(12) United States Patent
Boehm et al.

(10) Patent No.: US 9,598,430 B2
(45) Date of Patent: *Mar. 21, 2017

(54) GLP-1 RECEPTOR MODULATORS

(71) Applicant: Receptos, Inc., San Diego, CA (US)

(72) Inventors: Marcus F. Boehm, San Diego, CA (US); Esther Martinborough, San Diego, CA (US); Manisha Moorjani, San Diego, CA (US); Junko Tamiya, Carlsbad, CA (US); Liming Huang, San Diego, CA (US); Adam R. Yeager, La Mesa, CA (US); Enugurthi Brahmachary, San Diego, CA (US); Thomas Fowler, Melton Mowbray (GB); Andrew Novak, Long Eaton (GB); Premji Meghani, Loughborough (GB); Michael Knaggs, Burton-on-Trent (GB)

(73) Assignee: Celgene International II SÀRL, Couvet (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/958,513

(22) Filed: Dec. 3, 2015

(65) Prior Publication Data
US 2016/0214993 A1 Jul. 28, 2016

Related U.S. Application Data

(63) Continuation of application No. 14/302,260, filed on Jun. 11, 2014, now Pat. No. 9,260,427.
(Continued)

(51) Int. Cl.
*C07D 403/10* (2006.01)
*A61K 31/506* (2006.01)
(Continued)

(52) U.S. Cl.
CPC ......... *C07D 495/04* (2013.01); *A61K 31/155* (2013.01); *A61K 31/415* (2013.01); *A61K 31/4164* (2013.01); *A61K 31/4245* (2013.01); *A61K 31/4453* (2013.01); *A61K 31/4985* (2013.01); *A61K 31/505* (2013.01); *A61K 31/506* (2013.01); *A61K 31/551* (2013.01); *C07D 231/12* (2013.01); *C07D 233/64* (2013.01); *C07D 237/04* (2013.01); *C07D 239/26* (2013.01); *C07D 243/08* (2013.01); *C07D 271/06* (2013.01); *C07D 401/04* (2013.01); *C07D 401/12* (2013.01); *C07D 403/04* (2013.01); *C07D 403/10* (2013.01); *C07D 403/12* (2013.01); *C07D 403/14* (2013.01); *C07D 405/12* (2013.01); *C07D 409/12* (2013.01); *C07D 409/14* (2013.01); *C07D 413/04* (2013.01); *C07D 413/10* (2013.01); *C07D 413/12* (2013.01); *C07D 413/14* (2013.01); *C07D 417/04* (2013.01); *C07D 417/12* (2013.01); *C07D 471/04* (2013.01)

(58) Field of Classification Search
CPC .......................... C07D 403/10; A61K 31/506
USPC .................................. 544/333, 335; 514/256
See application file for complete search history.

(56) References Cited

U.S. PATENT DOCUMENTS

| 4,004,008 A | 1/1977 | Makovec et al. |
| 4,067,726 A | 1/1978 | Sasse et al. |

(Continued)

FOREIGN PATENT DOCUMENTS

| EP | 1 477 482 A1 | 11/2004 |
| EP | 1 700 850 A1 | 9/2006 |

(Continued)

OTHER PUBLICATIONS

Bundgaard, "Design of Prodrugs," Elsevier, pp. 1, 1985. (3 pages).
Devasthale et al., "Discovery of tertiary aminoacids as dual PPARα/γ agonists-I," *Bioorganic & Medicinal Chemistry Letters* 17:2312-2316, 2007.
Luo et al., "A new strategy for solid phase synthesis of a secondary amide library using sulfonamide linker via radical traceless cleavage," *Molecular Diversity* 6:33-41, 2003.
(Continued)

*Primary Examiner* — Deepak Rao
(74) *Attorney, Agent, or Firm* — Seed IP Law Group LLP

(57) ABSTRACT

Compounds are provided that modulate the glucagon-like peptide 1 (GLP-1) receptor, as well as methods of their synthesis, and methods of their therapeutic and/or prophylactic use. Such compounds can act as modulators or potentiators of GLP-1 receptor on their own, or with incretin peptides such as GLP-1(7-36) and GLP-1(9-36), or with peptide-based therapies, such as exenatide and liraglutide, and have the following general structure (where "⌇⌇⌇" represents either or both the R and S form of the compound):

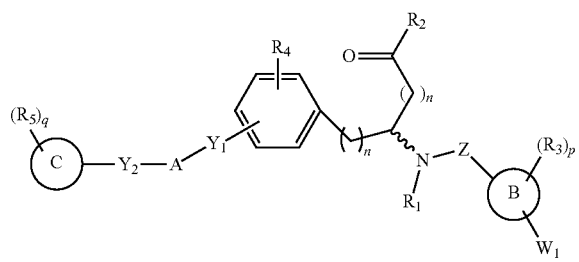

where A, B, C, $Y_1$, $Y_2$, Z, $R_1$, $R_2$, $R_3$, $R_4$, $R_5$, $W_1$, n, p and q are as defined herein.

56 Claims, No Drawings

Related U.S. Application Data

(60) Provisional application No. 61/833,737, filed on Jun. 11, 2013, provisional application No. 61/981,643, filed on Apr. 18, 2014.

(51) Int. Cl.

| | | |
|---|---|---|
| *C07D 495/04* | (2006.01) | |
| *C07D 403/12* | (2006.01) | |
| *C07D 401/04* | (2006.01) | |
| *C07D 403/04* | (2006.01) | |
| *C07D 239/26* | (2006.01) | |
| *C07D 405/12* | (2006.01) | |
| *C07D 409/12* | (2006.01) | |
| *C07D 409/14* | (2006.01) | |
| *C07D 413/04* | (2006.01) | |
| *C07D 413/12* | (2006.01) | |
| *C07D 417/12* | (2006.01) | |
| *C07D 271/06* | (2006.01) | |
| *C07D 231/12* | (2006.01) | |
| *C07D 233/64* | (2006.01) | |
| *C07D 243/08* | (2006.01) | |
| *C07D 413/14* | (2006.01) | |
| *C07D 417/04* | (2006.01) | |
| *C07D 471/04* | (2006.01) | |
| *A61K 31/155* | (2006.01) | |
| *A61K 31/415* | (2006.01) | |
| *A61K 31/4164* | (2006.01) | |
| *A61K 31/4245* | (2006.01) | |
| *A61K 31/4453* | (2006.01) | |
| *A61K 31/4985* | (2006.01) | |
| *A61K 31/505* | (2006.01) | |
| *A61K 31/551* | (2006.01) | |
| *C07D 237/04* | (2006.01) | |
| *C07D 401/12* | (2006.01) | |
| *C07D 403/14* | (2006.01) | |
| *C07D 413/10* | (2006.01) | |

(56) References Cited

U.S. PATENT DOCUMENTS

| | | |
|---|---|---|
| 5,424,286 A | 6/1995 | Eng |
| 6,174,905 B1 | 1/2001 | Suzuki et al. |
| 6,191,171 B1 | 2/2001 | DeLaszlo et al. |
| 6,583,139 B1 | 6/2003 | Thorsett et al. |
| 6,902,744 B1 | 6/2005 | Kolterman et al. |
| 7,297,761 B2 | 11/2007 | Beeley et al. |
| 7,368,427 B1 | 5/2008 | Dong et al. |
| 7,825,139 B2 | 11/2010 | Campbell et al. |
| 8,501,982 B2 | 8/2013 | Boehm et al. |
| 8,778,923 B2 | 7/2014 | Boehm et al. |
| 8,816,121 B2 | 8/2014 | Boehm et al. |
| 9,187,522 B2 * | 11/2015 | Boehm |
| 9,260,427 B2 | 2/2016 | Boehm et al. |
| 9,278,910 B2 | 3/2016 | Boehm et al. |
| 2001/0031772 A1 | 10/2001 | Schoenafinger et al. |
| 2004/0152750 A1 | 8/2004 | Kodra et al. |
| 2005/0222141 A1 | 10/2005 | Sagi et al. |
| 2007/0276034 A1 | 11/2007 | Esposito et al. |
| 2008/0300193 A1 | 12/2008 | Ahn et al. |
| 2010/0292143 A1 | 11/2010 | Bhuniya et al. |
| 2011/0306542 A1 | 12/2011 | Boehm et al. |
| 2013/0178420 A1 | 7/2013 | Boehm et al. |
| 2014/0031290 A1 | 1/2014 | Boehm et al. |
| 2014/0336185 A1 | 11/2014 | Boehm et al. |
| 2015/0038416 A1 | 2/2015 | Boehm et al. |
| 2016/0038487 A1 | 2/2016 | Boehm et al. |

FOREIGN PATENT DOCUMENTS

| | | |
|---|---|---|
| JP | 2003-525931 A | 9/2003 |
| JP | 2006-527233 A | 11/2006 |
| JP | 2009-102360 A | 5/2009 |
| JP | 2009-542752 A | 12/2009 |
| JP | 2010-180234 A | 8/2010 |
| WO | 99/06437 A1 | 2/1999 |
| WO | 99/10312 A1 | 3/1999 |
| WO | 01/21602 A1 | 3/2001 |
| WO | 01/66531 A1 | 9/2001 |
| WO | 03/048158 A1 | 6/2003 |
| WO | 2004/022561 A1 | 3/2004 |
| WO | 2005/077915 A1 | 8/2005 |
| WO | 2006/117743 A1 | 11/2006 |
| WO | 2006/127595 A1 | 11/2006 |
| WO | 2008/006561 A1 | 1/2008 |
| WO | 2011/094890 A1 | 8/2011 |
| WO | 2011/097300 A1 | 8/2011 |
| WO | 2011/156655 A2 | 12/2011 |
| WO | 2012/166951 A9 | 12/2012 |
| WO | 2013/090454 A2 | 6/2013 |
| WO | 2014/201172 A1 | 12/2014 |

OTHER PUBLICATIONS

Notice of Reasons for Rejection, mailed Nov. 26, 2015, for Japanese Application No. 2014-513706, 14 pages. (with English Translation).

Reid, "Practical Use of Glucagon-Like Peptide-1 Receptor Agonist Therapy in Primary Care," *Clinical Diabetes* 31(4):148-157, 2013.

Silverman, "The Organic Chemistry of Drug Design and Drug Action," Academic Press, Inc., pp. 352-400, 1992. (51 pages).

Banker et al., eds., "Modern Pharmaceutics $3^{rd}$ Ed", Marcel Dekker, New York, 1996, pp. 451 and 596, 3 pages.

Knudsen et al., "Small-molecule agonists for the glucagon-like peptide 1 receptor," *PNAS* 104(3): 937-942, Jan. 16, 2007.

International Search Report and Written Opinion, mailed Dec. 1, 2011, for International Application No. PCT/US2011/039873, 9 pages.

Thorsett et al., "Preparation of N-sulfonylated dipeptide derivatives as inhibitors of leukocyte adhesion mediated by VLA-4," Chem Abstracts Service Database accession No. 2003:485719, abstract, retrieved on Jul. 18, 2003 [3 pages].

Thorsen et al., "Preparation of N-sulfonylproline dipeptide derivatives and analogs as inhibitors of leukocyte adhesion mediated by VLA-4," Chem Abstracts Service Database accession No. 1999:113712, abstract, retrieved on Jul. 18, 2013 [3 pages].

Underwood et al., "Crystal Structure of Glucagon-like Peptide-1 in Complex with the Extracellular Domain of the Glucagon-like Peptide-1 Receptor," *Journal of Biological Chemistry* 285(1):723-730, Jan. 1, 2010.

West, "Solid state chemistry and its applications," John Wiley & Sons, New York, 1988, pp. 358 and 365, 3 pages.

Wolff, ed., "Burger's Medicinal Chemistry, Fourth Edition, Part 1, The Basis of Medicinal Chemistry," John Wiley & Sons, New York, 1979, pp. 336-337, 4 pages.

Wolff, ed., "Burger's Medicinal Chemistry and Drug Discovery, Fifth Edition, vol. 1: Principles and Practice," John Wiley & Sons, New York, 1995, pp. 975-977, 4 pages.

PubChem Compound, Compound Summary for CID 2980472, "N-benzyl-4-[(2-phenylacetyl)amino]benzamide," retrieve from https://pubchem.ncbi.nih.gov/summary/summary.cgi?cid=29804 . . . , retrieved on Sep. 10, 2014, 6 pages.

PubChem Compound, Compound Summary for CID 4884981, "SMR000154147," retrieved from https://pubchem.ncbi.nih.gov/summary/summary.cgi?cid=48849 . . . , retrieved on Sep. 10, 2014, 6 pages.

* cited by examiner

GLP-1 RECEPTOR MODULATORS

FIELD OF THE INVENTION

The invention relates to compounds that bind the glucagon-like peptide 1 (GLP-1) receptor, methods of their synthesis, and methods of their therapeutic and/or prophylactic use. The present invention is directed to compounds adapted to act as modulators of the GLP-1 receptor, and potentiators of incretin peptides, such as GLP-1(7-36) and GLP-1(9-36), as well as peptide-based therapies such as exenatide and liraglutide.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 800059_408D1_SEQUENCE_LISTING.txt. The text file is 1.6 KB, was created on Mar. 8, 2016, and is being submitted electronically via EFS-Web.

BACKGROUND

Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the brain (Kieffer T. J. and Habener, J. F. Endocrin. Rev. 20:876-913 (1999); Drucker, D. J., Endocrinology 142:521-7 (2001); Holst, J. J., Diabetes Metab. Res. Rev. 18:430-41 (2002)). The initial actions of GLP-1 observed were on the insulin-producing cells of the islets, where it stimulates glucose-dependent insulin secretion. Subsequently, multiple additional antidiabetogenic actions of GLP-1 were discovered including the stimulation of the growth and inhibition of the apoptosis of pancreatic beta cells (Drucker, D. J., Endocrinology 144:5145-8 (2003); Holz, G. G. and Chepurny O. G., Curr. Med. Chem. 10:2471-83 (2003); List, J. F. and Habener, J. F., Am. J. Physiol. Endocrinol. Metab. 286:E875-81 (2004)).

On activation, GLP-1 receptors couple to the α-subunit of G protein, with subsequent activation of adenylate cyclase and increase of cAMP levels, thereby potentiating glucose-stimulated insulin secretion. Therefore, GLP-1 is an attractive therapeutic target to lower blood glucose and preserve the β-cells of the pancreas of diabetic patients. Glucagon has been used for decades in medical practice within diabetes and several glucagon-like peptides are being developed for various therapeutic indications. GLP-1 analogs and derivatives are being developed for the treatment for patients suffering from diabetes.

SUMMARY OF THE INVENTION

The present invention is directed to compounds adapted to act as potentiators or modulators of GLP-1 receptor; methods of their preparation and methods of their use, such as in treatment of a malcondition mediated by GLP-1 receptor activation, or when modulation or potentiation of GLP-1 receptor is medically indicated.

Certain embodiments of the present invention comprise a compound having the structure of Formula I-R or I-S or a pharmaceutically acceptable isomer, enantiomer, racemate, salt, isotope, prodrug, hydrate or solvate thereof:

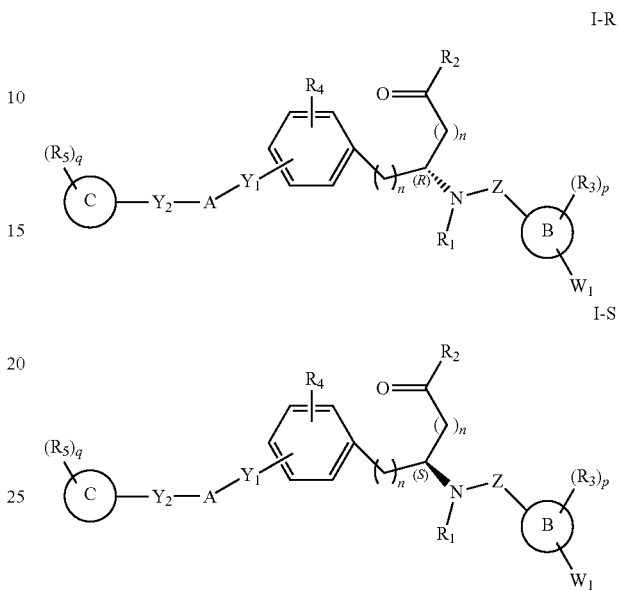

wherein
A is a 5-, 6- or 7-membered heterocyclyl having one, two or three heteroatoms where each such heteroatom is independently selected from O, N, and S, and where any ring atom of such heterocyclyl may be optionally substituted with one or more of $R_4$;
B is aryl, aralkyl, heterocyclyl, or heterocyclylalkyl;
C is aryl, aralkyl, heterocyclyl or heterocyclylalkyl, and when C is aryl A and C may be taken together to form a fused bicyclic ring system between the 5-, 6- or 7-membered heterocyclyl of A and the aryl of C;
$Y_1$ and $Y_2$ are both null, or one of $Y_1$ or $Y_2$ is —NH— or —O— and the other $Y_1$ or $Y_2$ is null;
Z is —C(O)— or —S(O)$_2$—;
each $R_1$ is independently H or $C_{1-4}$ alkyl;
$R_2$ is —OH, —O—$R_8$, —N($R_1$)—SO$_2$—$R_7$, —NR$_{41}$R$_{42}$, —N($R_1$)—(CR$_a$R$_b$)$_m$—COOR$_8$, —N($R_1$)—(CR$_a$R$_b$)$_m$—CO—N($R_1$)($R_{40}$), —N($R_1$)—(CR$_a$R$_b$)$_m$—N($R_1$)C(O)O($R_8$), —N($R_1$)—(CR$_a$R$_b$)$_m$—N($R_1$)($R_{40}$), —N($R_1$)—(CR$_a$R$_b$)$_m$—CO—N($R_1$)-heterocyclyl, or —N($R_1$)—(CR$_a$R$_b$)$_m$-heterocyclyl, which heterocyclyl may be optionally (singly or multiply) substituted with $R_7$;
each $R_3$ and $R_4$ is independently H, halo, alkyl, alkyl substituted (singly or multiply) with $R_{31}$, alkoxy, haloalkyl, perhaloalkyl, haloalkoxy, perhaloalkoxy, aryl, heterocyclyl, —OH, —OR$_7$, —CN, —NO$_2$, —NR$_1$R$_7$, —C(O)R$_7$, —C(O)NR$_1$R$_7$, —NR$_1$C(O)R$_7$, —SR$_7$, —S(O)R$_7$, —S(O)$_2$R$_7$, —OS(O)$_2$R$_7$, —S(O)$_2$NR$_1$R$_7$, —NR$_1$S(O)$_2$R$_7$, —(CR$_a$R$_b$)$_m$NR$_1$R$_7$, —(CR$_a$R$_b$)$_m$O(CR$_a$R$_b$)$_m$R$_7$, —(CR$_a$R$_b$)$_m$NR$_1$(CR$_a$R$_b$)$_m$R$_7$ or —(CR$_a$R$_b$)$_m$NR$_1$(CR$_a$R$_b$)$_m$COOR$_8$; or any two $R_3$ or $R_4$ groups on the same carbon atom taken together form oxo;
each $R_{31}$ is independently H, halo, hydroxyl, —NR$_{41}$R$_{42}$, or alkoxy;

each $R_{40}$ is independently H, $R_7$, alkyl which may be optionally (singly or multiply) substituted with $R_7$, or $R_{40}$ and $R_1$ taken together with the N atom to which they are attached form a 3- to 7-membered heterocyclyl which may be optionally (singly or multiply) substituted with $R_7$;

each $R_{41}$ and $R_{42}$ is independently $R_{40}$, —(CHR$_{40}$)$_n$—C(O)O—R$_{40}$, —(CHR$_{40}$)$_n$—C(O)—R$_{40}$, —(CH$_2$)$_n$—N(R$_1$)(R$_7$), aryl or heteroaryl any of which aryl or heteroaryl may be optionally (singly or multiply) substituted with $R_7$; or any two $R_{41}$ and $R_{42}$ taken together with the N atom to which they are attached form a 3- to 7-membered heterocyclyl which may be optionally (singly or multiply) substituted with $R_7$;

$W_1$ is null or -L$_1$-(CR$_a$R$_b$)$_m$-L$_1$-R$_6$;

each $L_1$ is independently, from the proximal to distal end of the structure of Formula I-R or I-S, null, —C(O)O—, —S(O$_2$)—, —S(O)—, —S—, —N(R$_1$)—C(O)—N(R$_1$)—, —N(R$_1$)—C(O)—O—, —C(O)— or —S(O$_2$)—NR$_1$—;

each $R_a$ and $R_b$ is independently H, halo, alkyl, alkoxy, aryl, aralkyl, heterocyclyl, heterocyclylalkyl (any of which alkyl, alkoxy, aryl, aralkyl, heterocyclyl or heterocyclylalkyl may be optionally (singly or multiply) substituted with $R_7$), —(CHR$_{40}$)$_m$C(O)OR$_{40}$, —(CHR$_{40}$)$_m$OR$_{40}$, —(CHR$_{40}$)$_m$SR$_{40}$, —(CHR$_{40}$)$_m$NR$_{41}$R$_{42}$, —(CHR$_{40}$)$_m$C(O)NR$_{41}$R$_{42}$, —(CHR$_{40}$)$_m$C(O)N(R$_1$)(CHR$_{40}$)$_m$—NR$_{41}$R$_{42}$, —(CHR$_{40}$)$_m$C(O)N(R$_1$)(CHR$_{40}$)$_m$C(O)NR$_{41}$R$_{42}$, —(CHR$_{40}$)$_m$C(O)N(R$_1$)—(CHR$_{40}$)$_m$C(O)OR$_{40}$, or —(CHR$_{40}$)$_m$—S—S—R$_{40}$; or any two $R_a$ and $R_b$ taken together with the carbon atom(s) to which they are attached form a cycloalkyl or heterocyclyl optionally substituted (singly or multiply) with $R_7$; or $R_1$ and any one of $R_a$ or $R_b$ taken together with the atoms to which they are attached form heterocyclyl optionally substituted (singly or multiply) with $R_7$;

$R_5$ is $R_7$, —(CR$_a$R$_b$)$_m$—(CR$_a$R$_b$)$_m$—R$_7$, or -(-L$_3$-(CR$_a$R$_b$)$_r$-L$_3$-R$_7$, wherein the carbon atoms of any two adjacent —(CR$_a$R$_b$)$_m$ or (CR$_a$R$_b$)$_r$ groups may be taken together to form a double bond (—(C(R$_a$)=C(R$_a$)—) or triple bond (—C≡C—);

$R_6$ is H, alkyl, aryl, heteroaryl, heterocyclyl, heterocloalkyl, any of which may be optionally substituted (singly or multiply) with $R_7$ or —(CR$_a$R$_b$)$_m$-L$_2$-(CR$_a$R$_b$)$_m$—R$_7$;

each $R_7$ is independently $R_{10}$; a ring moiety selected from cycloalkyl, aryl, aralkyl, heterocyclyl or heterocyclylalkyl, where such ring moiety is optionally (singly or multiply) substituted with $R_{10}$; or when a carbon atom bears two $R_7$ groups such two $R_7$ groups are taken together to form oxo or thioxo, or are taken together to form a ring moiety selected from cycloalkyl, aryl, heterocyclyl or heterocyclyl, wherein such ring moiety is optionally singly or multiply substituted with $R_{10}$;

each $R_{10}$ is independently H, halo, alkyl, haloalkyl, perhaloalkyl, —(CR$_a$R$_b$)$_m$OH, —(CR$_a$R$_b$)$_m$OR$_8$, —(CR$_a$R$_b$)$_m$CN, —(CR$_a$R$_b$)$_m$NH(C=NH)NH$_2$, —(CR$_a$R$_b$)$_m$NR$_1$R$_8$, —(CR$_a$R$_b$)$_m$O(CR$_a$R$_b$)$_m$R$_8$, —(CR$_a$R$_b$)$_m$NR$_1$(CR$_a$R$_b$)$_m$R$_8$, —(CR$_a$R$_b$)$_m$C(O)R$_8$, —(CR$_a$R$_b$)$_m$C(O)OR$_8$, —(CR$_a$R$_b$)$_m$C(O)NR$_1$R$_8$, —(CR$_a$R$_b$)$_m$NR$_1$(CR$_a$R$_b$)$_m$C(O)OR$_8$, —(CR$_a$R$_b$)$_m$NR$_1$C(O)R$_8$, —(CR$_a$R$_b$)$_m$C(O)NR$_1$S(O)$_2$R$_8$, —(CR$_a$R$_b$)$_m$SR$_8$, —(CR$_a$R$_b$)$_m$S(O)R$_8$, —(CR$_a$R$_b$)$_m$S(O)$_2$R$_8$, —(CR$_a$R$_b$)$_m$S(O)$_2$NR$_1$R$_8$ or —(CR$_a$R$_b$)$_m$NR$_1$S(O)$_2$R$_8$;

each $R_8$ is independently H, alkyl, aryl, —(CR$_a$R$_b$)$_m$-L$_2$-(CR$_a$R$_b$)$_m$—R$_1$ or -(-L$_3$-(CR$_a$R$_b$)$_r$-)$_s$-L$_3$-R$_1$;

$L_2$ is independently, from the proximal to distal end of the structure of Formula I-R or I-S, null, —O—, —OC(O)—, —NR$_1$—, —C(O)NR$_1$—, —N(R$_1$)—C(O)—, —S(O$_2$)—, —S(O)—, —S—, —C(O)— or —S(O$_2$)—N(R$_1$)—;

each $L_3$ is independently null, —O—, or —N(R$_1$)— each m is independently 0, 1, 2, 3, 4, 5 or 6;

each n is independently 0 or 1 or 2;

p is 0, 1, 2 or 3;

q is 0, 1, 2 or 3;

each r is independently 2, 3, or 4; and each s is independently 1, 2, 3, or 4.

In certain embodiments, a pharmaceutical composition comprising a compound of the invention together with at least one pharmaceutically acceptable carrier, diluent or excipient is provided.

In certain embodiments, a method of use of a compound of the invention comprising preparation of a medicament is provided.

In certain embodiments, the invention provides a pharmaceutical combination comprising a compound of the invention and a second medicament. In various such embodiments, the second medicament is an agonist or modulator for glucagon receptor, GIP receptor, GLP-2 receptor, or PTH receptor, or glucagon-like peptide 1 (GLP-1) receptor. In various such embodiments, the second medicament is exenatide, liraglutide, taspoglutide, albiglutide, or lixisenatide or other insulin regulating peptide. In various embodiment, the second medicament is medically indicated for the treatment of type II diabetes. In various embodiments, the second medicament is a biguanide, a sulfonylurea, a meglitinide, a thiazolidinedione, an α-glucosidase inhibitor, a bile acid sequestrant, and/or a dopamine-2 agonist, and in more specific embodiments is metformin (a biguanide) or sitagliptin (a DPPIV inhibitor).

In certain embodiments, a method of activation, potentiation or agonism of a GLP-1 receptor is provided comprising contacting the receptor with a compound, pharmaceutical composition or pharmaceutical combination of the invention.

In certain embodiments, a method is provided for treatment of a malcondition in a subject for which activation, potentiation or agonism of a GLP-1 receptor is medically indicated where such method comprises administering to such subject a compound, pharmaceutical composition or pharmaceutical combination of the invention. In various such embodiments, selective activation, potentiation or agonism of a GLP-1 receptor, is medically indicated. In various such embodiments, the malcondition comprises type I diabetes, type II diabetes, gestational diabetes, obesity, excessive appetite, insufficient satiety, or metabolic disorder.

In certain embodiments, the invention provides methods for synthesis of certain compounds including compounds of the invention. In certain other embodiments, the invention provides certain intermediate compounds associated with such methods of synthesis.

DETAILED DESCRIPTION OF THE INVENTION

Certain embodiments comprise a compound having the chiral structure of Formula I-R or I-S (with the chirality as indicated) or a pharmaceutically acceptable isomer, enantiomer, racemate, salt, isotope, prodrug, hydrate or solvate thereof:

Certain embodiments of the present invention comprise a compound having the structure of Formula I-R or I-S or a pharmaceutically acceptable isomer, enantiomer, racemate, salt, isotope, prodrug, hydrate or solvate thereof:

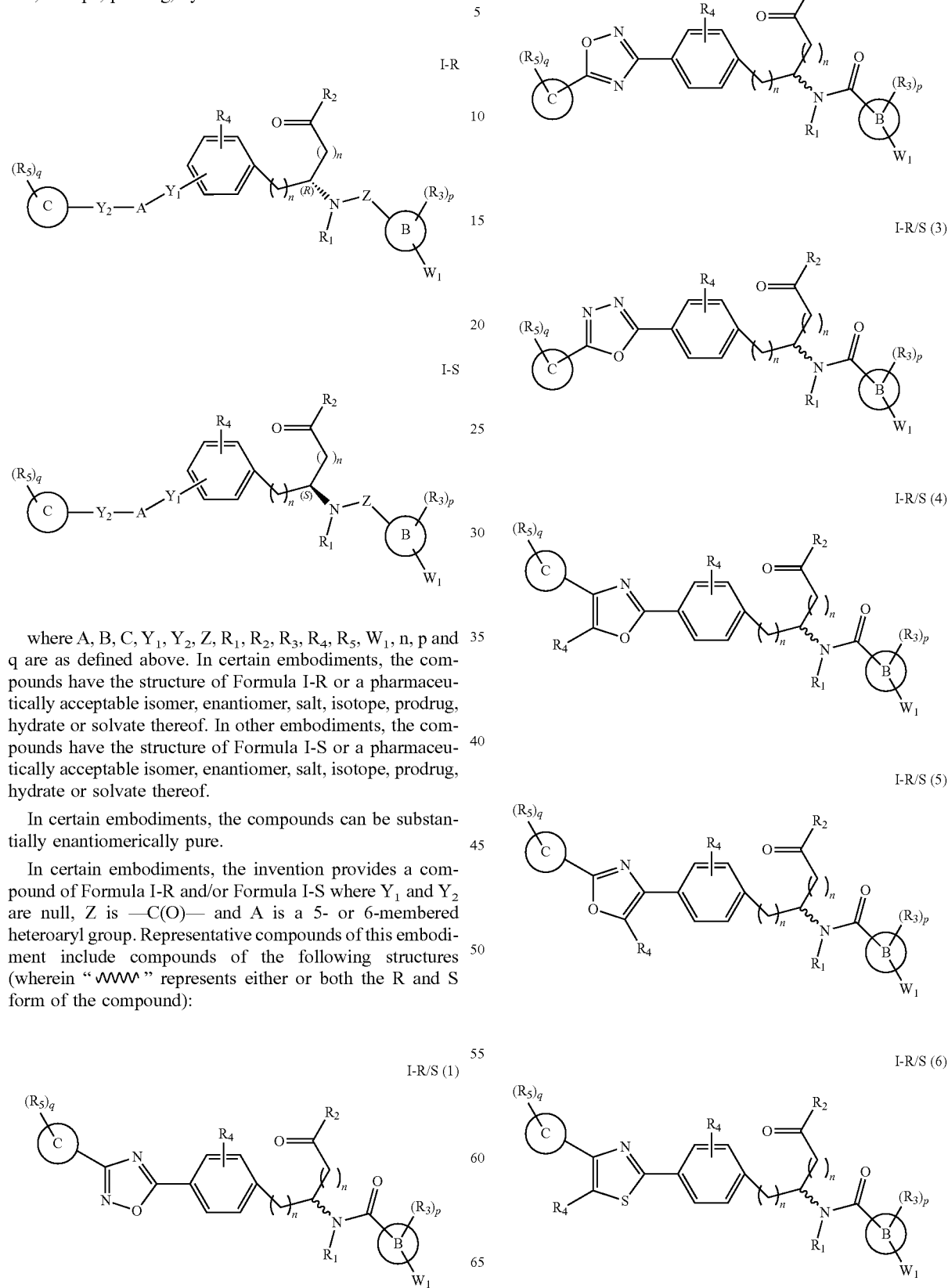

where A, B, C, $Y_1$, $Y_2$, Z, $R_1$, $R_2$, $R_3$, $R_4$, $R_5$, $W_1$, n, p and q are as defined above. In certain embodiments, the compounds have the structure of Formula I-R or a pharmaceutically acceptable isomer, enantiomer, salt, isotope, prodrug, hydrate or solvate thereof. In other embodiments, the compounds have the structure of Formula I-S or a pharmaceutically acceptable isomer, enantiomer, salt, isotope, prodrug, hydrate or solvate thereof.

In certain embodiments, the compounds can be substantially enantiomerically pure.

In certain embodiments, the invention provides a compound of Formula I-R and/or Formula I-S where $Y_1$ and $Y_2$ are null, Z is —C(O)— and A is a 5- or 6-membered heteroaryl group. Representative compounds of this embodiment include compounds of the following structures (wherein " ⌇⌇⌇ " represents either or both the R and S form of the compound):

-continued
I-R/S (7)
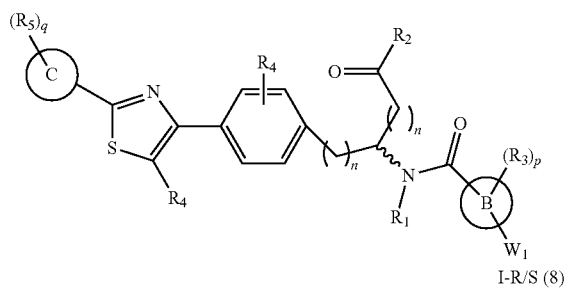
I-R/S (8)

I-R/S (9)
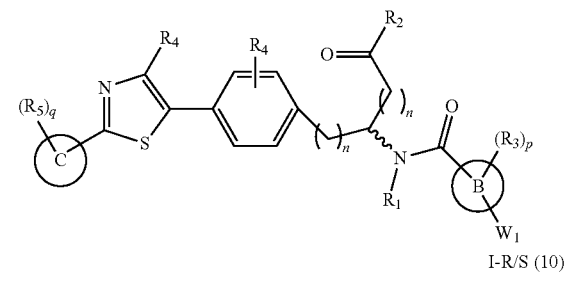
I-R/S (10)
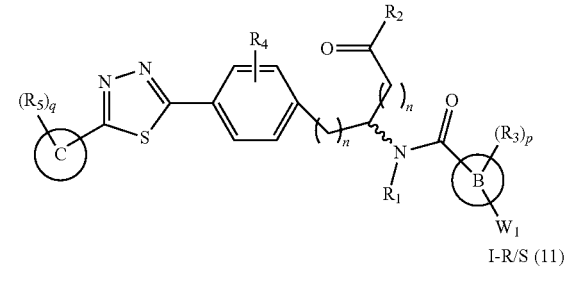
I-R/S (11)
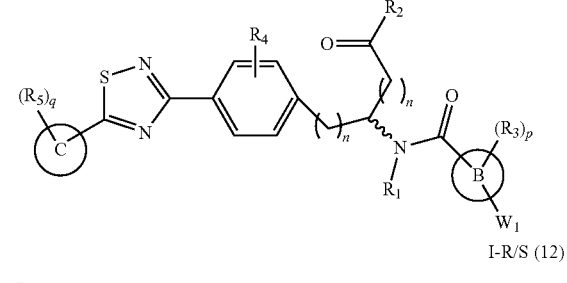
I-R/S (12)
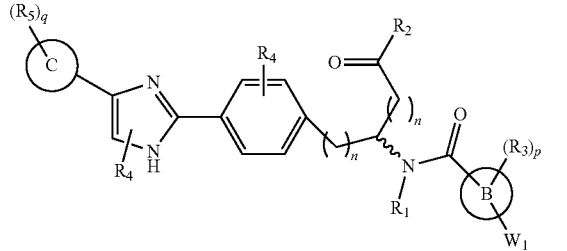
-continued
I-R/S (13)
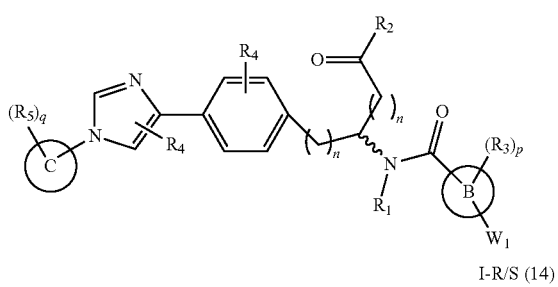
I-R/S (14)
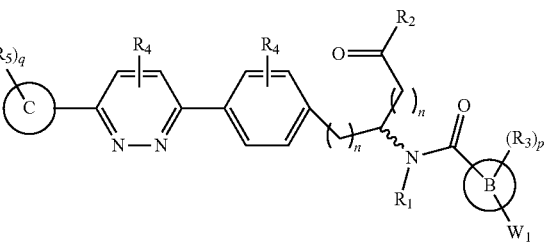
I-R/S (15)
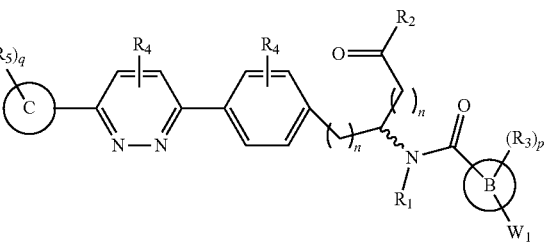
I-R/S (16)
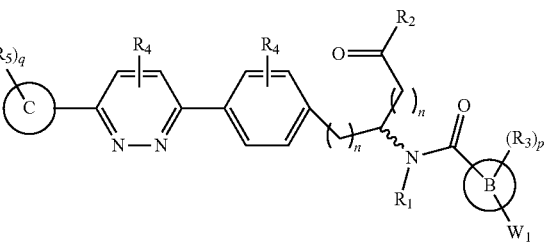
I-R/S (17)
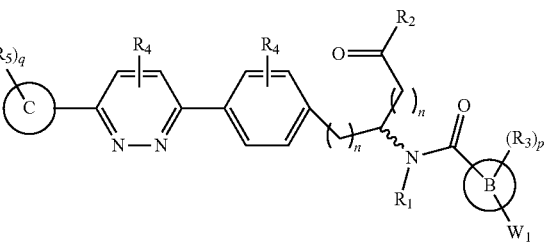
I-R/S (18)
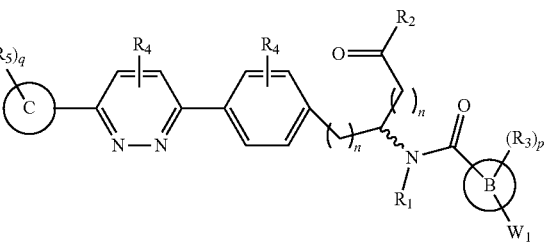

I-R/S (19)
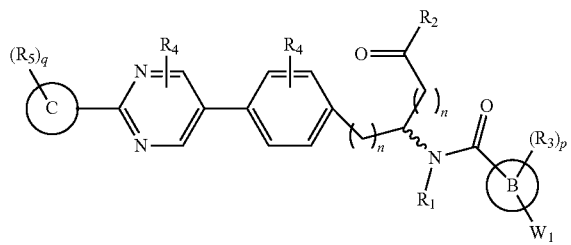

I-R/S (20)

I-R/S (21)
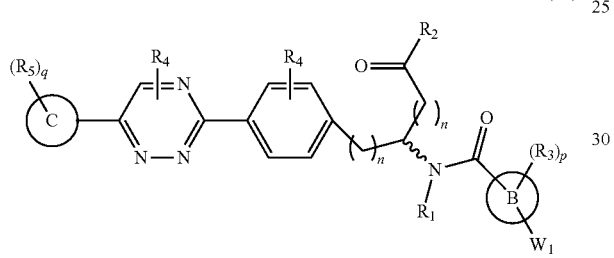

I-R/S (22)
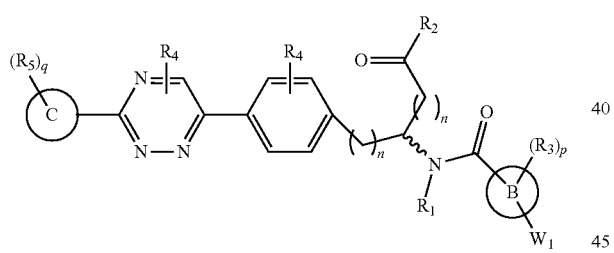

In certain embodiments, the invention provides a compound where $Y_1$ and $Y_2$ are null, Z is —C(O)— and A is a 5-, 6- or 7-membered non-aromatic heterocyclyl group. Representative compounds of this embodiment include compounds of the following structures (wherein " ⌇⌇⌇ " represents either or both the R and S form of the compound):

I-R/S (23)
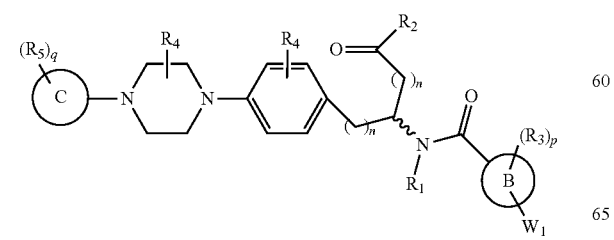

I-R/S (24)
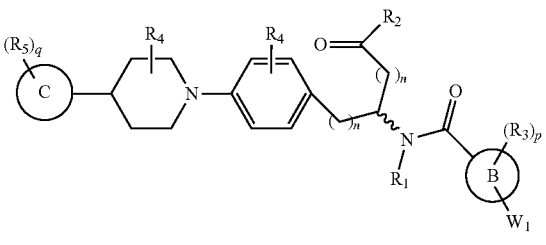

I-R/S (25)
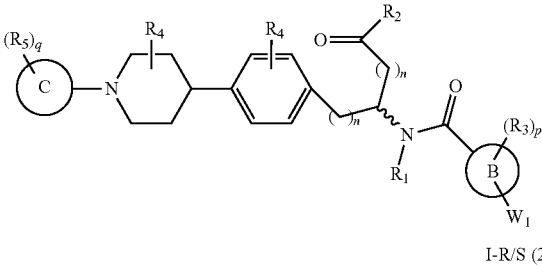

I-R/S (26)
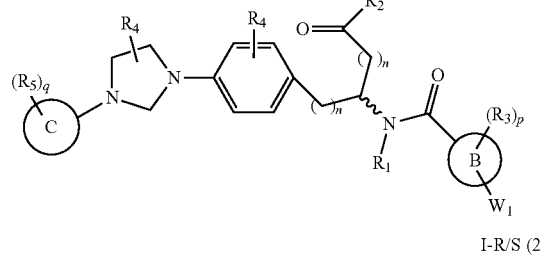

I-R/S (27)
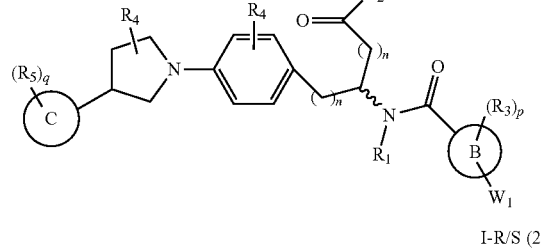

I-R/S (28)
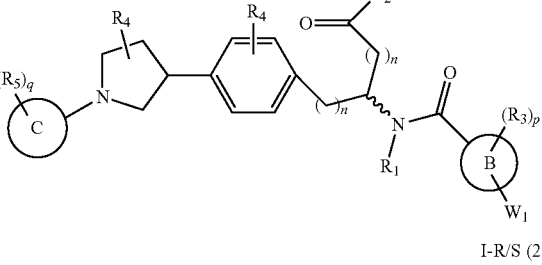

I-R/S (29)
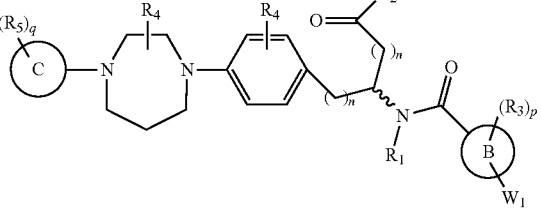

In certain embodiments, the invention provides compounds of each of structures I-R/S (1)-(29) where R$_4$ of the phenyl group is H.

In certain embodiments, the inventions provides compounds of each of structures I-R/S (1)-(29) where the A group (i.e., the 5-, 6- or 7-membered heterocyclyl) is not substituted by R$_4$, or substituted by R$_4$ where R$_4$ is alkyl, haloalkyl, alkoxy, —NR$_1$R$_7$ where R$_1$ and R$_7$ are independently hydrogen or alkyl, or substituted by two R$_4$ groups which taken together form oxo.

In certain embodiments, the invention provides a compound of Formula I-R and/or Formula I-S where Y$_1$ and Y$_2$ are null, Z is —C(O)— and C is aryl. Representative compounds of this embodiment include compounds of the following structures (wherein " $\mathcal{WW}$ " represents either or both the R and S form of the compound):

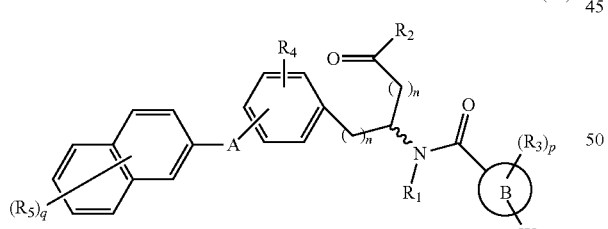

I-R/S (30)

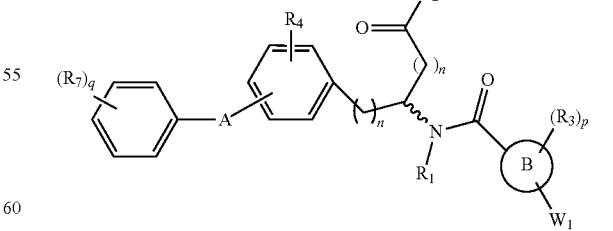

I-R/S (31)

I-R/S (32)

In certain embodiments, the invention provides compounds of each of structures I-R/S (30)-(32) where q is zero.

In certain embodiments, the invention provides compounds of each of structures I-R/S (30)-(32) where q is one, two or three.

In certain embodiments, the invention provides compounds of structure I-R/S (30) where q is one and R$_5$ is —(CR$_a$R$_b$)$_m$-L$_2$-(CR$_a$R$_b$)$_m$—R$_7$ or -(-L$_3$-(CR$_a$R$_b$)$_r$-)$_s$-L$_3$-R$_7$. Representative compounds of this embodiment include compounds of the following structure (wherein " $\mathcal{WW}$ " represents either or both the R and S form of the compound):

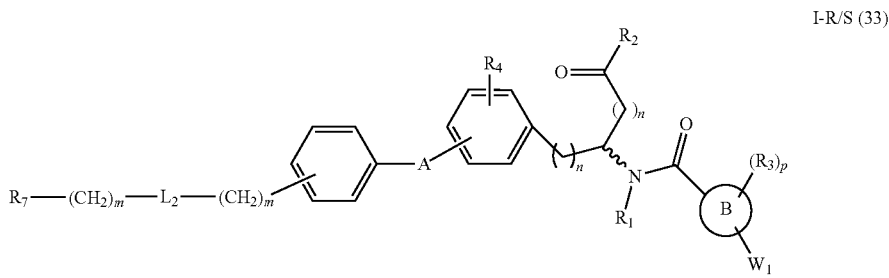

I-R/S (33)

In certain embodiments, the invention provides compounds of structure I-R/S (33) where R$_7$ is H or alkyl and L$_2$ is O. Representative compounds of this embodiment include compounds of the following structure (wherein " $\mathcal{WW}$ " represents either or both the R and S form of the compound):

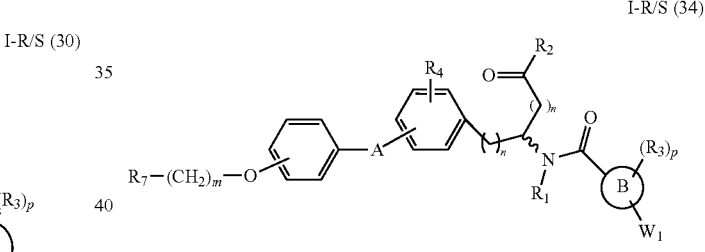

I-R/S (34)

In certain embodiments, the invention provides compounds of structure I-R/S (30) where R$_5$ is R$_7$. Representative compounds of this embodiment include compounds of the following structure (wherein " $\mathcal{WW}$ " represents either or both the R and S form of the compound):

I-R/S (35)

In certain embodiments, the invention provides compounds of structure I-R/S (35) where R$_7$ is halo, alkyl, haloalkyl, perhaloalkyl, alkoxy, —(CR$_a$R$_b$)$_m$OH, —(CR$_a$R$_b$)$_m$OR$_8$, —(CR$_a$R$_b$)$_m$CN, —(CR$_a$R$_b$)$_m$NH(C=NH)NH$_2$, —(CR$_a$R$_b$)$_m$NR$_1$R$_8$, —(CR$_a$R$_b$)$_m$O $(CR_aR_b)_m R_8$, —$(CR_aR_b)_mNR_1(CR_aR_b)_mR_8$, —$(CR_aR_b)_mC(O)R_8$, —$(CR_aR_b)_mC(O)OR_8$, —$(CR_aR_b)_mC(O)NR_1R_8$, —$(CR_aR_b)_mNR_1(CR_aR_b)_mC(O)OR_8$, —$(CR_aR_b)_mNR_1C(O)R_8$, —$(CR_aR_b)_mC(O)NR_1R_8$, —$(CR_aR_b)_mSR_8$, —$(CR_aR_b)_mS(O)R_8$, —$(CR_aR_b)_mS(O)_2R_8$, —$(CR_aR_b)_mS(O)_2NR_1R_8$, —$(CR_aR_b)_mNR_1S(O)_2R_8$.

In certain embodiments, the invention provides compounds of structure I-R/S (35) where $R_7$ is a ring moiety selected from cycloalkyl, aryl, aralkyl, heterocyclyl or heterocyclylalkyl, where such ring moiety is optionally (singly or multiply) substituted with halo, —OH, —CN, alkyl, alkoxy, haloalkyl or perhaloalkyl.

In certain embodiments, the invention provides a compound of Formula I-R and/or Formula I-S where $Y_1$ and $Y_2$ are null, Z is —C(O)— and C is heterocyclyl. Representative compounds of this embodiment include compounds of the following structures (wherein " ⌇⌇⌇ " represents either or both the R and S form of the compound):

I-R/S (36)

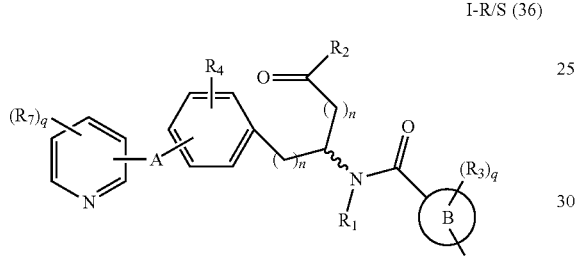

I-R/S (37)

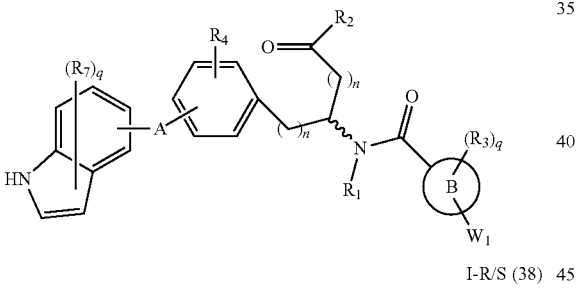

I-R/S (38)

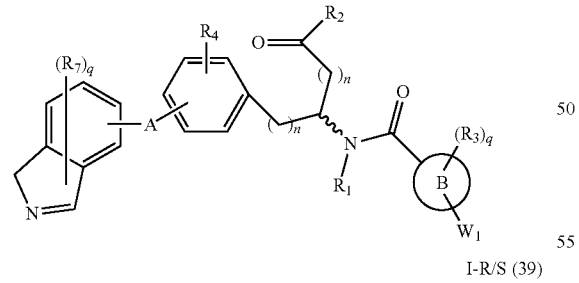

I-R/S (39)

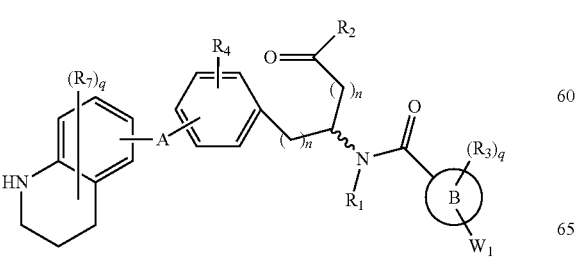

I-R/S (40)

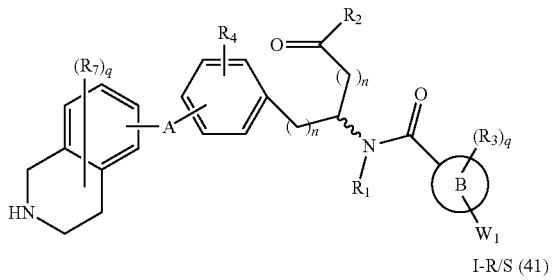

I-R/S (41)

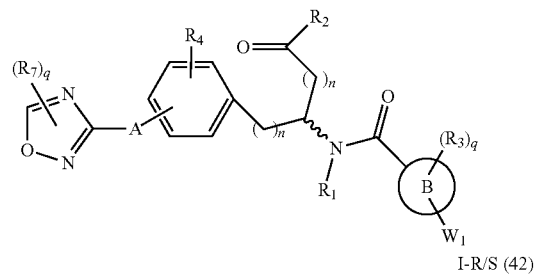

I-R/S (42)

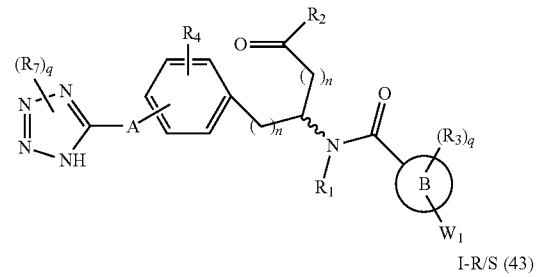

I-R/S (43)

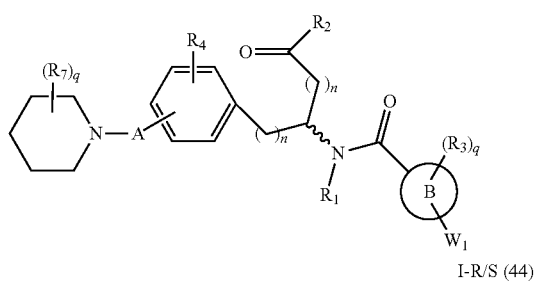

I-R/S (44)

In certain embodiments, the invention provides compounds of each of structures I-R/S (36)-(44) where $R_7$ is halo, alkyl, haloalkyl, perhaloalkyl, alkoxy, —$(CR_aR_b)_m$OH, —$(CR_aR_b)_mOR_8$, —$(CR_aR_b)_mCN$, —$(CR_aR_b)_mNH(C=NH)NH_2$, —$(CR_aR_b)_mNR_1R_8$, —$(CR_aR_b)_mO(CR_aR_b)_m R_8$, —$(CR_aR_b)_mNR_1(CR_aR_b)_mR_8$, —$(CR_aR_b)_mC(O)R_8$, —$(CR_aR_b)_mC(O)OR_8$, —$(CR_aR_b)_mC(O)NR_1R_8$, —$(CR_aR_b)_mNR_1(CR_aR_b)_mC(O)OR_8$, —$(CR_aR_b)_mNR_1C(O)R_8$, —$(CR_aR_b)_mC(O)NR_1R_8$, —$(CR_aR_b)_mSR_8$, —$(CR_aR_b)_mS(O)R_8$, —$(CR_aR_b)_mS(O)_2R_8$, —$(CR_aR_b)_mS(O)_2NR_1R_8$, —$(CR_aR_b)_mNR_1S(O)_2R_8$.

In certain embodiments, the invention provides compounds of each of structures I-R/S (36)-(44) where $R_7$ is a ring moiety selected from cycloalkyl, aryl, aralkyl, heterocyclyl or heterocyclylalkyl, where such ring moiety is optionally (singly or multiply) substituted with halo, —OH, —CN, alkyl, alkoxy, haloalkyl or perhaloalkyl.

In certain embodiments, the invention provides a compound of Formula I-R and/or Formula I-S where $Y_1$ and $Y_2$ are null, Z is —C(O)— and B is aryl or aralkyl. Representative compounds of this embodiment include compounds of the following structures (wherein "〰〰" represents either or both the R and S form of the compound):

I-R/S (45)

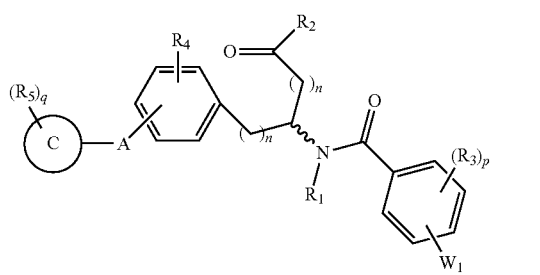

I-R/S (46)

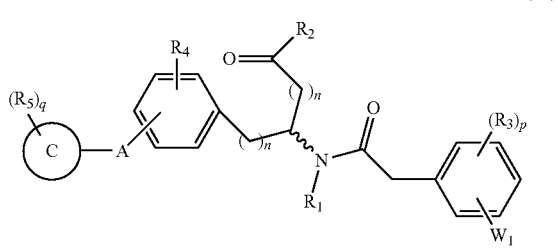

I-R/S (47)

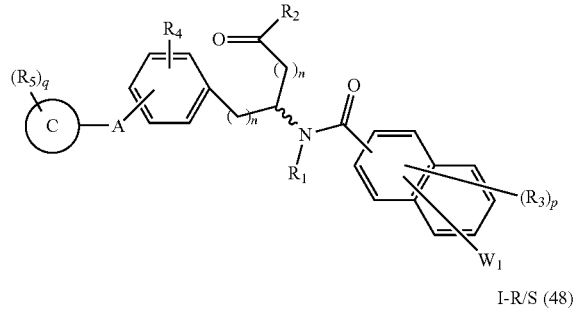

I-R/S (48)

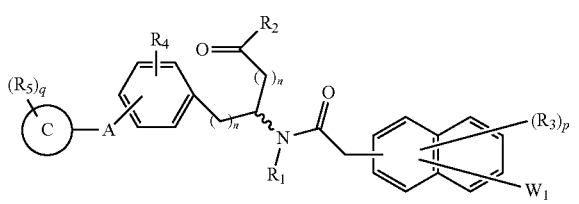

In certain embodiments, the invention provides compounds of each of structures I-R/S (45)-(48) where $W_1$ is null.

Representative compounds of this embodiment include compounds of the following structure (wherein "〰〰" represents either or both the R and S form of the compound):

I-R/S (49)

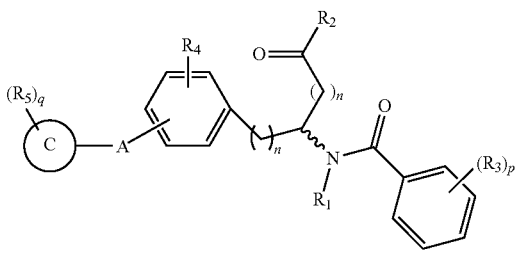

In certain embodiments, the invention provides compounds of structure I-R/S (49) where $R_3$ is halo, alkyl, alkyl substituted with $R_{31}$, alkoxy, haloalkyl, perhaloalkyl, haloalkoxy, perhaloalkoxy, aryl, heterocyclyl, —OH, —OR_7, —CN, —NO_2, —NR_1R_7, —C(O)R_7, —C(O)NR_1R_7, —NR_1C(O)R_7, —SR_7, —S(O)R_7, —S(O)_2R_7, —OS(O)_2R_7, —S(O)_2NR_1R_7, —NR_1S(O)_2R_7, —(CR_aR_b)_m NR_1R_7, —(CR_aR_b)_m O(CR_aR_b)_m R_7, —(CR_aR_b)_m NR_1 (CR_aR_b)_m R_7 or —(CR_aR_b)_m NR_1(CR_aR_b)_m COOR_8$.

In certain embodiments, the invention provides compounds of each of structures I-R/S (45)-(49) where $R_3$ is alkyl.

In certain embodiments, the invention provides a compound of Formula I-R and/or Formula I-S where $Y_1$ and $Y_2$ are null, Z is —C(O)— and B is heterocyclyl or heterocyclylalkyl. Representative compounds of this embodiment include compounds of the following structures (wherein "〰〰" represents either or both the R and S form of the compound):

I-R/S (50)

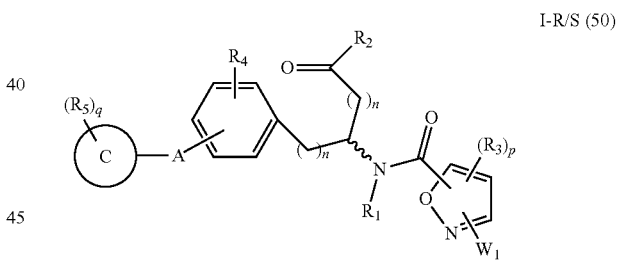

I-R/S (51)

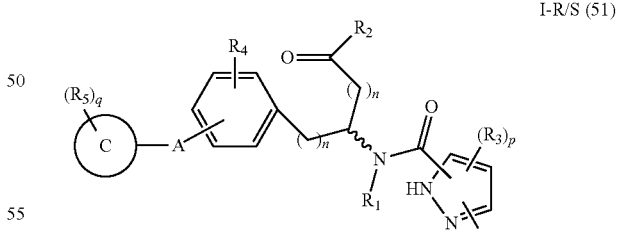

I-R/S (52)

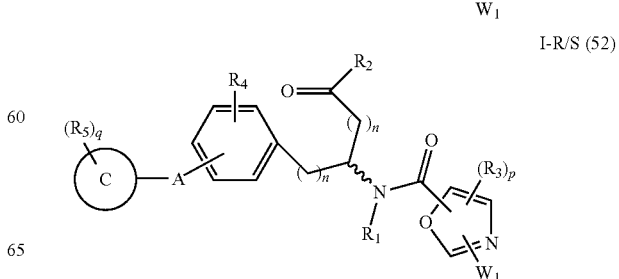

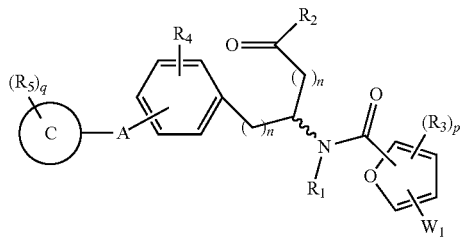

I-R/S (53)


I-R/S (54)

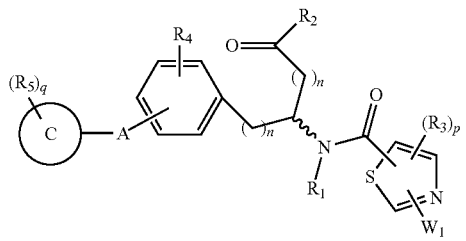

I-R/S (55)

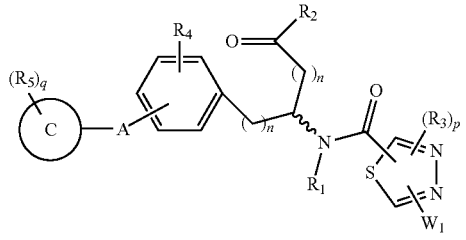

I-R/S (56)

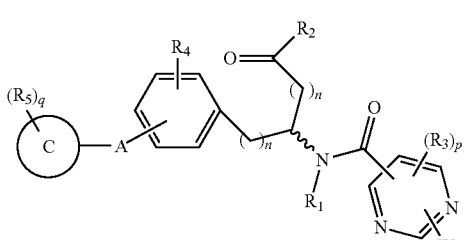

I-R/S (57)

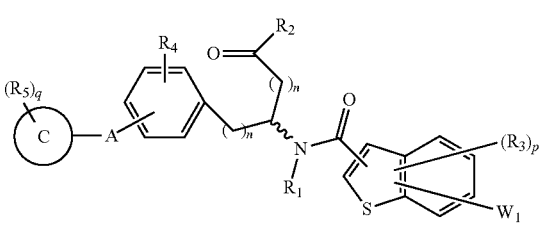

I-R/S (58)

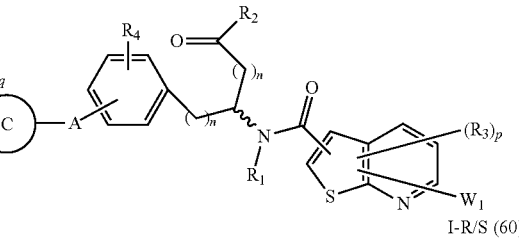

I-R/S (59)

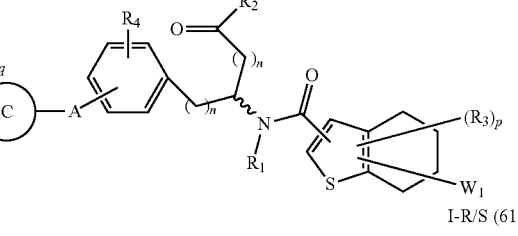

I-R/S (60)

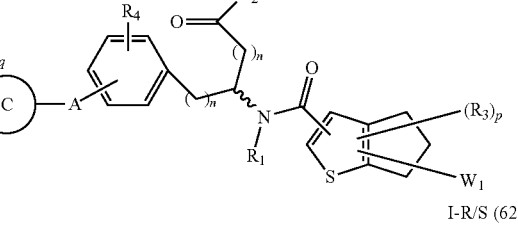

I-R/S (61)

I-R/S (62)

In certain embodiments, the invention provides compounds of each of structures I-R/S (50)-(62) where $W_1$ is null.

In certain embodiments, the invention provides compounds of each of structures I-R/S (50)-(62) where $W_1$ is null and $R_3$ is halo, alkyl, alkyl substituted with $R_{31}$, alkoxy, haloalkyl, perhaloalkyl, haloalkoxy, perhaloalkoxy, aryl, heterocyclyl, —OH, —OR$_7$, —CN, —NO$_2$, —NR$_1$R$_7$, —C(O)R$_7$, —C(O)NR$_1$R$_7$, —NR$_1$C(O)R$_7$, —SR$_7$, —S(O)R$_7$, —S(O)$_2$R$_7$, —OS(O)$_2$R$_7$, —S(O)$_2$NR$_1$R$_7$, —NR$_1$S(O)$_2$R$_7$, —(CR$_a$R$_b$)$_m$NR$_1$R$_7$, —(CR$_a$R$_b$)$_m$O(CR$_a$R$_b$)$_m$R$_7$, —(CR$_a$R$_b$)$_m$NR$_1$(CR$_a$R$_b$)$_m$R$_7$ or —(CR$_a$R$_b$)$_m$NR$_1$(CR$_a$R$_b$).

In certain embodiments, the invention provides compounds of each of structures I-R/S (50)-(62) where $W_1$ is null, p is 1 and $R_3$ is alkyl.

In certain embodiments, the invention provides compounds of each of structures I-R/S (1)-(62) where $R_2$ is —OH, —N(R$_1$)—(CR$_a$R$_b$)$_m$—COOH or —N(R$_1$)—SO$_2$—R$_7$; where $R_1$ is H; where $R_a$ and $R_b$ are independently H, alkyl, alkoxy, —(CHR$_{40}$)$_m$C(O)NR$_{41}$R$_{42}$, —(CHR$_{40}$)$_m$C(O)OR$_{40}$, —(CHR$_{40}$)$_m$NR$_{41}$R$_{42}$, —(CHR$_{40}$)$_m$SR$_{40}$, aryl optionally substituted with $R_7$, or wherein $R_1$ and any one of $R_a$ or $R_b$ taken together with the carbon(s) to which they are attached form heterocyclyl; $R_8$ is alkyl; and m is 1 or 2.

In certain embodiments, the invention provides compounds of the following structures (wherein "⌇⌇⌇" represents either or both the R and S form of the compound):

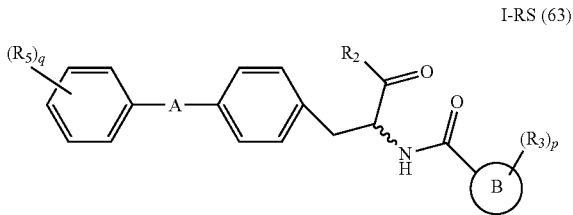

I-RS (63)

In certain embodiments, the invention provides compounds of structure I-R/S (63) where A is a 5-membered heteroaryl.

In certain embodiments, the invention provides compounds of structure I-R/S (63) where A is a 6-membered heteroaryl.

In certain embodiments, the invention provides compounds of structure I-R/S (63) where A is a 6-membered heteroaryl having one or two nitrogen atoms.

In certain embodiments, the invention provides compounds of structure I-R/S (63) where A is pyrimindinyl.

In certain embodiments, the invention provides compounds of structure I-R/S (63) where A is pyridinyl.

In certain embodiments, the invention provides compounds of structure I-R/S (63) where B is aryl.

In certain embodiments, the invention provides compounds of structure I-R/S (63) where B is phenyl.

In certain embodiments, the invention provides compounds of structure I-R/S (63) where B is heteroaryl.

In certain embodiments, the invention provides compounds of structure I-R/S (63) where B is thiophenyl.

In certain embodiments, the invention provides compounds of structure I-R/S (63) where $R_2$ is —OH.

In certain embodiments, the invention provides compounds of structure I-R/S (63) where $R_2$ is —N($R_1$)($CR_aR_b$)$_m$COOR$_8$.

In certain embodiments, the invention provides compounds of structure I-R/S (63) where $R_2$ is —N($R_1$)SO$_2$R$_7$.

In certain embodiments, the invention provides compounds of structure I-R/S (63) where $R_2$ is —NHCH$_2$COOH.

In certain embodiments, the invention provides compounds of structure I-R/S (63) where $R_2$ is —NH(CHR$_b$)COOH where $R_b$ is alkyl optionally substituted with $R_7$, —(CHR$_{40}$)$_m$OR$_{40}$, —(CHR$_{40}$)$_m$SR$_{40}$, —(CHR$_{40}$)$_m$NR$_{41}$R$_{42}$, —(CHR$_{40}$)$_m$C(O)NR$_{41}$R$_{42}$, —(CHR$_{40}$)$_m$C(O)N(R$_1$)(CHR$_{40}$)$_m$—NR$_{41}$R$_{42}$, —(CHR$_{40}$)$_m$C(O)N(R$_1$)(CHR$_{40}$)$_m$ C(O)NR$_{41}$R$_{42}$, —(CHR$_4$)$_m$C(O)N(R$_1$)(CHR$_{40}$)$_m$C(O)OR$_{40}$ or —(CHR$_{40}$)$_m$—S—S—R$_{40}$ In certain embodiments, the invention provides compounds of structure I-R/S (63) where $R_2$ is —NH(CR$_a$R$_b$)$_m$COOH where R$_a$ and R$_b$ are independently H, alkyl optionally substituted with R$_7$, —(CHR$_{40}$)$_m$OR$_{40}$, —(CHR$_{40}$)$_m$SR$_{40}$, —(CHR$_{40}$)$_m$NR$_{41}$R$_{42}$, —(CHR$_{40}$)$_m$C(O)NR$_{41}$R$_{42}$, —(CHR$_{40}$)$_m$C(O)N(R$_1$)(CHR$_{40}$)$_m$—NR$_{41}$R$_{42}$, —(CHR$_{40}$)$_m$C(O)N(R$_1$)—(CHR$_{40}$)$_m$C(O)NR$_{41}$R$_{42}$, —(CHR$_{40}$)$_m$C(O)N(R$_1$)(CHR$_{40}$)$_m$C(O)OR$_{40}$ or —(CHR$_{40}$)$_m$—S—S—R$_{40}$.

In certain embodiments, the invention provides compounds of structure I-R/S (63) where $R_2$ is —NR$_1$(CHR$_b$)$_m$COOH where R$_1$ and R$_b$ taken together form heterocyclyl.

In certain embodiments, the invention provides compounds of structure I-R/S (63) where $R_2$ is —NR$_1$(CR$_a$R$_b$)$_m$COOH where R$_1$ and one of R$_b$ taken together form heterocyclyl.

In certain embodiments, the invention provides compounds of structure I-R/S (63) where any two R$_a$ and R$_b$ taken together with the carbon to which they are attached form a cycloalkyl.

In certain embodiments, the invention provides compounds of structure I-R/S (63) where $R_2$ is —NH(CR$_a$R$_b$)$_m$COOH where one of R$_a$ and R$_b$ is H and the other R$_a$ and R$_b$ is aryl substituted with R$_7$.

In certain embodiments, the invention provides compounds of structure I-R/S (63) where p is 1 or 2 and each R$_3$ is independently alkyl, alkoxy, —OH, perhaloalkyl or —C(O)R$_8$.

In certain embodiments, the invention provides compounds of structure I-R/S (63) where p is 1 and each R$_3$ is alkyl.

In certain embodiments, the invention provides compounds of structure I-R/S (63) where q is 1 and R$_5$ is —(CR$_a$R$_b$)$_m$-L$_2$-(CR$_a$R$_b$)$_m$—R$_7$, and in more specific embodiments where q is 1 and R$_5$ is —(CH$_2$)$_m$-L$_2$-(CH$_2$)$_m$—R$_7$.

In certain embodiments, the invention provides compounds of structure I-R/S (63) where q is 1 and R$_5$ is alkoxy.

In certain embodiments, the invention provides compounds of the following structures (wherein "〰〰" represents either or both the R and S form of the compound):

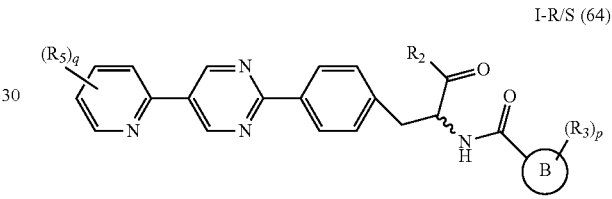

I-R/S (64)

In certain embodiments, the invention provides compounds of structure I-R/S (64) where B is phenyl or thiophenyl. Representative compounds of this embodiment include compounds of the following structure (wherein "〰〰" represents either or both the R and S form of the compound):

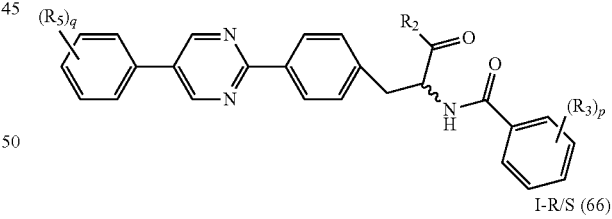

(I-R/S (65))

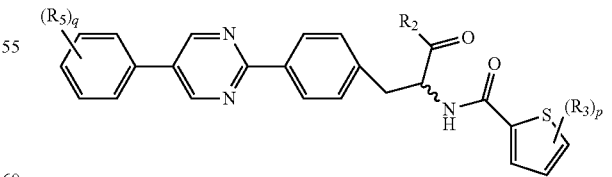

I-R/S (66)

In certain embodiments, the invention provides compounds of structure I-R/S (65)-(66) where p is 1 and R$_3$ is alkyl.

In certain embodiments, the invention provides compounds of structure I-R/S (65)-(66) where p is 1 and R$_3$ is tert-butyl.

In certain embodiments, the invention provides compounds of structure I-R/S (65)-(66) where q is 1 and R₅ is alkoxy.

In certain embodiments, the invention provides compounds of structure I-R/S (65)-(66) where q is 1 and R₅ is C₄₋₈ alkoxy.

In certain embodiments, the invention provides compounds of structure I-R/S (65)-(66) where q is 1 and R₅ is C₆₋₈ alkoxy.

In certain embodiments, the invention provides compounds of structure I-R/S (65)-(66) where q is 1 and R₅ is C₆ alkoxy In certain embodiments, the invention provides compounds of structure I-R/S (65)-(66) where q is 1 and R₅ is C₇ alkoxy.

In certain embodiments, the invention provides compounds of structure I-R/S (65)-(66) where q is 1 and R₅ is C₈ alkoxy.

In certain embodiments, the invention provides compounds of structure I-R/S (65)-(66) where q is 1 and R₅ is alkyl.

In certain embodiments, the invention provides compounds of structure I-R/S (65)-(66) where q is 1 and R₅ is C₁₋₄ alkyl.

In certain embodiments, the invention provides compounds of structure I-R/S (65)-(66) where q is 1 and R₅ is cycloalkyl.

In certain embodiments, the invention provides compounds of structure I-R/S (65)-(66) where q is 1 and R₅ is cyclopropyl.

In certain embodiments, the invention provides compounds of structure I-R/S (65)-(66) where p is 1, R₃ is alkyl, q is 1 and R₅ is alkoxy.

In certain embodiments, the invention provides compounds of structure I-R/S (65)-(66) where p is 1, R₃ is tert-butyl, q is 1 and R₅ is C₄₋₈ alkoxy.

In certain embodiments, the invention provides compounds of structure I-R/S (65)-(66) where p is 1, R₃ is tert-butyl, q is 1 and R₅ is C₆₋₈ alkoxy.

In certain embodiments, the invention provides compounds of structure I-R/S (65)-(66) where p is 1, R₃ is tert-butyl, q is 1 and R₅ is C₆ alkoxy.

In certain embodiments, the invention provides compounds of structure I-R/S (65)-(66) where p is 1, R₃ is tert-butyl, q is 1 and R₅ is C₇ alkoxy.

In certain embodiments, the invention provides compounds of structure I-R/S (65)-(66) where p is 1, R₃ is tert-butyl, q is 1 and R₅ is C₈ alkoxy.

In certain embodiments, the invention provides compounds of structure I-R/S (65)-(66) where p is 1, R₃ is tert-butyl, q is 1 and R₅ is alkyl.

In certain embodiments, the invention provides compounds of structure I-R/S (65)-(66) where p is 1, R₃ is tert-butyl, q is 1 and R₅ is C₁₋₄ alkyl.

In certain embodiments, the invention provides compounds of structure I-R/S (65)-(66) where p is 1, R₃ is tert-butyl, q is 1 and R₅ is cycloalkyl.

In certain embodiments, the invention provides compounds of structure I-R/S (65)-(66) where p is 1, R₃ is tert-butyl, q is 1 and R₅ is cyclopropyl.

In certain embodiments, the invention provides compounds of the following structures (wherein "〰〰" represents either or both the R and S form of the compound):

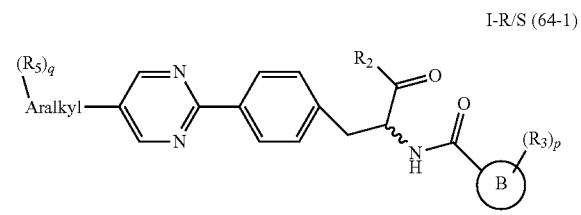

I-R/S (64-1)

In certain embodiments, the invention provides compounds of structure I-R/S (64-1) where B is phenyl or thiophenyl. Representative compounds of this embodiment include compounds of the following structure (wherein "〰〰" represents either or both the R and S form of the compound):

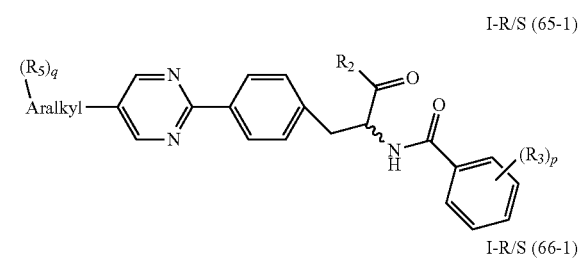

I-R/S (65-1)

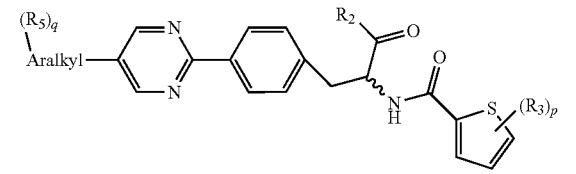

I-R/S (66-1)

In certain embodiments, the invention provides compounds of structure I-R/S (65-1)-(66-1) where aralkyl is benzyl (—CH₂phenyl), phenylethyl (—CH₂CH₂phenyl) or phenylethylene (—CH=CHphenyl).

In certain embodiments, the invention provides compounds of structure I-R/S (65-1)-(66-1) where aralkyl is benzyl (—CH₂phenyl).

In certain embodiments, the invention provides compounds of structure I-R/S (65-1)-(66-1) where aralkyl is phenylethyl (—CH₂CH₂phenyl).

In certain embodiments, the invention provides compounds of structure I-R/S (65-1)-(66-1) where aralkyl is phenylethylene (—CH=CHphenyl).

In certain embodiments, the invention provides compounds of structure I-R/S (65-1)-(66-1) where p is 1 and R₃ is alkyl.

In certain embodiments, the invention provides compounds of structure I-R/S (65-1)-(66-1) where p is 1 and R₃ is tert-butyl.

In certain embodiments, the invention provides compounds of structure I-R/S (65-1)-(66-1) where q is 1 and R₅ is alkoxy.

In certain embodiments, the invention provides compounds of structure I-R/S (65-1)-(66-1) where q is 1 and R₅ is C₄₋₈ alkoxy.

In certain embodiments, the invention provides compounds of structure I-R/S (65-1)-(66-1) where q is 1 and R₅ is C₆₋₈ alkoxy.

In certain embodiments, the invention provides compounds of structure I-R/S (65-1)-(66-1) where q is 1 and R₅ is C₆ alkoxy In certain embodiments, the invention provides compounds of structure I-R/S (65-1)-(66-1) where q is 1 and $R_5$ is $C_7$ alkoxy.

In certain embodiments, the invention provides compounds of structure I-R/S (65-1)-(66-1) where q is 1 and $R_5$ is $C_8$ alkoxy.

In certain embodiments, the invention provides compounds of structure I-R/S (65-1)-(66-1) where q is 1 and $R_5$ is alkyl.

In certain embodiments, the invention provides compounds of structure I-R/S (65-1)-(66-1) where q is 1 and $R_5$ is $C_{1-4}$ alkyl.

In certain embodiments, the invention provides compounds of structure I-R/S (65-1)-(66-1) where q is 1 and $R_5$ is cycloalkyl.

In certain embodiments, the invention provides compounds of structure I-R/S (65-1)-(66-1) where q is 1 and $R_5$ is cyclopropyl.

In certain embodiments, the invention provides compounds of structure I-R/S (65-1)-(66-1) where aralkyl is benzyl, phenylethyl or phenylethylene, p is 1, $R_3$ is alkyl, q is 1 and $R_5$ is alkoxy.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is $C_{4-8}$ alkoxy.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is $C_{6-8}$ alkoxy.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is $C_6$ alkoxy.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is $C_7$ alkoxy.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is $C_8$ alkoxy.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is alkyl.

In certain embodiments, the invention provides compounds of structure I-R/S (65-1)-(66-1) where aralkyl is phenylethylene, p is 1, $R_3$ is tert-butyl, q is 1 and $R_5$ is alkyl.

In certain embodiments, the invention provides compounds of structure I-R/S (65-1)-(66-1) where aralkyl is phenylethylene, p is 1, $R_3$ is tert-butyl, q is 1 and $R_5$ is $C_{1-4}$ alkyl.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is cycloalkyl.

In certain embodiments, the invention provides compounds of structure I-R/S (65-1)-(66-1) where aralkyl is benzyl, phenylethyl or phenylethylene, p is 1, $R_3$ is tert-butyl, q is 1 and $R_5$ is cyclopropyl.

In certain embodiments, the invention provides compounds of structure I-R/S (65)-(66) where $R_2$ is —N($R_1$)($CR_aR_b$)$_m$COOR$_8$. Representative compounds of this embodiment include compounds of the following structure (wherein " ~~~ " represents either or both the R and S form of the compound):

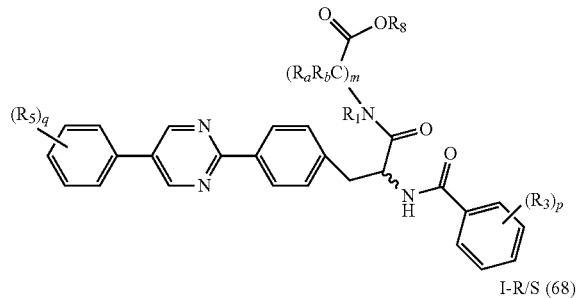

I-R/S (67)

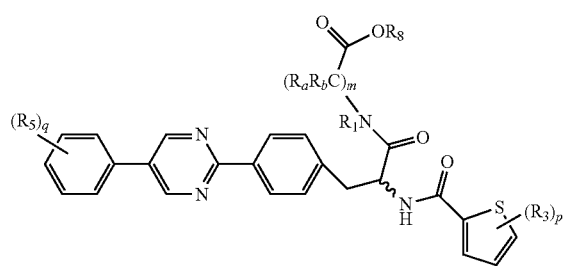

I-R/S (68)

In certain embodiments, the invention provides compounds of structure I-R/S (65-1)-(66-1) where $R_2$ is —N($R_1$)($CR_aR_b$)$_m$COOR$_8$. Representative compounds of this embodiment include compounds of the following structure (wherein " ~~~ " represents either or both the R and S form of the compound):

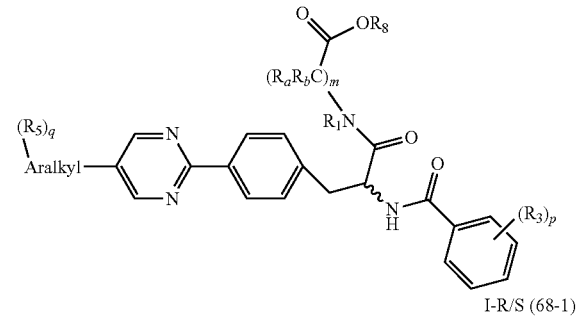

I-R/S (67-1)

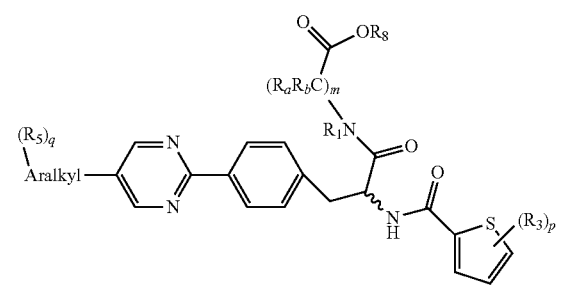

I-R/S (68-1)

In certain embodiments, the invention provides compounds of structure I-R/S (67), (67-1), (68) and (68-1) where $R_1$ is hydrogen.

In certain embodiments, the invention provides compounds of structure I-R/S (67), (67-1), (68) and (68-1) where $R_8$ is hydrogen.

In certain embodiments, the invention provides compounds of structure I-R/S (67), (67-1), (68) and (68-1) where m is 2, $R_1$ is hydrogen, each occurrence of $R_a$ and $R_b$ are hydrogen, and $R_8$ is hydrogen.

In certain embodiments, the invention provides compounds of structure I-R/S (67), (67-1), (68) and (68-1) where m is 2, a single $R_a$ (i.e., one of the two) is hydrogen, each occurrence of $R_b$ is hydrogen, and $R_8$ is hydrogen.

In certain embodiments, the invention provides compounds of structure I-R/S (67), (67-1), (68) and (68-1) where m is 1 and $R_1$, $R_a$, $R_b$ and $R_8$ are hydrogen.

In certain embodiments, the invention provides compounds of structure I-R/S (67), (67-1), (68) and (68-1) where m is 1, $R_a$ is alkyl and $R_1$, $R_b$ and $R_8$ are hydrogen.

In certain embodiments, the invention provides compounds of structure I-R/S (67), (67-1), (68) and (68-1) where m is 1, $R_a$ is methyl and $R_1$, $R_b$ and $R_8$ are hydrogen.

In certain embodiments, the invention provides compounds of structure I-R/S (67-1)-(68-1) where aralkyl is benzyl (—CH$_2$phenyl), phenylethyl (—CH$_2$CH$_2$phenyl) or phenylethylene (—CH=CHphenyl).

In certain embodiments, the invention provides compounds of structure I-R/S (67-1)-(68-1) where aralkyl is benzyl (—CH$_2$phenyl).

In certain embodiments, the invention provides compounds of structure I-R/S (67-1)-(68-1) where aralkyl is phenylethyl (—CH$_2$CH$_2$phenyl).

In certain embodiments, the invention provides compounds of structure I-R/S (67-1)-(68-1) where aralkyl is phenylethylene (—CH=CHphenyl).

In certain embodiments, the invention provides compounds of structure I-R/S (67), (67-1), (68) and (68-1) where p is 1 and $R_3$ is alkyl.

In certain embodiments, the invention provides compounds of structure I-R/S (67), (67-1), (68) and (68-1) where p is 1 and $R_3$ is tert-butyl.

In certain embodiments, the invention provides compounds of structure I-R/S (67), (67-1), (68) and (68-1) where q is 1 and $R_5$ is alkoxy.

In certain embodiments, the invention provides compounds of structure I-R/S (67), (67-1), (68) and (68-1) where q is 1 and $R_5$ is $C_{4-8}$alkoxy.

In certain embodiments, the invention provides compounds of structure I-R/S (67), (67-1), (68) and (68-1) where q is 1 and $R_5$ is $C_{6-8}$ alkoxy.

In certain embodiments, the invention provides compounds of structure I-R/S (67), (67-1), (68) and (68-1) where q is 1 and $R_5$ is $C_6$ alkoxy In certain embodiments, the invention provides compounds of structure I-R/S (67), (67-1), (68) and (68-1) where q is 1 and $R_5$ is $C_7$ alkoxy.

In certain embodiments, the invention provides compounds of structure I-R/S (67), (67-1), (68) and (68-1) where q is 1 and $R_5$ is $C_8$ alkoxy.

In certain embodiments, the invention provides compounds of structure I-R/S (67), (67-1), (68) and (68-1) where q is 1 and $R_5$ is alkyl.

In certain embodiments, the invention provides compounds of structure I-R/S (67), (67-1), (68) and (68-1) where q is 1 and $R_5$ is $C_{1-4}$ alkyl.

In certain embodiments, the invention provides compounds of structure I-R/S (67), (67-1), (68) and (68-1) where q is 1 and $R_5$ is cycloalkyl.

In certain embodiments, the invention provides compounds of structure I-R/S (67), (67-1), (68) and (68-1) where q is 1 and $R_5$ is cyclopropyl.

In certain embodiments, the invention provides compounds of structure I-R/S (67-1)-(68-1) where aralkyl is benzyl, phenylethyl or phenylethylene, p is 1, $R_3$ is alkyl, q is 1 and $R_5$ is alkoxy.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is $C_{4-8}$ alkoxy.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is $C_{6-8}$ alkoxy.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is $C_6$ alkoxy.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is $C_7$ alkoxy.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is $C_8$ alkoxy.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is alkyl.

In certain embodiments, the invention provides compounds of structure I-R/S (67-1)-(68-1) where aralkyl is phenylethylene, p is 1, $R_3$ is tert-butyl, q is 1 and $R_5$ is alkyl.

In certain embodiments, the invention provides compounds of structure I-R/S (67-1)-(68-1) where aralkyl is phenylethylene, p is 1, $R_3$ is tert-butyl, q is 1 and $R_5$ is $C_{1-4}$ alkyl.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is cycloalkyl.

In certain embodiments, the invention provides compounds of structure I-R/S (67-1)-(68-1) where aralkyl is benzyl, phenylethyl or phenylethylene, p is 1, $R_3$ is tert-butyl, q is 1 and $R_5$ is cyclopropyl.

In certain embodiments, the invention provides compounds of structure I-R/S (67)-(68) where m is 2, $R_1$ is hydrogen, each occurrence of $R_a$ and $R_b$ are hydrogen, and $R_8$ is hydrogen. Representative compounds of this embodiment include compounds of the following structure (wherein "⩘⩗⩘⩗" represents either or both the R and S form of the compound):

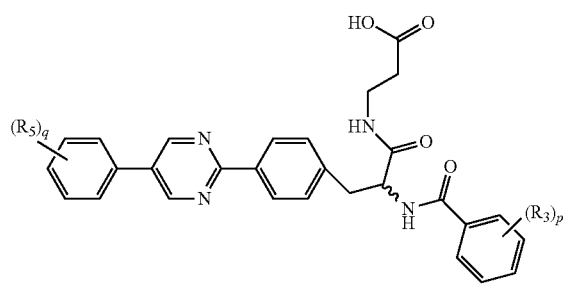

I-R/S (69)

-continued

I-R/S (70)

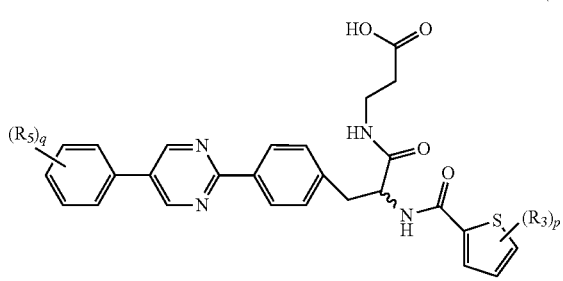

In certain embodiments, the invention provides compounds of structure I-R/S (69)-(70) where p is 1 and $R_3$ is alkyl.

In certain embodiments, the invention provides compounds of structure I-R/S (69)-(70) where p is 1 and $R_3$ is tert-butyl.

In certain embodiments, the invention provides compounds of structure I-R/S (69)-(70) where q is 1 and $R_5$ is alkoxy.

In certain embodiments, the invention provides compounds of structure I-R/S (69)-(70) where q is 1 and $R_5$ is $C_{4-8}$alkoxy.

In certain embodiments, the invention provides compounds of structure I-R/S (69)-(70) where q is 1 and $R_5$ is $C_7$ alkoxy.

In certain embodiments, the invention provides compounds of structure I-R/S (69)-(70) where p is 1, $R_3$ is alkyl, q is 1 and $R_5$ is $C_{4-8}$alkoxy.

In certain embodiments, the invention provides compounds of structure I-R/S (67)-(68) where m is 1 and $R_1$, $R_b$ and $R_8$ are hydrogen. Representative compounds of this embodiment include compounds of the following structure (wherein "⌇⌇⌇" represents either or both the R and S form of the compound):

I-R/S (71)

I-R/S (72)

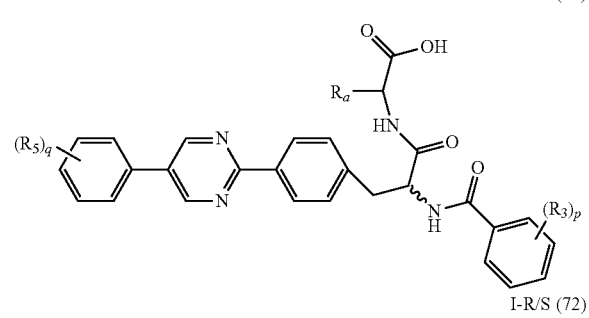

In certain embodiments, the invention provides compounds of structure I-R/S (67)-(68) where m is 2, a single $R_a$ (i.e., one of the two) is hydrogen, each occurrence of $R_b$ is hydrogen, and $R_8$ is hydrogen. Representative compounds of this embodiment include compounds of the following structure (wherein "⌇⌇⌇" represents either or both the R and S form of the compound):

I-R/S (73)

I-R/S (74)

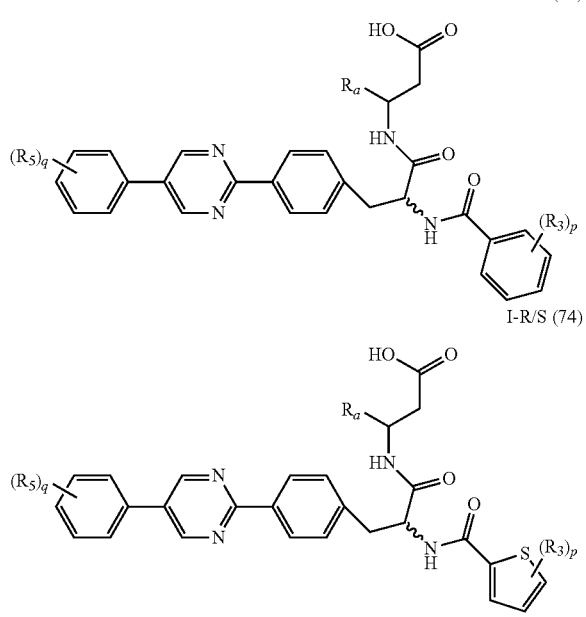

In certain embodiments, the invention provides compounds of structure I-R/S (71)-(74) where $R_a$ is alkyl optionally substituted with $R_7$, wherein alkyl includes straight and branched alkyl groups such as methyl, ethyl, n-propyl, iso-propyl, n-butyl, iso-butyl, sec-butyl and tert-butyl, as well as cycloalkyl groups such as cyclopropyl, cyclobutyl, cyclopentyl and cyclohexyl.

In certain embodiments, the invention provides compounds of structure I-R/S (71)-(74) where $R_a$ is methyl, ethyl, n-propyl, iso-propyl, n-butyl, iso-butyl, sec-butyl or tert-butyl.

In certain embodiments, the invention provides compounds of structure I-R/S (71)-(74) where $R_a$ is methyl.

In certain embodiments, the invention provides compounds of structure I-R/S (71)-(74) where $R_a$ is cyclopropyl, cyclobutyl, cyclopentyl or cyclohexyl.

In certain embodiments, the invention provides compounds of structure I-R/S (71)-(74) where $R_a$ is heterocycle or heterocyclylalkyl, either which may be optionally substituted with $R_7$.

In certain embodiments, the invention provides compounds of structure I-R/S (71)-(74) where $R_a$ is heterocycle, such as pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl, any of which may be optionally substituted with $R_7$.

In certain embodiments, the invention provides compounds of structure I-R/S (71)-(74) where $R_a$ is aryl or aralkyl, either of which may be optionally substituted with $R_7$.

In certain embodiments, the invention provides compounds of structure I-R/S (71)-(74) where $R_a$ is aryl or aralkyl, such as phenyl or benzyl.

In certain embodiments, the invention provides compounds of structure I-R/S (71)-(74) where $R_a$ is aryl or heteroaryl substituted with $R_7$.

In certain embodiments, the invention provides compounds of structure I-R/S (71)-(74) where $R_a$ is phenyl or benzyl substituted with hydroxyl.

In certain embodiments, the invention provides compounds of structure I-R/S (71)-(74) where $R_a$ is —CH(OH)C$_6$H$_5$.

In certain embodiments, the invention provides compounds of structure I-R/S (71)-(74) where $R_a$ is —(CHR$_{40}$)$_m$C(O)OR$_{40}$.

In certain embodiments, the invention provides compounds of structure I-R/S (71)-(74) where $R_a$ is —(CH$_2$)$_m$C(O)OH.

In certain embodiments, the invention provides compounds of structure I-R/S (71)-(74) where $R_a$ is —(CHR$_{40}$)$_m$OR$_{40}$.

In certain embodiments, the invention provides compounds of structure I-R/S (71)-(74) where $R_a$ is —(CH$_2$)$_m$OH.

In certain embodiments, the invention provides compounds of structure I-R/S (71)-(74) where $R_a$ is —CH$_2$OH.

In certain embodiments, the invention provides compounds of structure I-R/S (71)-(74) where $R_a$ is —(CHR$_{40}$)$_m$SR$_{40}$.

In certain embodiments, the invention provides compounds of structure I-R/S (71)-(74) where $R_a$ is —(CH$_2$)$_m$SR$_{40}$, where $R_{40}$ is H or alkyl.

In certain embodiments, the invention provides compounds of structure I-R/S (71)-(74) where $R_a$ is —(CHR$_{40}$)$_m$NR$_{41}$R$_{42}$.

In certain embodiments, the invention provides compounds of structure I-R/S (71)-(74) where $R_a$ is —(CH$_2$)$_m$NR$_{41}$R$_{42}$.

In certain embodiments, the invention provides compounds of structure I-R/S (71)-(74) where $R_a$ is —(CHR$_{40}$)$_m$C(O)NR$_{41}$R$_{42}$.

In certain embodiments, the invention provides compounds of structure I-R/S (71)-(74) where $R_a$ is —(CH$_2$)$_m$C(O)NR$_{41}$R$_{42}$.

In certain embodiments, the invention provides compounds of structure I-R/S (71)-(74) where $R_a$ is —CH$_2$C(O)NH$_2$ or —CH$_2$CH$_2$C(O)NH$_2$ In certain embodiments, the invention provides compounds of structure I-R/S (71)-(74) where $R_a$ is —(CHR$_{40}$)$_m$C(O)N(R$_1$)(CHR$_{40}$)$_m$NR$_{41}$R$_{42}$.

In certain embodiments, the invention provides compounds of structure I-R/S (71)-(74) where $R_a$ is —(CH$_2$)$_m$C(O)N(R$_1$)(CH$_2$)$_m$NR$_{41}$R$_{42}$.

In certain embodiments, the invention provides compounds of structure I-R/S (71)-(74) where $R_a$ is —(CHR$_{40}$)$_m$C(O)N(R$_1$)(CHR$_{40}$)$_m$C(O)NR$_{41}$R$_{42}$.

In certain embodiments, the invention provides compounds of structure I-R/S (71)-(74) where $R_a$ is —(CH$_2$)$_m$C(O)N(R$_1$)(CH$_2$)$_m$C(O)NR$_{41}$R$_{42}$.

In certain embodiments, the invention provides compounds of structure I-R/S (71)-(74) where $R_a$ is —(CHR$_{40}$)$_m$C(O)N(R$_1$)(CHR$_{40}$)$_m$C(O)OR$_{40}$.

In certain embodiments, the invention provides compounds of structure I-R/S (71)-(74) where $R_a$ is —(CH$_2$)$_m$C(O)N(R$_1$)(CH$_2$)$_m$C(O)OR$_{40}$.

In certain embodiments, the invention provides compounds of structure I-R/S (71)-(74) where $R_a$ is —(CHR$_{40}$)$_m$—S—S—R$_{40}$.

In certain embodiments, the invention provides compounds of structure I-R/S (71)-(74) where $R_a$ is —(CH$_2$)$_m$—S—S—R$_{40}$.

In certain embodiments, the invention provides compounds of structure I-R/S (71)-(74) wherein, within the $R_a$ group, $R_1$, $R_{40}$, $R_{41}$ and $R_{42}$ are hydrogen.

In certain embodiments, the invention provides compounds of structure I-R/S (71)-(74) wherein, within the $R_a$ group, m is 1.

In certain embodiments, the invention provides compounds of structure I-R/S (71)-(74) wherein, within the $R_a$ group, m is 2.

In certain embodiments, the invention provides compounds of structure I-R/S (71)-(74) where p is 1 and $R_3$ is alkyl.

In certain embodiments, the invention provides compounds of structure I-R/S (71)-(74) where p is 1 and $R_3$ is tert-butyl.

In certain embodiments, the invention provides compounds of structure I-R/S (71)-(74) where q is 1 and $R_5$ is alkoxy.

In certain embodiments, the invention provides compounds of structure I-R/S (71)-(74) where q is 1 and $R_5$ is C$_{4-8}$ alkoxy.

In certain embodiments, the invention provides compounds of structure I-R/S (71)-(74) where q is 1 and $R_5$ is C$_7$ alkoxy.

In certain embodiments, the invention provides compounds of structure I-R/S (71)-(74) where p is 1, $R_3$ is alkyl, q is 1 and $R_5$ is C$_{4-8}$ alkoxy.

In certain embodiments, the invention provides compounds of structure I-R/S (67)-(68) where m is 1, $R_b$ is hydrogen and $R_1$ and $R_a$ taken together with the atoms to which they are attached form a heterocyclyl optionally substituted (singly or multiply) with $R_7$. Representative compounds of this embodiment include compounds of the following structure (wherein "⟿" represents either or both the R and S form of the compound):

I-R/S (75)

I-R/S (76)
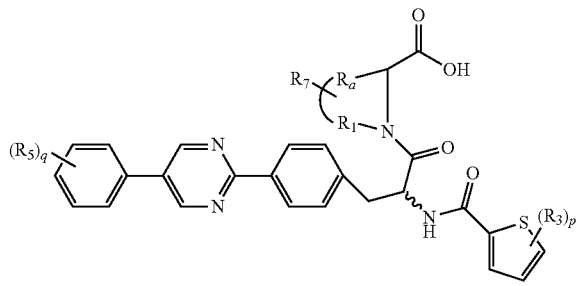

I-R/S (79)
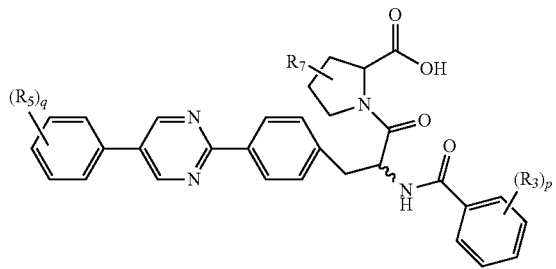

In certain embodiments, the invention provides compounds of structure I-R/S (67)-(68) where m is 2, $R_b$ of the second ($CR_aR_b$) group is hydrogen and $R_1$ and $R_a$ of the second ($CR_aR_b$) group taken together with the atoms to which they are attached form a heterocyclyl optionally substituted (singly or multiply) with $R_7$. Representative compounds of this embodiment include compounds of the following structure (wherein "∿∿∿" represents either or both the R and S form of the compound):

I-R/S (80)
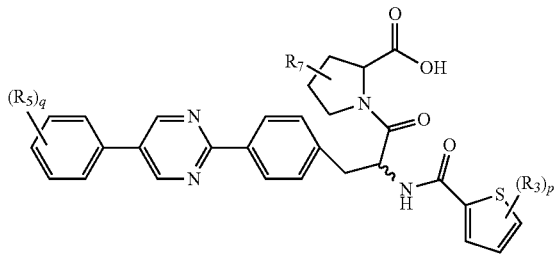

I-R/S (77)
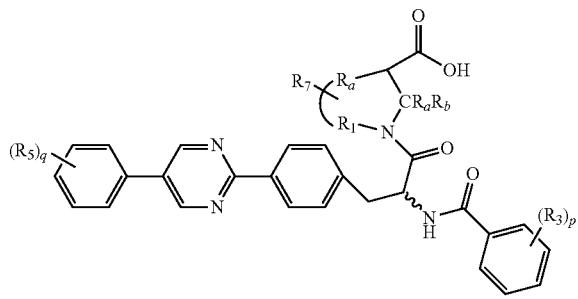

I-R/S (81)
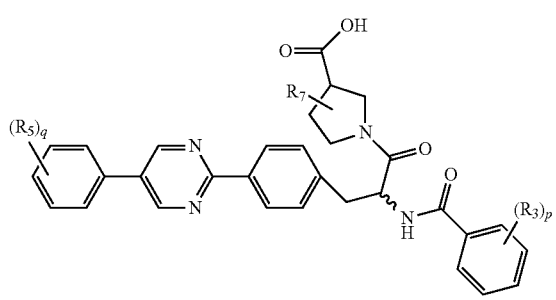

I-R/S (78)
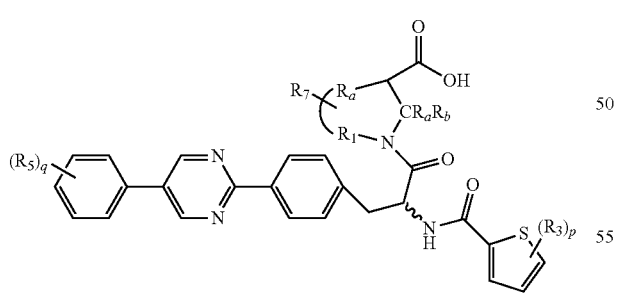

I-R/S (82)
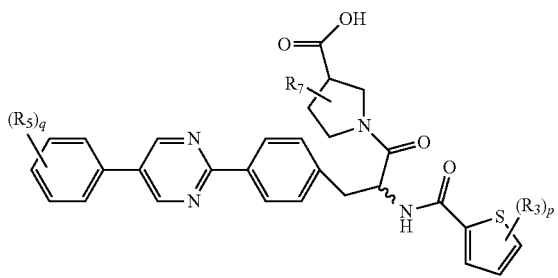

In certain embodiments, the invention provides compounds of structure I-R/S (75)-(78) where $R_1$ and $R_a$ taken together with the atoms to which they are attached form azetidinyl, pyrrolidinyl, piperidinyl optionally substituted (singly or multiply) with $R_7$. Representative compounds of this embodiment include compounds of the following structure (wherein "∿∿∿" represents either or both the R and S form of the compound):

(I-R/S (83))
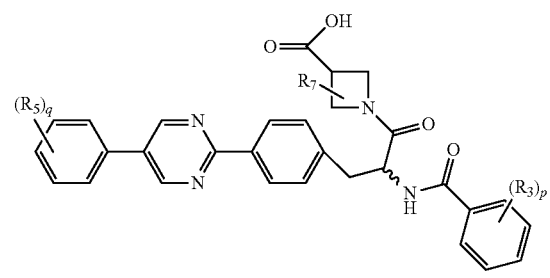

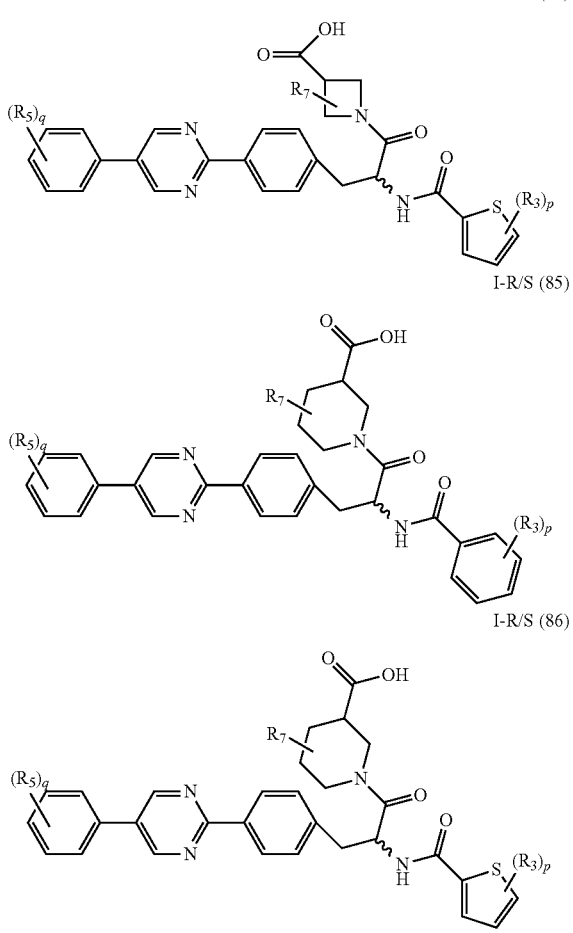

I-R/S (84)

I-R/S (85)

I-R/S (86)

In certain embodiments, the invention provides compounds of structure I-R/S (75)-(86) where p is 1 and $R_3$ is alkyl.

In certain embodiments, the invention provides compounds of structure I-R/S (75)-(86) where p is 1 and $R_3$ is tert-butyl.

In certain embodiments, the invention provides compounds of structure I-R/S (75)-(86) where q is 1 and $R_5$ is alkoxy.

In certain embodiments, the invention provides compounds of structure I-R/S (75)-(86) where q is 1 and $R_5$ is $C_{4-8}$ alkoxy.

In certain embodiments, the invention provides compounds of structure I-R/S (75)-(86) where q is 1 and $R_5$ is $C_7$ alkoxy.

In certain embodiments, the invention provides compounds of structure I-R/S (75)-(86) where p is 1, $R_3$ is alkyl, q is 1 and $R_5$ is $C_{4-8}$ alkoxy.

In certain embodiments, the invention provides compounds of structure I-R/S (75)-(86) where $R_7$ is absent.

In certain embodiments, the invention provides compounds of structure I-R/S (75)-(86) where $R_7$ is hydroxyl.

In certain embodiments, the invention provides compounds of structure I-R/S (75)-(86) where $R_7$ is absent, p is 1, $R_3$ is alkyl, q is 1 and $R_5$ is $C_{4-8}$ alkoxy.

In certain embodiments, the invention provides compounds of structure I-R/S (75)-(86) where $R_7$ is hydroxyl, p is 1, $R_3$ is alkyl, q is 1 and $R_5$ is $C_{4-8}$ alkoxy.

In certain embodiments, the invention provides compounds of structure I-R/S (65)-(66) where $R_2$ is —N($R_1$)—$SO_2$—$R_8$. Representative compounds of this embodiment include compounds of the following structure (wherein "〰〰" represents either or both the R and S form of the compound):

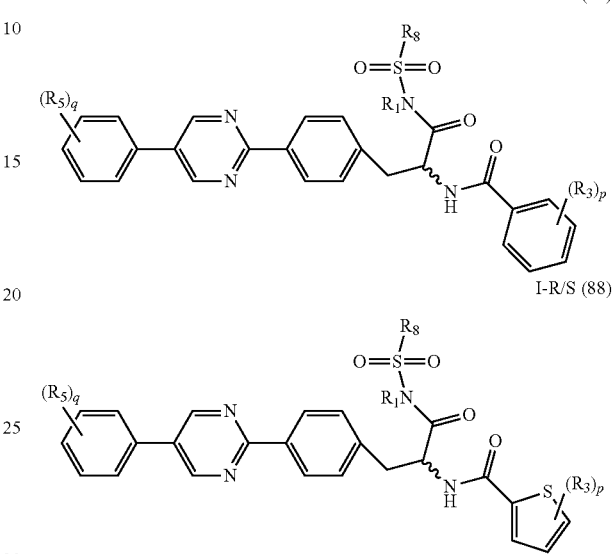

I-R/S (87)

I-R/S (88)

In certain embodiments, the invention provides compounds of structure I-R/S (87)-(88) where $R_1$ is hydrogen.

In certain embodiments, the invention provides compounds of structure I-R/S (87)-(88) where $R_1$ is hydrogen an $R_8$ is alkyl optionally substituted (singly or multiply) with $R_7$.

In certain embodiments, the invention provides compounds of structure I-R/S (65)-(66) where $R_2$ is —OH. Representative compounds of this embodiment include compounds of the following structure (wherein "〰〰" represents either or both the R and S form of the compound):

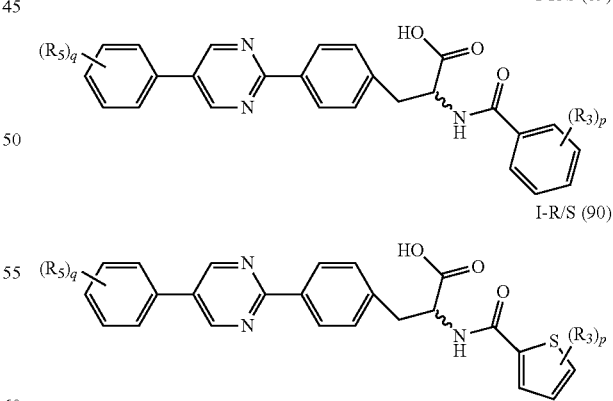

I-R/S (89)

I-R/S (90)

In certain embodiments, the invention provides compounds of structure I-R/S (65)-(66) where $R_2$ is —N($R_1$)($R_{42}$). Representative compounds of this embodiment include compounds of the following structure (wherein "〰〰" represents either or both the R and S form of the compound):

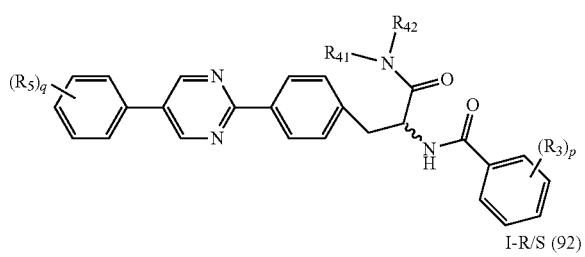

I-R/S (91)

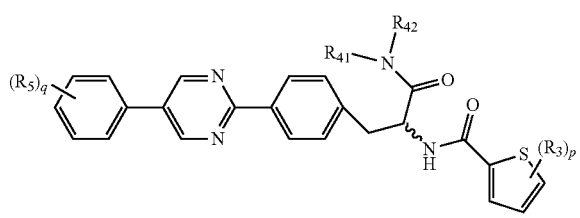

I-R/S (92)

In certain embodiments, the invention provides compounds of structure I-R/S (91)-(92) where $R_{41}$ and $R_{42}$ are independently $R_{40}$, —$(CHR_{40})_n$—C(O)OR$_{40}$, —$(CHR_{40})_n$—C(O)R$_{40}$, —$(CH_2)_nN(R_1)(R_7)$, aryl or heteroaryl, which aryl or heteroaryl is optionally substituted (singly or multiply) with $R_7$.

In certain embodiments, the invention provides compounds of structure I-R/S (91)-(92) where $R_{41}$ is hydrogen and $R_{42}$ is alkyl optionally substituted (singly or multiply) with $R_7$.

In certain embodiments, the invention provides compounds of structure I-R/S (91)-(92) where $R_{41}$ is hydrogen and $R_{42}$ is —$(CHR_{40})_nC(O)OR_{40}$.

In certain embodiments, the invention provides compounds of structure I-R/S (91)-(92) where $R_{41}$ is hydrogen and $R_{42}$ is —$(CHR_{40})_nC(O)R_{40}$.

In certain embodiments, the invention provides compounds of structure I-R/S (91)-(92) where $R_{41}$ is hydrogen and $R_{42}$ is —$(CH_2)_nN(R_1)(R_7)$.

In certain embodiments, the invention provides compounds of structure I-R/S (91)-(92) where $R_{41}$ is hydrogen and $R_{42}$ is aryl optionally substituted (singly or multiply) with $R_7$.

In certain embodiments, the invention provides compounds of structure I-R/S (91)-(92) where $R_{41}$ is hydrogen and $R_{42}$ is heteroaryl optionally substituted (singly or multiply) with $R_7$.

In certain embodiments, the invention provides compounds of structure I-R/S (91)-(92) where $R_{41}$ and $R_{42}$ taken together with the N atom to which they are attached form a 3- to 7-membered heterocyclyl optionally substituted (singly or multiply) with $R_7$.

In certain embodiments, the invention provides compounds of structure I-R/S (91)-(92) where $R_{41}$ and $R_{42}$ taken together with the N atom to which they are attached form pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, piperidinyl, piperazinyl, morpholinyl, pyrrolyl, pyrazolyl, triazolyl, tetrazolyl, oxazolyl, isoxazolyl, thiazolyl or pyridinyl, any of which may be optionally substituted (singly or multiply) with $R_7$.

In certain embodiments, the invention provides compounds of structure I-R/S (65)-(66) where $R_2$ is —N(R$_1$)(CR$_a$R$_b$)$_m$CON(R$_1$)(R$_{40}$). Representative compounds of this embodiment include compounds of the following structure (wherein "〰〰" represents either or both the R and S form of the compound):

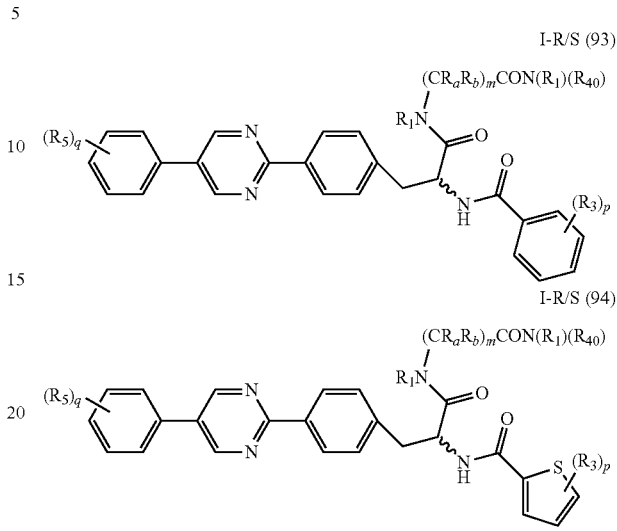

In certain embodiments, the invention provides compounds of structure I-R/S (93)-(94) where m is 1, $R_b$ is hydrogen and $R_1$ and $R_a$ taken together with the atoms to which they are attached form a heterocyclyl optionally substituted (singly or multiply) with $R_7$. Representative compounds of this embodiment include compounds of the following structure (wherein "〰〰" represents either or both the R and S form of the compound):

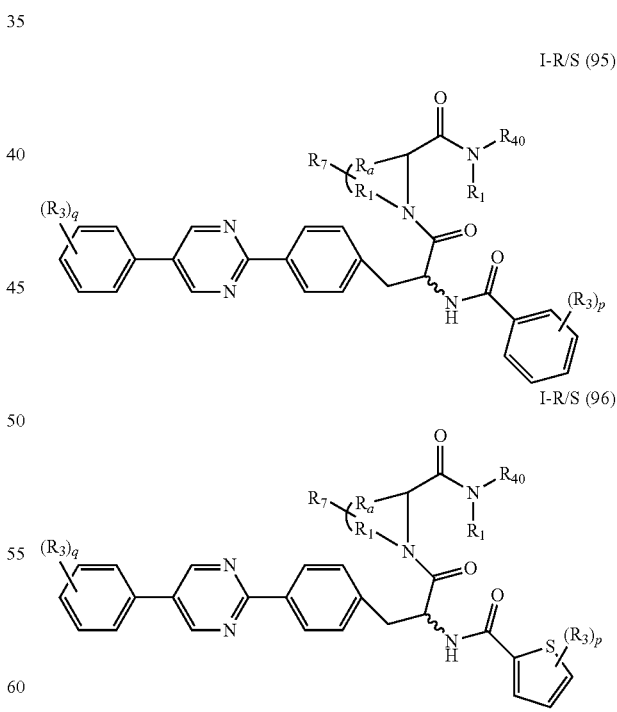

In certain embodiments, the invention provides compounds of structure I-R/S (93)-(94) where m is 2, $R_b$ of the second (CR$_a$R$_b$) group is hydrogen and $R_1$ and $R_a$ of the second (CR$_a$R$_b$) group taken together with the atoms to which they are attached form a heterocyclyl optionally substituted (singly or multiply) with R₇. Representative compounds of this embodiment include compounds of the following structure (wherein " ⌇⌇⌇ " represents either or both the R and S form of the compound):

I-R/S (97)

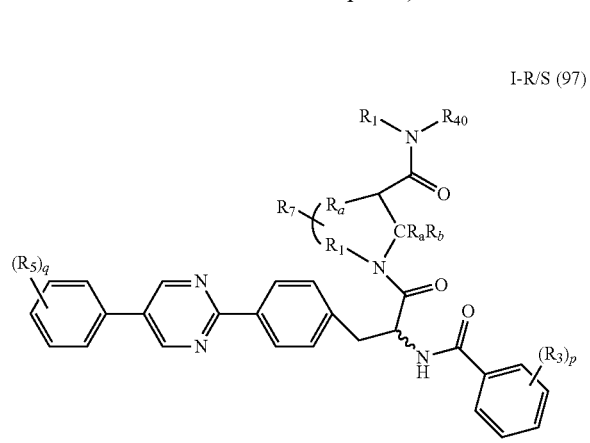

I-R/S (98)

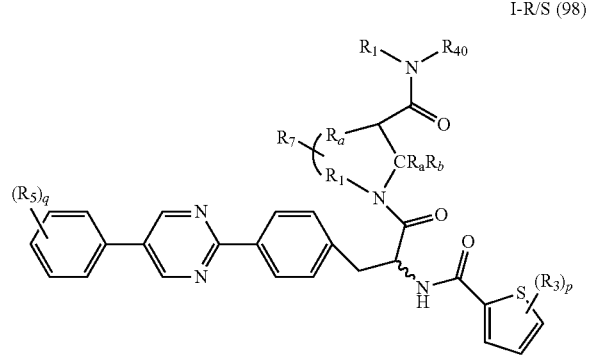

In certain embodiments, the invention provides compounds of structure I-R/S (95)-(98) where R₁ and R_a taken together with the atoms to which they are attached form azetidinyl, pyrrolidinyl, piperidinyl optionally substituted (singly or multiply) with R₇. Representative compounds of this embodiment include compounds of the following structure (wherein " ⌇⌇⌇ " represents either or both the R and S form of the compound):

I-R/S (99)

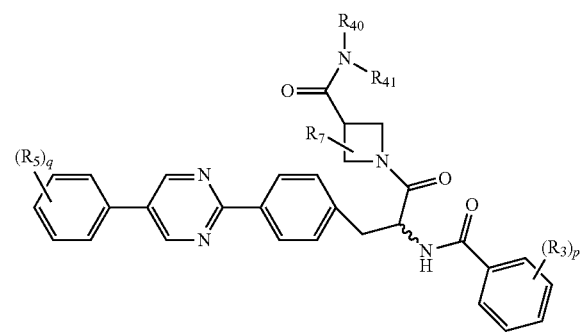

I-R/S (100)

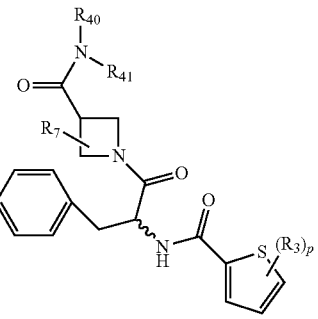

I-R/S (101)

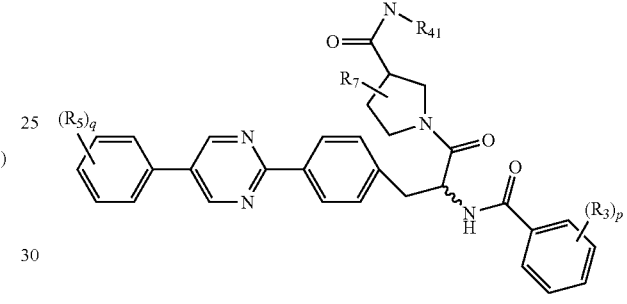

I-R/S (102)

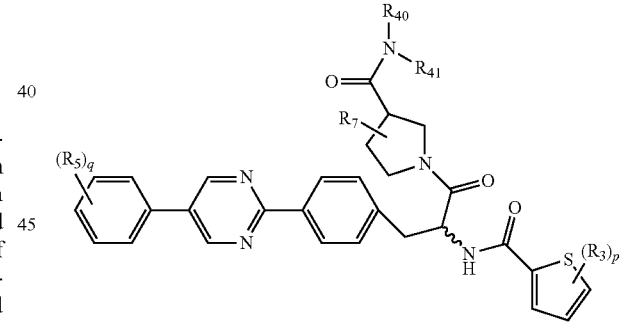

I-R/S (103)

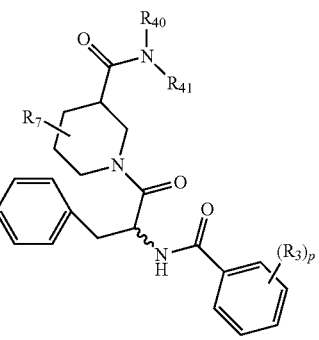

I-R/S (104)

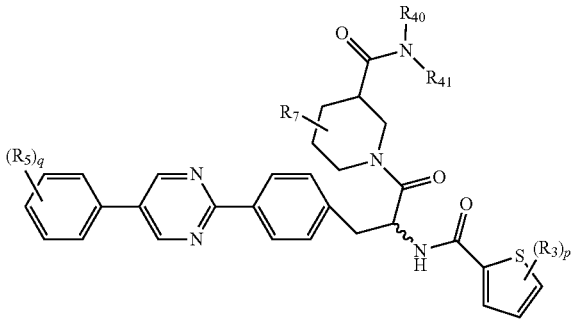

In certain embodiments, the invention provides compounds of structure I-R/S (93)-(104) where p is 1 and $R_3$ is alkyl.

In certain embodiments, the invention provides compounds of structure I-R/S (93)-(104) where p is 1 and $R_3$ is tert-butyl.

In certain embodiments, the invention provides compounds of structure I-R/S (93)-(104) where q is 1 and $R_5$ is alkoxy.

In certain embodiments, the invention provides compounds of structure I-R/S (93)-(104) where q is 1 and $R_5$ is $C_{4-8}$ alkoxy.

In certain embodiments, the invention provides compounds of structure I-R/S (93)-(104) where q is 1 and $R_5$ is $C_7$ alkoxy.

In certain embodiments, the invention provides compounds of structure I-R/S (93)-(104) where p is 1, $R_3$ is alkyl, q is 1 and $R_5$ is $C_{4-8}$ alkoxy.

In certain embodiments, the invention provides compounds of structure I-R/S (93)-(104) where $R_7$ is absent or hydroxyl.

In certain embodiments, the invention provides compounds of structure I-R/S (93)-(104) where $R_7$ is absent or hydroxyl, p is 1, $R_3$ is alkyl, q is 1 and $R_5$ is $C_{4-8}$ alkoxy.

In certain embodiments, the invention provides compounds of structure I-R/S (93)-(104) where $R_1$ is hydrogen.

In certain embodiments, the invention provides compounds of structure I-R/S (93)-(104) where $R_{40}$ is $R_7$.

In certain embodiments, the invention provides compounds of structure I-R/S (93)-(104) where $R_{40}$ is $R_7$, $R_7$ is —$(CR_aR_b)_mS(O)_2R_8$, and $R_8$ is —$(CR_aR_b)_m$-$L_2$-$(CR_aR_b)_m$—$R_1$.

In certain embodiments, the invention provides compounds of structure I-R/S (65)-(66) where $R_2$ is —$N(R_1)(CR_aR_b)_mN(R_1)C(O)O(R_8)$. Representative compounds of this embodiment include compounds of the following structure (wherein " ᴡᴡᴡ " represents either or both the R and S form of the compound):

I-R/S (105)

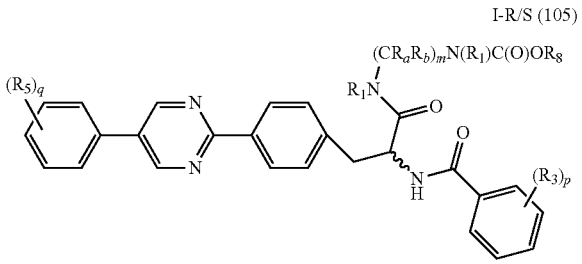

In certain embodiments, the invention provides compounds of structure I-R/S (65)-(66) where $R_2$ is —$N(R_1)(CR_aR_b)_mN(R_1)(R_7)$. Representative compounds of this embodiment include compounds of the following structure (wherein " ᴡᴡᴡ " represents either or both the R and S form of the compound):

I-R/S (106)

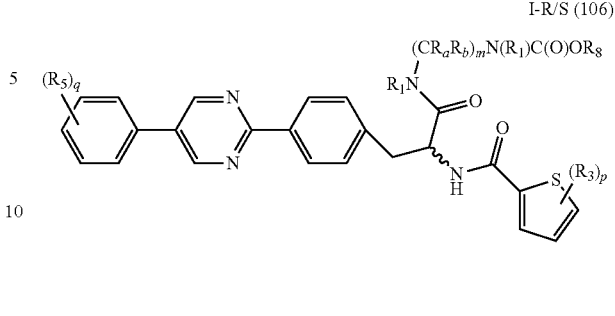

I-R/S (107)

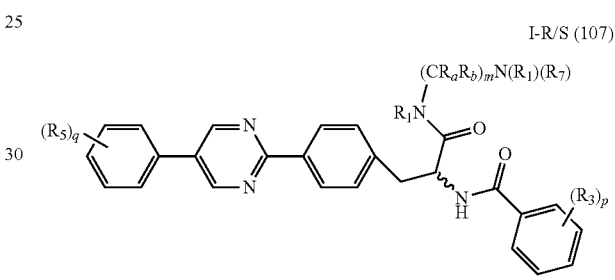

I-R/S (108)

In certain embodiments, the invention provides compounds of structure I-R/S (65)-(66) where $R_2$ is —$N(R_1)(CR_aR_b)_mCON(R_1)$heterocyclyl. Representative compounds of this embodiment include compounds of the following structure (wherein " ᴡᴡᴡ " represents either or both the R and S form of the compound):

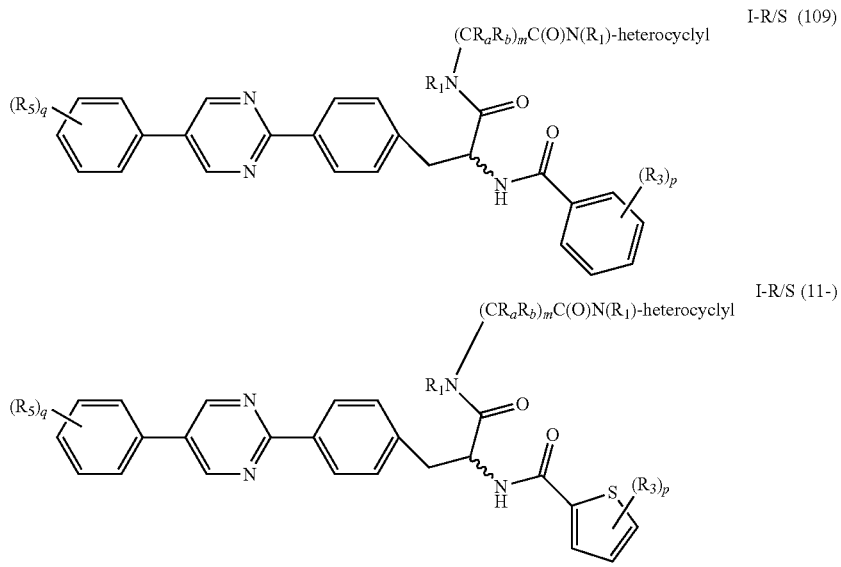

I-R/S (109)

I-R/S (11-)

In certain embodiments, the invention provides compounds of structure I-R/S (65)-(66) where $R_2$ is —N($R_1$)(CR$_a$R$_b$)$_m$-heterocyclyl, which heterocyclyl may be optionally substituted with $R_7$. Representative compounds of this embodiment include compounds of the following structure (wherein " ⌇⌇⌇ " represents either or both the R and S form of the compound):

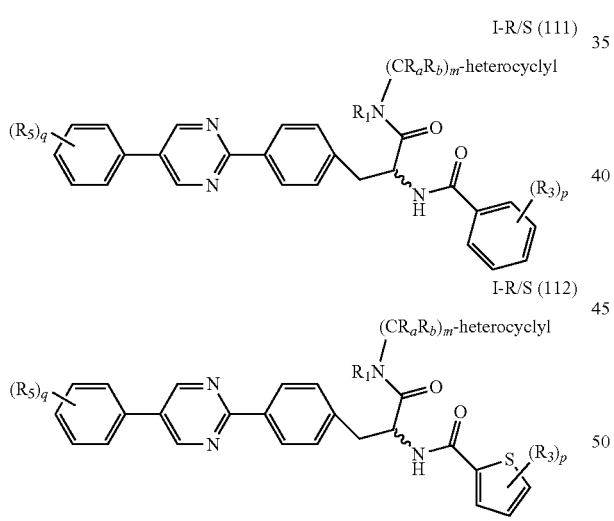

I-R/S (111)

I-R/S (112)

In certain embodiments, the invention provides compounds of structures I-R/S (65-1)-(66-1) where $R_2$ is as shown in each of structures I-R/S (69) through I-R/S (112). Such compounds are referred to herein as I-R/S (69-1) through I-R/S (112-1). For example, structures I-R/S (67-1)-(68-1) depict structures I-R/S (65-1)-(66-1) when $R_2$ is —N($R_1$)(CR$_a$R$_b$)$_m$COOR$_8$. In a similar manner, structures I-R/S (69-1) through I-R/S (112-1) correspond to structures I-R/S (69) through I-R/S (112), but with the specific $R_2$ group of structures I-R/S (69) through I-R/S (112) serving as the $R_2$ group of structures I-R/S (65-1)-(66-1).

In certain embodiments, the invention provides a compound of Formula I-R and/or Formula I-S where $Y_1$ and $Y_2$ are null and Z is —S(O)$_2$—. Representative compounds of this embodiment include compounds of the following structures (wherein " ⌇⌇⌇ " represents either or both the R and S form of the compound):

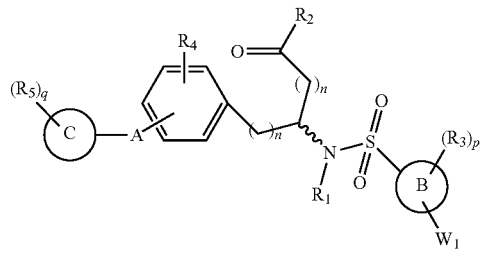

I-R/S (113)

In certain embodiments, the invention provides compounds of structure I-R/S (95) where A is pyrimidinyl, B is phenyl and C is phenyl. Representative compounds of this embodiment include compounds of the following structure (wherein " ⌇⌇⌇ " represents either or both the R and S form of the compound):

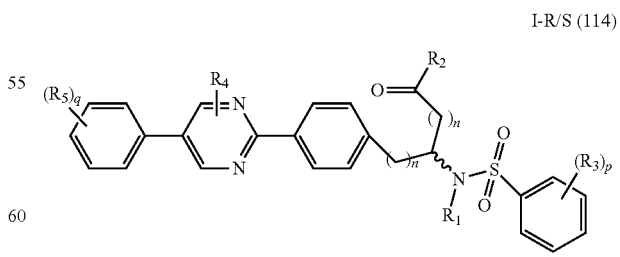

I-R/S (114)

In certain embodiments, the invention provides a compound of Formula I-R and/or Formula I-S where $Y_1$ is null, $Y_2$ is —O— and Z is —C(O)—. Representative compounds of this embodiment include compounds of the following structures (wherein " ⋎⋏⋎⋏ " represents either or both the R and S form of the compound):

I-R/S (115)

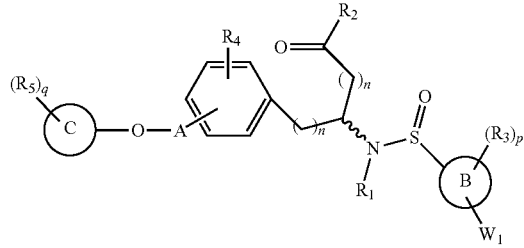

In certain embodiments, the invention provides a compound of Formula I-R and/or Formula I-S where $Y_1$ is NH, $Y_2$ is null and Z is —C(O)—. Representative compounds of this embodiment include compounds of the following structures (wherein " ⋎⋏⋎⋏ " represents either or both the R and S form of the compound):

I-R/S (116)

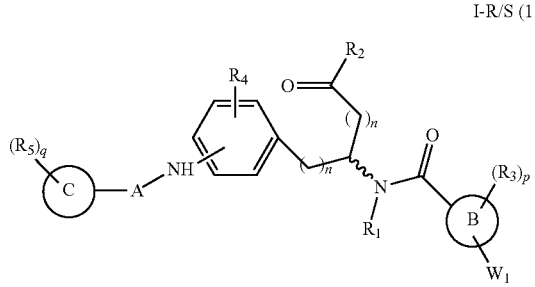

In certain embodiments, the invention provides a compound of Formula I-R and/or Formula I-S where C is aryl and A and C are taken together to form a fused bicyclic ring system between the 5-, 6- or 7-membered heterocyclyl of A and the aryl of C. Representative compounds of this embodiment include compounds of the following structures (wherein " ⋎⋏⋎⋏ " represents either or both the R and S form of the compound):

I-R/S (117)

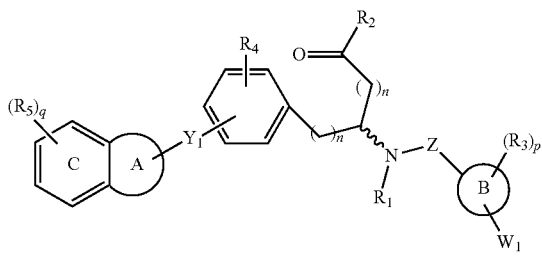

In certain embodiments, the invention provides compounds of structure I-R/S (99) where $Y_1$ is null and Z is —C(O)—. Representative compounds of this embodiment include compounds of the following structures where one or both of $X_A$ and $X_B$ is nitrogen (wherein " ⋎⋏⋎⋏ " represents either or both the R and S form of the compound)

I-R/S (118)

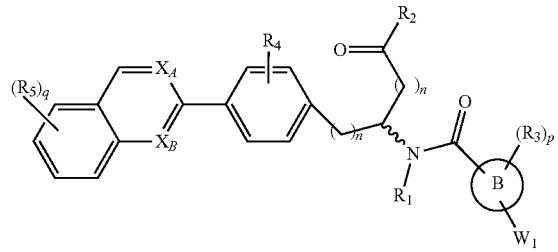

In certain embodiments, the invention provides a pharmaceutical composition comprising a compound of the invention together with at least one pharmaceutically acceptable carrier, diluent or excipient.

In certain embodiments, the invention provides a pharmaceutical composition comprising a compound of the invention and a second medicament. In certain of such embodiments, the second medicament is a GLP-1 agonist or a DPPIV inhibitor.

In certain embodiments, the invention provides a method of use of compounds of the invention for preparation of a medicament.

In certain embodiments, the invention provides a pharmaceutical combination comprising a compound of the invention and a second medicament. In various such embodiments, the second medicament is an agonist or modulator for glucagon receptor, GIP receptor, GLP-2 receptor, or PTH receptor, or glucagon-like peptide 1 (GLP-1) receptor. In various such embodiments, the second medicament is exenatide, liraglutide, taspoglutide, albiglutide, or lixisenatide or other insulin regulating peptide. In various such embodiments, the second medicament is a DPPIV inhibitor, such as sitagliptin. In various such embodiments, the second medicament is medically indicated for the treatment of type II diabetes. In various combinations, the second medicament is a sodium-glucose co-transporter (SGLT) inhibitor, such as a SGLT1 and/or SGLT2 inhibitor. In various such embodiments, the second medicament is a biguanide such as metformin, a sulfonylurea such as glibenclamide, glipizide, gliclazide, and glimepiride, a meglitinide such as repaglinide and mateglinide, a thiazolidinedione such as pioglitazone and rosiglitazone, an α-glucosidase inhibitor such as acarbose and miglitol, a bile acid sequestrant such as colesevelam, and/or a dopamine-2 agonist such as bromocriptine.

In certain embodiments, the invention provides a pharmaceutical composition comprising a compound of the invention and a second medicament, wherein the second medicament is metformin.

In certain embodiments, the invention provides a pharmaceutical composition comprising a compound of the invention and a second medicament, wherein the second medicament is sitagliptin.

In certain embodiments, a method is provided for activation, potentiation or agonism of a glucagon-like peptide 1 comprising contacting the receptor with an effective amount of a compound, pharmaceutical composition or pharmaceutical combination of the invention.

In further embodiments, a method is provided for activation or agonism of a GLP-1 receptor by contacting the receptor with an effective amount of an invention compound and GLP-1 peptides GLP-1(9-36) and GLP-1(7-36), pharmaceutical composition or pharmaceutical combination, wherein the GLP-1 receptor is disposed within a living mammal; in certain embodiments wherein such mammal is a human.

In certain embodiments, a method is provided for treatment of a malcondition in a subject for which activation, potentiation or agonism of a GLP-1 receptor is medically indicated, by administering an effective amount of an invention compound to the subject at a frequency and for a duration of time sufficient to provide a beneficial effect to the patient. In yet further embodiments, a method is provided for treatment of a malcondition in a patient for which activation, potentiation, or agonism of a GLP-1 receptor is medically indicated, by administering an effective amount of an invention compound to the patient at a frequency and for a duration of time sufficient to provide a beneficial effect to the patient, wherein the malcondition comprises type I diabetes, type II diabetes, gestational diabetes, obesity, excessive appetite, insufficient satiety, or metabolic disorder. In certain embodiments, the subject is a patient or a human being. In certain embodiments, the human being is afflicted with, or at risk of developing, a disease or condition selected from the group consisting of type I diabetes, type II diabetes, gestational diabetes, obesity, excessive appetite, insufficient satiety, and metabolic disorder. In certain of such embodiments, said disease is type I diabetes or type II diabetes.

In certain embodiments, the invention provides methods for synthesis of certain compounds including compounds of the invention as more fully illustrated herein. In certain other embodiments, the invention provides certain intermediate compounds associated with such methods of synthesis as illustrated herein.

In certain embodiments, methods are provided for use of an invention compound for preparation of a medicament adapted for treatment of a disorder or a malcondition wherein activation or inhibition of a GLP-1 receptor is medically indicated. In certain embodiments, the malcondition comprises type I diabetes, type II diabetes, gestational diabetes, obesity, excessive appetite, insufficient satiety, and metabolic disorder. Preferably said disease is type I diabetes or type II diabetes.

In certain embodiments, the method additionally comprises administering to the subject a second medicament selected from the group of biguanides, peptidic GLP-1 agonists and DPPIV inhibitors, wherein such second medicament is either a component of the pharmaceutical composition or a second pharmaceutical composition. In certain of such embodiments, the second medicament can be metformin, exenatide or sitagliptin.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g., apes and monkeys; cattle; horses; sheep; and goats. Non-mammals include, for example, fish and birds.

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist." Certain molecules bind to receptors at locations other than the binding sites of their natural ligands and such allosteric binding molecules may potentiate, activate or agonize the receptor and may enhance the effect of a natural ligand or a co-administered ligand.

A "GLP-1 compound" or "GLP-1 agonist" or "GLP-1 activator" or "GLP-1 inhibitor" or "GLP-1 antagonist" or "GLP-1 potentiator" or "GLP-1 modulator" as the terms are used herein refer to compounds that interact in some way with the GLP-1 receptor. They can be agonists, potentiators, or activators, or they can be antagonists or inhibitors. A "GLP-1 compound" of the invention can be selective for action of the GLP-1 receptor family.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically or diastereomerically pure means a level of enantiomeric or diasteromeric enrichment of one enantiomer with respect to the other enantiomer or diastereomer of at least about 80%, and more preferably in excess of 80%, 85%, 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by GLP-1 refers to the amount of a compound of the invention that is effective to bind to as an agonist or as an antagonist a GLP-1 receptor in the individual's tissues, wherein the GLP-1 is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of GLP-1 activity. A therapeutically effective amount is also one in which any toxic or detrimental effects of compounds of the invention are outweighed by the therapeutically beneficial effects. For example, in the context of treating a malcondition mediated by activation of a GLP-1 receptor, a therapeutically effective amount of a GLP-1 receptor agonist of the invention is an amount sufficient to control the malcondition, to mitigate the progress of the malcondition, or to relieve the symptoms of the malcondition. Examples of malconditions that can be so treated include, but not limited to, type II diabetes.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

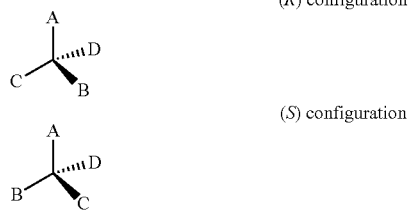

(R) configuration (S) configuration

"Isolated optical isomer" means a compound which has been substantially purified from the corresponding optical isomer(s) of the same formula. Preferably, the isolated isomer is at least about 80%, and preferably at least 80% or even at least 85% pure. In other embodiments, the isolated isomer is at least 90% pure or at least 98% pure, or at least about 99% pure, by weight.

Enantiomers are sometimes called optical isomers because a pure enantiomer rotates plane-polarized light in a particular direction. If the light rotates clockwise, then that enantiomer is labeled "(+)" or "d" for dextrorotatory, its counterpart will rotate the light counterclockwise and is labeled "(−)" or "l" for levorotatory.

The terms "racemate" and "racemic mixture" are frequently used interchangeably. A racemate is an equal mixture of two enantiomers. A racemate is labeled "(±)" because it is not optically active (i.e., will not rotate plane-polarized light in either direction since its constituent enantiomers cancel each other out).

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of type I diabetes, type II diabetes, gestational diabetes, obesity, excessive appetite, insufficient satiety, or metabolic disorder.

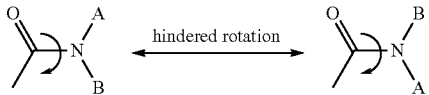

The preferred compounds of the present invention have a particular spatial arrangement of substituents on the aromatic rings, which are related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

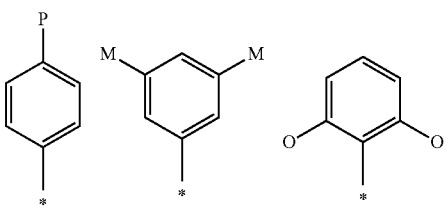

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds. Further, isotopes of the atoms depicted (such as deuterium and tritium in the case of hydrogen) are encompassed within the scope of this invention.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups include substituted aryl, heterocyclyl and heteroaryl groups. Substituted ring groups can be substituted by one or more substituents at any available ring position. In some embodiments, two substituents on a substituted ring group may taken together with the ring to which they are attached to form a ring, such that the two rings are fused together. For example, benzodioxolyl is a fused ring system formed by two substituents taken together on a phenyl group.

Such substituted ring groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The linking groups (e.g., L$_1$ and L$_2$) of Formula I-R or I-S are partial structures which may be represented by a formula, say, for example, —N(R$_1$)—C(O)—, which is read from left-to-right. Accordingly, the nitrogen atom of the —N(R$_1$)—C(O)— linker will be attached to the proximal end of the structure of Formula I-R or I-S, and the carbonyl carbon atom of the —N(R$_1$)—C(O)— linker will be attached to the distal end of the structure of Formula I-R or I-S.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons (C$_1$-C$_{12}$ alkyl), or, in some embodiments, from 1 to 8 carbon atoms (C$_1$-C$_8$ alkyl), or, in some embodiments, from 1 to 4 carbon atoms (C$_1$-C$_4$ alkyl). In the case of cycloalkyl groups, such groups have from 3-20 carbon atoms. Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Alkyl groups as used herein may optionally include one or more further substituent groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted one or more times with any of the groups listed above, for example, but not limited to, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —CH=CHCH$_2$CH$_3$, —CH=CH(CH$_2$)$_2$CH$_3$, —CH=CH(CH$_2$)$_3$CH$_3$, —CH=CH(CH$_2$)$_4$CH$_3$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups, as well as polycyclic and/or bridging ring systems such as adamantine.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms.

Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl, alkenyl or alkynyl groups as defined above in which a hydrogen atom of an alkyl, alkenyl or alkynyl group is replaced with an aryl group as defined above. Representative aralkyl groups include benzyl (—CH$_2$phenyl), phenylethyl (—CH$_2$CH$_2$phenyl) and phenylethylene (—CH═CHphenyl) groups and fused (cycloalkylaryl)alkyl groups such as 4-ethyl-indanyl. The aryl moiety or the alkyl, alkenyl or alkynyl moiety or both are optionally substituted with other groups, including but not limited to alkyl, halo, amino, hydroxy, cyano, carboxy, nitro, thio, or alkoxy groups.

Heterocyclyl or heterocyclic groups include aromatic and non-aromatic ring moieties containing 3 or more ring members, of which one or more is a heteroatom such as, but not limited to, N, O, S, or P. In some embodiments, heterocyclyl groups include 3 to 20 ring members, whereas other such groups have 3 to 15 ring members, including for example single ring systems containing 5, 6 or 7 ring members. At least one ring contains a heteroatom, but every ring in a polycyclic system need not contain a heteroatom. For example, a dioxolanyl ring and a benzodioxolanyl ring system (methylenedioxyphenyl ring system) are both heterocyclyl groups within the meaning herein. A heterocyclyl group designated as a C$_2$-heterocyclyl can be a 5-ring with two carbon atoms and three heteroatoms, a 6-ring with two carbon atoms and four heteroatoms, and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms.

The term "heterocyclyl" includes fused ring species including those having fused aromatic and non-aromatic groups. The phrase also includes polycyclic and/or bridging ring systems containing a heteroatom such as, but not limited to, quinuclidyl and 7-azabicyclo[2.2.1]heptane, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups, and in the case of two substituents on the same carbon atom of the heterocycle include oxo (═O) and thioxo (═S).

Heteroaryl groups are aromatic ring moieties containing 5 or more ring members, of which, one or more is a heteroatom such as, but not limited to, N, O, and S. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, pyridinyl, pyridazinyl, pyrimidyl, pyrazyl, pyrazinyl, pyrimidinyl, thiadiazolyl, imidazolyl, oxadiazolyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl (1,2,4-oxadiazolyl, 1,3,4-oxadiazolyl), thiadiazolyl (1,2,4-thiadiazolyl, 1,3,4-thiadiazolyl), isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl, pyrimidinyl (2-pyrimidinyl, 4-pyrimidinyl, 5-pyrimidinyl, 6pyrimidinyl), pyrazinyl, pyridazinyl (3-pyridazinyl, 4-pyridazinyl, 5-pyridazinyl), prazolo[1,5-a]pyridinyl, quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), isobenzofuranyl, 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo[d]isoxazolyl, carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl, alkenyl or alkynyl groups as defined above in which a hydrogen or carbon bond of an alkyl, alkenyl or alkynyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl, alkenyl or alkynyl moiety, or both.

Heteroarylalkyl groups are alkyl, alkenyl or alkynyl groups as defined above in which a hydrogen or carbon bond of an alkyl, alkenyl or alkynyl group is replaced with a bond to a heteroaryl group as defined above. Heteroarylalkyl groups can be substituted on the heteroaryl moiety, the alkyl, alkenyl or alkynyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

When two "R" groups are said to be joined together or taken together to form a ring, it is meant that together with the carbon atom or a non-carbon atom (e.g., nitrogen atom), to which they are bonded, they may form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrolidinyl, pyrrolyl, pyridinyl.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, n-heptyloxy, n-octyloxy n-nonyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "carbonyl," refers to a —C(O)— group.

"Halo," "halogen," and "halide" include fluorine, chlorine, bromine and iodine.

The term "perhaloalkyl" refers to an alkyl group where all of the hydrogen atoms are replaced by halogen atoms. Perhaloalkyl groups include, but are not limited to, —CF$_3$ and —C(CF$_3$)$_3$. The term "haloalkyl" refers to an alkyl group where some but not necessarily all of the hydrogen atoms are replaced by halogen atoms. Haloalkyl groups include but are not limited to —CHF$_2$ and —CH$_2$F.

The term "perhaloalkoxy" refers to an alkoxy group where all of the hydrogen atoms are replaced by halogen atoms. Perhaloalkoxy groups include, but are not limited to, —OCF$_3$ and —OC(CF$_3$)$_3$. The term "haloalkoxy" refers to an alkoxy group where some but not necessarily all of the hydrogen atoms are replaced by halogen atoms. Haloalkoxy groups include but are not limited to —OCHF$_2$ and —OCH$_2$F.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I compounds, for example in their purification by recrystallization. All of these salts may be prepared by conventional means from the corresponding compound according to Formula I by reacting, for example, the appropriate acid or base with the compound according to Formula I. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals.

"Isotopes" are well known in the art and refer to atoms with the same number of protons but different number of neutrons. For example, carbon 12, the most common form of carbon, has six protons and six neutrons, whereas carbon 14 has six protons and eight neutrons.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

The GLP-1 compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g., intravenous, oral, topical, suppository, or parenteral).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another GLP-1agonist or another type of therapeutic agent or second medicament, or both. Non-limiting examples of the GLP-1 receptor agonists include exenatide, liraglutide, taspoglutide, albiglutide, lixisenatide, and mixtures thereof.

In one embodiment, the GLP-1agonist is exenatide (Byetta®) or Byetta LAR®. Exenatide is described, for example, in U.S. Pat. Nos. 5,424,286; 6,902,744; 7,297,761, and others, the contents of each of which is herein incorporated by reference in its entirety.

In one embodiment, the GLP-1agonist is liraglutide (VICTOZA®) (also called NN-2211 and [Arg34, Lys26]-(N-epsilon-(gamma-Glu(N-alpha-hexadecanoyl))-GLP-1(7-37)), includes the sequence HAEGTFTSDVSSYLEGQAAKEFIAWKVRGRG (SEQ ID NO: 1) and is available from Novo Nordisk (Denmark) or Scios (Fremont, Calif. USA). See, e.g., Elbrond et al., 2002, Diabetes Care. August; 25(8):1398404; Agerso et al., 2002, Diabetologia. February; 45(2): 195-202).

In one embodiment, the GLP-1agonist is taspoglutide (CAS Registry No. 275371-94-3) and is available from Hoffman La-Roche. See, for example, U.S. Pat. No. 7,368,427, the contents of which are herein incorporated by reference in its entirety.

In one embodiment, the GLP-1 agonist isalbiglutide (SYNCRIA® from GlaxoSmithKline).

In another embodiment, the GLP-1 agonist is lixisenatide (Lyxumia® from Sanofi-Aventis/Zealand Pharma).

Non-limiting examples of the second medicaments are as disclosed above. In various such embodiments, the second medicament is exenatide, liraglutide, taspoglutide, albiglutide, or lixisenatide or other insulin regulating peptide. In various such embodiments, the second medicament is a DPPIV inhibitor. In various such embodiments, the second medicament is medically indicated for the treatment of type II diabetes. In various such embodiments, the second medicament is a biguanide, a sulfonylurea, a meglitinide, a thiazolidinedione, an α-glucosidase inhibitor, a bile acid sequestrant, and/or a dopamine-2 agonist.

In another embodiment, the second medicament is metformin.

In another embodiment, the second medicament is sitagliptin.

As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g., as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g., specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other GLP-1 modulators and/or ii) one or more other types of therapeutic agents or second medicaments which can be administered orally in the same dosage form, in a separate oral dosage form (e.g., sequentially or non-sequentially) or by injection together or separately (e.g., sequentially or non-sequentially). Examples of combination therapeutic agents include Metformin, Sitagliptin (MK-0431, Januvia) an oral antihyperglycemic (antidiabetic drug) of the dipeptidyl peptidase-4 (DPP-4) inhibitor class and Exenatide (Byetta) an incretin mimetic. In other embodiments, the second medicament is a biguanide such as metformin, a sulfonylurea such as glibenclamide, glipizide, gliclazide, and glimepiride, a meglitinide such as repaglinide and nateglinide, a thiazolidinedione such as pioglitazone and rosiglitazone, an α-glucosidase inhibitor such as acarbose and miglitol, a bile acid sequestrant such as colesevelam, and/or a dopamine-2 agonist such as bromocriptine.

Combinations of the invention include mixtures of compounds from i) and ii) in a single formulation and compounds from i) and ii) as separate formulations. Some combinations of the invention can be packaged as separate formulations in a kit. In some embodiments, two or more compounds from ii) are formulated together while a compound of the invention is formulated separately.

The dosages and formulations for the other agents to be employed, where applicable, will be as set out in the latest edition of the *Physicians' Desk Reference*, incorporated herein by reference.

In certain embodiments, the present invention encompasses compounds that bind with high affinity and specificity to the GLP-1 receptor in an agonist manner or as an activator or a potentiator. In certain embodiments a compound of the invention acts as a positive allosteric modulator of GLP-1 receptor.

In certain embodiments, the present invention provides a method for activating, potentiating, or agonizing (i.e., to have an agonic effect, to act as an agonist) a GLP-1 receptor, with a compound of the invention. The method involves contacting the receptor with a suitable concentration of an inventive compound to bring about activation of the receptor. The contacting can take place in vitro, for example in carrying out an assay to determine the GLP-1 receptor activation activity of an inventive compound undergoing experimentation related to a submission for regulatory approval.

In certain embodiments, the method for activating a GLP-1 receptor, can also be carried out in vivo, that is, within the living body of a mammal, such as a human patient or a test animal. The inventive compound can be supplied to the living organism via one of the routes as described above, e.g., orally, or can be provided locally within the body tissues. In the presence of the inventive compound, activation of the receptor takes place, and the effect thereof can be studied.

An embodiment of the present invention provides a method of treatment of a malcondition in a patient for which activation of an GLP-1 receptor is medically indicated, wherein the patient is administered the inventive compound in a dosage, at a frequency, and for a duration to produce a beneficial effect on the patient. The inventive compound can be administered by any suitable means, examples of which are described above.

In certain embodiments, the present invention is directed to compounds adapted to act as modulators or potentiators of Class B GPCRs. These compounds may have activity on their own or in the presence of receptor ligands. Receptors include incretin peptides including GLP-1(7-36) and GLP-1(9-36).

Methods of treatments provided by the invention include administration of a compound of the invention, alone or in combination with another pharmacologically active agent or second medicament to a subject or patient having a malcondition for which activation, potentiation or agonism of a glucagon-like peptide 1 receptor is medically indicated such as type I diabetes, type II diabetes, gestational diabetes, obesity, excessive appetite, insufficient satiety, or metabolic disorder.

General Synthetic Methods for Preparing Compounds

Molecular embodiments of the present invention can be synthesized using standard synthetic techniques known to those of skill in the art. Compounds of the present invention can be synthesized using the general synthetic procedures set forth in Schemes 1-37.

Scheme 1:

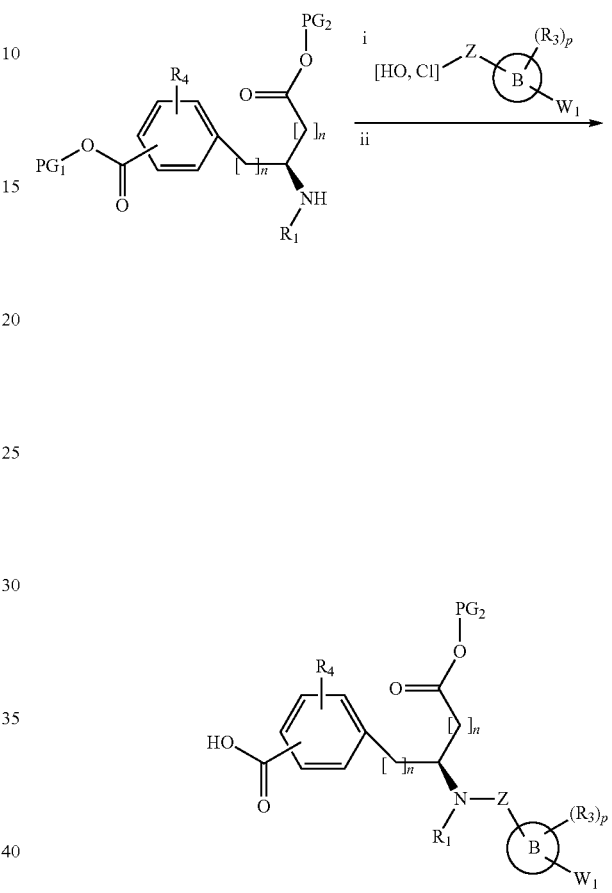

Reagents: $PG_1$ and $PG_2$ are protecting groups; (i) If Z = CO then amide coupling with acid chloride: DIEA, DCM or amide coupling with acid: EDC, HOBt, DMF or HATU, DMF; If Z = $SO_2$, then coupling with sulfonyl chloride: DIEA or $NEt_3$, DCM or DMF; (ii) Deprotection of $PG_1$ e.g., methyl ester deprotection: LiOH, dioxane, water.

The other enantiomer can be prepared in a similar manner using Scheme 1.

Scheme 2:

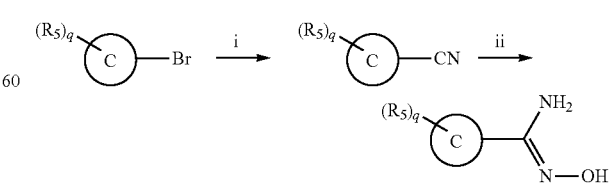

Reagents: (i) $Zn(CN)_2$, $Pd(PPh_3)_4$, NMP; (ii) $NH_2OH$ HCl, TEA, EtOH.

Scheme 3:

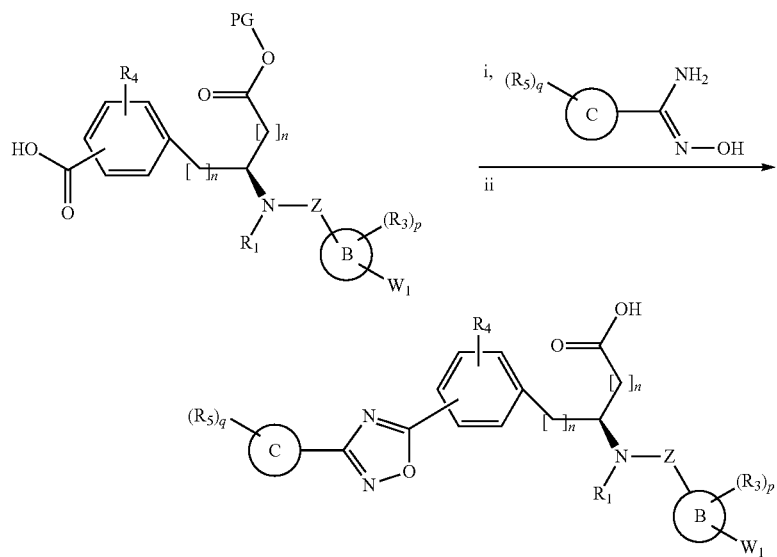

Reagents: PG is a protecting group; (i) EDC, HOBt, DMF then heat; (ii) Deprotection e.g., methyl ester deprotection: NaOH, MeOH, water.

The other enantiomer can be prepared in a similar manner using Scheme 3.

Scheme 4:

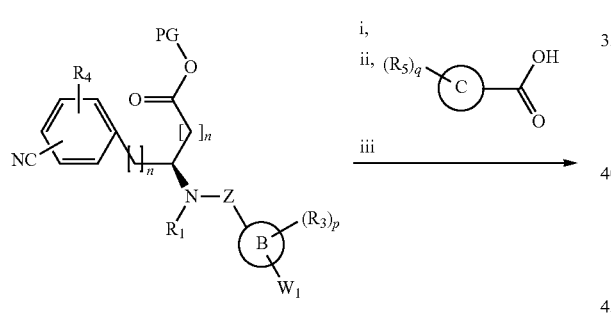

Reagents: PG is a protecting group; (i) NH$_2$OH, TEA, water or EtOH; (ii) EDC, HOBt, DMF then heat; (iii) Deprotection e.g., methyl ester deprotection: NaOH, MeOH, water.

The other enantiomer can be prepared in a similar manner using Scheme 4.

Scheme 5:

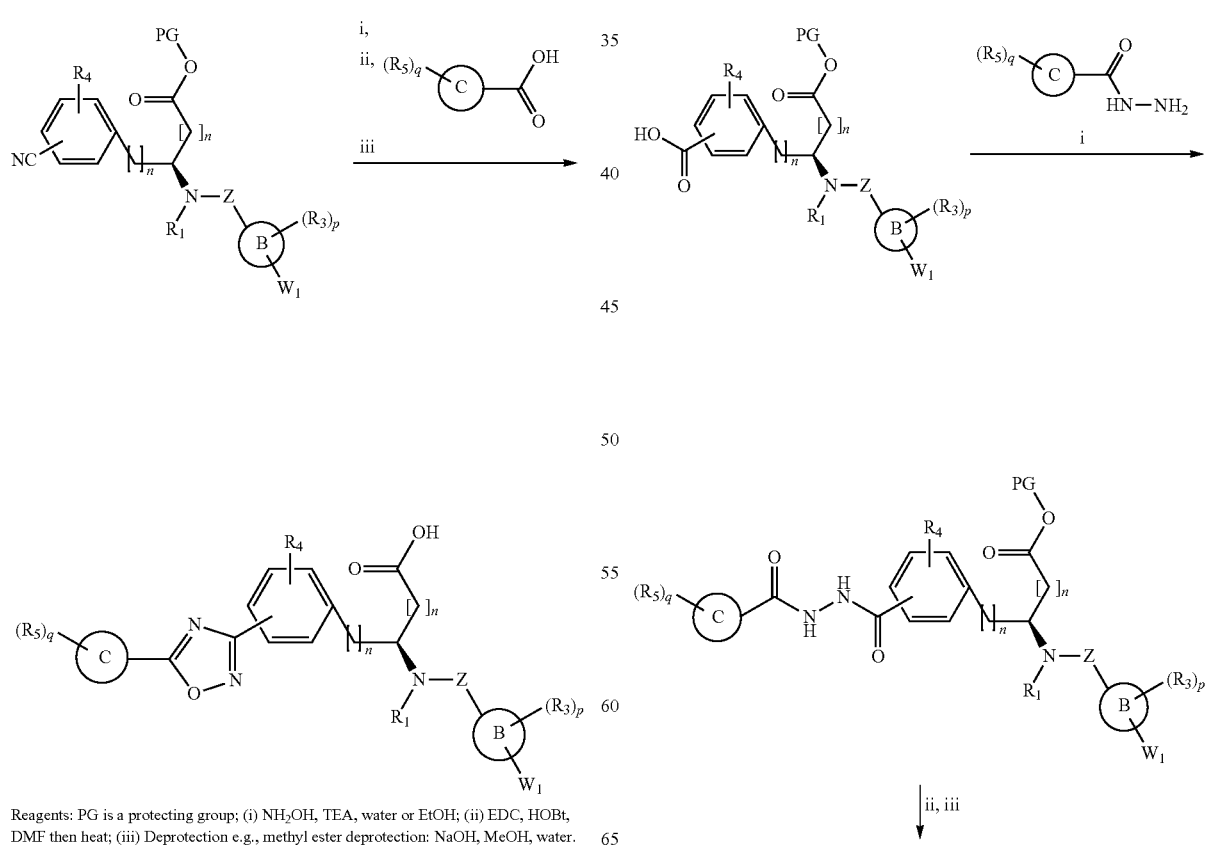

65

-continued

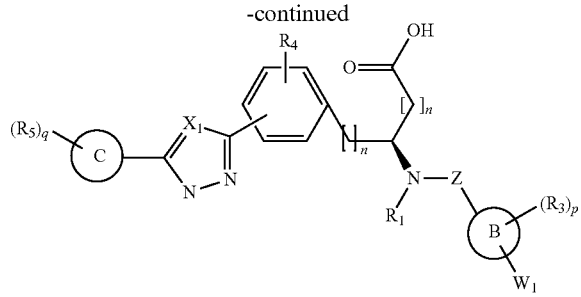

66

-continued

Reagents: $X_1$ = O or S; (i) N-Methylmorpholine, isobutyl chloroformate, THF, DMF; (ii) For $X_1$ = oxygen, then 2-Chloro-1,3-dimethylimidazolinium chloride, TEA, DCM; For $X_1$ = sulfur then 2,4-bis(4-methoxyphenyl)-1,3,2,4-dithiadiphosphetane 2,4-disulfide, THF; (iii) Deprotection e.g., methyl ester deprotection: NaOH, MeOH, water.

The other enantiomer can be prepared in a similar manner using Scheme 5.

Scheme 6:

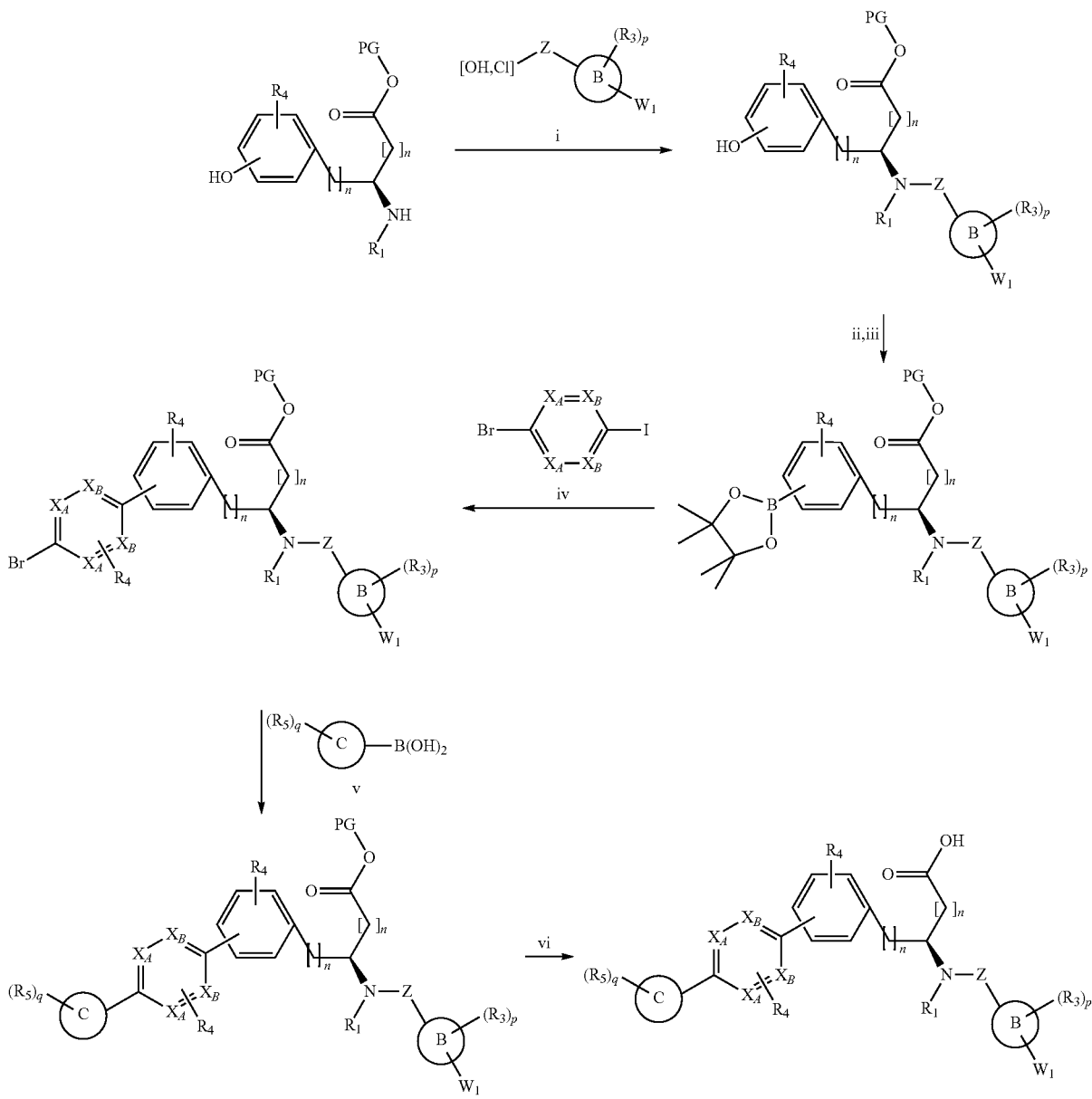

Reagents: PG is a protecting group and $X_A$ and $X_B$ are $CR_4$ or N; (i) For Z=CO, then amide coupling with acid chloride: DIEA, DCM or amide coupling with acid: EDC, HOBt, DMF or HATU, DMF; For Z=$SO_2$, then coupling with sulfonyl chloride DIEA or $NEt_3$, DCM or DMF (ii) DIEA, 1,1,1-trifluoro-N-phenyl-N-((trifluoromethyl) sulfonyl) methanesulfonamide, DCM; (iii) KOAc, bis-pinacolatoborane, $PdCl_2$(dppf) or Pd(dppf)$Cl_2$, $NaCO_3$, THF, ACN, water; (iv) Pd(dppf)$Cl_2$, $Na_2CO_3$, THF, ACN, water; (v) Pd(dppf)$Cl_2$, $NaCO_3$, THF, ACN, water; (vi) Deprotection eg., methyl ester deprotection: NaOH, MeOH, water.

The other enantiomer can be prepared in a similar manner using Scheme 6.
Scheme 7:
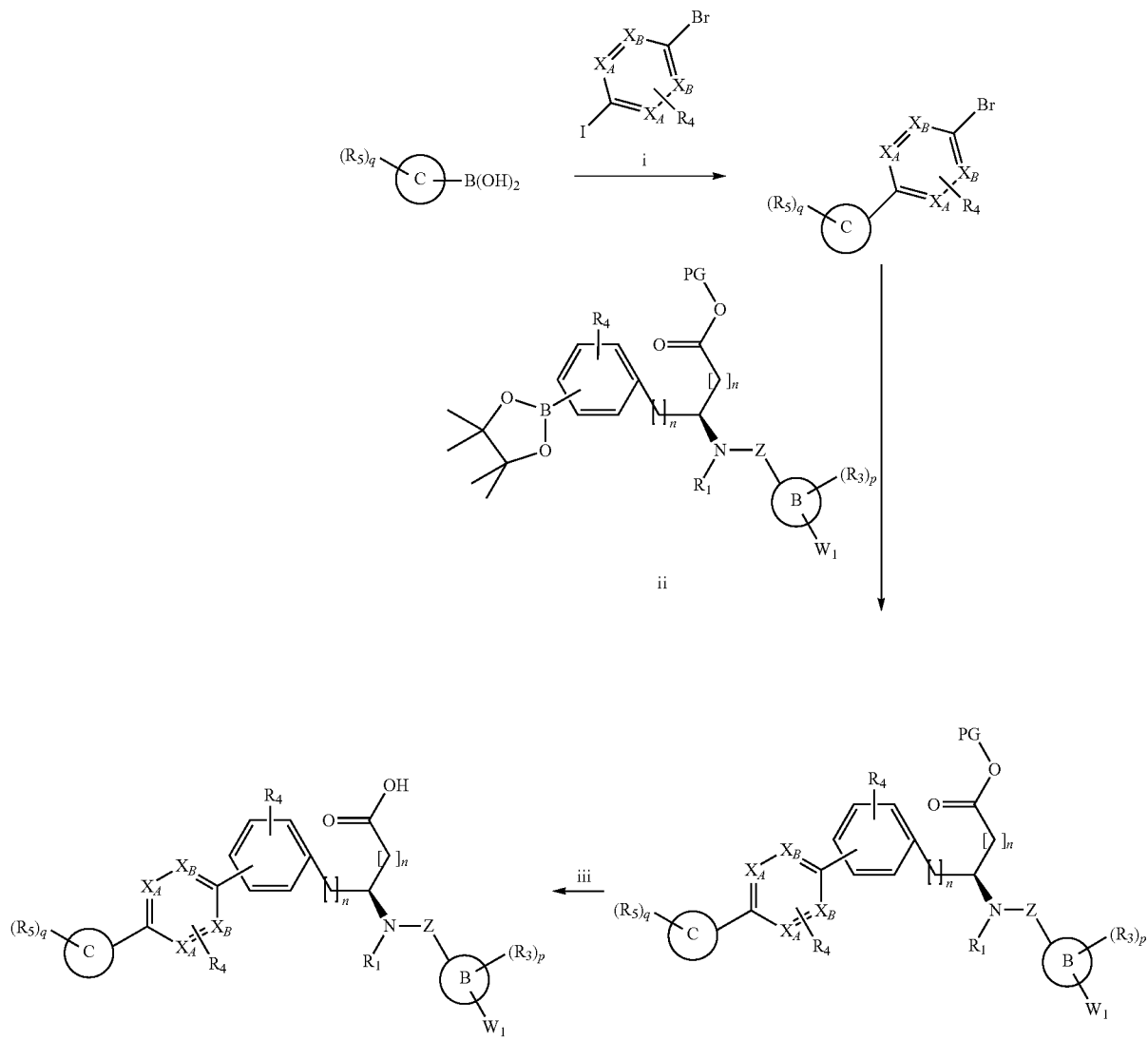
Reagents: PG is a protecting group and $X_A$ and $X_B$ are $CR_4$ or N; (i) Pd(dppf)Cl$_2$, Na$_2$CO$_3$, THF, ACN, water; (ii) Pd(dppf)Cl$_2$, NaCO$_3$, THF, ACN, water; (iii) Deprotection eg., methyl ester deprotection: NaOH, MeOH, water.
The other enantiomer can be prepared in a similar manner using Scheme 7.
Scheme 8:
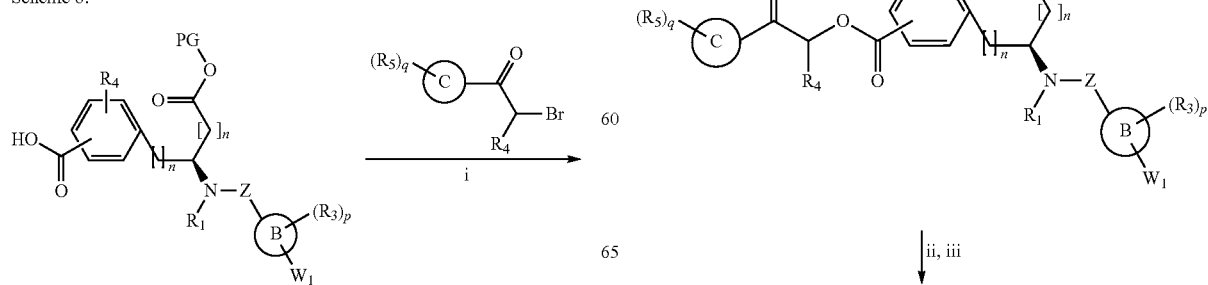

-continued

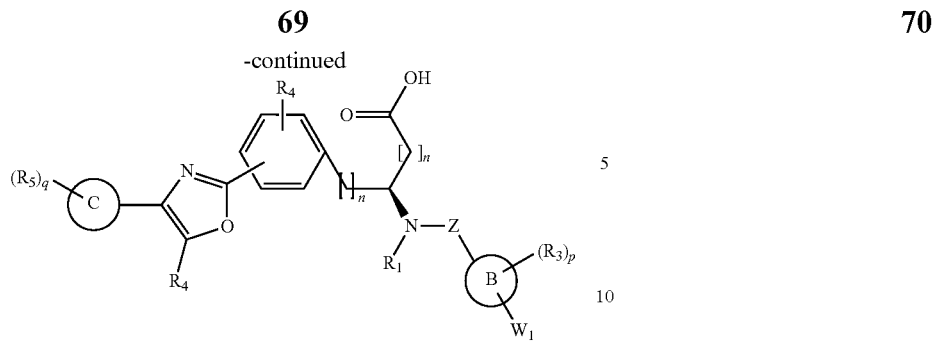

Reagents: PG is a protecting group; (i) DIEA or TEA, acetonitrile; (ii) Acetamide, boron trifluoride etherate, DCM; (iii) Deprotection e.g., methyl ester deprotection: NaOH, MeOH, water.

The other enantiomer can be prepared in a similar manner using Scheme 8.

Scheme 9:

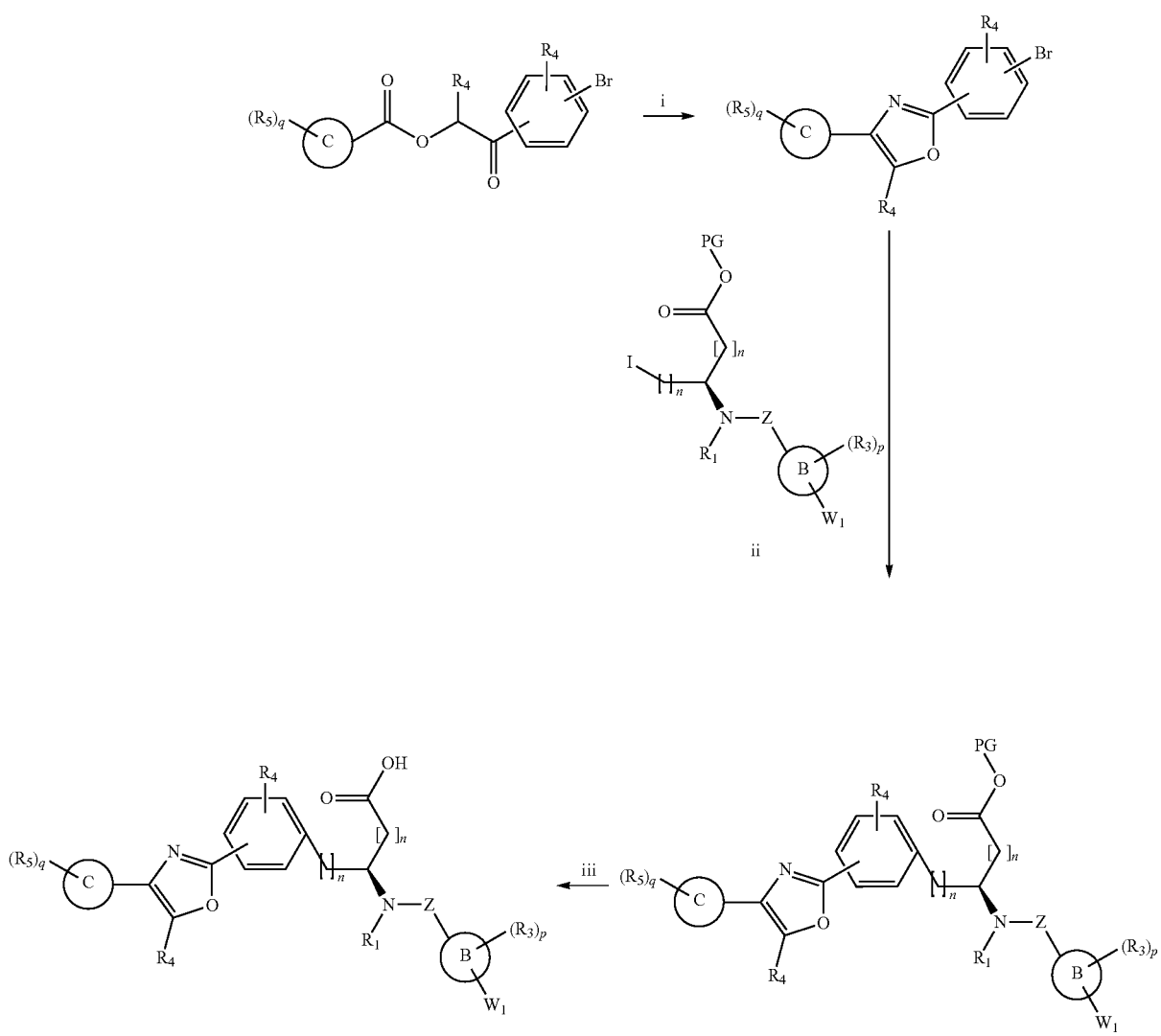

Reagent: PG is a protecting group; (i) Boron trifluoride etherate, acetamide, DCM; (ii) Zn, $I_2$, $Pd_2(dba)_3$, dicyclohexyl(2′,6′-dimethoxy-[1,1′-biphenyl]-2-yl)phosphine, DMF; (iii) Deprotection e.g., methyl ester deprotection: NaOH, MeOH, water.

The other enantiomer can be prepared in a similar manner using Scheme 9.

Scheme 10:

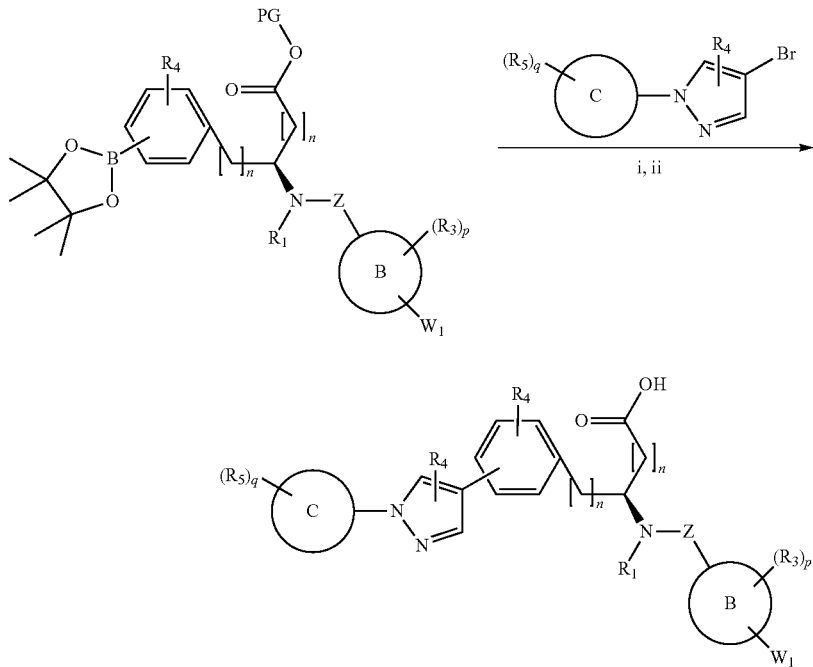

Reagents: PG is a protecting group; (i) Pd(dppf)Cl$_2$, Na$_2$CO$_3$, THF, ACN, water; (ii) Deprotection e.g. methyl ester deprotection: NaOH, MeOH, water.

The other enantiomer can be prepared in a similar manner using Scheme 10.

Scheme 11:

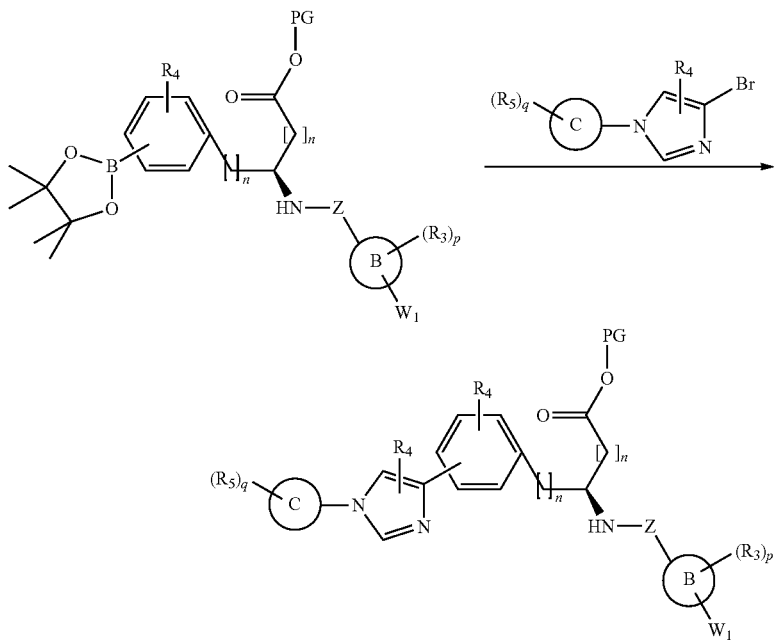

Reagents: PG is a protecting group: (i) Pd(dppf)Cl$_2$, Na$_2$CO$_3$, THF, ACN, water; (ii) Deprotection e.g., tert-butyl ester deprotection: DCM, TFA.

The other enantiomer can be prepared in a similar manner using Scheme 11.

Scheme 12:

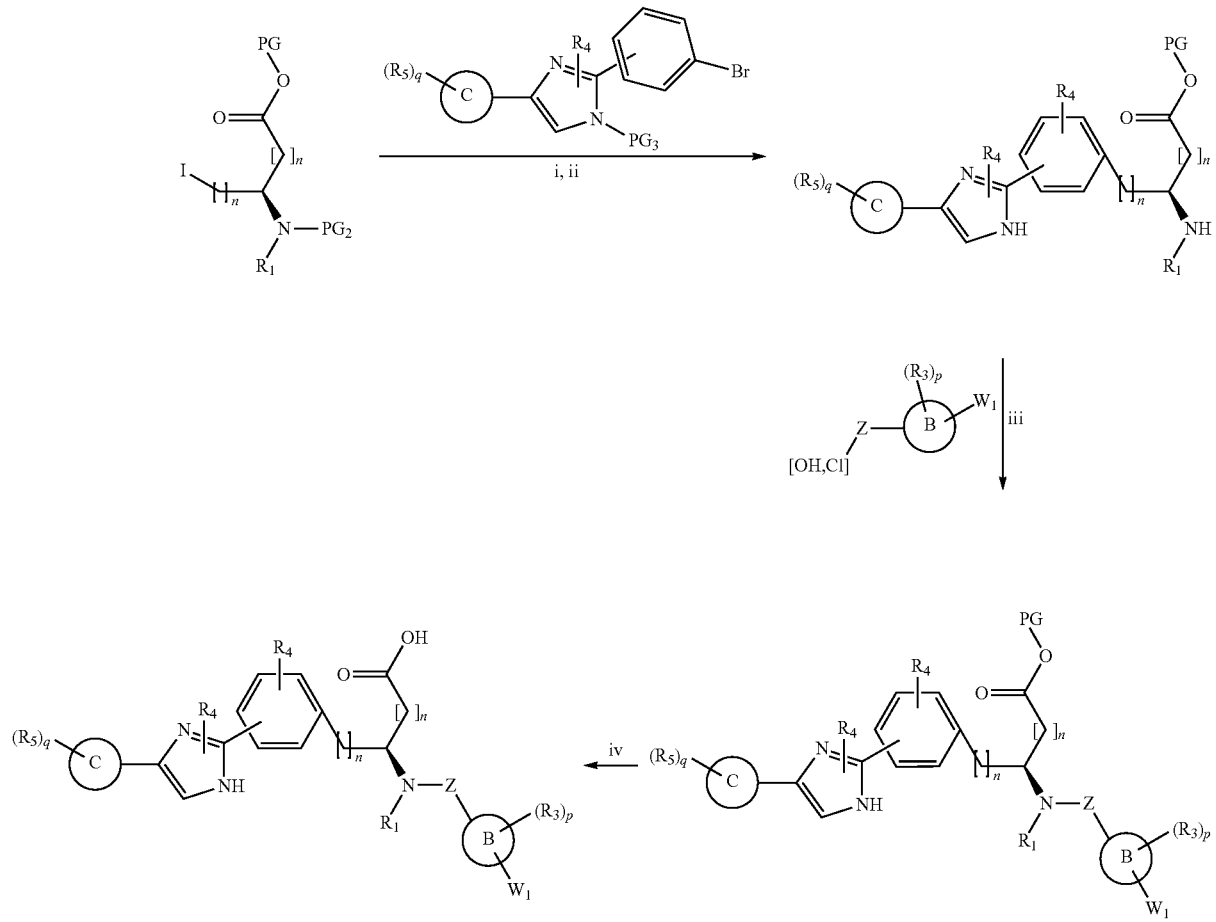

Reagent: PG, PG$_2$, and PG$_3$ are protecting group; (i) Zn, I$_2$, Pd$_2$(dba)$_3$, dicyclohexyl(2',6'-dimethoxy-[1,1'-biphenyl]-2-yl)phosphine, DMF; (ii) Deprotection of PG$_2$ e.g., tert-butyl carbonate and PG$_3$, e.g., SEM deprotection: DCM, TFA; (iii) If Z═CO then coupling with acid; base (DIEA, TEA, or NMM), coupling reagents (EDC, HOBt, or DCC, HOBt, or DCC, DMAP or HATU), solvent, (DMF or DCM); If Z═SO$_2$ then coupling with sulfonyl chloride: DIEA or TEA, DCM or DMF; (iv) Deprotection of PG, e.g., tert-butyl ester deprotection: DCM, TFA The other enantiomer can be prepared in a similar manner using Scheme 12.

Scheme 13:

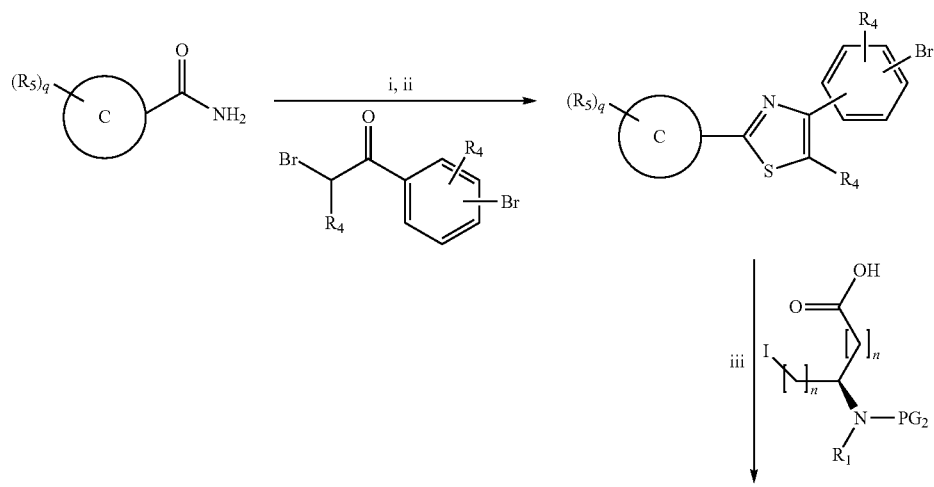

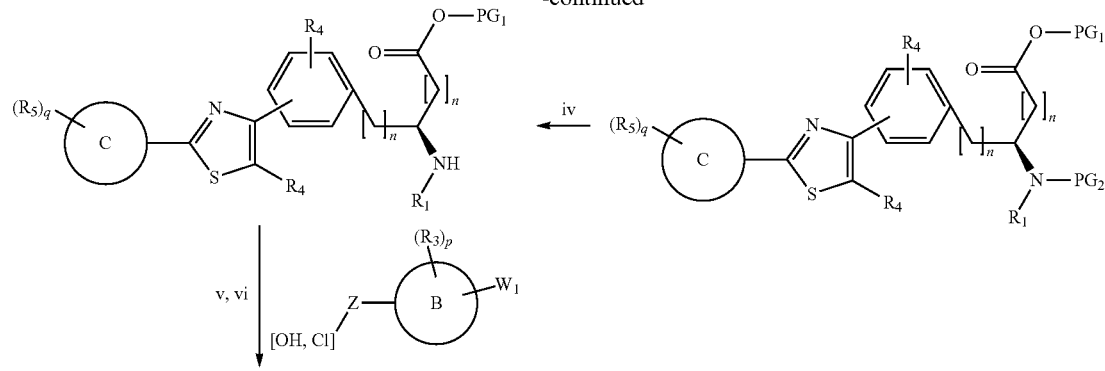

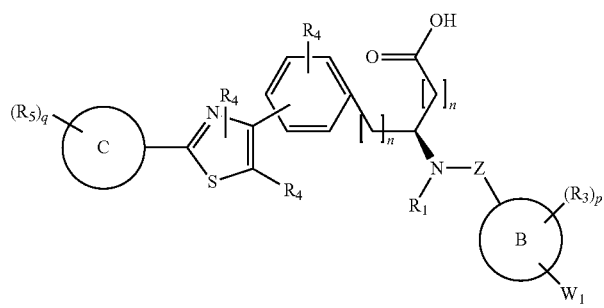

Reagents: PG and PG$_2$ are protecting groups; (i) 2,4-bis(4-phenoxyphenyl)-1,3,2,4-dithiaphosphetane 2,4-disulfate, DME, THF; (ii) isopropanol; (iii) Zn, I$_2$, Pd$_2$(dba)$_3$, dicyclohexyl(2′,6′-dimethoxy-[1,1′-biphenyl]-2-yl)phosphine, DMF; (iv) Deprotection of PG$_2$, e.g., tert-butyl ester deprotection: DCM, TFA; (v) If Z = CO then coupling with acid: base (DIEA, TEA, or NMM), coupling reagents (EDC, HOBt or DCC, HOBt, or DCC, DMAP or HATU), solvent (DMF or DCM; If Z = SO$_2$ then coupling with sulfonyl chloride: DIEA or TEA, DCM or DMF; (vi) Deprotection of PG$_1$, e.g., methyl ester deprotection: NaOH, MeOH, water.

The other enantiomer can be prepared in a similar manner using Scheme 13.

Scheme 14:

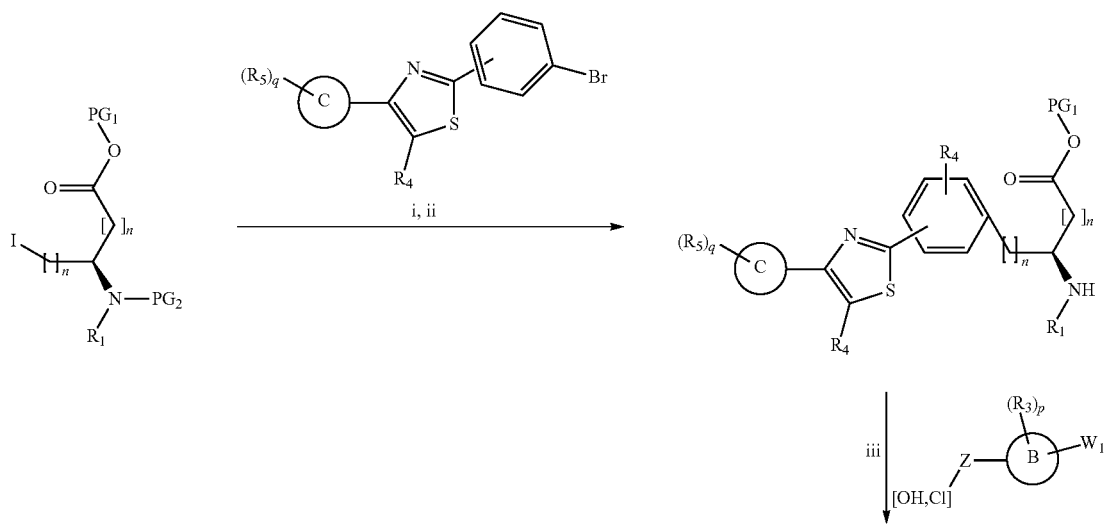

-continued

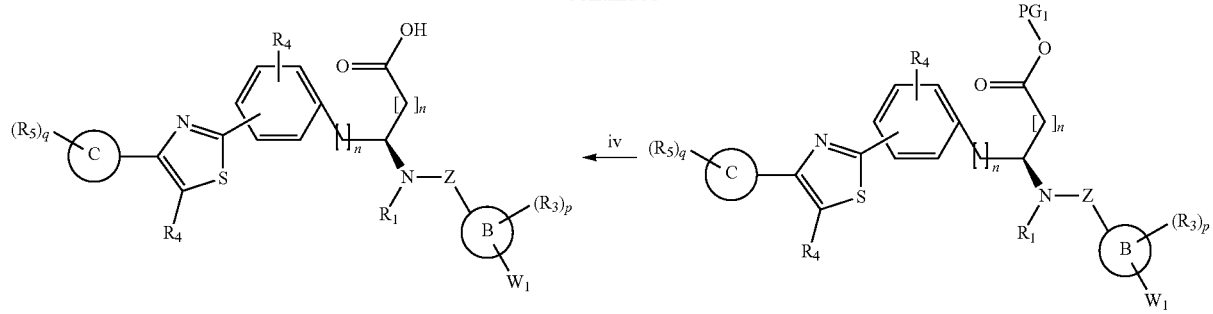

Reagent: PG₁ and PG₂ are protecting group; (i) Zn, I₂, Pd₂(dba)₃, dicyclohexyl(2',6'-dimethoxy-[1,1'-biphenyl]-2-yl)phosphine, DMF; (ii) Deprotection of PG₂, e.g., tert-butyl carbonate deprotection: DCM, TFA; (iii) If Z=CO then coupling with acid; base (DIEA, TEA, or NMM), coupling reagents (EDC, HOBt, or DCC, HOBt, or DCC, DMAP or HATU), solvent, (DMF or DCM); If Z=SO₂ then coupling with sulfonyl chloride: DIEA or TEA, DCM or DMF; (iv) Deprotection of PG₁, e.g., tert-butyl ester deprotection: DCM, TFA.

The other enantiomer can be prepared in a similar manner using Scheme 14.

Scheme 15:

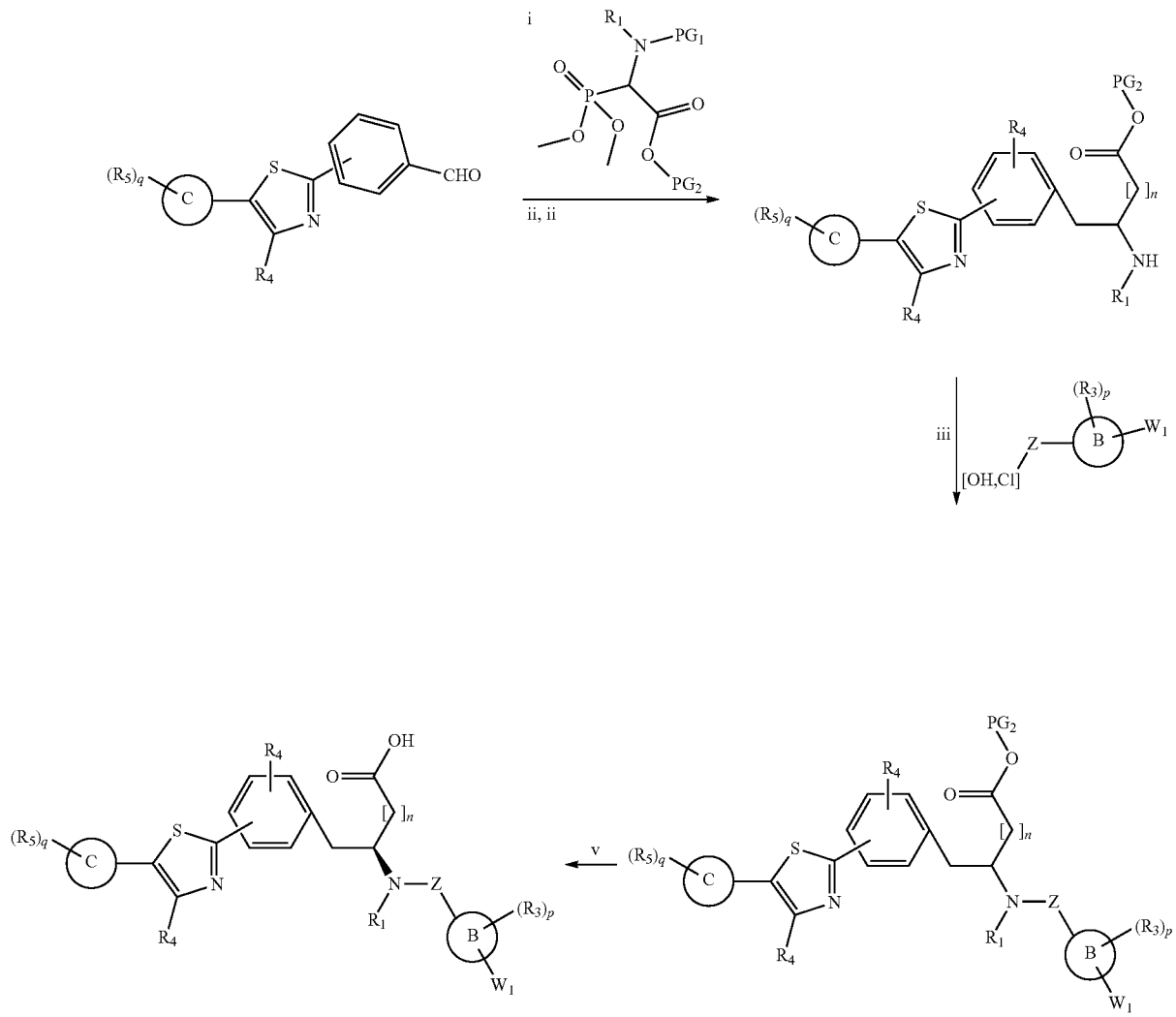

Reagent: PG₁ and PG₂ are protecting group; (i) 1,1,3,3-tetramethylguanidine, THF; (ii) H₂, Dioxane; (iii) Deprotection of PG₁ e.g.; boc-amine deprotection: DCM, TFA; (iv) If Z=CO then coupling with acid: base (DIEA, TEA, or NMM), coupling reagents (EDC, HOBt or DCC, HOBt, or DCC, DMAP or HATU), solvent (DMF of DCM); If Z=SO₂ then coupling with sulfonyl chloride; DIEA or TEA, DCM or DMF; (v) Deprotection of PG₂, e.g., tert-butyl ester deprotection: DCM, TFA.

Scheme 16:

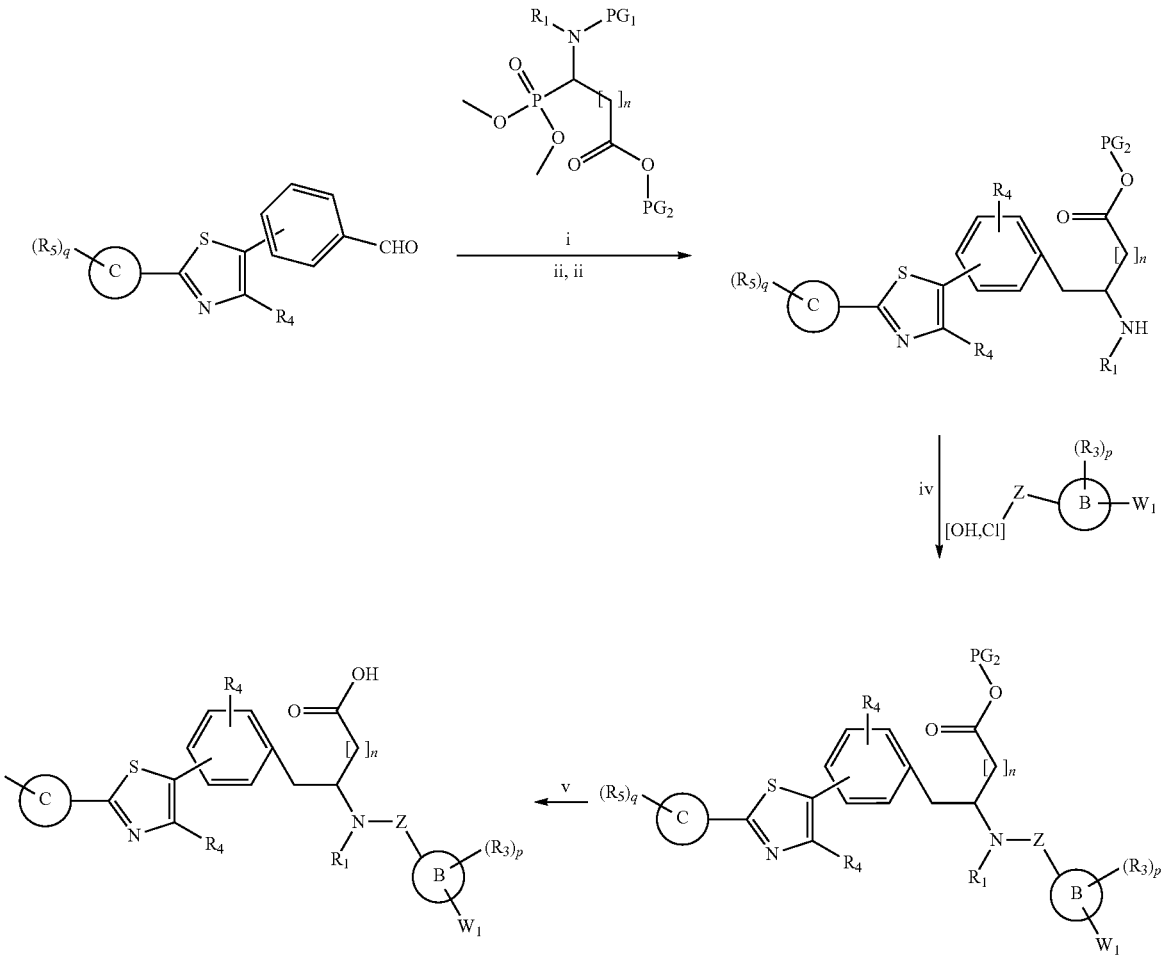

Reagent: $PG_1$ and $PG_2$ are protecting group; (i) 1,1,3,3-tetramethylguanidine, THF; (ii) $H_2$, Dioxane; (iii) Deprotection of $PG_1$ e.g.; boc amine deprotection: DCM, TFA; (iv) If Z═CO then coupling with acid: base (DIEA, TEA, or NMM), coupling reagents (EDC, HOBt or DCC, HOBt, or DCC, DMAP or HATU), solvent (DMF of DCM); If Z═$SO_2$ then coupling with sulfonyl chloride; DIEA or TEA, DCM or DMF; (v) Deprotection of $PG_2$, e.g., tert-butyl ester deprotection: DCM, TFA.

Scheme 17:

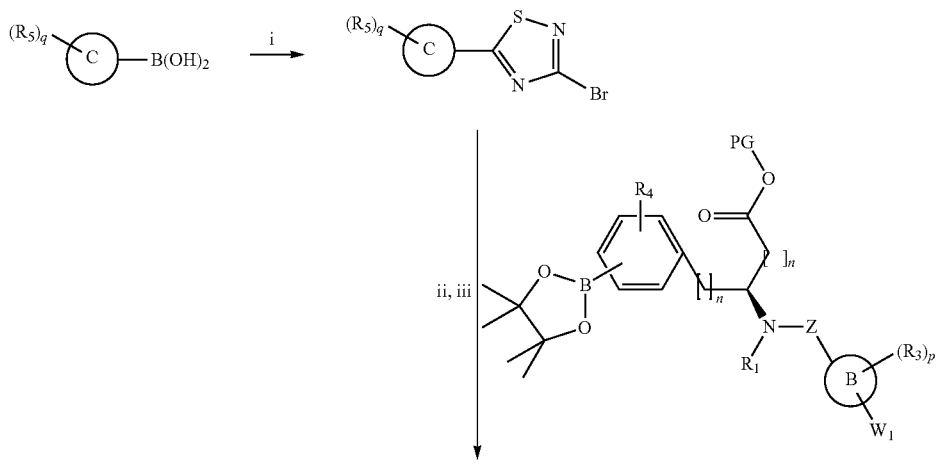

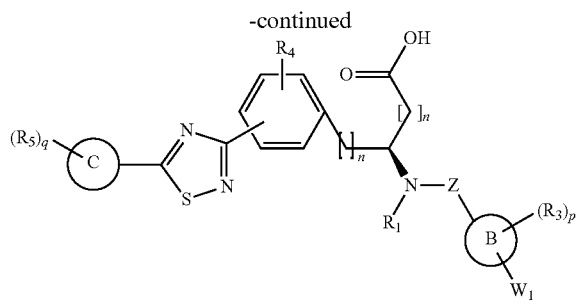

Reagents: PG is a protecting group; (i) 3-bromo-5-chloro-1,2,4-thiadiazole, NaHCO$_3$, Pd(dppf)Cl$_2$, water and THF, ACN or dioxane; (ii) NaHCO$_3$, Pd(dppf)Cl$_2$, water and THF, ACN or dioxane; (iii) Deprotection of PG, e.g., tert-butyl ester deprotection: DCM, TFA.

The other enantiomer can be prepared in a similar manner using Scheme 17.

Scheme 18:

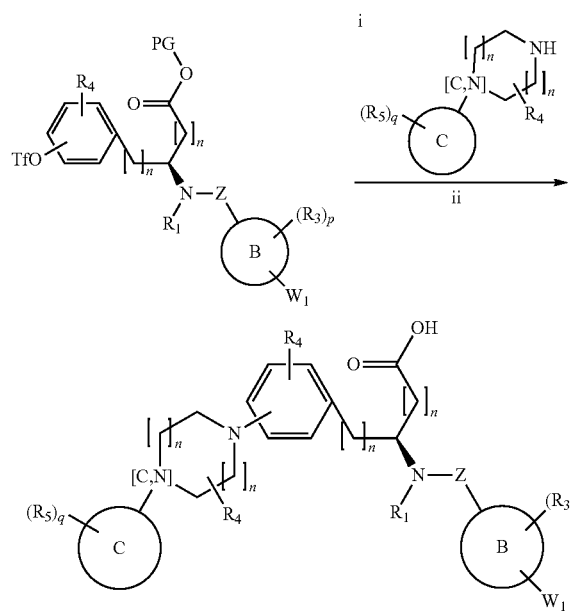

Reagents: PG is a protecting group;(i) NaO$^t$Bu or Cs$_2$CO$_3$, Pd(dppf)Cl$_2$ or Pd$_2$(dba)$_3$, 2-diclohexylphosphino-2'-(N,N-dimethylamino)biphenyl, water and THF, ACN or dioxane; (ii) Deprotection of PG, e.g. tert-butyl ester deprotection: DCM, TFA.

The other enantiomer can be prepared in a similar manner using Scheme 18.

Scheme 19:

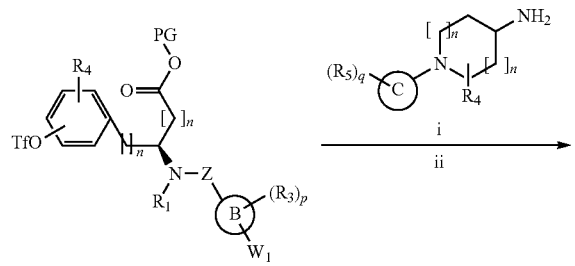

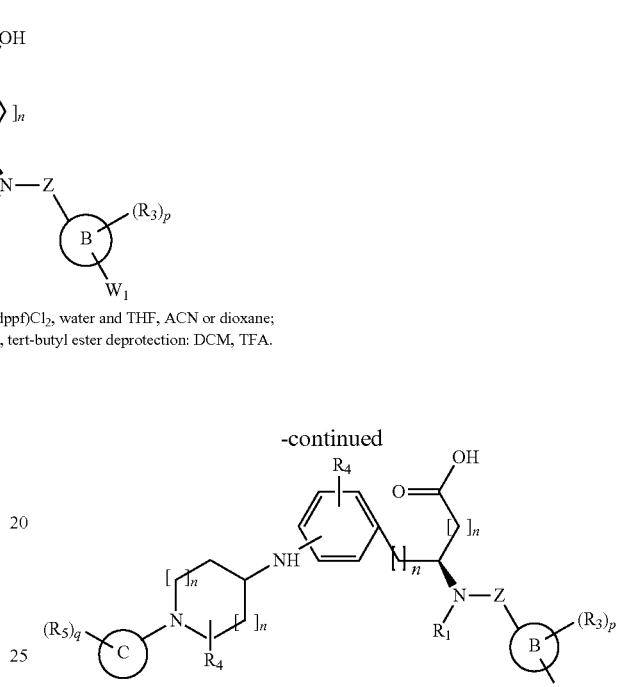

Reagents: PG is a protecting group; (i) NaO$^t$Bu or Cs$_2$CO$_3$, Pd(dppf)Cl$_2$, or Pd$_2$(dba)$_3$, 2-dicyclohexylphosphine-2'-(N,N-dimethylamino)phenyl, water and THF, ACN or dioxane; (ii) Deprotection of PG, e.g., tert-butyl ester deprotection: DCM, TFA.

The other enantiomer can be prepared in a similar manner using Scheme 19.

Scheme 20:

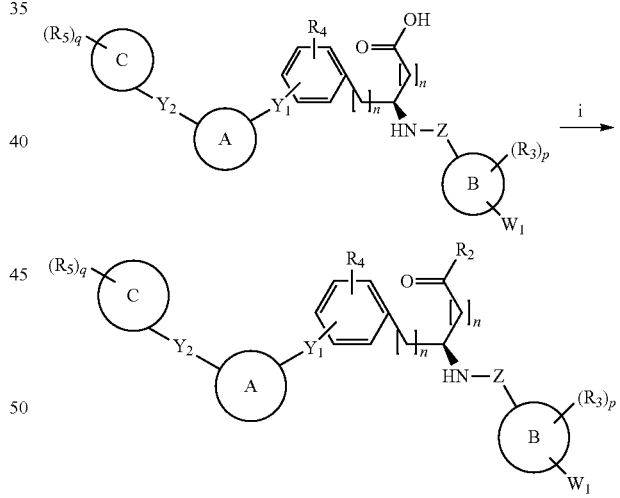

Reagents: PG is a protecting group;(i) (a) where R$_2$ is NH—(CR$_a$R$_b$)$_m$—COOH: NH$_2$—(CR$_a$R$_b$)$_m$—COOPG, HATU, DMF then deprotection e.g., tert-butyl ester deprotection: DCM, TFA;(b) where R$_2$ is NH—SO$_2$—R$_8$: R$_8$SO$_2$NH$_2$, DCC, DMAP, DCM (c) where R$_2$ is NR$_{41}$R$_{42}$: HNR$_{41}$R$_{42}$, HATU, DMF then deprotection e.g., tert-butyl ester deprotection: DCM, TFA; (d) where R$_2$ is N(R$_1$)—(CR$_a$R$_b$)m—CO—N(R$_1$)—heterocyclyl: HN(R$_1$)—(CR$_a$R$_b$)m—CO—N(R$_1$)—heterocyclyl, HATU, DMF then deprotection e.g., tert-butyl ester deprotection: DCM, TFA; (e) where R$_2$ is —N(R$_1$)—(CR$_a$R$_b$)$_m$—CO—N(R$_1$)(R$_7$): NH$_2$—(CR$_a$R$_b$)$_m$—COOPG, HATU, DMF then deprotection e.g., tert-butyl ester deprotection: DCM, TFA then HN(R$_1$)(R$_7$), HATU, DMAP, DCM (f) where R$_2$ is N(R$_1$)—(CR$_a$R$_b$)$_m$—heterocyclyl: HN(R$_1$)—(CR$_a$R$_b$)$_m$—heterocyclyl, HATU, DMF then deprotection e.g., tert-butyl ester deprotection: DCM, TFA.

The other enantiomer and diastereoisomer can be prepared in a similar manner using Scheme 20.

Scheme 21:

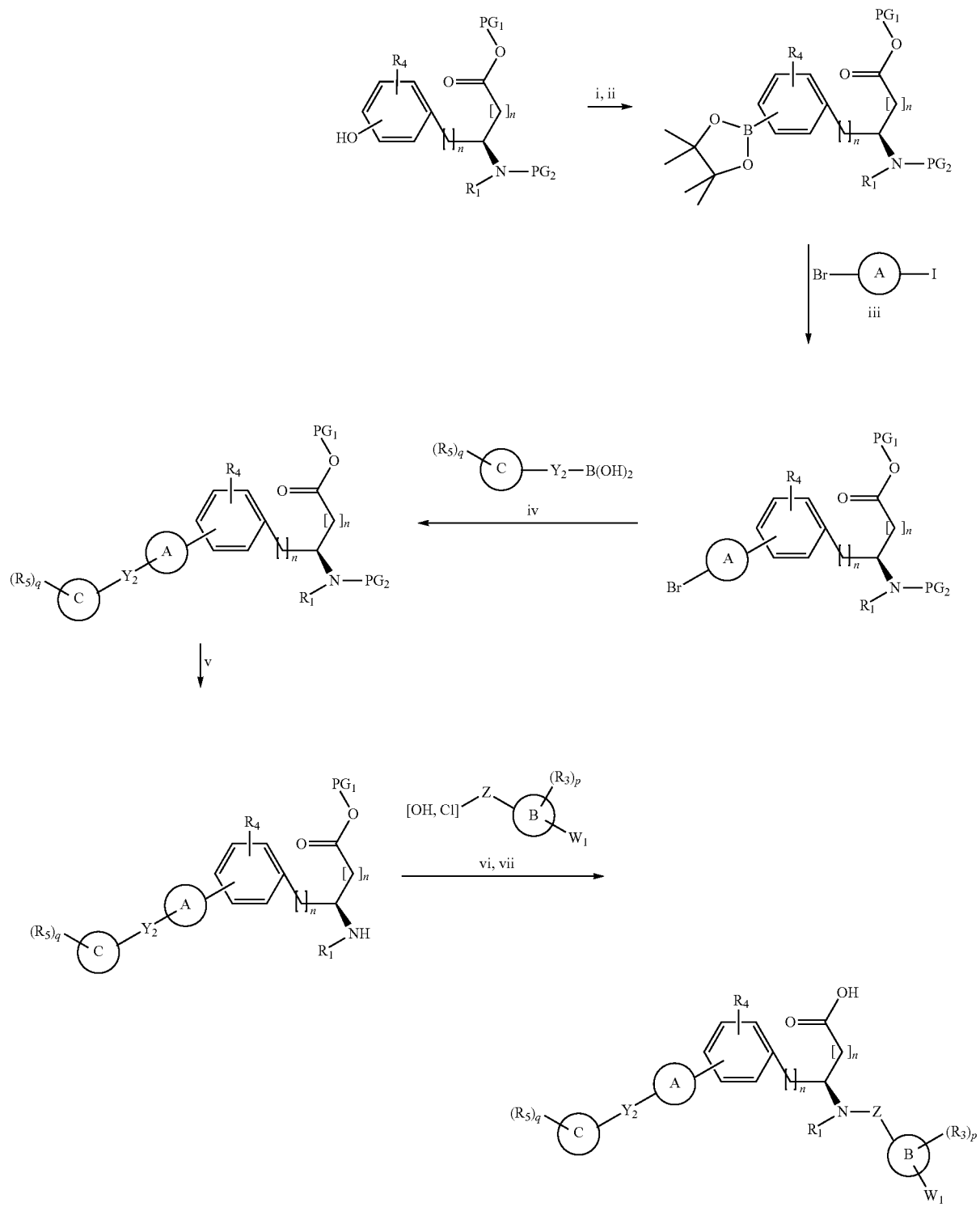

Reagents: PG$_1$ and PG$_2$ are protecting groups: (i) DIEA, 1,1,1-trifluoro-N-phenyl-N-((trifluoromethyl)sulfonyl)methanesulfonamide, DCM; (ii) KOAc, bis-pinacolatoborane, PdCl$_2$(dppf); (iii) Pd(dppf)Cl$_2$, NaCO$_3$, THF, ACN, water; (iv) Pd(dppf)Cl$_2$, NaCO$_3$, THF, ACN, water; (v) Deprotection of PG$_2$, e.g. CBZ: Pd/C, H$_2$, EA; (vi) If Z=CO then amide coupling with acid chloride; DIEA, DCM or amide coupling with acid: EDC, HOBt, DMF, or HATU, DMF; If Z=SO$_2$, then coupling with sulfonyl chloride: DIEA or NEt$_3$, DCM or DMF; (vii) Deprotection of PG$_1$, e.g., tert-butyl ester deprotection: DCM, TFA.

The other enantiomer can be prepared in a similar manner using Scheme 21.
Scheme 22:
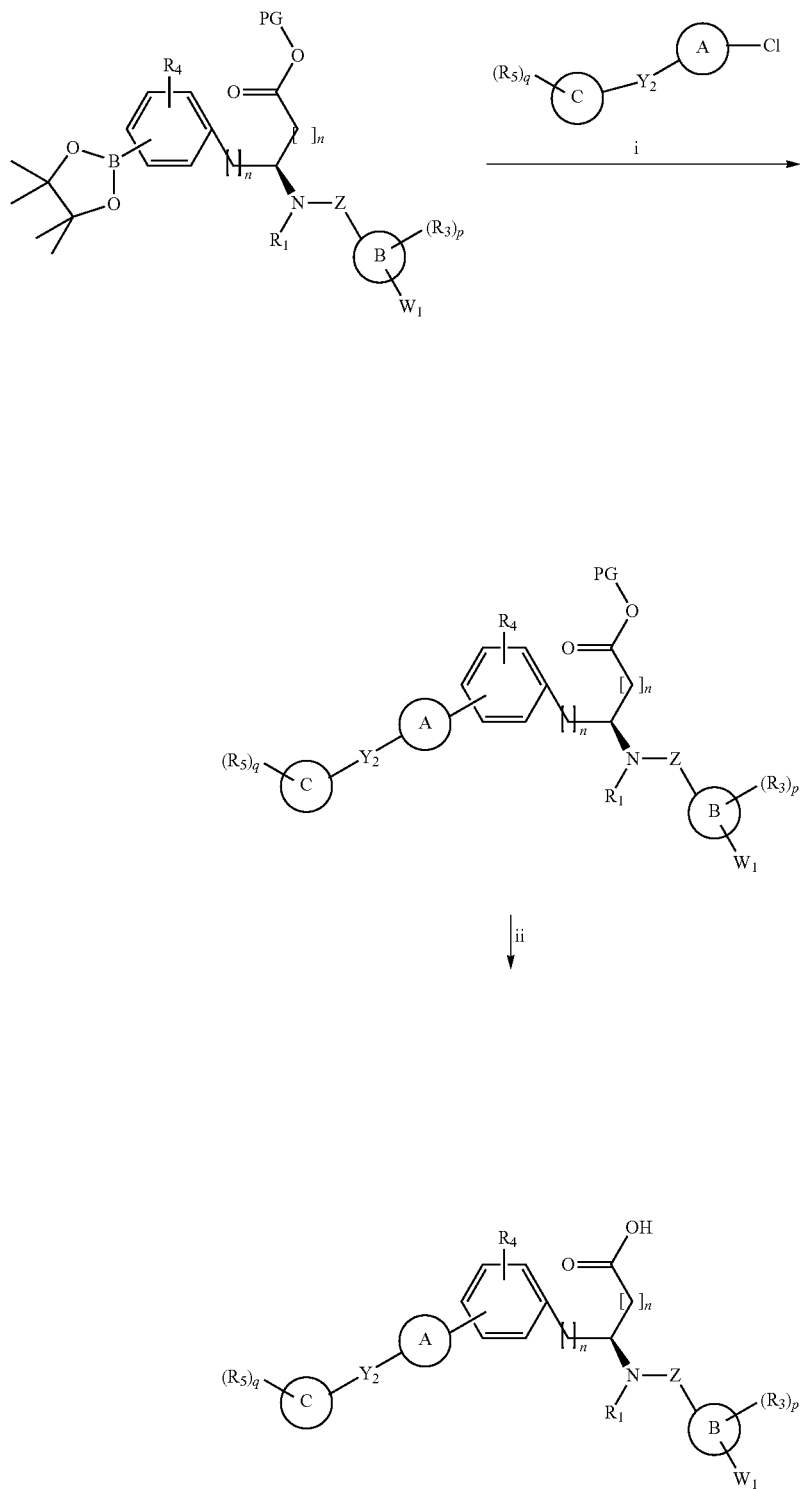
Reagents: PG is a protecting group; (i) Pd(dppf)Cl$_2$, NaCO$_3$, THF, ACN, water; (ii) Deprotection of PG, e.g., tert-butyl ester deprotection; DCM, TFA.
The other enantiomer can be prepared in a similar manner using Scheme 22.

Scheme 23:

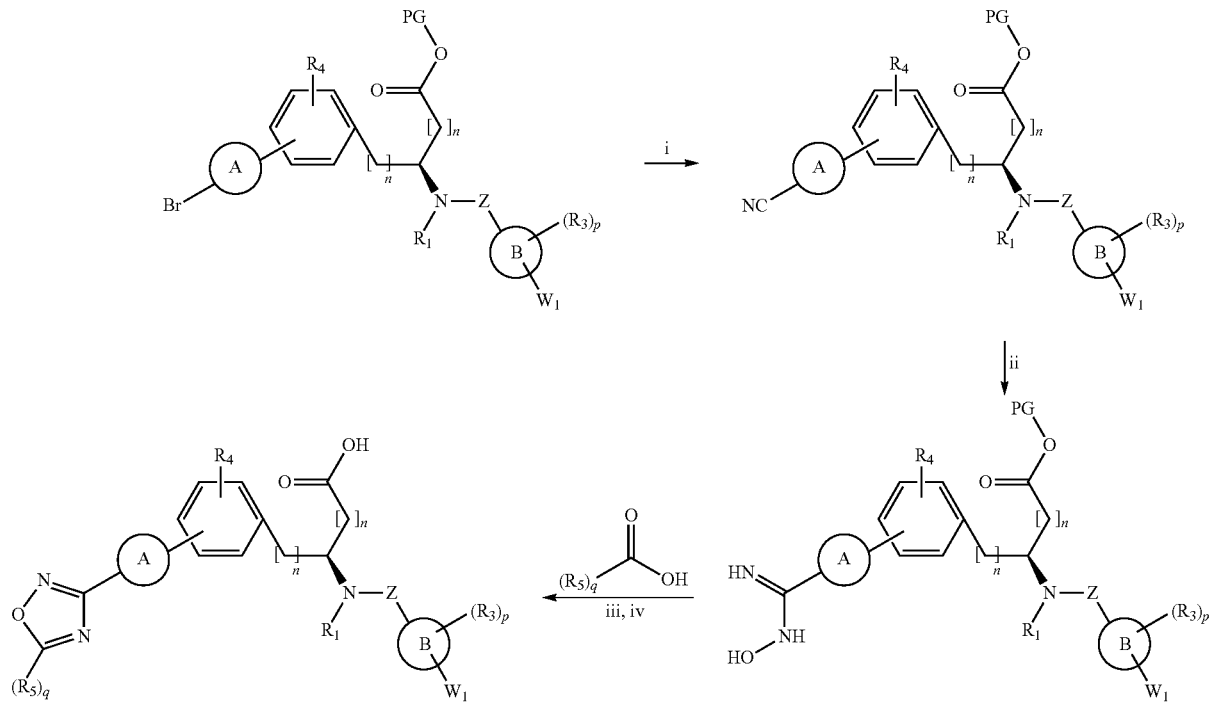

Reagents: PG is a protecting group; (i) Zn(CN)$_2$, Pd(Ph$_3$)$_4$, NMP; (ii) hydroxylamine, NEt$_3$, EtOH; (iii) EDC, HOBt, DMF then heat; (iv) Deprotection of PG, e.g., tert-butyl ester deprotection: DCM, TFA.

The other enantiomer can be prepared in a similar manner using Scheme 23.

Scheme 24:

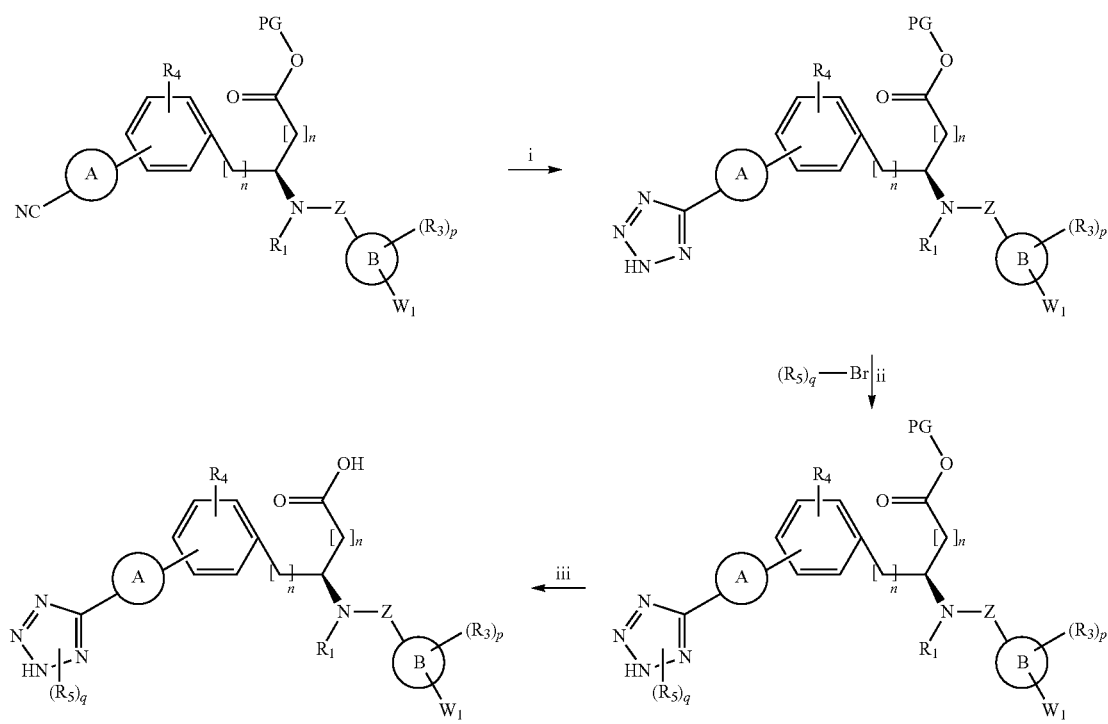

Reagents: PG is a protecting group; (i) NH$_4$Cl, NaN$_3$, DMF; (ii) CsCO$_3$, or K$_2$CO$_3$, DMF, acetone or acetonitrile; (iii) Deprotection of PG, e.g., tert-butyl ester deprotection: DCM, TFA.

The other enantiomer can be prepared in a similar manner using Scheme 24.

Scheme 25:

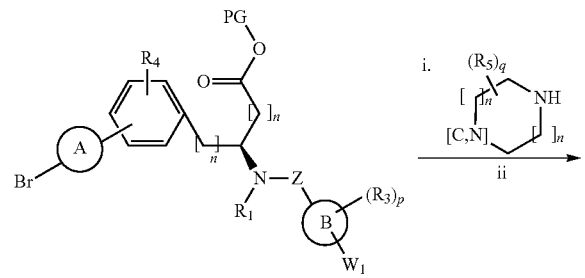

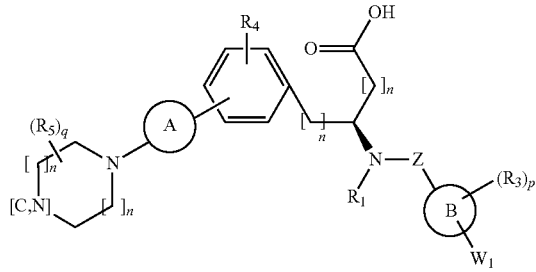

Reagents: PG is a protecting group; (i) sodium tert-butoxide, Pd$_2$(dba)$_3$, dioxane; (ii) Deprotection of PG, e.g., tert-butyl ester deprotection: DCM, TFA.

The other enantiomer can be prepared in a similar manner using Scheme 25.

Scheme 26:

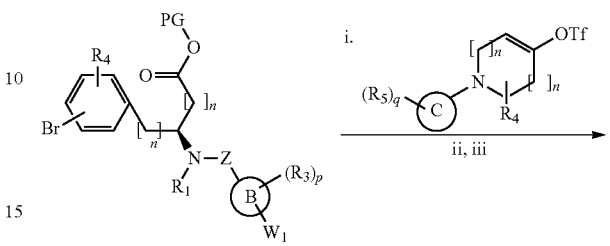

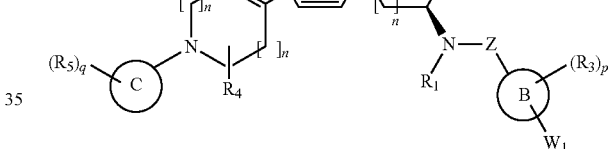

Reagents: PG is a protecting group; (i) NaO$^t$Bu or Cs$_2$CO$_3$, Pd$_2$(dppf)Cl$_2$ or Pd$_2$(dba)$_3$, 2-dicyclohexylphosphino-2'-(N,N-dimethylamino)biphenyl, water and THF, ACN or dioxane; (ii) Pd/C, H$_2$, EtOH, (iii) Deprotection of PG, e.g., tert-butyl ester deprotection: DCM, TFA.

The other enantiomer can be prepared in a similar manner using Scheme 26.

Scheme 27:

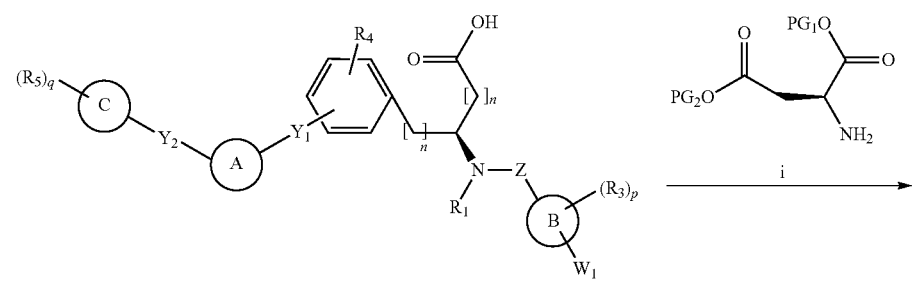

-continued
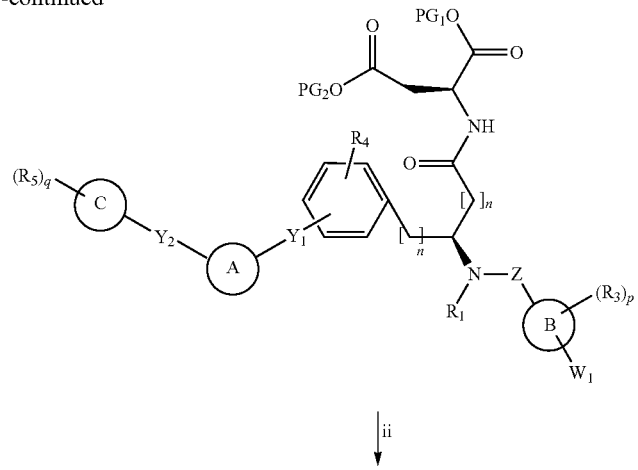
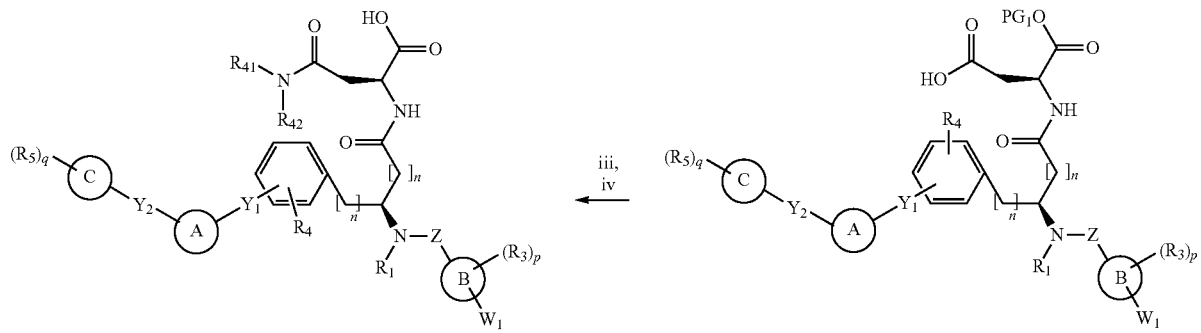
Reagents: PG₁ and PG₂ are protecting groups; (i) HATU, DMF, DIEA; (ii) Deprotection of PG₂, e.g. benzyl ester deprotection: Pd/C, H₂, MeOH; (iii) HNR₄₁R₄₂, HATU, DMF; (iv) Deprotection of PG₁, e.g., tert-butyl ester deprotection: dioxane, HCl or DCM, TFA.
The other enantiomer and diastereomers can be prepared in a similar manner using Scheme 27.
Scheme 28:
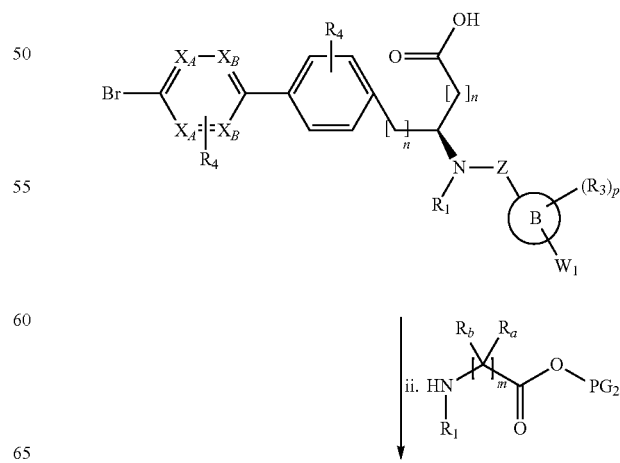
-continued
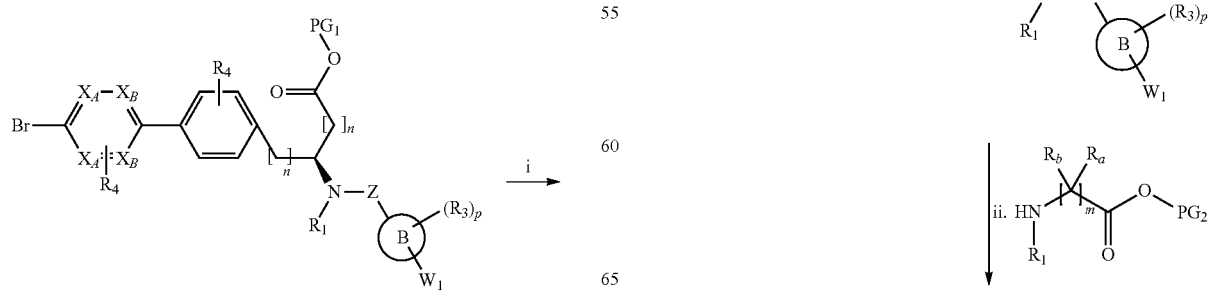

-continued

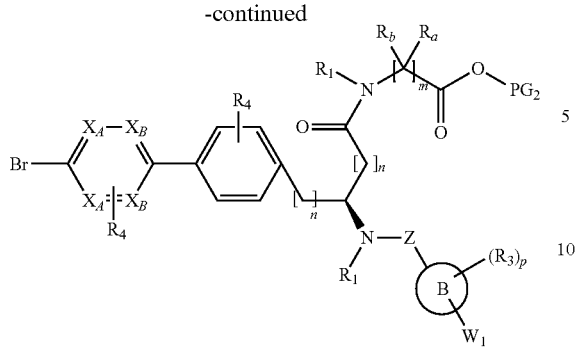

Reagents: PG$_1$ and PG$_2$ are protecting groups and X$_A$ and X$_B$ are CR$_4$ or N;
(i) Deprotection of PG$_1$, e.g., tert-butyl ester deprotection: DCM, TFA;
(ii) HATU, DIEA, DMF.

The other enantiomer can be prepared in a similar manner using Scheme 28.

Scheme 29:

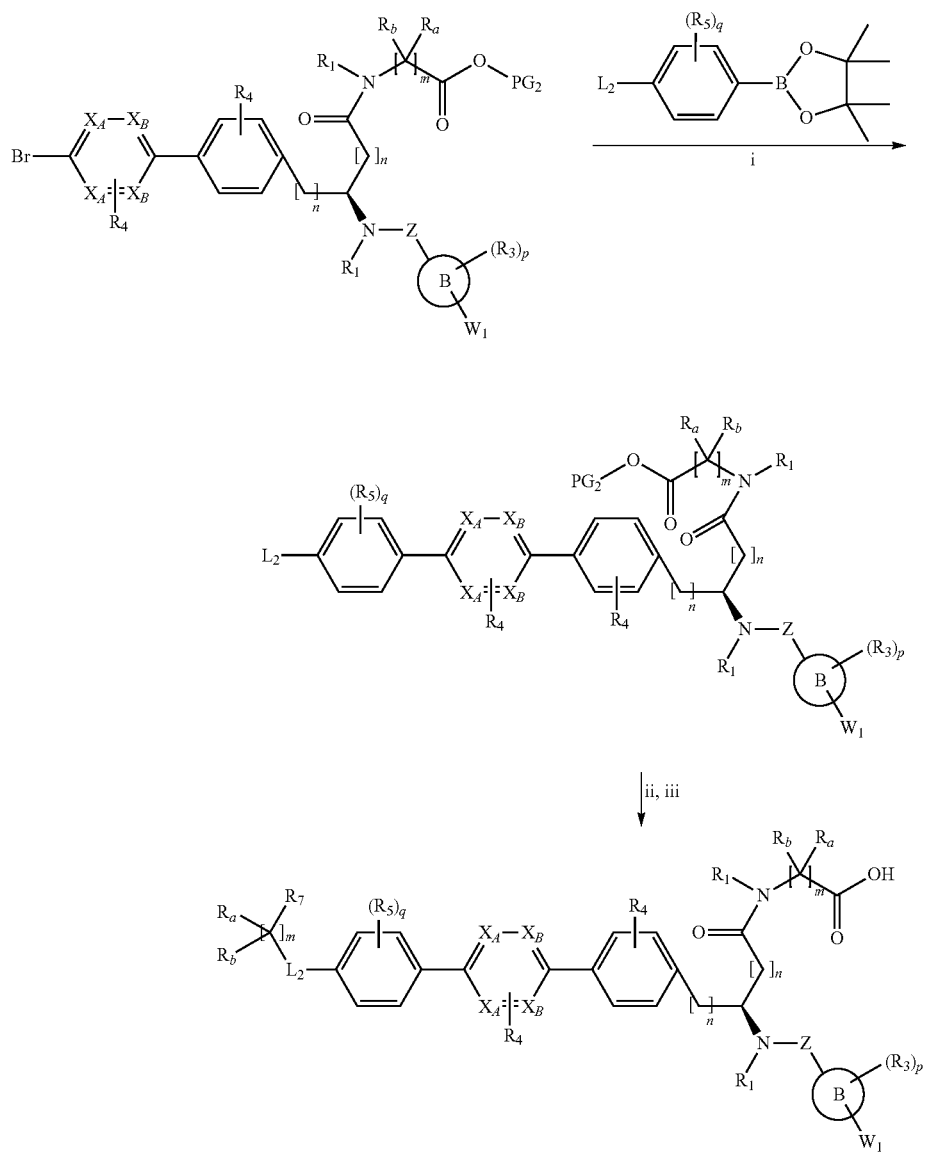

Reagents: PG$_1$ and PG$_2$ are protecting groups and X$_A$ and X$_B$ are CR$_4$ or N; (i) Pd(dppf)Cl$_2$, Na$_2$CO$_3$, THF, ACN, water; (ii) Br—(CR$_a$R$_b$)$_m$—R$_7$, K$_2$CO$_3$, DMF; (iii) Deprotection of PG$_2$, e.g., tert-butyl ester deprotection: DCM, TFA.

The other enantiomer can be prepared in a similar manner using Scheme 29.

Scheme 30:
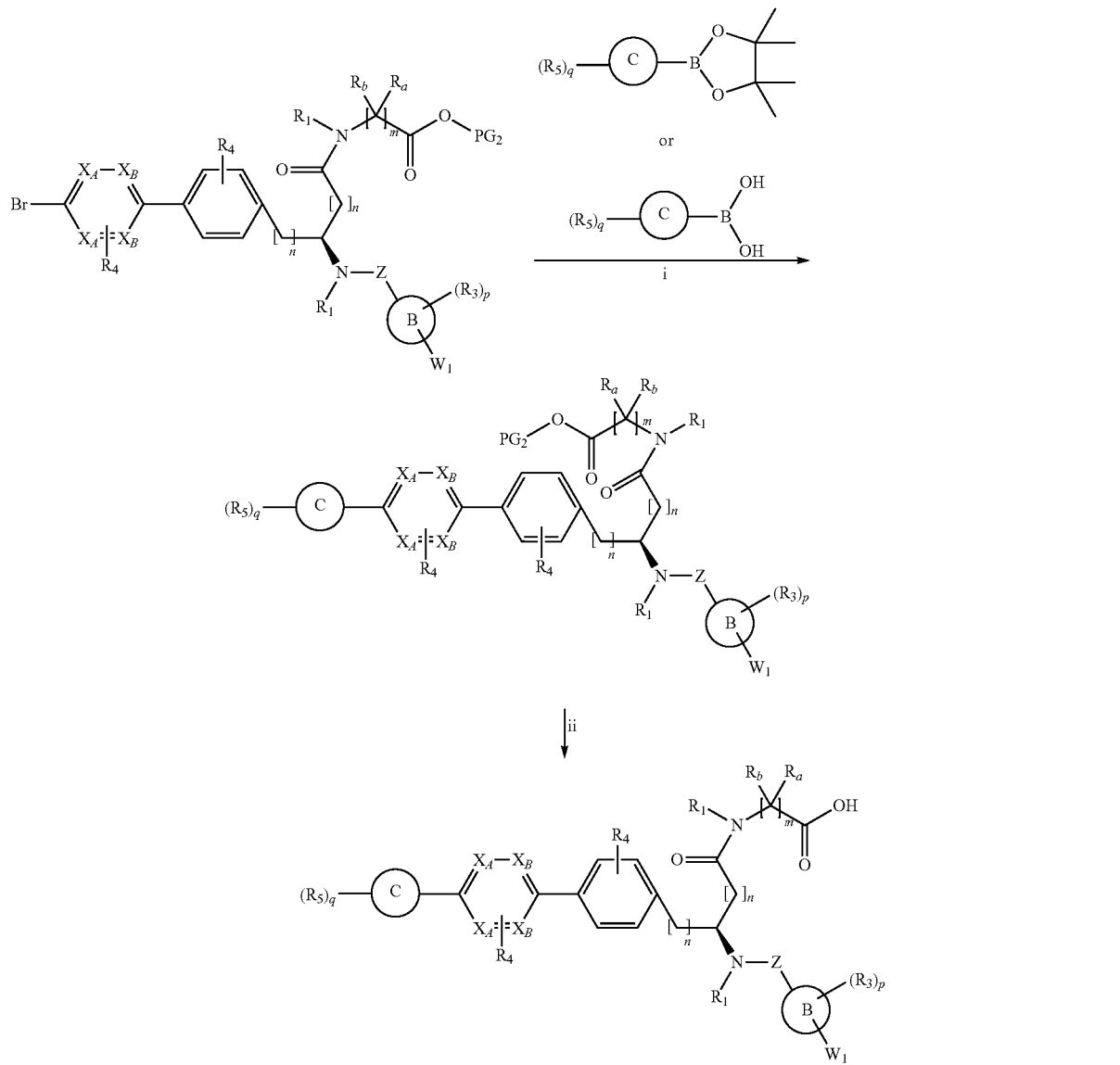
Reagents: PG$_1$ and PG$_2$ are protecting groups and X$_A$ and X$_B$ are CR$_4$ or N; (i) Pd(dppf)Cl$_2$, Na$_2$CO$_3$, THF, acetonitrile, water; (ii) Deprotection of PG$_2$, e.g., tert-butyl ester deprotection: DCM, TFA.
The other enantiomer can be prepared in a similar manner using Scheme 30.
Scheme 31:
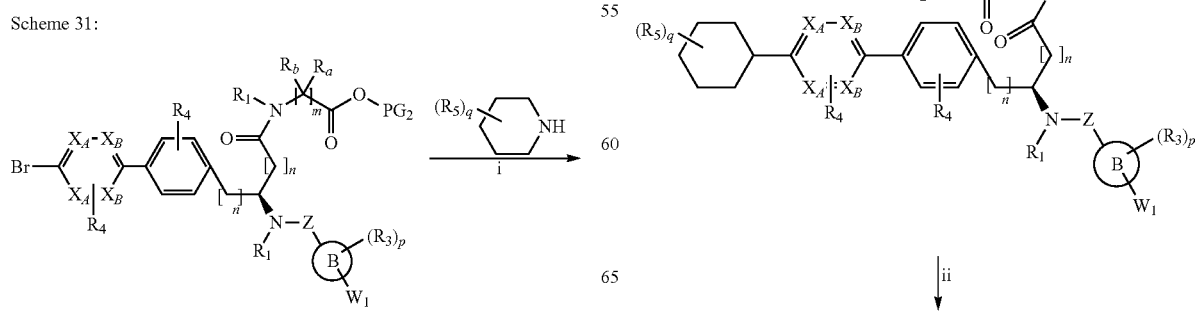
-continued -continued

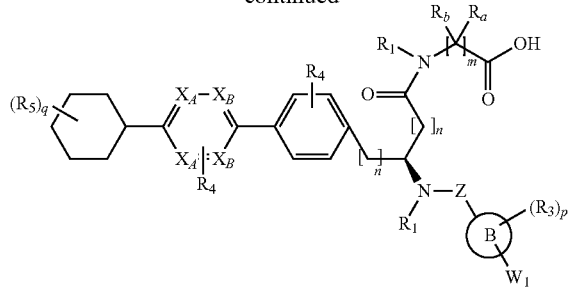

Reagents: $PG_1$ and $PG_2$ are protecting groups and $X_A$ and $X_B$ are $CR_4$ or N; (i) $Pd_2(dba)_3$, 2-dicyclohexylphosphino-2'-(N,N-dimethylamino)biphenyl, NaOtBu, dioxane; (ii) Deprotection of $PG_2$, e.g., tert-butyl ester deprotection: DCM, TFA.

The other enantiomer can be prepared in a similar manner using Scheme 31.

Scheme 32:

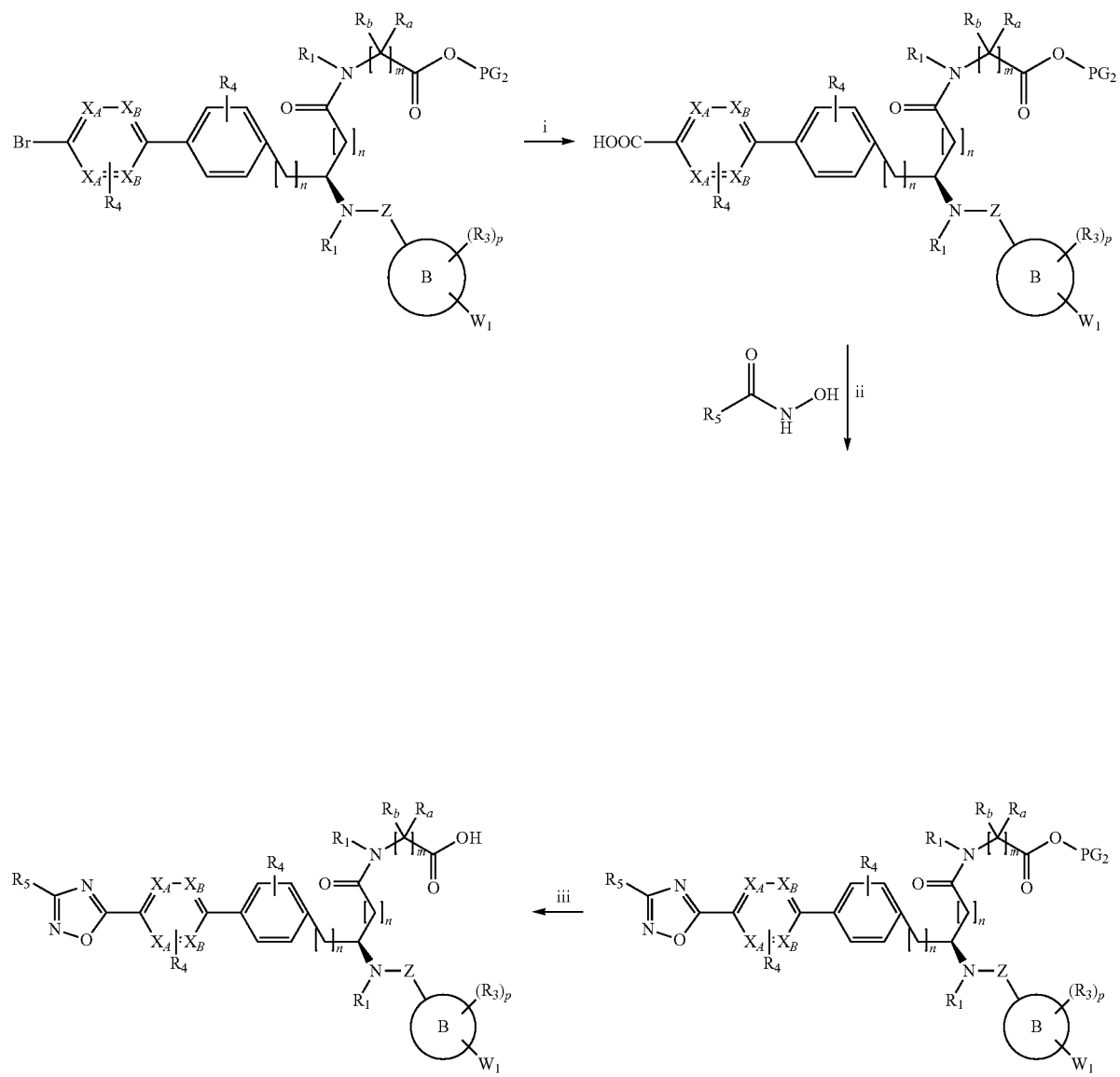

Reagents: $PG_1$ and $PG_2$ are protecting groups and $X_A$ and $X_B$ are $CR_4$ or N;
(i) Lithium formate, DIEA, $Ac_2O$, DMF, then, $PDCl_2$(dppf);
(ii) HOBt, EDC, DMF, EtOH;
(iii) Deprotection of $PG_2$, e.g., tert-butyl ester deprotection: DCM, TFA.

The other enantiomer can be prepared in a similar manner using Scheme 32.

Scheme 33:

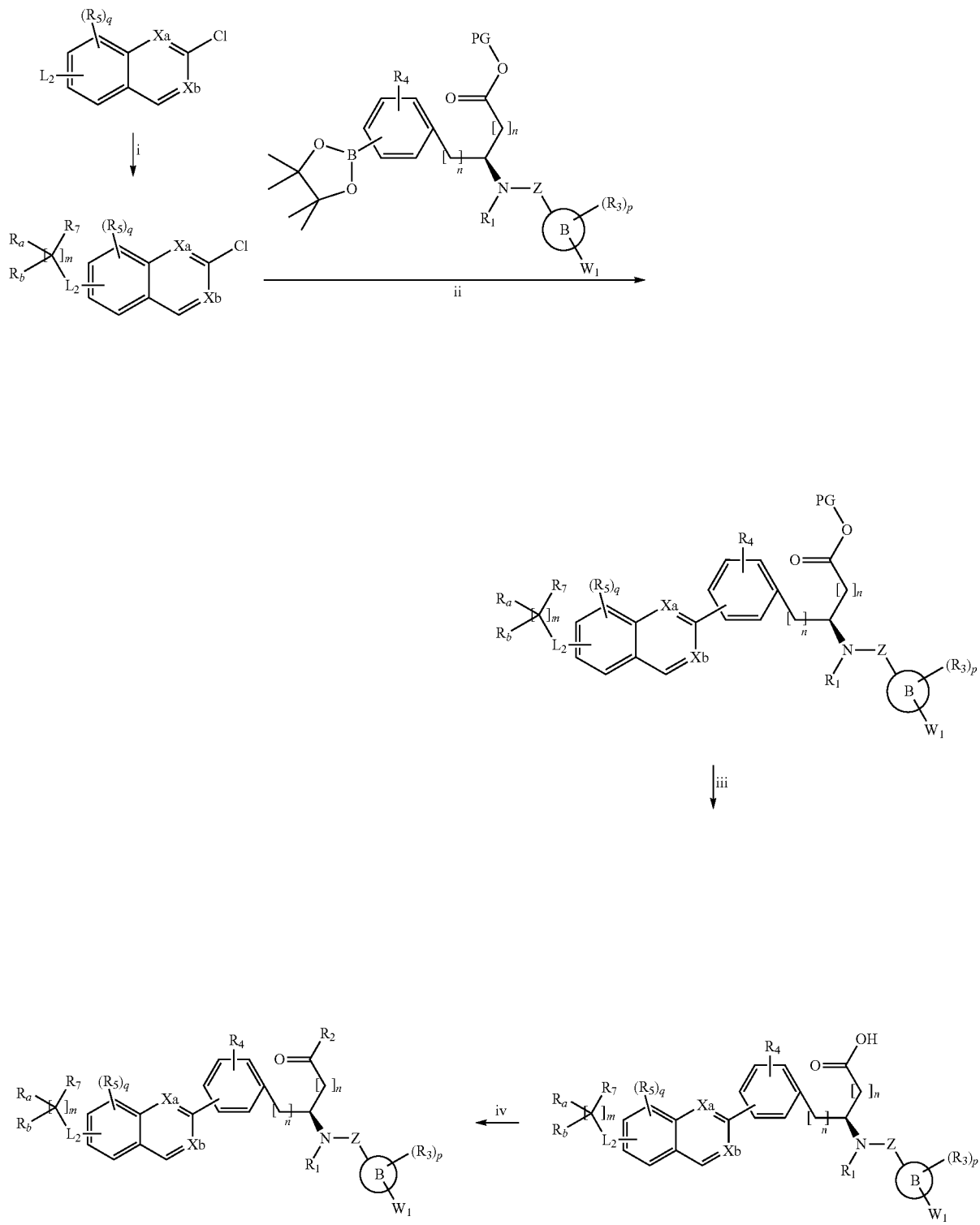

Reagents: PG is a protecting group and $X_A$ and $X_B$ are $CR_4$ or N; (i) Br—$(CR_aR_b)_m$—$R_7$, $K_2CO_3$, DMF; (ii) Pd(dppf)Cl$_2$, Na$_2$CO$_3$, THF, ACN, water; (iii) Deprotection of PG, e.g., tert-butyl ester deprotection: DCM, TFA; (iv) (a) where $R_2$ is NH—$(CR_aR_b)_m$—COOH: NH$_2$—$(CR_aR_b)_m$—COOPG, HATU, DMF then deprotection e.g., tert-butyl ester deprotection: DCM, TFA; (b) where $R_2$ is NR$_{41}$R$_{42}$: HNR$_{41}$R$_{42}$, HATU, DMF then deprotection e.g., tert-butyl ester deprotection: DCM, TFA.

The other enantiomer can be prepared in a similar manner using Scheme 33.

Scheme 34:

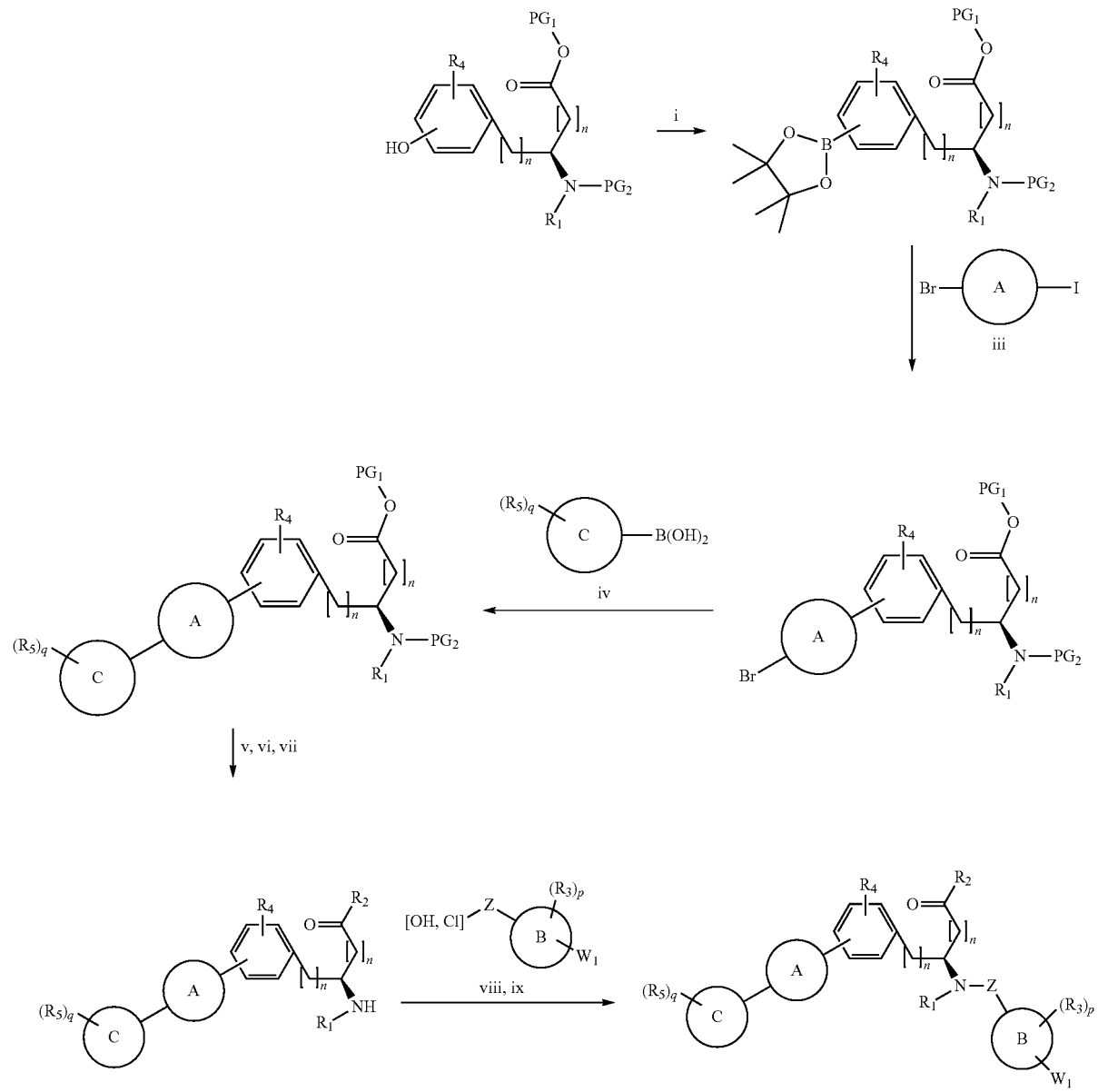

Reageants: PG$_1$, PG$_2$ and PG$_3$ are protecting groups;
(i) DIEA, 1,1,1-trifluoro-N-phenyl-N-((trifluoromethyl)sulfonyl)methanesulfonamide, DCM;
(ii) KOAc, bis-pinacolatoborane, PdCl$_2$(dppf);
(iii) Pd(dppf)Cl$_2$, Na$_2$CO$_3$, THF, ACN, water;
(iv) Pd(dppf)Cl$_2$, Na$_2$CO$_3$, THF, ACN, water;
(v) Deprotection of PG$_1$, e.g., tert-butyl ester deprotection: DCM, TFA;
(vi) (i) (a) where R$_2$ is NH—(CR$_a$R$_b$)$_m$—COOH: NH$_2$—(CR$_a$R$_b$)$_m$—COOPG, HATU, DMF then deprotection e.g., tert-butyl ester deprotection: DCM, TFA;
  (b) where R$_2$ is NH—SO$_2$—R$_8$: R$_8$SO$_2$NH$_2$, DCC, DMAP, DCM
  (c) where R$_2$ is NR$_{41}$R$_{42}$: HNR$_{41}$R$_{42}$, HATU, DMF then deprotection e.g., tert-butyl ester deprotection: DCM, TFA:
  (d) where R$_2$ is N(R$_1$)—(CR$_a$R$_b$)m—CO—N(R$_1$)—heterocyclyl: HN(R$_1$)—(CR$_a$R$_b$)m—CO—N(R$_1$)—heterocyclyl,
      HATU, DMF then deprotection e.g., tert-butyl ester deprotection: DCM, TFA;
  (e) R$_2$ is —N(R$_1$)—(CR$_a$R$_b$)$_m$—CO—N(R$_1$)(R$_7$): NH$_2$—(CR$_a$R$_b$)$_m$—COOPG$_3$,
      HATU, DMF then deprotection e.g., tert-butyl ester deprotection: DCM, TFA then HN(R$_1$)(R$_7$), HATU, DMAP, DCM
  (f) where R$_2$ is N(R$_1$)—heterocyclyl: HN(R$_1$)—heterocyclyl, HATU, DMF then deprotection e.g., tert-butyl ester deprotection: DCM, TFA.
(vii) Deprotection of PG$_2$, e.g. CBZ: Pd/C, H$_2$, EA;
(viii) If Z = CO then amide coupling with acid chloride: DIEA, DCM or amide coupling with acid: EDC, HOBt, DMF or HATU, DMF;
If Z = SO$_2$, then coupling with sulfonyl chloride: DIEA or NEt$_3$, DCM or DMF;
(ix) Deprotection of PG$_3$, e.g.,tert-butyl ester deprotection: DCM, TFA.

The other enantiomer can be prepared in a similar manner using Scheme 34.

Scheme 35:

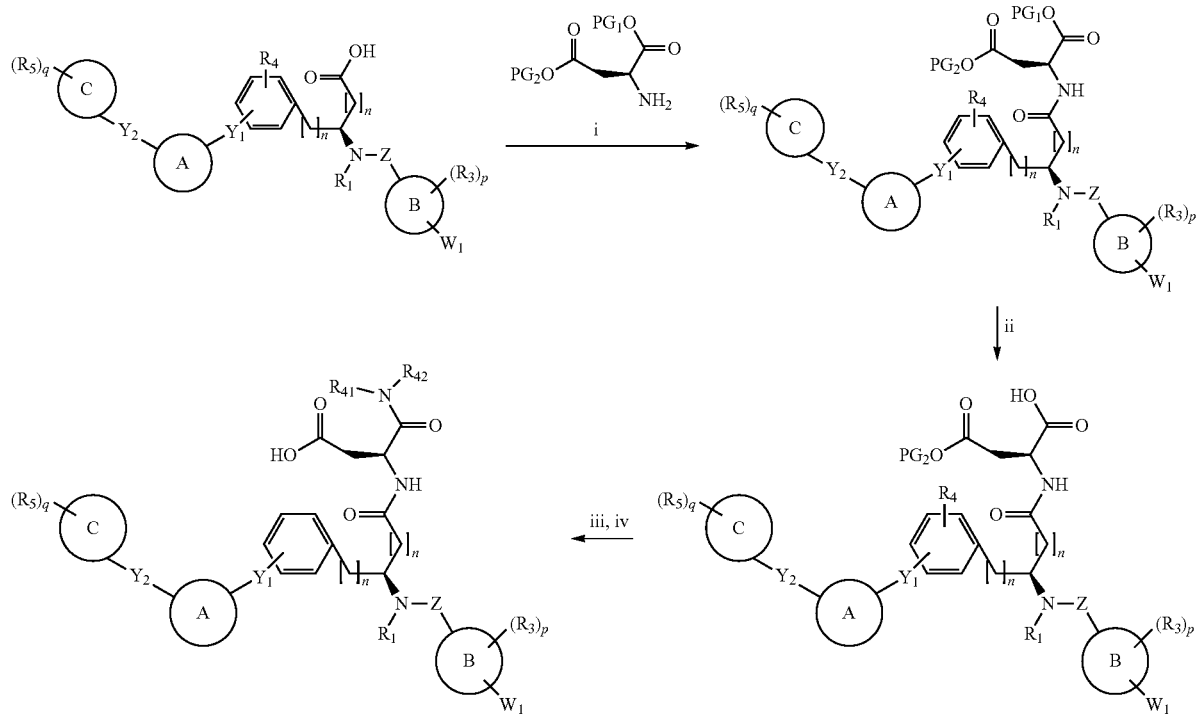

Reagents: PG$_1$ and PG$_2$ are protecting group; (i) HATU, DMF, DIEA; (ii) Deprotection of PG$_1$, e.g., tert-butyl ester deprotection: dioxane, HCl or DCM, TFA, (iii) HNR$_{41}$R$_{42}$, HATU, DMF; (iv) Deprotection of PG$_2$ e.g. benzyl ester deprotection: Pd/C, H$_2$, MeOH.

The other enantiomer and diastereomers can be prepared in a similar manner using Scheme 35.

Scheme 36:

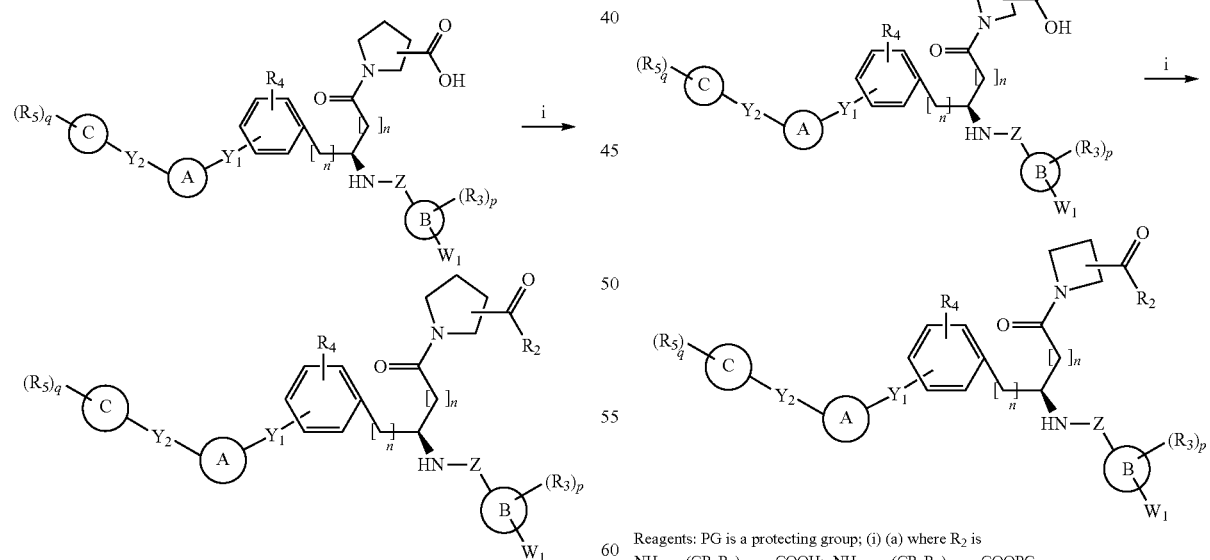

Reagents: PG is a protecting group; (i) (a) where R$_2$ is NH—(CR$_a$R$_b$)$_m$—COOH: NH$_2$—(CR$_a$R$_b$)$_m$—COOPG, HATU, DMF then deprotection e.g., tert-butyl ester deprotection: DCM, TFA; (b) where R$_2$ is NH$_2$-heterocyclyl, NH—SO$_2$—R$_8$: R$_8$SO$_2$NH$_2$, DCC or EDC, DMAP, DCM (c) where R$_2$ is NR$_{41}$R$_{42}$: HNR$_{41}$R$_{42}$, HATU, DMF then deprotection e.g., tert-butyl ester deprotection: DCM, TFA.

The other enantiomer and diastereoisomers can be prepared in a similar manner using Scheme 36.

Scheme 37:

Reagents: PG is a protecting group; (i) (a) where R$_2$ is NH—(CR$_a$R$_b$)$_m$—COOH: NH$_2$—(CR$_a$R$_b$)$_m$—COOPG, HATU, DMF then deprotection e.g., tert-butyl ester deprotection: DCM, TFA; (b) where R$_2$ is NH—SO$_2$—R$_8$: R$_8$SO$_2$NH$_2$, DCC, DMAP, DCM (c) where R$_2$ is NR$_{41}$R$_{42}$: HNR$_{41}$R$_{42}$, HATU, DMF then deprotection e.g., tert-butyl ester deprotection: DCM, TFA.

The other enantiomer and diastereoisomers can be prepared in a similar manner using Scheme 37.

Scheme 38:

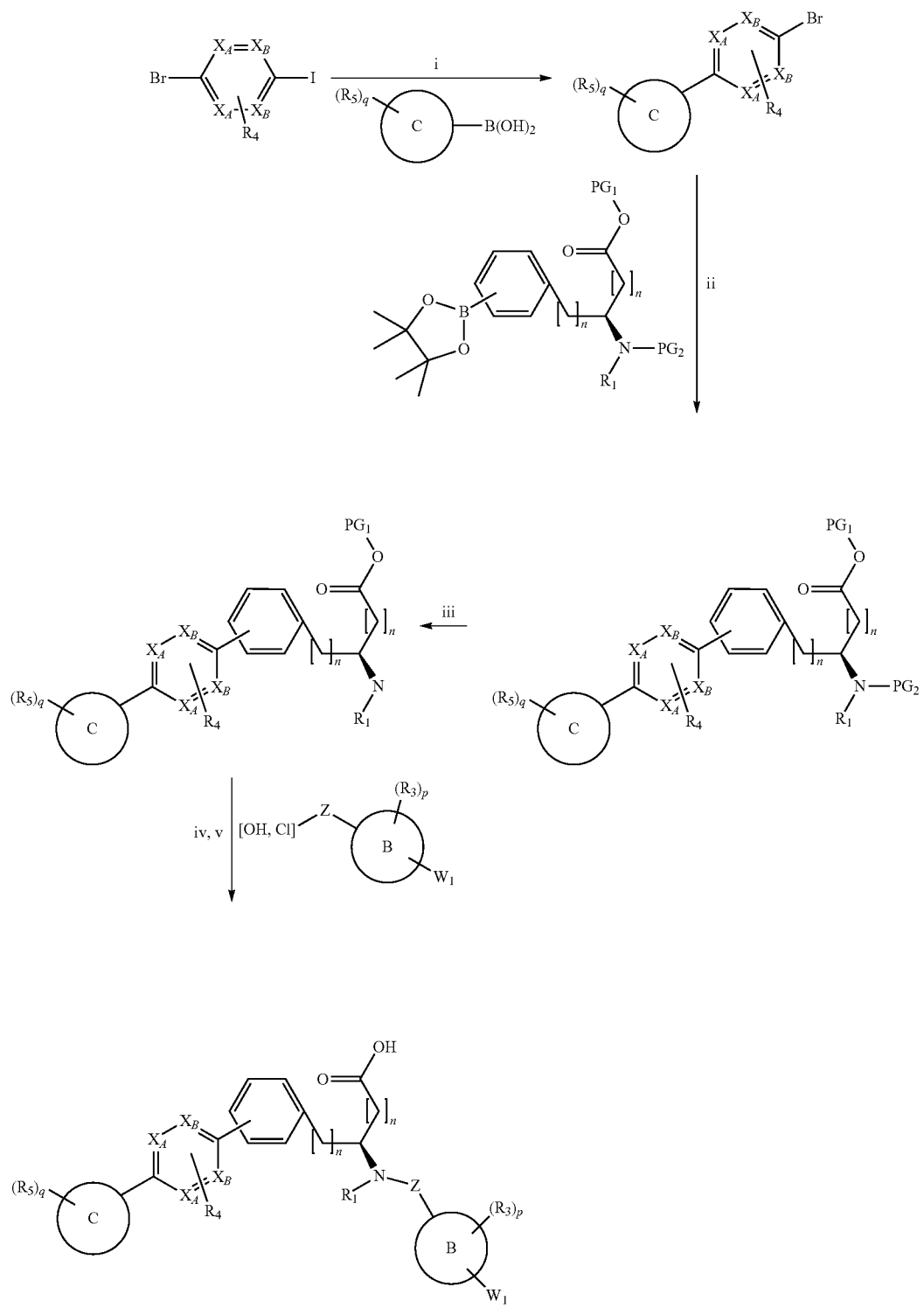

Reagents: PG$_1$ and PG$_2$ are protecting groups and X$_A$ and X$_B$ are CR$_4$ or N; (i) Pd(dppf)Cl$_2$, Na$_2$CO$_3$, THF, ACN, water; (ii) Pd(dppf)Cl$_2$, Na$_2$CO$_3$, THF, ACN, water; (iii) Deprotection of PG$_2$, e.g. CBZ: Pd/C, H$_2$, EA; (iv) If Z = CO then amide coupling with acid chloride: DIEA, DCM or amide coupling with acid: EDC, HOBt, DMF or HATU, DMF; If Z = SO$_2$, then coupling with sulfonyl chloride: DIEA or NEt$_3$, DCM or DMF; (v) Deprotection of PG$_1$, e.g., tert-butyl ester deprotection: DCM, TFA.

The other enantiomer can be prepared in a similar manner using Scheme 38.

Scheme 39:

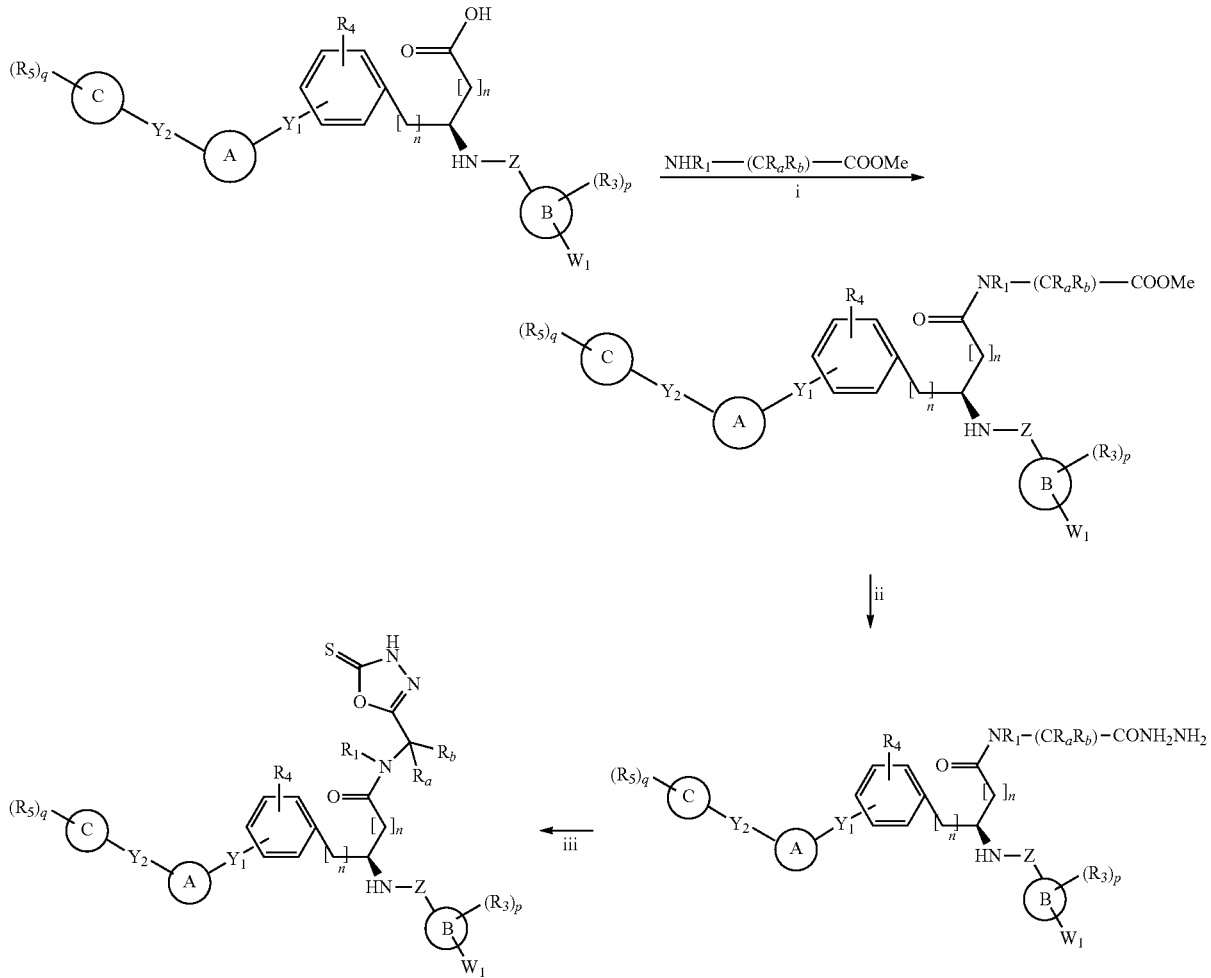

Reagents: (i) HATU, DMF; (ii) hydrazine hydrate, THF, EtOH; (iii) thiocarbonyldiimadazole, DIEA, THF.

The other enantiomer and diastereoisomers can be prepared in a similar manner using Scheme 39.

Examples

The invention is further illustrated by the following examples. The examples below are non-limiting are merely representative of various aspects of the invention.
General Methods
NMR Spectra $^{1}$H NMR (400 MHz) and $^{13}$C NMR (100 MHz) were obtained in solution of deuteriochloroform (CDCl$_3$) or dimethyl sulfoxide (d$_6$-DMSO). NMR spectra were processed using MestReNova 6.0.3-5604.
LCMS Data Mass spectra (LCMS) were obtained using one of 6 systems. System 1a: Agilent 1100/6110 HPLC system equipped with a Thompson ODS-A, 100 A, 5μ (50×4.6 mm) column using water with 0.1% formic acid as the mobile phase A, acetonitrile with 0.1% formic acid as the mobile phase B, water with 5 mM ammonium acetate as the mobile phase C, and acetonitrile with 5 mM ammonium acetate as the mobile phase D with a flow rate of 1 mL/min. Method 1: 20-100% mobile phase B (80-0% A) over 2.5 min then held at 100% B for 2.5 min. Method 2: 5% mobile phase B (95% A) for 1 min, 5-95% B over 9 min, then held at 95% B for 5 min. Method 3: 20-100% mobile phase B (80-0% A) over 2.5 min then held at 100% B for 4.5 min. Method 12: 5% D (95% C) for 1 min. then 5-95% D over 9 min. and held at 95% D for 5 min. System 1b: Agilent 1100/6110 HPLC system equipped with a Agilent Poroshell 120 EC-C8, 2.7μ (50×3 mm) column using water with 5 mM ammonium acetate as the mobile phase C, and acetonitrile with 5 mM ammonium acetate as the mobile phase D with a flow rate of 1 mL/min. Method 13: 5% D (95% C) to 95% D over 12 min. then held at 95% D for 2.8 min. and to 5% D over 0.2 min. System 1c: Agilent 1100/6110 HPLC system equipped with a Agilent Poroshell 120 EC-C18, 2.7μ (50×3 mm) column using water with 5 mM ammonium acetate as the mobile phase C, and acetonitrile with 5 mM ammonium acetate as the mobile phase D with a flow rate of 1 mL/min. Method 14: 5% D (95% C) to 95% D over 12 min. then held at 95% D for 2.8 min. and then to 5% D over 0.2 min. Method 15: 20% D (80% C) to 95% D over 3 min. and hold at 95% D 1.8 min. then to 20% D over 0.2 min. Method 16: 20% D (80% C) to 95% D over 3.0 min. and hold at 95% D for 3.8 min. then 20% D over 0.2 min. System 2: Agilent 1200 LCMS equipped with an Agilent Zorbax Extend RRHT 1.8 μm (4.6×30 mm) column using water with 0.1% formic acid as mobile phase A and acetonitrile with 0.1% formic acid as mobile phase B. Method 4: 5-95% mobile phase B over 3.0 min with a flow rate of 2.5 mL/min, then held at 95% for 0.5 min with a flow rate of 4.5 mL/min. Method 5: 5-95% mobile phase B over 14 min with a flow rate of 2.5 mL/min, then held at 95% for 0.5 min with a flow rate of 4.5 mL/min. System 3: Waters Fractionlynx LCMS system equipped with an Agilent Zorbax Extend RRHT 1.8 μm, (4.6×30 mm) column using water with 0.1% formic acid as mobile phase A and acetonitrile with 0.1% formic acid as mobile phase B. Method 6: 5-95% mobile phase B over 3.0 min with a flow rate of 2.5 mL/min, then held at 95% for 0.5 min with a flow rate of 4.5 mL/min. Method 7: 5-95% mobile phase B over 14 min with a flow rate of 2.5 mL/min, then held at 95% for 0.5 min with a flow rate of 4.5 mL/min. System 4: Agilent 1260 LCMS equipped with an Agilent Zorbax Extend RRHT 1.8 μm (4.6×30 mm) column using water with 0.1% formic acid as mobile phase A and acetonitrile with 0.1% formic acid as mobile phase B. Method 8: 5-95% mobile phase B over 3.0 min with a flow rate of 2.5 mL/min, then held at 95% for 0.5 min with a flow rate of 4.5 mL/min. Method 9: 5-95% mobile phase B over 14 min with a flow rate of 2.5 mL/min, then held at 95% for 0.5 min with a flow rate of 4.5 mL/min. System 5: Agilent 1260 LCMS equipped with a Waters Xselect CSH C18 3.5 μm (4.6×50 mm) column using water with 0.1% formic acid as mobile phase A and acetonitrile with 0.1% formic acid as mobile phase B. Method 10: The gradient was 5-95% mobile phase B over 13.0 min with a flow rate of 2.5 mL/min, then held at 95% for 1.0 min with a flow rate of 4.5 mL/min. Method 11: The gradient was 5-95% mobile phase B over 3.0 min with a flow rate of 2.5 mL/min, then held at 95% for 0.6 min with an flow rate of 4.5 mL/min. System 6: Waters Acquity UPLC system equipped with a Acquity UPLC BEH C18, 1.7 μm (2.1×50 mm) or Phenomenex Kinetex C18, 1.7 μm (2.1×50 mm) column using water with 10 mM ammonium formate as mobile phase A, acetonitrile as mobile phase B with a flow rate of 0.5 mL/min. Method 17: 10% mobile phase B (90% A) for 0.5 min, 10-95% B over 3 min, then held at 95% B for 1.1 min, 95-10% B over 0.1 min then held for 0.3 min and the total run time is 5 min. Method 18: 20% mobile phase B (80% A) for 0.5 min, 20-95% B over 3 min, then held at 95% B for 1.1 min, 95-20% B over 0.1 min, then held for 0.3 min and the total run time is 5 min. Method 19: 30% mobile phase B (70% A) for 0.5 min, 30-95% B over 2.2 min, then held at 95% B for 1.9 min, 95-30% B over 0.1 min, then held for 0.3 min and the total run time is 5 min. Method 20: 40% mobile phase B (60% A) for 0.5 min, 40-95% B over 1.9 min, then held at 95% B for 2.2 min, 95-40% B over 0.1 min, then held for 0.3 min and the total run time is 5 min. Method 21: 20% mobile phase B (80% A) for 0.5 min, 20-95% B over 2.7 min, then held at 95% B for 1.4 min, 95-20% B over 0.1 min, then held for 0.3 min and the total run time is 5 min. Method 22: 40% mobile phase B (60% A) for 0.5 min, 40-95% B over 1.6 min, then held at 95% B for 2.5 min, 95-40% B over 0.1 min, then held for 0.3 min and the total run time is 5 min.

Hydrogenations

Hydrogenation reactions were performed using a Thales Nanotechnology H-Cube reactor equipped with the specified CatCart or using standard laboratory techniques.

Reaction Conditions and Abbreviations

Pyridine, dichloromethane (DCM), tetrahydrofuran (THF), and toluene used in the procedures were from Aldrich Sure-Seal bottles or Acros AcroSeal dry solvent and kept under nitrogen ($N_2$). All reactions were stirred magnetically and temperatures are external reaction temperatures. The following abbreviations are used: ethyl acetate (EA), 1-methy-2-pyrrolidinone (NMP), triethylamine (TEA), N-hydroxybenzotriazole (HOBt), 1-ethyl-3-(3-dimethylaminopropyl) carbodiimide hydrochloride (EDC), N,N-dimethylformamide (DMF), dimethyl acetamide (DMA), Di-tert-butyl dicarbonate ($Boc_2O$), N,N-Diisopropylethylamine (DIEA), acetic acid (AcOH), hydrochloric acid (HCl), O-(7-azabenzotriazol-1-yl-N,N,N',N'-tetramethyluronium hexafluorophosphate (HATU), 4-dimethylaminopyridine (DMAP), tert-butanol (t-BuOH), sodium hydride (NaH), sodium triacetoxyborohydride (Na(OAc)$_3$BH), ethanol (EtOH), methanol (MeOH), acetonitrile (ACN).

Purifications

Chromatographies were carried out using a Combiflash Rf flash purification system (Teledyne Isco) equipped with Redisep (Teledyne Isco), Telos (Kinesis) or Grace Resolv (Grace Davison Discovery Sciences) silica gel ($SiO_2$) columns. Preparative HPLC purifications were performed using one or two systems. System 1: Varian ProStar/PrepStar system equipped with a Waters SunFire Prep C18 OBD, 5 μm (19×150 mm) column using water containing 0.05% trifluoroacetic acid as mobile phase A, and acetonitrile with 0.05% trifluoroacetic acid as mobile phase B. The gradient was 40-95% mobile phase B over 10 min, held at 95% for 5-10 min, and then return to 40% over 2 min with flow rate of 18 mL/min. Fractions were collected using a Varian Prostar fraction collector by UV detection at 254 nm and were evaporated using a Savant SpeedVac Plus vacuum pump or a Genevac EZ-2. System 2: Waters Fractionlynx system equipped with an Agilent Prep-C18, 5 μm (21.2×50 mm) column using water containing 0.1% formic acid as mobile phase A, and acetonitrile with 0.1% formic acid as mobile phase B. The gradient was 45-95% mobile phase B over 7.5 min, held at 95% for 1 min, and then returned to 45% over 1.5 min with a flow rate of 28 mL/min. Fractions were collected by UV detection at 254 nm or by mass and evaporated using a Genevac EZ-2.

Chiral Methods

Chiral Method:

Enantiomeric excess was determined by integration of peaks that were separated on a Diacel Chiralpak IA, 4.6×250 mm column, 5 μm particle size. The solvents used were "Solvent A": 4:1 (hexanes with 0.2% TFA): DCM, and "Solvent B": EtOH. The flow rate was held at 1.0 mL/min with the following gradient: Increase Solvent B from 2-10% over 30 min, hold Solvent B at 10% for 15 min.

Chiral Method 2:

Enantiomeric excess was determined by integration of peaks that were separated on a Daicel Chiralpak IC, 4.6×250 mm column, 5 μm particle size running an isocratic mixture of 76% (0.2% TFA in iso-hexanes), 19% DCM and 5% EtOH at a flow rate of 1.5 mL/min.

Chiral Preparative HPLC:

This was carried out using a Gilson preparative HPLC system equipped with a Daicel Chiralpak IC column, 20×250 mm column, 5 μm particle size running an isocratic mixture of mobile phase A (60% (0.2% TFA in iso-hexanes) and 40% DCM) at 15 mL/min and at-column-dilution with mobile phase B (EtOH) at 1.5 mL/min. Fractions were collected by UV detection at 254 nm and evaporated using a Genevac EZ-2.

Experimental Procedures

General Procedures

General Procedure 1: Preparation of Nitriles.

A stirred a solution of bromide or triflate (1 eq), zinc cyanide (2 eq) and tetrakis (triphenylphosphine) palladium (1-5 mol %) in dry NMP (0.5-1 M) was degassed with $N_2$. The reaction was heated to 100° C. for 18 h while stirring under $N_2$. The reaction mixture was cooled and poured into water and DCM. The solid material was removed by filtration and the filtrate was extracted with water. The organic layer was dried over $MgSO_4$ and concentrated. The crude product was purified by chromatography.

General Procedure 2: Preparation of Amidoximes.

To a stirring solution of nitrile (1 eq) in EtOH was added hydroxylamine (50% solution in $H_2O$, 5 eq) and TEA (1.1 eq). The mixture was heated for 2-12 h at 80-85° C. then concentrated. The resulting solid was dissolved in EA, washed with water, then dried with $Na_2SO_4$, concentrated and used without further purification. Alternatively, to a stirring solution of nitrile (1 eq) and TEA (2-3 eq) in DMF or EtOH was added hydroxylamine hydrochloride (2-3 eq). The mixture was stirred at room temperature up to 80° C. for up to 24 h then concentrated. The resulting solid was dissolved in EA or DCM, washed with water or brine, then dried with $Na_2SO_4$, concentrated, and used without further purification.

General Procedure 3: Preparation of Amides Via Acid Chlorides.

To a solution of amine (1 eq) and base (either DIEA or TEA) (2-3 eq) in DCM (0.06-0.30 M) was treated with the appropriate acid chloride (1.0-1.5 eq). The reaction mixture was stirred until the reaction was complete. The reaction was diluted with DCM and washed with saturated aqueous $NaHCO_3$. The organic layer was dried over $MgSO_4$ and concentrated. The product was purified by chromatography. Alternatively, the crude reaction mixture can be carried on to the next step without further purification.

General Procedure 4: Hydrolysis of Esters to Acids.

To a stirring solution of ester (1 eq) in THF or dioxane and water, was added NaOH or LiOH (1-3 eq). The reaction mixture was stirred at up to 60° C. for up to 18 h. The reaction mixture was neutralized with AcOH or HCl and either diluted with water or concentrated. If the reaction mixture was diluted with water, then HCl was added to acidify the reaction mixture to a pH of approximately 2. The resulting precipitate was isolated by filtration to yield product which can be purified by chromatography, preparative HPLC, or used without purification. If the reaction mixture was concentrated, the crude material was diluted with DCM or EA and washed with brine. The organic layer was concentrated and purified by chromatography or preparative HPLC to give final product. Alternatively, the crude material can be carried forward without purification.

General Procedure 5: Preparation of Oxadiazoles Via Acids or Acid Chlorides. Oxadiazoles Via Acids:

To a solution of acid (1 eq) in DMF was added HOBt (2 eq) and EDC (2 eq). After stirring for 2 h, amidoxime (2 eq) was added and the mixture was stirred at room temperature for up to 12 h. The reaction mixture was then heated to 100° C. for up to 12 h. Alternatively, after stirring at room temperature, the reaction mixture was diluted with DCM, washed with $NaHCO_3$, then dried with $Na_2SO_4$ and concentrated. The resulting residue was dissolved in EtOH and heated in a microwave for 35 min at 110° C. The solvent was removed and the final product was purified by preparative HPLC.

Oxadiazoles via Acid Chlorides: To synthesize oxadiazoles via acid chlorides, dioxanes and DIEA (1.5 eq) were added to a stirred solution of amidoxime (1 eq) followed by an acid chloride (1.1 eq). The reaction mixture was stirred at room temperature for 30 min then at 120° C. for up to 6 h. The reaction mixture was allowed to cool to room temperature, diluted with EA and washed with brine. The organics were concentrated and the residue purified by chromatography.

General Procedure 6: Removal of Tert-Butyl Carbamate.

A solution of the tert-butyl carbamate (1 eq) in DCM (0.06 M) was treated with TFA (0.16-0.33 M) or HCl in ether (0.16-0.33 M). The reaction mixture was stirred at either room temperature or 30° C. until complete. The solvent was removed and the product was purified by chromatography or preparative HPLC.

General Procedure 7: Preparation of Amides Via Peptide Coupling.

A solution of amine (1.0 eq) and base (DIEA, TEA or NMM) (0-3.0 eq) in DCM or DMF (0.08-0.10 M) was treated with the appropriate carboxylic acid (1.0-1.5 eq). To this mixture was added the coupling reagent. The coupling reagent could be HATU (1.05-2.5 eq) optionally with DMAP (0.01-1 eq), EDC (1.5 eq) with HOBt (1.5 eq) or DMAP (0.01-1 eq), DCC (1.1 eq) with HOBt (1.1 eq) or DCC (1.5 eq) with DMAP (2.0 eq). The reaction mixture was stirred until the reaction was complete. The reaction was diluted with EA and washed with saturated aqueous $NaHCO_3$. The organic layer was dried over $MgSO_4$ and concentrated. The product was purified by chromatography or alternatively can be carried on to the next step without further purification.

General Procedure 8: Deprotection of Esters to Acids, Deprotection of Boc-Amines, and/or Protodesilylation of Protected Alcohols A solution of the tert-butyl ester or Boc-amine (1.00 eq) in DCM (0.06 M) was treated with TFA (0.16-0.33 M) or 1-4N HCl in ether or dioxane (10.0-20.0 eq). The reaction mixture was stirred at either room temperature or 30° C. until complete. The solvent was removed and the product was purified by chromatography or preparative HPLC. This procedure was also applicable for protodesilylation of tert-butyl, dimethylsilyl protected alcohols.

A solution of the methyl ester (1.00 eq) in dioxane (0.04-0.08 M) was treated with 1-6N aqueous HCl (10-100 eq). The reaction mixture was stirred at either room temperature or 30° C. until complete. The solvent was removed and the product was purified by chromatography or preparative HPLC.

General Procedure 9: Formation of Triflate.

A solution of the phenol (1.0 eq) in DCM (0.25 M) was treated with 1,1-trifluoro-N-phenyl-N-((trifluoromethyl)sulfonyl)methanesulfonamide (1.1 eq). The reaction mixture was stirred at room temperature until complete. The reaction was stirred with water and saturated aqueous $NaHCO_3$. The organic layers was dried and concentrated. The material was purified by chromatography or alternatively used without purification.

General Procedure 10: Palladium-Catalyzed Coupling Reactions.

A solution of boronic acid or boronate ester (1.0-1.3 eq), halide (1.0-1.3 eq), sodium bicarbonate or sodium carbonate decahydrate (2.0-2.5 eq), and dichloro[1,1'-bis(di-tert-butylphosphino)ferrocene]palladium(II) or Pd(dppf)$Cl_2$ were combined in THF, acetonitrile, or dioxane (0.1-0.2 M) and water (0.25-0.50 M). The reaction was heated at 80 to 100° C. until complete. The reaction was diluted with EA and washed with saturated aqueous $NaHCO_3$. The organic layer was dried over $MgSO_4$ and concentrated. The product can be purified by chromatography, preparative HPLC, or carried on to the next step without further purification.

General Procedure 11: Palladium-Catalyzed Aryl Amidation.

A solution of aryl bromide or triflate (1.00 eq), sodium tert-butoxide or cesium carbonate (1-2 eq) and amine (1.0-1.5 eq) in dioxane or THF (0.05M) was degassed using $N_2$ bubbling for 10 min. $Pd_2(dba)_3$ (0.10 eq) and 2-dicyclohexylphosphino-2'-(N,N-dimethylamino)biphenyl (0.15 eq) are added and the reaction mixture was heated for 45-60 min at 100-120° C. in a microwave reactor or up to 80° C. with conventional heating for up to 18 h. The reaction was diluted with EA and washed with saturated aqueous $NaHCO_3$. The organic layer was dried over $Na_2SO_4$ and concentrated. The product can be purified by chromatography, preparative HPLC, or carried on to the next step without further purification.

General Procedure 12: Alklation of Phenols, Imidazoles, Lactams and Amines.

To a solution of a phenolic intermediate in DMF, acetone or ACN (0.1 M) were added the appropriate bromoalkane (1.5 eq) or tosylate and either $CsCO_3$ (1.5-2.0 eq) or $K_2CO_3$ (1.5-2.0 eq). The reaction mixture was heated at 40-70° C. for up to 18 h, then diluted with DCM and washed with $H_2O$. The organic layer was dried over $Na_2SO_4$ and concentrated. The product can be purified by chromatography, preparative HPLC, or carried on to the next step without further purification.

General Procedure 13: Sulfonate or Sulfonamide Formation.

To a solution of alcohol or amine in DCM (0.02 M) was added the sulfonyl chloride (2 eq) and triethylamine (3 eq). The reaction was stirred at room temperature until complete. The reaction was diluted with DCM and washed with saturated aqueous $NaHCO_3$. The organic layer was dried over $MgSO_4$ and concentrated. The product can be purified by chromatography, preparative HPLC, or carried on to the next step without further purification.

General Procedure 14: Reduction of Aryl Nitro to an Aryl Amine.

To a stirring solution of aryl nitro (1 eq) in THF purged with $N_2$ was added palladium on carbon. The reaction mixture was subjected to an $H_2$ atmosphere for up to 4 h. The reaction mixture can be filtered over a pad of celite and solvent concentrated. The crude material was carried forward without further purification.

General Procedure 15: Preparation of a Secondary or Tertiary Amine Via Reductive Amination.

To a stirring solution of aldehyde or ketone (0.9-1.0 eq) in DCM or 1,2-dichloroethane or THF was added an amine (0.9-1.1 eq). After stirring at room temperature for up to 2 h, one drop of acetic acid (optional) was added followed by sodium triacetoxyborohydride (1.5-2.0 eq) and the reaction mixture was stirred overnight. In some cases it is necessary to filter the reaction mixture, redissolve and add additional reducing agent to drive the reaction to completion. The crude reaction mixture was quenched with $NaHCO_3$ and stirred for 5 min. The aqueous layer was extracted with DCM and the organic layer was dried over $MgSO_4$ and concentrated. The final product was isolated by chromatography.

General Procedure 16: Preparation of 2-Iodopyrimidines

To a stirring solution of a 2-chloro pyrimidine (1 eq) in 57% aqueous hydrogen iodide (1 mL) was added sodium iodide (2 eq). The reaction mixture was stirred at ambient temperature until the starting material was consumed. The reaction mixture was quenched with $NaHCO_3$ (5 mL) then extracted with EA (3×5 mL). The combined organic layer was washed with brine (10 mL), dried over $MgSO_4$ and concentrated. The crude product was used in the subsequent step without purification.

General Procedure 17. Preparation of 2-Iodopyridines

To a stirring solution of a 2-chloropyridine (1 eq) in acetonitrile (2 mL) was added sodium iodide (6 eq). The reaction mixture was heated to 40° C. and acetyl chloride (0.6 eq) was added. The reaction mixture was stirred until the staring material was consumed. The reaction was quenched with $NaHCO_3$ (5 mL) and extracted with EA (3×5 mL). The combined organic layer was washed with brine (10 mL), dried over $MgSO_4$ and concentrated. The crude product was used in the subsequent step without purification.

General Procedure 18: Deprotection of Cbz to Amine or Deprotection of Benzyl Esters to Acids.

Conventional Hydrogenations: To a stirring solution of Cbz-protected amine or benzyl protected ester (1.0 eq) in EA, THF, EtOH, or MeOH (0.01-0.05 M) was added Pd/C and the reaction was stirred under hydrogen until complete. The catalyst was filtered and the solvent was removed. The product was purified by chromatography or alternatively can be carried onto the next step without further purification.

Hydrogenation using H-cube: A solution of Cbz-protected amine or benzyl protected ester (1.0 eq) in dioxane or THF (0.01-0.03 M) was passed over a 10% Pd/C CatCart in a Thales Nanotechnology H-Cube reactor at 1 mL/min. The solvent was evaporated and the product was carried to the next step without further purification.

General Procedure 19: Preparation of Aryl-Acids from Aryl Bromides

To a stirring solution of oven-dried lithium formate (3 eq) and DIEA (2 eq) under $N_2$ in DMF (0.1 M) was added acetic anhydride (2 eq). After 30 minutes, the mixture was degassed by $N_2$ bubbling for 15 min and then added to a similarly degassed solution of aryl bromide (1 eq) and $PdCl_2(dppf)$ (0.1 eq) in DMF (0.1 M). The resulting mixture was heated in a microwave reactor for 1 hr at 120° C. After cooling, the mixture was diluted with DCM and washed with water. The organic layer was dried ($Na_2SO_4$) and concentrated. The resulting crude material was purified by chromatography.

General Procedure 20: Alkylation of Phenols Via Mitsunobu Condensation of Alcohols To a stirring solution of phenol (1 eq) in THF was added an alcohol (1.1 eq), triphenyl phosphine (1.1 eq) and diisopropyl azodicarboxylate (1.1 eq). The reaction mixture was stirred overnight, concentrated and purified by preparative HPLC.

General Procedure 21: Palladium Catalyzed Coupling (Sonogashira Coupling)

To a Suspension of Alkyne (1 Eq), Iodide (1.2 Eq), and Diethylamine (5 Eq) in anhydrous diethyl ether (0.2 M) was added CuI (0.1 eq) followed by $Pd(PPh_3)_2Cl_2$ (0.05 eq). The reaction mixture was stirred under $N_2$ at room temperature for 24 h. The reaction mixture was diluted with ethyl acetate, washed with saturated aqueous ammonium chloride then brine, and dried over $MgSO_4$. The crude product was purified by silica gel column chromatography.

General Procedure 22: Methyl or Ethyl Ester Formation

To a stirring suspension of amino acid (1 eq) in MeOH or EtOH (0.5 M) was added TMS-Cl (4-10 eq) and the mixture stirred at ambient temperature (RT-reflux) for 4-24 h. The reaction mixture was cooled and concentrated/purified to yield desired ester.

General Procedure 23: BOC Protection.

To a stirring suspension of amino ester (1 eq) in DCM (0.25 M) at 0° C. was added DIEA (1.1 eq) and di-tert-butyl dicarbonate (1.2 eq). The reaction was stirred for between 4-24 h before being washed with water and dried over MgSO$_4$. The final product was isolated by chromatography.
General Procedure 24: Swern Oxidation To a stirring solution of oxalyl chloride (1.6 eq) in DCM (0.17 M) at −78° C. was added DMSO (3.2 eq) and the reaction stirred for 10 mins. A solution of alcohol (1 eq) in DCM was then added by cannula and the reaction stirred at −78° C. for 2 h before the addition of DIEA (5 eq). The solution was warmed to 0° C., stirred for an additional 60 minutes then washed with saturated ammonium chloride solution. The organic layer was dried over MgSO$_4$ and concentrated. The crude product was purified by column chromatography or used directly
General Procedure 25: Sodium Borohydride Reduction To a stirring solution of ketone (1 eq) in MeOH (0.17 M) at −78° C. was added NaBH$_4$ (0.7 eq). The reaction was stirred for 30 min before the addition of saturated ammonium chloride solution and warming to room temperature. MeOH was removed by reduced pressure distillation and the aqueous extracted with DCM. The combined organic extracts were dried over MgSO$_4$ and concentrated. The final product was isolated by chromatography.
General Procedure 26: t-Butyl Ester Formation To a stirring suspension of acid (1 eq) in DME (0.5 mL) at −10° C. was added concentrated sulfuric acid (6 eq) followed by 2-methylprop-1-ene (100 eq). The mixture was sealed in a pressure vessel and stirred at 0° C. for 18 h. The reaction was then cooled to −10° C. and the vessel opened. The reaction was warmed to RT over 30 minutes over which time all the isobutylene evaporated. The reaction was diluted with EA and saturated sodium bicarbonate was added to pH 8 with vigorous stirring. The phases were separated and the aqueous re-extracted with EA. The combined organic extracts were dried over MgSO$_4$ and concentrated. The final product was isolated by chromatography.
General Procedure 27: Boronic Acid Synthesis.

To a stirring solution of bromide (1 eq) in THF (0.14 M) at −78° C. was added butyllithium (1.5 eq) and the solution stirred for 20 mins. Trimethyl borate (1.1 eq) was added and the reaction warmed to RT. The mixture was quenched with water and extracted with ethyl acetate. The combined organics were washed successively with 1 N HCl and saturated brine (50 ml), dried over MgSO$_4$ and concentrated. The final product was isolated by chromatography.
General Procedure 28. Hydrazide Formation To a stirring solution of methy ester (1 eq) in 1:1 THF: EtOH (0.05 M) was added hydrazine hydrate (10 eq) and the solution stirred for 16 h. The product was precipitated with water and isolated by filtration.
General Procedure 29: Oxadiazole Thione Formation To a stirring solution of hydrazide (1 eq) and DIEA in THF (0.027 M) was added thiocarbonyldiimidazole (1.2 eq) and the solution stirred for 2 h. The mixture was warmed to 45° C. for a further 1 h then quenched with aqueous AcOH and extracted with DCM. The organics were dried through a hydrophobic frit and concentrated. The final product was isolated by chromatography.
General Procedure 30: Amino Alcohol Synthesis.

To a stirring solution of diisopropylamine (1.15 eq) in THF (0.34 M) at 0° C. was added butyllithium (1.1 eq of a 2.4 M solution in hexanes). After 30 mins, the mixture was cooled to −78° C. and treated with tert-butyl 2-((diphenylmethylene)amino)acetate (1 eq). After 30 mins, chlorotrimethylsilane (3 eq) was added and the mixture allowed to warm to room temperature. The resulting solution was added to a stirring solution of aldehyde (1 eq) and zinc chloride (0.05 eq of a 0.5 M solution in diethyl ether) in THF (0.36 M). After 16 h, the mixture was quenched with 10% aqueous citric acid and stirred for a further 16 h. The product was isolated by direct strong-cation-exchange ion-exchange chromatography of the reaction mixture and used without further purification.

Synthesis of Representative Compounds 4-(heptyloxy)benzonitrile

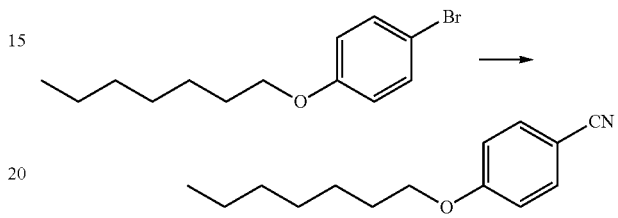

Prepared using General Procedure 1: A stirred a solution of 1-bromo-4-(heptyloxy)benzene (2.0 g, 7.37 mmol), zinc cyanide (1.73 g, 14.74 mmol) and tetrakis (triphenylphosphine) palladium (76.12 mg, 0.07 mol) in dry NMP (20 mL) was degassed with N$_2$. The reaction was heated to 100° C. for 18 h while stirring under nitrogen. The reaction mixture was cooled and poured into water (100 mL) and DCM (20 mL). The solid material was removed by filtration and the filtrate was extracted with water (3×20 mL). The organic layer was dried over MgSO$_4$ and concentrated. The crude product was purified by chromatography (EA/hexanes) to afford 1.15 g (73%) of 4-(heptyloxy)benzonitrile as a light yellow solid. LCMS-ESI (m/z) calculated for C$_{14}$H$_{19}$NO: 217.1. found 218.1 [M+H]$^+$, t$_R$=11.14 min (Method 2). $^1$H NMR (400 MHz, CDCl$_3$) δ 7.64-7.50 (m, 2H), 7.05-6.83 (m, 2H), 3.99 (t, J=6.5 Hz, 2H), 1.89-1.69 (m, 2H), 1.58-1.12 (m, 8H), 0.90 (dd, J=9.1, 4.5 Hz, 3H). $^{13}$C NMR (101 MHz CDCl$_3$) δ 162.47, 133.91, 132.78, 132.12, 129.13, 119.31, 115.18, 103.58, 68.41, 31.73, 28.98, 25.89, 22.58, 14.07.

(Z)-4-(heptyloxy)-N'-hydroxybenzimidamide

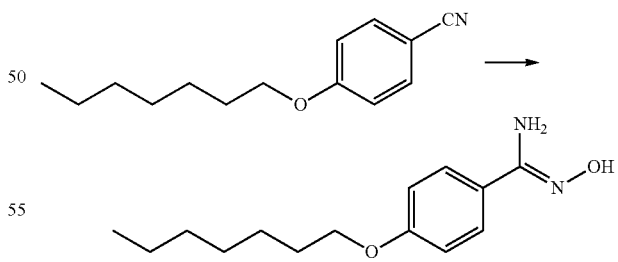

Prepared using General Procedure 2: To a stirring solution of 4-(heptyloxy)benzonitrile (1.0 g, 4.6 mmol) in EtOH (15 mL) were added hydroxylamine hydrochloride (0.96 g, 13.8 mmol) and TEA (2.22 g, 23.0 mmol). The reaction was heated to 85° C. for 2 h. The solvent was removed under reduced pressure and the residue was diluted with water (20 mL) and extracted with DCM (3×10 mL). The combined organic layers were concentrated under reduced pressure. The crude material was crystallized from isopropanol (20 mL) to afford 1.05 g (91%) of (Z)-4-(heptyloxy)-N'-hydroxybenzimidamide as a white solid. LCMS-ESI (m/z) calculated for $C_{14}H_{22}N_2O_2$: 250.2. found 251.3 [M+H]$^+$, $t_R$=1.70 min (Method 1). $^1$H NMR (400 MHz, CDCl$_3$) δ 9.45 (s, 1H), 7.59 (d, J=8.6 Hz, 2H), 6.93 (t, J=14.7 Hz, 2H), 5.82-5.48 (m, 2H), 3.97 (t, J=6.5 Hz, 2H), 1.83-1.55 (m, 2H), 1.56-1.05 (m, 8H), 0.87 (t, J=6.7 Hz, 3H). $^{13}$C NMR (101 MHz CDCl$_3$) δ 159.19, 150.53, 126.64, 125.55, 113.87, 67.40, 31.21, 28.62, 28.40, 25.44, 22.02, 13.92.

(S)-methyl 4-(2-amino-3-methoxy-3-oxopropyl)benzoate

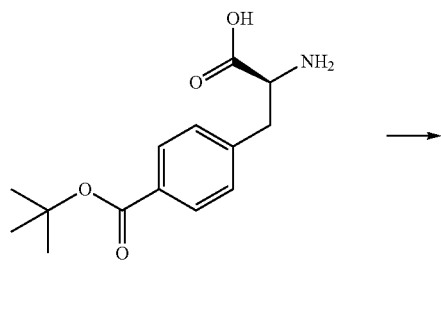

To a solution of (S)-2-amino-3-(4-(tert-butoxycarbonyl)phenyl)propanoic acid (500.0 mg, 1.88 mmol) in MeOH (20 mL) at 0° C. was slowly added thionyl chloride (447.64 mg, 3.77 mmol). The reaction was stirred for 1 h at 0° C. then warmed to room temperature and stirred for 1 h. The solvent was removed under reduced pressure. The reaction mixture was washed with saturated aqueous NaHCO$_3$ (20 ml) and extracted with DCM (3×10 ml). The organic layer was dried over MgSO$_4$ and concentrated. The crude product was purified by chromatography (EA/hexanes) to afford 425 mg (95%) of (S)-methyl 4-(2-amino-3-methoxy-3-oxopropyl)benzoate as the HCl salt. LCMS-ESI (m/z) calculated for $C_{12}H_{15}NO_4$: 237.1. found 238.0 [M+H]$^+$, $t_R$=1.01 min (Method 1). $^1$H NMR (400 MHz, CDCl$_3$) δ 8.55 (s, 3H), 7.94 (d, J=8.3 Hz, 2H), 7.41 (d, J=8.3 Hz, 2H), 4.37 (t, J=6.8 Hz, 1H), 3.86 (s, 3H), 3.68 (s, 3H), 3.20 (dd, J=11.8, 6.8 Hz, 2H).

(S)-methyl 4-(2-(4-(tert-butyl)benzamido)-3-methoxy-3-oxopropyl)benzoate

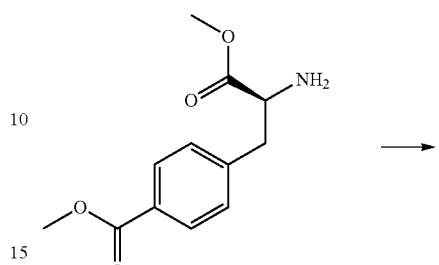

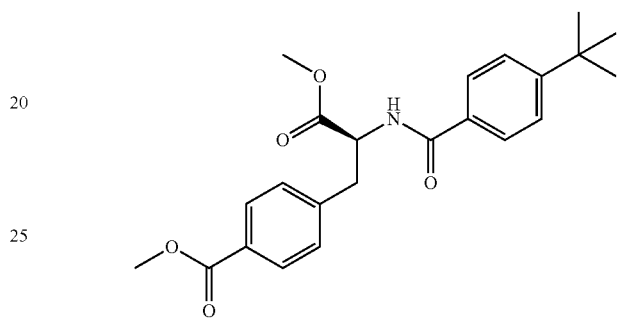

Prepared using General Procedure 3: To the solution of (S)-methyl 4-(2-amino-3-methoxy-3-oxopropyl)benzoate (425.0 mg, 1.79 mmol) in DCM (10 mL) and DIEA (463.0 mg, 3.58 mmol) was added 4-(tert-butyl)benzoyl chloride (556.6 mg, 2.83 mmol) at room temperature. The reaction was stirred for 2 h and the reaction was partitioned between DCM and saturated aqueous NaHCO$_3$. The organic layer was dried over MgSO$_4$ and concentrated. The crude product was purified by chromatography (EA/hexanes) to afford 317 mg (45%) of (S)-methyl 4-(2-(4-(tert-butyl)benzamido)-3-methoxy-3-oxopropyl)benzoate. LCMS-ESI (m/z) calculated for $C_{23}H_{27}NO_5$: 397.2. found 398.1 [M+H]$^+$, $t_R$=2.31 min (Method 1). $^1$H NMR (400 MHz, CDCl$_3$) δ 7.97-7.75 (m, 2H), 7.67-7.51 (m, 2H), 7.46-7.26 (m, 2H), 7.14 (d, J=8.3 Hz, 2H), 6.60 (d, J=7.4 Hz, 1H), 5.03 (dt, J=7.4, 5.7 Hz, 1H), 3.82 (s, 3H), 3.68 (s, 3H), 3.28 (dd, J=13.7, 5.8 Hz, 1H), 3.18 (dd, J=13.7, 5.5 Hz, 1H), 1.24 (s, 9H).

(S)-4-(2-(4-(tert-butyl)benzamido)-3-methoxy-3-oxopropyl)benzoic acid (INT-1)

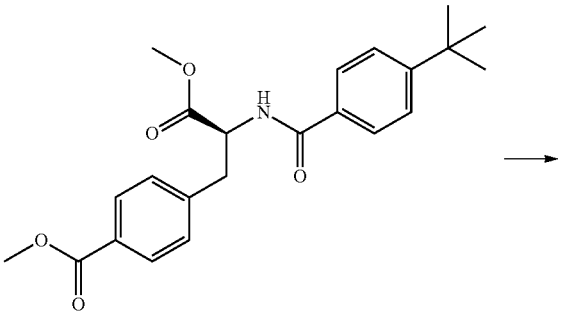

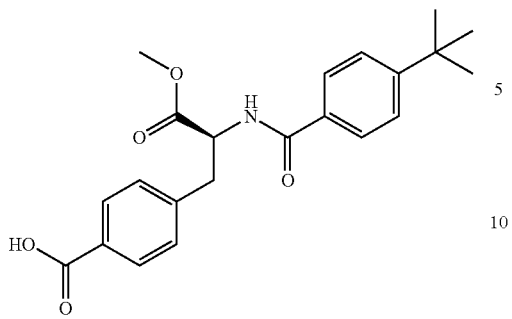

Prepared using General Procedure 4: To a stirred solution of (S)-methyl 4-(2-(4-(tert-butyl)benzamido)-3-methoxy-3-oxopropyl)benzoate (316.6 mg, 0.79 mmol) in dioxane (15 mL) and water (1 mL) at 0° C. was added lithium hydroxide monohydrate (93.52 mg, 2.23 mmol). After 2 h, the solution was neutralized with 1 M HCl to pH 7.0. The mixture was partitioned between DCM (15 mL) and saturated aqueous $NaHCO_3$ (10 mL). The organic layer was washed with saturated aqueous $NaHCO_3$ (3×10 mL) and brine (10 mL). The organic layer was dried over $MgSO_4$ and concentrated to afford 208 mg (69%) of (S)-4-(2-(4-(tert-butyl)benzamido)-3-methoxy-3-oxopropyl)benzoic acid, INT-1. LCMS-ESI (m/z) calculated for $C_{22}H_{25}NO_5$: 383.2. found 384.1 [M+H]$^+$, $t_R$=2.13 min. (Method 1). $^1$H NMR (400 MHz, DMSO) δ 12.86 (s, 1H), 8.80 (d, J=8.0 Hz, 1H), 7.87-7.78 (m, 2H), 7.75-7.65 (m, 2H), 7.50-7.35 (m, 4H), 4.72 (ddd, J=10.3, 8.0, 5.1 Hz, 1H), 3.65 (s, 3H), 3.28-3.05 (m, 2H), 1.29 (s, 9H). $^{13}$C NMR (101 MHz, DMSO) δ 173.00, 167.21, 166.29, 154.39, 143.10, 130.85, 129.34, 129.27, 129.21, 129.03, 127.21, 125.39, 125.10, 53.75, 52.04, 34.64, 30.92, 30.88.

(S)-methyl 2-(4-(tert-butyl)benzamido)-3-(4-(3-(4-(heptyloxy)phenyl)-1,2,4-oxadiazol-5-yl)phenyl) propanoate

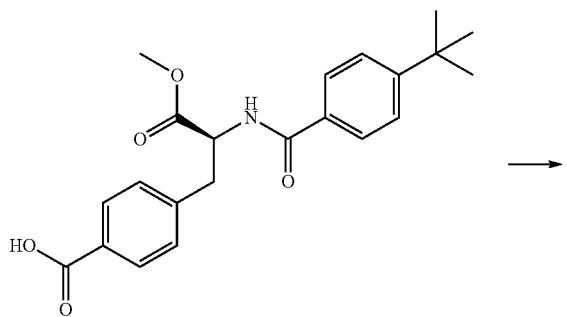

⟶

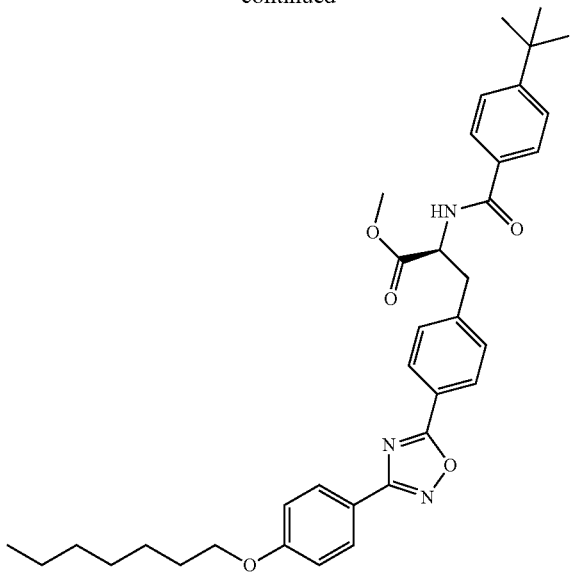

Prepared using General Procedure 5: To a solution of (S)-4-(2-(4-(tert-butyl)benzamido)-3-methoxy-3-oxopropyl)benzoic acid, INT-1 (10.0 mg, 0.026 mmol) in anhydrous DMF (1 mL) was added HOBt (5.27 mg, 0.39 mmol) and EDC (7.48 mg, 0.39 mmol). After stirring for 2 h, (Z)-4-(heptyloxy)-N'-hydroxybenzimidamide (9.76 mg, 0.39 mmol) was added. The reaction mixture was stirred at room temperature for 2 h, partitioned between saturated aqueous $NaHCO_3$ (5 ml) and EA (5 mL), and concentrated under reduced pressure to afford the intermediate (S)-methyl 2-(4-(tert-butyl)benzamido)-3-(4-(((4-(heptyloxy)benzimidamido) oxy)carbonyl) phenyl) propanoate. The intermediate was dissolved in DMF (1 mL) and heated to 100° C. for 18 h. The reaction mixture was cooled to room temperature and partitioned between EA (5 mL) and saturated aqueous $NaHCO_3$ (5 mL). The organic layer was extracted with water (2×5 mL) and brine (5 mL). The organic layer was dried over $MgSO_4$ and concentrated. The brown oil was purified by preparative HPLC to afford 4.5 mg (29%) of (S)-methyl 2-(4-(tert-butyl)benzamido)-3-(4-(3-(4-(heptyloxy)phenyl)-1,2,4-oxadiazol-5-yl) phenyl) propanoate. LCMS-ESI (m/z) calculated for $C_{36}H_{43}N_3O_5$: 597.3; no m/z observed, $t_R$=12.75 min (Method 2). $^1$H NMR (400 MHz, DMSO) δ 8.85 (d, J=8.0 Hz, 1H), 8.09 (d, J=8.3 Hz, 2H), 8.00 (d, J=8.9 Hz, 2H), 7.74 (d, J=8.5 Hz, 2H), 7.59 (d, J=8.4 Hz, 2H), 7.48 (d, J=8.6 Hz, 2H), 7.12 (d, J=8.9 Hz, 2H), 4.87-4.56 (m, 1H), 4.06 (t, J=6.5 Hz, 2H), 3.67 (s, 3H), 3.32-3.13 (m, 4H), 1.74 (dd, J=14.2, 6.5 Hz, 2H), 1.51-1.37 (m, 2H), 1.33 (s, 4H), 1.26 (d, J=20.2 Hz, 9H), 0.88 (t, J=6.9 Hz, 3H). $^{13}$C NMR (101 MHz, DMSO) δ 175.00, 171.91, 167.89, 166.27, 161.21, 154.37, 143.68, 130.78, 130.30, 128.76, 127.80, 127.18, 125.07, 121.69, 118.21, 115.07, 67.72, 53.61, 52.05, 36.15, 34.60, 31.20, 30.87, 28.54, 28.39, 25.40, 22.02, 13.93.

(S)-2-(4-(tert-butyl)benzamido)-3-(4-(3-(4-(heptyloxy)phenyl)-1,2,4-oxadiazol-5-yl)phenyl)propanoic acid (Compound 1)

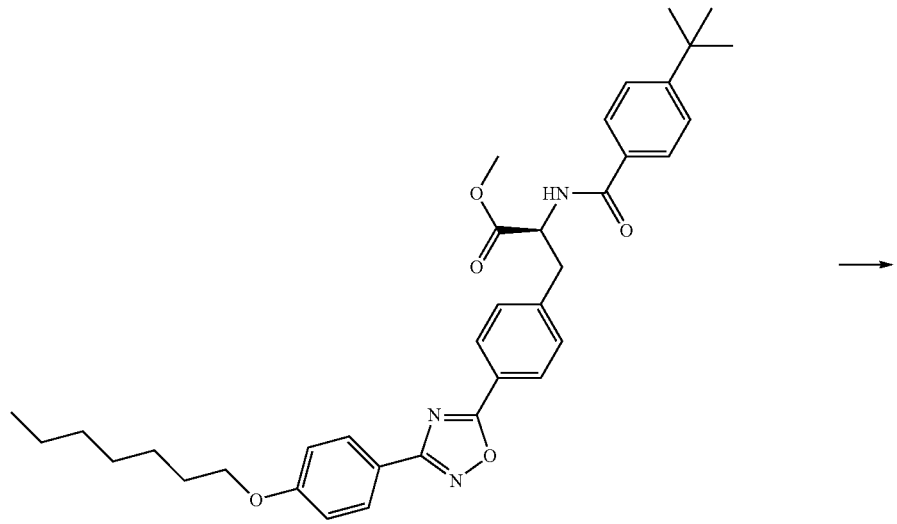

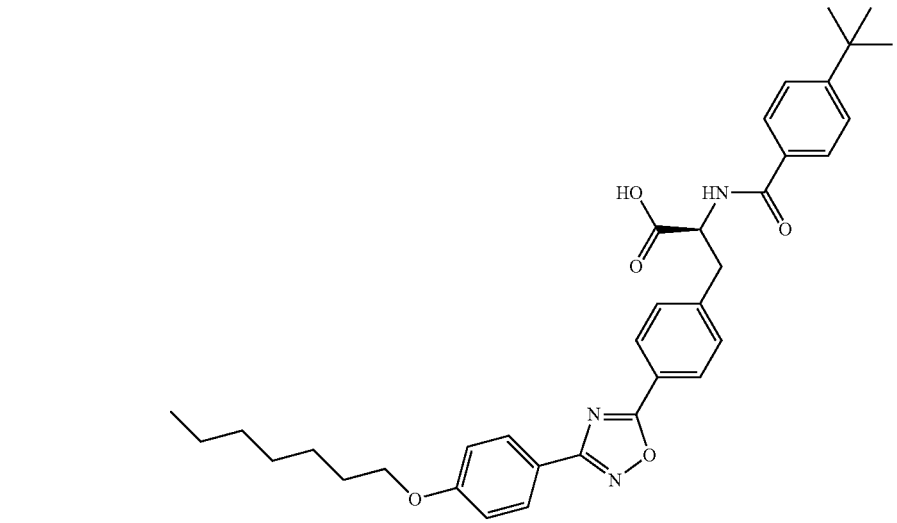

Prepared using General Procedure 4: To a solution of (S)-methyl 2-(4-(tert-butyl)benzamido)-3-(4-(3-(4-(heptyloxy)phenyl)-1,2,4-oxadiazol-5-yl)phenyl) propanoate (4.52 mg, 0.008 mmol) in MeOH (2 mL) was added of 1 N NaOH (1 mL). The reaction mixture was stirred at 50° C. for 3 h. The resulting mixture was purified by preparative HPLC to afford 0.36 mg (8%) of (S)-2-(4-(tert-butyl)benzamido)-3-(4-(3-(4-(heptyloxy)phenyl)-1,2,4-oxadiazol-5-yl)phenyl) propanoic acid. LCMS-ESI (m/z) calculated for $C_{35}H_{41}N_3O_5$: 583.7; no m/z observed, $t_R$=12.59 min (Method 2).

(S)-methyl 2-amino-3-(4-cyanophenyl)propanoate

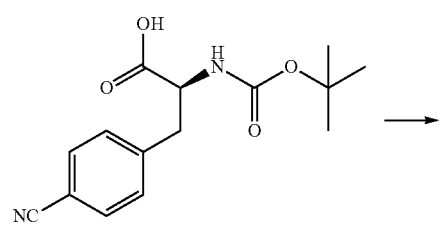

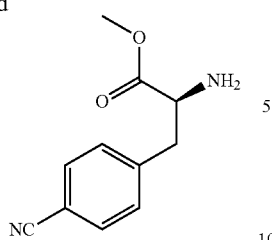

To a solution of (S)-2-((tert-butoxycarbonyl)amino)-3-(4-cyanophenyl)propanoic acid (1.0 g, 3.44 mmol) in MeOH (20 mL) at 0° C. was slowly added thionyl chloride (818.1 mg, 6.89 mmol) over 1 h. The reaction was warmed to room temperature and stirred for 1 h. The solvent was removed under reduced pressure. The reaction mixture was washed with saturated aqueous NaHCO$_3$ (20 ml) and extracted with DCM (3×10 ml). The organic layer was dried over MgSO$_4$ and concentrated. The crude product was purified by chromatography (EA/hexanes) to afford 789 mg (97%) of (S)-methyl 2-amino-3-(4-cyanophenyl)propanoate as the HCl salt. LCMS-ESI (M/z) calculated for C$_{11}$H$_{12}$N$_2$O$_2$: 204.1. found 205.0 [M+H]$^+$, t$_R$=3.25 min (Method 1). $^1$H NMR (400 MHz, CDCl$_3$) δ 8.69 (s, 3H), 7.83 (d, J=8.3 Hz, 2H), 7.51 (t, J=8.8 Hz, 2H), 4.37 (t, J=6.7 Hz, 1H), 3.68 (s, 3H), 3.23 (qd, J=14.4, 7.7 Hz, 2H).

(S)-methyl 2-(4-(tert-butyl)benzamido)-3-(4-cyanophenyl)propanoate

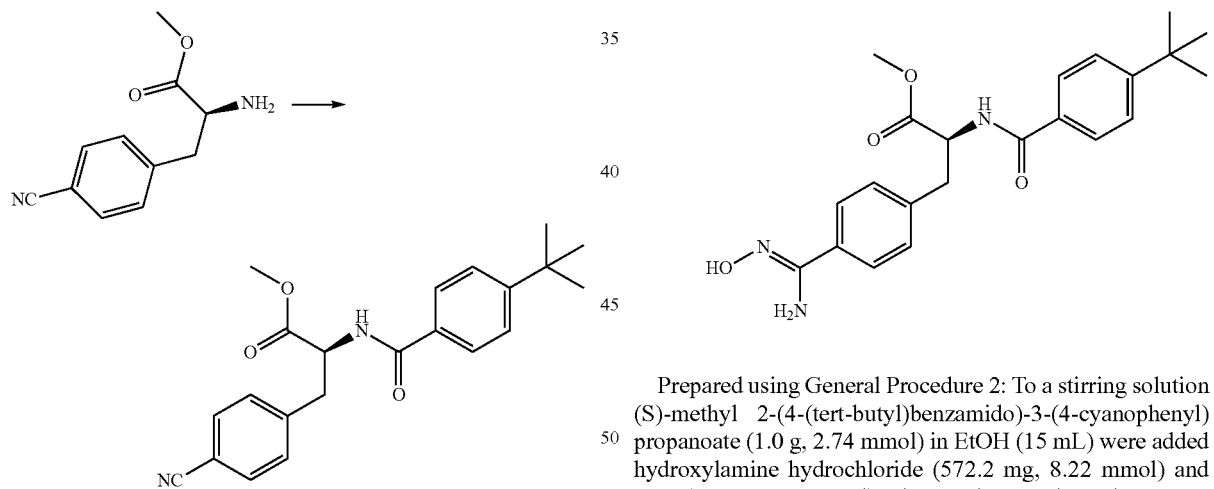

Prepared using General Procedure 3: To the solution of (S)-methyl 2-amino-3-(4-cyanophenyl)propanoate (789.2 mg, 3.32 mmol) in DCM (15 mL) and DIEA (1.29 g, 9.96 mmol) was added 4-(tert-butyl)benzoyl chloride (981.3 mg, 4.99 mmol) at room temperature. The reaction was stirred for 2 h and the reaction was partitioned between DCM and saturated aqueous NaHCO$_3$. The organic layer was dried over mgSO$_4$ and concentrated. The crude product was purified by chromatography (EA/hexanes) to afford 1.06 g (88%) of (S)-methyl 2-(4-(tert-butyl)benzamido)-3-(4-cyanophenyl)propanoate. LCMS-ESI (m/z calculated for C$_{22}$H$_{24}$N$_2$O$_3$: 364.2. found 365.3 [M+H]$^+$, t$_R$=3.55 min (Method 1). $^1$H NMR (400 MHz, CDCl$_3$) δ 8.81 (d, J=8.0 Hz, 1H), 7.85-7.60 (m, 4H), 7.49 (dd, J=15.1, 8.4 Hz, 4H), 4.85-4.60 (m, 1H), 3.65 (s, 3H), 3.30-3.23 (m, 1H), 3.18 (dd, J=13.7, 10.6 Hz, 1H), 1.29 (s, 9H).

(S,Z)-methyl 2-(4-(tert-butyl)benzamido)-3-(4-(N'-hydroxycarbamimidoyl) phenyl) propanoate (INT-2)

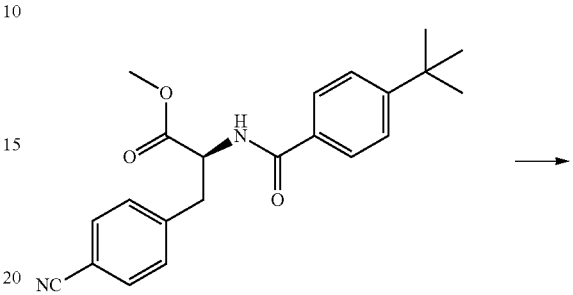

Prepared using General Procedure 2: To a stirring solution (S)-methyl 2-(4-(tert-butyl)benzamido)-3-(4-cyanophenyl) propanoate (1.0 g, 2.74 mmol) in EtOH (15 mL) were added hydroxylamine hydrochloride (572.2 mg, 8.22 mmol) and TEA (1.38 g, 13.7 mmol). The reaction was heated to 85° C. for 2 h. The solvent was removed under reduced pressure and the residue was diluted with water (20 mL) and extracted with DCM (3×10 mL). The combined organic layers were concentrated under reduced pressure. The crude material was crystallized from isopropanol (20 mL) to afford 1.04 g (95%) of (S,Z)-methyl 2-(4-(tert-butyl)benzamido)-3-(4-(N'-hydroxycarbamimidoyl)phenyl)propanoate (INT-2) as a white solid. LCMS-ESI (m/z): calcd for: C$_{22}$H$_{27}$N$_3$O$_4$, 397.2. found 398.1 [M+1]$^+$, t$_R$=2.26 min (Method 1). $^1$H NMR (400 MHz, DMSO) δ 10.19 (s, 1H), 9.57 (s, 1H), 8.78 (d, J=7.9 Hz, 1H), 7.74 (d, J=8.4 Hz, 2H), 7.58 (d, J=8.2 Hz, 2H), 7.48 (d, J=8.4 Hz, 2H), 7.30 (d, J=8.3 Hz, 2H), 4.79-4.49 (m, 1H), 3.65 (s, 3H), 3.15 (dt, J=13.6, 6.0 Hz, 2H), 1.75 (d, J=13.6 Hz, 1H), 1.29 (s, 9H).

(S)-methyl 2-(4-(tert-butyl)benzamido)-3-(4-(5-(4-(heptyloxy)phenyl)-1,2,4-oxadiazol-3-yl)phenyl)propanoate

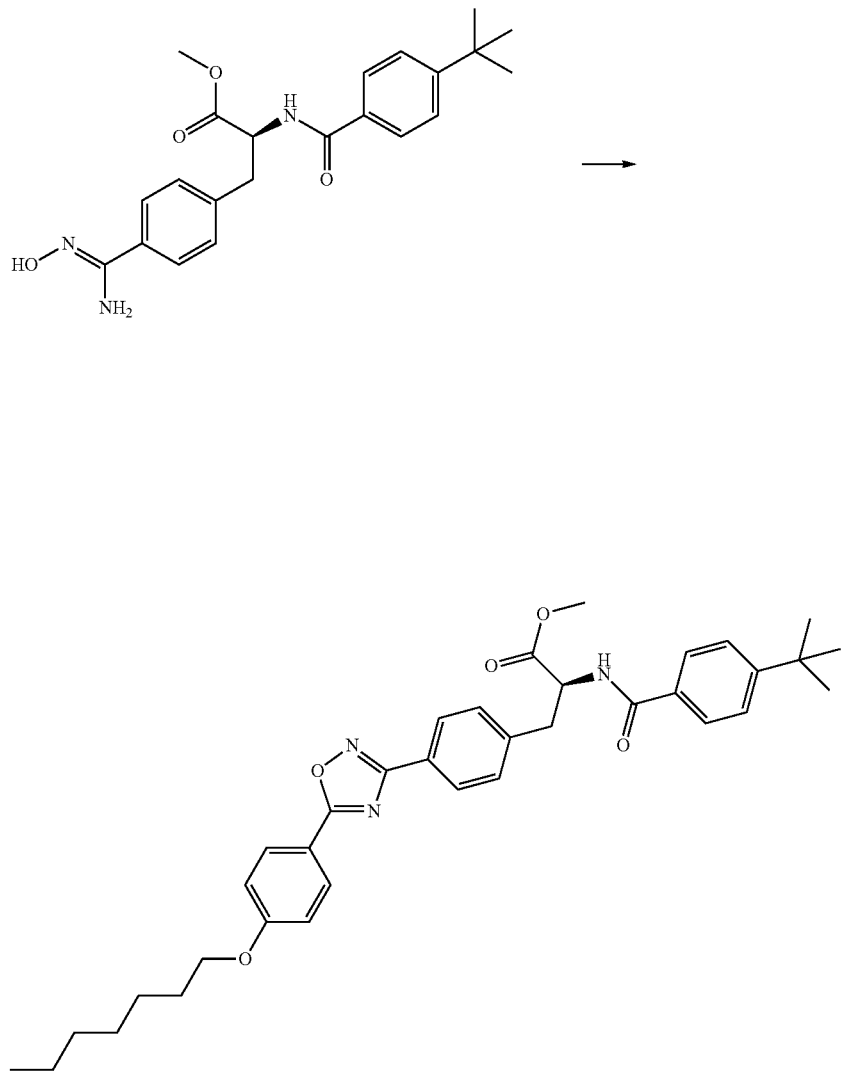

Prepared using General Procedure 5: To a solution of 4-(heptyloxy)benzoic acid (400.0 mg, 1.54 mmol) in anhydrous DMF (6 mL) were added HOBt (312.3 mg, 2.31 mmol) and EDC (442.75 mg, 2.31 mmol). After stirring for 2 h, (S, Z)-methyl 2-(4-(tert-butyl)benzamido)-3-(4-(N'-hydroxycarbamimidoyl)phenyl)-propanoate, INT-2 (673.3 mg, 1.69 mmol) was added. The reaction mixture was stirred at room temperature for 2 h, partitioned between saturated aqueous $NaHCO_3$ (15 mL) and EA (15 mL), and concentrated under reduced pressure to afford the intermediate (S)-methyl 2-(4-(tert-butyl)benzamido)-3-(4-(N-((4-(heptyloxy)benzoyl)oxy)carbamimidoyl)phenyl)propanoate. The intermediate was dissolved in DMF (10 mL) and heated to 100° C. for 18 h. The reaction mixture was cooled to room temperature and partitioned between EA (10 mL) and saturated aqueous $NaHCO_3$ (50 mL). The organic layer was extracted with water (2×10 mL) and brine (10 mL). The organic layer was dried over $MgSO_4$ and concentrated. The brown oil was purified by chromatography (EA/hexanes) to afford 710 mg (77%) of (S)-methyl 2-(4-(tert-butyl)benzamido)-3-(4-(5-(4-(heptyloxy)phenyl)-1,2,4-oxadiazol-3-yl)phenyl)propanoate as a white solid. LCMS-ESI (m/z) calculated for $C_{36}H_{43}N_3O_5$: 597.3; no m/z observed, $t_R$=12.80 min (Method 2). $^1$H NMR (400 MHz, DMSO) δ 8.84 (d, J=8.0 Hz, 1H), 8.08 (t, J=17.2 Hz, 2H), 7.97 (dd, J=18.2, 8.5 Hz, 2H), 7.74 (d, J=8.5 Hz, 2H), 7.50 (dd, J=18.6, 8.3 Hz, 4H), 7.18 (d, J=8.9 Hz, 2H), 4.85-4.63 (m, 1H), 4.09 (dd, J=13.8, 7.3 Hz, 2H), 3.67 (s, 3H), 3.24 (ddd, J=23.8, 15.7, 7.3 Hz, 4H), 2.08 (s, 4H), 1.74 (dd, J=14.1, 6.9 Hz, 2H), 1.42 (dd, J=13.6, 6.3 Hz, 2H), 1.30 (d, J=14.5 Hz, 9H), 0.88 (t, J=6.8 Hz, 3H). $^{13}$C NMR (101 MHz, DMSO) δ 174.05, 170.87, 133.81, 165.14, 161.43, 153.21, 140.51, 129.70, 128.85, 128.78, 126.06, 125.84, 123.93, 123.39, 114.36, 114.25, 66.86, 52.66, 50.88, 34.32, 33.47, 30.06, 29.74, 27.33, 27.24, 24.23, 20.89, 12.80.

(S)-2-(4-(tert-butyl)benzamido)-3-(4-(5-(4-(heptyloxy)phenyl)-1,2,4-oxadiazol-3-yl)phenyl)propanoic acid (Compound 2)

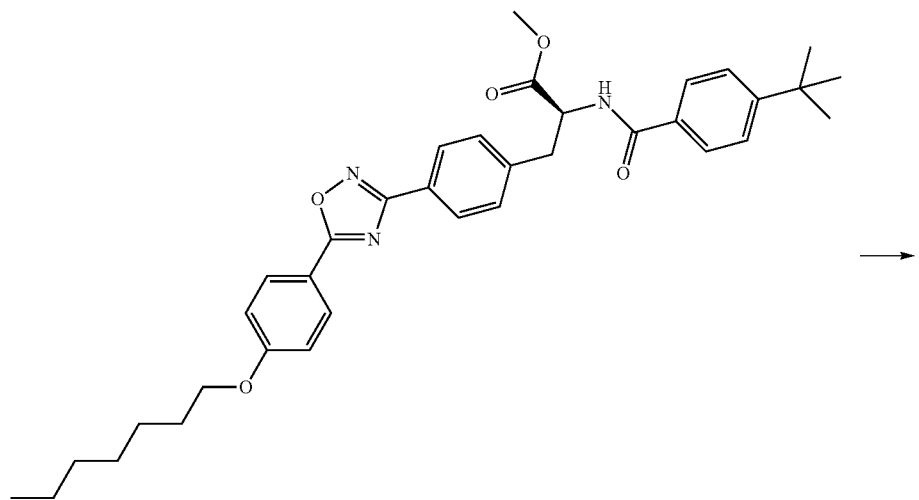

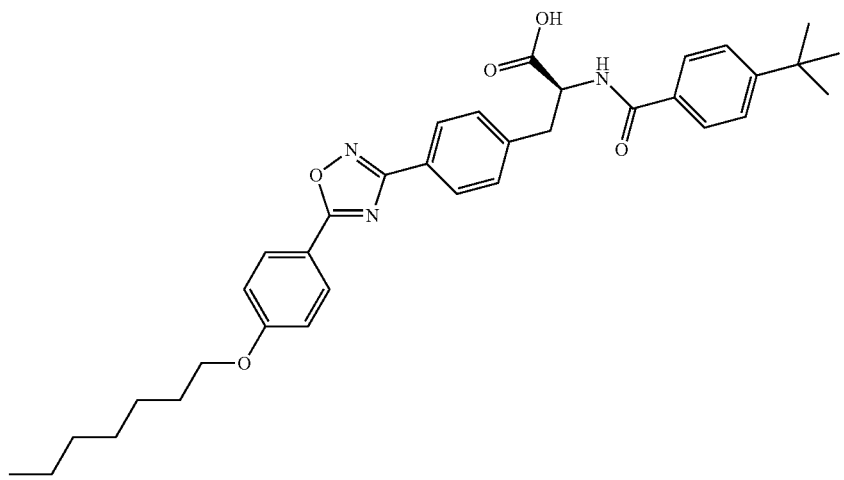

Prepared using General Procedure 4: To a solution of (S)-methyl 2-(4-(tert-butyl)benzamido)-3-(4-(5-(4-(heptyloxy)phenyl)-1,2,4-oxadiazol-3-yl)phenyl)propanoate (710.0 mg, 1.19 mmol) in MeOH (20 mL) was added 1 N NaOH (10 mL). The reaction mixture was stirred at 50° C. for 3 h. The resulting mixture was purified by chromatography (DCM/MeOH) to afford 218 mg (31%) of (S)-2-(4-(tert-butyl)benzamido)-3-(4-(5-(4-(heptyloxy)phenyl)-1,2,4-oxadiazol-3-yl)phenyl)propanoic acid as white solid. LCMS-ESI (m/z) calculated for $C_{35}H_{41}N_3O_5$; 583.3; no m/z observed, $t_R$=12.16 min (Method 2). $^1$H NMR (400 MHz, DMSO) δ 8.69 (d, J=8.3 Hz, 1H), 8.16-8.02 (m, 2H), 7.98 (d, J=8.3 Hz, 2H), 7.74 (d, J=8.5 Hz, 2H), 7.53 (d, J=8.3 Hz, 2H), 7.47 (d, J=8.5 Hz, 2H), 7.18 (d, J 9.0 Hz, 2H), 4.70 (ddd, J 10.8, 8.4, 4.5 Hz, 1H), 4.09 (t, J 6.5 Hz, 2H), 3.30 (dd, J 13.8, 4.2 Hz, 1H), 3.17 (dd, J 13.8, 10.7 Hz, 1H), 1.74 (dd, J 14.5, 6.7 Hz, 2H) 1.42 (dd, J 13.8, 6.1 Hz, 2H), 1.37-1.14 (m, 14H), 0.87 (t, J 6.9 Hz, 3H). $^{13}$C NMR (101 MHz, DMSO) δ 175.16, 173.00, 167.96, 166.19, 162.55, 154.18, 142.11, 131.08, 129.95, 129.89, 127.14, 126.92, 125.01, 124.39, 115.49, 115.37, 67.98, 53.72, 36.19, 34.58, 31.19, 30.89, 28.46, 28.37, 25.36, 22.01, 13.92.

Compounds 3-11 and 13-61 were prepared from (S,Z)-methyl 2-(4-(tert-butyl)benzamido)-3-(4-(N'-hydroxycarbamimidoyl)phenyl)propanoate INT-2 using General Procedures 5 and 4 sequentially.

Compounds 62-66 were prepared from (S,Z)-methyl 2-(4-(tert-butyl)benzamido)-3-(4-(N'-hydroxycarbamimidoyl)phenyl)propanoate INT-2 using General Procedures 5, 6, and 4 sequentially.

(S)-2-(2-(4-(tert-butyl)benzamido)-3-(4-(5-(4-(heptyloxy)phenyl)-1,2,4-oxadiazol-3-yl)phenyl)propanamido)acetic acid (Compound 67)

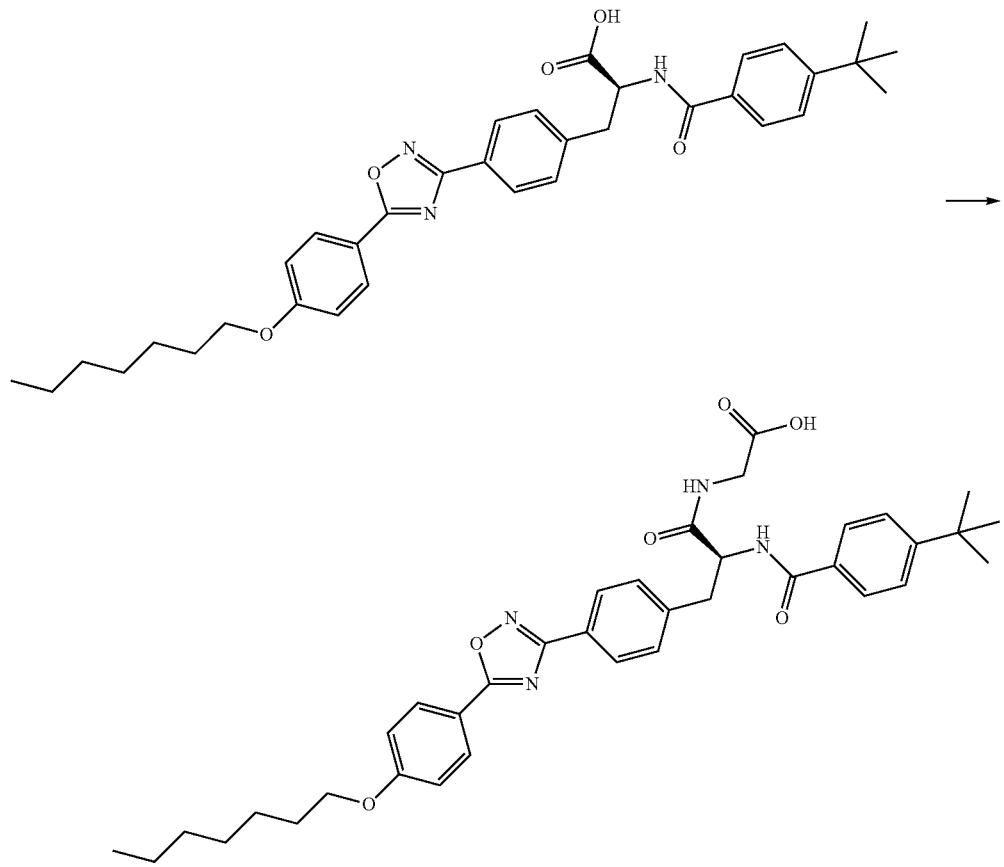

Prepared using General Procedures 7 and 8: To a solution of (S)-2-(4-(tert-butyl)benzamido)-3-(4-(5-(4-(heptyloxy)phenyl)-1,2,4-oxadiazol-3-yl)phenyl)propanoic acid, Compound 2 (10.0 mg, 0.017 mmol) in anhydrous DMF (1 mL) was added HOBt (3.52 mg, 0.027 mmol) and EDCI (4.88 mg, 0.027 mmol) at room temperature. After 2 h, tert-butyl 2-aminoacetate (3.49 mg, 0.027 mmol) was added and the reaction mixture stirred at room temperature for 2 h. LCMS analysis showed complete conversion to the intermediate. The reaction mixture was partitioned between NaHCO$_3$ aqueous (5 ml) and DCM (1 mL), the organic layer was collected and concentrated by vacuum and then was re-dissolved in 1 mL of DCM and 0.1 mL of TFA. The mixture was heated to 30° C. for 3 h. The final compound was purified by HPLC to afford 9.6 mg (88%) of (S)-2-(2-(4-(tert-butyl)benzamido)-3-(4-(5-(4-(heptyloxy)phenyl)-1,2,4-oxadiazol-3-yl)phenyl)propanamido)acetic acid. LCMS-ESI (m/z) calculated for $C_{37}H_{44}N_4O_6$ 640.3; no m/z observed, $t_R$=11.51 min (Method 2). $^1$H NMR (400 MHz, DMSO) δ: 8.60 (d, J=8.4 Hz, 1H), 8.47 (t, J=5.7 Hz, 1H), 8.10 (d, J=8.8 Hz, 2H), 7.96 (d, J=8.2 Hz, 2H), 7.75 (d, J=8.4 Hz, 2H), 7.57 (d, J=8.0 Hz, 2H), 7.45 (d, J=8.4 Hz, 2H), 7.17 (d, J=8.8 Hz, 2H), 4.83 (d, J=8.1 Hz, 1H), 4.09 (t, J=6.4 Hz, 2H), 3.94-3.69 (m, 2H), 3.34 (s, 2H), 3.26 (d, J=13.5 Hz, 1H), 3.15-3.01 (m, 1H), 1.83-1.65 (m, 2H), 1.50-1.15 (m, 16H), 0.87 (t, J=6.7 Hz, 3H). $^{13}$C NMR (101 MHz, DMSO) δ: 175.12, 171.58, 171.13, 167.99, 166.02, 162.54, 154.10, 142.44, 131.16, 130.02, 129.89, 127.23, 126.81, 124.91, 124.25, 115.50, 115.36, 67.97, 54.23, 40.10, 37.12, 34.57, 31.19, 30.88, 28.46, 28.37, 25.36, 22.02, 13.93.

Compound 68 was prepared from Compound 5 using General Procedures 7, and 8 sequentially.

Compound 69 was prepared from (S, Z)-methyl 2-(4-(tert-butyl)benzamido)-3-(4-(N'-hydroxycarbamimidoyl)phenyl)propanoate Compound 2 using General Procedure 7.

Compound 70 was prepared from (S, Z)-methyl 2-(4-(tert-butyl)benzamido)-3-(4-(N'-hydroxycarbamimidoyl)phenyl)propanoate Compound 2 using General Procedures 7 and 8 sequentially.

Compounds 71 and 72 were prepared from Methyl 2-amino-2-(4-bromophenyl)acetate hydrochloride using General Procedures 7, 1, 2, 5, and 4 sequentially.

Compounds 73 and 74 were prepared from (S)-methyl 2-amino-4-(4-hydroxyphenyl)butanoate hydrobromide using General Procedures 7, 9, 1, 2, 5, and 4 sequentially.

Compound 75 was prepared from (S)-methyl 3-amino-4-(4-hydroxyphenyl)butanoate hydrochloride using General Procedures 7, 9, 1, 2, 5, and 4 sequentially.

4-(heptyloxy)benzohydrazide

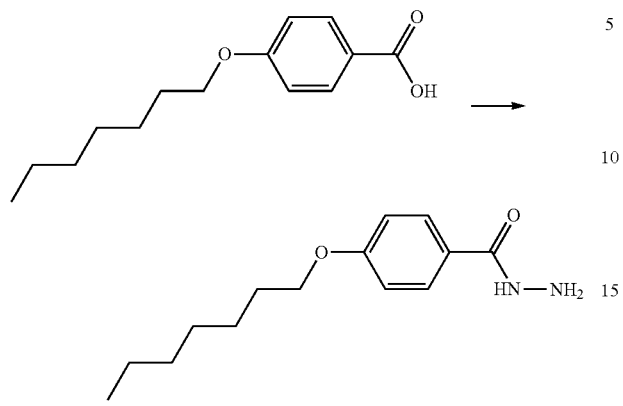

To a stirred solution of 4-(heptyloxy)benzoic acid (679 mg, 2.87 mmol) in THF (5 mL) was added 1,1'-carbonyldiimidazole (559 mg, 3.45 mmol). After stirring at room temperature for 2 h, the solution was added to a stirred mixture of hydrazine hydrate (0.729 mL, 5.75 mmol) in THF (2 mL) and stirred a further 2 h. The reaction mixture was poured onto water (20 mL) and stirred for 30 min. The resulting precipitate was collected by filtration, washed with water (2×10 mL) then acetonitrile (3 mL) to afford 0.54 g (71%) of 4-(heptyloxy)benzohydrazide as a white solid. LCMS-ESI (m/z) calculated for $C_{14}H_{22}N_2O_2$: 250.3 found 251.0 $[M+H]^+$, $t_R$=2.05 min. (Method 4).

(S)-methyl 2-(4-(tert-butyl)benzamido)-3-(4-(2-(4-(heptyloxy)benzoyl)hydrazine-carbonyl)phenyl)propanoate (INT-3)

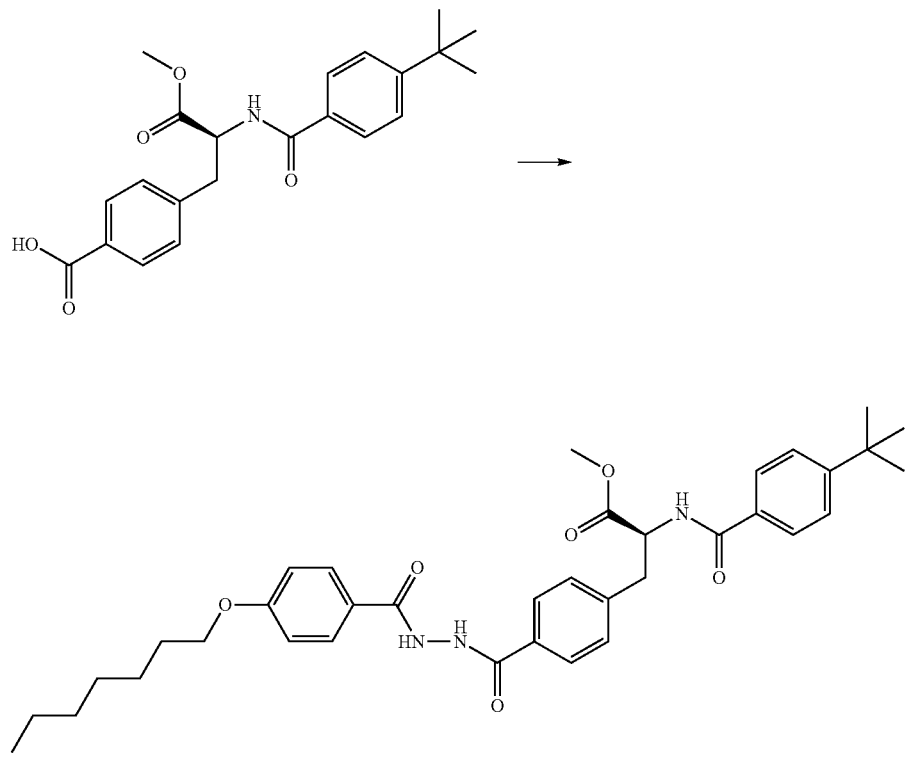

To a stirring solution of (S)-4-(2-(4-(tert-butyl)benzamido)-3-methoxy-3-oxopropyl)benzoic acid INT-1 (260 mg, 0.68 mmol) in THF (5 mL) were added 4-methylmorpholine (0.15 mL, 1.36 mmol) and isobutyl carbonochloridate (0.09 mL, 0.71 mmol). After stirring at room temperature for 2 h, 4-(heptyloxy)benzohydrazide (187 mg, 0.75 mmol) was added and stirring continued for another 2 h. The reaction mixture was poured onto $NaHCO_3$ (50 mL) and extracted with DCM (3×20 mL). The combined organics were dried over $MgSO_4$ and evaporated. The crude product was purified by column chromatography (100% EA in iso-hexanes) to afford 297 mg (71%) of (S)-methyl 2-(4-(tert-butyl)benzamido)-3-(4-(2-(4-(heptyloxy)benzoyl)hydrazinecarbonyl)phenyl)propanoate INT-3 as an off-white foam. LCMS-ESI (m/z) calculated for $C_{36}H_{45}N_3O_6$: 615.8 found 616.0 $[M+H]^+$, $t_R$=2.89 min. (Method 4).

(S)-Methyl 2-(4-(tert-butyl)benzamido)-3-(4-(5-(4-(heptyloxy)phenyl)-1,3,4-oxadiazol-2-yl)phenyl)propanoate

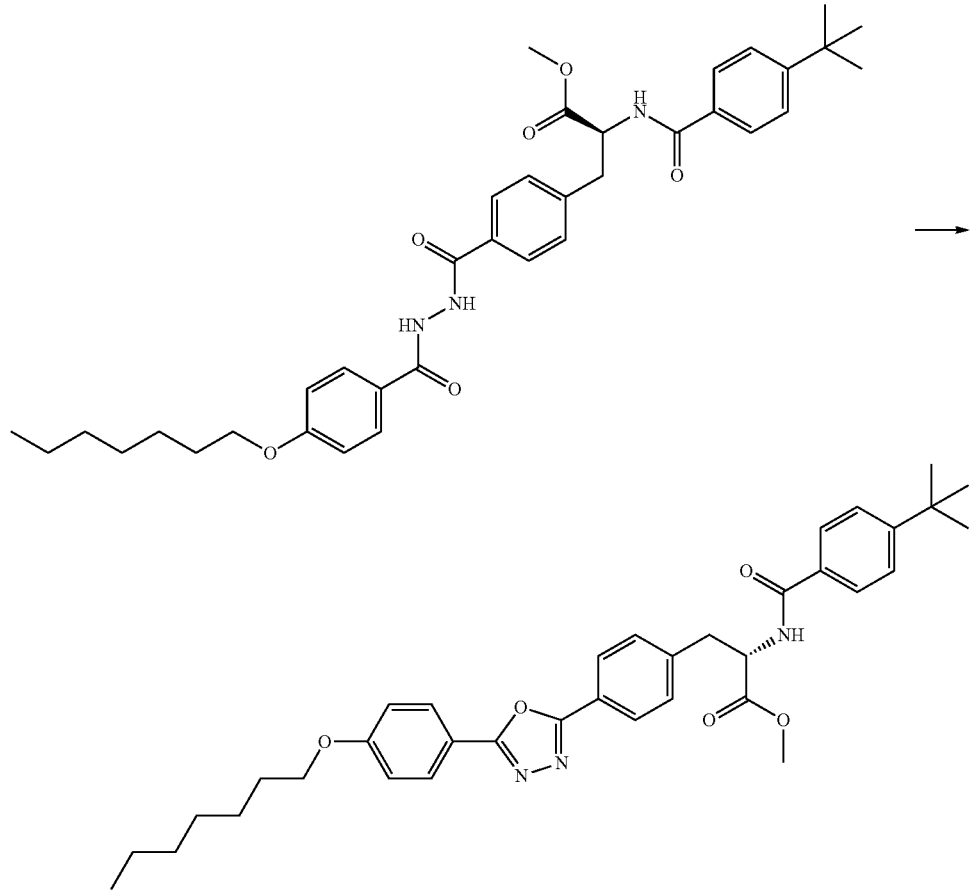

To a stirring solution (S)-methyl 2-(4-(tert-butyl)benzamido)-3-(4-(2-(4-(heptyloxy)benzoyl)hydrazinecarbonyl)phenyl)propanoate INT-3 (127 mg, 0.21 mmol) and TEA (0.09 mL, 0.62 mmol) in DCM (4 mL) was added 2-chloro-1,3-dimethylimidazolidinium chloride (41.8 mg, 0.25 mmol). The reaction mixture was stirred at room temperature for 18 h then warmed to 40° C. for 1 h. The reaction mixture was cooled to room temperature, diluted with $NaHCO_3$ (15 mL), shaken, split through a hydrophobic frit and evaporated to afford 120 mg (95%) of (S)-methyl 2-(4-(tert-butyl)benzamido)-3-(4-(5-(4-(heptyloxy)phenyl)-1,3,4-oxadiazol-2-yl)phenyl)propanoate as a white solid. LCMS-ESI (m/z) calculated for $C_{36}H_{43}N_3O_5$: 597.8. found 598.0 $[M+H]^+$, $t_R$=3.25 min. (Method 4).

Compound 76 was prepared using (S)-methyl 2-(4-(tert-butyl)benzamido)-3-(4-(5-(4-(heptyloxy)phenyl)-1,3,4-oxadiazol-2-yl)phenyl)propanoate and General Procedure 4.

2-bromo-1-(4-(heptyloxy)phenyl)ethanone (INT-4)

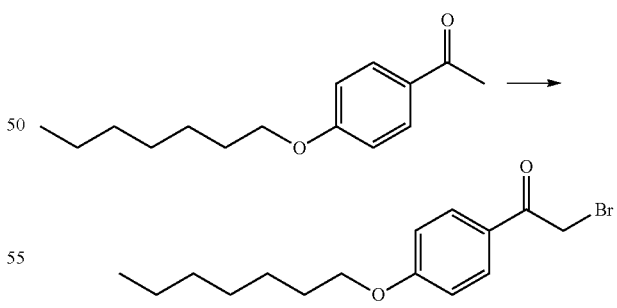

To a stirring solution of 1-(4-(heptyloxy)phenyl)ethanone (500 mg, 2.13 mmol) in THF (8.5 mL) under nitrogen was added phenyltrimethylammonium tribromide (842 mg, 2.24 mmol). The reaction mixture was stirred at room temperature for 2 h, filtered under vacuum and the captured solid washed with THF. The combined liquors were concentrated to afford 919 mg (100%) of 2-bromo-1-(4-(heptyloxy)phenyl)ethanone INT-4 as a yellow oil. LCMS-ESI (m/z) calculated for $C_{15}H_{21}BrO_2$: 313.2. found 313.0 $[M+H]^+$, $t_R$=2.12 min. (Method 4).

(S)-2-(4-(heptyloxy)phenyl)-2-oxoethyl 4-(2-(4-(tert-butyl)benzamido)-3-methoxy-3-oxopropyl)benzoate

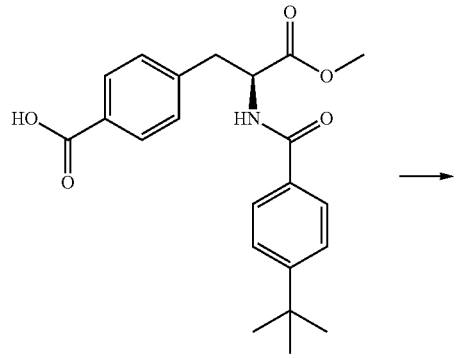

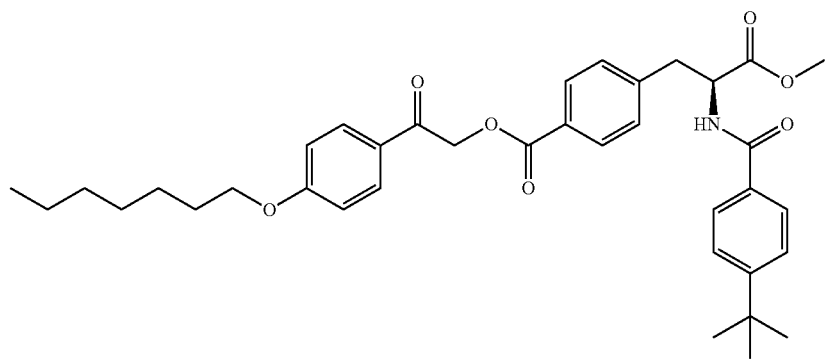

A solution of 2-bromo-1-(4-(heptyloxy)phenyl)ethanone, INT-4 (166 mg, 0.45 mmol) in acetonitrile (1 mL) was added to a solution of (S)-4-(2-(4-(tert-butyl)benzamido)-3-methoxy-3-oxopropyl)benzoic acid INT-1 (190 mg, 0.50 mmol) and TEA (75.0 μl, 0.54 mmol) in acetonitrile (4 mL). The reaction mixture was stirred at room temperature for 18 h then poured onto 0.5 M citric acid (30 mL) and extracted with EA (3×25 mL). The combined organics were dried over MgSO$_4$, filtered and concentrated. The residue was triturated with Et$_2$O (10 mL) and the filtrate concentrated to afford 159 mg (49%) of (S)-2-(4-(heptyloxy)phenyl)-2-oxoethyl 4-(2-(4-(tert-butyl)benzamido)-3-methoxy-3-oxopropyl)benzoate as a white solid. LCMS-ESI (m/z) calculated for C$_{37}$H$_{45}$NO$_7$: 615.8. found 616.0 [M+H]$^+$, t$_R$=2.76 min. (Method 4).

(S)-methyl 2-(4-(tert-butyl)benzamido)-3-(4-(4-(4-(heptyloxy)phenyl)oxazol-2-yl)phenyl)propanoate

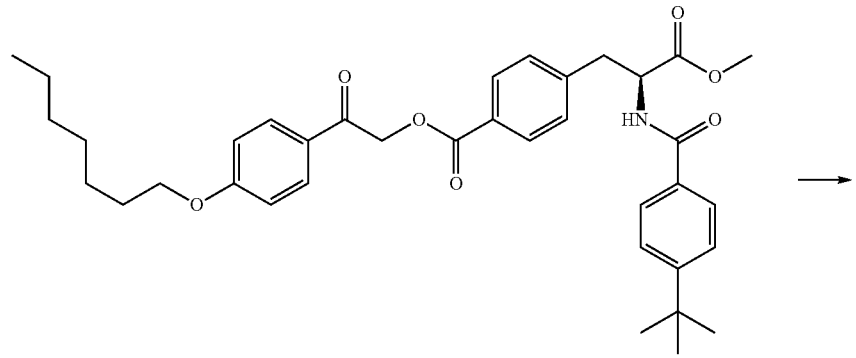

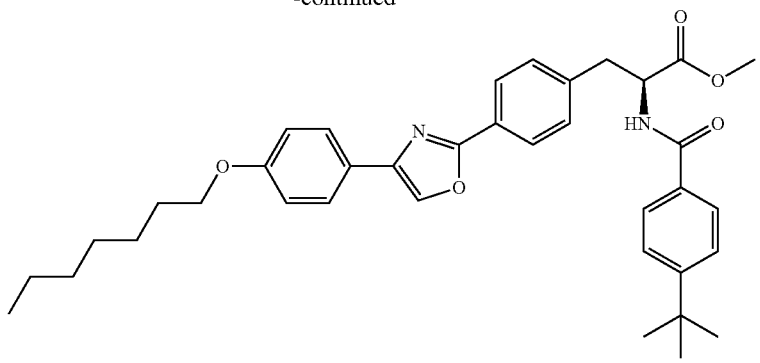

To boron trifluoride diethyl etherate (33.3 μl, 0.27 mmol) was added a mixture of acetamide (763 mg, 12.9 mmol) and (S)-2-(4-(heptyloxy)phenyl)-2-oxoethyl 4-(2-(4-(tert-butyl)benzamido)-3-methoxy-3-oxopropyl)benzoate (159 mg, 0.26 mmol). The reaction mixture was stirred at 140° C. for 1 h. The reaction mixture was allowed to cool to room temperature, diluted with EA (15 mL) and extracted with NaHCO$_3$ (3×15 mL) and brine (15 mL). The combined organics were dried over MgSO$_4$, filtered and concentrated. The residue was recrystallized from Et$_2$O (5 mL), filtered and rinsed with Et$_2$O. The filtrate was concentrated to afford 55 mg (16%) of (S)-methyl 2-(4-(tert-butyl)benzamido)-3-(4-(4-(4-(heptyloxy)phenyl)oxazol-2-yl)phenyl)propanoate as an orange oil. LCMS-ESI (m/z) calculated for C$_{37}$H$_{44}$N$_2$O$_5$: 596.8. found 597.0 [M+H]$^+$, t$_R$=3.11 min. (Method 4).

Compound 77 was prepared from (S)-methyl 2-(4-(tert-butyl)benzamido)-3-(4-(4-(4-(heptyloxy)phenyl)oxazol-2-yl)phenyl)propanoate using General Procedure 4.

2-(4-bromophenyl)-2-oxoethyl 4-(heptyloxy)benzoate

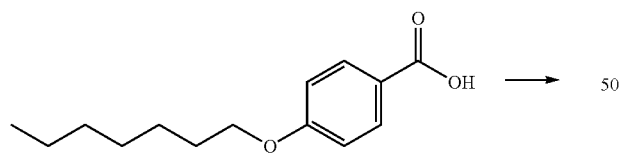

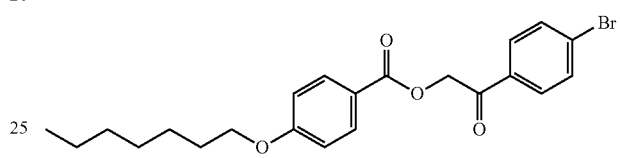

To stirring mixture of 4-(heptyloxy)benzoic acid (2.0 g, 8.46 mmol) in acetonitrile (30 mL) at room temperature was added TEA (1.24 mL, 8.87 mmol) drop wise. The reaction mixture was stirred at room temperature for 1 h, poured onto 0.05 M citric acid (100 mL) and EA (10 mL) then stirred for 10 min. The precipitate was isolated by filtration, washed with water (30 mL) and iso-hexanes (2×10 mL) then dried in air to afford 3.8 g (98%) of 2-(4-bromophenyl)-2-oxoethyl 4-(heptyloxy)benzoate. LCMS-ESI (m/z) calculated for C$_{22}$H$_{25}$BrO$_4$: 433.3. found 455.0/457.0 [M+Na]$^+$, t$_R$=3.21 min. (Method 4).

4-(4-bromophenyl)-2-(4-(heptyloxy)phenyl)oxazole

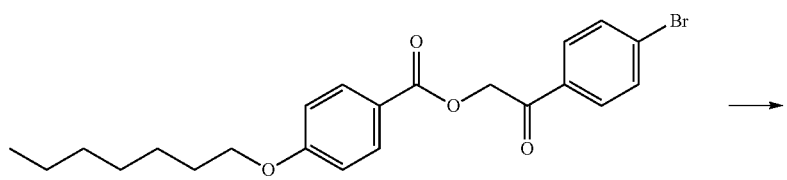

-continued

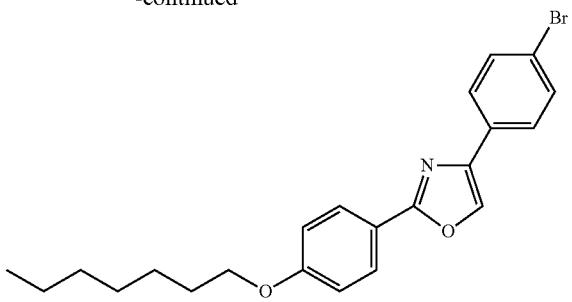

To boron trifluoride etherate (0.322 mL, 2.5 mmol) was added 2-(4-bromophenyl)-2-oxoethyl 4-(heptyloxy)benzoate (1.0 g, 2.3 mmol) and acetamide (4.91 g, 83.0 mmol) in DCM (10 mL). The reaction mixture was heated to 50° C. then 140° C. for 16 h, DCM was distilled off. The reaction mixture was cooled, diluted with acetonitrile and stirred at room temperature for 1 h. The precipitate was isolated by filtration to afford 273 mg (23%) of 4-(4-bromophenyl)-2-(4-(heptyloxy)phenyl)oxazole as a brown solid. LCMS-ESI (m/z) calculated for $C_{22}H_{24}BrNO_2$: 414.3. found 414.0 [M+H]$^+$, $t_R$=3.00 min. (Method 4).

(S)-methyl 2-((tert-butoxycarbonyl)amino)-3-(4-(2-(4-(heptyloxy)phenyl)oxazol-4-yl)phenyl)propanoate

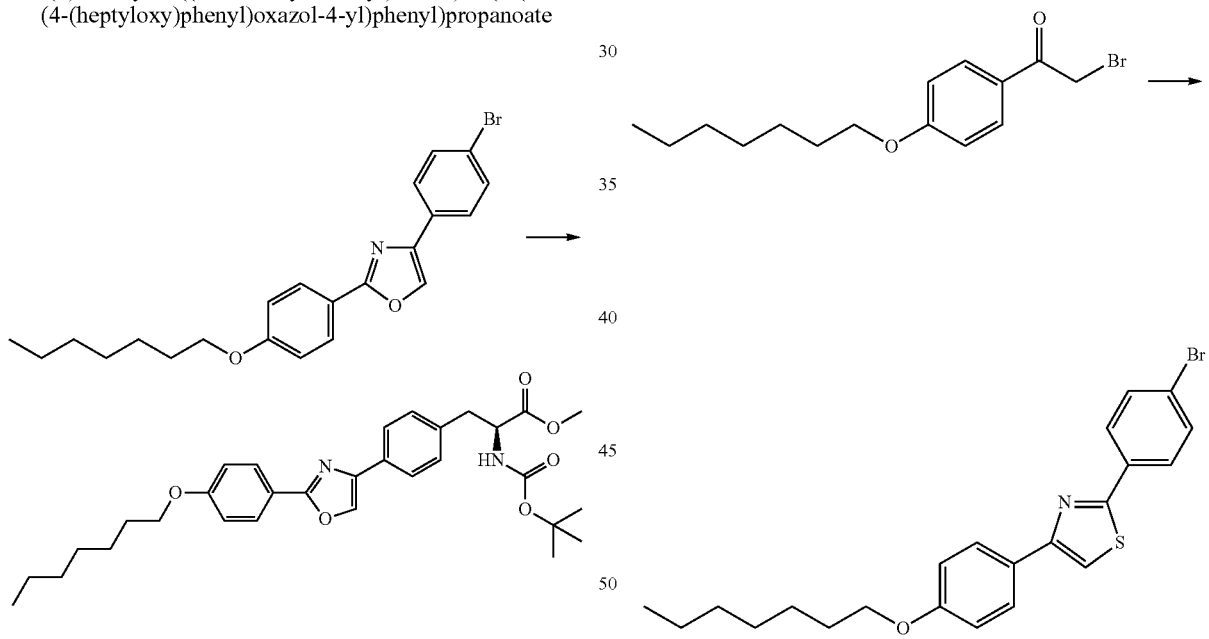

To zinc (104 mg, 1.59 mmol) stirring in DMF (1.5 mL) was added iodine (20.2 mg, 0.08 mmol). After the color disappeared, (R)-methyl 2-((tert-butoxycarbonyl)amino)-3-iodopropanoate (175 mg, 0.53 mmol) and further iodine (20.2 mg, 0.08 mmol) were added. After 30 min, the mixture was de-gassed by bubbling through N$_2$ then treated with 4-(4-bromophenyl)-2-(4-(heptyloxy)phenyl)oxazole (220 mg, 0.53 mmol), Pd$_2$dba$_3$ (12.2 mg, 0.01 mmol) and dicyclohexyl(2',6'-dimethoxy-[1,1'-biphenyl]-2-yl)phosphine (10.9 mg, 0.03 mmol) followed by THF (1 mL). The reaction mixture was heated to 50° C. for 2 h, cooled to room temperature and purified by column chromatography (gradient of 15-95% EA in iso-hexanes) to afford 188 mg (65%) of (S)-methyl 2-((tert-butoxycarbonyl)amino)-3-(4-(2-(4-(heptyloxy)phenyl)oxazol-4-yl)phenyl)propanoate. LCMS-ESI (m/z) calculated for $C_{31}H_{40}N_2O_6$: 536.6. found 537.0 [M+H]$^+$, $t_R$=3.72 min. (Method 11).

Compound 78 was prepared from (S)-methyl 2-((tert-butoxycarbonyl)amino)-3-(4-(2-(4-(heptyloxy)phenyl)oxazol-4-yl)phenyl)propanoate and 4-(tert-butyl)benzoic acid using General Procedures 8, 7 then 4.

2-(4-bromophenyl)-4-(4-(heptyloxy)phenyl) thiazole

To a stirring solution of 2-bromo-1-(4-(heptyloxy)phenyl) ethanone INT-4 (1.37 g, 4.38 mmol) in EtOH (10 mL) were added 4-bromobenzothioamide (0.95 g, 4.38 mmol) and isopropanol (10 mL). The reaction mixture was stirred at room temperature for 16 h. The solid was isolated by filtration, washed with EtOH (5 mL) then taken up in DCM (10 mL) and NaHCO$_3$ (20 mL) and stirred for 1 h at room temperature. The solid was isolated by filtration, washed with water (2×10 mL) and acetonitrile (2×4 mL) then dried to afford 1.02 g (52%) of 2-(4-bromophenyl)-4-(4-(heptyloxy)phenyl)thiazole as a white micro-crystalline solid. LCMS-ESI (m/z) calculated for $C_{22}H_{24}BrNO_S$: 429.1. found 430.0 [M+H]$^+$, $t_R$=3.20 min. (Method 4).

(S)-Methyl 2-((tert-butoxycarbonyl)amino)-3-(4-(4-(4-(heptyloxy)phenyl)thiazol-2-yl)phenyl)propanoate

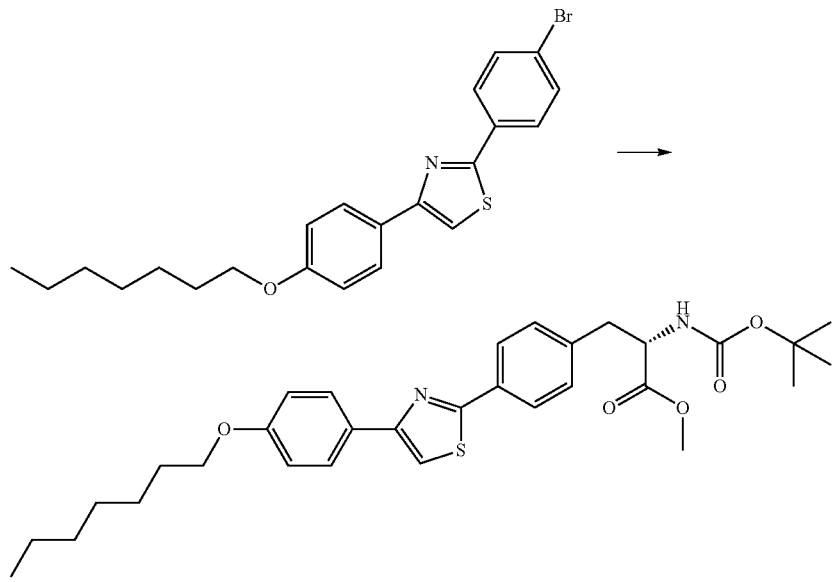

To a stirring suspension of zinc (228 mg, 3.49 mmol) in DMF (2 mL) was added diiodine (44 mg, 0.17 mmol). When the color was discharged, (R)-methyl 2-((tert-butoxycarbonyl)amino)-3-iodopropanoate (382 mg, 1.16 mmol) and further diiodine (44.2 mg, 0.17 mmol) were added. After stirring at room temperature for 30 min, the reaction mixture was de-gassed by bubbling through $N_2$ then 2-(4-bromophenyl)-4-(4-(heptyloxy)phenyl)thiazole (500 mg, 1.16 mmol), dicyclohexyl(2',6'-dimethoxy-[1,1'-biphenyl]-2-yl)phosphine (23.8 mg, 0.06 mmol), $Pd_2dba_3$ (26 mg, 0.03 mmol) and DMF (2 mL) were added. The reaction mixture was heated to 50° C. for 3 h, cooled and purified by column chromatography (10-80% EA in iso-hexanes) to afford 620 mg (96%) of (S)-methyl 2-((tert-butoxycarbonyl)amino)-3-(4-(4-(4-(heptyloxy)phenyl) thiazol-2-yl)phenylpropanoate. LCMS-ESI (m/z) calculated for $C_{31}H_{40}N_2O_5S$: 552.3; no ion observed, $t_R$=3.37 min. (Method 4).

Compound 79 was prepared from (S)-methyl 2-((tert-butoxycarbonyl)amino)-3-(4-(4-(4-(heptyloxy) phenyl) thiazol-2-yl) phenyl propanoate and 4-(tert-butyl)benzoic acid using General Procedures 8, 7 then 4.

4-(heptyloxy)benzothioamide

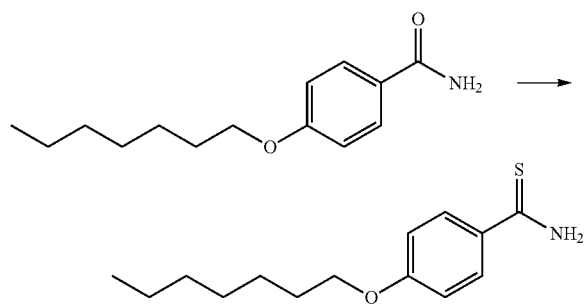

To stirring suspension of 4-(heptyloxy)benzamide (1.24 g, 5.29 mmol) in DME (20 mL) and THF (10 mL) was added 2,4-bis(4-phenoxyphenyl)-1,3,2,4-dithiadiphosphetane 2,4-disulfide (2.80 g, 5.29 mmol). The reaction mixture was stirred at room temperature for 16 h. The reaction mixture was concentrated onto silica and purified by column chromatography (0-60% EA in iso-hexanes) to afford 1.4 g (62%) of 4-(heptyloxy)benzothioamide as a yellow waxy solid. LCMS-ESI (m/z) calculated for $C_{14}H_{21}NOS$: 251.4. found 252.0 $[M+H]^+$, $t_R$=3.13 min. (Method 6).

4-(4-bromophenyl)-2-(4-(heptyloxy)phenyl) thiazole

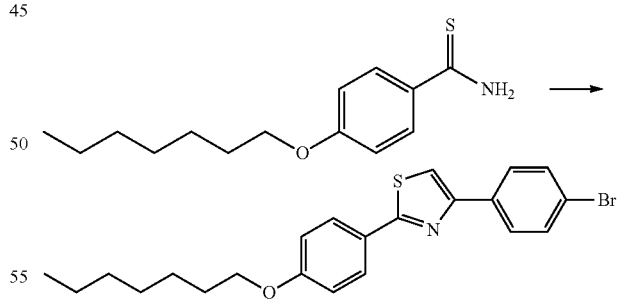

To a stirring mixture of 4-(heptyloxy)benzothioamide (1.30 g, 5.17 mmol) in isopropanol (20 mL) was added 2-bromo-1-(4-bromophenyl)ethanone (1.44 g, 5.17 mmol). The precipitate was collected by filtration and washed with EtOH (2×5 mL). The filter cake was slurried with $NaHCO_3$ (2×20 mL), water (2×20 mL) then EtOH (2×5 mL) and dried to afford 926 mg (41%) of 4-(4-bromophenyl)-2-(4-(heptyloxy)phenyl)thiazole as a pale yellow powder. LCMS-ESI (m/z) calculated for $C_{22}H_{24}BrNOS$: 429.1. found 430.0 $[M+H]^+$, $t_R$=3.41 min. (Method 4).

(S)-Methyl 2-((tert-butoxycarbonyl)amino)-3-(4-(2-(4-(heptyloxy)phenyl) thiazol-4-yl)phenyl)propanoate

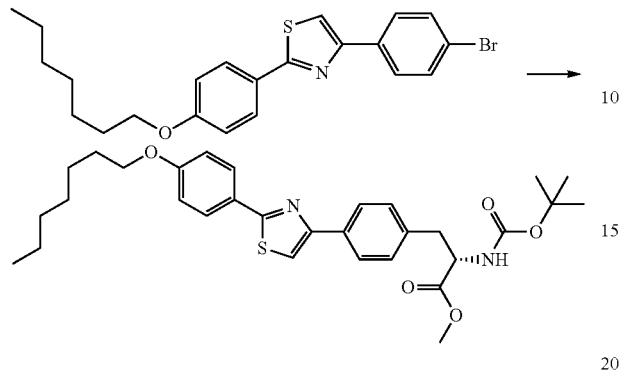

To a stirring mixture of zinc (182 mg, 2.79 mmol) in DMF (2 mL) was added diiodine (35.4 mg, 0.14 mmol). When the color was discharged, further diiodine (35.4 mg, 0.14 mmol) and (R)-methyl 2-((tert-butoxycarbonyl)amino)-3-iodopropanoate (306 mg, 0.93 mmol) were added. After 30 min, DMF (1 mL) was added and the mixture de-gassed by bubbling through $N_2$. To the reaction mixture were added 4-(4-bromophenyl)-2-(4-(heptyloxy)phenyl)thiazole (400 mg, 0.93 mmol), $Pd_2dba_3$ (21 mg, 0.02 mmol) and dicyclohexyl(2',6'-dimethoxy-[1,1'-biphenyl]-2-yl)phosphine (19 mg, 0.05 mmol), the mixture was further de-gassed then heated to 50° C. for 3 h. The reaction mixture was cooled and purified by column chromatography (10-80% EA in iso-hexanes). The product obtained was taken into DCM (4 mL) and washed with water (20 mL) and dried through a hydrophobic frit. The organics were suspended in ACN (4 mL) and concentrated to afford 432 mg (83%) of (S)-methyl 2-((tert-butoxycarbonyl)amino)-3-(4-(2-(4-(heptyloxy)phenyl)thiazol-4-yl)phenyl)propanoate as a yellow foam. LCMS-ESI (m/z) calculated for $C_{31}H_{40}N_2O_5S$: 552.7; no ion observed, $t_R$=3.36 min. (Method 4).

Compound 80 was prepared from (S)-methyl 2-((tert-butoxycarbonyl)amino)-3-(4-(2-(4-(heptyloxy)phenyl)thiazol-4-yl)phenyl)propanoate and 4-(tert-butyl)benzoic acid using General Procedures 8, 7 then 4.

4-(5-(4-(heptyloxy)phenyl) thiazol-2-yl)benzaldehyde

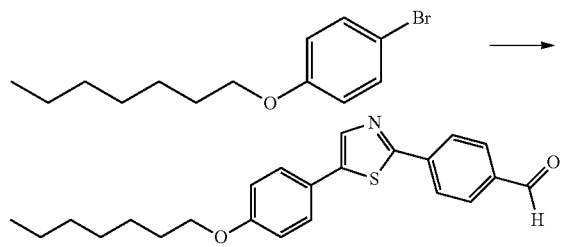

To a stirring suspension of 4-(thiazol-2-yl)benzaldehyde (349 mg, 1.84 mmol), tricyclohexylphosphine (27 mg, 0.07 mmol), pivalic acid (64.2 µl, 0.55 mmol), potassium carbonate (382 mg, 2.77 mmol) and palladium (II) acetate (8 mg, 0.04 mmol) in DMA (5.15 mL) under nitrogen was added a solution of 1-bromo-4-(heptyloxy)benzene (500 mg, 1.84 mmol) in DMA (1 mL). The reaction mixture was evacuated and purged with nitrogen 3 times then heated at 100° C. for 6 h. Once cooled, the reaction mixture was diluted with EA (40 mL), washed with water (3×40 mL) and brine (40 mL). The organic phase was dried over $MgSO_4$, filtered and concentrated in vacuo to afford a brown-green solid. The crude product was purified by chromatography (0-50% EA in hexanes) to afford 270 mg (37%) of 4-(5-(4-(heptyloxy)phenyl)thiazol-2-yl)benzaldehyde as an iridescent yellow solid. LCMS-ESI (m/z) calculated for $C_{23}H_{25}NO_2S$: 379.5. found 380.0 $[M+H]^+$, $t_R$=2.99 min. (Method 8).

Methyl 2-((tert-butoxycarbonyl)amino)-3-(4-(5-(4-(heptyloxy)phenyl)thiazol-2-yl)phenyl) acrylate

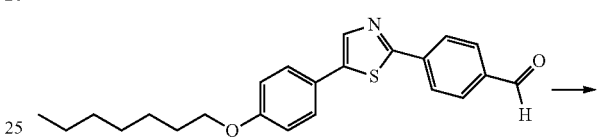

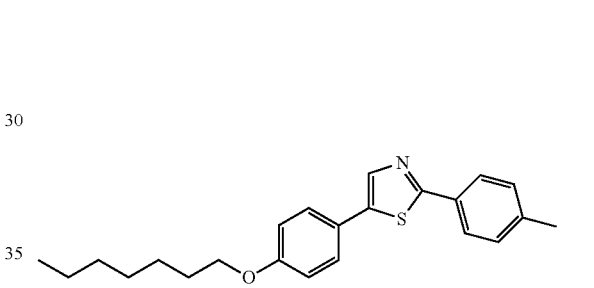

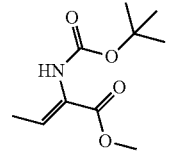

A stirring mixture of 1,1,3,3-tetramethylguanidine (86 µl, 0.69 mmol) was added to a suspension of 4-(5-(4-(heptyloxy)phenyl)thiazol-2-yl)benzaldehyde (260 mg, 0.685 mmol) and methyl 2-((tert-butoxycarbonyl)amino)-2-(dimethoxyphosphoryl)acetate (185 mg, 0.62 mmol) in anhydrous THF (10 mL) under nitrogen, at −70° C. The reaction mixture was stirred at −70° C. for 1 h then at room temperature for 18 h. The reaction mixture was diluted with DCM (50 mL), washed with water (50 mL), passed through a phase separation cartridge and the organic phase concentrated in vacuo to afford a yellow solid. The solid was triturated with EA/EtOH (20 mL) and the collected solid washed with EtOH (10 mL) and $Et_2O$ to afford 284 mg (79%) of methyl 2-((tert-butoxycarbonyl)amino)-3-(4-(5-(4-(heptyloxy)phenyl)thiazol-2-yl)phenyl) acrylate as a yellow solid. LCMS-ESI (m/z) calculated for $C_{31}H_{38}N_2O_5S$: 550.7. found 551.0 $[M+H]^+$, $t_R$=3.11 min. (Method 8).

Methyl 2-((tert-butoxycarbonyl)amino)-3-(4-(5-(4-(heptytyloxy)phenyl)thiazol-2-yl)phenyl) propanoate

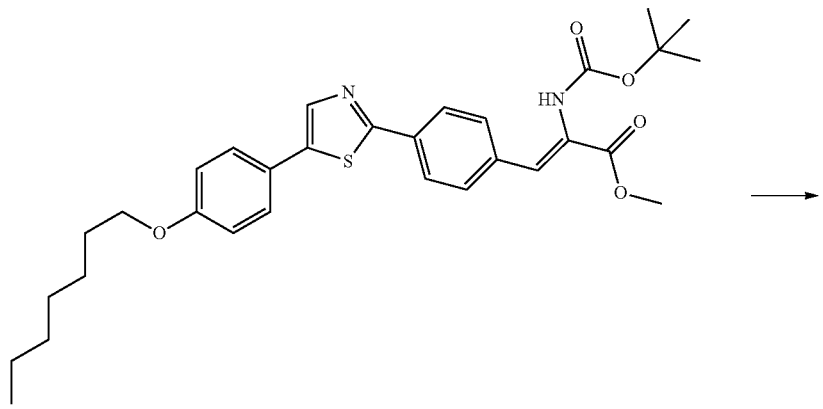

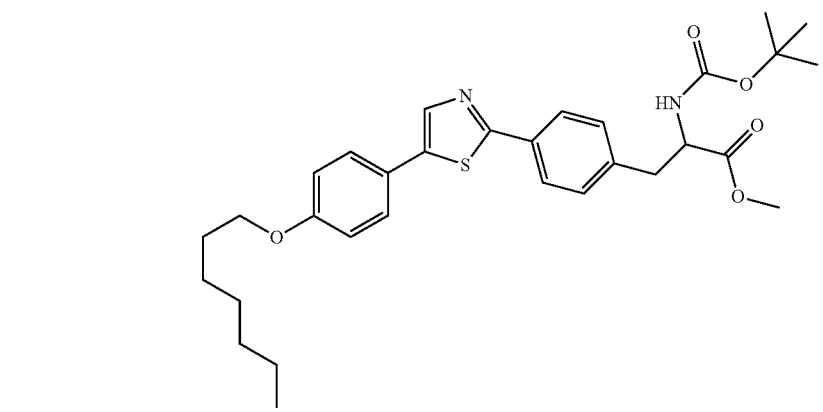

A stirring mixture of Methyl 2-((tert-butoxycarbonyl)amino)-3-(4-(5-(4-(heptyloxy)phenyl)thiazol-2-yl)phenyl) acrylate (50 mg, 0.091 mmol) dissolved in dioxane (5 mL) was hydrogenated using an H-Cube hydrogenator (10% Pd/C, 30×4 mm, full hydrogen, 40° C., 1 mL/min). The reaction mixture was concentrated in vacuo to afford 21 mg (29%) of methyl 2-((tert-butoxycarbonyl)amino)-3-(4-(5-(4-(heptyloxy)phenyl)thiazol-2-yl)phenyl)propanoate as a yellow solid. LCMS-ESI (m/z) calculated for $C_{31}H_{40}N_2O_5S$: 552.7. found 553.0 [M+H]$^+$, $t_R$=1.85 min. (Method 8).

Compound 81 was prepared from Methyl 2-((tert-butoxycarbonyl)amino)-3-(4-(5-(4-(heptyloxy) phenyl) thiazol-2-yl) phenyl) propanoate and 4-(tert-butyl)benzoyl chloride using General Procedures 8, 3 then 4.

Compound 82 was prepared in a similar fashion to Compound 81 using 4-(2-(4-(heptyloxy) phenyl) thiazol-5-yl)benzaldehyde in place of 4-(5-(4-(heptyloxy)phenyl)thiazol-2-yl) benzaldehyde.

(S)-methyl 2-(4-(tert-butyl)benzamido)-3-(4-(5-(4-(heptyloxy)phenyl)-1,3,4-thiadiazol-2-yl)phenyl) propanoate

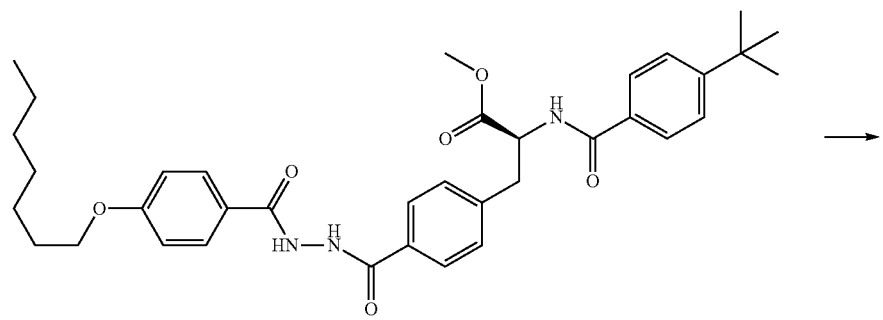

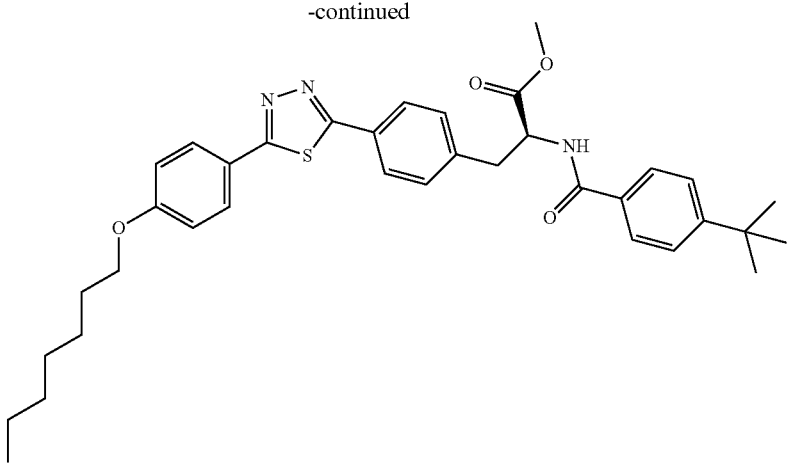

Prepared using INT-3: To a stirring solution of 2,4-bis(4-methoxyphenyl)-1,3,2,4-dithiadiphosphetane 2,4-disulfide (65.7 mg, 0.16 mmol) in THF (3 mL) was added (S)-methyl 2-(4-(tert-butyl)benzamido)-3-(4-(2-(4-(heptyloxy)benzoyl)hydrazinecarbonyl)phenyl)propanoate INT-3 (100.0 mg, 0.16 mmol) and the mixture heated to 65° C. After 1 h, the reaction mixture was concentrated and purified by column chromatography (10-100% EA in iso-hexanes) to afford 37.0 mg (29%) of (S)-methyl 2-(4-(tert-butyl)benzamido)-3-(4-(5-(4-(heptyloxy)phenyl)-1,3,4-thiadiazol-2-yl)phenyl)propanoate as a yellow solid. LCMS-ESI (m/z) calculated for $C_{36}H_{43}N_3O_4S$: 613.8; no ion observed, $t_R$=3.31 min. (Method 4).

Compound 83 was prepared from (S)-methyl 2-(4-(tert-butyl) benzamido)-3-(4-(5-(4-(heptyloxy) phenyl)-1,3,4-thiadiazol-2-yl)phenyl)propanoate using General Procedure 4.

Compound 84 was prepared using 3-bromo-5-chloro-1,2,4-thiadiazole, (4-(heptyloxy)phenyl)boronic acid and INT-13 using General Procedures 10, 10, and 8 sequentially.

(S)-tert-butyl 2-(((benzyloxy)carbonyl)amino)-3-(4-(((trifluoromethyl)sulfonyl)oxy)-phenyl) propanoate (INT-5)

Prepared using General Procedure 9: A stirred solution of (S)-tert-butyl 2-(((benzyloxy)carbonyl)amino)-3-(4-hydroxyphenyl)propanoate hydrate (25 g, 64.2 mmol) in DCM (100 mL) was treated with $MgSO_4$ (4.01 g, 33.7 mmol). After 15 min, the mixture was filtered and washed with DCM (2×20 mL). The organics were treated with N-ethyl-N-isopropylpropan-2-amine (17.41 g, 134.7 mmol) and stirred. This solution was treated with 1,1,1-trifluoro-N-phenyl-N-((trifluoromethyl)sulfonyl)methanesulfonamide (26.44 g, 74.01 mmol) and the mixture was allowed to stir overnight at room temperature. The mixture was treated with water (50 mL) and saturated aqueous $NaHCO_3$ (20 mL) and stirred vigorously for 10 min. The layers were separated and the organic layer was further washed with saturated aqueous $NaHCO_3$ (2×50 mL), water (50 mL), and saturated aqueous $NaHCO_3$ (50 mL) and concentrated. The compound was purified by chromatography (EA/hexanes) to afford 26.85 g (79%) of (S)-tert-butyl 2-(((benzyloxy)carbonyl)amino)-3-(4-(((trifluoromethyl)sulfonyl)oxy)phenyl) propanoate INT-5. LCMS-ESI (m/z) calculated for $C_{22}H_{24}F_3NO_7S$: 503.1. found 526.1 [M+Na]$^+$, $t_R$=4.12 min (Method 3).

(S)-tert-butyl 2-(((benzyloxy)carbonyl)amino)-3-(4-(4,4,5,5-tetramethyl-1, 3, 2-dioxaborolan-2-yl)phenyl)propanoate (INT-6)

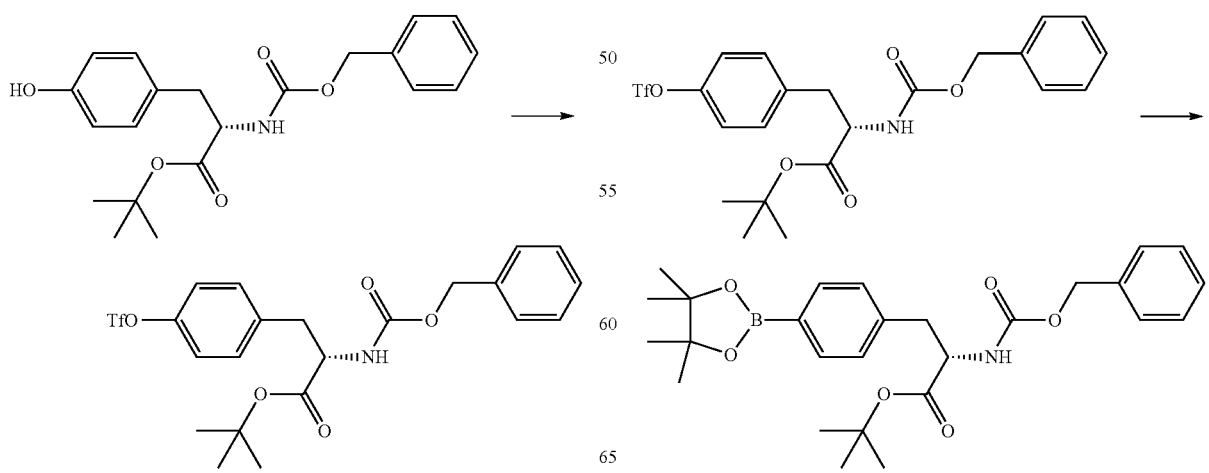

A solution of (S)-tert-butyl 2-(((benzyloxy) carbonyl)amino)-3-(4-(((trifluoromethyl)sulfonyl)oxy)phenyl)propanoate INT-5 (26.85 g, 53.4 mmol), potassium acetate (15.71 g, 160.1 mmol), bis-pinacolatoborane (27.1 g, 106.7 mmol) and DMSO (100 mL) was degassed with a steady flow of nitrogen gas for 5 minutes. To this solution was added PdCl$_2$(dppf) (1.95 g, 2.67 mmol) and the solution further degassed and kept under an atmosphere of nitrogen. The mixture was heated at 100° C. for 18 h then cooled to room temperature and diluted with EA (50 mL) and washed with saturated aqueous NaHCO$_3$ (20 mL), water (3×30 mL), dried over MgSO$_4$, filtered, and the solvent removed under reduced pressure. The compound was purified by column chromatography to give 11.10 g (41%) of (S)-tert-butyl 2-(((benzyloxy)carbonyl)amino)-3-(4-(4,4,5,5-tetramethyl-1,3,2-dioxaborolan-2-yl)phenyl)propanoate INT-6 as an oil. LCMS-ESI (m/z) calculated for C$_{27}$H$_{36}$BNO$_6$: 481.3. found 504.3 [M+Na]$^+$, t$_R$=4.21 min (Method 3). $^1$H NMR (400 MHz, DMSO) δ 7.72 (d, J=8.3 Hz, 1H), 7.60 (d, J=8.0 Hz, 2H), 7.42-7.11 (m, 6H), 4.98 (s, 2H), 4.22-4.08 (m, 1H), 3.03 (dd, J=13.7, 5.2 Hz, 1H), 2.85 (dd, J=13.6, 10.1 Hz, 1H), 1.36 (s, 6H), 1.30 (s, 9H), 1.22-1.13 (m, 6H).

(S)-Tert-butyl 2-(((benzyloxy)carbonyl)amino)-3-(4-(5-bromopyrimidin-2-yl)phenyl) propanoate (INT-7)

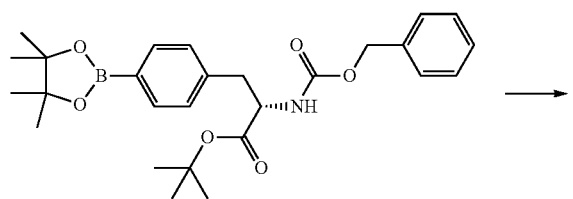

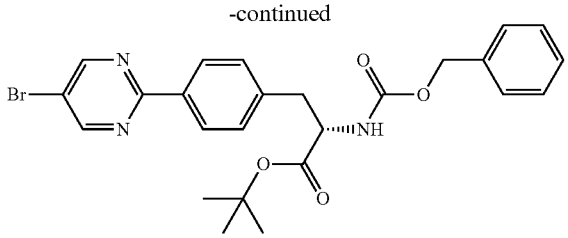

Prepared using General Procedure 10: A stirred mixture of (S)-tert-butyl 2-(((benzyloxy)carbonyl)amino)-3-(4-(4,4,5,5-tetramethyl-1,3,2-dioxaborolan-2-yl)phenyl) propanoate INT-6 (21.7 g, 45.0 mmol) and 5-bromo-2-iodopyrimidine (15.4 g, 54.0 mmol) in dioxane (400 mL) with sodium carbonate decahydrate (25.7 g, 90 mmol) in water (100 mL) was de-gassed. PdCl$_2$(dppf) (0.99 g, 1.4 mmol) was added and the mixture further de-gassed then heated to reflux for 5 h. The mixture was allowed to cool while stirring overnight. The mixture was poured onto water (1 L) and EA (300 mL) and stirred for 30 min. The mixture was filtered and the layers were separated. The aqueous layer was further extracted with EA (2×200 mL) and the combined organic layers were washed with water (2×100 mL) then brine (50 mL), dried over MgSO$_4$ and concentrated. Column chromatography (EA/hexanes) gave 14.84 g (63%) of (S)-tert-butyl 2-(((benzyloxy)carbonyl)amino)-3-(4-(5-bromopyrimidin-2-yl)phenyl) propanoate INT-7. LCMS-ESI (m/z) calculated for C$_{25}$H$_{26}$BrN$_3$O$_4$: 511.1. found 534.0 [M+Na]$^+$, t$_R$=2.97 min (Method 11).

(S)-Tert-butyl 2-(((benzyloxy)carbonyl)amino)-3-(4-(5-(4-(heptyloxy)phenyl)pyrimidin-2-yl) phenyl) propanoate (INT-8)

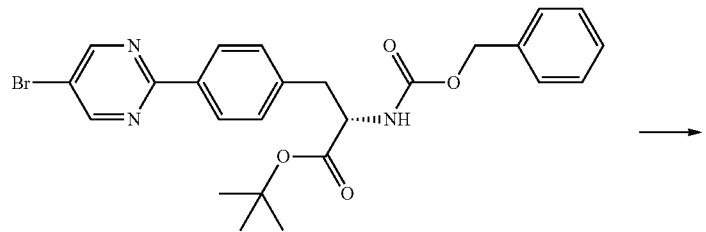

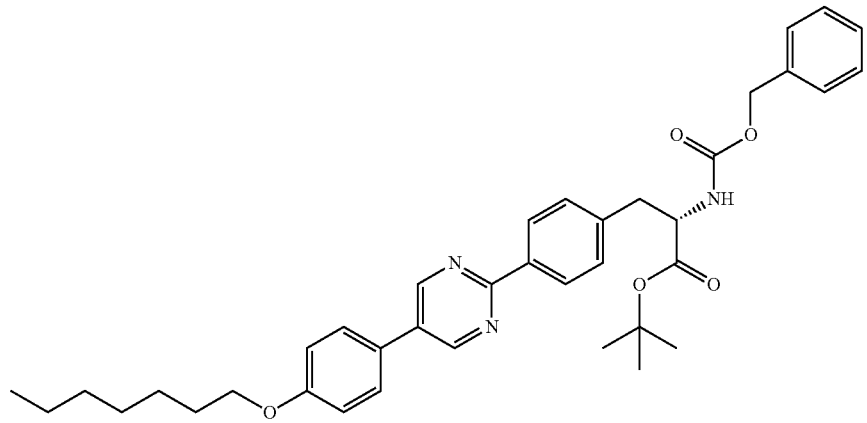

Prepared using General Procedure 10: A stirred solution of (S)-tert-butyl 2-(((benzyloxy)carbonyl)amino)-3-(4-(5-bromopyrimidin-2-yl)phenyl)propanoate INT-7 (759 mg, 1.48 mmol), (4-(heptyloxy)phenyl)boronic acid (455 mg, 1.93 mmol) and sodium bicarbonate (311 mg, 3.70 mmol) in acetonitrile (5 ml), THF (5 ml), and water (4 ml) was degassed with $N_2$ for 5 min. Pd(dppf)$Cl_2$ (108 mg, 0.15 mmol) was added and the reaction was heated to 110° C. in the microwave for 50 min. The reaction was diluted with EA and water then filtered. The organic phase was dried over MgSO4, filtered, and concentrated. The crude product was purified by chromatography on silica gel (EA/hexanes) to afford 591 mg (62%) of (S)-tert-butyl 2-(((benzyloxy)carbonyl)amino)-3-(4-(5-(4-(heptyloxy)phenyl)pyrimidin-2-yl)phenyl) propanoate INT-8 as a yellow solid. LCMS-ESI (m/z) calculated for $C_{38}H_{45}N_3O_5$: 623.8; no m/z observed, $t_R$=3.42 min (Method 8).

(S)-Tert-butyl 2-amino-3-(4-(5-(4-(heptyloxy)phenyl)pyrimidin-2-yl)phenyl) propanoate (INT-9)

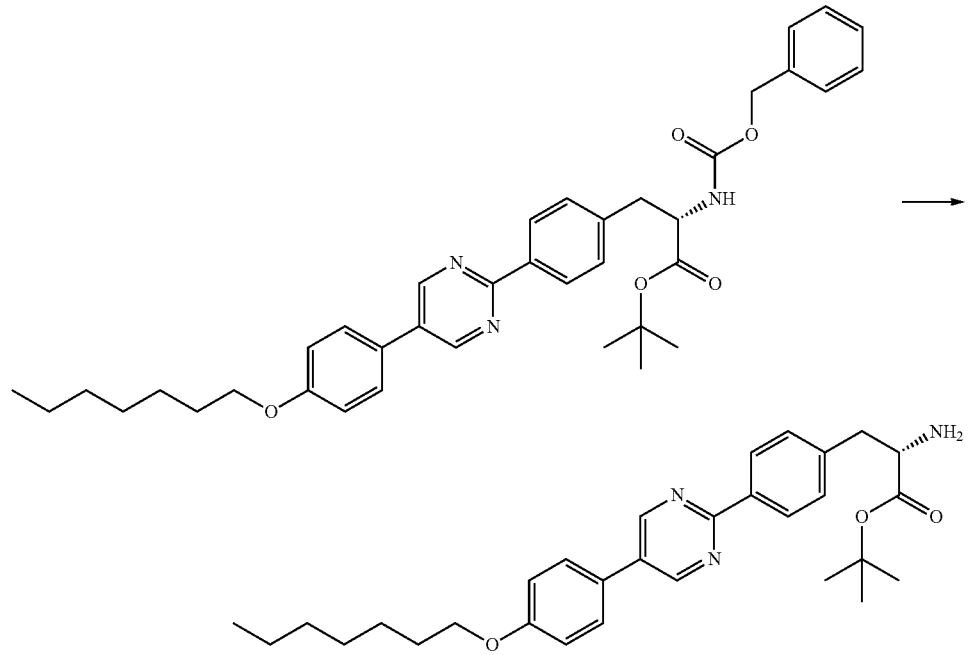

To a stirred solution of (S)-tert-butyl 2-(((benzyloxy)carbonyl)amino)-3-(4-(5-(4-(heptyloxy)phenyl)pyrimidin-2-yl)phenyl)propanoate INT-8 (591 mg, 0.95 mmol) in EA (25 ml) was added Pd/C (101 mg, 0.09 mmol) and the suspension degassed with $H_2$. The mixture was stirred vigorously under an atmosphere of $H_2$ overnight then filtered through celite and the filtrate was concentrated to give 405 mg (83%) of (S)-tert-butyl 2-amino-3-(4-(5-(4-(heptyloxy)phenyl)pyrimidin-2-yl)phenyl)propanoate INT-9. LCMS-ESI (m/z) calculated for $C_{30}H_{39}N_3O_3$: 489.3. found: 490.2 [M+H]$^+$, $t_R$=2.35 min (Method 8).

(S)-2-(4-(tert-butyl)benzamido)-3-(4-(5-(4-(heptyloxy)phenyl)pyrimidin-2-yl)phenyl)propanoic acid
(Compound 85)

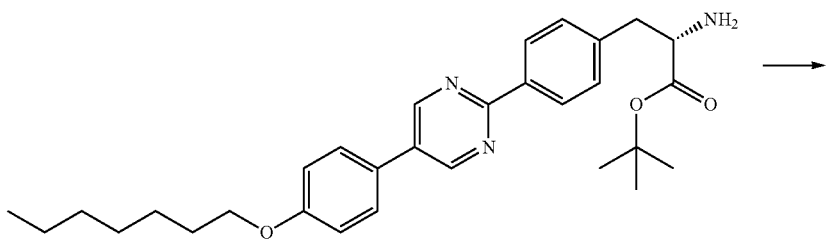

-continued

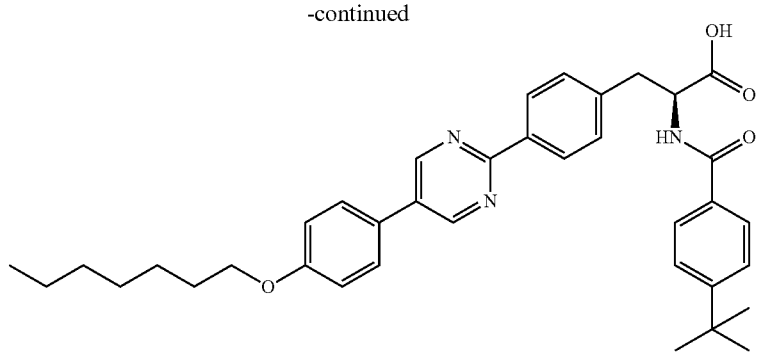

A stirred solution of (S)-tert-butyl 2-amino-3-(4-(5-(4-(heptyloxy)phenyl)pyrimidin-2-yl)phenyl)propanoate INT-9 (1.34 g, 2.74 mmol) and 4-(tert-butyl)benzoic acid (0.54 g, 3.01 mmol) in DMF (5 mL) and N-ethyl-N-isopropylpropan-2-amine (1.01 ml, 5.47 mmol) was treated with HATU (1.09 g, 2.87 mmol). After stirring for 1 h, the mixture was treated with water (60 mL) and iso-hexanes (20 mL) and stirred for 1 h. The product was collected by filtration, washed with water (3×10 mL) then iso-hexanes (10 mL) and dried in the vacuum oven. The ester was taken up in DCM (5 mL) and treated with TFA (5 mL). After 2 h, the mixture was treated with toluene (5 mL) and evaporated. The residue was taken up in DMSO (6 mL) then treated with water (20 mL) and stirred for 1 h. The product was collected by filtration, washed with water (3×15 mL) then acetonitrile (2×5 mL), and dried in the vacuum oven to give 1.40 g (85%) of (S)-2-(4-(tert-butyl)benzamido)-3-(4-(5-(4-(heptyloxy)phenyl)pyrimidin-2-yl)phenyl)propanoic acid Compound 85 as a white solid. LCMS-ESI (m/z) calculated for $C_{37}H_{43}N_3O_4$; 593.3. found: 594.0 $[M+H]^+$, $t_R$=11.18 min (Method 9) and 97% e.e. (Chiral Method). $^1$H NMR (400 MHz, DMSO-d6) δ 12.79 (br, s, 1H), 9.16 (s, 2H), 8.66 (d, J=8.2 Hz, 1H), 8.45-8.27 (m, 2H), 7.89-7.69 (m, 4H), 7.57-7.38 (m, 4H), 7.18-7.02 (m, 2H), 4.77-4.62 (m, 1H), 4.03 (t, J=6.5 Hz, 2H), 3.30-3.24 (m, 1H), 3.22-3.12 (m, 1H), 1.80-1.68 (m, 2H), 1.48-1.20 (m, 17H), 0.96-0.82 (m, 3H).

Compounds 86-102, 104-158 and 296 were prepared from (S)-tert-butyl 2-amino-3-(4-(5-(4-(heptyloxy) phenyl) pyrimidin-2-yl)phenyl)propanoate INT-8 using General Procedures 3 or 7 followed by 4 or 8.

(S)-Tert-butyl 2-(((benzyloxy)carbonyl)amino)-3-(4-(5-(4-(tert-butyl)phenyl)pyrimidin-2-yl) phenyl) propanoate (INT-10)

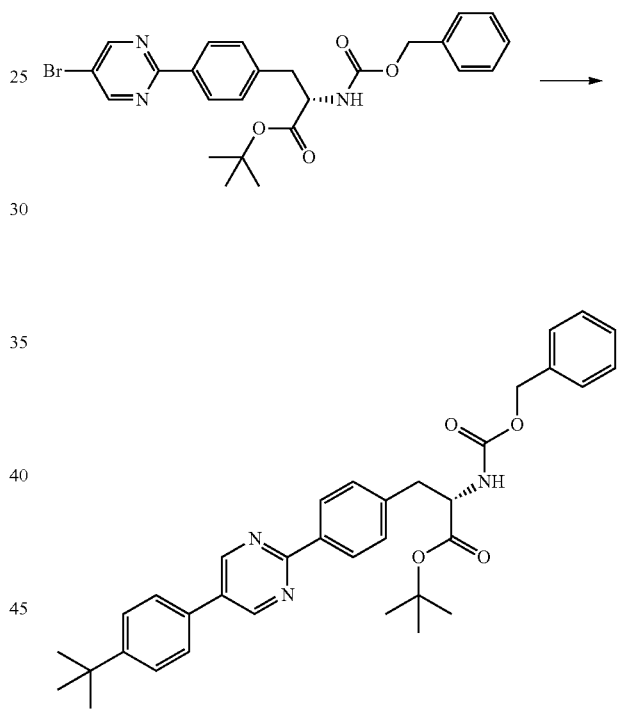

Prepared using General Procedure 10: A stirred solution of (S)-tert-butyl 2-(((benzyloxy)carbonyl)amino)-3-(4-(5-bromopyrimidin-2-yl)phenyl)propanoate INT-7 (0.96 g, 1.86 mmol), (4-(tert-butyl)phenyl)boronic acid (0.43 g, 2.42 mmol) and sodium bicarbonate (0.39 g, 4.66 mmol) in acetonitrile (5 ml), THF (5 ml) and water (5 ml) was degassed with $N_2$ for 5 min. Pd(dppf)Cl$_2$ (0.136 g, 0.186 mmol) was added and the reaction was heated to 110° C. in the microwave for 45 min. The reaction was diluted with EA (50 mL) and filtered over celite. The organic phase was washed with water (100 mL) and concentrated. The crude product was purified by chromatography on silica gel (EA/isohexanes) to afford 757 mg (70%) of (S)-tert-butyl 2-(((benzyloxy)carbonyl)amino)-3-(4-(5-(4-(tert-butyl)phenyl)pyrimidin-2-yl) phenyl) propanoate INT-10 as a white powder. LCMS-ESI (m/z) calculated for $C_{35}H_{39}N_3O_4$: 565.3; no m/z observed, $t_R$=3.39 min (Method 8).

(S)-Tert-butyl 2-amino-3-(4-(5-(4-(tert-butyl)phenyl)pyrimidin-2-yl)phenyl)-propanoate (INT-11)

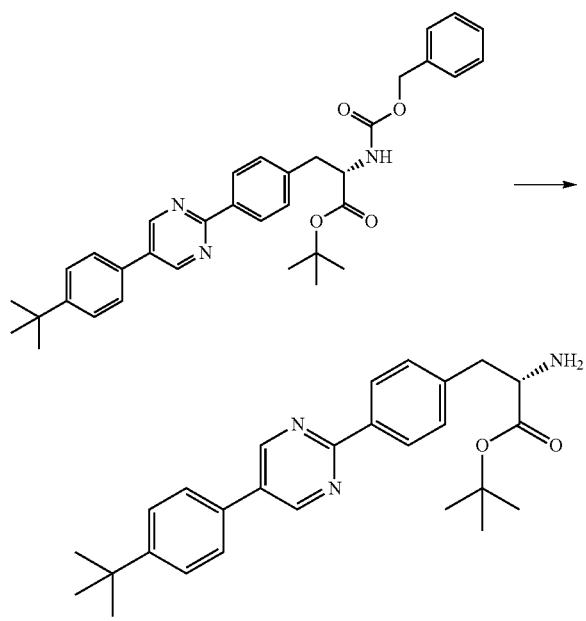

To a stirred solution of (S)-tert-butyl 2-(((benzyloxy)carbonyl)amino)-3-(4-(5-(4-(tert-butyl)phenyl)pyrimidin-2-yl)phenyl)propanoate INT-10 (757 mg, 1.34 mmol) in EA (100 ml) was added Pd/C (142 mg, 0.13 mmol) and the suspension degassed with $H_2$. The mixture was stirred vigorously under an atmosphere of $H_2$ overnight then filtered through celite and the filtrate was concentrated to give 532 mg (88%) of (S)-tert-butyl 2-amino-3-(4-(5-(4-(tert-butyl)phenyl)pyrimidin-2-yl)phenyl)propanoateINT-11. LCMS-ESI (m/z) calculated for $C_{27}H_{33}N_3O_2$: 431.3. found: 432.0 $[M+H]^+$, $t_R$=2.01 min (Method 4).

Compounds 159-181 were prepared from (S)-tert-butyl 2-amino-3-(4-(5-(4-(tert-butyl) phenyl)pyrimidin-2-yl)phenyl)propanoate INT-11 using General Procedures 3 or 7 followed by 4 or 8.

Compound 182 was prepared in a manner analogous to 165 starting from (R)-tert-butyl 2-(((benzyloxy)carbonyl)amino)-3-(4-hydroxyphenyl)propanoate.

Compound 183 was prepared from (S)-3-(4-(5-(4-(heptyloxy)phenyl)pyrimidin-2-yl)-2-(4-hydroxybenzamido)propanoic acid, Compound 114 using General Procedure 13.

Compounds 184-190 were prepared from (S)-tert-butyl 2-amino-3-(4-(5-(4-(heptyloxy)phenyl)pyrimidin-2-yl)phenyl)propanoate INT-9 using General Procedures 13 and 8 sequentially.

Compound 191 was prepared in a manner analogous to 85 starting from (R)-tert-butyl 2-(((benzyloxy)carbonyl)amino)-3-(4-hydroxyphenyl)propanoate.

(S)-2-(5-(tert-butyl)thiophene-2-carboxamido)-3-(4-(5-(4-(heptyloxy)phenyl)-pyrimidin-2-yl)phenyl)propanoic acid (Compound 192)

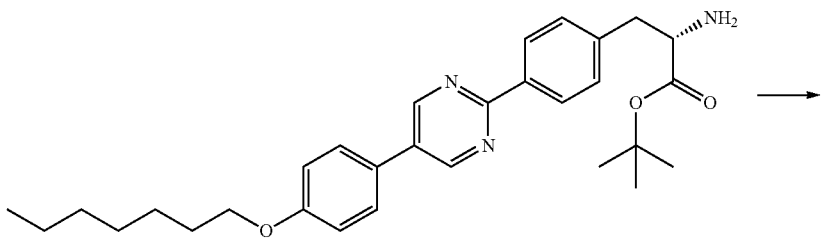

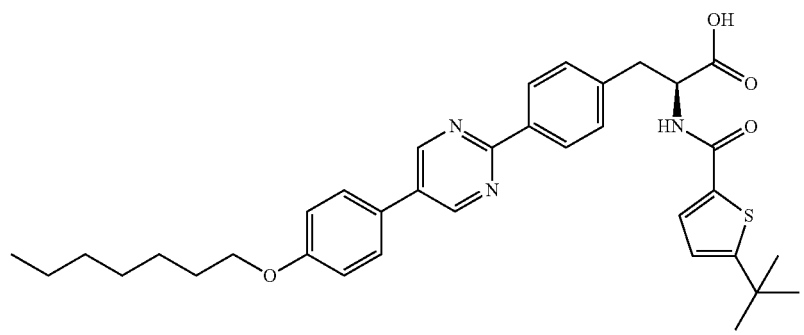

A stirring solution of (S)-tert-butyl 2-amino-3-(4-(5-(4-(heptyloxy)phenyl)pyrimidin-2-yl)phenyl)propanoate INT-9 (5.50 g, 11.23 mmol) and 5-(tert-butyl)thiophene-2-carboxylic acid (2.13 g, 11.57 mmol) in DMF (50 mL) and DIEA (6.22 ml, 33.70 mmol) was treated portion wise with HATU (4.48 g, 11.79 mmol). After stirring for 1 h, the mixture was treated with water (200 mL) and iso-hexanes (20 mL) and stirred for 10 min. The product was collected by filtration, washed with iso-hexanes (2×30 mL), water (2×50 mL) then MeOH (20 mL) and iso-hexanes (30 mL). The ester was taken up in DCM (50 mL) and treated with TFA (10 mL). After 1 h, additional TFA (15 mL) was added. After a further 5 h, the mixture was treated with toluene (20 mL) and concentrated. The residue was washed with acetonitrile (25 mL) then taken up in DMSO (20 mL) then treated with water (100 mL) and stirred for 1 h. The product was collected by filtration, washed with water (4×50 mL) then acetonitrile (3×30 mL), and dried in a vacuum oven to give 5.30 g (75%) of (S)-2-(5-(tert-butyl)thiophene-2-carboxamido)-3-(4-(5-(4-(heptyloxy)phenyl)pyrimidin-2-yl)phenyl)propanoic acid, Compound 192 as an off-white solid. LCMS-ESI (m/z) calculated for $C_{35}H_{41}N_3O_4S$: 599.3; no m/z observed, $t_R$=11.10 min (Method 10). The chiral purity was 98% e.e. (Chiral Method). $^1$H NMR (400 MHz, DMSO-d6) δ 12.87 (s, 1H), 9.17 (s, 2H), 8.68 (d, J=8.3 Hz, 1H), 8.47-8.17 (m, 2H), 7.96-7.71 (m, 2H), 7.64 (d, J=3.8 Hz, 1H), 7.55-7.29 (m, 2H), 7.26-7.02 (m, 2H), 6.93 (d, J=3.8 Hz, 1H), 4.79-4.48 (m, 1H), 4.03 (t, J=6.5 Hz, 2H), 3.27 (dd, J=13.9, 4.5 Hz, 1H), 3.12 (dd, J=13.9, 10.6 Hz, 1H), 1.90-1.58 (m, 2H), 1.58-1.01 (m, 17H), 1.01-0.69 (m, 3H).

Compound 193 was prepared in a manner analogous to 192 starting from (R)-tert-butyl 2-(((benzyloxy)carbonyl)amino)-3-(4-hydroxyphenyl)propanoate.

Tert-butyl (4-(tert-butyl)benzoyl)-L-tyrosinate

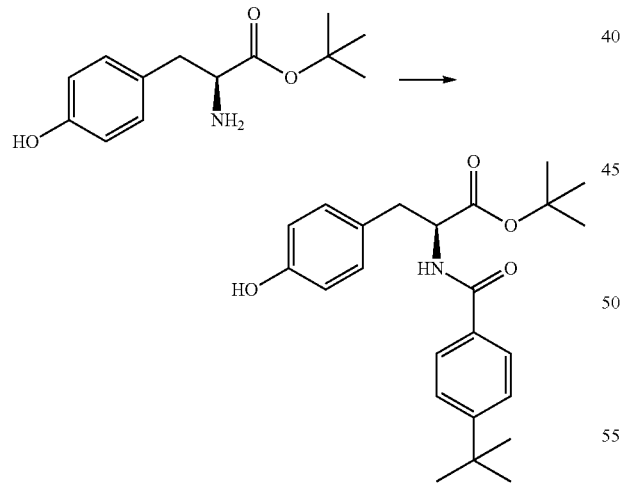

Prepared using General Procedure 7. Into a solution of 4-(tert-butyl)benzoic acid (8.3 g, 46.4 mmol) in DMF (100 mL) were added HATU (19.2 g, 50.6 mmol), TEA (17.6 mL, 126.4 mmol) and (S)-tert-butyl 2-amino-3-(4-hydroxyphenyl) propanoate (10.0 g, 42.1 mmol). After 5 h, the reaction mixture was diluted with EA, washed with saturated aqueous NaHCO$_3$ and brine, then dried (Na$_2$SO$_4$), concentrated, and purified by chromatography (EA/hexanes) to provide 12.9 g (69%) of tert-butyl (4-(tert-butyl)benzoyl)-L-tyrosinate. LCMS-ESI (m/z) calculated for $C_{24}H_{31}NO_4$: 397.5; no m/z observed, $t_R$=3.59 min (Method 1). $^1$H NMR (400 MHz, CDCl$_3$) δ7.71-7.65 (m, 2H), 7.47-7.39 (m, 2H), 7.04 (t, J=5.7 Hz, 2H), 6.78-6.70 (m, 2H), 6.59 (d, J=7.5 Hz, 1H), 4.91 (dt, J=7.5, 5.6 Hz, 1H), 3.15 (qd, J=14.0, 5.6 Hz, 2H), 1.45 (s, 9H), 1.33 (s, 9H).

Tert-butyl (S)-2-(4-(tert-butyl)benzamido)-3-(4-(((trifluoromethyl)sulfonyl)oxy) phenylpropanoate (INT-12)

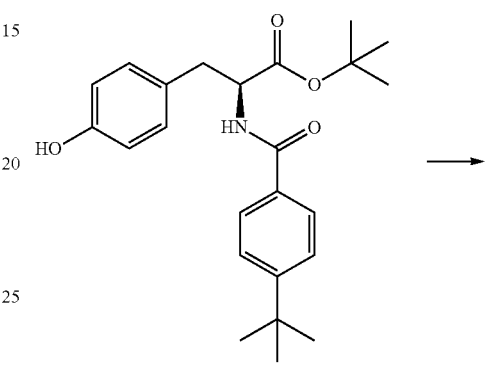

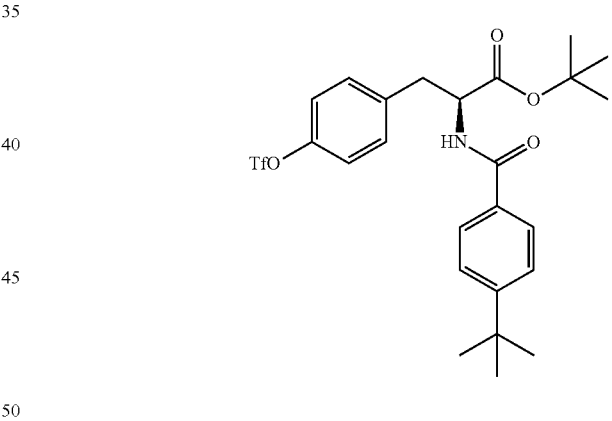

Prepared using General Procedure 9. Into a solution of tert-butyl (4-(tert-butyl)benzoyl)-L-tyrosinate (8.0 g, 17.9 mmol) were added DIEA (3.7 mL, 1.2 mmol) and N-Phenyl bis(trifluoromethanesulfonimide) (7.0 g, 19.7 mmol). After stirring for 36 h, the reaction mixture was diluted with DCM then washed with 10% aqueous citric acid and saturated aqueous NaHCO$_3$. The organic layer was dried over Na$_2$SO$_4$, and concentrated to provide 9.5 g (100%) tert-butyl (S)-2-(4-(tert-butyl)benzamido)-3-(4-(((trifluoromethyl)sulfonyl)oxy) phenyl) propanoate INT-12, which was used without further purification. LCMS-ESI (m/z) calculated for $C_{25}H_{30}F_3NO_6S$: 529.6; no m/z observed, $t_R$=4.42 min (Method 1). $^1$H NMR (400 MHz, CDCl$_3$) δ 7.71-7.65 (m, 2H), 7.49-7.43 (m, 2H), 7.32-7.26 (m, 2H), 7.22-7.16 (m, 2H), 6.69 (d, J=7.0 Hz, 1H), 4.94 (dt, J=6.9, 5.9 Hz, 1H), 3.24 (t, J=7.1 Hz, 2H), 1.41 (s, 9H), 1.33 (s, 9H).

159

Tert-butyl (S)-2-(4-(tert-butyl)benzamido)-3-(4-(4,4,5,5-tetramethyl-1,3,2-dioxaborolan-2-yl)phenyl)propanoate (INT-13)

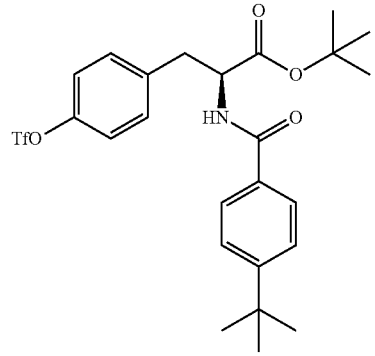

Into a degassed solution of (S)-2-(4-(tert-butyl)benzamido)-3-(4-(((trifluoromethyl)sulfonyl)oxy) phenyl) propanoate INT-12 (9.5 g, 24 mmol), KOAc (7.0 g, 72 mmol), and bis-pinacolatoborane (9.1 g, 36 mmol) in DMSO (20 mL) was added Pd(dppf)Cl$_2$ (0.87 g, 1 mmol). The reaction mixture was heated at 100° C. for 12 h under an atmosphere of N$_2$. The reaction mixture was diluted with EA then washed with saturated aqueous NaHCO$_3$ and H$_2$O. The organic layer was dried over Na$_2$SO$_4$, concentrated, and purified by chromatography (EA/hexanes) to provide 7.2 g (60%) of tert-butyl (S)-2-(4-(tert-butyl)benzamido)-3-(4-(4,4,5,5-tetramethyl-1,3,2-dioxaborolan-2-yl)phenyl)propanoate INT-13. LCMS-ESI (m/z) calculated for C$_{30}$H$_{42}$BNO$_5$: 507.5; no m/z observed, t$_R$=4.53 min (Method 1). $^1$H NMR (400 MHz, CDCl$_3$) δ 7.74 (d, J=8.0 Hz, 2H), 7.72-7.67 (m, 2H), 7.48-7.43 (m, 2H), 7.21 (d, J=8.0 Hz, 2H), 6.59 (d, J=7.4 Hz, 1H), 5.05-4.92 (m, 1H), 3.27 (qd, J=13.7, 5.4 Hz, 2H), 1.47 (s, 9H), 1.36 (m, 21H).

160

Tert-butyl (S)-3-(4-(5-bromopyrimidin-2-yl)phenyl)-2-(4-(tert-butyl)benzamido)propanoate (INT-14)

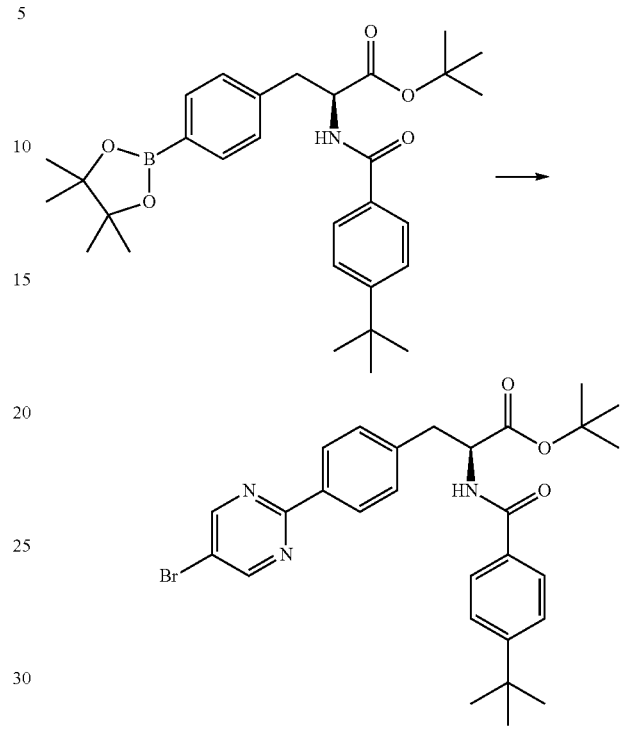

Prepared using General Procedure 10. Into a degassed solution of (S)-2-(4-(tert-butyl)benzamido)-3-(4-(4,4,5,5-tetramethyl-1,3,2-dioxaborolan-2-yl)phenyl)propanoate INT-13 (1.0 g, 2.0 mmol), Na$_2$HCO$_3$ (420 mg, 3.9 mmol), and 5-bromo-2-iodopyrimidine (615 mg, 2.2 mmol) in 2/2/1 ACN/THF/H$_2$O was added Pd(dppf)Cl$_2$ (140 mg, 0.2 mmol). The reaction mixture was heated at 110° C. for 1 h in a microwave reactor. The reaction mixture was concentrated, dissolved in DCM and washed with H$_2$O. The organic layer was dried over Na$_2$SO$_4$, concentrated, and purified by chromatography EA/hexanes) to provide 630 mg (58%) of tert-butyl (S)-3-(4-(5-bromopyrimidin-2-yl)phenyl)-2-(4-(tert-butyl)benzamido)propanoate INT-14. LCMS-ESI (m/z) calculated for C$_{28}$H$_{32}$BrN$_4$O$_3$: 538.5; no m/z observed, t$_R$=4.66 min (Method 1). $^1$H NMR (400 MHz, CDCl$_3$) δ 8.84-8.78 (s, 2H), 8.31 (t, J=7.0 Hz, 2H), 7.75-7.64 (m, 2H), 7.46-7.38 (m, 2H), 7.30 (dd, J=12.9, 7.1 Hz, 2H), 6.65 (d, J=7.2 Hz, 1H), 5.10-4.94 (m, 1H), 3.43-3.20 (m, 2H), 1.45 (s, 9H), 1.32 (s, 9H).

Compounds 194-236 were prepared from tert-butyl (S)-3-(4-(5-bromopyrimidin-2-yl) phenyl)-2-(4-(tert-butyl)benzamido)propanoate INT-14 using General Procedures 10 and 8 sequentially.

Tert-butyl (5-(tert-butyl)thiophene-2-carbonyl)-L-tyrosinate

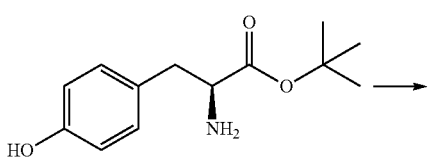

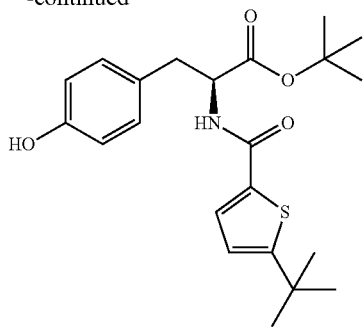

Prepared using General Procedure 7. Into a solution of 5-(tert-butyl)thiophene-2-carboxylic acid (1.93 g, 10.0 mmol) in DMF (20 mL) were added HATU (4.56 g, 12.0 mmol) and TEA (4.18 mL, 30.0 mmol). The mixture was stirred at room temperature for 30 min and (S)-tert-butyl 2-amino-3-(4-hydroxyphenyl) propanoate (2.37 g, 10.0 mmol) was added. After 1 h, the reaction mixture was poured into 400 mL of ice-water and the solid was filtered. The solid was dissolved in DCM and EA, dried over MgSO$_4$, concentrated, and purified by chromatography (EA/hexanes) to provide 3.6 g (89%) of tert-butyl (5-(tert-butyl)thiophene-2-carbonyl)-L-tyrosinate. LCMS-ESI (m/z) calculated for $C_{22}H_{29}NO_4S$: 403.2. found: 426.1 [M+Na]$^+$, $t_R$=9.07 min (Method 2).

Tert-butyl (S)-2-(5-(tert-butyl)thiophene-2-carboxamido)-3-(4-(((trifluoromethyl)sulfonyl)oxy) phenyl) propanoate (INT-15)

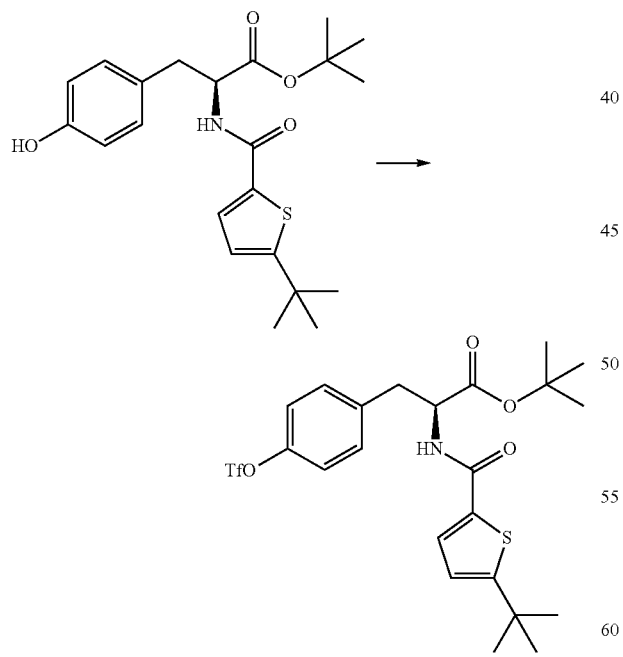

Prepared using General Procedure 9. Into a solution of tert-butyl (5-(tert-butyl)thiophene-2-carbonyl)-L-tyrosinate (3.52 g, 8.72 mmol) were added DIEA (4.56 mL, 26.17 mmol) and N-phenyl bis(trifluoromethanesulfonimide) (3.27 g, 9.16 mmol). After stirring for 18 h, the reaction mixture was diluted with DCM then washed with saturated aqueous NaHCO$_3$. The organic layer was dried over MgSO$_4$ and concentrated. The crude product was purified by chromatography to provide 4.10 g (87.6%) of tert-butyl (S)-2-(5-(tert-butyl)thiophene-2-carboxamido)-3-(4-(((trifluoromethyl)sulfonyl)oxy)phenyl)propanoate INT-15. LCMS-ESI (m/z) calculated for $C_{23}H_{28}F_3NO_6S_2$: 535.1; no m/z observed, $t_R$=4.22 min (Method 3).

Tert-butyl (S)-2-(5-(tert-butyl)thiophene-2-carboxamido)-3-(4-(4,4,5,5-tetramethyl-1, 3,2-dioxaborolan-2-yl)phenyl)propanoate (INT-16)

Into a degassed solution of tert-butyl (S)-2-(5-(tert-butyl)thiophene-2-carboxamido)-3-(4-(((trifluoromethyl)sulfonyl)oxy)phenyl)propanoateINT-15 (3.89 g, 7.26 mmol), KOAc (2.14 g, 21.79 mmol), and bis-pinacolatoborane (2.40 g, 9.44 mmol) in DMSO (50 mL) was added Pd(dppf)Cl$_2$ (0.27 g, 0.36 mmol). The reaction mixture was heated at 100° C. for 18 h under an atmosphere of N$_2$. The reaction mixture was poured into 600 mL of ice-water and the solid was filtered. The precipitate was diluted with EA, dried over MgSO$_4$, concentrated, and purified by chromatography (EA/hexanes) to provide 3.68 g (99%) of tert-butyl (S)-2-(5-(tert-butyl)thiophene-2-carboxamido)-3-(4-(4,4,5,5-tetramethyl-1,3,2-dioxaborolan-2-yl)phenyl)propanoate INT-16. LCMS-ESI (m/z) calculated for $C_{28}H_{40}BNO_5S$: 513.3; no m/z observed, $t_R$=4.51 min (Method 3).

163
Tert-butyl (S)-3-(4-(5-bromopyrimidin-2-yl)phenyl)-2-(5-(tert-butyl)thiophene-2-carboxamido)propanoate (INT-17)

164
Tert-butyl (S)-2-(4-(tert-butyl)benzamido)-3-(4-(5-cyanopyrimidin-2-yl)phenyl)-propanoate (INT-18)

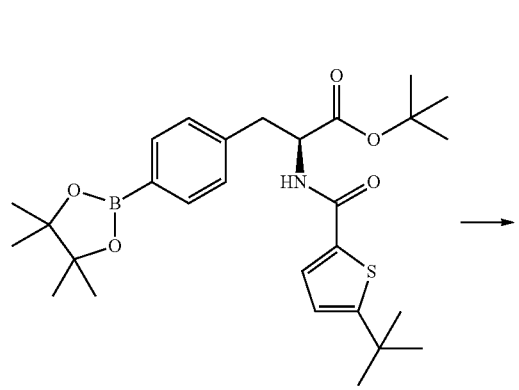

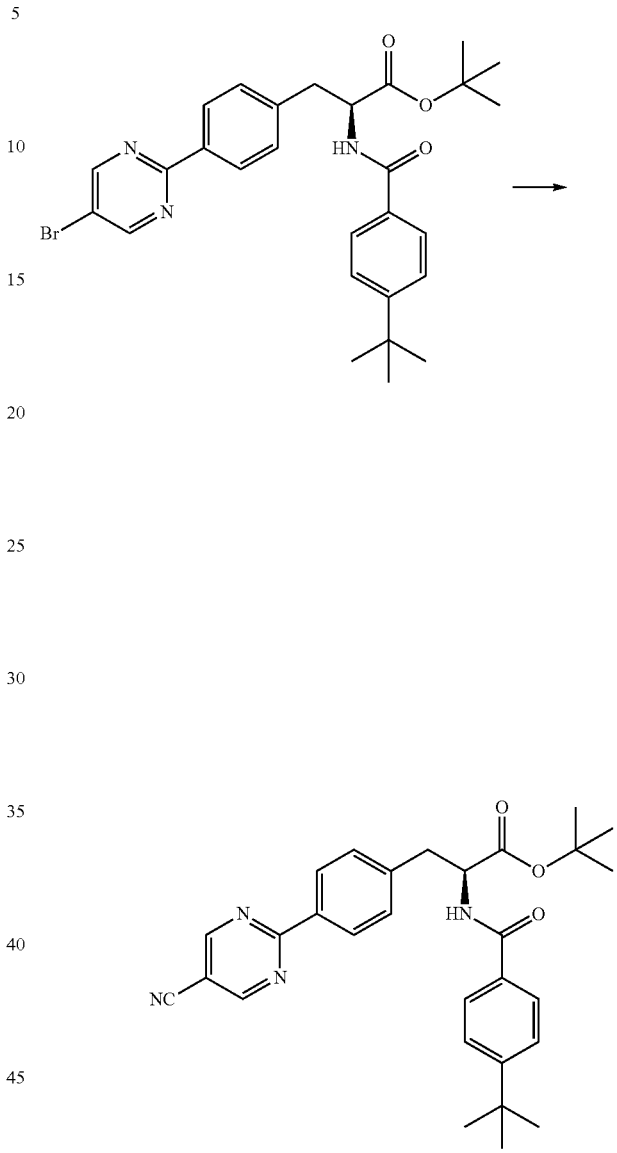

Prepared using General Procedure 10. Into a degassed solution of tert-butyl (S)-2-(5-(tert-butyl)thiophene-2-carboxamido)-3-(4-(4,4,5,5-tetramethyl-1,3,2-dioxaborolan-2-yl)phenyl)propanoate INT-16 (510 mg, 1.0 mmol) and 5-bromo-2-iodopyrimidine (570 mg, 2.0 mmol) in 2/2/1 ACN/THF/saturated aqueous $NaHCO_3$ (10 mL) was added $Pd(dppf)Cl_2$ (30 mg, 0.4 mmol). The reaction mixture was heated at 120° C. for 1 h in a microwave reactor. The reaction mixture was diluted with water (100 mL) and EA (50 mL) and filtered over Celite. The aqueous layer was extracted with EA (3×30 mL) and the combined organic layer was dried over $MgSO_4$, concentrated, and purified by chromatography (EA/hexanes) to provide 342 mg (63%) of tert-butyl (S)-3-(4-(5-bromopyrimidin-2-yl)phenyl)-2-(5-(tert-butyl)thiophene-2-carboxamido)propanoate INT-17. LCMS-ESI (m/z) calculated for $C_{26}H_{30}BrN_3O_3$: 543.1. found: 488.0 [M-tBu+H]$^+$, $t_R$=10.95 min (Method 2).

Compounds 237-247 were prepared from tert-butyl (S)-3-(4-(5-bromopyrimidin-2-yl)phenyl)-2-(5-(tert-butyl)thiophene-2-carboxamido)propanoate INT-17 using General Procedures 10 and 8 sequentially.

Prepared using General Procedure 1. Into a degassed solution of (S)-3-(4-(5-bromopyrimidin-2-yl)phenyl)-2-(4-(tert-butyl)benzamido)propanoate INT-14 (100 mg, 0.190 mmol), and $Zn(CN)_2$ (44 mg, 0.370 mmol) in NMP (5 mL) was added $Pd(Ph_3)_4$ (2 mg, 0.002 mmol). The mixture was heated for 45 min at 80° C. in a microwave reactor then partitioned between DCM and $H_2O$. The organic layer was dried over $Na_2SO_4$, concentrated, and purified by chromatography (EA/hexanes) to provide 75 mg (84%) of tert-butyl (S)-2-(4-(tert-butyl)benzamido)-3-(4-(5-cyanopyrimidin-2-yl)phenyl)propanoate INT-18. LCMS-ESI (m/z) calculated for $C_{29}H_{32}N_4O_3$: 484.60; no m/z observed, $t_R$=4.17 min (Method 1). $^1$H NMR (400 MHz, $CDCl_3$) δ 8.97 (s, 2H), 8.38 (d, J=7.9 Hz, 2H), 7.67 (d, J=8.0 Hz, 2H), 7.46-7.35 (m, 2H), 7.33 (d, J=7.9 Hz, 2H), 6.77 (d, J=6.8 Hz, 1H), 4.96 (d, J=6.1 Hz, 1H), 3.27 (dd, J=13.1, 8.0 Hz, 2H), 1.37 (d, J=34.5 Hz, 9H), 1.26 (d, J=21.0 Hz, 9H).

165

Tert-butyl (S)-2-(4-(tert-butyl)benzamido)-3-(4-(5-(N-hydroxycarbamimidoyl)-pyrimidin-2-yl)phenyl)propanoate

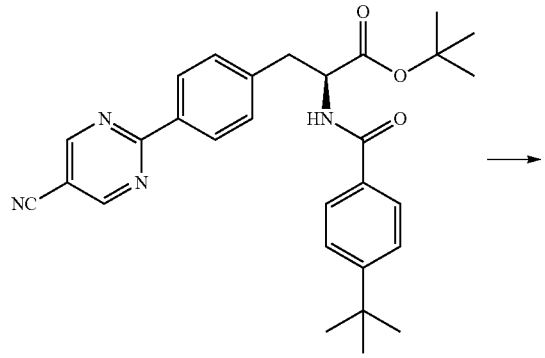

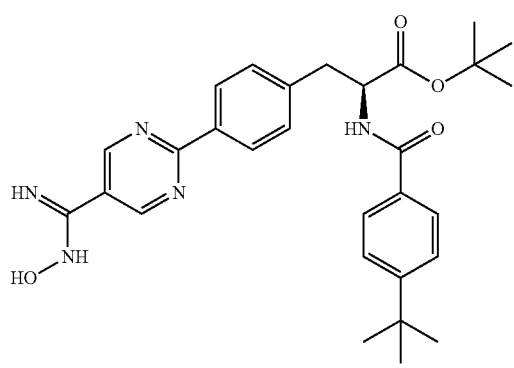

Prepared using General Procedure 2. A solution of (S)-2-(4-(tert-butyl)benzamido)-3-(4-(5-cyanopyrimidin-2-yl)phenyl)propanoate INT-18 (35 mg, 0.07 mmol), hydroxylamine (25 μL, 0.36 mmol, 50% solution in H$_2$O), and NEt$_3$ (11 μL, 0.08 mmol) in EtOH (5 mL) was heated at 80° C. for 1.5 h. The reaction mixture was concentrated, dissolved in DCM and washed with H$_2$O to provide 22 mg of tert-butyl (S)-2-(4-(tert-butyl)benzamido)-3-(4-(5-(N-hydroxycarbamimidoyl) pyrimidin-2-yl)phenyl)propanoate. LCMS-ESI (m/z) calculated for C$_{29}$H$_{35}$N$_5$O$_4$: 517.6. found 462.2 [M-$^t$Bu+H]$^+$, t$_R$=3.72 min (Method 1). $^1$H NMR (400 MHz, CDCl$_3$) δ 9.19 (s, 2H), 8.42 (d, J=8.2 Hz, 2H), 7.67 (dd, J=8.5, 2.1 Hz, 2H), 7.40 (dd, J=9.2, 8.0 Hz, 2H), 7.34 (dd, J=10.3, 8.4 Hz, 2H), 6.74 (dd, J=7.1, 4.7 Hz, 1H), 5.00 (q, J=5.6 Hz, 1H), 2.83 (d, J=5.3 Hz, 2H), 1.44 (s, 9H), 1.28 (d, J=22.0 Hz, 9H).

166

Tert-butyl (S)-2-(4-(tert-butyl)benzamido)-3-(4-(5-(5-hexyl-1,2,4-oxadiazol-3-yl)pyrimidin-2-yl)phenyl)propanoate (Compound 248)

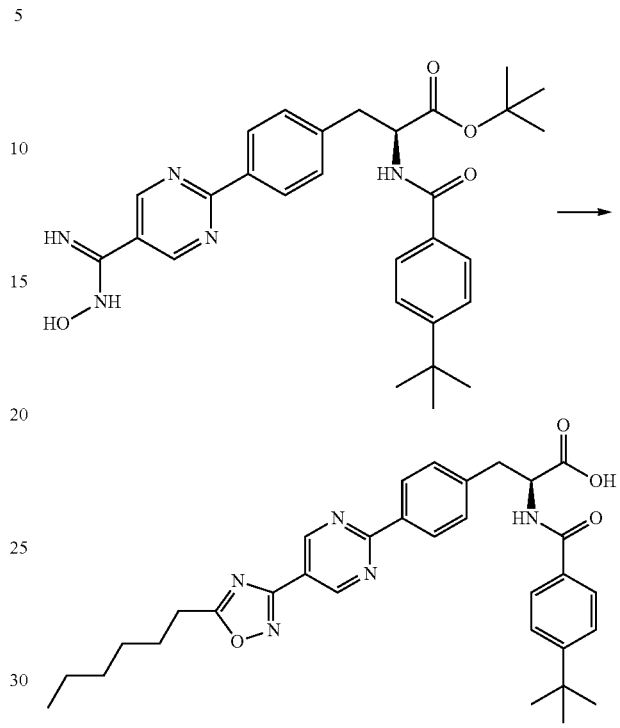

Prepared using General Procedure 5. A solution of heptanoic acid (7 mg, 0.05 mmol), HOBt (12 mg, 0.09 mmol) and EDC (13 mg, 0.09 mmol) was heated at 80° C. for 2 h. The reaction mixture was diluted with EtOAc and washed with NaHCO$_3$. The organic layer was dried over Na$_2$SO$_4$ and concentrated. The resulting mixture was dissolved in EtOH (2 mL) and heated for 45 min at 80° C. in a microwave reactor. The mixture was concentrated and purified by preparatory HPLC to provide 1.5 mg of tert-butyl (S)-2-(4-(tert-butyl)benzamido)-3-(4-(5-(5-hexyl-1,2,4-oxadiazol-3-yl)pyrimidin-2-yl)phenyl)propanoate. LCMS-ESI (m/z) calculated for C$_{36}$H$_{45}$N$_5$O$_4$: 611.8; no m/z observed, t$_R$=5.5 min (Method 1). $^1$H NMR (400 MHz, CDCl$_3$) δ 9.45 (s, 2H), 8.44 (d, J=8.3 Hz, 2H), 7.71 (d, J=8.5 Hz, 2H), 7.48 (d, J=8.5 Hz, 2H), 7.38 (d, J=8.3 Hz, 2H), 6.80 (d, J=7.3 Hz, 1H), 5.04 (dd, J=12.7, 5.5 Hz, 1H), 3.37 (ddd, J=18.9, 13.8, 5.5 Hz, 2H), 3.02 (t, J=7.6 Hz, 2H), 1.92 (dt, J=15.3, 7.5 Hz, 2H), 1.49 (s, 9H), 1.44-1.28 (m, 15H), 0.93 (t, J=7.1 Hz, 3H).

(S)-2-(4-(tert-butyl)benzamido)-3-(4-(5-(5-hexyl-1,2,4-oxadiazol-3-yl) pyrimidin-2-yl) phenyl)propanoate was deprotected using General Procedure 8 to provide 1.4 mg (6% overall) of (S)-2-(4-(tert-butyl)benzamido)-3-(4-(5-(5-hexyl-1,2,4-oxadiazol-3-yl)pyrimidin-2-yl)phenyl) propanoic acid Compound 248. LCMS-ESI (m/z) calculated for C$_{32}$H$_{37}$N$_5$O$_4$: 555.68; no m/z observed, t$_R$=11.03 min (Method 2). $^1$H NMR (400 MHz, CDCl$_3$) δ 9.41 (s, 2H), 8.47 (d, J=8.2 Hz, 2H), 7.66 (d, J=8.4 Hz, 2H), 7.42 (dd, J=15.1, 8.4 Hz, 4H), 6.60 (d, J=6.8 Hz, 1H), 5.21-4.95 (m, 1H), 3.43 (ddd, J=20.0, 14.0, 5.6 Hz, 2H), 3.05-2.90 (m, 2H), 1.98-1.76 (m, 2H), 1.55-1.22 (m, 15H), 0.91 (t, J=7.0 Hz, 3H).

167

Tert-butyl (S)-2-(5-(tert-butyl)thiophene-2-carbox-
amido)-3-(4-(5-(4-hydroxyphenyl)pyrimidin-2-yl)
phenyl)propanoate

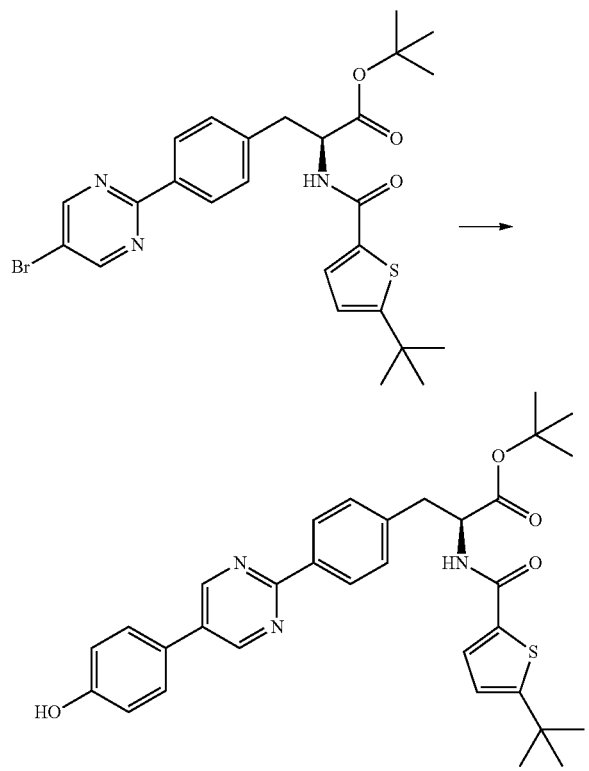

168

Prepared using General Procedure 10. To a degassed solution of tert-butyl (S)-3-(4-(5-bromopyrimidin-2-yl) phenyl)-2-(5-(tert-butyl)thiophene-2-carboxamido) propanoate INT-17 (180 mg, 0.3 mmol), sodium carbonate (70 mg, 0.7 mmol) and 4-hydroxyphenylboronic acid (55 mg, 0.4 mmol) in 5 mL of 2/2/1 ACN/THF/H$_2$O was added Pd(dppf)Cl$_2$ (24 mg, 0.03 mmol). The reaction mixture was heated at 110° C. for 45 min in a microwave reactor. The mixture was filtered through celite, concentrated, then dissolved in DCM and washed with H$_2$O. The organic layer was concentrated and purified by prep HPLC to provide 131 mg (78%) of tert-butyl (S)-2-(5-(tert-butyl)thiophene-2-carboxamido)-3-(4-(5-(4-hydroxyphenyl) pyrimidin-2-yl)phenyl) propanoate. LCMS-ESI (m/z) calculated for C$_{32}$H$_{35}$N$_3$O$_4$S: 557.7; no m/z observed, t$_R$=4.08 min (Method 1). $^1$H NMR (400 MHz, CDCl$_3$) δ 8.98 (s, 2H), 8.35 (d, J=8.1 Hz, 2H), 7.49 (d, J=8.6 Hz, 2H), 7.40-7.31 (m, 3H), 6.94 (d, J=8.5 Hz, 2H), 6.81 (d, J=3.8 Hz, 1H), 6.51 (d, J=7.5 Hz, 1H), 5.00 (dd, J=12.9, 5.8 Hz, 1H), 3.28 (qd, J=13.8, 5.6 Hz, 2H), 1.47 (s, 9H), 1.39 (s, 9H).

(S)-2-(5-(tert-butyl)thiophene-2-carboxamido)-3-(4-
(5-(4-(decyloxy)phenyl)-pyrimidin-2-yl)phenyl)pro-
panoic acid (Compound 249)

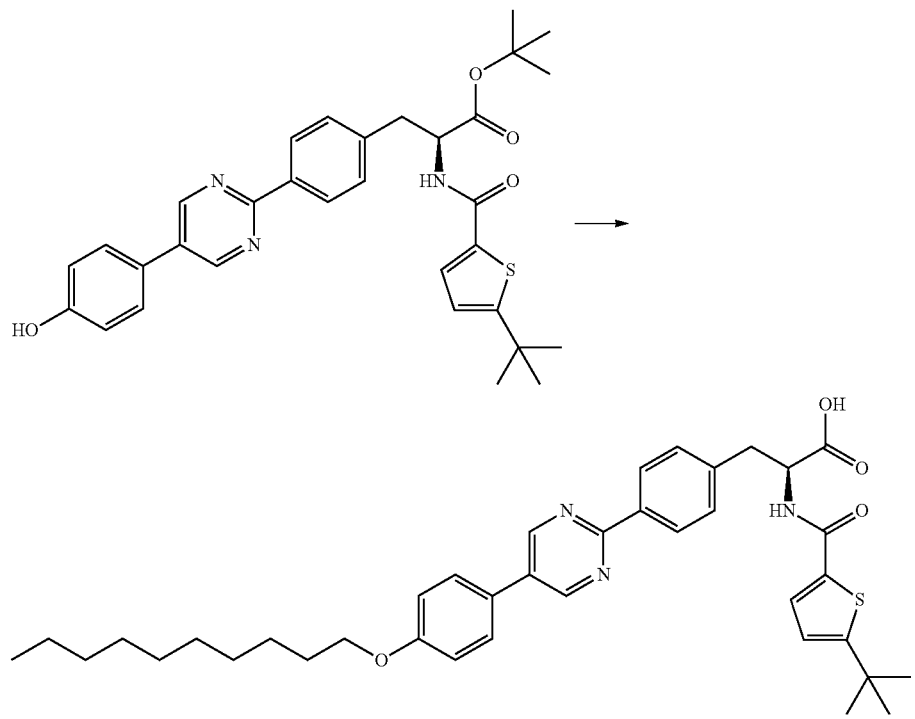

Prepared using General Procedures 12. To a solution of tert-butyl (S)-2-(5-(tert-butyl)thiophene-2-carboxamido)-3-(4-(5-(4-(hydroxyphenyl) pyrimidin-2-yl)phenyl)propanoate (20 mg, 0.04 mmol) in DMF (0.5 mL) were added 1-bromodecane (8 μL, 0.05 mmol) and $K_2CO_3$ (8 mg, 0.05 mmol). The reaction mixture was heated at 40° C. for 18 h, then diluted with DCM and washed with $H_2O$. The organic layer was dried over $Na_2SO_4$ and concentrated. The crude material was deprotected using General Procedure 8 then purified by preparatory HPLC to provide 3.9 mg (17%) of (S)-2-(5-(tert-butyl)thiophene-2-carboxamido)-3-(4-(5-(4-(decyloxy)phenyl)pyrimidin-2-yl)phenyl)propanoic acid compound 249. LCMS-ESI (m/z) calculated for $C_{38}H_{47}N_3O_4S$: 641.9; no m/z observed, $t_R$=13.49 min (Method 2). $^1$H NMR (400 MHz, $CDCl_3$) δ 9.01 (s, 2H), 8.36 (d, J=8.1 Hz, 2H), 7.56 (d, J=8.7 Hz, 2H), 7.44 (d, J=8.2 Hz, 2H), 7.33 (d, J=3.8 Hz, 1H), 7.03 (d, J=8.8 Hz, 2H), 6.80 (d, J=3.8 Hz, 1H), 6.54 (d, J=6.8 Hz, 1H), 5.13 (d, J=6.8 Hz, 1H), 4.01 (t, J=6.6 Hz, 2H), 3.44 (d, J=4.9 Hz, 2H), 1.91-1.72 (m, 2H), 1.47 (dd, J=15.0, 7.3 Hz, 2H), 1.38 (s, 9H), 1.28 (s, 12H), 0.88 (t, J=6.8 Hz, 3H).

Compounds 250-252 were prepared from tert-butyl (S)-2-(5-(tert-butyl)thiophene-2-carboxamido)-3-(4-(5-(4-hydroxyphenyl) pyrimidin-2-yl)phenyl) propanoate using General Procedure 12 followed by General Procedure 8.

(S)-2-(4-(tert-butyl)benzamido)-3-(4-(5-(4-(tert-butyl)piperidin-1-yl)pyrimidin-2-yl)phenyl)propanoic acid (Compound 253)

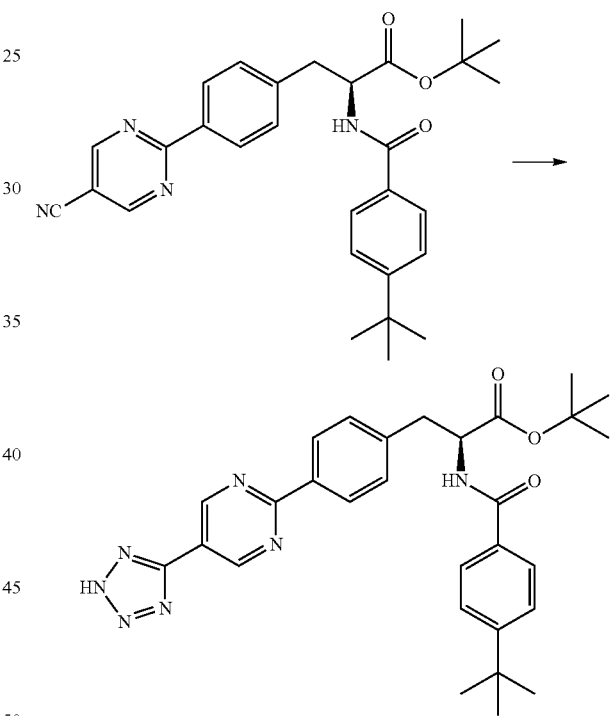

Prepared using General Procedure 11. Into a degassed solution of INT-14 (50 mg, 0.09 mmol), sodium tert-butoxide (18 mg, 0.19 mmol) and 4-tert-butylpiperidine HCl (23 mg, 0.11 mmol) in dioxane (2.5 mL) were added $Pd_2(dba)_3$ (9 mg, 0.01 mmol) and 2-dicyclohexylphosphino-2'-(N,N-dimethylamino)biphenyl (6 mg, 0.015 mmol). The reaction mixture was heated for 45 min at 120° C. in a microwave reactor. The mixture was diluted with EA and washed with $NaHCO_3$. The organic layer was dried over $Na_2SO_4$, concentrated, and purified by preparatory HPLC. The isolated intermediate was deprotected using General Procedure 8 to provide 2.9 mg (6%) of (S)-2-(4-(tert-butyl)benzamido)-3-(4-(5-(4-(tert-butyl)piperidin-1-yl)pyrimidin-2-yl)phenyl) propanoic acid Compound 253. LCMS-ESI (m/z) calculated for $C_{33}H_{42}N_4O_3$: 542.7. found 543.3 [M+H]$^+$, $t_R$=10.79 min (Purity). $^1$H NMR (400 MHz, $CDCl_3$) δ 8.52 (s, 2H), 8.23 (d, J=8.0 Hz, 2H), 7.72 (d, J=8.4 Hz, 2H), 7.44 (dd, J=11.3, 8.4 Hz, 4H), 6.79 (d, J=6.8 Hz, 1H), 5.18 (d, J=6.5 Hz, 1H), 3.89 (d, J=11.9 Hz, 2H), 3.47 (d, J=5.2 Hz, 2H), 2.83 (t, J=11.5 Hz, 2H), 1.88 (d, J=12.0 Hz, 2H), 1.52-1.37 (m, 2H), 1.34 (s, 9H), 1.24 (dd, J=24.7, 12.8 Hz, 1H), 0.92 (s, 9H).

Compound 254 was prepared from INT-14 using General Procedure 11 then General Procedure 8.

Tert-butyl (S)-3-(4-(5-(2H-tetrazol-5-yl)pyrimidin-2-yl)phenyl)-2-(4-(tert-butyl)-benzamido) propanoate

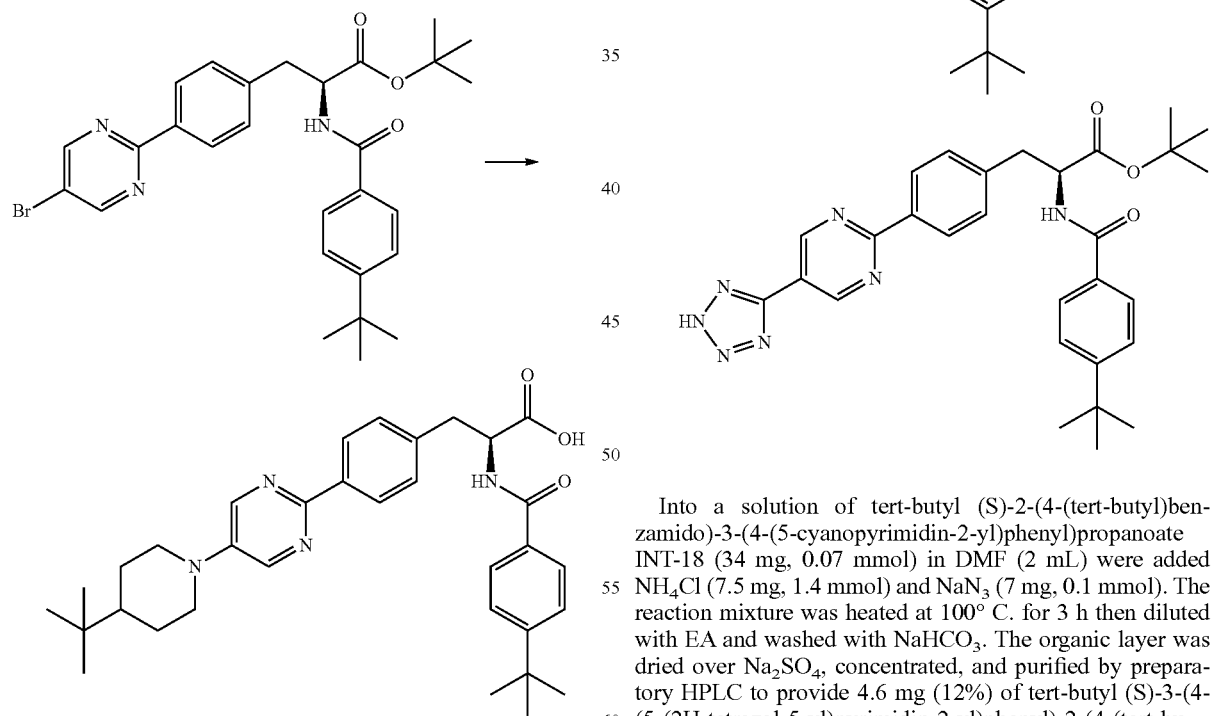

Into a solution of tert-butyl (S)-2-(4-(tert-butyl)benzamido)-3-(4-(5-cyanopyrimidin-2-yl)phenyl)propanoate INT-18 (34 mg, 0.07 mmol) in DMF (2 mL) were added $NH_4Cl$ (7.5 mg, 1.4 mmol) and $NaN_3$ (7 mg, 0.1 mmol). The reaction mixture was heated at 100° C. for 3 h then diluted with EA and washed with $NaHCO_3$. The organic layer was dried over $Na_2SO_4$, concentrated, and purified by preparatory HPLC to provide 4.6 mg (12%) of tert-butyl (S)-3-(4-(5-(2H-tetrazol-5-yl)pyrimidin-2-yl)phenyl)-2-(4-(tert-butyl)benzamido)propanoate. LCMS-ESI (m/z) calculated for $C_{29}H_{33}N_7O_3$: 527.6; no m/z observed, $t_R$=3.83 min (Method 1). $^1$H NMR (400 MHz, $CDCl_3$) δ 9.35 (s, 2H), 8.42 (d, J=8.1 Hz, 2H), 7.75 (d, J=8.4 Hz, 2H), 7.47 (d, J=8.5 Hz, 2H), 7.43 (d, J=8.2 Hz, 2H), 7.11 (d, J=7.8 Hz, 1H), 5.13 (dd, J=14.4, 7.1 Hz, 1H), 3.28 (ddd, J=21.0, 13.6, 6.7 Hz, 2H), 1.47 (d, J=6.8 Hz, 9H), 1.33 (s, 9H).

Compound 255 was prepared from tert-butyl (S)-3-(4-(5-(2H-tetrazol-5-yl)pyrimidin-2-yl)phenyl)-2-(4-(tert-butyl)benzamido)propanoate using General Procedure 12 then General Procedure 8.

Compound 256 was prepared from INT-14 and 5-(4,4,5,5-tetramethyl-1,3,2-dioxaborolan-2-yl)isoindolin-1-one using General Procedures 10, 12 and 8.

Compound 257 was prepared from INT-14 and 6-Hydroxypyridine-3-boronic acid pinacol ester using General Procedures 10, 12 and 8.

Compound 258 was prepared from INT-13 and 5-(benzyloxy)-2-chloropyrimidine using General Procedure 10, followed by General Procedure 8.

Compounds 259 and 260 were prepared from INT-14 and the appropriate boronic acid using General Procedures 10 then 8.

Tert-butyl 4-(4-(heptyloxy)phenyl)-3-oxopiperazine-1-carboxylate

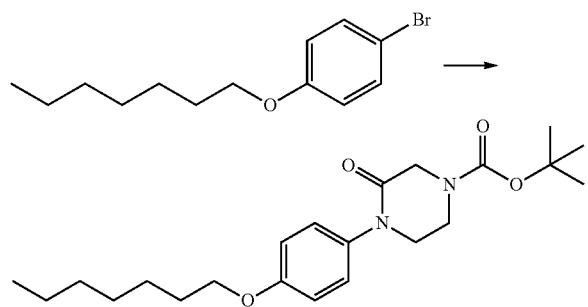

To a stirring solution of 1-bromo-4-(heptyloxy)benzene (447 mg, 1.65 mmol) in dioxane (5 mL) were added tert-butyl 3-oxopiperazine-1-carboxylate (330 mg, 1.65 mmol), copper I iodide (31.4 mg, 0.17 mmol), (1R,2R)—N1,N2-dimethylcyclohexane-1,2-diamine (234 mg, 1.65 mmol) and potassium carbonate (456 mg, 3.30 mmol). The reaction mixture was heated at 120° C. for 16 h. The reaction mixture was passed through a plug of celite, eluted with EA (50 mL). The organics were washed with ammonium chloride (25 mL), water (25 mL) and brine (25 mL) then dried over $MgSO_4$ and concentrated to afford 602 mg (89%) of tert-butyl 4-(4-(heptyloxy)phenyl)-3-oxopiperazine-1-carboxylate. LCMS-ESI (m/z) calculated for $C_{22}H_{34}N_2O_4$: 390.5. found 319.0 $[M+H]^+$, $t_R$=2.90 min. (Method 4).

1-(4-(heptyloxy)phenyl)piperazin-2-one

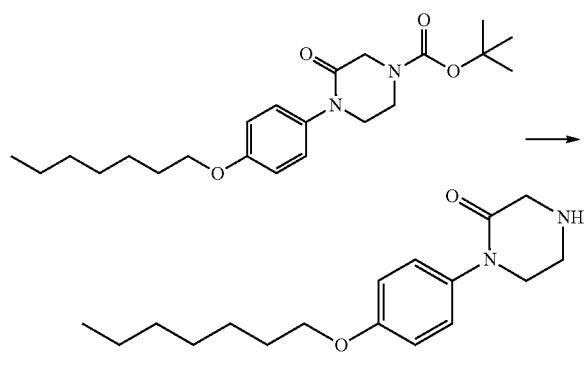

To tert-butyl 4-(4-(heptyloxy)phenyl)-3-oxopiperazine-1-carboxylate (540 mg, 1.38 mmol) was added 4M HCl in dioxane (2.07 mL, 8.30 mmol). The reaction mixture was stirred at room temperature for 2 h. The precipitate was filtered, washed with hexane (5 mL) and dried. The crude product was purified by column chromatography (79/20/1 DCM/MeOH/NH$_4$) to afford 325 mg (80%) of 1-(4-(heptyloxy)phenyl)piperazin-2-one as a colorless solid. LCMS-ESI (m/z) calculated for $C_{17}H_{26}N_2O_2$: 290.4. found 291.0 $[M+H]^+$, $t_R$=1.49 min. (Method 4).

Compound 261 was prepared from INT-12 and 1-(4-(heptyloxy)phenyl)piperazin-2-one using General Procedures 11 and 8.

Compound 262 was prepared in a similar fashion from INT-12 and 1-(4-(heptyloxy)phenyl)imidazolidin-2-one using General Procedures 11 and 8.

Compound 263 was prepared using (S)-methyl 2-amino-3-(4-nitrophenyl)propanoate hydrochloride, 4-(tert-butyl)benzoic acid and 1-(4-(heptyloxy)phenyl)piperidin-4-one using General Procedures 7, 14, 15 then 4.

Tert-butyl 4-(4-(heptyloxy)phenyl)-4-hydroxypiperidine-1-carboxylate

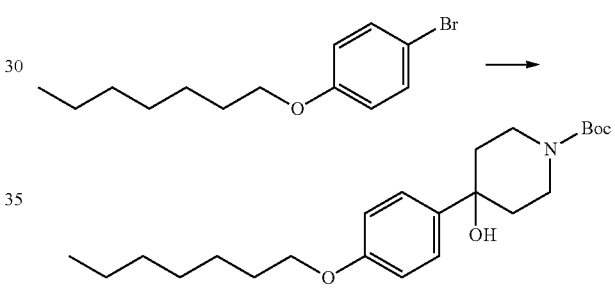

To a stirring solution of 1-bromo-4-(heptyloxy)benzene (668 mg, 2.46 mmol) in THF (5 mL) at −78° C. was added butyllithium (985 µl, 2.46 mmol). After 30 min, a solution of tert-butyl 4-oxopiperidine-1-carboxylate (491 mg, 2.46 mmol) in THF (2 mL) was added. After 10 min, the cooling bath was removed and the reaction mixture stirred for 16 h. The reaction mixture was poured onto NH$_4$Cl (50 mL) and extracted with Et$_2$O (3×20 mL). The combined organics were washed with water (20 mL), dried over MgSO$_4$ and evaporated. The crude product was purified by column chromatography (5-70% AcMe in iso-hexanes) to afford 0.4 g (33%) of tert-butyl 4-(4-(heptyloxy)phenyl)-4-hydroxypiperidine-1-carboxylate. LCMS-ESI (m/z) calculated for $C_{23}H_{37}NO_4$: 391.5. found 414.0 $[M+Na]^+$, $t_R$=2.24 min. (Method 4).

4-(4-(heptyloxy)phenyl)piperidine (INT-19)

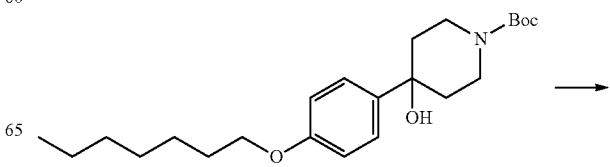

-continued

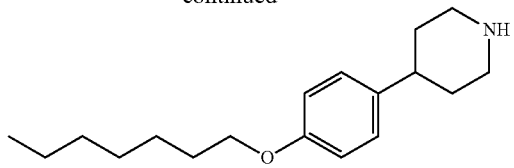

To a stirring solution of tert-butyl 4-(4-(heptyloxy)phenyl)-4-hydroxypiperidine-1-carboxylate (388 mg, 0.99 mmol) and triethylsilane (791 μl, 4.95 mmol) in DCM (2 mL) cooled to −30° C. was slowly added 2,2,2-trifluoroacetic acid (379 μl, 4.95 mmol) in a drop-wise fashion. The reaction mixture was allowed to warm slowly and stirring continued for 16 h. The reaction mixture was poured onto ice-water/NaOH (50 mL/5 mL, 2 M) and extracted with DCM (3×20 mL). The combined organic extracts were washed successively with water (50 mL) and NaHCO$_3$ (20 mL), dried over MgSO$_4$ and evaporated to afford 166 mg (58%) of 4-(4-(heptyloxy)phenyl)piperidine INT-19 as a white, waxy solid. LCMS-ESI (m/z) calculated for $C_{18}H_{29}NO$: 275.4. found 276.0 [M+H]$^+$, $t_R$=2.88 min. (Method 11).

Compound 264 was prepared using INT-12 and INT-19 using General Procedures 11 then 8.

Compound 265 was prepared in a similar fashion to 264 using INT-12 and 3-(4-(heptyloxy)phenyl)pyrrolidine using General Procedures 11 then 8.

Compound 266 was prepared using INT-12 and 1-([1,1'-biphenyl]-4-yl)piperazine using General Procedures 11 then 8.

Compound 267 was prepared using INT-12, tert-butyl 4-(4-hydroxyphenyl)piperazine-1-carboxylate and 1-bromoheptane using General Procedures 12, 8, 11 then 8.

Compound 268 was prepared using INT-12, tert-butyl 1,4-diazepane-1-carboxylate and 1-bromo-4-(heptyloxy)benzene using General Procedures 11, 8, 11 then 8.

Compound 269 was prepared using 5-bromo-2-iodopyridine, INT-13 and (4-(heptyloxy)phenyl)boronic acid using General Procedures 10, 10, and 8 sequentially.

Compound 270 was prepared using 5-bromo-2-iodopyridine, (4-(heptyloxy)phenyl)boronic acid and INT-13 using General Procedures 10, 10, and 8 sequentially.

Compound 271 was prepared using 5-bromo-2-iodopyrimidine, (4-(heptyloxy)phenyl)boronic acid and INT-13 using General Procedures 10, 10, and 8 sequentially.

Compound 272 was prepared using 2-bromo-5-iodopyrazine, (4-(heptyloxy)phenyl)boronic acid and INT-13 using General Procedures 10, 10, and 8 sequentially.

Compound 273 was prepared using 3-chloro-6-iodopyridazine, (4-(heptyloxy)phenyl)boronic acid and INT-13 using General Procedures 10, 10, and 8 sequentially.

3-(4-bromophenyl)-6-(4-(heptyloxy)phenyl)-1,2,4-triazine (INT-20)

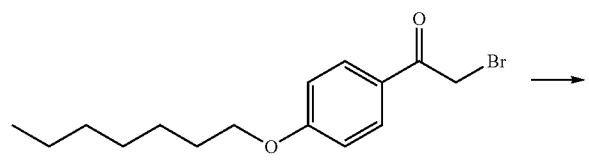

-continued

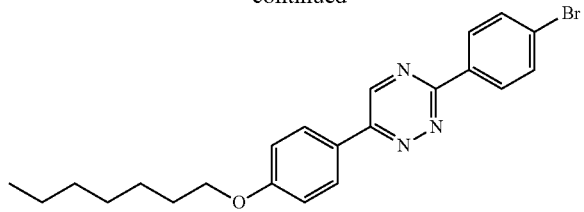

To a stirring solution of 4-bromobenzohydrazide (1.85 g, 8.62 mmol) in ethanol (10 mL) was added acetic acid (1 mL). The reaction mixture was stirred at 60° C. for 30 min then 2-bromo-1-(4-(heptyloxy)phenyl)ethanone (1.35 g, 4.31 mmol) INT-4 and sodium acetate (0.389 g, 4.74 mmol) were added and the mixture heated to reflux for 30 min. The reaction mixture was cooled to room temperature and the resultant precipitate was filtered and washed with isohexanes (20 mL) then dried. The solid was dissolved in NMP and heated to 120° C. for 16 h. The crude material was cooled to room temperature, diluted with Et$_2$O (4 mL), filtered, triturated with ethanol (3×2 mL), filtered and dried to afford 241 mg (13%) of 3-(4-bromophenyl)-6-(4-(heptyloxy)phenyl)-1,2,4-triazine INT-20 as an orange solid. LCMS-ESI (m/z) calculated for $C_{22}H_{24}BrN_3O$: 425.1. found 426.3 [M+H]$^+$, $t_R$=3.40 min (Method 8).

Compound 274 was prepared in a similar fashion to 79 using 3-(4-bromophenyl)-6-(4-(heptyloxy)phenyl)-1,2,4-triazine INT-20 in place of 2-(4-bromophenyl)-4-(4-(heptyloxy)phenyl)thiazole.

6-(4-bromophenyl)-3-(4-(heptyloxy)phenyl)-1,2,4-triazine (INT-21)

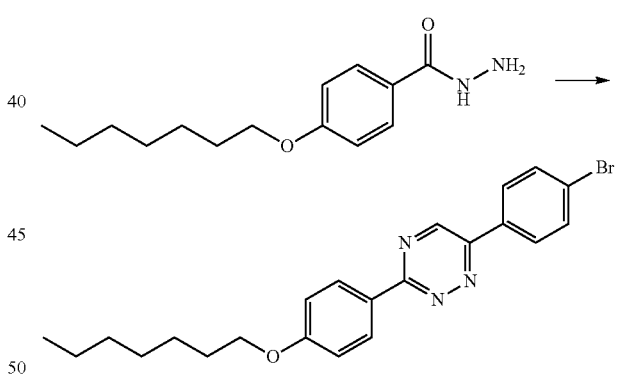

To a stirring solution of 4-(heptyloxy)benzohydrazide (400 mg, 1.60 mmol) in ethanol (15 mL) was added acetic acid (1 mL). The reaction mixture was stirred at 60° C. for 30 min then 2-bromo-1-(4-bromophenyl)ethanone (222 mg, 0.80 mmol) and sodium acetate (72.1 mg, 0.88 mmol) were added and the solution heated to reflux for 2 h. The reaction mixture was cooled to room temperature and the resultant crystals were filtered, washed with iso-hexanes (20 mL) then dried to afford 108 mg (31%) of 6-(4-bromophenyl)-3-(4-(heptyloxy)phenyl)-1,2,4-triazine INT-21. LCMS-ESI (m/z) calculated for $C_{22}H_{24}BrN_3O$: 425.1. found 426.1 [M+H]$^+$, $t_R$=3.38 min (Method 8).

Compound 275 was prepared in a similar fashion to 274 using 6-(4-bromophenyl)-3-(4-(heptyloxy)phenyl)-1,2,4-triazine INT-21 in place of 3-(4-bromophenyl)-6-(4-(heptyloxy)phenyl)-1,2,4-triazine.

Compound 276 was prepared using 274 using General Procedures 7 and 8.

Compounds 277 and 278 were prepared using INT-16 and 5-bromo-2-iodopyridine using General Procedures 10, 10, and 8 sequentially.

Compounds 279 and 280 were prepared using INT-16 and 3-chloro-6-iodopyridazine using General Procedures 10, 10, and 8 sequentially.

Compounds 281 and 282 were prepared using INT-16 and 2-bromo-5-iodopyrazine using General Procedures 10, 10, and 8 sequentially.

poured onto aq. citric acid and EA then stirred for 10 min before the solid was collected by filtration. The cake was washed with water and iso-hexanes then dried to provide 905 mg (57%) of 2-(4-(heptyloxy)phenyl)-2-oxoethyl 4-bromobenzoate. LCMS-ESI (m/z) calculated for $C_{22}H_{25}BrO_4$: 432.1. found 433.2 $[M+H]^+$, $t_R$=3.24 min (Method 8).

2-(4-bromophenyl)-5-(4-(heptyloxy)phenyl)-1H-imidazole

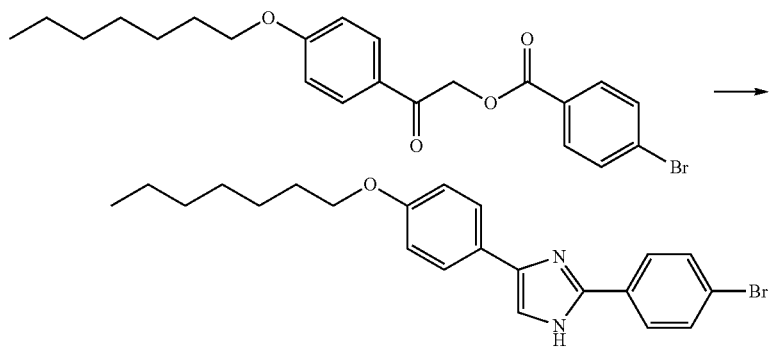

Compound 283 was prepared from Compound 279 and tert-butyl glycinate using General Procedures 7 and 8 sequentially.

Compound 284 was prepared from Compound 281 and tert-butyl glycinate using General Procedures 7 and 8 sequentially.

Compound 285 was prepared from Compound 277 and tert-butyl glycinate using General Procedures 7 and 8 sequentially.

2-(4-(heptyloxy)phenyl)-2-oxoethyl 4-bromobenzoate

To a solution of 2-(4-(heptyloxy)phenyl)-2-oxoethyl 4-bromobenzoate (905 mg, 2.09 mmol) in toluene (6 ml) was added $CH_3COONH_4$ (1600 mg, 20.9 mmol). After heating overnight at 115° C., the reaction mixture was diluted with aq. $NaHCO_3$ and extracted into DCM. The organic layers were combined, dried over $MgSO_4$, filtered, and the solvent was removed under reduced pressure. The crude reaction mixture was purified by chromatography (EA/hexanes) to provide 370 mg (33%) of 2-(4-bromophenyl)-5-(4-(heptyloxy)phenyl)-1H-imidazole. LCMS-ESI (m/z) calculated for $C_{22}H_{25}BrN_2O$: 412.1. found 413.2 $[M+H]^+$, $t_R$=2.33 min (Method 8).

2-(4-bromophenyl)-5-(4-(heptyloxy)phenyl)-1-((2-(trimethylsilyl)ethoxy)methyl)-1H-imidazole

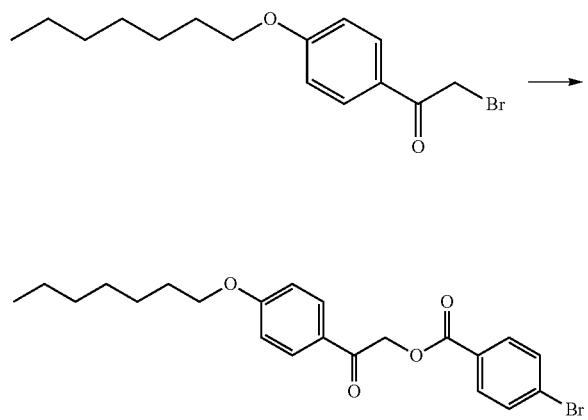

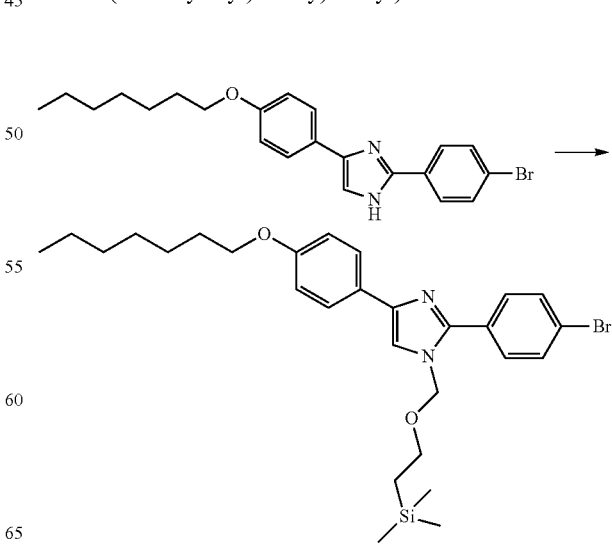

To a solution of 2-bromo-1-(4-(heptyloxy)phenyl)ethanone INT-4 (1.3 g, 4.2 mmol) and 4-bromobenzoic acid (0.70 g, 3.5 mmol) in ACN (30 mL) was added TEA (0.72 ml, 5.2 mmol). After stirring overnight, the mixture was To a solution of 2-(4-bromophenyl)-5-(4-(heptyloxy)phenyl)-1H-imidazole (370 g, 900 mmol) in DMF (4 ml) was added NaH (40 mg, 980 mmol). After 2 h, 2-(trimethylsilyl)ethoxymethyl chloride (160 g, 990 mmol) in THF (2 ml) was added dropwise and reaction mixture was stirred overnight. The reaction mixture was diluted with EA and washed with aq. NaHCO$_3$. The organics were dried over MgSO$_4$, filtered, and the solvent was removed under reduced pressure. The crude product was purified by chromatography (EA/hexane) to afford 32 mg (65%) of 2-(4-bromophenyl)-5-(4-(heptyloxy)phenyl)-1-((2-(trimethylsilyl)ethoxy)methyl)-1H-imidazole as a tan solid. LCMS-ESI (m/z) calculated for C$_{28}$H$_{39}$BrN$_2$O$_2$Si: 542.2. found 543.3 [M+H]$^+$, t$_R$=3.35 min (Method 8).

(S)-methyl 2-((tert-butoxycarbonyl)amino)-3-(4-(4-(4-(heptyloxy)phenyl)-1-((2-(trimethylsilyl)ethoxy)methyl)-1H-imidazol-2-yl)phenyl)propanoate A stirred suspension of zinc (68 mg, 1.03 mmol) in DMF (2 mL) was treated with I$_2$ (12 mg, 0.05 mmol). After the color disappeared, ((R)-methyl 2-((tert-butoxycarbonyl)amino)-3-iodopropanoate (110 mg, 0.34 mmol) and further I$_2$ (12 mg, 0.05 mmol) were added. After 30 min, the mixture was de-gassed then 2-(4-bromophenyl)-5-(4-(heptyloxy)phenyl)-1-((2-(trimethylsilyl)ethoxy)methyl)-1H-imidazole (170 mg, 0.31 mmol), dicyclohexyl(2',6'-dimethoxy-[1,1'-biphenyl]-2-yl)phosphine (7 mg, 0.02 mmol) and Pd$_2$(dba)$_3$ (8 mg, 7.8 mol) were added. After further de-gassing, DMF (2 mL) was added and the reaction mixture was heated at 50° C. overnight. The reaction mixture purified by column chromatography (EA/hexane) to provide 55 mg (25%) of (S)-methyl 2-((tert-butoxycarbonyl)amino)-3-(4-(4-(4-(heptyloxy)phenyl)-1-((2-(trimethylsilyl)ethoxy)methyl)-1H-imidazol-2-yl)phenyl)propanoate as a colorless oil. LCMS-ESI (m/z) calculated for C$_{37}$H$_{55}$N$_3$O$_6$Si: 665.9. found 666.4 [M+H]$^+$, t$_R$=3.10 min (Method 8).

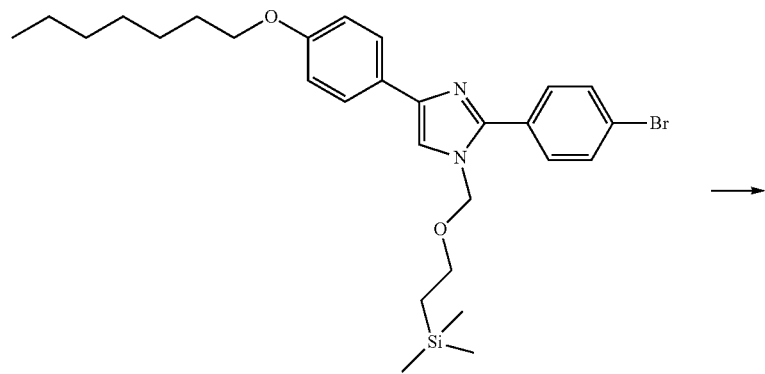

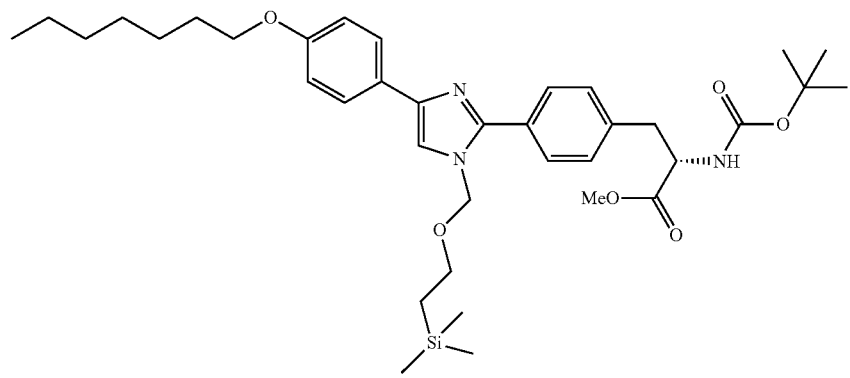

(S)-methyl 2-amino-3-(4-(4-(4-(heptyloxy)phenyl)-1H-imidazol-2-yl)phenyl)-propanoate To a solution of 4-(tert-butyl)benzoic acid (25 mg, 0.14 mmol), (S)-methyl 2-amino-3-(4-(4-(4-(heptyloxy)phenyl)-1H-imidazol-2-yl)phenyl)propanoate (55 mg, 0.13 mmol),

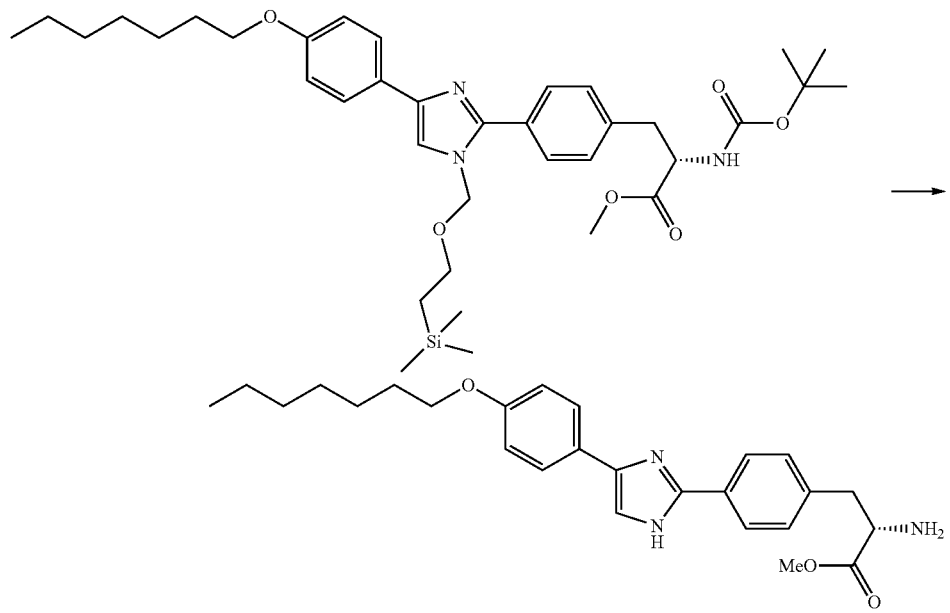

(S)-methyl 2-amino-3-(4-(4-(4-(heptyloxy)phenyl)-1H-imidazol-2-yl)phenyl)propanoate was prepared from (S)-methyl 2-((tert-butoxycarbonyl)amino)-3-(4-(4-(4-(heptyloxy)phenyl)-1-((2-(trimethylsilyl)ethoxy)methyl)-1H-imidazol-2-yl) phenyl) propanoate using General Procedure 8. LCMS-ESI (m/z) calculated for $C_{26}H_{33}N_3O_3$: 435.6. found 436.3 [M+H]$^+$, $t_R$=1.43 min (Method 8).

(S)-2-(4-(tert-butyl)benzamido)-3-(4-(4-(4-(heptyloxy)phenyl)-1H-imidazol-2-yl)phenyl)propanoic acid hydrochloride (Compound 286)

and TEA (53 μl, 0.38 mmol) in DMF (1 mL) was added HATU (53 mg, 0.14 mmol). The reaction mixture was stirred at room temperature for 2 h, diluted in DCM, and washed aq. NaHCO$_3$. The organic layer was dried, concentrated and purified by chromatography (EA/hexane) to provide 14 mg (17%) of methyl (S)-2-(4-(tert-butyl)benzamido)-3-(4-(4-(4-(heptyloxy)phenyl)-1H-imidazol-2-yl)phenyl)propanoate. LCMS-ESI (m/z) calculated for $C_{37}H_{45}N_3O_4$: 595.8. found 596.4 [M+H]$^+$, $t_R$=2.33 min. (Method 8).

The isolated ester intermediate was deprotected using General Procedure 4 to provide 14 mg (17.5%) of (S)-2-(4-(tert-butyl)benzamido)-3-(4-(4-(4-(heptyloxy)phenyl)-1H-

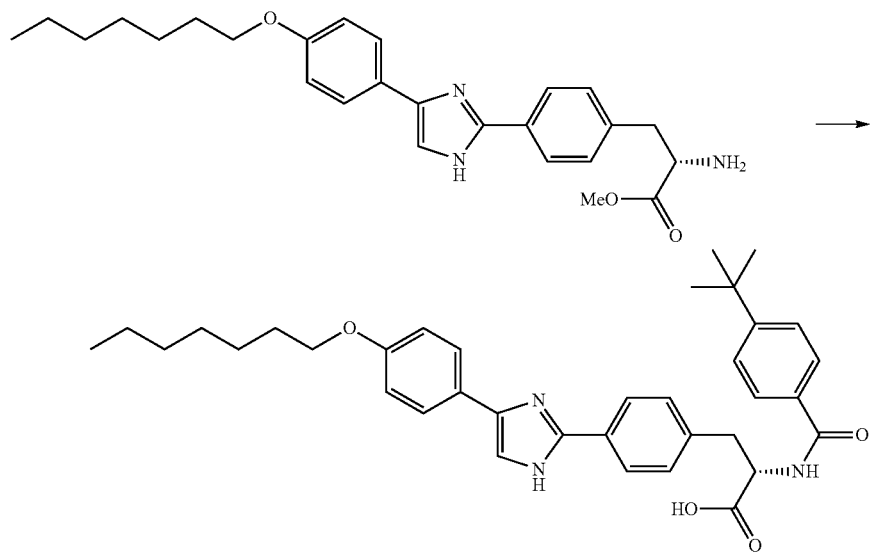

imidazol-2-yl)phenyl)propanoic acid hydrochloride Compound 286 as a light tan solid. LCMS-ESI (m/z) calculated for $C_{36}H_{43}N_3O_4$: 581.8. found 582.4 $[M+H]^+$, $t_R$=6.56 min (Method 9).

4-bromo-1-(4-(heptyloxy)phenyl)-1H-imidazole

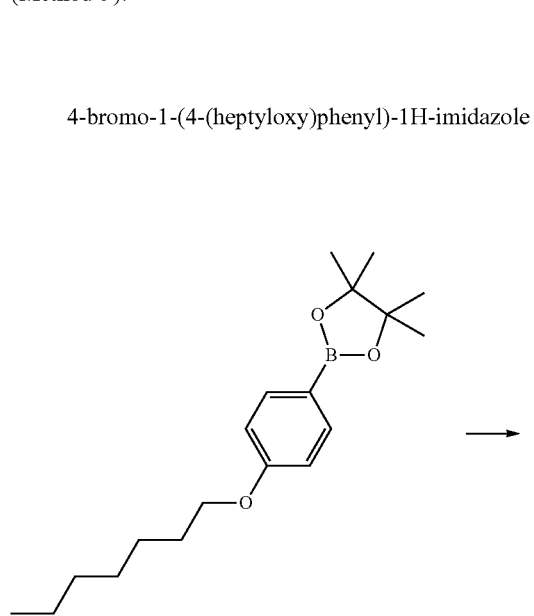

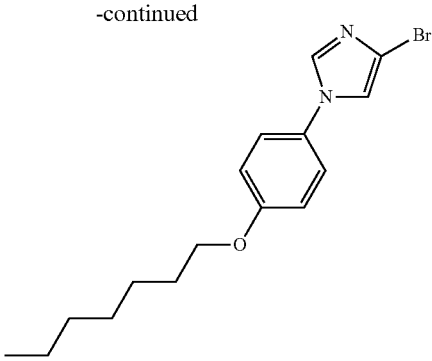

Into a vial was charged (4-(heptyloxy)phenyl)boronic acid (1.00 g, 4.24 mmol), 4-bromo-1H-imidazole (0.31 g, 2.1 mmol), Cu-(TMEDA)$_2$(OH)$_2$Cl$_2$ (0.10 g, 0.21 mmol) and DCM (12 ml). After stirring at room temperature for 42 h, the mixture was purified by chromatography (EA/hexane) to provide 80 mg of impure product. Further purification by chromatography (CAN/DCM) provided 42 mg (6%) of 4-bromo-1-(4-(heptyloxy)phenyl)-1H-imidazole as a colourless oil. LCMS-ESI (m/z) calculated for $C_{16}H_{21}BrN_2O$: 336.1. found 337.1 $[M+H]^+$, $t_R$=2.71 min (Method 8).

(S)-2-(4-(tert-butyl)benzamido)-3-(4-(1-(4-(heptyloxy)phenyl)-1H-imidazol-4-yl)phenyl)propanoic acid (Compound 287)

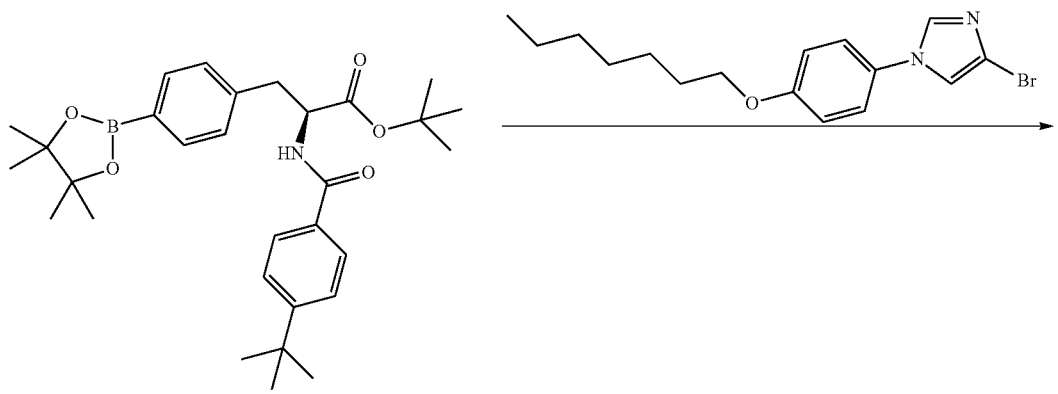

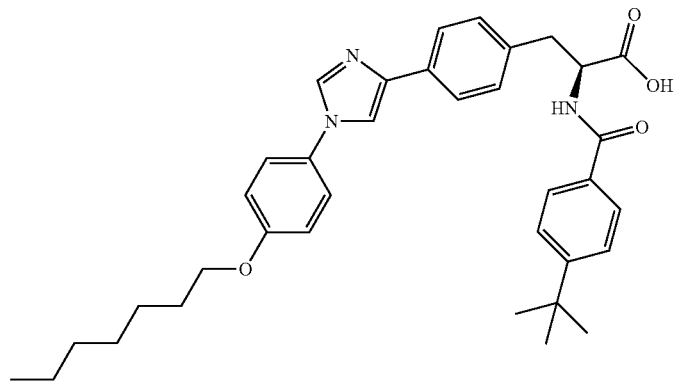

Prepared using General Procedure 10. Into a vial containing INT-13 (96 mg, 0.19 mmol) and 4-bromo-1-(4-(heptyloxy)phenyl)-1H-imidazole (64 mg, 0.19 mmol) in 2/2/1 THF/CAN/H$_2$O (3 mL) was added Na$_2$CO$_3$ (40 mg, 0.38 mmol). The reaction mixture was degassed and Pd(dppf)Cl$_2$ (14 mg, 0.02 mmol) was added. After heating at 120° C. for 30 min in a microwave reactor, the mixture was diluted with EA, washed with aq. NaHCO$_3$, dried over MgSO$_4$ and concentrated. Purification by chromatography (EA/hexanes) provided 14 mg (12%) of the intermediate tert-butyl (S)-2-(4-(tert-butyl)benzamido)-3-(4-(1-(4-(heptyloxy)phenyl)-1H-imidazol-4-yl)phenyl)propanoate as a white solid.

The intermediate was deprotected according to General Procedure 8 to provide 9 mg (8%) of (S)-2-(4-(tert-butyl)benzamido)-3-(4-(1-(4-(heptyloxy)phenyl)-1H-imidazol-4-yl)phenyl)propanoic acid, Compound 287 as a white solid. LCMS-ESI (m/z) calculated for C$_{36}$H$_{43}$N$_3$O$_4$: 581.3. found 582.2 [M+H]$^+$, t$_R$=8.33 min (Method 9).

(S)-2-(4-(tert-butyl)benzamido)-3-(4-(1-(4'-methyl-[1,1'-biphenyl]-4-yl)-1H-pyrazol-4-yl)phenyl)propanoic acid (Compound 288)

Prepared using General Procedure 10. Into a vial containing INT-13 (100 mg, 0.20 mmol) and 4-bromo-1-(4'-methyl-[1,1'-biphenyl]-4-yl)-1H-pyrazole (63 mg, 0.201 mmol) in 2/1 ACN/H$_2$O (3 mL) was added sat aq. NaHCO$_3$ (670 μL, 0.60 mmol). The reaction mixture was degassed and Pd(dppf)Cl$_2$ (15 mg, 0.02 mmol) was added. After heating at 120° C. for 60 min in a microwave reactor, the mixture was diluted with DCM, washed with aq. NaHCO$_3$, passed through a phase separation cartridge, and concentrated. Purification by chromatography (EA/hexane) provided 58 mg (47%) of the intermediate tert-butyl (S)-2-(4-(tert-butyl)benzamido)-3-(4-(1-(4'-methyl-[1,1'-biphenyl]-4-yl)-1H-pyrazol-4-yl)phenyl)propanoate as a white solid. LCMS-ESI (m/z) calculated for C$_{40}$H$_{43}$N$_3$O$_3$: 613.8. found 614.0 [M+H]$^+$, t$_R$=3.02 min (Method 8). The intermediate was stirred in 4M HCl/dioxane for 132 h and filtered. The resulting solid was washed with hexane to provide 13 mg of solid product. The filtrate was loaded onto a strong anion exchange (SAX) column, washed with MeOH, and eluted with 5% AcOH in MeOH. The elution liquors were combined with the trituration solid and concentrated in vacuo to afford 18 mg (32%) of (S)-2-(4-(tert-butyl)benzamido)-3-(4-(1-(4'-methyl-[1,1'-biphenyl]-4-yl)-1H-pyrazol-4-yl)phenyl)propanoic acid 288 as a white solid. LCMS-ESI (m/z) calculated for C$_{36}$H$_{35}$N$_3$O$_3$: 557.3. found 558.0 [M+H]$^+$, t$_R$=9.37 min (Method 9).

Methyl 2-(4-bromophenyl)-2-(5-(tert-butyl)thiophene-2-carboxamido)acetate

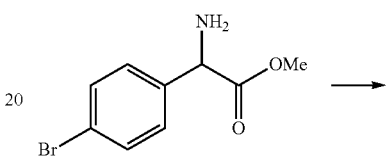

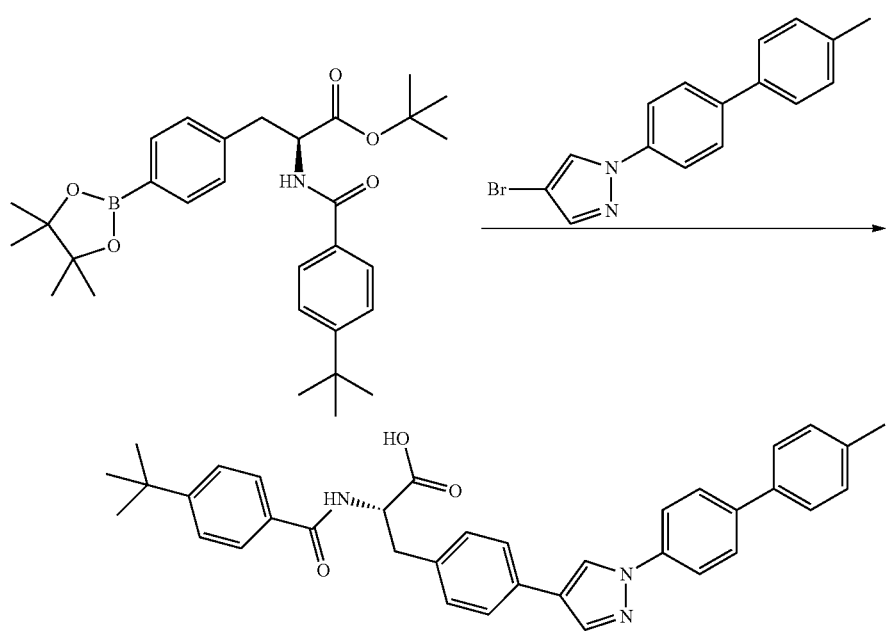

-continued

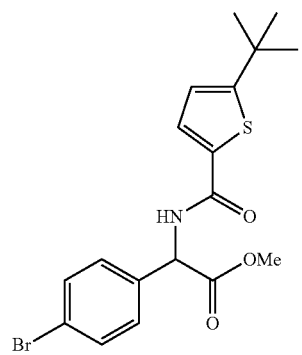

Prepared using General Procedure 7. To a solution of methyl 2-amino-2-(4-bromophenyl)acetate, HCl (730 mg, 2.6 mmol), 5-(tert-butyl)thiophene-2-carboxylic acid (480 mg, 2.6 mmol) and TEA (1090 µl, 7.8 mmol) in DMF (10 mL) was added HATU (1090 mg, 2.9 mmol). After stirring overnight, the reaction mixture was diluted with EA (100 mL) and washed with 1M HCl (100 mL) and brine. The organic layer was dried over $Mg_2SO_4$, concentrated, and purified by chromatography (EA/hexane) to provide 900 mg (76%) of methyl 2-(4-bromophenyl)-2-(5-(tert-butyl)thiophene-2-carboxamido)acetate as a white powder. LCMS-ESI (m/z) calculated for $C_{18}H_{20}BrNO_3S$: 410.3. found 412.0 $[M+2]^+$, $t_R$=2.71 min (Method 8).

Methyl 2-(5-(tert-butyl)thiophene-2-carboxamido)-2-(4-(4,4,5,5-tetramethyl-1, 3, 2-dioxaborolan-2-yl)phenyl)acetate 2-(4-(5-bromopyrimidin-2-yl)phenyl)-2-(5-(tert-butyl)thiophene-2-carboxamido)acetic acid

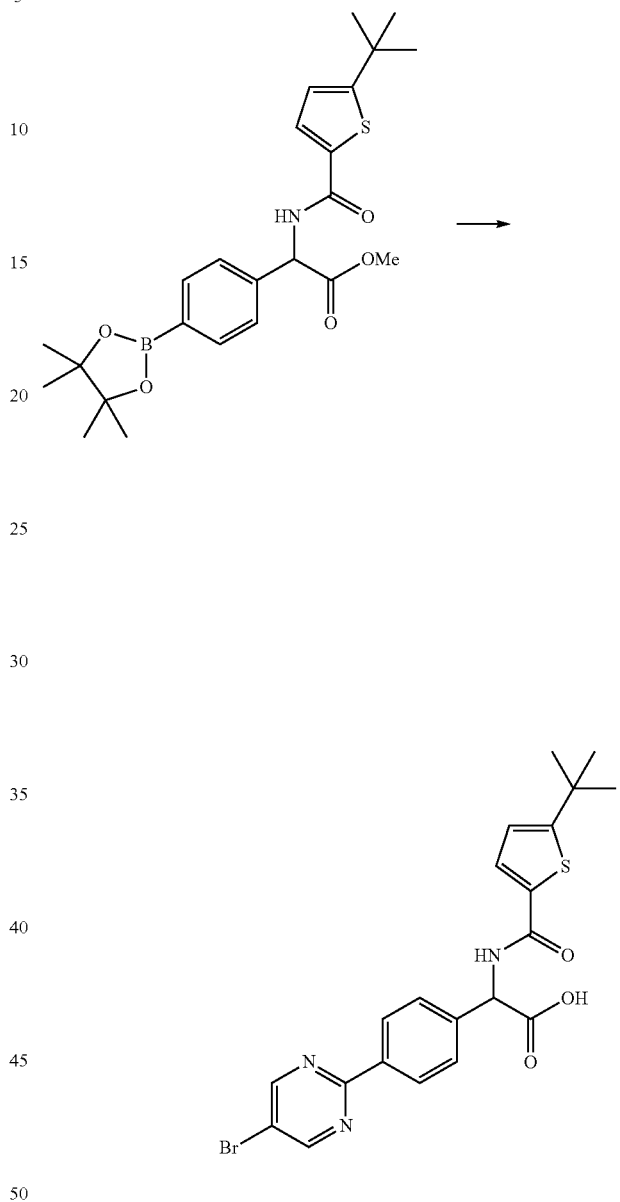

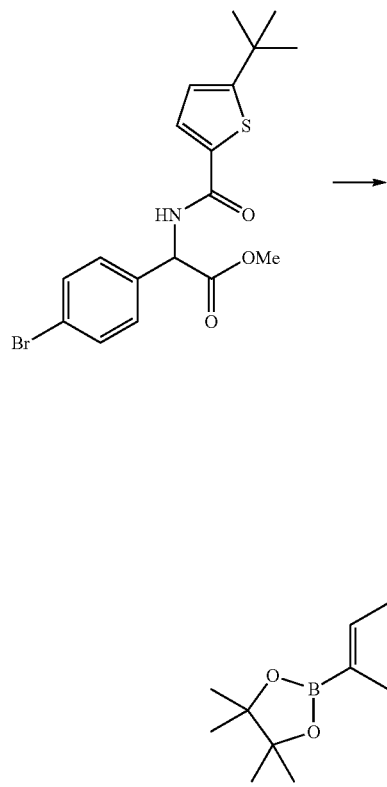

Prepared using General Procedure 10. A solution of 2-(4-bromophenyl)-2-(5-(tert-butyl)thiophene-2-carboxamido)acetate (900 mg, 2.2 mmol), KOAc (650 mg, 6.6 mmol) and 4,4,4',4',5,5,5',5'-octamethyl-2,2'-bi(1,3,2-dioxaborolane) (670 mg, 2.6 mmol) in DMSO (10 mL) at 40° C. was de-gassed. $PdCl_2$dppf (80 mg, 0.11 mmol) was added and the mixture was heated at 100° C. for 3 h. The reaction mixture was purified by chromatography (EA/hexane with 1% TEA) to provide 491 mg (41%) of methyl 2-(5-(tert-butyl)thiophene-2-carboxamido)-2-(4-(4,4,5,5-tetramethyl-1,3,2-dioxaborolan-2-yl)phenyl)acetate. LCMS-ESI (m/z) calculated for $C_{24}H_{32}BNO_5S$: 457.4. found 458.0 $[M+H]^+$, $t_R$=2.89 min (Method 8).

Prepared using General Procedure 10. A mixture of methyl 2-(5-(tert-butyl)thiophene-2-carboxamido)-2-(4-(4,4,5,5-tetramethyl-1,3,2-dioxaborolan-2-yl)phenyl)acetate (320 mg, 0.71 mmol) and 5-bromo-2-iodopyrimidine (220 mg, 0.78 mmol) in THF (2 mL) and ACN (2 mL) was treated with saturated aq. $NaHCO_3$ (1600 µl, 1.40 mmol) and de-gassed ($N_2$ bubbling). $PdCl_2$dppf (26 mg, 0.04 mmol) was added and the mixture was heated at 120° C. for 30 min in a microwave reactor. The mixture was poured onto $H_2O$ (30 mL), acidified with AcOH and extracted with EA (3×15 mL). The combined organics were dried over $MgSO_4$, evaporated, and purified by chromatography (EA/hexane with 1% AcOH) to provide 160 mg (46%) of 2-(4-(5-bromopyrimidin-2-yl)phenyl)-2-(5-(tert-butyl)thiophene-2-carboxamido)acetic acid as a white solid. LCMS-ESI (m/z) calculated for $C_{21}H_{20}BrN_3O_3S$: 473.0. found 474.0 $[M+H]^+$, $t_R$=2.68 min (Method 8).

(S)-2-(5-(tert-butyl)thiophene-2-carboxamido)-3-(4-(5-(4-(heptyloxy)phenyl)-pyrimidin-2-yl)phenyl) propanoic acid (Compound 289)

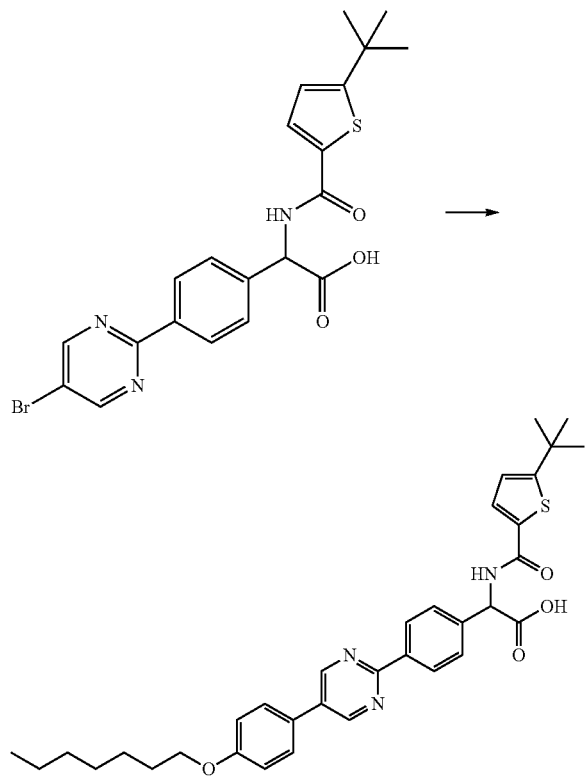

Prepared using General Procedure 10. A solution of 2-(4-(5-bromopyrimidin-2-yl)phenyl)-2-(5-(tert-butyl)thiophene-2-carboxamido)acetic acid (160 mg, 0.34 mmol), (4-(heptyloxy)phenyl)boronic acid (94 mg, 0.40 mmol) and sat aq. $NaHCO_3$ (930 µl, 0.84 mmol) in ACN (1.5 mL) and THF (1.5 mL) was degassed ($N_2$ bubbling). $PdCl_2(dppf)$ (262 mg, 0.34 mmol) was added and the reaction mixture was heated at 110° C. in a microwave reactor for 50 min. The reaction was partitioned between EA and $H_2O$. The organic layer was dried over $MgSO_4$, filtered, concentrated and purified by chromatography (EA/hexane with 1% AcOH) to afford 113 mg (55%) of 2-(5-(tert-butyl)thiophene-2-carboxamido)-2-(4-(5-(4-(heptyloxy)phenyl)pyrimidin-2-yl)phenyl)acetic acid Compound 289 as a white solid. LCMS-ESI (m/z) calculated for $C_{34}H_{39}N_3O_4S$: 585.3. found 586.0 $[M+H]^+$, $t_R$=3.37 min (Method 9).

(S)—N-(1-amino-3-(4-(5-(4-(heptyloxy)phenyl)pyrimidin-2-yl)phenyl)-1-oxopropan-2-yl)-4-(tert-butyl)benzamide

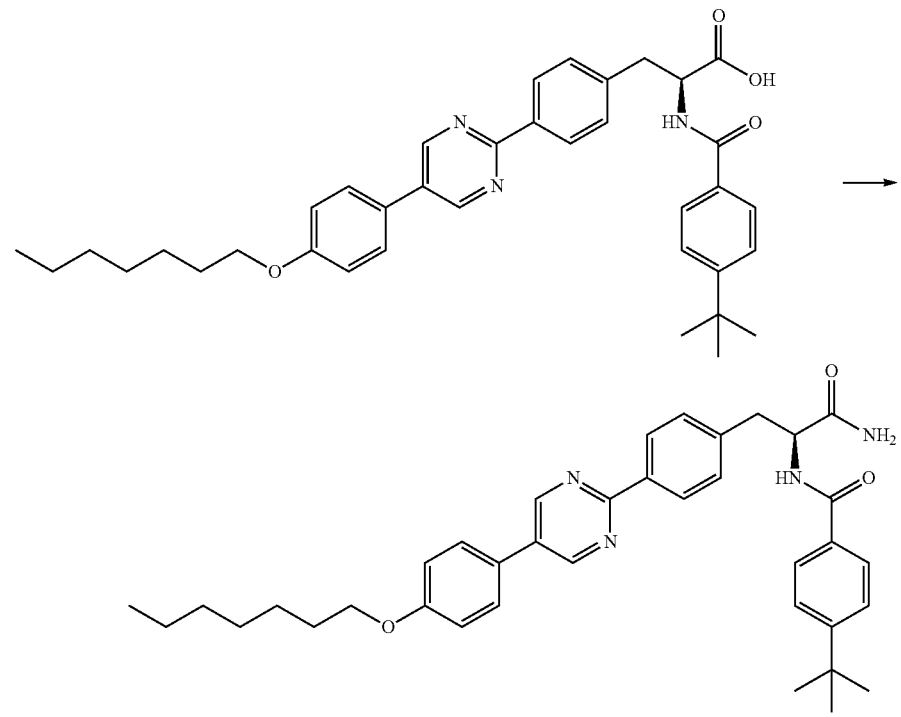

189

A solution of Compound 85 (245 mg, 0.413 mmol) in DMF (5 mL) was treated with NH$_4$Cl (180 mg, 3.3 mmol), DIEA (760 μl, 4.1 mmol) and HATU (170 mg, 0.4 mmol). After stirring overnight, the reaction mixture was diluted with EA (50 mL), washed with aq. 0.5 M HCl (100 mL) and brine (20 mL), then dried over MgSO$_4$ and concentrated. The residue was re-slurried from ACN (4 mL) to afford 204 mg (77%) of (S)—N-(1-amino-3-(4-(5-(4-(heptyloxy)phenyl)pyrimidin-2-yl)phenyl)-1-oxopropan-2-yl)-4-(tert-butyl)benzamide as a fine white solid. LCMS-ESI (m/z) calculated for C$_{37}$H$_{44}$N$_4$O$_3$: 592.3. found 593.0 [M+H]$^+$, $t_R$=3.43 min (Method 6).

(S)-methyl 3-(4-(tert-butyl)benzamido)-4-(4-hydroxyphenyl)butanoate

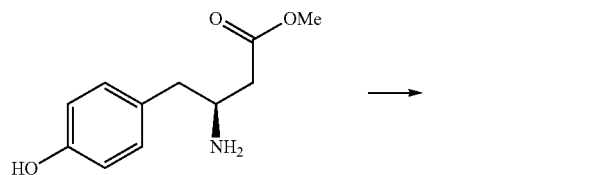

Prepared using General Procedure 7. A solution of (S)-methyl 3-amino-4-(4-hydroxyphenyl)butanoate hydrochloride (2.1 g, 8.7 mmol), 4-(tert-butyl)benzoic acid (1.6 g, 9.0 mmol) and DIEA (3.5 ml, 18.8 mmol) in DMF (20 mL) and DCM (20 mL) was treated with HATU (3.3 g, 8.5 mmol). After 1 h, the mixture was poured onto 1M HCl (100 mL) and extracted with EA (3×50 mL). The combined organic extracts were washed successively with 1M HCl (50 mL), water (50 mL) and brine (20 mL), then dried over MgSO$_4$ and concentrated. The resulting residue was purified by chromatography (EA/hexane) to provide 2.3 g (72%) of (S)-methyl 3-(4-(tert-butyl)benzamido)-4-(4-hydroxyphenyl)butanoate as white needles. LCMS-ESI (m/z) calculated for C$_{22}$H$_{27}$NO: 369.4. found 370.0 [M+H]$^+$, $t_R$=2.52 min (Method 6).

190

(S)-methyl 3-(4-(tert-butyl)benzamido)-4-(4-(((trifluoromethyl)sulfonyl)oxy)-phenyl)butanoate

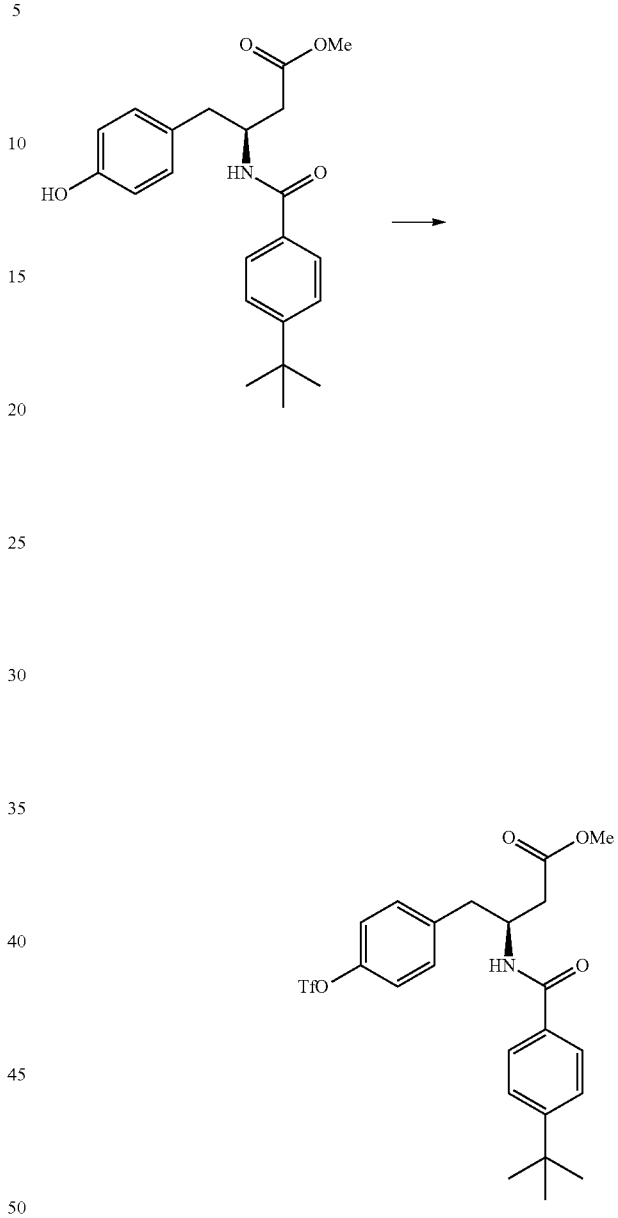

Prepared using General Procedure 9. A stirred solution of (S)-methyl 3-(4-(tert-butyl)benzamido)-4-(4-hydroxyphenyl)butanoate (2.30 g, 6.3 mmol) in DCM (25 mL) was treated with DIEA (1.4 ml, 7.6 mmol) then 1,1,1-trifluoro-N-phenyl-N-((trifluoromethyl)sulfonyl)methanesulfonamide (2.5 g, 6.9 mmol). After 18 h, the reaction mixture was diluted with DCM (100 mL), H$_2$O (50 mL) and NaHCO$_3$ (75 mL) and stirred for 1 h. The organic layer was isolated, washed with NaHCO$_3$ (100 mL), dried over MgSO$_4$, concentrated, and purified by chromatography (EA/hexane) to provide 2.5 g (75%) of (S)-methyl 3-(4-(tert-butyl)benzamido)-4-(4-(((trifluoromethyl)sulfonyl)oxy)phenyl)butanoate as a thick oil. LCMS-ESI (m/z) calculated for C$_{23}$H$_{26}$F$_3$NO$_6$S: 501.5. found 502 [M+H]$^+$, $t_R$=3.20 min (Method 6).

191

(S)-methyl 3-(4-(tert-butyl)benzamido)-4-(4-(4,4,5,5-tetramethyl-1,3,2-dioxaborolan-2-yl)phenyl)butanoate

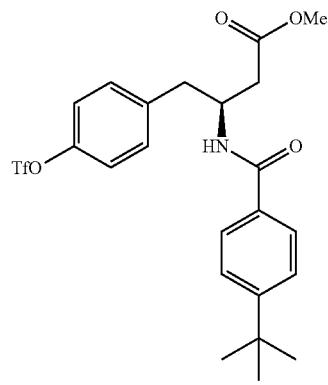

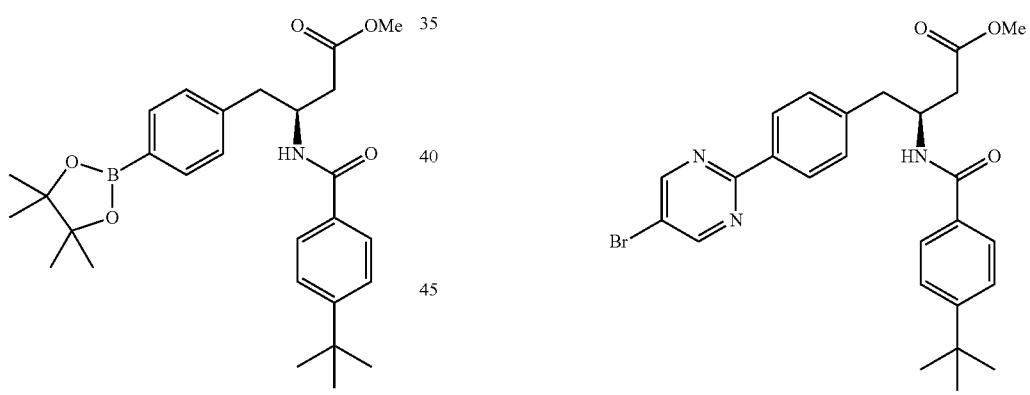

To a vial under a $N_2$ atmosphere were added 4,4,4',4',5,5,5',5'-octamethyl-2,2'-bi(1,3,2-dioxaborolane) (530 mg, 2.1 mmol), (S)-methyl 3-(4-(tert-butyl)benzamido)-4-(4-(((trifluoromethyl)sulfonyl)oxy)phenyl)butanoate (810 mg, 1.6 mmol), KOAc (280 mg, 4.8 mmol) and DMSO (14 mL). The solution was degassed. Pd(dppf)Cl$_2$ (59 mg, 0.08 mmol) was added and the solution was heated to 80° C. for 6 h. The reaction mixture was cooled to room temperature, diluted with EA (100 mL) and washed with sat aq. NaHCO$_3$ (50 ml) and brine (50 mL). The organic layer was dried over MgSO$_4$, concentrated and purified by chromatography (EA/hexane) to afford 446 mg (57%) of (S)-methyl 3-(4-(tert-butyl)benzamido)-4-(4-(4,4,5,5-tetramethyl-1,3,2-dioxaborolan-2-yl)phenyl) as a colorless crystalline solid. LCMS-ESI (m/z) calculated for $C_{28}H_{38}BNO_5$: 479.4. found 480.3 [M+H]$^+$, $t_R$=2.86 min (Method 6).

192

(S)-methyl 4-(4-(5-bromopyrimidin-2-yl)phenyl)-3-(4-(tert-butyl)benzamido)-butanoate

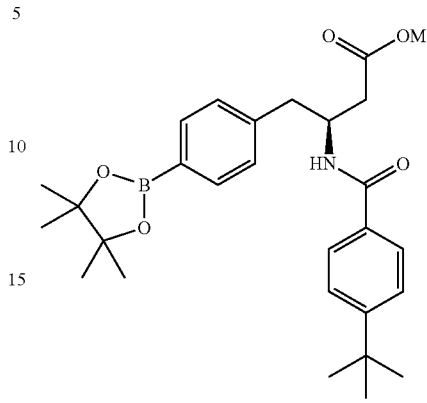

Prepared using General Procedure 10. Into a vial were added (S)-methyl 3-(4-(tert-butyl)benzamido)-4-(4-(4,4,5,5-tetramethyl-1,3,2-dioxaborolan-2-yl)phenyl) (390 mg, 0.81 mmol), 5-bromo-2-iodopyrimidine (240 mg, 0.85 mmol), Na$_2$CO$_3$ (170 mg, 1.6 mmol), THF (1.5 mL), ACN (1.5 mL) and H$_2$O (0.75 mL). The solution was degassed and PdCl$_2$(dppf) (60 mg, 0.08 mmol) was added. The reaction mixture was heated in a microwave reactor at 110° C. for 60 min. The sample was cooled, diluted with EA (50 mL), and washed with sat aq. NaHCO$_3$ (30 mL). The organic layers were dried over MgSO$_4$, filtered, concentrated, and purified by chromatography (EA/hexane) to afford 205 mg (49%) of (S)-methyl 4-(4-(5-bromopyrimidin-2-yl)phenyl)-3-(4-(tert-butyl)benzamido)butanoate as a colourless solid. LCMS-ESI (m/z) calculated for $C_{26}H_{28}BrN_3O_3$: 510.4. found 512.2 [M+H]$^+$, $t_R$=2.77 min (Method 6).

(S)-3-(4-(tert-butyl)benzamido)-4-(4-(5-(4-(hepty-loxy)phenyl)pyrimidin-2-yl)phenyl)butanoic acid
(Compound 291)

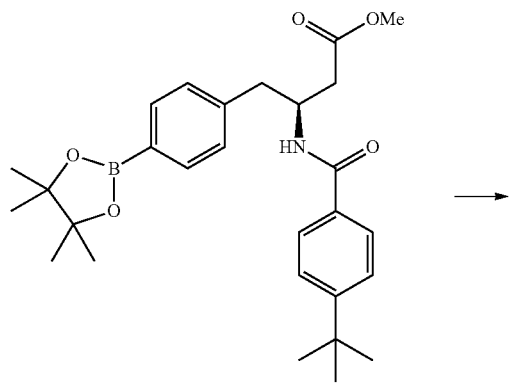

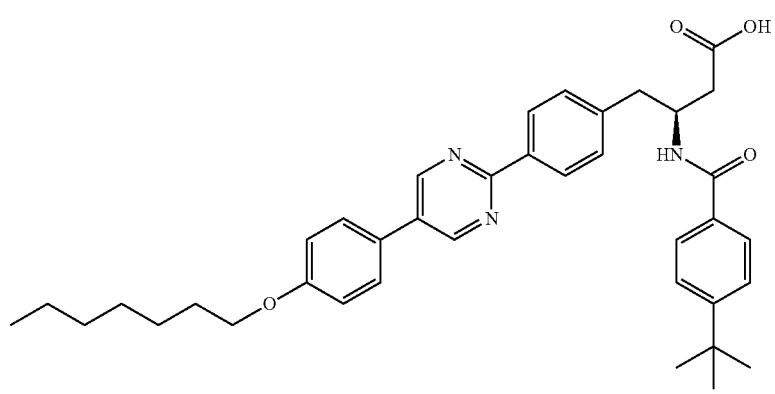

Prepared using General Procedures 10 and 4. Into a vial were added (S)-methyl 4-(4-(5-bromopyrimidin-2-yl)phenyl)-3-(4-(tert-butyl)benzamido)butanoate (180 mg, 0.35 mmol), (4-(heptyloxy)phenyl)boronic acid (98 mg, 0.41 mmol), Na$_2$CO$_3$ (73 mg, 0.69 mmol), ACN (1.2 mL), THF (1.2 mL) and H$_2$O (0.7 mL). The solution was degassed, Pd(dppf)Cl$_2$ (25 mg, 0.03 mmol) was added, and the reaction mixture was heated in a microwave reactor at 110° C. for 80 min. The reaction mixture was diluted with EA (50 mL) and washed with sat aq. NaHCO$_3$ (30 mL). The organics layer was dried over MgSO$_4$, concentrated, and purified by chromatography (EA/hexane) to afford 44 mg of methyl ester intermediate. The solid was dissolved in THF (1 mL) and 1M LiOH (1 mL). The solution was stirred at ambient temperature for 1 h, concentrated, and 1M HCl (1.5 mL) was added. The solid was collected by filtration, washing with water (2×5 mL) and hexane (2×5 mL) to provide 19 mg (9%) of (S)-3-(4-(tert-butyl)benzamido)-4-(4-(5-(4-(heptyloxy)phenyl)pyrimidin-2-yl)phenyl)butanoic acid Compound 291 as a colorless solid. LCMS-ESI (m/z) calculated for C$_{38}$H$_{45}$N$_3$O$_4$: 607.8. found 608.4 [M+H]$^+$, t$_R$=10.99 min (Method 10).

5-bromo-2-chloro-4-methoxypyrimidine

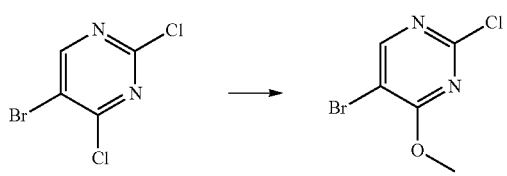

To a stirred solution of 5-bromo-2,4-dichloropyrimidine (500 mg, 2.19 mmol) in MeOH (5 mL) was added a 30% solution of sodium methoxide (0.40 mL, 2.26 mmol). The reaction mixture was stirred at room temperature for 2 h then concentrated. The residue was dissolved in water (5 mL) and extracted with EA (3×5 mL). The combined organic layer was washed with brine, dried over MgSO$_4$ and concentrated to afford 432 mg (88%) of 5-bromo-2-chloro-4-methoxypyrimidine as white solid. LCMS-ESI (m/z) calculated for C$_5$H$_4$BrClN$_2$O: 223.4. found 224.2 [M+H]$^+$, t$_R$=7.66 min. (Method 2).

5-bromo-2-iodo-4-methoxypyrimidine

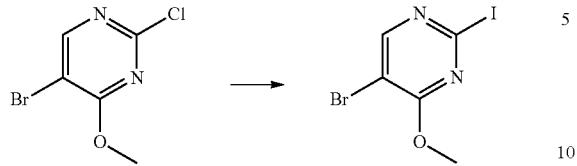

Prepared using General Procedure 16: To a stirred solution of 5-bromo-2-chloro-4-methoxypyrimidine (100 mg, 0.447 mmol) in 57% aq. HI (1.0 mL) was added sodium iodide (125 mg, 0.838 mmol). The reaction mixture was stirred at 40° C. for 16 h, cooled, then quenched with NaHCO$_3$ (5 mL) and extracted with EA (3×5 mL). The combined organics were washed with brine, dried over MgSO$_4$ and concentrated to afford 22.0 mg (16%) of 5-bromo-2-iodo-4-methoxypyrimidine as an off-white solid. LCMS-ESI (m/z) calculated for C$_5$H$_4$BrIN$_2$O: 314.9. found 315.9 [M+H]$^+$, t$_R$=8.22 min. (Method 2). $^1$H NMR (400 MHz, DMSO) δ 8.25 (s, 1H), 4.07 (s, 3H).

Tert-butyl (S)-3-(4-(5-bromo-4-methoxypyrimidin-2-yl)phenyl)-2-(4-(tert-butyl)benzamido)propanoate

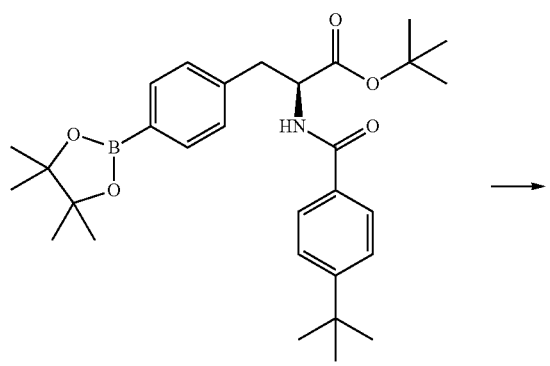

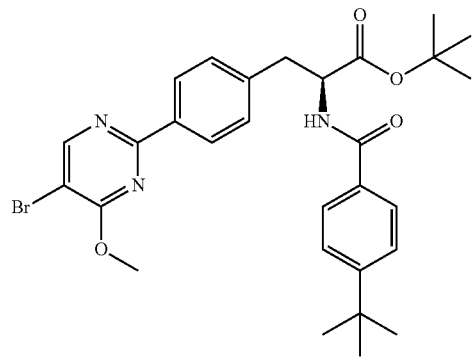

Prepared using General Procedure 10: A mixture of tert-butyl (S)-2-(4-(tert-butyl)benzamido)-3-(4-(4,4,5,5-tetramethyl-1,3,2-dioxaborolan-2-yl)phenyl)propanoate INT-13 (30.0 mg, 0.06 mmol), 5-bromo-2-iodo-4-methoxypyrimidine (22.3 mg, 0.07 mmol), and sodium carbonate (12.5 mg, 0.12 mmol) in acetonitrile (0.80 mL), THF (0.80 mL) and H$_2$O (0.40 mL) was degassed for 10 min. Pd(dppf)Cl$_2$:CH$_2$Cl$_2$ (5 mg, 0.005 mmol) was added and the reaction mixture heated at 110° C. in a microwave for 30 min. Once cooled, the reaction was diluted with NaHCO$_3$ (5 mL), extracted with EA (3×5 mL) and the combined organics dried over MgSO$_4$ and concentrated. The residue was purified by column chromatography (EA/hexanes) to afford 20.0 mg (60%) of tert-butyl (S)-3-(4-(5-bromo-4-methoxypyrimidin-2-yl)phenyl)-2-(4-(tert-butyl)benzamido)propanoate as a white solid. LCMS-ESI (m/z) calculated for C$_{29}$H$_{34}$BrN$_3$O$_4$: 568.5. found 514.2 [M-tBu+H]$^+$, t$_R$=11.0 min. (Method 2).

Tert-butyl (S)-2-(4-(tert-butyl)benzamido)-3-(4-(5-(4-(heptyloxy)phenyl)-4-methoxypyrimidin-2-yl)phenyl)propanoate

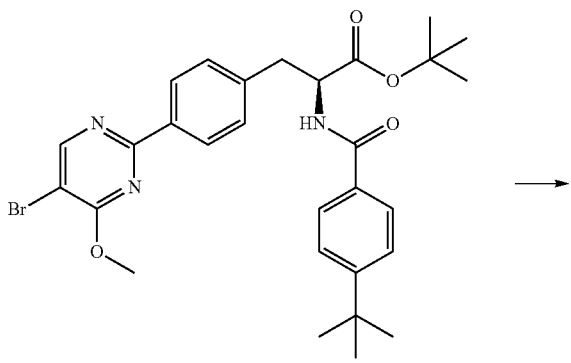

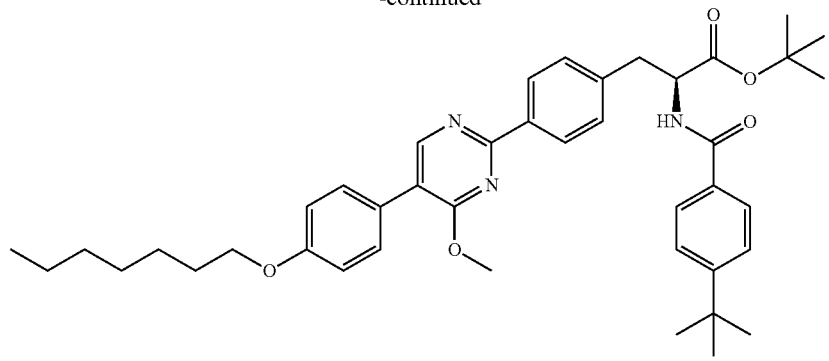

Prepared using General Procedure 10: A mixture of tert-butyl (S)-3-(4-(5-bromo-4-methoxypyrimidin-2-yl)phenyl)-2-(4-(tert-butyl)benzamido)propanoate (18.0 mg, 0.031 mmol), (4-(heptyloxy)phenyl)boronic acid (10.0 mg, 0.042 mmol) and sodium carbonate (8.97 mg, 0.084 mmol) in acetonitrile (0.80 mL), THF (0.80 mL) and H$_2$O (0.40 mL) was degassed for 10 min. Pd(dppf)Cl$_2$:CH$_2$Cl$_2$ (3.09 mg, 0.003 mmol) was added and the reaction mixture heated at 110° C. in a microwave for 30 min. Once cooled, the reaction was diluted with NaHCO$_3$ (5 mL) and extracted with EA (3×5 mL). The combined organics were dried over MgSO$_4$ and concentrated. The residue was purified by column chromatography (EA:hexanes) to afford 20.0 mg (60%) of tert-butyl (S)-2-(4-(tert-butyl)benzamido)-3-(4-(5-(4-(heptyloxy)phenyl)-4-methoxypyrimidin-2-yl)phenyl)propanoate as pale yellow solid. LCMS-ESI (m/z) calculated for C$_{42}$H$_{53}$N$_3$O$_5$: 679.8; no ion observed, t$_R$=13.83 min. (Method 2).

(S)-2-(4-(tert-butyl)benzamido)-3-(4-(5-(4-(heptyloxy)phenyl)-4-methoxypyrimidin-2-yl)phenyl)propanoic acid (Compound 292)

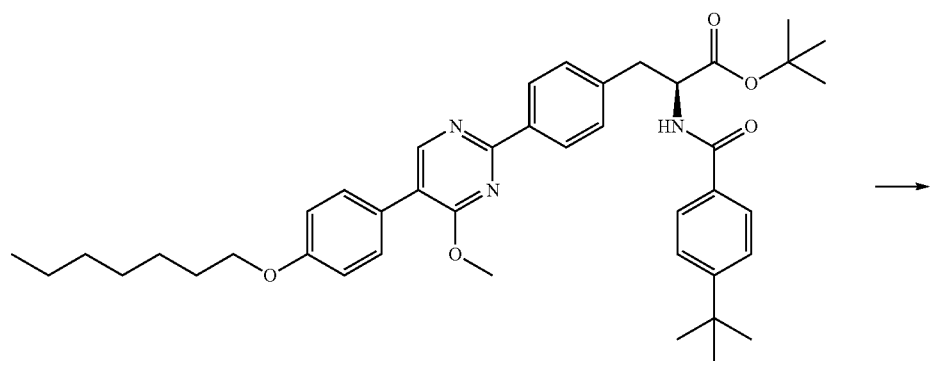

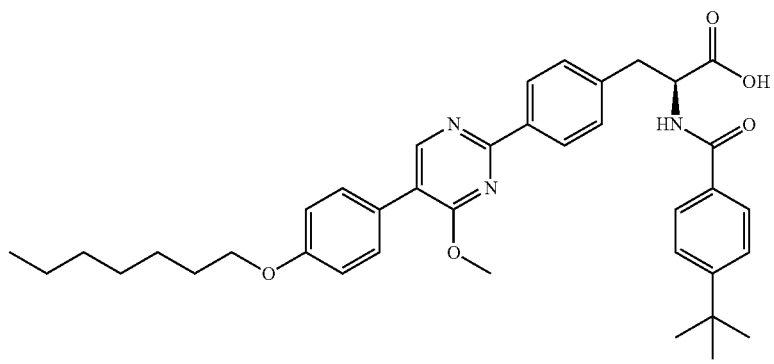

Prepared using General Procedure 8: A solution of tert-butyl (S)-2-(4-(tert-butyl)benzamido)-3-(4-(5-(4-(heptyloxy)phenyl-4-methoxypyrimidin-2-yl)phenyl)propanoate (20.0 mg, 0.029 mmol) in DCM (1 mL) was treated with TFA (0.350 mL). The reaction mixture was stirred at room temperature for 12 h. The solvent was concentrated and the product was purified preparative HPLC to yield 15.0 mg (82%) of (S)-2-(4-(tert-butyl)benzamido)-3-(4-(5-(4-(heptyloxy)phenyl)-4-methoxypyrimidin-2-yl)phenyl)propanoic acid, Compound 292 as pale yellow solid. LCMS-ESI (m/z) calculated for $C_{38}H_{45}N_3O_5$: 623.8; no ion observed, $t_R$=12.17 min. (Method 2).

Compound 293 was prepared using tert-butyl (S)-2-(4-(tert-butyl)benzamido)-3-(4-(4,4,5,5-tetramethyl-1,3,2-dioxaborolan-2-yl)phenyl)propanoate INT-13 and 5-bromo-2-chloro-N,N-dimethylpyrimidin-4-amine using General Procedures 10, 10 and 8 sequentially.

Compound 294 was prepared using tert-butyl (S)-2-(4-(tert-butyl)benzamido)-3-(4-(4,4,5,5-tetramethyl-1,3,2-dioxaborolan-2-yl)phenyl)propanoate INT-13 and 5-bromo-2-iodo-4-methylpyridine using General Procedures 10, 10 and 8 sequentially 5-bromo-2-iodo-4-(trifluoromethyl)pyridine

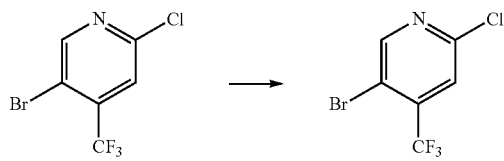 [SMILES: FC(F)(F)c1cc(Cl)ncc1Br ; FC(F)(F)c1cc(Cl)ncc1Br]

Prepared using General Procedure 17: To a stirred a solution of 5-bromo-2-chloro-4-(trifluoromethyl)pyridine (150 mg, 0.576 mmol) in acetonitrile (2 mL) was added sodium iodide (518 mg, 3.45 mmol). The reaction mixture was heated to 40° C. and acetyl chloride (26.0 mg, 0.345 mmol) was added. The reaction mixture was stirred at 40° C. for 90 min. Once cooled, the reaction was quenched with $NaHCO_3$ (5 mL) and extracted with EA (3×5 mL). The combined organics were washed with brine (10 mL), dried over $MgSO_4$ and concentrated to give 80.0 mg (40%) of 5-bromo-2-iodo-4-(trifluoromethyl)pyridine as a white crystalline solid which was used in the subsequent step without purification. LCMS-ESI (m/z) calculated for $C_6H_2BrF_3IN$: 351.9. found 352.5 [M+H]$^+$, $t_R$=3.91 min. (Method 1).

Compound 295 was prepared by employing tert-butyl (S)-2-(4-(tert-butyl)benzamido)-3-(4-(4,4,5,5-tetramethyl-1,3,2-dioxaborolan-2-yl)phenyl)propanoate INT-13 and 5-bromo-2-iodo-4-(trifluoromethyl)pyridine using General Procedures 10, 10 and 8 sequentially.

(S)-(2-(4-(tert-butyl)benzamido)-3-(4-(5-(4-(heptyloxy)phenyl)pyrimidin-2-yl)phenyl)propanoyl)glycine (Compound 297)

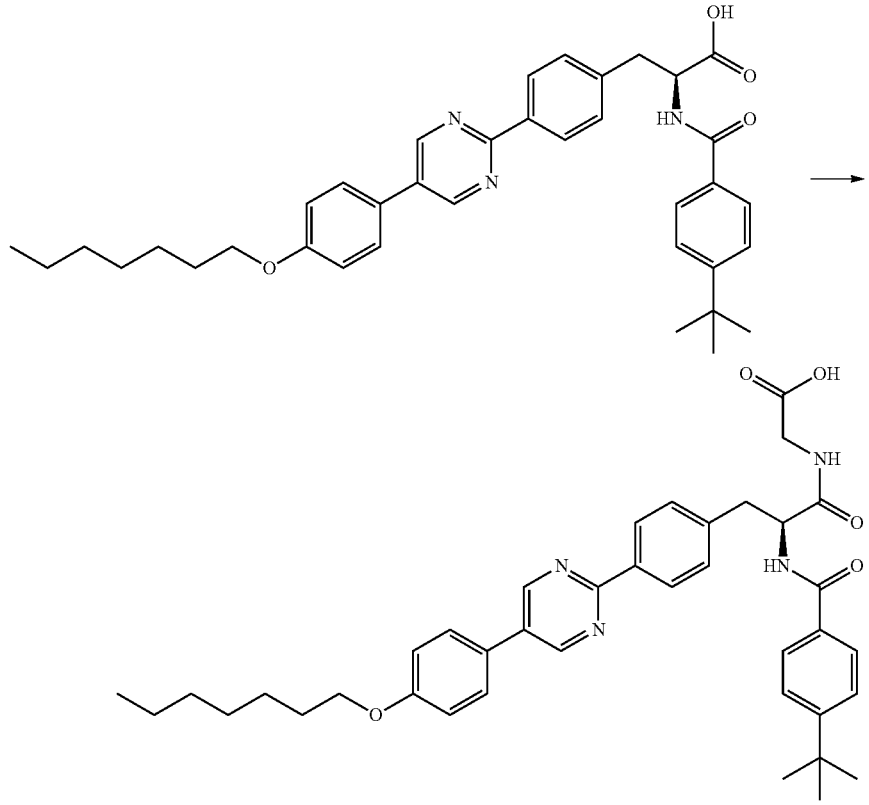

Prepared using General Procedures 7 and 8: To a solution of (S)-2-(4-(tert-butyl)benzamido)-3-(4-(5-(4-(heptyloxy)phenyl)pyrimidin-2-yl)phenyl)propanoic acid Compound 85 (185 mg, 0.312 mmol), tert-butyl 2-aminoacetate hydrochloride (52.2 mg, 0.312 mmol), and DIEA (163 µl, 0.935 mmol) in DMF (3 mL) was added HATU (124 mg, 0.327 mmol). The mixture was stirred for 1 h at room temperature. The crude material was diluted in EA (50 mL), washed with saturated aqueous sodium bicarbonate (20 mL) and brine (20 mL). The organic layer was dried over MgSO$_4$, filtered, and the solvent removed under reduced pressure. The crude product was purified by chromatography (EA/hexanes) to afford the intermediate tert-butyl ester (110 mg).

The tert-butyl ester was dissolved in DCM (1 mL) and TFA (2 mL) was added. The solution was stirred at room temperature for 3 h and the solvent was removed under reduced pressure. The crude mixture was dissolved in DMSO (0.8 mL) and precipitated by the addition of water (3 mL). The precipitate was filtered, washed with water (3 mL) and hexane (2×2 mL) to yield 58 mg (28%) of (S)-(2-(4-(tert-butyl)benzamido)-3-(4-(5-(4-(heptyloxy)phenyl)pyrimidin-2-yl)phenyl)propanoyl)glycine, Compound 297 as a colorless solid. LCMS-ESI (m/z) calculated for C$_{39}$H$_{46}$N$_4$O$_5$: 650.4. found 651.4 [M+H]$^+$, t$_R$=10.43 min (Method 10). The chiral purity was calculated at 92% e.e. (Chiral Method). $^1$H NMR (400 MHz, DMSO-d6) δ 12.62 (s, 1H), 9.15 (s, 2H), 8.60 (d, J=8.6 Hz, 1H), 8.49-8.40 (m, 1H), 8.35-8.25 (m, 2H), 7.84-7.70 (m, 4H), 7.58-7.49 (m, 2H), 7.48-7.41 (m, 2H), 7.16-7.02 (m, 2H), 4.90-4.75 (m, 1H), 4.03 (t, J=6.5 Hz, 2H), 3.93-3.75 (m, 2H), 3.25 (dd, J=13.8, 3.8 Hz, 1H), 3.09 (dd, J=13.7, 11.2 Hz, 1H), 1.79-1.68 (m, 2H), 1.51-1.21 (m, 17H), 0.94-0.80 (m, 3H).

(S)-3-(2-(4-(tert-butyl)benzamido)-3-(4-(5-(4-(heptyloxy)phenyl)pyrimidin-2-yl)phenyl)propanamido)propanoic acid (Compound 298)

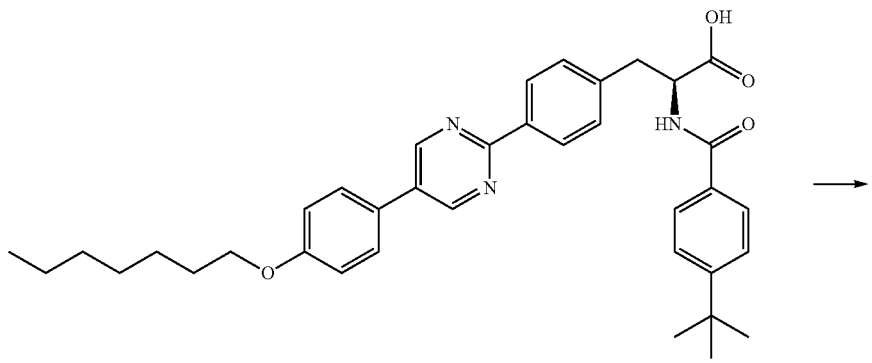

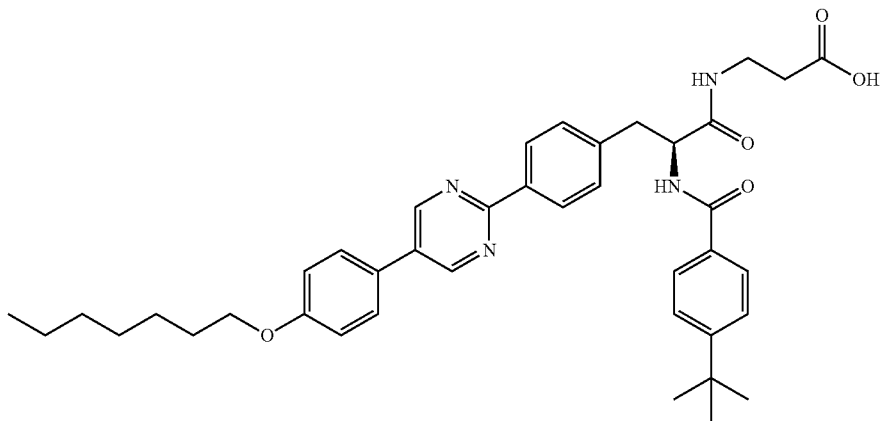

Prepared using General Procedures 7 and 8: HATU (116 mg, 0.31 mmol) was added to a stirring solution of (S)-2-(4-(tert-butyl)benzamido)-3-(4-(5-(4-(heptyloxy)phenyl)pyrimidin-2-yl)phenyl)propanoic acid Compound 85 (173 mg, 0.29 mmol), tert-butyl 3-aminopropanoate hydrochloride (53 mg, 0.29 mmol) and DIEA (153 µl, 0.87 mmol) in DMF (3 mL). The crude material was diluted in EA (50 mL), washed with saturated aqueous sodium bicarbonate (20 mL) and brine (20 mL). The organic layer was dried over MgSO$_4$, filtered, and the solvent removed under reduced pressure. The crude product was purified by chromatography (EA/hexanes) to afford the intermediate tert-butyl ester (122 mg).

The tert-butyl ester was dissolved in DCM (1 mL) and TFA (2 mL) was added. The reaction mixture was stirred at room temperature for 3 h and the solvent was removed under reduced pressure. The crude mixture was dissolved in DMSO (0.8 mL) and precipitated by the addition of water (3 mL). The precipitate was filtered, washed with water (3 mL) and hexane (2×2 mL) to yield 48 mg (25%) of (S)-3-(2-(4-(tert-butyl)benzamido)-3-(4-(5-(4-(heptyloxy)phenyl)pyrimidin-2-yl)phenyl)propanamido)propanoic acid, Compound 298 as a colorless solid. LCMS-ESI (m/z) calculated for $C_{40}H_{48}N_4O_5$: 664.4. found 665.4 [M+H]$^+$, $t_R$=10.36 min (Method 10). The chiral purity was calculated at 92% e.e. (Chiral Method, isocratic with 40% Solvent A, 60% Solvent B). $^1$H NMR (400 MHz, DMSO-d6) δ12.26 (s, 1H), 9.15 (s, 2H), 8.51 (d, J=8.5 Hz, 1H), 8.40-8.25 (m, 2H), 8.25-8.14 (m, 1H), 7.96-7.65 (m, 4H), 7.65-7.36 (m, 4H), 7.28-6.99 (m, 2H), 4.84-4.64 (m, 1H), 4.03 (t, J=6.5 Hz, 2H), 3.32-3.24 (m, 2H), 3.17 (dd, J=13.7, 4.4 Hz, 1H), 3.06 (dd, J=13.7, 10.4 Hz, 1H), 2.41 (t, J=6.9 Hz, 2H), 1.81-1.68 (m, 2H), 1.50-1.20 (m, 17H), 0.88 (t, J=6.7 Hz, 3H).

(S)-4-(tert-butyl)-N-(3-(4-(5-(4-(heptyloxy)phenyl)pyrimidin-2-yl)phenyl)-1-(methylsulfonamido)-1-oxopropan-2-yl)benzamide (Compound 299)

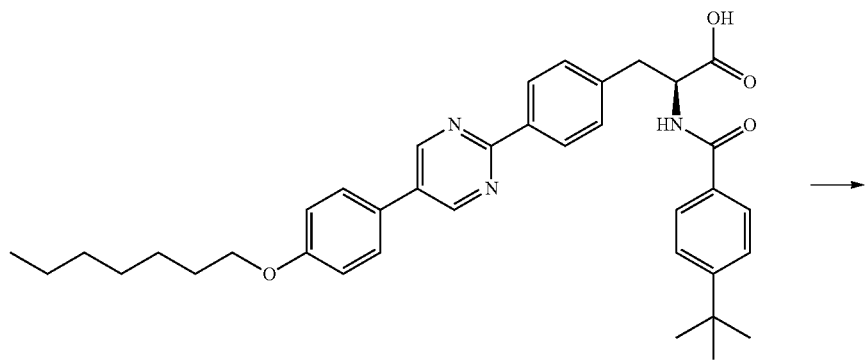

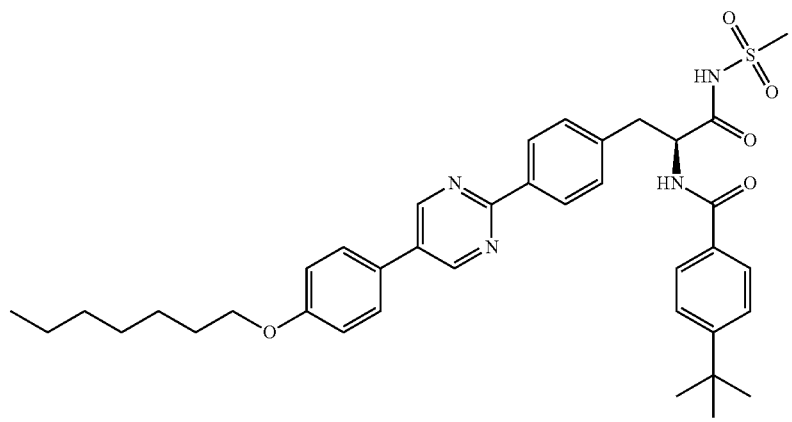

To a solution of (S)-2-(4-(tert-butyl)benzamido)-3-(4-(5-(4-(heptyloxy)phenyl)pyrimidin-2-yl)phenyl)propanoic acid Compound 85 (78.0 mg, 0.13 mmol), methanesulfonamide (20.0 mg, 0.21 mmol), and DMAP (16.1 mg, 0.13 mmol) in DMF (1.5 mL) was added EDC (40.3 mg, 0.21 mmol) and the solution stirred overnight at room temperature. The reaction mixture was diluted in EA (50 mL), washed with aqueous saturated sodium bicarbonate (2×20 mL) and brine (20 mL). The organic layer was dried over MgSO$_4$, filtered, and the solvent removed under reduced pressure. The crude product was purified by chromatography (hexane/EA) to afford 36 mg (40%) of (S)-4-(tert-butyl)-N-(3-(4-(5-(4-(heptyloxy)phenyl)pyrimidin-2-yl)phenyl)-1-(methylsulfonamido)-1-oxopropan-2-yl)benzamide, Compound 299 as a colorless solid. LCMS-ESI (m/z) calculated for $C_{38}H_{46}N_4O_5S$: 670.3. found 671.3 [M+H]$^+$, $t_R$=11.01 min (Method 10).

Compounds 300-304 were prepared from (S)-2-(4-(tert-butyl)benzamido)-3-(4-(5-(4-(heptyloxy)phenyl)pyrimidin-2-yl)phenyl)propanoic acid Compound 85 using General Procedures 3 or 7 followed by 4 or 8.

Compounds 305-317 were prepared from (S)-3-(4-(5-(4-(heptyloxy)phenyl)pyrimidin-2-yl)phenyl)-2-(4-isopropylbenzamido)propanoic acid Compound 94 using General Procedures 3 or 7 followed by 4 or 8.

Compound 318 was prepared from (S)-2-(4-(tert-butyl)benzamido)-3-(4-(5-(4-(hexyloxy)phenyl)pyrimidin-2-yl)phenyl)propanoic acid Compound 225 using General Procedures 7 followed by 8.

(S)-(2-(5-(tert-butyl)thiophene-2-carboxamido)-3-(4-(5-(4-(heptyloxy)phenyl)pyrimidin-2-yl)phenyl)propanoyl)glycine (Compound 319)

Prepared using General Procedures 7 and 4: TEA (93 µl, 0.67 mmol) was added to a solution of (S)-2-(5-(tert-butyl)thiophene-2-carboxamido)-3-(4-(5-(4-(heptyloxy)phenyl)pyrimidin-2-yl)phenyl)propanoic acid Compound 192 (100 mg, 0.167 mmol), methyl 2-aminoacetate hydrochloride (23.03 mg, 0.18 mmol) and HATU (76 mg, 0.20 mmol) in DMF (2 mL). The solution was stirred at room temperature for 18 h. The reaction mixture was diluted with EA (25 mL) and washed with saturated aqueous NaHCO$_3$ (2×25 mL) and 1 M HCl (2×25 mL). The organic phase was dried over MgSO$_4$, filtered, and concentrated. The solid was purified by chromatography (EA/hexanes) to afford the methyl ester intermediate as a colorless solid.

The solid was dissolved in THF (3 mL) and 1 M LiOH (333 µl, 0.33 mmol) was added. The resultant yellow solution was stirred at room temperature for 1 h. The reaction mixture was acidified to pH 1 using 1M HCl and the THF removed in vacuo. The residue was suspended in water and the mixture filtered under vacuum. The solid was azeotroped with MeOH and dried in a vacuum oven to afford 48 mg (44%) of (S)-(2-(5-(tert-butyl)thiophene-2-carboxamido)-3-(4-(5-(4-(heptyloxy)phenyl)pyrimidin-2-yl)phenyl)propanoyl)glycine, Compound 319 as a yellow solid. LCMS-ESI (m/z) calculated for $C_{37}H_{44}N_4O_5S$: 656.3. found 657.0 [M+H]$^+$, $t_R$=10.34 min (Method 10). The chiral purity was calculated at 95% e.e. (Chiral Method). $^1$H NMR (400 MHz, DMSO-d6) δ 12.61 (s, 1H), 9.16 (s, 2H), 8.62 (d, J=8.7 Hz, 1H), 8.51-8.41 (m, 1H), 8.36-8.26 (m, 2H), 7.84-7.75 (m, 2H), 7.68 (d, J=3.8 Hz, 1H), 7.55-7.43 (m, 2H), 7.14-7.05 (m, 2H), 6.92 (d, J=3.8 Hz, 1H), 4.84-4.72 (m, 1H), 4.03 (t, J=6.5 Hz, 2H), 3.89-3.73 (m, 2H), 3.22 (dd, J=13.9, 3.7 Hz, 1H), 3.10-2.96 (m, 1H), 1.78-1.66 (m, 2H), 1.31 (s, 17H), 0.94-0.81 (m, 3H).

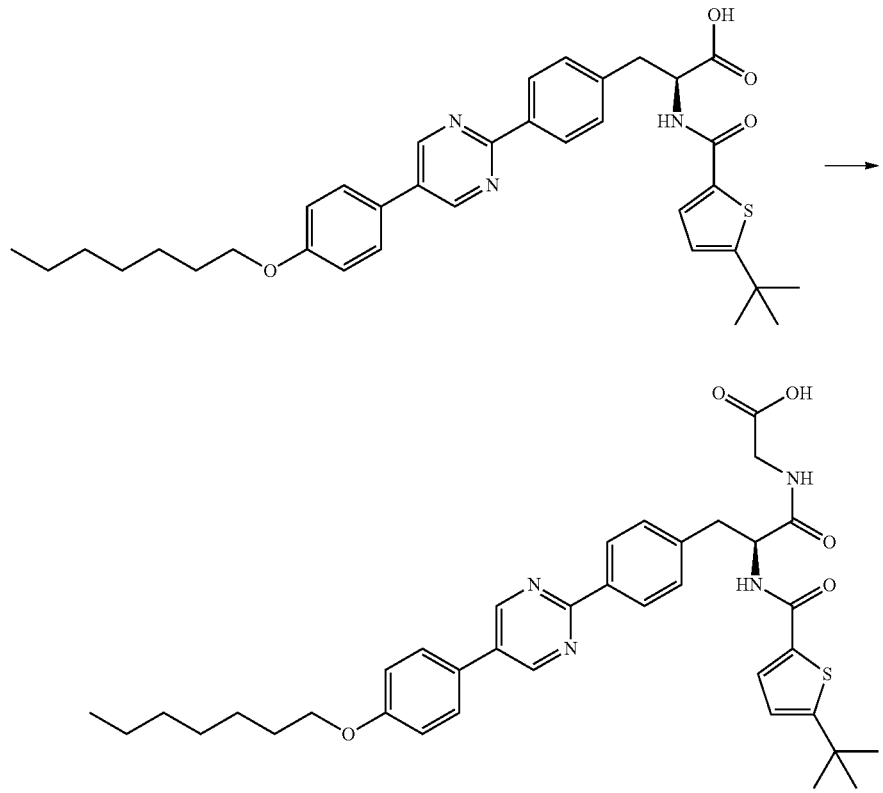

((S)-2-(5-(tert-butyl)thiophene-2-carboxamido)-3-(4-(5-(4-(heptyloxy)phenyl)pyrimidin-2-yl)phenyl)propanoyl)-L-glutamine (Compound 320)

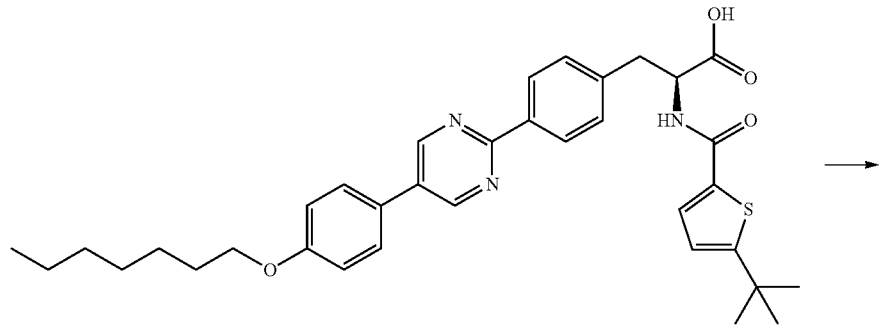

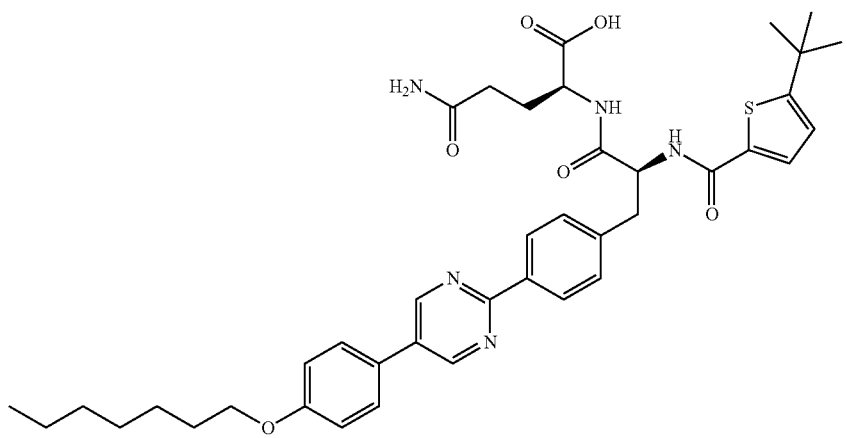

Prepared using General Procedures 7 and 8: To a stirred solution of (S)-2-(5-(tert-butyl)thiophene-2-carboxamido)-3-(4-(5-(4-(heptyloxy)phenyl)pyrimidin-2-yl)phenyl)propanoic acid Compound 192 (250 mg, 0.42 mmol), (S)-tert-butyl 2,5-diamino-5-oxopentanoate hydrochloride (109 mg, 0.46 mmol) and TEA (145 µl, 1.04 mmol) in DMF (4 mL) was added HATU (190 mg, 0.50 mmol) and the reaction mixture was stirred at room temperature for 2 h. The reaction mixture was diluted with EA (50 mL), washed with 1M HCl (50 mL) and brine (100 mL), dried over $MgSO_4$, and concentrated.

The crude product was dissolved in DCM (5 mL) and TFA (3 mL) was added. After 3 h, toluene (10 mL) was added and the solvent removed. The compound was purified by preparative HPLC to afford 78 mg (25%) of ((S)-2-(5-(tert-butyl)thiophene-2-carboxamido)-3-(4-(5-(4-(heptyloxy)phenyl)pyrimidin-2-yl)phenyl)propanoyl)-L-glutamine, Compound 320 as a white powder. LCMS-ESI (m/z) calculated for $C_{40}H_{49}N_5O_6S$: 727.3. found 728.0 $[M+H]^+$, $t_R$=10.71 min (Method 10). The chiral purity was 90% d.e. (Chiral Method). $^1$H NMR (400 MHz, DMSO-d6) δ 9.15 (s, 2H), 8.56 (d, J=8.6 Hz, 1H), 8.42-8.34 (m, 1H), 8.34-8.27 (m, 2H), 7.84-7.75 (m, 2H), 7.66 (d, J=3.9 Hz, 1H), 7.54-7.48 (m, 2H), 7.32 (s, 1H), 7.12-7.04 (m, 2H), 6.90 (d, J=3.8 Hz, 1H), 6.77 (s, 1H), 4.81-4.65 (m, 1H), 4.19-4.11 (m, 1H), 4.03 (t, J=6.5 Hz, 2H), 3.20 (dd, J=14.1, 3.5 Hz, 1H), 3.07-2.96 (m, 1H), 2.24-2.09 (m, 2H), 2.06-1.93 (M, 1H), 1.90-1.79 (m, 1H), 1.78-1.68 (m, 2H), 1.47-1.20 (m, 17H), 0.93-0.82 (m, 3H).

Compounds 321-326 were prepared from Compound 192 using General Procedures 3 or 7 followed by 4 or 8.

(S)-2-(((benzyloxy)carbonyl)amino)-3-(4-(5-(4-(hep-tyloxy)phenyl) pyrimidin-2-yl) phenyl) propanoic acid (INT-22)

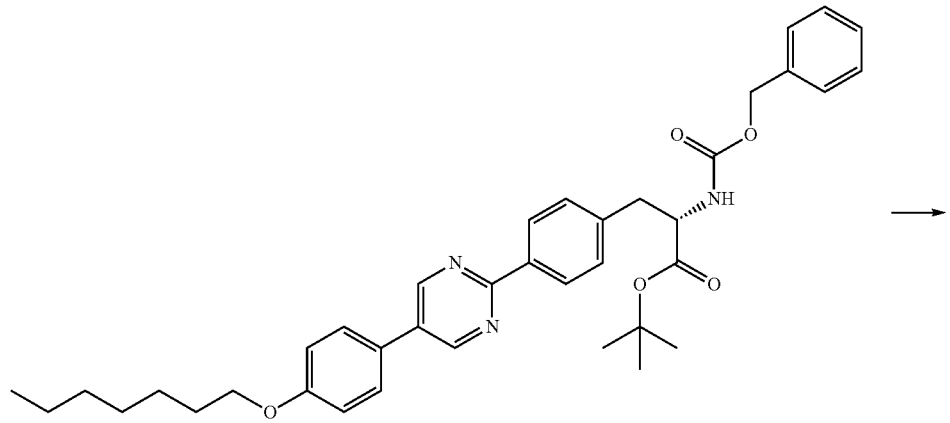

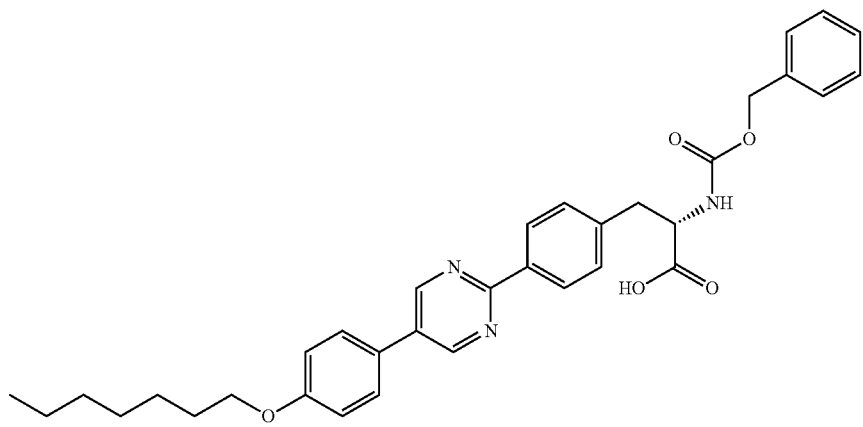

Prepared using General Procedure 8. To a stirred solution of (S)-tert-butyl 2-(((benzyloxy)carbonyl)amino)-3-(4-(5-(4-(heptyloxy)phenyl)pyrimidin-2-yl) phenyl) propanoate INT-8 (6.4 g, 10.26 mmol) in DCM (30 mL) was added TFA (20 mL) and the mixture was stirred at room temperature for 3 h. Toluene (50 mL then 2×30 mL) was added and the solvent as removed under vacuum. The material was sonicated in DCM (20 mL) and acetonitrile (30 mL) was added. The DCM was partially removed under a flow of air until a precipitate began to appear. The suspension was stirred for a further 2 h and the yellow solid was isolated by filtration and washed with additional iso-hexanes (100 mL). The solid was dried under suction then at under vacuum at 40° C. overnight to afford 5.5 g (90%) (S)-2-(((benzyloxy)carbonyl)amino)-3-(4-(5-(4-(heptyloxy)phenyl)pyrimidin-2-yl) phenyl) propanoic acid INT-22 as a yellow solid. LCMS-ESI (m/z) calculated for $C_{34}H_{37}N_3O_5$: 567.3. found 568.3 $[M+H]^+$, $t_R$=10.11 min (Method 10).

Tert-butyl ((S)-2-(((benzyloxy)carbonyl)amino)-3-(4-(5-(4-(heptyloxy)phenyl)pyrimidin-2-yl)phenyl)propanoyl)-D-alaninate (INT-23)

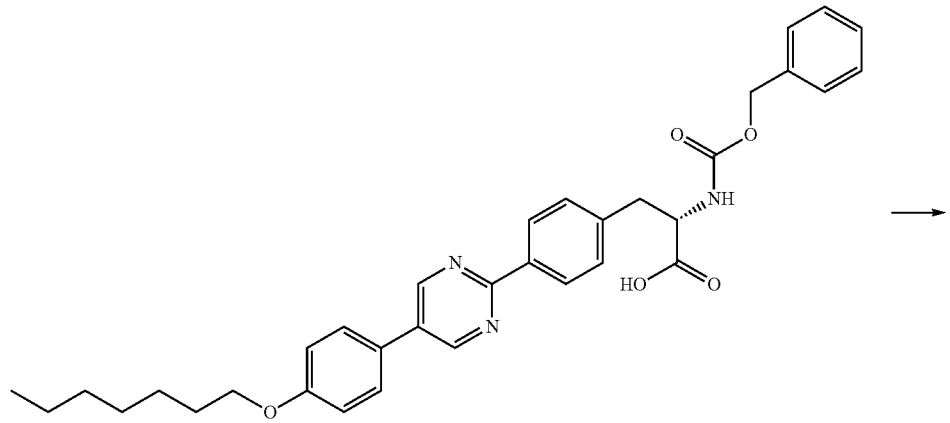

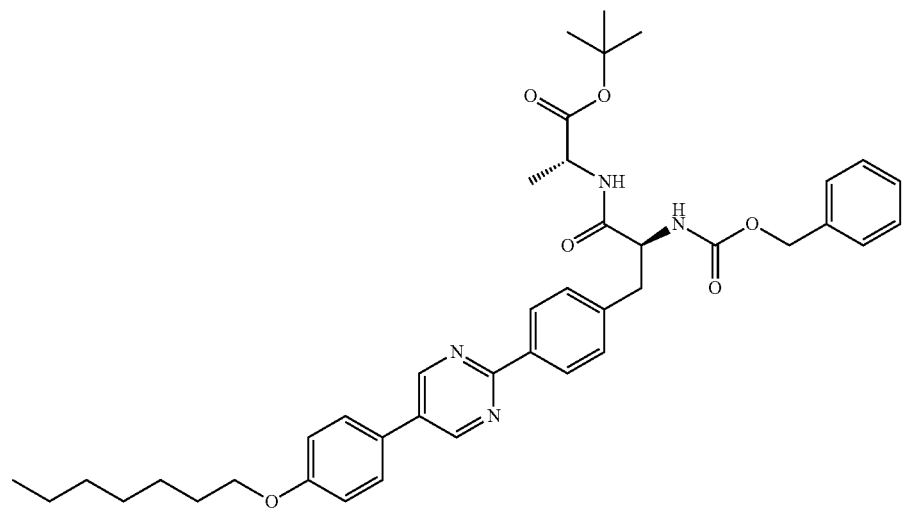

Prepared using General Procedure 7. To a stirred solution of (S)-2-(((benzyloxy)carbonyl)amino)-3-(4-(5-(4-(heptyloxy)phenyl)pyrimidin-2-yl)phenyl)propanoic acid (1000 mg, 1.762 mmol) and (R)-tert-butyl 2-aminopropanoate HCl (352 mg, 1.938 mmol) in DMF (8 mL). The solution was cooled to 0° C. and TEA (737 μl, 5.28 mmol) was added. To this mixture was slowly added HATU (804 mg, 2.114 mmol) over 5 mins then the reaction mixture was allowed to warm to room temperature. The reaction mixture was diluted with EA (150 mL) and washed with 1M HCl (100 mL) then brine (100 mL). The organic layer was isolated and dried over MgSO$_4$. The solvents were removed to give a white solid and ACN (50 mL) was added and the suspension was sonicated. The fine suspension was stirred for 30 mins then filtered and washed with iso-hexanes to afford 881 mg (70.5%) of tert-butyl ((S)-2-(((benzyloxy)carbonyl)amino)-3-(4-(5-(4-(heptyloxy)phenyl)pyrimidin-2-yl)phenyl)propanoyl)-D-alaninate INT-23 as a white powder. LCMS-ESI (m/z) calculated for $C_{41}H_{50}N_4O_6$: 694.4; no m/z observed, $t_R$=3.39 min (Method 11). The chiral purity was calculated at >99% e.e. (Chiral Method).

Tert-butyl ((S)-2-amino-3-(4-(5-(4-(heptyloxy)phenyl)pyrimidin-2-yl)phenyl)propanoyl)-D-alaninate (INT-24)

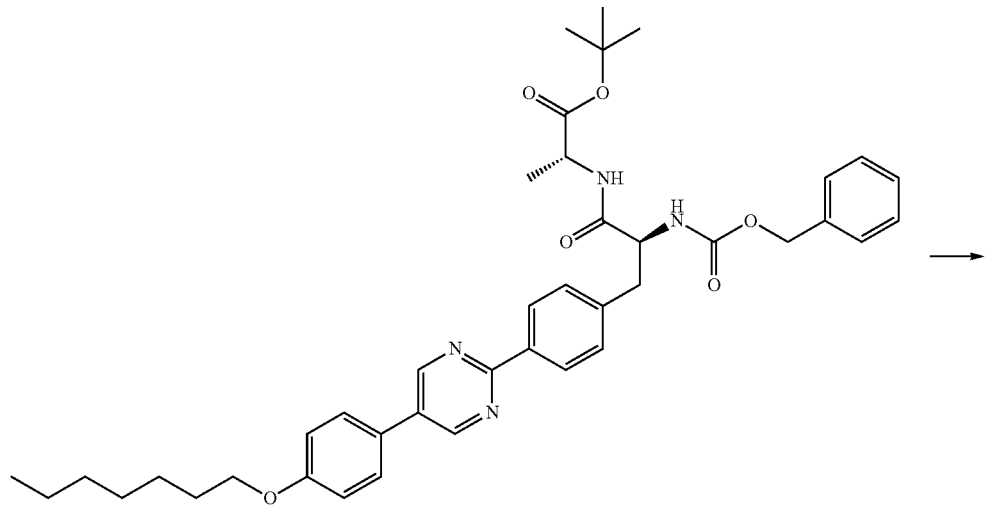

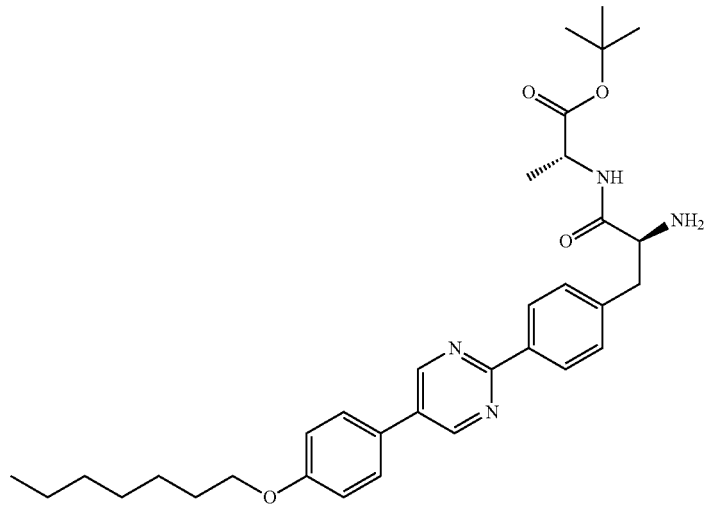

Prepared using General Procedure 18: To a stirred solution of tert-butyl ((S)-2-(((benzyloxy)carbonyl)amino)-3-(4-(5-(4-(heptyloxy)phenyl)pyrimidin-2-yl)phenyl)propanoyl)-D-alaninate (860 mg, 1.238 mmol) in THF (30 mL) was added palladium on carbon (10 wt %) as a slurry in EtOH (4 mL). To this mixture was added acetic acid (1 mL) and the reaction mixture was hydrogenated at 4 bar pressure at room temperature. The reaction mixture was diluted with THF (50 mL) and filtered through Celite. The crude product was loaded onto a column in 5% AcOH in MeOH/THF. The column was washed with MeOH/THF/DCM and then the product was eluted with 0.7 M ammonia in MeOH/THF/DCM. The resultant mixture was concentrated in vacuo to afford 565 mg (77%) of tert-butyl ((S)-2-amino-3-(4-(5-(4-(heptyloxy)phenyl)pyrimidin-2-yl)phenyl)propanoyl)-D-alaninate INT-24 as a yellow solid. LCMS-ESI (m/z) calculated for $C_{33}H_{44}N_4O_4$: 560.3; no m/z observed, $t_R$=2.61 min (Method 11).

Tert-butyl ((S)-2-(5-(tert-butyl)thiophene-2-carboxamido)-3-(4-(5-(4-(heptyloxy)phenyl) pyrimidin-2-yl)phenyl)propanoyl)-D-alaninate

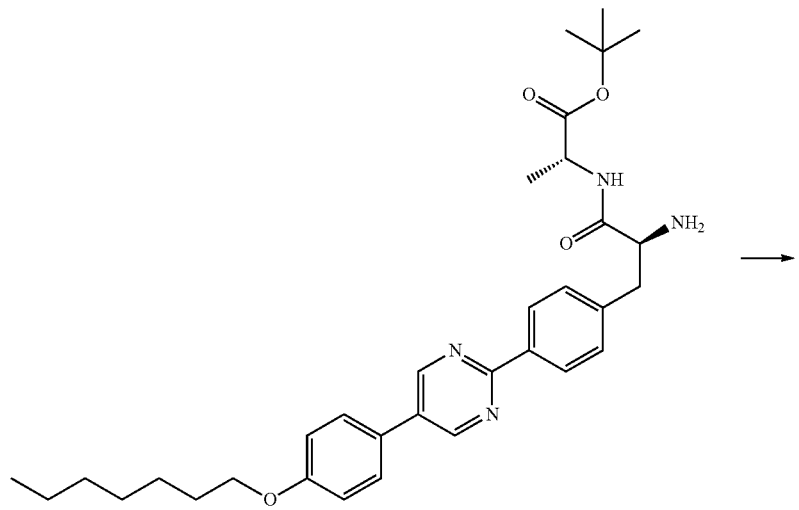

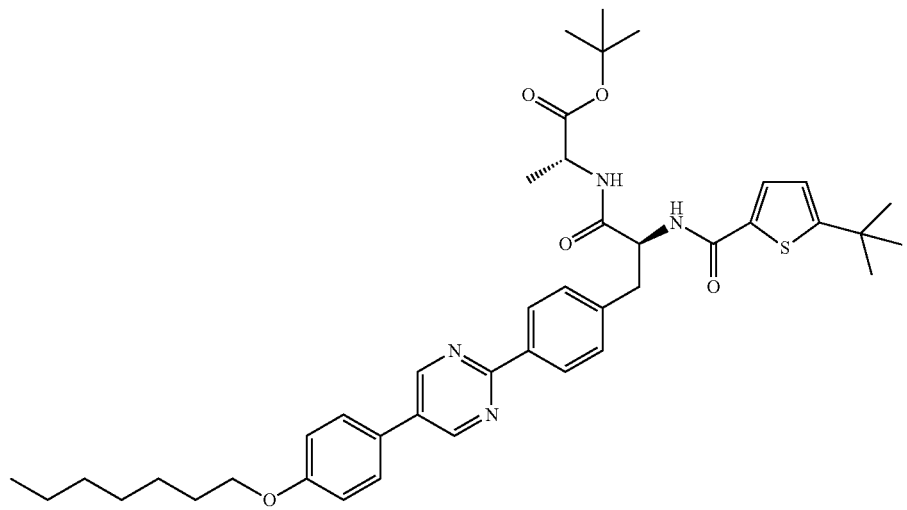

Prepared using General Procedure 7. To a stirred solution of tert-butyl ((S)-2-amino-3-(4-(5-(4-(heptyloxy)phenyl)pyrimidin-2-yl)phenyl)propanoyl)-D-alaninate (418 mg, 0.75 mmol), 5-(tert-butyl)thiophene-2-carboxylic acid (137 mg, 0.75 mmol) in DMF (8 mL) was added TEA (208 µl, 1.49 mmol). The mixture was cooled to 0° C. and HATU (298 mg, 0.78 mmol) was added in 2 portions over 5 mins. The mixture was stirred at room temperature for 2 h. The reaction mixture was diluted with EA (150 mL) and washed with saturated aqueous $NaHCO_3$ (100 mL), 1N HCl (100 mL), and brine (100 mL). The organic layer was dried over $MgSO_4$ then concentrated. The crude product was purified by chromatography 0-30% ACN in DCM to afford 382 mg (69%) of tert-butyl ((S)-2-(5-(tert-butyl)thiophene-2-carboxamido)-3-(4-(5-(4-(heptyloxy)phenyl) pyrimidin-2-yl) phenyl)propanoyl)-D-alaninate as a white solid. LCMS-ESI (m/z) calculated for $C_{42}H_{54}N_4O_5S$: 726.4; no m/z observed, $t_R$=3.47 min (Method 11).

((S)-2-(5-(tert-butyl)thiophene-2-carboxamido)-3-(4-(5-(4-(heptyloxy)phenyl)pyrimidin-2-yl)phenyl)propanoyl)-D-alanine (Compound 327)

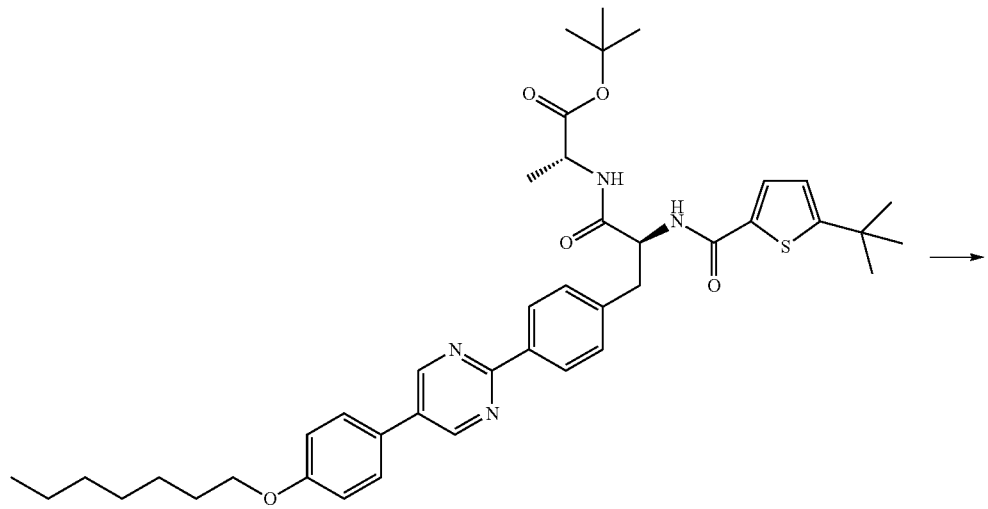

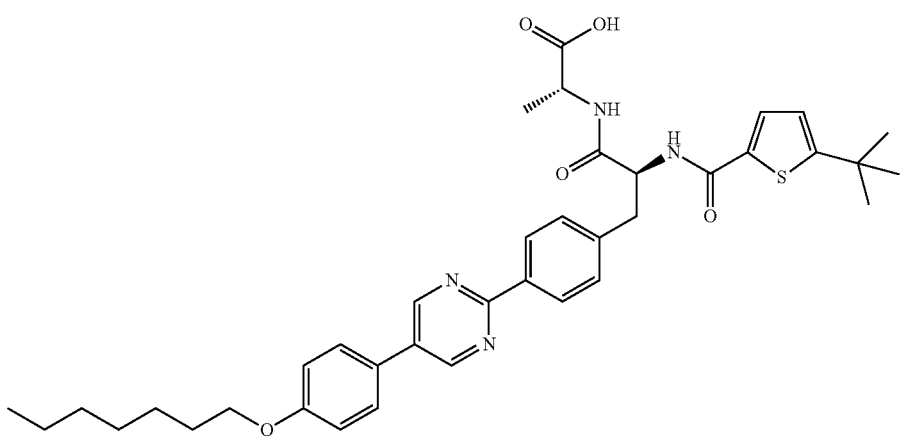

Prepared using General Procedure 8. To a stirred solution of tert-butyl ((S)-2-(5-(tert-butyl)thiophene-2-carboxamido)-3-(4-(5-(4-(heptyloxy)phenyl)pyrimidin-2-yl)phenyl) propanoyl)-D-alaninate (375 mg, 0.495 mmol) in DCM (8 mL) was added TFA (4 mL) and the mixture was stirred at room temperature for 3 h. The reaction mixture was azeotroped with toluene (2×30 mL) to give a viscous oily solid. DMSO (5 mL) was added and the solution was sonicated. To this solution was added water (60 mL) and the mixture was sonicated for 5 mins then stirred at room temperature for 20 mins. The white solid was isolated by filtration and washed with additional water (20 mL) and isohexanes (30 mL). The material was dried under vacuum, suspended in ACN (20 mL), then diluted with diethyl ether (30 mL) and stirred for 20 mins. The suspension was filtered and the wet solid was dried under vacuum to give 189.3 mg (55%) of ((S)-2-(5-(tert-butyl)thiophene-2-carboxamido)-3-(4-(5-(4-(heptyloxy)phenyl)pyrimidin-2-yl)phenyl) propanoyl)-D-alanine Compound 327 as a white powder. LCMS-ESI (m/z) calculated for $C_{38}H_{46}N_4O_5S$: 670.3. found 671.0 $[M+H]^+$, $t_R$=13.32 min (Method 10). The chiral purity was calculated at >99% e.e. (Chiral Method). [1] NMR (400 MHz, DMSO-d6) δ 12.64 (s, 1H), 9.16 (s, 2H), 8.56 (d, J=8.8 Hz, 1H), 8.48 (d, J=7.4 Hz, 1H), 8.35-8.26 (m, 2H), 7.84-7.76 (m, 2H), 7.70 (d, J=3.9 Hz, 1H), 7.54-7.45 (m, 2H), 7.13-7.05 (m, 2H), 6.92 (d, J=3.8 Hz, 1H), 4.86-4.77 (m, 1H), 4.29-4.18 (m, 1H), 4.03 (t, J=6.5 Hz, 2H), 3.20-3.10 (m, 1H), 3.08-2.94 (m, 1H), 1.80-1.68 (m, 2H), 1.51-1.22 (m, 20H), 0.94-0.83 (m, 3H).

(S)-tert-butyl 1-((S)-2-(((benzyloxy)carbonyl)
amino)-3-(4-(5-(4-(heptyloxy)phenyl)pyrimidin-2-
yl)phenyl)propanoyl)pyrrolidine-2-carboxylate
(INT-25)

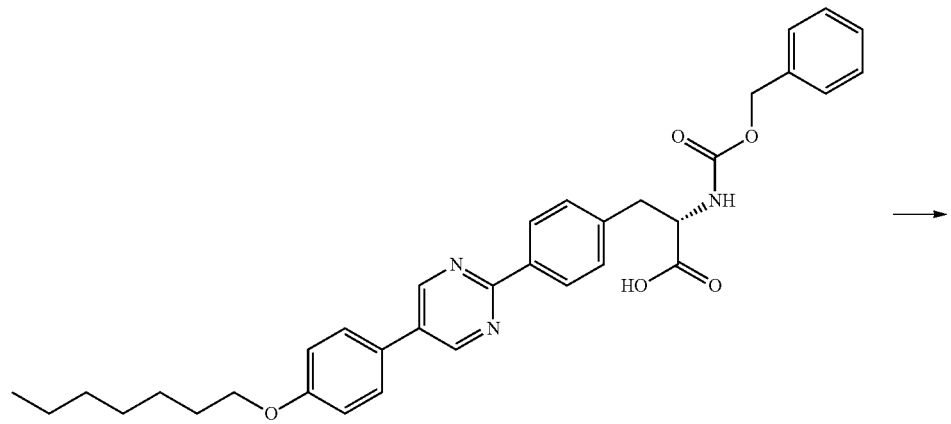

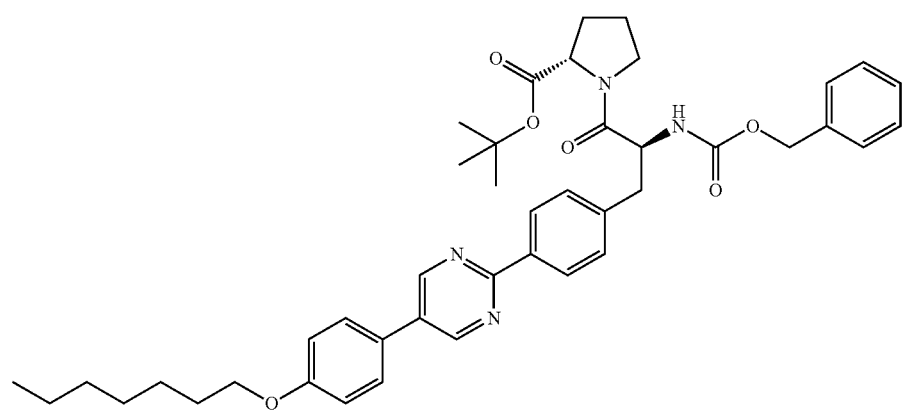

Prepared using General Procedure 7. A stirred solution of (S)-2-(((benzyloxy)carbonyl)amino)-3-(4-(5-(4-(heptyloxy)phenyl)pyrimidin-2-yl)phenyl)propanoic acid (419 mg, 0.738 mmol), (S)-tert-butyl pyrrolidine-2-carboxylate HCl (153 mg, 0.738 mmol) and TEA (257 µl, 1.845 mmol) in DMF (6 mL) was cooled to 0° C. and HATU (295 mg, 0.775 mmol) was slowly added over 5 minutes. The reaction was stirred at room temperature for 2 h, then diluted with 1M citric acid (30 mL) and iso-hexanes (20 mL). EA (100 mL) was added and the organic layer was isolated, washed with brine (100 mL), dried with $MgSO_4$. The solvent was removed and the crude product was purified by chromatography 0-20% ACN in DCM to afford 436 mg (81%) of (S)-tert-butyl 1-((S)-2-(((benzyloxy)carbonyl)amino)-3-(4-(5-(4-(heptyloxy)phenyl)pyrimidin-2-yl)phenyl)propanoyl) pyrrolidine-2-carboxylate INT-25 as a viscous oil. LCMS-ESI (m/z) calculated for $C_{43}H_{52}N_4O_6$: 720.4; no m/z observed, $t_R$=11.45 min (Method 10).

(S)-tert-butyl 1-((S)-2-amino-3-(4-(5-(4-(heptyloxy)
phenyl)pyrimidin-2-yl)phenyl)propanoyl)pyrroli-
dine-2-carboxylate (INT-26)

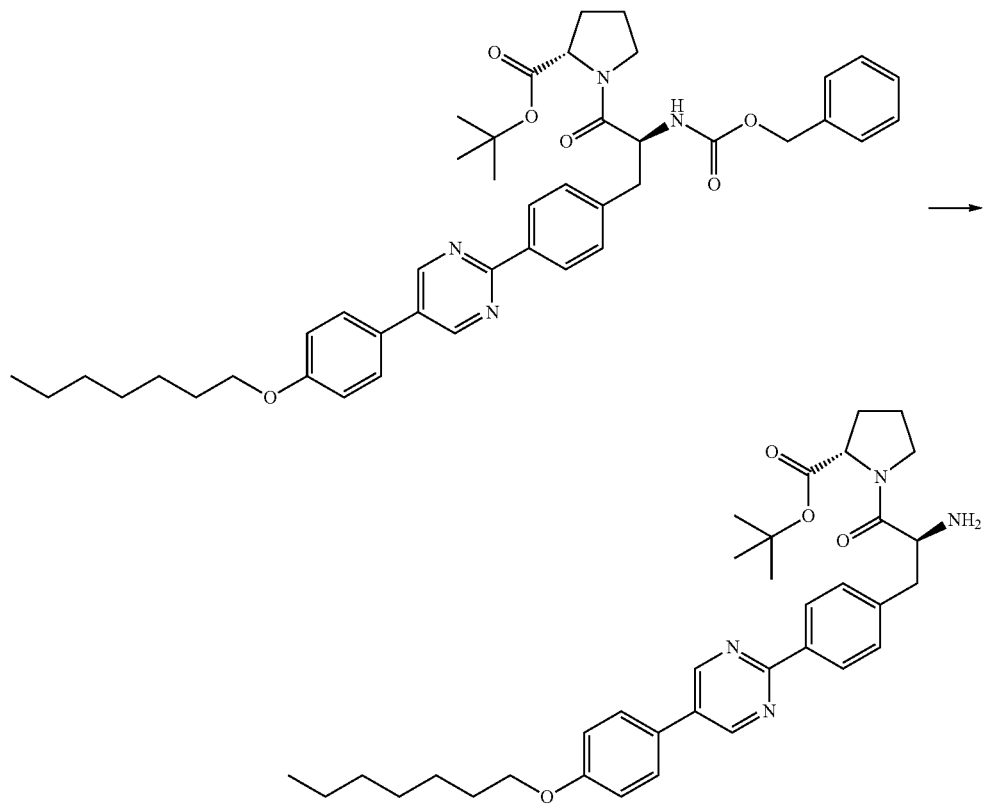

Prepared using General Procedure 18: A solution of (S)-tert-butyl 1-((S)-2-(((benzyloxy)carbonyl)amino)-3-(4-(5-(4-(heptyloxy)phenyl)pyrimidin-2-yl)phenyl)propanoyl) pyrrolidine-2-carboxylate (436 mg, 0.6 mmol) in THF (25 mL) was hydrogenated in the H-Cube using a 10% Pd/C CatCart at 60° C. (Full hydrogen, 1 mL/min). The reaction mixture was passed over the catalyst a second time at 65° C. The solvent was removed to give 307 mg (83%) of (S)-tert-butyl 1-((S)-2-amino-3-(4-(5-(4-(heptyloxy)phenyl)pyrimi-din-2-yl)phenyl)propanoyl)pyrrolidine-2-carboxylate INT-26 as a white powder. LCMS-ESI (m/z) calculated for $C_{35}H_{46}N_4O_4$: 586.4. found 587.4 [M+H]$^+$, $t_R$=6.99 min (Method 10).

(S)-tert-butyl 1-((S)-2-(5-(tert-butyl)thiophene-2-
carboxamido)-3-(4-(5-(4-(heptyloxy)phenyl)pyrimi-
din-2-yl)phenyl) propanoyl)pyrrolidine-2-carboxy-
late

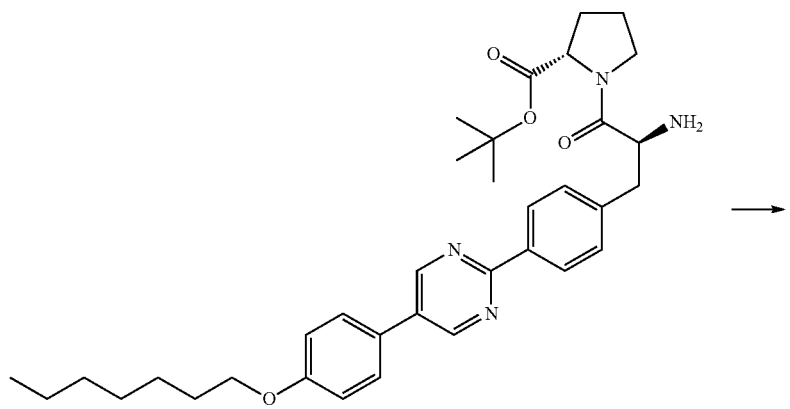

-continued

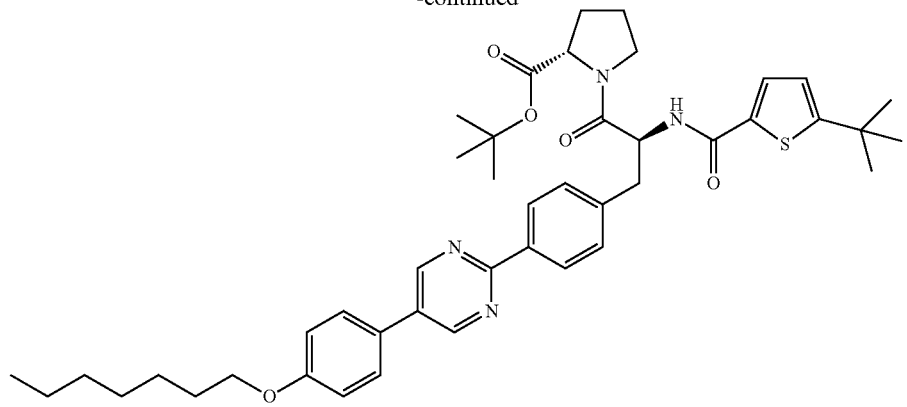

Prepared using General Procedure 7: A stirred solution of (S)-tert-butyl 1-((S)-2-amino-3-(4-(5-(4-(heptyloxy)phenyl)pyrimidin-2-yl)phenyl)propanoyl)pyrrolidine-2-carboxylate (306 mg, 0.522 mmol) and 5-(tert-butyl)thiophene-2-carboxylic acid (106 mg, 0.574 mmol) in DMF (6 mL) was added TEA (145 µl, 1.043 mmol), cooled to 0° C., then HATU (218 mg, 0.574 mmol) was slowly added over 5 minutes. The reaction was stirred at room temperature for 2 h, then diluted with EA (70 mL), washed with saturated aqueous $NaHCO_3$ (70 mL) and brine (100 mL). The solvent was dried over $MgSO_4$ and removed. The crude product was purified by chromatography 0-30% ACN in DCM to afford 363 mg (92%) of (S)-tert-butyl 1-((S)-2-(5-(tert-butyl)thiophene-2-carboxamido)-3-(4-(5-(4-(heptyloxy)phenyl)pyrimidin-2-yl)phenyl) propanoyl)pyrrolidine-2-carboxylate as a sticky solid. LCMS-ESI (m/z) calculated for $C_{44}H_{56}N_4O_5S$: 752.4; no m/z observed, $t_R$=11.99 min (Method 10).

(S)-1-((S)-2-(5-(tert-butyl)thiophene-2-carboxamido)-3-(4-(5-(4-(heptyloxy)phenyl)pyrimidin-2-yl)phenyl)propanoyl)pyrrolidine-2-carboxylic acid
(Compound 328)

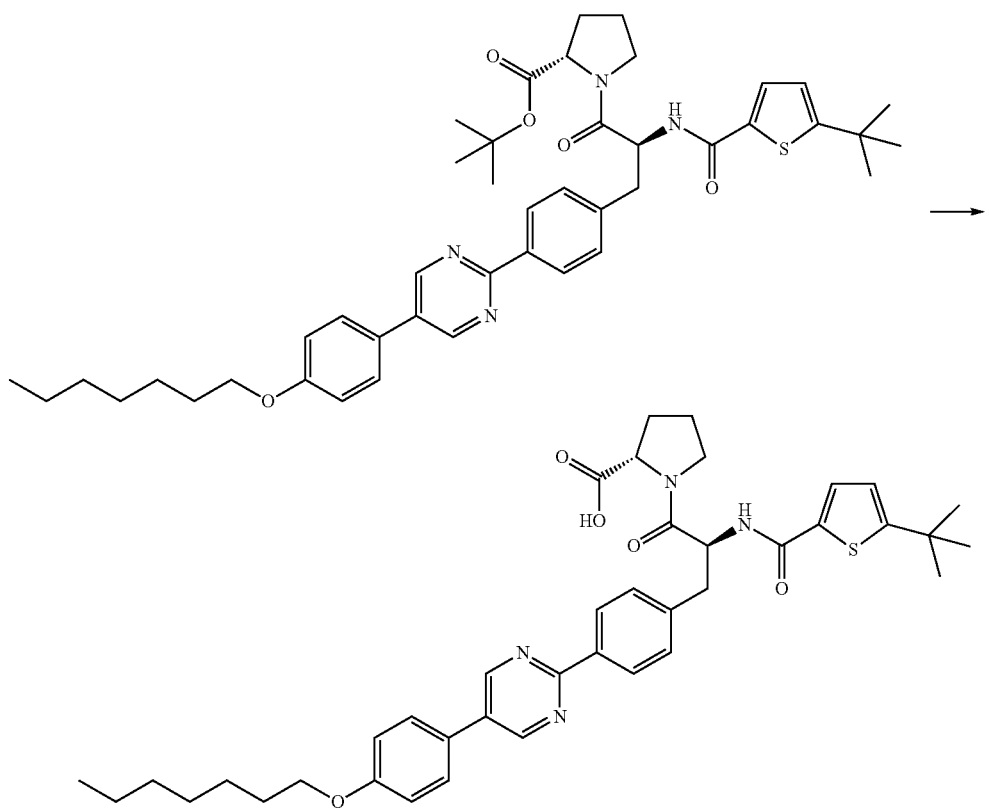

Prepared using General Procedure 8. To a stirred solution of (S)-tert-butyl 1-((S)-2-(5-(tert-butyl)thiophene-2-carboxamido)-3-(4-(5-(4-(heptyloxy)phenyl)pyrimidin-2-yl)phenyl) propanoyl)pyrrolidine-2-carboxylate (350 mg, 0.465 mmol) in DCM (5 mL) was added TFA (5 mL) and stirred at room temperature for 2 h. The reaction mixture was diluted with toluene (10 mL) and solvent removed. The residue was dissolved in EA (50 mL), THF (5 mL) and acetone (10 mL) and washed with a mixture of saturated aqueous NaHCO₃ (10 mL) and brine (40 mL). The aqueous layer was removed and acetic acid (5 mL) was added. The organic layer was washed with brine (50 mL) and dried over MgSO₄. The solvent was removed and residual acetic acid was removed under high vacuum overnight. The material was dissolved in DCM (5 mL) and ACN (5 mL) was added. The material was stirred under a flow of air for 1 hour and the suspension was filtered and the solid washed with additional ACN (5 mL) and iso-hexanes (20 mL) to give 134 mg (41%) of (S)-1-((S)-2-(5-(tert-butyl)thiophene-2-carboxamido)-3-(4-(5-(4-(heptyloxy)phenyl)-pyrimidin-2-yl)phenyl)propanoyl)pyrrolidine-2-carboxylic acid Compound 328 as a yellow powder. LCMS-ESI (m/z) calculated for $C_{40}H_{48}N_4O_5S$: 696.3. found 697.3 $[M+H]^+$, $t_R$=10.59 min (Method 10). The chiral purity was calculated at >93% e.e. (Chiral Method). ¹H NMR (400 MHz, DMSO-d6) δ 12.47 (s, 1H), 9.17 (s, 2H), 8.74 (d, J=8.3 Hz, 1H), 8.38-8.27 (m, 2H), 7.86-7.76 (m, 2H), 7.71 (d, J=3.9 Hz, 1H), 7.57-7.48 (m, 2H), 7.14-7.02 (m, 2H), 6.92 (d, J=3.9 Hz, 1H), 4.94-4.86 (m, 1H), 4.33-4.27 (m, 1H), 4.04 (t, J=6.5 Hz, 2H), 3.86-3.74 (m, 1H), 3.69-3.59 (m, 1H), 3.19-3.01 (m, 2H), 2.24-2.13 (m, 1H), 2.01-1.84 (m, 3H), 1.80-1.68 (m, 2H), 1.52-1.23 (m, 17H), 0.93-0.85 (m, 3H).

Compounds 329-350 were prepared from Compound 192 using General Procedures 3 or 7 followed by 4 or 8.

Compounds 351-368 were prepared from Compound 165 using General Procedures 7 followed by 4 or 8.

Compound 369 was prepared from Compound 139 using General Procedures 7 followed by 8.

Compound 370 was prepared from Compound 167 using General Procedures 7 followed by 8.

Compound 371 was prepared from Compound 142 using General Procedures 7 followed by 8.

Compound 372 was prepared from Compound 143 using General Procedures 7 followed by 8.

Compound 373 was prepared from Compound 182 using General Procedures 7 followed by 8.

Compounds 374-379 were prepared from Compound 193 using General Procedures 3 or 7 followed by 4 or 8.

Compound 380 was prepared from Compound 191 using General Procedures 7 followed by 8.

(S)-4-(tert-butyl)-N-(3-(4-(5-(4-(heptyloxy)phenyl) pyrimidin-2-yl)phenyl)-1-((2-(methylsulfonamido)-2-oxoethyl)amino)-1-oxopropan-2-yl)benzamide (Compound 381)

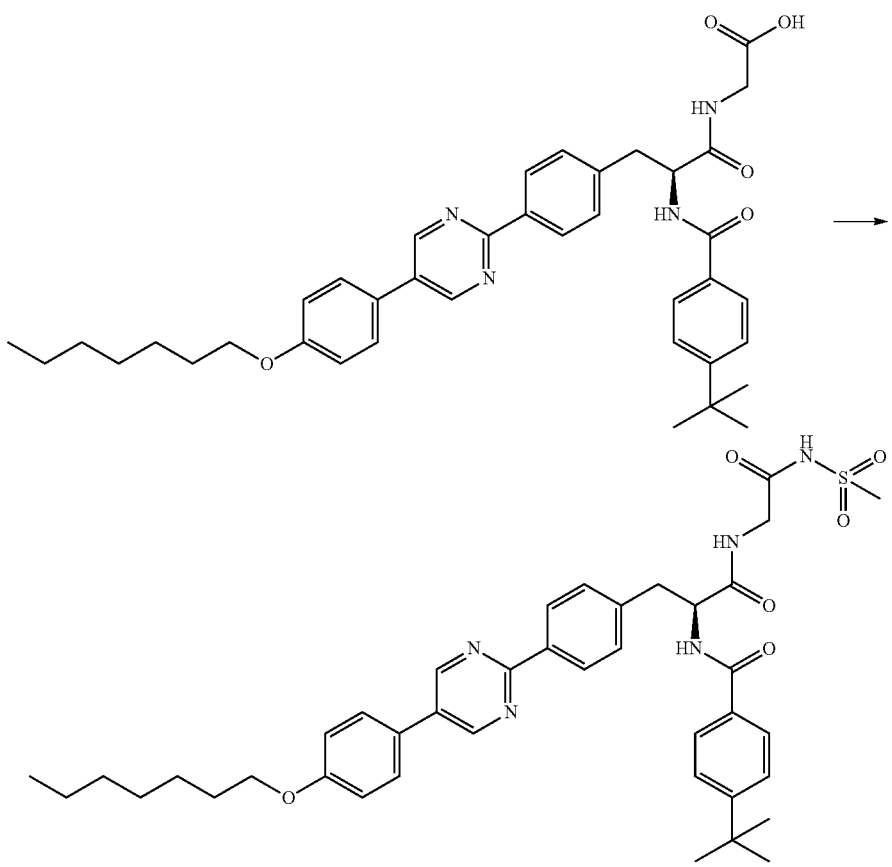

TEA (32.1 μl, 0.23 mmol) was added to a suspension of (S)-(2-(4-(tert-butyl)benzamido)-3-(4-(5-(4-(heptyloxy) phenyl)pyrimidin-2-yl)phenyl)propanoyl)glycine Compound 297 (75.0 mg, 0.11 mmol), methanesulfonamide (12.1 mg, 0.13 mmol), HATU (52.6 mg, 0.14 mmol) and DMAP (1.41 mg, 0.01 mmol) in DCM (2 mL). The resultant yellow suspension was stirred at room temperature for 3 h. The reaction mixture was washed with saturated aqueous NaHCO₃ (2 mL) and the mixture passed through a phase separation cartridge. The organic phase was concentrated in vacuo to afford a yellow solid. The crude product was purified by chromatography (EA/1% AcOH in hexanes) to afford 9 mg (11%) (S)-4-(tert-butyl)-N-(3-(4-(5-(4-(heptyloxy)phenyl)pyrimidin-2-yl)phenyl)-1-((2-(methylsulfonamido)-2-oxoethyl)amino)-1-oxopropan-2-yl)benzamide, Compound 381 as a yellow solid. LCMS-ESI (m/z) calculated for $C_{40}H_{49}N_5O_6S$: 727.3. found 728.0 $[M+H]^+$, $t_R$=10.51 min (Method 10).

Compounds 382-390 were prepared from Compound 192 using the appropriate combination of General Procedures 4, 7, and 8 as needed.

Ethyl 2-amino-3-(3-fluoro-4-(4,4,5,5-tetramethyl-1, 3, 2-dioxaborolan-2-yl)phenyl)propanoate

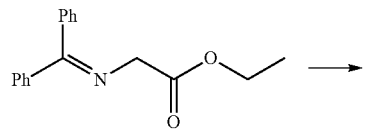

To a stirred solution of ethyl 2-((diphenylmethylene)amino)acetate (300 mg, 1.12 mmol) in anhydrous THF (3 mL) at −78° C. was added 0.5 M KHMDS in toluene (2.46 mL, 1.23 mmol). After stirring for 15 min, 2-(4-(bromomethyl)-2-fluorophenyl)-4,4,5,5-tetramethyl-1,3,2-dioxaborolane (353 mg, 1.12 mmol) was added. The reaction mixture was stirred at −78° C. for 3 h and warmed to −20° C. To the mixture was added 6 N Hydrochloric acid (0.5 mL) and the mixture was stirred overnight at room temperature. The reaction mixture was diluted with water (5 mL) and 1 N HCl (5 mL) and then extracted with diethyl ether. The aqueous layer was basified with 1N NaOH and then extracted with EtOAc (3×10 mL). The combined organic extract was washed with water, brine and then dried over MgSO$_4$. Filtration and concentration gave 177 mg (46%) of ethyl 2-amino-3-(3-fluoro-4-(4,4,5,5-tetramethyl-1,3,2-dioxaborolan-2-yl)phenyl)propanoate which was used in the next step without purification. LCMS-ESI (m/z) calculated for $C_{17}H_{25}BFNO_4$: 337.2. found 338.2 $[M+H]^+$, $t_R$=2.78 min (Method 1).

Compound 391 was prepared using ethyl 2-amino-3-(3-fluoro-4-(4,4,5,5-tetramethyl-1,3,2-dioxaborolan-2-yl)phenyl)propanoate and 5-(tert-butyl)thiophene-2-carbonyl chloride using General Procedure 3 followed by treatment with 5-(4-(tert-butyl)phenyl)-2-iodopyrimidine and General Procedure 10.

Compounds 392-396 were prepared from Compound 192 using, as needed, the appropriate combination of General Procedures 4, 7, and 8.

(S)-2-(4-(3-(tert-butoxy)-2-(4-(tert-butyl)benzamido)-3-oxopropyl)phenyl)pyrimidine-5-carboxylic acid

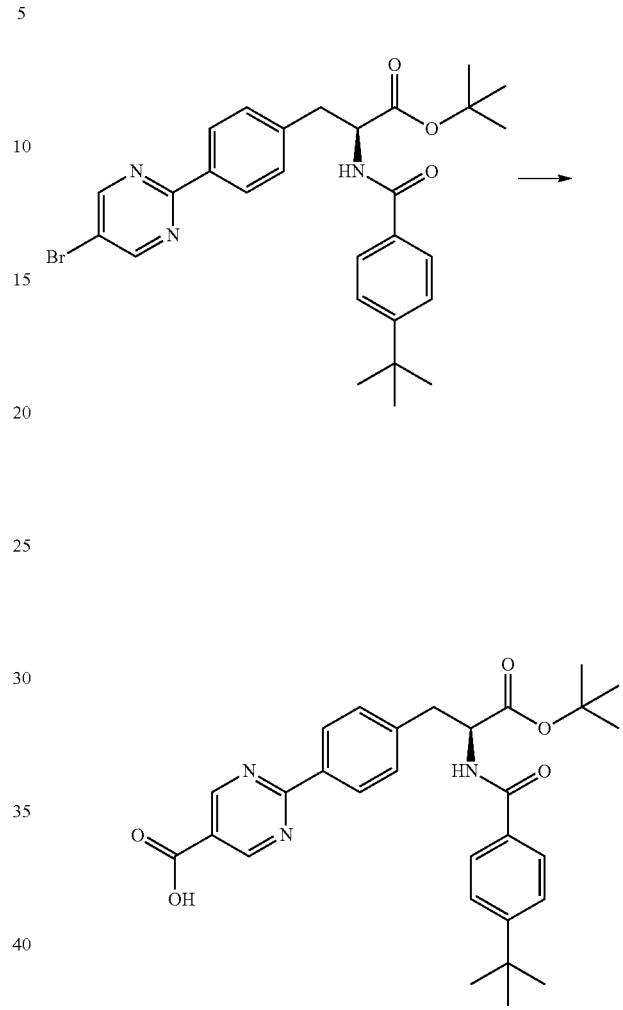

Prepared using General Procedure 10. Into an oven-dried vial containing lithium formate (58 mg (1.1 mmol) in DMF (5 mL) were added DIEA (400 μL, 2.2 mmol) and acetic anhydride (210 μL, 2.2 mmol). After stirring for 1 h, the reaction mixture was degassed by N$_2$ bubbling. A second, degassed solution containing (S)-tert-butyl 3-(4-(5-bromopyrimidin-2-yl)phenyl)-2-(4-(tert-butyl)benzamido)propanoate, INT-14 (200 mg, 0.4 mmol) and PdCl$_2$(dppf) (27 mg, 0.04 mmol) in DMF (5 mL) was added via cannula. The resulting mixture was heated for 1 h at 120° C. in a microwave reactor. The reaction mixture was diluted with 10% citric acid and extracted with EA. The organic extract was dried (Na$_2$SO$_4$), concentrated, and purified by chromatography (EA/hexane) to provide 166 mg (88%) of (S)-2-(4-(3-(tert-butoxy)-2-(4-(tert-butyl)benzamido)-3-oxopropyl)phenyl)pyrimidine-5-carboxylic acid as a brown solid. LCMS-ESI (m/z) calculated for $C_{29}H_{33}BN_3O_5$: 503.6. found 504.2 $[M+H]^+$, $t_R$=3.87 min (Method 1). $^1$H NMR (400 MHz, CDCl$_3$) δ 9.24 (s, 2H), 8.42 (d, J=8.2 Hz, 2H), 7.75 (t, J=11.9 Hz, 2H), 7.45 (d, J=8.4 Hz, 2H), 7.34 (d, J=8.2 Hz, 2H), 6.91 (t, J=11.5 Hz, 1H), 5.12 (dd, J=12.9, 5.5 Hz, 1H), 3.32 (qd, J=13.8, 5.4 Hz, 2H), 1.50 (s, 9H), 1.29 (d, J=29.8 Hz, 9H).

229

Tert-butyl (S)-2-(4-(tert-butyl)benzamido)-3-(4-(5-(2-heptanoylhydrazine-1-carbonyl)pyrimidin-2-yl)phenyl)propanoate

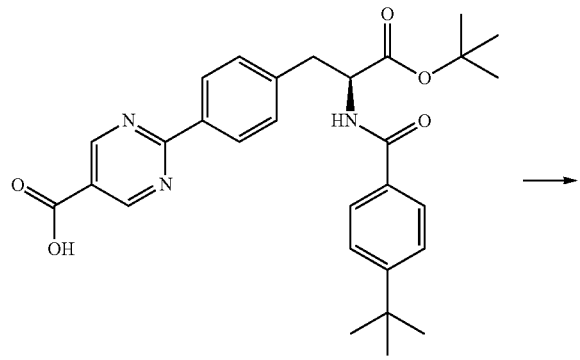

230

Prepared using General Procedure 7. Into a stirring solution of (S)-2-(4-(3-(tert-butoxy)-2-(4-(tert-butyl)benzamido)-3-oxopropyl)phenyl)pyrimidine-5-carboxylic acid (50 mg, 0.10 mmol) in DCM (2 mL) were added EDC (34 mg, 0.20 mmol), DMAP (3 mg, 0.02 mmol) and heptanehydrazide (16 mg, 0.11 mmol). After 18 h, the reaction mixture was diluted with NaHCO$_3$ and extracted with DCM (2×). The organic layers were combined, dried (Na$_2$SO$_4$), concentrated and purified by chromatography (EA/Hexane) to provide 38 mg (61%) of tert-butyl (S)-2-(4-(tert-butyl)benzamido)-3-(4-(5-(2-heptanoylhydrazine-1-carbonyl)pyrimidin-2-yl)phenyl)propanoate. LCMS-ESI (m/z) calculated for C$_{36}$H$_{47}$BN$_5$O$_5$: 629.8; no m/z observed, t$_R$=3.84 min (Method 1). $^1$H NMR (400 MHz, CDCl$_3$) δ 9.17 (s, 2H), 8.42 (d, J=8.2 Hz, 2H), 7.69 (d, J=8.4 Hz, 2H), 7.43 (d, J=8.4 Hz, 2H), 7.34 (d, J=8.2 Hz, 2H), 6.70 (d, J=7.3 Hz, 1H), 5.01 (dd, J=12.6, 5.8 Hz, 1H), 3.41-3.20 (m, 2H), 2.35 (t, J=7.5 Hz, 2H), 1.81-1.61 (m, 2H), 1.59 (d, J=14.0 Hz, 2H), 1.45 (s, 4H), 1.42-1.22 (m, 18H), 0.88 (t, J=6.8 Hz, 3H).

Tert-butyl (S)-2-(4-(tert-butyl)benzamido)-3-(4-(5-(5-hexyl-1,3,4-thiadiazol-2-yl)pyrimidin-2-yl)phenyl)propanoate

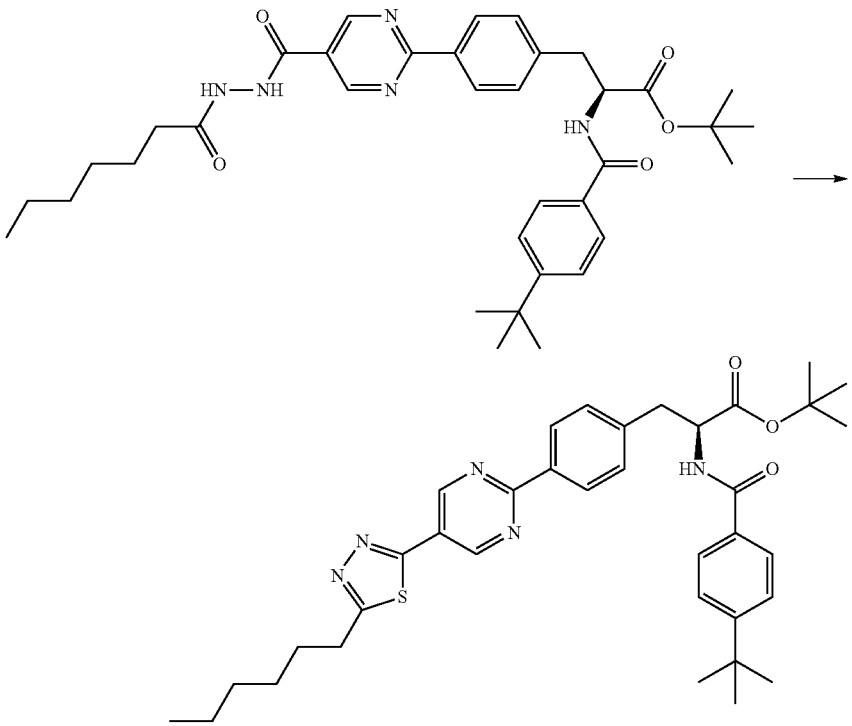

-continued

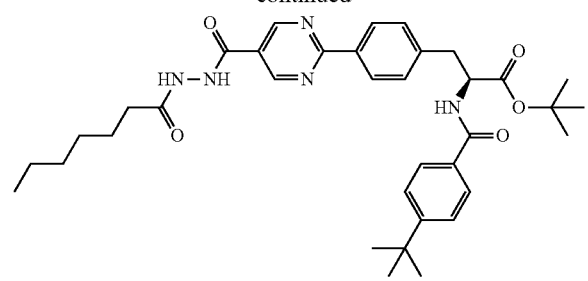

To a solution of tert-butyl (S)-2-(4-(tert-butyl)benzamido)-3-(4-(5-(2-heptanoylhydrazine-1-carbonyl)pyrimidin-2-yl)phenyl)propanoate (38 mg, 0.06 mmol) in THF (1.5 mL) was added 2,4-bis(4-methoxyphenyl)-1,3,2,4-dithiadiphosphetane 2,4-disulfide (24 mg, 0.06 mmol). After 1.5 h, the reaction mixture was concentrated and purified by preparative HPLC to provide 10 mg (27%) of tert-butyl (S)-2-(4-(tert-butyl)benzamido)-3-(4-(5-(5-hexyl-1,3,4-thiadiazol-2-yl) pyrimidin-2-yl) phenyl) propanoate. LCMS-ESI (m/z) calculated for C$_{36}$H$_{45}$N$_5$O$_3$S: 627.9; no m/z observed, t$_R$=3.89 min (Method 1). $^1$H NMR (400 MHz, CDCl$_3$) δ 9.29 (s, 2H), 8.44 (d, J=8.2 Hz, 2H), 7.75-7.66 (m, 2H), 7.50-7.41 (m, 2H), 7.35 (d, J=8.3 Hz, 2H), 6.68 (d, J=7.3 Hz, 1H), 5.02 (dd, J=12.7, 5.6 Hz, 1H), 3.33 (qd, J=13.8, 5.5 Hz, 2H), 3.26-3.15 (m, 2H), 1.87 (dt, J=15.3, 7.6 Hz, 2H), 1.46 (d, J=5.1 Hz, 10H), 1.41-1.23 (m, 14H), 0.96-0.85 (m, 3H).

(S)-2-(4-(tert-butyl)benzamido)-3-(4-(5-(5-hexyl-1,3,4-thiadiazol-2-yl)pyrimidin-2-yl)phenyl)propanoic acid (Compound 397)

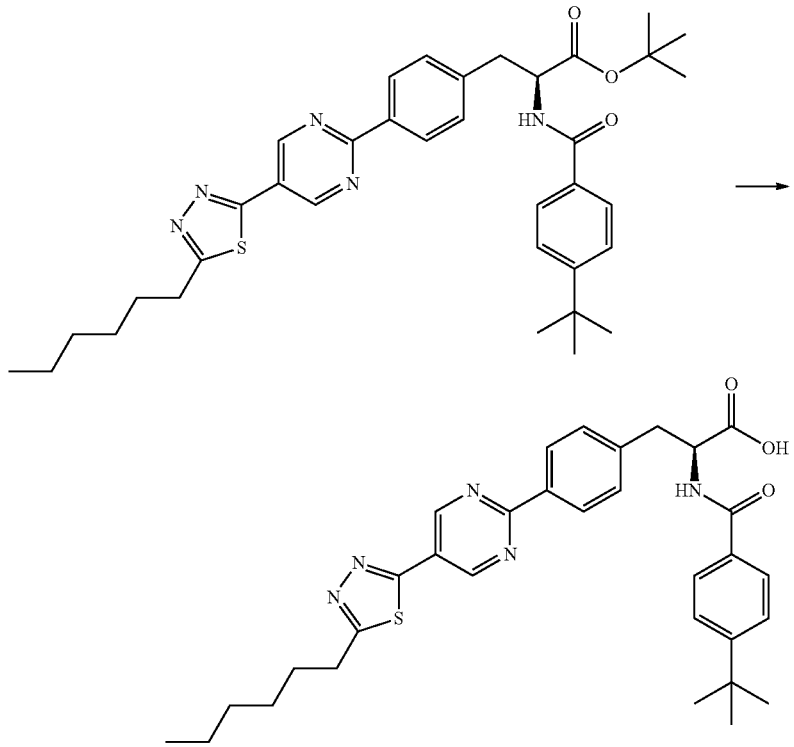

Prepared using General Procedure 8 from tert-butyl (S)-2-(4-(tert-butyl)benzamido)-3-(4-(5-(5-hexyl-1,3,4-thiadiazol-2-yl) pyrimidin-2-yl) phenyl) propanoate. LCMS-ESI (m/z) calculated for $C_{32}H_{37}N_5O_3S$: 571.4. found 571.7 [M+H]$^+$, $t_R$=10.66 min (Method 2). $^1$H NMR (400 MHz, CDCl$_3$) δ 9.30 (d, J=2.6 Hz, 2H), 8.48 (d, J=8.2 Hz, 2H), 7.67 (d, J=8.4 Hz, 2H), 7.43 (dd, J=13.7, 8.3 Hz, 4H), 6.61 (d, J=6.8 Hz, 1H), 5.20-5.04 (m, 1H), 3.45 (ddd, J=36.2, 13.9, 5.6 Hz, 2H), 3.20 (t, J=7.6 Hz, 2H), 1.95-1.75 (m, 2H), 1.54-1.36 (m, 2H), 1.39-1.19 (m, 13H), 0.91 (t, J=7.0 Hz, 3H).

(R)-tert-butyl 2-((S)-2-(4-(tert-butyl)benzamido)-3-(4-(5-(4-(heptyloxy)phenyl)pyrimidin-2-yl)phenyl) propanamido)propanoate

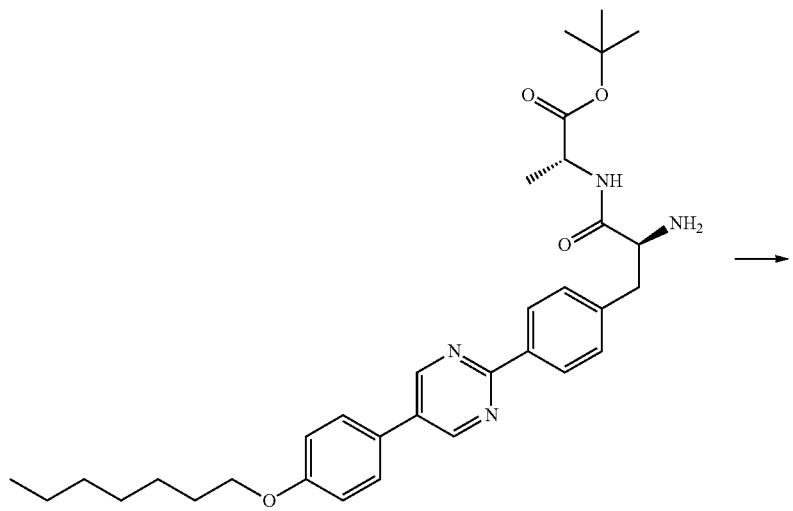

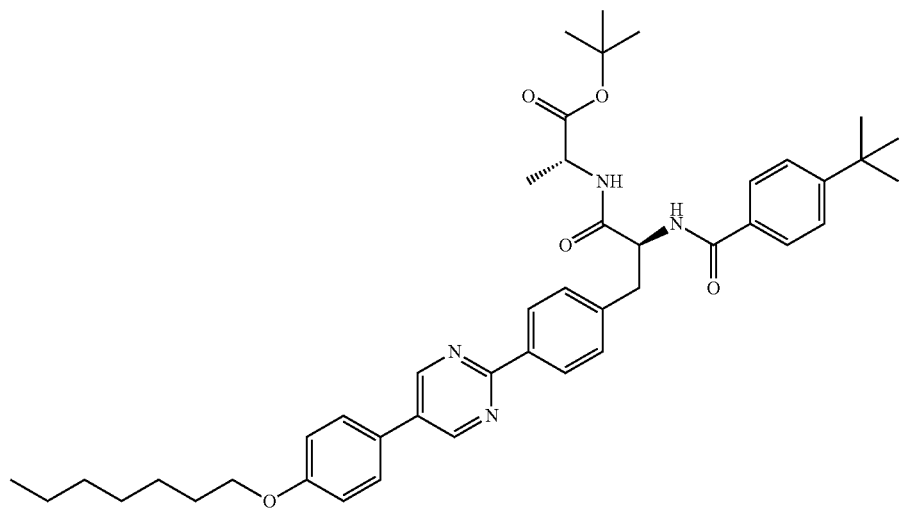

Prepared using General Procedure 7. A stirred solution of (R)-tert-butyl 2-((S)-2-amino-3-(4-(5-(4-(heptyloxy)phenyl)pyrimidin-2-yl)phenyl)propanamido)propanoate (122 mg, 0.218 mmol), 4-(tert-butyl)benzoic acid (38.8 mg, 0.218 mmol) and TEA (60.7 μl, 0.435 mmol) in DMF (4 mL) was cooled to 0° C. and HATU (87 mg, 0.228 mmol) was slowly added over 5 minutes. The reaction was stirred at room temperature for 2 h, then diluted with EA (100 mL), washed with saturated aqueous $NaHCO_3$ (100 mL) and brine (100 mL). The solvent was dried over $MgSO_4$ and removed. The crude product was purified by chromatography 0-30% ACN in DCM to afford 123 mg (78%) of (R)-tert-butyl 2-((S)-2-(4-(tert-butyl)benzamido)-3-(4-(5-(4-(heptyloxy)phenyl)pyrimidin-2-yl)phenyl)propanamido)propanoate as a white solid. LCMS-ESI (m/z) calculated for $C_{44}H_{56}N_4O_5$: 720.4; no m/z observed, $t_R$=3.47 min (Method 11).

(R)-2-((S)-2-(4-(tert-butyl)benzamido)-3-(4-(5-(4-(heptyloxy)phenyl)pyrimidin-2-yl)phenyl) propanamido)propanoic acid (Compound 398)

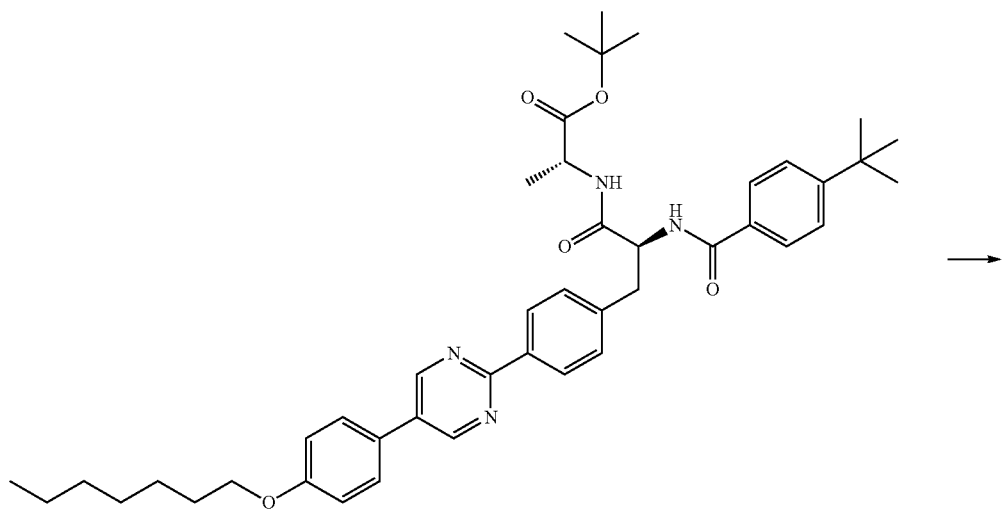

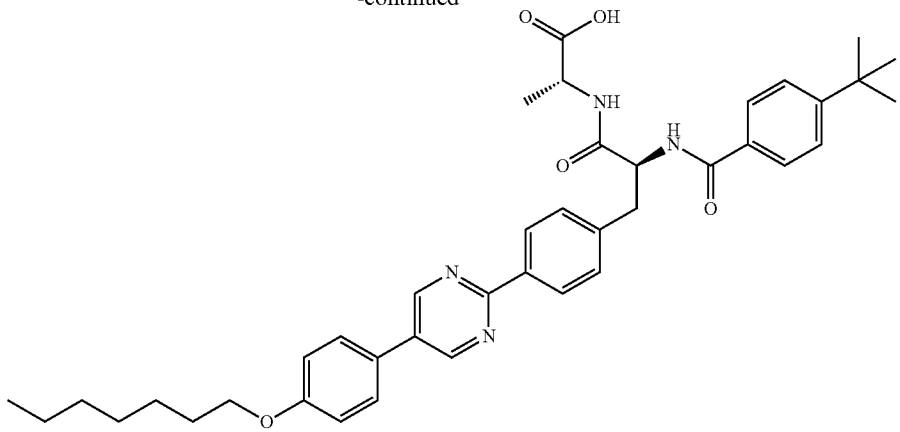

Prepared using General Procedure 8. To a stirred solution of (R)-tert-butyl 2-((S)-2-(4-(tert-butyl)benzamido)-3-(4-(5-(4-(heptyloxy)phenyl)pyrimidin-2-yl)phenyl)propanamido) propanoate (120 mg, 0.166 mmol) in DCM (4 mL) was added TFA (3 mL) and stirred for 2 h. The reaction mixture was diluted with toluene (15 mL) and solvent removed. DMSO (3 mL) was added and the solution was sonicated. This solution was added to vigorously stirring water (30 mL) and the white solid was isolated by filtration and washed with additional ACN (10 mL). The material was dried under high vacuum for 24 h to afford 75 mg (66%) of (R)-2-((S)-2-(4-(tert-butyl)benzamido)-3-(4-(5-(4-(heptyloxy)phenyl) pyrimidin-2-yl)phenyl)propanamido)propanoic acid Compound 398 as a white powder. LCMS-ESI (m/z) calculated for $C_{40}H_{48}N_4O_5$: 664.4. found 665.0 [M+H]$^+$, $t_R$=12.33 min (Method 10). The chiral purity was calculated at >99% e.e. (Chiral Method). $^1$H NMR (400 MHz, DMSO-d6) δ 12.64 (s, 1H), 9.15 (s, 2H), 8.52 (d, J=8.7 Hz, 1H), 8.45 (d, J=7.4 Hz, 1H), 8.35-8.20 (m, 2H), 7.85-7.68 (m, 4H), 7.56-7.50 (m, 2H), 7.49-7.39 (m, 2H), 7.14-7.03 (m, 2H), 4.93-4.80 (m, 1H), 4.38-4.17 (m, 1H), 4.03 (t, J=6.5 Hz, 2H), 3.22-3.12 (m, 1H), 3.12-3.02 (m, 1H), 1.81-1.67 (m, 2H), 1.53-1.24 (m, 20H), 0.95-0.80 (m, 3H).

Compounds 399-409 were prepared using, as needed, the appropriate combination of General Procedures 4, 7, 8, and 18.

(S)-4-amino-2-((S)-2-(5-(tert-butyl)thiophene-2-carboxamido)-3-(4-(5-(4-(heptyloxy)phenyl)pyrimidin-2-yl)phenyl)propanamido) butanoic acid (Compound 410)

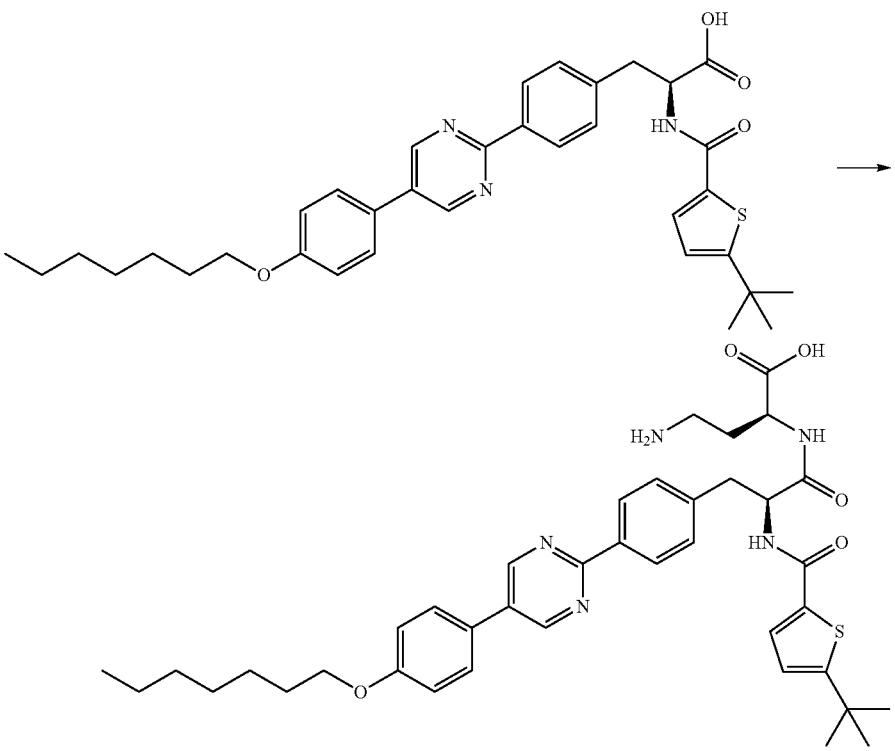

Prepared using General Procedures 7, 4, and 8: A stirring solution of (S)-2-(5-(tert-butyl)thiophene-2-carboxamido)-3-(4-(5-(4-(heptyloxy)phenyl)pyrimidin-2-yl)phenyl)propanoic acid Compound 192 (25 mg, 0.042 mmol), (S)-methyl 2-amino-4-((tert-butoxycarbonyl)amino)butanoate hydrochloride (12 mg, 0.042 mmol), and TEA (0.015 mL, 0.105 mmol) at 0° C. was treated with HATU (17 mg, 0.046 mmol) in DMF (1 mL). The solution was stirred at room temperature for 18 h. The reaction mixture was diluted with DCM (5 mL) and washed with saturated aqueous NaHCO$_3$ (5 mL), water (5 mL), and brine (5 mL). The organic phase was dried over MgSO$_4$, filtered, and concentrated to afford the methyl ester intermediate. The ester was dissolved in THF (2 mL) and MeOH (1 mL) and 1 N aqueous NaOH (0.1 ml, 0.1 mmol) was added. The solution was stirred at 60° C. for 5 h. The reaction mixture was concentrated then dissolved in DCM (0.5 mL) and treated with 1N HCl in ether (0.42 mL, 0.42 mmol). The reaction was stirred at 27° C. for 18 h. The compound was purified by preparative HPLC to afford 21 mg (60.0%) of (S)-4-amino-2-((S)-2-(5-(tert-butyl)thiophene-2-carboxamido)-3-(4-(5-(4-(heptyloxy)phenyl)pyrimidin-2-yl)phenyl)propanamido)butanoic acid as the trifluoroacetate salt. LCMS-ESI (m/z) calculated for C$_{39}$H$_{49}$N$_5$O$_5$S: 699.4. found 700.3 [M+H]$^+$, $t_R$=9.24 min (Method 12). $^1$H NMR (400 MHz, DMSO) δ 12.95 (s, 1H), 9.15 (s, 2H), 8.63-8.55 (m, 2H), 8.32 (d, J=8.1 Hz, 2H), 7.78 (d, J=8.7 Hz, 2H), 7.76-7.63 (m, 4H), 7.51 (d, J=8.2 Hz, 2H), 7.09 (d, J=8.7 Hz, 2H), 6.91 (d, J=3.7 Hz, 1H), 4.87-4.66 (m, 1H), 4.50-4.31 (m, 1H), 4.03 (t, J=6.5 Hz, 2H), 3.23-3.12 (m, 1H), 3.12-3.00 (m, 1H), 2.95-2.77 (m, 2H), 2.18-2.02 (m, 1H), 2.02-1.84 (m, 1H), 1.83-1.64 (m, 2H), 1.50-1.38 (m, 2H), 1.38-1.14 (m, 15H), 0.87 (t, J=6.7 Hz, 3H).

Compounds 411-418 were prepared using, as needed, the appropriate combination of General Procedures 4, 7, 8, and 18.

Compounds 419-423 and 435 were prepared in a similar fashion to Compound 381.

Compounds 424-433 were prepared using, as needed, the appropriate combination of General Procedures 4, 7, 8, and 18.

Compound 434 was prepared from Compound 422 using General Procedure 4.

Compounds 436-440 were prepared using, as needed, the appropriate combination of General Procedures 4, 7, 8, and 18.

Compounds 441 and 442 were prepared from Compound 192 using General Procedures 3 and 8.

Compound 443 was prepared from tert-butyl (S)-3-(2-(4-(tert-butyl)benzamido)-3-(4-(5-(4-hydroxyphenyl)pyrimidin-2-yl)phenyl)propanamido)propanoate using General Procedures 12 then 8.

Compounds 444-455 were prepared using, as needed, the appropriate combination of General Procedures 4, 7, 8, and 18.

Compounds 456-458 were prepared from tert-butyl (S)-3-(2-(4-(tert-butyl)benzamido)-3-(4-(5-(4-hydroxyphenyl)pyrimidin-2-yl)phenyl)propanamido)propanoate using General Procedures 12 then 8.

Compounds 459-464 were prepared from Compound 192 using, as needed, the appropriate combination of General Procedures 4, 7, and 8.

Compounds 465-466 were prepared from Compound 85 using, as needed, the appropriate combination of General Procedures 4, 7, and 8.

2-((S)-2-(4-(tert-butyl)benzamido)-3-(4-(5-(4-(heptyloxy)phenyl)pyrimidin-2-yl)phenyl)propanamido)-3-(1H-1,2,4-triazol-1-yl)propanoic acid (Compound 467)

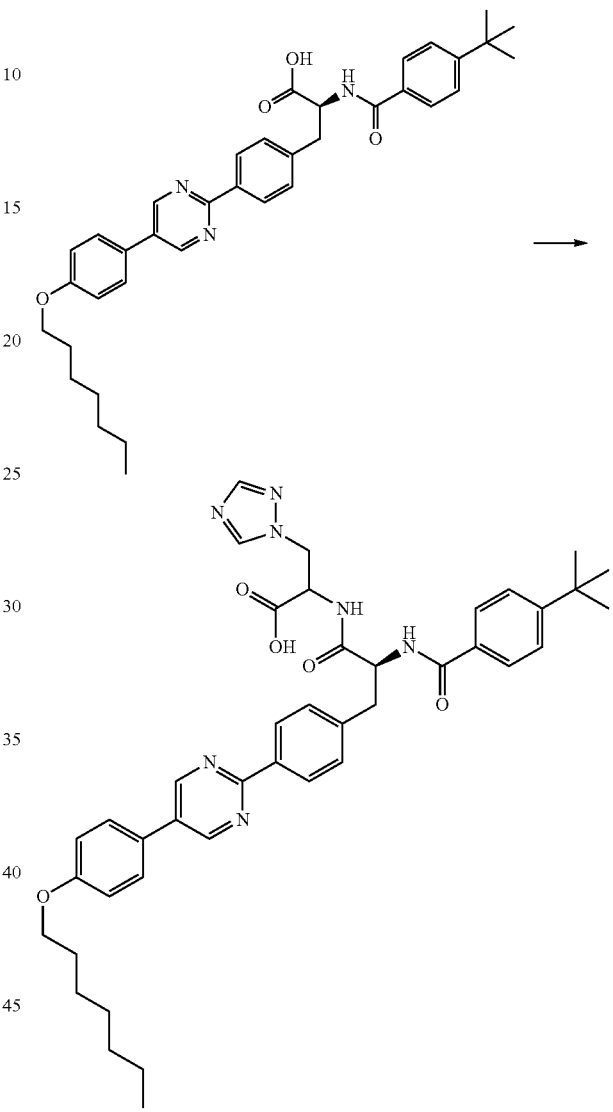

Prepared using General Procedure 7 and then 4. (S)-2-(4-(tert-butyl)benzamido)-3-(4-(5-(4-(heptyloxy)phenyl)pyrimidin-2-yl)phenyl)propanoic acid (90 mg, 0.152 mmol) and (S)-methyl 2-amino-3-(1H-1,2,4-triazol-1-yl)propanoate (25.8 mg, 0.152 mmol) in DMF (2.5 mL) was added TEA (52.8 µl, 0.379 mmol) and then cooled to 0° C. To this mixture was added HATU (57.6 mg, 0.152 mmol) and left at room temperature for 2 h. The reaction mixture was quenched by the addition of 0.1 M Citric acid (aq. 15 mL) and the solid precipitated was allowed to slurry for 30 mins. The solid was filtered, washed with water (10 mL), isohexanes (10 mL) and then dried. Then the solid was dissolved in mixture of THF (4 mL) and MeOH (2 mL). To this solution was added 2M aq. NaOH (380 µL, 0.76 mmol) and the mixture was stirred vigorously at room temperature for 1 h. The reaction mixture was diluted with 0.1 M aq. citric acid (20 mL) and stirred for 1 h. The solid formed was filtered and washed with water (10 mL) and isohexanes (10 mL). The crude product was purified by column chromatography (0-20% MeOH in EA) to afford 12 mg (11%) of 2-((S)-2-(4-(tert-butyl)benzamido)-3-(4-(5-(4-(heptyloxy)phenyl)pyrimidin-2-yl)phenyl)propanamido)-3-(1H-1,2,4-triazol-1-yl)propanoic acid as a white powder. LCMS-ESI (m/z) calculated for $C_{42}H_{49}N_7O_5$: 731.9; no m/z observed, $t_R$=9.75 min (Method 10). $^1$H NMR (400 MHz, DMSO-d6) δ13.21 (s, 1H), 9.20 (s, 2H), 8.70 (d, J 8.1 Hz, 0.5H), 8.60 (dd, J 8.4, 4.6 Hz, 1H), 8.56 (d, J=7.8 Hz, 0.5H), 8.52 (d, J=7.1 Hz, 1H), 8.37-8.34 (m, 2H), 8.01 (d, J=6.9 Hz, 1H), 7.85-7.82 (m, 2H), 7.80-7.78 (m, 2H), 7.56-7.49 (m, 4H), 7.14 (d, J=8.9 Hz, 2H), 4.87-4.74 (m, 2H), 4.71-4.55 (m, 2H), 4.08 (t, J=6.5 Hz, 2H), 3.24-2.97 (m, 2H), 1.82-1.75 (m, 2H), 1.51-1.29 (m, 17H), 0.95-0.91 (m, 3H).

Compounds 468 and 469 were prepared from Compound 85 using, as needed, the appropriate combination of General Procedures 4, 7, and 8.

Compound 470 was prepared from (S)-tert-butyl 2-amino-3-(4-(5-(4-(heptyloxy)phenyl)pyrimidin-2-yl)phenyl)propanoate INT-9 using General Procedures 7 and 8.

(S)-3-(4-(5-bromopyrimidin-2-yl)phenyl)-2-(4-(tert-butyl)benzamido)propanoic acid (INT-27)

Tert-butyl (S)-3-(3-(4-(5-bromopyrimidin-2-yl)phenyl)-2-(4-(tert-butyl)benzamido)propanamido)propanoate (INT-28)

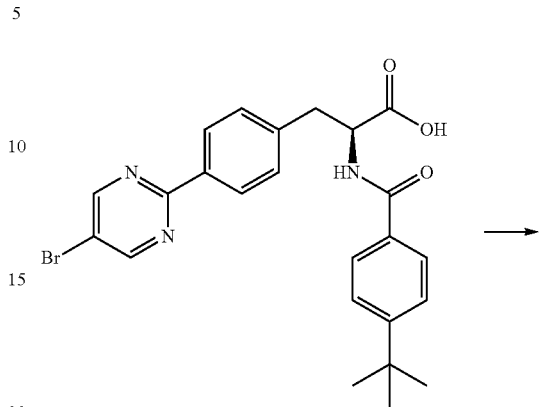

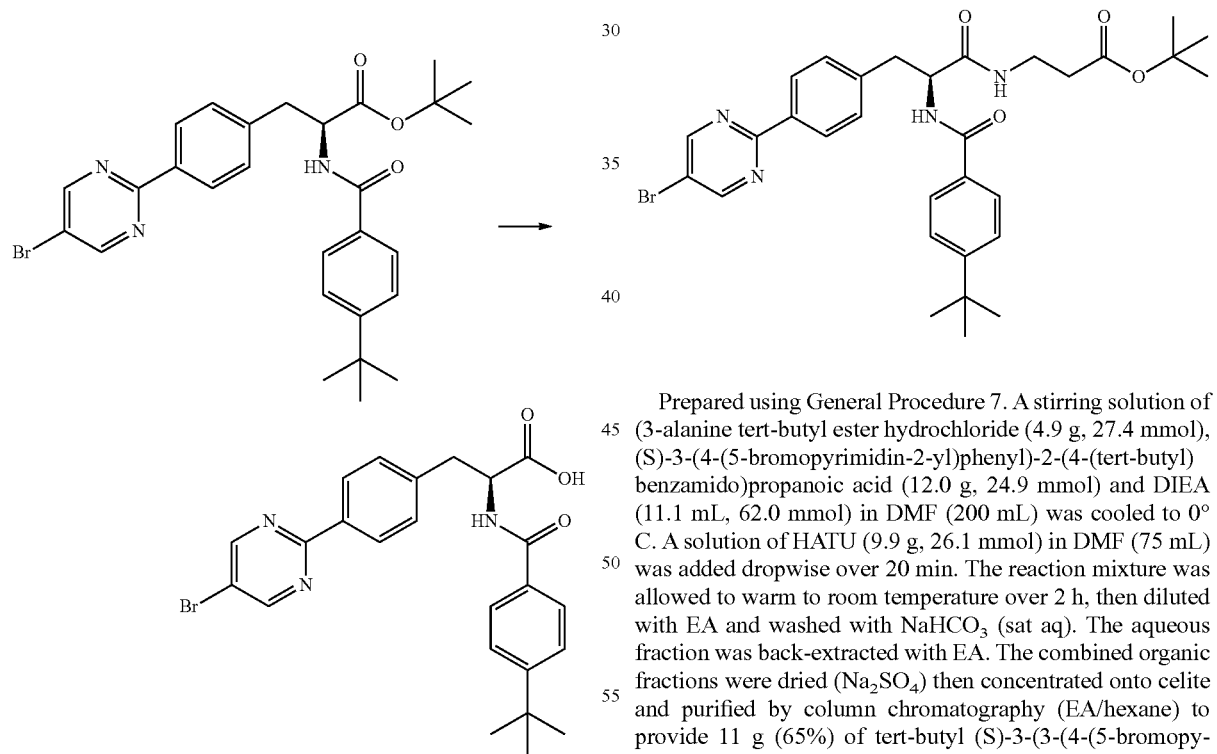

Prepared using General Procedure 8. LCMS-ESI (m/z) calculated for $C_{24}H_{24}BrN_3O_3$: 482.3. found 481.1 [M−H]$^+$, $t_R$=2.6 min (Method 15), and 98.7% e.e. (Chiral Method, isocratic with 2% Solvent A, 98% Solvent B). $^1$H NMR (400 MHz, CDCl$_3$) δ 8.87 (s, 2H), 8.32 (d, J=8.3 Hz, 2H), 7.64 (d, J=8.5 Hz, 2H), 7.45 (d, J=8.5 Hz, 2H), 7.36 (d, J=8.3 Hz, 2H), 6.64 (d, J=6.9 Hz, 1H), 5.16 (dd, J=12.7, 5.7 Hz, 1H), 3.42 (ddd, J=38.8, 14.0, 5.7 Hz, 2H), 1.32 (s, 9H).

Prepared using General Procedure 7. A stirring solution of β-alanine tert-butyl ester hydrochloride (4.9 g, 27.4 mmol), (S)-3-(4-(5-bromopyrimidin-2-yl)phenyl)-2-(4-(tert-butyl)benzamido)propanoic acid (12.0 g, 24.9 mmol) and DIEA (11.1 mL, 62.0 mmol) in DMF (200 mL) was cooled to 0° C. A solution of HATU (9.9 g, 26.1 mmol) in DMF (75 mL) was added dropwise over 20 min. The reaction mixture was allowed to warm to room temperature over 2 h, then diluted with EA and washed with NaHCO$_3$ (sat aq). The aqueous fraction was back-extracted with EA. The combined organic fractions were dried (Na$_2$SO$_4$) then concentrated onto celite and purified by column chromatography (EA/hexane) to provide 11 g (65%) of tert-butyl (S)-3-(3-(4-(5-bromopyrimidin-2-yl)phenyl)-2-(4-(tert-butyl)benzamido)propanamido)propanoate INT-28. LCMS-ESI (m/z) calculated for $C_{31}H_{37}BrN_4O_4$; 609.6. found 610.2 [M+H]$^+$, $t_R$=3.99 min (Method 15), and 87.1% e.e. (Chiral Method, isocratic with 20% Solvent A, 80% Solvent B). $^1$H NMR (400 MHz, CDCl$_3$) δ 8.80 (s, 2H), 8.32 (t, J=6.5 Hz, 2H), 7.74-7.62 (m, 2H), 7.41 (d, J=8.5 Hz, 2H), 7.35 (t, J=7.9 Hz, 2H), 6.91 (d, J=7.7 Hz, 1H), 6.53 (t, J=5.9 Hz, 1H), 4.93-4.81 (m, 1H), 3.52-3.34 (m, 2H), 3.34-3.14 (m, 2H), 2.46-2.24 (m, 2H), 1.34 (d, J=5.2 Hz, 9H), 1.31 (d, J=5.2 Hz, 9H).

241

Tert-butyl (S)-3-(2-(4-(tert-butyl)benzamido)-3-(4-(5-(4-hydroxyphenyl)pyrimidin-2-yl)phenyl)propanamido)propanoate (INT-29)

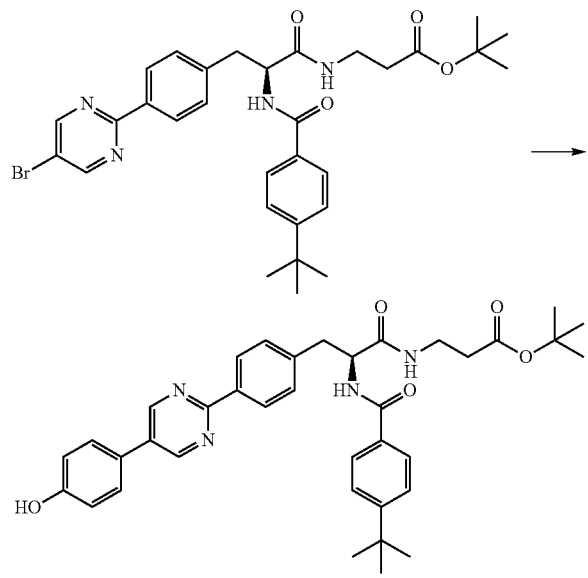

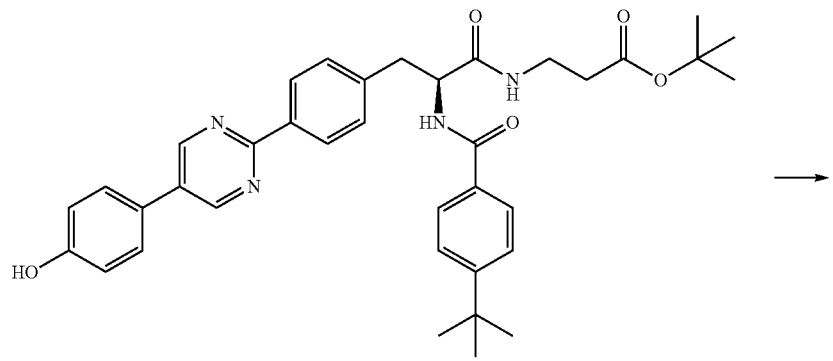

242

Prepared using General Procedure 10 from tert-butyl (S)-3-(3-(4-(5-bromopyrimidin-2-yl)phenyl)-2-(4-(tert-butyl)benzamido)propanamido)propanoate and 4-hydroxyphenyl boronic acid. LCMS-ESI (m/z) calculated for $C_{37}H_{42}BN_4O_5$: 622.8. found 621.3 [M–H]$^+$, $t_R$=3.53 min. (Method 15), and 80.1% e.e. (Chiral Method, isocratic with 20% Solvent A, 80% Solvent B). $^1$H NMR (400 MHz, CDCl$_3$) δ 8.96 (s, 2H), 8.42 (d, J=8.0 Hz, 2H), 7.70 (d, J=8.2 Hz, 2H), 7.56-7.32 (m, 6H), 6.95 (d, J=8.2 Hz, 2H), 6.82 (d, J=7.6 Hz, 1H), 6.35 (s, 1H), 4.88 (d, J=6.9 Hz, 1H), 3.46 (s, 2H), 3.39-3.12 (m, 2H), 2.48-2.15 (m, 2H), 1.36 (s, 9H), 1.33 (s, 9H).

Compound 471 was prepared from tert-butyl (S)-3-(2-(4-(tert-butyl)benzamido)-3-(4-(5-(4-hydroxyphenyl)pyrimidin-2-yl)phenyl)propanamido)propanoate using General Procedures 12 then 8.

Tert-butyl (S)-3-(2-(4-(tert-butyl)benzamido)-3-(4-(5-(4-((5-methylhexyl)oxy)phenyl)pyrimidin-2-yl)phenyl)propanamido)propanoate

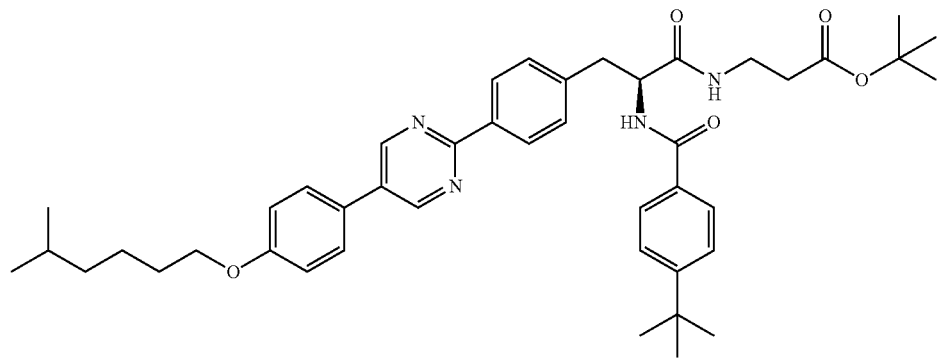

243

Prepared using General Procedure 12 from tert-butyl (S)-3-(2-(4-(tert-butyl)benzamido)-3-(4-(5-(4-hydroxyphenyl)pyrimidin-2-yl)phenyl)propanamido)propanoate and 1-bromo-5-methyl hexane. LCMS-ESI (m/z) calculated for $C_{44}H_{56}N_4O_5$: 720.9. found 721.4 $[M+H]^+$, $t_R$=5.39 min. (Method 16).

244

(S)-3-(2-(4-(tert-butyl)benzamido)-3-(4-(5-(4-((5-methylhexyl)oxy)phenyl)pyrimidin-2-yl)phenyl) propanamido)propanoic acid (Compound 472)

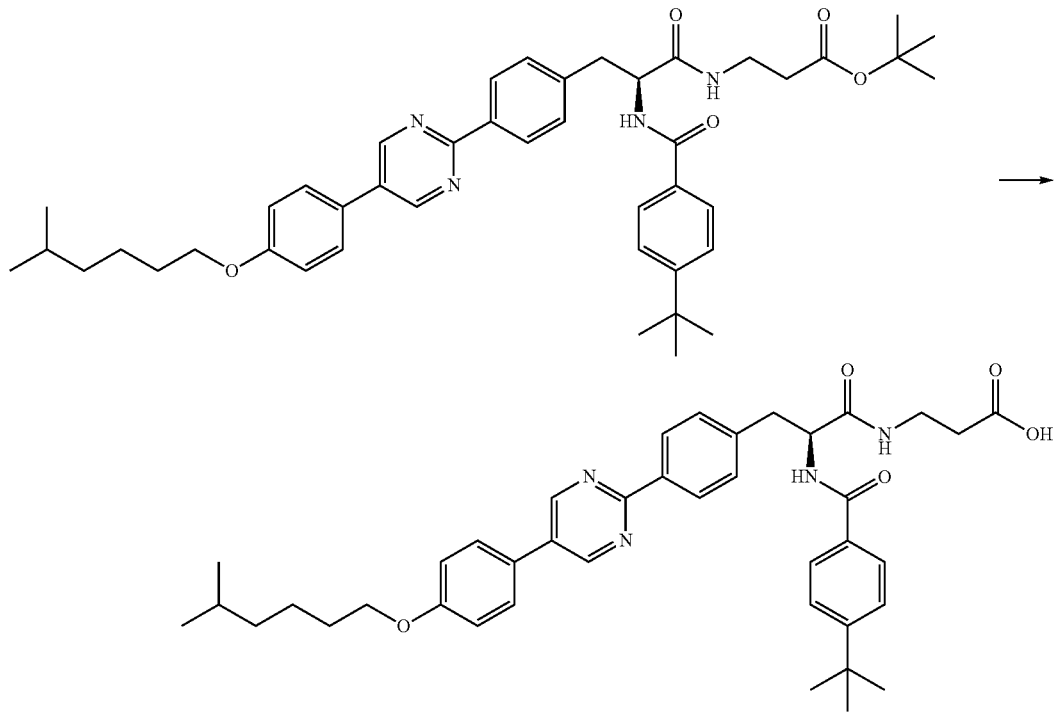

Prepared using General Procedure 8 from tert-butyl (S)-3-(2-(4-(tert-butyl)benzamido)-3-(4-(5-(4-((5-methylhexyl)oxy)phenyl)pyrimidin-2-yl)phenyl)propanamido)propanoate. LCMS-ESI (m/z) calculated for $C_{40}H_{45}N_4O_5$: 664.9. found 664.8 $[M+H]^+$, $t_R$=10.32 min. (Method 14).

Compound 473 was prepared from tert-butyl (S)-3-(2-(4-(tert-butyl)benzamido)-3-(4-(5-(4-hydroxyphenyl)pyrimidin-2-yl)phenyl)propanamido)-propanoate using General Procedures 12 then 8.

Tert-butyl (S)-3-(2-(4-(tert-butyl)benzamido)-3-(4-(5-(4-(2-cyclohexylethoxy)phenyl)-pyrimidin-2-yl)phenyl)propanamido)propanoate

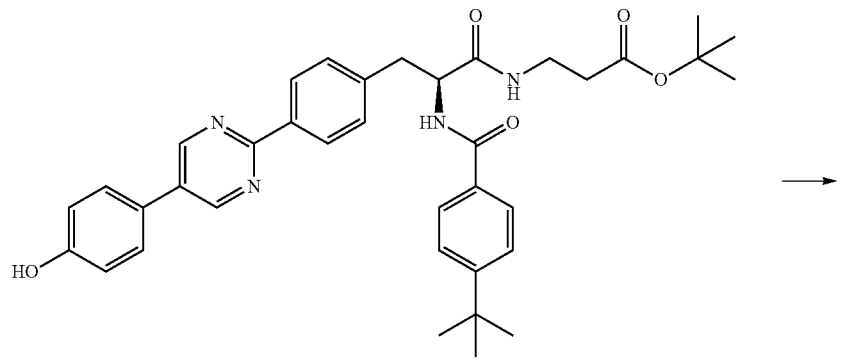

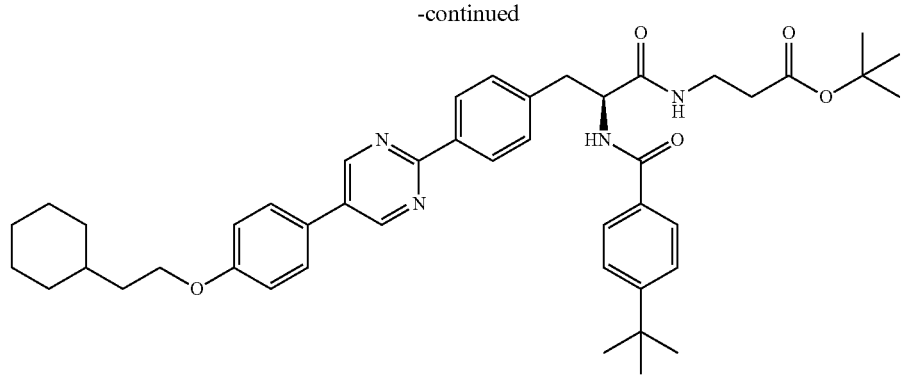

Prepared using General Procedure 12 from tert-butyl (S)-3-(2-(4-(tert-butyl)benzamido)-3-(4-(5-(4-hydroxyphenyl)pyrimidin-2-yl)phenyl)propanamido)propanoate and (2-bromoethyl)cyclohexane. LCMS-ESI (m/z) calculated for $C_{45}H_{56}N_4O_5$: 732.9. found 733.5 [M+H]$^+$, $t_R$=5.59 min. (Method 16).

(S)-3-(2-(4-(tert-butyl)benzamido)-3-(4-(5-(4-(2-cyclohexylethoxy)phenyl)pyrimidin-2-yl)phenyl) propanamido)propanoic acid (Compound 474)

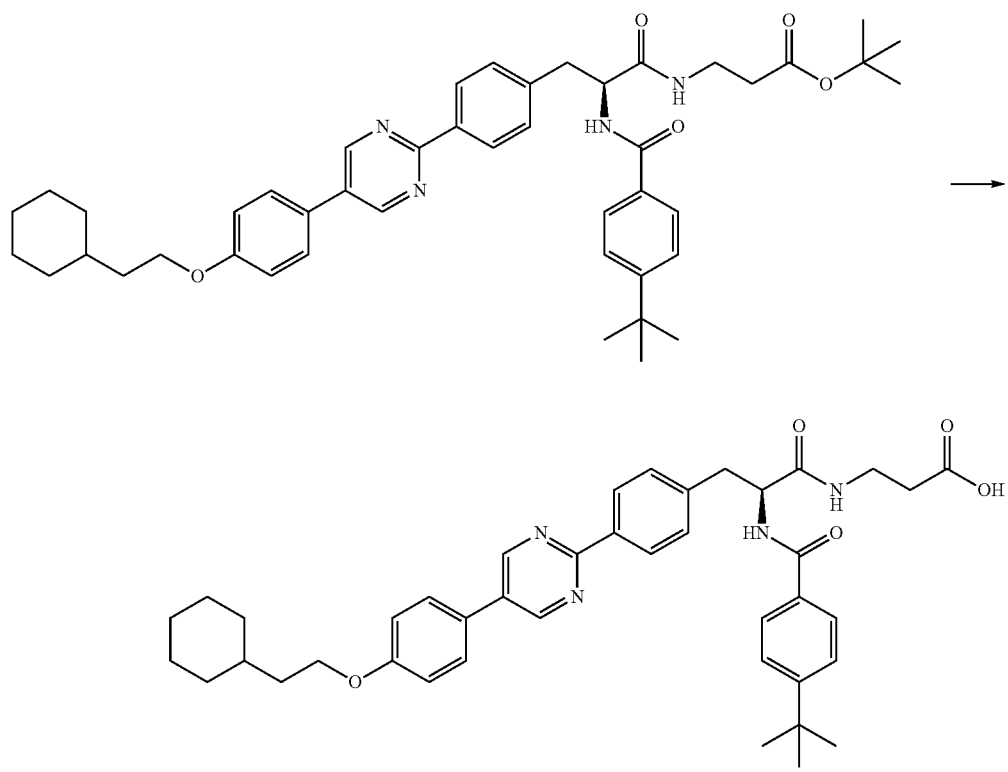 [SMILES: CC(C)(C)OC(=O)CCNC(=O)[C@H](Cc1ccc(-c2ncc(-c3ccc(OCCC4CCCCC4)cc3)cn2)cc1)NC(=O)c1ccc(C(C)(C)C)cc1 ; CC(C)(C)c1ccc(C(=O)N[C@@H](Cc2ccc(-c3ncc(-c4ccc(OCCC5CCCCC5)cc4)cn3)cc2)C(=O)NCCC(=O)O)cc1]

Prepared using General Procedure 8 from tert-butyl (S)-3-(2-(4-(tert-butyl)benzamido)-3-(4-(5-(4-(2-cyclohexylethoxy)phenyl)pyrimidin-2-yl)phenyl)propanamido)propanoate. LCMS-ESI (m/z) calculated for $C_{41}H_{48}N_4O_5$: 676.9 found 677.4 [M+H]$^+$, $t_R$=10.61 min. (Method 14).

Compounds 475 and 476 were prepared from Compound 85 using General Procedures 7, 4, then 8.

4-Benzyl 1-(tert-butyl) ((S)-2-(4-(tert-butyl)benzamido)-3-(4-(5-(4-(heptyloxy)phenyl)-pyrimidin-2-yl)phenyl)propanoyl)-L-aspartate (INT-30)

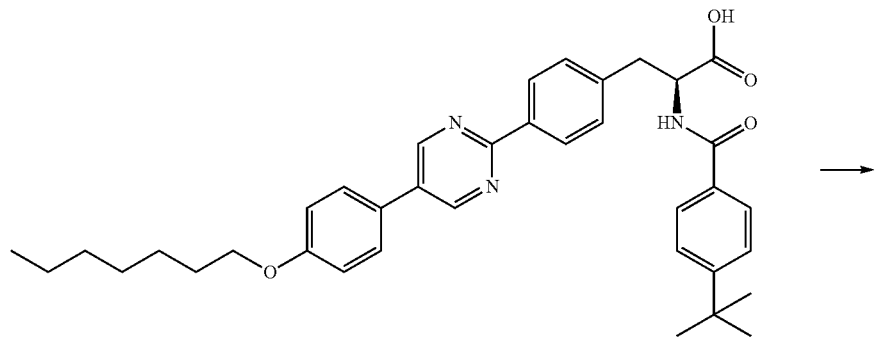

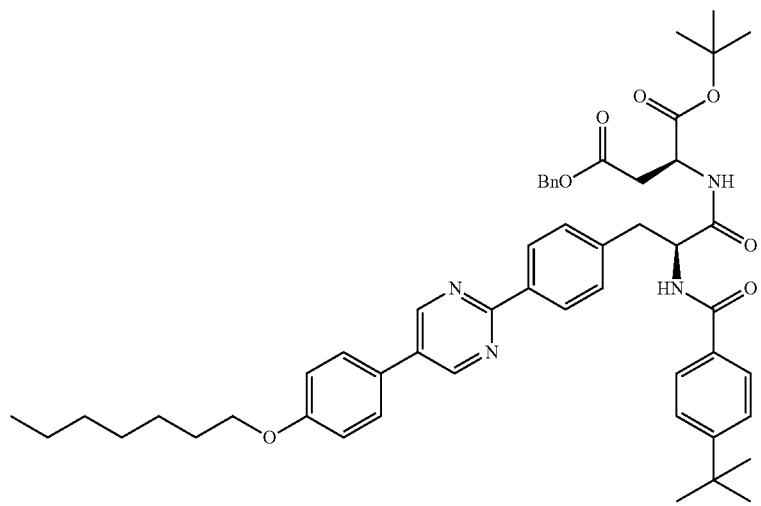

Prepared using General Procedure 7: To a stirred solution of (S)-2-(4-(tert-butyl)benzamido)-3-(4-(5-(4-(heptyloxy)phenyl)pyrimidin-2-yl)phenyl)propanoic acid Compound 85 (594 mg, 1.00 mmol), L-aspartic acid β-benzyl ester α-tert-butyl ester hydrochloride (398.4 mg, 1.20 mmol) in DMF (6 mL) was added DIEA (554 μl, 3.00 mmol). The mixture was cooled to 0° C. and HATU (418 mg, 1.10 mmol) in DMF (4 mL) was added over 5 mins. The mixture was stirred at 0° C. for 1 h. The reaction mixture was added to water (200 mL) and the precipitate was filtered. The precipitate was dissolved in DCM (20 mL), dried over $MgSO_4$, and concentrated. The crude product was purified by chromatography 0-100% EA in hexane to afford 751 mg (88%) of 4-benzyl 1-(tert-butyl) ((S)-2-(4-(tert-butyl)benzamido)-3-(4-(5-(4-(heptyloxy)phenyl)pyrimidin-2-yl)phenyl)propanoyl)-L-aspartate INT-30 as a white solid. LCMS-ESI (m/z) calculated for $C_{52}H_{62}N_4O_7$: 854.5. found 855.5 $[M+H]^+$, $t_R$=6.22 min (Method 16).

(S)-4-(tert-butoxy)-3-((S)-2-(4-(tert-butyl)benzamido)-3-(4-(5-(4-(heptyloxy)phenyl)-pyrimidin-2-yl)phenyl)propanamido)-4-oxobutanoic acid (INT-31)

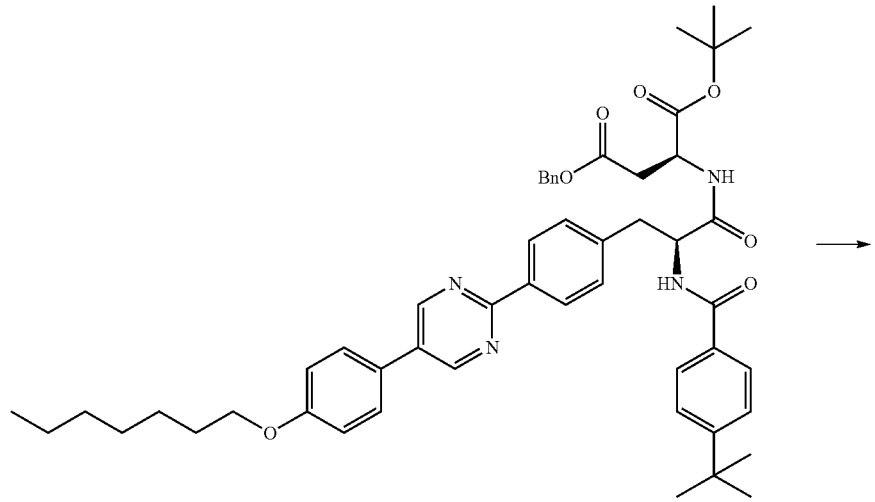

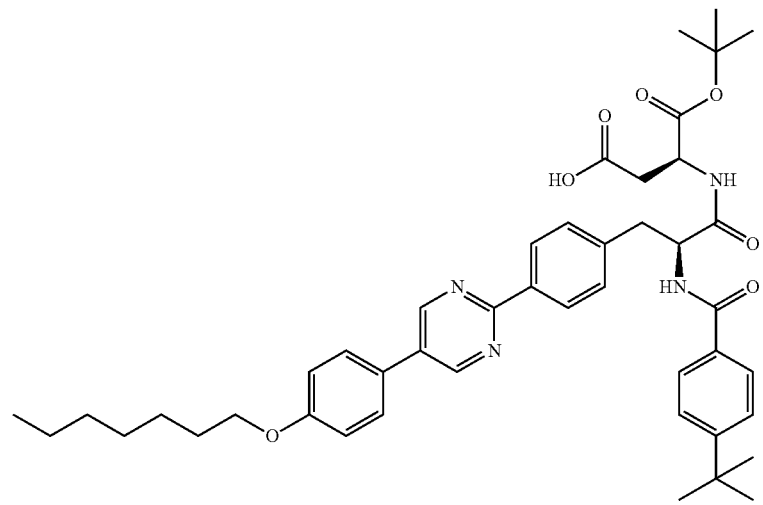

Prepared using General Procedures 18: To 4-benzyl 1-(tert-butyl) ((S)-2-(4-(tert-butyl)benzamido)-3-(4-(5-(4-(heptyloxy)phenyl)pyrimidin-2-yl)phenyl)propanoyl)-L-aspartate (50 mg, 0.058 mmol) in THF (2 mL) was added 10% Pd/C (10 mg). The reaction vessel was flushed with hydrogen gas and the reaction was stirred vigorously under hydrogen for 2 h at room temperature. The reaction mixture was filtered to remove the catalyst and the solvent was removed to give 38 mg (86%) of (S)-4-(tert-butoxy)-3-((S)-2-(4-(tert-butyl)benzamido)-3-(4-(5-(4-(heptyloxy)phenyl)pyrimidin-2-yl)phenyl)propanamido)-4-oxobutanoic acid INT-31 as a white solid. LCMS-ESI (m/z) calculated for $C_{45}H_{56}N_4O_7$: 764.4. found 765.4 [M+H]$^+$, $t_R$=4.24 min (Method 16).

N²—((S)-2-(4-(tert-butyl)benzamido)-3-(4-(5-(4-(heptyloxy)phenyl)pyrimidin-2-yl)phenyl)propanoyl)-N⁴-methyl-L-asparagine (Compound 477)

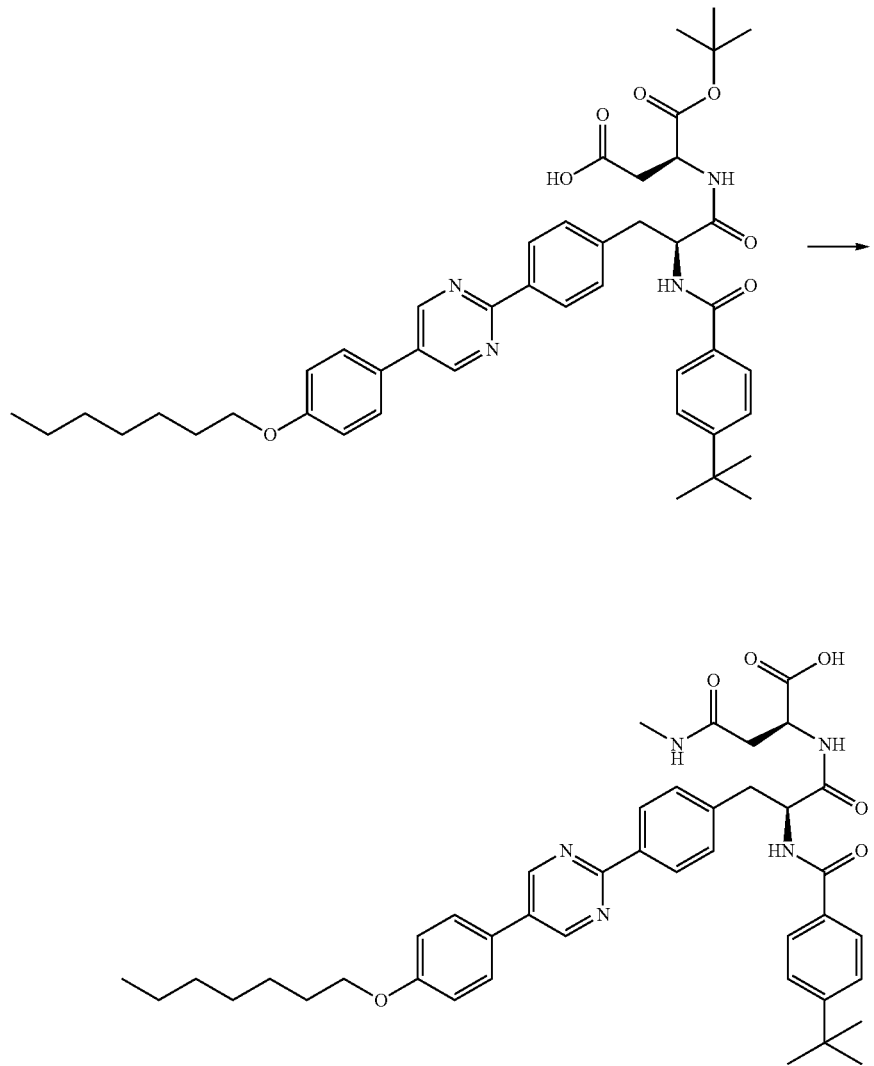

Prepared using General Procedure 7 and 8: To a stirred solution of (S)-4-(tert-butoxy)-3-((S)-2-(4-(tert-butyl)benzamido)-3-(4-(5-(4-(heptyloxy)phenyl)pyrimidin-2-yl)phenyl)propanamido)-4-oxobutanoic acid (19 mg, 0.025 mmol), methylamine (40 wt % in water, 5.8 μL, 0.075 mmol) in DMF (0.25 mL) was added DIEA (13.8 μl, 0.075 mmol). The mixture was cooled to 0° C. and HATU (19 mg, 0.05 mmol) was added. The mixture was stirred at room temperature for 18 h. The reaction mixture was added to water (2 mL) and the precipitate was filtered. The precipitate was dissolved in DCM (2 mL), dried over MgSO₄, and concentrated. The crude ester was dissolved in DCM (1 mL) and TFA (0.2 mL) was added. The reaction was stirred overnight. The solvent was removed and the crude material was purified by preparative HPLC to afford 5 mg (25%) of N²-((s)-2-(4-(tert-butyl)benzamido)-3-(4-(5-(4-(heptyloxy)phenyl)pyrimidin-2-yl)phenyl)propanoyl)-N⁴-methyl-L-asparagine. LCMS-ESI (m/z) calculated for $C_{42}H_{51}N_5O_6$; 721.4. found 722.4 [M+H]⁺, $t_R$=8.67 min (Method 14). ¹H NMR (400 MHz, DMSO) δ 12.62 (s, 1H), 9.14 (s, 2H), 8.53 (d, J=8.5 Hz, 1H), 8.36 (d, J=7.9 Hz, 1H), 8.29 (d, J=8.2 Hz, 2H), 7.86 (d, J=4.6 Hz, 1H), 7.78 (d, J=8.7 Hz, 2H), 7.72 (d, J=8.3 Hz, 2H), 7.51 (d, J=8.3 Hz, 2H), 7.44 (d, J=8.4 Hz, 2H), 7.08 (d, J=8.8 Hz, 2H), 4.89-4.73 (m, 1H), 4.66-4.53 (m, 1H), 4.03 (t, J=6.5 Hz, 3H), 3.26-3.18 (m, 1H), 3.11-3.00 (m, 1H), 2.64-2.53 (m, 5H), 1.80-1.67 (m, 2H), 1.51-1.38 (m, 2H), 1.38-1.21 (m, 15H), 0.87 (t, J=6.8 Hz, 3H).

Compounds 478-487 were prepared from (S)-4-(tert-butoxy)-3-((S)-2-(4-(tert-butyl)benzamido)-3-(4-(5-(4-(heptyloxy)phenyl)pyrimidin-2-yl)phenyl)propanamido)-4-oxobutanoic acid using General Procedures 7 and 8.

Compound 488 was prepared from Compound 85 using General Procedures 7 and 4.

Compounds 489 and 490 were prepared from tert-butyl (S)-3-(2-(4-(tert-butyl)benzamido)-3-(4-(5-(4-hydroxyphenyl)pyrimidin-2-yl)phenyl)propanamido)propanoate using General Procedures 12 then 8.

Compound 491 was prepared from Compound 85 using General Procedures 7 then 4.

253

Tert-butyl ((S)-3-(4-(5-bromopyrimidin-2-yl)phenyl)-2-(4-(tert-butyl)benzamido)-propanoyl)-D-alaninate (INT-32)

254

(S)-2-(4-(3-((3-(tert-butoxy)-3-oxopropyl)amino)-2-(4-(tert-butyl)benzamido)-3-oxopropyl)phenyl)pyrimidine-5-carboxylic acid (INT-33)

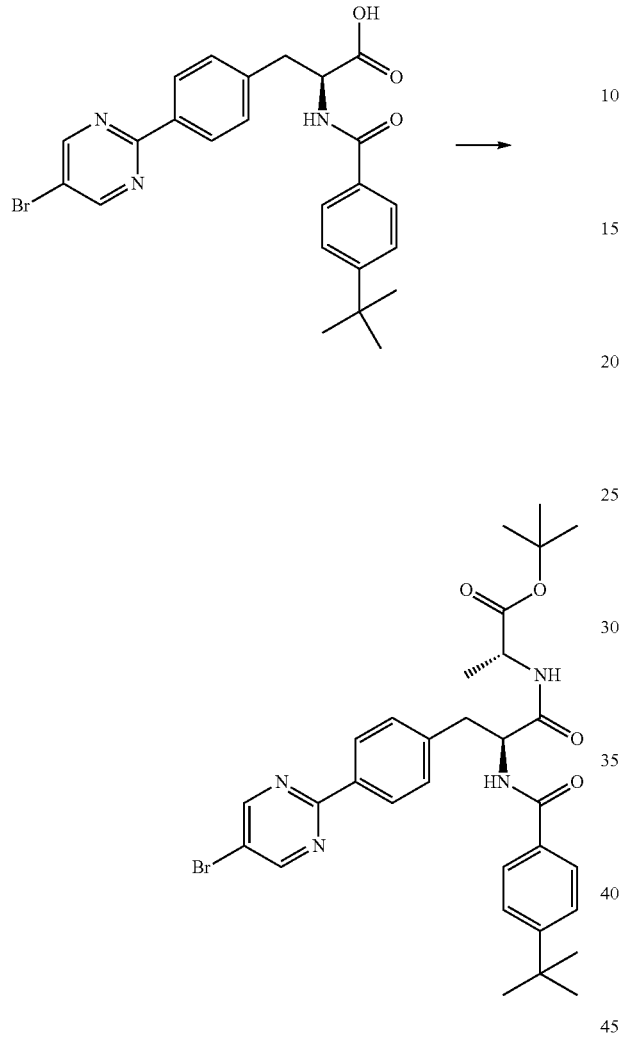

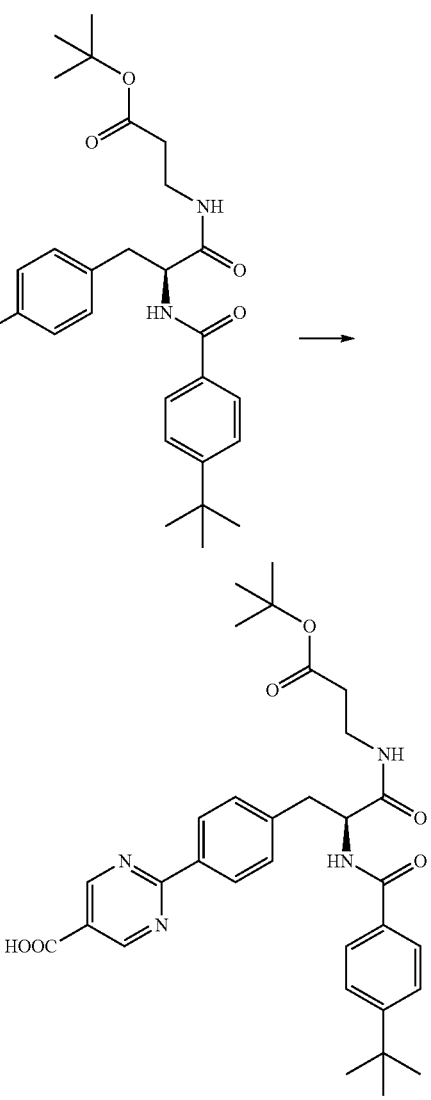

To a stirring solution of (S)-3-(4-(5-bromopyrimidin-2-yl)phenyl)-2-(4-(tert-butyl)benzamido)propanoic acid INT-27 (1.50 g, 3.10 mmol) in DMF (15 mL) were added tert-butyl D-alaninate (680.0 mg, 3.73 mmol) and Et$_3$N (802.3 mg, 6.2 mmol). The reaction was stirred for 1 hour at 0° C. and then HATU (877.5 mg, 3.37 mmol) in 2 mL DMF was added. The reaction was stirred for 1 hour at 0° C. and then warmed to room temperature with stirring for 18 hours. The reaction solution was extracted with aqueous NaHCO$_3$ (3×20 mL). The combined organics were dried over MgSO$_4$ and evaporated. The crude product was purified by column chromatography (50%) EA in hexanes) to afford 1.44 g (76%) of tert-butyl ((S)-3-(4-(5-bromopyrimidin-2-yl)phenyl)-2-(4-(tert-butyl)benzamido)-propanoyl)-D-alaninate INT-32 as a solid powder. LCMS-ESI (m/z) calculated for C$_{31}$H$_{37}$BrN$_4$O$_4$: 609.6. found 610.2 [M+H]$^+$, t$_R$=4.05 min. (Method 16). $^1$H NMR (400 MHz, DMSO) δ 9.03 (s, 2H), 8.49 (d, J=8.7 Hz, 1H), 8.41 (d, J=7.2 Hz, 1H), 8.24 (d, J=8.2 Hz, 2H), 7.73 (t, J=7.4 Hz, 2H), 7.54-7.37 (m, 4H), 4.85 (td, J=10.1, 4.6 Hz, 1H), 4.16 (t, J=7.2 Hz, 1H), 3.24-2.97 (m, 2H), 1.50-1.29 (m, 9H), 1.32-1.17 (m, 12H).

Prepared using General Procedure 19. Oven-dried lithium formate (136 mg, 2.6 mmol), DIEA (700 µL, 3.9 mmol), and Ac$_2$O (370 µL, 3.9 mmol) were dissolved in anhydrous DMF (10 mL) in a flame-dried flask under N$_2$. After stirring for 30 min, the solution was degassed via N$_2$ bubbling. In a separate flask, INT-28 (400 mg, 0.7 mmol, azeotropically dried from THF) was dissolved in DMF (10 mL) and degassed via N$_2$ bubbling. Into the INT-28 solution was added PdCl$_2$(dppf) (48 mg, 0.07 mmol) and the resulting solution was transferred via cannula into the lithium formate solution. The flask was sealed and heated at 120° C. for 4 h in a microwave reactor. The reaction mixture was diluted with EA (250 mL) and washed with 10% citric acid (250 mL) and then washed with H$_2$O (250 mL) and purified by chromatography (EA/hexanes) to afford 400 mg (99%) of (S)-2-(4-(3-((3-(tert-butoxy)-3-oxopropyl)amino)-2-(4-(tert-butyl)benzamido)-3-oxopropyl)phenyl)pyrimidine-5- carboxylic acid INT-33. LCMS-ESI (m/z) calculated for $C_{32}H_{38}N_4O_6$: 574.7. found 575.3 $[M+H]^+$, $t_R$=2.41 min. (Method 15).

Methyl 2-(4-bromophenyl)-2-(4-(tert-butyl)benzamido)acetate

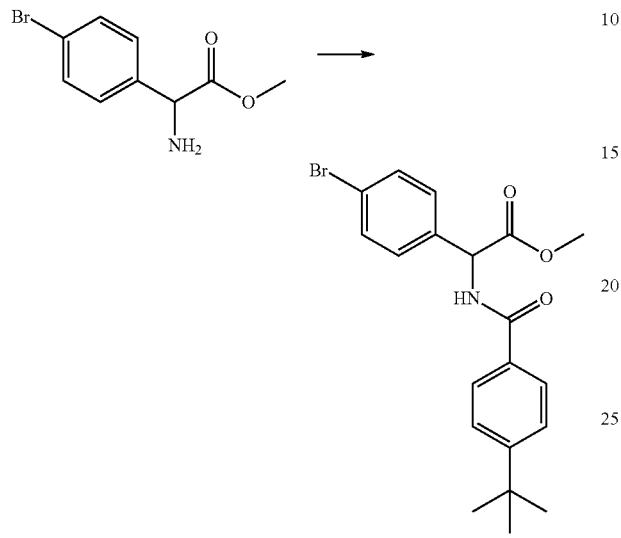

Prepared using General Procedure 7. To a stirring solution of methyl 2-amino-2-(4-bromophenyl)acetate (421 mg, 1.5 mmol), 4-(tert-butyl)benzoic acid (321 mg, 1.8 mmol), and DIEA (831 µl, 4.5 mmol) in DMF (3 mL) cooled to 0° C. was slowly added a solution of HATU (380 mg, 1.65 mmol) in DMF (1.5 mL) in a drop-wise fashion. The reaction mixture was allowed to warm slowly and stirring continued for 4 h. The reaction mixture was poured onto ice-water and the solid was filtered. The solid was dissolved in DCM (10 mL), dried over MgSO$_4$ and evaporated to afford 532 mg (88%) of methyl 2-(4-bromophenyl)-2-(4-(tert-butyl)benzamido)acetate. LCMS-ESI (m/z) calculated for $C_{20}H_{22}BrNO_3$: 403.0. found 404.1 $[M+H]^+$, $t_R$=3.61 min. (Method 16).

Methyl 2-(4-(tert-butyl)benzamido)-2-(4-(4,4,5,5-tetramethyl-1, 3, 2-dioxaborolan-2-yl)phenyl)acetate (INT-34)

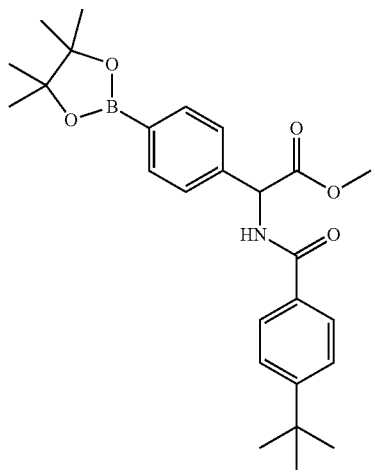

Prepared using General Procedure 10. A solution of methyl 2-(4-bromophenyl)-2-(4-(tert-butyl)benzamido)acetate (202 mg, 0.5 mmol), KOAc (147 mg, 1.5 mmol) and 4,4,4',4',5,5,5',5'-octamethyl-2,2'-bi(1,3,2-dioxaborolane) (165 mg, 0.65 mmol) in DMSO (3 mL) was de-gassed. PdCl$_2$dppf (18 mg, 0.025 mmol) was added and the mixture was heated at 90° C. for 1.5 h. The crude reaction mixture was poured onto ice-water and the solid was filtered. The solid was dissolved in DCM (5 mL), dried over MgSO$_4$, evaporated and purified by chromatography (EA/hexane) to provide 71 mg (31%) of methyl 2-(4-(tert-butyl)benzamido)-2-(4-(4,4,5,5-tetramethyl-1,3,2-dioxaborolan-2-yl)phenyl)acetate INT-34. LCMS-ESI (m/z) calculated for $C_{26}H_{34}BNO_5$: 451.3. found 452.2 $[M+H]^+$, $t_R$=3.83 min (Method 16).

(S)-3-(4-(5-bromopyrimidin-2-yl)phenyl)-2-(5-(tert-butyl)thiophene-2 carboxamido)-propanoic acid

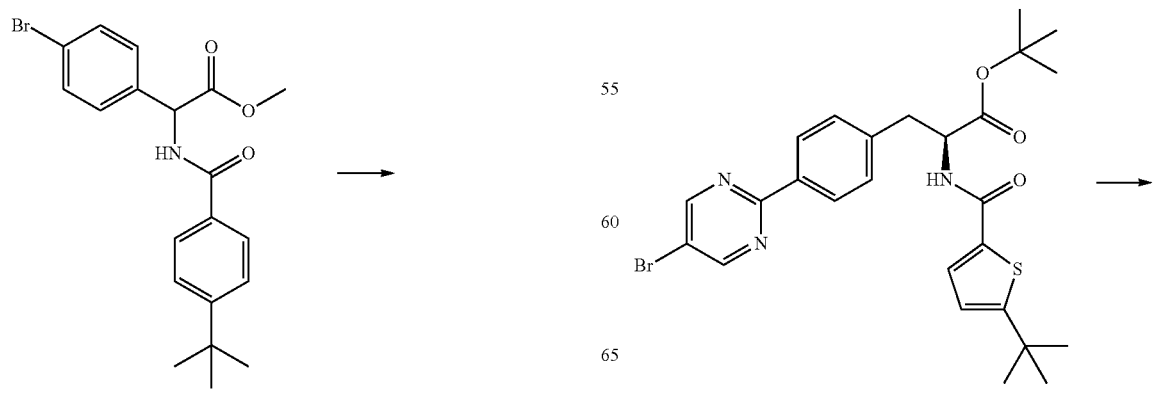

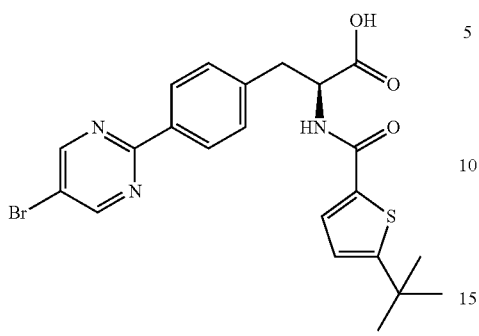
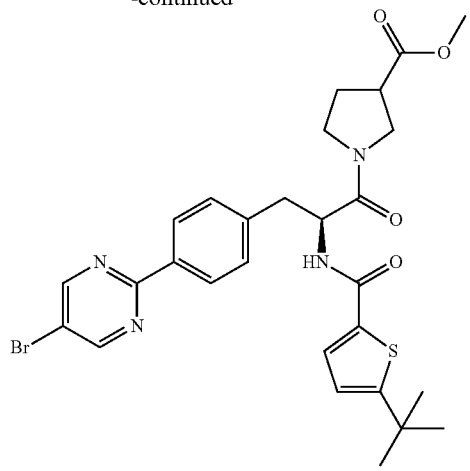

To a stirring solution of tert-butyl (S)-3-(4-(5-bromopyrimidin-2-yl)phenyl)-2-(5-(tert-butyl)thiophene-2-carboxamido)propanoate INT-17 (15.7 g, 28.8 mmol) in DCM (30 mL) was treated with TFA (30.0 g, 263.1 mmol). The reaction mixture was stirred at room temperature for 18 hours to complete. The solvent was evaporated and then co-evaporated with toluene (3×20 mL) to remove trace TFA. The compound was dried under vacuum overnight to afford 13.7 g (97%) of (S)-3-(4-(5-bromopyrimidin-2-yl)phenyl)-2-(5-(tert-butyl)thiophene-2-carboxamido)propanoic acid as powder. LCMS-ESI (m/z) calculated for $C_{22}H_{22}BrN_3O_3S$: 487.1. found 488.1 $[M+H]^+$, $t_R$=2.55 min. (Method 16). $^1$H NMR (400 MHz, DMSO) δ 9.05 (d, J=5.0 Hz, 2H), 8.64 (d, J=8.4 Hz, 1H), 8.25 (d, J=8.1 Hz, 2H), 7.62 (d, J=3.8 Hz, 1H), 7.45 (d, J=8.2 Hz, 2H), 6.92 (d, J=3.8 Hz, 2H), 4.64 (td, J=10.5, 4.5 Hz, 1H), 3.26 (dd, J=13.8, 4.4 Hz, 1H), 3.11 (dd, J=13.7, 10.7 Hz, 1H), 1.32 (s, 9H).

To a stirring solution of methyl (S)-pyrrolidine-3-carboxylate (357.0 mg, 2.16 mmol) in DMF (10 mL) were added DIEA (465.26 mg, 3.60 mmol) and (S)-3-(4-(5-bromopyrimidin-2-yl)phenyl)-2-(5-(tert-butyl)thiophene-2-carboxamido)propanoic acid (700.0 mg, 1.44 mmol). The solution was cooled to 0° C. at ice bath and then HATU (677.55 mg, 2.88 mmol) in 2 mL DMF solution was slowly added. The reaction was stirred 1 hour at 0° C. and then warmed to RT with stirring for 2 hours. The reaction solution was extracted with DCM (3×20 mL) and aqueous NaHCO₃ (3×10 mL). The combined organics were dried over MgSO₄ and evaporated. The final compound was purified by column chromatography (40% DCM in hexane) to afford 501.0 mg (58%) of methyl (S)-1-((S)-3-(4-(5-bromopyrimidin-2-yl)phenyl)-2-(5-(tert-butyl)thiophene-2-carboxamido)propanoyl)pyrrolidine-3-carboxylate INT-35 as a powder. LCMS-ESI (m/z calculated for $C_{28}H_{31}BrN_4O_4S$: 598.1. found 599.3 $[M+H]^+$, $t_R$=3.553 min. (Method 16). $^1$H NMR (400 MHz, DMSO) δ 9.05 (d, J=1.1 Hz, 2H), 8.77 (dd, J=11.5, 8.3 Hz, 1H), 8.25 (d, J=7.7 Hz, 2H), 7.72 (d, J=3.5 Hz, 1H), 7.46 (d, J=8.3 Hz, 2H), 6.92 (d, J=3.8 Hz, 1H), 4.98-4.73 (m, 1H), 3.88 (dd, J=10.3, 8.0 Hz, 1H), 3.71 (dd, J=15.5, 7.5 Hz, 1H), 3.50 (ddd, J=18.3, 12.2, 5.4 Hz, 2H), 3.38 (dd, J=17.3, 7.6 Hz, 1H), 3.23 (ddd, J=28.0, 15.0, 8.7 Hz, 1H), 3.18-2.85 (m, 3H), 2.17-1.96 (m, 2H), 1.87 (td, J=15.2, 7.4 Hz, 1H), 1.32 (s, 9H).

Methyl (S)-1-((S)-3-(4-(5-bromopyrimidin-2-yl)phenyl)-2-(5-(tert-butyl)thiophene-2-carboxamido)propanoyl)pyrrolidine-3-carboxylate (INT-35)

Tert-butyl ((S)-3-(4-(5-bromopyrimidin-2-yl)phenyl)-2-(5-(tert-butyl)thiophene-2-carboxamido)propanoyl)-D-alaninate

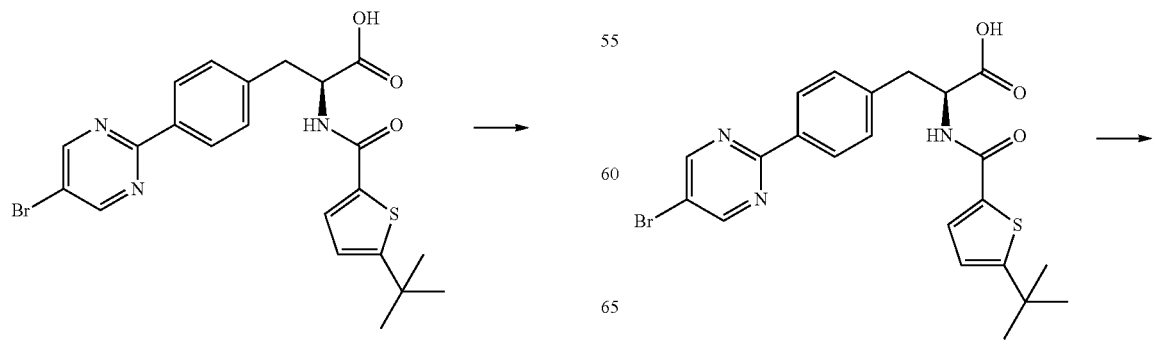

Tert-butyl ((S)-2-(5-(tert-butyl)thiophene-2-carboxamido)-3-(4-(5-(4-hydroxyphenyl)-pyrimidin-2-yl)phenyl)propanoyl)-D-alaninate (INT-36)

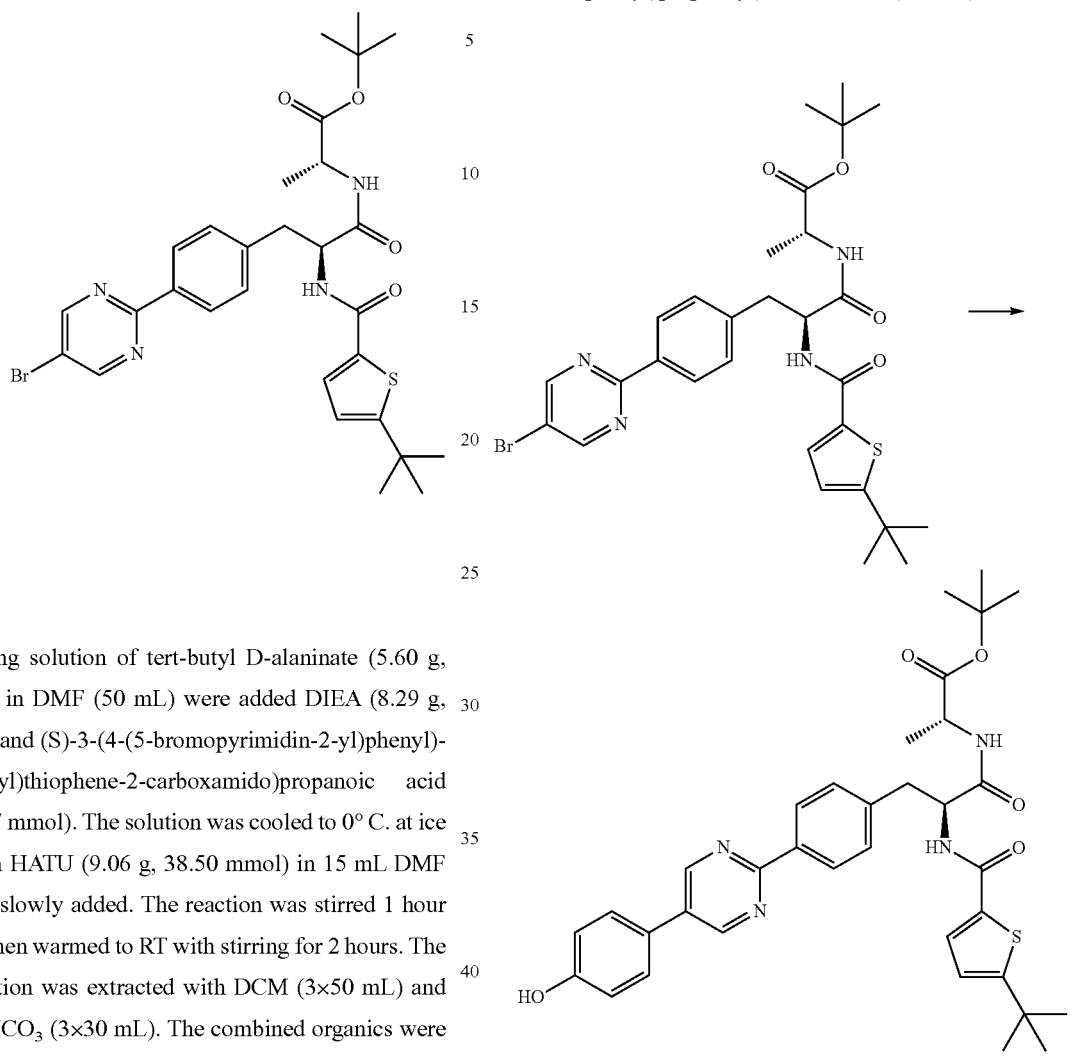

To a stirring solution of tert-butyl D-alaninate (5.60 g, 30.80 mmol) in DMF (50 mL) were added DIEA (8.29 g, 64.18 mmol) and (S)-3-(4-(5-bromopyrimidin-2-yl)phenyl)-2-(5-(tert-butyl)thiophene-2-carboxamido)propanoic acid (12.5 g, 25.67 mmol). The solution was cooled to 0° C. at ice bath and then HATU (9.06 g, 38.50 mmol) in 15 mL DMF solution was slowly added. The reaction was stirred 1 hour at 0° C. and then warmed to RT with stirring for 2 hours. The reaction solution was extracted with DCM (3×50 mL) and aqueous NaHCO$_3$ (3×30 mL). The combined organics were dried over MgSO$_4$ and evaporated. The final compound was purified by column chromatography (40% DCM in hexane) to afford 14.7 g (94%) of tert-butyl ((S)-3-(4-(5-bromopyrimidin-2-yl)phenyl)-2-(5-(tert-butyl)thiophene-2-carboxamido)propanoyl)-D-alaninateas solid powder. LCMS-ESI (m/z) calculated for C$_{29}$H$_{35}$BRN$_4$O$_4$S: 614.2. found 615.3 [M+H]$^+$, t$_R$=3.914 min. (Method 16). $^1$H NMR (400 MHz, CDCl$_3$) δ 8.83 (d, J=3.6 Hz, 2H), 8.36 (d, J=8.2 Hz, 2H), 7.39 (d, J=8.2 Hz, 2H), 7.34 (d, J=3.8 Hz, 1H), 6.81 (d, J=3.8 Hz, 1H), 6.66 (d, J=7.6 Hz, 1H), 6.34 (d, J=7.2 Hz, 1H), 4.88 (d, J=5.9 Hz, 1H), 4.41 (t, J=7.2 Hz, 1H), 3.31 (dd, J=13.6, 5.8 Hz, 1H), 3.20 (dd, J=13.6, 7.8 Hz, 1H), 1.51-1.32 (m, 18H), 1.27 (d, J=7.1 Hz, 3H). $^{13}$C NMR (101 MHz, DMSO) δ 172.02, 171.31, 162.28, 162.13, 161.42, 158.55, 142.27, 136.34, 134.66, 130.20, 128.82, 127.92, 123.07, 118.63, 80.90, 54.45, 48.86, 39.59, 39.38, 32.39, 28.04, 17.68.

To a 100 ml flask were added (4-hydroxyphenyl)boronic acid (224.6 mg, 1.6 mmol), sodium carbonate decahydrate (96.0 mg, 1.6 mmol), tert-butyl ((S)-3-(4-(5-bromopyrimidin-2-yl)phenyl)-2-(5-(tert-butyl)thiophene-2-carboxamido)propanoyl)-D-alaninate (500.0 mg, 1.6 mmol), Pd(dppf)Cl$_2$ (58.5 mg, 0.08 mmol), THF (2.0 mL), CH$_3$CN (2.0 ml) and water (1.0 mL). The solution was degassed using N$_2$ bubbling for 10 min. The reaction mixture was heated to 80° C. for 2 hours. The reaction mixture was dried under reduced pressure to remove the solvent and diluted in DCM (20 mL). The mixture was extracted with DCM (3×20 mL) and aqueous NaHCO$_3$ (3×10 mL). The combined organics were dried over MgSO$_4$ and evaporated. The final compound was purified by column chromatography (40% DCM in hexane) to afford 462.3 mg (91%) of tert-butyl ((S)-2-(5-(tert-butyl)thiophene-2-carboxamido)-3-(4-(5-(4-hydroxyphenyl)pyrimidin-2-yl)phenyl)propanoyl)-D-alaninate INT-36 as a solid. LCMS-ESI (m/z) calculated for C$_{35}$H$_{40}$N$_4$O$_5$S: 628.3. found 629.3 [M+H]$^+$, t$_R$=3.447 min. (Method 16). $^1$H NMR (400 MHz, DMSO) δ 9.79 (s, 1H), 9.12 (s, 2H), 8.55 (t, J=16.2 Hz, 1H), 8.43 (d, J=7.2 Hz, 1H), 8.30 (d, J=8.1 Hz, 2H), 7.69 (t, J=7.5 Hz, 3H), 7.50 (dd, J=15.4, 8.3 Hz, 2H), 7.00-6.85 (m, 2H), 6.75 (t, J=9.9 Hz, 1H), 4.80 (td, J=9.7, 4.7 Hz, 1H), 4.15 (p, J=7.2 Hz, 1H), 3.10 (ddd, J=39.3, 19.4, 11.8 Hz, 2H), 1.40 (d, J=6.6 Hz, 9H), 1.31 (s, 9H), 1.23 (t, J=11.1 Hz, 3H).

Methyl (S)-1-((S)-2-(5-(tert-butyl)thiophene-2-carboxamido)-3-(4-(5-(4-hydroxyphenyl)pyrimidin-2-yl)phenyl)propanoyl)pyrrolidine-3-carboxylate (INT-37)

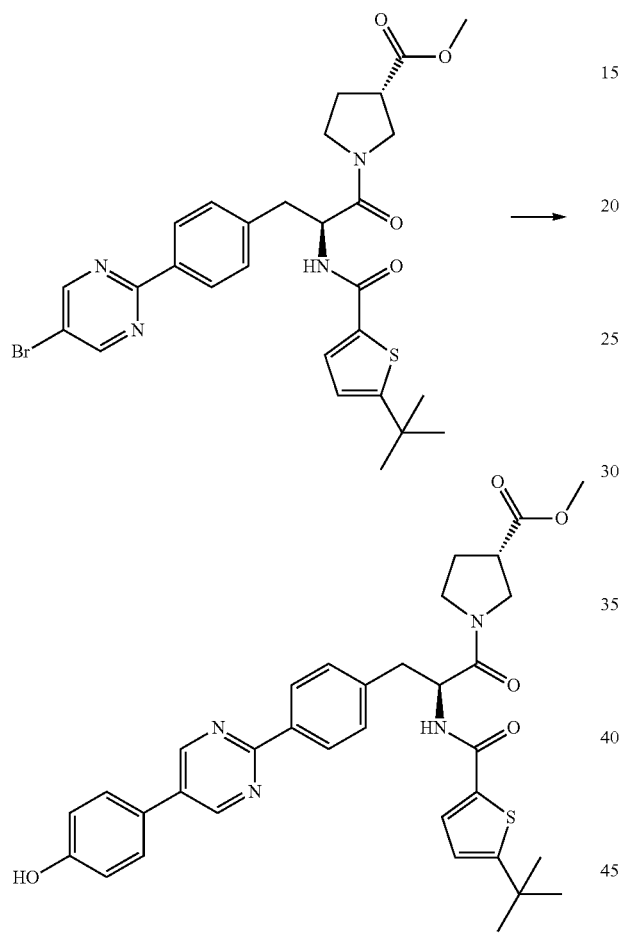

To a 10 ml flask were added (4-hydroxyphenyl)boronic acid (60.7 mg, 0.44 mmol), sodium carbonate decahydrate (26.4 mg, 0.44 mmol), methyl (S)-1-((S)-3-(4-(5-bromopyrimidin-2-yl)phenyl)-2-(5-(tert-butyl)thiophene-2-carboxamido)propanoyl)pyrrolidine-3-carboxylate INT-35 (130.0 mg, 0.44 mmol), Pd(dppf)Cl₂ (16.09 mg, 0.022 mmol), THF (2.0 mL), CH₃CN (2.0 ml) and water (1.0 mL). The solution was degassed using N₂ bubbling for 10 min. The reaction mixture was heated to 80° C. for 2 hours. The reaction mixture was dried under reduced pressure to remove the solvent and diluted in DCM (20 mL). The mixture was extracted with DCM (3×10 mL) and aqueous NaHCO₃ (3×10 mL). The combined organics were dried over MgSO₄ and evaporated. The final compound was purified by column chromatography (50% DCM in hexane) to afford 102.0 mg (76%) of methyl (S)-1-((S)-2-(5-(tert-butyl)thiophene-2-carboxamido)-3-(4-(5-(4-hydroxyphenyl)pyrimidin-2-yl)phenyl)propanoyl)pyrrolidine-3-carboxylate INT-37 as a solid powder. LCMS-ESI (m/z) calculated for C₃₄H₃₆N₄O₅S: 612.3. found 613.3 [M+H]⁺, $t_R$=3.138 min. (Method 16). ¹H NMR (400 MHz, DMSO) δ 9.81 (s, 1H), 9.13 (d, J=1.5 Hz, 2H), 8.77 (dd, J=11.4, 8.1 Hz, 1H), 8.31 (d, J=8.2 Hz, 2H), 7.73 (d, J=3.8 Hz, 1H), 7.69 (d, J=8.4 Hz, 2H), 7.46 (d, J=8.3 Hz, 2H), 6.99-6.84 (m, 3H), 4.88 (s, 1H), 3.72 (d, J=8.9 Hz, 1H), 3.62 (s, 1H), 3.59 (d, J=6.4 Hz, 1H), 3.50 (ddd, J=18.7, 12.0, 5.8 Hz, 1H), 3.36 (d, J=7.5 Hz, 1H), 3.27-3.16 (m, 1H), 3.18-2.97 (m, 3H), 2.15-1.95 (m, 2H), 1.88 (dd, J=12.5, 7.5 Hz, 1H), 1.32 (s, 9H).

Tert-butyl (S)-1-(3-(4-(5-bromopyrimidin-2-yl)phenyl)-2-(5-(tert-butyl)thiophene-2-carboxamido)propanoyl)azetidine-3-carboxylate (INT-38)

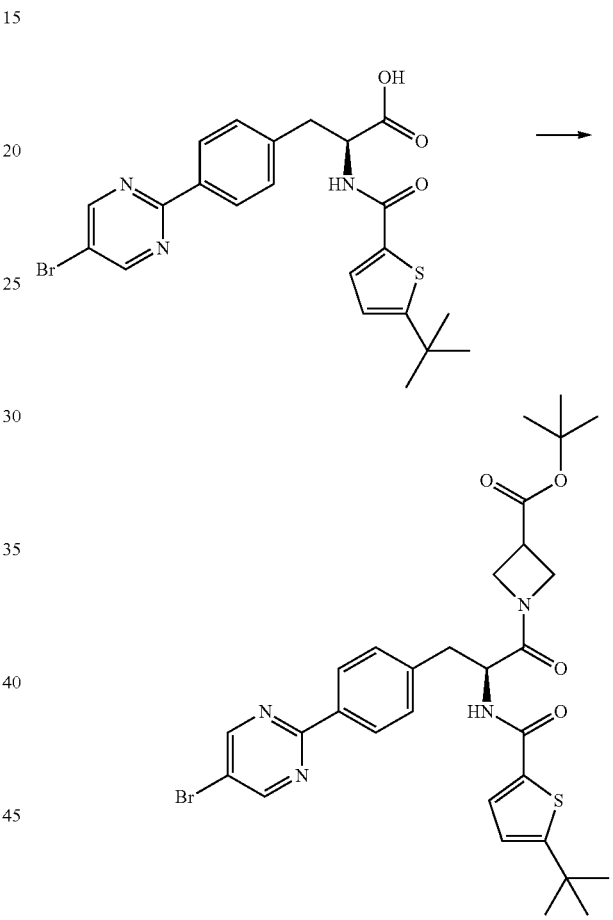

To a stirring solution of tert-butyl azetidine-3-carboxylate (64.55 mg, 0.41 mmol) in DMF (1 mL) were added DIEA (169.6 mg, 1.31 mmol), and (S)-3-(4-(5-bromopyrimidin-2-yl)phenyl)-2-(5-(tert-butyl)thiophene-2-carboxamido)propanoic acid (100.0 mg, 0.21 mmol). The solution was cooled to 0° C. at ice bath and then HATU (74.11 mg, 1.31 mmol) in 1 mL DMF solution was slowly added. The reaction was stirred 1 hour at 0° C. and then warmed to RT with stirring for 2 hours. The reaction solution was extracted with DCM (3×10 mL) and aqueous NaHCO₃ (3×10 mL). The combined organics were dried over MgSO₄ and evaporated. to afford 117.6 mg (85%) of tert-butyl (S)-1-(3-(4-(5-bromopyrimidin-2-yl)phenyl)-2-(5-(tert-butyl)thiophene-2-carboxamido)propanoyl)azetidine-3-carboxylate INT-38 as a solid powder without further purification for next step. LCMS-ESI (m/z) calculated for C₃₀H₃₅BrN₄O₄S: 626.2. found 627.2 [M+H]⁺, $t_R$=3.884 min. (Method 16).

Methyl (S)-1-((S)-2-(((benzyloxy)carbonyl)amino)-
3-(4-(5-(4-(heptyloxy)phenyl)pyrimidin-2-yl)phenyl)
propanoyl)pyrrolidine-3-carboxylate

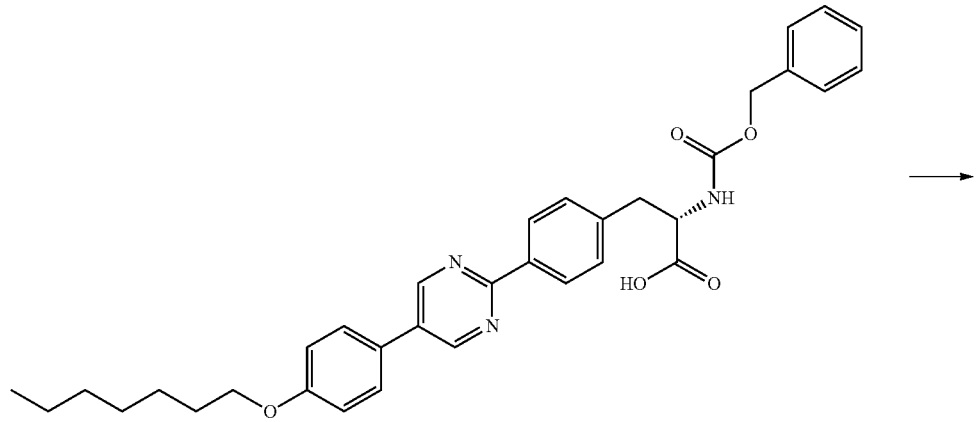

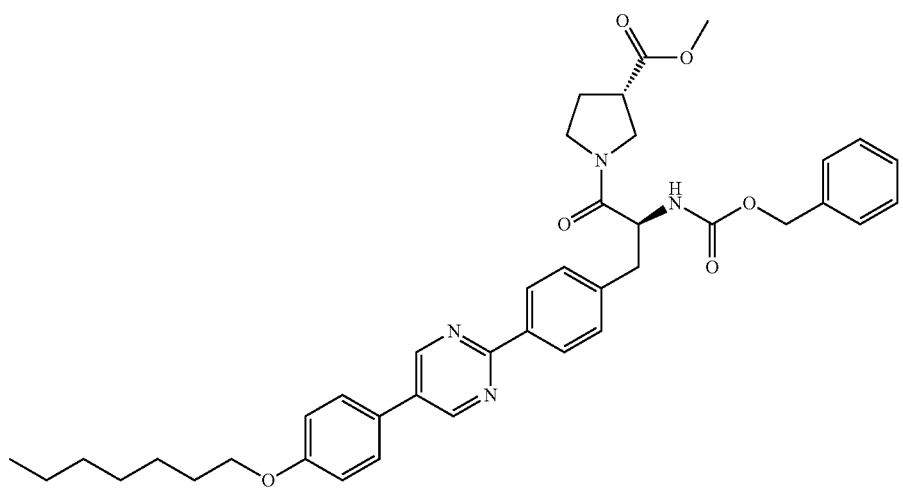

Prepared using General Procedure 7. To a stirring solution of (S)-2-(((benzyloxy)carbonyl)amino)-3-(4-(5-(4-(heptyloxy)phenyl)pyrimidin-2-yl)phenyl)propanoic acid INT-22 (2082 mg, 2.75 mmol), methyl (S)-pyrrolidine-3-carboxylate HCl (545 mg, 3.30 mmol), and DIEA (1523 µl, 8.25 mmol) in DMF (6 mL) cooled to 0° C. was slowly added a solution of HATU (1254 mg, 3.30 mmol) in DMF (5 mL) in a drop-wise fashion The reaction mixture was allowed to warm slowly and stirring continued for 4 h. The reaction mixture was poured onto ice-water and the solid was filtered. The solid was dissolved in EA (50 mL), dried over MgSO$_4$, evaporated and purified by chromatography (EA/hexane) to provide 932 mg (52%) of methyl (S)-1-((S)-2-(((benzyloxy)carbonyl)amino)-3-(4-(5-(4-(heptyloxy)phenyl)pyrimidin-2-yl)phenyl)propanoyl)pyrrolidine-3-carboxylate. LCMS-ESI (m/z) calculated for $C_{40}H_{46}N_4O_6$: 678.3. found 679.3 [M+H]$^+$, $t_R$=4.50 min (Method 16).

Methyl (S)-1-((S)-2-amino-3-(4-(5-(4-(heptytyloxy)phenyl)pyrimidin-2-yl)propanoyl) pyrrolidine-3-carboxylate (INT-39)

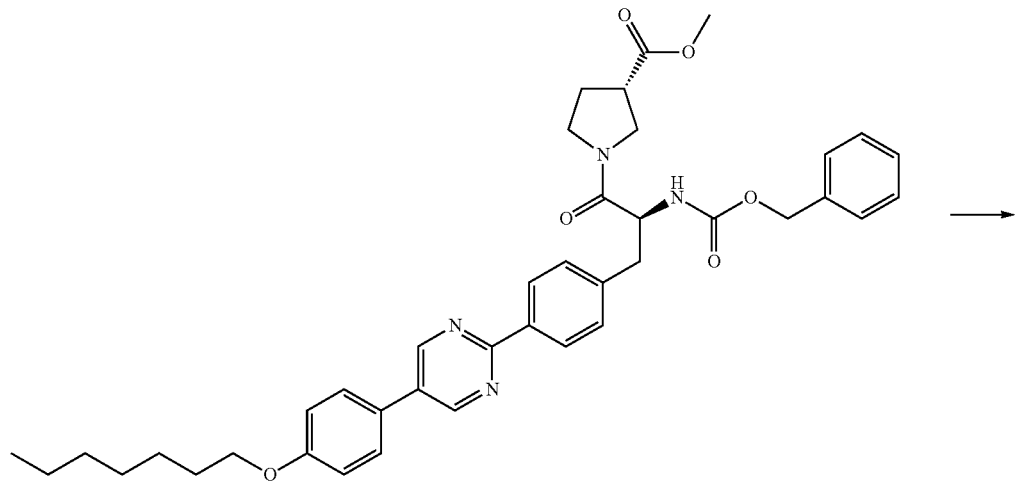

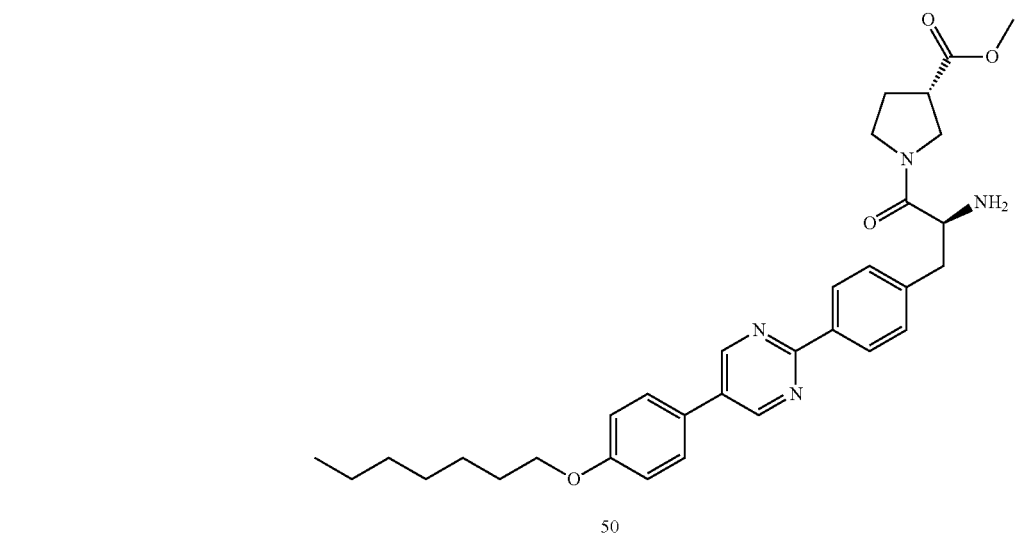

Prepared using General Procedure 18: To a stirred solution of methyl (S)-1-((S)-2-(((benzyloxy)carbonyl)amino)-3-(4-(5-(4-(heptyloxy)phenyl)pyrimidin-2-yl)phenyl)propanoyl)pyrrolidine-3-carboxylate (962 mg, 1.42 mmol) in MeOH (10 mL) was added palladium on carbon (10 wt %, 150 mg). The reaction mixture was flushed with hydrogen and stirred under hydrogen at room temperature for 1.5 h. The reaction mixture was filtered through Celite and concentrated to give 752 mg (97%) of methyl (S)-1-((S)-2-amino-3-(4-(5-(4-(heptyloxy)phenyl)pyrimidin-2-yl)phenyl)propanoyl) pyrrolidine-3-carboxylate INT-39. LCMS-ESI (m/z) calculated for $C_{32}H_{40}N_4O_4$: 544.3. found 545.3 [M+H]$^+$, $t_R$=3.61 min (Method 16).

(S)-2-(((benzyloxy)carbonyl)amino)-3-(4-(5-bromopyrimidin-2-yl)phenyl)propanoic acid

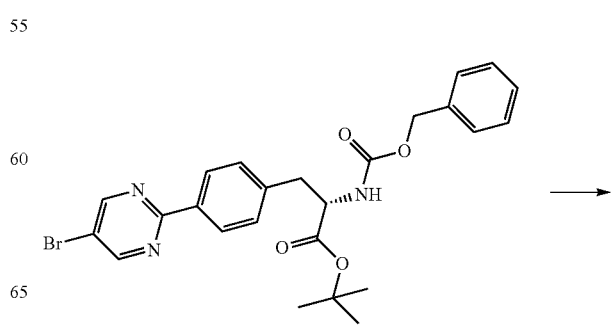

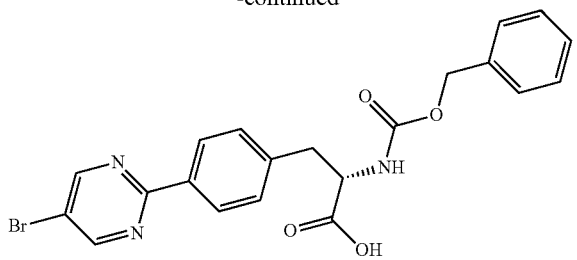

Prepared using General Procedure 8: To a stirred solution of (S)-tert-butyl 2-(((benzyloxy)carbonyl)amino)-3-(4-(5-bromopyrimidin-2-yl)phenyl)propanoate (1.08 g, 2.11 mmol) INT-7 in DCM (10 mL) was added TFA (5 mL). After 16 h the mixture was diluted with toluene (10 mL) and evaporated. Further toluene (2×10 mL) was evaporated from the residue to afford 962 mg (100%) of (S)-2-(((benzyloxy)carbonyl)amino)-3-(4-(5-bromopyrimidin-2-yl)phenyl)propanoic acid as an off-white solid. LCMS-ESI (m/z) calculated for $C_{21}H_{18}BrN_3O_4$: 455.1. found 456.0 [M+H]$^+$, $t_R$=5.81 min (Method 10).

Tert-butyl ((S)-2-(((benzyloxy)carbonyl)amino)-3-(4-(5-bromopyrimidin-2-yl)phenyl)propanoyl)-D-alaninate (INT-42)

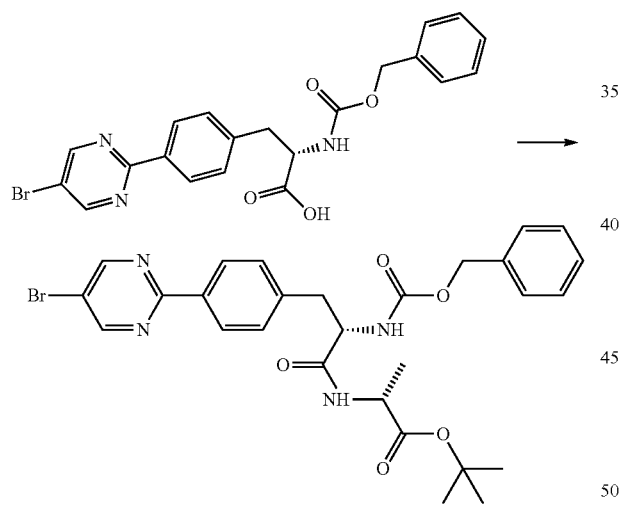

Prepared using General Procedure 7: To a stirred solution of (S)-2-(((benzyloxy)carbonyl)amino)-3-(4-(5-bromopyrimidin-2-yl)phenyl)propanoic acid (962 mg, 2.11 mmol) and (R)-tert-butyl 2-aminopropanoate hydrochloride (383 mg, 2.11 mmol) in DMF (20 mL) was added DIEA (1.2 mL, 6.32 mmol). The mixture was cooled to 0° C. and HATU (802 mg, 2.11 mmol) was added portionwise. The cooling bath was removed and the mixture was allowed to warm to room temperature. After 1 h the mixture was poured onto citric acid (100 mL of a 0.1 M aqueous solution) and iso-hexanes (20 mL) and the resulting precipitate collected by filtration, washing successively with water (2×10 mL), ACN (3 mL) and iso-hexanes (2×5 mL) to afford 1.1 g (89%) of tert-butyl ((S)-2-(((benzyloxy)carbonyl)amino)-3-(4-(5-bromopyrimidin-2-yl)phenyl)propanoyl)-D-alaninate INT-42 as a white solid. LCMS-ESI (m/z) calculated for $C_{28}H_{31}BrN_4O_5$: 582.2. found 605.2 [M+Na]$^+$, $t_R$=7.94 min (Method 10).

2-amino-2-(2, 5-dimethyloxazol-4-yl)acetic acid hydrochloride

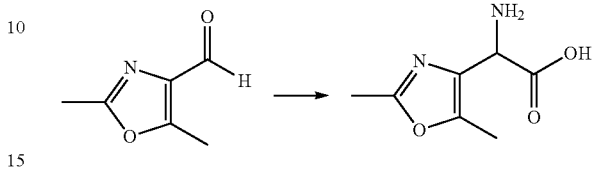

To a stirred solution of 2,5-dimethyloxazole-4-carbaldehyde (272 mg, 2.17 mmol) and ammonium carbonate (564 mg, 5.87 mmol) in EtOH (6 mL) and water (2 mL) at 50° C. was added dropwise over 20 minutes a solution of potassium cyanide (177 mg, 2.72 mmol) in water (3.8 mL). The solution was stirred at 60° C. for 16 h. The EtOH was distilled off at 80° C. and HCl added (0.2 mL of a 37% aqueous solution). The mixture was allowed to cool to room temperature and the precipitate collected by filtration, washing successively with water (5 mL) and iso-hexanes (2×5 mL). This was dissolved in MeOH (14 mL) with stirring and treated with potassium hydroxide (5.2 mL of a 2.5 M aqueous solution, 13.1 mmol) and the solution stirred at 60° C. for 100 h. The mixture was allowed to cool and acidified with HCl. Solvents were evaporated and the residue treated with MeOH (10 mL). The mixture was filtered and the filtrate evaporated to afford 205 mg (55%) of 2-amino-2-(2,5-dimethyloxazol-4-yl)acetic acid hydrochloride as an orange oil. LCMS-ESI (m/z) calculated for $C_7H_{10}N_2O_3$: 170.1. found 171.1 [M+H]$^+$, $t_R$=0.23 min (Method 11). $^1$H NMR (400 MHz, DMSO) δ 8.71 (br s, 3H), 5.13 (s, 1H), 2.38 (s, 3H), 2.34 (s, 3H).

Methyl 2-amino-2-(2,5-dimethyloxazol-4-yl)acetate hydrochloride (INT-43)

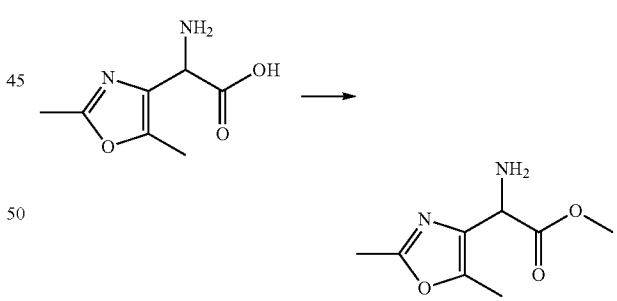

Prepared using General Procedure 22: To a stirred solution of 2-amino-2-(2,5-dimethyloxazol-4-yl)acetic acid hydrochloride (150 mg, 0.726 mmol) in MeOH (5 mL) was added HCl (1.2 mL of a 37% aqueous solution, 14.5 mmol) and the mixture heated under reflux for 4 h. The mixture was allowed to cool and solvents evaporated. The residue was treated with MeOH (12 mL) and filtered. The filtrate was evaporated to afford 135 mg (84%) of methyl 2-amino-2-(2,5-dimethyloxazol-4-yl)acetate hydrochloride INT-43. LCMS-ESI (m/z) calculated for $C_8H_{12}N_2O_3$: 184.1. found 185.1 [M+H]$^+$, $t_R$=0.23 min (Method 11). $^1$H NMR (400 MHz, DMSO) δ 8.94 (br s, 3H), 5.35 (s, 1H), 3.73 (s, 3H), 2.38 (s, 3H), 2.36 (s, 3H).

4-Benzyl 1-(tert-butyl) ((S)-2-(5-(tert-butyl)thiophene-2-carboxamido)-3-(4-(5-(4-(heptyloxy)phenyl)pyrimidin-2-yl)phenyl)propanoyl)phenyl)propanoyl)-L-aspartate (INT-47)

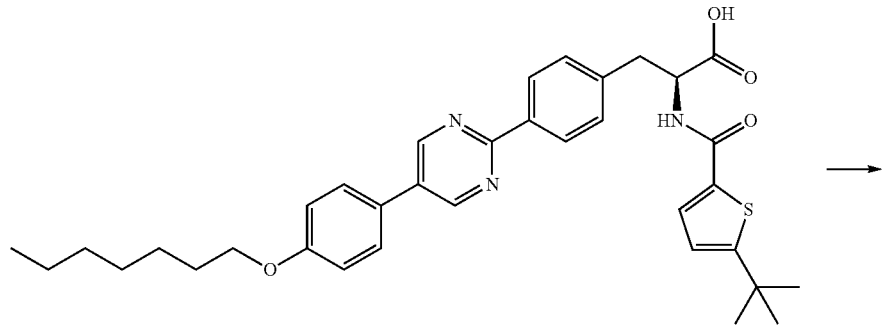

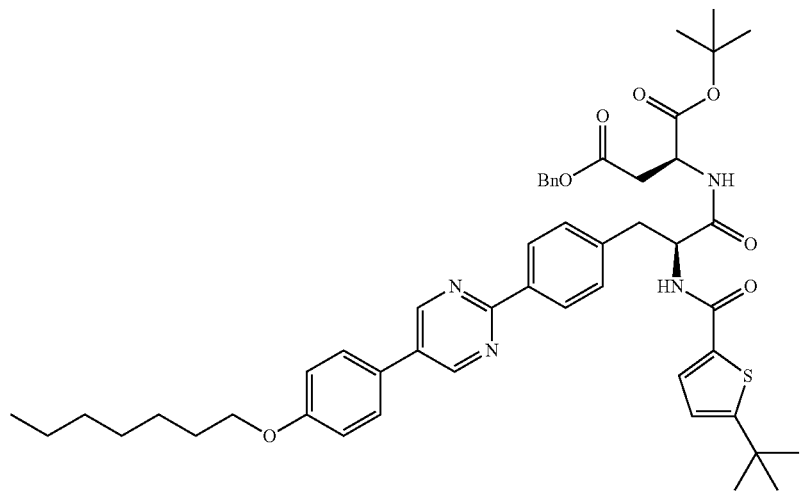

Prepared using General Procedure 7: To a stirred solution of (S)-2-(5-(tert-butyl)thiophene-2-carboxamido)-3-(4-(5-(4-(heptyloxy)phenyl)pyrimidin-2-yl)phenyl)propanoic acid Compound 192 (600 mg, 1.00 mmol), L-aspartic acid β-benzyl ester α-tert-butyl ester hydrochloride (398.4 mg, 1.20 mmol) in DMF (6 mL) was added DIEA (554 µl, 3.00 mmol). The mixture was cooled to 0° C. and HATU (418 mg, 1.10 mmol) in DMF (4 mL) was added over 5 mins. The mixture was stirred at 0° C. for 0.5 h. The reaction mixture was added to water (250 mL) and the precipitate was filtered. The precipitate was dissolved in DCM (20 mL), dried over MgSO$_4$, and concentrated. The crude product was purified by chromatography 0-100% EA in hexane to afford 789 mg (92%) of 4-benzyl 1-(tert-butyl) ((S)-2-(5-(tert-butyl)thiophene-2-carboxamido)-3-(4-(5-(4-(heptyloxy)phenyl)pyrimidin-2-yl)phenyl)propanoyl)-L-aspartate INT-47 as a white solid. LCMS-ESI (m/z) calculated for $C_{50}H_{60}N_4O_7S$: 860.4. found 861.4 [M+H]$^+$, $t_R$=6.028 min (Method 16).

(S)-4-(tert-butoxy)-3-((S)-2-(5-(tert-butyl)thiophene-2-carboxamido)-3-(4-(5-(4-(heptyloxy)phenyl)pyrimidin-2-yl)phenyl)propanamido)-4-oxobutanoic acid (INT-44)

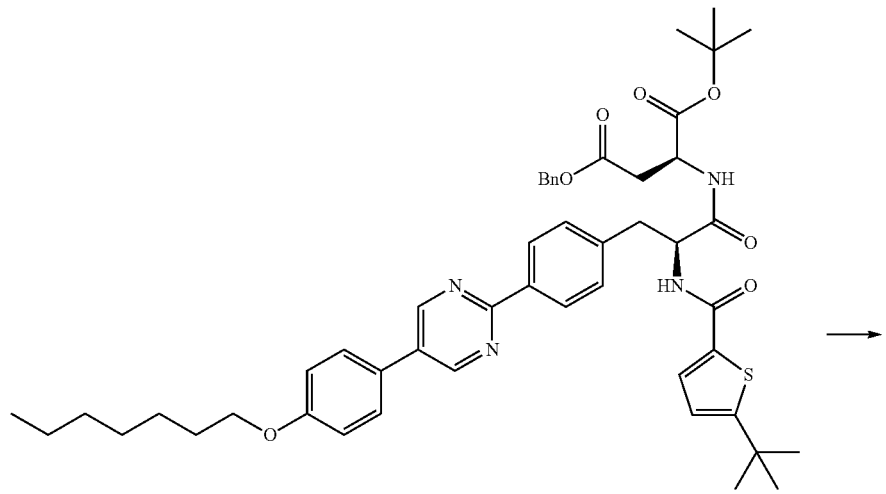

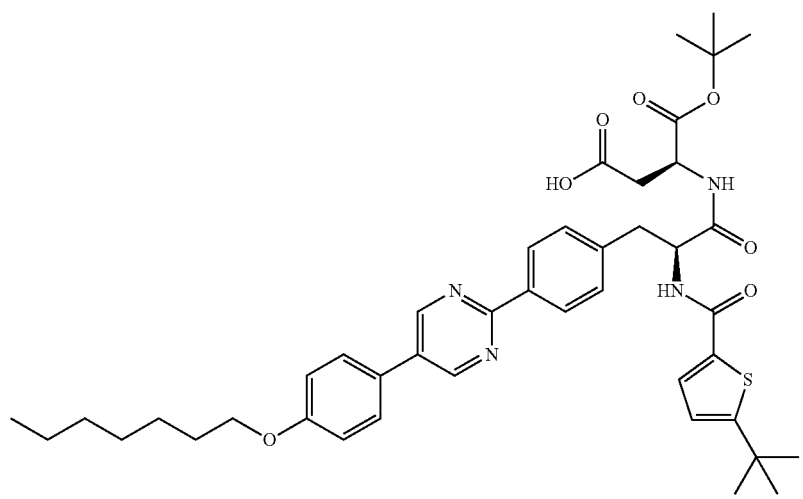

Prepared using General Procedures 18: To 4-benzyl 1-(tert-butyl) ((S)-2-(5-(tert-butyl)thiophene-2-carboxamido)-3-(4-(5-(4-(heptyloxy)phenyl)pyrimidin-2-yl)phenyl)propanoyl)-L-aspartate INT-47 (345 mg, 0.4 mmol) in THF (5 mL) was added 10% Pd/C (60 mg). The reaction vessel was flushed with hydrogen gas and the reaction was stirred vigorously under hydrogen overnight at room temperature. The reaction mixture was filtered to remove the catalyst, the solvent was removed, and the crude product was purified by chromatography 0-100% EA in hexane to afford 228 mg (66%) of (S)-4-(tert-butoxy)-3-((S)-2-(5-(tert-butyl)thiophene-2-carboxamido)-3-(4-(5-(4-(heptyloxy)phenyl)pyrimidin-2-yl)phenyl)propanamido)-4-oxobutanoic acid INT-44 as a white solid. LCMS-ESI (m/z) calculated for $C_{43}H_{54}N_4O_7S$: 770.4. found 771.3 [M+H]+, $t_R$=4.21 min (Method 16).

Tert-butyl ((S)-2-(4-(tert-butyl)benzamido)-3-(4-(5-(4-hydroxyphenyl)pyrimidin-2-yl)phenyl)propanoyl)-D-alaninate (INT-45)

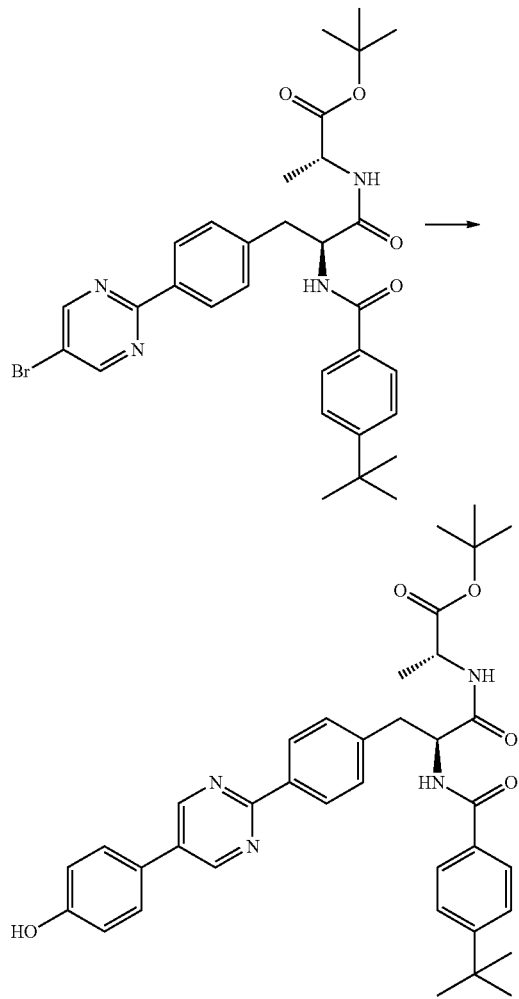

To a 10 ml flask were added (4-hydroxyphenyl)boronic acid (317.23 mg, 2.30 mmol), sodium carbonate decahydrate (138.0 mg, 2.3 mmol), tert-butyl ((S)-3-(4-(5-bromopyrimidin-2-yl)phenyl)-2-(4-(tert-butyl)benzamido)propanoyl)-D-alaninate INT-32 (700.0 mg, 1.15 mmol), Pd(dppf)Cl$_2$ (87.8 mg, 0.12 mmol), THF (10 mL), CH$_3$CN (10 ml) and water (5 mL). The solution was degassed using N$_2$ bubbling for 10 min. The reaction mixture was heated to 80° C. for 2 hours. The mixture was extracted with DCM (3×20 mL) and aqueous NaHCO$_3$ (3×10 mL). The combined organics were dried over MgSO$_4$ and evaporated. The final compound was purified by column chromatography (40% DCM in hexane) to afford 595.0 mg (83%) of tert-butyl ((S)-2-(4-(tert-butyl)benzamido)-3-(4-(5-(4-hydroxyphenyl)pyrimidin-2-yl)phenyl)propanoyl)-D-alaninate INT-45 as solid. LCMS-ESI (m/z) calculated for C$_{37}$H$_{42}$N$_4$O$_5$: 622.3. found 623.3 [M+H]$^+$, t$_R$=3.635 min. (Method 16). $^1$H NMR (400 MHz, DMSO) δ 9.79 (s, 1H), 9.11 (s, 2H), 8.50 (d, J=8.7 Hz, 1H), 8.41 (d, J=7.2 Hz, 1H), 8.30 (d, J=8.2 Hz, 2H), 7.75 (d, J=8.4 Hz, 2H), 7.68 (d, J=8.6 Hz, 2H), 7.51 (d, J=8.2 Hz, 2H), 7.46 (d, J=8.4 Hz, 2H), 6.92 (d, J=8.6 Hz, 2H), 4.85 (td, J=9.9, 4.6 Hz, 1H), 4.17 (p, J=7.1 Hz, 1H), 3.24-3.00 (m, 2H), 1.46-1.34 (m, 9H), 1.32-1.19 (m, 12H).

Tert-butyl N$^2$-(((9H-fluoren-9-yl)methoxy)carbonyl)-N$^4$-methyl-D-asparaginate

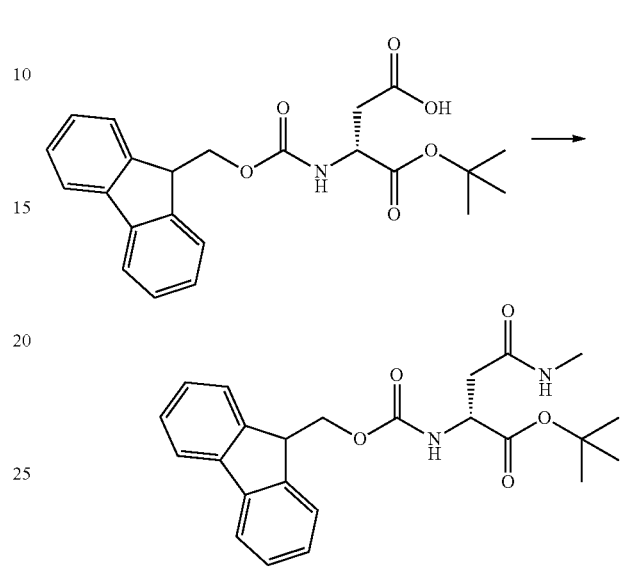

Prepared using General Procedures 7: To (R)-3-((((9H-fluoren-9-yl)methoxy)carbonyl)amino)-4-(tert-butoxy)-4-oxobutanoic acid (205.7 mg, 0.5 mmol) in DMF (5 mL) at 0° C. was added HATU (380 mg, 1.0 mmol). After stirring for 3 min, DIEA (277 µL, 1.5 mmol) and methylamine (40 wt % in water, 116 µL, 1.5 mmol) were added. The reaction mixture was stirred at room temperature for 1 h. The reaction mixture was added to water (75 mL) and the precipitate was filtered and dried to give 201 mg (95%) of tert-butyl N$^2$-(((9H-fluoren-9-yl)methoxy)carbonyl)-N$^4$-methyl-D-asparaginate as a colorless semi-solid. LCMS-ESI (m/z) calculated for C$_{24}$H$_{28}$N$_2$O$_5$: 424.2. found 425.2 [M+H]$^+$, t$_R$=3.22 min (Method 16).

Tert-butyl N$^4$-methyl-D-asparaginate (INT-46)

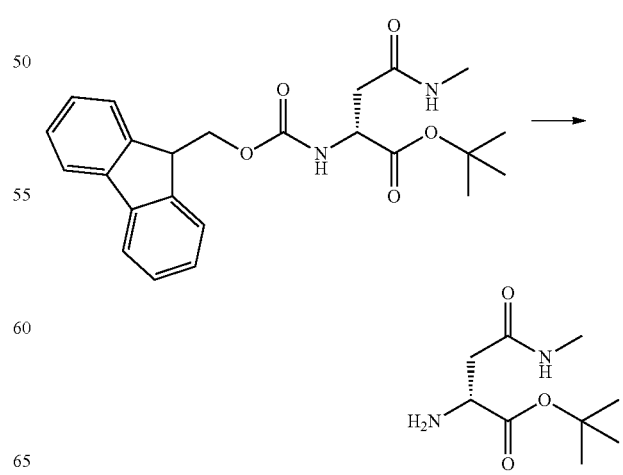

To tert-butyl N²-(((9H-fluoren-9-yl)methoxy)carbonyl)-N⁴-methyl-D-asparaginate (200 mg, 0.47 mmol) in DCM (0.93 mL) was added piperidine (233 μL, 2.35 mmol). The reaction mixture was stirred at room temperature for 1 h. All solvent was removed to give 215 mg of tert-butyl N⁴-methyl-D-asparaginate as a mixture with 1-((9H-fluoren-9-yl)methyl)piperidine. The mixture was used without purification in the next reaction. LCMS-ESI (m/z) calculated for $C_9H_{18}N_2O_3$: 202.1. found 203.1 [M+H]⁺, $t_R$=0.534 min (Method 16).

Tert-butyl (S)-1-(2-(5-(tert-butyl)thiophene-2-carboxamido)-3-(4-(5-(4-hydroxyphenyl)-pyrimidin-2-yl)phenyl)propanoyl)azetidine-3-carboxylate (INT-48)

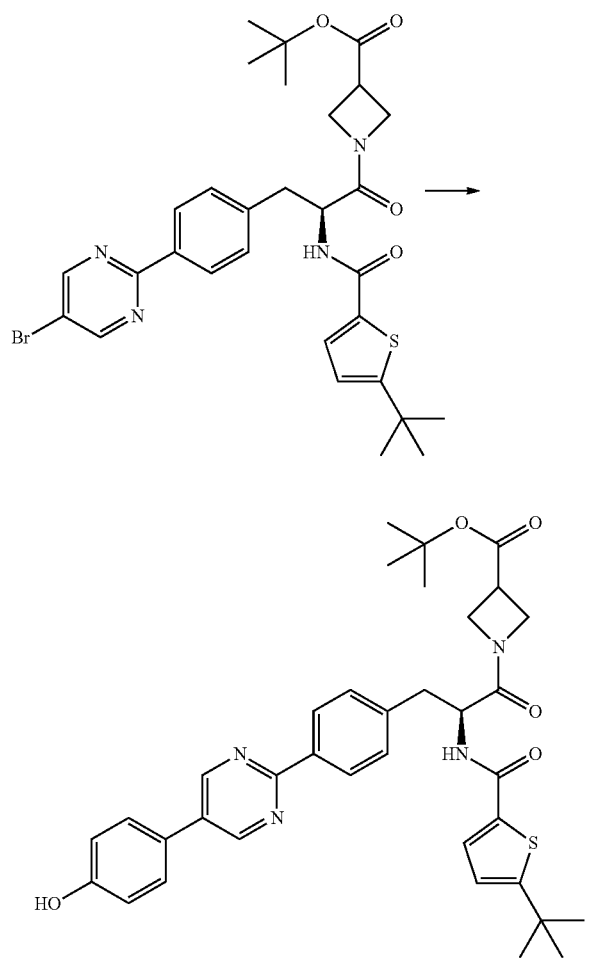

Prepared using General Procedure 10. Into a solution of INT-38 (60 mg, 0.1 mmol) in dioxane (2 mL) and H₂O (1 mL) were added sodium carbonate, decahydrate (60 mg, 0.2 mmol), 4-hydroxyphenylboronic acid (17 mg, 0.1 mmol) and PdCl₂(dppf) (7 mg, 0.01 mmol). The mixture was heated at 80° C. for 2.5 h then cooled to room temp, diluted with H₂O (100 mL) and extracted into EA (2×100 mL). The resulting organic layers were combined, dried (Na₂SO₄) and concentrated to yield 75 mg (117%) of crude tert-butyl (S)-1-(2-(5-(tert-butyl)thiophene-2-carboxamido)-3-(4-(5-(4-hydroxyphenyl)pyrimidin-2-yl)phenyl)propanoyl)azetidine-3-carboxylate (INT-48) which was used without further purification. LCMS-ESI (m/z) calculated for $C_{36}H_{40}N_4O_5S$: 640.8. found 341.3[M+H]⁺, $t_R$=3.42 min. (Method 15).

Compound 492 was prepared from (S)-2-(((benzyloxy)carbonyl)amino)-3-(4-(5-(4-(heptyloxy)phenyl)pyrimidin-2-yl)phenyl)propanoic acid INT-22 and (S)-methyl 2-amino-6-((tert-butoxycarbonyl)amino)hexanoate hydrochloride using General Procedures 7, 18, 7, 4 and 8 sequentially.

Compounds 493, 494 and 500 were prepared from (S)-1-((S)-2-(5-(tert-butyl)thiophene-2-carboxamido)-3-(4-(5-(4-(heptyloxy)phenyl) pyrimidin-2-yl) phenyl)propanoyl) pyrrolidine-2-carboxylic acid Compound 328 using General Procedures 7 and 4 sequentially.

Compounds 495 and 496 were prepared from(S)-1-((S)-2-(5-(tert-butyl)thiophene-2-carboxamido)-3-(4-(5-(4-(heptyloxy)phenyl) pyrimidin-2-yl) phenyl)propanoyl)pyrrolidine-2-carboxylic acid Compound 328 using General Procedure 7.

Compound 497 was prepared from(S)-1-((S)-2-(5-(tert-butyl)thiophene-2-carboxamido)-3-(4-(5-(4-(heptyloxy) phenyl) pyrimidin-2-yl) phenyl)propanoyl)-pyrrolidine-2-carboxylic acid Compound 328 using General Procedures 7 and 8 sequentially.

Compounds 498 and 499 were prepared from (S)-2-(((benzyloxy)carbonyl)amino)-3-(4-(5-(4-(heptyloxy)phenyl)pyrimidin-2-yl)phenyl)propanoic acid INT-22 using General Procedures 7, 18, 7 and 8 sequentially.

Compounds 501, 592-602, 604, 607-621, 625-629, 631, 633, 634, 636-641, 644, 655, 668 and 669 were prepared from Compound 192 using General Procedures 7 then 4.

Compound 502 was prepared from INT-30 using General Procedure 8.

Compounds 503-507, 579, and 580 were prepared from Compound 502 using General Procedures 7 then 18.

Compounds 508-511 were prepared from INT-31 using General Procedures 7 then 8.

Compounds 512-523 were prepared from INT-44 using General Procedures 7 then 8.

Compound 524 was prepared from INT-47 using General Procedure 8.

Compounds 525-533 were prepared from Compound 524 using General Procedures 7 then 18.

Compound 534 was prepared from Compound 524 using General Procedures 7, 18, then 8.

Compound 535 was prepared from Compound 192 using General Procedures 3 then 8.

Compound 536 was prepared from (S)-2-(4-(tert-butyl)benzamido)-3-(4-(5-(4-(heptyloxy)phenyl)pyrimidin-2-yl) phenyl)propanoic acid Compound 85 and 2-amino-2-(2,5-dimethyloxazol-4-yl)acetic acid hydrochloride INT-43 using General Procedures 7 and 4 sequentially.

Compounds 537 and 554 were prepared from Compound 85 using General Procedures 7 then 8.

Compounds 538-553, 555-578, 583-588, 622-624, 632 and 660-662 were prepared from Compound 85 using General Procedures 7 then 4.

Compound 581 was prepared from Compound 85 using General Procedures 7, 4 then 18.

Compound 582 was prepared from Compound 85 using General Procedures 7, 8 then 4.

277
Tert-butyl (R)-3-((((9H-fluoren-9-yl)methoxy)carbonyl)amino)-4-(methylamino)-4-oxobutanoate

278
Tert-butyl (R)-3-amino-4-(methylamino)-4-oxobutanoate

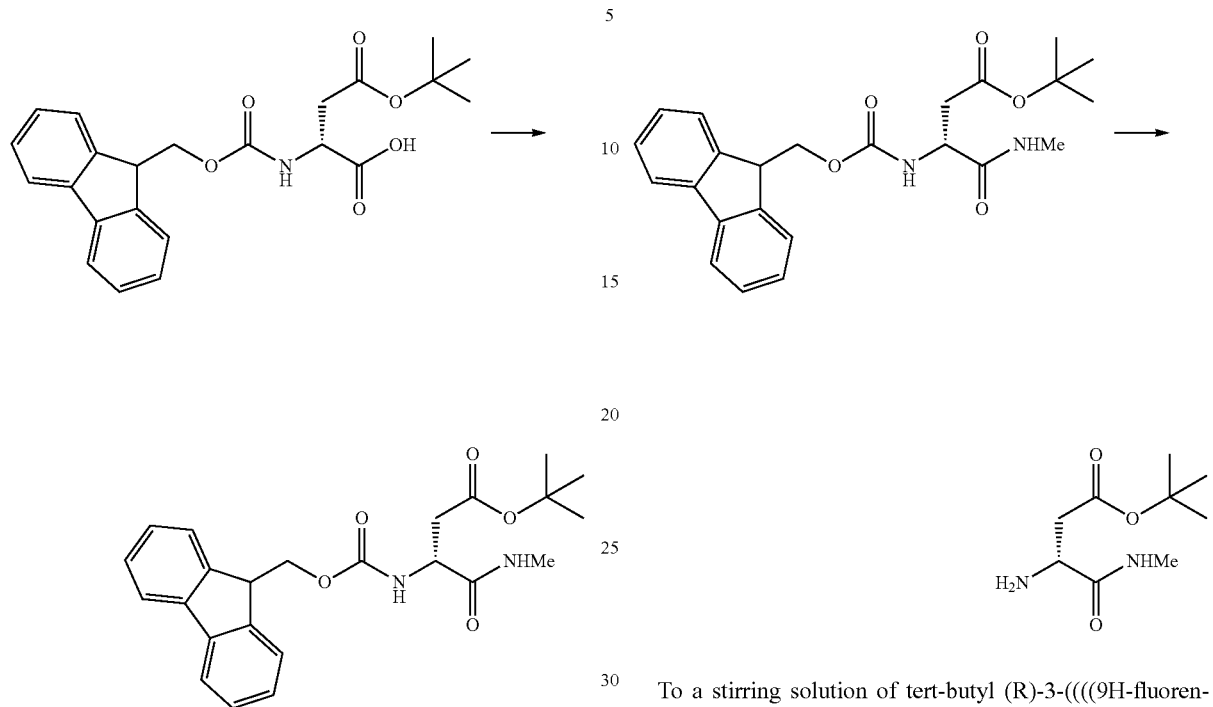

Prepared using General Procedure 7. To a stirring solution of (R)-2-((((9H-fluoren-9-yl)methoxy)carbonyl)amino)-4-(tert-butoxy)-4-oxobutanoic acid (308 mg, 0.75 mmol), methylamine (40 wt % in water, 174 µL, 2.25 mmol), and DIEA (415 µl, 2.25 mmol) in DMF (7.5 mL) cooled to 0° C. was added HATU (569 mg, 1.5 mmol). The reaction mixture was allowed to warm slowly and stirring continued for 18 h. The reaction mixture was poured onto ice-water and the solid was filtered. The solid was dissolved in DCM (10 mL), dried over $MgSO_4$ and evaporated. The crude product was purified by column chromatography to afford 226 mg (71%) of tert-butyl (R)-3-((((9H-fluoren-9-yl)methoxy)carbonyl)amino)-4-(methylamino)-4-oxobutanoate. LCMS-ESI (m/z) calculated for $C_{24}H_{28}N_2O_5$: 424.2. found 447.1 $[M+Na]^+$, $t_R$=3.12 min. (Method 16).

To a stirring solution of tert-butyl (R)-3-((((9H-fluoren-9-yl)methoxy)carbonyl)amino)-4-(methylamino)-4-oxobutanoate (226 mg, 0.53 mmol), in DCM (1.05 mL) was added piperidine (263 µL, 2.7 mmol). The reaction mixture was stirred for 1 h at room temperature. The solvent was evaporated to afford 250 mg (100%) of tert-butyl (R)-3-amino-4-(methylamino)-4-oxobutanoate as a mixture with 1-((9H-fluoren-9-yl)methyl)piperidine. The mixture was used without purification in the next reaction. LCMS-ESI (m/z) calculated for $C_9H_{18}N_2O_3$: 202.1. found 225.1 $[M+Na]^+$, $t_R$=0.50 min. (Method 15).

Compound 589 was prepared from Compound 85 and tert-butyl (R)-3-amino-4-(methylamino)-4-oxobutanoate using General Procedures 7 then 8.

Tert-butyl (S)-1-(2-(((benzyloxy)carbonyl)amino)-3-(4-(5-(4-(heptyloxy)phenyl)pyrimidin-2-yl)phenyl)propanoyl)azetidine-3-carboxylate

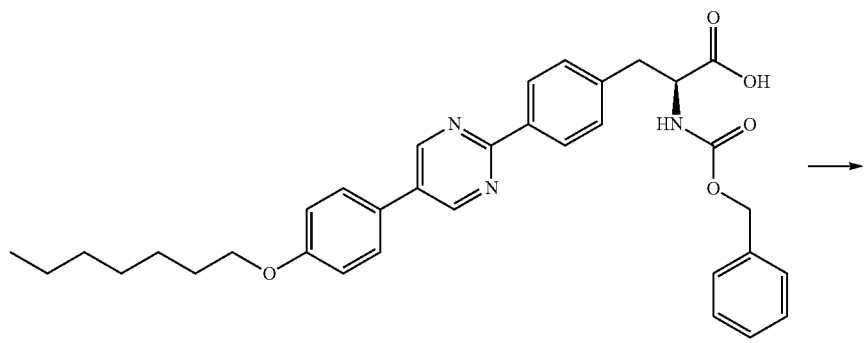

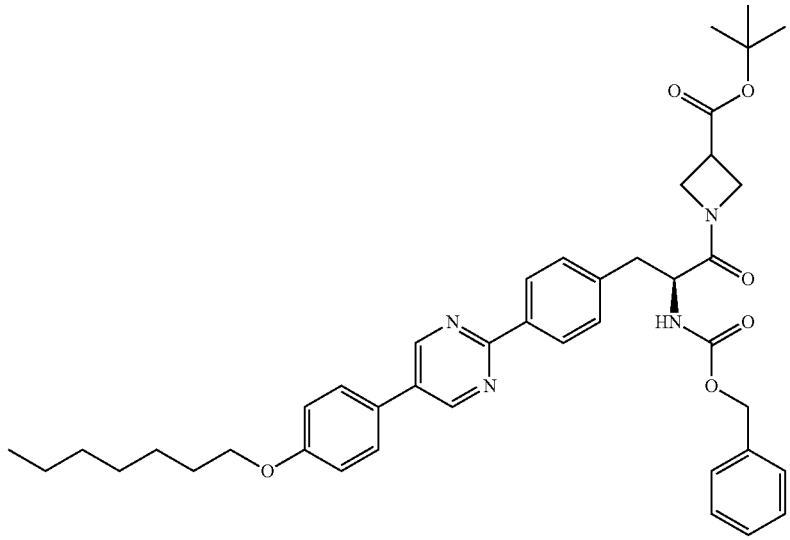

Prepared using General Procedure 7: A stirred solution of (S)-2-(((benzyloxy)carbonyl)amino)-3-(4-(5-(4-(heptyloxy)phenyl)pyrimidin-2-yl)phenyl) propanoic acid INT-22 (1 g, 1.76 mmol), tert-butyl azetidine-3-carboxylate (0.554 g, 1.76 mmol) and DIEA (1.30 mL, 7.05 mmol) in DMF (20 mL) at 0° C. was treated with HATU (0.703 g, 1.85 mmol), added portionwise. After 10 min, the cooling bath was removed. After a further 1 h the mixture was poured onto 0.2 M HCl (100 mL) and extracted with EA (3×30 mL). The combined organic extracts were washed with brine (20 mL), dried over MgSO$_4$ and evaporated. Column chromatography (EA/DCM/iso-hexanes) gave 708 mg (58%) of tert-butyl (S)-1-(2-(((benzyloxy)carbonyl)amino)-3-(4-(5-(4-(heptyloxy)phenyl)pyrimidin-2-yl)phenyl)propanoyl)azetidine-3-carboxylate as an off-white solid. LCMS-ESI (m/z) calculated for $C_{42}H_{50}N_4O_6$: 706.4. found 707.1 [M+H]$^+$, $t_R$=3.60 min (Method 6).

Tert-butyl (S)-1-(2-(4-(tert-butyl)benzamido)-3-(4-(5-(4-(heptyloxy)phenyl)pyrimidin-2-yl)phenyl)propanoyl)azetidine-3-carboxylate

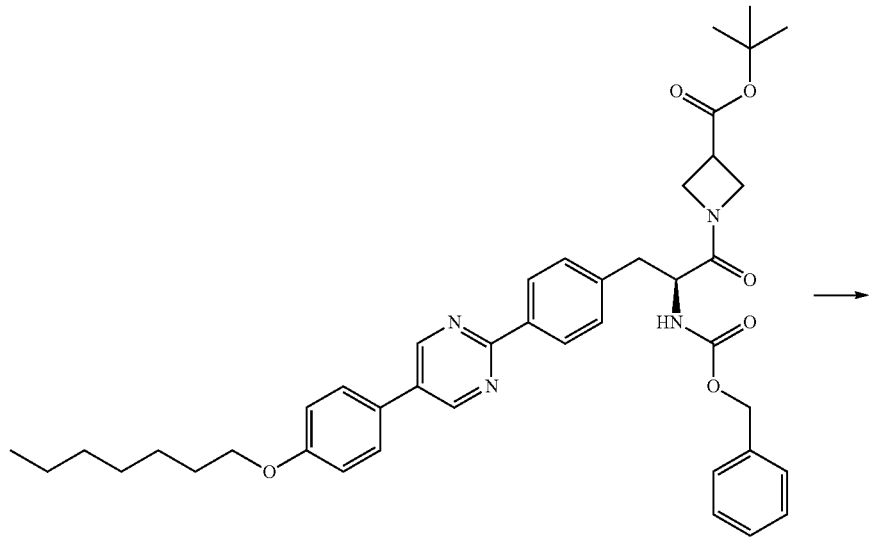

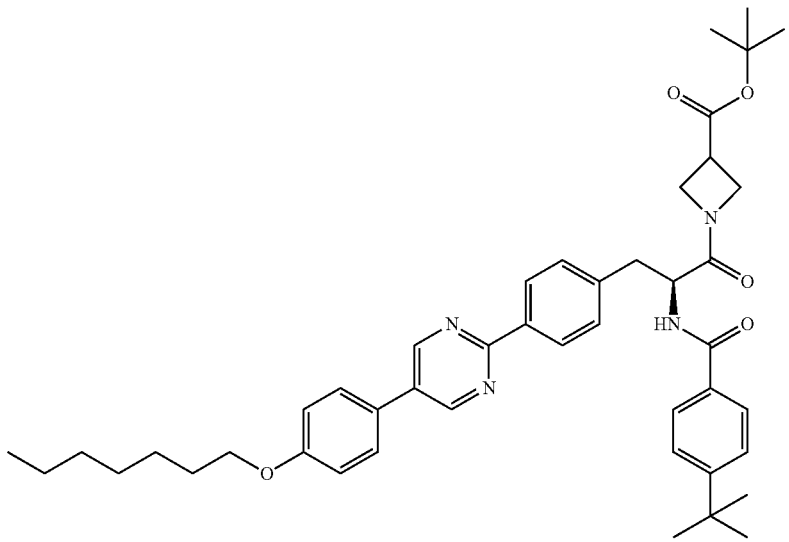

Prepared using General Procedures 18 and 7: To a stirred solution of (S)-tert-butyl 1-(2-(((benzyloxy)carbonyl)amino)-3-(4-(5-(4-(heptyloxy)phenyl)pyrimidin-2-yl)phenyl)propanoyl)azetidine-3-carboxylate (708 mg, 1.00 mmol) and triethylsilane (352 μL, 2.20 mmol) in DCM (10 mL) was added a solution of diacetoxypalladium (22.5 mg, 0.100 mmol) and triethylamine (43 μL, 0.30 mmol) in DCM (2 mL). After 16 h, the mixture was filtered through Celite and solvents evaporated. The residue was taken up in DMF (6 mL) and the resulting solution added to a stirred solution of active ester prepared by the action of HATU (399 mg, 1.05 mmol) and DIEA (0.55 mL, 3.00 mmol) on 4-(tert-butyl)benzoic acid (196 mg, 1.10 mmol) in DMF (5 mL) over 10 min. After 1 h, the mixture was poured onto 0.5 M HCl (100 mL) and extracted with EA (3×50 mL). The combined organic extracts were washed with brine (20 mL), dried over MgSO$_4$ and evaporated. Column chromatography (EA/DCM/iso-hexanes) gave 583 mg (80%) of tert-butyl (S)-1-(2-(4-(tert-butyl)benzamido)-3-(4-(5-(4-(heptyloxy)phenyl)pyrimidin-2-yl)phenyl)propanoyl)azetidine-3-carboxylate. LCMS-ESI (m/z) calculated for $C_{45}H_{56}N_4O_5$: 732.4; no m/z observed, $t_R$=3.99 min (Method 11).

(S)-1-(2-(4-(tert-butyl)benzamido)-3-(4-(5-(4-(heptyloxy)phenyl)pyrimidin-2-yl)phenyl)propanoyl)azetidine-3-carboxylic acid (Compound 590)

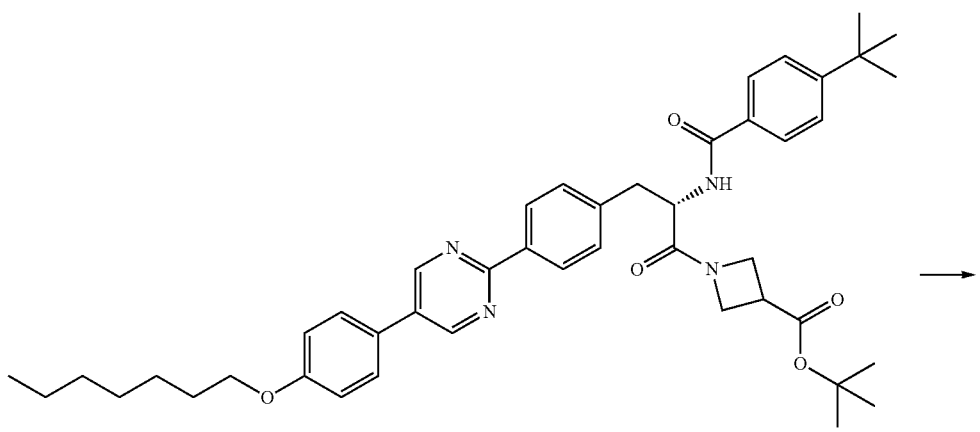

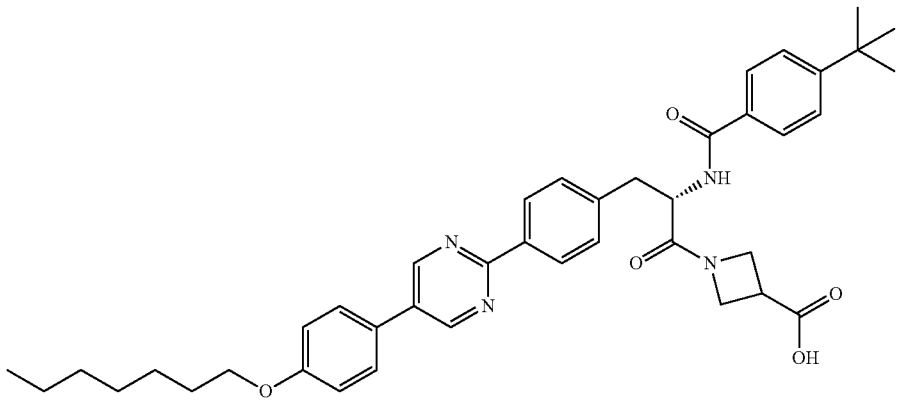

Prepared using General Procedure 8: To a stirred solution of (S)-tert-butyl 1-(2-(4-(tert-butyl)benzamido)-3-(4-(5-(4-(heptyloxy)phenyl)pyrimidin-2-yl)phenyl)propanoyl)azetidine-3-carboxylate (580 mg, 0.791 mmol) in DCM (6 mL) was added TFA (2 mL). After 3 h, the mixture was diluted with toluene (20 mL) and the solvents evaporated. Column chromatography (acetic acid/EA/DCM/iso-hexanes) gave moderately pure product. This was further purified by re-slurry from DCM/ACN then iso-propyl acetate. The resulting solid was again purified by column chromatography (acetic acid/EA/DCM/iso-hexanes) then reslurried from diethyl ether to afford 212 mg (40%) of (S)-1-(2-(4-(tert-butyl)benzamido)-3-(4-(5-(4-(heptyloxy)phenyl)pyrimidin-2-yl)phenyl)-propanoyl)azetidine-3-carboxylic acid Compound 590. LCMS-ESI (m/z) calculated for $C_{41}H_{48}N_4O_5$; 676.4; no m/z observed, $t_R$=10.23 min (Method 10). The chiral purity was >95% e.e (chiral Method). $^1$H NMR (400 MHz, DMSO-d6) δ 12.80 (s, 1H), 9.16 (d, J=1.5 Hz, 2H), 8.75 (dd, J=8.1, 3.7 Hz, 1H), 8.36-8.31 (m, 2H), 7.85-7.75 (m, 4H), 7.49-7.46 (m, 4H), 7.11-7.05 (m, 2H), 4.74-4.68 (m, 1H), 4.45 (t, J=8 Hz, 0.5H), 4.33-4.30 (m, 0.5H), 4.24-4.16 (m, 1H), 4.06-4.00 (m, 3H), 3.47-3.40 (m, 1H), 3.90 (ddd, J=13.5, 9.7, 6.0 Hz, 1H), 3.18-3.05 (m, 2H), 1.77-1.70 (m, 2H), 1.46-1.24 (m, 17H), 0.89-0.86 (m, 3H).

Compound 591 was prepared from Compound 85 and INT-46 using General Procedures 7 then 8.

Compounds 603, 605, 645-648, 652, 653, 656-659 and 664 were prepared from Compound 192 using General Procedures 7 then 8.

Compound 606 was prepared from Compound 192 using General Procedures 7, 4 then 8.

Compound 630 was prepared from Compound 192 and tert-butyl (R)-3-amino-4-(methylamino)-4-oxobutanoate using General Procedures 7 then 8.

(S)-methyl 1-(2-(((benzyloxy)carbonyl)amino)-3-(4-(5-(4-(heptyloxy)phenyl)pyrimidin-2-yl)phenyl)propanoyl)azetidine-3-carboxylate

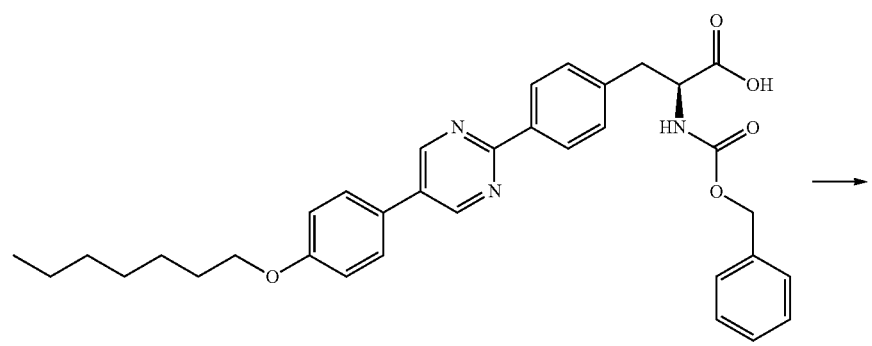

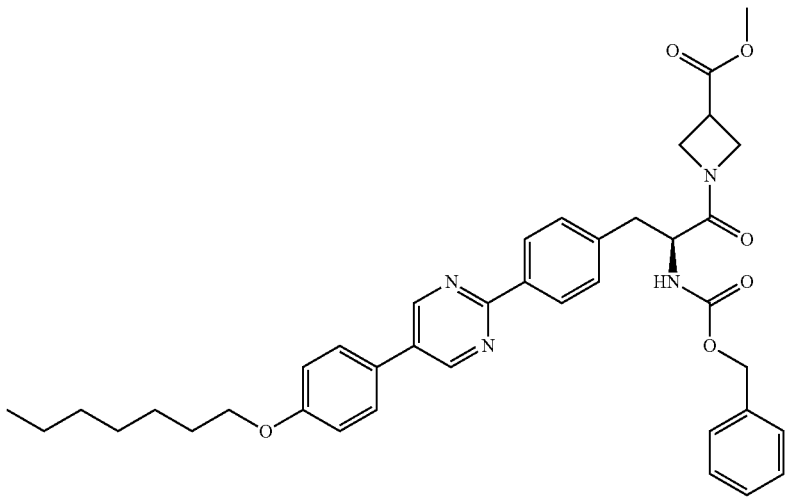

Prepared using General Procedure 7: To a stirred solution of (S)-2-(((benzyloxy)carbonyl)amino)-3-(4-(5-(4-(heptyloxy)phenyl)pyrimidin-2-yl)phenyl)-propanoic acid INT-22 (2.2 g, 3.88 mmol) and methyl azetidine-3-carboxylate, HCl (0.705 g, 4.65 mmol) in DMF (25 mL) was added DIEA (2.7 mL, 15.5 mmol) and the mixture cooled to 0° C. HATU (1.621 g, 4.26 mmol) was added portion-wise over 10 minutes. After 3 h further methyl azetidine-3-carboxylate, HCl (0.223 g, 1.938 mmol) and HATU (0.456 g, 1.938 mmol) were added. The mixture was allowed to stir at room temperature for 100 h. The mixture was treated with citric acid (50 mL of a 0.1 M aqueous solution) and water (20 mL) and extracted with EA (2×100 mL). The combined organic extracts were washed with brine (80 mL), dried over MgSO$_4$ and solvents evaporated. Column chromatography (EA/iso-hexanes) gave 1.45 g (56%) of (S)-methyl 1-(2-(((benzyloxy)carbonyl)amino)-3-(4-(5-(4-(heptyloxy)phenyl)pyrimidin-2-yl)phenyl)propanoyl)azetidine-3-carboxylate as a colourless glass. LCMS-ESI (m/z) calculated for $C_{39}H_{44}N_4O_6$: 664.3. found 665.3 [M+H]$^+$, $t_R$=3.37 min (Method 6).

(S)-methyl 1-(2-amino-3-(4-(5-(4-(heptyloxy)phenyl)pyrimidin-2-yl)phenyl)propanoyl)-azetidine-3-carboxylate

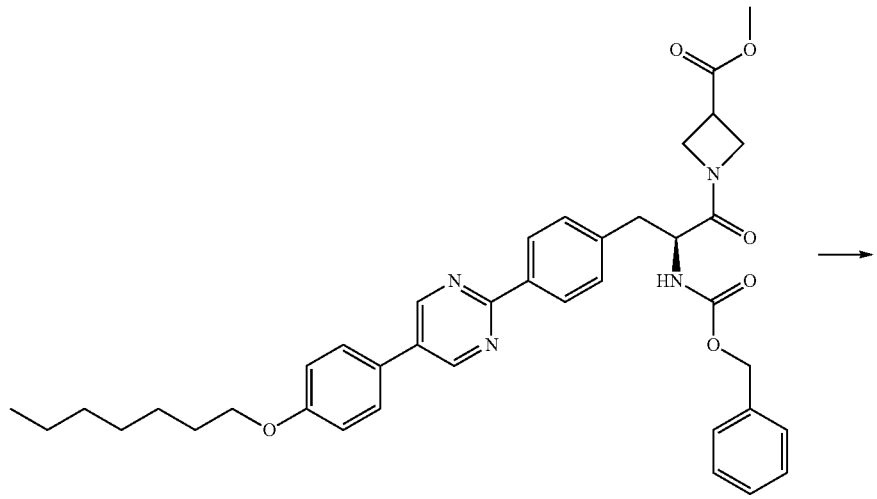

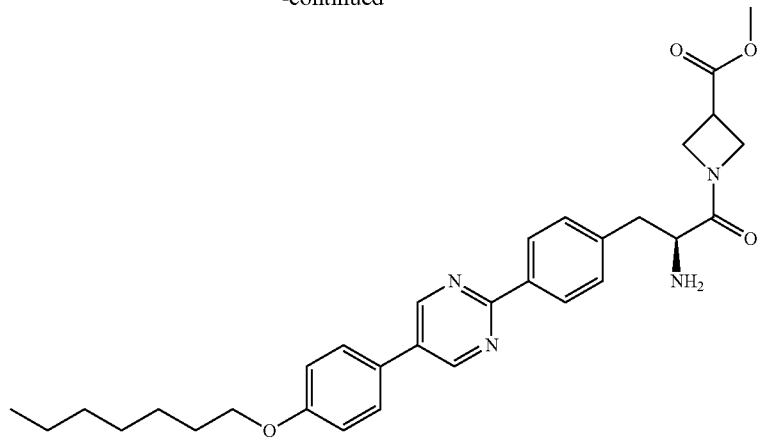

Prepared using General Procedure 18: A solution of (S)-methyl 1-(2-(((benzyloxy)carbonyl)amino)-3-(4-(5-(4-(heptyloxy)phenyl)pyrimidin-2-yl)phenyl)-propanoyl)azetidine-3-carboxylate (1.2 g, 1.81 mmol) in MeOH (150 mL) was passed over a 10% Pd/C CatCart (55×4 mm) at 65° C. in a Thales Nanotechnology H-Cube reactor at 2.1 mL/min. The solvent was evaporated and the residue purified by column chromatography (Ammonia/MeOH/DCM) to afford 604 mg (63%) of (S)-methyl 1-(2-amino-3-(4-(5-(4-(heptyloxy)phenyl)pyrimidin-2-yl)phenyl)propanoyl)azetidine-3-carboxylate. LCMS-ESI (m/z) calculated for $C_{31}H_{38}N_4O_4$: 530.3. found 531.0 $[M+H]^+$, $t_R$=1.60 min (Method 6).

Methyl (S)-1-(2-(5-(tert-butyl)thiophene-2-carboxamido)-3-(4-(5-(4-(heptyloxy)phenyl)-pyrimidin-2-yl)phenyl)propanoyl)azetidine-3-carboxylate

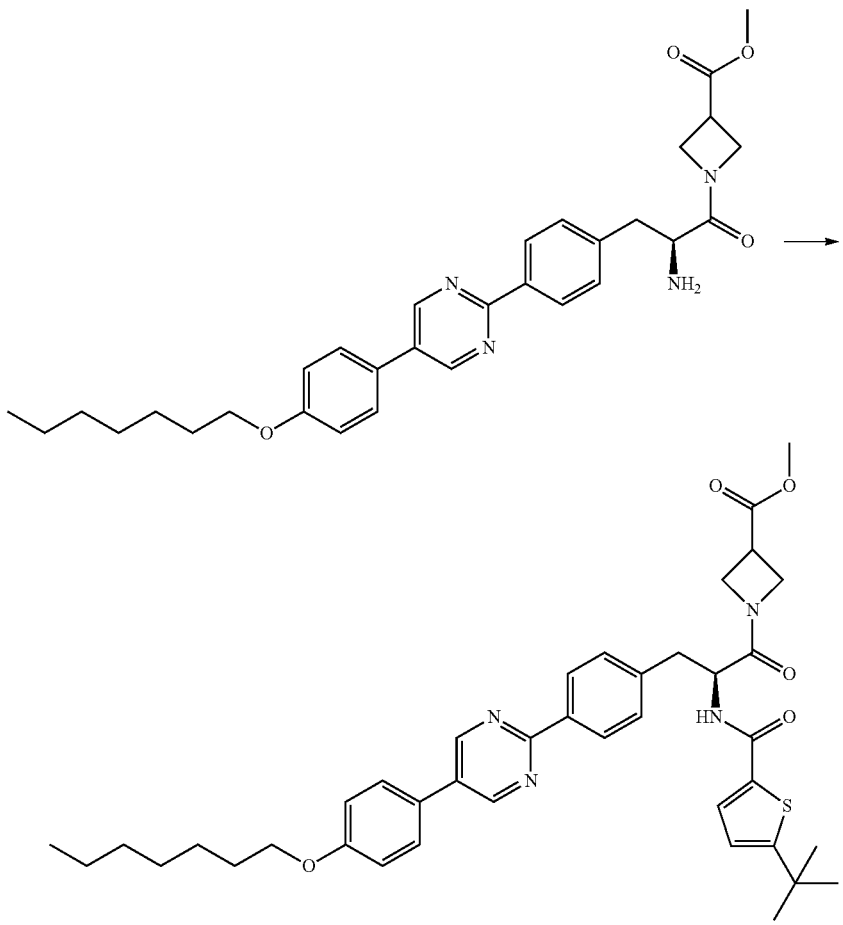

To a stirred solution of (S)-methyl 1-(2-amino-3-(4-(5-(4-(heptyloxy)phenyl)pyrimidin-2-yl)phenyl)propanoyl)azetidine-3-carboxylate (360 mg, 0.678 mmol) and 5-(tert-butyl)thiophene-2-carboxylic acid (125 mg, 0.678 mmol) in DMF (6 mL, 77 mmol) was added DIEA (0.47 mL, 2.71 mmol) and the mixture cooled to 0° C. HATU (284 mg, 0.746 mmol) was added portion-wise and the reaction stirred at room temperature for 1 h. The mixture was poured onto citric acid (70 mL of a 10% w/w aqueous solution) and extracted with EA (2×100 mL). The combined organic extracts were washed with brine (50 mL), dried over MgSO$_4$ and solvents evaporated. Column chromatography (EA/iso-hexanes) gave 389 mg (82%) of (S)-methyl 1-(2-(5-(tert-butyl)thiophene-2-carboxamido)-3-(4-(5-(4-(heptyloxy)phenyl)pyrimidin-2-yl)phenyl)propanoyl)azetidine-3-carboxylate as a pale yellow solid. LCMS-ESI (m/z) calculated for $C_{40}H_{48}N_4O_5S$: 696.3. found 697.0 [M+H]$^+$, $t_R$=3.60 min (Method 6).

(S)-1-(2-(5-(tert-butyl)thiophene-2-carboxamido)-3-(4-(5-(4-(heptyloxy)phenyl)pyrimidin-2-yl)phenyl)propanoyl)azetidine-3-carboxylic acid (Compound 635)

To a stirred solution of (S)-methyl 1-(2-(5-(tert-butyl)thiophene-2-carboxamido)-3-(4-(5-(4-(heptyloxy)phenyl)pyrimidin-2-yl)phenyl)propanoyl)azetidine-3-carboxylate (341 mg, 0.489 mmol) in THF (10 mL) was added sulfuric acid (3 mL of a 5 M aqueous solution, 15 mmol). After 24 h, the mixture was diluted with water (100 mL) and extracted with EA (2×100 mL). The combined organic extracts were washed with brine (50 mL), dried over MgSO$_4$ and solvents evaporated. Column chromatography (AcOH/EA/DCM/iso-hexanes) gave 233 mg (70%) of (S)-1-(2-(5-(tert-butyl)thiophene-2-carboxamido)-3-(4-(5-(4-(heptyloxy)phenyl)pyrimidin-2-yl)phenyl)propanoyl)azetidine-3-carboxylic acid Compound 635 as a white solid. LCMS-ESI (m/z) calculated for $C_{39}H_{46}N_4O_5S$: 682.3; no m/z observed, $t_R$=10.17 min (Method 10). The chiral purity was >98% e.e. (Chiral Method). $^1$H NMR (400 MHz, DMSO-d6) δ 12.75 (s, 1H), 9.17 (d, J=1.8 Hz, 2H), 8.77 (app dd, J=8.3, 2.7 Hz, 1H), 8.32 (dd, J=8.2, 4.7 Hz, 2H), 7.79 (d, J=8.7 Hz, 2H), 7.70 (d, J=3.9 Hz, 1H), 7.47-7.52 (m, 2H), 7.11-7.07 (m, 2H), 6.93 (app dd, J=3.9, 1.4 Hz, 1H), 4.70-4.63 (m, 1H), 4.43 (t, J=9.0 Hz, 0.5H), 4.30 (dd, J=8.7, 6.0 Hz, 0.5H), 4.21 (t, J=8.9 Hz, 0.5H), 4.15 (dd, J=8.5, 6.3 Hz, 0.5H), 4.08-3.99 (m, 3H), 3.47-3.40 (m, 1H), 3.93-3.87 (m, 1H), 3.15-3.01 (m, 2H), 1.77-1.70 (m, 2H), 1.49-1.16 (m, 17H), 0.88 (t, J=6.8 Hz, 3H).

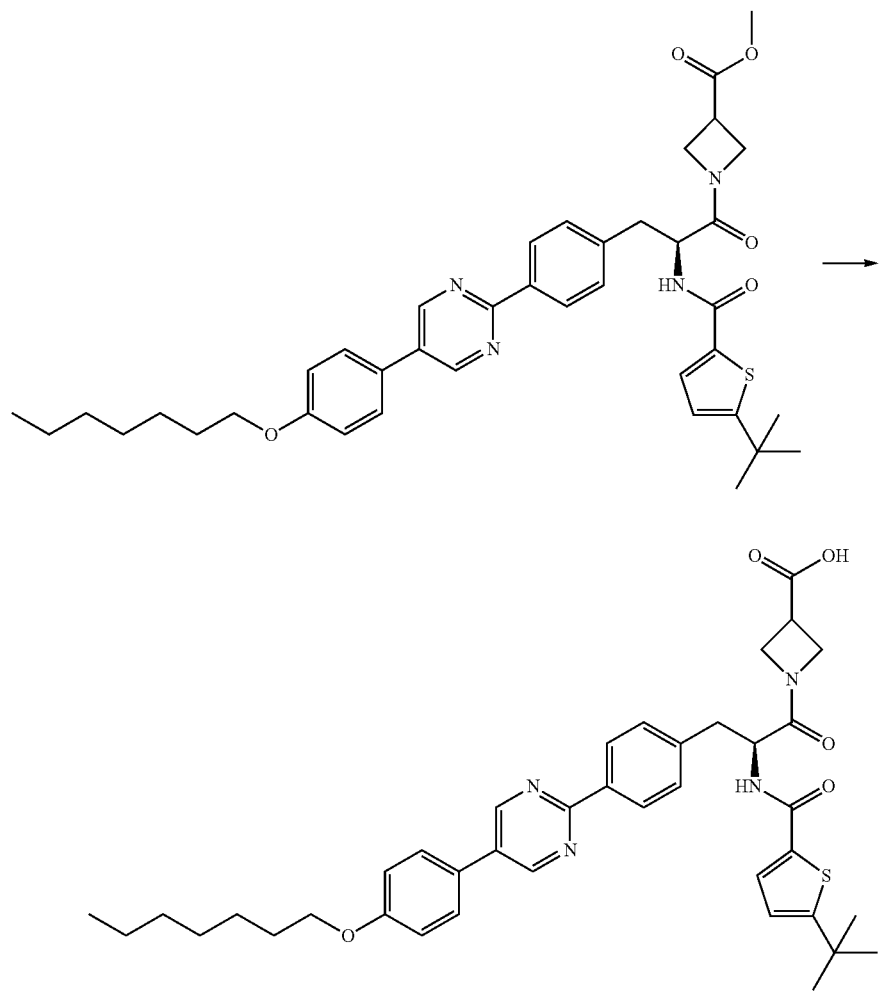

Compound 642 was prepared from (2S,3R)-2-amino-3-hydroxy-3-phenylpropanoic acid and (S)-2-(5-(tert-butyl)

thiophene-2-carboxamido)-3-(4-(5-(4-(heptyloxy)phenyl)-pyrimidin-2-yl)phenyl)propanoic acid Compound 192 using General Procedures 26, 7 and 8 sequentially.

Compounds 650 and 654 were prepared from Compound 635 using General Procedure 7.

Compound 649 was prepared from Compound 654 using General Procedure 4.

Threo-methyl 2-amino-3-hydroxy-3-phenylpropanoate HCl

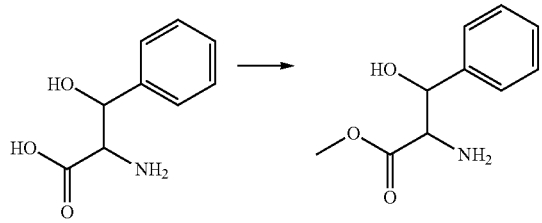

Prepared using General Procedure 22: To a stirred solution of threo-2-amino-3-hydroxy-3-phenylpropanoic acid (7 g, 38.6 mmol) in MeOH (20 mL) was added chlorotrimethylsilane (19.8 mL, 155 mmol). The mixture was heated under reflux for 16 h then solvents evaporated to afford 8.95 g (100%) of threo-methyl 2-amino-3-hydroxy-3-phenylpropanoate HCl. LCMS-ESI (m/z) calculated for $C_{10}H_{13}NO_3$; 195.1. found 196.0 $[M+H]^+$, $t_R$=0.18 min (Method 10). $^1$H NMR (400 MHz, DMSO-d6) δ 8.45 (s, 3H), 7.42-7.31 (m, 5H), 5.03 (d, J=5.4 Hz, 1H), 4.18 (app t, J=5.4 Hz, 1H), 3.63 (s, 3H).

Threo-methyl 2-((tert-butoxycarbonyl)amino)-3-hydroxy-3-phenylpropanoate

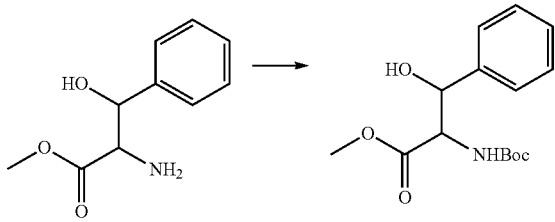 [SMILES: COC(=O)C(N)C(O)c1ccccc1 ; COC(=O)C(NC(=O)OC(C)(C)C)C(O)c1ccccc1]

Prepared using General Procedure 23: To a stirred mixture of threo-methyl 2-amino-3-hydroxy-3-phenylpropanoate, HCl (1.1 g, 4.75 mmol), MeOH (10 mL) and NaHCO$_3$ (8.44 mL of a 0.9 M aqueous solution, 7.60 mmol) was added di-tert-butyl dicarbonate (1.451 g, 6.65 mmol). After 3 h, the bulk of the MeOH was evaporated under reduced pressure and the aqueous extracted with diethyl ether (2×40 mL). The combined organic extracts were dried over MgSO$_4$ and solvents evaporated. The residue was re-slurried from isohexanes and the solid collected by filtration to afford 1.1 g (78%) of threo-methyl 2-((tert-butoxycarbonyl)amino)-3-hydroxy-3-phenylpropanoate. LCMS-ESI (m/z) calculated for $C_{15}H_{21}NO_5$: 295.1. found 318.0 $[M+Na]^+$, $t_R$=4.45 min (Method 10).

Methyl 2-((tert-butoxycarbonyl)amino)-3-oxo-3-phenylpropanoate

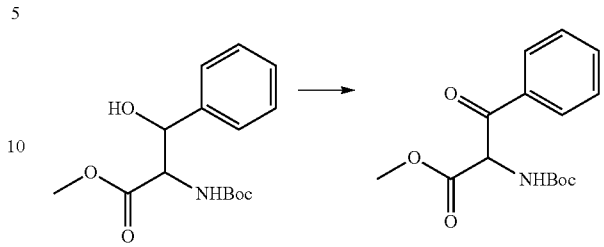

Prepared using General Procedure 24: To a stirred solution of oxalyl chloride (0.47 ml, 5.42 mmol) in DCM (50 mL) at −78° C. was added DMSO (0.77 mL, 10.8 mmol) and the reaction stirred for 10 mins. This was then treated with a pre-cooled solution of threo-methyl 2-((tert-butoxycarbonyl)amino)-3-hydroxy-3-phenylpropanoate (1 g, 3.39 mmol) in DCM (20 mL). After 2 h, DIEA (2.96 mL, 16.93 mmol) was added and the mixture allowed to warm to 0° C. After 1 h, the mixture was washed with NH$_4$Cl (2×20 mL of a saturated aqueous solution) and the organics dried over MgSO$_4$ and solvents evaporated to afford 964 mg (97%) of methyl 2-((tert-butoxycarbonyl)amino)-3-oxo-3-phenylpropanoate. LCMS-ESI (m/z) calculated for $C_{15}H_{19}NO_5$: 293.1. found 316.0 $[M+Na]^+$, $t_R$=2.15 min (Method 11).

Erythro-methyl 2-((tert-butoxycarbonyl)amino)-3-hydroxy-3-phenylpropanoate

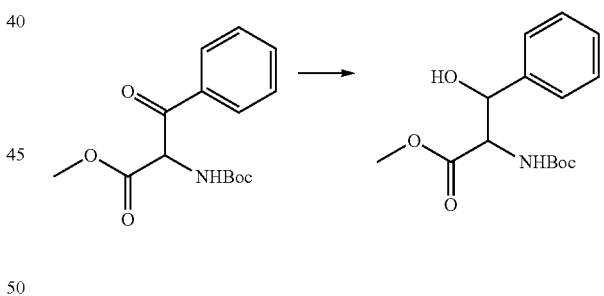

Prepared using General Procedure 25: To a stirred solution of methyl 2-((tert-butoxycarbonyl)amino)-3-oxo-3-phenylpropanoate (0.5 g, 1.705 mmol) in MeOH (10 mL) at −78° C. was added sodium borohydride (0.045 g, 1.193 mmol). After 0.5 h, the reaction was quenched with NH$_4$Cl (8 mL of a saturated aqueous solution) and the MeOH evaporated under reduce pressure. The mixture was extracted with DCM (2×30 mL) and the combined organic extracts dried over MgSO$_4$ and solvents evaporated. The residue was purified by column chromatography (EA/isohexanes) to afford 312 mg (62%) of erythro-methyl 2-((tert-butoxycarbonyl)amino)-3-hydroxy-3-phenylpropanoate. LCMS-ESI (m/z) calculated for $C_{15}H_{21}NO_5$: 295.1. found 318.0 $[M+Na]^+$, $t_R$=1.84 min (Method 11).

Erythro-methyl 2-amino-3-hydroxy-3-phenylpropanoate

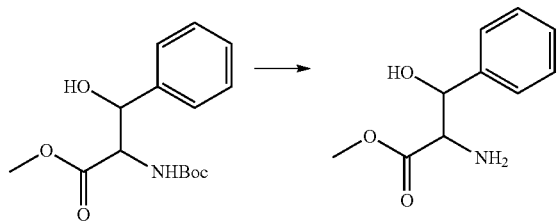 [SMILES: COC(=O)C(NC(=O)OC(C)(C)C)C(O)c1ccccc1 ; COC(=O)C(N)C(O)c1ccccc1]

Prepared using General Procedure 8: To a stirred solution of erythro-methyl 2-((tert-butoxycarbonyl)amino)-3-hydroxy-3-phenylpropanoate (0.3 g, 1.02 mmol) in DCM (15 mL) was added TFA (1.57 mL, 20.32 mmol). After 3 h, solvents were evaporated and the residue purified by strong-cation-exchange ion exchange chromatography to afford 195 mg (98%) of erythro-methyl 2-amino-3-hydroxy-3-phenylpropanoate as a white solid. LCMS-ESI (m/z) calculated for $C_{10}H_{13}NO_3$: 195.2. found 196.0 $[M+Na]^+$, $t_R$=0.19 min (Method 11).

Compound 651 was prepared from erythro-2-amino-3-hydroxy-3-phenylpropanoic acid and (S)-2-(5-(tert-butyl)thiophene-2-carboxamido)-3-(4-(5-(4-(heptyloxy)phenyl)-pyrimidin-2-yl)phenyl)propanoic acid Compound 192 using General Procedures 7 and 4 sequentially.

Compound 663 was prepared from Compound 192 and INT-46 using General Procedures 7 then 8.

Compound 665 was prepared from erythro-2-amino-3-hydroxy-3-phenylpropanoic acid and (S)-2-(5-(tert-butyl)thiophene-2-carboxamido)-3-(4-(5-(4-(heptyloxy)phenyl)-pyrimidin-2-yl)phenyl)propanoic acid Compound 192 using General Procedures 7 and 4 sequentially, followed by chiral preparative HPLC.

Methyl (2, 3-erythro)-2-((S)-2-(5-(tert-butyl)thiophene-2-carboxamido)-3-(4-(5-(4-(heptyloxy)phenyl)pyrimidin-2-yl)phenyl)propanamido)-3-hydroxy-3-phenylpropanoate

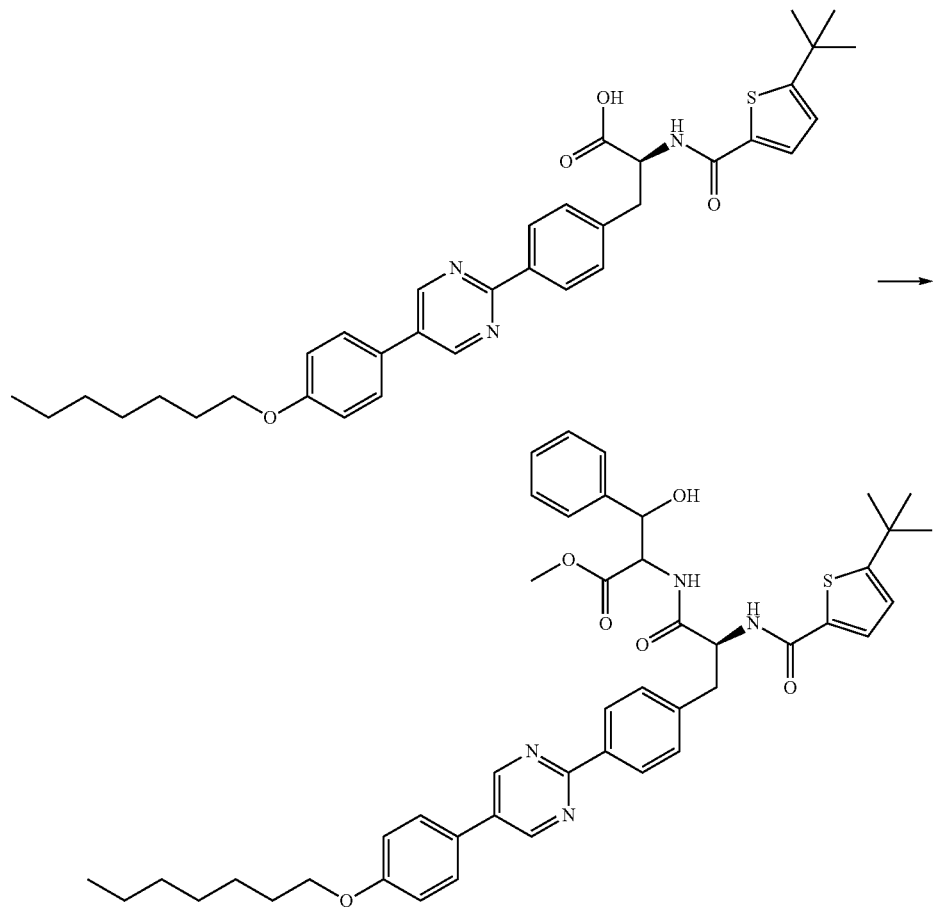

Prepared using General Procedure 7: To a stirred solution of (S)-2-(5-(tert-butyl)thiophene-2-carboxamido)-3-(4-(5-(4-(heptyloxy)phenyl)pyrimidin-2-yl)phenyl)-propanoic acid Compound 192 (578 mg, 0.963 mmol) and erythro-methyl 2-amino-3-hydroxy-3-phenylpropanoate (188 mg, 0.963 mmol) in DMF (8 mL) was added DIEA (503 μL, 2.89 mmol). The mixture was cooled to 0° C. and treated with HATU (384 mg, 1.01 mmol), added portionwise. The cooling bath was removed and the reaction allowed to stir for 2 h. The mixture was treated with citric acid (100 mL of a 10% w/v aqueous solution) and extracted with EA (3×20 mL).

The combined organic extracts were dried over MgSO₄ and solvents evaporated. Column chromatography (EA/isohexanes) gave 654 mg (87%) of methyl(2,3-erythro)-2-((S)-2-(5-(tert-butyl)thiophene-2-carboxamido)-3-(4-(5-(4-(heptyloxy)phenyl)pyrimidin-2-yl)phenyl)propanamido)-3-hydroxy-3-phenylpropanoate as a white solid. LCMS-ESI (m/z) calculated for $C_{45}H_{52}N_4O_6S$: 776.4; no m/z observed, $t_R$=3.24 min (Method 11).

(2R,3R)-2-((S)-2-(5-(tert-butyl)thiophene-2-carboxamido)-3-(4-(5-(4-(heptyloxy)phenyl)-pyrimidin-2-yl)phenyl)propanamido)-3-hydroxy-3-phenylpropanoic acid (Compound 666)

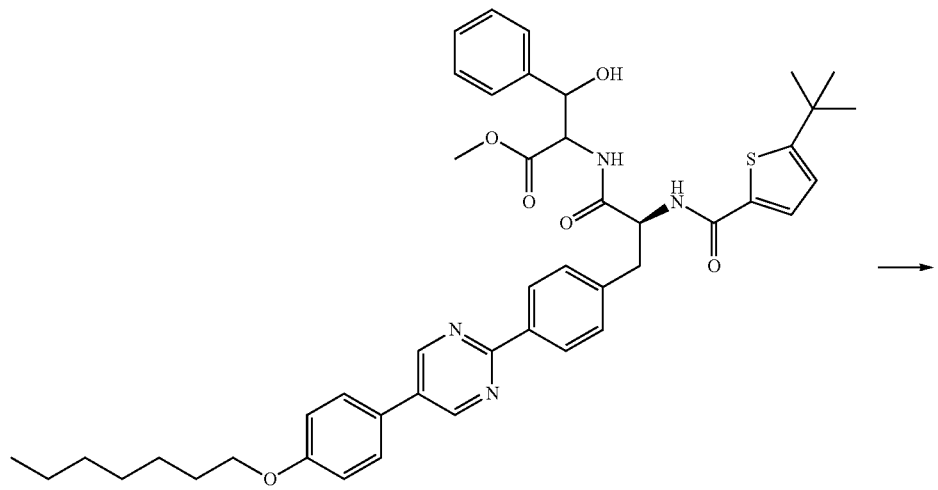

10% w/v aqueous solution) and extracted with DCM (3×30 mL). The combined organic extracts were dried over MgSO₄ and solvents evaporated. The residue was purified by column chromatography (AcOH/MeOH/DCM) then preparative chiral HPLC to afford 15 mg (5%) of (2R,3R)-2-((S)-2-(5-(tert-butyl)thiophene-2-carboxamido)-3-(4-(5-(4-(heptyloxy)-phenyl)pyrimidin-2-yl)phenyl)propanamido)-3-hydroxy-3-phenylpropanoic acid Compound 666. LCMS-ESI (m/z) calculated for $C_{44}H_{50}N_4O_6S$: 762.4; no m/z observed, $t_R$=10.68 min (Method 10). The chiral purity was >70% d.e. (Chiral Method 2). ¹H NMR (400 MHz, DMSO-d6) δ 12.71 (s, 1H), 9.15 (s, 2H), 8.51 (d, J=9.3 Hz, 1H), 8.42 (d, J=9.0 Hz, 1H), 8.27-8.23 (m, 2H), 7.80-7.77 (m, 2H), 7.61 (d, J=3.9 Hz, 1H), 7.42-7.37 (m, 4H), 7.27-7.20 (m, 3H), 7.10-7.08 (m, 2H), 6.89 (d, J=3.9 Hz, 1H), 5.81 (s, 1H), 4.80 (d, J=8.8 Hz, 1H), 4.68-4.62 (m, 1H), 4.55 (t, J=9.0 Hz, 1H), 4.04 (t, J=6.5 Hz, 2H), 2.59-2.52 (m, 2H), 1.80-1.68 (m, 2H), 1.43-1.29 (m, 17H), 0.94-0.83 (m, 3H).

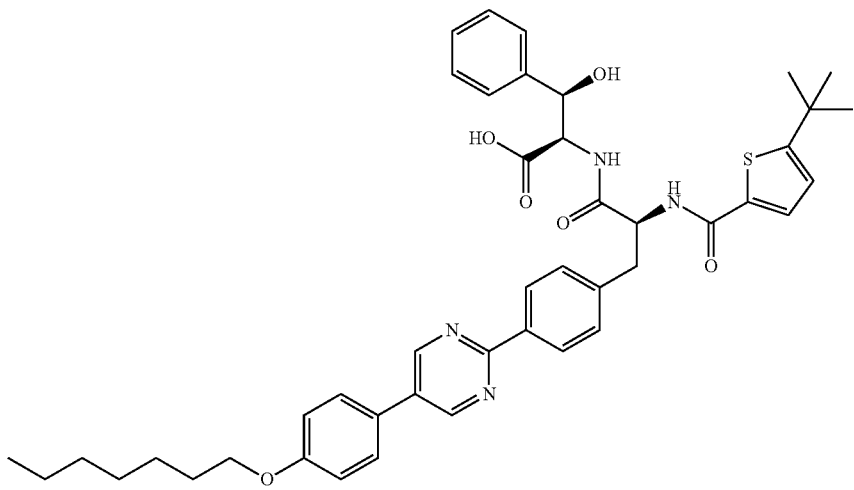

Prepared using General Procedure 4: To a stirred solution of methyl(2,3-erythro)-2-((S)-2-(5-(tert-butyl)thiophene-2-carboxamido)-3-(4-(5-(4-(heptyloxy)-phenyl)pyrimidin-2-yl)phenyl)propanamido)-3-hydroxy-3-phenylpropanoate (327 mg, 0.421 mmol) in THF (5 mL) was added LiOH (231 μL of a 2 M aqueous solution, 0.463 mmol). After 30 minutes the mixture was poured into citric acid (25 mL of a (2R,3S)-2-((S)-2-(5-(tert-butyl)thiophene-2-carboxamido)-3-(4-(5-(4-(heptyloxy)phenyl)pyrimidin-2-yl)phenyl)propanamido)-3-hydroxy-3-phenylpropanoic acid (Compound 667)

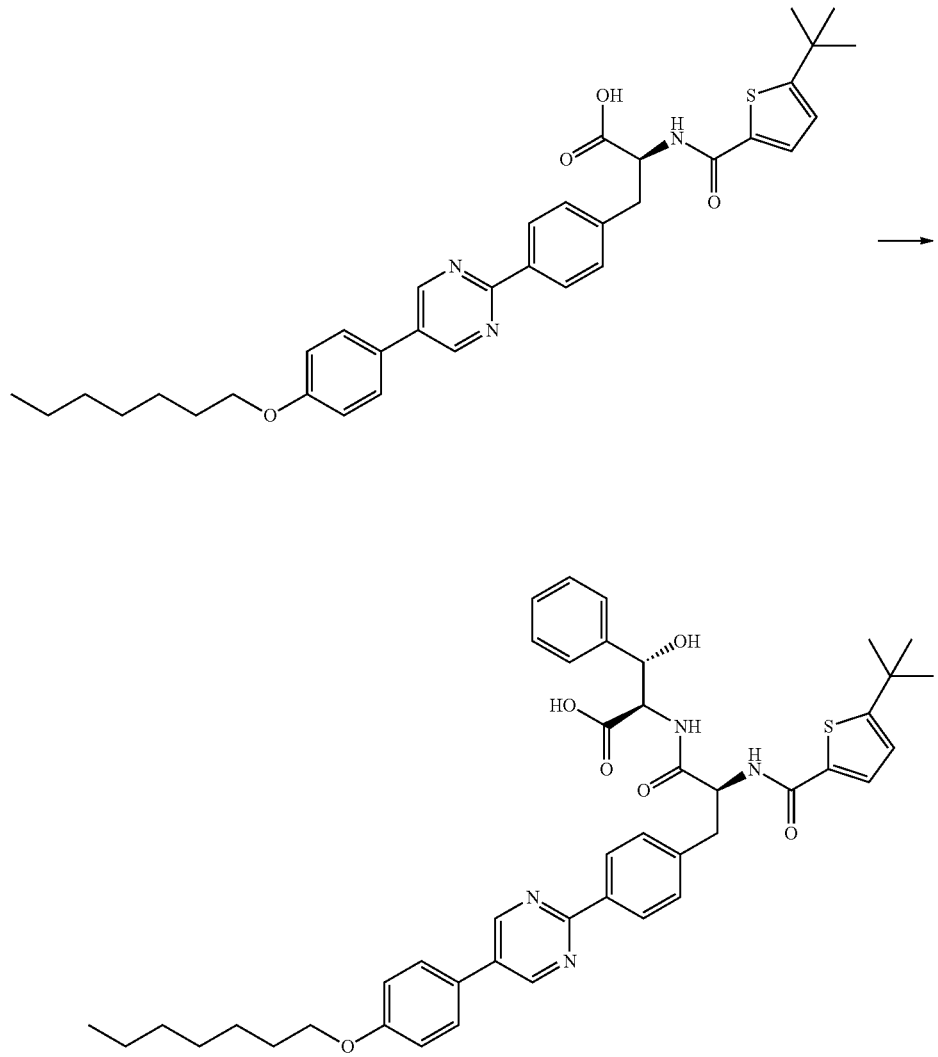

Prepared using General Procedures 7 and 4: To a stirred solution of threo-methyl 2-amino-3-hydroxy-3-phenylpropanoate (50 mg, 0.256 mmol) and (S)-2-(5-(tert-butyl)thiophene-2-carboxamido)-3-(4-(5-(4-(heptyloxy)phenyl)pyrimidin-2-yl)phenyl)propanoic acid Compound 192 (140 mg, 0.233 mmol) in DMF (3 mL) was added DIEA (122 µL, 0.699 mmol) and the mixture cooled to 0° C. HATU (97 mg, 0.256 mmol) was added portionwise and the mixture allowed to warm to room temperature over 2 h. The mixture was treated with citric acid (40 mL of a 5% w/v aqueous solution) and the liquid decanted. The aqueous was extracted with EA (50 mL) and this used to dissolve the solid residue. This solution was diluted with toluene (5 mL) and solvents evaporated. The residue was purified by column chromatography (ACN/DCM). The intermediate ester thus obtained was dissolved in THF/MeOH (1:1, 3 mL) and allowed to stir with LiOH (0.23 mL of a 2 M aqueous solution, 0.46 mmol). After 16 h, further LiOH (0.58 mL of a 2 M aqueous solution, 1.17 mmol) was charged. After an additional 1 h, the mixture was treated with citric acid (20 mL of a 10% w/v aqueous solution) and the precipitate collected by filtration. Purification by preparative chiral HPLC gave 5 mg (3%) of (2R,3S)-2((S)-2-(5-(tert-butyl)thiophene-2-carboxamido)-3-(4-(5-(4-(heptyloxy)phenyl)pyrimidin-2-yl)-phenyl)propanamido)-3-hydroxy-3-phenylpropanoic acid Compound 667. LCMS-ESI (m/z) calculated for $C_{44}H_{50}N_4O_6S$: 762.4; no m/z observed, $t_R$=10.63 min (Method 10). The chiral purity was <80% d.e. (chiral Method 2). $^1$H NMR (400 MHz, DMSO-d6) δ 12.71 (s, 1H), 9.08 (s, 2H), 8.30 (dd, J=17.6, 9.1 Hz, 2H), 8.24-8.13 (m, 2H), 7.78-7.66 (m, 2H), 7.53 (d, J=3.9 Hz, 1H), 7.32 (app ddd, J=16.7, 7.6, 1.8 Hz, 4H), 7.25-7.08 (m, 3H), 7.08-6.90 (m, 2H), 6.83 (d, J=3.8 Hz, 1H), 5.81 (d, J=4.6 Hz, 1H), 5.17 (s, 1H), 4.72 (ddd, J=11.0, 9.0, 3.9 Hz, 1H), 4.50 (dd, J=9.2, 2.8 Hz, 1H), 3.96 (t, J=6.5 Hz, 2H), 2.78 (dd, J=13.8, 3.7 Hz, 1H), 2.68-2.54 (m, 1H), 1.75-1.59 (m, 2H), 1.42-1.12 (m, 17H), 0.89-0.75 (m, 3H).

Compound 670 was prepared from INT-34 and 5-(4-(heptyloxy)phenyl)-2-iodopyrimidine using General Procedure 10.

Compound 671 was prepared from 2-chloroquinolin-6-ol and 1-bromoheptane using General Procedure 12, General Procedure 10 using INT-13, then General Procedure 8.

Compound 672 was prepared from 3-chloroisoquinolin-7-ol and 1-bromoheptane using General Procedure 12, General Procedure 10 using INT-13, and General Procedure 8.

Compound 673 was prepared from 2-chloroquinazolin-6-ol and 1-bromoheptane using General Procedure 12, General Procedure 10 using INT-13, then General Procedure 8.

Compound 674 and 693 were prepared from INT-28 using General Procedure 11 then 8.

Compounds 675-691, 694, 695 and 696 were prepared from INT-28 using General Procedures 10 and 8.

Compounds 692, 744-748, 751-755, 758-760 were prepared from commercial nitriles using General Procedure 2, then General Procedure 5 using INT-33 and General Procedure 8.

Compounds 697-705 were prepared by coupling commercial phenol boronic acids and INT-28 using General Procedure 10 followed by General Procedures 12 and 8.

Compounds 706-716, and 803 were prepared from INT-29 using General Procedures 12 and 8.

Compounds 717-742 and 800 were prepared from INT-32 using General Procedures 10 then 8.

Compounds 743, 749, 750, 756 and 757 were prepared from INT-33 using General Procedure 5 and 8.

Compounds 761-769 were prepared from INT-35 using General Procedures 10 then 4.

Compounds 770 and 771 were prepared from INT-36 using General Procedures 12 then 8.

Compounds 772-774 were prepared from INT-37 using General Procedures 12 then 4.

Compound 775 was prepared from INT-38 using General Procedures 10 then 8.

Compound 776 was prepared from (3-methyl-4-hydroxyphenyl)boronic acid and INT-38 using General Procedure 10, then with 1-bromoheptane using General Procedure 12 then 8.

Compounds 777-789 were prepared from INT-38 using General Procedures 10 then 8.

Compound 790 was prepared from (4-hydroxy-2-methylphenyl)boronic acid and (R)-tert-butyl 2-((S)-2-(((benzyloxy)carbonyl)amino)-3-(4-(5-bromopyrimidin-2-yl)phenyl)propanamido)propanoate INT-42 using General Procedures 10, 12, 18, 7 and 8 sequentially.

Compound 791 was prepared from 4-bromo-3,5-dimethylphenol and (R)-tert-butyl 2-((S)-2-(((benzyloxy)carbonyl)amino)-3-(4-(5-bromopyrimidin-2-yl)phenyl)propanamido)propanoate INT-42 using General Procedures 12, 27, 10, 18, 7 and 8 sequentially.

Compounds 792-794 were prepared from INT-45 using General Procedures 12 then 8.

Compounds 795-797 and 799 were prepared from INT-48 using General Procedures 12 then 8.

Tert-butyl(S)-1-(2-(5-(tert-butyl)thiophene-2-carboxamido)-3-(4-(5-(4-((4-methylpentyl)oxy)phenyl-)pyrimidin-2-yl)phenyl)propanoyl) azetidine-3-carboxylate

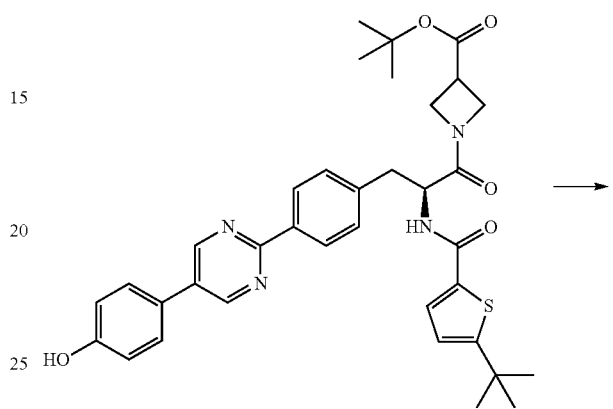

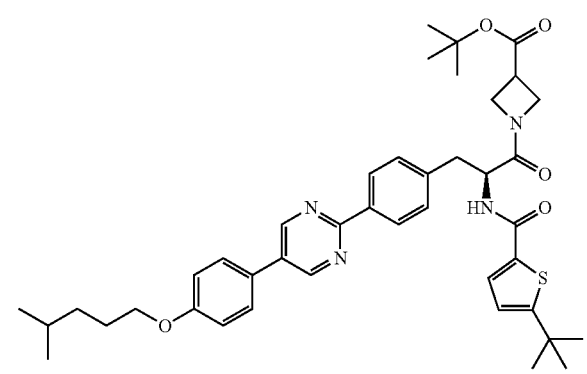

Prepared using General Procedure 12: To a stirred solution of INT-48 (300 mg, 0.479 mmol) in DMF (5 mL) was added $Cs_2CO_3$ (197 mg, 0.58 mmol) and 1-bromo-4-methylpentane (158 mg, 0.96 mmol). The reaction mixture was stirred for 18 h at 65° C. then diluted with aq. $NaHCO_3$ (100 ml, saturated) and extracted with EA (2×100 mL). The combined organic layers were dried ($Na_2SO_4$), concentrated, and purified by column chromatography (EA/hexane) to afford 188 mg (54%) of tert-butyl (S)-1-(2-(5-(tert-butyl)thiophene-2-carboxamido)-3-(4-(5-(4-((4-methylpentyl)oxy)phenyl)pyrimidin-2-yl)phenyl)propanoyl)azetidine-3-carboxylate. LCMS-ESI (m/z) calculated for $C_{42}H_{52}N_4O_5S$: 724.96. found 725.3 [M+H]$^+$, $t_R$=12.71 min (Method 16). $^1$H NMR (400 MHz, $CDCl_3$) δ 8.97 (d, J=7.5 Hz, 2H), 8.45 (d, J=5.5 Hz, 2H), 7.55 (s, 2H), 7.49-7.31 (m, 3H), 7.05 (d, J=6.6 Hz, 2H), 6.82 (s, 1H), 6.68 (d, J=28.8 Hz, 1H), 4.82 (s, 1H), 4.30 (s, 0.5H), 4.07 (m, 5.5H), 3.56 (s, 0.5H), 3.31-3.09 (m, 2H), 2.91 (s, 0.5H), 1.83 (s, 2H), 1.60 (d, J=25.3 Hz, 1H), 1.40 (s, 16H), 1.29 (s, 4H), 0.95 (s, 6H).

(S)-1-(2-(5-(tert-butyl)thiophene-2-carboxamido)-3-(4-(5-(4-((4-methylpentyl)oxy)phenyl)-pyrimidin-2-yl)phenyl)propanoyl)azetidine-3-carboxylic acid (798)

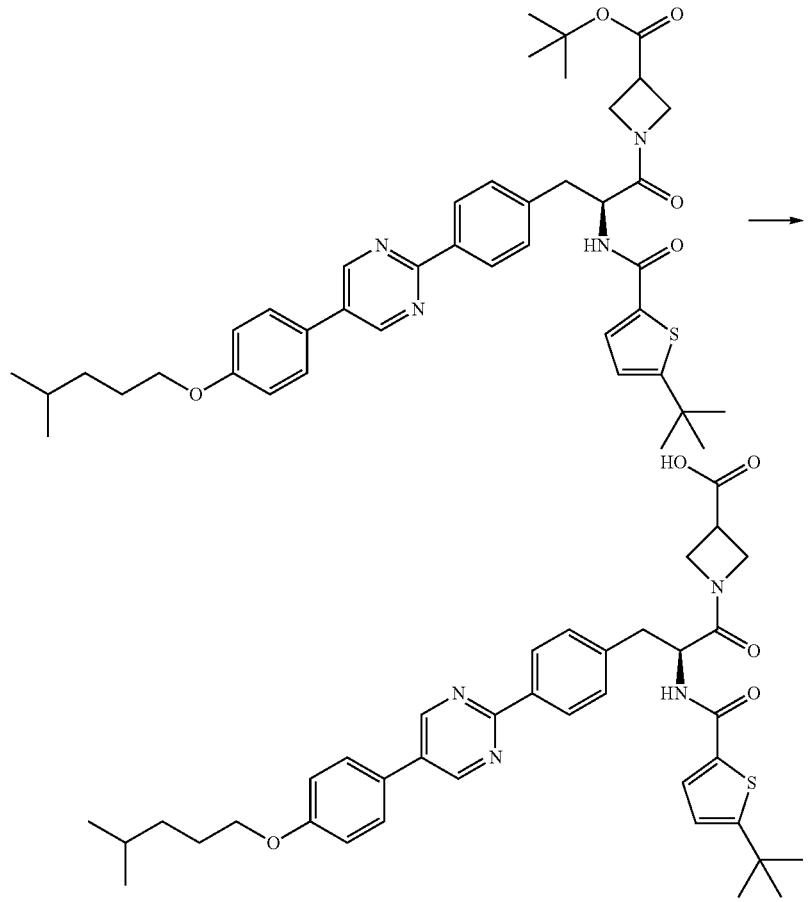

Prepared using General Procedure 8: To a stirred solution of tert-butyl (S)-1-(2-(5-(tert-butyl)thiophene-2-carboxamido)-3-(4-(5-(4-((4-methylpentyl)oxy)phenyl)pyrimidin-2-yl)phenyl)propanoyl)azetidine-3-carboxylate (188 mg, 0.26 mmol), in DCM (2 mL) was added TFA (2 mL). The mixture was stirred for 4 h then concentrated. The resulting solid was dissolved in DCM (10 mL) and concentrated (5×) to remove excess TFA, affording 169 mg (98%) of 1-(2-(5-(tert-butyl)thiophene-2-carboxamido)-3-(4-(5-(4-((4-methylpentyl)oxy)phenyl)pyrimidin-2-yl)phenyl)propanoyl)azetidine-3-carboxylic acid 798 as a yellow solid. LCMS-ESI (m/z) calculated for $C_{38}H_{44}N_4O_5S$: 668.85. found 669.3 [M+H]$^+$, $t_R$=9.121 min (Method 16). $^1$H NMR (400 MHz, CDCl$_3$) δ 9.17 (s, 2H), 8.12 (d, J=7.8 Hz, 2H), 7.58 (m, 3H), 7.45 (m, 1H), 7.42 (m, 2H), 7.06 (m, 2H), 6.84 (m, 1H), 4.71 (d, J=7.7 Hz, 1H), 4.33-4.14 (m, 2H), 4.08 (dd, J=19.8, 9.1 Hz, 2H), 4.03 (t, J=6.6 Hz, 2H), 3.30 (dd, J=12.5, 4.2 Hz, 1H), 3.06 (t, J=11.9 Hz, 1H), 2.91 (s, 1H), 1.91-1.76 (m, 2H), 1.64 (dt, J=13.0, 6.6 Hz, 1H), 1.43-1.33 (m, 11H), 0.95 (d, J=6.6 Hz, 6H).

Compound 801 was prepared from Compound 2 using General Procedures 7 then 8.

Compound 802 was prepared from Compound 83 using General Procedures 7 then 8.

Compound 804 was prepared from Compound 267 using General Procedures 7 and 8.

Compounds 806 and 807 were prepared from compound 671 using General Procedures 7 then 8.

Compound 808 was prepared from compound 672 using General Procedures 7 then 8.

Compound 809 and 810 were prepared from 673 using General Procedures 7 then 8.

Compound 811 was prepared from (S)-tert-butyl 2-(((benzyloxy)carbonyl)amino)-3-(4-(4,4,5,5-tetramethyl-1,3,2-dioxaborolan-2-yl)phenyl)propanoate INT-6 and 5-bromo-2-iodopyridine using General Procedures 10, 10, 8, 7, 18, 7 and 8 sequentially.

Compound 812 was prepared from 2-bromo-5-iodo-3-methylpyridine and (S)-tert-butyl 2-(((benzyloxy)carbonyl)amino)-3-(4-(4,4,5,5-tetramethyl-1,3,2-dioxaborolan-2-yl)phenyl)propanoate INT-6 using General Procedures 10, 10, 8, 7, 18, 7 and 8 sequentially.

Compounds 813-830 and 832-843 were prepared from INT-24 using General Procedures 7 then 8.

Compounds 844 853 and 855-868 were prepared from INT-39 using General Procedures 7 then 8.

Compounds 869 and 870 were prepared from Compound 90 using General Procedures 7 then 8.

Compounds 871-879 were prepared from Compound 192 using General Procedures 7 then 8.

Compounds 880-882 and 888 were prepared from Compound 192 using General Procedures 7 then 4.

Compound 883 was prepared from Compound 192 and methyl (2S, 3S)-2-amino-3-((tert-butoxycarbonyl)amino)-3-phenylpropanoate using General Procedures 7, 4 then 8.

Compounds 884, 885 and 887 were prepared from Compound 349 using General Procedure 7.

Compound 886 was prepared from Compound 192 using General Procedure 7.

Compound 889 was prepared from Compound 192 using General Procedures 7 then 8.

Methyl 2-amino-3-methoxy-3-phenylpropanoate

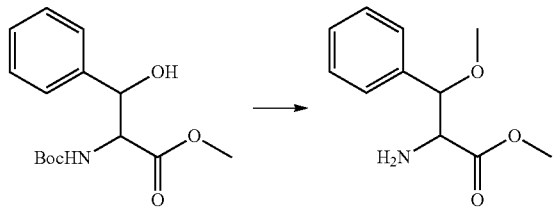 [SMILES: COC(=O)C(NC(=O)OC(C)(C)C)C(O)c1ccccc1 ; COC(=O)C(N)C(OC)c1ccccc1]

To a stirring solution of threo-methyl 2-((tert-butoxycarbonyl)amino)-3-hydroxy-3-phenylpropanoate (148 mg, 0.5 mmol) in DCM (5 mL) was added proton sponge (430 µL, 2.0 mmol), 4 Å molecular sieves (520 mg) and trimethyloxonium tetrafluoroborate (260 mg). The reaction mixture was stirred vigorously at room temperature for 24 hours and the solids were removed by filtration. The filtrate was washed with 10% aqueous copper sulfate (10 mL), saturated aqueous ammonium chloride (10 mL), saturated aqueous sodium bicarbonate (10 mL), and brine (10 mL). The organic layer was dried over magnesium sulfate and concentrated. The crude compound was purified by column chromatography (0-100% EA in hexanes) to afford 86 mg of methyl 2-((tert-butoxycarbonyl)amino)-3-methoxy-3-phenylpropanoate which was dissolved in DCM (1 mL) and treated with TFA (425 µL). After 1 hour, all solvent was removed to give 96 mg (59%) of methyl 2-amino-3-methoxy-3-phenylpropanoate. LCMS-ESI (m/z) calculated for $C_{11}H_{15}NO_3$: 209.1. found 210.1 [M+H]$^+$, $t_R$=1.46 min (Method 16).

Compound 890 was prepared from methyl 2-amino-3-methoxy-3-phenylpropanoate and Compound 192 using General Procedures 7 then 4.

Compound 891 was prepared from 1-tert-butyl 3-methyl piperazine-1,3-dicarboxylate and Compound 192 using General Procedures 7, 4 then 8.

Compound 892 was prepared from 1,3-pyrrolidinedicarboxylic acid, 5-methyl-, 1-(1,1-dimethylethyl) ester using General Procedures 22 then 8, and Compound 192 using General Procedures 7 then 4.

Compound 893 was prepared from Compound 85 and 1,3-pyrrolidinedicarboxylic acid, 5-methyl-, 1-(1,1-dimethylethyl) ester using General Procedures 22, 8, 7 then 4.

Compound 894 was prepared from 3-(aminomethyl)-1-methylpyrrolidin-3-ol and Compound 192 using General Procedure 7.

Compound 895 was prepared from Compound 192 and (2R,3R)-methyl 2-amino-3-hydroxybutanoate hydrochloride using General Procedures 7, 28 and 29 sequentially.

Compounds 896-899 were prepared from 2-amino-3-phenylbutanoic acid using General Procedure 22, and INT-22 using General Procedures 7, 18, 7 and 4 sequentially.

Compounds 900-908 and 911-918 were prepared from a suitable aminoalcohol, prepared using General Procedure 30, and Compound 192 using General Procedures 7 and 8 sequentially.

Compound 909 was prepared from (2S, 3S)-2-((tert-butoxycarbonyl)amino)-3-phenylbutanoic acid using General Procedure 22, and Compound 192 using General Procedures 7 and 4 sequentially.

Compound 910 was prepared from (2R,3R)-2-((tert-butoxycarbonyl)amino)-3-phenylbutanoic acid using General Procedure 22, and Compound 192 using General Procedures 7 and 4 sequentially.

Compounds 919-922, 944 and 945 were prepared from INT-48 using General Procedures 12 then 8.

Tert-butyl 2-((S)-3-(4-(5-bromopyrimidin-2-yl)phenyl)-2-(5-(tert-butyl)thiophene-2-carboxamido)propanamido)-3-(tert-butoxy)-3-phenylpropanoate

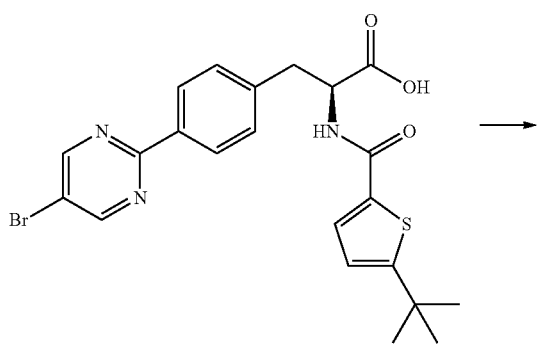

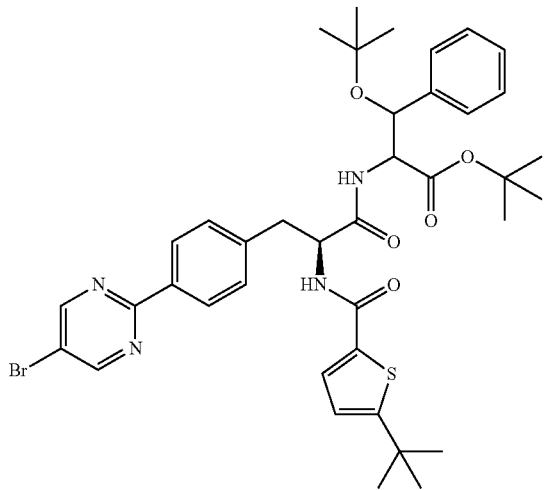

Prepared using General Procedure 7. To a stirring solution of tert-butyl 2-amino-3-(tert-butoxy)-3-phenylpropanoate (198 mg, 0.7 mmol) in DMF (5 mL) were added DIEA (267 μL, 1.54 mmol), and INT-17 (300 mg, 0.6 mmol). The solution was cooled to 0° C. at ice bath and then HATU (245 mg, 0.6 mmol) was added. The reaction was stirred for 1 hour at 0° C. and then warmed to RT with stirring for 2 hours. The reaction solution was diluted with aqueous NaHCO$_3$ (50 mL) and extracted with EA (3×50 mL). The combined organics were dried over Na$_2$SO$_4$ and purified by chromatography (EA/Hexanes) to afford 308 mg (67%) of tert-butyl 2-((S)-3-(4-(5-bromopyrimidin-2-yl)phenyl)-2-(5-(tert-butyl)thiophene-2-carboxamido)propanamido)-3-(tert-butoxy)-3-phenylpropanoate. LCMS-ESI (m/z) calculated for C$_{39}$H$_{47}$BrN$_4$O$_5$S: 763.79. found 764.2 [M+H]$^+$, t$_R$=4.64 min. (Method 15).

Compounds 925-934 and 943 were prepared from tert-butyl 2-((S)-3-(4-(5-bromopyrimidin-2-yl)phenyl)-2-(5-(tert-butyl)thiophene-2-carboxamido)propanamido)-3-(tert-butoxy)-3-phenylpropanoate using General Procedure 10 then 8.

Tert-butyl 3-(tert-butoxy)-2-((S)-2-(5-(tert-butyl)thiophene-2-carboxamido)-3-(4-(5-(4-hydroxyphenyl)pyrimidin-2-yl)phenyl)propanamido)-3-phenylpropanoate (INT-51)

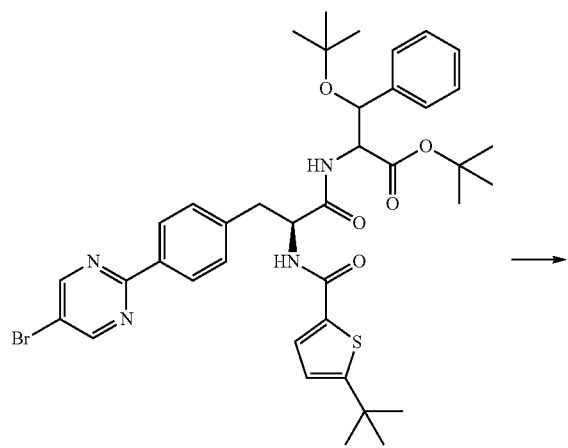

To a 100 ml flask were added (4-hydroxyphenyl)boronic acid (63 mg, 0.5 mmol), sodium carbonate decahydrate (217 mg, 0.8 mmol), tert-butyl 2-((S)-3-(4-(5-bromopyrimidin-2-yl)phenyl)-2-(5-(tert-butyl)thiophene-2-carboxamido)propanamido)-3-(tert-butoxy)-3-phenylpropanoate (290 mg, 0.4 mmol), Pd(dppf)Cl$_2$ (28 mg, 0.04 mmol), dioxane (10.0 mL), and water (2.0 mL). The reaction mixture was heated to 80° C. overnight. The reaction mixture was dried under reduced pressure to remove the solvent and diluted in DCM (20 mL). The mixture was washed with aqueous NaHCO$_3$ (3×10 mL). The combined organics were dried over Na$_2$SO$_4$ and evaporated to afford 309 mg (106%) of crude tert-butyl 3-(tert-butoxy)-2-((S)-2-(5-(tert-butyl)thiophene-2-carboxamido)-3-(4-(5-(4-hydroxyphenyl)pyrimidin-2-yl)phenyl)propanamido)-3-phenylpropanoate INT-51 which was used without further purification. LCMS-ESI (m/z) calculated for C$_{45}$H$_{52}$N$_4$O$_6$S: 776.9. found 721 [M-$^t$BuO]+, t$_R$=11.03 min. (Method 14).

Compounds 923, 924 and 935-942 were prepared from INT-51 using General Procedure 12 followed by General Procedure 8.

Compound 946 was prepared from 2-bromo-5-iodo-3-methylpyridine and 4-(heptyloxy)phenyl boronic acid using General Procedure 10, and then with INT-6 using General Procedures 10, 18, 7 and 8 sequentially.

Compounds 947-960 were prepared from INT-49 using General Procedures 7 then 4.

Compounds 961-978 were prepared from Compound 192 using General Procedure 7.

Compounds 984-989, 991 and 1047 were prepared from Compound 192 using General Procedures 7 then 8.

Compounds 979-983 and 990 were prepared from Compound 24 using General Procedures 7 then 8.

Compounds 992-1046 and 1050-1055 were prepared from tert-butyl ((S)-3-(4-(5-bromopyrimidin-2-yl)phenyl)-2-(5-(tert-butyl)thiophene-2-carboxamido)propanoyl)-D-alaninate using General Procedures 10 then 8.

Compounds 1048 and 1049 were prepared from Compound 192 using General Procedures 7 then 8.

Selected compounds and their corresponding analytical data are shown in Table 1, where the LCMS data was collected using the method indicated.

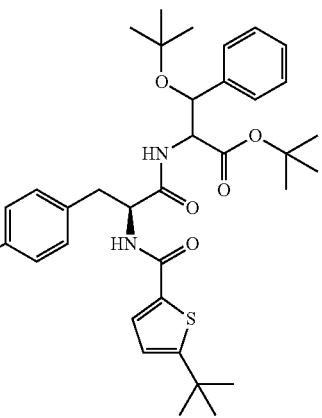

TABLE 1

| STRUCTURE | COMPOUND NUMBER | LCMS RETENTION TIME (min) | PURITY METHOD |
|---|---|---|---|
| *(structure)* | 1 | 12.42 | 2 |
| *(structure)* | 2 | 12.17 | 2 |
| *(structure)* | 3 | 11.65 | 2 |

TABLE 1-continued

| STRUCTURE | COMPOUND NUMBER | LCMS RETENTION TIME (min) | PURITY METHOD |
|---|---|---|---|
| 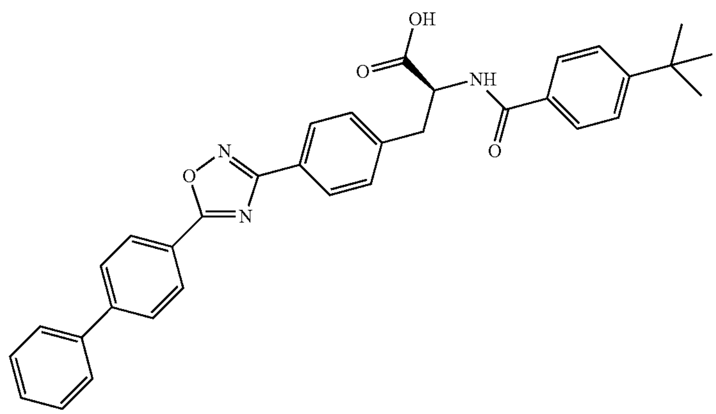 [SMILES: CC(C)(C)c1ccc(C(=O)N[C@@H](Cc2ccc(-c3noc(-c4ccc(-c5ccccc5)cc4)n3)cc2)C(=O)O)cc1] | 4 | 11.13 | 2 |
| 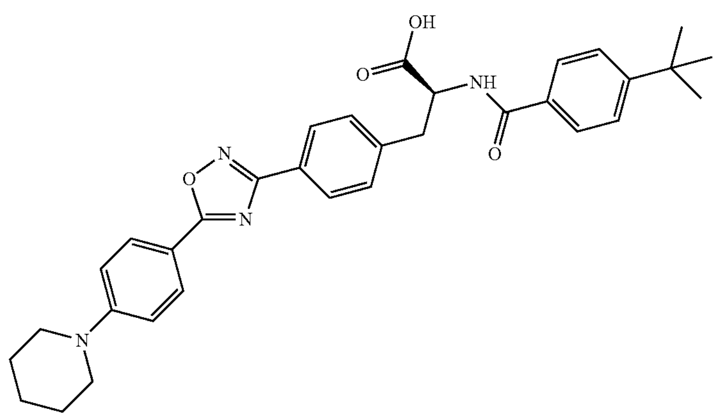 [SMILES: CC(C)(C)c1ccc(C(=O)N[C@@H](Cc2ccc(-c3noc(-c4ccc(N5CCCCC5)cc4)n3)cc2)C(=O)O)cc1] | 5 | 10.65 | 2 |
| 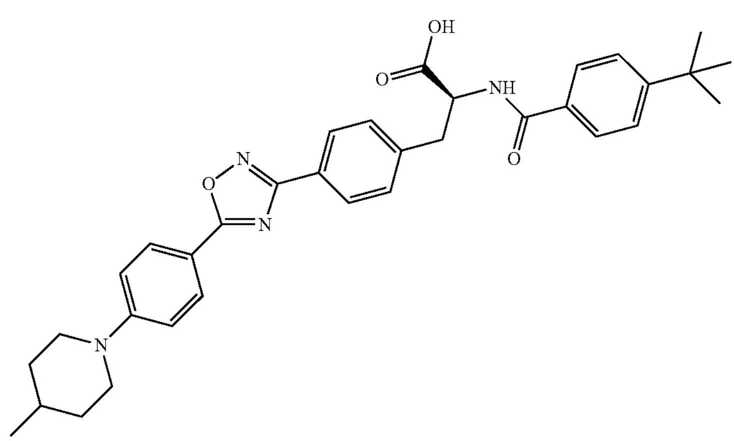 [SMILES: CC1CCN(c2ccc(-c3nc(-c4ccc(C[C@H](NC(=O)c5ccc(C(C)(C)C)cc5)C(=O)O)cc4)no3)cc2)CC1] | 6 | 11.66 | 2 |

TABLE 1-continued

| STRUCTURE | COMPOUND NUMBER | LCMS RETENTION TIME (min) | PURITY METHOD |
|---|---|---|---|
| 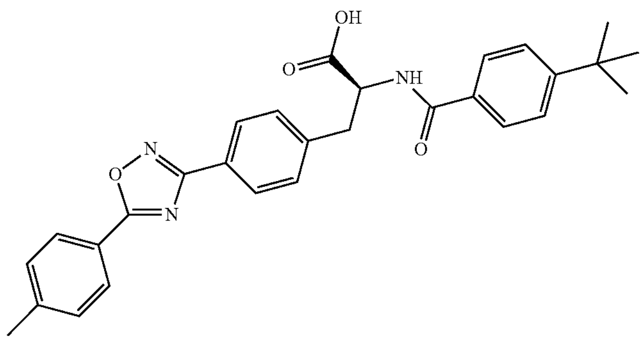 [SMILES: Cc1ccc(-c2nc(-c3ccc(C[C@H](NC(=O)c4ccc(C(C)(C)C)cc4)C(=O)O)cc3)no2)cc1] | 7 | 10.04 | 2 |
| 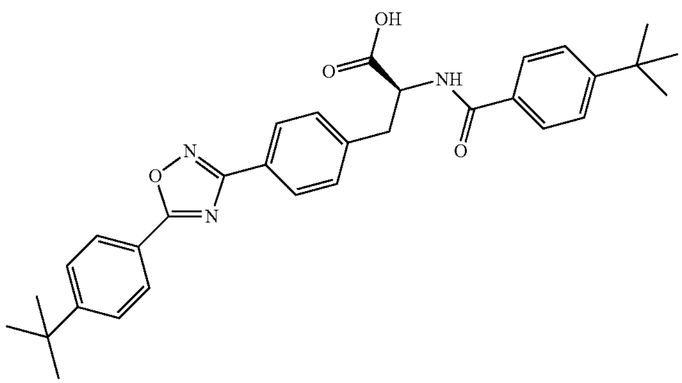 [SMILES: CC(C)(C)c1ccc(C(=O)N[C@@H](Cc2ccc(-c3noc(-c4ccc(C(C)(C)C)cc4)n3)cc2)C(=O)O)cc1] | 8 | 10.92 | 2 |
| 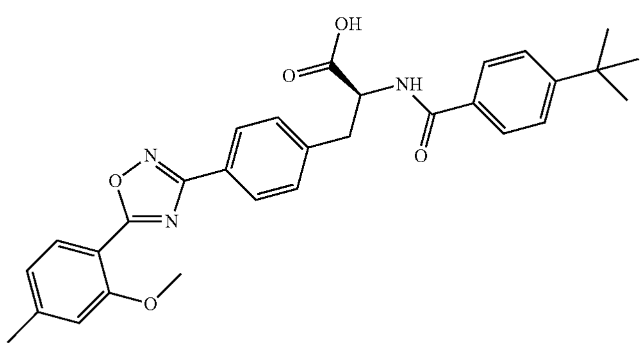 [SMILES: COc1cc(C)ccc1-c1nc(-c2ccc(C[C@H](NC(=O)c3ccc(C(C)(C)C)cc3)C(=O)O)cc2)no1] | 9 | 9.58 | 2 |
| 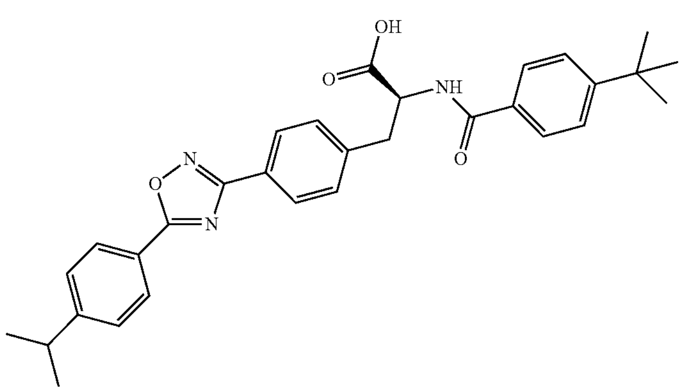 [SMILES: CC(C)c1ccc(-c2nc(-c3ccc(C[C@H](NC(=O)c4ccc(C(C)(C)C)cc4)C(=O)O)cc3)no2)cc1] | 10 | 10.69 | 2 |

TABLE 1-continued

| STRUCTURE | COMPOUND NUMBER | LCMS RETENTION TIME (min) | PURITY METHOD |
|---|---|---|---|
| 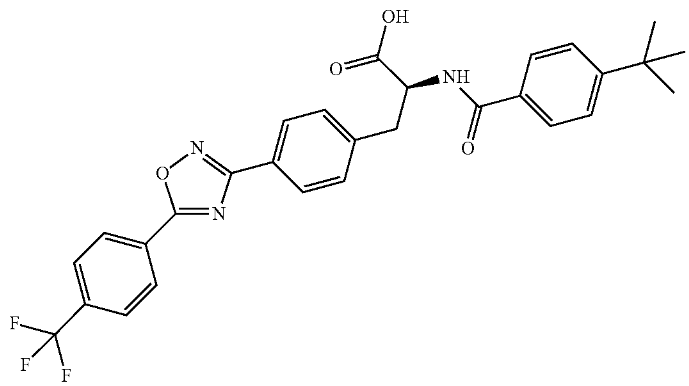 [SMILES: CC(C)(C)c1ccc(C(=O)N[C@@H](Cc2ccc(-c3noc(-c4ccc(C(F)(F)F)cc4)n3)cc2)C(=O)O)cc1] | 11 | 10.13 | 2 |
| 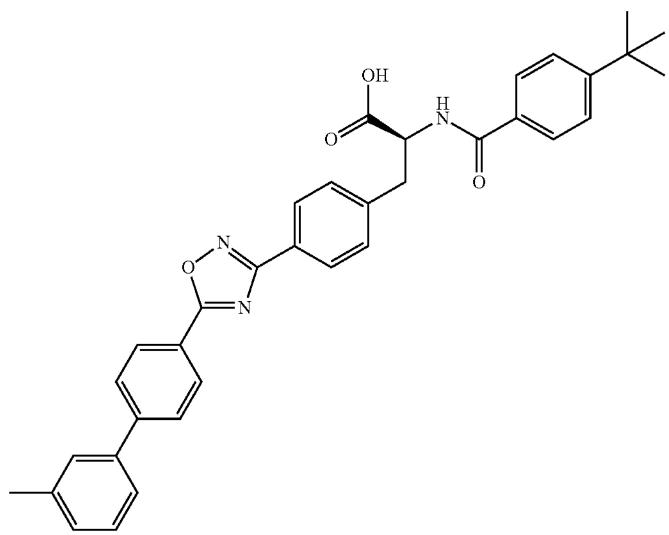 [SMILES: Cc1cccc(-c2ccc(-c3nc(-c4ccc(C[C@H](NC(=O)c5ccc(C(C)(C)C)cc5)C(=O)O)cc4)no3)cc2)c1] | 13 | 11.46 | 2 |
| 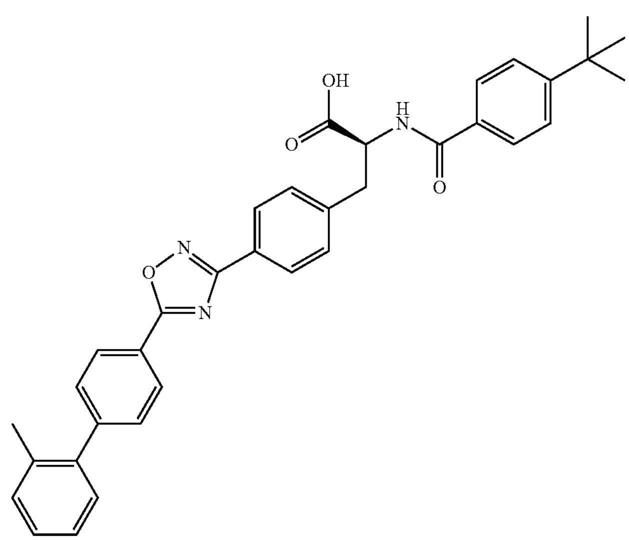 [SMILES: Cc1ccccc1-c1ccc(-c2nc(-c3ccc(C[C@H](NC(=O)c4ccc(C(C)(C)C)cc4)C(=O)O)cc3)no2)cc1] | 14 | 11.45 | 2 |

TABLE 1-continued
| STRUCTURE | COMPOUND NUMBER | LCMS RETENTION TIME (min) | PURITY METHOD |
|---|---|---|---|
| 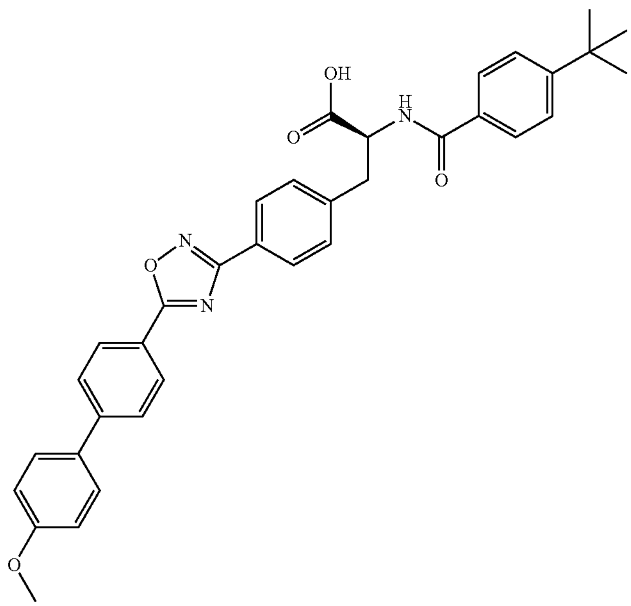 [SMILES: COc1ccc(-c2ccc(-c3nc(-c4ccc(C[C@H](NC(=O)c5ccc(C(C)(C)C)cc5)C(=O)O)cc4)no3)cc2)cc1] | 15 | 10.95 | 2 |
| 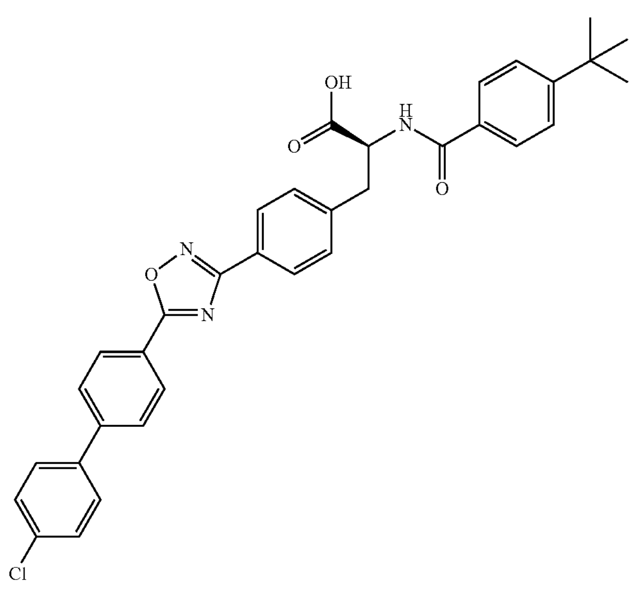 [SMILES: CC(C)(C)c1ccc(C(=O)N[C@@H](Cc2ccc(-c3noc(-c4ccc(-c5ccc(Cl)cc5)cc4)n3)cc2)C(=O)O)cc1] | 16 | 11.55 | 2 |

TABLE 1-continued
| STRUCTURE | COMPOUND NUMBER | LCMS RETENTION TIME (min) | PURITY METHOD |
|---|---|---|---|
| 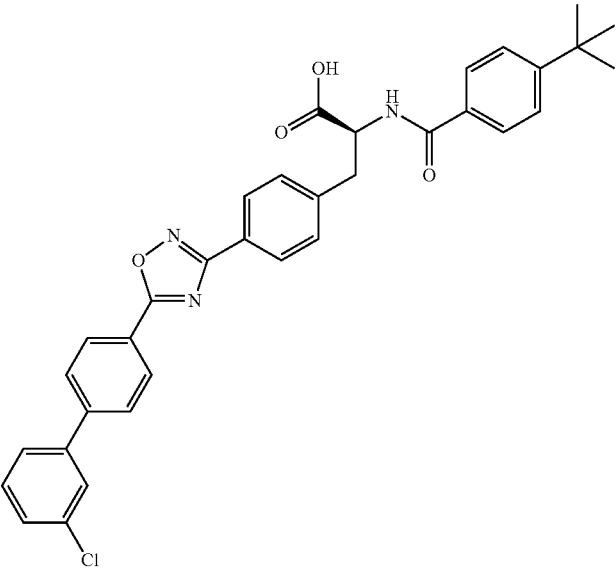 [SMILES: CC(C)(C)c1ccc(C(=O)N[C@@H](Cc2ccc(-c3noc(-c4ccc(-c5cccc(Cl)c5)cc4)n3)cc2)C(=O)O)cc1] | 17 | 11.04 | 2 |
| 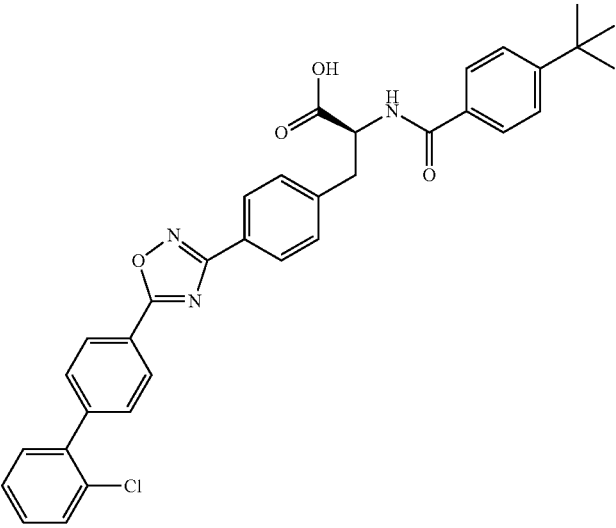 [SMILES: CC(C)(C)c1ccc(C(=O)N[C@@H](Cc2ccc(-c3noc(-c4ccc(-c5ccccc5Cl)cc4)n3)cc2)C(=O)O)cc1] | 18 | 10.66 | 2 |

TABLE 1-continued
| STRUCTURE | COMPOUND NUMBER | LCMS RETENTION TIME (min) | PURITY METHOD |
|---|---|---|---|
| 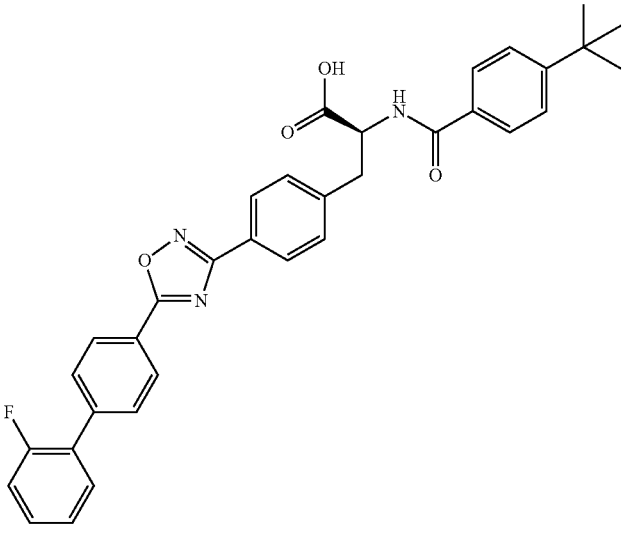 [SMILES: CC(C)(C)c1ccc(C(=O)N[C@@H](Cc2ccc(-c3noc(-c4ccc(-c5ccccc5F)cc4)n3)cc2)C(=O)O)cc1] | 19 | 10.69 | 2 |
| 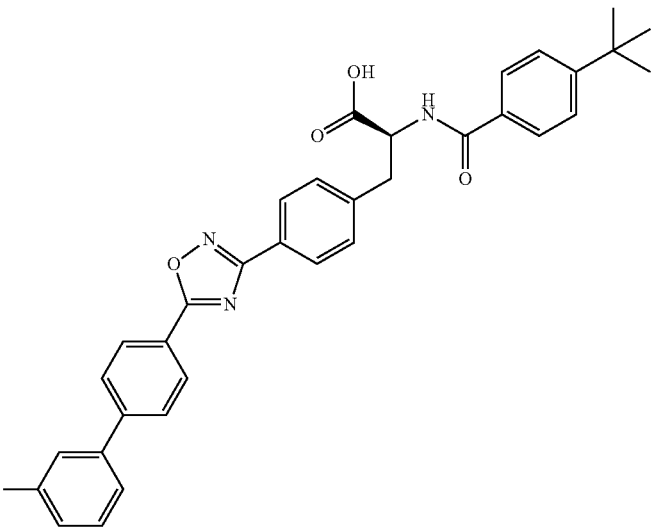 | 20 | 10.78 | 2 |

TABLE 1-continued

| STRUCTURE | COMPOUND NUMBER | LCMS RETENTION TIME (min) | PURITY METHOD |
|---|---|---|---|
| (structure) | 21 | 10.74 | 2 |
| (structure) | 22 | 10.75 | 2 |

TABLE 1-continued

| STRUCTURE | COMPOUND NUMBER | LCMS RETENTION TIME (min) | PURITY METHOD |
|---|---|---|---|
| 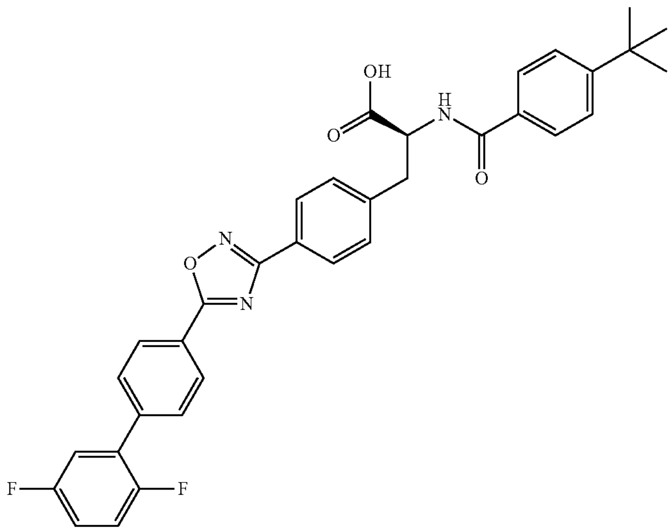 [SMILES: CC(C)(C)c1ccc(C(=O)N[C@@H](Cc2ccc(-c3noc(-c4ccc(-c5cc(F)ccc5F)cc4)n3)cc2)C(=O)O)cc1] | 23 | 10.66 | 2 |
| 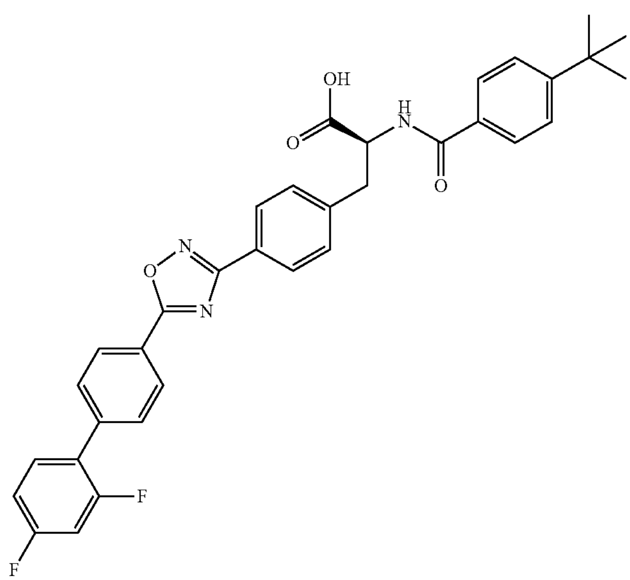 [SMILES: CC(C)(C)c1ccc(C(=O)N[C@@H](Cc2ccc(-c3noc(-c4ccc(-c5ccc(F)cc5F)cc4)n3)cc2)C(=O)O)cc1] | 24 | 10.72 | 2 |

TABLE 1-continued

| STRUCTURE | COMPOUND NUMBER | LCMS RETENTION TIME (min) | PURITY METHOD |
|---|---|---|---|
| 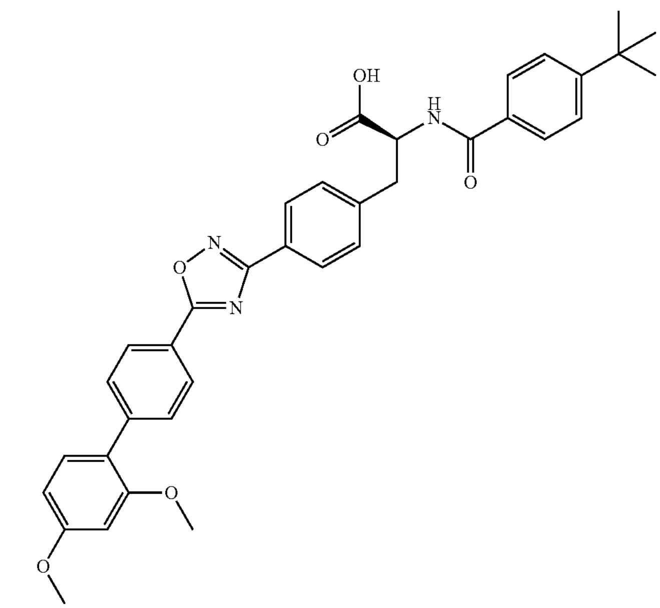 [SMILES: COc1ccc(-c2ccc(-c3nc(-c4ccc(C[C@H](NC(=O)c5ccc(C(C)(C)C)cc5)C(=O)O)cc4)no3)cc2)c(OC)c1] | 25 | 10.50 | 2 |
| 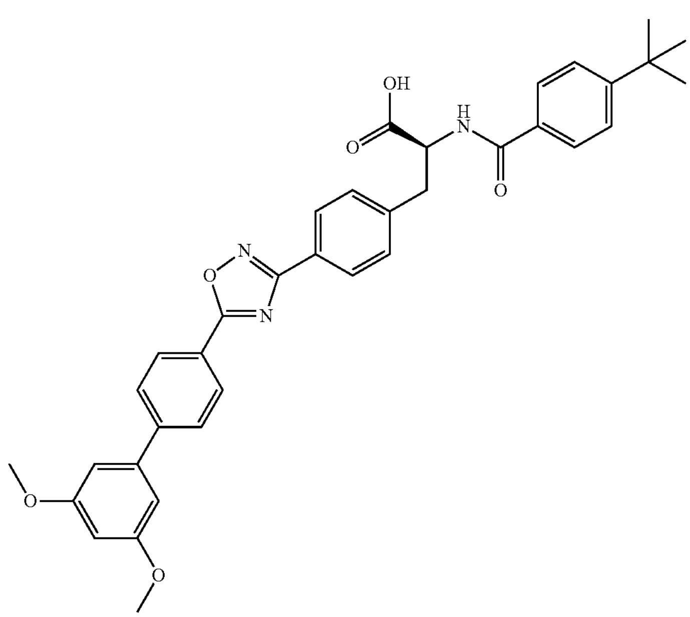 [SMILES: COc1cc(OC)cc(-c2ccc(-c3nc(-c4ccc(C[C@H](NC(=O)c5ccc(C(C)(C)C)cc5)C(=O)O)cc4)no3)cc2)c1] | 26 | 10.53 | 2 |

TABLE 1-continued
| STRUCTURE | COMPOUND NUMBER | LCMS RETENTION TIME (min) | PURITY METHOD |
|---|---|---|---|
| 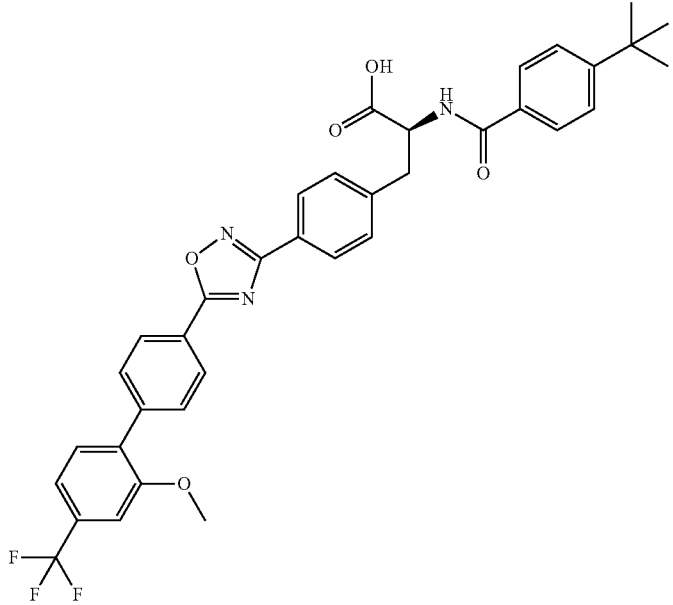 [SMILES: COc1cc(C(F)(F)F)ccc1-c1ccc(-c2nc(-c3ccc(C[C@H](NC(=O)c4ccc(C(C)(C)C)cc4)C(=O)O)cc3)no2)cc1] | 27 | 11.48 | 2 |
| 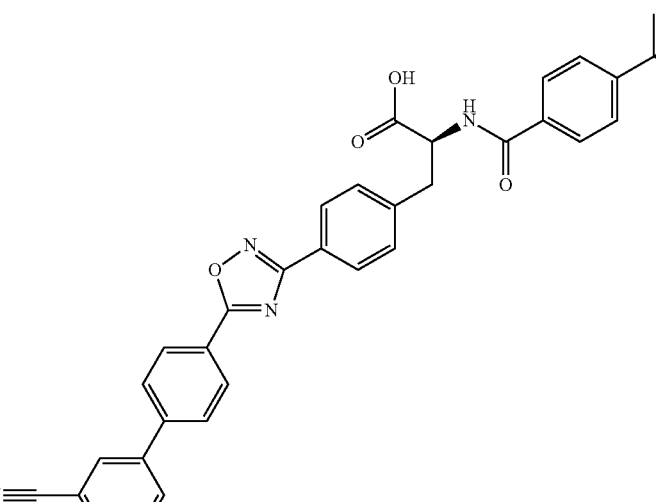 | 28 | 10.05 | 2 |

TABLE 1-continued

| STRUCTURE | COMPOUND NUMBER | LCMS RETENTION TIME (min) | PURITY METHOD |
|---|---|---|---|
| 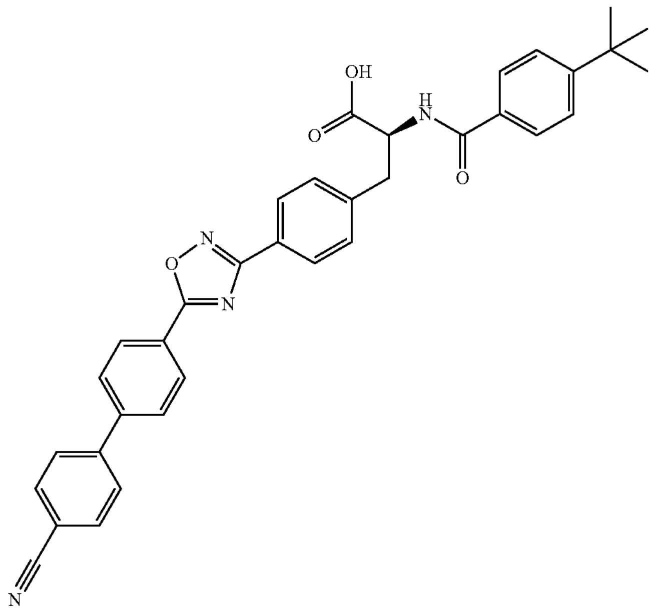 [SMILES: CC(C)(C)c1ccc(C(=O)N[C@@H](Cc2ccc(-c3noc(-c4ccc(-c5ccc(C#N)cc5)cc4)n3)cc2)C(=O)O)cc1] | 29 | 10.07 | 2 |
| 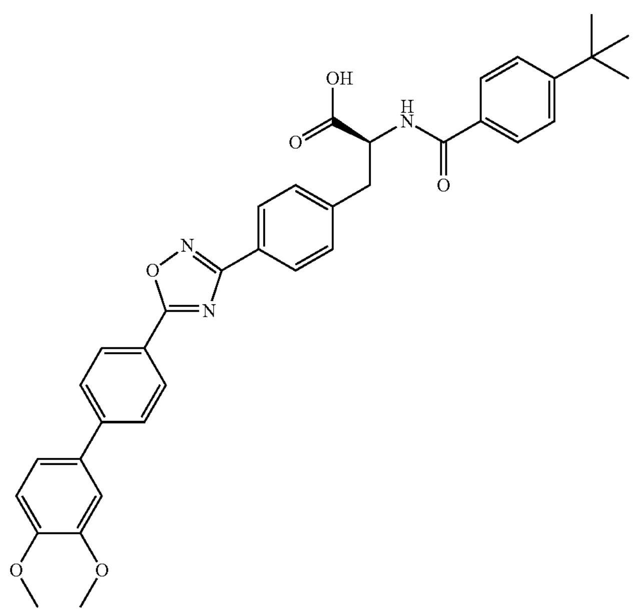 [SMILES: COc1ccc(-c2ccc(-c3nc(-c4ccc(C[C@H](NC(=O)c5ccc(C(C)(C)C)cc5)C(=O)O)cc4)no3)cc2)cc1OC] | 30 | 10.03 | 2 |

TABLE 1-continued
| STRUCTURE | COMPOUND NUMBER | LCMS RETENTION TIME (min) | PURITY METHOD |
|---|---|---|---|
| 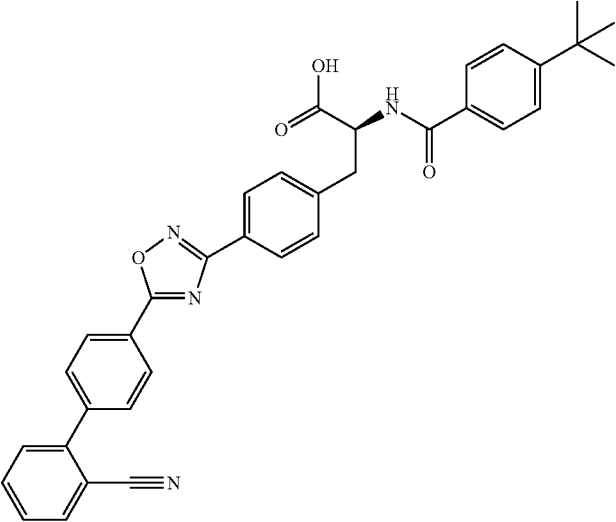 [SMILES: CC(C)(C)c1ccc(C(=O)N[C@@H](Cc2ccc(-c3noc(-c4ccc(-c5ccccc5C#N)cc4)n3)cc2)C(=O)O)cc1] | 31 | 9.83 | 2 |
| 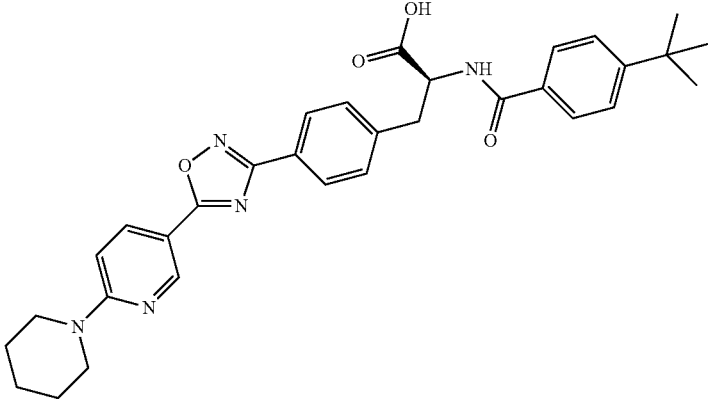 [SMILES: CC(C)(C)c1ccc(C(=O)N[C@@H](Cc2ccc(-c3noc(-c4ccc(N5CCCCC5)nc4)n3)cc2)C(=O)O)cc1] | 32 | 10.77 | 2 |
| 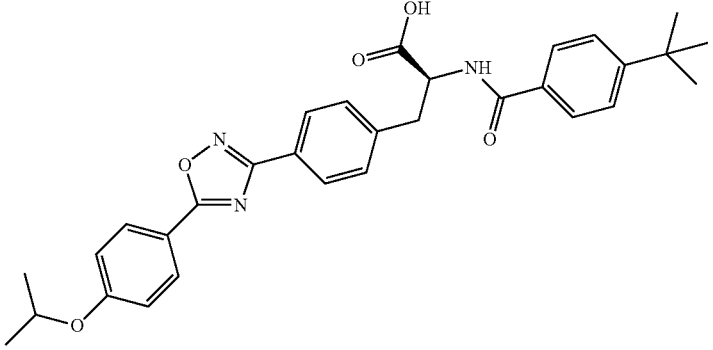 [SMILES: CC(C)Oc1ccc(-c2nc(-c3ccc(C[C@H](NC(=O)c4ccc(C(C)(C)C)cc4)C(=O)O)cc3)no2)cc1] | 33 | 10.75 | 2 |

TABLE 1-continued
| STRUCTURE | COMPOUND NUMBER | LCMS RETENTION TIME (min) | PURITY METHOD |
|---|---|---|---|
| 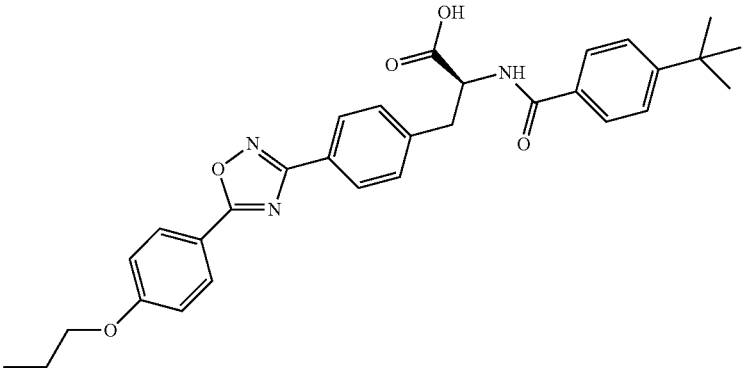 [SMILES: CCCOc1ccc(-c2nc(-c3ccc(C[C@H](NC(=O)c4ccc(C(C)(C)C)cc4)C(=O)O)cc3)no2)cc1] | 34 | 11.00 | 2 |
| 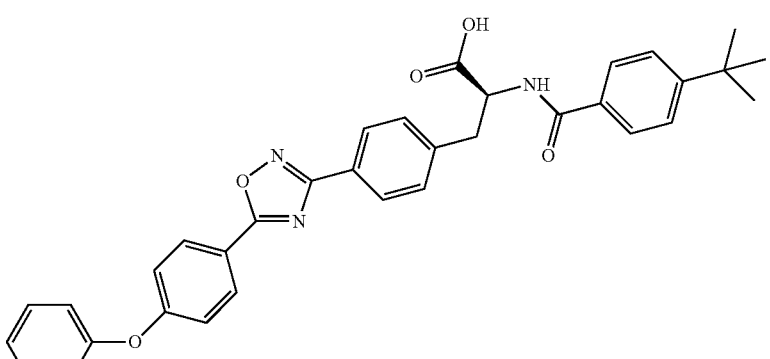 | 35 | 11.09 | 2 |
| 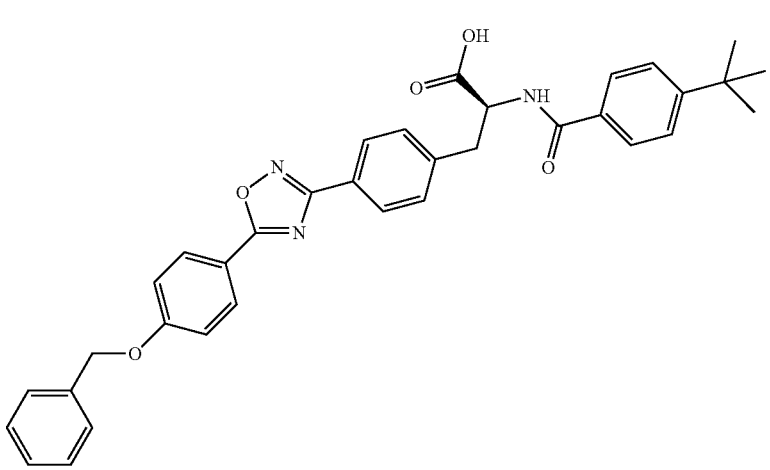 [SMILES: CC(C)(C)c1ccc(C(=O)N[C@@H](Cc2ccc(-c3noc(-c4ccc(OCc5ccccc5)cc4)n3)cc2)C(=O)O)cc1] | 36 | 9.19 | 2 |

TABLE 1-continued

| STRUCTURE | COMPOUND NUMBER | LCMS RETENTION TIME (min) | PURITY METHOD |
|---|---|---|---|
| 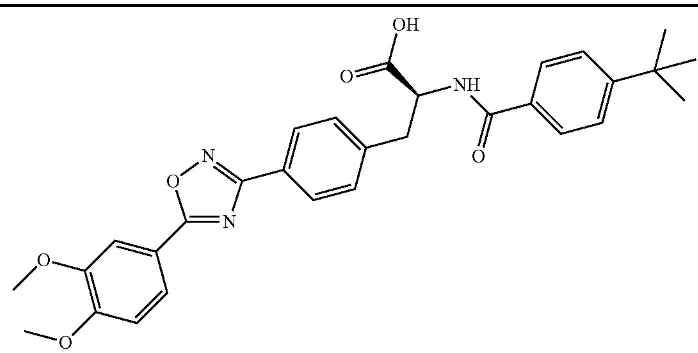 | 37 | 10.98 | 2 |
| 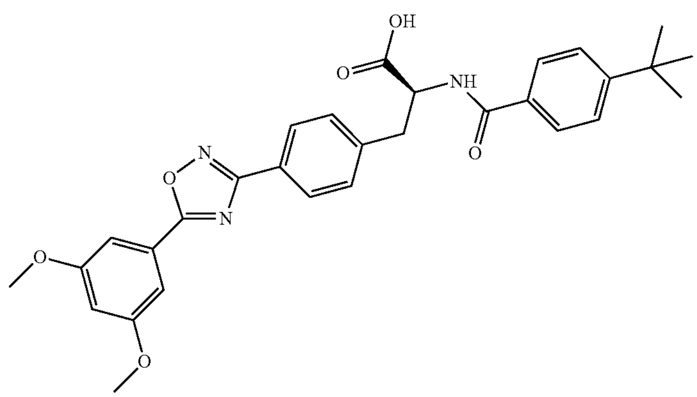 [SMILES: COc1cc(OC)cc(-c2nc(-c3ccc(C[C@H](NC(=O)c4ccc(C(C)(C)C)cc4)C(=O)O)cc3)no2)c1] | 38 | 9.93 | 2 |
| 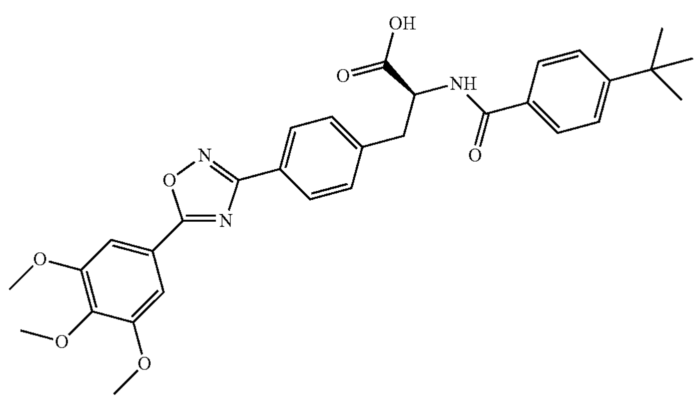 [SMILES: COc1cc(-c2nc(-c3ccc(C[C@H](NC(=O)c4ccc(C(C)(C)C)cc4)C(=O)O)cc3)no2)cc(OC)c1OC] | 39 | 9.30 | 2 |
| 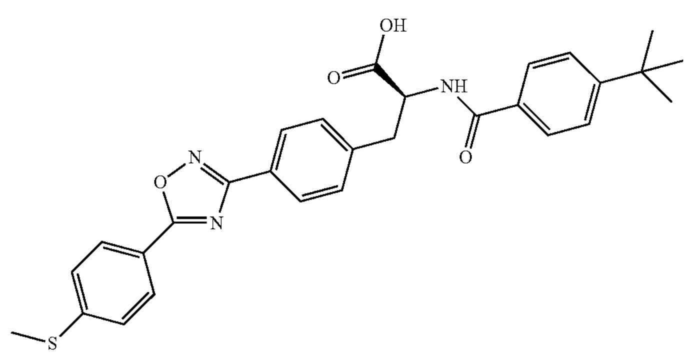 [SMILES: CSc1ccc(-c2nc(-c3ccc(C[C@H](NC(=O)c4ccc(C(C)(C)C)cc4)C(=O)O)cc3)no2)cc1] | 40 | 9.87 | 2 |

TABLE 1-continued

| STRUCTURE | COMPOUND NUMBER | LCMS RETENTION TIME (min) | PURITY METHOD |
|---|---|---|---|
| 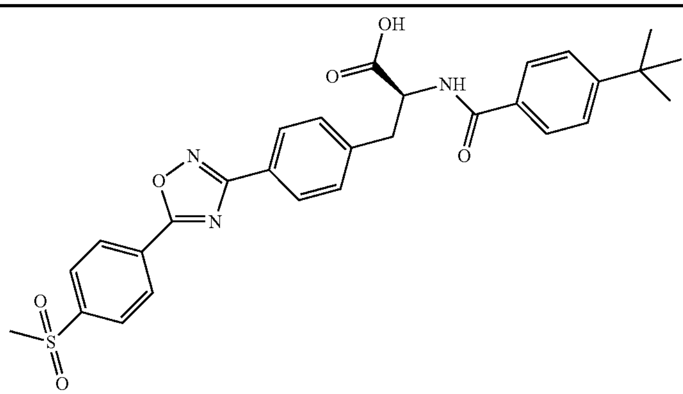 | 41 | 8.29 | 2 |
| 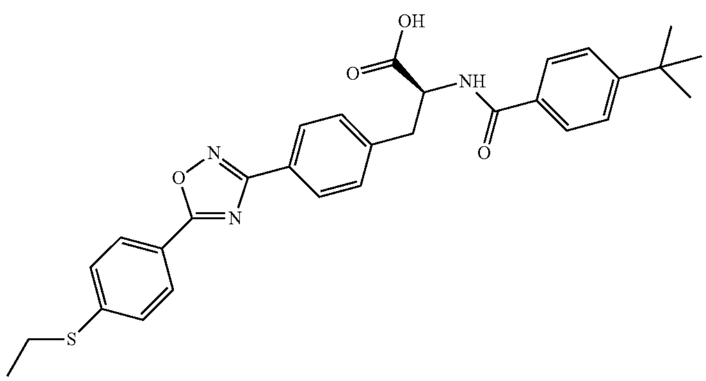 [SMILES: CCSc1ccc(-c2nc(-c3ccc(C[C@H](NC(=O)c4ccc(C(C)(C)C)cc4)C(=O)O)cc3)no2)cc1] | 42 | 10.32 | 2 |
| 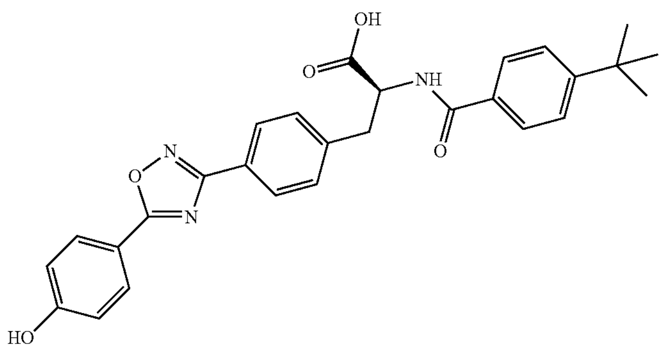 [SMILES: CC(C)(C)c1ccc(C(=O)N[C@@H](Cc2ccc(-c3noc(-c4ccc(O)cc4)n3)cc2)C(=O)O)cc1] | 43 | 8.20 | 2 |
| 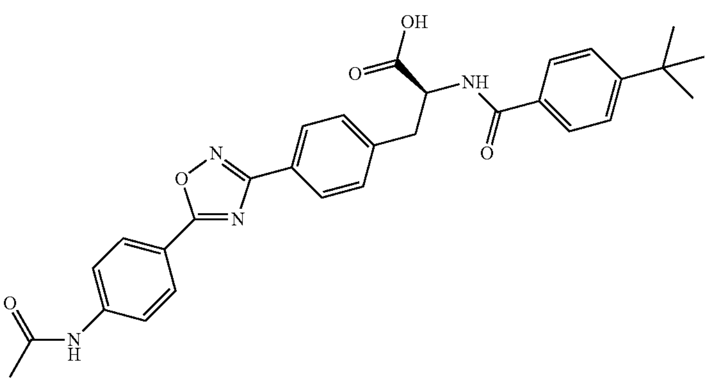 [SMILES: CC(=O)Nc1ccc(-c2nc(-c3ccc(C[C@H](NC(=O)c4ccc(C(C)(C)C)cc4)C(=O)O)cc3)no2)cc1] | 44 | 8.14 | 2 |

TABLE 1-continued

| STRUCTURE | COMPOUND NUMBER | LCMS RETENTION TIME (min) | PURITY METHOD |
|---|---|---|---|
| 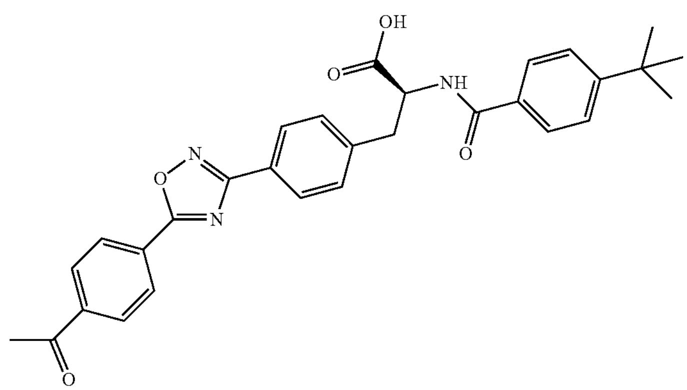 [SMILES: CC(=O)c1ccc(-c2nc(-c3ccc(C[C@H](NC(=O)c4ccc(C(C)(C)C)cc4)C(=O)O)cc3)no2)cc1] | 45 | 9.29 | 2 |
| 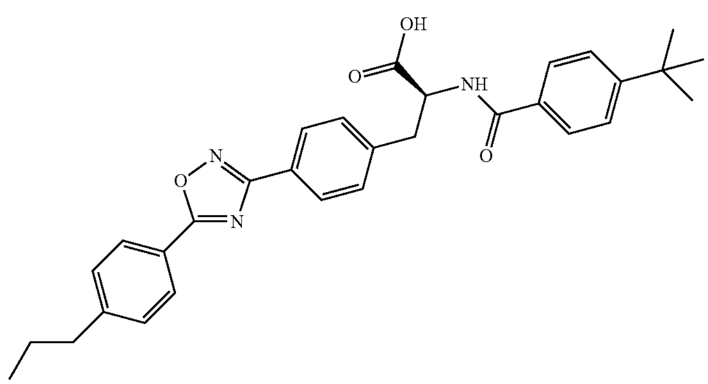 [SMILES: CCCc1ccc(-c2nc(-c3ccc(C[C@H](NC(=O)c4ccc(C(C)(C)C)cc4)C(=O)O)cc3)no2)cc1] | 46 | 11.40 | 2 |
| 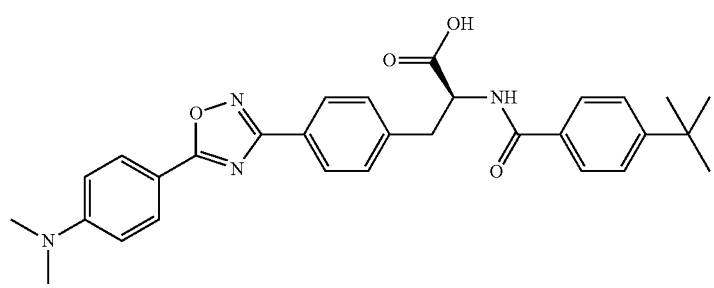 [SMILES: CN(C)c1ccc(-c2nc(-c3ccc(C[C@H](NC(=O)c4ccc(C(C)(C)C)cc4)C(=O)O)cc3)no2)cc1] | 47 | 10.07 | 2 |
| 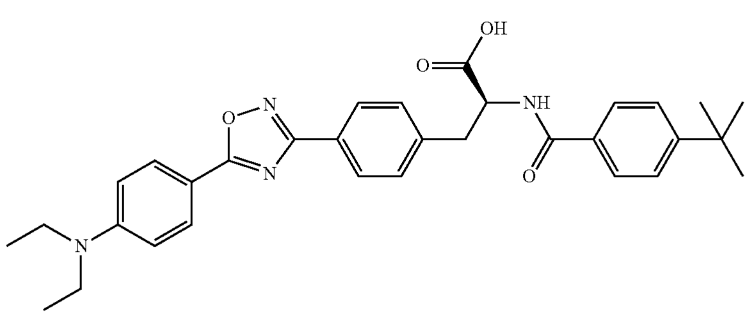 [SMILES: CCN(CC)c1ccc(-c2nc(-c3ccc(C[C@H](NC(=O)c4ccc(C(C)(C)C)cc4)C(=O)O)cc3)no2)cc1] | 48 | 10.38 | 2 |

TABLE 1-continued
| STRUCTURE | COMPOUND NUMBER | LCMS RETENTION TIME (min) | PURITY METHOD |
|---|---|---|---|
| 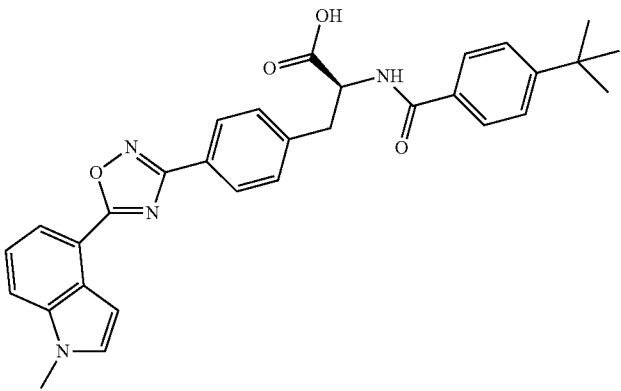 [SMILES: Cn1ccc2c(-c3nc(-c4ccc(C[C@H](NC(=O)c5ccc(C(C)(C)C)cc5)C(=O)O)cc4)no3)cccc21] | 49 | 9.78 | 2 |
| 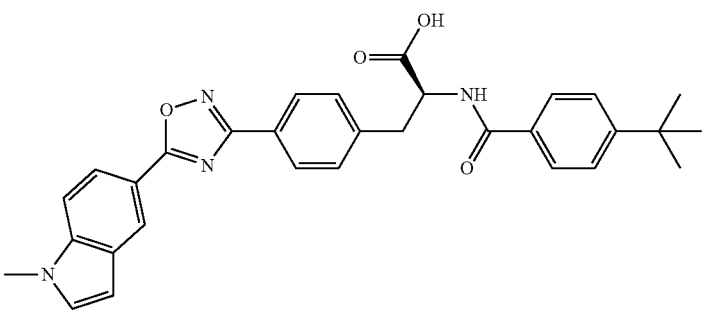 [SMILES: Cn1ccc2cc(-c3nc(-c4ccc(C[C@H](NC(=O)c5ccc(C(C)(C)C)cc5)C(=O)O)cc4)no3)ccc21] | 50 | 9.79 | 2 |
| 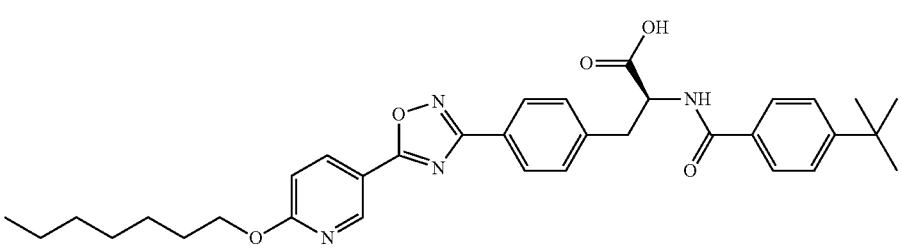 [SMILES: CCCCCCCOc1ccc(-c2nc(-c3ccc(C[C@H](NC(=O)c4ccc(C(C)(C)C)cc4)C(=O)O)cc3)no2)cn1] | 51 | 11.93 | 2 |
| 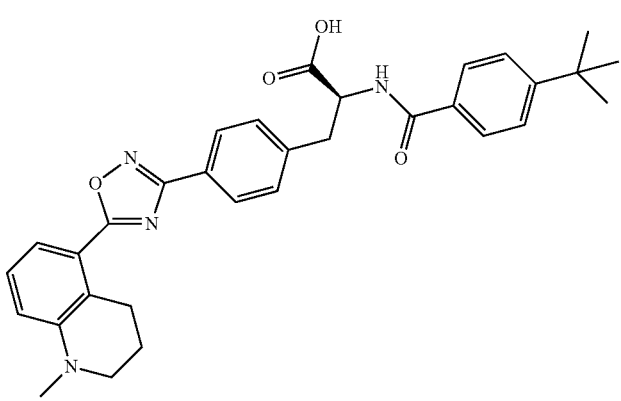 [SMILES: CN1CCCc2c(-c3nc(-c4ccc(C[C@H](NC(=O)c5ccc(C(C)(C)C)cc5)C(=O)O)cc4)no3)cccc21] | 52 | 10.36 | 2 |

TABLE 1-continued

| STRUCTURE | COMPOUND NUMBER | LCMS RETENTION TIME (min) | PURITY METHOD |
|---|---|---|---|
| 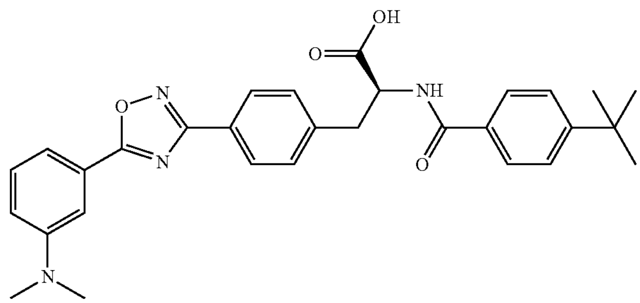 [SMILES: CN(C)c1cccc(-c2nc(-c3ccc(C[C@H](NC(=O)c4ccc(C(C)(C)C)cc4)C(=O)O)cc3)no2)c1] | 53 | 10.23 | 2 |
| 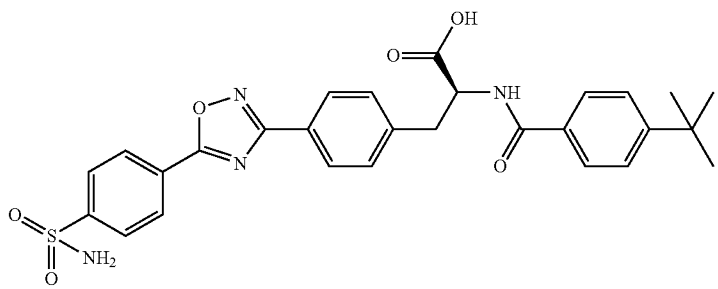 [SMILES: CC(C)(C)c1ccc(C(=O)N[C@@H](Cc2ccc(-c3noc(-c4ccc(S(N)(=O)=O)cc4)n3)cc2)C(=O)O)cc1] | 54 | 7.85 | 2 |
| 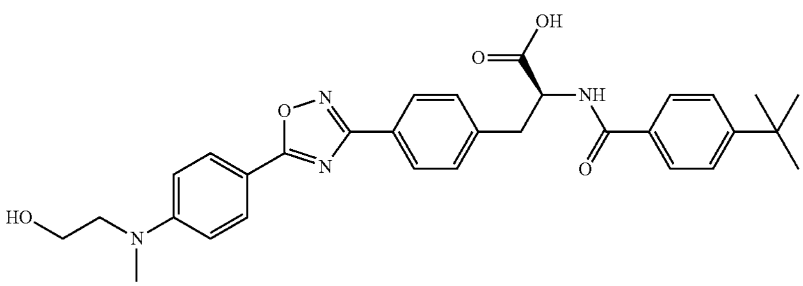 [SMILES: CN(CCO)c1ccc(-c2nc(-c3ccc(C[C@H](NC(=O)c4ccc(C(C)(C)C)cc4)C(=O)O)cc3)no2)cc1] | 55 | 8.17 | 2 |
| 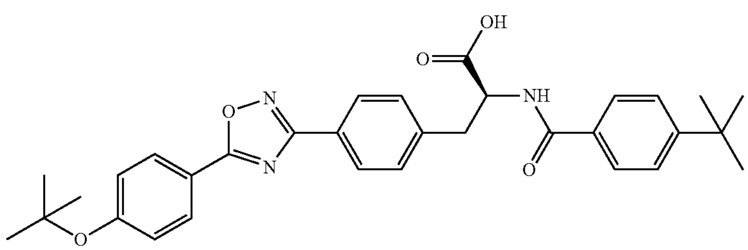 [SMILES: CC(C)(C)Oc1ccc(-c2nc(-c3ccc(C[C@H](NC(=O)c4ccc(C(C)(C)C)cc4)C(=O)O)cc3)no2)cc1] | 56 | 10.44 | 2 |
| 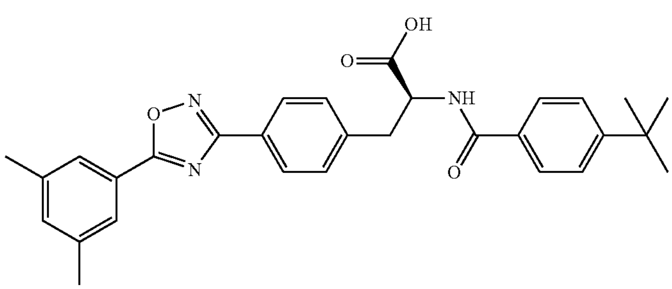 [SMILES: Cc1cc(C)cc(-c2nc(-c3ccc(C[C@H](NC(=O)c4ccc(C(C)(C)C)cc4)C(=O)O)cc3)no2)c1] | 57 | 10.46 | 2 |

TABLE 1-continued

| STRUCTURE | COMPOUND NUMBER | LCMS RETENTION TIME (min) | PURITY METHOD |
|---|---|---|---|
| 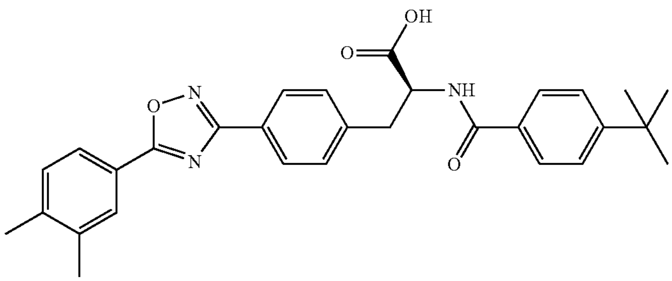 [SMILES: Cc1ccc(-c2nc(-c3ccc(C[C@H](NC(=O)c4ccc(C(C)(C)C)cc4)C(=O)O)cc3)no2)cc1C] | 58 | 10.25 | 2 |
| 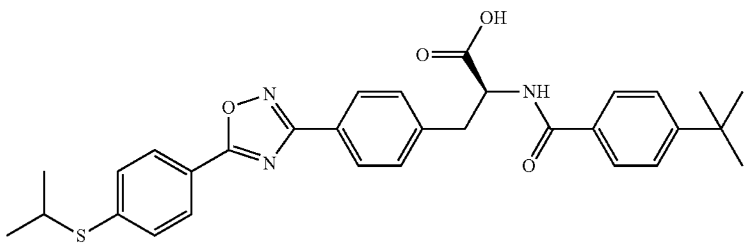 [SMILES: CC(C)Sc1ccc(-c2nc(-c3ccc(C[C@H](NC(=O)c4ccc(C(C)(C)C)cc4)C(=O)O)cc3)no2)cc1] | 59 | 10.85 | 2 |
| 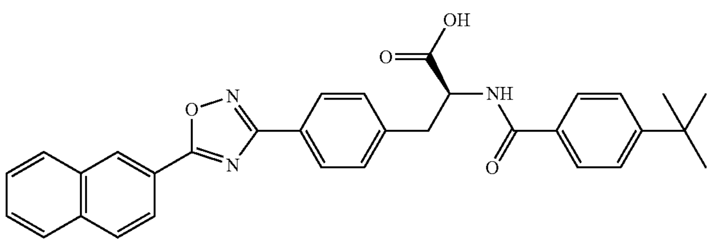 [SMILES: CC(C)(C)c1ccc(C(=O)N[C@@H](Cc2ccc(-c3noc(-c4ccc5ccccc5c4)n3)cc2)C(=O)O)cc1] | 60 | 10.33 | 2 |
| 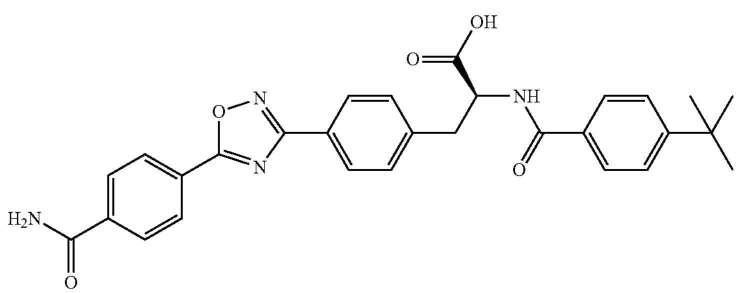 [SMILES: CC(C)(C)c1ccc(C(=O)N[C@@H](Cc2ccc(-c3noc(-c4ccc(C(N)=O)cc4)n3)cc2)C(=O)O)cc1] | 61 | 7.66 | 2 |
| 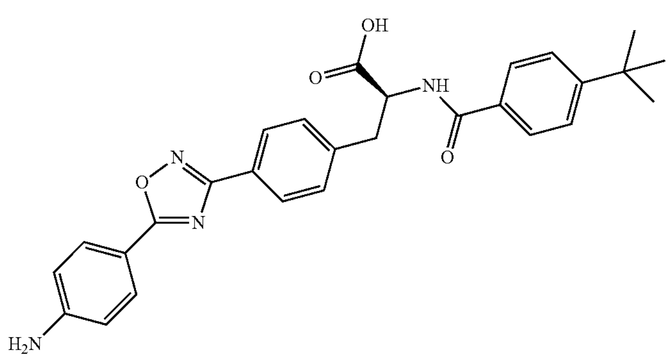 [SMILES: CC(C)(C)c1ccc(C(=O)N[C@@H](Cc2ccc(-c3noc(-c4ccc(N)cc4)n3)cc2)C(=O)O)cc1] | 62 | 8.28 | 2 |

TABLE 1-continued

| STRUCTURE | COMPOUND NUMBER | LCMS RETENTION TIME (min) | PURITY METHOD |
|---|---|---|---|
| 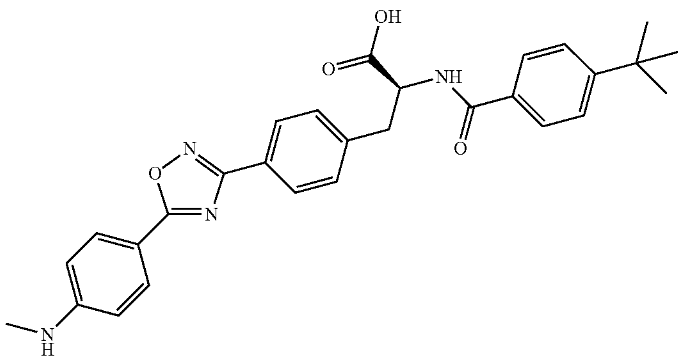 [SMILES: CNc1ccc(-c2nc(-c3ccc(C[C@H](NC(=O)c4ccc(C(C)(C)C)cc4)C(=O)O)cc3)no2)cc1] | 63 | 9.34 | 2 |
| 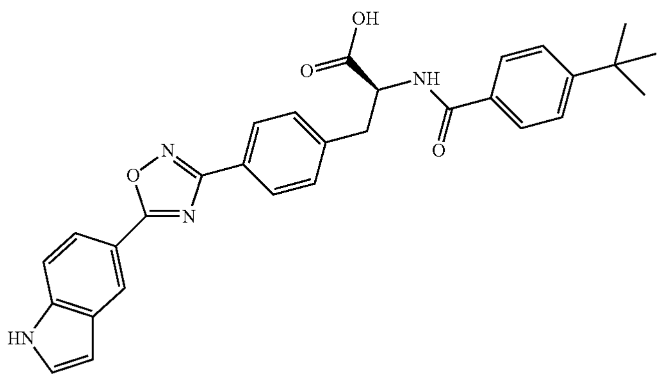 [SMILES: CC(C)(C)c1ccc(C(=O)N[C@@H](Cc2ccc(-c3noc(-c4ccc5[nH]ccc5c4)n3)cc2)C(=O)O)cc1] | 64 | 9.05 | 2 |
| 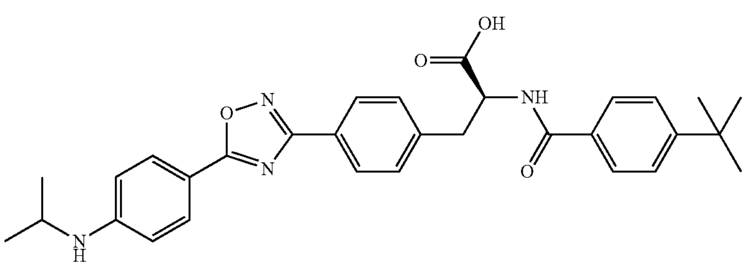 [SMILES: CC(C)Nc1ccc(-c2nc(-c3ccc(C[C@H](NC(=O)c4ccc(C(C)(C)C)cc4)C(=O)O)cc3)no2)cc1] | 65 | 9.69 | 2 |
| 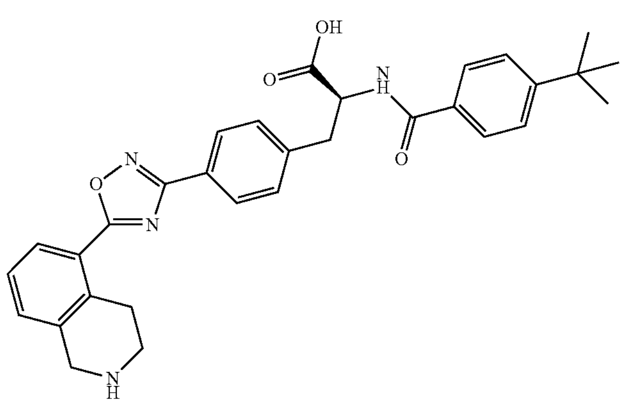 [SMILES: CC(C)(C)c1ccc(C(=O)N[C@@H](Cc2ccc(-c3noc(-c4cccc5c4CCNC5)n3)cc2)C(=O)O)cc1] | 66 | 6.46 | 2 |

TABLE 1-continued

| STRUCTURE | COMPOUND NUMBER | LCMS RETENTION TIME (min) | PURITY METHOD |
|---|---|---|---|
| 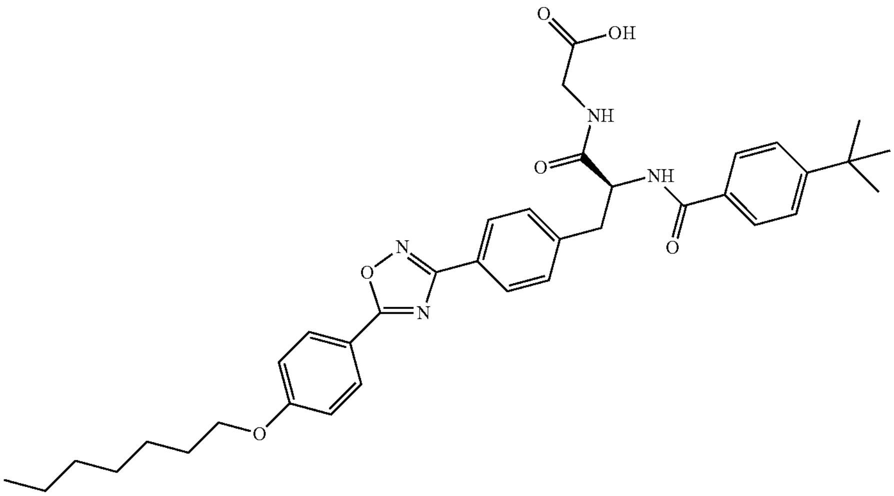 [SMILES: CCCCCCCOc1ccc(-c2nc(-c3ccc(C[C@H](NC(=O)c4ccc(C(C)(C)C)cc4)C(=O)NCC(=O)O)cc3)no2)cc1] | 67 | 11.51 | 2 |
| 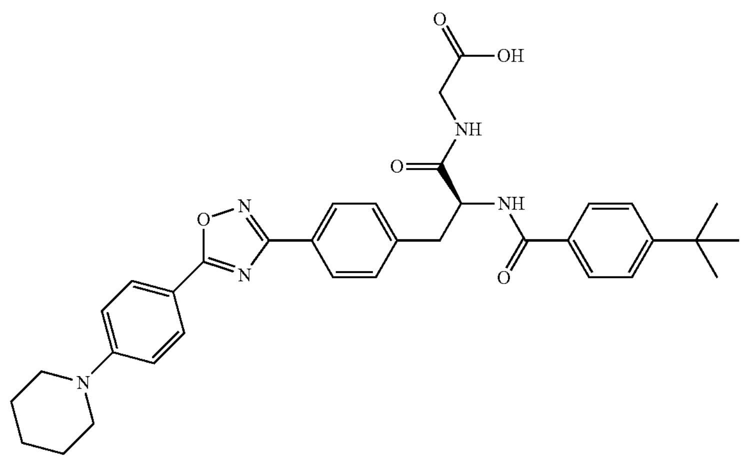 [SMILES: CC(C)(C)c1ccc(C(=O)N[C@@H](Cc2ccc(-c3noc(-c4ccc(N5CCCCC5)cc4)n3)cc2)C(=O)NCC(=O)O)cc1] | 68 | 10.10 | 2 |
| 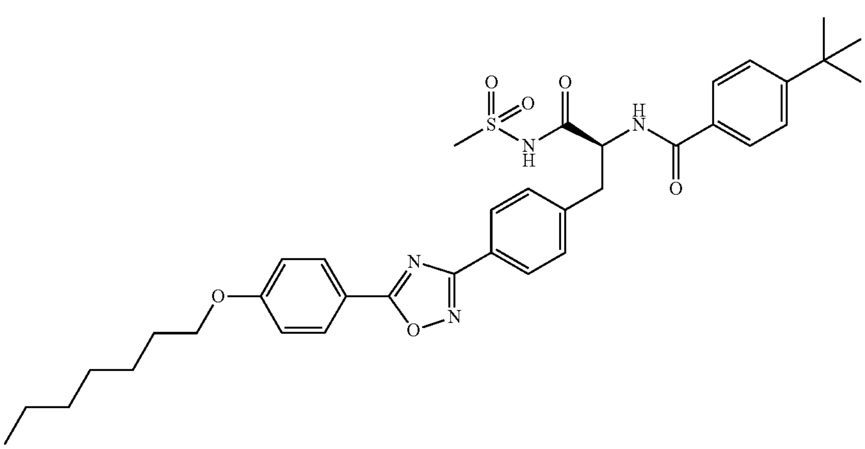 [SMILES: CCCCCCCOc1ccc(-c2nc(-c3ccc(C[C@H](NC(=O)c4ccc(C(C)(C)C)cc4)C(=O)NS(C)(=O)=O)cc3)no2)cc1] | 69 | 11.90 | 2 |

TABLE 1-continued
| STRUCTURE | COMPOUND NUMBER | LCMS RETENTION TIME (min) | PURITY METHOD |
|---|---|---|---|
| 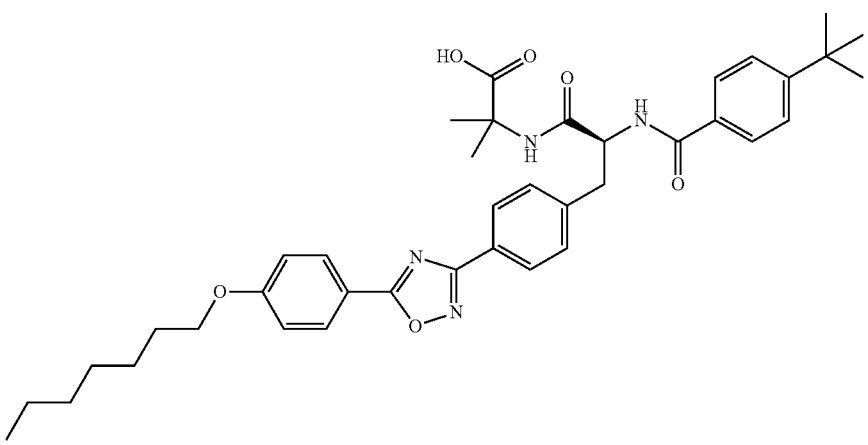 [SMILES: CCCCCCCOc1ccc(-c2nc(-c3ccc(C[C@H](NC(=O)c4ccc(C(C)(C)C)cc4)C(=O)NC(C)(C)C(=O)O)cc3)no2)cc1] | 70 | 11.67 | 2 |
| 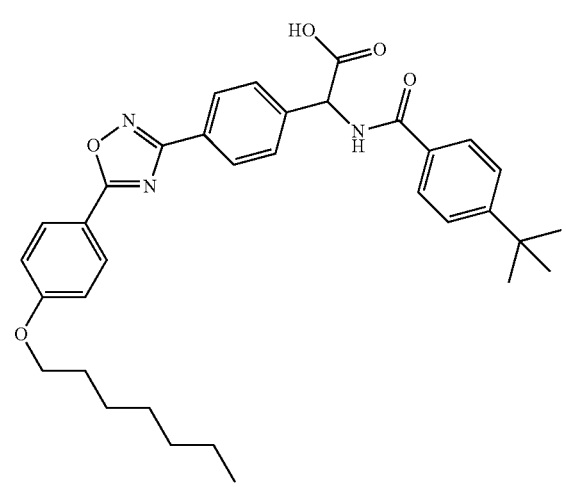 [SMILES: CCCCCCCOc1ccc(-c2nc(-c3ccc(C(NC(=O)c4ccc(C(C)(C)C)cc4)C(=O)O)cc3)no2)cc1] | 71 | 11.05 | 9 |
| 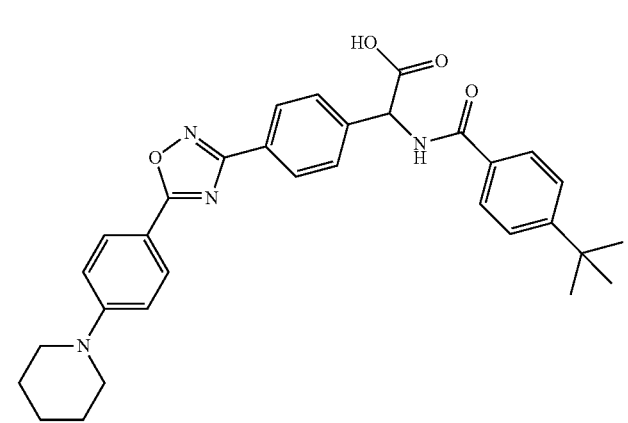 [SMILES: CC(C)(C)c1ccc(C(=O)NC(C(=O)O)c2ccc(-c3noc(-c4ccc(N5CCCCC5)cc4)n3)cc2)cc1] | 72 | 9.22 | 9 |

TABLE 1-continued

| STRUCTURE | COMPOUND NUMBER | LCMS RETENTION TIME (min) | PURITY METHOD |
|---|---|---|---|
| 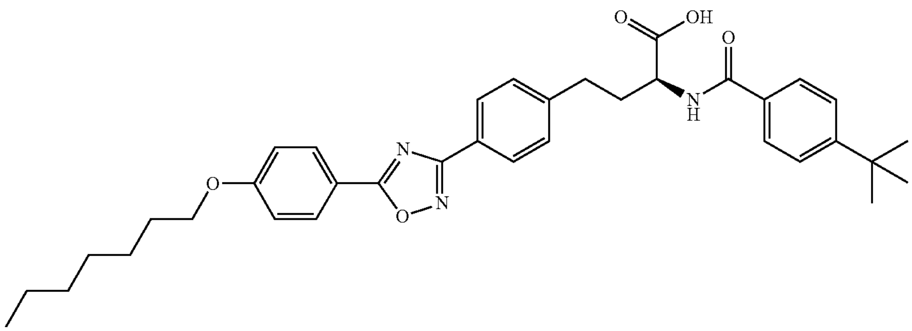 [SMILES: CCCCCCCOc1ccc(-c2nc(-c3ccc(CC[C@H](NC(=O)c4ccc(C(C)(C)C)cc4)C(=O)O)cc3)no2)cc1] | 73 | 11.42 | 9 |
| 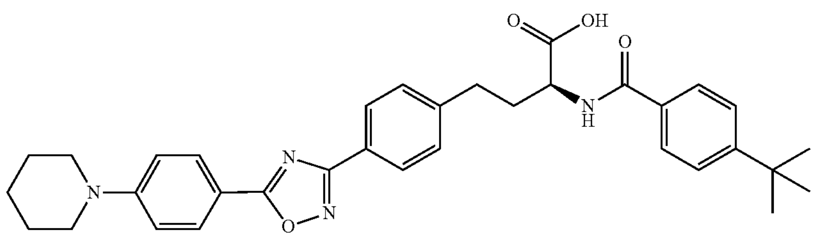 [SMILES: CC(C)(C)c1ccc(C(=O)N[C@@H](CCc2ccc(-c3noc(-c4ccc(N5CCCCC5)cc4)n3)cc2)C(=O)O)cc1] | 74 | 9.61 | 9 |
| 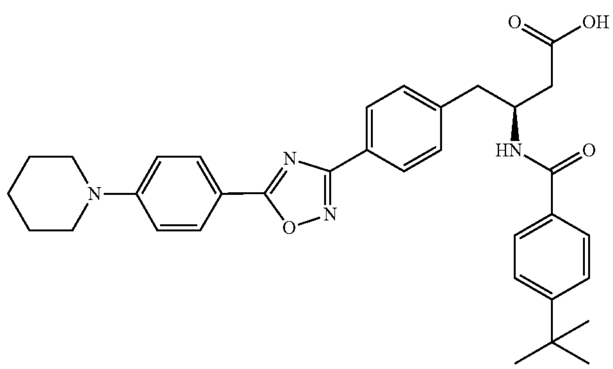 [SMILES: CC(C)(C)c1ccc(C(=O)N[C@H](CC(=O)O)Cc2ccc(-c3noc(-c4ccc(N5CCCCC5)cc4)n3)cc2)cc1] | 75 | 9.13 | 9 |
| 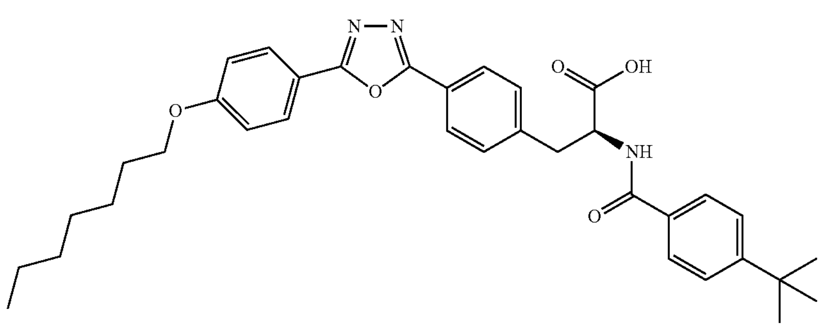 [SMILES: CCCCCCCOc1ccc(-c2nnc(-c3ccc(C[C@H](NC(=O)c4ccc(C(C)(C)C)cc4)C(=O)O)cc3)o2)cc1] | 76 | 10.06 | 9 |

TABLE 1-continued

| STRUCTURE | COMPOUND NUMBER | LCMS RETENTION TIME (min) | PURITY METHOD |
|---|---|---|---|
| 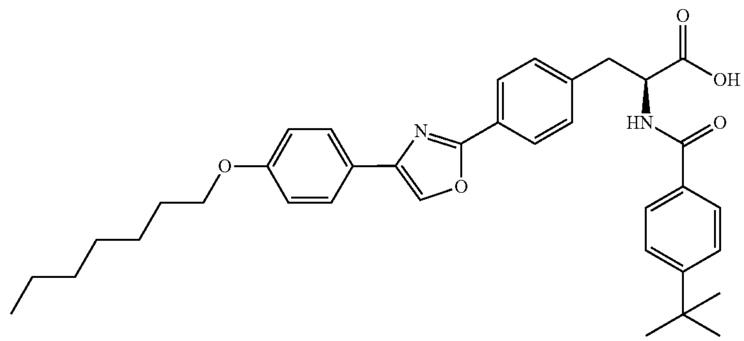 [SMILES: CCCCCCCOc1ccc(-c2coc(-c3ccc(C[C@H](NC(=O)c4ccc(C(C)(C)C)cc4)C(=O)O)cc3)n2)cc1] | 77 | 10.87 | 9 |
| 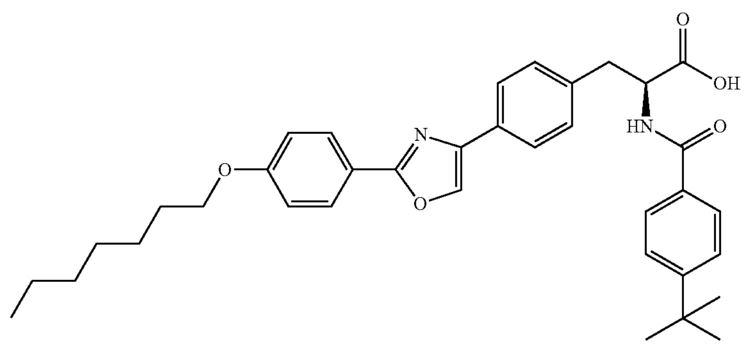 [SMILES: CCCCCCCOc1ccc(-c2nc(-c3ccc(C[C@H](NC(=O)c4ccc(C(C)(C)C)cc4)C(=O)O)cc3)co2)cc1] | 78 | 11.03 | 9 |
| 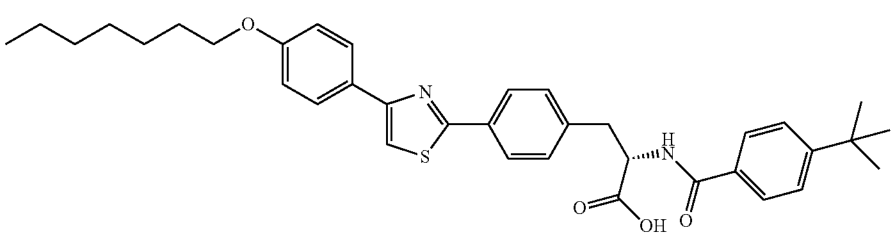 [SMILES: CCCCCCCOc1ccc(-c2csc(-c3ccc(C[C@H](NC(=O)c4ccc(C(C)(C)C)cc4)C(=O)O)cc3)n2)cc1] | 79 | 11.30 | 9 |
| 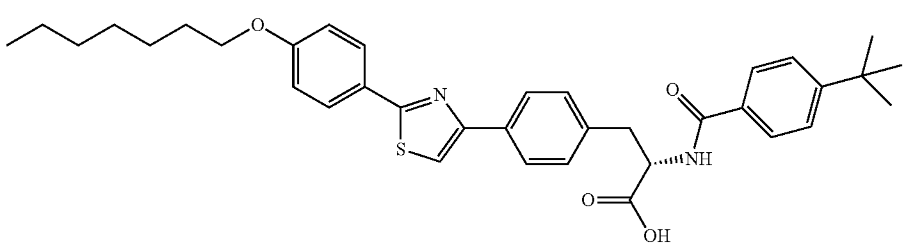 [SMILES: CCCCCCCOc1ccc(-c2nc(-c3ccc(C[C@H](NC(=O)c4ccc(C(C)(C)C)cc4)C(=O)O)cc3)cs2)cc1] | 80 | 11.57 | 9 |

TABLE 1-continued

| STRUCTURE | COMPOUND NUMBER | LCMS RETENTION TIME (min) | PURITY METHOD |
|---|---|---|---|
| 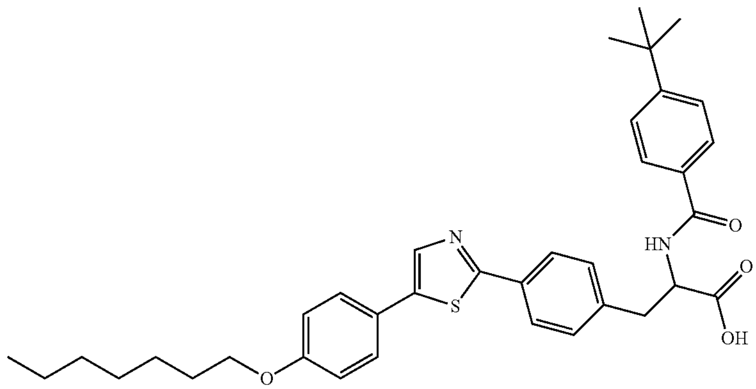 [SMILES: CCCCCCCOc1ccc(-c2cnc(-c3ccc(CC(NC(=O)c4ccc(C(C)(C)C)cc4)C(=O)O)cc3)s2)cc1] | 81 | 11.23 | 9 |
| 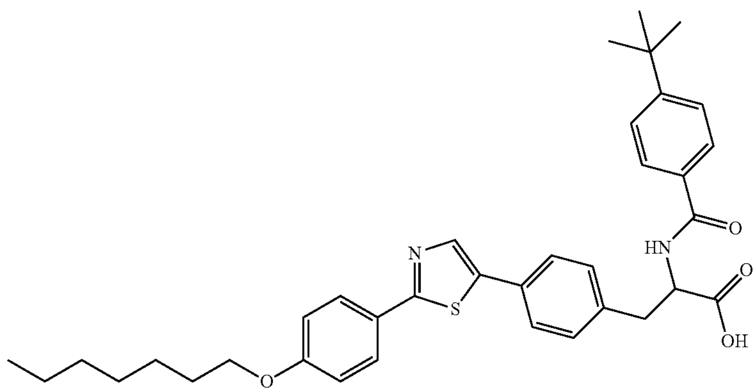 [SMILES: CCCCCCCOc1ccc(-c2ncc(-c3ccc(CC(NC(=O)c4ccc(C(C)(C)C)cc4)C(=O)O)cc3)s2)cc1] | 82 | 11.21 | 9 |
| 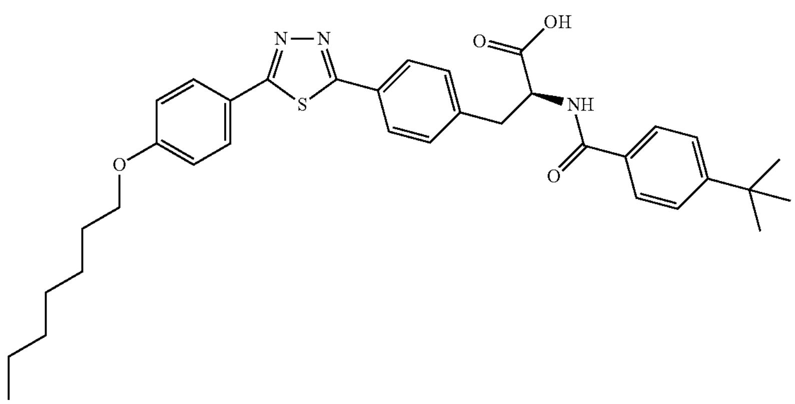 [SMILES: CCCCCCCOc1ccc(-c2nnc(-c3ccc(C[C@H](NC(=O)c4ccc(C(C)(C)C)cc4)C(=O)O)cc3)s2)cc1] | 83 | 10.60 | 9 |
| 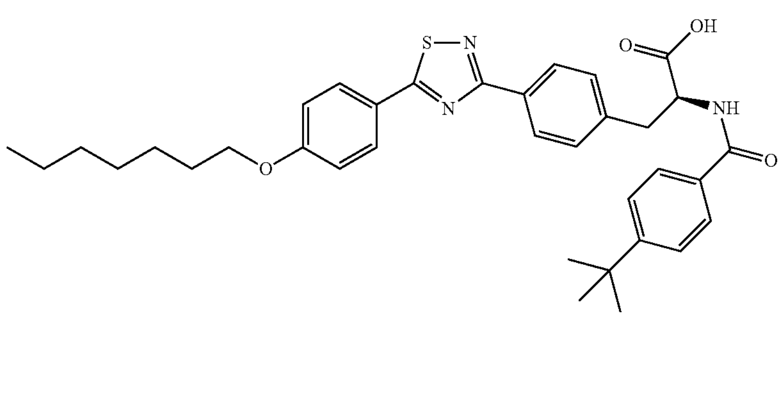 [SMILES: CCCCCCCOc1ccc(-c2nc(-c3ccc(C[C@H](NC(=O)c4ccc(C(C)(C)C)cc4)C(=O)O)cc3)ns2)cc1] | 84 | 11.56 | 9 |

TABLE 1-continued

| STRUCTURE | COMPOUND NUMBER | LCMS RETENTION TIME (min) | PURITY METHOD |
|---|---|---|---|
| 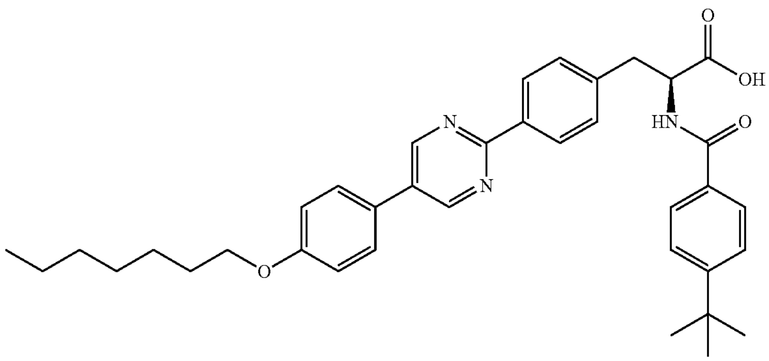 [SMILES: CCCCCCCOc1ccc(-c2cnc(-c3ccc(C[C@H](NC(=O)c4ccc(C(C)(C)C)cc4)C(=O)O)cc3)nc2)cc1] | 85 | 11.18 | 9 |
| 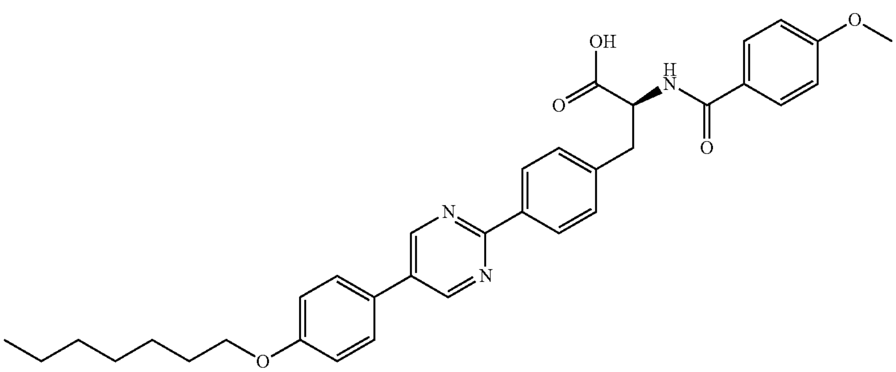 [SMILES: CCCCCCCOc1ccc(-c2cnc(-c3ccc(C[C@H](NC(=O)c4ccc(OC)cc4)C(=O)O)cc3)nc2)cc1] | 86 | 9.46 | 9 |
| 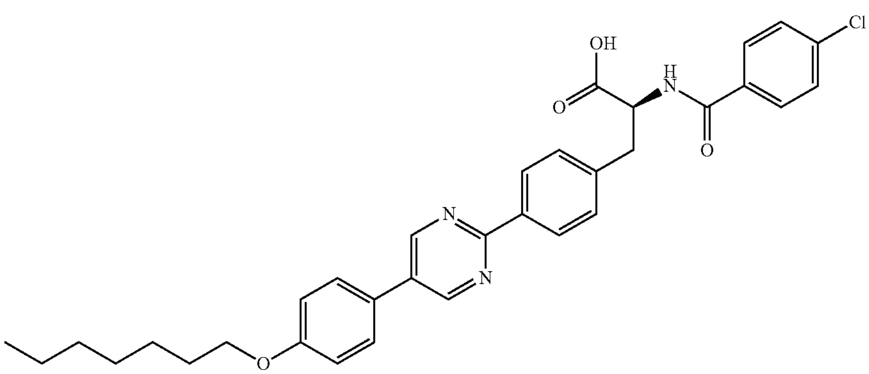 [SMILES: CCCCCCCOc1ccc(-c2cnc(-c3ccc(C[C@H](NC(=O)c4ccc(Cl)cc4)C(=O)O)cc3)nc2)cc1] | 87 | 10.09 | 9 |
| 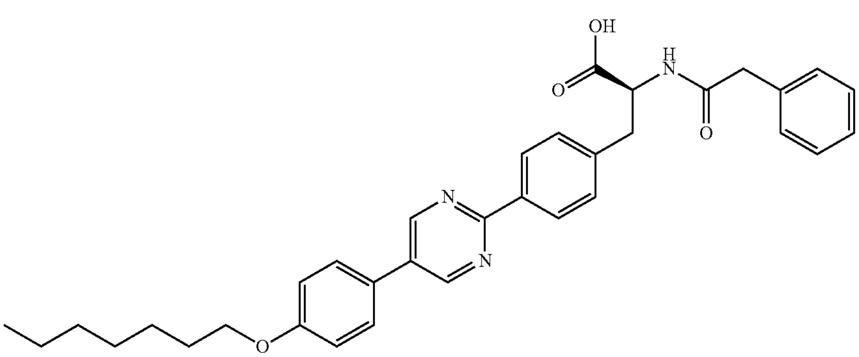 [SMILES: CCCCCCCOc1ccc(-c2cnc(-c3ccc(C[C@H](NC(=O)Cc4ccccc4)C(=O)O)cc3)nc2)cc1] | 88 | 9.51 | 9 |

TABLE 1-continued

| STRUCTURE | COMPOUND NUMBER | LCMS RETENTION TIME (min) | PURITY METHOD |
|---|---|---|---|
| 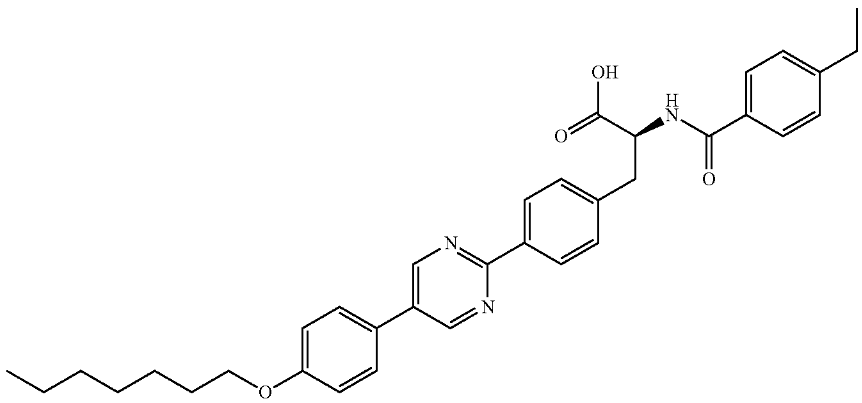 [SMILES: CCCCCCCOc1ccc(-c2cnc(-c3ccc(C[C@H](NC(=O)c4ccc(CC)cc4)C(=O)O)cc3)nc2)cc1] | 89 | 10.26 | 9 |
| 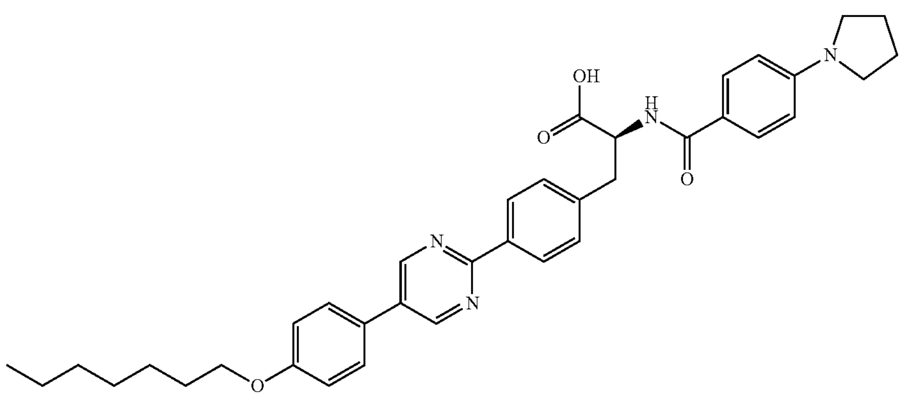 [SMILES: CCCCCCCOc1ccc(-c2cnc(-c3ccc(C[C@H](NC(=O)c4ccc(N5CCCC5)cc4)C(=O)O)cc3)nc2)cc1] | 90 | 10.33 | 9 |
| 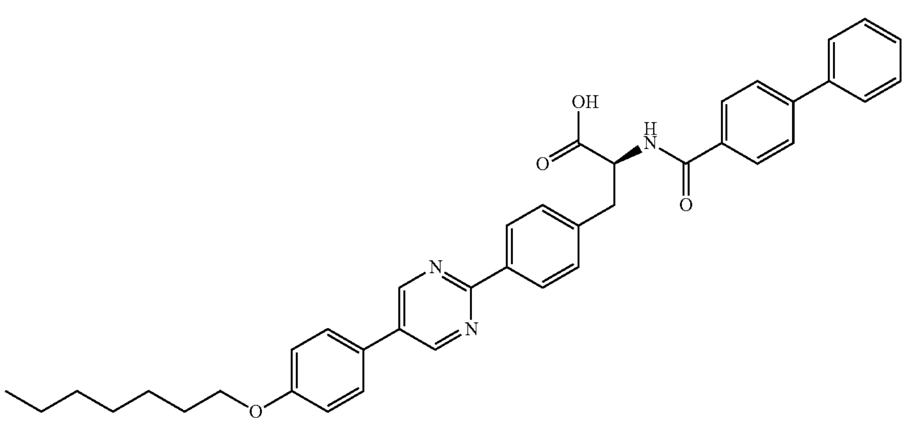 [SMILES: CCCCCCCOc1ccc(-c2cnc(-c3ccc(C[C@H](NC(=O)c4ccc(-c5ccccc5)cc4)C(=O)O)cc3)nc2)cc1] | 91 | 10.64 | 9 |

TABLE 1-continued
| STRUCTURE | COMPOUND NUMBER | LCMS RETENTION TIME (min) | PURITY METHOD |
|---|---|---|---|
| 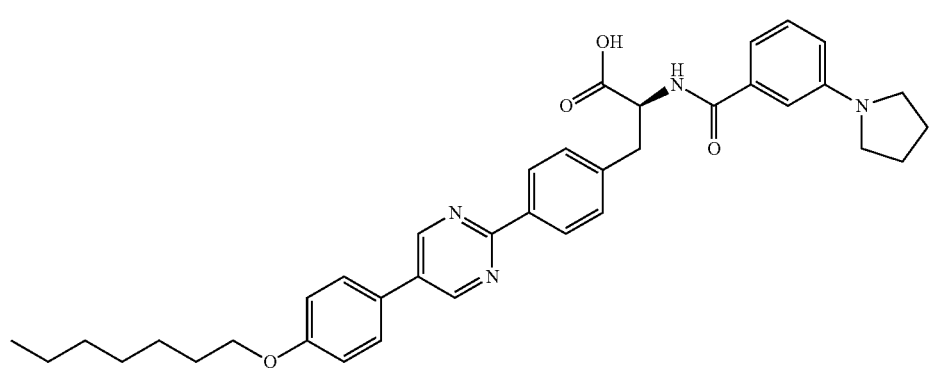 [SMILES: CCCCCCCOc1ccc(-c2cnc(-c3ccc(C[C@H](NC(=O)c4cccc(N5CCCC5)c4)C(=O)O)cc3)nc2)cc1] | 92 | 10.48 | 9 |
| 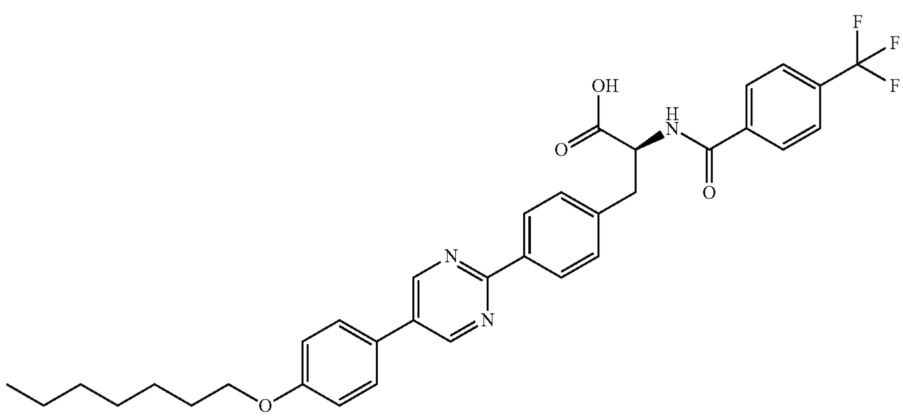 [SMILES: CCCCCCCOc1ccc(-c2cnc(-c3ccc(C[C@H](NC(=O)c4ccc(C(F)(F)F)cc4)C(=O)O)cc3)nc2)cc1] | 93 | 10.63 | 9 |
| 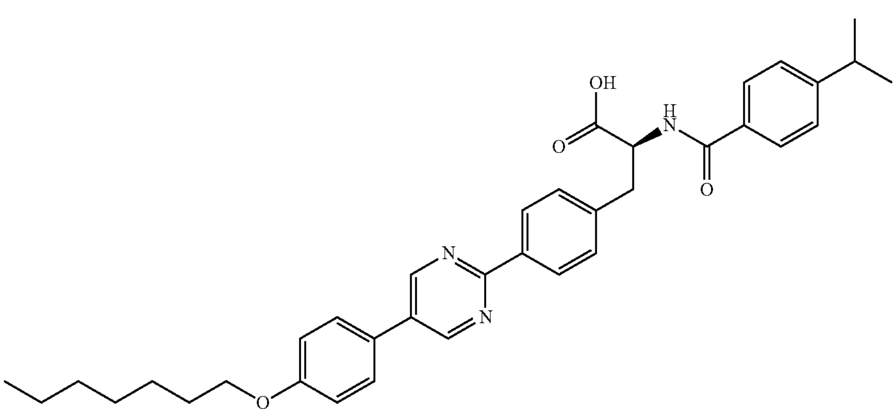 | 94 | 10.85 | 10 |

TABLE 1-continued

| STRUCTURE | COMPOUND NUMBER | LCMS RETENTION TIME (min) | PURITY METHOD |
|---|---|---|---|
| 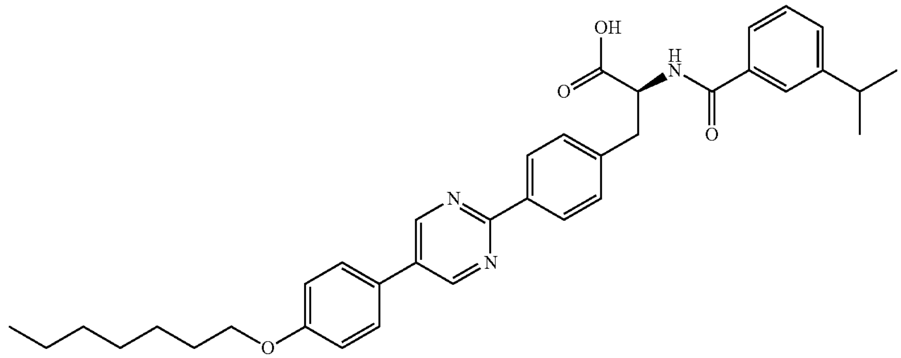 [SMILES: CCCCCCCOc1ccc(-c2cnc(-c3ccc(C[C@H](NC(=O)c4cccc(C(C)C)c4)C(=O)O)cc3)nc2)cc1] | 95 | 10.58 | 9 |
| 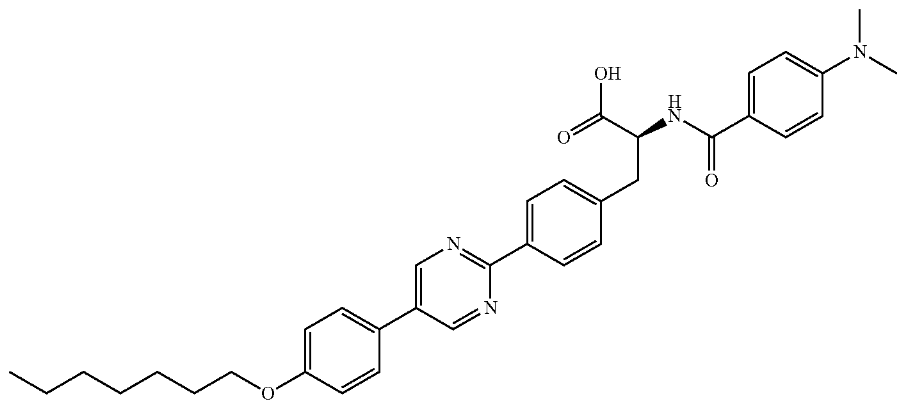 [SMILES: CCCCCCCOc1ccc(-c2cnc(-c3ccc(C[C@H](NC(=O)c4ccc(N(C)C)cc4)C(=O)O)cc3)nc2)cc1] | 96 | 9.69 | 9 |
| 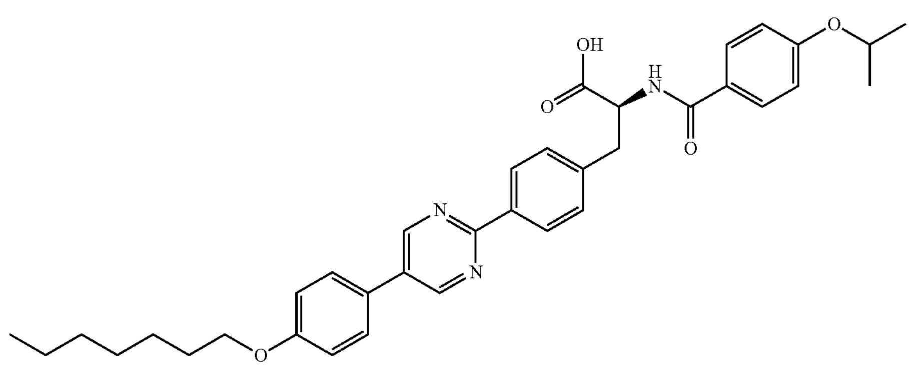 [SMILES: CCCCCCCOc1ccc(-c2cnc(-c3ccc(C[C@H](NC(=O)c4ccc(OC(C)C)cc4)C(=O)O)cc3)nc2)cc1] | 97 | 10.22 | 9 |
| 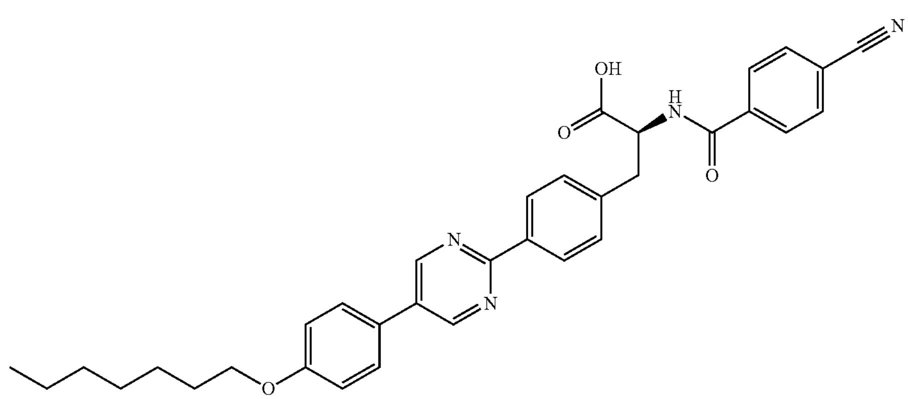 [SMILES: CCCCCCCOc1ccc(-c2cnc(-c3ccc(C[C@H](NC(=O)c4ccc(C#N)cc4)C(=O)O)cc3)nc2)cc1] | 98 | 9.36 | 9 |

TABLE 1-continued

| STRUCTURE | COMPOUND NUMBER | LCMS RETENTION TIME (min) | PURITY METHOD |
|---|---|---|---|
| 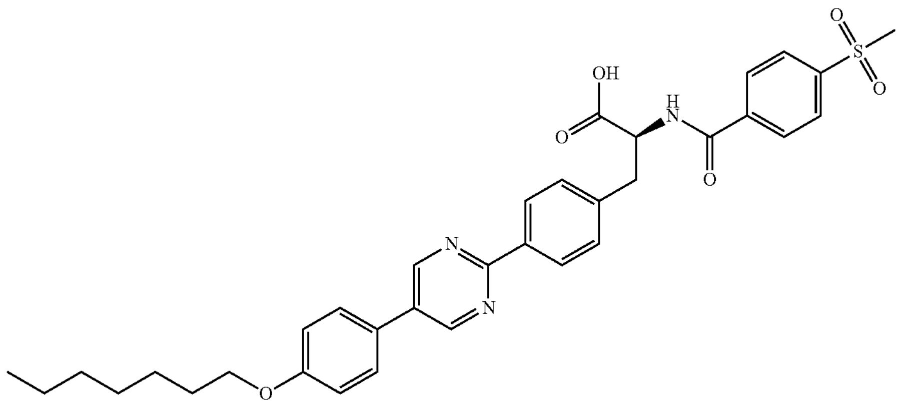 [SMILES: CCCCCCCOc1ccc(-c2cnc(-c3ccc(C[C@H](NC(=O)c4ccc(S(C)(=O)=O)cc4)C(=O)O)cc3)nc2)cc1] | 99 | 8.75 | 9 |
| 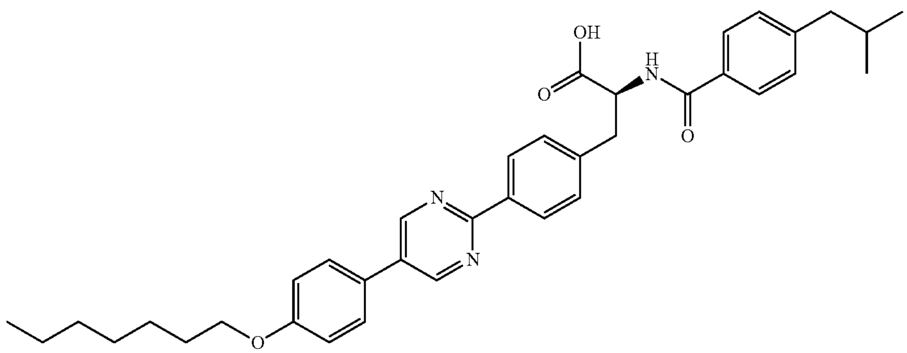 [SMILES: CCCCCCCOc1ccc(-c2cnc(-c3ccc(C[C@H](NC(=O)c4ccc(CC(C)C)cc4)C(=O)O)cc3)nc2)cc1] | 100 | 11.08 | 9 |
| 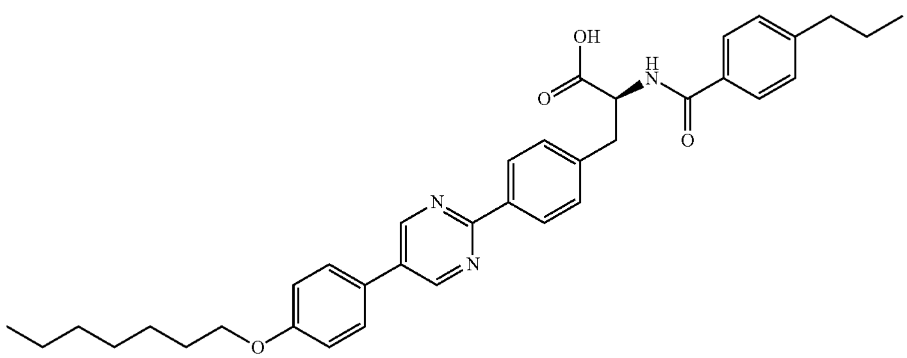 [SMILES: CCCCCCCOc1ccc(-c2cnc(-c3ccc(C[C@H](NC(=O)c4ccc(CCC)cc4)C(=O)O)cc3)nc2)cc1] | 101 | 10.70 | 9 |
| 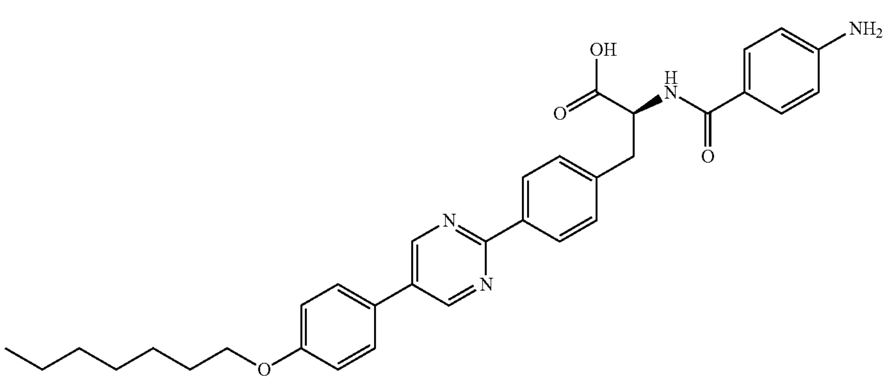 [SMILES: CCCCCCCOc1ccc(-c2cnc(-c3ccc(C[C@H](NC(=O)c4ccc(N)cc4)C(=O)O)cc3)nc2)cc1] | 102 | 8.51 | 9 |

TABLE 1-continued

| STRUCTURE | COMPOUND NUMBER | LCMS RETENTION TIME (min) | PURITY METHOD |
|---|---|---|---|
| 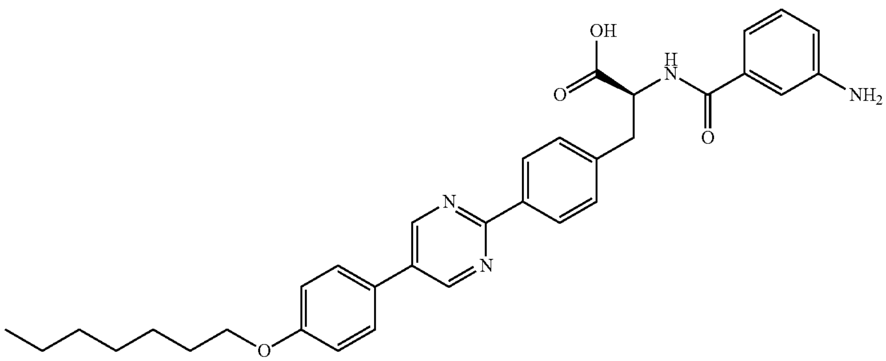 [SMILES: CCCCCCCOc1ccc(-c2cnc(-c3ccc(C[C@H](NC(=O)c4cccc(N)c4)C(=O)O)cc3)nc2)cc1] | 104 | 8.44 | 9 |
| 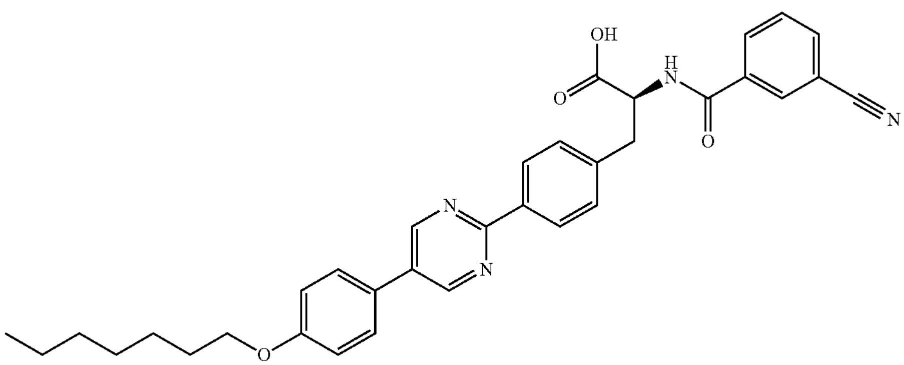 [SMILES: CCCCCCCOc1ccc(-c2cnc(-c3ccc(C[C@H](NC(=O)c4cccc(C#N)c4)C(=O)O)cc3)nc2)cc1] | 105 | 9.46 | 9 |
| 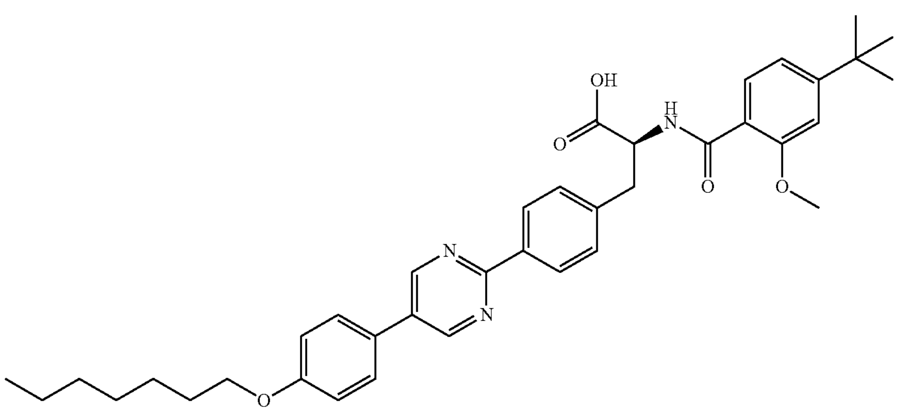 [SMILES: CCCCCCCOc1ccc(-c2cnc(-c3ccc(C[C@H](NC(=O)c4ccc(C(C)(C)C)cc4OC)C(=O)O)cc3)nc2)cc1] | 106 | 11.27 | 9 |
| 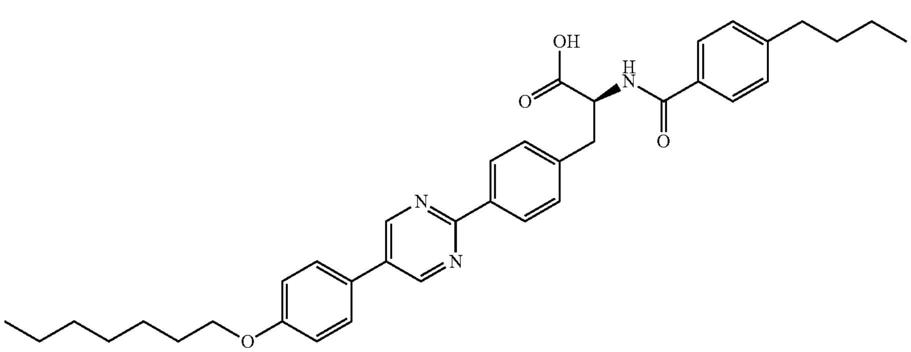 [SMILES: CCCCCCCOc1ccc(-c2cnc(-c3ccc(C[C@H](NC(=O)c4ccc(CCCC)cc4)C(=O)O)cc3)nc2)cc1] | 107 | 11.13 | 9 |

TABLE 1-continued

| STRUCTURE | COMPOUND NUMBER | LCMS RETENTION TIME (min) | PURITY METHOD |
|---|---|---|---|
| 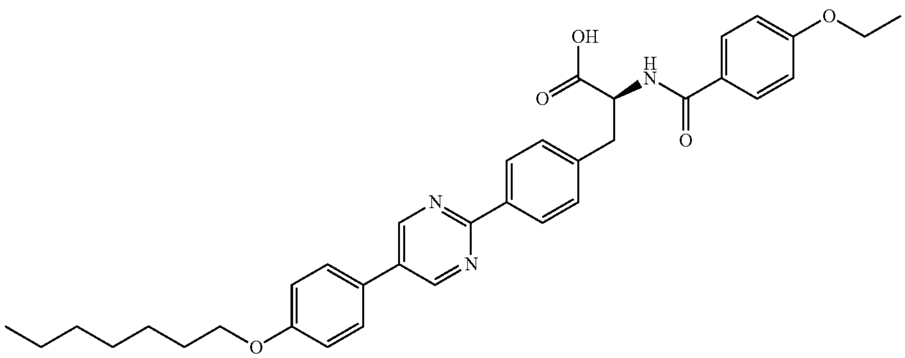 [SMILES: CCCCCCCOc1ccc(-c2cnc(-c3ccc(C[C@H](NC(=O)c4ccc(OCC)cc4)C(=O)O)cc3)nc2)cc1] | 108 | 9.88 | 9 |
| 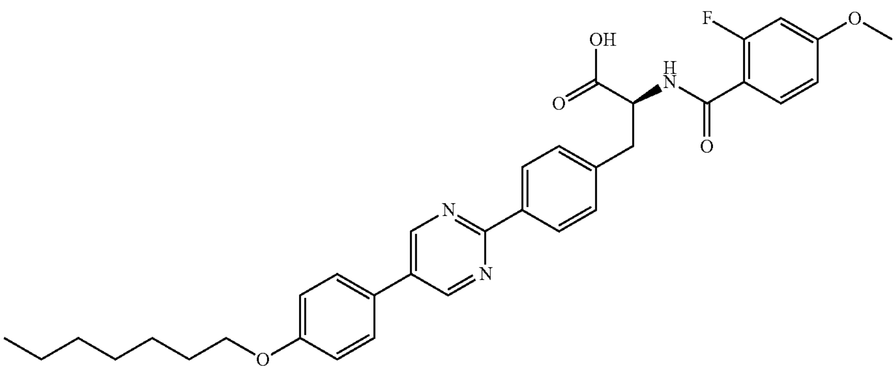 [SMILES: CCCCCCCOc1ccc(-c2cnc(-c3ccc(C[C@H](NC(=O)c4ccc(OC)cc4F)C(=O)O)cc3)nc2)cc1] | 109 | 9.87 | 9 |
| 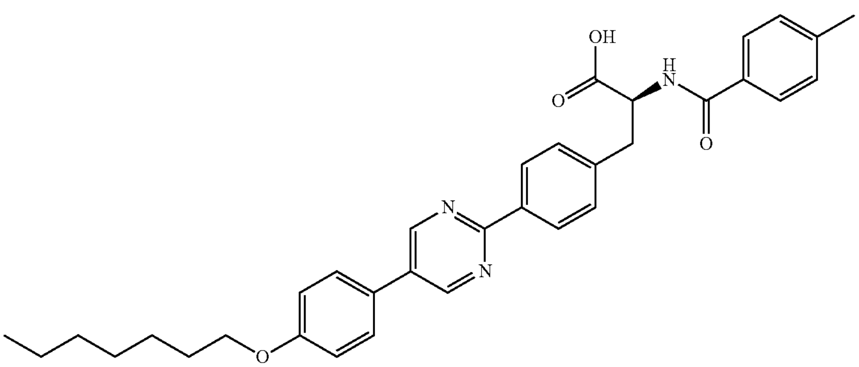 [SMILES: CCCCCCCOc1ccc(-c2cnc(-c3ccc(C[C@H](NC(=O)c4ccc(C)cc4)C(=O)O)cc3)nc2)cc1] | 110 | 9.90 | 9 |
| 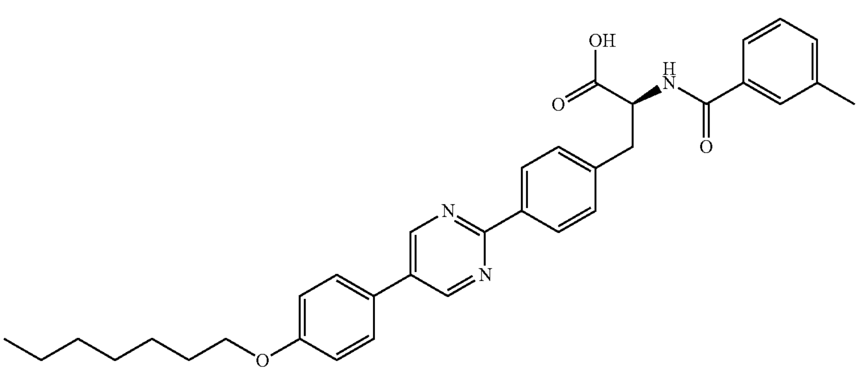 [SMILES: CCCCCCCOc1ccc(-c2cnc(-c3ccc(C[C@H](NC(=O)c4cccc(C)c4)C(=O)O)cc3)nc2)cc1] | 111 | 9.86 | 9 |

TABLE 1-continued
| STRUCTURE | COMPOUND NUMBER | LCMS RETENTION TIME (min) | PURITY METHOD |
|---|---|---|---|
| 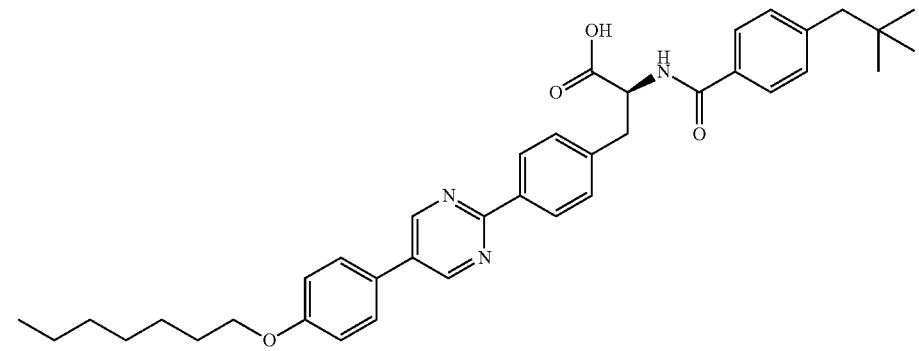 [SMILES: CCCCCCCOc1ccc(-c2cnc(-c3ccc(C[C@H](NC(=O)c4ccc(CC(C)(C)C)cc4)C(=O)O)cc3)nc2)cc1] | 112 | 11.34 | 9 |
| 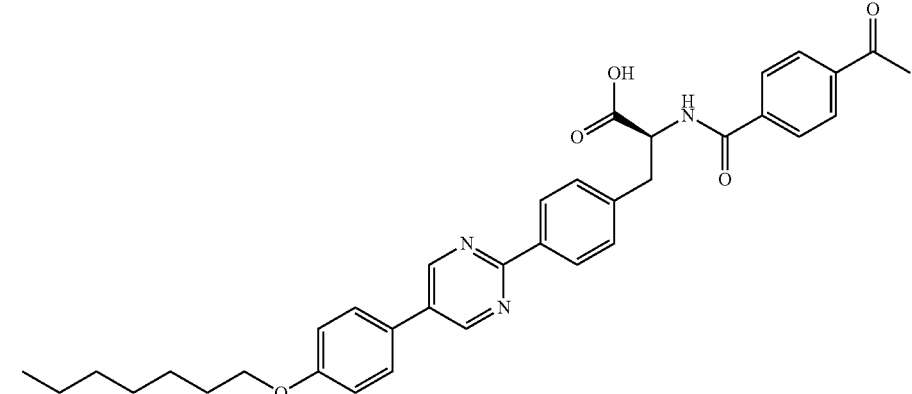 | 113 | 9.19 | 9 |
| 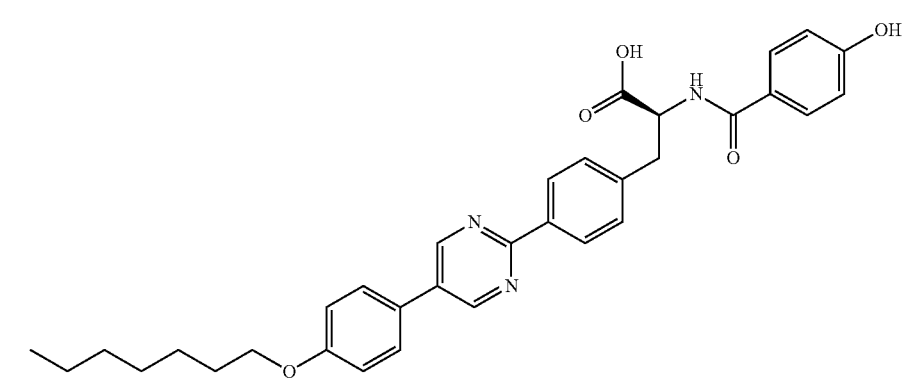 [SMILES: CCCCCCCOc1ccc(-c2cnc(-c3ccc(C[C@H](NC(=O)c4ccc(O)cc4)C(=O)O)cc3)nc2)cc1] | 114 | 8.49 | 9 |

TABLE 1-continued

| STRUCTURE | COMPOUND NUMBER | LCMS RETENTION TIME (min) | PURITY METHOD |
|---|---|---|---|
| 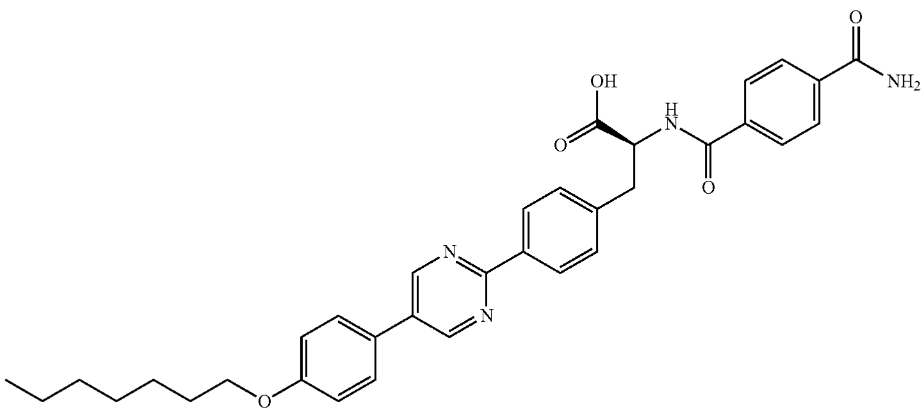 [SMILES: CCCCCCCOc1ccc(-c2cnc(-c3ccc(C[C@H](NC(=O)c4ccc(C(N)=O)cc4)C(=O)O)cc3)nc2)cc1] | 115 | 7.95 | 9 |
| 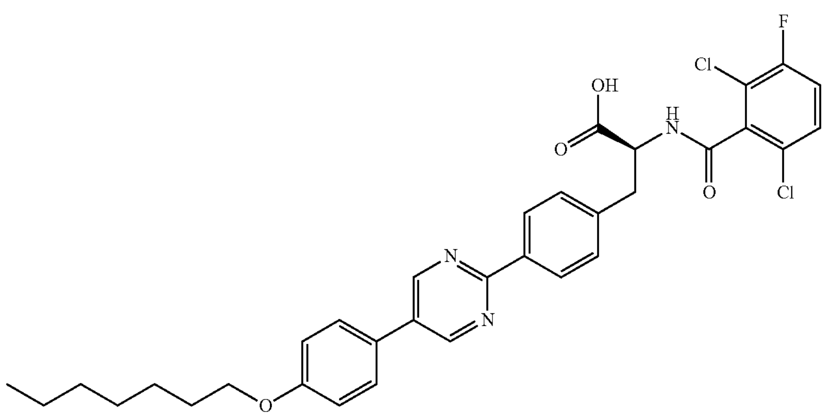 [SMILES: CCCCCCCOc1ccc(-c2cnc(-c3ccc(C[C@H](NC(=O)c4c(Cl)ccc(F)c4Cl)C(=O)O)cc3)nc2)cc1] | 116 | 11.14 | 2 |
| 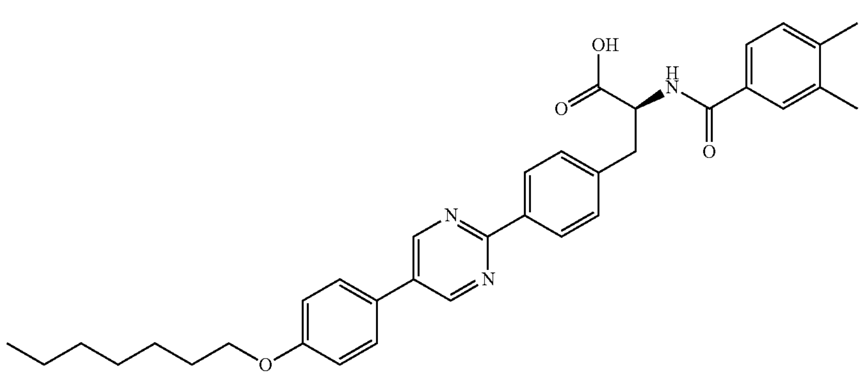 [SMILES: CCCCCCCOc1ccc(-c2cnc(-c3ccc(C[C@H](NC(=O)c4ccc(C)c(C)c4)C(=O)O)cc3)nc2)cc1] | 117 | 10.15 | 9 |

TABLE 1-continued
| STRUCTURE | COMPOUND NUMBER | LCMS RETENTION TIME (min) | PURITY METHOD |
|---|---|---|---|
| 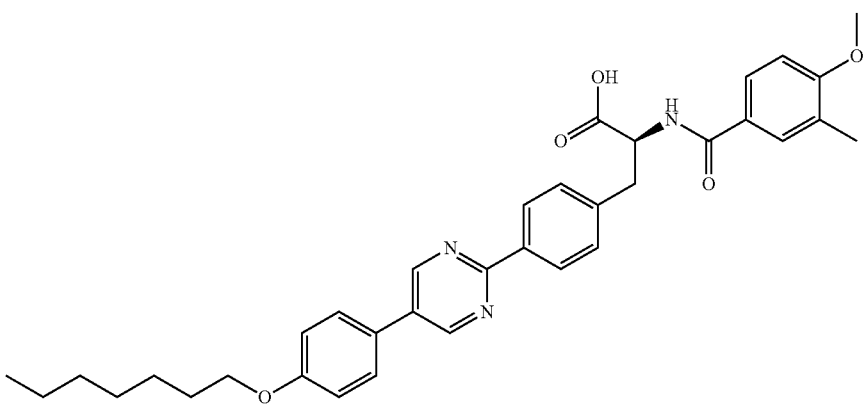 [SMILES: CCCCCCCOc1ccc(-c2cnc(-c3ccc(C[C@H](NC(=O)c4ccc(OC)c(C)c4)C(=O)O)cc3)nc2)cc1] | 118 | 9.90 | 9 |
| 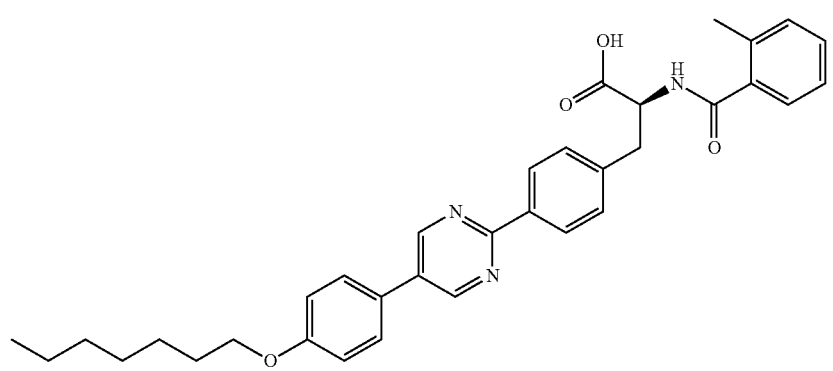 [SMILES: CCCCCCCOc1ccc(-c2cnc(-c3ccc(C[C@H](NC(=O)c4ccccc4C)C(=O)O)cc3)nc2)cc1] | 119 | 9.67 | 9 |
| 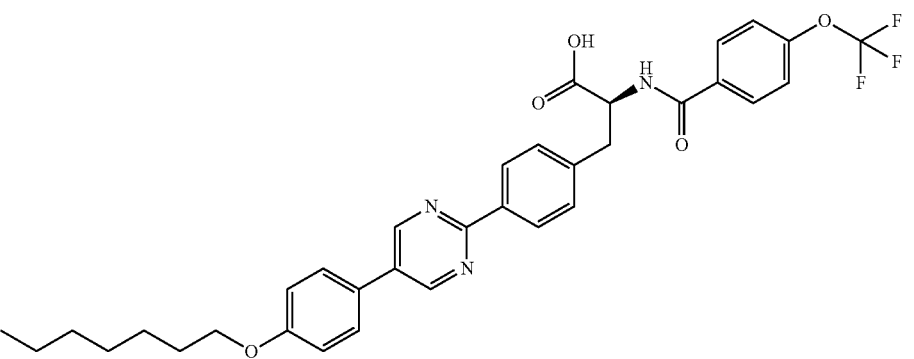 [SMILES: CCCCCCCOc1ccc(-c2cnc(-c3ccc(C[C@H](NC(=O)c4ccc(OC(F)(F)F)cc4)C(=O)O)cc3)nc2)cc1] | 120 | 10.41 | 9 |

TABLE 1-continued

| STRUCTURE | COMPOUND NUMBER | LCMS RETENTION TIME (min) | PURITY METHOD |
|---|---|---|---|
| 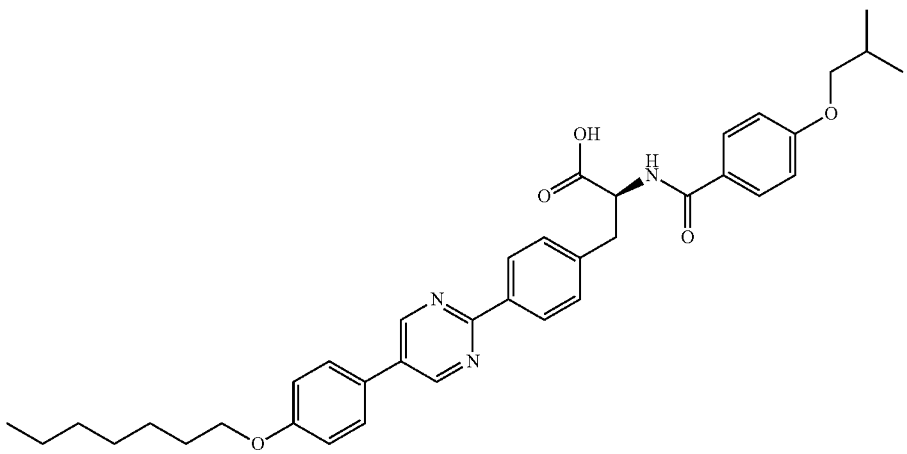 [SMILES: CCCCCCCOc1ccc(-c2cnc(-c3ccc(C[C@H](NC(=O)c4ccc(OCC(C)C)cc4)C(=O)O)cc3)nc2)cc1] | 121 | 10.86 | 9 |
| 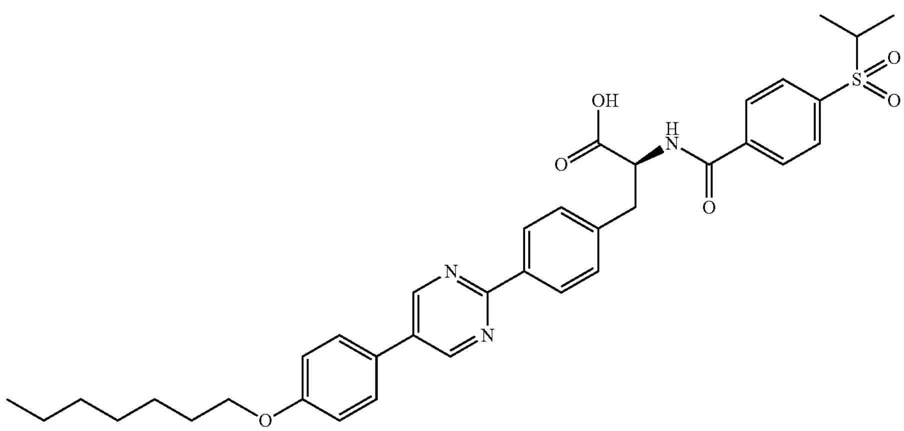 [SMILES: CCCCCCCOc1ccc(-c2cnc(-c3ccc(C[C@H](NC(=O)c4ccc(S(=O)(=O)C(C)C)cc4)C(=O)O)cc3)nc2)cc1] | 122 | 9.30 | 9 |
| 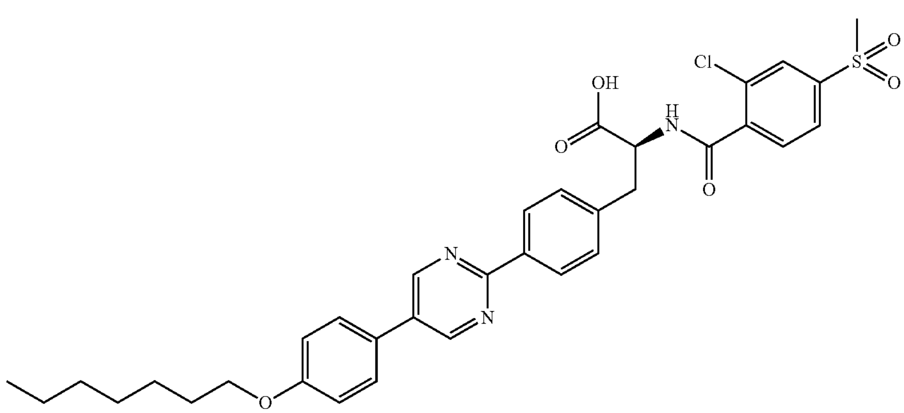 [SMILES: CCCCCCCOc1ccc(-c2cnc(-c3ccc(C[C@H](NC(=O)c4ccc(S(C)(=O)=O)cc4Cl)C(=O)O)cc3)nc2)cc1] | 123 | 9.02 | 9 |

TABLE 1-continued
| STRUCTURE | COMPOUND NUMBER | LCMS RETENTION TIME (min) | PURITY METHOD |
|---|---|---|---|
| 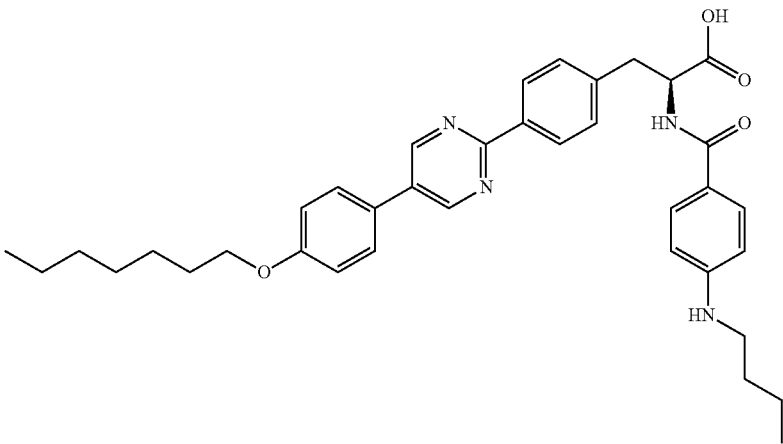 [SMILES: CCCCCCCOc1ccc(-c2cnc(-c3ccc(C[C@H](NC(=O)c4ccc(NCCCC)cc4)C(=O)O)cc3)nc2)cc1] | 124 | 10.38 | 9 |
| 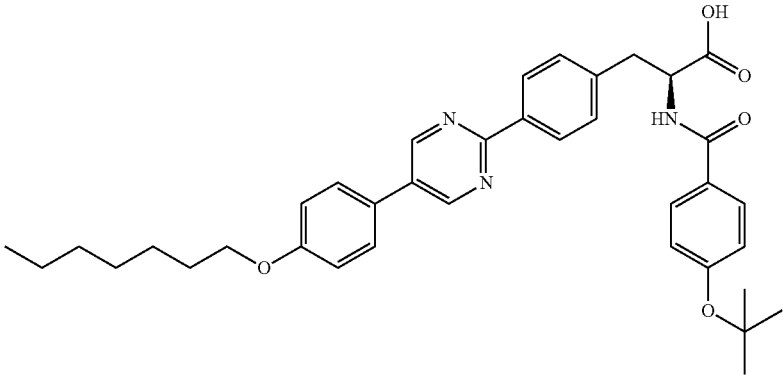 [SMILES: CCCCCCCOc1ccc(-c2cnc(-c3ccc(C[C@H](NC(=O)c4ccc(OC(C)(C)C)cc4)C(=O)O)cc3)nc2)cc1] | 125 | 10.51 | 9 |
| 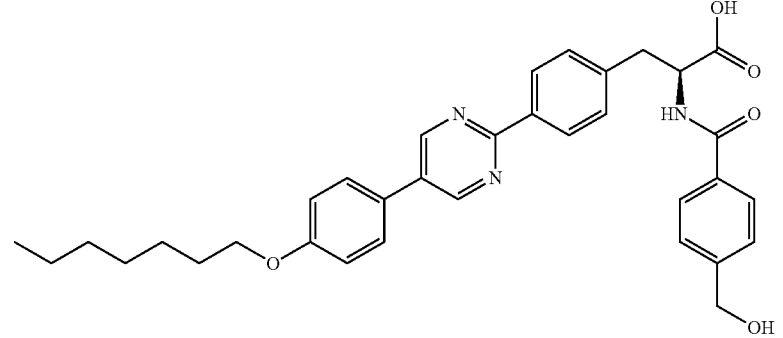 [SMILES: CCCCCCCOc1ccc(-c2cnc(-c3ccc(C[C@H](NC(=O)c4ccc(CO)cc4)C(=O)O)cc3)nc2)cc1] | 126 | 8.38 | 9 |
| 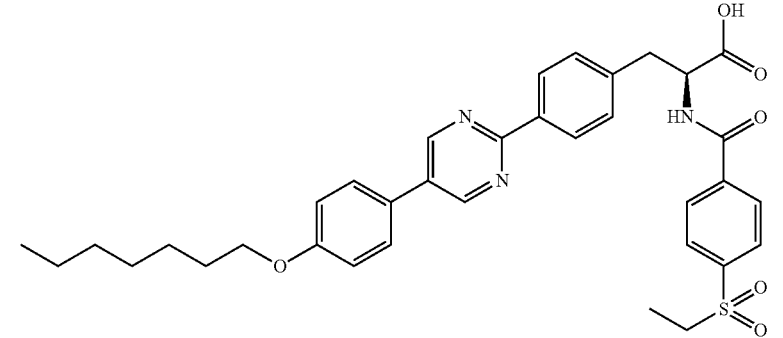 [SMILES: CCCCCCCOc1ccc(-c2cnc(-c3ccc(C[C@H](NC(=O)c4ccc(S(=O)(=O)CC)cc4)C(=O)O)cc3)nc2)cc1] | 127 | 8.95 | 9 |

TABLE 1-continued

| STRUCTURE | COMPOUND NUMBER | LCMS RETENTION TIME (min) | PURITY METHOD |
|---|---|---|---|
| 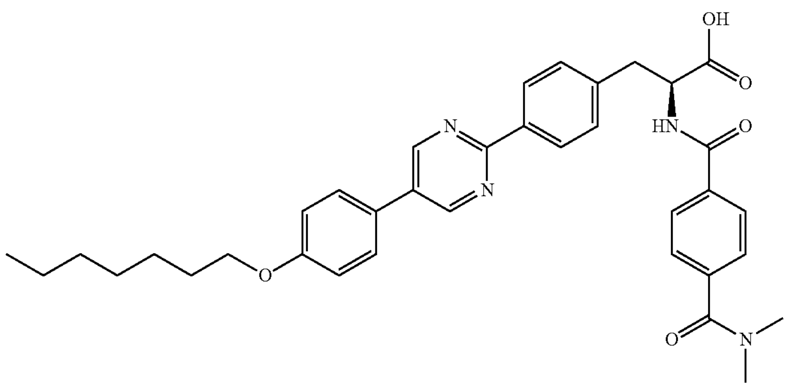 [SMILES: CCCCCCCOc1ccc(-c2cnc(-c3ccc(C[C@H](NC(=O)c4ccc(C(=O)N(C)C)cc4)C(=O)O)cc3)nc2)cc1] | 128 | 8.42 | 9 |
| 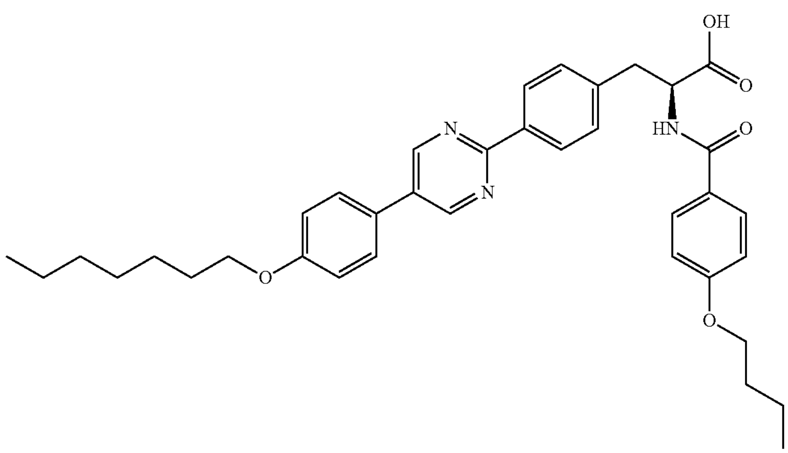 [SMILES: CCCCCCCOc1ccc(-c2cnc(-c3ccc(C[C@H](NC(=O)c4ccc(OCCCC)cc4)C(=O)O)cc3)nc2)cc1] | 129 | 11.13 | 10 |
| 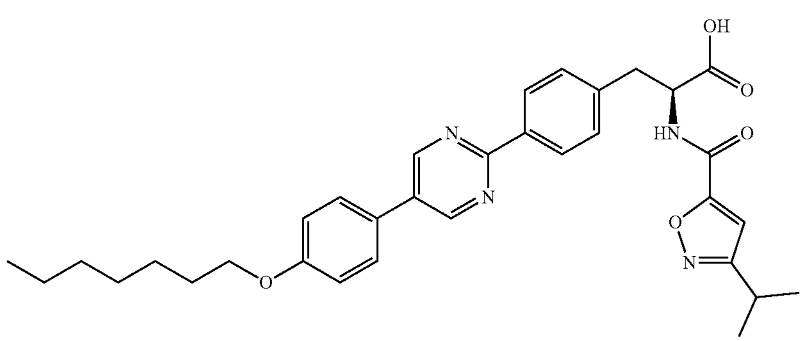 [SMILES: CCCCCCCOc1ccc(-c2cnc(-c3ccc(C[C@H](NC(=O)c4cc(C(C)C)no4)C(=O)O)cc3)nc2)cc1] | 130 | 10.23 | 10 |

TABLE 1-continued

| STRUCTURE | COMPOUND NUMBER | LCMS RETENTION TIME (min) | PURITY METHOD |
|---|---|---|---|
| 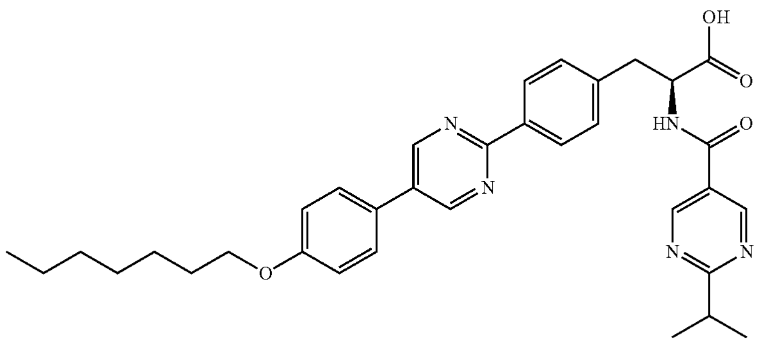 [SMILES: CCCCCCCOc1ccc(-c2cnc(-c3ccc(C[C@H](NC(=O)c4cnc(C(C)C)nc4)C(=O)O)cc3)nc2)cc1] | 131 | 9.70 | 10 |
| 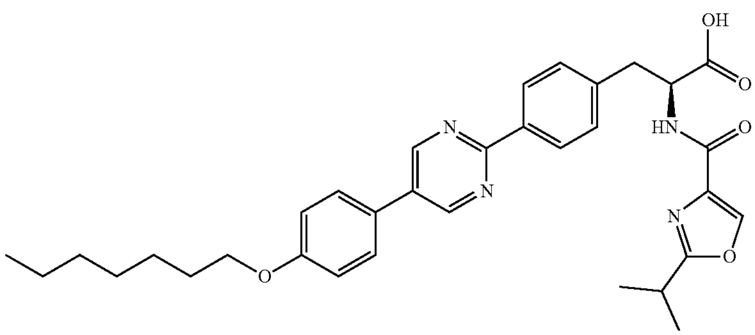 [SMILES: CCCCCCCOc1ccc(-c2cnc(-c3ccc(C[C@H](NC(=O)c4coc(C(C)C)n4)C(=O)O)cc3)nc2)cc1] | 132 | 10.27 | 10 |
| 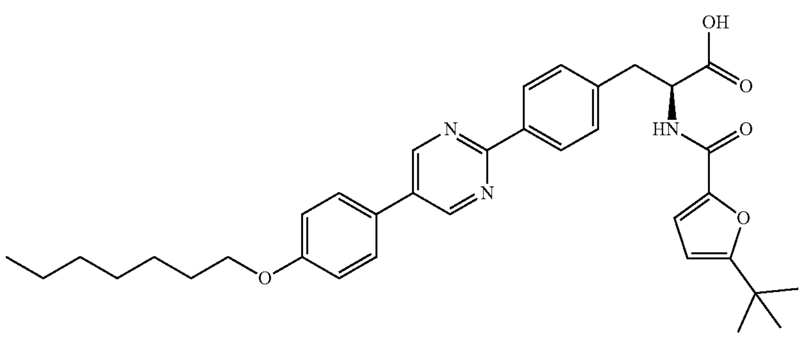 [SMILES: CCCCCCCOc1ccc(-c2cnc(-c3ccc(C[C@H](NC(=O)c4ccc(C(C)(C)C)o4)C(=O)O)cc3)nc2)cc1] | 133 | 10.87 | 10 |
| 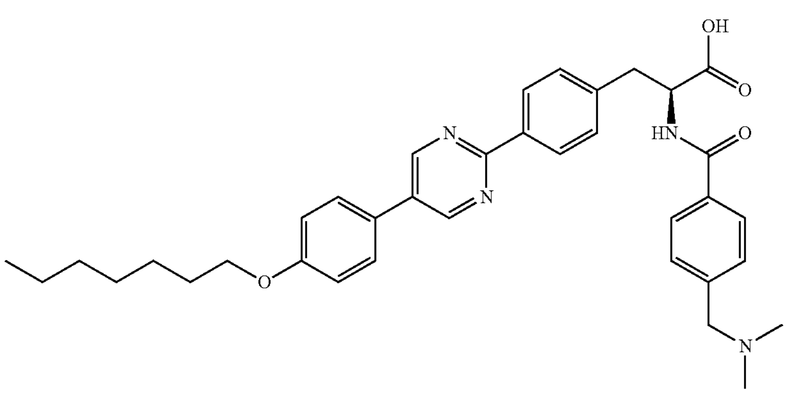 [SMILES: CCCCCCCOc1ccc(-c2cnc(-c3ccc(C[C@H](NC(=O)c4ccc(CN(C)C)cc4)C(=O)O)cc3)nc2)cc1] | 134 | 6.44 | 10 |

TABLE 1-continued

| STRUCTURE | COMPOUND NUMBER | LCMS RETENTION TIME (min) | PURITY METHOD |
|---|---|---|---|
| 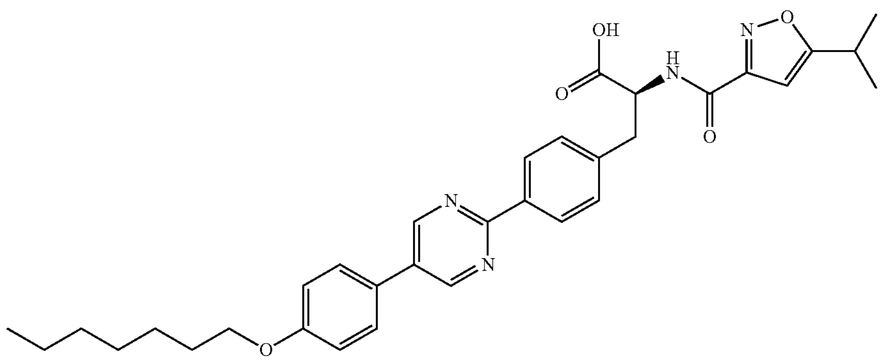 [SMILES: CCCCCCCOc1ccc(-c2cnc(-c3ccc(C[C@H](NC(=O)c4cc(C(C)C)on4)C(=O)O)cc3)nc2)cc1] | 135 | 10.67 | 10 |
| 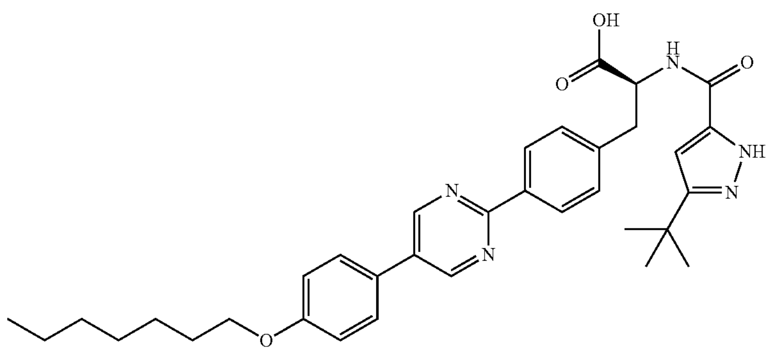 [SMILES: CCCCCCCOc1ccc(-c2cnc(-c3ccc(C[C@H](NC(=O)c4cc(C(C)(C)C)n[nH]4)C(=O)O)cc3)nc2)cc1] | 136 | 9.85 | 10 |
| 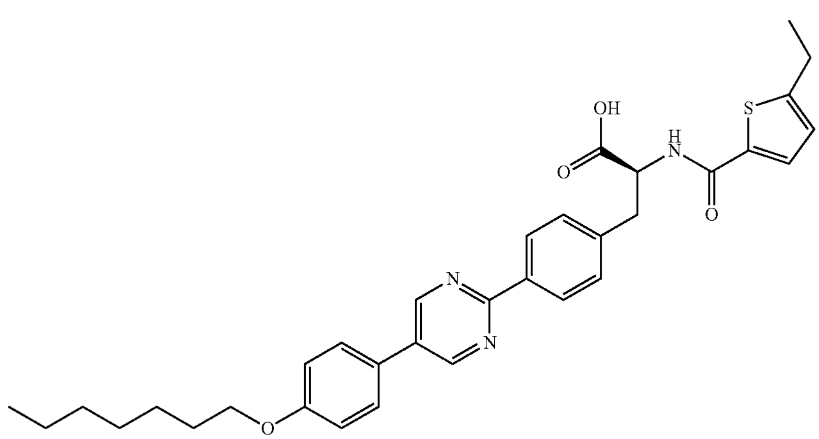 | 137 | 10.48 | 10 |

TABLE 1-continued

| STRUCTURE | COMPOUND NUMBER | LCMS RETENTION TIME (min) | PURITY METHOD |
|---|---|---|---|
| 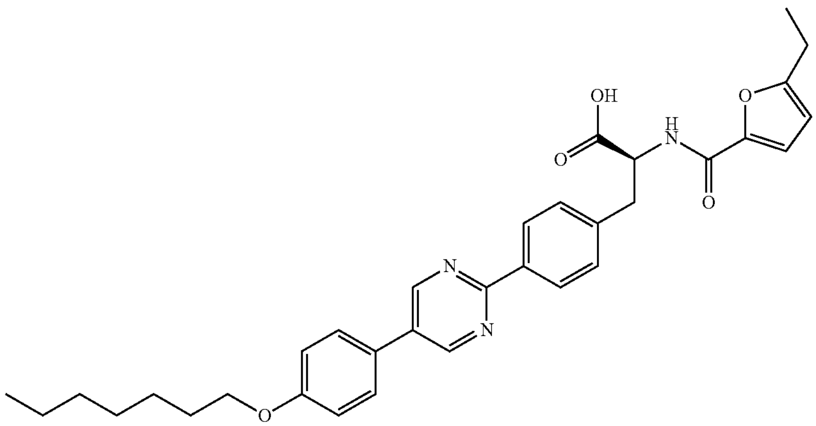 [SMILES: CCCCCCCOc1ccc(-c2cnc(-c3ccc(C[C@H](NC(=O)c4ccc(CC)o4)C(=O)O)cc3)nc2)cc1] | 138 | 10.13 | 10 |
| 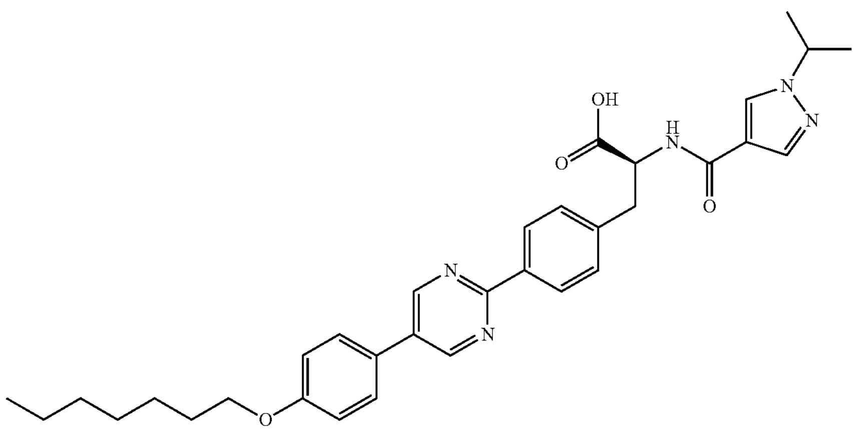 [SMILES: CCCCCCCOc1ccc(-c2cnc(-c3ccc(C[C@H](NC(=O)c4cnn(C(C)C)c4)C(=O)O)cc3)nc2)cc1] | 139 | 9.09 | 10 |
| 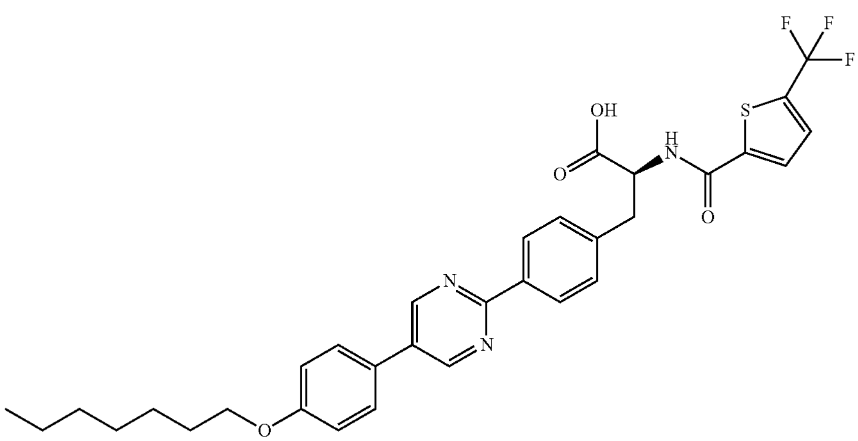 [SMILES: CCCCCCCOc1ccc(-c2cnc(-c3ccc(C[C@H](NC(=O)c4ccc(C(F)(F)F)s4)C(=O)O)cc3)nc2)cc1] | 140 | 10.76 | 10 |

TABLE 1-continued

| STRUCTURE | COMPOUND NUMBER | LCMS RETENTION TIME (min) | PURITY METHOD |
|---|---|---|---|
| 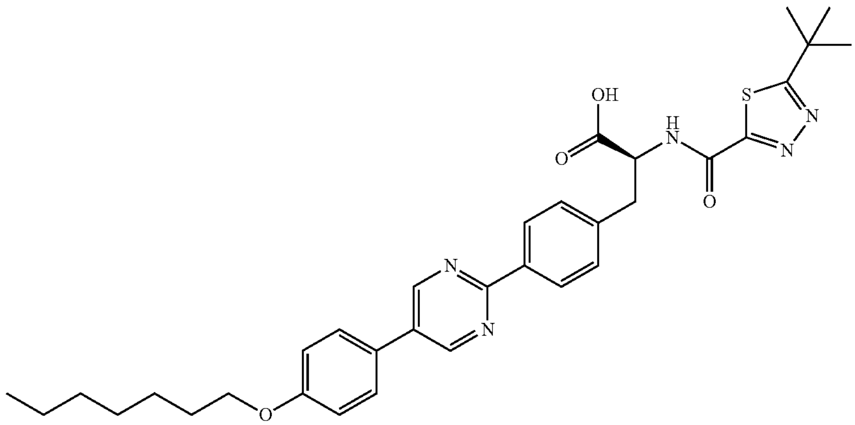 [SMILES: CCCCCCCOc1ccc(-c2cnc(-c3ccc(C[C@H](NC(=O)c4nnc(C(C)(C)C)s4)C(=O)O)cc3)nc2)cc1] | 141 | 10.83 | 10 |
| 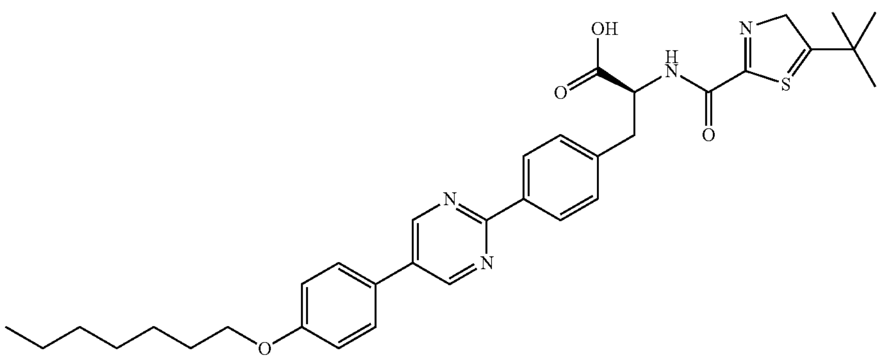 | 142 | 10.42 | 10 |
| 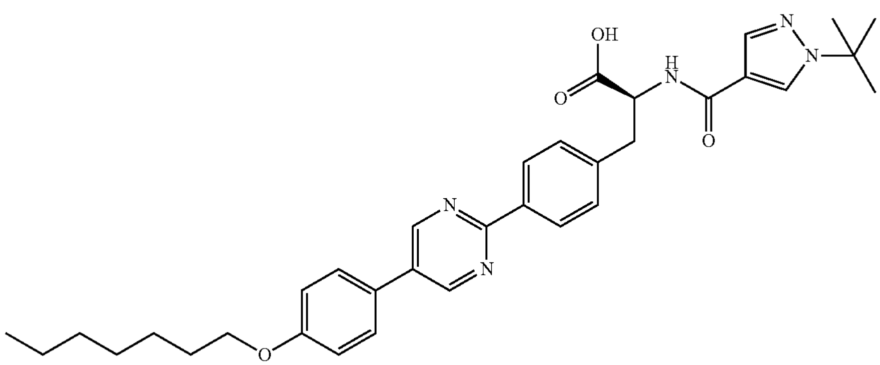 [SMILES: CCCCCCCOc1ccc(-c2cnc(-c3ccc(C[C@H](NC(=O)c4cnn(C(C)(C)C)c4)C(=O)O)cc3)nc2)cc1] | 143 | 9.47 | 10 |
| 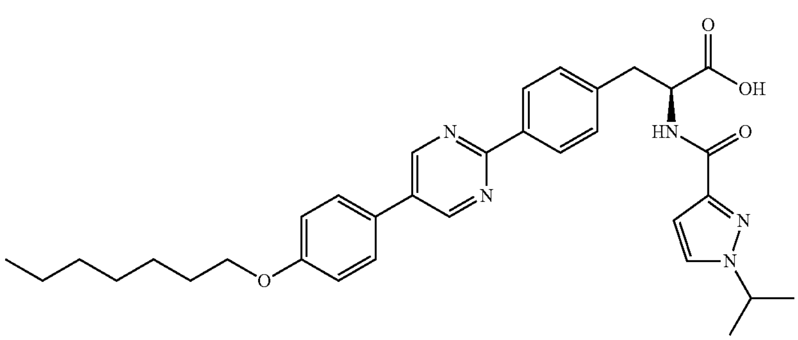 [SMILES: CCCCCCCOc1ccc(-c2cnc(-c3ccc(C[C@H](NC(=O)c4ccn(C(C)C)n4)C(=O)O)cc3)nc2)cc1] | 144 | 9.83 | 10 |

TABLE 1-continued

| STRUCTURE | COMPOUND NUMBER | LCMS RETENTION TIME (min) | PURITY METHOD |
|---|---|---|---|
| 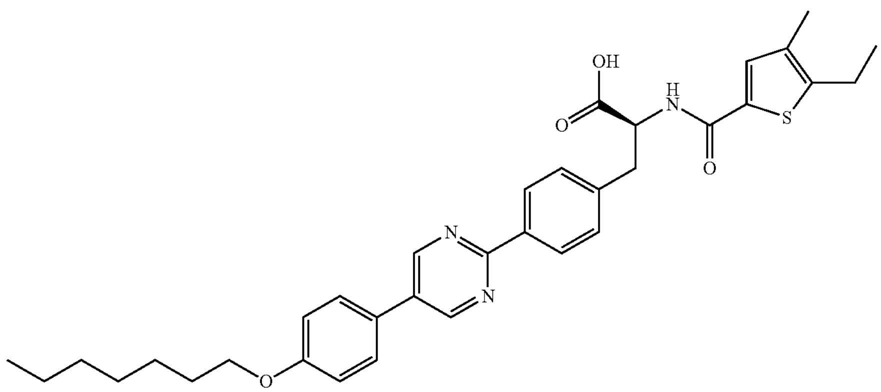 [SMILES: CCCCCCCOc1ccc(-c2cnc(-c3ccc(C[C@H](NC(=O)c4cc(C)c(CC)s4)C(=O)O)cc3)nc2)cc1] | 145 | 10.79 | 10 |
| 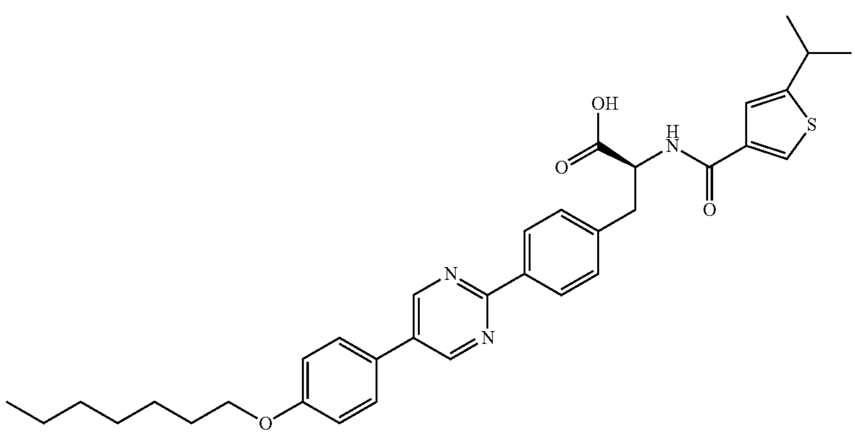 [SMILES: CCCCCCCOc1ccc(-c2cnc(-c3ccc(C[C@H](NC(=O)c4csc(C(C)C)c4)C(=O)O)cc3)nc2)cc1] | 146 | 10.77 | 10 |
| 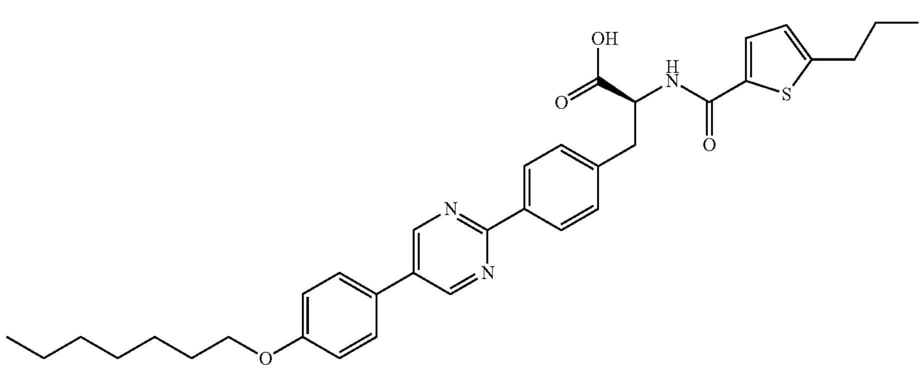 [SMILES: CCCCCCCOc1ccc(-c2cnc(-c3ccc(C[C@H](NC(=O)c4ccc(CCC)s4)C(=O)O)cc3)nc2)cc1] | 147 | 10.86 | 10 |

TABLE 1-continued
| STRUCTURE | COMPOUND NUMBER | LCMS RETENTION TIME (min) | PURITY METHOD |
|---|---|---|---|
| 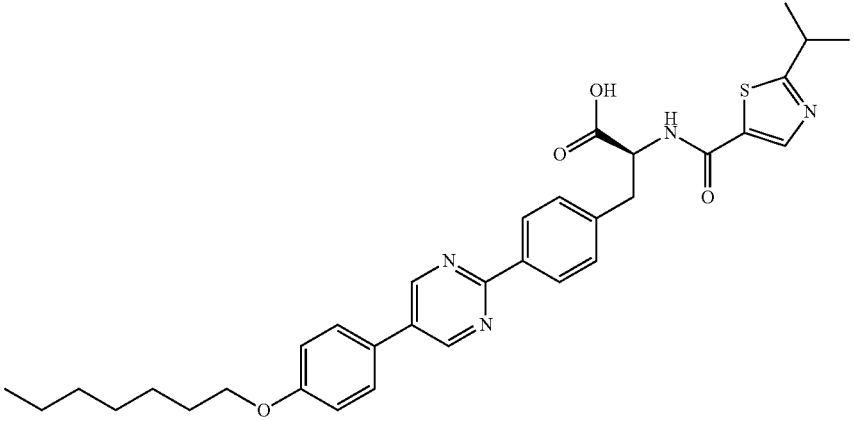 [SMILES: CCCCCCCOc1ccc(-c2cnc(-c3ccc(C[C@H](NC(=O)c4cnc(C(C)C)s4)C(=O)O)cc3)nc2)cc1] | 148 | 10.17 | 10 |
| 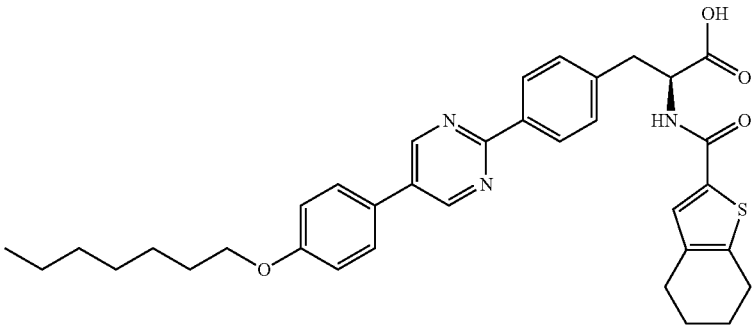 [SMILES: CCCCCCCOc1ccc(-c2cnc(-c3ccc(C[C@H](NC(=O)c4cc5c(s4)CCCC5)C(=O)O)cc3)nc2)cc1] | 149 | 11.95 | 2 |
| 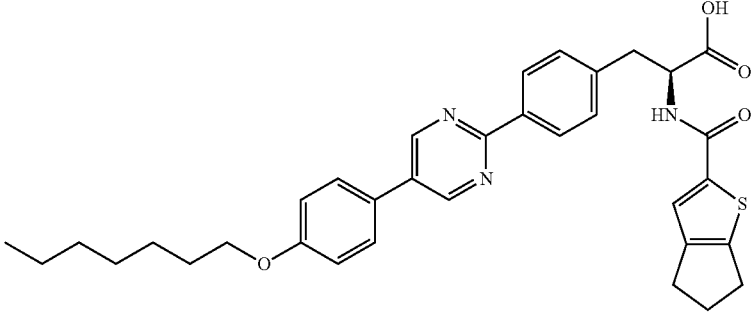 [SMILES: CCCCCCCOc1ccc(-c2cnc(-c3ccc(C[C@H](NC(=O)c4cc5c(s4)CCC5)C(=O)O)cc3)nc2)cc1] | 150 | 11.83 | 2 |
| 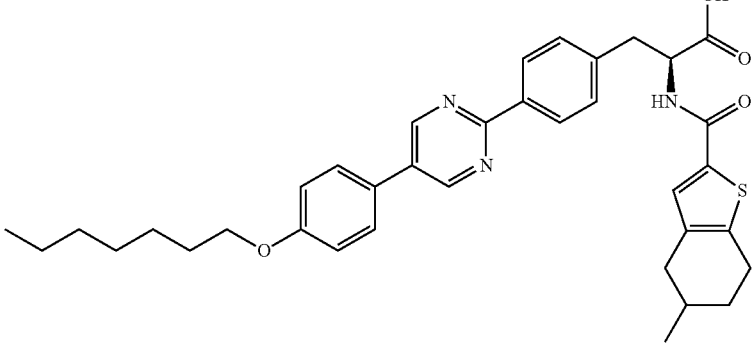 | 151 | 12.41 | 2 |

TABLE 1-continued

| STRUCTURE | COMPOUND NUMBER | LCMS RETENTION TIME (min) | PURITY METHOD |
|---|---|---|---|
| 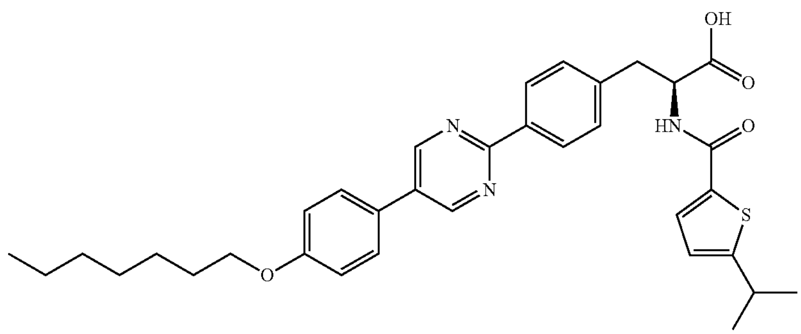 [SMILES: CCCCCCCOc1ccc(-c2cnc(-c3ccc(C[C@H](NC(=O)c4ccc(C(C)C)s4)C(=O)O)cc3)nc2)cc1] | 152 | 12.06 | 2 |
| 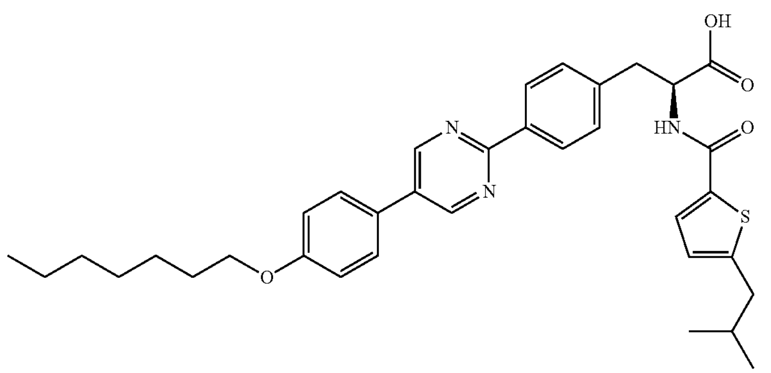 [SMILES: CCCCCCCOc1ccc(-c2cnc(-c3ccc(C[C@H](NC(=O)c4ccc(CC(C)C)s4)C(=O)O)cc3)nc2)cc1] | 153 | 12.37 | 2 |
| 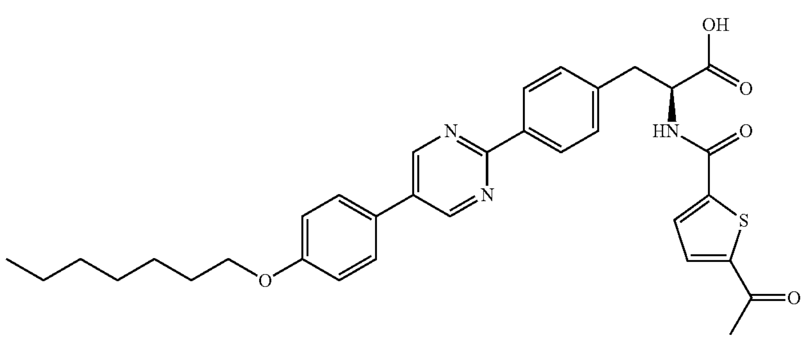 [SMILES: CCCCCCCOc1ccc(-c2cnc(-c3ccc(C[C@H](NC(=O)c4ccc(C(C)=O)s4)C(=O)O)cc3)nc2)cc1] | 154 | 11.19 | 2 |
| 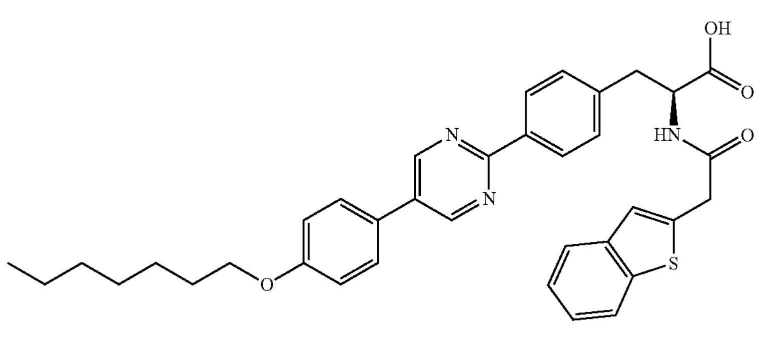 [SMILES: CCCCCCCOc1ccc(-c2cnc(-c3ccc(C[C@H](NC(=O)Cc4cc5ccccc5s4)C(=O)O)cc3)nc2)cc1] | 155 | 11.73 | 2 |

TABLE 1-continued

| STRUCTURE | COMPOUND NUMBER | LCMS RETENTION TIME (min) | PURITY METHOD |
|---|---|---|---|
| 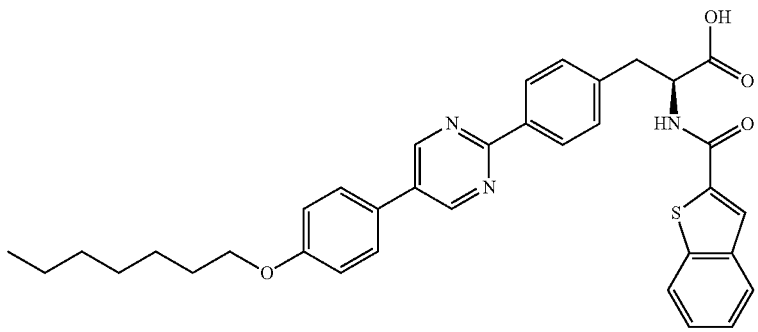 [SMILES: CCCCCCCOc1ccc(-c2cnc(-c3ccc(C[C@H](NC(=O)c4cc5ccccc5s4)C(=O)O)cc3)nc2)cc1] | 156 | 11.40 | 10 |
| 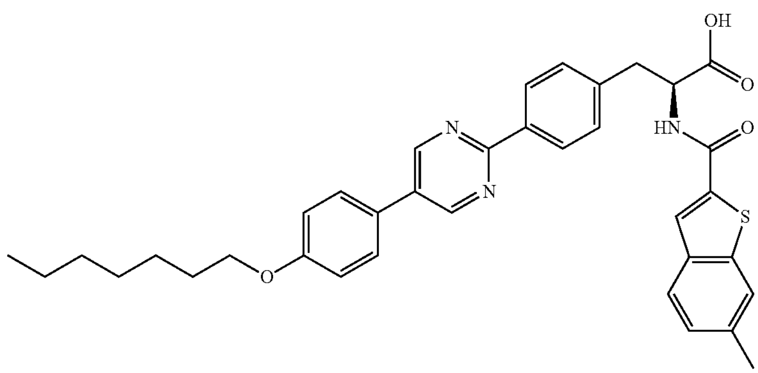 [SMILES: CCCCCCCOc1ccc(-c2cnc(-c3ccc(C[C@H](NC(=O)c4cc5ccc(C)cc5s4)C(=O)O)cc3)nc2)cc1] | 157 | 11.93 | 2 |
| 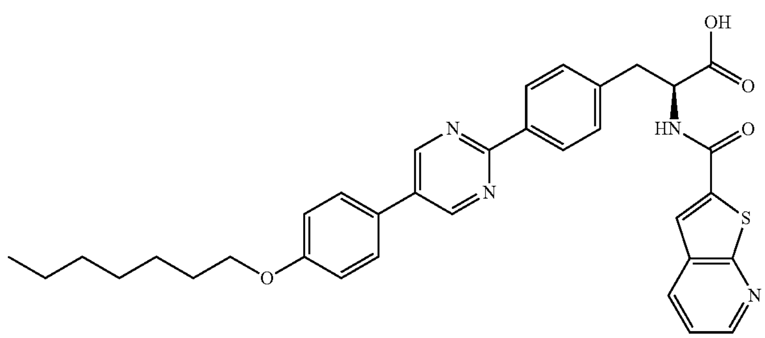 [SMILES: CCCCCCCOc1ccc(-c2cnc(-c3ccc(C[C@H](NC(=O)c4cc5cccnc5s4)C(=O)O)cc3)nc2)cc1] | 158 | 11.13 | 2 |
| 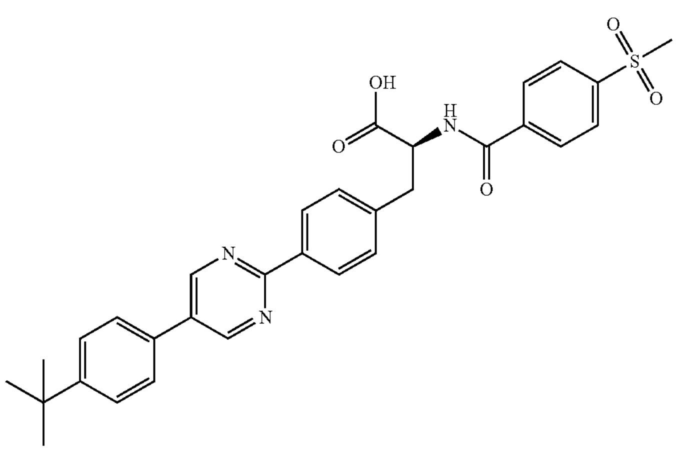 [SMILES: CC(C)(C)c1ccc(-c2cnc(-c3ccc(C[C@H](NC(=O)c4ccc(S(C)(=O)=O)cc4)C(=O)O)cc3)nc2)cc1] | 159 | 7.23 | 9 |

TABLE 1-continued

| STRUCTURE | COMPOUND NUMBER | LCMS RETENTION TIME (min) | PURITY METHOD |
|---|---|---|---|
| 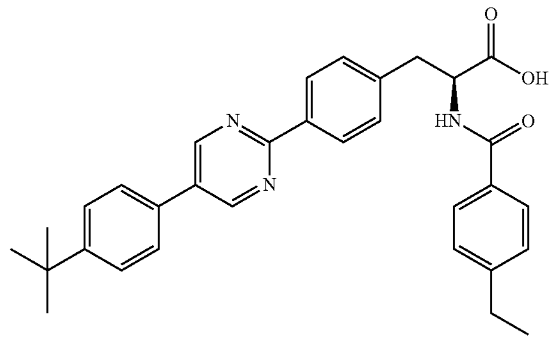 [SMILES: CCc1ccc(C(=O)N[C@@H](Cc2ccc(-c3ncc(-c4ccc(C(C)(C)C)cc4)cn3)cc2)C(=O)O)cc1] | 160 | 8.85 | 9 |
| 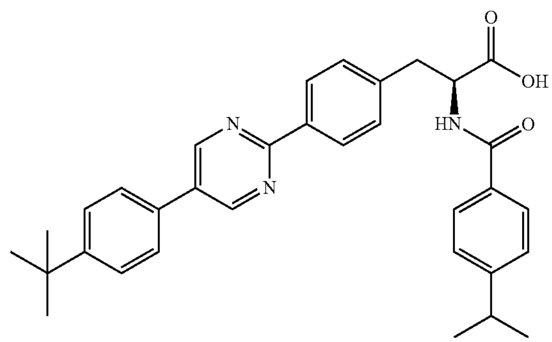 [SMILES: CC(C)c1ccc(C(=O)N[C@@H](Cc2ccc(-c3ncc(-c4ccc(C(C)(C)C)cc4)cn3)cc2)C(=O)O)cc1] | 161 | 9.24 | 9 |
| 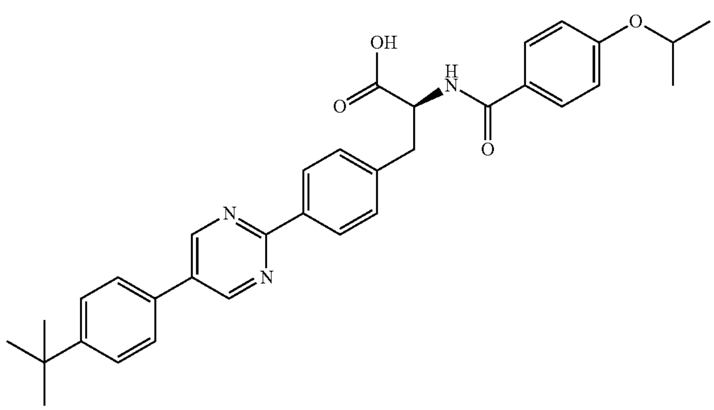 [SMILES: CC(C)Oc1ccc(C(=O)N[C@@H](Cc2ccc(-c3ncc(-c4ccc(C(C)(C)C)cc4)cn3)cc2)C(=O)O)cc1] | 162 | 8.83 | 9 |
| 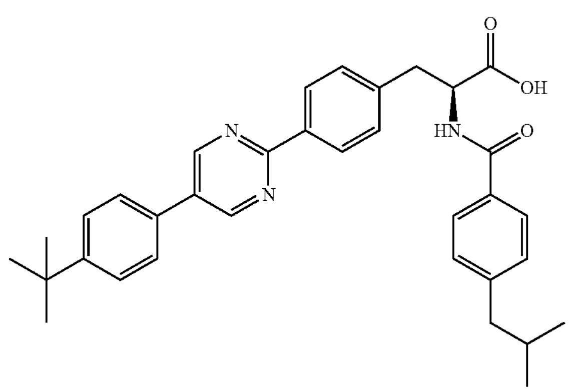 [SMILES: CC(C)Cc1ccc(C(=O)N[C@@H](Cc2ccc(-c3ncc(-c4ccc(C(C)(C)C)cc4)cn3)cc2)C(=O)O)cc1] | 163 | 9.78 | 9 |

TABLE 1-continued

| STRUCTURE | COMPOUND NUMBER | LCMS RETENTION TIME (min) | PURITY METHOD |
|---|---|---|---|
| 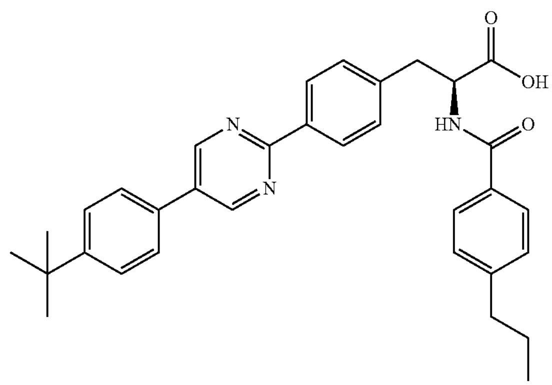 [SMILES: CCCc1ccc(C(=O)N[C@@H](Cc2ccc(-c3ncc(-c4ccc(C(C)(C)C)cc4)cn3)cc2)C(=O)O)cc1] | 164 | 10.44 | 2 |
| 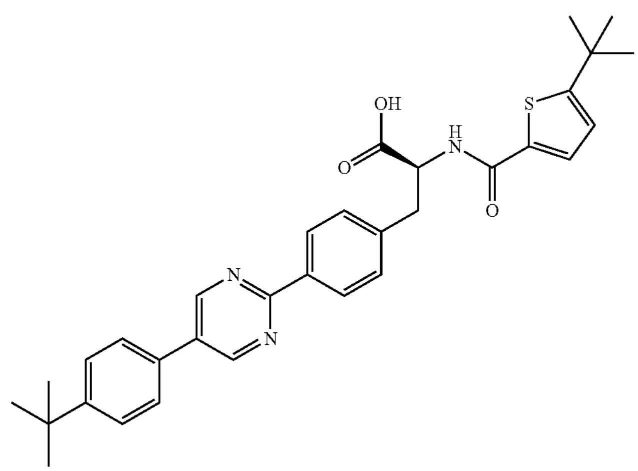 [SMILES: CC(C)(C)c1ccc(-c2cnc(-c3ccc(C[C@H](NC(=O)c4ccc(C(C)(C)C)s4)C(=O)O)cc3)nc2)cc1] | 165 | 9.69 | 10 |
| 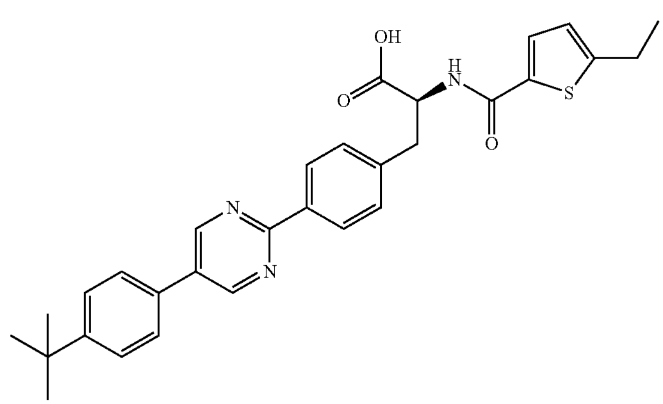 [SMILES: CCc1ccc(C(=O)N[C@@H](Cc2ccc(-c3ncc(-c4ccc(C(C)(C)C)cc4)cn3)cc2)C(=O)O)s1] | 166 | 8.97 | 10 |

TABLE 1-continued
| STRUCTURE | COMPOUND NUMBER | LCMS RETENTION TIME (min) | PURITY METHOD |
|---|---|---|---|
| 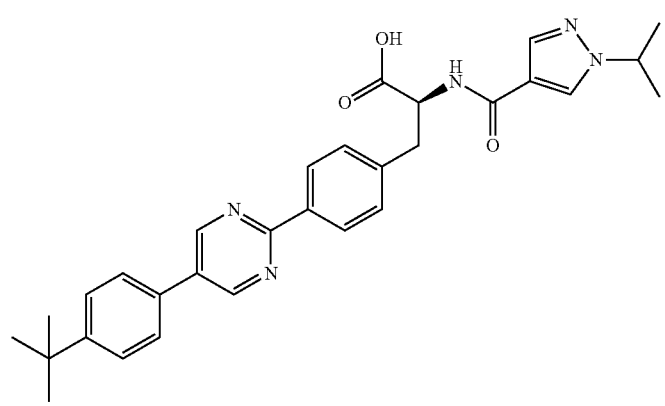 [SMILES: CC(C)n1cc(C(=O)N[C@@H](Cc2ccc(-c3ncc(-c4ccc(C(C)(C)C)cc4)cn3)cc2)C(=O)O)cn1] | 167 | 7.54 | 10 |
| 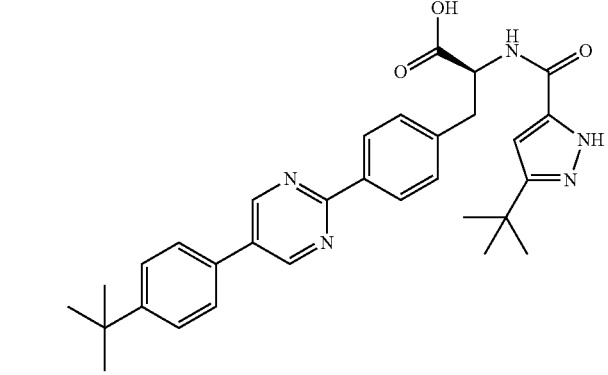 [SMILES: CC(C)(C)c1ccc(-c2cnc(-c3ccc(C[C@H](NC(=O)c4cc(C(C)(C)C)n[nH]4)C(=O)O)cc3)nc2)cc1] | 168 | 8.35 | 10 |
| 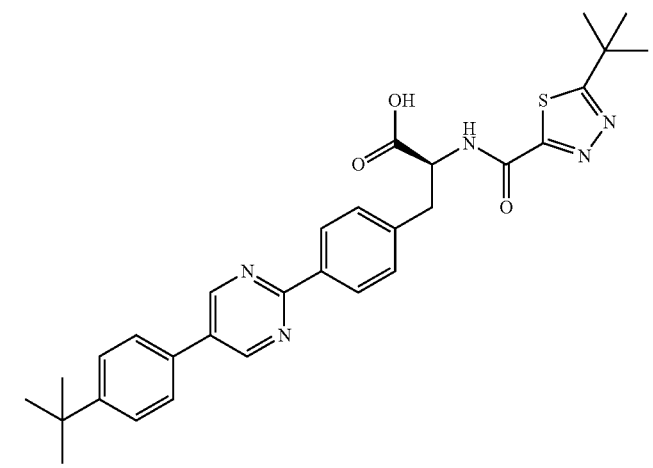 | 169 | 9.32 | 10 |

TABLE 1-continued
| STRUCTURE | COMPOUND NUMBER | LCMS RETENTION TIME (min) | PURITY METHOD |
|---|---|---|---|
| 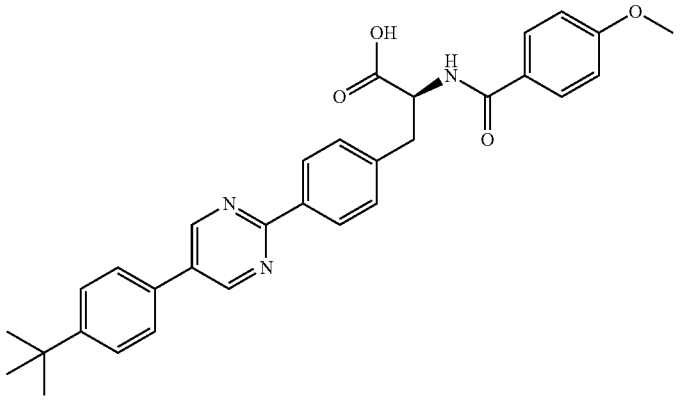 [SMILES: COc1ccc(C(=O)N[C@@H](Cc2ccc(-c3ncc(-c4ccc(C(C)(C)C)cc4)cn3)cc2)C(=O)O)cc1] | 170 | 8.23 | 10 |
| 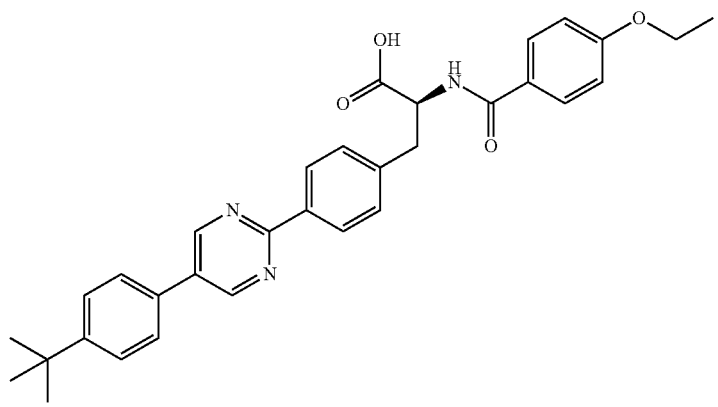 [SMILES: CCOc1ccc(C(=O)N[C@@H](Cc2ccc(-c3ncc(-c4ccc(C(C)(C)C)cc4)cn3)cc2)C(=O)O)cc1] | 171 | 8.67 | 10 |
| 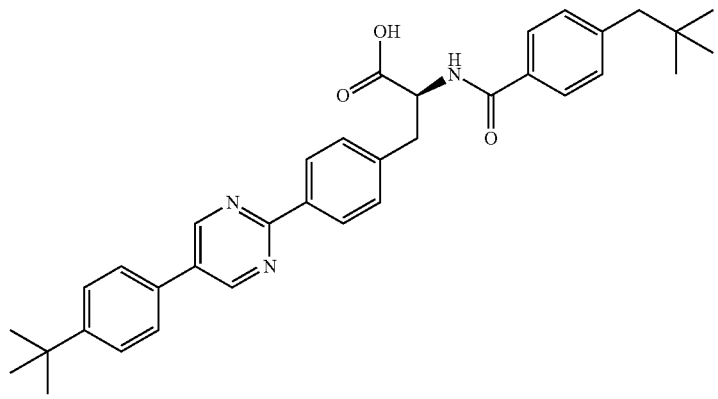 [SMILES: CC(C)(C)Cc1ccc(C(=O)N[C@@H](Cc2ccc(-c3ncc(-c4ccc(C(C)(C)C)cc4)cn3)cc2)C(=O)O)cc1] | 172 | 10.31 | 10 |

TABLE 1-continued

| STRUCTURE | COMPOUND NUMBER | LCMS RETENTION TIME (min) | PURITY METHOD |
|---|---|---|---|
| 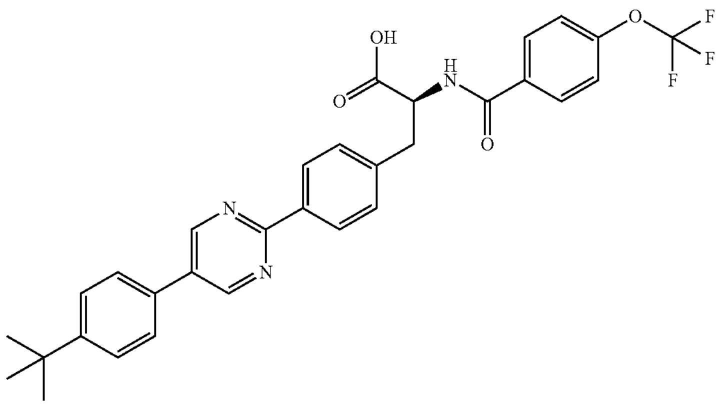 [SMILES: CC(C)(C)c1ccc(-c2cnc(-c3ccc(C[C@H](NC(=O)c4ccc(OC(F)(F)F)cc4)C(=O)O)cc3)nc2)cc1] | 173 | 9.27 | 10 |
| 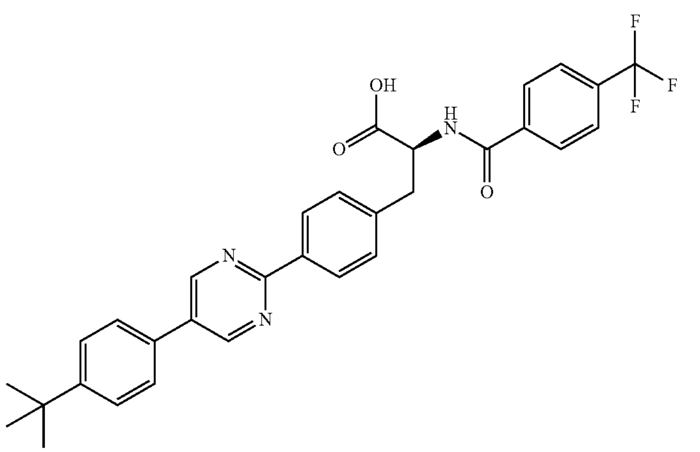 [SMILES: CC(C)(C)c1ccc(-c2cnc(-c3ccc(C[C@H](NC(=O)c4ccc(C(F)(F)F)cc4)C(=O)O)cc3)nc2)cc1] | 174 | 9.17 | 10 |
| 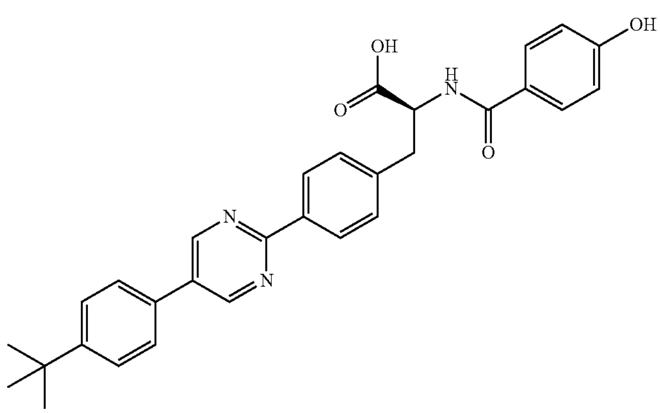 [SMILES: CC(C)(C)c1ccc(-c2cnc(-c3ccc(C[C@H](NC(=O)c4ccc(O)cc4)C(=O)O)cc3)nc2)cc1] | 175 | 7.34 | 10 |

TABLE 1-continued

| STRUCTURE | COMPOUND NUMBER | LCMS RETENTION TIME (min) | PURITY METHOD |
|---|---|---|---|
| 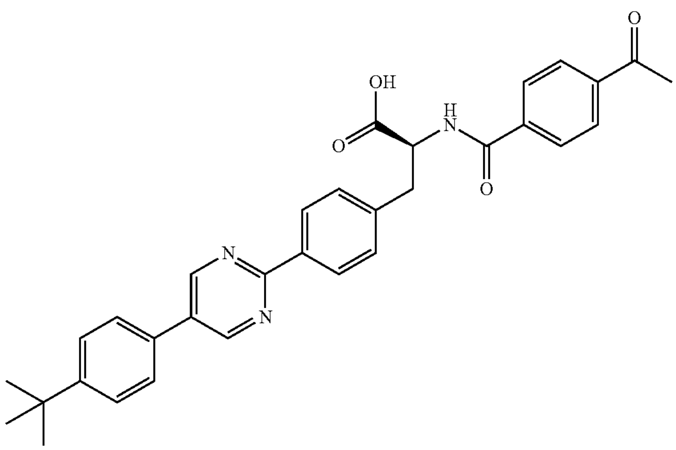 [SMILES: CC(=O)c1ccc(C(=O)N[C@@H](Cc2ccc(-c3ncc(-c4ccc(C(C)(C)C)cc4)cn3)cc2)C(=O)O)cc1] | 176 | 7.97 | 10 |
| 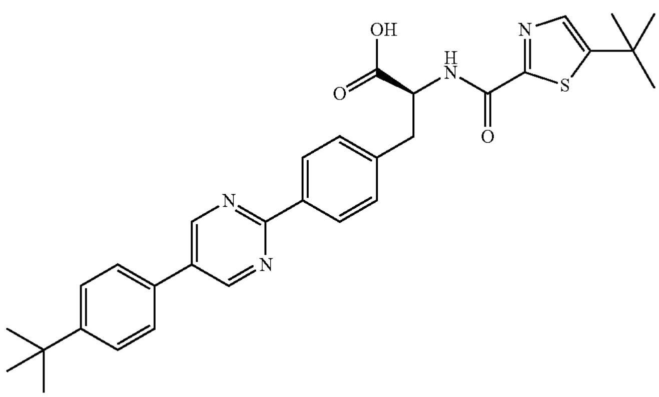 [SMILES: CC(C)(C)c1ccc(-c2cnc(-c3ccc(C[C@H](NC(=O)c4ncc(C(C)(C)C)s4)C(=O)O)cc3)nc2)cc1] | 177 | 8.87 | 10 |
| 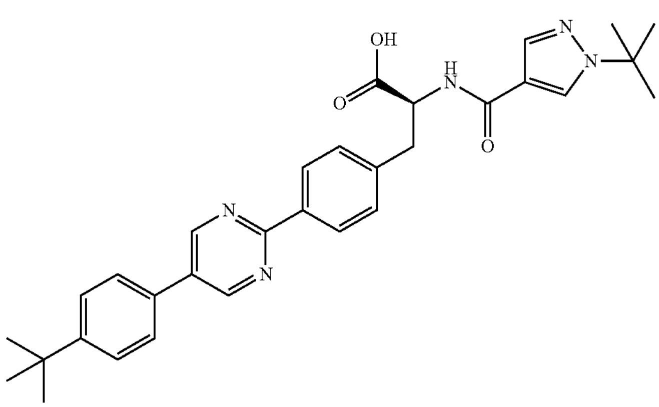 [SMILES: CC(C)(C)c1ccc(-c2cnc(-c3ccc(C[C@H](NC(=O)c4cnn(C(C)(C)C)c4)C(=O)O)cc3)nc2)cc1] | 178 | 7.94 | 10 |

TABLE 1-continued

| STRUCTURE | COMPOUND NUMBER | LCMS RETENTION TIME (min) | PURITY METHOD |
|---|---|---|---|
| 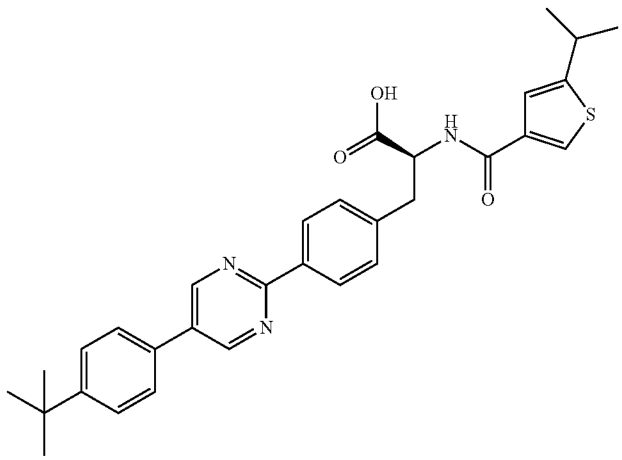 [SMILES: CC(C)c1cc(C(=O)N[C@@H](Cc2ccc(-c3ncc(-c4ccc(C(C)(C)C)cc4)cn3)cc2)C(=O)O)cs1] | 179 | 9.31 | 10 |
| 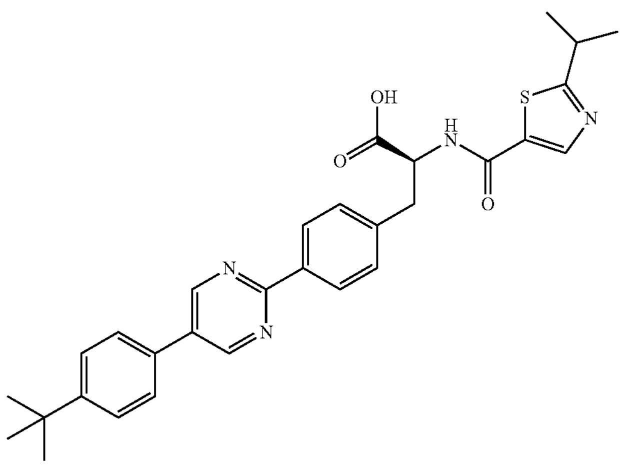 [SMILES: CC(C)c1ncc(C(=O)N[C@@H](Cc2ccc(-c3ncc(-c4ccc(C(C)(C)C)cc4)cn3)cc2)C(=O)O)s1] | 180 | 8.79 | 10 |
| 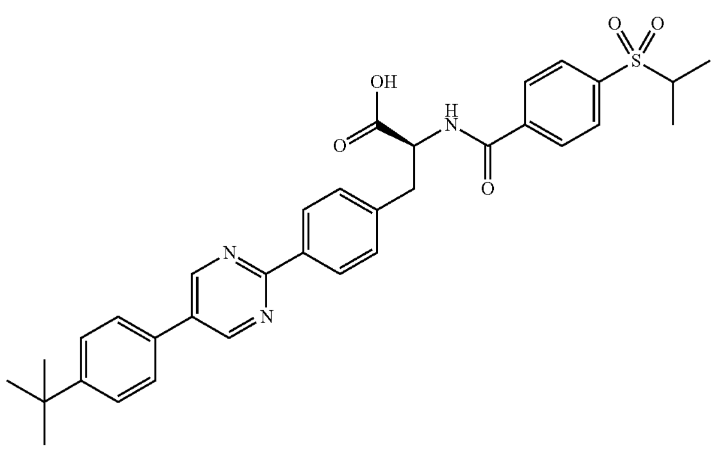 [SMILES: CC(C)S(=O)(=O)c1ccc(C(=O)N[C@@H](Cc2ccc(-c3ncc(-c4ccc(C(C)(C)C)cc4)cn3)cc2)C(=O)O)cc1] | 181 | 8.11 | 10 |

TABLE 1-continued

| STRUCTURE | COMPOUND NUMBER | LCMS RETENTION TIME (min) | PURITY METHOD |
|---|---|---|---|
| 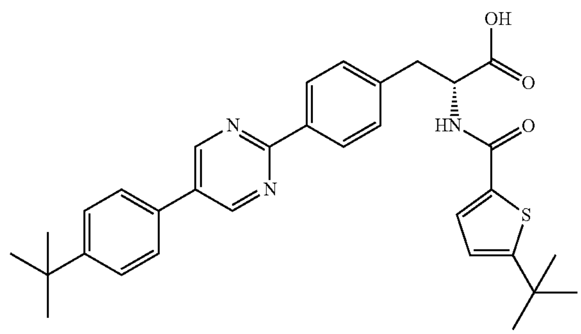 | 182 | 9.75 | 10 |
| 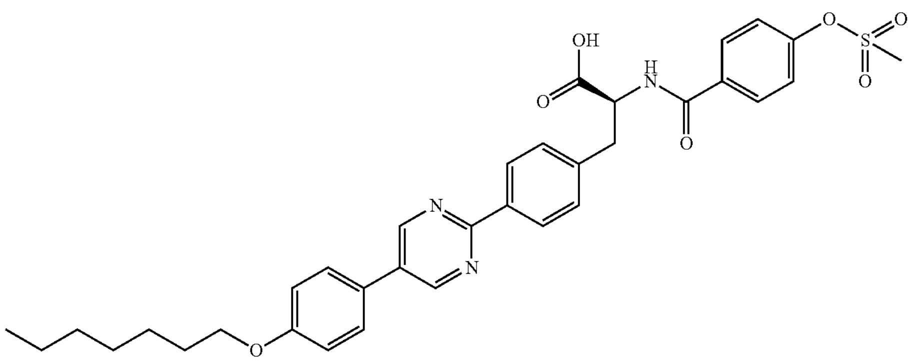 [SMILES: CCCCCCCOc1ccc(-c2cnc(-c3ccc(C[C@H](NC(=O)c4ccc(OS(C)(=O)=O)cc4)C(=O)O)cc3)nc2)cc1] | 183 | 9.13 | 9 |
| 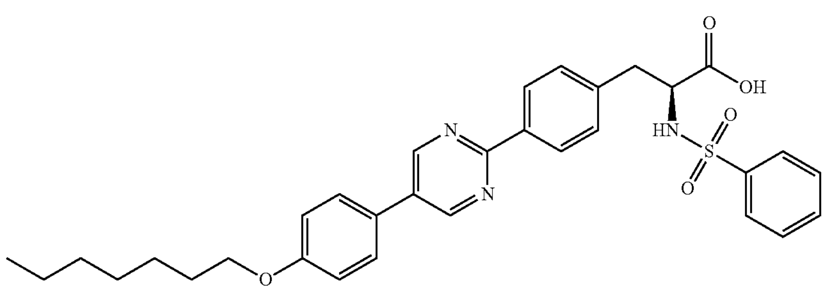 [SMILES: CCCCCCCOc1ccc(-c2cnc(-c3ccc(C[C@H](NS(=O)(=O)c4ccccc4)C(=O)O)cc3)nc2)cc1] | 184 | 10.87 | 2 |
| 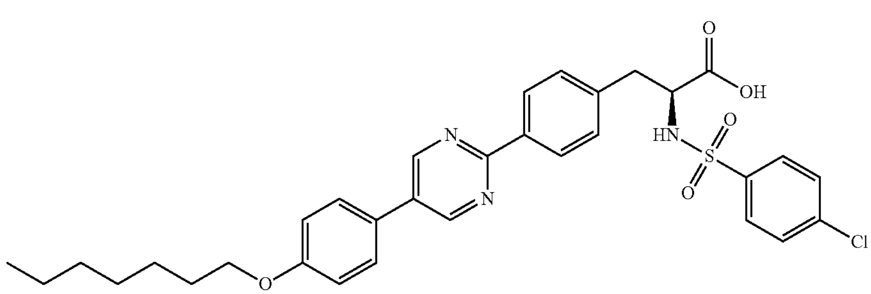 [SMILES: CCCCCCCOc1ccc(-c2cnc(-c3ccc(C[C@H](NS(=O)(=O)c4ccc(Cl)cc4)C(=O)O)cc3)nc2)cc1] | 185 | 11.32 | 2 |

TABLE 1-continued

| STRUCTURE | COMPOUND NUMBER | LCMS RETENTION TIME (min) | PURITY METHOD |
|---|---|---|---|
| 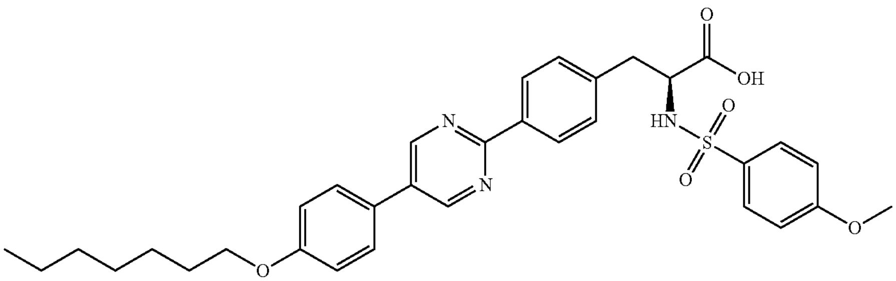 [SMILES: CCCCCCCOc1ccc(-c2cnc(-c3ccc(C[C@H](NS(=O)(=O)c4ccc(OC)cc4)C(=O)O)cc3)nc2)cc1] | 186 | 11.02 | 2 |
| 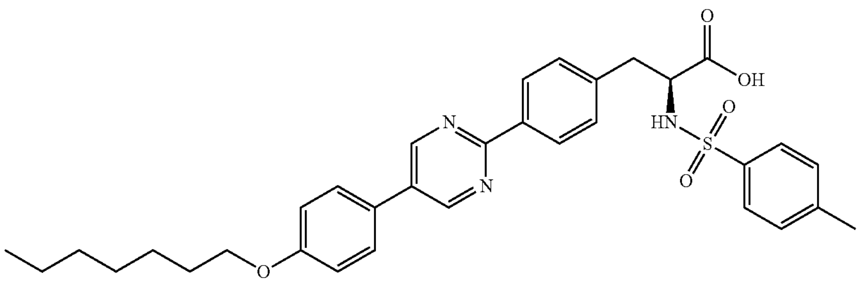 [SMILES: CCCCCCCOc1ccc(-c2cnc(-c3ccc(C[C@H](NS(=O)(=O)c4ccc(C)cc4)C(=O)O)cc3)nc2)cc1] | 187 | 11.21 | 2 |
| 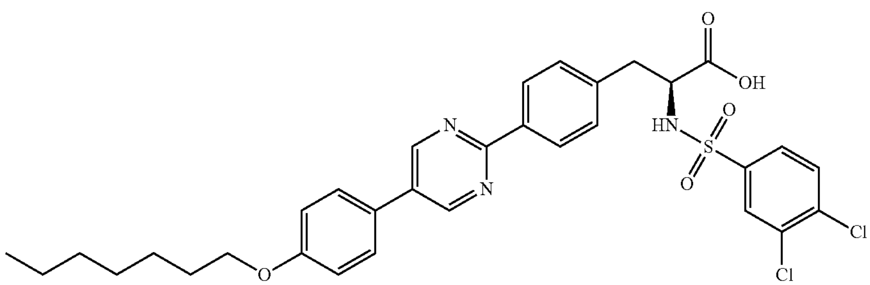 [SMILES: CCCCCCCOc1ccc(-c2cnc(-c3ccc(C[C@H](NS(=O)(=O)c4ccc(Cl)c(Cl)c4)C(=O)O)cc3)nc2)cc1] | 188 | 11.56 | 2 |
| 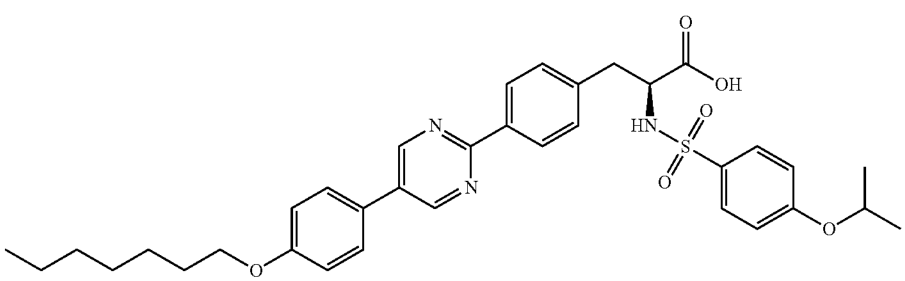 [SMILES: CCCCCCCOc1ccc(-c2cnc(-c3ccc(C[C@H](NS(=O)(=O)c4ccc(OC(C)C)cc4)C(=O)O)cc3)nc2)cc1] | 189 | 11.25 | 2 |
| 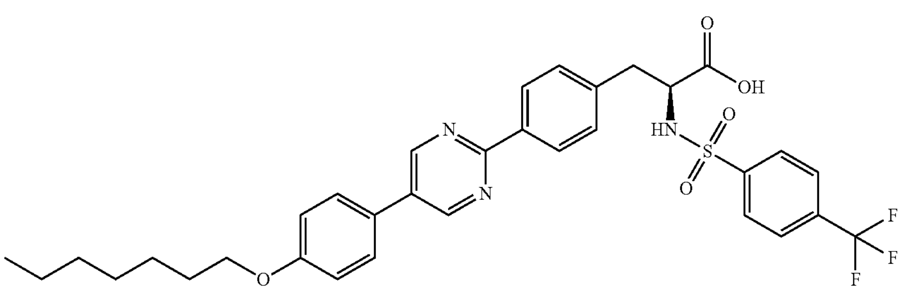 [SMILES: CCCCCCCOc1ccc(-c2cnc(-c3ccc(C[C@H](NS(=O)(=O)c4ccc(C(F)(F)F)cc4)C(=O)O)cc3)nc2)cc1] | 190 | 11.42 | 2 |

TABLE 1-continued

| STRUCTURE | COMPOUND NUMBER | LCMS RETENTION TIME (min) | PURITY METHOD |
|---|---|---|---|
| (structure) | 191 | 11.59 | 10 |
| (structure) | 192 | 11.10 | 10 |
| (structure) | 193 | 11.17 | 10 |
| (structure) | 194 | 7.39 | 9 |

TABLE 1-continued
| STRUCTURE | COMPOUND NUMBER | LCMS RETENTION TIME (min) | PURITY METHOD |
|---|---|---|---|
| 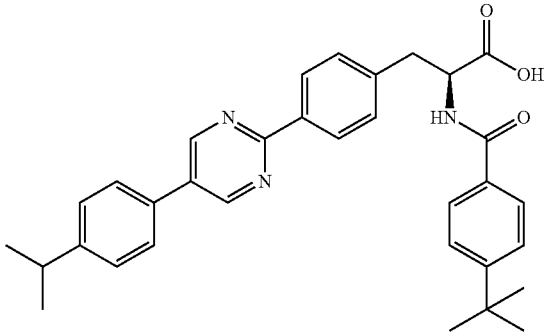 [SMILES: CC(C)c1ccc(-c2cnc(-c3ccc(C[C@H](NC(=O)c4ccc(C(C)(C)C)cc4)C(=O)O)cc3)nc2)cc1] | 195 | 9.15 | 9 |
| 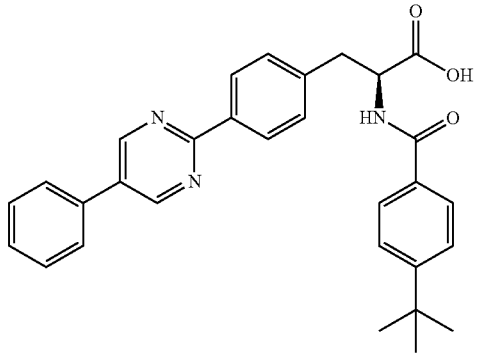 [SMILES: CC(C)(C)c1ccc(C(=O)N[C@@H](Cc2ccc(-c3ncc(-c4ccccc4)cn3)cc2)C(=O)O)cc1] | 196 | 9.30 | 2 |
| 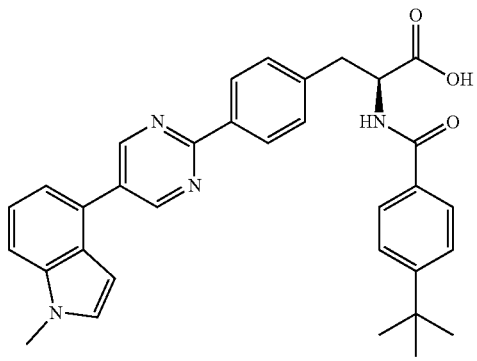 [SMILES: Cn1ccc2c(-c3cnc(-c4ccc(C[C@H](NC(=O)c5ccc(C(C)(C)C)cc5)C(=O)O)cc4)nc3)cccc21] | 197 | 9.41 | 2 |
| 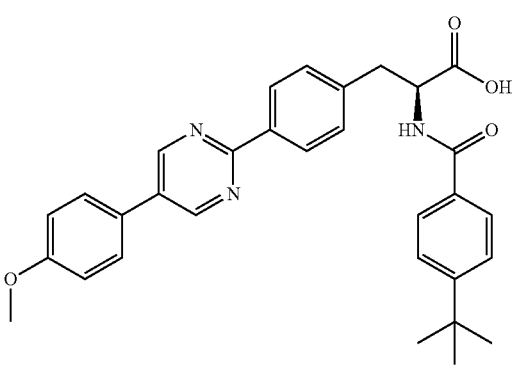 [SMILES: COc1ccc(-c2cnc(-c3ccc(C[C@H](NC(=O)c4ccc(C(C)(C)C)cc4)C(=O)O)cc3)nc2)cc1] | 198 | 9.40 | 2 |

TABLE 1-continued
| STRUCTURE | COMPOUND NUMBER | LCMS RETENTION TIME (min) | PURITY METHOD |
|---|---|---|---|
| 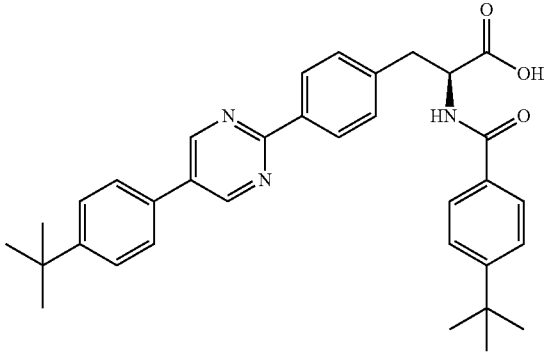 [SMILES: CC(C)(C)c1ccc(C(=O)N[C@@H](Cc2ccc(-c3ncc(-c4ccc(C(C)(C)C)cc4)cn3)cc2)C(=O)O)cc1] | 199 | 10.53 | 2 |
| 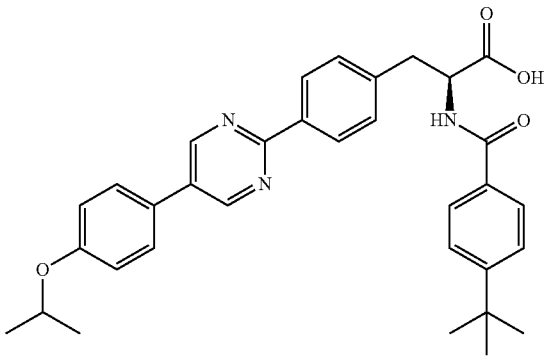 [SMILES: CC(C)Oc1ccc(-c2cnc(-c3ccc(C[C@H](NC(=O)c4ccc(C(C)(C)C)cc4)C(=O)O)cc3)nc2)cc1] | 200 | 10.11 | 2 |
| 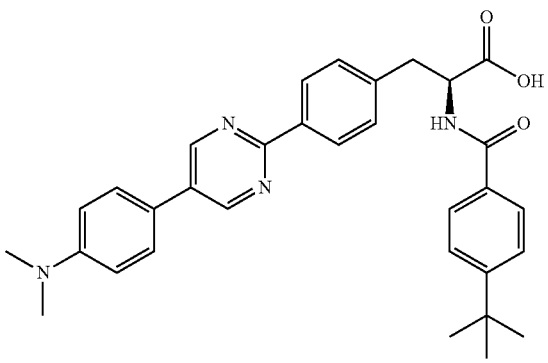 [SMILES: CN(C)c1ccc(-c2cnc(-c3ccc(C[C@H](NC(=O)c4ccc(C(C)(C)C)cc4)C(=O)O)cc3)nc2)cc1] | 201 | 9.58 | 2 |
| 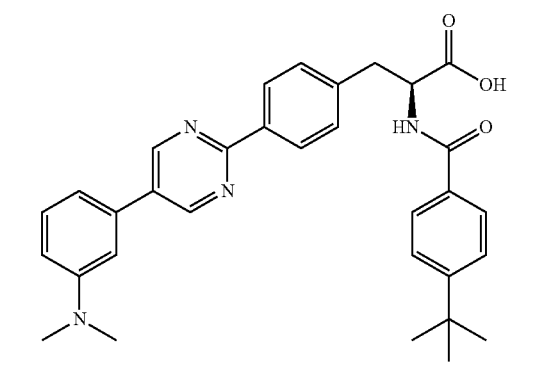 [SMILES: CN(C)c1cccc(-c2cnc(-c3ccc(C[C@H](NC(=O)c4ccc(C(C)(C)C)cc4)C(=O)O)cc3)nc2)c1] | 202 | 9.51 | 2 |

TABLE 1-continued

| STRUCTURE | COMPOUND NUMBER | LCMS RETENTION TIME (min) | PURITY METHOD |
|---|---|---|---|
| 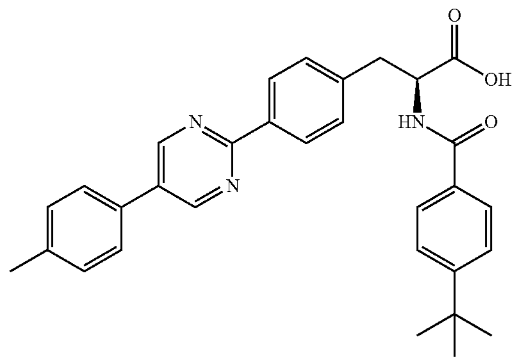 [SMILES: Cc1ccc(-c2cnc(-c3ccc(C[C@H](NC(=O)c4ccc(C(C)(C)C)cc4)C(=O)O)cc3)nc2)cc1] | 203 | 10.05 | 2 |
| 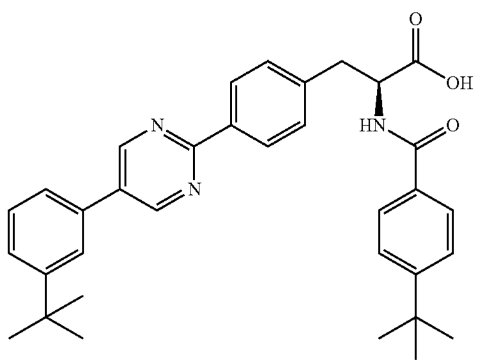 [SMILES: CC(C)(C)c1ccc(C(=O)N[C@@H](Cc2ccc(-c3ncc(-c4cccc(C(C)(C)C)c4)cn3)cc2)C(=O)O)cc1] | 204 | 10.55 | 2 |
| 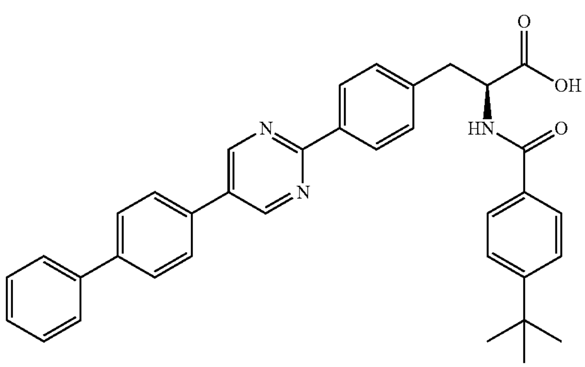 [SMILES: CC(C)(C)c1ccc(C(=O)N[C@@H](Cc2ccc(-c3ncc(-c4ccc(-c5ccccc5)cc4)cn3)cc2)C(=O)O)cc1] | 205 | 10.36 | 2 |
| 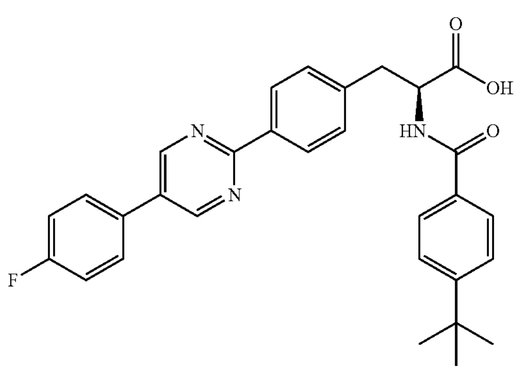 | 206 | 9.36 | 2 |

TABLE 1-continued
| STRUCTURE | COMPOUND NUMBER | LCMS RETENTION TIME (min) | PURITY METHOD |
|---|---|---|---|
| 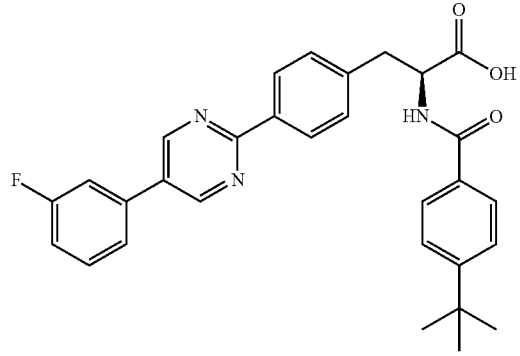 | 207 | 9.41 | 2 |
| 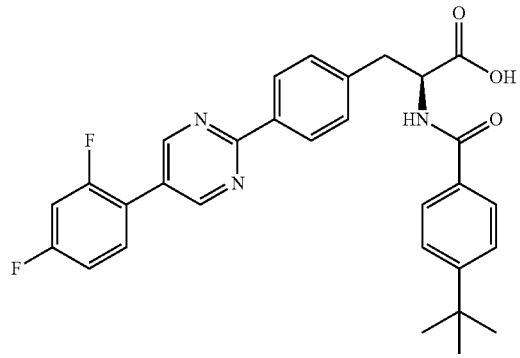 | 208 | 9.49 | 2 |
| 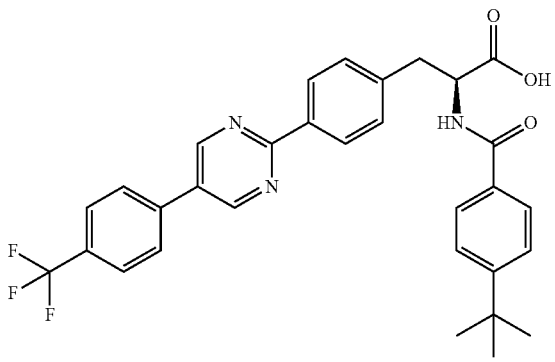 [SMILES: CC(C)(C)c1ccc(C(=O)N[C@@H](Cc2ccc(-c3ncc(-c4ccc(C(F)(F)F)cc4)cn3)cc2)C(=O)O)cc1] | 209 | 9.85 | 2 |
| 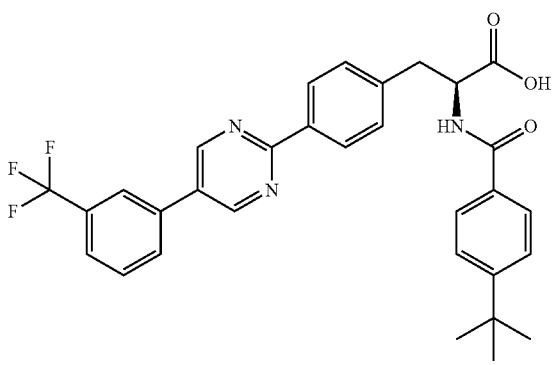 [SMILES: CC(C)(C)c1ccc(C(=O)N[C@@H](Cc2ccc(-c3ncc(-c4cccc(C(F)(F)F)c4)cn3)cc2)C(=O)O)cc1] | 210 | 9.69 | 2 |

TABLE 1-continued

| STRUCTURE | COMPOUND NUMBER | LCMS RETENTION TIME (min) | PURITY METHOD |
|---|---|---|---|
| 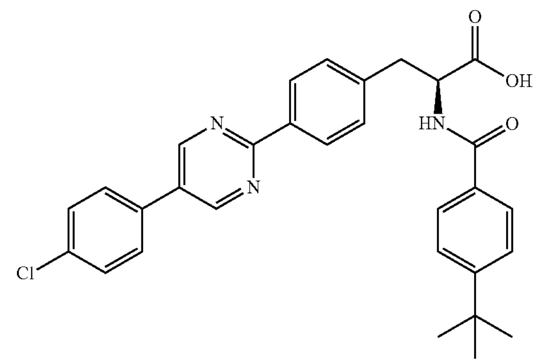 [SMILES: CC(C)(C)c1ccc(C(=O)N[C@@H](Cc2ccc(-c3ncc(-c4ccc(Cl)cc4)cn3)cc2)C(=O)O)cc1] | 211 | 9.81 | 2 |
| 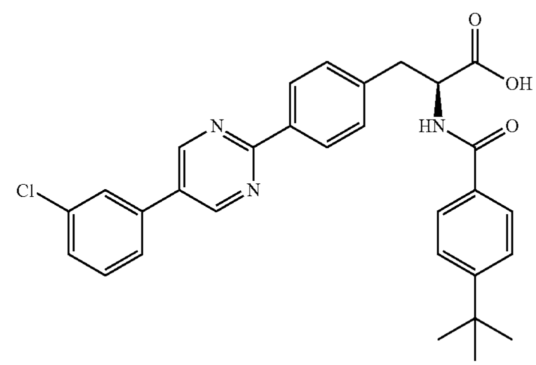 [SMILES: CC(C)(C)c1ccc(C(=O)N[C@@H](Cc2ccc(-c3ncc(-c4cccc(Cl)c4)cn3)cc2)C(=O)O)cc1] | 212 | 10.13 | 2 |
| 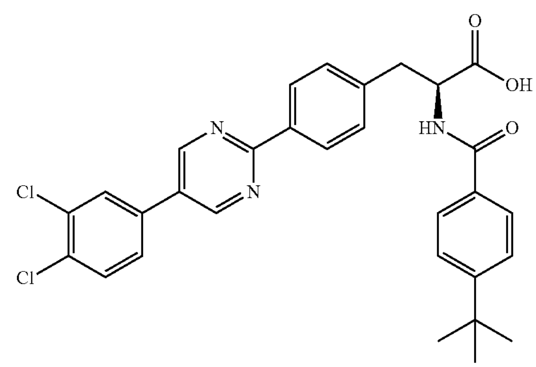 [SMILES: CC(C)(C)c1ccc(C(=O)N[C@@H](Cc2ccc(-c3ncc(-c4ccc(Cl)c(Cl)c4)cn3)cc2)C(=O)O)cc1] | 213 | 10.28 | 2 |
| 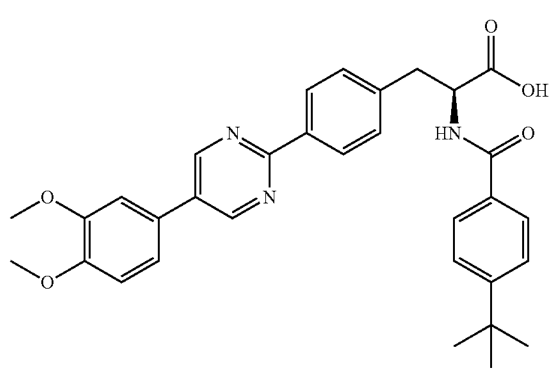 [SMILES: COc1ccc(-c2cnc(-c3ccc(C[C@H](NC(=O)c4ccc(C(C)(C)C)cc4)C(=O)O)cc3)nc2)cc1OC] | 214 | 8.69 | 2 |

TABLE 1-continued

| STRUCTURE | COMPOUND NUMBER | LCMS RETENTION TIME (min) | PURITY METHOD |
|---|---|---|---|
| 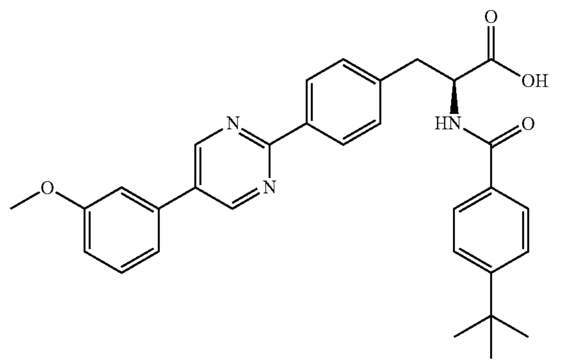 [SMILES: COc1cccc(-c2cnc(-c3ccc(C[C@H](NC(=O)c4ccc(C(C)(C)C)cc4)C(=O)O)cc3)nc2)c1] | 215 | 9.37 | 2 |
| 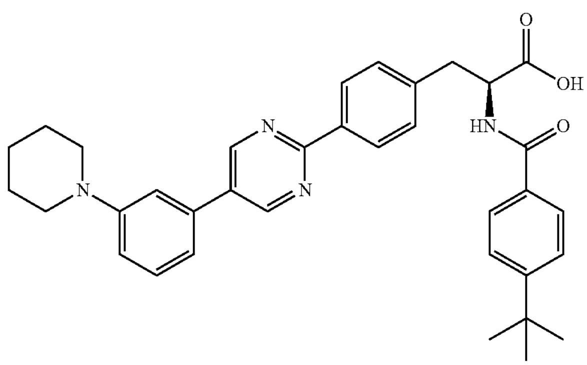 [SMILES: CC(C)(C)c1ccc(C(=O)N[C@@H](Cc2ccc(-c3ncc(-c4cccc(N5CCCCC5)c4)cn3)cc2)C(=O)O)cc1] | 216 | 8.75 | 2 |
| 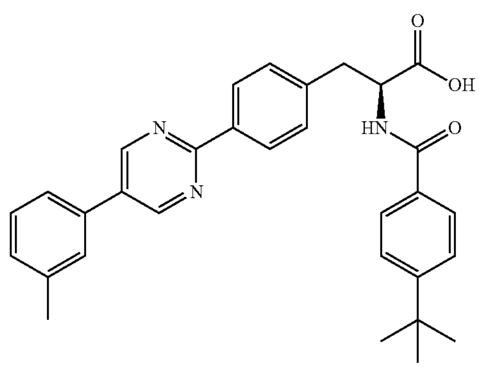 [SMILES: Cc1cccc(-c2cnc(-c3ccc(C[C@H](NC(=O)c4ccc(C(C)(C)C)cc4)C(=O)O)cc3)nc2)c1] | 217 | 9.83 | 2 |
| 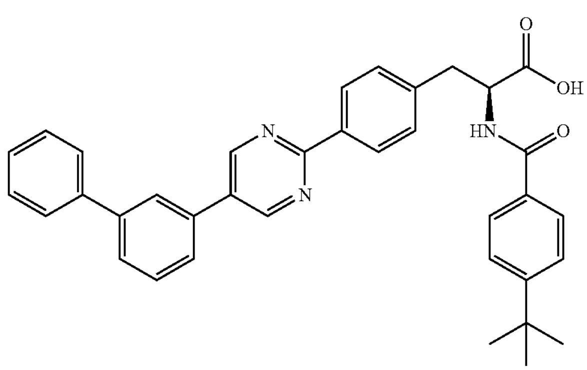 [SMILES: CC(C)(C)c1ccc(C(=O)N[C@@H](Cc2ccc(-c3ncc(-c4cccc(-c5ccccc5)c4)cn3)cc2)C(=O)O)cc1] | 218 | 10.31 | 2 |

TABLE 1-continued

| STRUCTURE | COMPOUND NUMBER | LCMS RETENTION TIME (min) | PURITY METHOD |
|---|---|---|---|
| 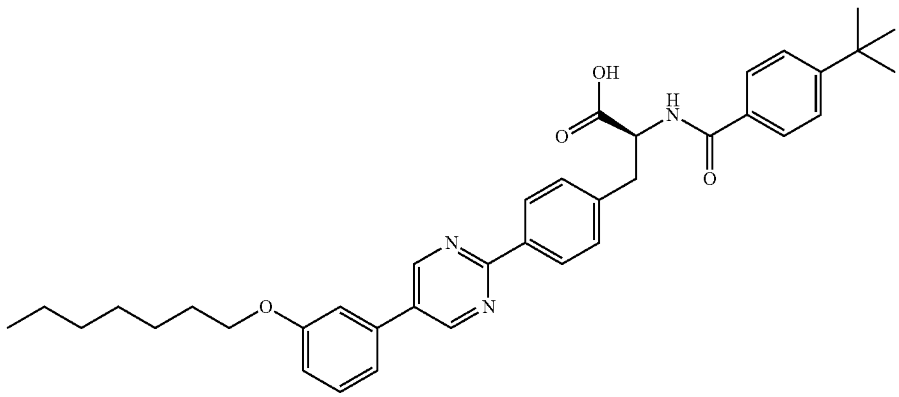 [SMILES: CCCCCCCOc1cccc(-c2cnc(-c3ccc(C[C@H](NC(=O)c4ccc(C(C)(C)C)cc4)C(=O)O)cc3)nc2)c1] | 219 | 11.69 | 2 |
| 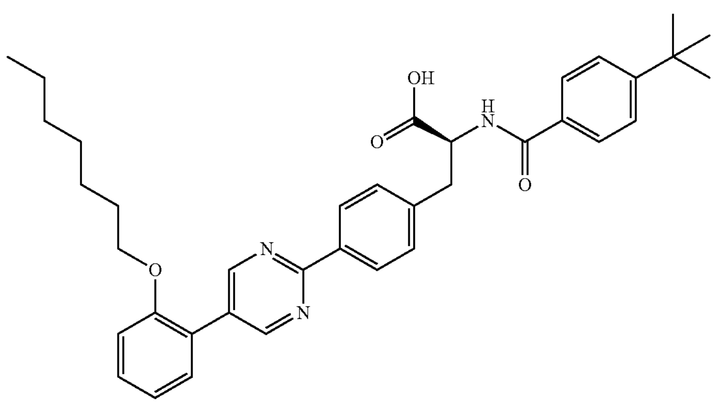 [SMILES: CCCCCCCOc1ccccc1-c1cnc(-c2ccc(C[C@H](NC(=O)c3ccc(C(C)(C)C)cc3)C(=O)O)cc2)nc1] | 220 | 11.97 | 2 |
| 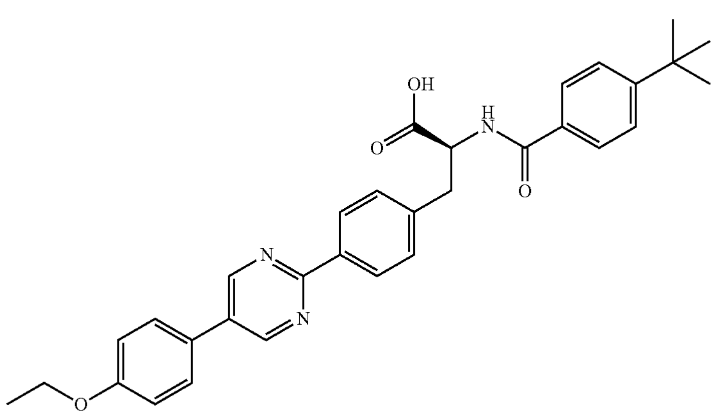 [SMILES: CCOc1ccc(-c2cnc(-c3ccc(C[C@H](NC(=O)c4ccc(C(C)(C)C)cc4)C(=O)O)cc3)nc2)cc1] | 221 | 9.89 | 2 |

TABLE 1-continued

| STRUCTURE | COMPOUND NUMBER | LCMS RETENTION TIME (min) | PURITY METHOD |
|---|---|---|---|
| 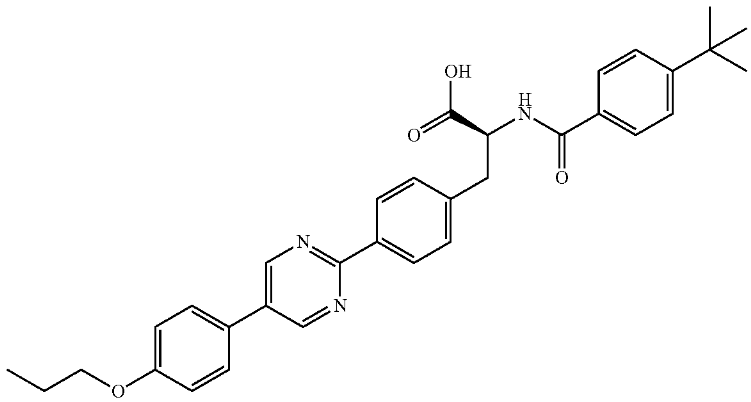 [SMILES: CCCOc1ccc(-c2cnc(-c3ccc(C[C@H](NC(=O)c4ccc(C(C)(C)C)cc4)C(=O)O)cc3)nc2)cc1] | 222 | 10.27 | 2 |
| 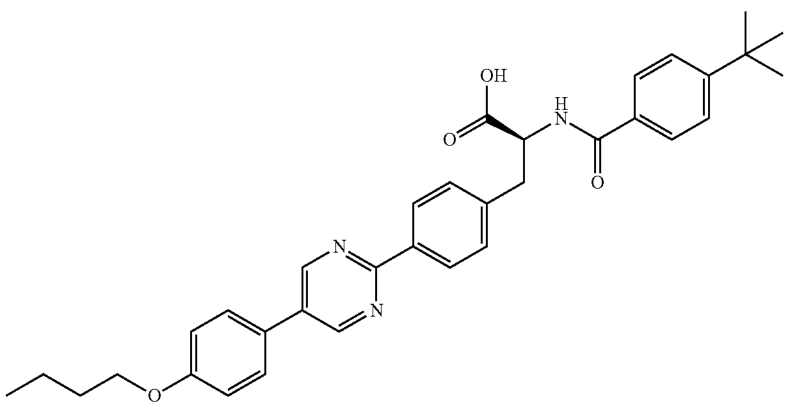 [SMILES: CCCCOc1ccc(-c2cnc(-c3ccc(C[C@H](NC(=O)c4ccc(C(C)(C)C)cc4)C(=O)O)cc3)nc2)cc1] | 223 | 10.46 | 2 |
| 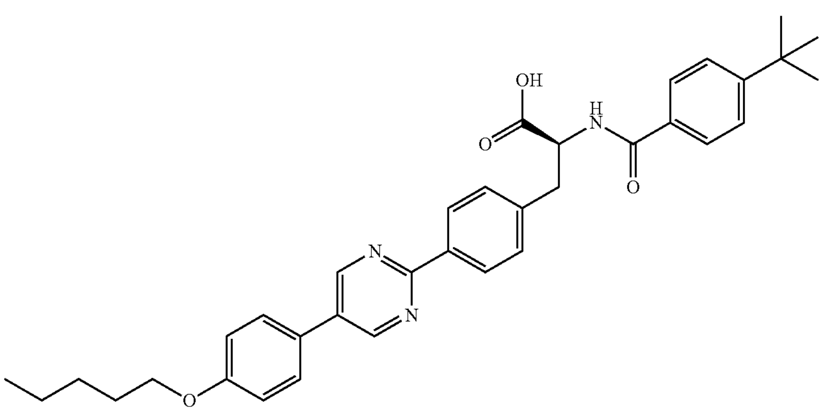 [SMILES: CCCCCOc1ccc(-c2cnc(-c3ccc(C[C@H](NC(=O)c4ccc(C(C)(C)C)cc4)C(=O)O)cc3)nc2)cc1] | 224 | 10.82 | 2 |

TABLE 1-continued

| STRUCTURE | COMPOUND NUMBER | LCMS RETENTION TIME (min) | PURITY METHOD |
|---|---|---|---|
| 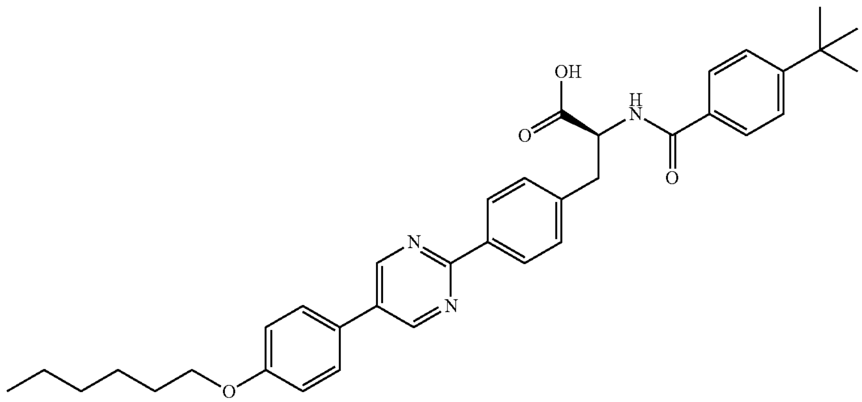 [SMILES: CCCCCCOc1ccc(-c2cnc(-c3ccc(C[C@H](NC(=O)c4ccc(C(C)(C)C)cc4)C(=O)O)cc3)nc2)cc1] | 225 | 11.81 | 2 |
| 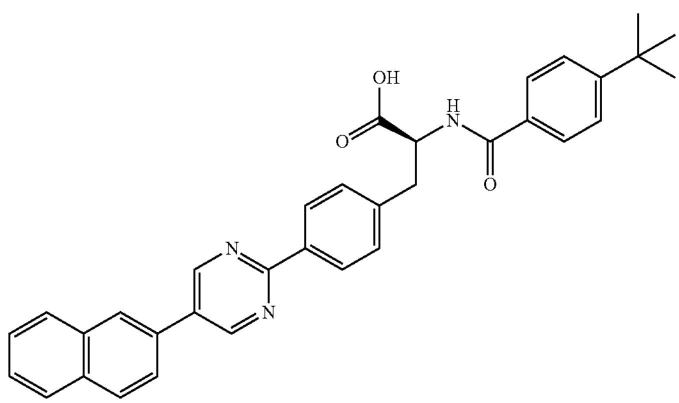 [SMILES: CC(C)(C)c1ccc(C(=O)N[C@@H](Cc2ccc(-c3ncc(-c4ccc5ccccc5c4)cn3)cc2)C(=O)O)cc1] | 226 | 10.15 | 2 |
| 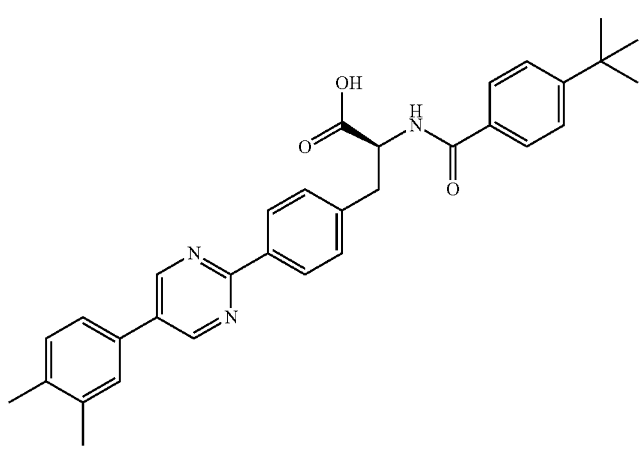 [SMILES: Cc1ccc(-c2cnc(-c3ccc(C[C@H](NC(=O)c4ccc(C(C)(C)C)cc4)C(=O)O)cc3)nc2)cc1C] | 227 | 10.31 | 2 |

TABLE 1-continued

| STRUCTURE | COMPOUND NUMBER | LCMS RETENTION TIME (min) | PURITY METHOD |
|---|---|---|---|
| 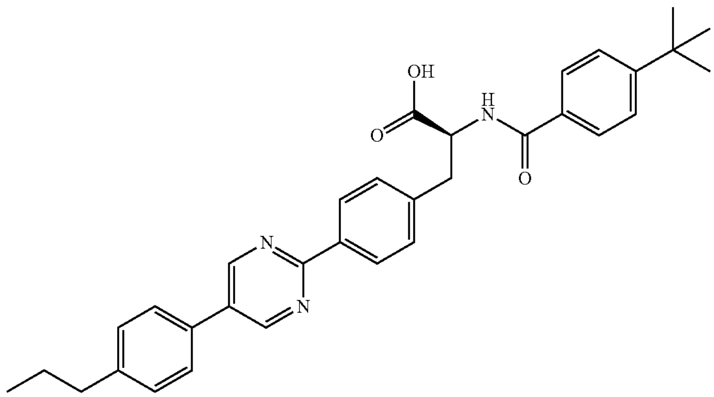 [SMILES: CCCc1ccc(-c2cnc(-c3ccc(C[C@H](NC(=O)c4ccc(C(C)(C)C)cc4)C(=O)O)cc3)nc2)cc1] | 228 | 10.74 | 2 |
| 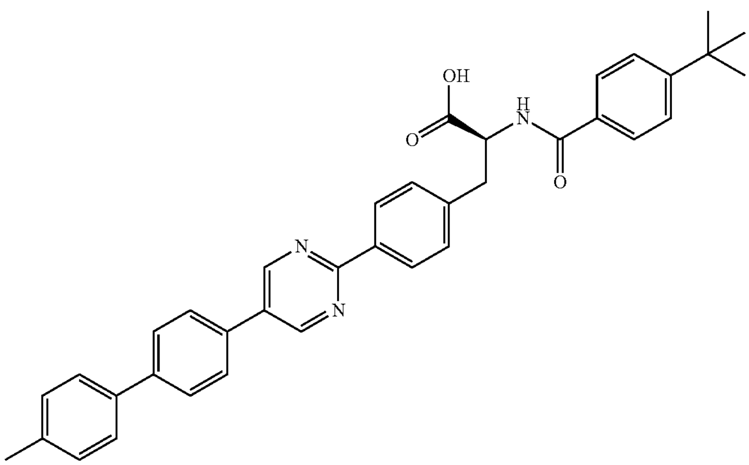 [SMILES: Cc1ccc(-c2ccc(-c3cnc(-c4ccc(C[C@H](NC(=O)c5ccc(C(C)(C)C)cc5)C(=O)O)cc4)nc3)cc2)cc1] | 229 | 11.03 | 2 |
| 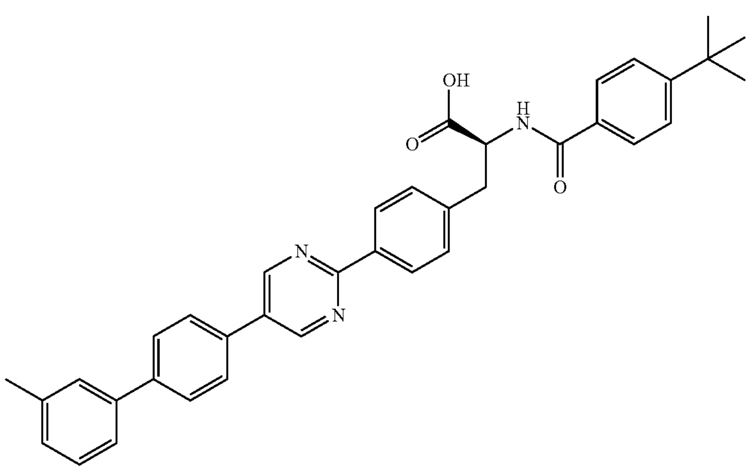 [SMILES: Cc1cccc(-c2ccc(-c3cnc(-c4ccc(C[C@H](NC(=O)c5ccc(C(C)(C)C)cc5)C(=O)O)cc4)nc3)cc2)c1] | 230 | 10.87 | 2 |

TABLE 1-continued
| STRUCTURE | COMPOUND NUMBER | LCMS RETENTION TIME (min) | PURITY METHOD |
|---|---|---|---|
| 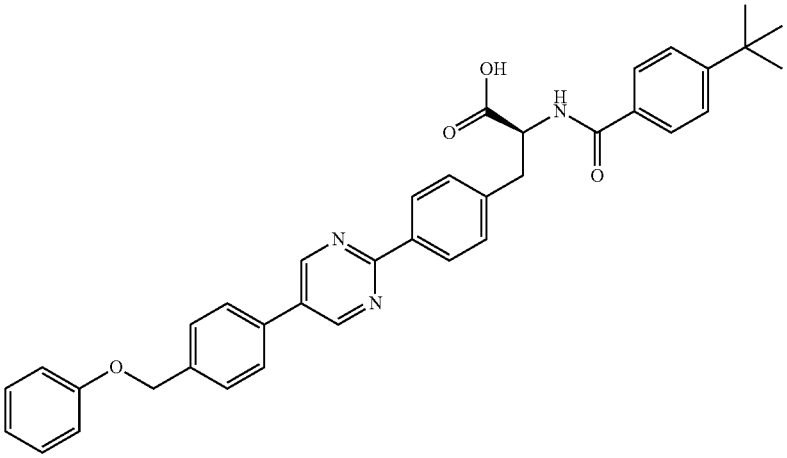 [SMILES: CC(C)(C)c1ccc(C(=O)N[C@@H](Cc2ccc(-c3ncc(-c4ccc(COc5ccccc5)cc4)cn3)cc2)C(=O)O)cc1] | 231 | 10.29 | 2 |
| 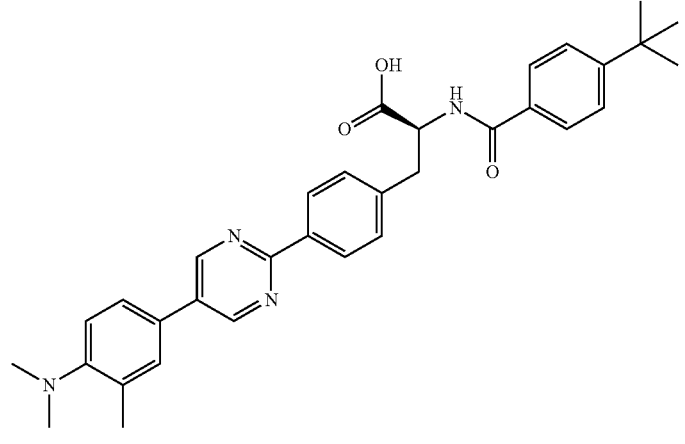 [SMILES: Cc1cc(-c2cnc(-c3ccc(C[C@H](NC(=O)c4ccc(C(C)(C)C)cc4)C(=O)O)cc3)nc2)ccc1N(C)C] | 232 | 7.95 | 2 |
| 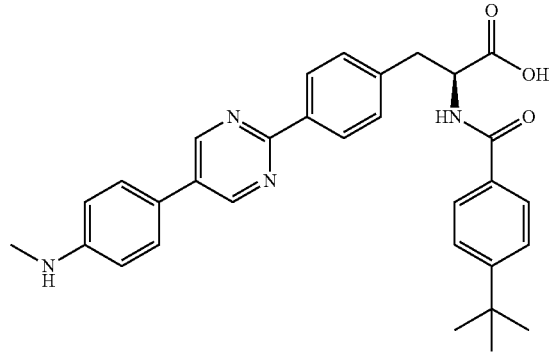 [SMILES: CNc1ccc(-c2cnc(-c3ccc(C[C@H](NC(=O)c4ccc(C(C)(C)C)cc4)C(=O)O)cc3)nc2)cc1] | 233 | 8.64 | 2 |

TABLE 1-continued

| STRUCTURE | COMPOUND NUMBER | LCMS RETENTION TIME (min) | PURITY METHOD |
|---|---|---|---|
| 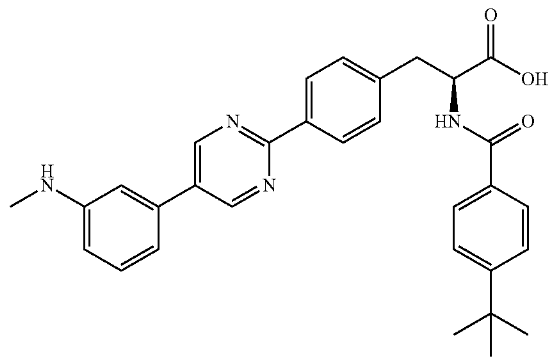 [SMILES: CNc1cccc(-c2cnc(-c3ccc(C[C@H](NC(=O)c4ccc(C(C)(C)C)cc4)C(=O)O)cc3)nc2)c1] | 234 | 8.34 | 2 |
| 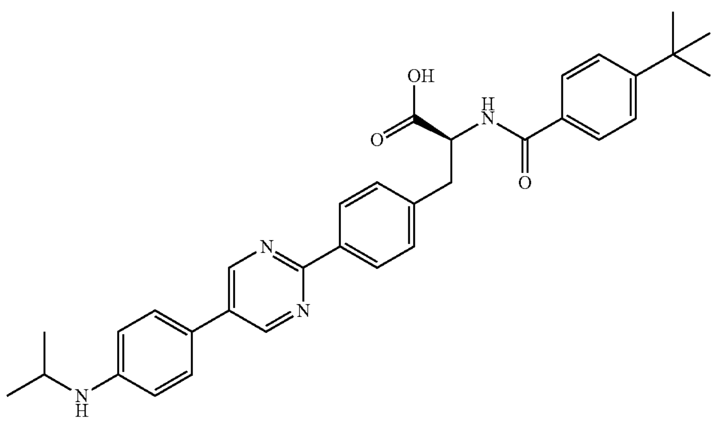 [SMILES: CC(C)Nc1ccc(-c2cnc(-c3ccc(C[C@H](NC(=O)c4ccc(C(C)(C)C)cc4)C(=O)O)cc3)nc2)cc1] | 235 | 8.94 | 2 |
| 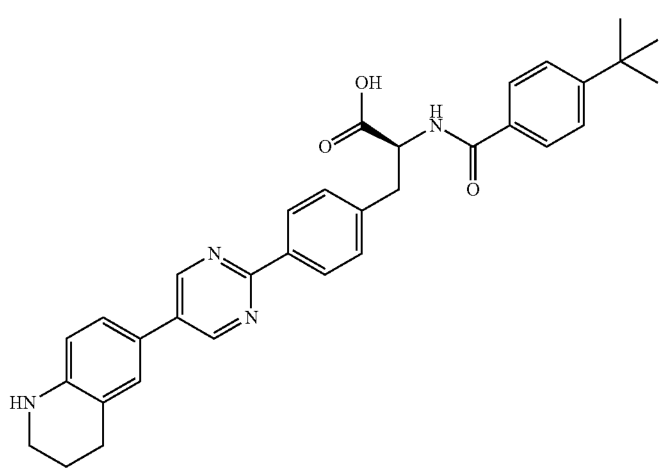 [SMILES: CC(C)(C)c1ccc(C(=O)N[C@@H](Cc2ccc(-c3ncc(-c4ccc5c(c4)CCCN5)cn3)cc2)C(=O)O)cc1] | 236 | 9.02 | 2 |

TABLE 1-continued
| STRUCTURE | COMPOUND NUMBER | LCMS RETENTION TIME (min) | PURITY METHOD |
|---|---|---|---|
| 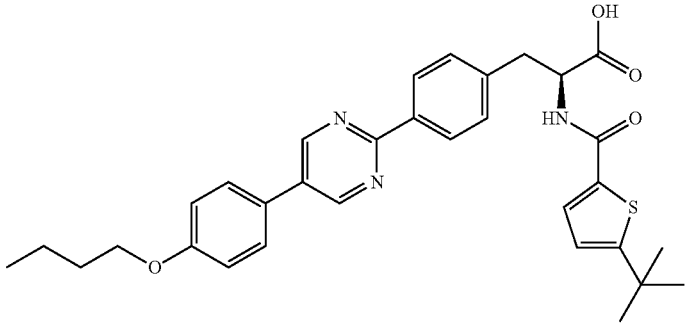 [SMILES: CCCCOc1ccc(-c2cnc(-c3ccc(C[C@H](NC(=O)c4ccc(C(C)(C)C)s4)C(=O)O)cc3)nc2)cc1] | 237 | 10.95 | 2 |
| 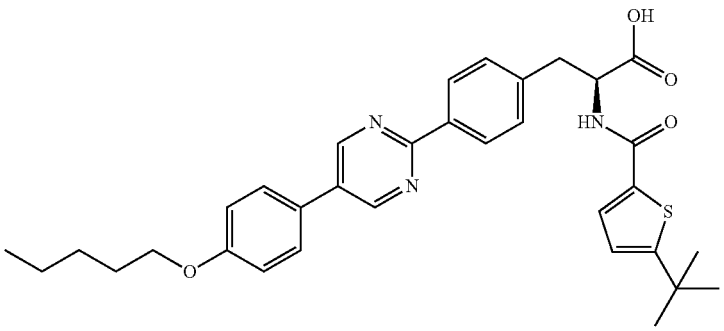 [SMILES: CCCCCOc1ccc(-c2cnc(-c3ccc(C[C@H](NC(=O)c4ccc(C(C)(C)C)s4)C(=O)O)cc3)nc2)cc1] | 238 | 11.19 | 2 |
| 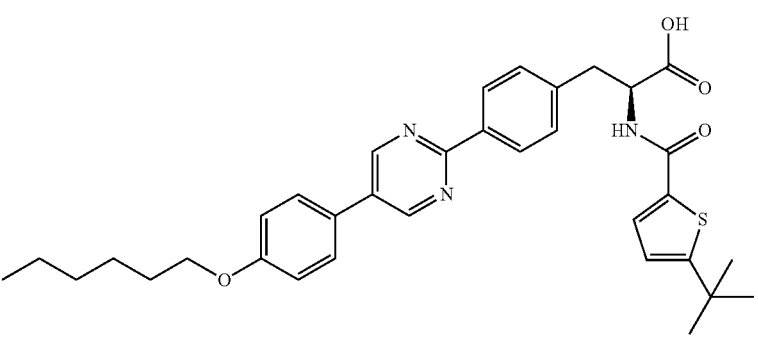 [SMILES: CCCCCCOc1ccc(-c2cnc(-c3ccc(C[C@H](NC(=O)c4ccc(C(C)(C)C)s4)C(=O)O)cc3)nc2)cc1] | 239 | 11.53 | 2 |
| 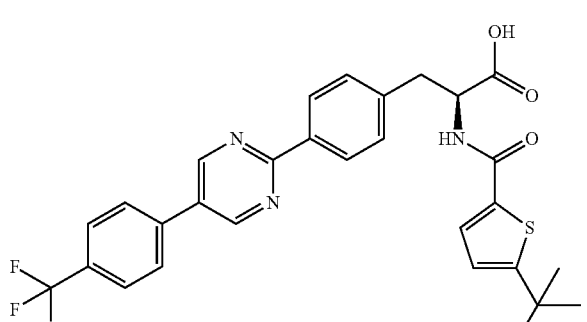 | 240 | 10.18 | 2 |

TABLE 1-continued

| STRUCTURE | COMPOUND NUMBER | LCMS RETENTION TIME (min) | PURITY METHOD |
|---|---|---|---|
| 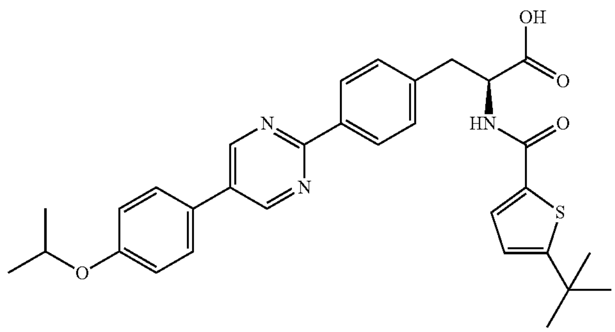 [SMILES: CC(C)Oc1ccc(-c2cnc(-c3ccc(C[C@H](NC(=O)c4ccc(C(C)(C)C)s4)C(=O)O)cc3)nc2)cc1] | 241 | 10.30 | 2 |
| 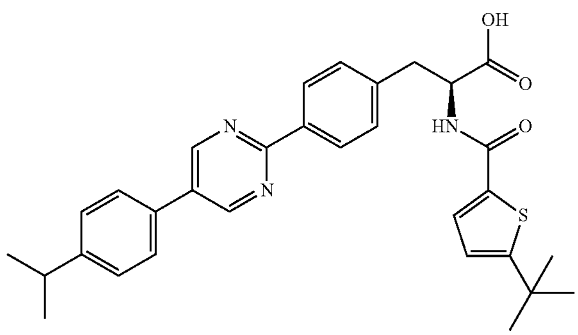 [SMILES: CC(C)c1ccc(-c2cnc(-c3ccc(C[C@H](NC(=O)c4ccc(C(C)(C)C)s4)C(=O)O)cc3)nc2)cc1] | 242 | 10.79 | 2 |
| 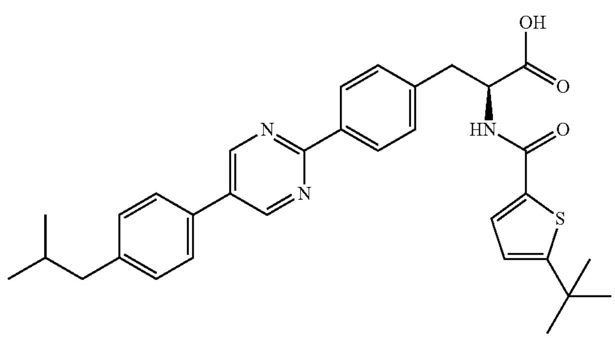 [SMILES: CC(C)Cc1ccc(-c2cnc(-c3ccc(C[C@H](NC(=O)c4ccc(C(C)(C)C)s4)C(=O)O)cc3)nc2)cc1] | 243 | 11.26 | 2 |
| 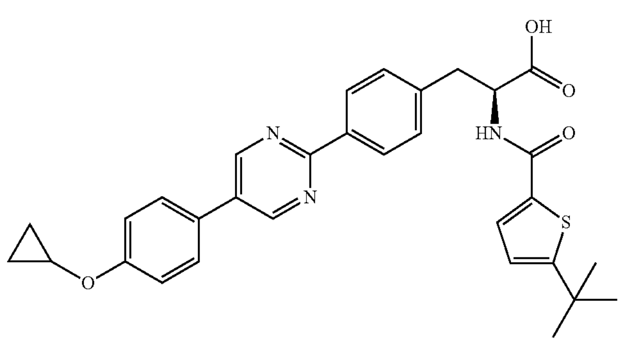 [SMILES: CC(C)(C)c1ccc(C(=O)N[C@@H](Cc2ccc(-c3ncc(-c4ccc(OC5CC5)cc4)cn3)cc2)C(=O)O)s1] | 244 | 10.10 | 2 |

TABLE 1-continued
| STRUCTURE | COMPOUND NUMBER | LCMS RETENTION TIME (min) | PURITY METHOD |
|---|---|---|---|
| 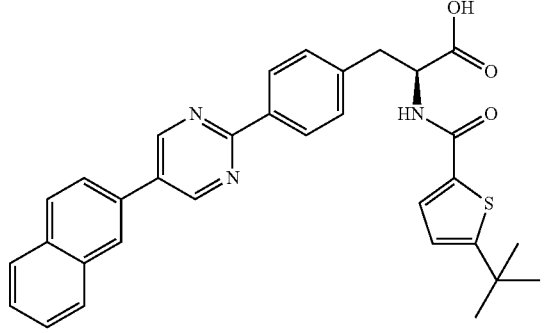 [SMILES: CC(C)(C)c1ccc(C(=O)N[C@@H](Cc2ccc(-c3ncc(-c4ccc5ccccc5c4)cn3)cc2)C(=O)O)s1] | 245 | 10.58 | 2 |
| 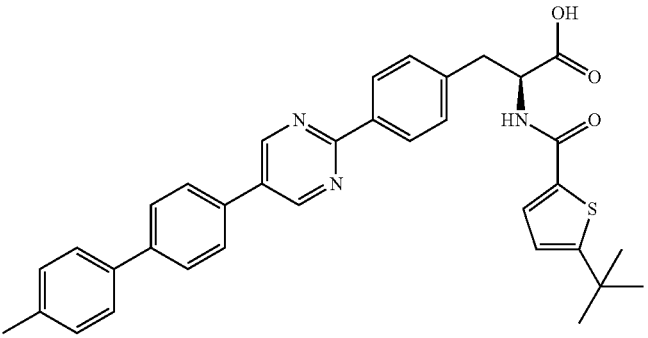 [SMILES: Cc1ccc(-c2ccc(-c3cnc(-c4ccc(C[C@H](NC(=O)c5ccc(C(C)(C)C)s5)C(=O)O)cc4)nc3)cc2)cc1] | 246 | 11.33 | 2 |
| 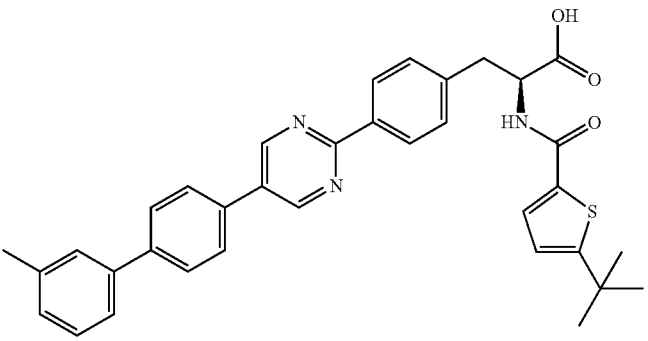 [SMILES: Cc1cccc(-c2ccc(-c3cnc(-c4ccc(C[C@H](NC(=O)c5ccc(C(C)(C)C)s5)C(=O)O)cc4)nc3)cc2)c1] | 247 | 11.19 | 2 |
| 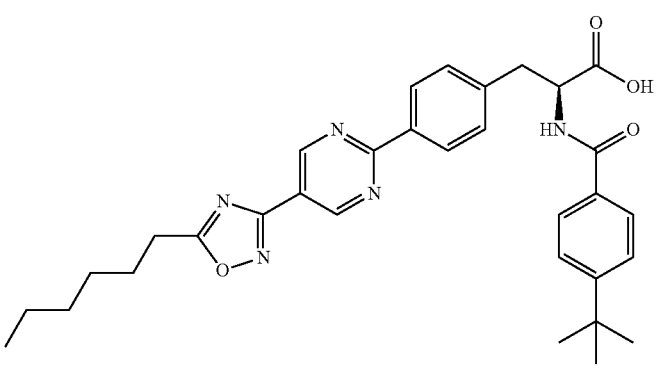 [SMILES: CCCCCCc1nc(-c2cnc(-c3ccc(C[C@H](NC(=O)c4ccc(C(C)(C)C)cc4)C(=O)O)cc3)nc2)no1] | 248 | 11.03 | 2 |

TABLE 1-continued

| STRUCTURE | COMPOUND NUMBER | LCMS RETENTION TIME (min) | PURITY METHOD |
|---|---|---|---|
| 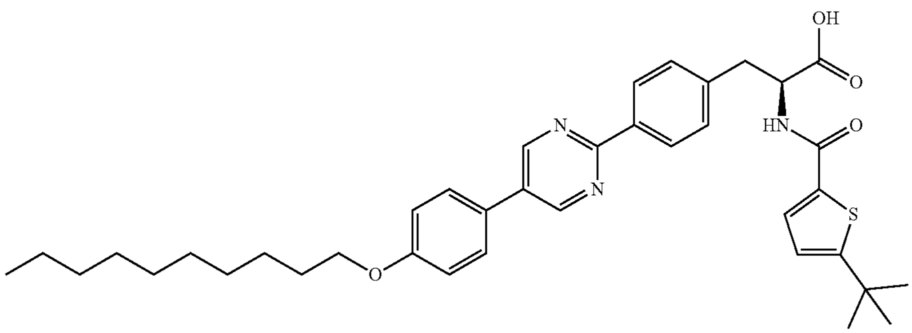 [SMILES: CCCCCCCCCCOc1ccc(-c2cnc(-c3ccc(C[C@H](NC(=O)c4ccc(C(C)(C)C)s4)C(=O)O)cc3)nc2)cc1] | 249 | 13.49 | 2 |
| 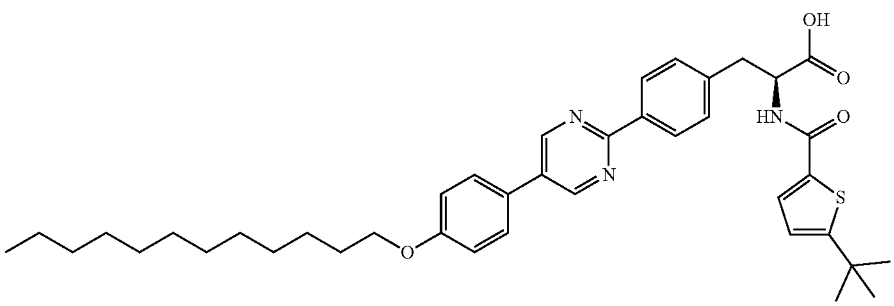 [SMILES: CCCCCCCCCCCCOc1ccc(-c2cnc(-c3ccc(C[C@H](NC(=O)c4ccc(C(C)(C)C)s4)C(=O)O)cc3)nc2)cc1] | 250 | 14.78 | 2 |
| 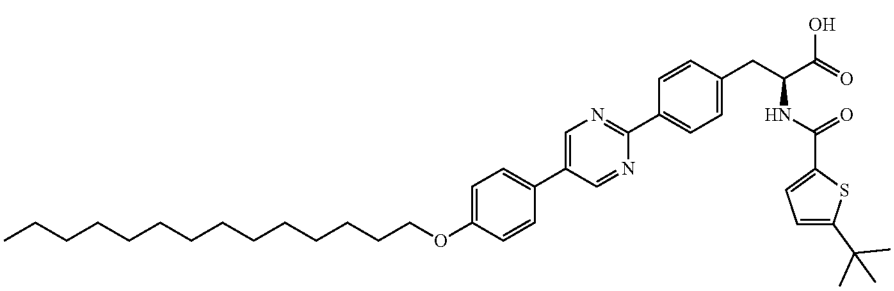 [SMILES: CCCCCCCCCCCCCCOc1ccc(-c2cnc(-c3ccc(C[C@H](NC(=O)c4ccc(C(C)(C)C)s4)C(=O)O)cc3)nc2)cc1] | 251 | 16.51 | 2 |
| 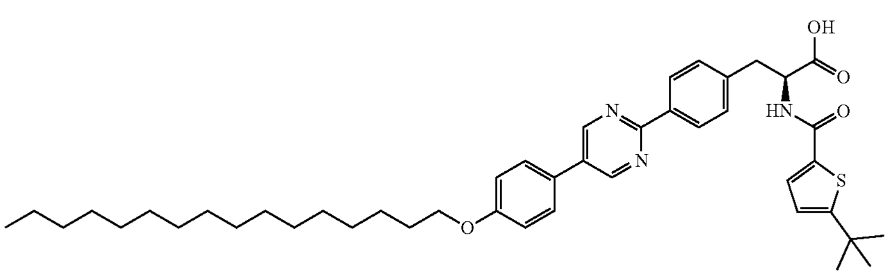 [SMILES: CCCCCCCCCCCCCCCCOc1ccc(-c2cnc(-c3ccc(C[C@H](NC(=O)c4ccc(C(C)(C)C)s4)C(=O)O)cc3)nc2)cc1] | 252 | 19.99 | 2 |

TABLE 1-continued
| STRUCTURE | COMPOUND NUMBER | LCMS RETENTION TIME (min) | PURITY METHOD |
|---|---|---|---|
| 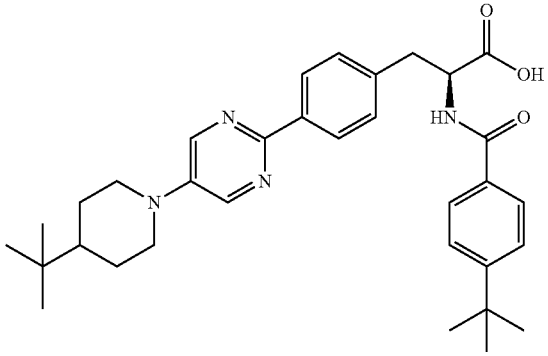 [SMILES: CC(C)(C)c1ccc(C(=O)N[C@@H](Cc2ccc(-c3ncc(N4CCC(C(C)(C)C)CC4)cn3)cc2)C(=O)O)cc1] | 253 | 10.79 | 2 |
| 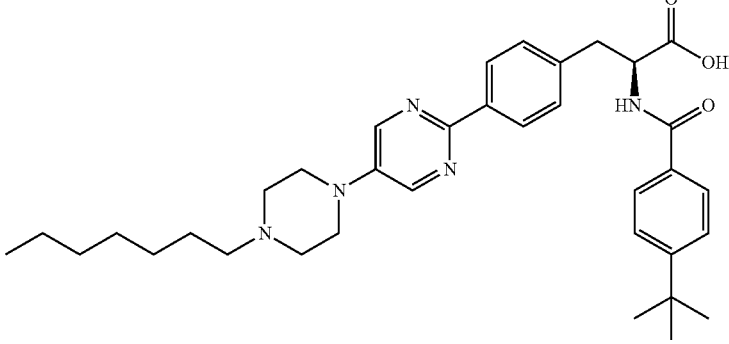 | 254 | 7.29 | 2 |
| 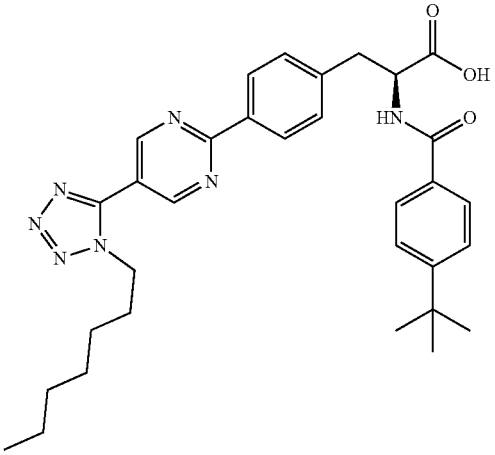 [SMILES: CCCCCCCn1nnnc1-c1cnc(-c2ccc(C[C@H](NC(=O)c3ccc(C(C)(C)C)cc3)C(=O)O)cc2)nc1] | 255 | 10.63 | 2 |

TABLE 1-continued

| STRUCTURE | COMPOUND NUMBER | LCMS RETENTION TIME (min) | PURITY METHOD |
|---|---|---|---|
| 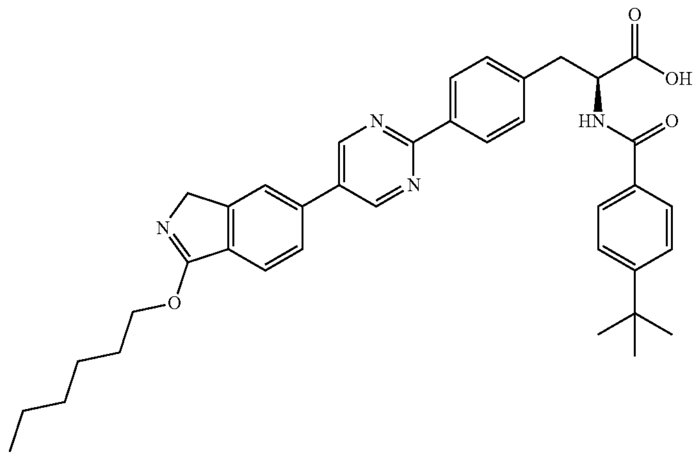 [SMILES: CCCCCCOC1=NCc2cc(-c3cnc(-c4ccc(C[C@H](NC(=O)c5ccc(C(C)(C)C)cc5)C(=O)O)cc4)nc3)ccc21] | 256 | 10.99 | 2 |
| 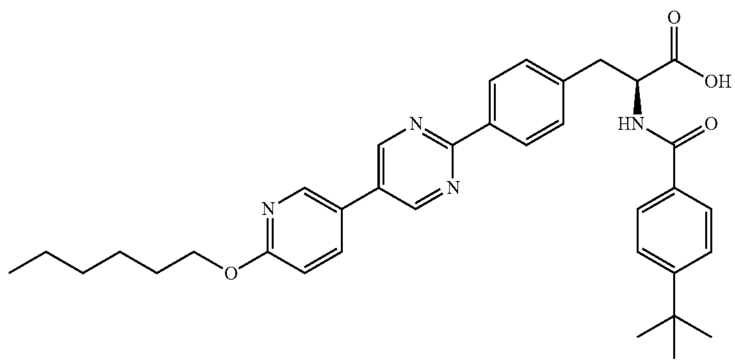 [SMILES: CCCCCCOc1ccc(-c2cnc(-c3ccc(C[C@H](NC(=O)c4ccc(C(C)(C)C)cc4)C(=O)O)cc3)nc2)cn1] | 257 | 11.05 | 2 |
| 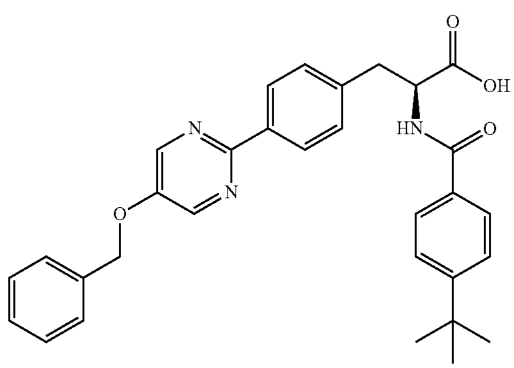 [SMILES: CC(C)(C)c1ccc(C(=O)N[C@@H](Cc2ccc(-c3ncc(OCc4ccccc4)cn3)cc2)C(=O)O)cc1] | 258 | 9.10 | 2 |
| 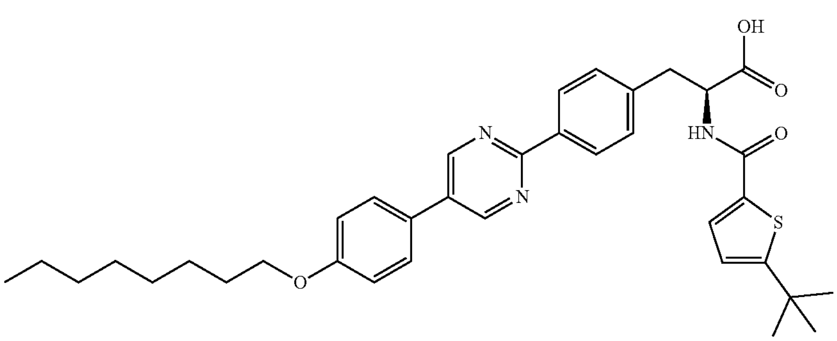 [SMILES: CCCCCCCCOc1ccc(-c2cnc(-c3ccc(C[C@H](NC(=O)c4ccc(C(C)(C)C)s4)C(=O)O)cc3)nc2)cc1] | 259 | 12.41 | 2 |

TABLE 1-continued

| STRUCTURE | COMPOUND NUMBER | LCMS RETENTION TIME (min) | PURITY METHOD |
|---|---|---|---|
| 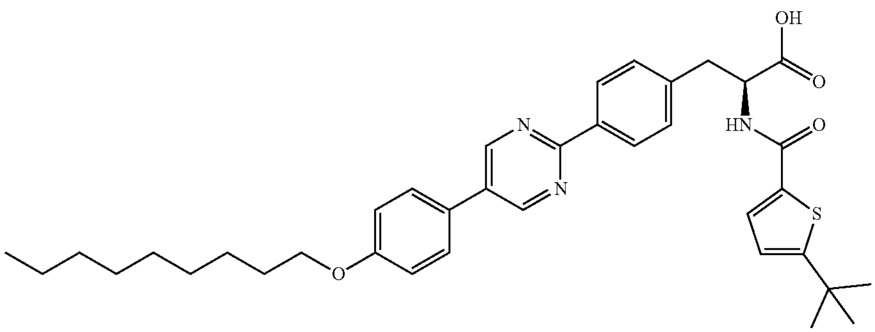 [SMILES: CCCCCCCCCOc1ccc(-c2cnc(-c3ccc(C[C@H](NC(=O)c4ccc(C(C)(C)C)s4)C(=O)O)cc3)nc2)cc1] | 260 | 12.85 | 2 |
| 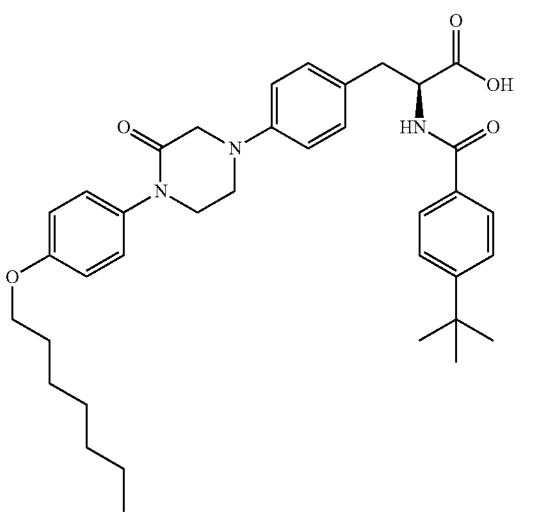 [SMILES: CCCCCCCOc1ccc(N2CCN(c3ccc(C[C@H](NC(=O)c4ccc(C(C)(C)C)cc4)C(=O)O)cc3)CC2=O)cc1] | 261 | 9.20 | 10 |
| 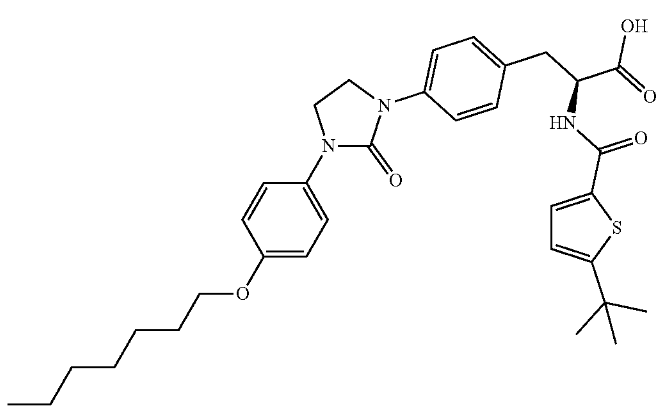 [SMILES: CCCCCCCOc1ccc(N2CCN(c3ccc(C[C@H](NC(=O)c4ccc(C(C)(C)C)s4)C(=O)O)cc3)C2=O)cc1] | 262 | 10.23 | 10 |

TABLE 1-continued

| STRUCTURE | COMPOUND NUMBER | LCMS RETENTION TIME (min) | PURITY METHOD |
|---|---|---|---|
| 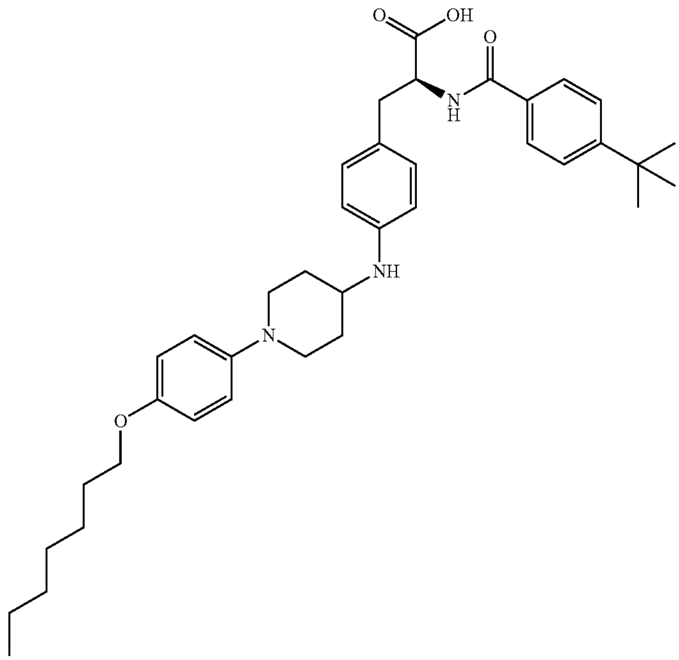 [SMILES: CCCCCCCOc1ccc(N2CCC(Nc3ccc(C[C@H](NC(=O)c4ccc(C(C)(C)C)cc4)C(=O)O)cc3)CC2)cc1] | 263 | 7.31 | 9 |
| 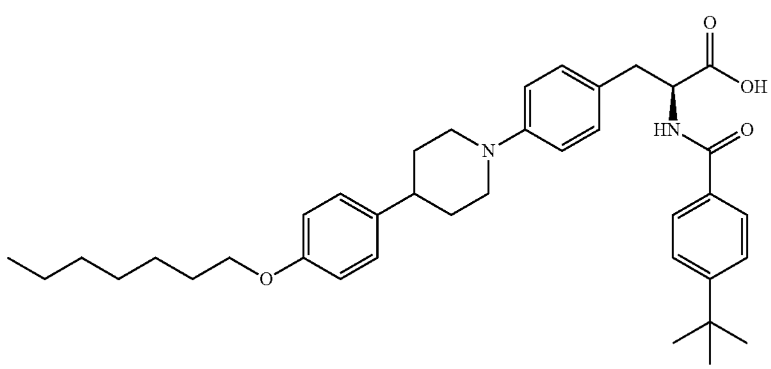 [SMILES: CCCCCCCOc1ccc(C2CCN(c3ccc(C[C@H](NC(=O)c4ccc(C(C)(C)C)cc4)C(=O)O)cc3)CC2)cc1] | 264 | 9.29 | 9 |
| 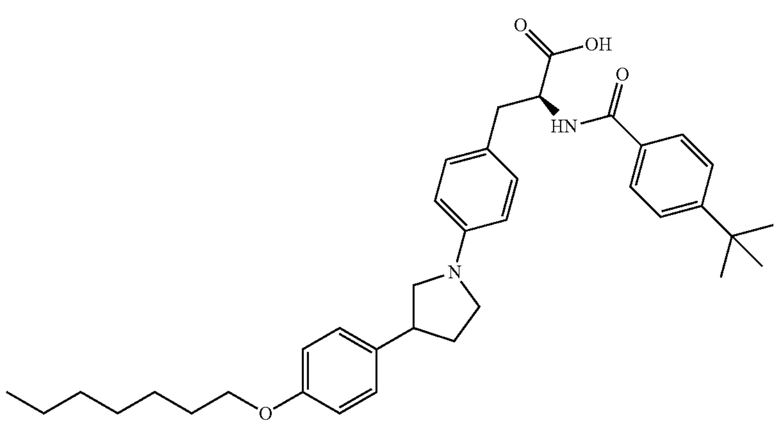 [SMILES: CCCCCCCOc1ccc(C2CCN(c3ccc(C[C@H](NC(=O)c4ccc(C(C)(C)C)cc4)C(=O)O)cc3)C2)cc1] | 265 | 11.47 | 9 |

TABLE 1-continued

| STRUCTURE | COMPOUND NUMBER | LCMS RETENTION TIME (min) | PURITY METHOD |
|---|---|---|---|
| 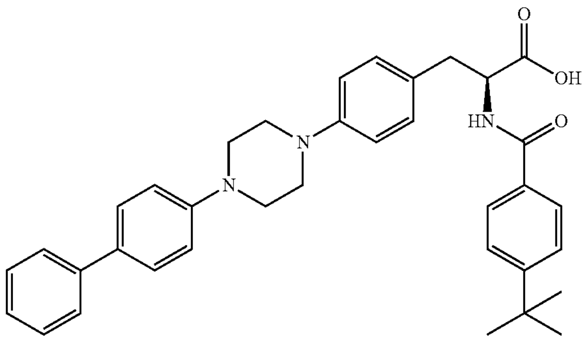 [SMILES: CC(C)(C)c1ccc(C(=O)N[C@@H](Cc2ccc(N3CCN(c4ccc(-c5ccccc5)cc4)CC3)cc2)C(=O)O)cc1] | 266 | 8.88 | 9 |
| 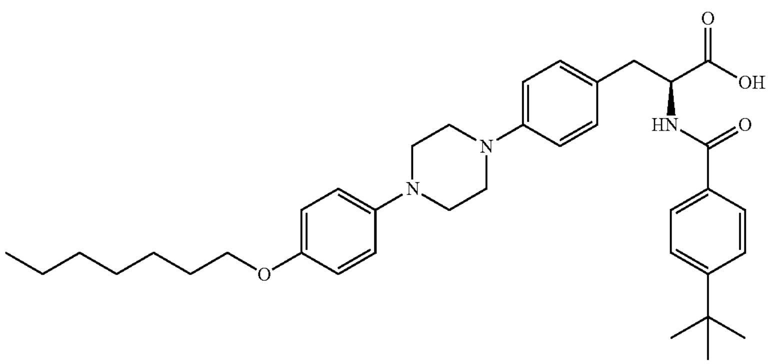 [SMILES: CCCCCCCOc1ccc(N2CCN(c3ccc(C[C@H](NC(=O)c4ccc(C(C)(C)C)cc4)C(=O)O)cc3)CC2)cc1] | 267 | 9.89 | 9 |
| 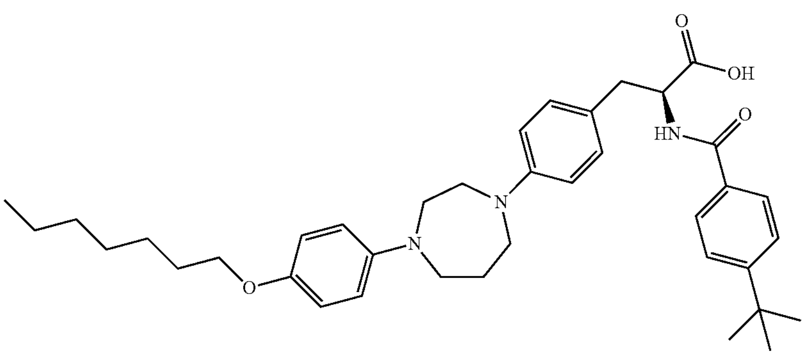 [SMILES: CCCCCCCOc1ccc(N2CCCN(c3ccc(C[C@H](NC(=O)c4ccc(C(C)(C)C)cc4)C(=O)O)cc3)CC2)cc1] | 268 | 10.33 | 10 |
| 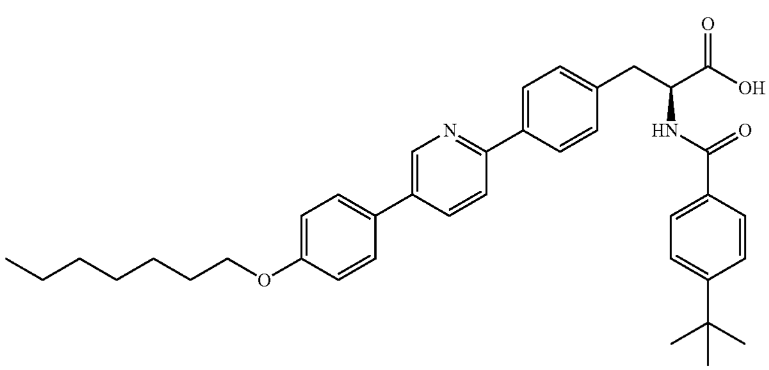 | 269 | 10.54 | 9 |

TABLE 1-continued

| STRUCTURE | COMPOUND NUMBER | LCMS RETENTION TIME (min) | PURITY METHOD |
|---|---|---|---|
| 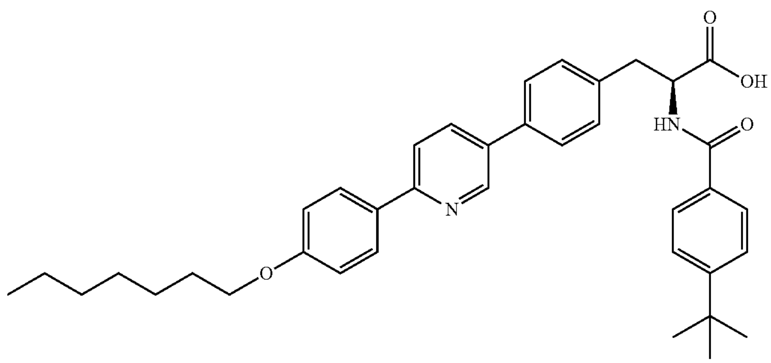 [SMILES: CCCCCCCOc1ccc(-c2ccc(-c3ccc(C[C@H](NC(=O)c4ccc(C(C)(C)C)cc4)C(=O)O)cc3)cn2)cc1] | 270 | 10.37 | 9 |
| 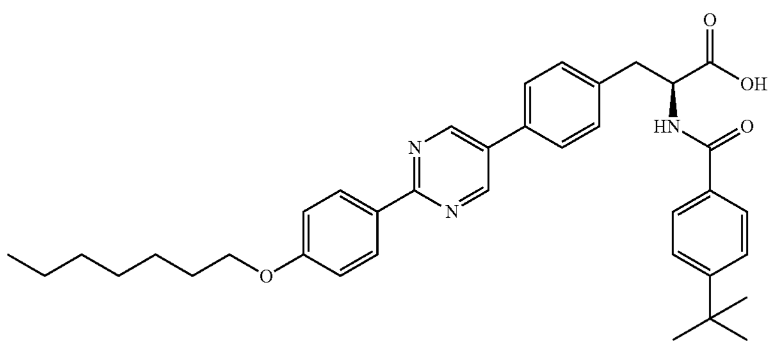 [SMILES: CCCCCCCOc1ccc(-c2ncc(-c3ccc(C[C@H](NC(=O)c4ccc(C(C)(C)C)cc4)C(=O)O)cc3)cn2)cc1] | 271 | 10.92 | 9 |
| 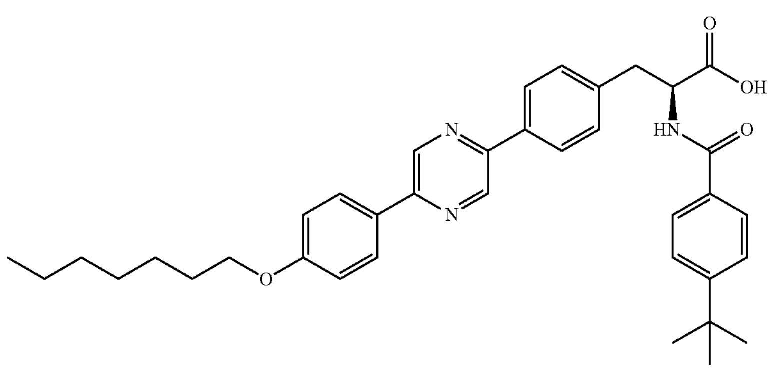 | 272 | 11.07 | 9 |
| 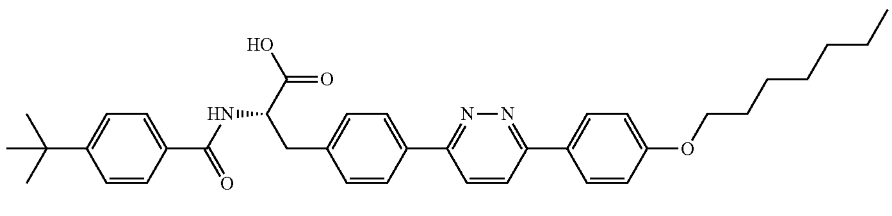 [SMILES: CCCCCCCOc1ccc(-c2ccc(-c3ccc(C[C@H](NC(=O)c4ccc(C(C)(C)C)cc4)C(=O)O)cc3)nn2)cc1] | 273 | 10.13 | 9 |

TABLE 1-continued

| STRUCTURE | COMPOUND NUMBER | LCMS RETENTION TIME (min) | PURITY METHOD |
|---|---|---|---|
| 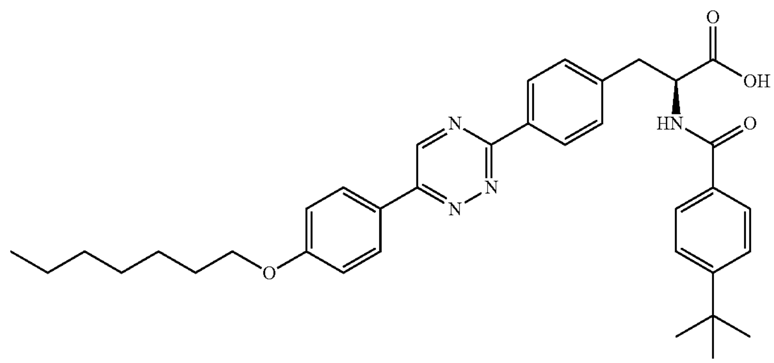 [SMILES: CCCCCCCOc1ccc(-c2cnc(-c3ccc(C[C@H](NC(=O)c4ccc(C(C)(C)C)cc4)C(=O)O)cc3)nn2)cc1] | 274 | 10.61 | 9 |
| 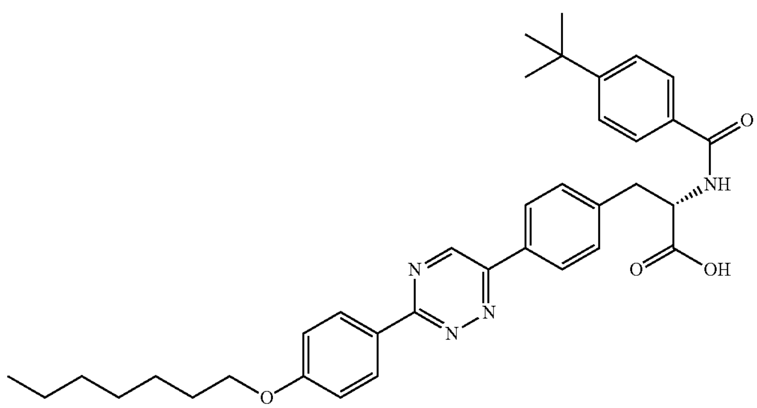 [SMILES: CCCCCCCOc1ccc(-c2ncc(-c3ccc(C[C@H](NC(=O)c4ccc(C(C)(C)C)cc4)C(=O)O)cc3)nn2)cc1] | 275 | 10.77 | 9 |
| 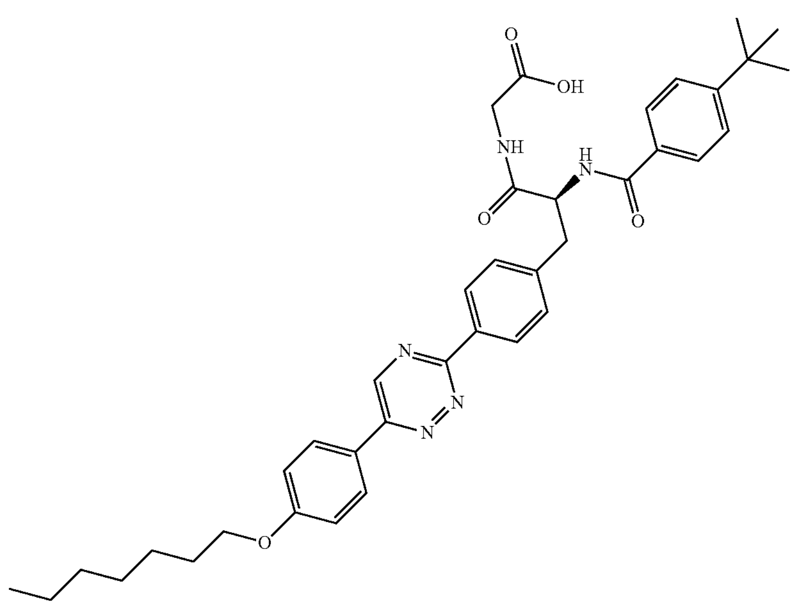 [SMILES: CCCCCCCOc1ccc(-c2cnc(-c3ccc(C[C@H](NC(=O)c4ccc(C(C)(C)C)cc4)C(=O)NCC(=O)O)cc3)nn2)cc1] | 276 | 10.92 | 2 |

TABLE 1-continued

| STRUCTURE | COMPOUND NUMBER | LCMS RETENTION TIME (min) | PURITY METHOD |
|---|---|---|---|
| 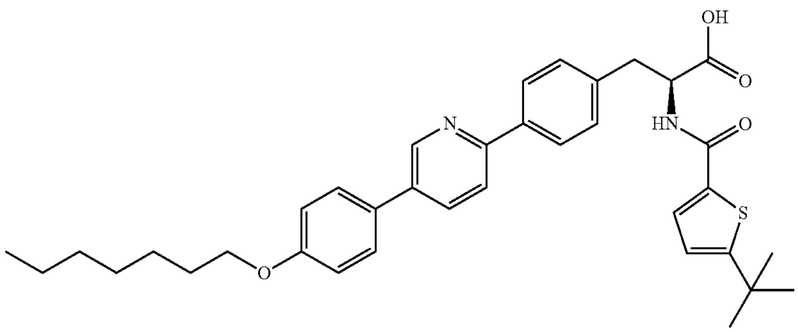 | 277 | 11.90 | 2 |
| 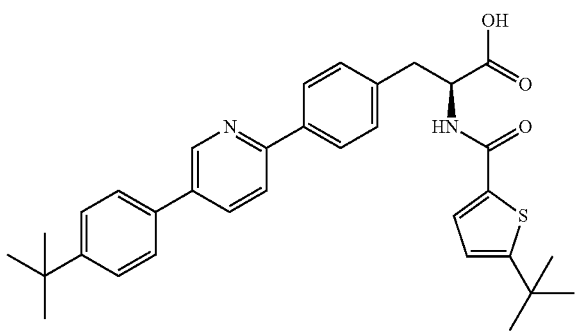 | 278 | 10.90 | 2 |
| 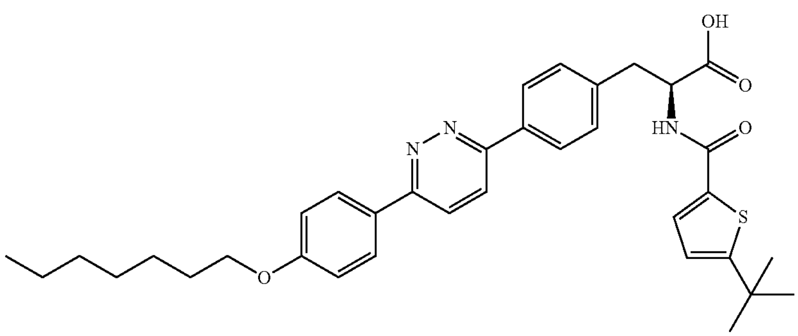 [SMILES: CCCCCCCOc1ccc(-c2ccc(-c3ccc(C[C@H](NC(=O)c4ccc(C(C)(C)C)s4)C(=O)O)cc3)nc2)cc1] | 279 | 11.12 | 2 |
| 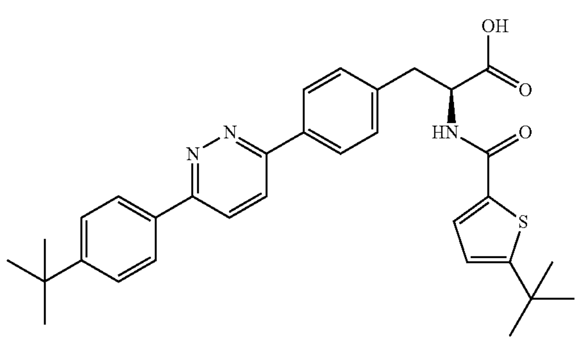 [SMILES: CC(C)(C)c1ccc(-c2ccc(-c3ccc(C[C@H](NC(=O)c4ccc(C(C)(C)C)s4)C(=O)O)cc3)nn2)cc1] | 280 | 10.30 | 2 |

TABLE 1-continued

| STRUCTURE | COMPOUND NUMBER | LCMS RETENTION TIME (min) | PURITY METHOD |
|---|---|---|---|
| 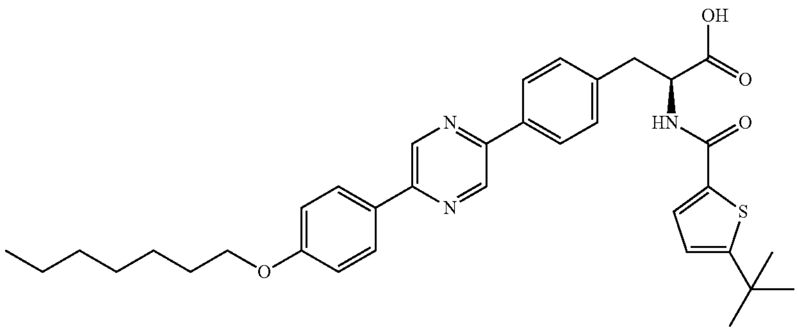 [SMILES: CCCCCCCOc1ccc(-c2cnc(-c3ccc(C[C@H](NC(=O)c4ccc(C(C)(C)C)s4)C(=O)O)cc3)cn2)cc1] | 281 | 12.30 | 2 |
| 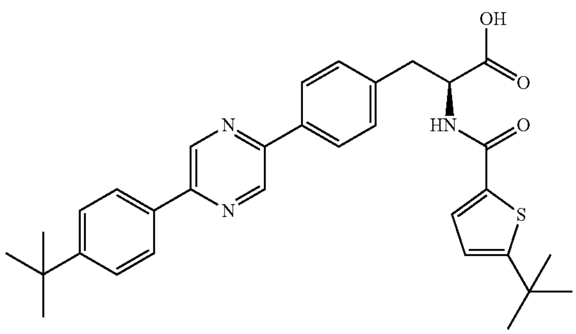 [SMILES: CC(C)(C)c1ccc(-c2cnc(-c3ccc(C[C@H](NC(=O)c4ccc(C(C)(C)C)s4)C(=O)O)cc3)cn2)cc1] | 282 | 10.91 | 2 |
| 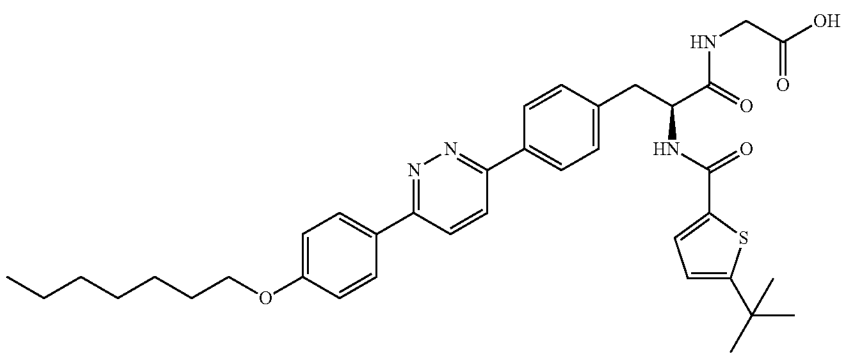 [SMILES: CCCCCCCOc1ccc(-c2ccc(-c3ccc(C[C@H](NC(=O)c4ccc(C(C)(C)C)s4)C(=O)NCC(=O)O)cc3)nn2)cc1] | 283 | 11.00 | 2 |
| 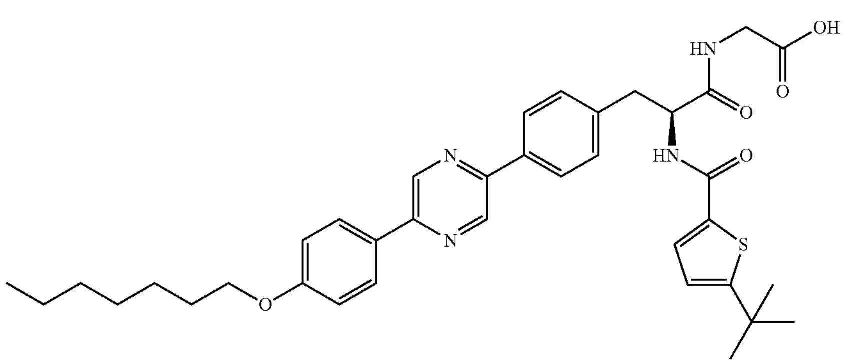 [SMILES: CCCCCCCOc1ccc(-c2cnc(-c3ccc(C[C@H](NC(=O)c4ccc(C(C)(C)C)s4)C(=O)NCC(=O)O)cc3)cn2)cc1] | 284 | 11.58 | 2 |

TABLE 1-continued

| STRUCTURE | COMPOUND NUMBER | LCMS RETENTION TIME (min) | PURITY METHOD |
|---|---|---|---|
| 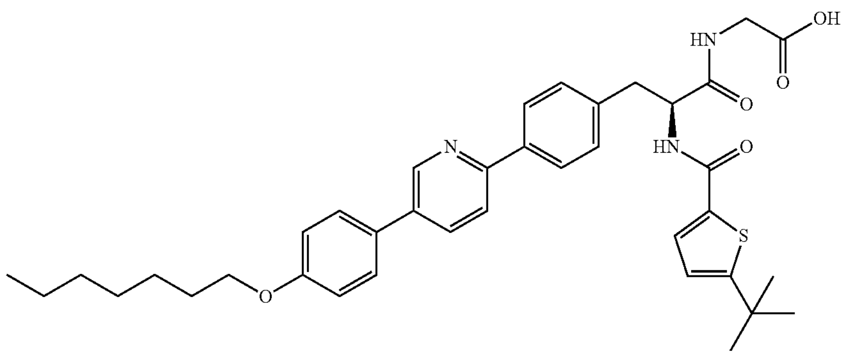 | 285 | 11.10 | 2 |
| 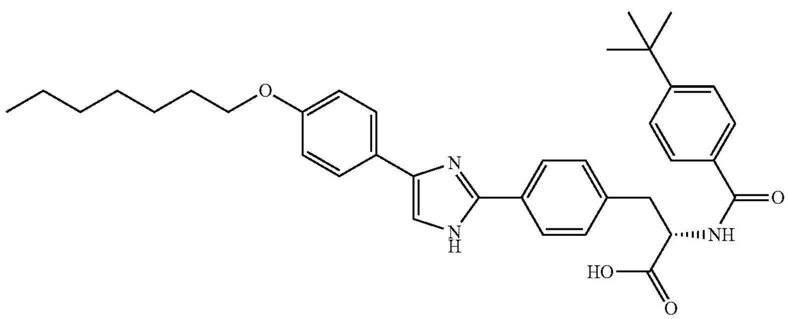 [SMILES: CCCCCCCOc1ccc(-c2c[nH]c(-c3ccc(C[C@H](NC(=O)c4ccc(C(C)(C)C)cc4)C(=O)O)cc3)n2)cc1] | 286 | 6.56 | 9 |
| 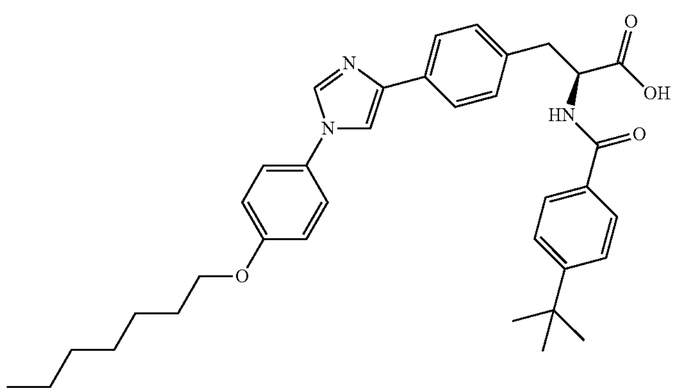 [SMILES: CCCCCCCOc1ccc(-n2cnc(-c3ccc(C[C@H](NC(=O)c4ccc(C(C)(C)C)cc4)C(=O)O)cc3)c2)cc1] | 287 | 8.33 | 9 |
| 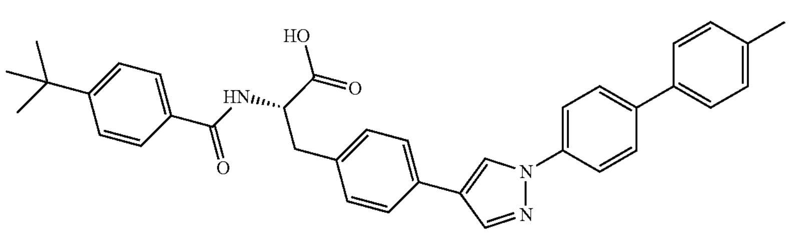 [SMILES: Cc1ccc(-c2ccc(-n3cc(-c4ccc(C[C@H](NC(=O)c5ccc(C(C)(C)C)cc5)C(=O)O)cc4)cn3)cc2)cc1] | 288 | 9.37 | 9 |

TABLE 1-continued
| STRUCTURE | COMPOUND NUMBER | LCMS RETENTION TIME (min) | PURITY METHOD |
|---|---|---|---|
| 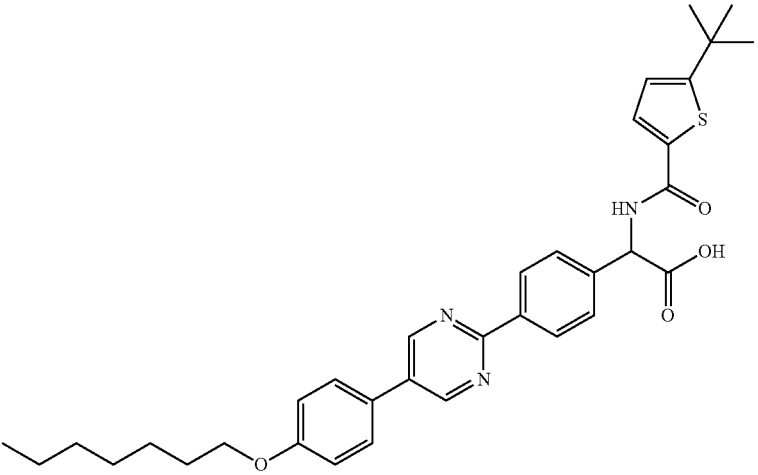 [SMILES: CCCCCCCOc1ccc(-c2cnc(-c3ccc(C(NC(=O)c4ccc(C(C)(C)C)s4)C(=O)O)cc3)nc2)cc1] | 289 | 3.37 | 9 |
| 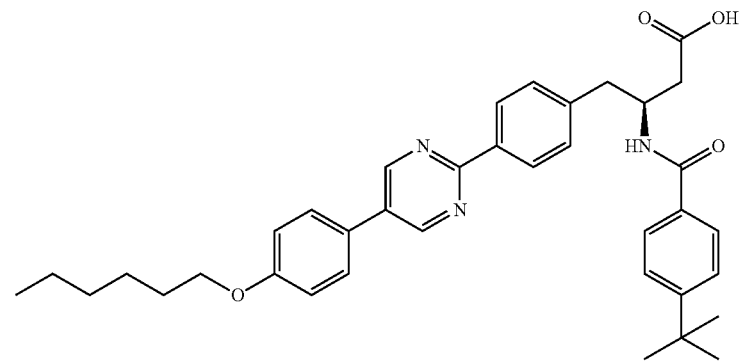 [SMILES: CCCCCCOc1ccc(-c2cnc(-c3ccc(C[C@@H](CC(=O)O)NC(=O)c4ccc(C(C)(C)C)cc4)cc3)nc2)cc1] | 291 | 10.99 | 10 |
| 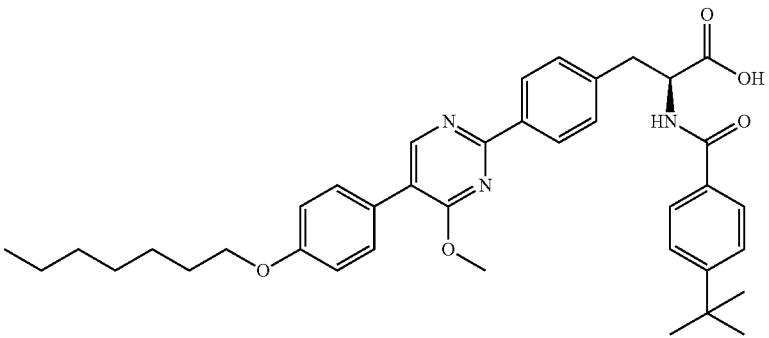 [SMILES: CCCCCCCOc1ccc(-c2cnc(-c3ccc(C[C@H](NC(=O)c4ccc(C(C)(C)C)cc4)C(=O)O)cc3)nc2OC)cc1] | 292 | 12.17 | 2 |

TABLE 1-continued

| STRUCTURE | COMPOUND NUMBER | LCMS RETENTION TIME (min) | PURITY METHOD |
|---|---|---|---|
| 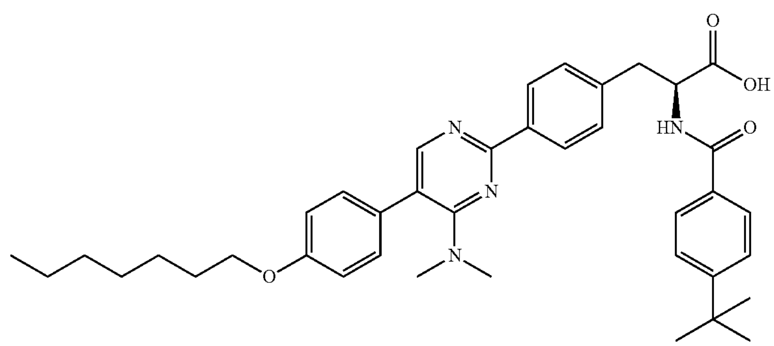 [SMILES: CCCCCCCOc1ccc(-c2cnc(-c3ccc(C[C@H](NC(=O)c4ccc(C(C)(C)C)cc4)C(=O)O)cc3)nc2N(C)C)cc1] | 293 | 9.21 | 2 |
| 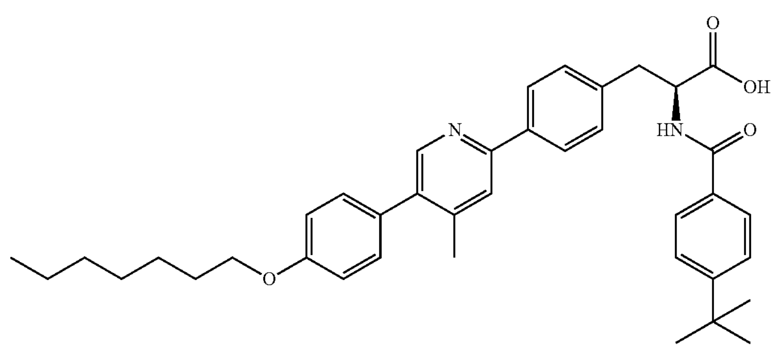 [SMILES: CCCCCCCOc1ccc(-c2cnc(-c3ccc(C[C@H](NC(=O)c4ccc(C(C)(C)C)cc4)C(=O)O)cc3)cc2C)cc1] | 294 | 11.59 | 2 |
| 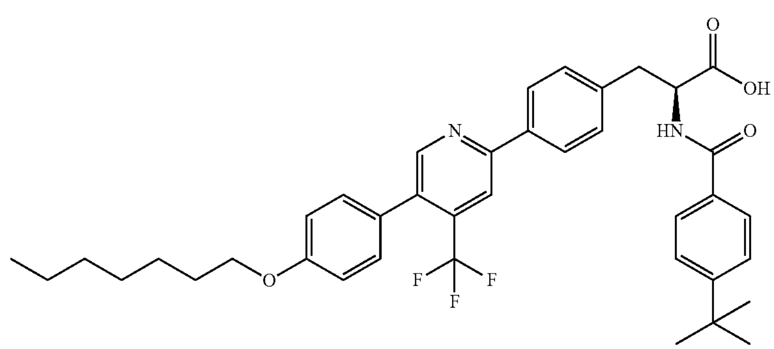 [SMILES: CCCCCCCOc1ccc(-c2cnc(-c3ccc(C[C@H](NC(=O)c4ccc(C(C)(C)C)cc4)C(=O)O)cc3)cc2C(F)(F)F)cc1] | 295 | 12.56 | 2 |
| 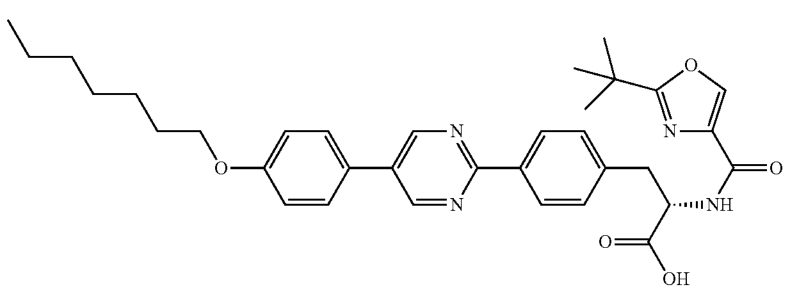 [SMILES: CCCCCCCOc1ccc(-c2cnc(-c3ccc(C[C@H](NC(=O)c4coc(C(C)(C)C)n4)C(=O)O)cc3)nc2)cc1] | 296 | 11.25 | 10 |

TABLE 1-continued
| STRUCTURE | COMPOUND NUMBER | LCMS RETENTION TIME (min) | PURITY METHOD |
|---|---|---|---|
| 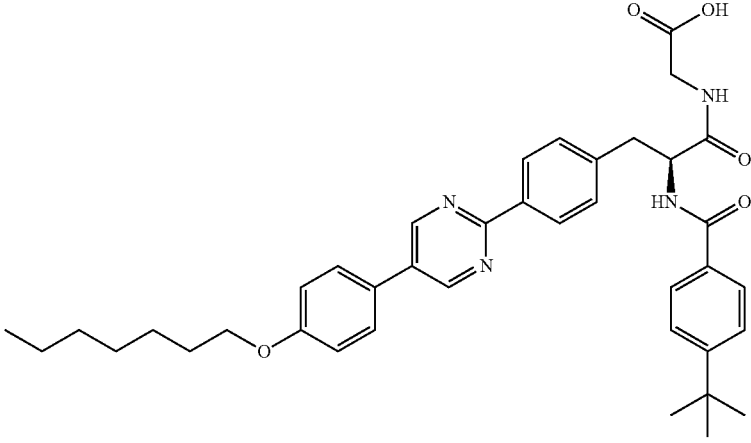 [SMILES: CCCCCCCOc1ccc(-c2cnc(-c3ccc(C[C@H](NC(=O)c4ccc(C(C)(C)C)cc4)C(=O)NCC(=O)O)cc3)nc2)cc1] | 297 | 10.43 | 10 |
| 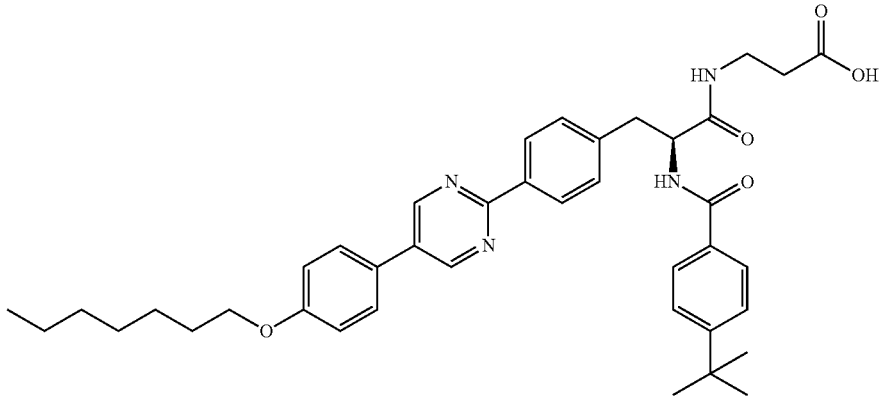 [SMILES: CCCCCCCOc1ccc(-c2cnc(-c3ccc(C[C@H](NC(=O)c4ccc(C(C)(C)C)cc4)C(=O)NCCC(=O)O)cc3)nc2)cc1] | 298 | 10.36 | 10 |
| 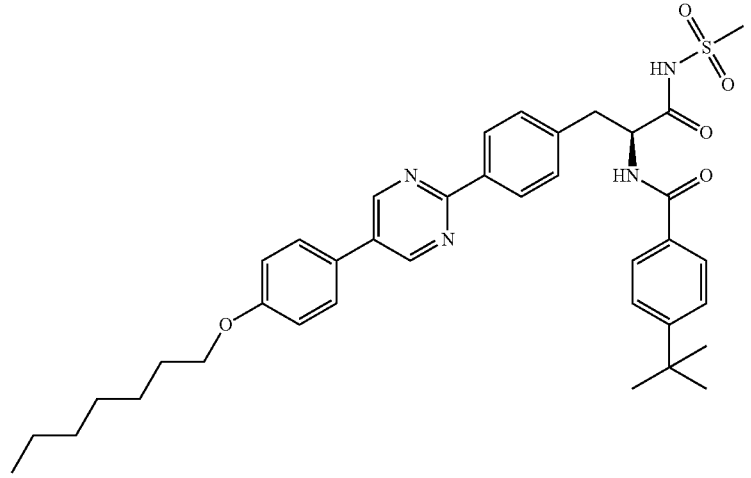 [SMILES: CCCCCCCOc1ccc(-c2cnc(-c3ccc(C[C@H](NC(=O)c4ccc(C(C)(C)C)cc4)C(=O)NS(C)(=O)=O)cc3)nc2)cc1] | 299 | 11.01 | 10 |

TABLE 1-continued

| STRUCTURE | COMPOUND NUMBER | LCMS RETENTION TIME (min) | PURITY METHOD |
|---|---|---|---|
| 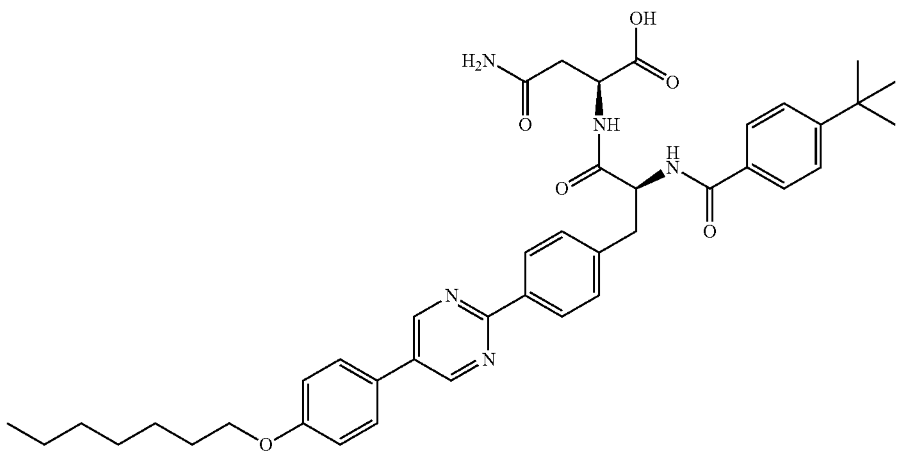 [SMILES: CCCCCCCOc1ccc(-c2cnc(-c3ccc(C[C@H](NC(=O)c4ccc(C(C)(C)C)cc4)C(=O)N[C@@H](CC(N)=O)C(=O)O)cc3)nc2)cc1] | 300 | 11.24 | 2 |
| 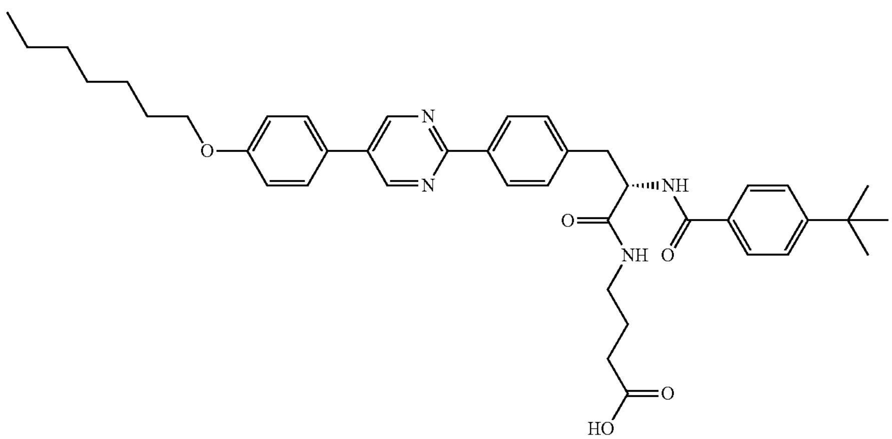 [SMILES: CCCCCCCOc1ccc(-c2cnc(-c3ccc(C[C@H](NC(=O)c4ccc(C(C)(C)C)cc4)C(=O)NCCCC(=O)O)cc3)nc2)cc1] | 301 | 10.34 | 10 |
| 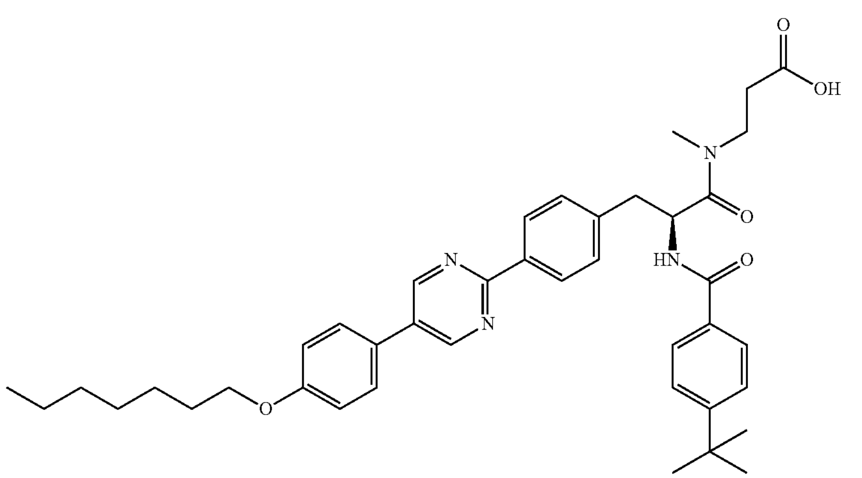 [SMILES: CCCCCCCOc1ccc(-c2cnc(-c3ccc(C[C@H](NC(=O)c4ccc(C(C)(C)C)cc4)C(=O)N(C)CCC(=O)O)cc3)nc2)cc1] | 302 | 10.67 | 10 |

TABLE 1-continued

| STRUCTURE | COMPOUND NUMBER | LCMS RETENTION TIME (min) | PURITY METHOD |
|---|---|---|---|
| 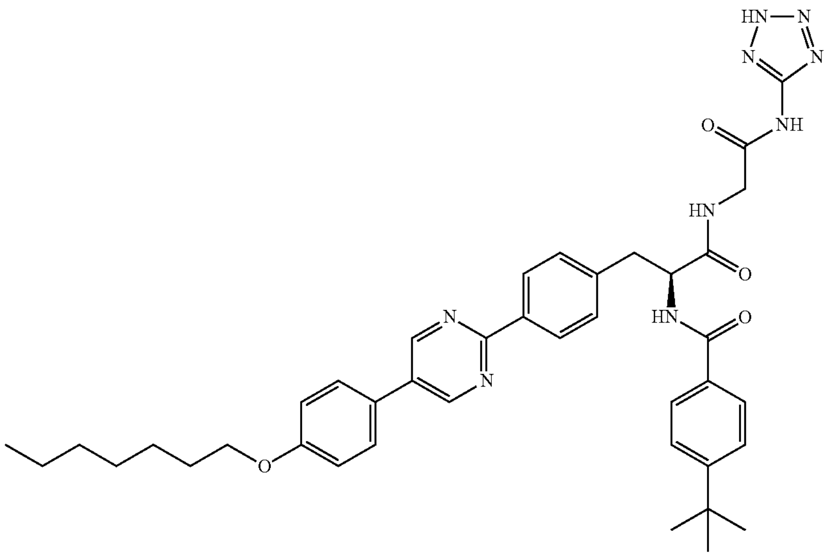 [SMILES: CCCCCCCOc1ccc(-c2cnc(-c3ccc(C[C@H](NC(=O)c4ccc(C(C)(C)C)cc4)C(=O)NCC(=O)Nc4nn[nH]n4)cc3)nc2)cc1] | 303 | 10.16 | 10 |
| 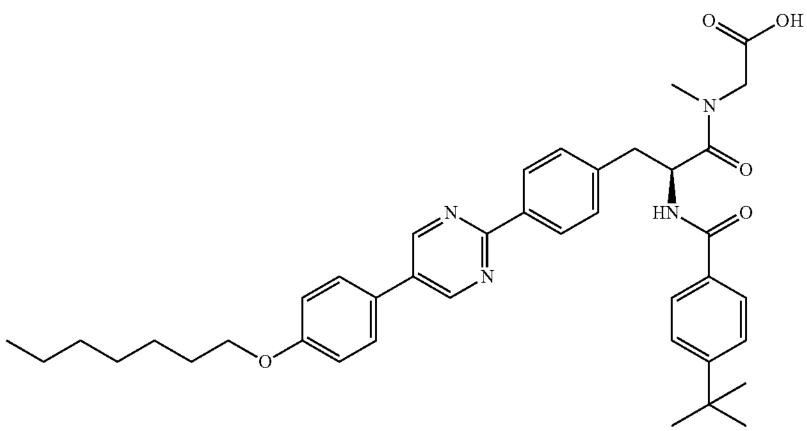 [SMILES: CCCCCCCOc1ccc(-c2cnc(-c3ccc(C[C@H](NC(=O)c4ccc(C(C)(C)C)cc4)C(=O)N(C)CC(=O)O)cc3)nc2)cc1] | 304 | 10.74 | 10 |
| 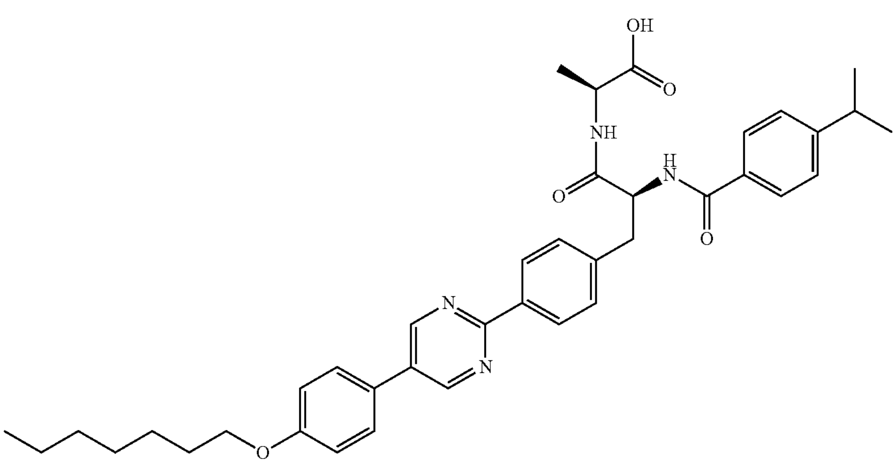 [SMILES: CCCCCCCOc1ccc(-c2cnc(-c3ccc(C[C@H](NC(=O)c4ccc(C(C)C)cc4)C(=O)N[C@@H](C)C(=O)O)cc3)nc2)cc1] | 305 | 11.39 | 2 |

TABLE 1-continued

| STRUCTURE | COMPOUND NUMBER | LCMS RETENTION TIME (min) | PURITY METHOD |
|---|---|---|---|
| 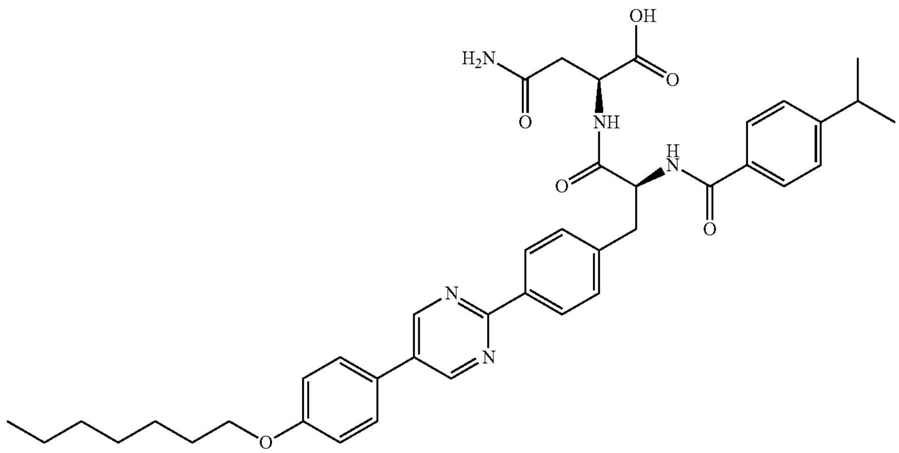 [SMILES: CCCCCCCOc1ccc(-c2cnc(-c3ccc(C[C@H](NC(=O)c4ccc(C(C)C)cc4)C(=O)N[C@@H](CC(=O)O)C(=O)O)cc3)nc2)cc1] | 306 | 11.20 | 2 |
| 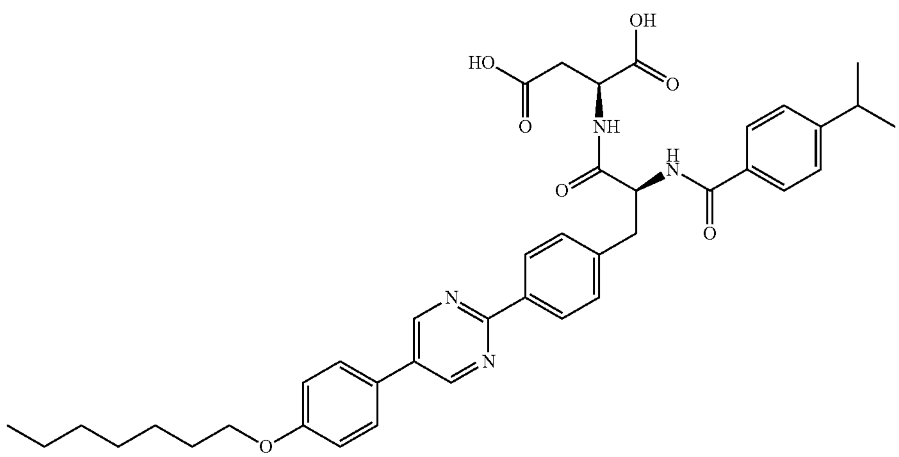 | 307 | 11.35 | 2 |
| 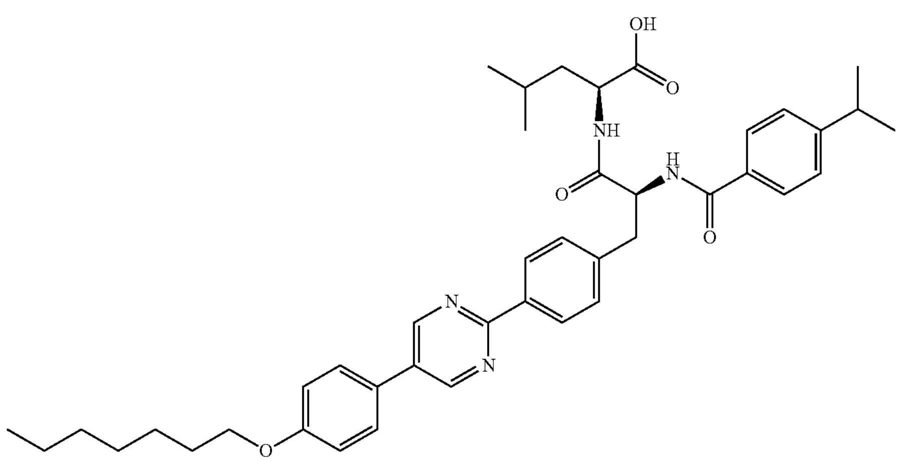 [SMILES: CCCCCCCOc1ccc(-c2cnc(-c3ccc(C[C@H](NC(=O)c4ccc(C(C)C)cc4)C(=O)N[C@@H](CC(C)C)C(=O)O)cc3)nc2)cc1] | 308 | 11.61 | 2 |

TABLE 1-continued
| STRUCTURE | COMPOUND NUMBER | LCMS RETENTION TIME (min) | PURITY METHOD |
|---|---|---|---|
| 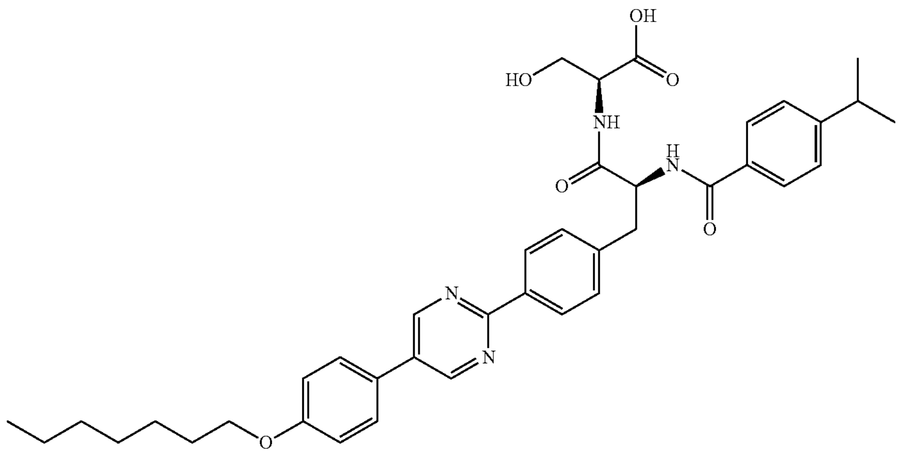 [SMILES: CCCCCCCOc1ccc(-c2cnc(-c3ccc(C[C@H](NC(=O)c4ccc(C(C)C)cc4)C(=O)N[C@@H](CO)C(=O)O)cc3)nc2)cc1] | 309 | 11.47 | 2 |
| 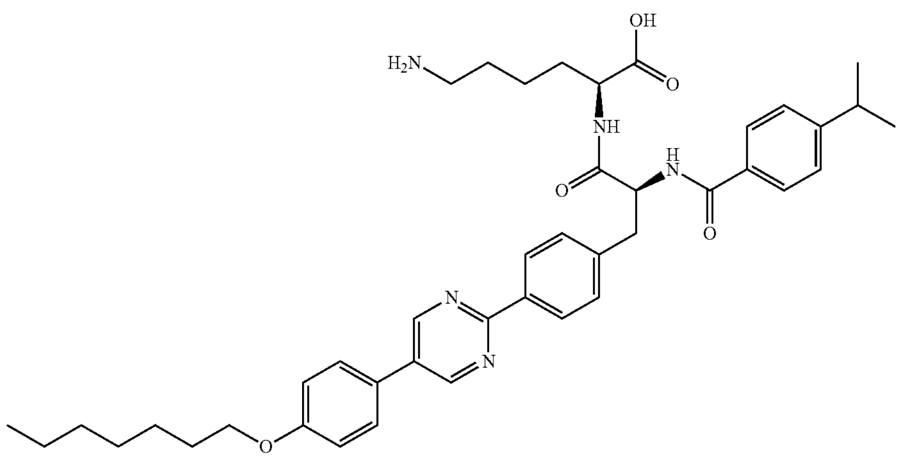 [SMILES: CCCCCCCOc1ccc(-c2cnc(-c3ccc(C[C@H](NC(=O)c4ccc(C(C)C)cc4)C(=O)N[C@@H](CCCCN)C(=O)O)cc3)nc2)cc1] | 310 | 9.14 | 2 |
| 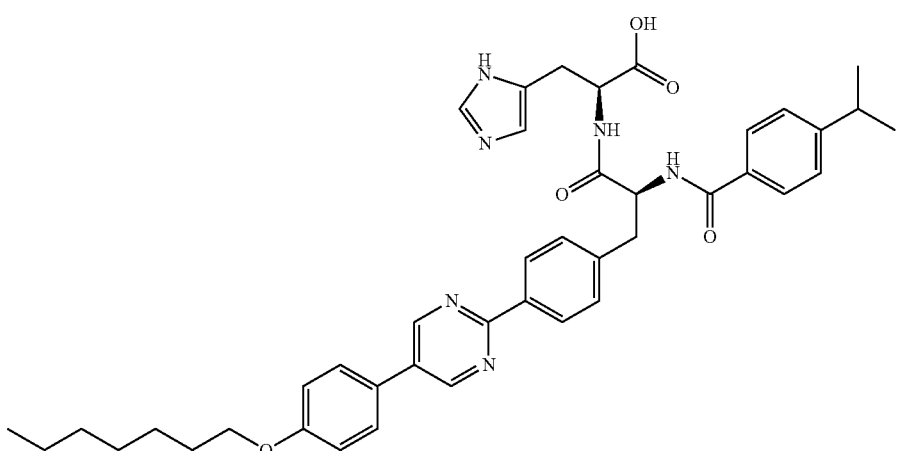 | 311 | 9.52 | 2 |

TABLE 1-continued

| STRUCTURE | COMPOUND NUMBER | LCMS RETENTION TIME (min) | PURITY METHOD |
|---|---|---|---|
| 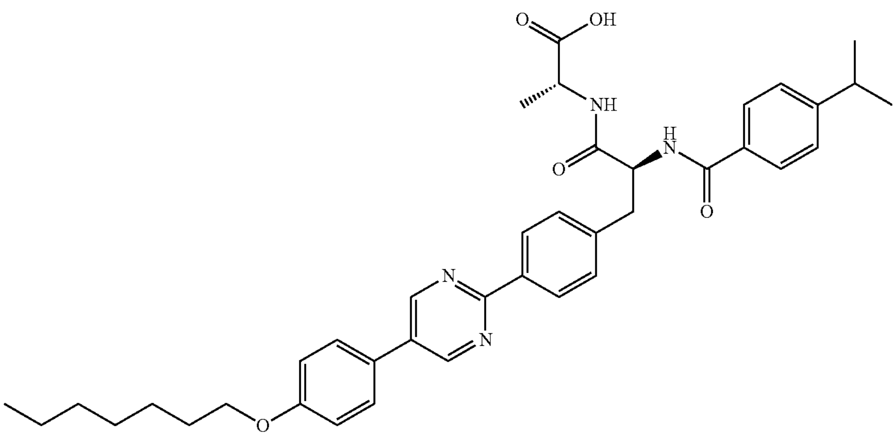 [SMILES: CCCCCCCOc1ccc(-c2cnc(-c3ccc(C[C@H](NC(=O)c4ccc(C(C)C)cc4)C(=O)N[C@H](C)C(=O)O)cc3)nc2)cc1] | 312 | 11.75 | 2 |
| 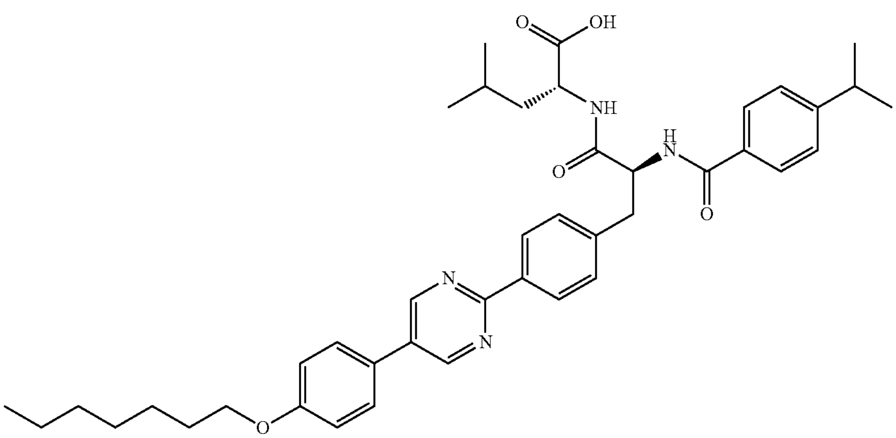 [SMILES: CCCCCCCOc1ccc(-c2cnc(-c3ccc(C[C@H](NC(=O)c4ccc(C(C)C)cc4)C(=O)N[C@H](CC(C)C)C(=O)O)cc3)nc2)cc1] | 313 | 12.36 | 2 |
| 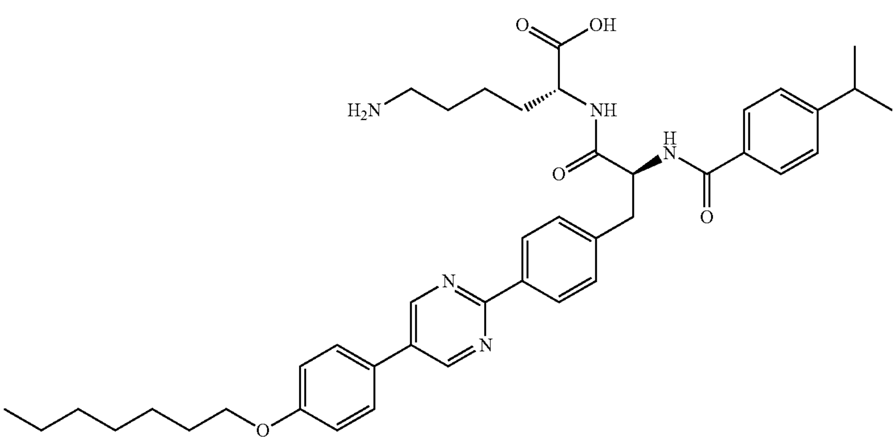 [SMILES: CCCCCCCOc1ccc(-c2cnc(-c3ccc(C[C@H](NC(=O)c4ccc(C(C)C)cc4)C(=O)N[C@H](CCCCN)C(=O)O)cc3)nc2)cc1] | 314 | 9.14 | 2 |

TABLE 1-continued

| STRUCTURE | COMPOUND NUMBER | LCMS RETENTION TIME (min) | PURITY METHOD |
|---|---|---|---|
| 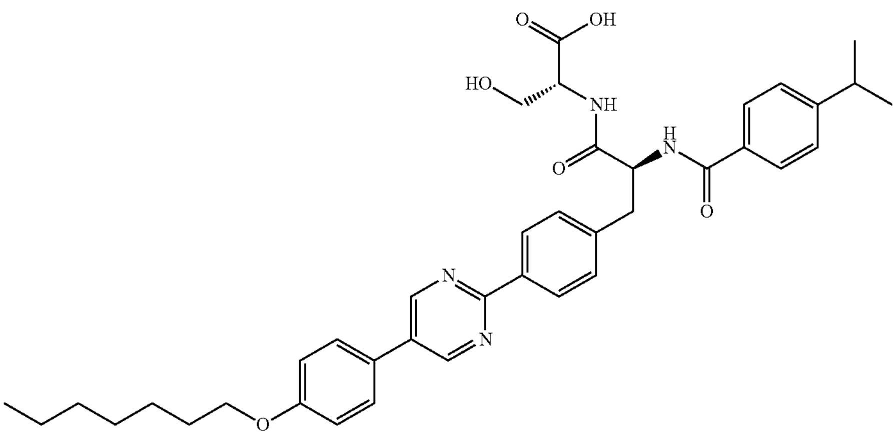 [SMILES: CCCCCCCOc1ccc(-c2cnc(-c3ccc(C[C@H](NC(=O)c4ccc(C(C)C)cc4)C(=O)N[C@H](CO)C(=O)O)cc3)nc2)cc1] | 315 | 11.45 | 2 |
| 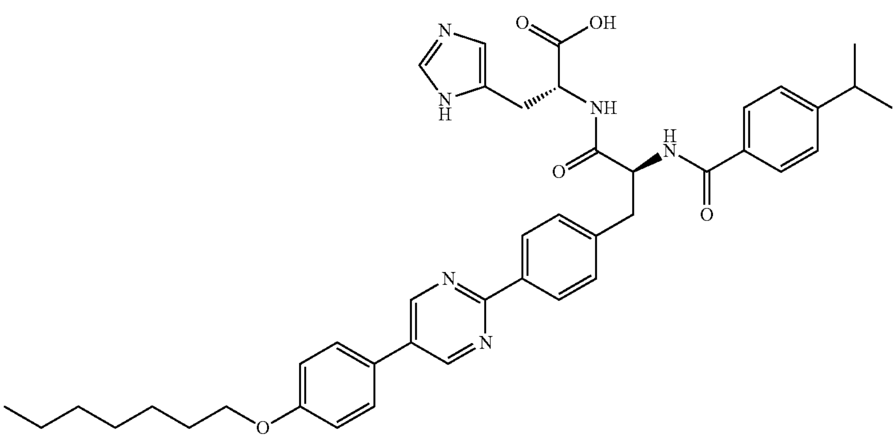 [SMILES: CCCCCCCOc1ccc(-c2cnc(-c3ccc(C[C@H](NC(=O)c4ccc(C(C)C)cc4)C(=O)N[C@H](Cc4cnc[nH]4)C(=O)O)cc3)nc2)cc1] | 316 | 9.55 | 2 |
| 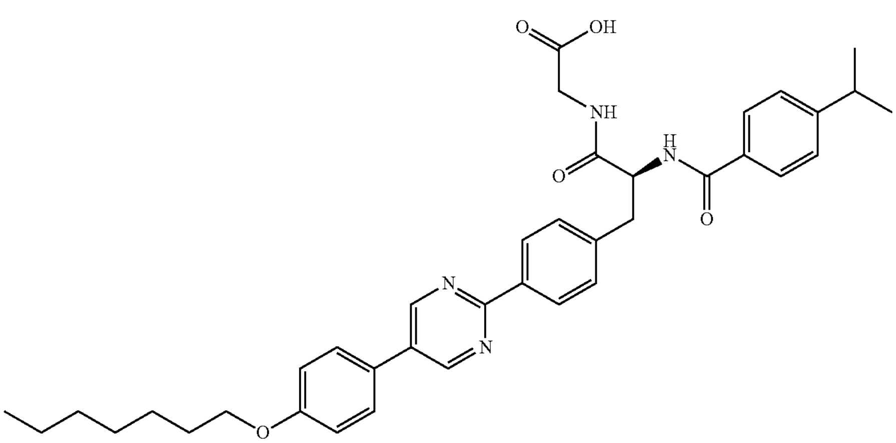 [SMILES: CCCCCCCOc1ccc(-c2cnc(-c3ccc(C[C@H](NC(=O)c4ccc(C(C)C)cc4)C(=O)NCC(=O)O)cc3)nc2)cc1] | 317 | 11.18 | 2 |

TABLE 1-continued

| STRUCTURE | COMPOUND NUMBER | LCMS RETENTION TIME (min) | PURITY METHOD |
|---|---|---|---|
| 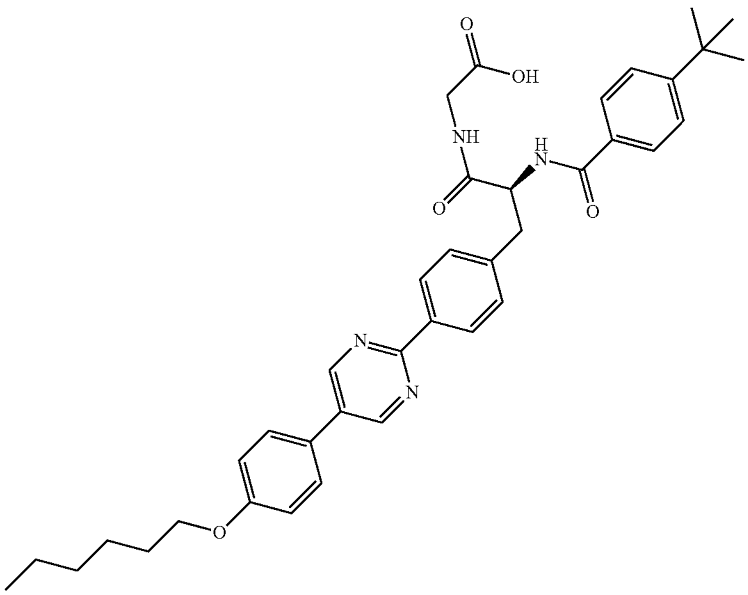 [SMILES: CCCCCCOc1ccc(-c2cnc(-c3ccc(C[C@H](NC(=O)c4ccc(C(C)(C)C)cc4)C(=O)NCC(=O)O)cc3)nc2)cc1] | 318 | 11.26 | 2 |
| 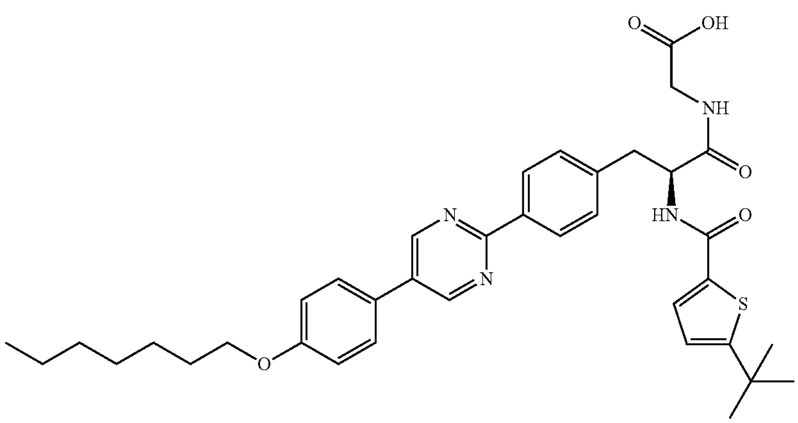 [SMILES: CCCCCCCOc1ccc(-c2cnc(-c3ccc(C[C@H](NC(=O)c4ccc(C(C)(C)C)s4)C(=O)NCC(=O)O)cc3)nc2)cc1] | 319 | 10.34 | 10 |
| 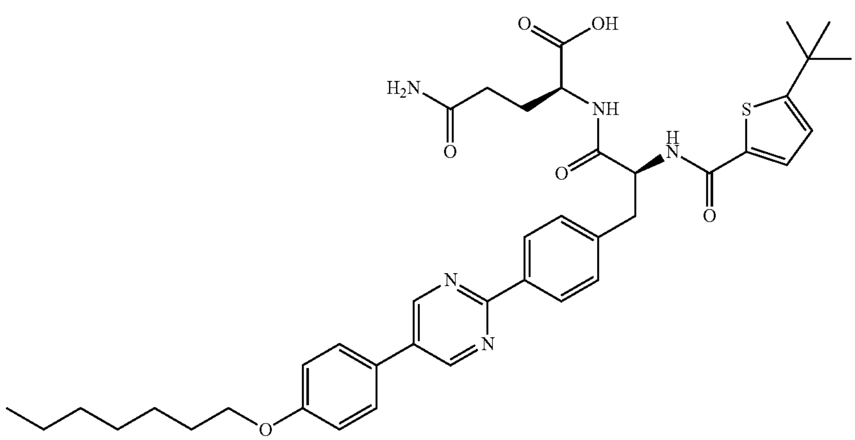 [SMILES: CCCCCCCOc1ccc(-c2cnc(-c3ccc(C[C@H](NC(=O)c4ccc(C(C)(C)C)s4)C(=O)N[C@@H](CCC(N)=O)C(=O)O)cc3)nc2)cc1] | 320 | 10.71 | 2 |

TABLE 1-continued
| STRUCTURE | COMPOUND NUMBER | LCMS RETENTION TIME (min) | PURITY METHOD |
|---|---|---|---|
| 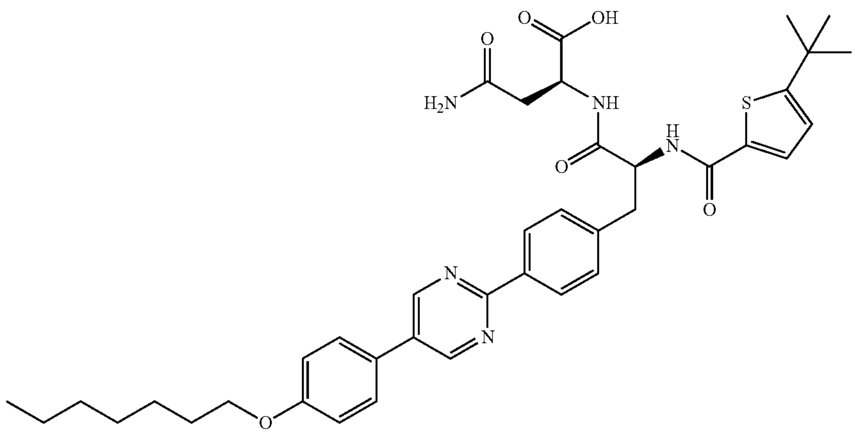 [SMILES: CCCCCCCOc1ccc(-c2cnc(-c3ccc(C[C@H](NC(=O)c4ccc(C(C)(C)C)s4)C(=O)N[C@@H](CC(N)=O)C(=O)O)cc3)nc2)cc1] | 321 | 11.20 | 2 |
| 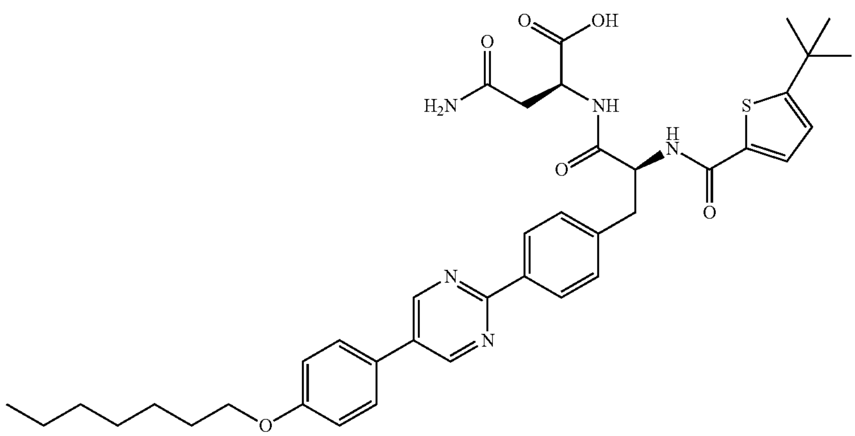 [SMILES: CCCCCCCOc1ccc(-c2cnc(-c3ccc(C[C@H](NC(=O)c4ccc(C(C)(C)C)s4)C(=O)N[C@@H](CC(N)=O)C(=O)O)cc3)nc2)cc1] | 322 | 11.43 | 2 |
| 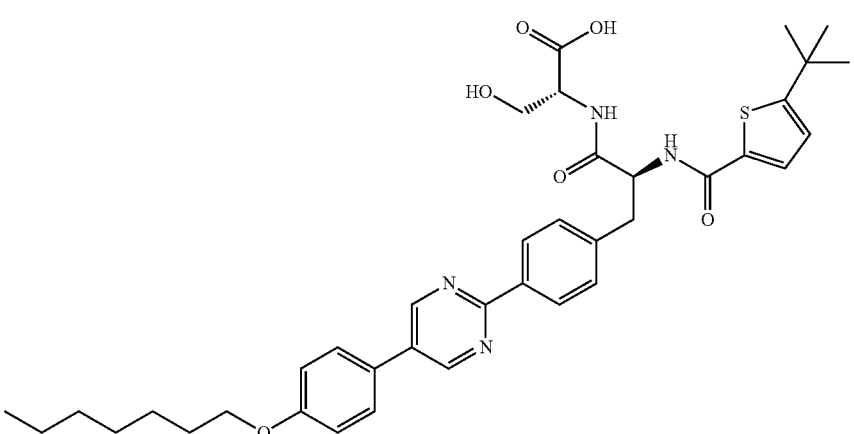 | 323 | 11.31 | 2 |

TABLE 1-continued

| STRUCTURE | COMPOUND NUMBER | LCMS RETENTION TIME (min) | PURITY METHOD |
|---|---|---|---|
| 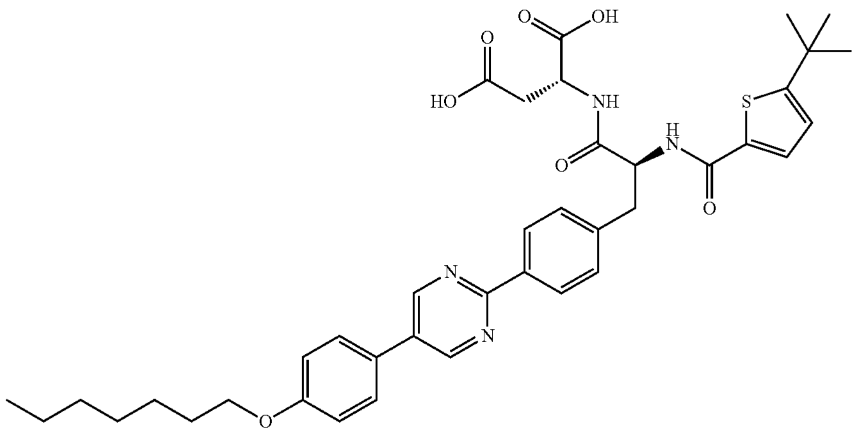 [SMILES: CCCCCCCOc1ccc(-c2cnc(-c3ccc(C[C@H](NC(=O)c4ccc(C(C)(C)C)s4)C(=O)N[C@H](CC(=O)O)C(=O)O)cc3)nc2)cc1] | 324 | 11.38 | 2 |
| 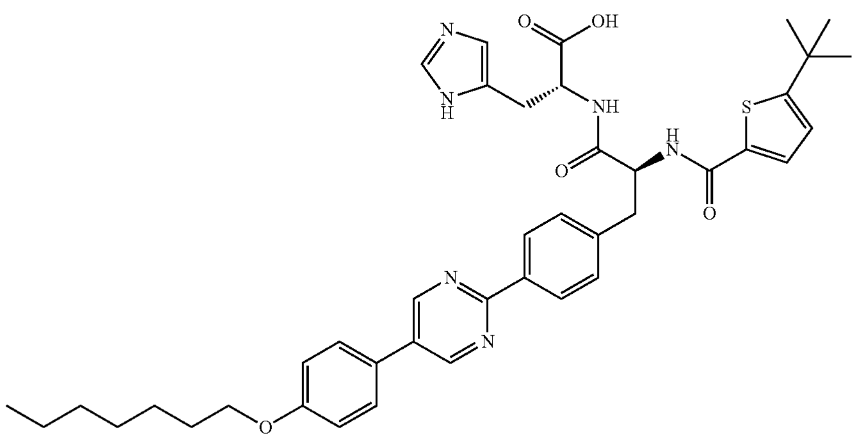 [SMILES: CCCCCCCOc1ccc(-c2cnc(-c3ccc(C[C@H](NC(=O)c4ccc(C(C)(C)C)s4)C(=O)N[C@H](Cc4cnc[nH]4)C(=O)O)cc3)nc2)cc1] | 325 | 9.87 | 2 |
| 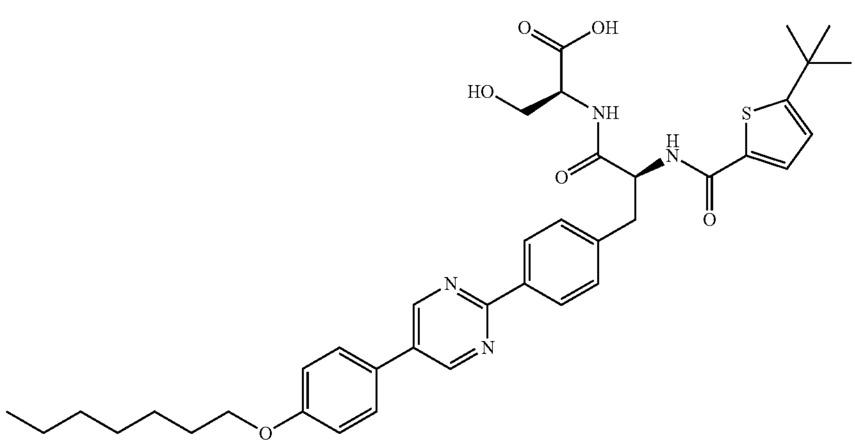 [SMILES: CCCCCCCOc1ccc(-c2cnc(-c3ccc(C[C@H](NC(=O)c4ccc(C(C)(C)C)s4)C(=O)N[C@@H](CO)C(=O)O)cc3)nc2)cc1] | 326 | 11.34 | 2 |

TABLE 1-continued

| STRUCTURE | COMPOUND NUMBER | LCMS RETENTION TIME (min) | PURITY METHOD |
|---|---|---|---|
| 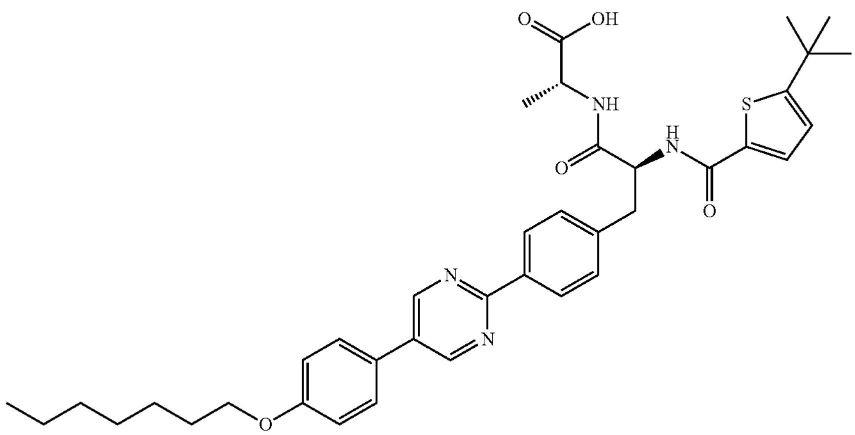 [SMILES: CCCCCCCOc1ccc(-c2cnc(-c3ccc(C[C@H](NC(=O)c4ccc(C(C)(C)C)s4)C(=O)N[C@H](C)C(=O)O)cc3)nc2)cc1] | 327 | 13.32 | 10 |
| 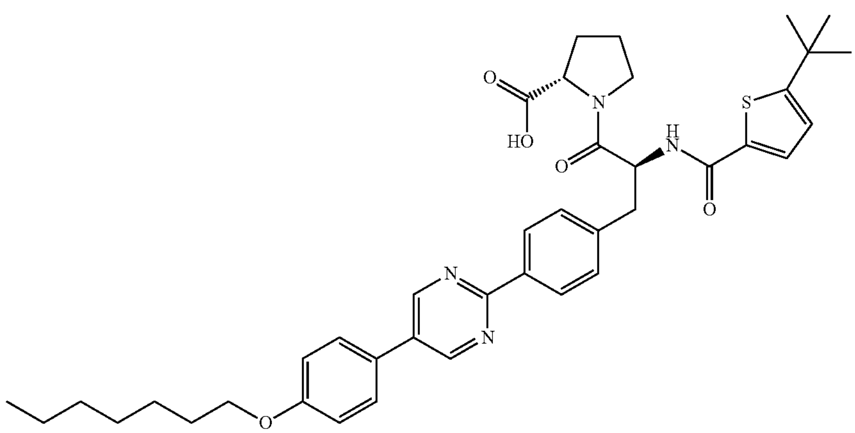 [SMILES: CCCCCCCOc1ccc(-c2cnc(-c3ccc(C[C@H](NC(=O)c4ccc(C(C)(C)C)s4)C(=O)N4CCC[C@H]4C(=O)O)cc3)nc2)cc1] | 328 | 10.59 | 10 |
| 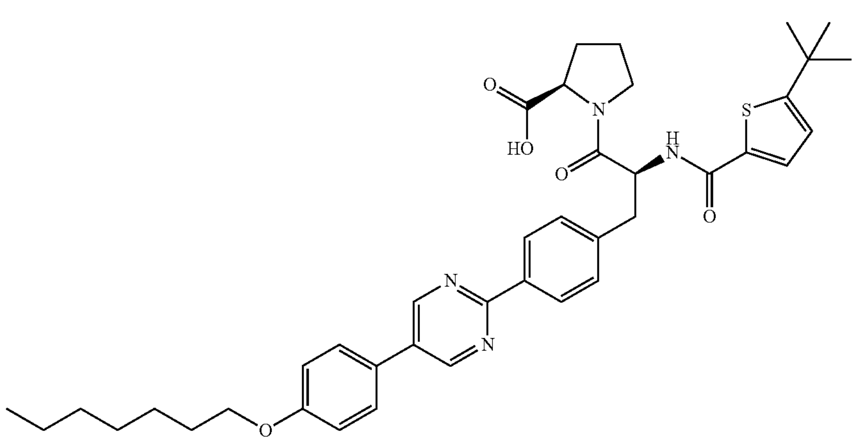 [SMILES: CCCCCCCOc1ccc(-c2cnc(-c3ccc(C[C@H](NC(=O)c4ccc(C(C)(C)C)s4)C(=O)N4CCC[C@@H]4C(=O)O)cc3)nc2)cc1] | 329 | 11.90 | 2 |

TABLE 1-continued
| STRUCTURE | COMPOUND NUMBER | LCMS RETENTION TIME (min) | PURITY METHOD |
|---|---|---|---|
| 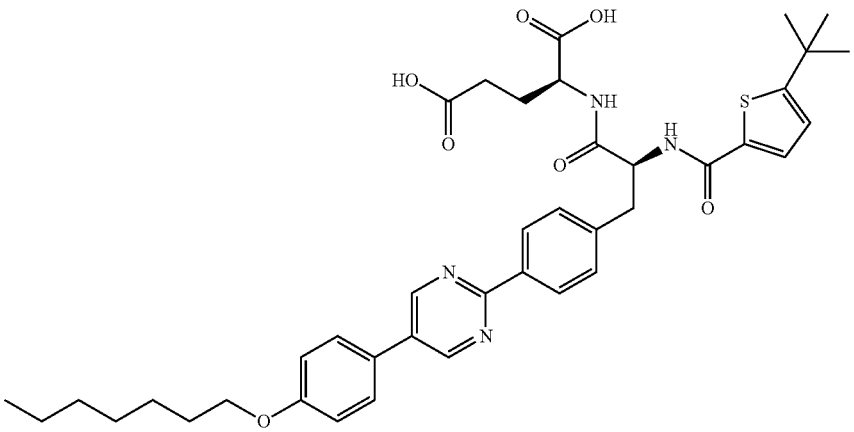 [SMILES: CCCCCCCOc1ccc(-c2cnc(-c3ccc(C[C@H](NC(=O)c4ccc(C(C)(C)C)s4)C(=O)N[C@@H](CCC(=O)O)C(=O)O)cc3)nc2)cc1] | 330 | 11.32 | 2 |
| 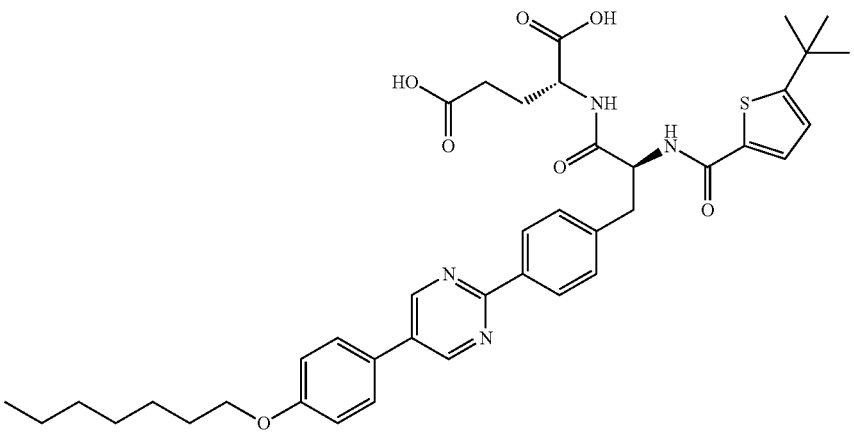 [SMILES: CCCCCCCOc1ccc(-c2cnc(-c3ccc(C[C@H](NC(=O)c4ccc(C(C)(C)C)s4)C(=O)N[C@H](CCC(=O)O)C(=O)O)cc3)nc2)cc1] | 331 | 10.92 | 2 |
| 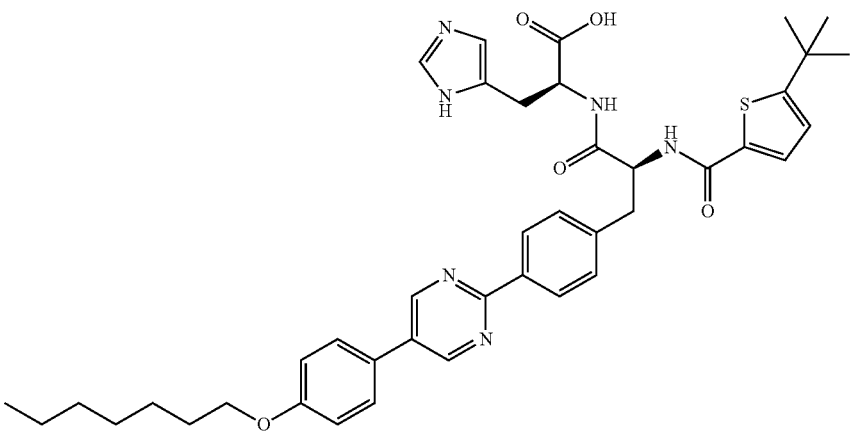 [SMILES: CCCCCCCOc1ccc(-c2cnc(-c3ccc(C[C@H](NC(=O)c4ccc(C(C)(C)C)s4)C(=O)N[C@@H](Cc4cnc[nH]4)C(=O)O)cc3)nc2)cc1] | 332 | 9.53 | 2 |

TABLE 1-continued
| STRUCTURE | COMPOUND NUMBER | LCMS RETENTION TIME (min) | PURITY METHOD |
|---|---|---|---|
| 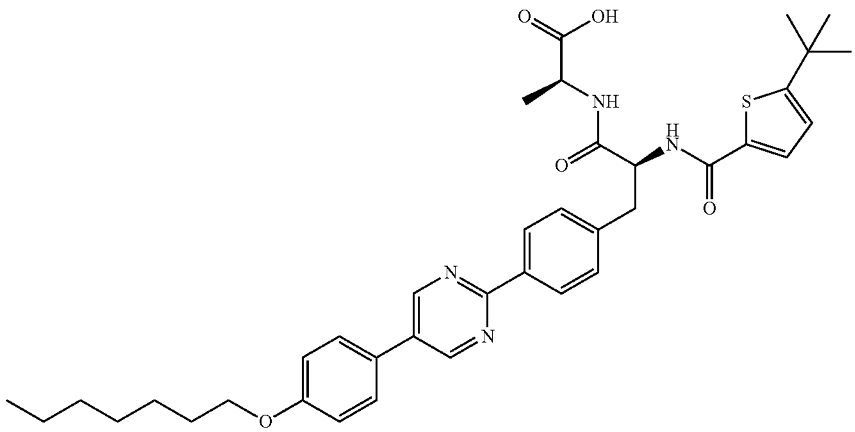 [SMILES: CCCCCCCOc1ccc(-c2cnc(-c3ccc(C[C@H](NC(=O)c4ccc(C(C)(C)C)s4)C(=O)N[C@@H](C)C(=O)O)cc3)nc2)cc1] | 333 | 11.53 | 2 |
| 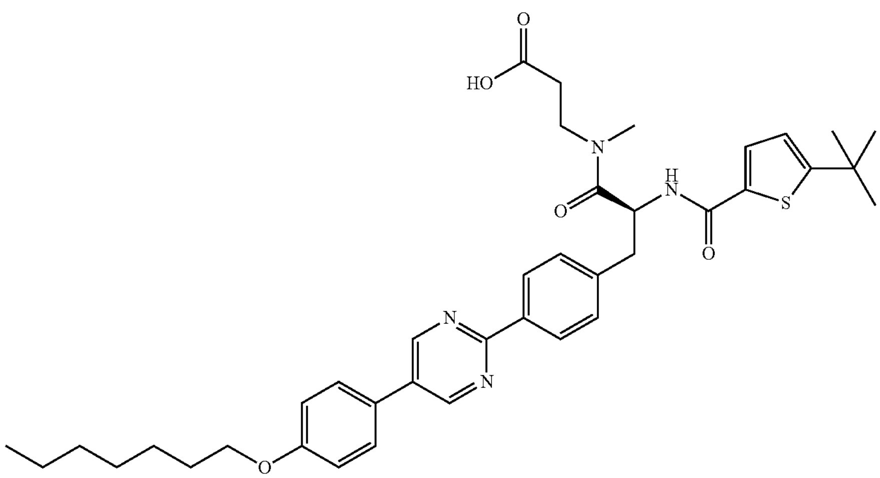 [SMILES: CCCCCCCOc1ccc(-c2cnc(-c3ccc(C[C@H](NC(=O)c4ccc(C(C)(C)C)s4)C(=O)N(C)CCC(=O)O)cc3)nc2)cc1] | 334 | 10.61 | 10 |
| 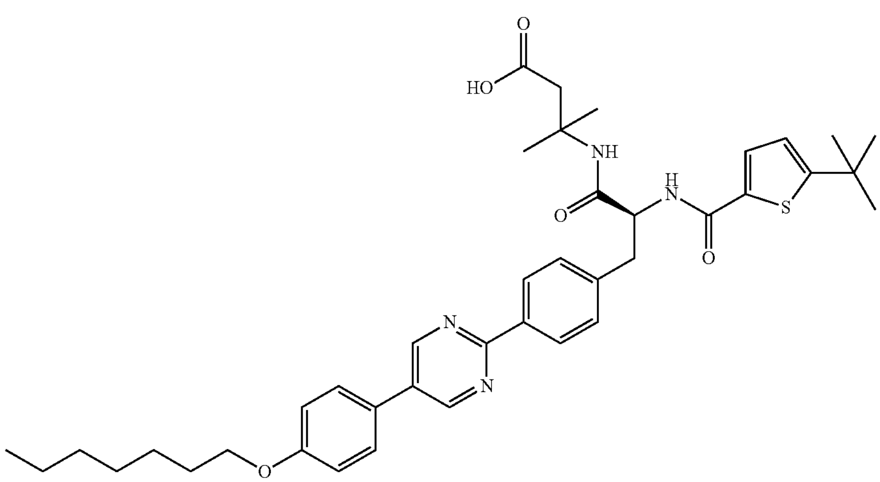 [SMILES: CCCCCCCOc1ccc(-c2cnc(-c3ccc(C[C@H](NC(=O)c4ccc(C(C)(C)C)s4)C(=O)NC(C)(C)CC(=O)O)cc3)nc2)cc1] | 335 | 10.87 | 10 |

TABLE 1-continued

| STRUCTURE | COMPOUND NUMBER | LCMS RETENTION TIME (min) | PURITY METHOD |
|---|---|---|---|
| 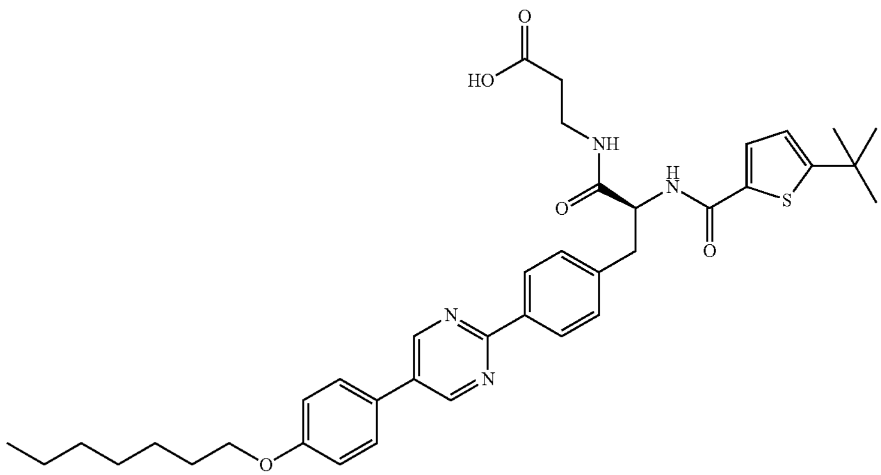 [SMILES: CCCCCCCOc1ccc(-c2cnc(-c3ccc(C[C@H](NC(=O)c4ccc(C(C)(C)C)s4)C(=O)NCCC(=O)O)cc3)nc2)cc1] | 336 | 10.26 | 10 |
| 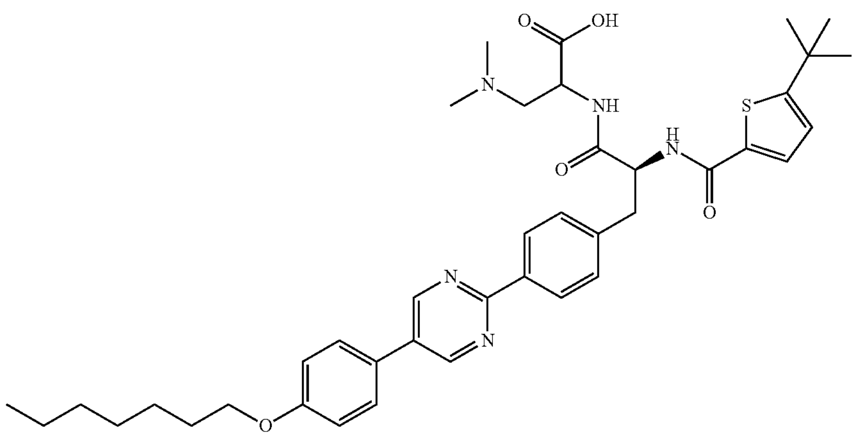 [SMILES: CCCCCCCOc1ccc(-c2cnc(-c3ccc(C[C@H](NC(=O)c4ccc(C(C)(C)C)s4)C(=O)NC(CN(C)C)C(=O)O)cc3)nc2)cc1] | 337 | 10.30 | 2 |
| 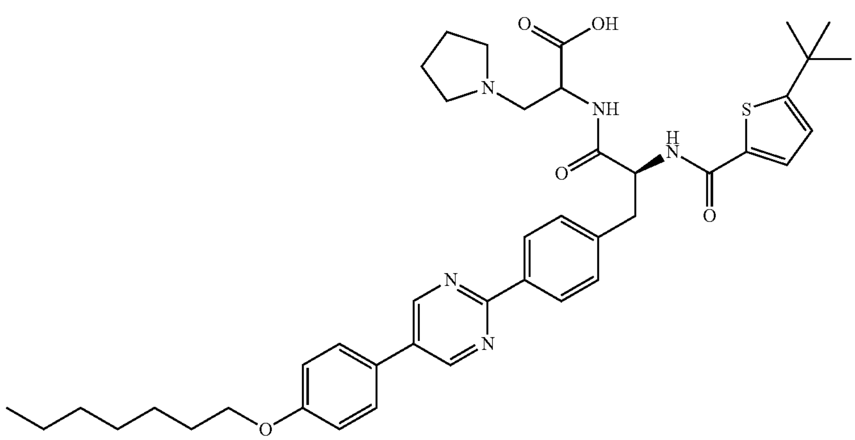 [SMILES: CCCCCCCOc1ccc(-c2cnc(-c3ccc(C[C@H](NC(=O)c4ccc(C(C)(C)C)s4)C(=O)NC(CN4CCCC4)C(=O)O)cc3)nc2)cc1] | 338 | 10.36 | 2 |

TABLE 1-continued

| STRUCTURE | COMPOUND NUMBER | LCMS RETENTION TIME (min) | PURITY METHOD |
|---|---|---|---|
| 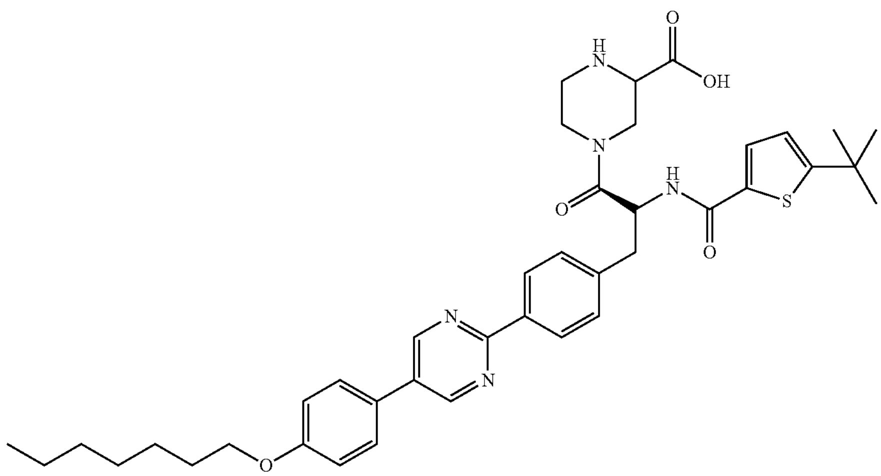 | 339 | 8.59 | 10 |
| 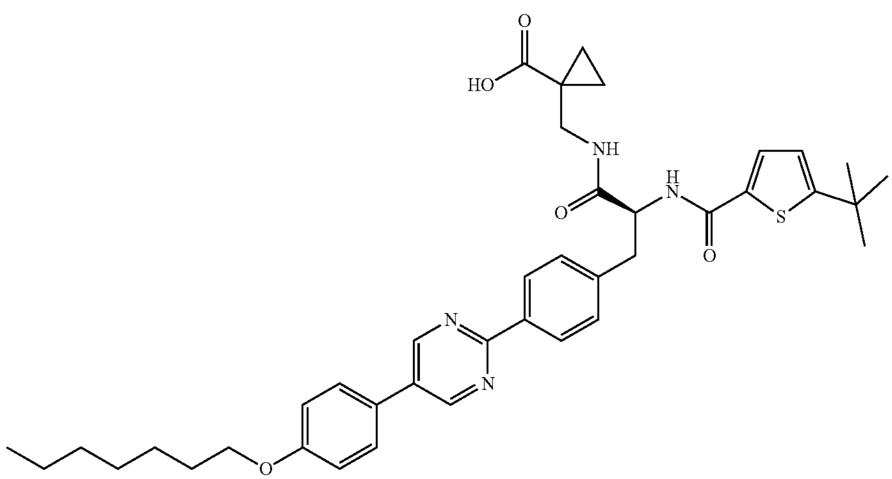 [SMILES: CCCCCCCOc1ccc(-c2cnc(-c3ccc(C[C@H](NC(=O)c4ccc(C(C)(C)C)s4)C(=O)NCC4(C(=O)O)CC4)cc3)nc2)cc1] | 340 | 10.73 | 10 |
| 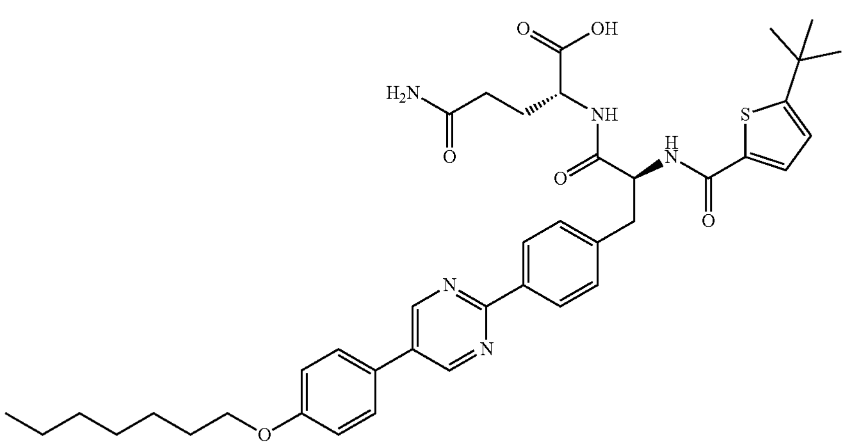 [SMILES: CCCCCCCOc1ccc(-c2cnc(-c3ccc(C[C@H](NC(=O)c4ccc(C(C)(C)C)s4)C(=O)N[C@H](CCC(N)=O)C(=O)O)cc3)nc2)cc1] | 341 | 11.28 | 2 |

TABLE 1-continued
| STRUCTURE | COMPOUND NUMBER | LCMS RETENTION TIME (min) | PURITY METHOD |
|---|---|---|---|
| 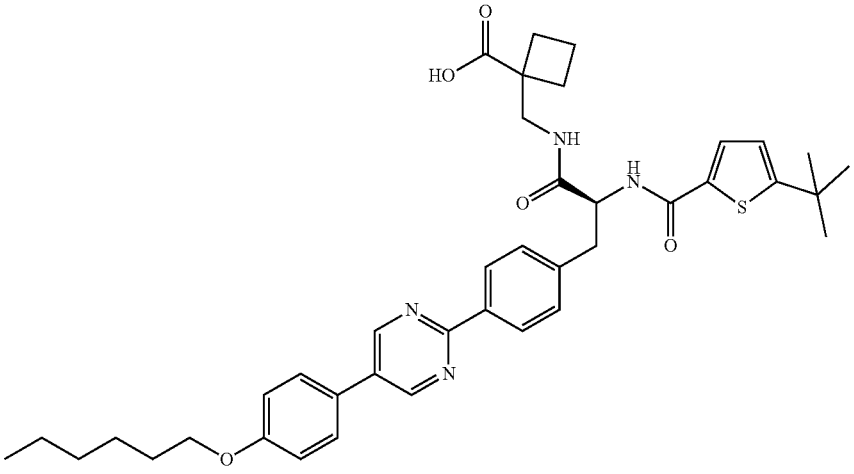 [SMILES: CCCCCCOc1ccc(-c2cnc(-c3ccc(C[C@H](NC(=O)c4ccc(C(C)(C)C)s4)C(=O)NCC4(C(=O)O)CCC4)cc3)nc2)cc1] | 342 | 11.16 | 10 |
| 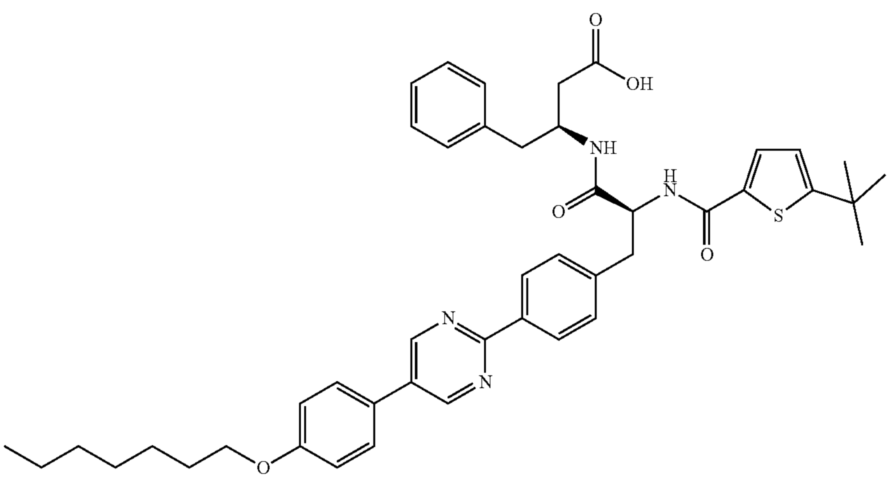 [SMILES: CCCCCCCOc1ccc(-c2cnc(-c3ccc(C[C@H](NC(=O)c4ccc(C(C)(C)C)s4)C(=O)N[C@H](CC(=O)O)Cc4ccccc4)cc3)nc2)cc1] | 343 | 11.72 | 10 |
| 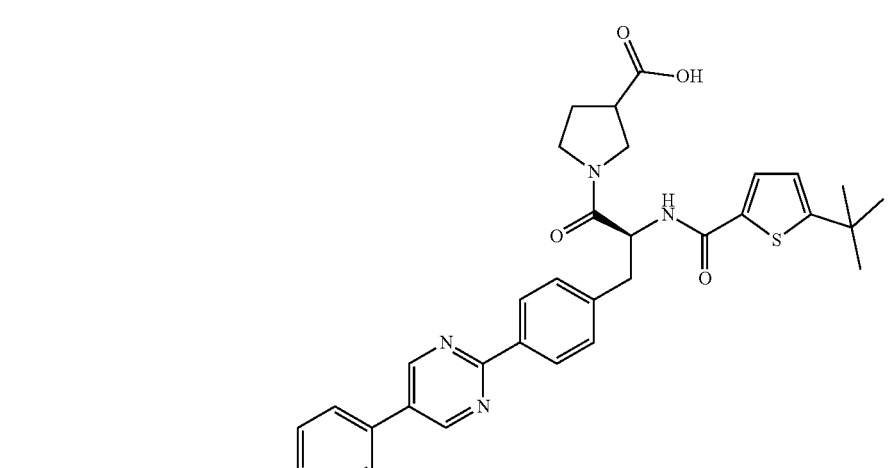 | 344 | 11.13 | 10 |

TABLE 1-continued
| STRUCTURE | COMPOUND NUMBER | LCMS RETENTION TIME (min) | PURITY METHOD |
|---|---|---|---|
| 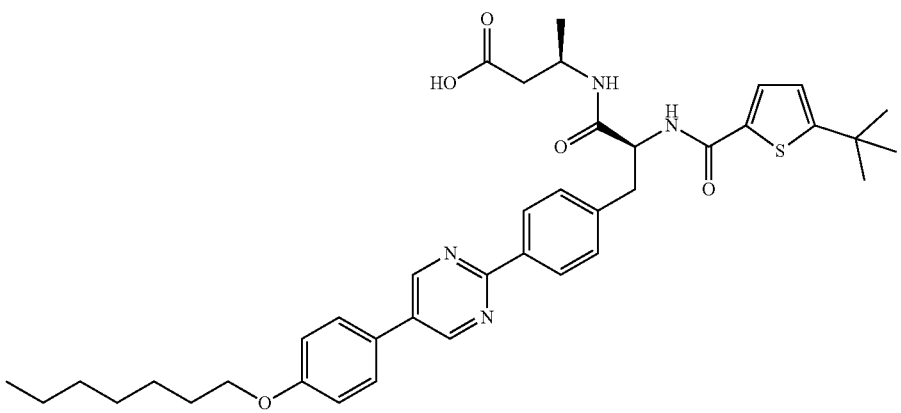 [SMILES: CCCCCCCOc1ccc(-c2cnc(-c3ccc(C[C@H](NC(=O)c4ccc(C(C)(C)C)s4)C(=O)N[C@H](C)CC(=O)O)cc3)nc2)cc1] | 345 | 10.83 | 10 |
| 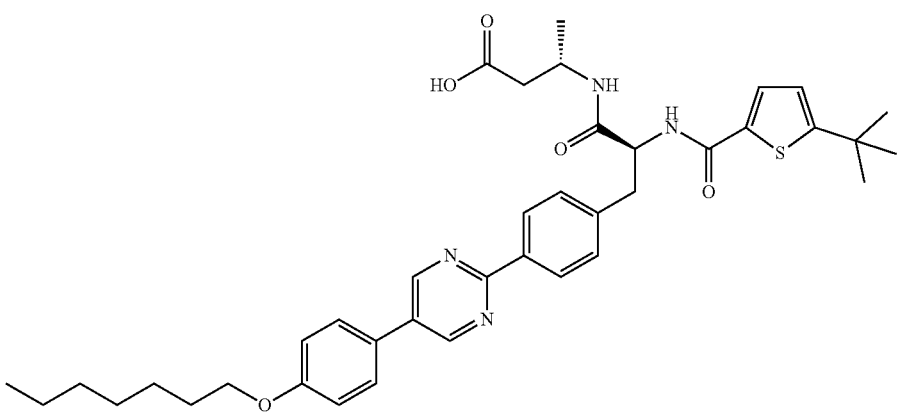 [SMILES: CCCCCCCOc1ccc(-c2cnc(-c3ccc(C[C@H](NC(=O)c4ccc(C(C)(C)C)s4)C(=O)N[C@@H](C)CC(=O)O)cc3)nc2)cc1] | 346 | 11.03 | 10 |
| 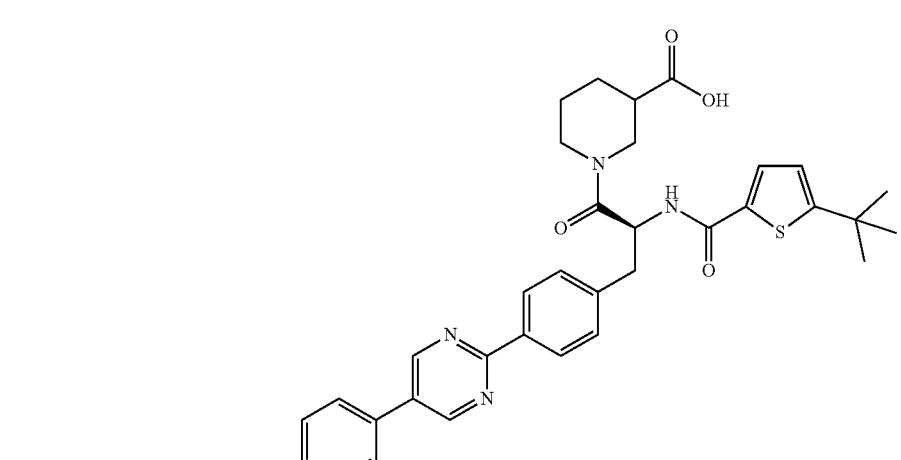 | 347 | 11.60 | 10 |

TABLE 1-continued

| STRUCTURE | COMPOUND NUMBER | LCMS RETENTION TIME (min) | PURITY METHOD |
|---|---|---|---|
| 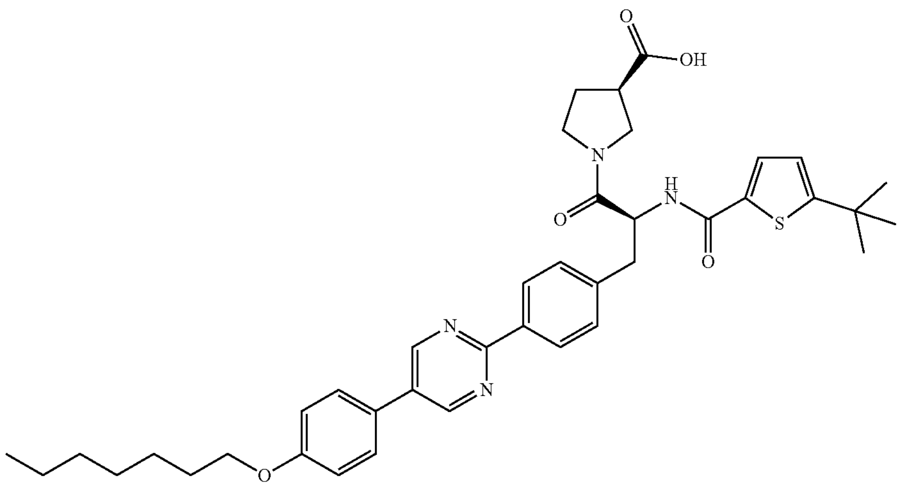 [SMILES: CCCCCCCOc1ccc(-c2cnc(-c3ccc(C[C@H](NC(=O)c4ccc(C(C)(C)C)s4)C(=O)N4CC[C@@H](C(=O)O)C4)cc3)nc2)cc1] | 348 | 11.38 | 10 |
| 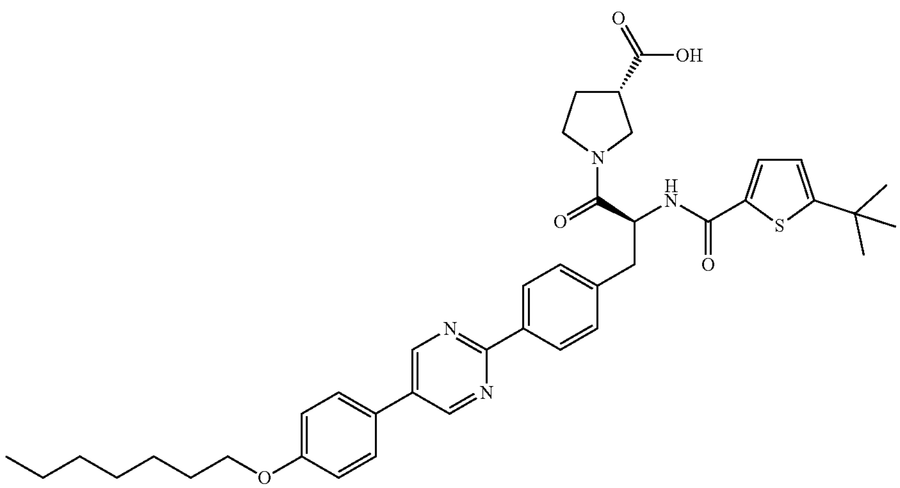 [SMILES: CCCCCCCOc1ccc(-c2cnc(-c3ccc(C[C@H](NC(=O)c4ccc(C(C)(C)C)s4)C(=O)N4CC[C@H](C(=O)O)C4)cc3)nc2)cc1] | 349 | 10.99 | 10 |
| 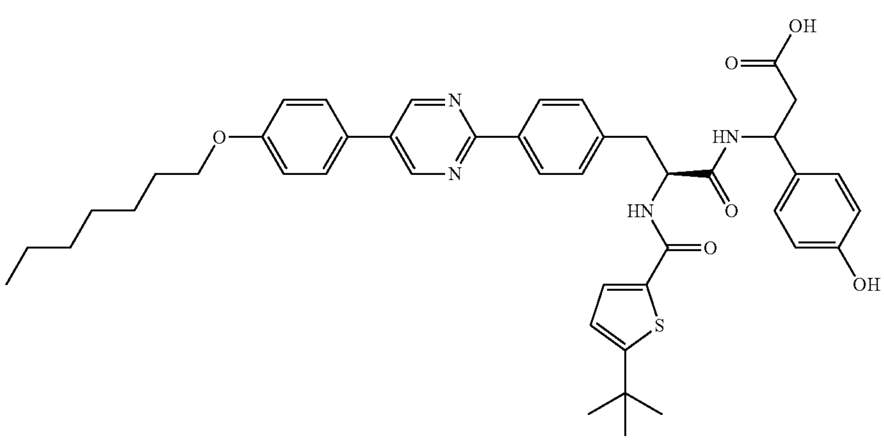 [SMILES: CCCCCCCOc1ccc(-c2cnc(-c3ccc(C[C@H](NC(=O)c4ccc(C(C)(C)C)s4)C(=O)NC(CC(=O)O)c4ccc(O)cc4)cc3)nc2)cc1] | 350 | 10.91 | 10 |

TABLE 1-continued

| STRUCTURE | COMPOUND NUMBER | LCMS RETENTION TIME (min) | PURITY METHOD |
|---|---|---|---|
| (structure) | 351 | 9.93 | 10 |
| (structure) | 352 | 8.59 | 10 |
| (structure) | 353 | 9.91 | 2 |

TABLE 1-continued

| STRUCTURE | COMPOUND NUMBER | LCMS RETENTION TIME (min) | PURITY METHOD |
|---|---|---|---|
| 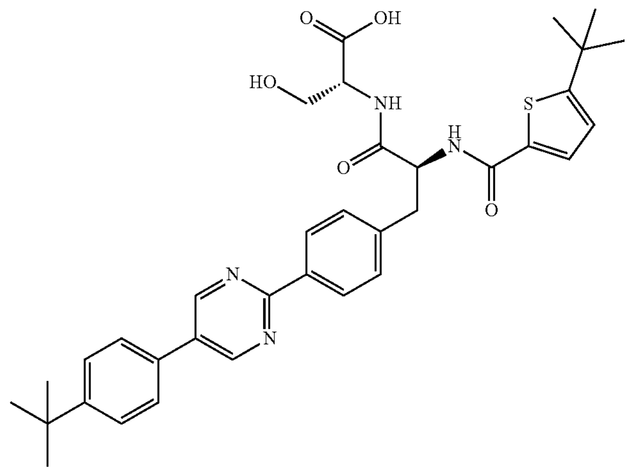 [SMILES: CC(C)(C)c1ccc(-c2cnc(-c3ccc(C[C@H](NC(=O)c4ccc(C(C)(C)C)s4)C(=O)N[C@H](CO)C(=O)O)cc3)nc2)cc1] | 354 | 10.23 | 2 |
| 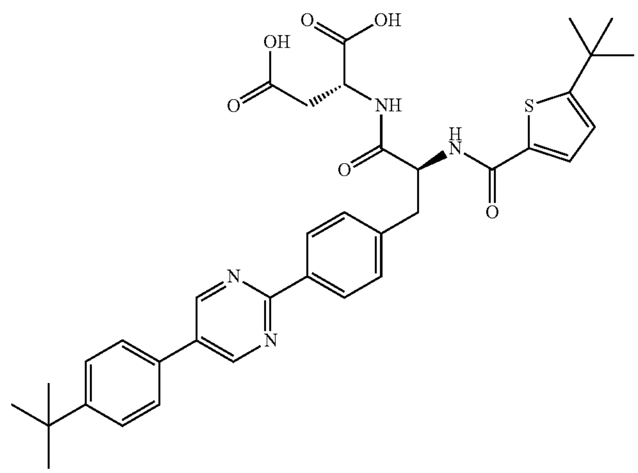 [SMILES: CC(C)(C)c1ccc(-c2cnc(-c3ccc(C[C@H](NC(=O)c4ccc(C(C)(C)C)s4)C(=O)N[C@H](CC(=O)O)C(=O)O)cc3)nc2)cc1] | 355 | 10.17 | 2 |
| 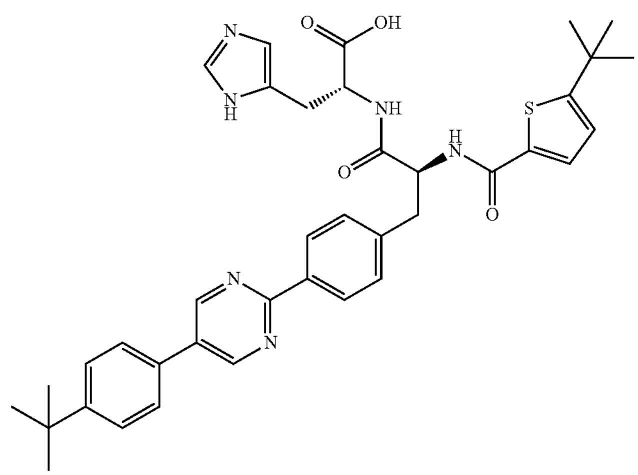 [SMILES: CC(C)(C)c1ccc(-c2cnc(-c3ccc(C[C@H](NC(=O)c4ccc(C(C)(C)C)s4)C(=O)N[C@H](Cc4cnc[nH]4)C(=O)O)cc3)nc2)cc1] | 356 | 8.40 | 2 |

TABLE 1-continued

| STRUCTURE | COMPOUND NUMBER | LCMS RETENTION TIME (min) | PURITY METHOD |
|---|---|---|---|
| 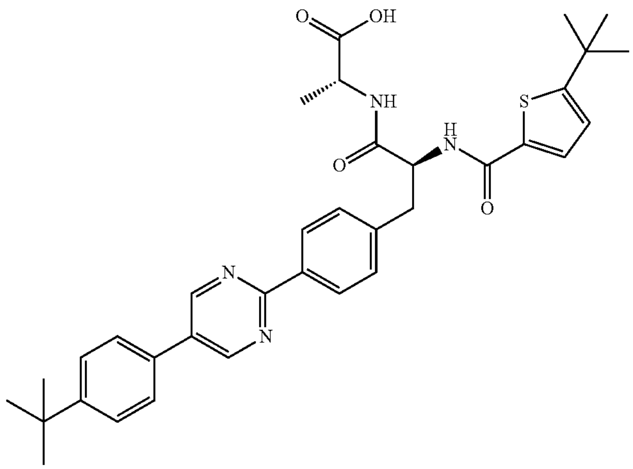 [SMILES: C[C@@H](NC(=O)[C@H](Cc1ccc(-c2ncc(-c3ccc(C(C)(C)C)cc3)cn2)cc1)NC(=O)c1ccc(C(C)(C)C)s1)C(=O)O] | 357 | 10.72 | 2 |
| 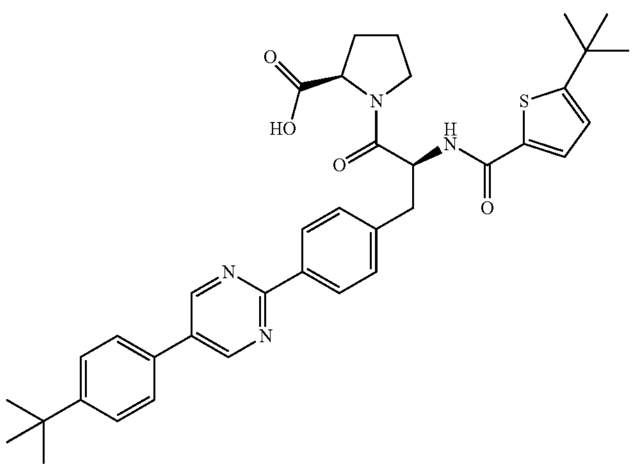 [SMILES: CC(C)(C)c1ccc(-c2cnc(-c3ccc(C[C@H](NC(=O)c4ccc(C(C)(C)C)s4)C(=O)N4CCC[C@@H]4C(=O)O)cc3)nc2)cc1] | 358 | 10.95 | 2 |
| 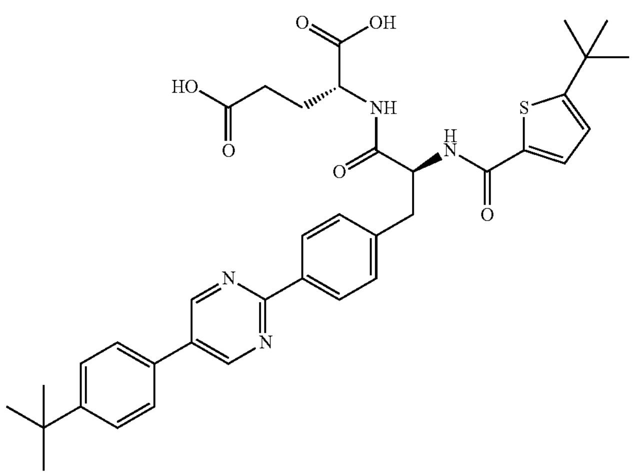 [SMILES: CC(C)(C)c1ccc(-c2cnc(-c3ccc(C[C@H](NC(=O)c4ccc(C(C)(C)C)s4)C(=O)N[C@H](CCC(=O)O)C(=O)O)cc3)nc2)cc1] | 359 | 10.17 | 2 |

TABLE 1-continued

| STRUCTURE | COMPOUND NUMBER | LCMS RETENTION TIME (min) | PURITY METHOD |
|---|---|---|---|
| 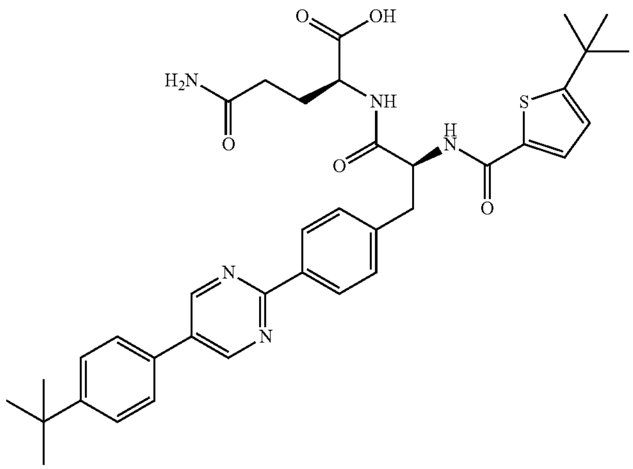 [SMILES: CC(C)(C)c1ccc(-c2cnc(-c3ccc(C[C@H](NC(=O)c4ccc(C(C)(C)C)s4)C(=O)N[C@@H](CCC(N)=O)C(=O)O)cc3)nc2)cc1] | 360 | 10.17 | 2 |
| 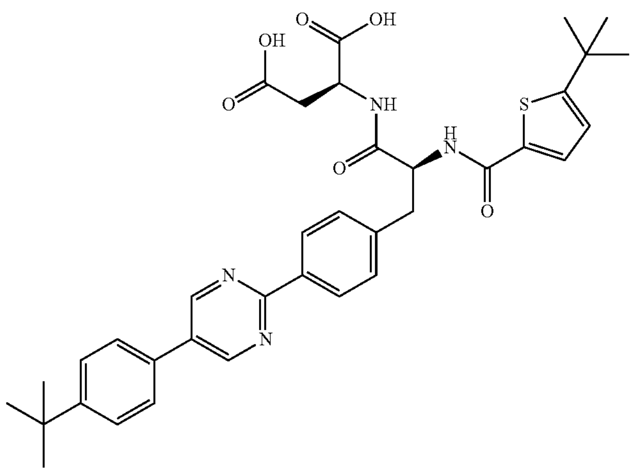 [SMILES: CC(C)(C)c1ccc(-c2cnc(-c3ccc(C[C@H](NC(=O)c4ccc(C(C)(C)C)s4)C(=O)N[C@@H](CC(=O)O)C(=O)O)cc3)nc2)cc1] | 361 | 10.20 | 2 |
| 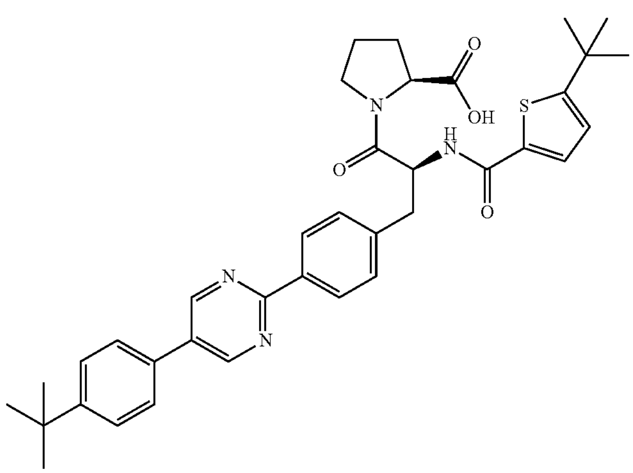 [SMILES: CC(C)(C)c1ccc(-c2cnc(-c3ccc(C[C@H](NC(=O)c4ccc(C(C)(C)C)s4)C(=O)N4CCC[C@H]4C(=O)O)cc3)nc2)cc1] | 362 | 10.98 | 2 |

US 9,598,430 B2

521 522

TABLE 1-continued

| STRUCTURE | COMPOUND NUMBER | LCMS RETENTION TIME (min) | PURITY METHOD |
|---|---|---|---|
| (structure) | 363 | 10.20 | 2 |
| (structure) | 364 | 10.67 | 2 |
| (structure) | 365 | 9.14 | 2 |

TABLE 1-continued

| STRUCTURE | COMPOUND NUMBER | LCMS RETENTION TIME (min) | PURITY METHOD |
|---|---|---|---|
| (structure) | 366 | 8.65 | 2 |
| (structure) | 367 | 10.78 | 2 |
| (structure) | 368 | 10.84 | 2 |

| STRUCTURE | COMPOUND NUMBER | LCMS RETENTION TIME (min) | PURITY METHOD |
|---|---|---|---|
| 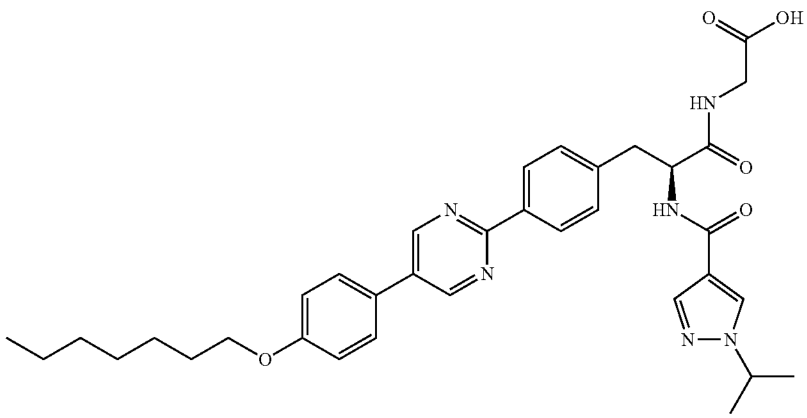 [SMILES: CCCCCCCOc1ccc(-c2cnc(-c3ccc(C[C@H](NC(=O)c4cnn(C(C)C)c4)C(=O)NCC(=O)O)cc3)nc2)cc1] | 369 | 8.62 | 10 |
| 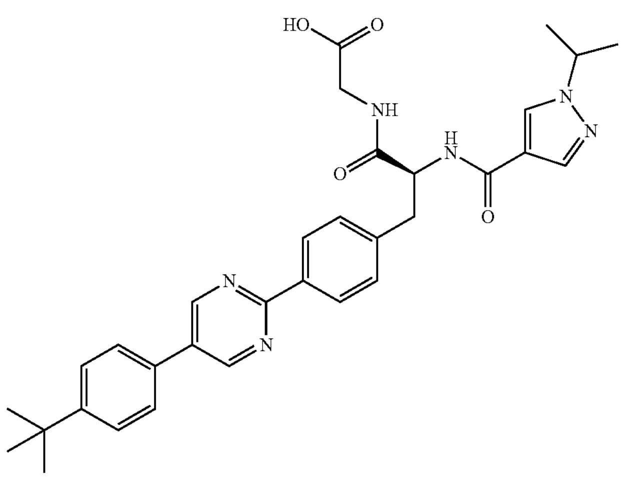 [SMILES: CC(C)n1cc(C(=O)N[C@@H](Cc2ccc(-c3ncc(-c4ccc(C(C)(C)C)cc4)cn3)cc2)C(=O)NCC(=O)O)cn1] | 370 | 7.02 | 10 |
| 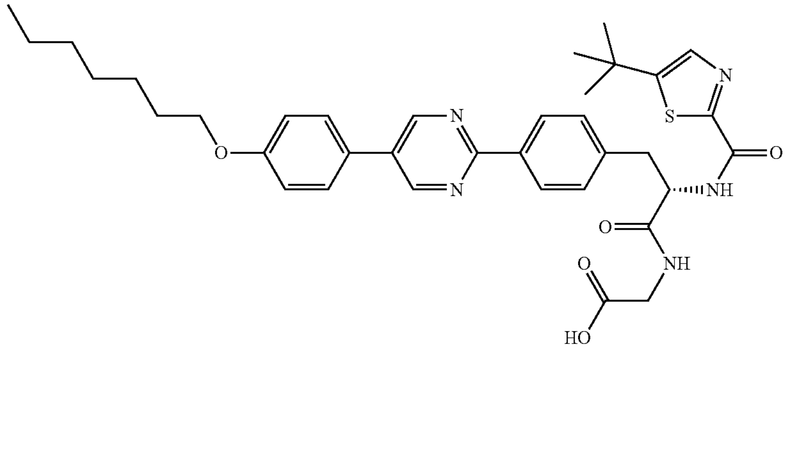 [SMILES: CCCCCCCOc1ccc(-c2cnc(-c3ccc(C[C@H](NC(=O)c4ncc(C(C)(C)C)s4)C(=O)NCC(=O)O)cc3)nc2)cc1] | 371 | 10.12 | 10 |

TABLE 1-continued
| STRUCTURE | COMPOUND NUMBER | LCMS RETENTION TIME (min) | PURITY METHOD |
|---|---|---|---|
| 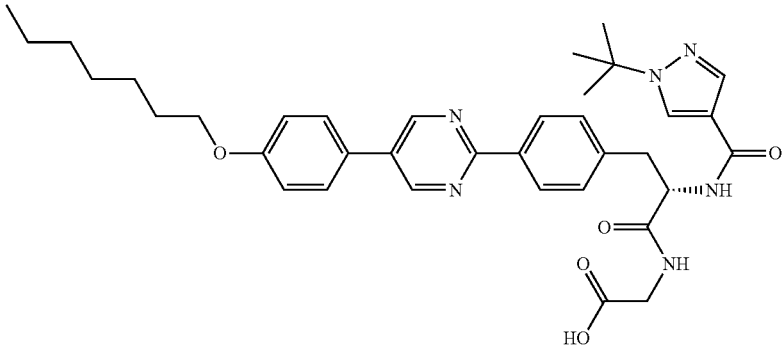 [SMILES: CCCCCCCOc1ccc(-c2cnc(-c3ccc(C[C@H](NC(=O)c4cnn(C(C)(C)C)c4)C(=O)NCC(=O)O)cc3)nc2)cc1] | 372 | 9.42 | 10 |
| 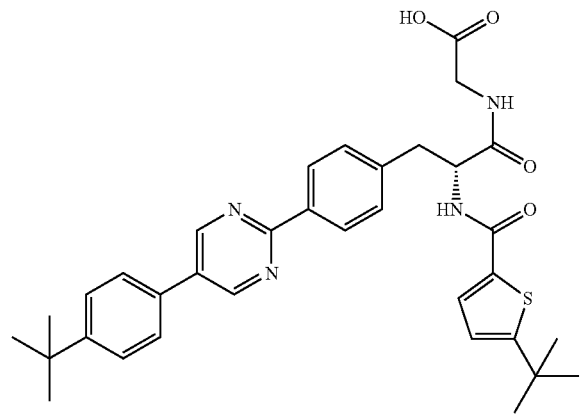 [SMILES: CC(C)(C)c1ccc(-c2cnc(-c3ccc(C[C@@H](NC(=O)c4ccc(C(C)(C)C)s4)C(=O)NCC(=O)O)cc3)nc2)cc1] | 373 | 9.14 | 10 |
| 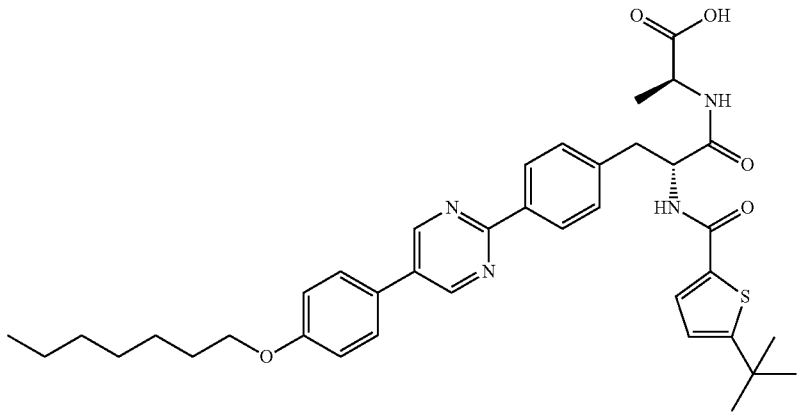 [SMILES: CCCCCCCOc1ccc(-c2cnc(-c3ccc(C[C@@H](NC(=O)c4ccc(C(C)(C)C)s4)C(=O)N[C@@H](C)C(=O)O)cc3)nc2)cc1] | 374 | 10.78 | 10 |

| STRUCTURE | COMPOUND NUMBER | LCMS RETENTION TIME (min) | PURITY METHOD |
|---|---|---|---|
| 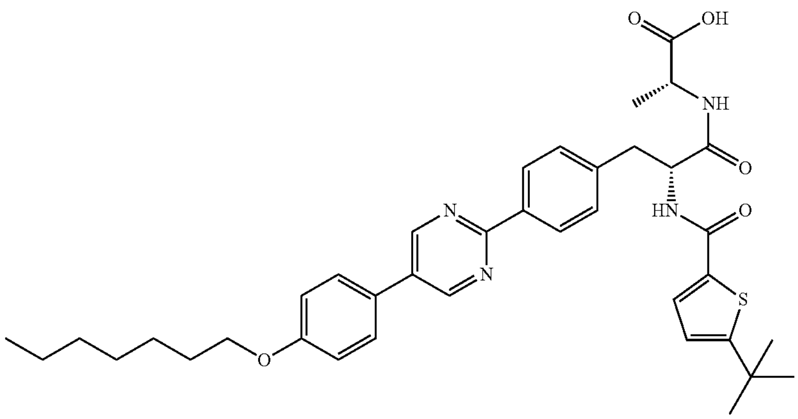 [SMILES: CCCCCCCOc1ccc(-c2cnc(-c3ccc(C[C@@H](NC(=O)c4ccc(C(C)(C)C)s4)C(=O)N[C@H](C)C(=O)O)cc3)nc2)cc1] | 375 | 10.82 | 10 |
| 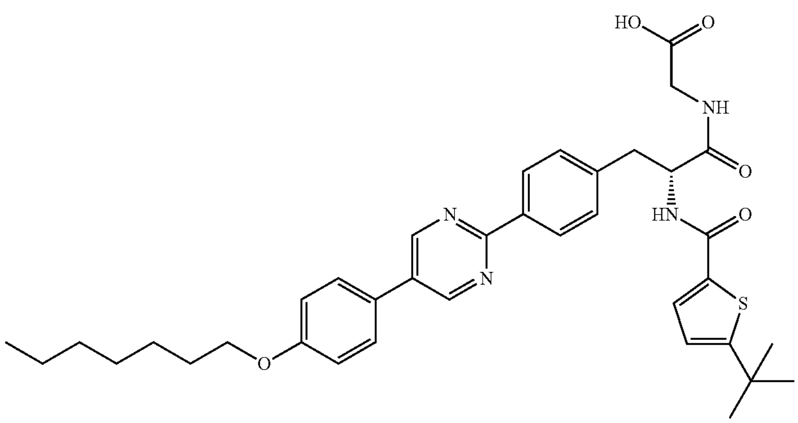 [SMILES: CCCCCCCOc1ccc(-c2cnc(-c3ccc(C[C@@H](NC(=O)c4ccc(C(C)(C)C)s4)C(=O)NCC(=O)O)cc3)nc2)cc1] | 376 | 10.61 | 10 |
| 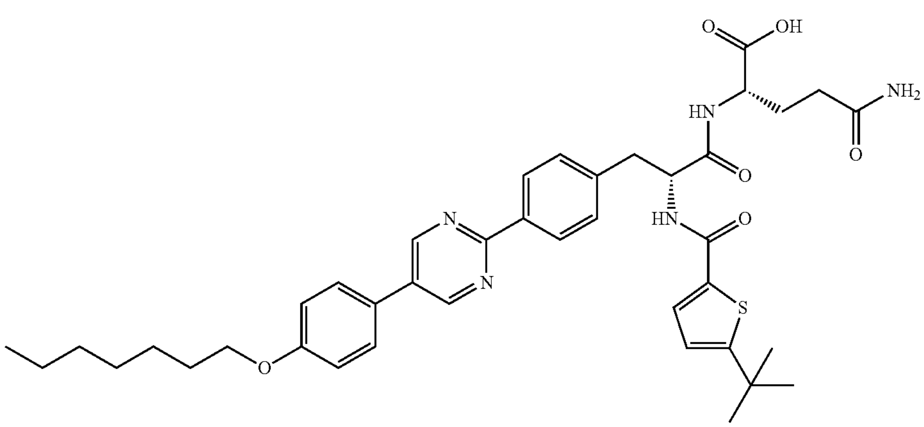 [SMILES: CCCCCCCOc1ccc(-c2cnc(-c3ccc(C[C@@H](NC(=O)c4ccc(C(C)(C)C)s4)C(=O)N[C@@H](CCC(N)=O)C(=O)O)cc3)nc2)cc1] | 377 | 10.16 | 10 |

TABLE 1-continued
| STRUCTURE | COMPOUND NUMBER | LCMS RETENTION TIME (min) | PURITY METHOD |
|---|---|---|---|
| 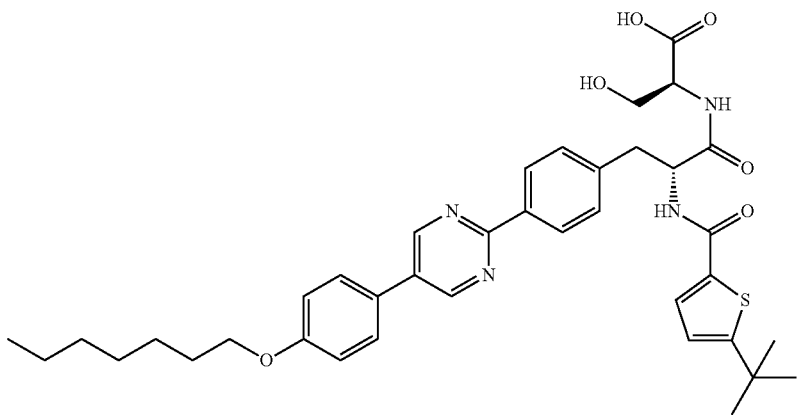 [SMILES: CCCCCCCOc1ccc(-c2cnc(-c3ccc(C[C@@H](NC(=O)c4ccc(C(C)(C)C)s4)C(=O)N[C@@H](CO)C(=O)O)cc3)nc2)cc1] | 378 | 10.36 | 10 |
| 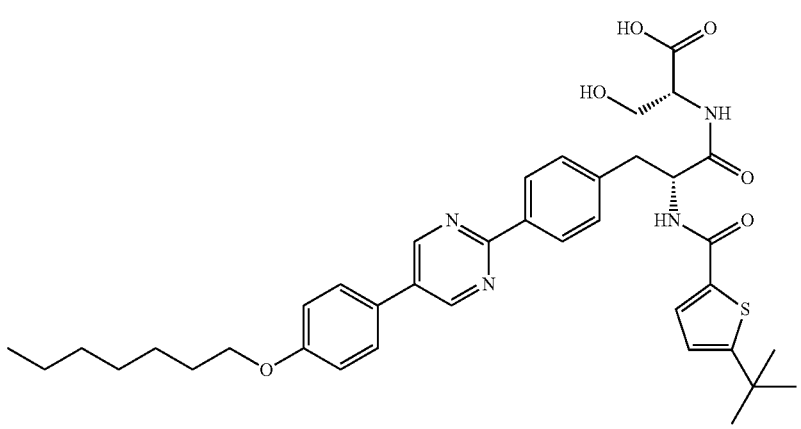 [SMILES: CCCCCCCOc1ccc(-c2cnc(-c3ccc(C[C@@H](NC(=O)c4ccc(C(C)(C)C)s4)C(=O)N[C@H](CO)C(=O)O)cc3)nc2)cc1] | 379 | 10.46 | 10 |
| 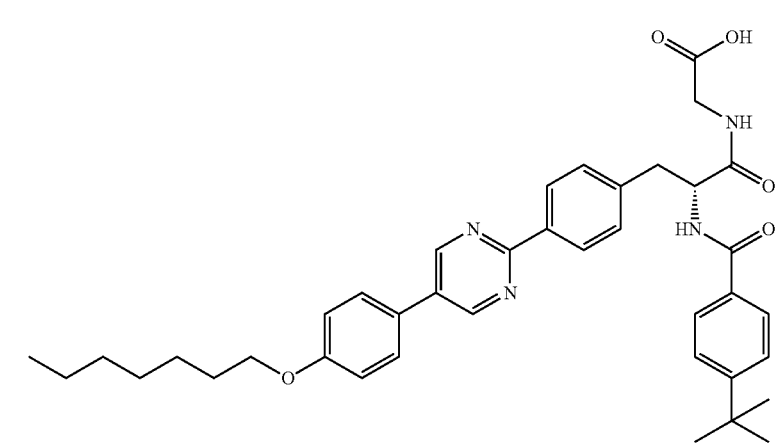 [SMILES: CCCCCCCOc1ccc(-c2cnc(-c3ccc(C[C@@H](NC(=O)c4ccc(C(C)(C)C)cc4)C(=O)NCC(=O)O)cc3)nc2)cc1] | 380 | 10.74 | 10 |

TABLE 1-continued
| STRUCTURE | COMPOUND NUMBER | LCMS RETENTION TIME (min) | PURITY METHOD |
|---|---|---|---|
| 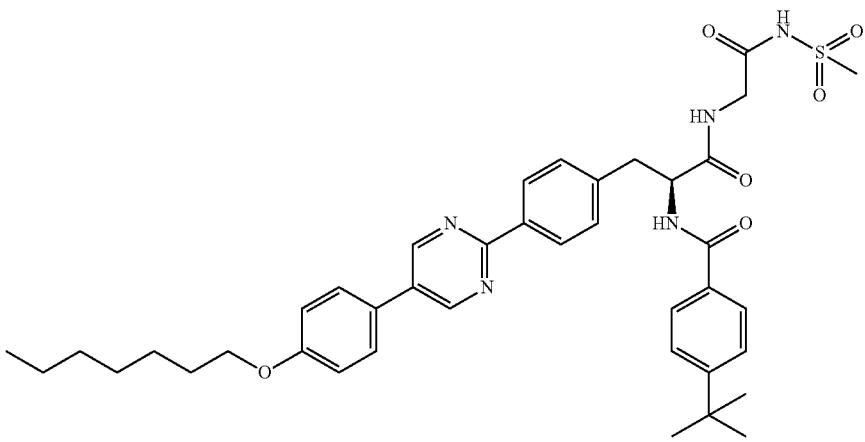 [SMILES: CCCCCCCOc1ccc(-c2cnc(-c3ccc(C[C@H](NC(=O)c4ccc(C(C)(C)C)cc4)C(=O)NCC(=O)NS(C)(=O)=O)cc3)nc2)cc1] | 381 | 10.51 | 10 |
| 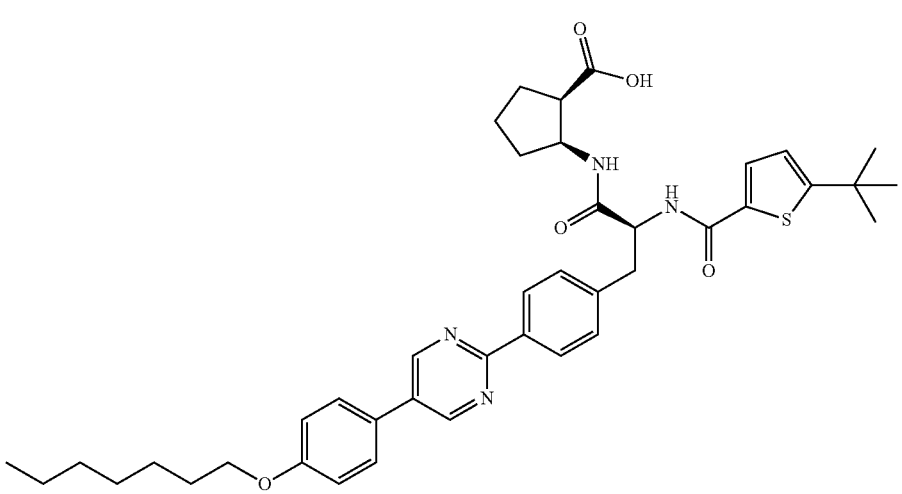 [SMILES: CCCCCCCOc1ccc(-c2cnc(-c3ccc(C[C@H](NC(=O)c4ccc(C(C)(C)C)s4)C(=O)N[C@H]4CCC[C@H]4C(=O)O)cc3)nc2)cc1] | 382 | 11.40 | 10 |
| 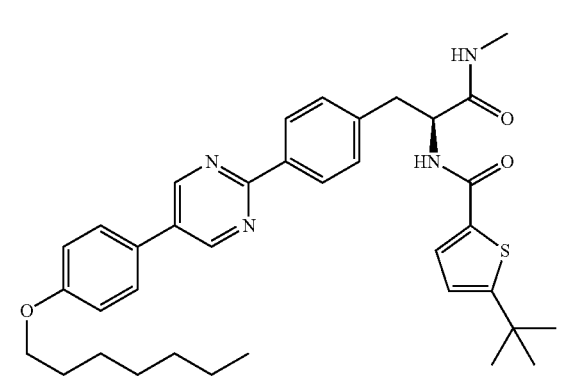 [SMILES: CCCCCCCOc1ccc(-c2cnc(-c3ccc(C[C@H](NC(=O)c4ccc(C(C)(C)C)s4)C(=O)NC)cc3)nc2)cc1] | 383 | 12.06 | 2 |

TABLE 1-continued

| STRUCTURE | COMPOUND NUMBER | LCMS RETENTION TIME (min) | PURITY METHOD |
|---|---|---|---|
| 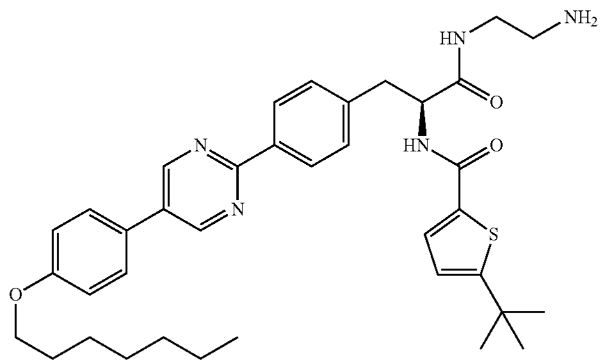 [SMILES: CCCCCCCOc1ccc(-c2cnc(-c3ccc(C[C@H](NC(=O)c4ccc(C(C)(C)C)s4)C(=O)NCCN)cc3)nc2)cc1] | 384 | 9.29 | 2 |
| 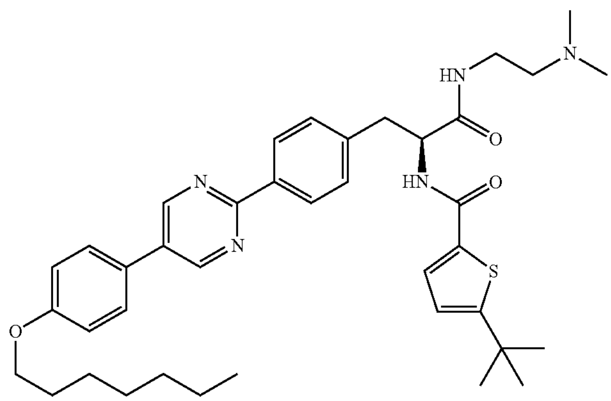 [SMILES: CCCCCCCOc1ccc(-c2cnc(-c3ccc(C[C@H](NC(=O)c4ccc(C(C)(C)C)s4)C(=O)NCCN(C)C)cc3)nc2)cc1] | 385 | 9.43 | 2 |
| 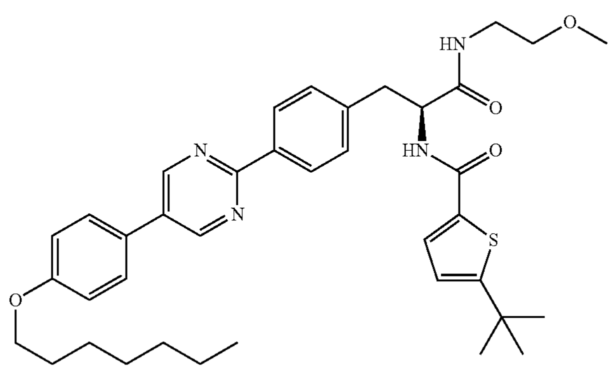 [SMILES: CCCCCCCOc1ccc(-c2cnc(-c3ccc(C[C@H](NC(=O)c4ccc(C(C)(C)C)s4)C(=O)NCCOC)cc3)nc2)cc1] | 386 | 12.10 | 2 |

TABLE 1-continued

| STRUCTURE | COMPOUND NUMBER | LCMS RETENTION TIME (min) | PURITY METHOD |
|---|---|---|---|
| 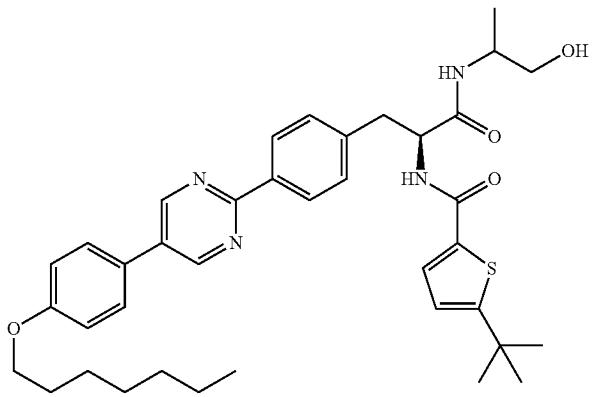 [SMILES: CCCCCCCOc1ccc(-c2cnc(-c3ccc(C[C@H](NC(=O)c4ccc(C(C)(C)C)s4)C(=O)NC(C)CO)cc3)nc2)cc1] | 387 | 11.83 | 2 |
| 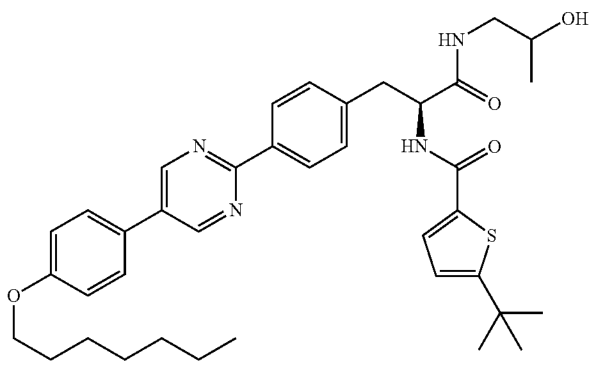 [SMILES: CCCCCCCOc1ccc(-c2cnc(-c3ccc(C[C@H](NC(=O)c4ccc(C(C)(C)C)s4)C(=O)NCC(C)O)cc3)nc2)cc1] | 388 | 11.85 | 2 |
| 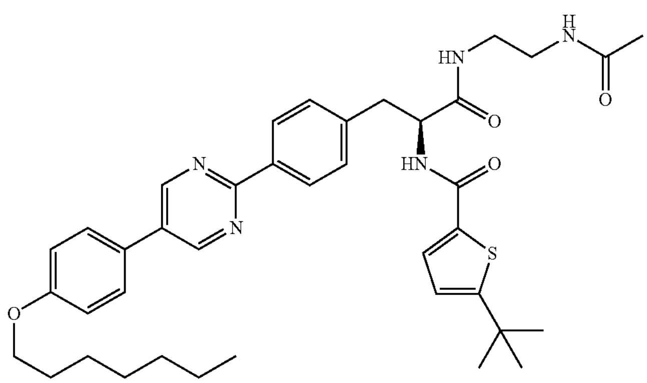 [SMILES: CCCCCCCOc1ccc(-c2cnc(-c3ccc(C[C@H](NC(=O)c4ccc(C(C)(C)C)s4)C(=O)NCCNC(C)=O)cc3)nc2)cc1] | 389 | 11.63 | 2 |
| 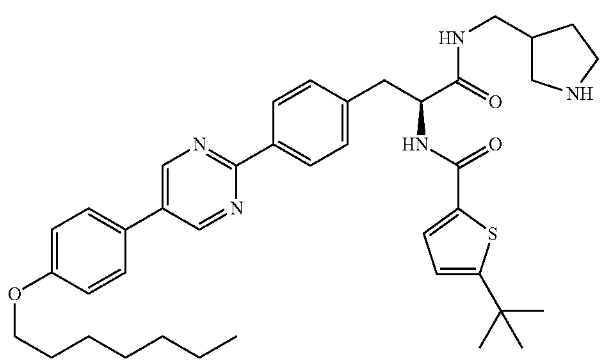 [SMILES: CCCCCCCOc1ccc(-c2cnc(-c3ccc(C[C@H](NC(=O)c4ccc(C(C)(C)C)s4)C(=O)NCC4CCNC4)cc3)nc2)cc1] | 390 | 9.35 | 2 |

TABLE 1-continued

| STRUCTURE | COMPOUND NUMBER | LCMS RETENTION TIME (min) | PURITY METHOD |
|---|---|---|---|
| 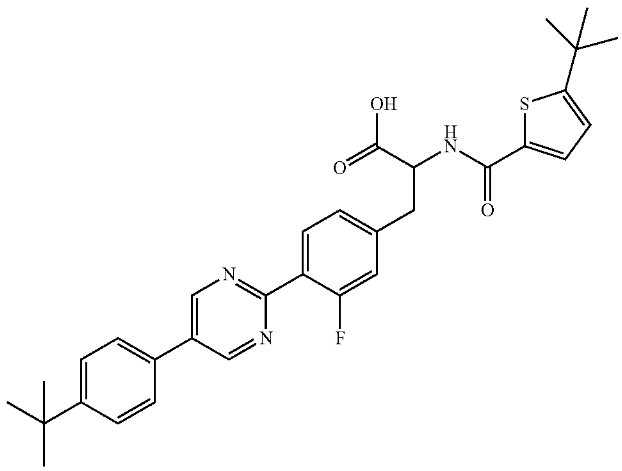 [SMILES: CC(C)(C)c1ccc(-c2cnc(-c3ccc(CC(NC(=O)c4ccc(C(C)(C)C)s4)C(=O)O)cc3F)nc2)cc1] | 391 | 10.75 | 2 |
| 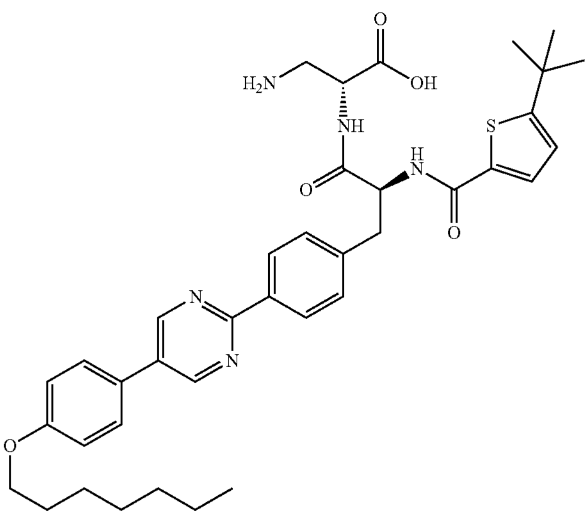 [SMILES: CCCCCCCOc1ccc(-c2cnc(-c3ccc(C[C@H](NC(=O)c4ccc(C(C)(C)C)s4)C(=O)N[C@H](CN)C(=O)O)cc3)nc2)cc1] | 392 | 10.33 | 2 |
| 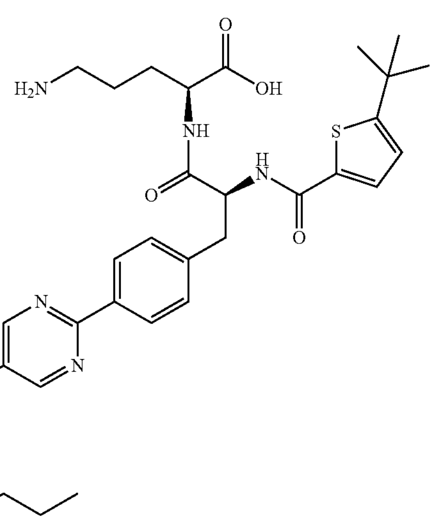 | 393 | 9.56 | 2 |

TABLE 1-continued

| STRUCTURE | COMPOUND NUMBER | LCMS RETENTION TIME (min) | PURITY METHOD |
|---|---|---|---|
| 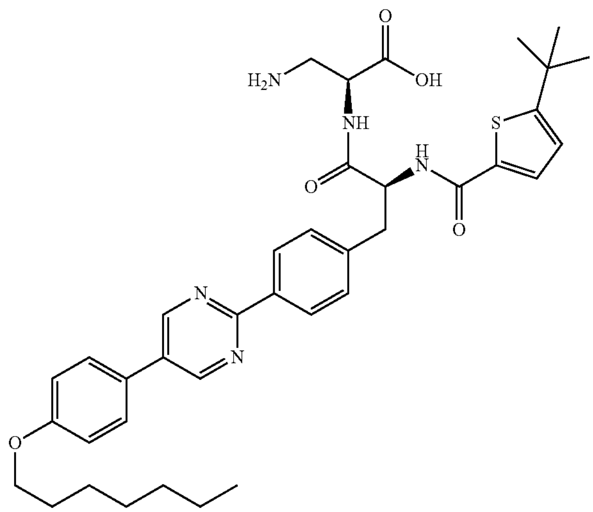 [SMILES: CCCCCCCOc1ccc(-c2cnc(-c3ccc(C[C@H](NC(=O)c4ccc(C(C)(C)C)s4)C(=O)N[C@@H](CN)C(=O)O)cc3)nc2)cc1] | 394 | 9.96 | 2 |
| 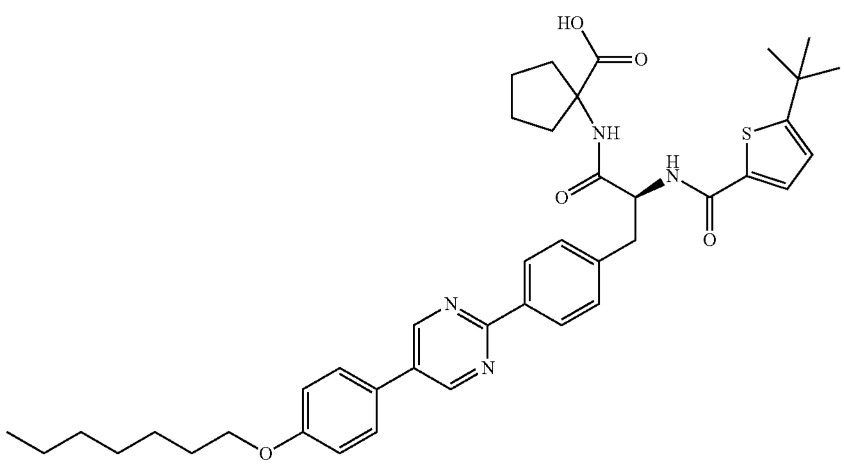 [SMILES: CCCCCCCOc1ccc(-c2cnc(-c3ccc(C[C@H](NC(=O)c4ccc(C(C)(C)C)s4)C(=O)NC4(C(=O)O)CCCC4)cc3)nc2)cc1] | 395 | 9.49 | 12 |
| 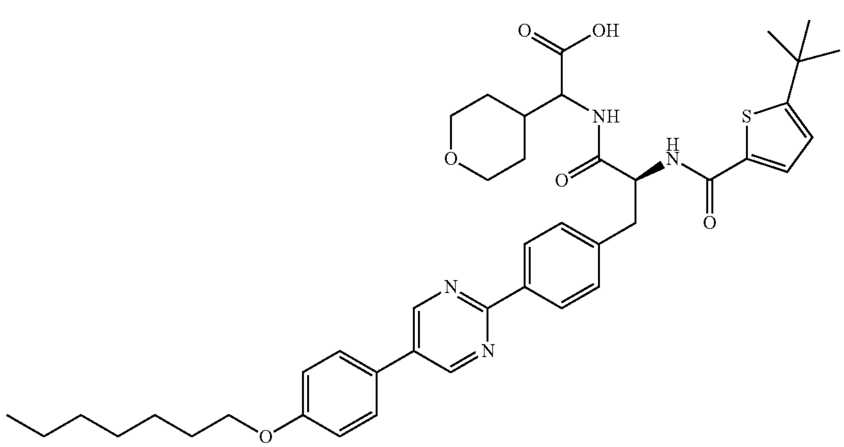 [SMILES: CCCCCCCOc1ccc(-c2cnc(-c3ccc(C[C@H](NC(=O)c4ccc(C(C)(C)C)s4)C(=O)NC(C(=O)O)C4CCOCC4)cc3)nc2)cc1] | 396 | 9.61 | 12 |

TABLE 1-continued

| STRUCTURE | COMPOUND NUMBER | LCMS RETENTION TIME (min) | PURITY METHOD |
|---|---|---|---|
| 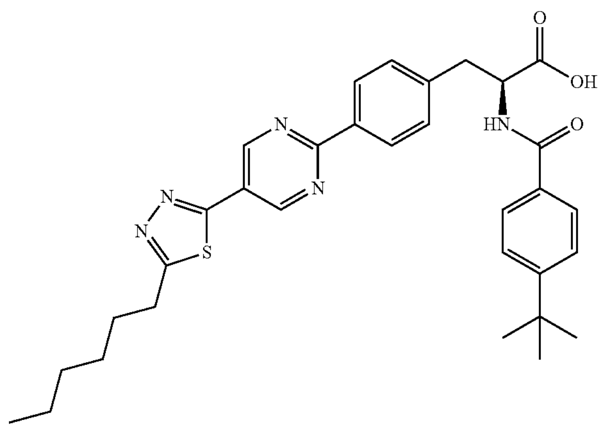 [SMILES: CCCCCCc1nnc(-c2cnc(-c3ccc(C[C@H](NC(=O)c4ccc(C(C)(C)C)cc4)C(=O)O)cc3)nc2)s1] | 397 | 10.66 | 2 |
| 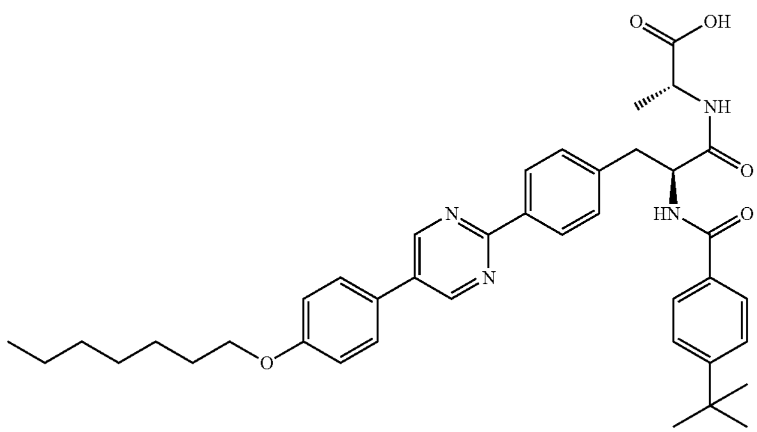 [SMILES: CCCCCCCOc1ccc(-c2cnc(-c3ccc(C[C@H](NC(=O)c4ccc(C(C)(C)C)cc4)C(=O)N[C@H](C)C(=O)O)cc3)nc2)cc1] | 398 | 12.33 | 10 |
| 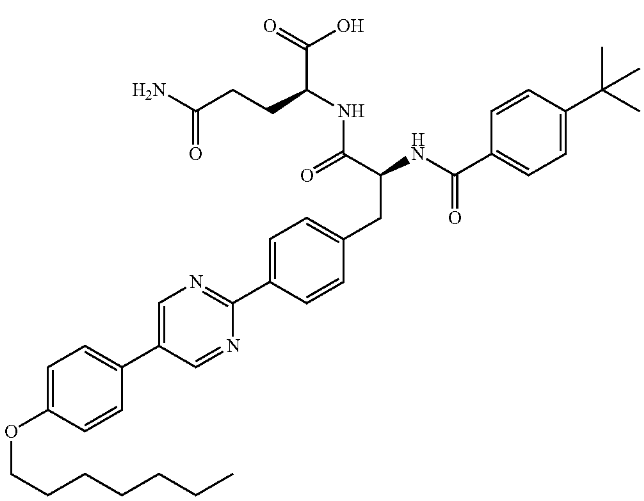 [SMILES: CCCCCCCOc1ccc(-c2cnc(-c3ccc(C[C@H](NC(=O)c4ccc(C(C)(C)C)cc4)C(=O)N[C@@H](CCC(N)=O)C(=O)O)cc3)nc2)cc1] | 399 | 9.53 | 10 |

TABLE 1-continued

| STRUCTURE | COMPOUND NUMBER | LCMS RETENTION TIME (min) | PURITY METHOD |
|---|---|---|---|
| (structure) | 400 | 10.40 | 10 |
| (structure) | 401 | 8.83 | 2 |
| (structure) | 402 | 8.19 | 2 |

TABLE 1-continued
| STRUCTURE | COMPOUND NUMBER | LCMS RETENTION TIME (min) | PURITY METHOD |
|---|---|---|---|
| 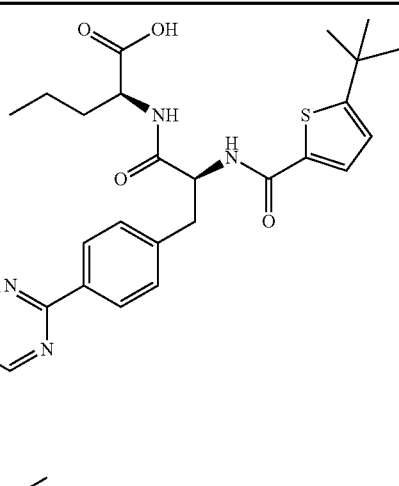 | 403 | 8.26 | 2 |
| 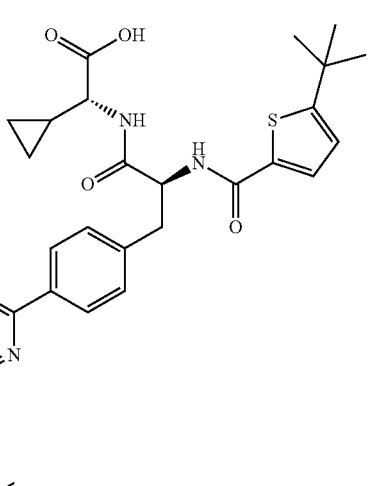 | 404 | 8.66 | 2 |
| 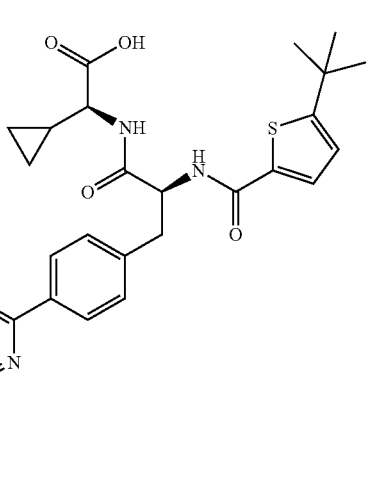 | 405 | 7.85 | 2 |

TABLE 1-continued

| STRUCTURE | COMPOUND NUMBER | LCMS RETENTION TIME (min) | PURITY METHOD |
|---|---|---|---|
| 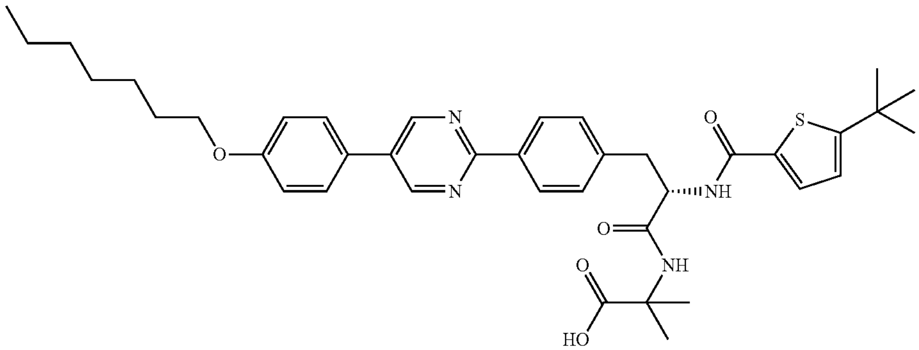 [SMILES: CCCCCCCOc1ccc(-c2cnc(-c3ccc(C[C@H](NC(=O)c4ccc(C(C)(C)C)s4)C(=O)NC(C)(C)C(=O)O)cc3)nc2)cc1] | 406 | 10.47 | 10 |
| 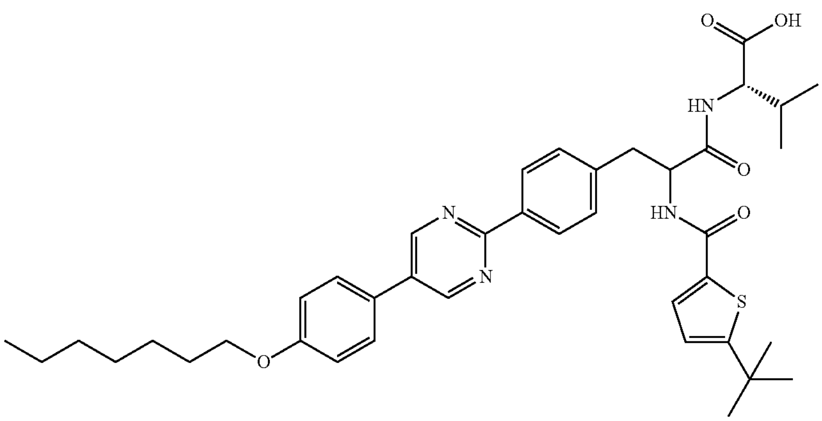 [SMILES: CCCCCCCOc1ccc(-c2cnc(-c3ccc(CC(NC(=O)c4ccc(C(C)(C)C)s4)C(=O)N[C@H](C(=O)O)C(C)C)cc3)nc2)cc1] | 407 | 9.06 | 12 |
| 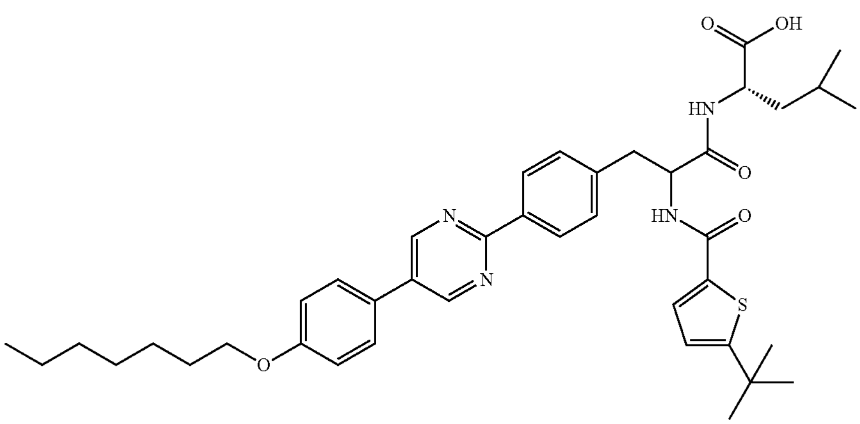 [SMILES: CCCCCCCOc1ccc(-c2cnc(-c3ccc(CC(NC(=O)c4ccc(C(C)(C)C)s4)C(=O)N[C@@H](CC(C)C)C(=O)O)cc3)nc2)cc1] | 408 | 9.55 | 12 |
| 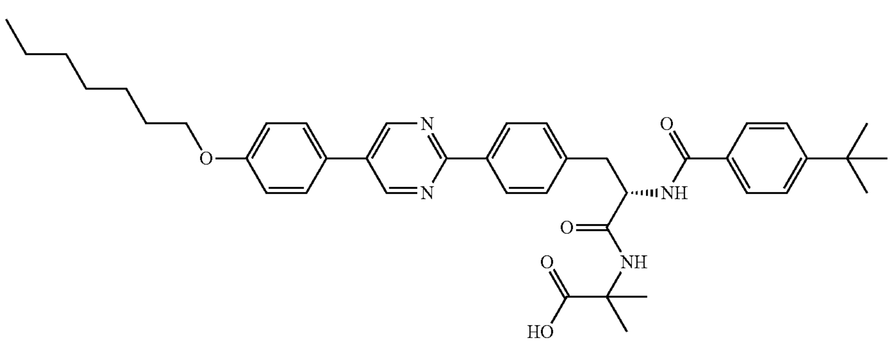 [SMILES: CCCCCCCOc1ccc(-c2cnc(-c3ccc(C[C@H](NC(=O)c4ccc(C(C)(C)C)cc4)C(=O)NC(C)(C)C(=O)O)cc3)nc2)cc1] | 409 | 10.50 | 10 |

TABLE 1-continued
| STRUCTURE | COMPOUND NUMBER | LCMS RETENTION TIME (min) | PURITY METHOD |
|---|---|---|---|
| 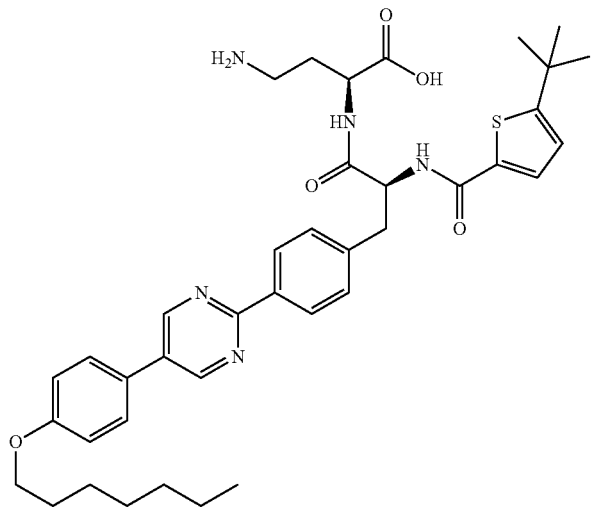 [SMILES: CCCCCCCOc1ccc(-c2cnc(-c3ccc(C[C@H](NC(=O)c4ccc(C(C)(C)C)s4)C(=O)N[C@@H](CCN)C(=O)O)cc3)nc2)cc1] | 410 | 7.66 | 10 |
| 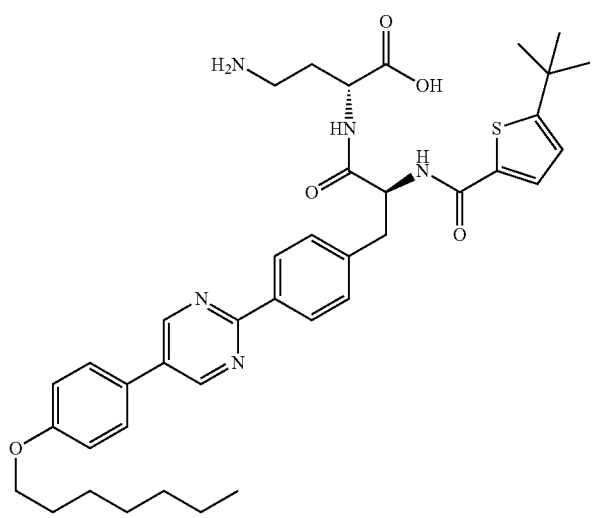 [SMILES: CCCCCCCOc1ccc(-c2cnc(-c3ccc(C[C@H](NC(=O)c4ccc(C(C)(C)C)s4)C(=O)N[C@H](CCN)C(=O)O)cc3)nc2)cc1] | 411 | 9.43 | 12 |

TABLE 1-continued

| STRUCTURE | COMPOUND NUMBER | LCMS RETENTION TIME (min) | PURITY METHOD |
|---|---|---|---|
| 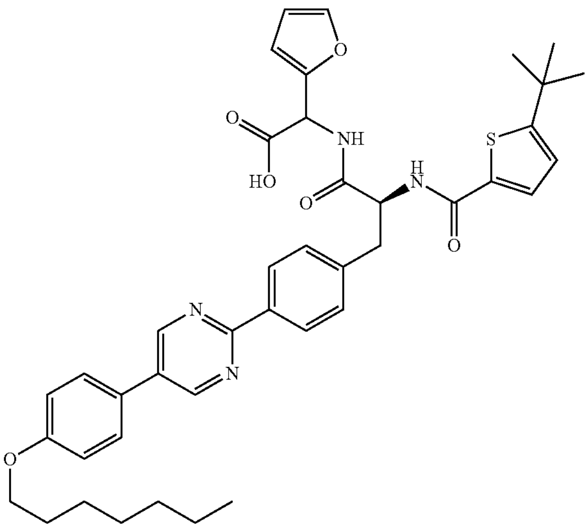 [SMILES: CCCCCCCOc1ccc(-c2cnc(-c3ccc(C[C@H](NC(=O)c4ccc(C(C)(C)C)s4)C(=O)NC(C(=O)O)c4ccco4)cc3)nc2)cc1] | 412 | 8.90 | 12 |
| 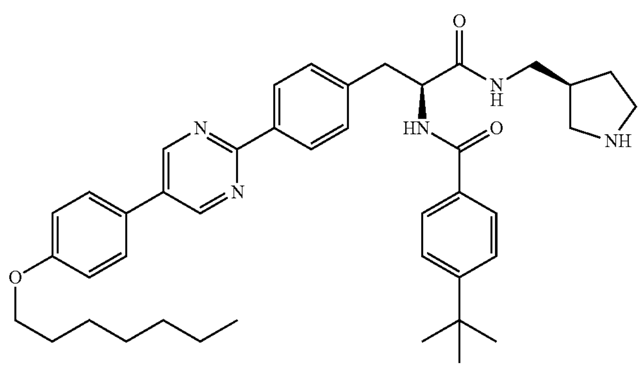 [SMILES: CCCCCCCOc1ccc(-c2cnc(-c3ccc(C[C@H](NC(=O)c4ccc(C(C)(C)C)cc4)C(=O)NC[C@H]4CCNC4)cc3)nc2)cc1] | 413 | 8.95 | 13 |
| 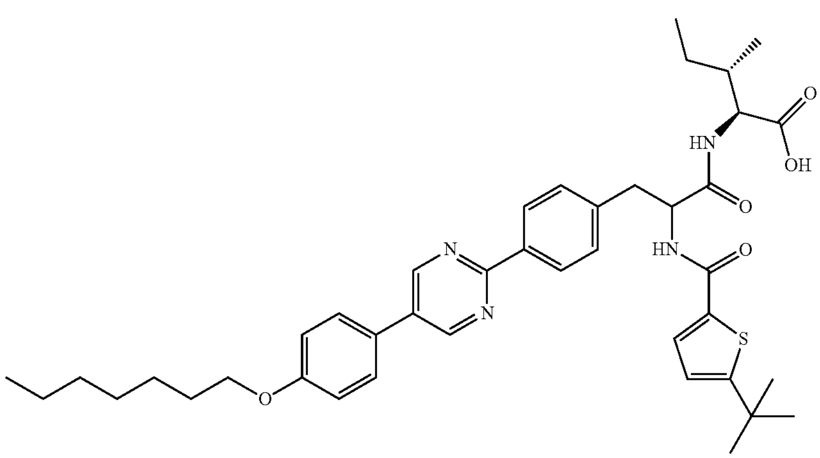 [SMILES: CCCCCCCOc1ccc(-c2cnc(-c3ccc(CC(NC(=O)c4ccc(C(C)(C)C)s4)C(=O)N[C@H](C(=O)O)[C@@H](C)CC)cc3)nc2)cc1] | 414 | 9.14 | 13 |

TABLE 1-continued

| STRUCTURE | COMPOUND NUMBER | LCMS RETENTION TIME (min) | PURITY METHOD |
|---|---|---|---|
| 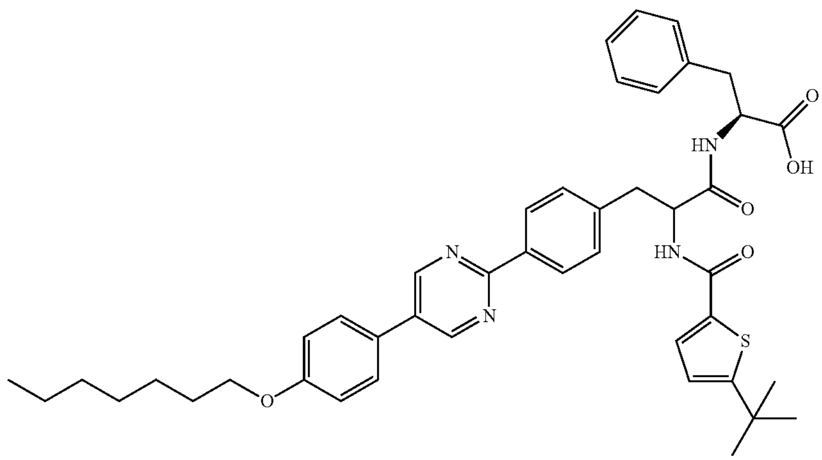 [SMILES: CCCCCCCOc1ccc(-c2cnc(-c3ccc(CC(NC(=O)c4ccc(C(C)(C)C)s4)C(=O)N[C@@H](Cc4ccccc4)C(=O)O)cc3)nc2)cc1] | 415 | 9.12 | 13 |
| 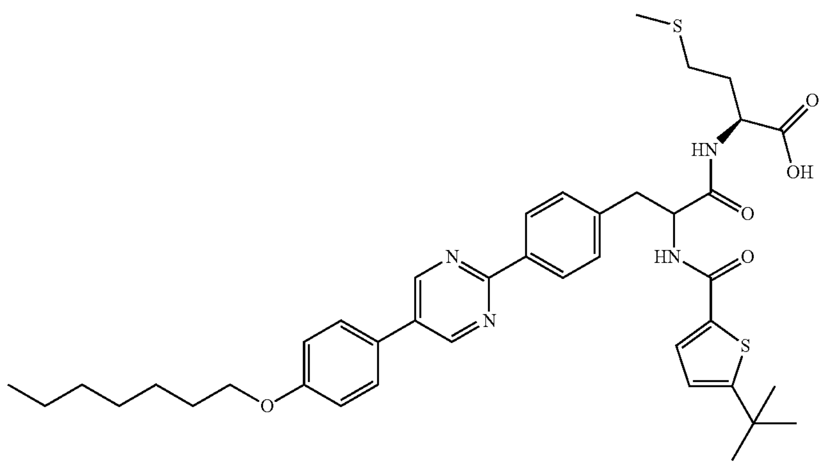 [SMILES: CCCCCCCOc1ccc(-c2cnc(-c3ccc(CC(NC(=O)c4ccc(C(C)(C)C)s4)C(=O)N[C@@H](CCSC)C(=O)O)cc3)nc2)cc1] | 416 | 8.93 | 13 |
| 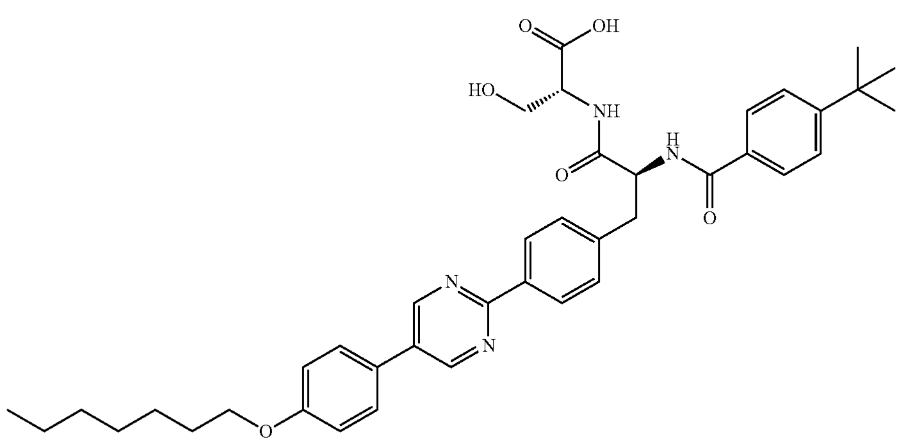 [SMILES: CCCCCCCOc1ccc(-c2cnc(-c3ccc(C[C@H](NC(=O)c4ccc(C(C)(C)C)cc4)C(=O)N[C@H](CO)C(=O)O)cc3)nc2)cc1] | 417 | 9.99 | 10 |

TABLE 1-continued

| STRUCTURE | COMPOUND NUMBER | LCMS RETENTION TIME (min) | PURITY METHOD |
|---|---|---|---|
| 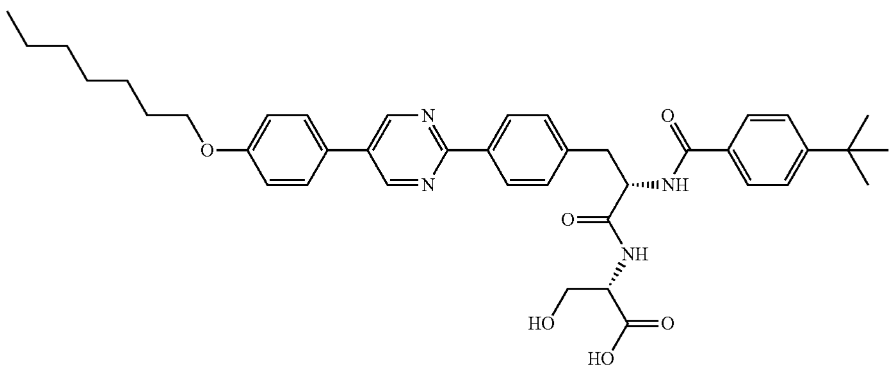 [SMILES: CCCCCCCOc1ccc(-c2cnc(-c3ccc(C[C@H](NC(=O)c4ccc(C(C)(C)C)cc4)C(=O)N[C@@H](CO)C(=O)O)cc3)nc2)cc1] | 418 | 9.80 | 10 |
| 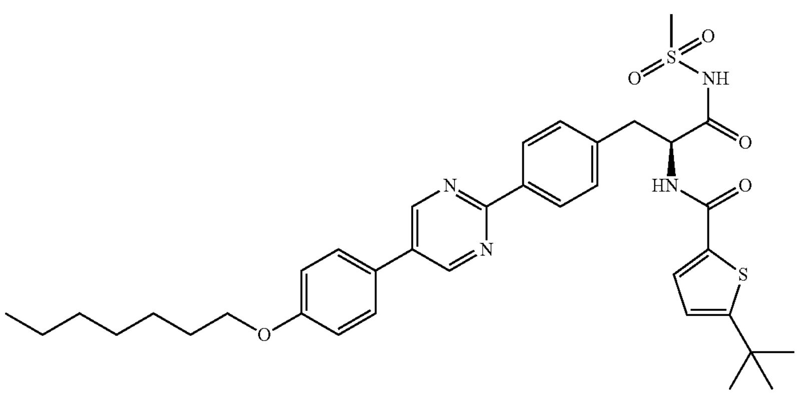 [SMILES: CCCCCCCOc1ccc(-c2cnc(-c3ccc(C[C@H](NC(=O)c4ccc(C(C)(C)C)s4)C(=O)NS(C)(=O)=O)cc3)nc2)cc1] | 419 | 8.77 | 13 |
| 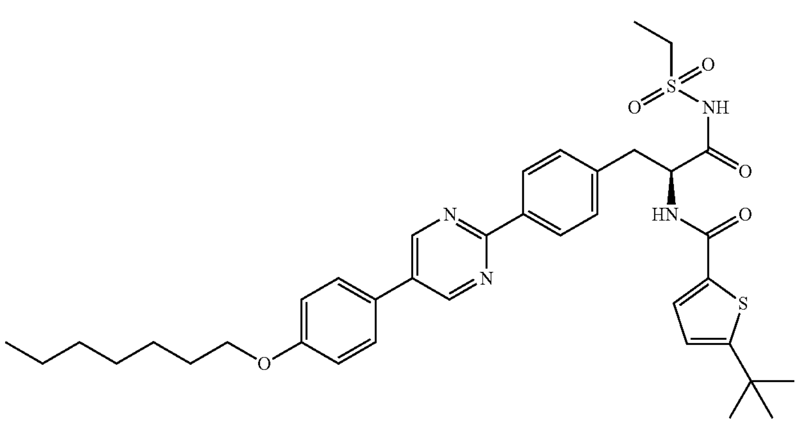 [SMILES: CCCCCCCOc1ccc(-c2cnc(-c3ccc(C[C@H](NC(=O)c4ccc(C(C)(C)C)s4)C(=O)NS(=O)(=O)CC)cc3)nc2)cc1] | 420 | 9.33 | 13 |

TABLE 1-continued

| STRUCTURE | COMPOUND NUMBER | LCMS RETENTION TIME (min) | PURITY METHOD |
|---|---|---|---|
| 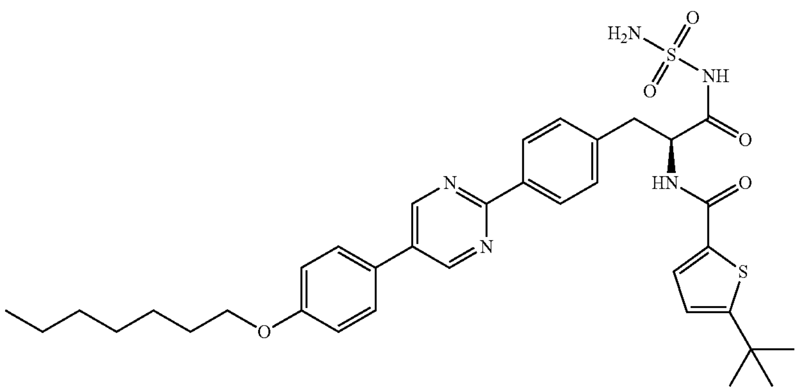 [SMILES: CCCCCCCOc1ccc(-c2cnc(-c3ccc(C[C@H](NC(=O)c4ccc(C(C)(C)C)s4)C(=O)NS(N)(=O)=O)cc3)nc2)cc1] | 421 | 9.28 | 13 |
| 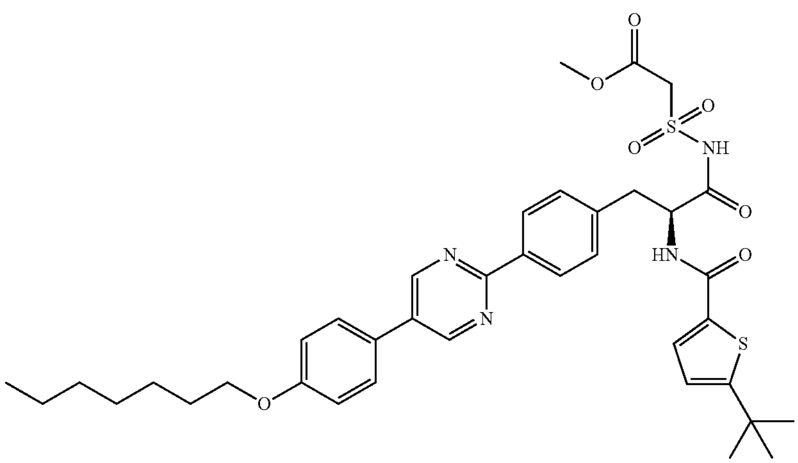 [SMILES: CCCCCCCOc1ccc(-c2cnc(-c3ccc(C[C@H](NC(=O)c4ccc(C(C)(C)C)s4)C(=O)NS(=O)(=O)CC(=O)OC)cc3)nc2)cc1] | 422 | 9.46 | 13 |
| 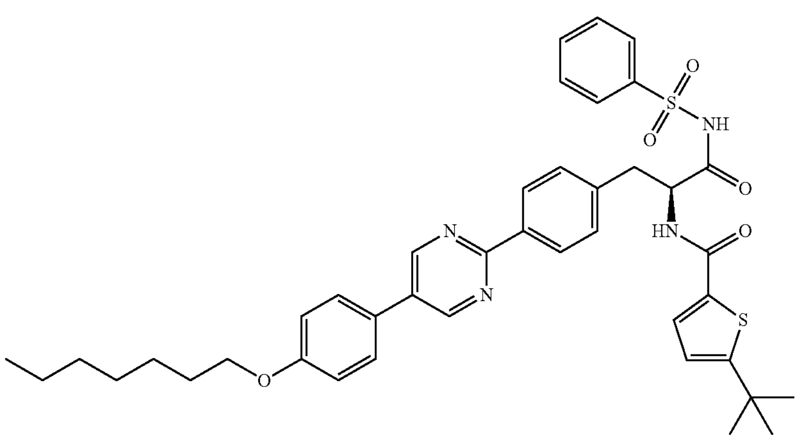 [SMILES: CCCCCCCOc1ccc(-c2cnc(-c3ccc(C[C@H](NC(=O)c4ccc(C(C)(C)C)s4)C(=O)NS(=O)(=O)c4ccccc4)cc3)nc2)cc1] | 423 | 9.72 | 13 |

TABLE 1-continued
| STRUCTURE | COMPOUND NUMBER | LCMS RETENTION TIME (min) | PURITY METHOD |
|---|---|---|---|
| 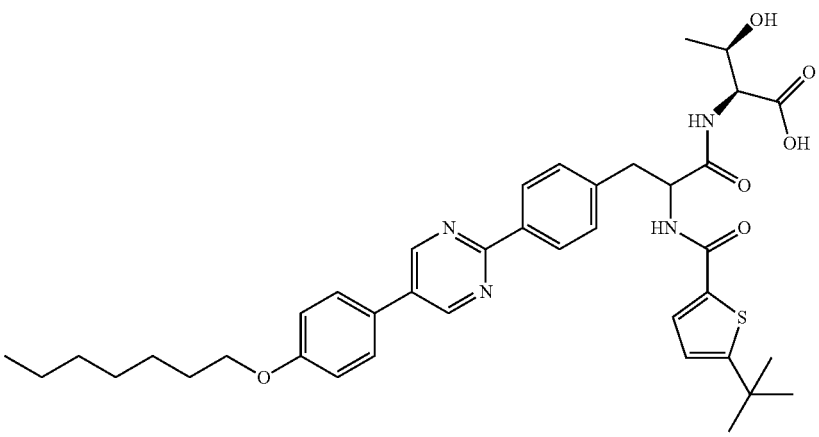 [SMILES: CCCCCCCOc1ccc(-c2cnc(-c3ccc(CC(NC(=O)c4ccc(C(C)(C)C)s4)C(=O)N[C@H](C(=O)O)[C@@H](C)O)cc3)nc2)cc1] | 424 | 8.77 | 13 |
| 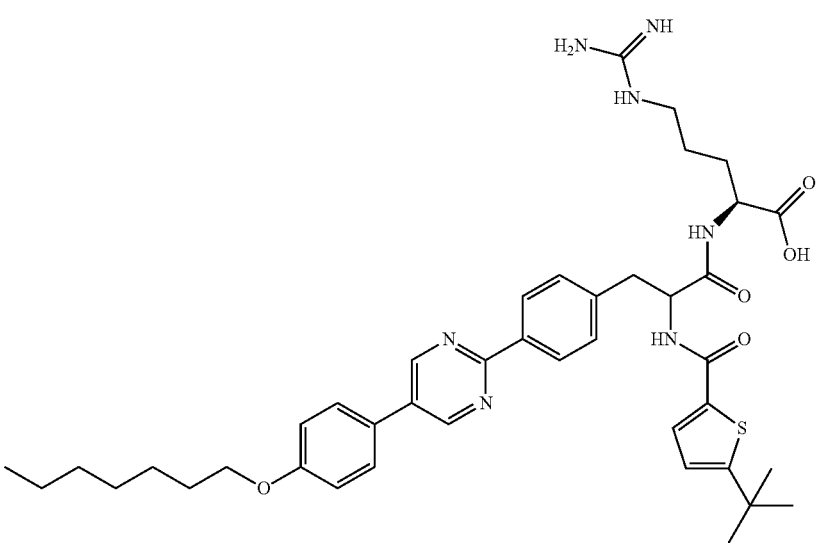 [SMILES: CCCCCCCOc1ccc(-c2cnc(-c3ccc(CC(NC(=O)c4ccc(C(C)(C)C)s4)C(=O)N[C@@H](CCCNC(=N)N)C(=O)O)cc3)nc2)cc1] | 425 | 8.92 | 13 |
| 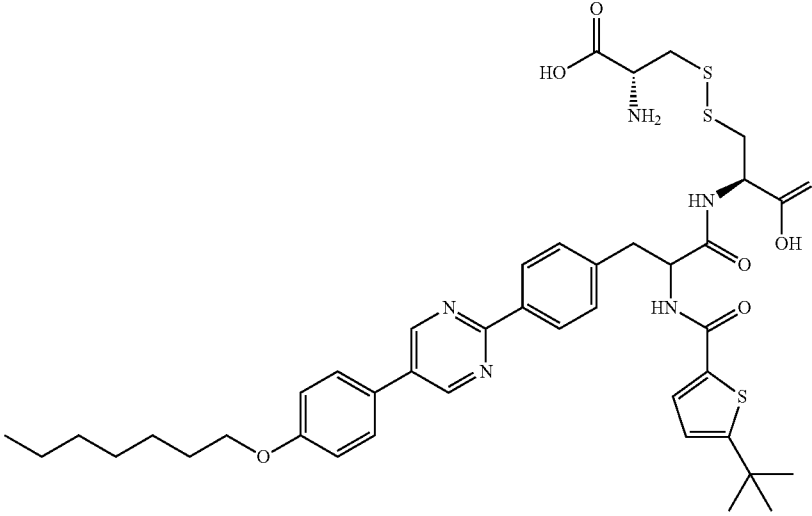 | 426 | 8.39 | 13 |

TABLE 1-continued
| STRUCTURE | COMPOUND NUMBER | LCMS RETENTION TIME (min) | PURITY METHOD |
|---|---|---|---|
| 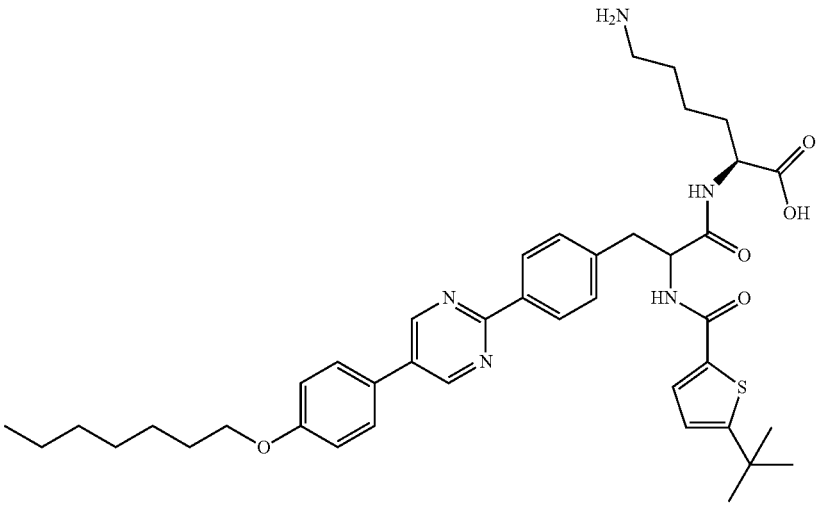 [SMILES: CCCCCCCOc1ccc(-c2cnc(-c3ccc(CC(NC(=O)c4ccc(C(C)(C)C)s4)C(=O)N[C@@H](CCCCN)C(=O)O)cc3)nc2)cc1] | 427 | 8.89 | 13 |
| 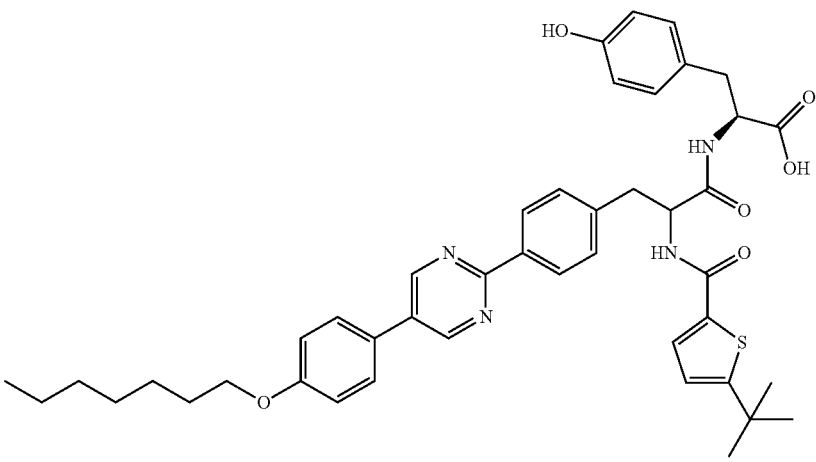 [SMILES: CCCCCCCOc1ccc(-c2cnc(-c3ccc(CC(NC(=O)c4ccc(C(C)(C)C)s4)C(=O)N[C@@H](Cc4ccc(O)cc4)C(=O)O)cc3)nc2)cc1] | 428 | 8.88 | 13 |
| 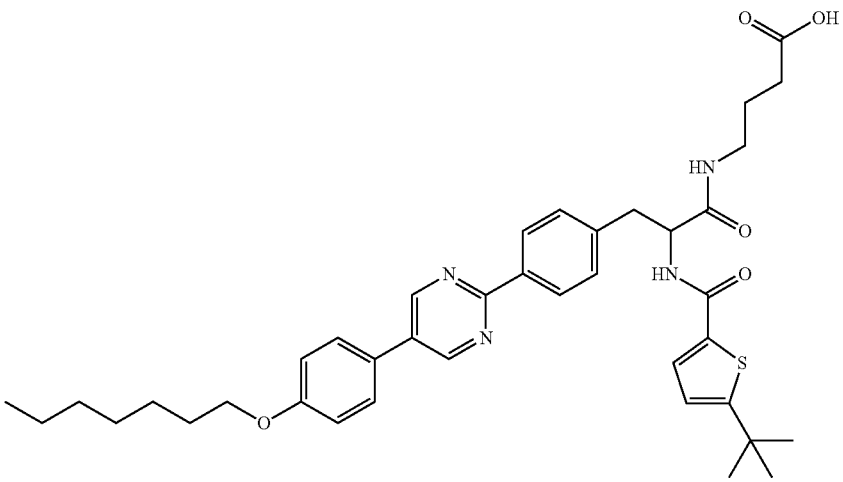 [SMILES: CCCCCCCOc1ccc(-c2cnc(-c3ccc(CC(NC(=O)c4ccc(C(C)(C)C)s4)C(=O)NCCCC(=O)O)cc3)nc2)cc1] | 429 | 9.13 | 13 |

TABLE 1-continued

| STRUCTURE | COMPOUND NUMBER | LCMS RETENTION TIME (min) | PURITY METHOD |
|---|---|---|---|
| 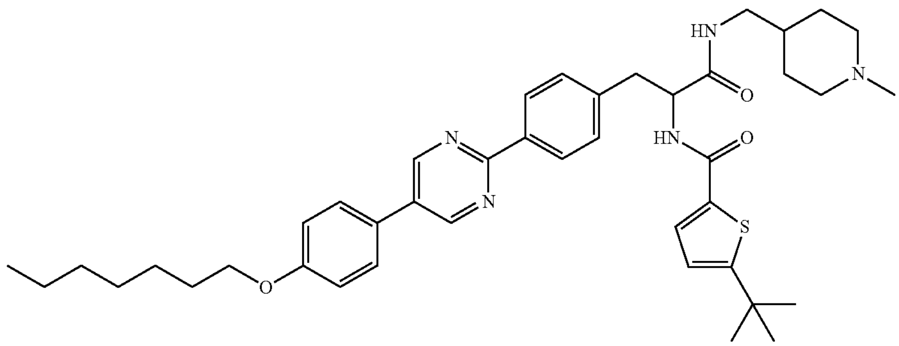 [SMILES: CCCCCCCOc1ccc(-c2cnc(-c3ccc(CC(NC(=O)c4ccc(C(C)(C)C)s4)C(=O)NCC4CCN(C)CC4)cc3)nc2)cc1] | 430 | 8.94 | 13 |
| 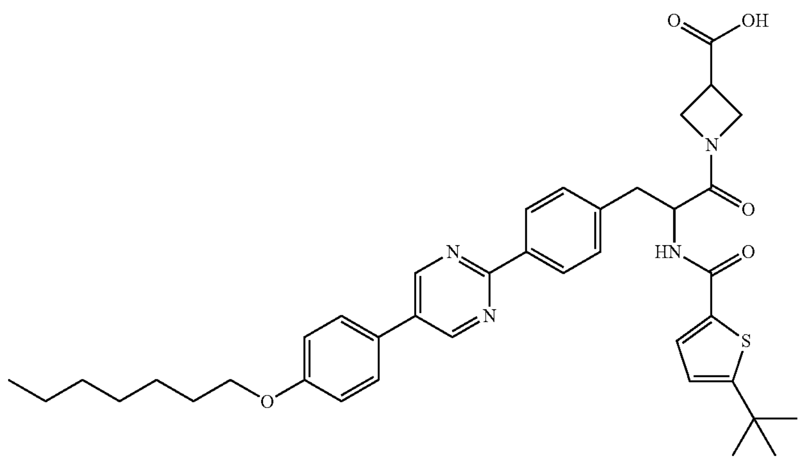 [SMILES: CCCCCCCOc1ccc(-c2cnc(-c3ccc(CC(NC(=O)c4ccc(C(C)(C)C)s4)C(=O)N4CC(C(=O)O)C4)cc3)nc2)cc1] | 431 | 8.82 | 13 |
| 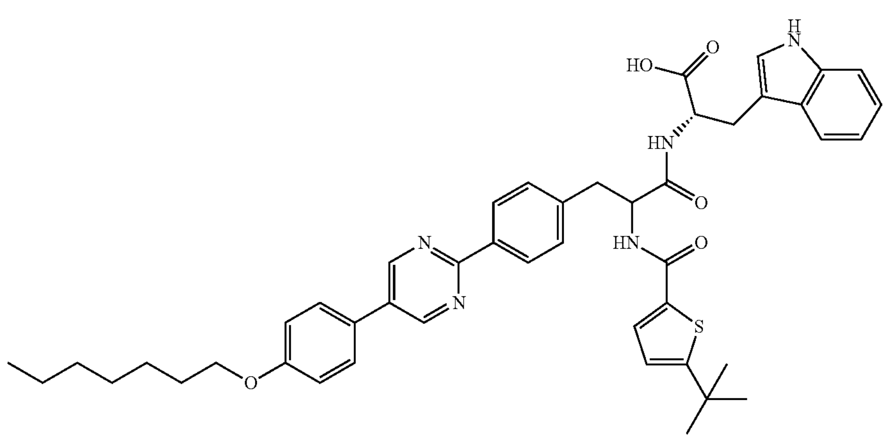 [SMILES: CCCCCCCOc1ccc(-c2cnc(-c3ccc(CC(NC(=O)c4ccc(C(C)(C)C)s4)C(=O)N[C@@H](Cc4c[nH]c5ccccc45)C(=O)O)cc3)nc2)cc1] | 432 | 9.66 | 13 |

TABLE 1-continued
| STRUCTURE | COMPOUND NUMBER | LCMS RETENTION TIME (min) | PURITY METHOD |
|---|---|---|---|
| 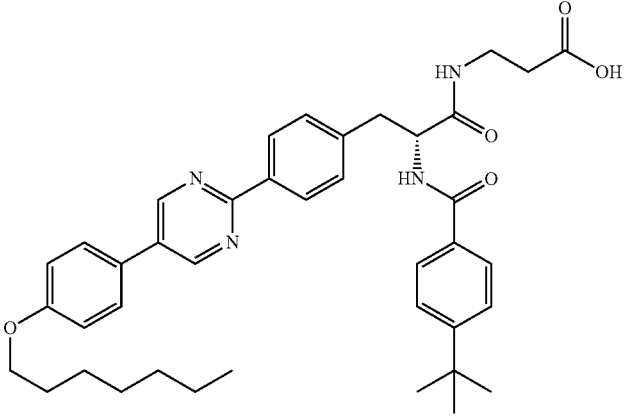 [SMILES: CCCCCCCOc1ccc(-c2cnc(-c3ccc(C[C@@H](NC(=O)c4ccc(C(C)(C)C)cc4)C(=O)NCCC(=O)O)cc3)nc2)cc1] | 433 | 10.22 | 10 |
| 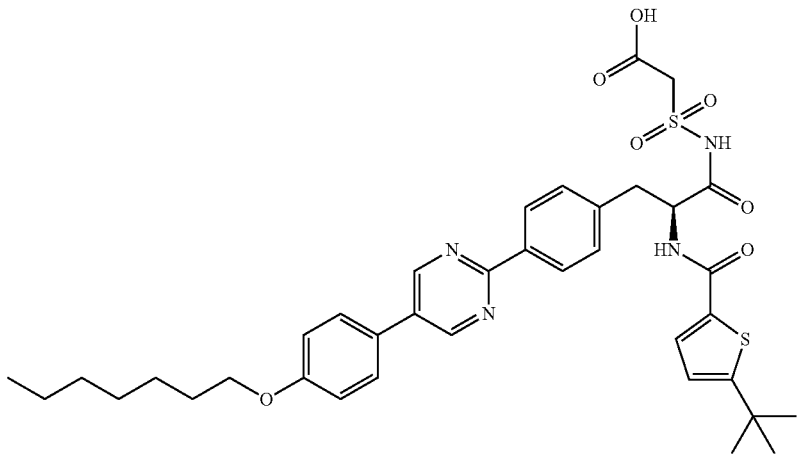 [SMILES: CCCCCCCOc1ccc(-c2cnc(-c3ccc(C[C@H](NC(=O)c4ccc(C(C)(C)C)s4)C(=O)NS(=O)(=O)CC(=O)O)cc3)nc2)cc1] | 434 | 8.09 | 13 |
| 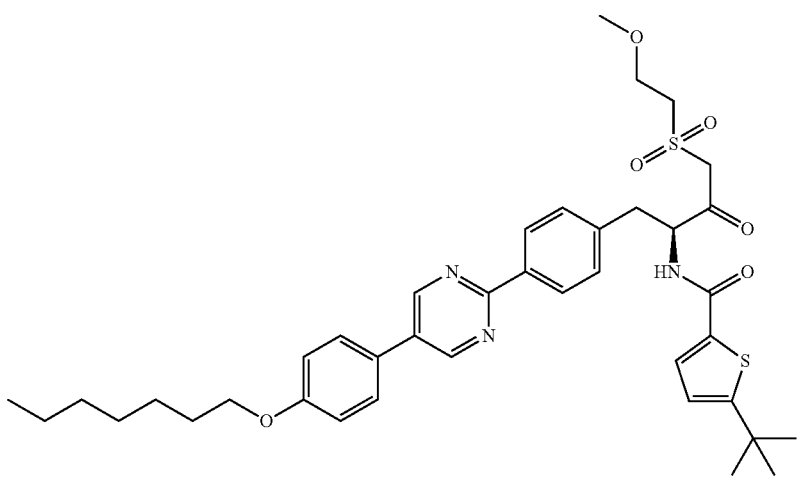 [SMILES: CCCCCCCOc1ccc(-c2cnc(-c3ccc(C[C@H](NC(=O)c4ccc(C(C)(C)C)s4)C(=O)CS(=O)(=O)CCOC)cc3)nc2)cc1] | 435 | 9.44 | 13 |

TABLE 1-continued

| STRUCTURE | COMPOUND NUMBER | LCMS RETENTION TIME (min) | PURITY METHOD |
|---|---|---|---|
| (structure) | 436 | 10.40 | 10 |
| (structure) | 437 | 10.36 | 10 |
| (structure) | 438 | 9.46 | 13 |

| STRUCTURE | COMPOUND NUMBER | LCMS RETENTION TIME (min) | PURITY METHOD |
|---|---|---|---|
| 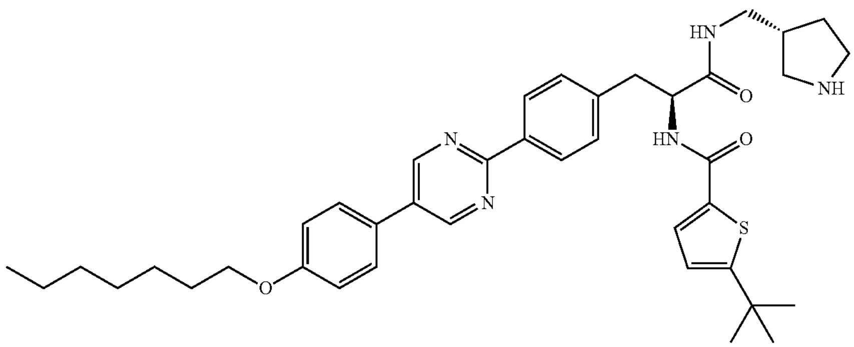 [SMILES: CCCCCCCOc1ccc(-c2cnc(-c3ccc(C[C@H](NC(=O)c4ccc(C(C)(C)C)s4)C(=O)NC[C@@H]4CCNC4)cc3)nc2)cc1] | 439 | 9.47 | 13 |
| 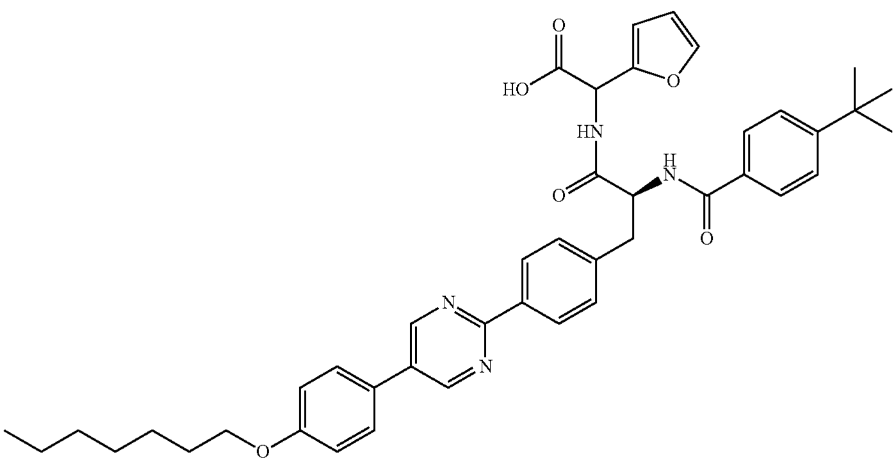 [SMILES: CCCCCCCOc1ccc(-c2cnc(-c3ccc(C[C@H](NC(=O)c4ccc(C(C)(C)C)cc4)C(=O)NC(C(=O)O)c4ccco4)cc3)nc2)cc1] | 440 | 8.98 | 12 |
| 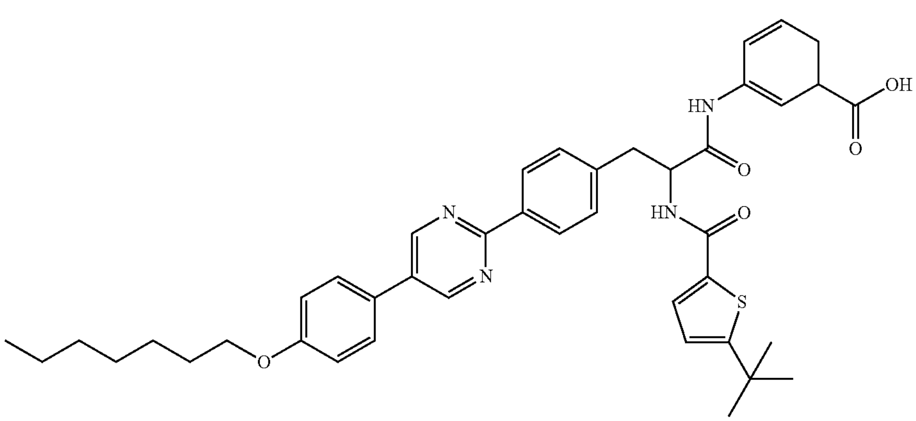 [SMILES: CCCCCCCOc1ccc(-c2cnc(-c3ccc(CC(NC(=O)c4ccc(C(C)(C)C)s4)C(=O)NC4=CC(C(=O)O)CC=C4)cc3)nc2)cc1] | 441 | 9.58 | 13 |

TABLE 1-continued

| STRUCTURE | COMPOUND NUMBER | LCMS RETENTION TIME (min) | PURITY METHOD |
|---|---|---|---|
| 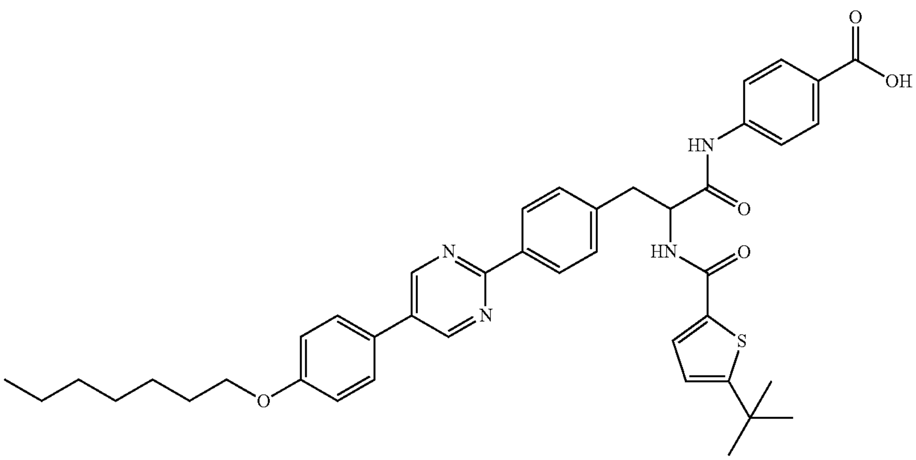 [SMILES: CCCCCCCOc1ccc(-c2cnc(-c3ccc(CC(NC(=O)c4ccc(C(C)(C)C)s4)C(=O)Nc4ccc(C(=O)O)cc4)cc3)nc2)cc1] | 442 | 9.72 | 13 |
| 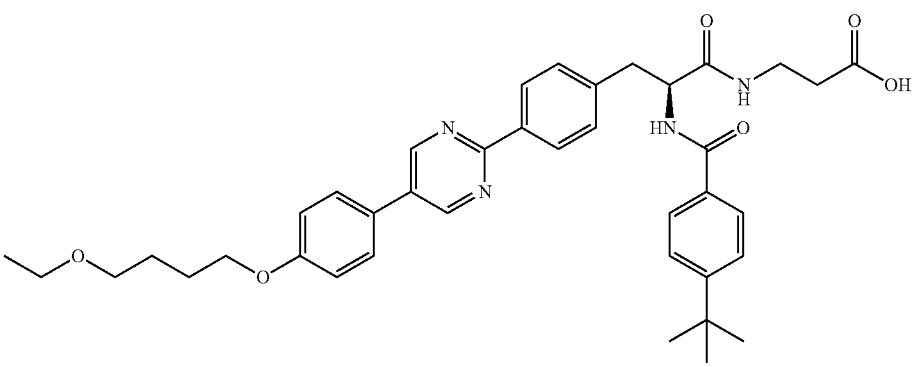 [SMILES: CCOCCCCOc1ccc(-c2cnc(-c3ccc(C[C@H](NC(=O)c4ccc(C(C)(C)C)cc4)C(=O)NCCC(=O)O)cc3)nc2)cc1] | 443 | 8.23 | 14 |
| 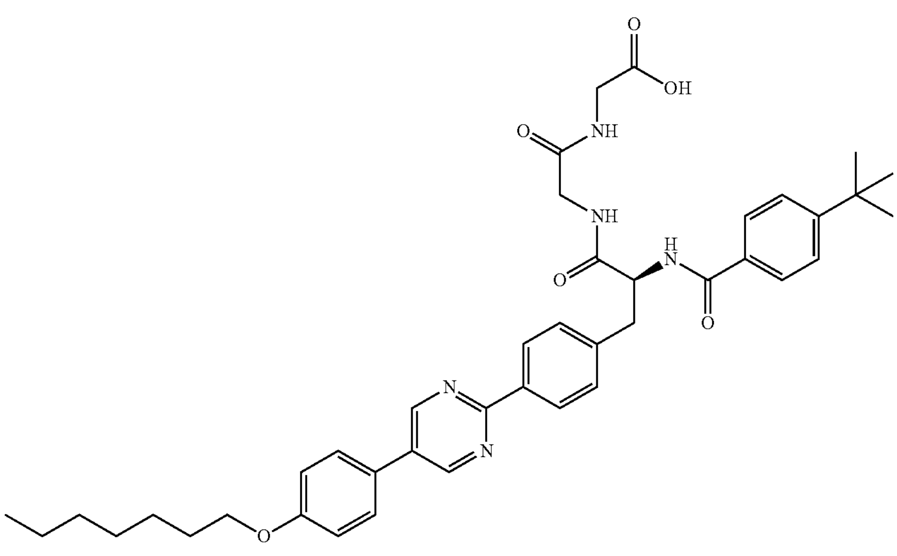 [SMILES: CCCCCCCOc1ccc(-c2cnc(-c3ccc(C[C@H](NC(=O)c4ccc(C(C)(C)C)cc4)C(=O)NCC(=O)NCC(=O)O)cc3)nc2)cc1] | 444 | 9.97 | 14 |

TABLE 1-continued
| STRUCTURE | COMPOUND NUMBER | LCMS RETENTION TIME (min) | PURITY METHOD |
|---|---|---|---|
| 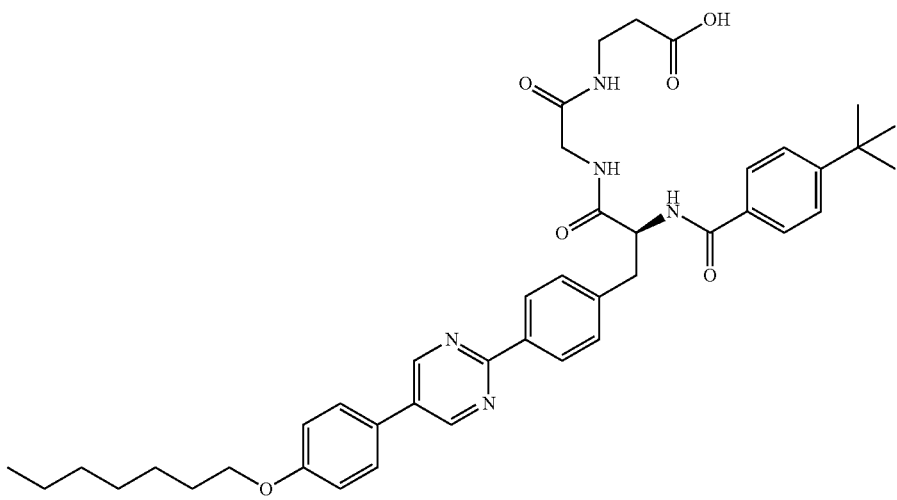 [SMILES: CCCCCCCOc1ccc(-c2cnc(-c3ccc(C[C@H](NC(=O)c4ccc(C(C)(C)C)cc4)C(=O)NCC(=O)NCCC(=O)O)cc3)nc2)cc1] | 445 | 10.21 | 14 |
| 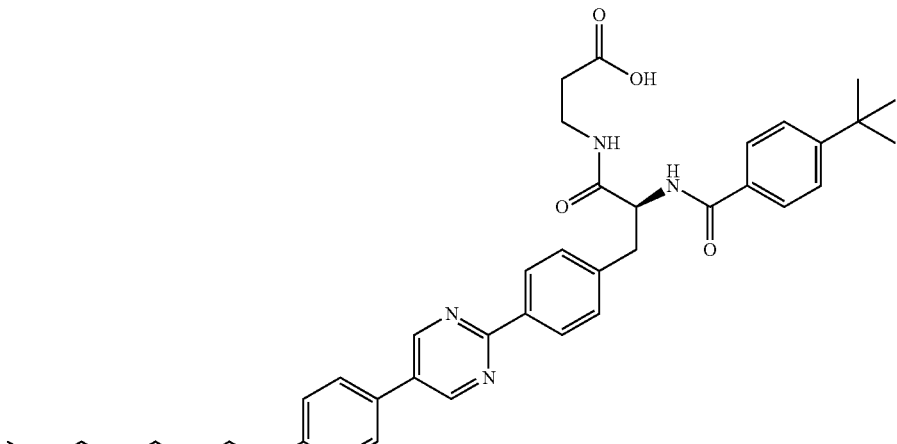 | 446 | 10.23 | 14 |
| 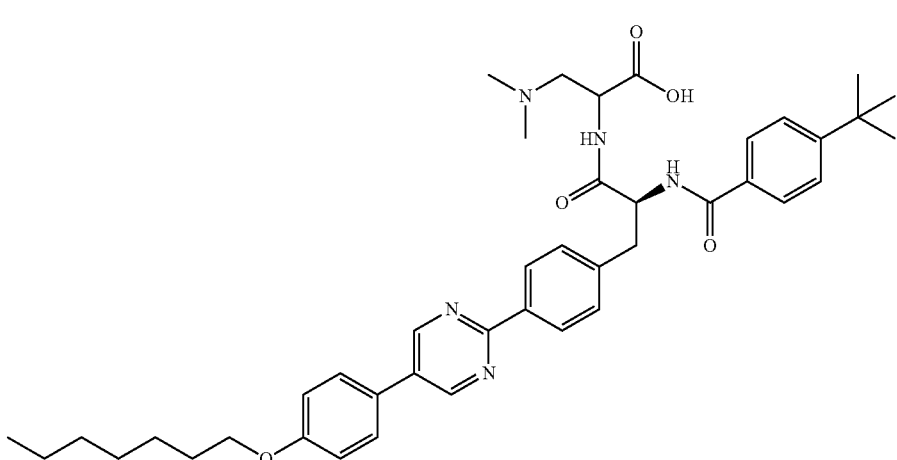 | 447 | 10.40 | 12 |

TABLE 1-continued

| STRUCTURE | COMPOUND NUMBER | LCMS RETENTION TIME (min) | PURITY METHOD |
|---|---|---|---|
| 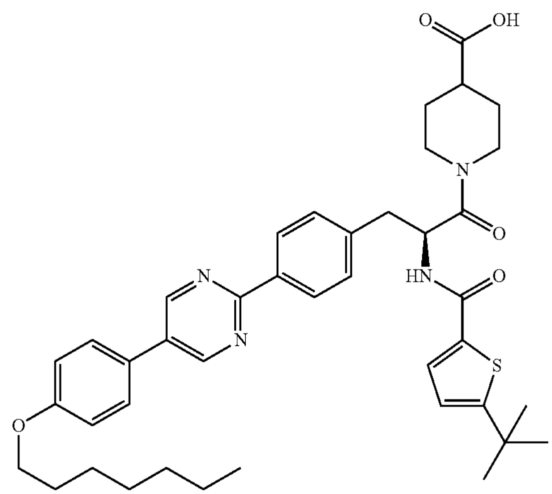 [SMILES: CCCCCCCOc1ccc(-c2cnc(-c3ccc(C[C@H](NC(=O)c4ccc(C(C)(C)C)s4)C(=O)N4CCC(C(=O)O)CC4)cc3)nc2)cc1] | 448 | 11.29 | 14 |
| 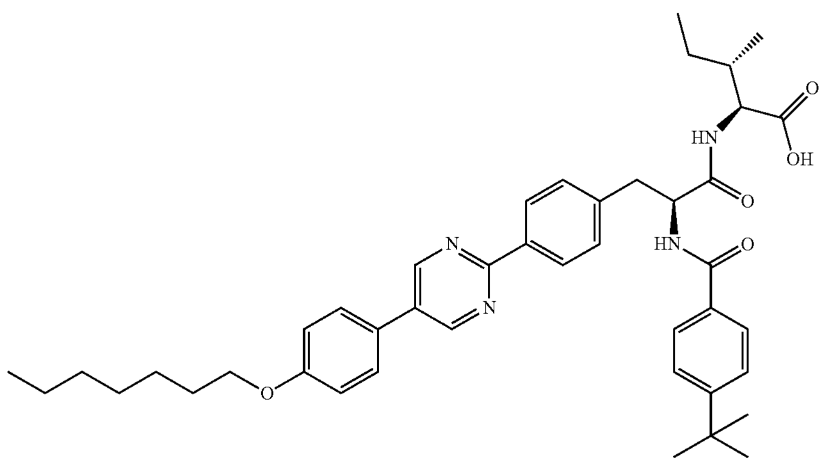 [SMILES: CCCCCCCOc1ccc(-c2cnc(-c3ccc(C[C@H](NC(=O)c4ccc(C(C)(C)C)cc4)C(=O)N[C@H](C(=O)O)[C@@H](C)CC)cc3)nc2)cc1] | 449 | 11.08 | 14 |
| 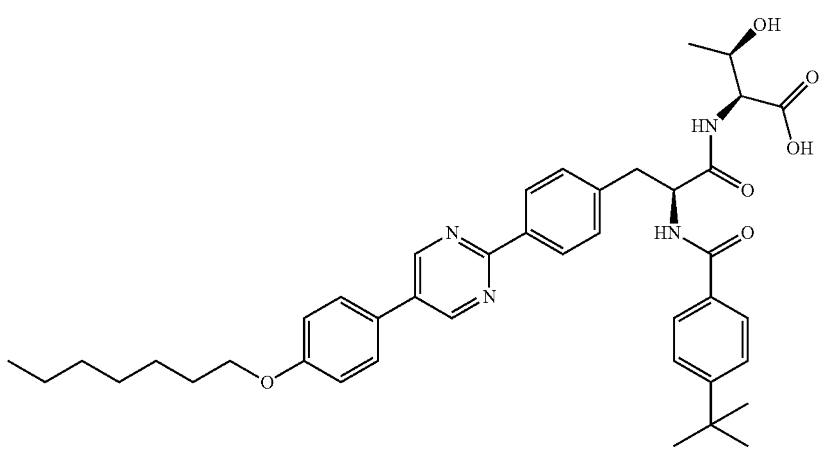 [SMILES: CCCCCCCOc1ccc(-c2cnc(-c3ccc(C[C@H](NC(=O)c4ccc(C(C)(C)C)cc4)C(=O)N[C@H](C(=O)O)[C@@H](C)O)cc3)nc2)cc1] | 450 | 10.25 | 14 |

TABLE 1-continued
| STRUCTURE | COMPOUND NUMBER | LCMS RETENTION TIME (min) | PURITY METHOD |
|---|---|---|---|
| 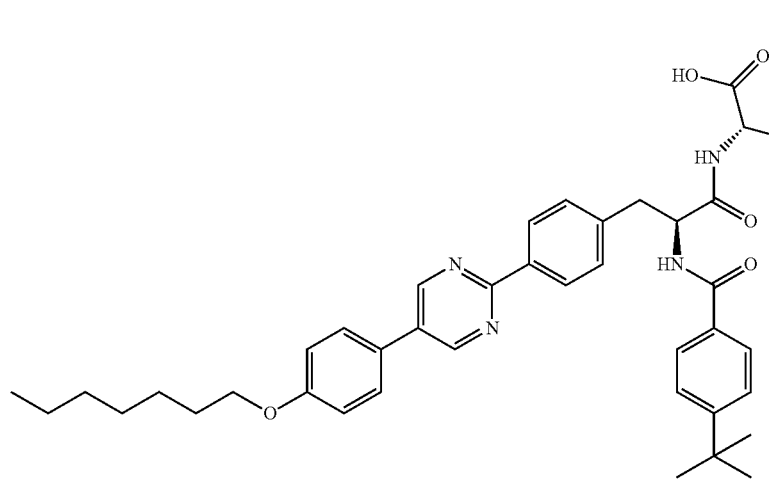 | 451 | 10.45 | 14 |
| 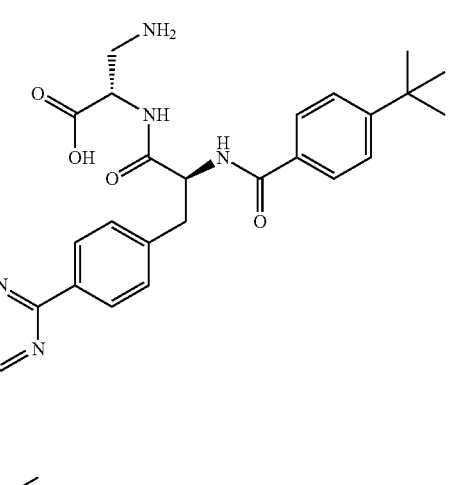 | 452 | 8.21 | 10 |

TABLE 1-continued

| STRUCTURE | COMPOUND NUMBER | LCMS RETENTION TIME (min) | PURITY METHOD |
|---|---|---|---|
| 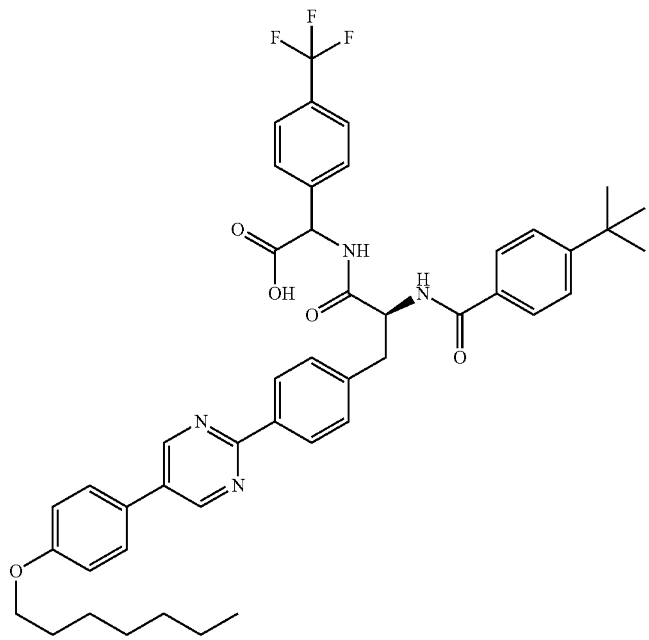 [SMILES: CCCCCCCOc1ccc(-c2cnc(-c3ccc(C[C@H](NC(=O)c4ccc(C(C)(C)C)cc4)C(=O)NC(C(=O)O)c4ccc(C(F)(F)F)cc4)cc3)nc2)cc1] | 453 | 11.44 | 10 |
| 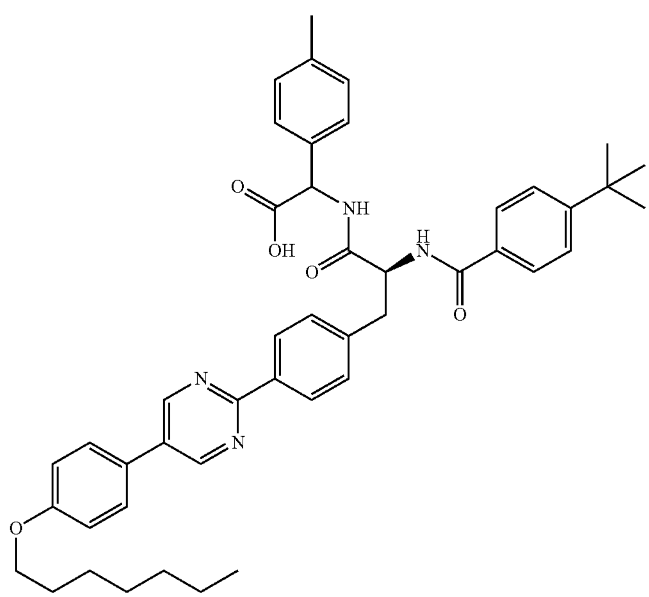 [SMILES: CCCCCCCOc1ccc(-c2cnc(-c3ccc(C[C@H](NC(=O)c4ccc(C(C)(C)C)cc4)C(=O)NC(C(=O)O)c4ccc(C)cc4)cc3)nc2)cc1] | 454 | 11.13 | 10 |

TABLE 1-continued

| STRUCTURE | COMPOUND NUMBER | LCMS RETENTION TIME (min) | PURITY METHOD |
|---|---|---|---|
| 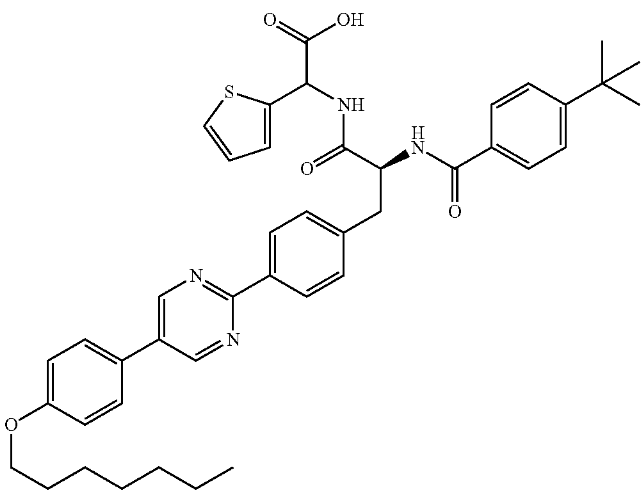 [SMILES: CCCCCCCOc1ccc(-c2cnc(-c3ccc(C[C@H](NC(=O)c4ccc(C(C)(C)C)cc4)C(=O)NC(C(=O)O)c4cccs4)cc3)nc2)cc1] | 455 | 10.97 | 10 |
| 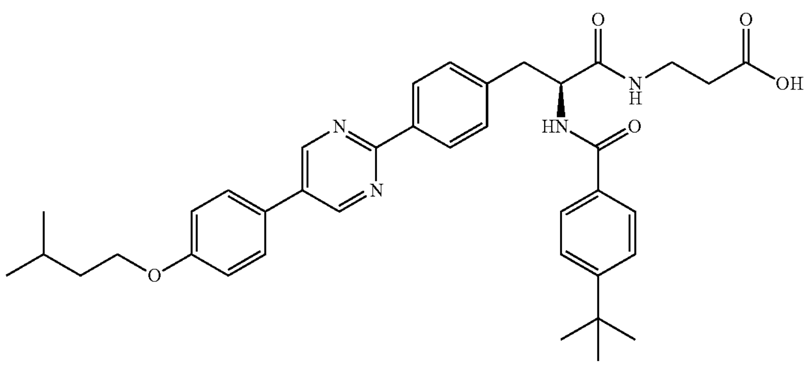 [SMILES: CC(C)CCOc1ccc(-c2cnc(-c3ccc(C[C@H](NC(=O)c4ccc(C(C)(C)C)cc4)C(=O)NCCC(=O)O)cc3)nc2)cc1] | 456 | 9.29 | 14 |
| 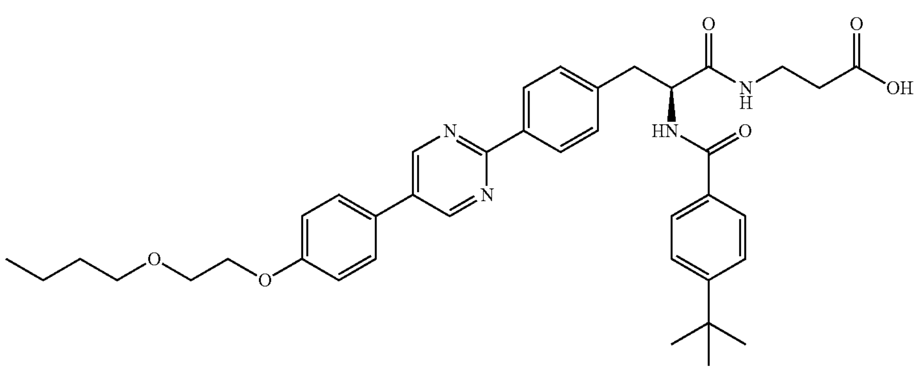 [SMILES: CCCCOCCOc1ccc(-c2cnc(-c3ccc(C[C@H](NC(=O)c4ccc(C(C)(C)C)cc4)C(=O)NCCC(=O)O)cc3)nc2)cc1] | 457 | 8.50 | 14 |

TABLE 1-continued

| STRUCTURE | COMPOUND NUMBER | LCMS RETENTION TIME (min) | PURITY METHOD |
|---|---|---|---|
| 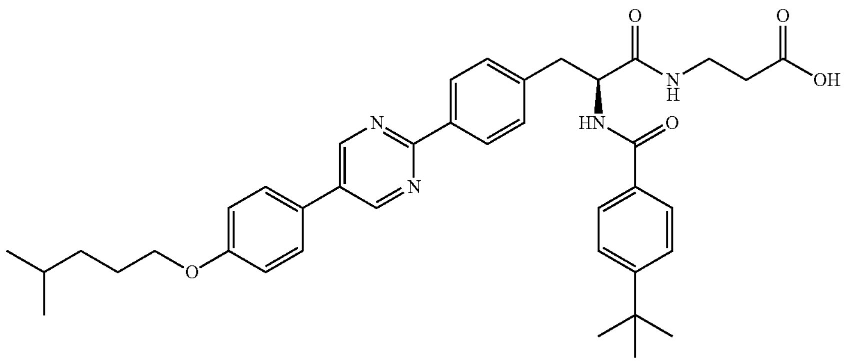 [SMILES: CC(C)CCCOc1ccc(-c2cnc(-c3ccc(C[C@H](NC(=O)c4ccc(C(C)(C)C)cc4)C(=O)NCCC(=O)O)cc3)nc2)cc1] | 458 | 9.85 | 14 |
| 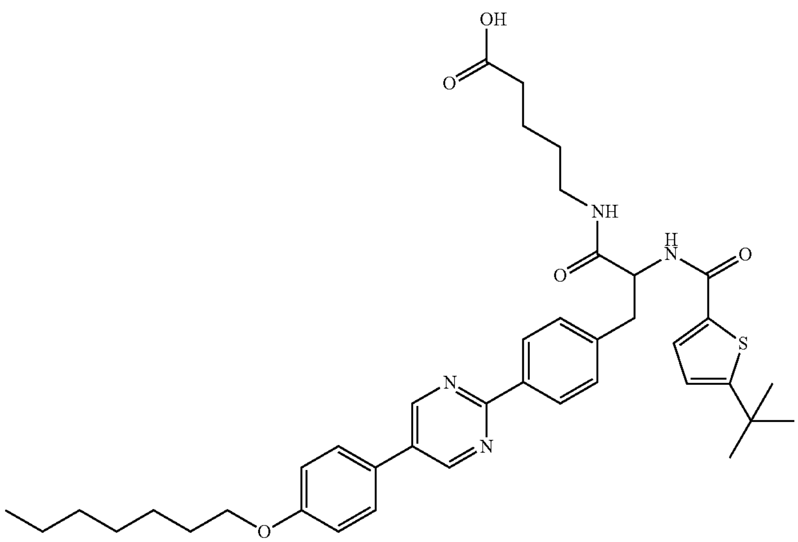 [SMILES: CCCCCCCOc1ccc(-c2cnc(-c3ccc(CC(NC(=O)c4ccc(C(C)(C)C)s4)C(=O)NCCCCC(=O)O)cc3)nc2)cc1] | 459 | 11.07 | 14 |
| 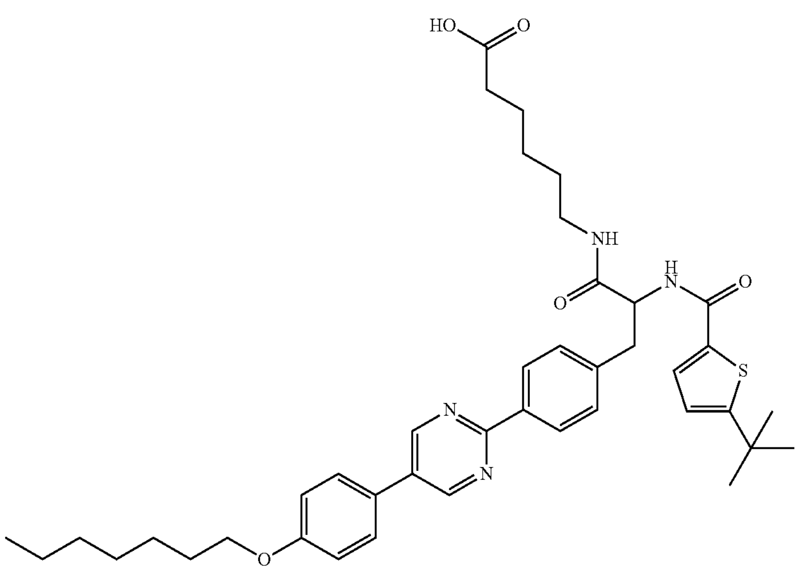 [SMILES: CCCCCCCOc1ccc(-c2cnc(-c3ccc(CC(NC(=O)c4ccc(C(C)(C)C)s4)C(=O)NCCCCCC(=O)O)cc3)nc2)cc1] | 460 | 11.42 | 14 |

TABLE 1-continued

| STRUCTURE | COMPOUND NUMBER | LCMS RETENTION TIME (min) | PURITY METHOD |
|---|---|---|---|
| (structure) | 461 | 10.68 | 14 |
| (structure) | 462 | 11.49 | 14 |
| (structure) | 463 | 10.52 | 14 |

TABLE 1-continued

| STRUCTURE | COMPOUND NUMBER | LCMS RETENTION TIME (min) | PURITY METHOD |
|---|---|---|---|
| 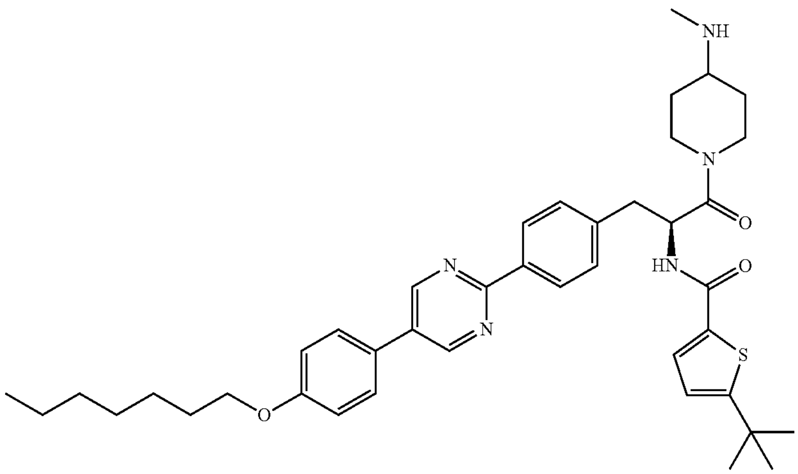 [SMILES: CCCCCCCOc1ccc(-c2cnc(-c3ccc(C[C@H](NC(=O)c4ccc(C(C)(C)C)s4)C(=O)N4CCC(NC)CC4)cc3)nc2)cc1] | 464 | 10.81 | 14 |
| 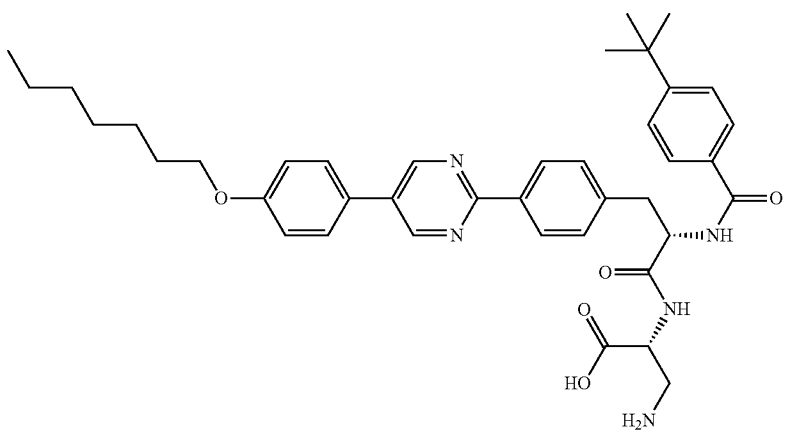 [SMILES: CCCCCCCOc1ccc(-c2cnc(-c3ccc(C[C@H](NC(=O)c4ccc(C(C)(C)C)cc4)C(=O)N[C@H](CN)C(=O)O)cc3)nc2)cc1] | 465 | 8.26 | 10 |
| 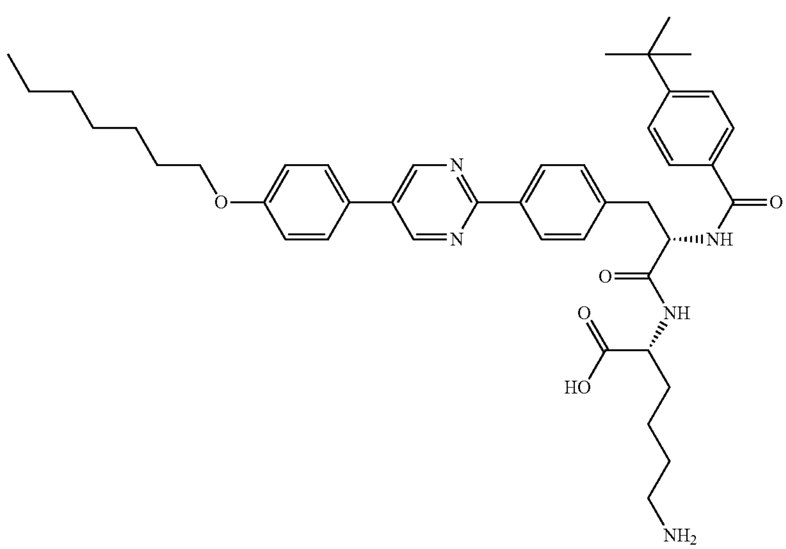 [SMILES: CCCCCCCOc1ccc(-c2cnc(-c3ccc(C[C@H](NC(=O)c4ccc(C(C)(C)C)cc4)C(=O)N[C@H](CCCCN)C(=O)O)cc3)nc2)cc1] | 466 | 7.58 | 10 |

TABLE 1-continued

| STRUCTURE | COMPOUND NUMBER | LCMS RETENTION TIME (min) | PURITY METHOD |
|---|---|---|---|
| 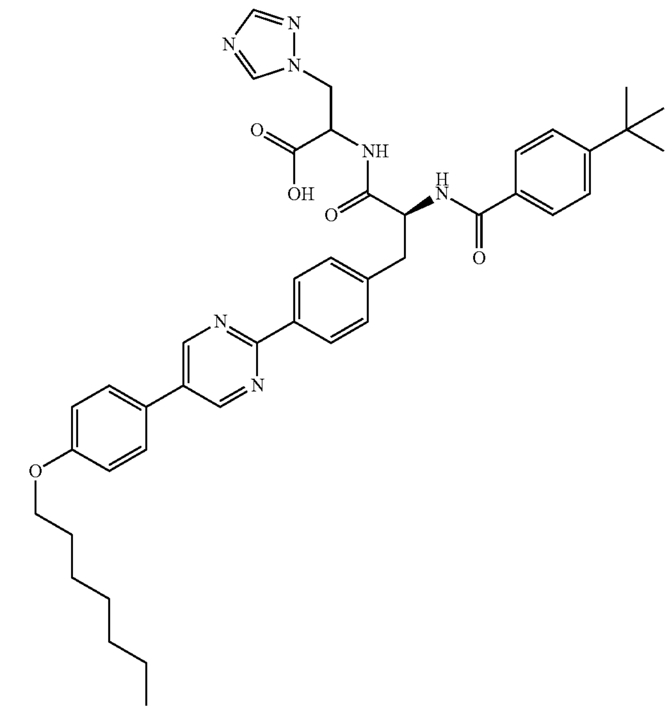 [SMILES: CCCCCCCOc1ccc(-c2cnc(-c3ccc(C[C@H](NC(=O)c4ccc(C(C)(C)C)cc4)C(=O)NC(Cn4cncn4)C(=O)O)cc3)nc2)cc1] | 467 | 9.75 | 10 |
| 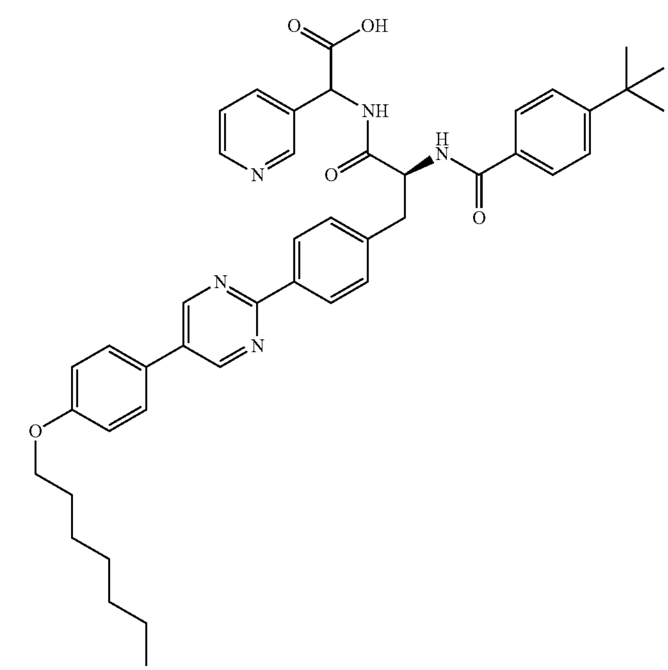 [SMILES: CCCCCCCOc1ccc(-c2cnc(-c3ccc(C[C@H](NC(=O)c4ccc(C(C)(C)C)cc4)C(=O)NC(C(=O)O)c4cccnc4)cc3)nc2)cc1] | 468 | 9.34 | 10 |

TABLE 1-continued

| STRUCTURE | COMPOUND NUMBER | LCMS RETENTION TIME (min) | PURITY METHOD |
|---|---|---|---|
| 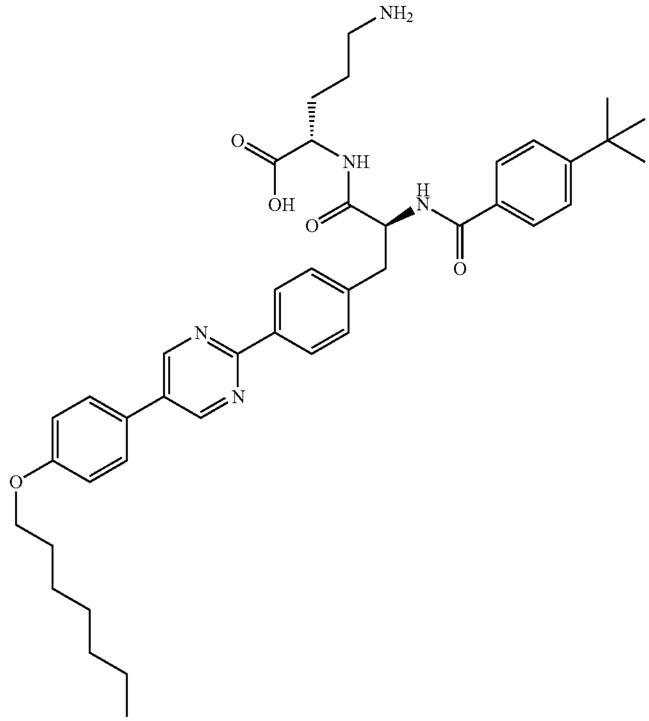 [SMILES: CCCCCCCOc1ccc(-c2cnc(-c3ccc(C[C@H](NC(=O)c4ccc(C(C)(C)C)cc4)C(=O)N[C@@H](CCCN)C(=O)O)cc3)nc2)cc1] | 469 | 7.59 | 10 |
| 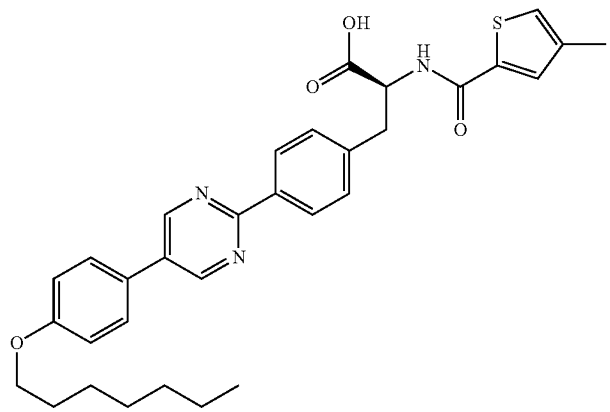 [SMILES: CCCCCCCOc1ccc(-c2cnc(-c3ccc(C[C@H](NC(=O)c4cc(C)cs4)C(=O)O)cc3)nc2)cc1] | 470 | 8.94 | 14 |
| 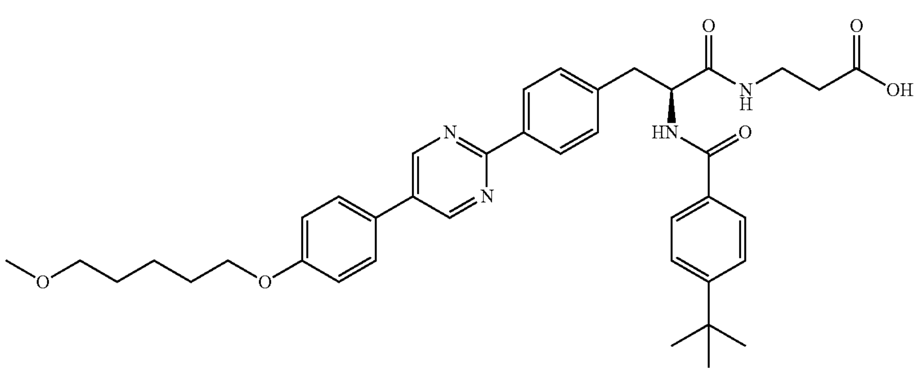 [SMILES: COCCCCCOc1ccc(-c2cnc(-c3ccc(C[C@H](NC(=O)c4ccc(C(C)(C)C)cc4)C(=O)NCCC(=O)O)cc3)nc2)cc1] | 471 | 8.21 | 14 |

TABLE 1-continued

| STRUCTURE | COMPOUND NUMBER | LCMS RETENTION TIME (min) | PURITY METHOD |
|---|---|---|---|
| 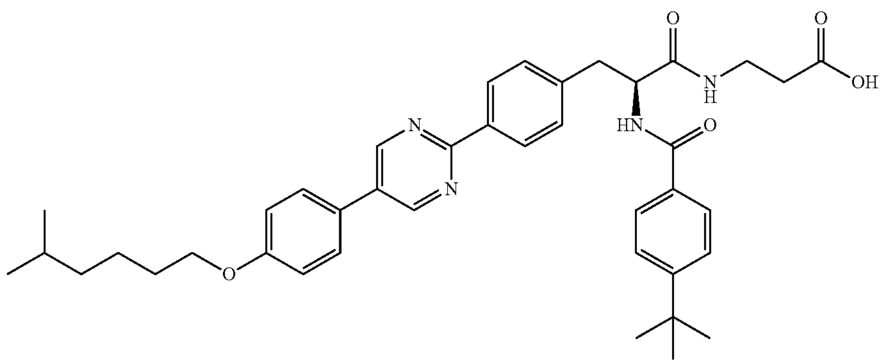 [SMILES: CC(C)CCCCOc1ccc(-c2cnc(-c3ccc(C[C@H](NC(=O)c4ccc(C(C)(C)C)cc4)C(=O)NCCC(=O)O)cc3)nc2)cc1] | 472 | 10.33 | 14 |
| 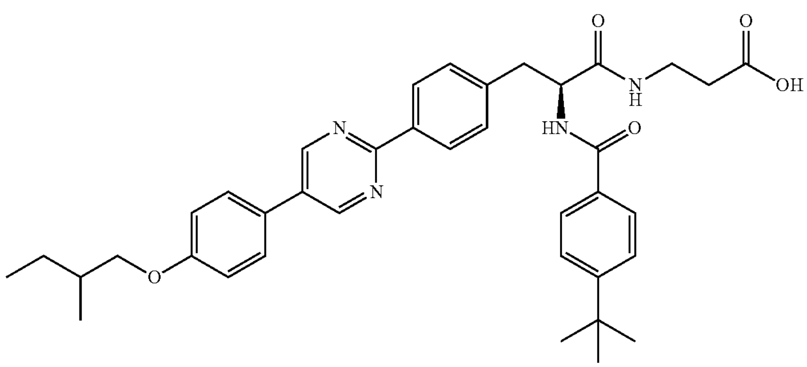 [SMILES: CCC(C)COc1ccc(-c2cnc(-c3ccc(C[C@H](NC(=O)c4ccc(C(C)(C)C)cc4)C(=O)NCCC(=O)O)cc3)nc2)cc1] | 473 | 9.43 | 14 |
| 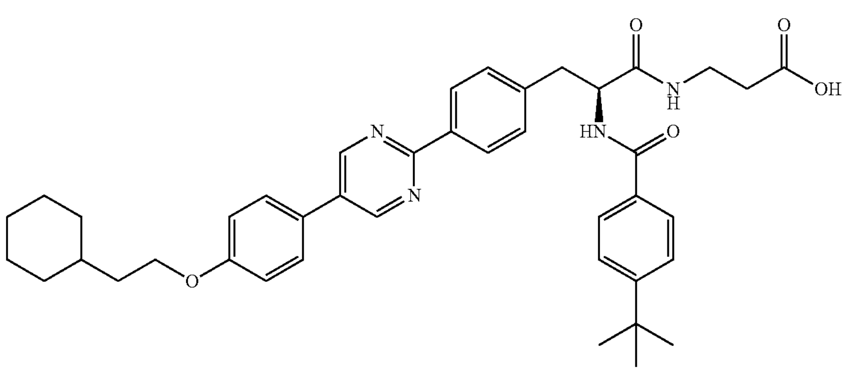 [SMILES: CC(C)(C)c1ccc(C(=O)N[C@@H](Cc2ccc(-c3ncc(-c4ccc(OCCC5CCCCC5)cc4)cn3)cc2)C(=O)NCCC(=O)O)cc1] | 474 | 10.61 | 14 |

TABLE 1-continued

| STRUCTURE | COMPOUND NUMBER | LCMS RETENTION TIME (min) | PURITY METHOD |
|---|---|---|---|
| 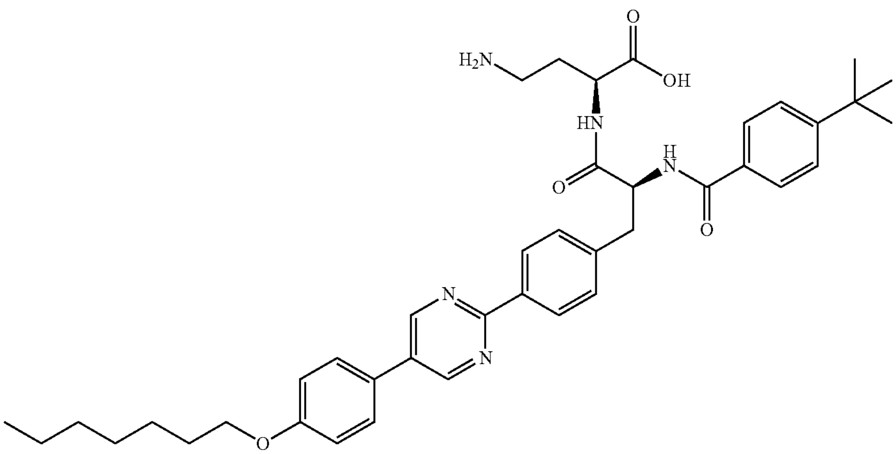 [SMILES: CCCCCCCOc1ccc(-c2cnc(-c3ccc(C[C@H](NC(=O)c4ccc(C(C)(C)C)cc4)C(=O)N[C@@H](CCN)C(=O)O)cc3)nc2)cc1] | 475 | 10.27 | 14 |
| 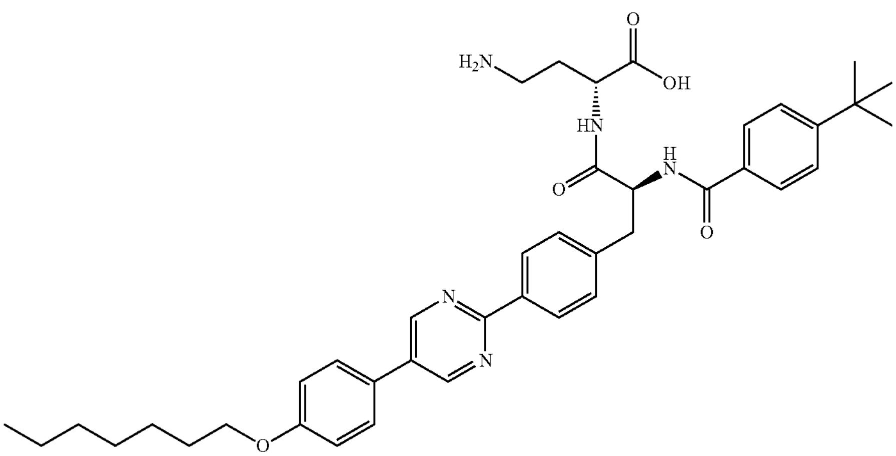 [SMILES: CCCCCCCOc1ccc(-c2cnc(-c3ccc(C[C@H](NC(=O)c4ccc(C(C)(C)C)cc4)C(=O)N[C@H](CCN)C(=O)O)cc3)nc2)cc1] | 476 | 10.22 | 14 |
| 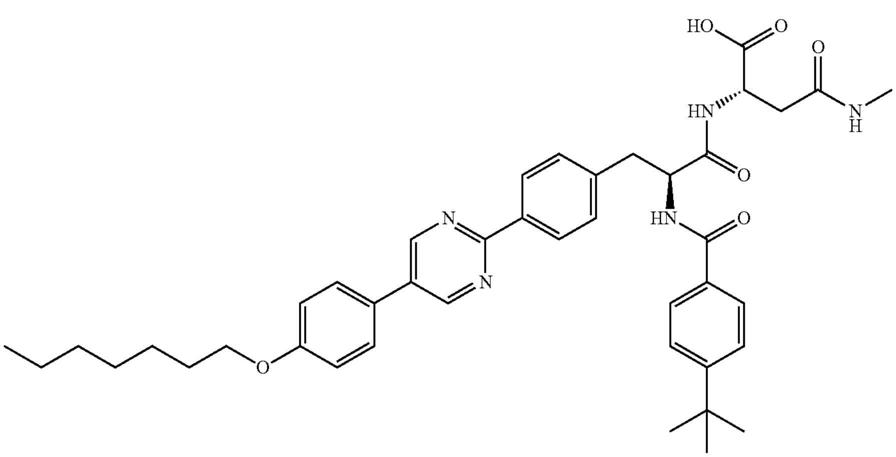 [SMILES: CCCCCCCOc1ccc(-c2cnc(-c3ccc(C[C@H](NC(=O)c4ccc(C(C)(C)C)cc4)C(=O)N[C@@H](CC(=O)NC)C(=O)O)cc3)nc2)cc1] | 477 | 8.67 | 12 |

TABLE 1-continued

| STRUCTURE | COMPOUND NUMBER | LCMS RETENTION TIME (min) | PURITY METHOD |
|---|---|---|---|
| 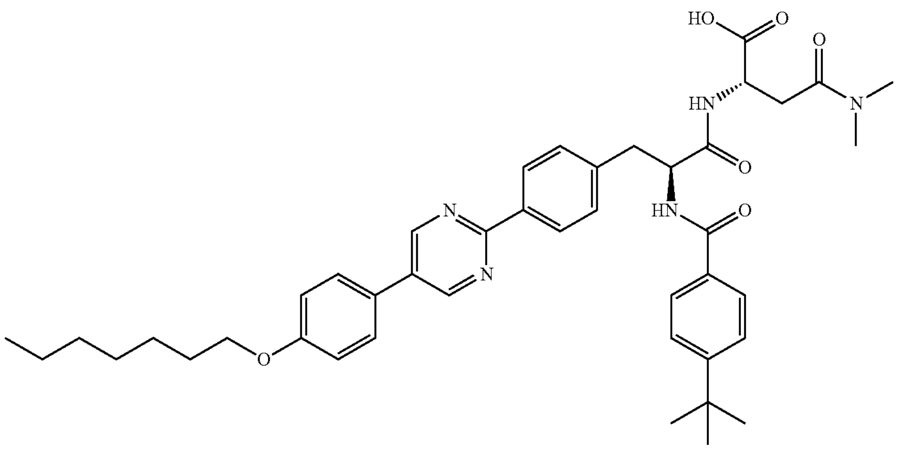 [SMILES: CCCCCCCOc1ccc(-c2cnc(-c3ccc(C[C@H](NC(=O)c4ccc(C(C)(C)C)cc4)C(=O)N[C@@H](CC(=O)N(C)C)C(=O)O)cc3)nc2)cc1] | 478 | 8.94 | 12 |
| 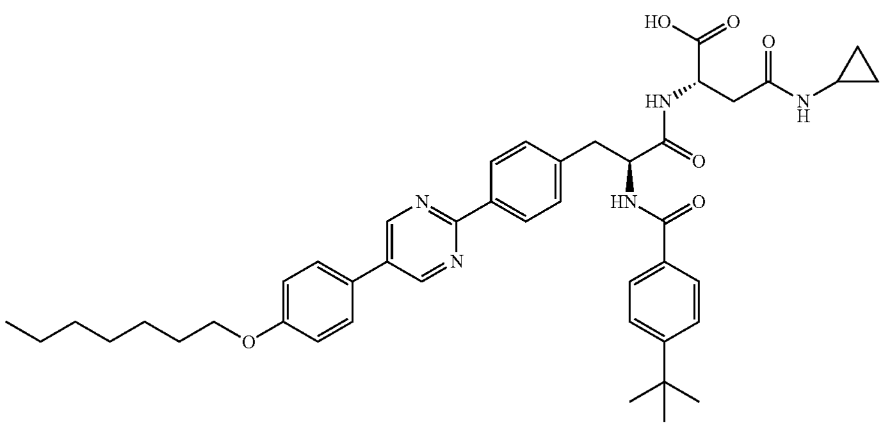 [SMILES: CCCCCCCOc1ccc(-c2cnc(-c3ccc(C[C@H](NC(=O)c4ccc(C(C)(C)C)cc4)C(=O)N[C@@H](CC(=O)NC4CC4)C(=O)O)cc3)nc2)cc1] | 479 | 10.13 | 14 |
| 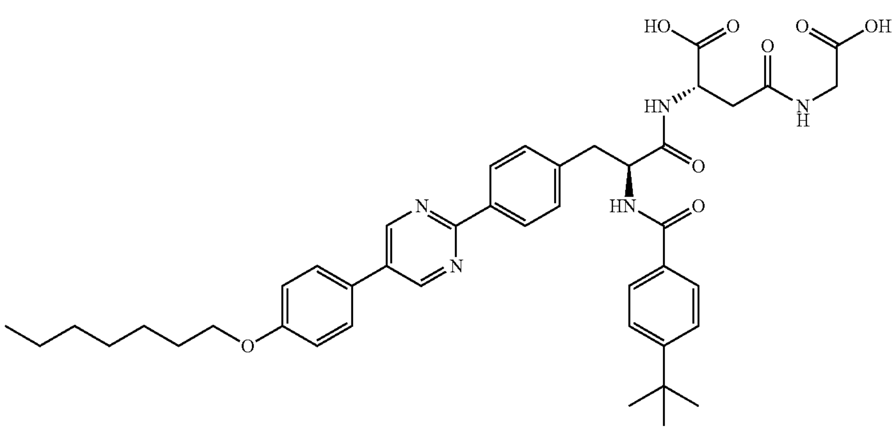 [SMILES: CCCCCCCOc1ccc(-c2cnc(-c3ccc(C[C@H](NC(=O)c4ccc(C(C)(C)C)cc4)C(=O)N[C@@H](CC(=O)NCC(=O)O)C(=O)O)cc3)nc2)cc1] | 480 | 8.55 | 14 |

TABLE 1-continued

| STRUCTURE | COMPOUND NUMBER | LCMS RETENTION TIME (min) | PURITY METHOD |
|---|---|---|---|
| 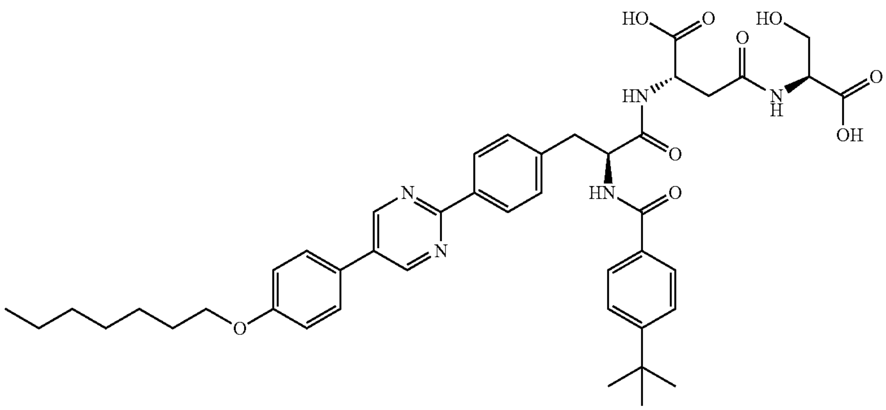 [SMILES: CCCCCCCOc1ccc(-c2cnc(-c3ccc(C[C@H](NC(=O)c4ccc(C(C)(C)C)cc4)C(=O)N[C@@H](CC(=O)N[C@@H](CO)C(=O)O)C(=O)O)cc3)nc2)cc1] | 481 | 8.43 | 14 |
| 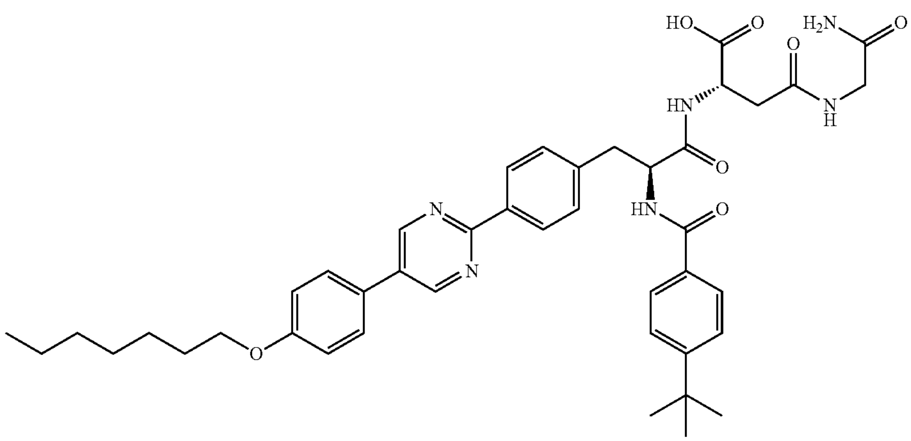 [SMILES: CCCCCCCOc1ccc(-c2cnc(-c3ccc(C[C@H](NC(=O)c4ccc(C(C)(C)C)cc4)C(=O)N[C@@H](CC(=O)NCC(N)=O)C(=O)O)cc3)nc2)cc1] | 482 | 9.52 | 14 |
| 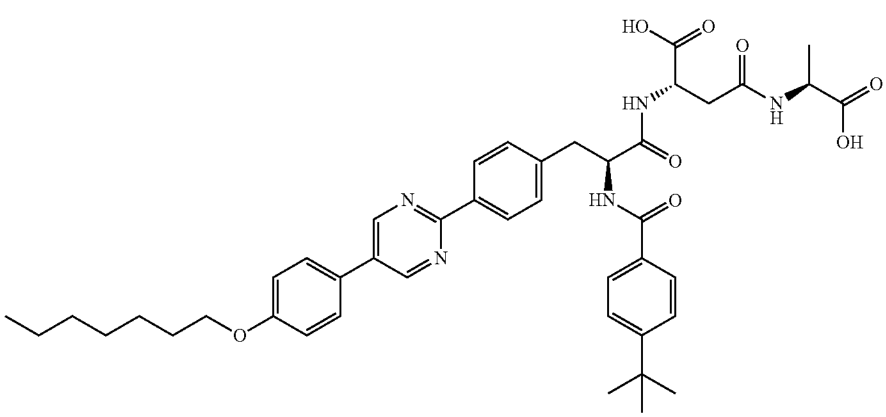 [SMILES: CCCCCCCOc1ccc(-c2cnc(-c3ccc(C[C@H](NC(=O)c4ccc(C(C)(C)C)cc4)C(=O)N[C@@H](CC(=O)N[C@@H](C)C(=O)O)C(=O)O)cc3)nc2)cc1] | 483 | 8.75 | 14 |

TABLE 1-continued

| STRUCTURE | COMPOUND NUMBER | LCMS RETENTION TIME (min) | PURITY METHOD |
|---|---|---|---|
| 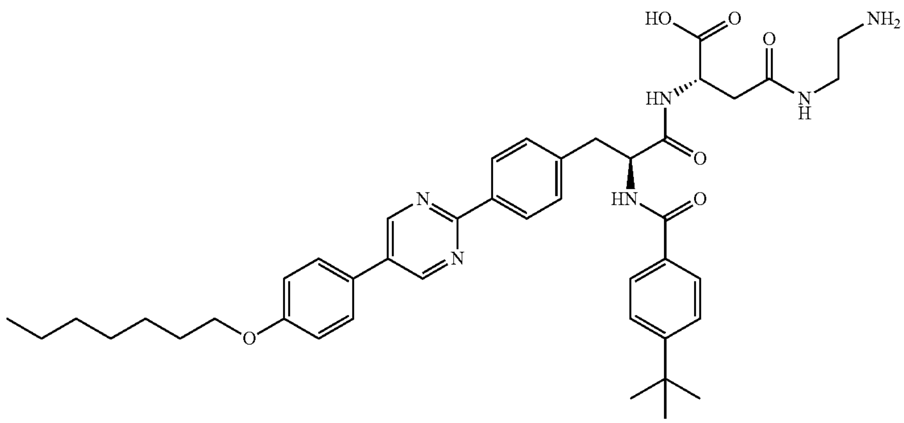 [SMILES: CCCCCCCOc1ccc(-c2cnc(-c3ccc(C[C@H](NC(=O)c4ccc(C(C)(C)C)cc4)C(=O)N[C@@H](CC(=O)NCCN)C(=O)O)cc3)nc2)cc1] | 484 | 10.15 | 14 |
| 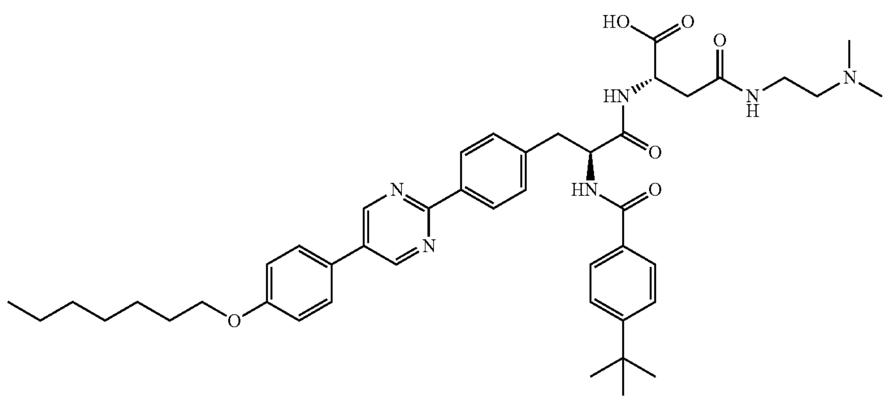 [SMILES: CCCCCCCOc1ccc(-c2cnc(-c3ccc(C[C@H](NC(=O)c4ccc(C(C)(C)C)cc4)C(=O)N[C@@H](CC(=O)NCCN(C)C)C(=O)O)cc3)nc2)cc1] | 485 | 10.38 | 14 |
| 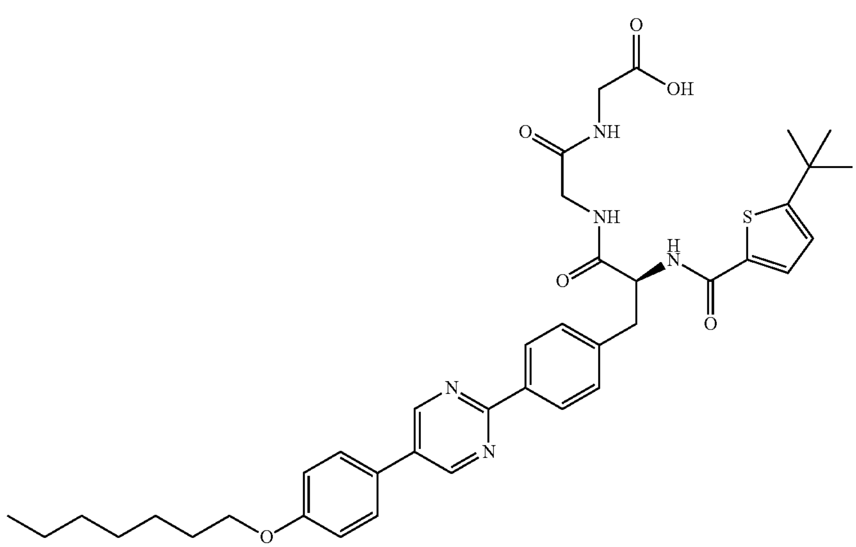 [SMILES: CCCCCCCOc1ccc(-c2cnc(-c3ccc(C[C@H](NC(=O)c4ccc(C(C)(C)C)s4)C(=O)NCC(=O)NCC(=O)O)cc3)nc2)cc1] | 486 | 9.85 | 14 |

TABLE 1-continued

| STRUCTURE | COMPOUND NUMBER | LCMS RETENTION TIME (min) | PURITY METHOD |
|---|---|---|---|
| 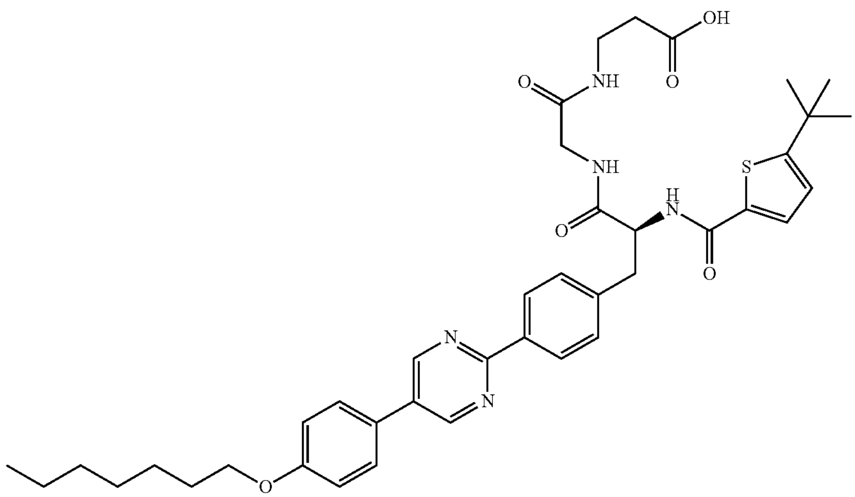 [SMILES: CCCCCCCOc1ccc(-c2cnc(-c3ccc(C[C@H](NC(=O)c4ccc(C(C)(C)C)s4)C(=O)NCC(=O)NCCC(=O)O)cc3)nc2)cc1] | 487 | 10.11 | 14 |
| 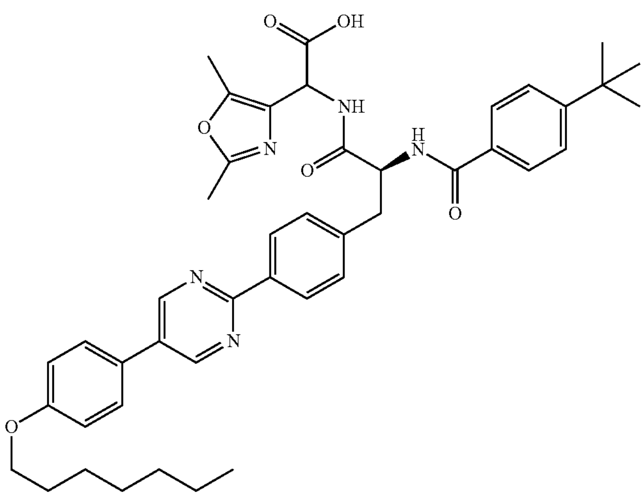 [SMILES: CCCCCCCOc1ccc(-c2cnc(-c3ccc(C[C@H](NC(=O)c4ccc(C(C)(C)C)cc4)C(=O)NC(C(=O)O)c4nc(C)oc4C)cc3)nc2)cc1] | 488 | 10.69 | 10 |
| 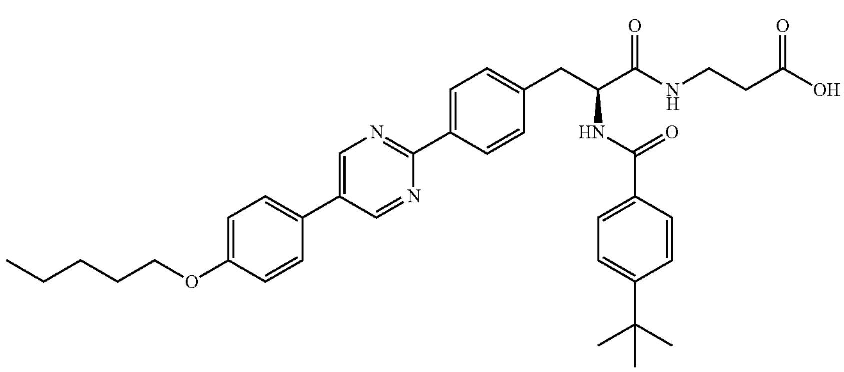 [SMILES: CCCCCOc1ccc(-c2cnc(-c3ccc(C[C@H](NC(=O)c4ccc(C(C)(C)C)cc4)C(=O)NCCC(=O)O)cc3)nc2)cc1] | 489 | 9.44 | 14 |

TABLE 1-continued

| STRUCTURE | COMPOUND NUMBER | LCMS RETENTION TIME (min) | PURITY METHOD |
|---|---|---|---|
| 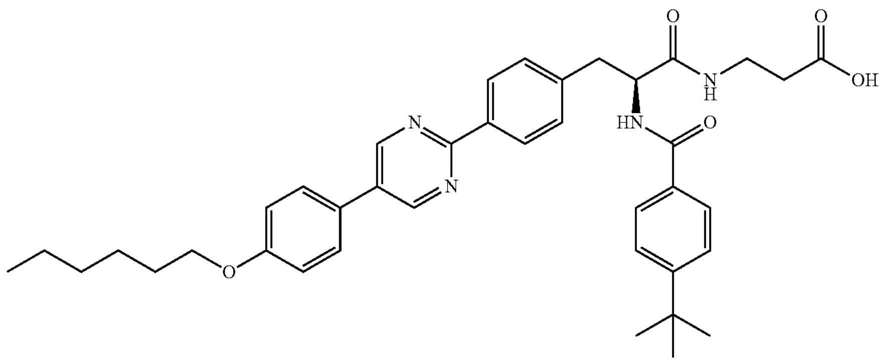 [SMILES: CCCCCCOc1ccc(-c2cnc(-c3ccc(C[C@H](NC(=O)c4ccc(C(C)(C)C)cc4)C(=O)NCCC(=O)O)cc3)nc2)cc1] | 490 | 9.94 | 14 |
| 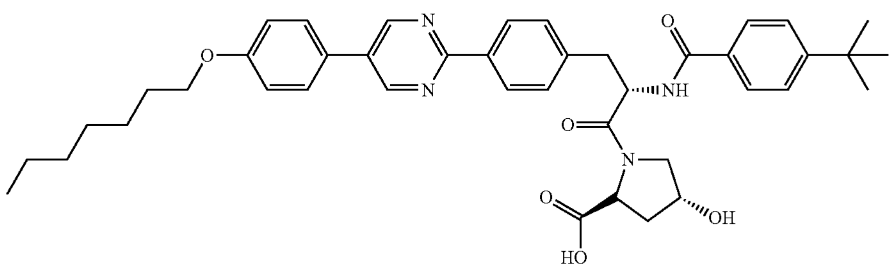 | 491 | 9.91 | 10 |
| 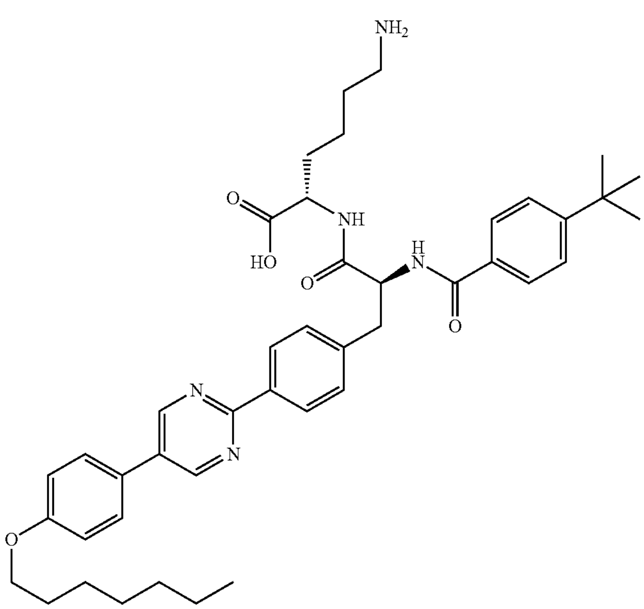 [SMILES: CCCCCCCOc1ccc(-c2cnc(-c3ccc(C[C@H](NC(=O)c4ccc(C(C)(C)C)cc4)C(=O)N[C@@H](CCCCN)C(=O)O)cc3)nc2)cc1] | 492 | 7.56 | 10 |

TABLE 1-continued

| STRUCTURE | COMPOUND NUMBER | LCMS RETENTION TIME (min) | PURITY METHOD |
|---|---|---|---|
| 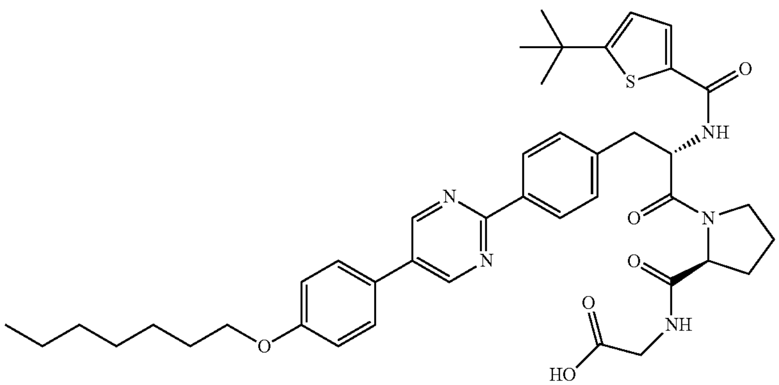 [SMILES: CCCCCCCOc1ccc(-c2cnc(-c3ccc(C[C@H](NC(=O)c4ccc(C(C)(C)C)s4)C(=O)N4CCC[C@H]4C(=O)NCC(=O)O)cc3)nc2)cc1] | 493 | 10.05 | 10 |
| 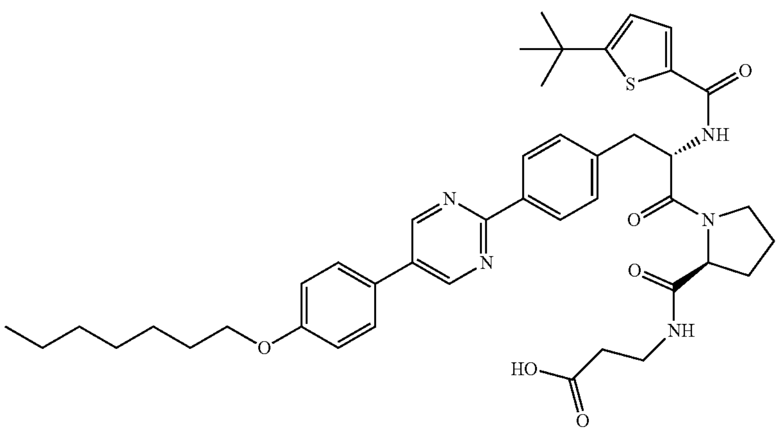 [SMILES: CCCCCCCOc1ccc(-c2cnc(-c3ccc(C[C@H](NC(=O)c4ccc(C(C)(C)C)s4)C(=O)N4CCC[C@H]4C(=O)NCCC(=O)O)cc3)nc2)cc1] | 494 | 9.97 | 10 |
| 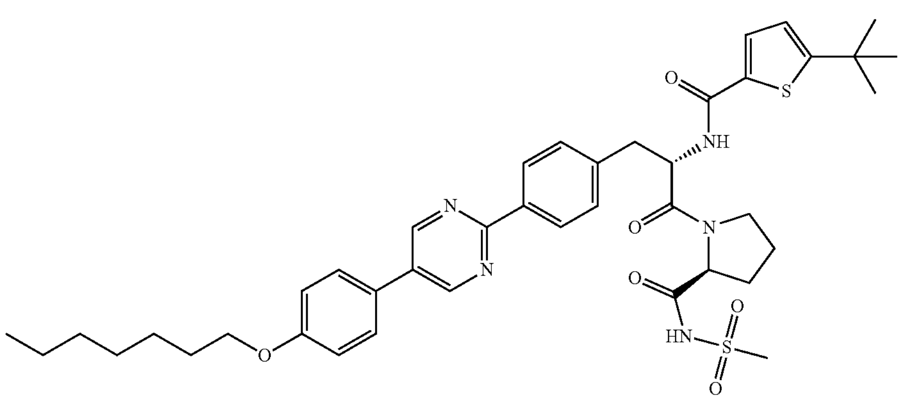 [SMILES: CCCCCCCOc1ccc(-c2cnc(-c3ccc(C[C@H](NC(=O)c4ccc(C(C)(C)C)s4)C(=O)N4CCC[C@H]4C(=O)NS(C)(=O)=O)cc3)nc2)cc1] | 495 | 10.68 | 10 |

TABLE 1-continued
| STRUCTURE | COMPOUND NUMBER | LCMS RETENTION TIME (min) | PURITY METHOD |
|---|---|---|---|
| 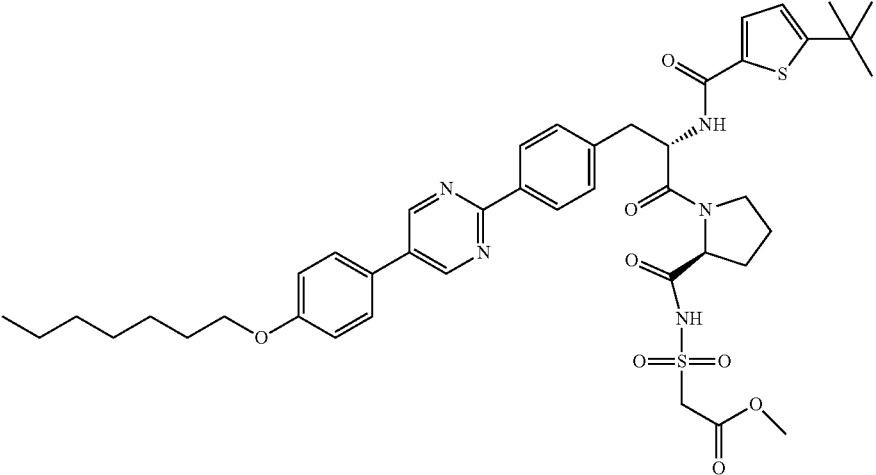 [SMILES: CCCCCCCOc1ccc(-c2cnc(-c3ccc(C[C@H](NC(=O)c4ccc(C(C)(C)C)s4)C(=O)N4CCC[C@H]4C(=O)NS(=O)(=O)CC(=O)OC)cc3)nc2)cc1] | 496 | 10.92 | 10 |
| 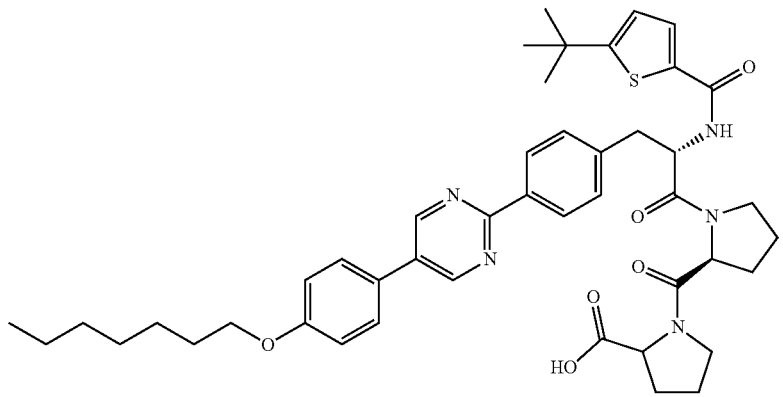 [SMILES: CCCCCCCOc1ccc(-c2cnc(-c3ccc(C[C@H](NC(=O)c4ccc(C(C)(C)C)s4)C(=O)N4CCC[C@H]4C(=O)N4CCCC4C(=O)O)cc3)nc2)cc1] | 497 | 10.33 | 10 |
| 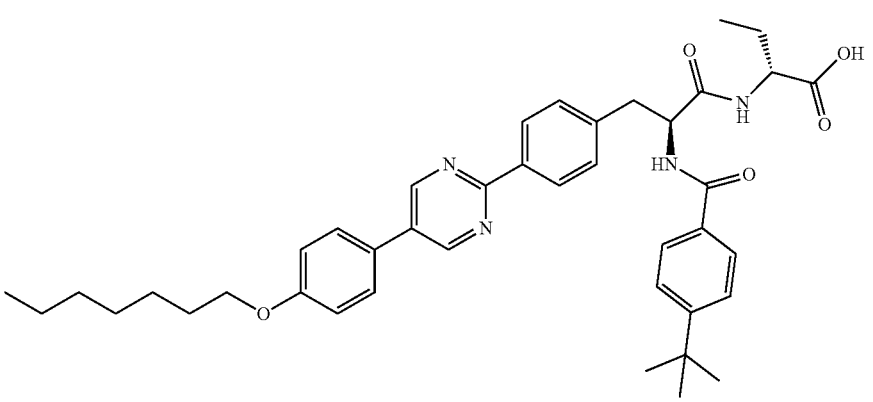 [SMILES: CCCCCCCOc1ccc(-c2cnc(-c3ccc(C[C@H](NC(=O)c4ccc(C(C)(C)C)cc4)C(=O)N[C@H](CC)C(=O)O)cc3)nc2)cc1] | 498 | 10.67 | 10 |

TABLE 1-continued

| STRUCTURE | COMPOUND NUMBER | LCMS RETENTION TIME (min) | PURITY METHOD |
|---|---|---|---|
| 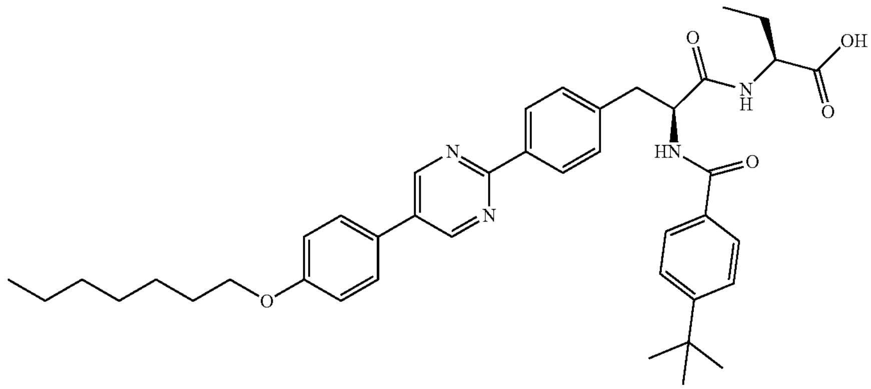 [SMILES: CCCCCCCOc1ccc(-c2cnc(-c3ccc(C[C@H](NC(=O)c4ccc(C(C)(C)C)cc4)C(=O)N[C@@H](CC)C(=O)O)cc3)nc2)cc1] | 499 | 10.63 | 10 |
| 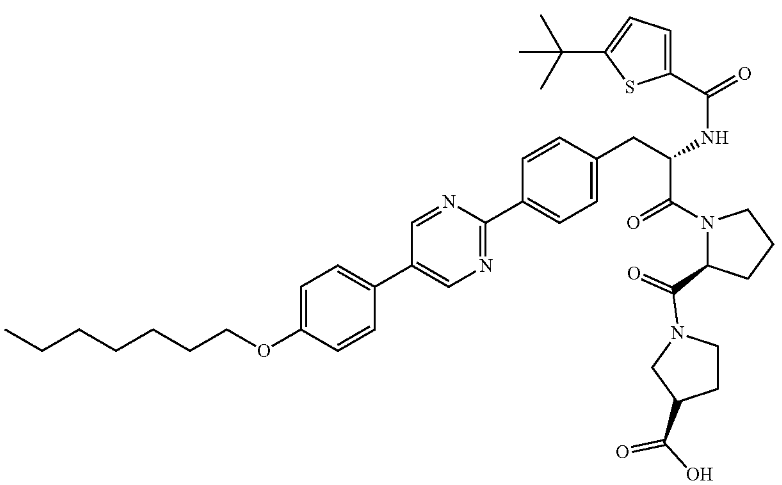 | 500 | 10.14 | 10 |
| 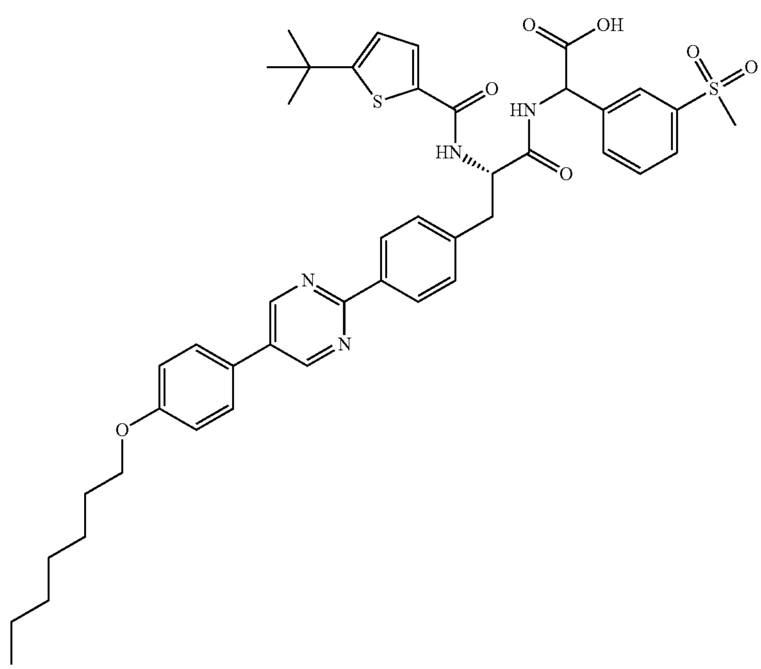 [SMILES: CCCCCCCOc1ccc(-c2cnc(-c3ccc(C[C@H](NC(=O)c4ccc(C(C)(C)C)s4)C(=O)NC(C(=O)O)c4cccc(S(C)(=O)=O)c4)cc3)nc2)cc1] | 501 | 10.57 | 10 |

TABLE 1-continued

| STRUCTURE | COMPOUND NUMBER | LCMS RETENTION TIME (min) | PURITY METHOD |
|---|---|---|---|
| 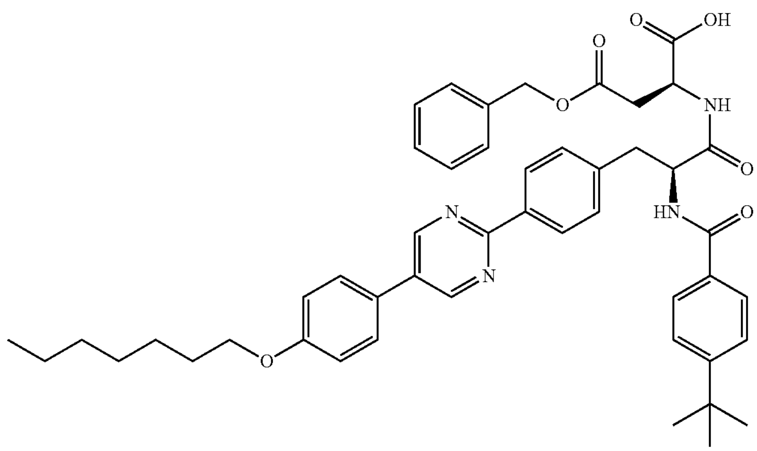 [SMILES: CCCCCCCOc1ccc(-c2cnc(-c3ccc(C[C@H](NC(=O)c4ccc(C(C)(C)C)cc4)C(=O)N[C@@H](CC(=O)OCc4ccccc4)C(=O)O)cc3)nc2)cc1] | 502 | 10.23 | 14 |
| 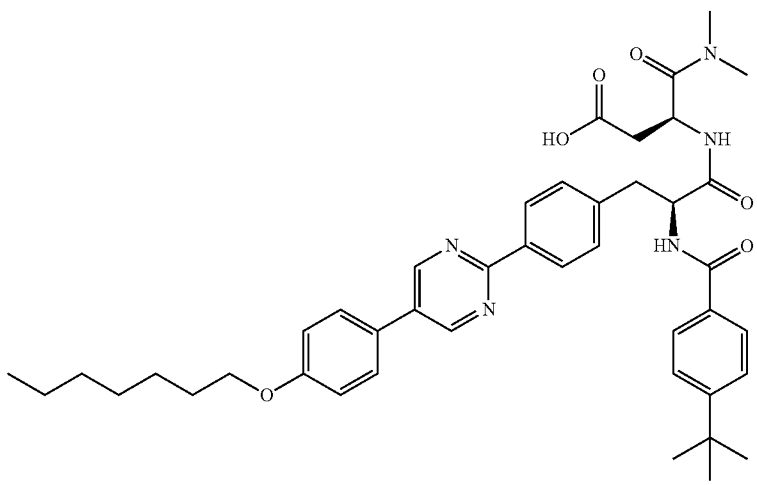 [SMILES: CCCCCCCOc1ccc(-c2cnc(-c3ccc(C[C@H](NC(=O)c4ccc(C(C)(C)C)cc4)C(=O)N[C@@H](CC(=O)O)C(=O)N(C)C)cc3)nc2)cc1] | 503 | 10.20 | 14 |
| 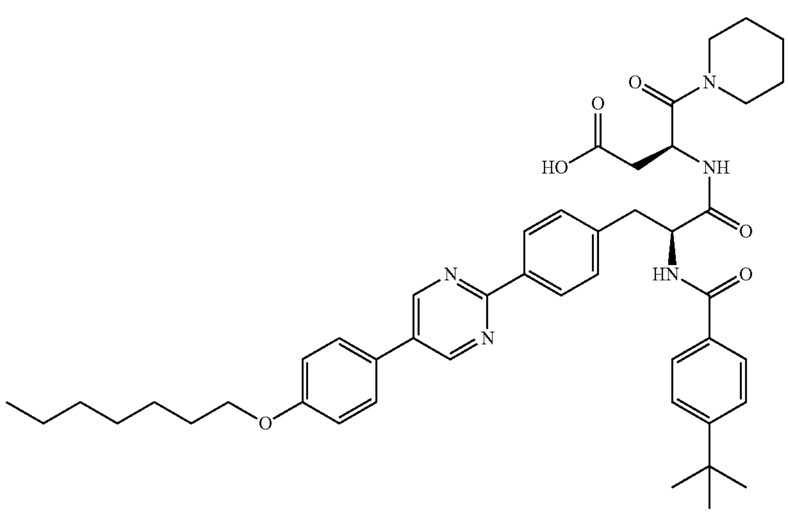 [SMILES: CCCCCCCOc1ccc(-c2cnc(-c3ccc(C[C@H](NC(=O)c4ccc(C(C)(C)C)cc4)C(=O)N[C@@H](CC(=O)O)C(=O)N4CCCCC4)cc3)nc2)cc1] | 504 | 10.78 | 14 |

TABLE 1-continued
| STRUCTURE | COMPOUND NUMBER | LCMS RETENTION TIME (min) | PURITY METHOD |
|---|---|---|---|
| 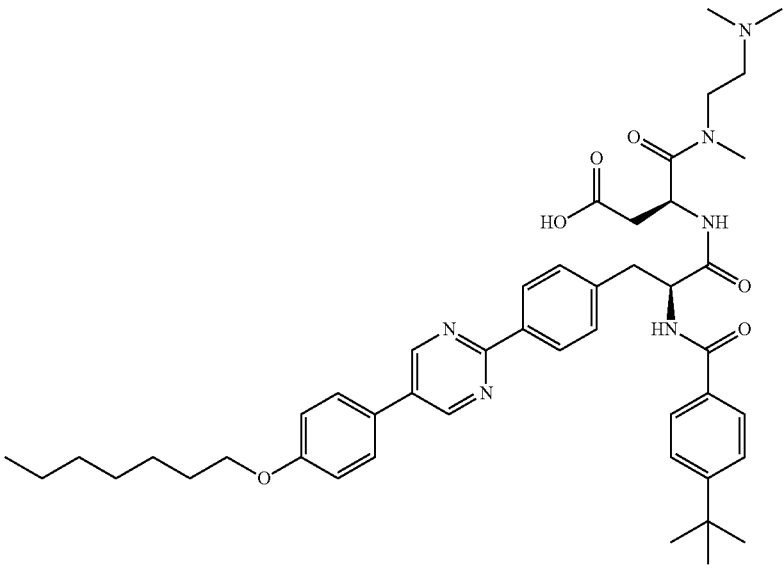 [SMILES: CCCCCCCOc1ccc(-c2cnc(-c3ccc(C[C@H](NC(=O)c4ccc(C(C)(C)C)cc4)C(=O)N[C@@H](CC(=O)O)C(=O)N(C)CCN(C)C)cc3)nc2)cc1] | 505 | 10.40 | 14 |
| 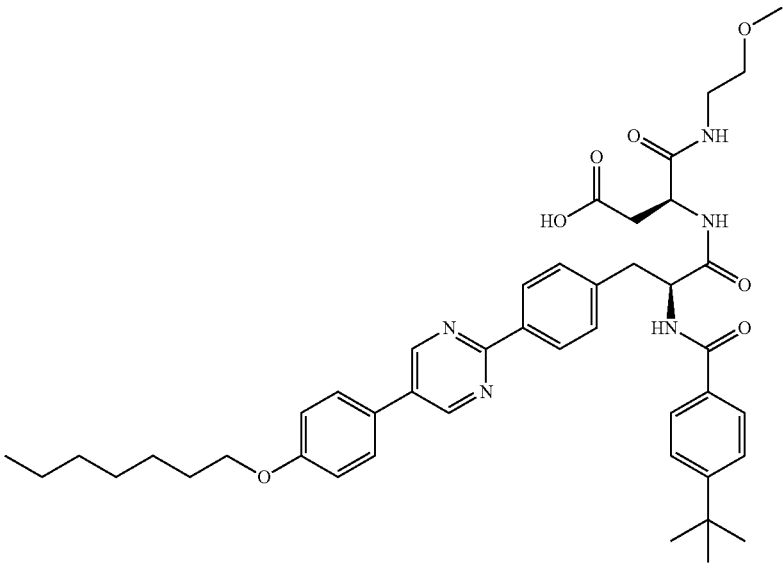 [SMILES: CCCCCCCOc1ccc(-c2cnc(-c3ccc(C[C@H](NC(=O)c4ccc(C(C)(C)C)cc4)C(=O)N[C@@H](CC(=O)O)C(=O)NCCOC)cc3)nc2)cc1] | 506 | 10.24 | 14 |

TABLE 1-continued

| STRUCTURE | COMPOUND NUMBER | LCMS RETENTION TIME (min) | PURITY METHOD |
|---|---|---|---|
| 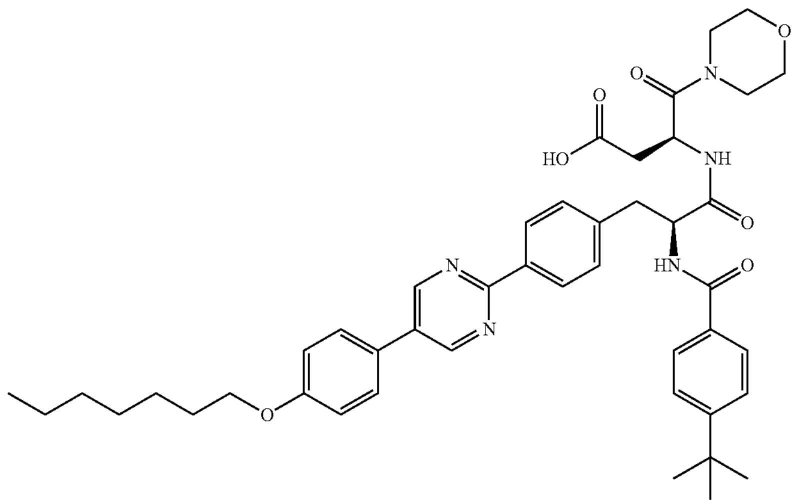 [SMILES: CCCCCCCOc1ccc(-c2cnc(-c3ccc(C[C@H](NC(=O)c4ccc(C(C)(C)C)cc4)C(=O)N[C@@H](CC(=O)O)C(=O)N4CCOCC4)cc3)nc2)cc1] | 507 | 9.82 | 14 |
| 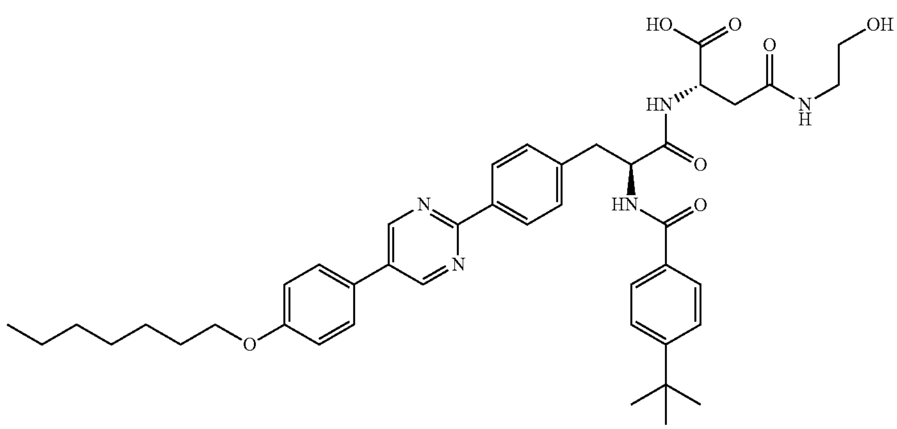 [SMILES: CCCCCCCOc1ccc(-c2cnc(-c3ccc(C[C@H](NC(=O)c4ccc(C(C)(C)C)cc4)C(=O)N[C@@H](CC(=O)NCCO)C(=O)O)cc3)nc2)cc1] | 508 | 9.75 | 2 |
| 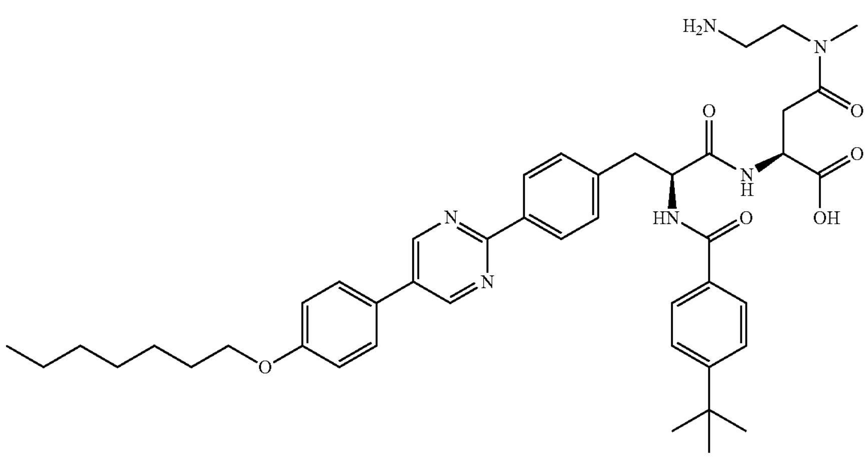 [SMILES: CCCCCCCOc1ccc(-c2cnc(-c3ccc(C[C@H](NC(=O)c4ccc(C(C)(C)C)cc4)C(=O)N[C@@H](CC(=O)N(C)CCN)C(=O)O)cc3)nc2)cc1] | 509 | 10.26 | 2 |

TABLE 1-continued

| STRUCTURE | COMPOUND NUMBER | LCMS RETENTION TIME (min) | PURITY METHOD |
|---|---|---|---|
| 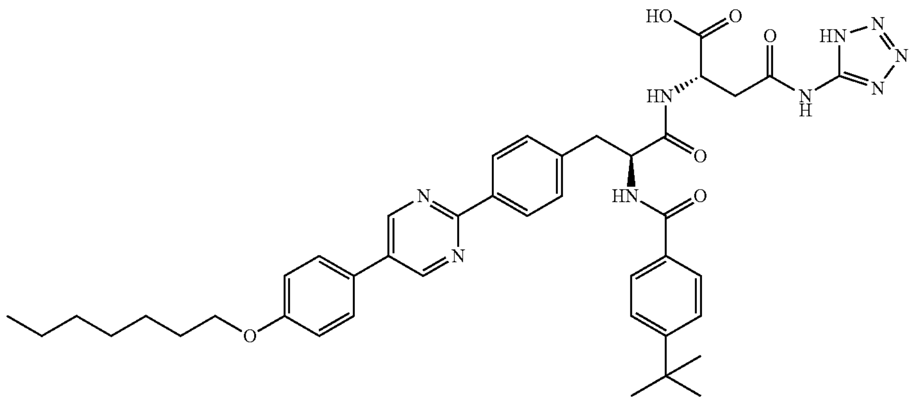 [SMILES: CCCCCCCOc1ccc(-c2cnc(-c3ccc(C[C@H](NC(=O)c4ccc(C(C)(C)C)cc4)C(=O)N[C@@H](CC(=O)Nc4nnn[nH]4)C(=O)O)cc3)nc2)cc1] | 510 | 9.04 | 2 |
| 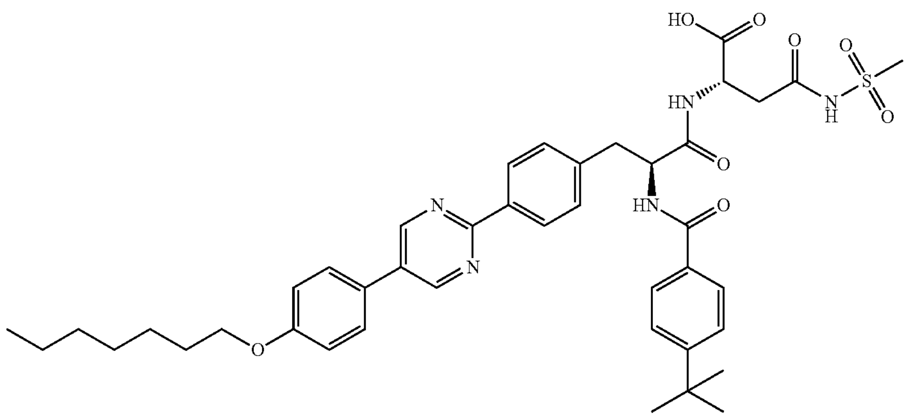 [SMILES: CCCCCCCOc1ccc(-c2cnc(-c3ccc(C[C@H](NC(=O)c4ccc(C(C)(C)C)cc4)C(=O)N[C@@H](CC(=O)NS(C)(=O)=O)C(=O)O)cc3)nc2)cc1] | 511 | 9.44 | 2 |
| 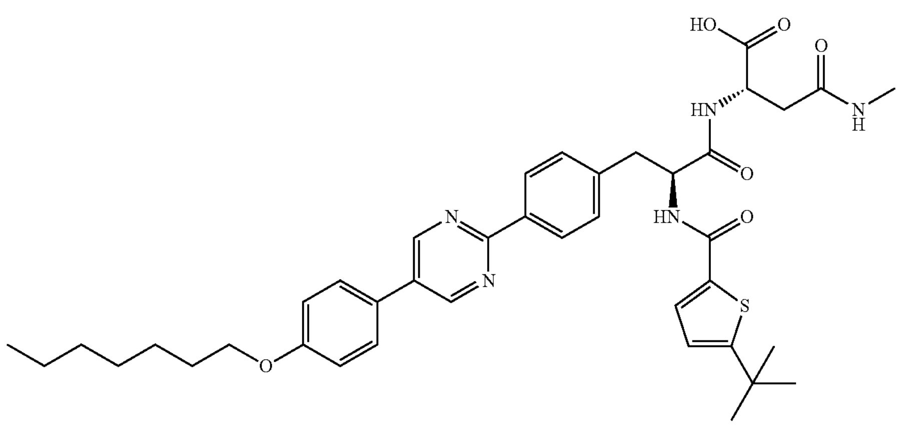 [SMILES: CCCCCCCOc1ccc(-c2cnc(-c3ccc(C[C@H](NC(=O)c4ccc(C(C)(C)C)s4)C(=O)N[C@@H](CC(=O)NC)C(=O)O)cc3)nc2)cc1] | 512 | 9.80 | 2 |

TABLE 1-continued

| STRUCTURE | COMPOUND NUMBER | LCMS RETENTION TIME (min) | PURITY METHOD |
|---|---|---|---|
| 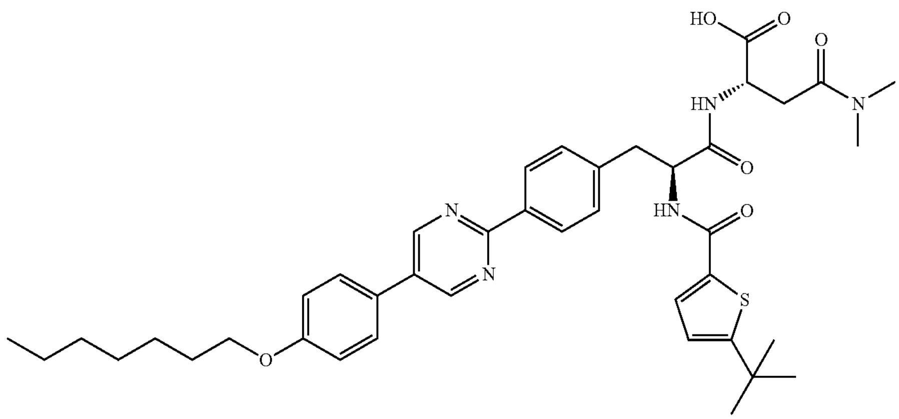 [SMILES: CCCCCCCOc1ccc(-c2cnc(-c3ccc(C[C@H](NC(=O)c4ccc(C(C)(C)C)s4)C(=O)N[C@@H](CC(=O)N(C)C)C(=O)O)cc3)nc2)cc1] | 513 | 9.95 | 2 |
| 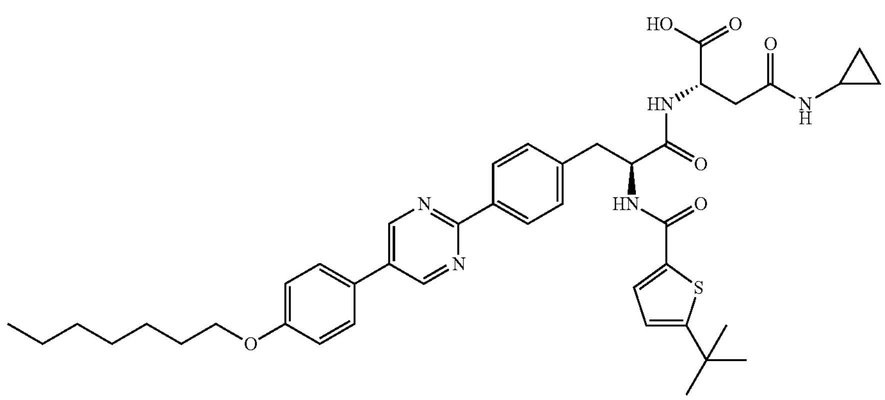 [SMILES: CCCCCCCOc1ccc(-c2cnc(-c3ccc(C[C@H](NC(=O)c4ccc(C(C)(C)C)s4)C(=O)N[C@@H](CC(=O)NC4CC4)C(=O)O)cc3)nc2)cc1] | 514 | 10.10 | 2 |
| 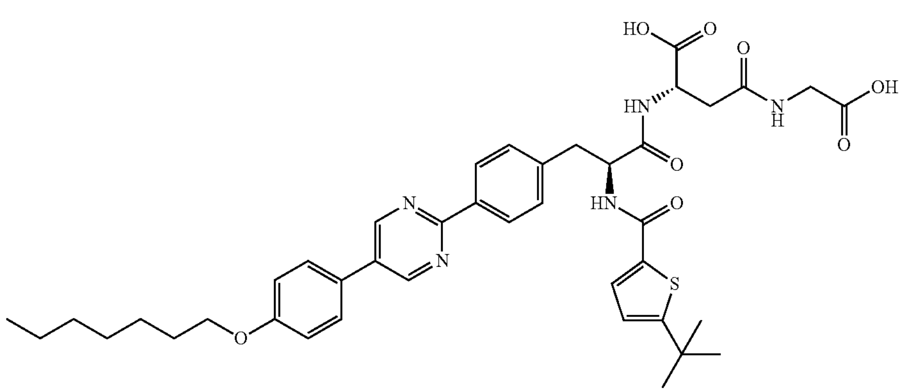 [SMILES: CCCCCCCOc1ccc(-c2cnc(-c3ccc(C[C@H](NC(=O)c4ccc(C(C)(C)C)s4)C(=O)N[C@@H](CC(=O)NCC(=O)O)C(=O)O)cc3)nc2)cc1] | 515 | 8.50 | 2 |

TABLE 1-continued

| STRUCTURE | COMPOUND NUMBER | LCMS RETENTION TIME (min) | PURITY METHOD |
|---|---|---|---|
| 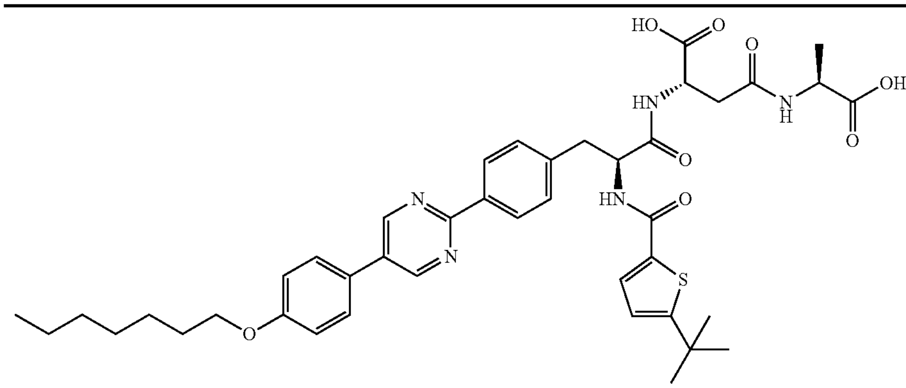 | 516 | 8.57 | 2 |
| 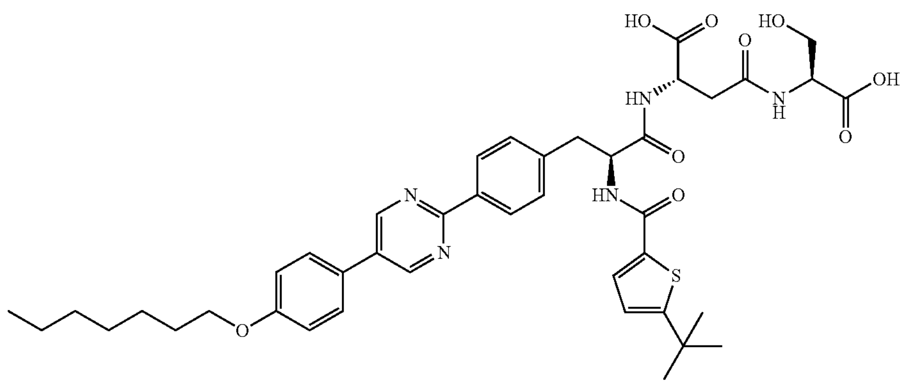 [SMILES: CCCCCCCOc1ccc(-c2cnc(-c3ccc(C[C@H](NC(=O)c4ccc(C(C)(C)C)s4)C(=O)N[C@@H](CC(=O)N[C@@H](CO)C(=O)O)C(=O)O)cc3)nc2)cc1] | 517 | 8.46 | 2 |
| 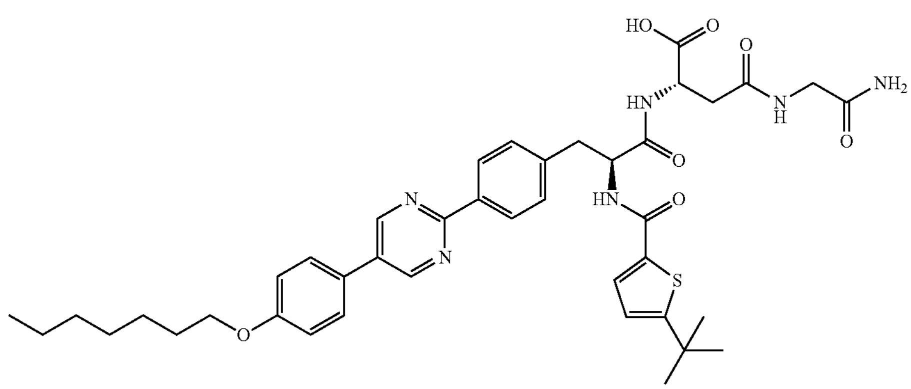 [SMILES: CCCCCCCOc1ccc(-c2cnc(-c3ccc(C[C@H](NC(=O)c4ccc(C(C)(C)C)s4)C(=O)N[C@@H](CC(=O)NCC(N)=O)C(=O)O)cc3)nc2)cc1] | 518 | 9.55 | 2 |
| 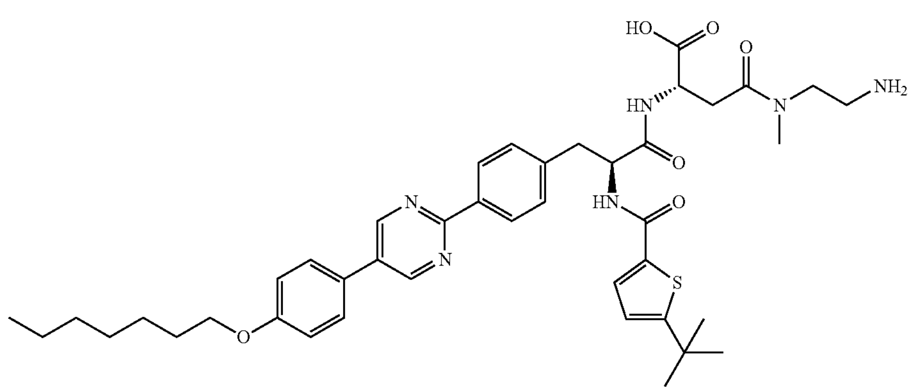 [SMILES: CCCCCCCOc1ccc(-c2cnc(-c3ccc(C[C@H](NC(=O)c4ccc(C(C)(C)C)s4)C(=O)N[C@@H](CC(=O)N(C)CCN)C(=O)O)cc3)nc2)cc1] | 519 | 10.04 | 2 |

TABLE 1-continued

| STRUCTURE | COMPOUND NUMBER | LCMS RETENTION TIME (min) | PURITY METHOD |
|---|---|---|---|
| 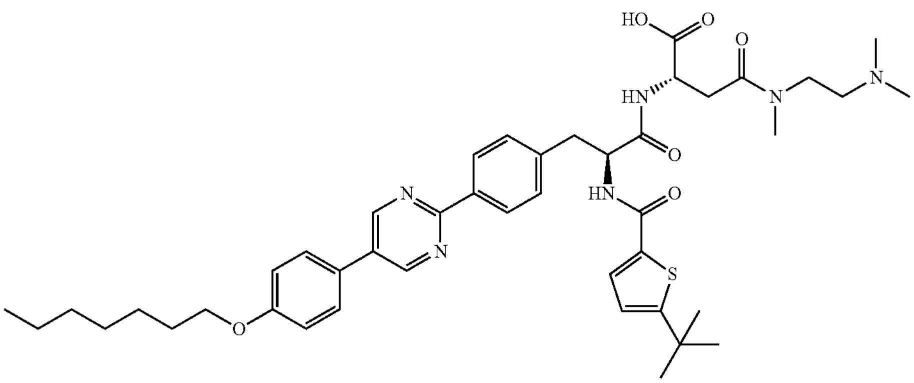 [SMILES: CCCCCCCOc1ccc(-c2cnc(-c3ccc(C[C@H](NC(=O)c4ccc(C(C)(C)C)s4)C(=O)N[C@@H](CC(=O)N(C)CCN(C)C)C(=O)O)cc3)nc2)cc1] | 520 | 10.23 | 2 |
| 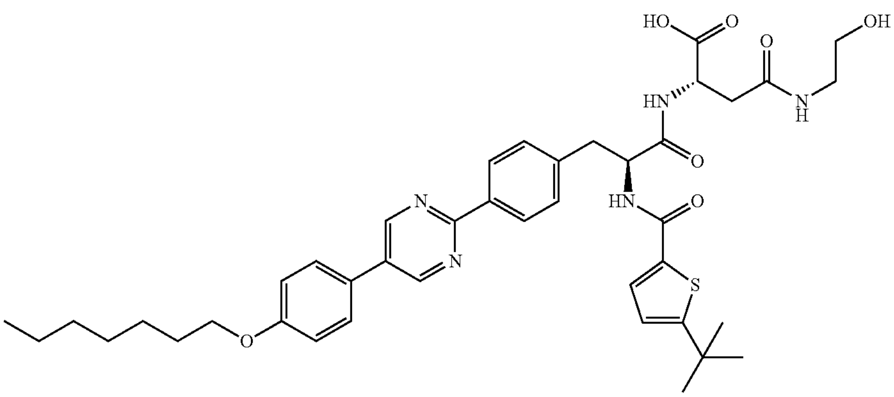 [SMILES: CCCCCCCOc1ccc(-c2cnc(-c3ccc(C[C@H](NC(=O)c4ccc(C(C)(C)C)s4)C(=O)N[C@@H](CC(=O)NCCO)C(=O)O)cc3)nc2)cc1] | 521 | 9.56 | 14 |
| 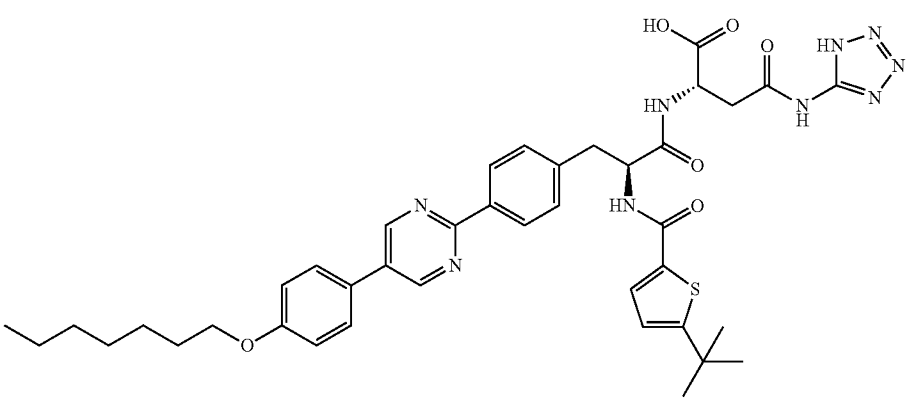 [SMILES: CCCCCCCOc1ccc(-c2cnc(-c3ccc(C[C@H](NC(=O)c4ccc(C(C)(C)C)s4)C(=O)N[C@@H](CC(=O)Nc4nnn[nH]4)C(=O)O)cc3)nc2)cc1] | 522 | 8.78 | 14 |

TABLE 1-continued

| STRUCTURE | COMPOUND NUMBER | LCMS RETENTION TIME (min) | PURITY METHOD |
|---|---|---|---|
| 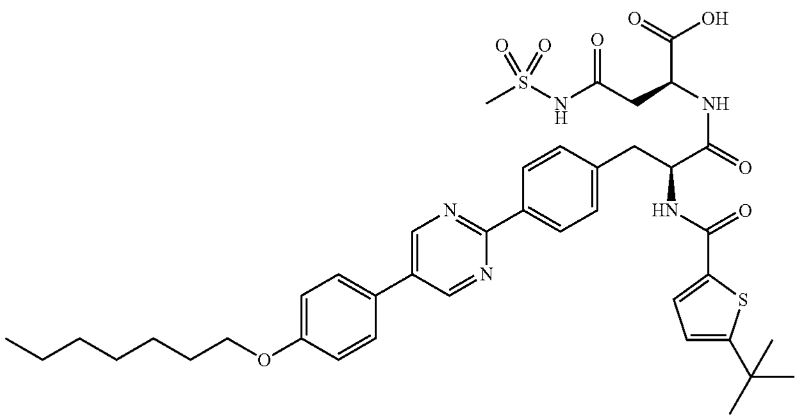 [SMILES: CCCCCCCOc1ccc(-c2cnc(-c3ccc(C[C@H](NC(=O)c4ccc(C(C)(C)C)s4)C(=O)N[C@@H](CC(=O)NS(C)(=O)=O)C(=O)O)cc3)nc2)cc1] | 523 | 9.25 | 14 |
| 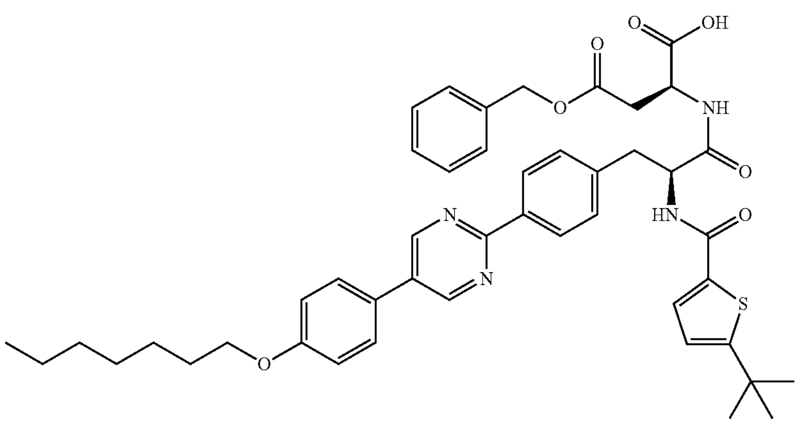 [SMILES: CCCCCCCOc1ccc(-c2cnc(-c3ccc(C[C@H](NC(=O)c4ccc(C(C)(C)C)s4)C(=O)N[C@@H](CC(=O)OCc4ccccc4)C(=O)O)cc3)nc2)cc1] | 524 | 10.065 | 14 |
| 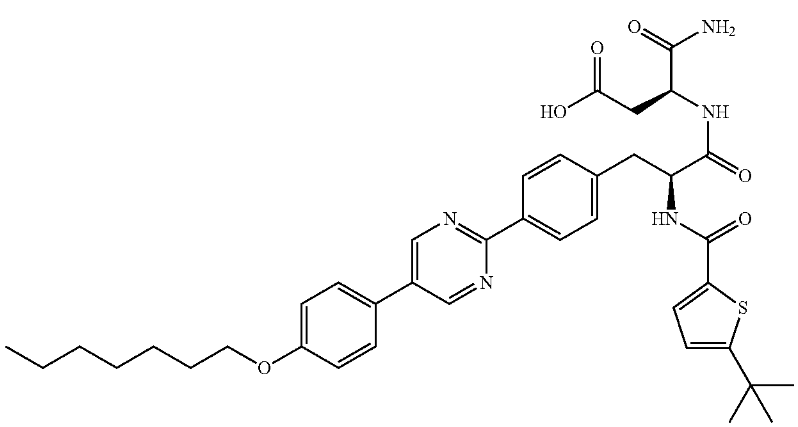 [SMILES: CCCCCCCOc1ccc(-c2cnc(-c3ccc(C[C@H](NC(=O)c4ccc(C(C)(C)C)s4)C(=O)N[C@@H](CC(=O)O)C(N)=O)cc3)nc2)cc1] | 525 | 10.02 | 14 |

TABLE 1-continued

| STRUCTURE | COMPOUND NUMBER | LCMS RETENTION TIME (min) | PURITY METHOD |
|---|---|---|---|
| 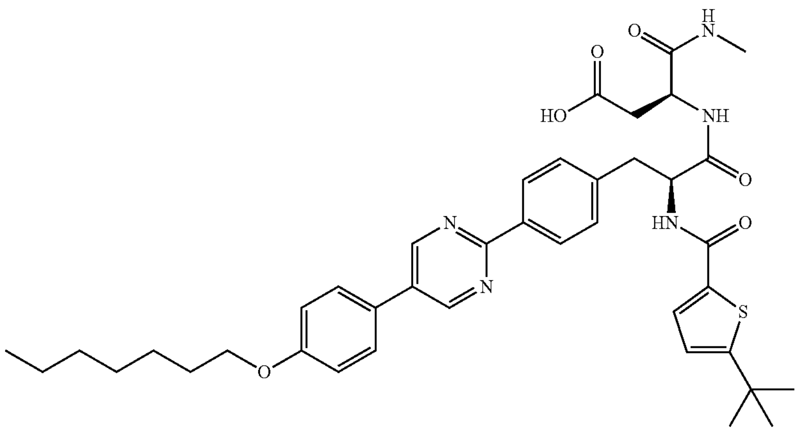 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)NC)cc3)nc2)cc1] | 526 | 10.28 | 14 |
| 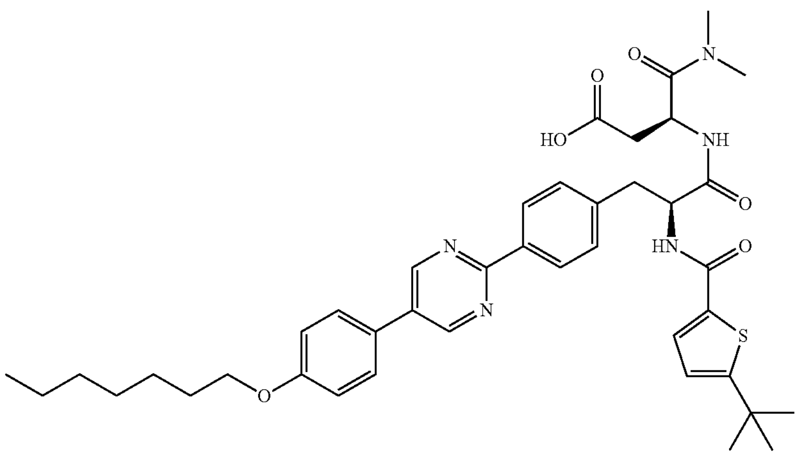 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)N(C)C)cc3)nc2)cc1] | 527 | 10.47 | 14 |
| 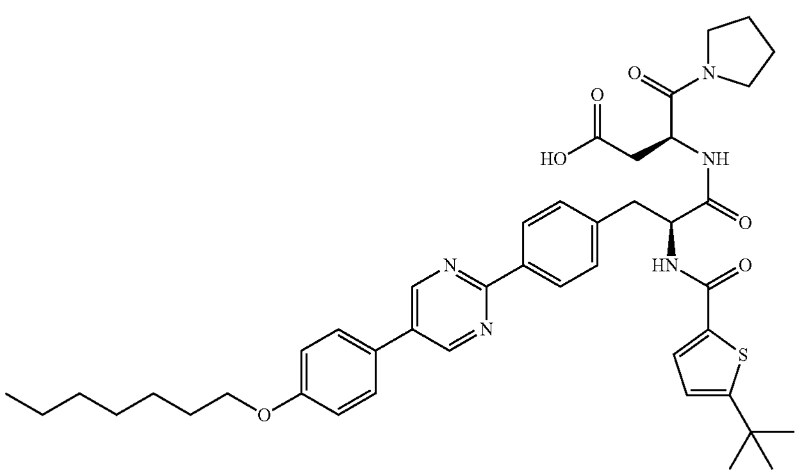 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)N4CCCC4)cc3)nc2)cc1] | 528 | 10.68 | 14 |

TABLE 1-continued

| STRUCTURE | COMPOUND NUMBER | LCMS RETENTION TIME (min) | PURITY METHOD |
|---|---|---|---|
| 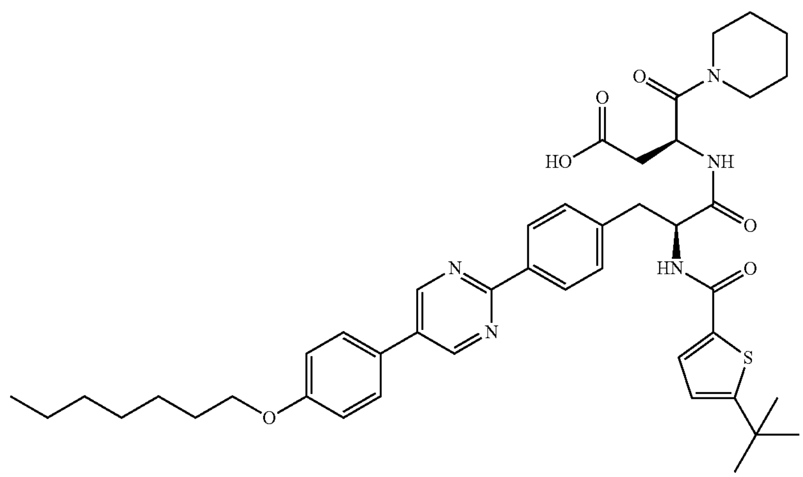 | 529 | 10.16 | 14 |
| 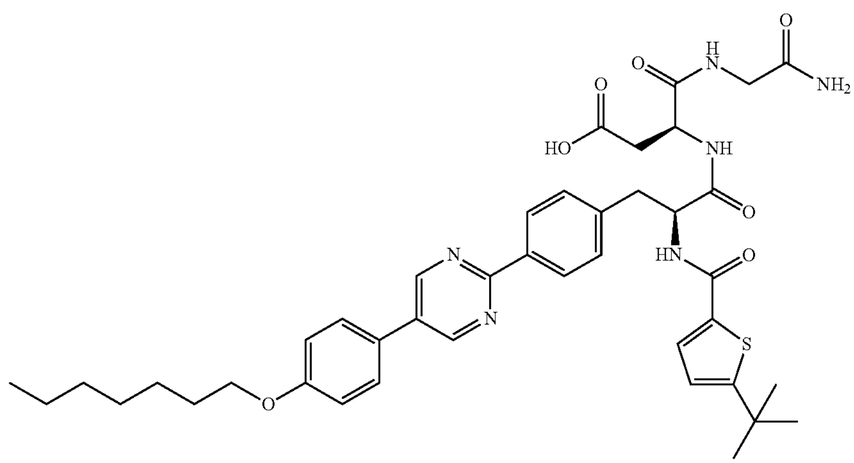 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)NCC(N)=O)cc3)nc2)cc1] | 530 | 9.67 | 14 |
| 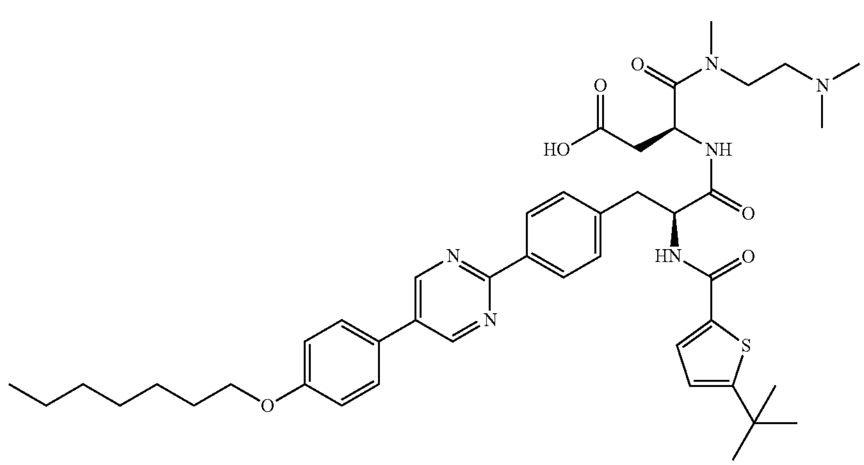 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)N(C)CCN(C)C)cc3)nc2)cc1] | 531 | 10.29 | 14 |

TABLE 1-continued

| STRUCTURE | COMPOUND NUMBER | LCMS RETENTION TIME (min) | PURITY METHOD |
|---|---|---|---|
| 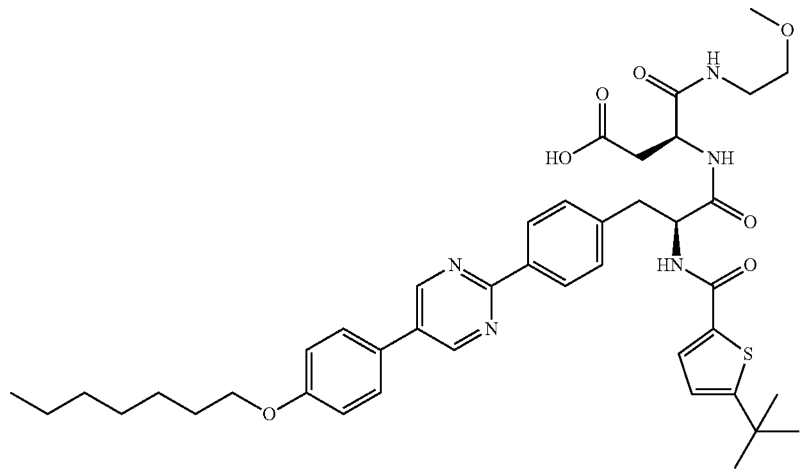 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)NCCOC)cc3)nc2)cc1] | 532 | 10.36 | 14 |
| 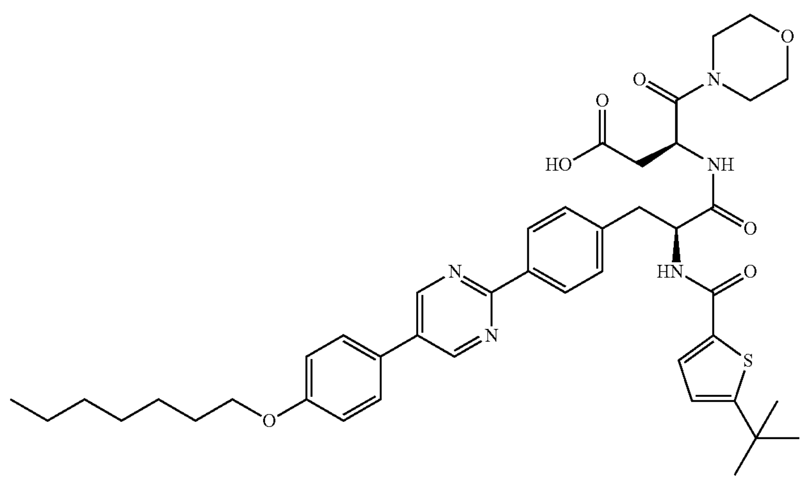 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)N4CCOCC4)cc3)nc2)cc1] | 533 | 10.39 | 14 |
| 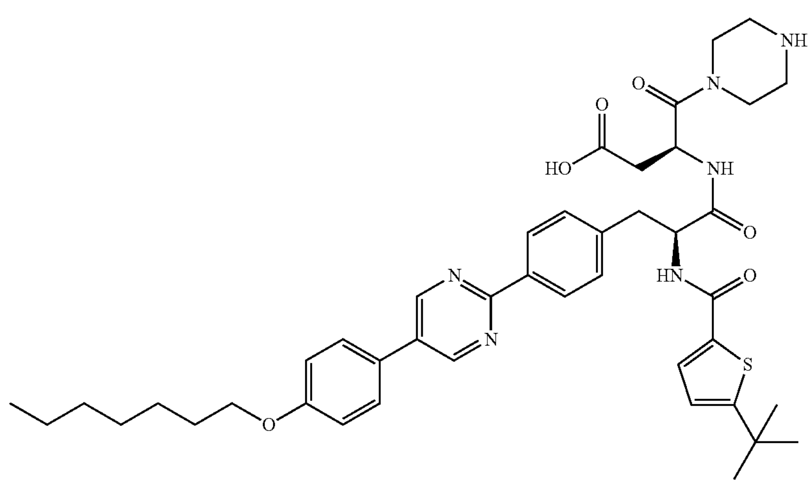 [SMILES: CCCCCCCOc1ccc(-c2cnc(-c3ccc(C[C@H](NC(=O)c4ccc(C(C)(C)C)s4)C(=O)N[C@@H](CC(=O)O)C(=O)N4CCNCC4)cc3)nc2)cc1] | 534 | 9.75 | 14 |

TABLE 1-continued

| STRUCTURE | COMPOUND NUMBER | LCMS RETENTION TIME (min) | PURITY METHOD |
|---|---|---|---|
| (structure) | 535 | 10.94 | 14 |
| (structure) | 536 | 10.69 | 10 |
| (structure) | 537 | 10.75 | 14 |

TABLE 1-continued
| STRUCTURE | COMPOUND NUMBER | LCMS RETENTION TIME (min) | PURITY METHOD |
|---|---|---|---|
| 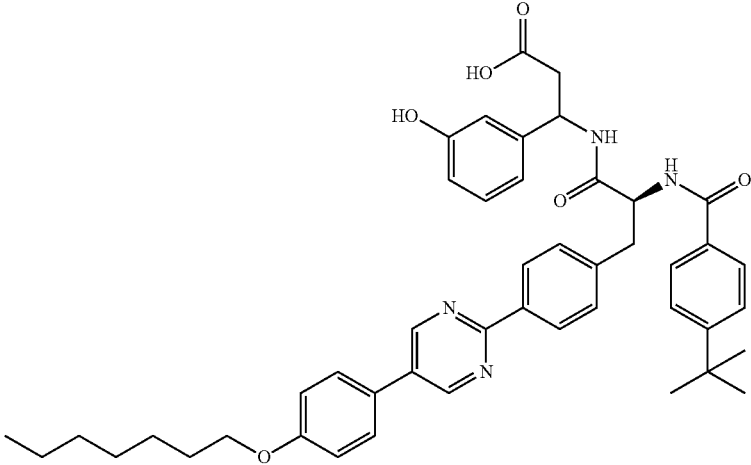 [SMILES: CCCCCCCOc1ccc(-c2cnc(-c3ccc(C[C@H](NC(=O)c4ccc(C(C)(C)C)cc4)C(=O)NC(CC(=O)O)c4cccc(O)c4)cc3)nc2)cc1] | 538 | 10.74 | 14 |
| 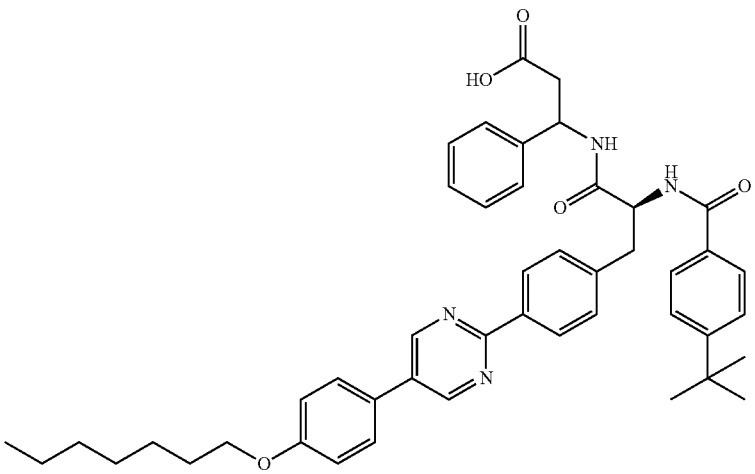 [SMILES: CCCCCCCOc1ccc(-c2cnc(-c3ccc(C[C@H](NC(=O)c4ccc(C(C)(C)C)cc4)C(=O)NC(CC(=O)O)c4ccccc4)cc3)nc2)cc1] | 539 | 10.36 | 14 |
| 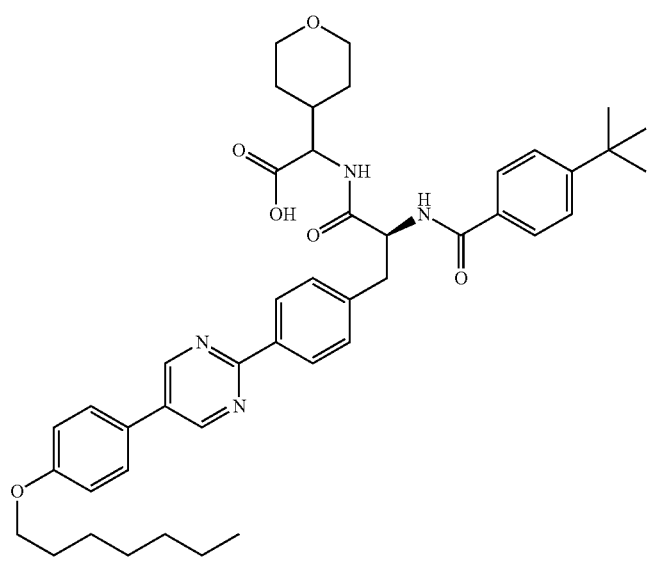 [SMILES: CCCCCCCOc1ccc(-c2cnc(-c3ccc(C[C@H](NC(=O)c4ccc(C(C)(C)C)cc4)C(=O)NC(C(=O)O)C4CCOCC4)cc3)nc2)cc1] | 540 | 10.29 | 10 |

TABLE 1-continued

| STRUCTURE | COMPOUND NUMBER | LCMS RETENTION TIME (min) | PURITY METHOD |
|---|---|---|---|
| 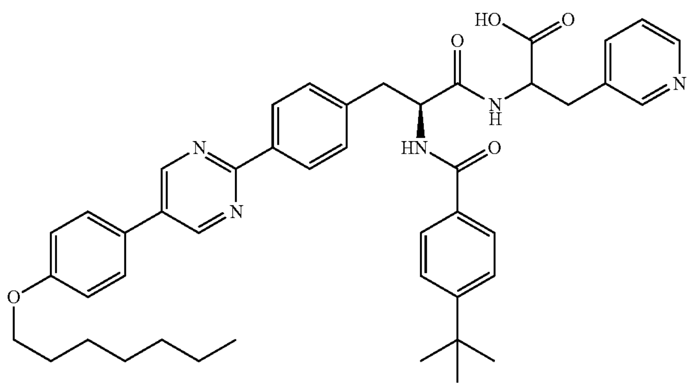 [SMILES: CCCCCCCOc1ccc(-c2cnc(-c3ccc(C[C@H](NC(=O)c4ccc(C(C)(C)C)cc4)C(=O)NC(Cc4cccnc4)C(=O)O)cc3)nc2)cc1] | 541 | 8.64 | 10 |
| 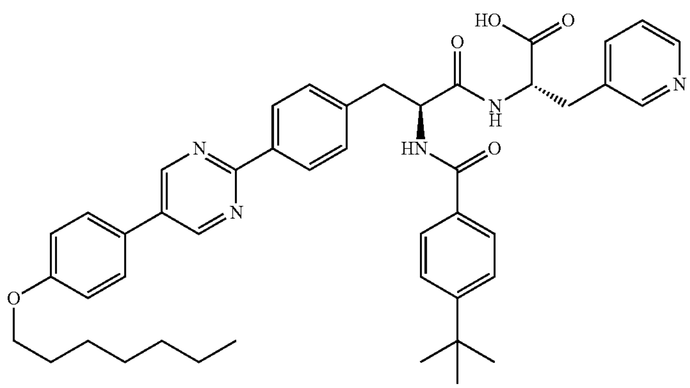 [SMILES: CCCCCCCOc1ccc(-c2cnc(-c3ccc(C[C@H](NC(=O)c4ccc(C(C)(C)C)cc4)C(=O)N[C@@H](Cc4cccnc4)C(=O)O)cc3)nc2)cc1] | 542 | 9.35 | 10 |
| 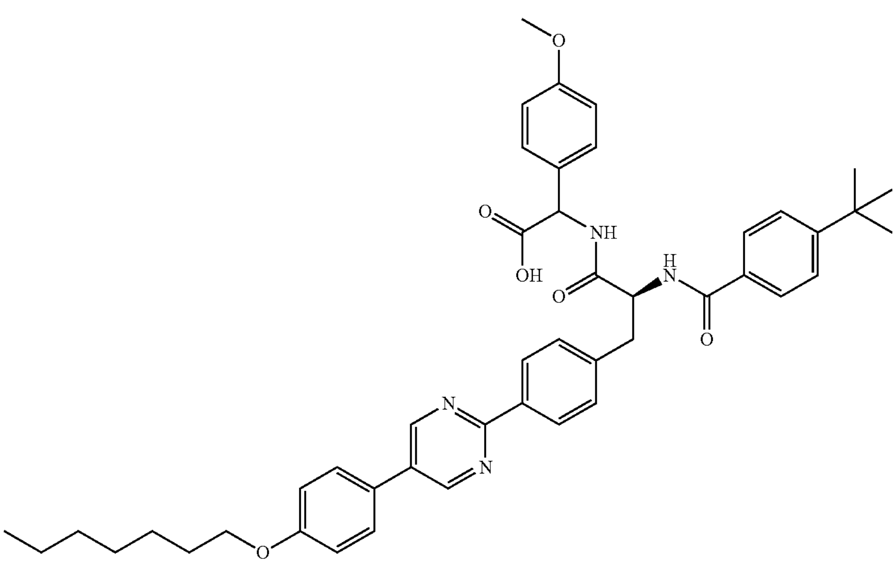 [SMILES: CCCCCCCOc1ccc(-c2cnc(-c3ccc(C[C@H](NC(=O)c4ccc(C(C)(C)C)cc4)C(=O)NC(C(=O)O)c4ccc(OC)cc4)cc3)nc2)cc1] | 543 | 10.84 | 10 |

TABLE 1-continued

| STRUCTURE | COMPOUND NUMBER | LCMS RETENTION TIME (min) | PURITY METHOD |
|---|---|---|---|
| 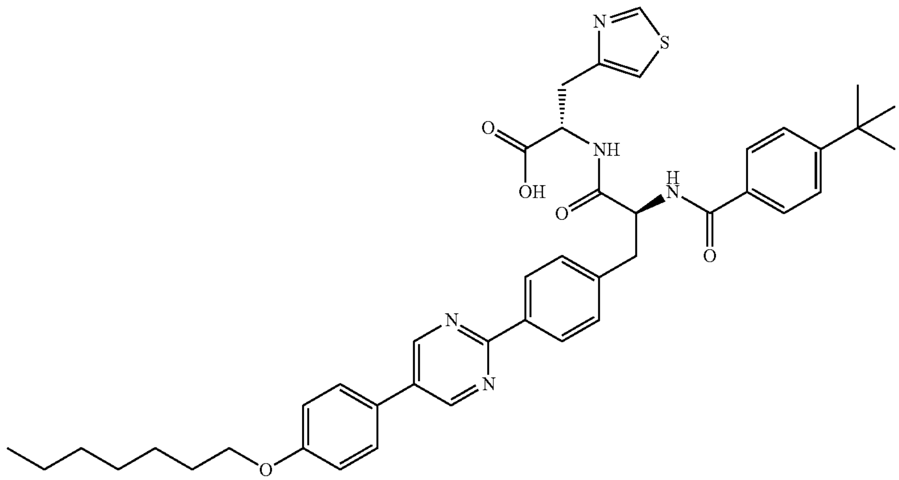 [SMILES: CCCCCCCOc1ccc(-c2cnc(-c3ccc(C[C@H](NC(=O)c4ccc(C(C)(C)C)cc4)C(=O)N[C@@H](Cc4cscn4)C(=O)O)cc3)nc2)cc1] | 544 | 10.34 | 10 |
| 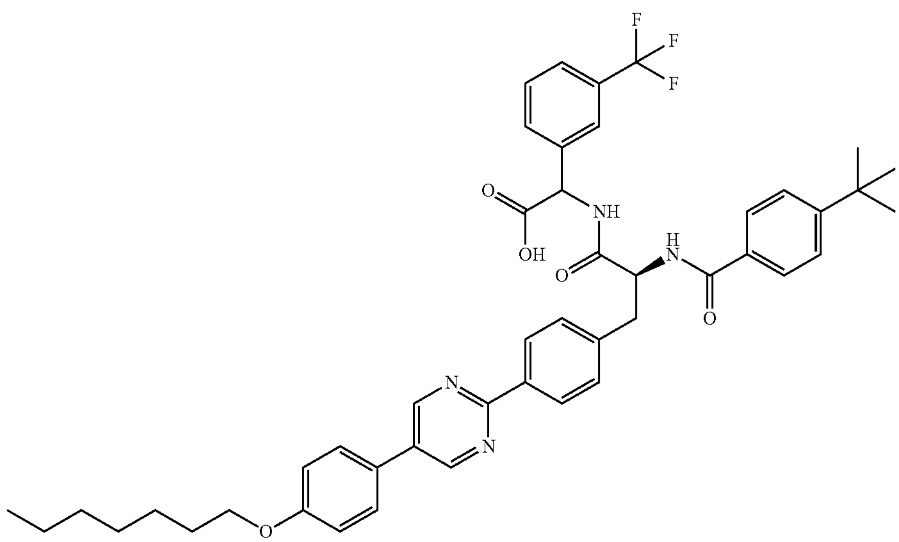 [SMILES: CCCCCCCOc1ccc(-c2cnc(-c3ccc(C[C@H](NC(=O)c4ccc(C(C)(C)C)cc4)C(=O)NC(C(=O)O)c4cccc(C(F)(F)F)c4)cc3)nc2)cc1] | 545 | 10.40 | 10 |
| 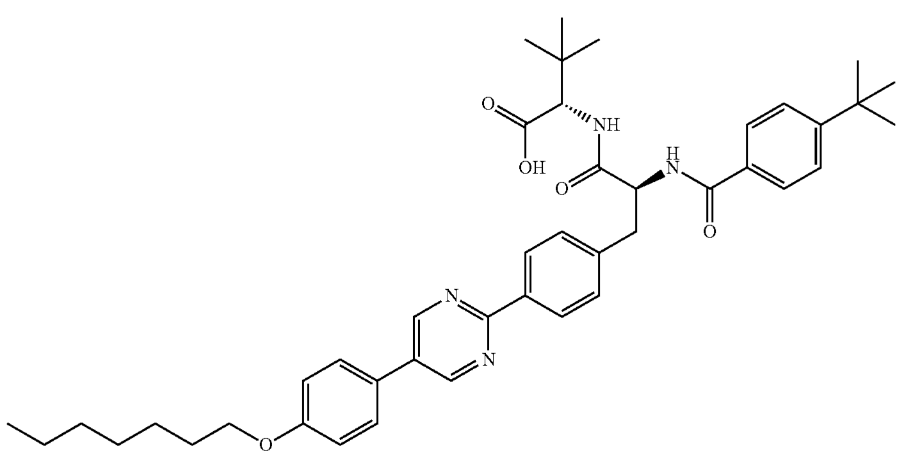 [SMILES: CCCCCCCOc1ccc(-c2cnc(-c3ccc(C[C@H](NC(=O)c4ccc(C(C)(C)C)cc4)C(=O)N[C@H](C(=O)O)C(C)(C)C)cc3)nc2)cc1] | 546 | 10.21 | 10 |

TABLE 1-continued

| STRUCTURE | COMPOUND NUMBER | LCMS RETENTION TIME (min) | PURITY METHOD |
|---|---|---|---|
| 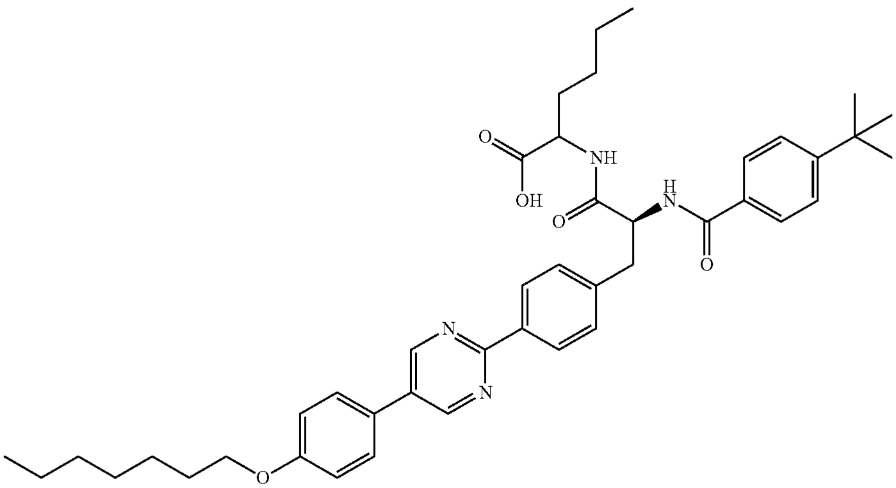 [SMILES: CCCCCCCOc1ccc(-c2cnc(-c3ccc(C[C@H](NC(=O)c4ccc(C(C)(C)C)cc4)C(=O)NC(CCCC)C(=O)O)cc3)nc2)cc1] | 547 | 10.14 | 10 |
| 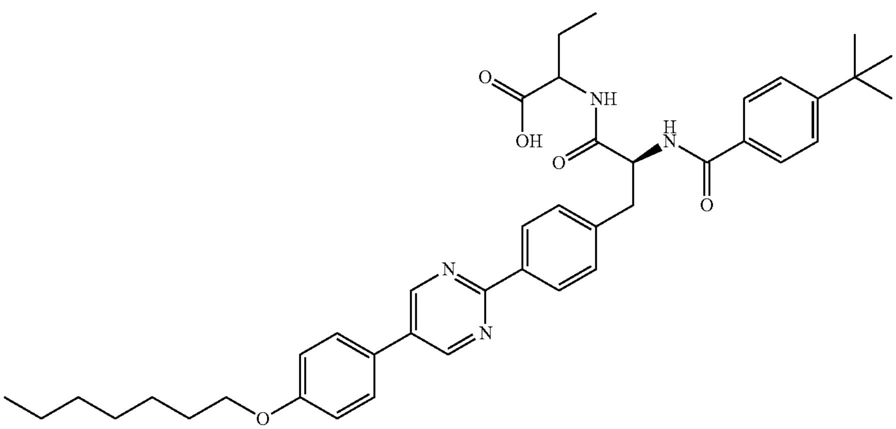 [SMILES: CCCCCCCOc1ccc(-c2cnc(-c3ccc(C[C@H](NC(=O)c4ccc(C(C)(C)C)cc4)C(=O)NC(CC)C(=O)O)cc3)nc2)cc1] | 548 | 10.94 | 10 |
| 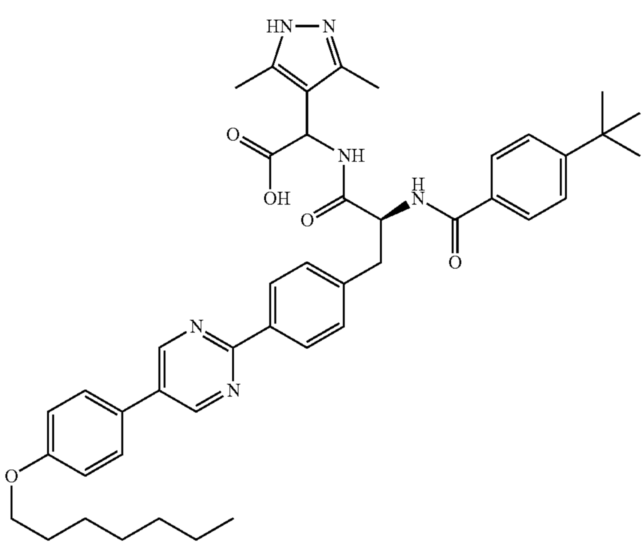 [SMILES: CCCCCCCOc1ccc(-c2cnc(-c3ccc(C[C@H](NC(=O)c4ccc(C(C)(C)C)cc4)C(=O)NC(C(=O)O)c4c(C)n[nH]c4C)cc3)nc2)cc1] | 549 | 9.75 | 10 |

TABLE 1-continued
| STRUCTURE | COMPOUND NUMBER | LCMS RETENTION TIME (min) | PURITY METHOD |
|---|---|---|---|
| 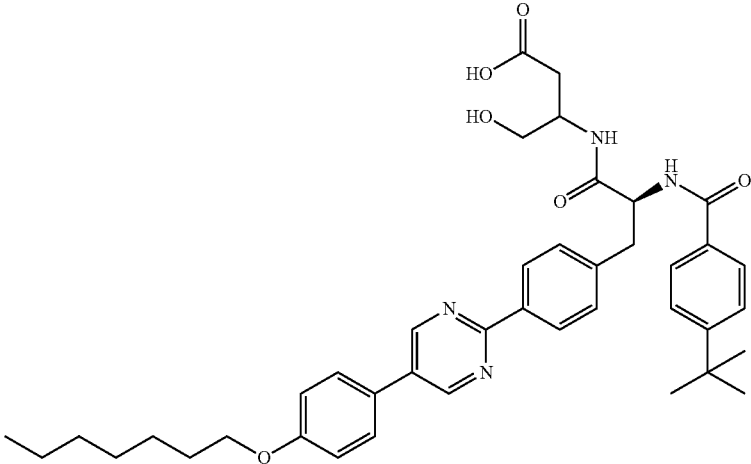 [SMILES: CCCCCCCOc1ccc(-c2cnc(-c3ccc(C[C@H](NC(=O)c4ccc(C(C)(C)C)cc4)C(=O)NC(CO)CC(=O)O)cc3)nc2)cc1] | 550 | 10.08 | 14 |
| 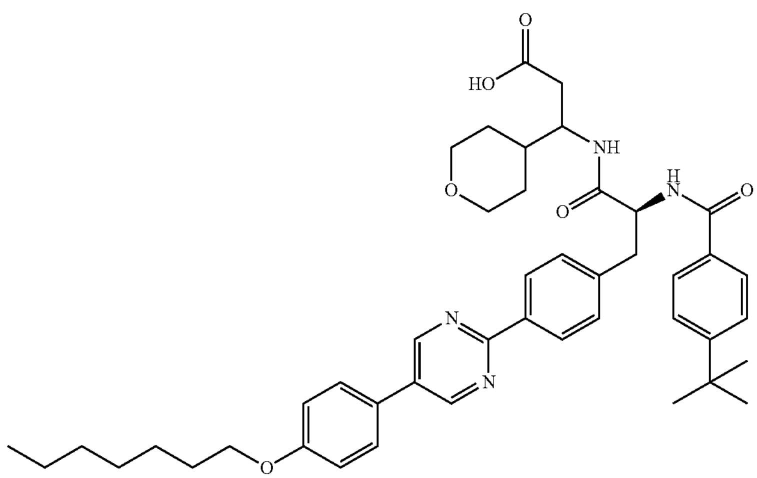 [SMILES: CCCCCCCOc1ccc(-c2cnc(-c3ccc(C[C@H](NC(=O)c4ccc(C(C)(C)C)cc4)C(=O)NC(CC(=O)O)C4CCOCC4)cc3)nc2)cc1] | 551 | 10.56 | 14 |
| 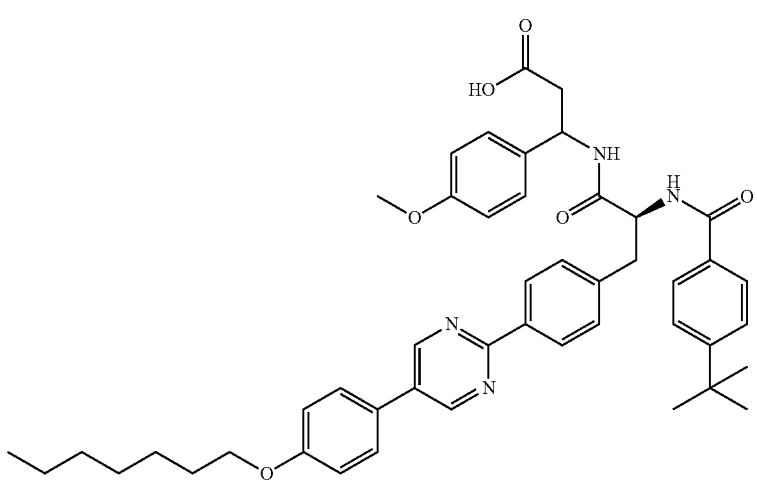 [SMILES: CCCCCCCOc1ccc(-c2cnc(-c3ccc(C[C@H](NC(=O)c4ccc(C(C)(C)C)cc4)C(=O)NC(CC(=O)O)c4ccc(OC)cc4)cc3)nc2)cc1] | 552 | 10.15 | 14 |

TABLE 1-continued

| STRUCTURE | COMPOUND NUMBER | LCMS RETENTION TIME (min) | PURITY METHOD |
|---|---|---|---|
| 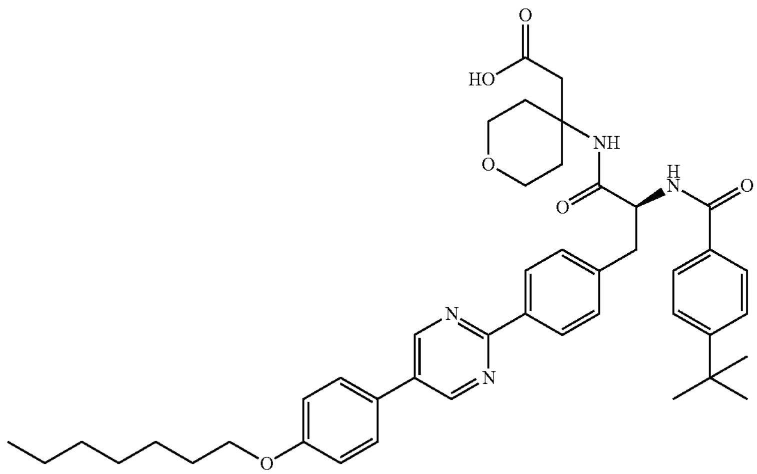 [SMILES: CCCCCCCOc1ccc(-c2cnc(-c3ccc(C[C@H](NC(=O)c4ccc(C(C)(C)C)cc4)C(=O)NC4(CC(=O)O)CCOCC4)cc3)nc2)cc1] | 553 | 10.01 | 14 |
| 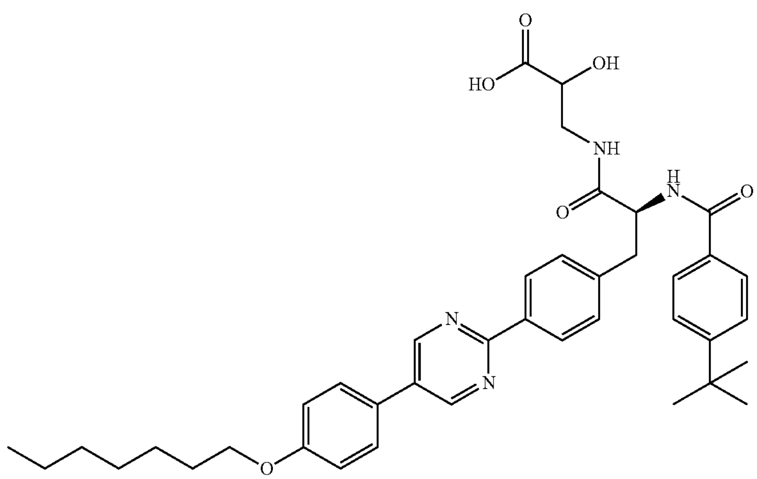 [SMILES: CCCCCCCOc1ccc(-c2cnc(-c3ccc(C[C@H](NC(=O)c4ccc(C(C)(C)C)cc4)C(=O)NCC(O)C(=O)O)cc3)nc2)cc1] | 554 | 9.91 | 14 |
| 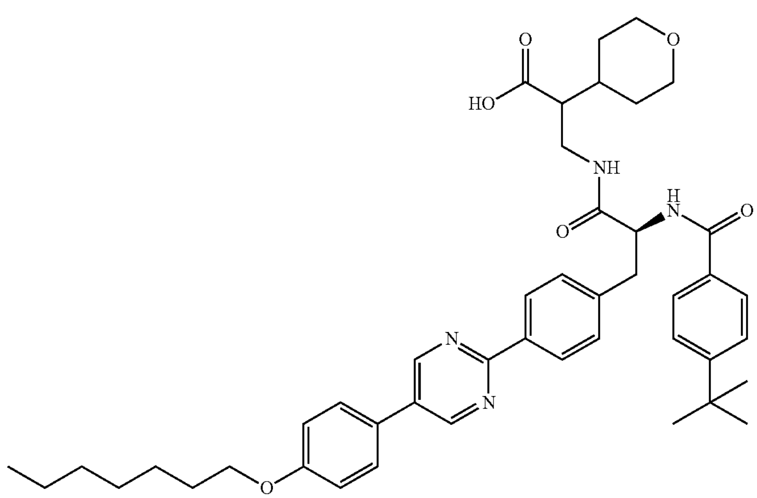 [SMILES: CCCCCCCOc1ccc(-c2cnc(-c3ccc(C[C@H](NC(=O)c4ccc(C(C)(C)C)cc4)C(=O)NCC(C(=O)O)C4CCOCC4)cc3)nc2)cc1] | 555 | 10.44 | 14 |

TABLE 1-continued
| STRUCTURE | COMPOUND NUMBER | LCMS RETENTION TIME (min) | PURITY METHOD |
|---|---|---|---|
| 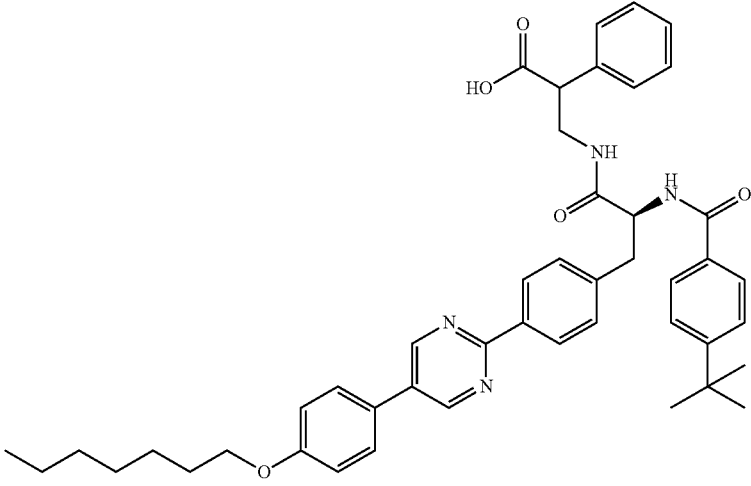 [SMILES: CCCCCCCOc1ccc(-c2cnc(-c3ccc(C[C@H](NC(=O)c4ccc(C(C)(C)C)cc4)C(=O)NCC(C(=O)O)c4ccccc4)cc3)nc2)cc1] | 556 | 10.94 | 14 |
| 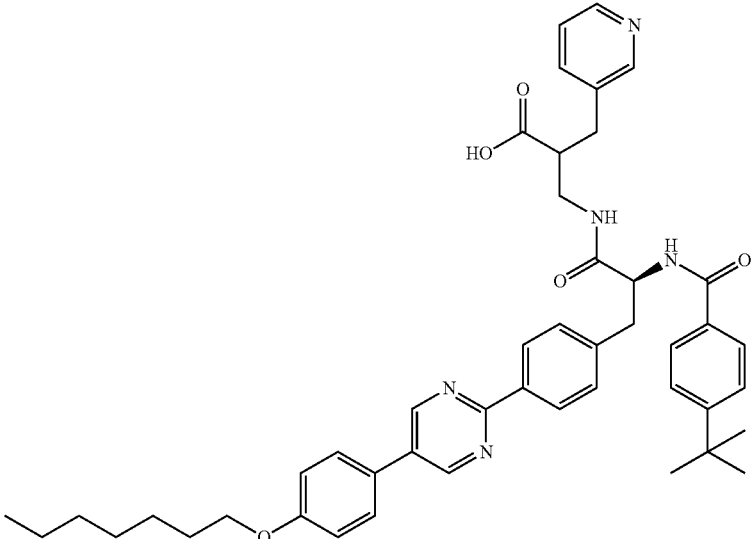 | 557 | 10.16 | 14 |

TABLE 1-continued
| STRUCTURE | COMPOUND NUMBER | LCMS RETENTION TIME (min) | PURITY METHOD |
|---|---|---|---|
| 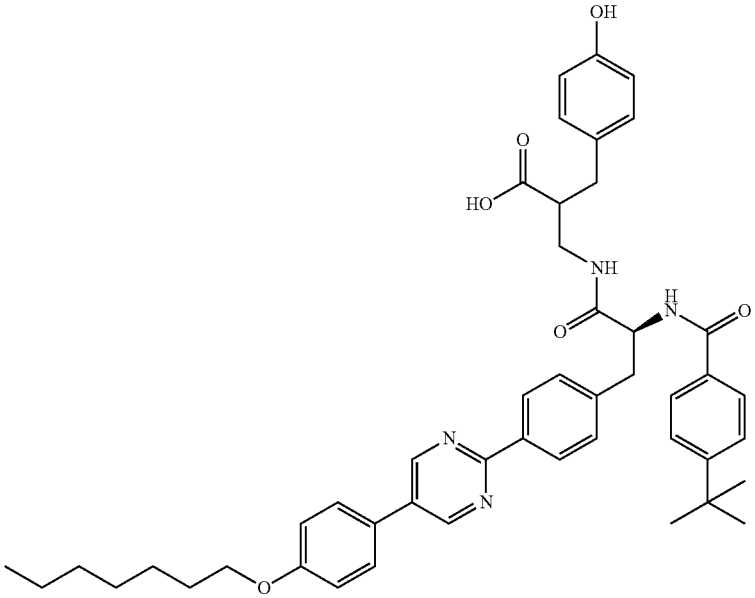 [SMILES: CCCCCCCOc1ccc(-c2cnc(-c3ccc(C[C@H](NC(=O)c4ccc(C(C)(C)C)cc4)C(=O)NCC(Cc4ccc(O)cc4)C(=O)O)cc3)nc2)cc1] | 558 | 10.66 | 14 |
| 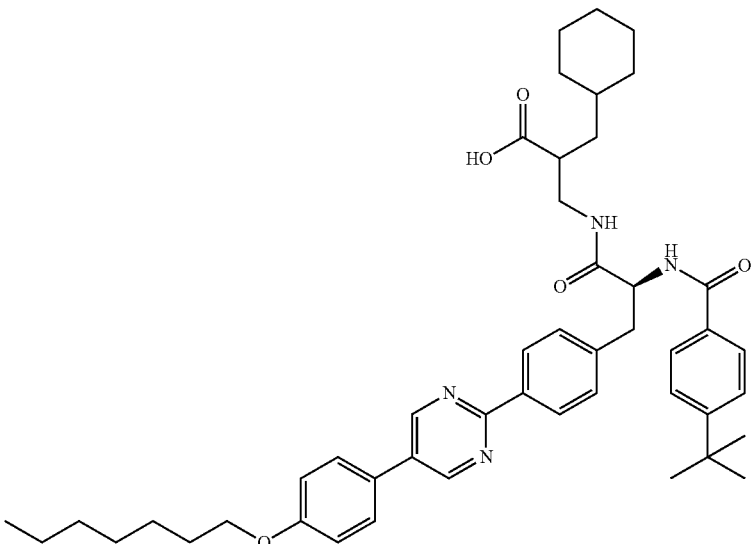 | 559 | 10.69 | 14 |

TABLE 1-continued
| STRUCTURE | COMPOUND NUMBER | LCMS RETENTION TIME (min) | PURITY METHOD |
|---|---|---|---|
| 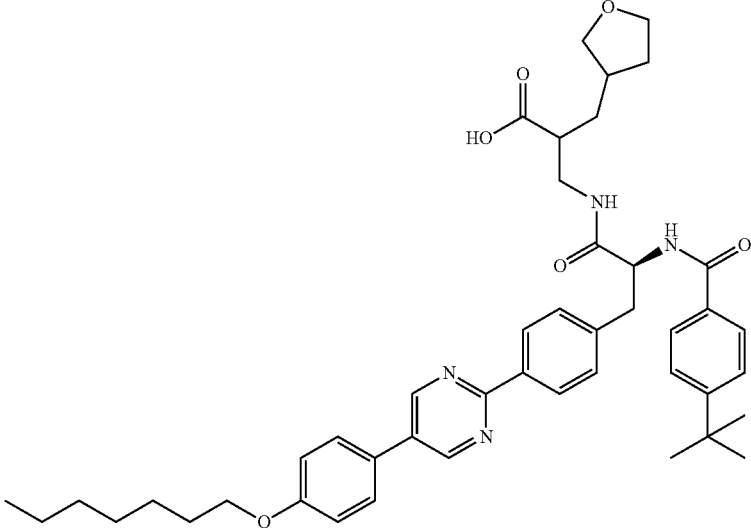 [SMILES: CCCCCCCOc1ccc(-c2cnc(-c3ccc(C[C@H](NC(=O)c4ccc(C(C)(C)C)cc4)C(=O)NCC(CC4CCOC4)C(=O)O)cc3)nc2)cc1] | 560 | 10.41 | 14 |
| 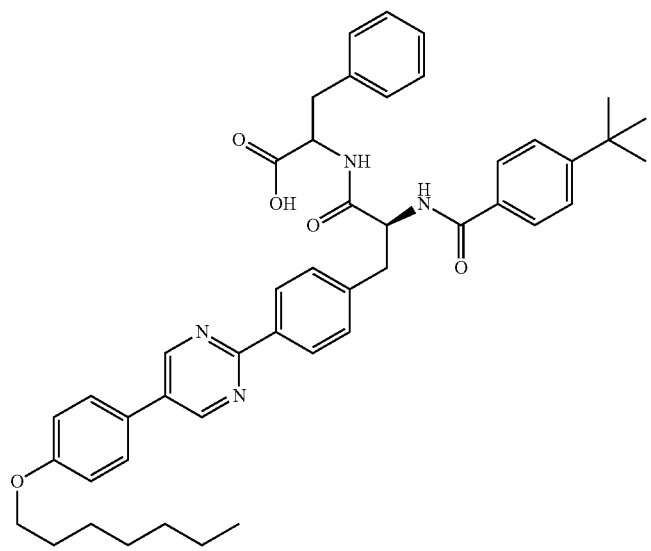 [SMILES: CCCCCCCOc1ccc(-c2cnc(-c3ccc(C[C@H](NC(=O)c4ccc(C(C)(C)C)cc4)C(=O)NC(Cc4ccccc4)C(=O)O)cc3)nc2)cc1] | 561 | 10.24 | 10 |

TABLE 1-continued
| STRUCTURE | COMPOUND NUMBER | LCMS RETENTION TIME (min) | PURITY METHOD |
|---|---|---|---|
| 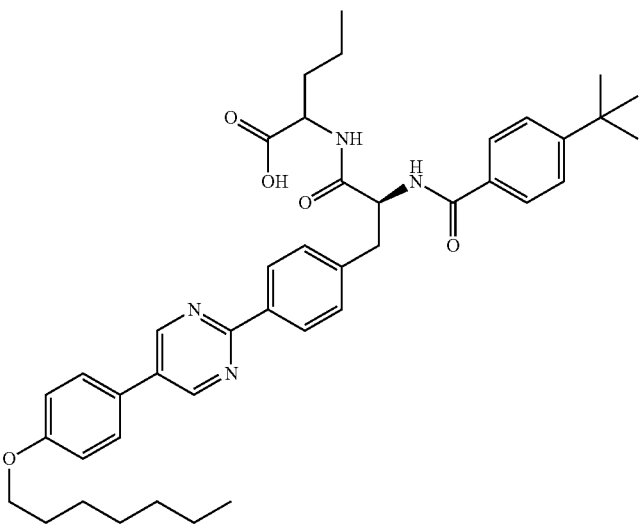 [SMILES: CCCCCCCOc1ccc(-c2cnc(-c3ccc(C[C@H](NC(=O)c4ccc(C(C)(C)C)cc4)C(=O)NC(CCC)C(=O)O)cc3)nc2)cc1] | 562 | 10.98 | 10 |
| 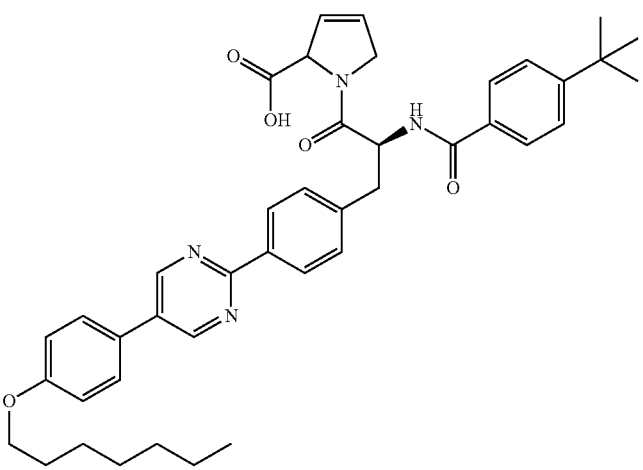 [SMILES: CCCCCCCOc1ccc(-c2cnc(-c3ccc(C[C@H](NC(=O)c4ccc(C(C)(C)C)cc4)C(=O)N4CC=CC4C(=O)O)cc3)nc2)cc1] | 563 | 10.71 | 10 |

TABLE 1-continued
| STRUCTURE | COMPOUND NUMBER | LCMS RETENTION TIME (min) | PURITY METHOD |
|---|---|---|---|
| 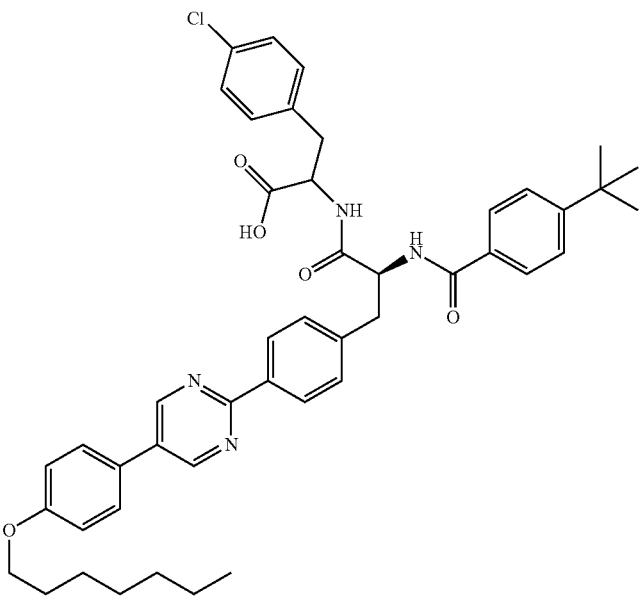 [SMILES: CCCCCCCOc1ccc(-c2cnc(-c3ccc(C[C@H](NC(=O)c4ccc(C(C)(C)C)cc4)C(=O)NC(Cc4ccc(Cl)cc4)C(=O)O)cc3)nc2)cc1] | 564 | 10.62 | 10 |
| 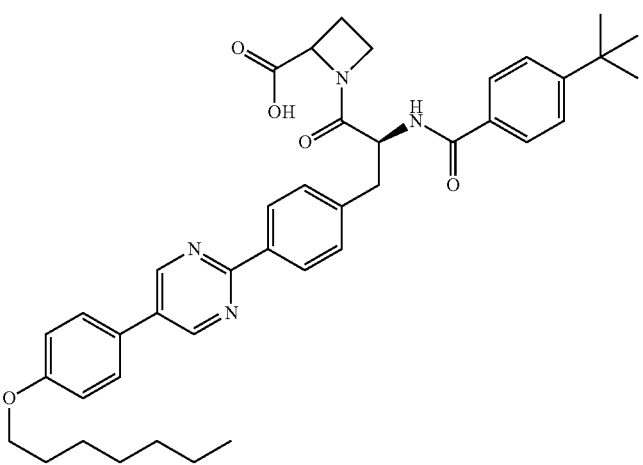 [SMILES: CCCCCCCOc1ccc(-c2cnc(-c3ccc(C[C@H](NC(=O)c4ccc(C(C)(C)C)cc4)C(=O)N4CCC4C(=O)O)cc3)nc2)cc1] | 565 | 10.50 | 10 |

TABLE 1-continued

| STRUCTURE | COMPOUND NUMBER | LCMS RETENTION TIME (min) | PURITY METHOD |
|---|---|---|---|
| 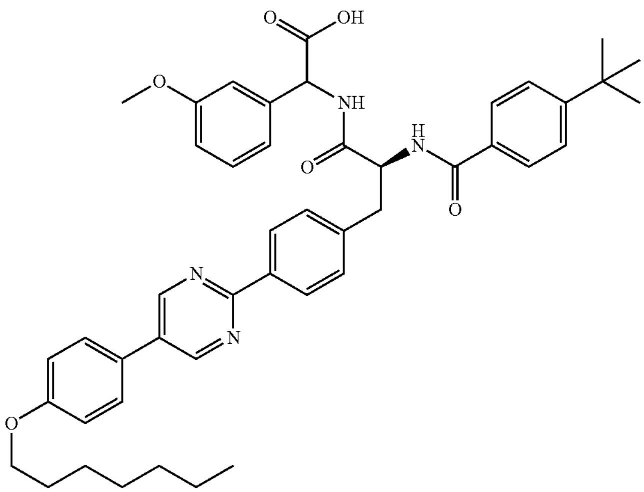 [SMILES: CCCCCCCOc1ccc(-c2cnc(-c3ccc(C[C@H](NC(=O)c4ccc(C(C)(C)C)cc4)C(=O)NC(C(=O)O)c4cccc(OC)c4)cc3)nc2)cc1] | 566 | 10.13 | 10 |
| 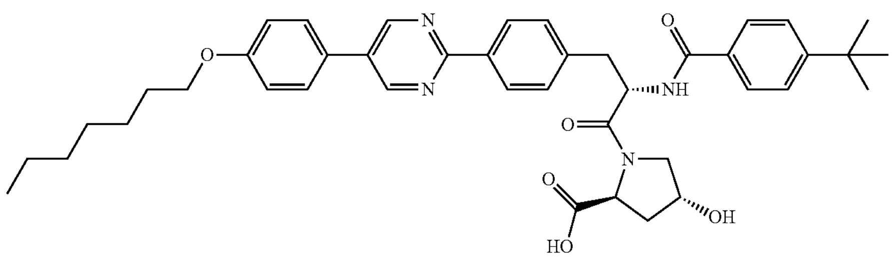 [SMILES: CCCCCCCOc1ccc(-c2cnc(-c3ccc(C[C@H](NC(=O)c4ccc(C(C)(C)C)cc4)C(=O)N4C[C@H](O)C[C@H]4C(=O)O)cc3)nc2)cc1] | 567 | 9.91 | 10 |
| 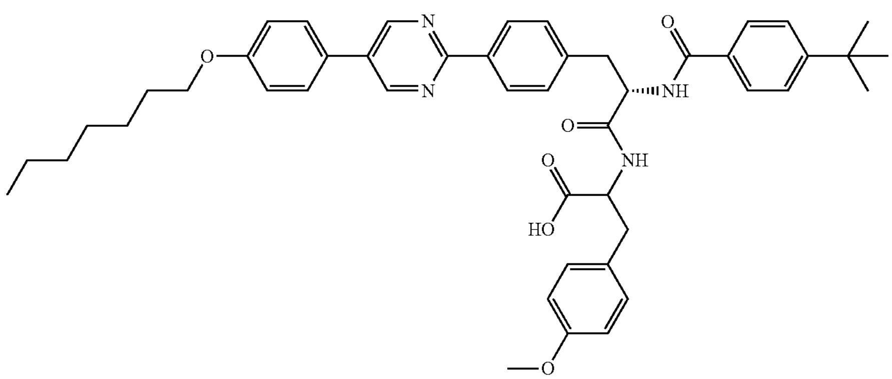 [SMILES: CCCCCCCOc1ccc(-c2cnc(-c3ccc(C[C@H](NC(=O)c4ccc(C(C)(C)C)cc4)C(=O)NC(Cc4ccc(OC)cc4)C(=O)O)cc3)nc2)cc1] | 568 | 10.15 | 10 |
| 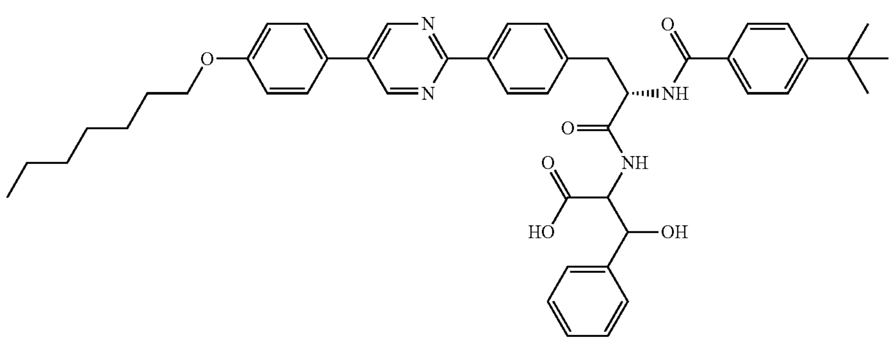 [SMILES: CCCCCCCOc1ccc(-c2cnc(-c3ccc(C[C@H](NC(=O)c4ccc(C(C)(C)C)cc4)C(=O)NC(C(=O)O)C(O)c4ccccc4)cc3)nc2)cc1] | 569 | 10.79 | 10 |

TABLE 1-continued

| STRUCTURE | COMPOUND NUMBER | LCMS RETENTION TIME (min) | PURITY METHOD |
|---|---|---|---|
| 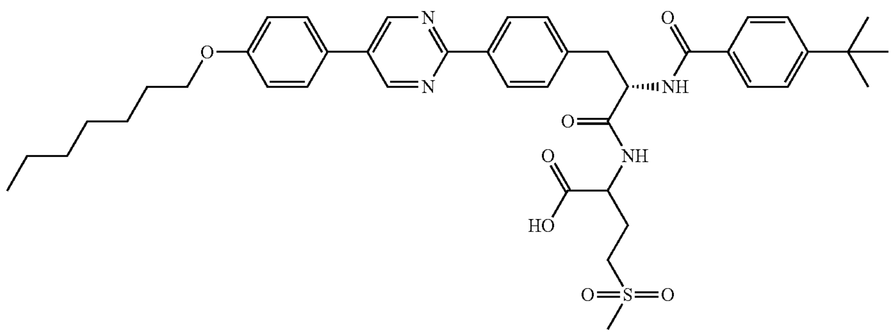 [SMILES: CCCCCCCOc1ccc(-c2cnc(-c3ccc(C[C@H](NC(=O)c4ccc(C(C)(C)C)cc4)C(=O)NC(CCS(C)(=O)=O)C(=O)O)cc3)nc2)cc1] | 570 | 10.90 | 10 |
| 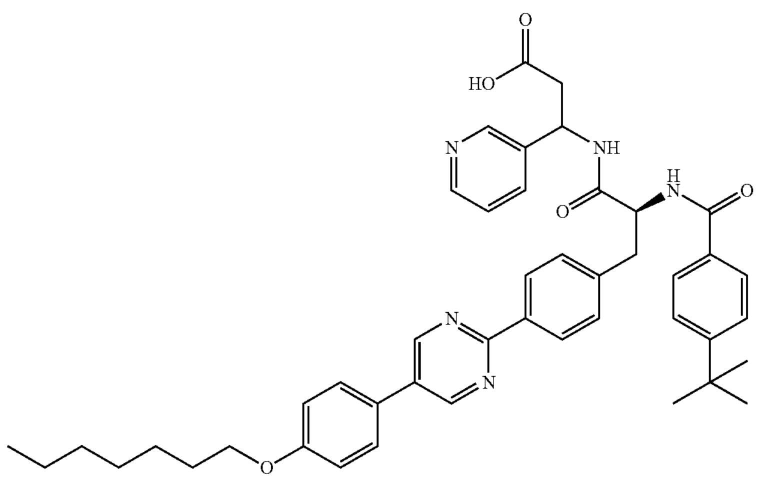 [SMILES: CCCCCCCOc1ccc(-c2cnc(-c3ccc(C[C@H](NC(=O)c4ccc(C(C)(C)C)cc4)C(=O)NC(CC(=O)O)c4cccnc4)cc3)nc2)cc1] | 571 | 10.22 | 14 |
| 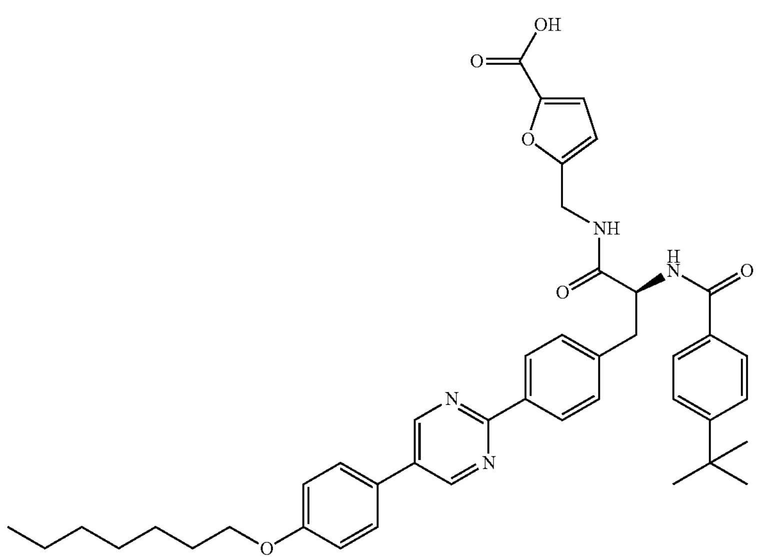 [SMILES: CCCCCCCOc1ccc(-c2cnc(-c3ccc(C[C@H](NC(=O)c4ccc(C(C)(C)C)cc4)C(=O)NCc4ccc(C(=O)O)o4)cc3)nc2)cc1] | 572 | 10.35 | 14 |

TABLE 1-continued
| STRUCTURE | COMPOUND NUMBER | LCMS RETENTION TIME (min) | PURITY METHOD |
|---|---|---|---|
| 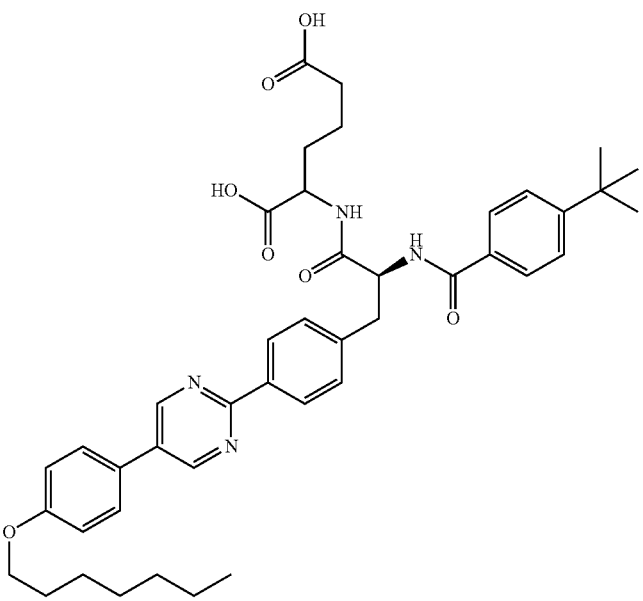 [SMILES: CCCCCCCOc1ccc(-c2cnc(-c3ccc(C[C@H](NC(=O)c4ccc(C(C)(C)C)cc4)C(=O)NC(CCCC(=O)O)C(=O)O)cc3)nc2)cc1] | 573 | 10.05 | 10 |
| 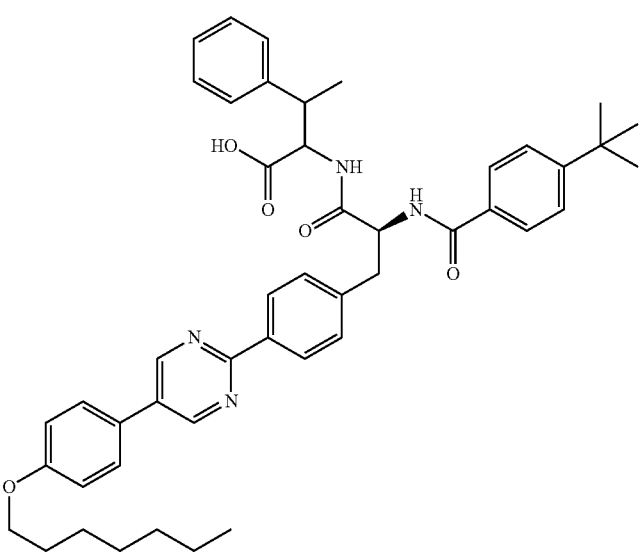 [SMILES: CCCCCCCOc1ccc(-c2cnc(-c3ccc(C[C@H](NC(=O)c4ccc(C(C)(C)C)cc4)C(=O)NC(C(=O)O)C(C)c4ccccc4)cc3)nc2)cc1] | 574 | 11.47 | 10 |

TABLE 1-continued
| STRUCTURE | COMPOUND NUMBER | LCMS RETENTION TIME (min) | PURITY METHOD |
|---|---|---|---|
| 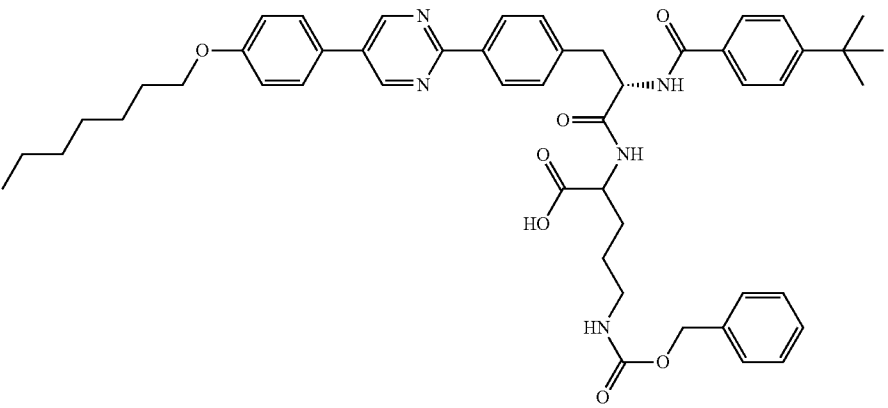 [SMILES: CCCCCCCOc1ccc(-c2cnc(-c3ccc(C[C@H](NC(=O)c4ccc(C(C)(C)C)cc4)C(=O)NC(CCCNC(=O)OCc4ccccc4)C(=O)O)cc3)nc2)cc1] | 575 | 10.02 | 10 |
| 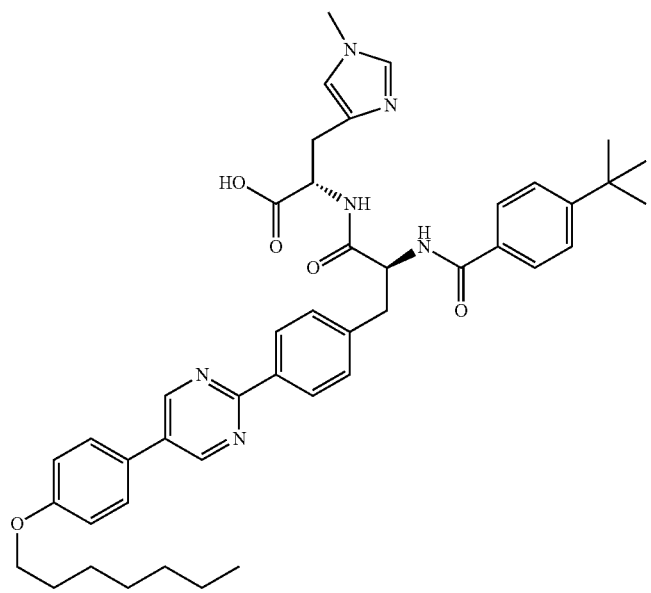 [SMILES: CCCCCCCOc1ccc(-c2cnc(-c3ccc(C[C@H](NC(=O)c4ccc(C(C)(C)C)cc4)C(=O)N[C@@H](Cc4cn(C)cn4)C(=O)O)cc3)nc2)cc1] | 576 | 9.09 | 10 |

TABLE 1-continued
| STRUCTURE | COMPOUND NUMBER | LCMS RETENTION TIME (min) | PURITY METHOD |
|---|---|---|---|
| 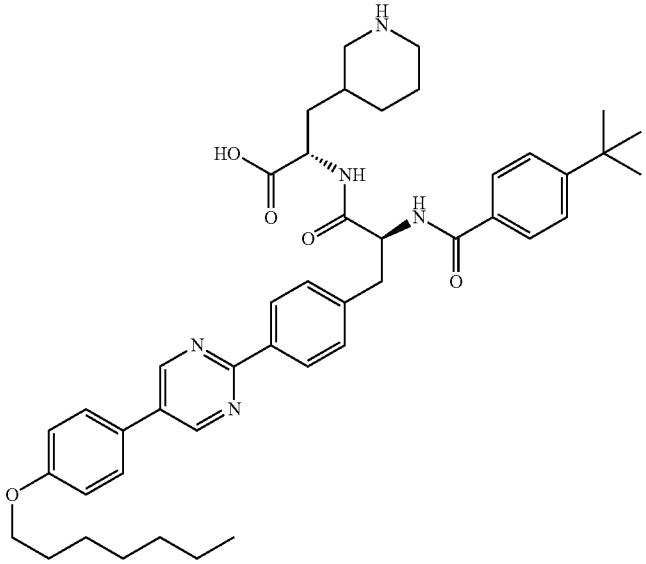 [SMILES: CCCCCCCOc1ccc(-c2cnc(-c3ccc(C[C@H](NC(=O)c4ccc(C(C)(C)C)cc4)C(=O)N[C@@H](CC4CCCNC4)C(=O)O)cc3)nc2)cc1] | 577 | 7.06 | 10 |
| 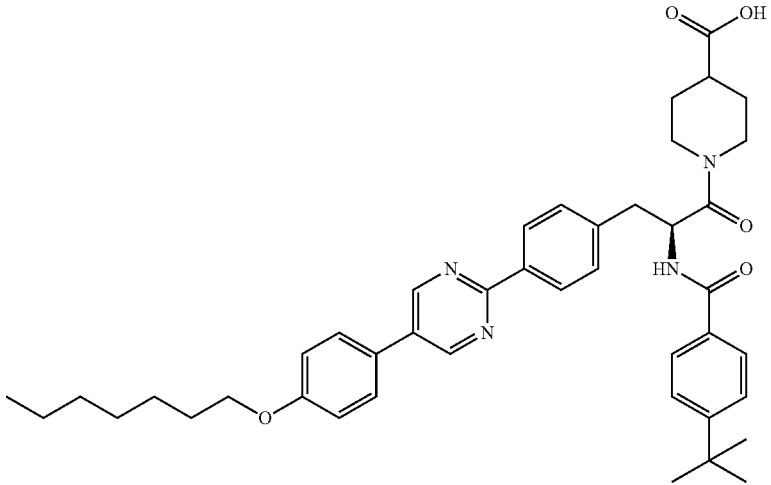 [SMILES: CCCCCCCOc1ccc(-c2cnc(-c3ccc(C[C@H](NC(=O)c4ccc(C(C)(C)C)cc4)C(=O)N4CCC(C(=O)O)CC4)cc3)nc2)cc1] | 578 | 10.11 | 14 |
| 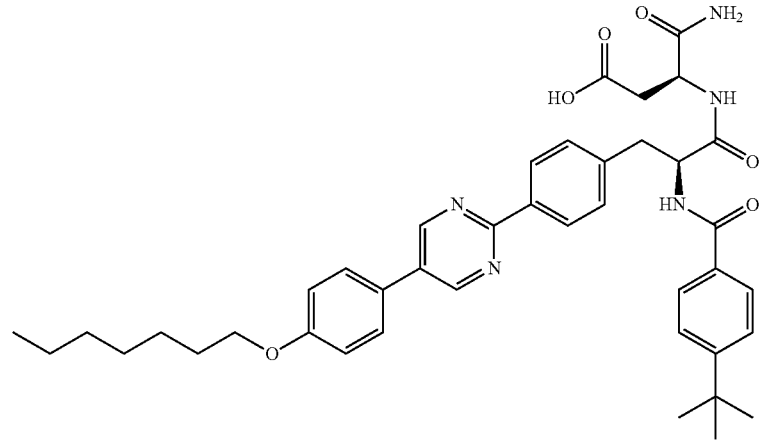 [SMILES: CCCCCCCOc1ccc(-c2cnc(-c3ccc(C[C@H](NC(=O)c4ccc(C(C)(C)C)cc4)C(=O)N[C@@H](CC(=O)O)C(N)=O)cc3)nc2)cc1] | 579 | 9.895 | 14 |

TABLE 1-continued

| STRUCTURE | COMPOUND NUMBER | LCMS RETENTION TIME (min) | PURITY METHOD |
|---|---|---|---|
| 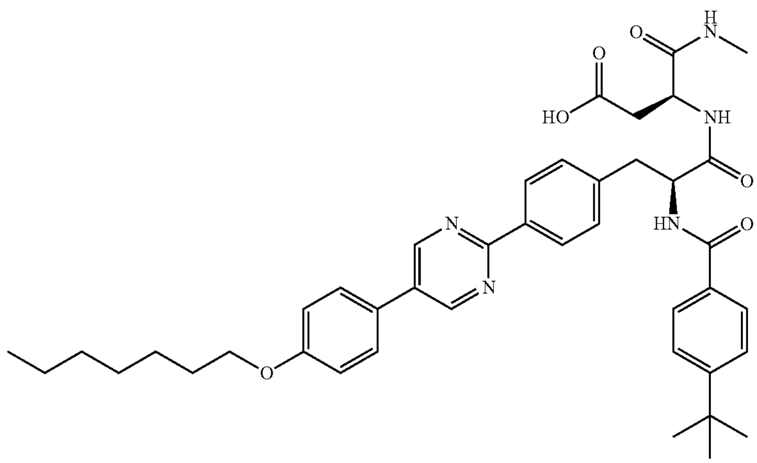 [SMILES: CCCCCCCOc1ccc(-c2cnc(-c3ccc(C[C@H](NC(=O)c4ccc(C(C)(C)C)cc4)C(=O)N[C@@H](CC(=O)O)C(=O)NC)cc3)nc2)cc1] | 580 | 10.064 | 14 |
| 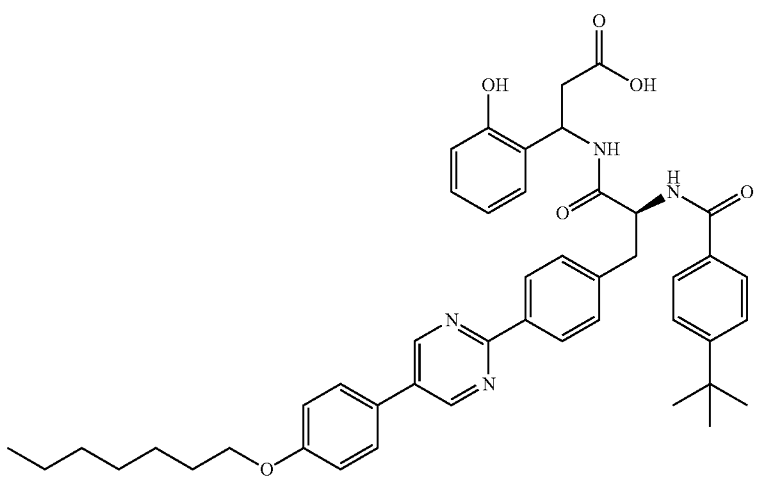 [SMILES: CCCCCCCOc1ccc(-c2cnc(-c3ccc(C[C@H](NC(=O)c4ccc(C(C)(C)C)cc4)C(=O)NC(CC(=O)O)c4ccccc4O)cc3)nc2)cc1] | 581 | 10.72 | 14 |
| 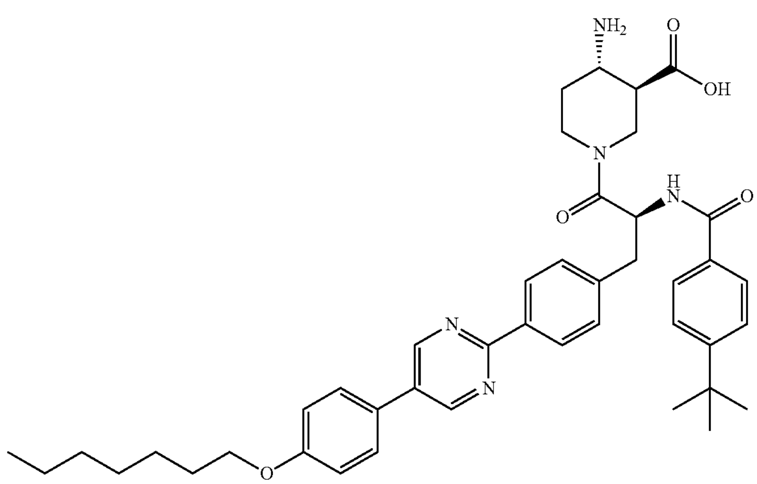 [SMILES: CCCCCCCOc1ccc(-c2cnc(-c3ccc(C[C@H](NC(=O)c4ccc(C(C)(C)C)cc4)C(=O)N4CC[C@H](N)[C@@H](C(=O)O)C4)cc3)nc2)cc1] | 582 | 10.23 | 14 |

TABLE 1-continued

| STRUCTURE | COMPOUND NUMBER | LCMS RETENTION TIME (min) | PURITY METHOD |
|---|---|---|---|
| 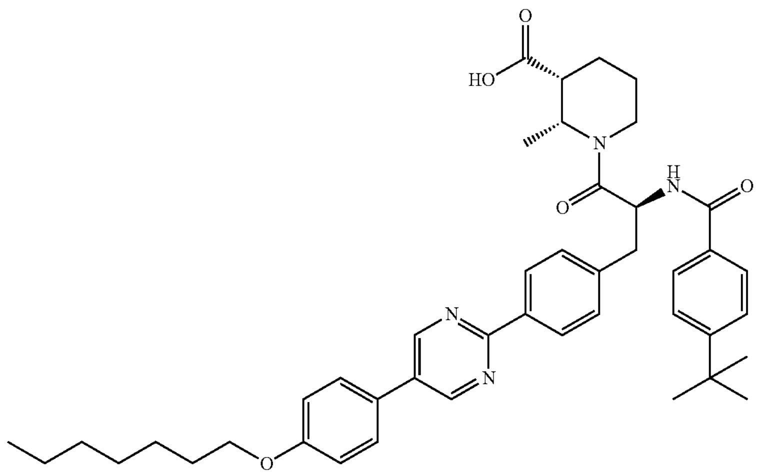 [SMILES: CCCCCCCOc1ccc(-c2cnc(-c3ccc(C[C@H](NC(=O)c4ccc(C(C)(C)C)cc4)C(=O)N4CCC[C@@H](C(=O)O)[C@H]4C)cc3)nc2)cc1] | 583 | 10.89 | 14 |
| 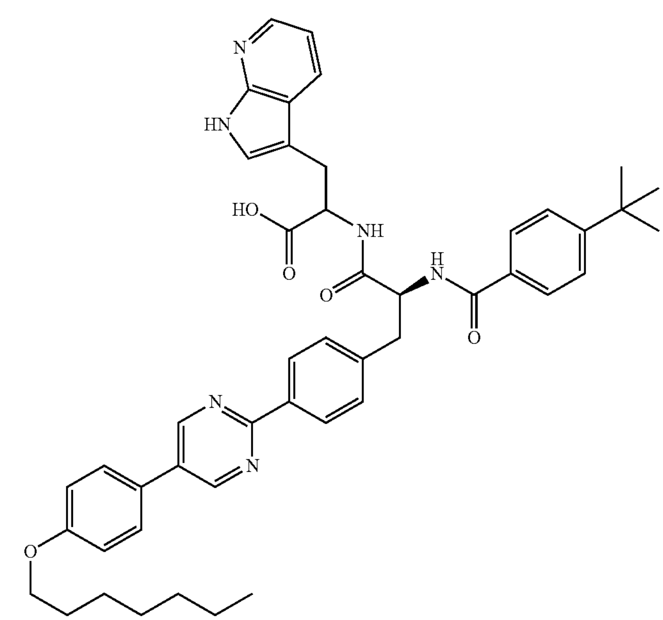 [SMILES: CCCCCCCOc1ccc(-c2cnc(-c3ccc(C[C@H](NC(=O)c4ccc(C(C)(C)C)cc4)C(=O)NC(Cc4c[nH]c5ncccc45)C(=O)O)cc3)nc2)cc1] | 584 | 9.60 | 10 |

TABLE 1-continued

| STRUCTURE | COMPOUND NUMBER | LCMS RETENTION TIME (min) | PURITY METHOD |
|---|---|---|---|
| 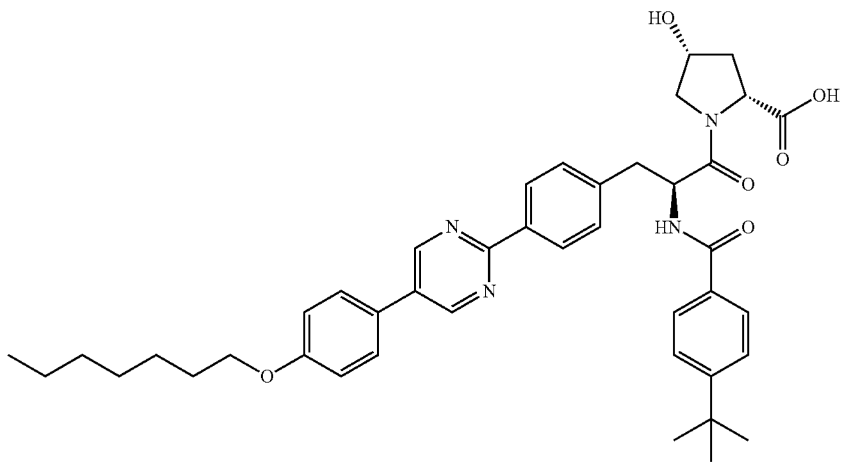 [SMILES: CCCCCCCOc1ccc(-c2cnc(-c3ccc(C[C@H](NC(=O)c4ccc(C(C)(C)C)cc4)C(=O)N4C[C@H](O)C[C@@H]4C(=O)O)cc3)nc2)cc1] | 585 | 10.03 | 10 |
| 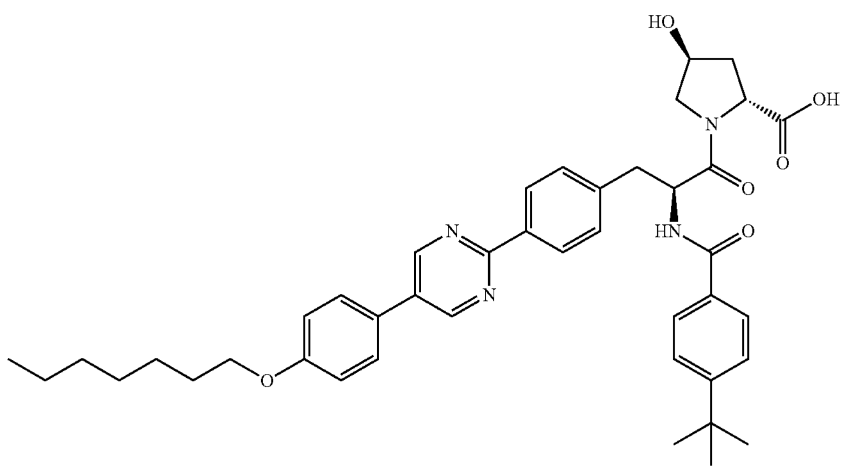 [SMILES: CCCCCCCOc1ccc(-c2cnc(-c3ccc(C[C@H](NC(=O)c4ccc(C(C)(C)C)cc4)C(=O)N4C[C@@H](O)C[C@@H]4C(=O)O)cc3)nc2)cc1] | 586 | 9.93 | 10 |
| 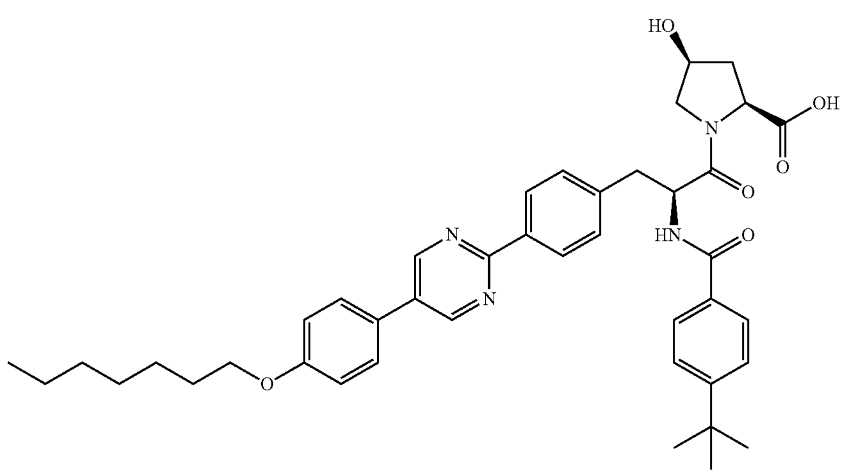 [SMILES: CCCCCCCOc1ccc(-c2cnc(-c3ccc(C[C@H](NC(=O)c4ccc(C(C)(C)C)cc4)C(=O)N4C[C@@H](O)C[C@H]4C(=O)O)cc3)nc2)cc1] | 587 | 10.01 | 10 |

TABLE 1-continued

| STRUCTURE | COMPOUND NUMBER | LCMS RETENTION TIME (min) | PURITY METHOD |
|---|---|---|---|
| 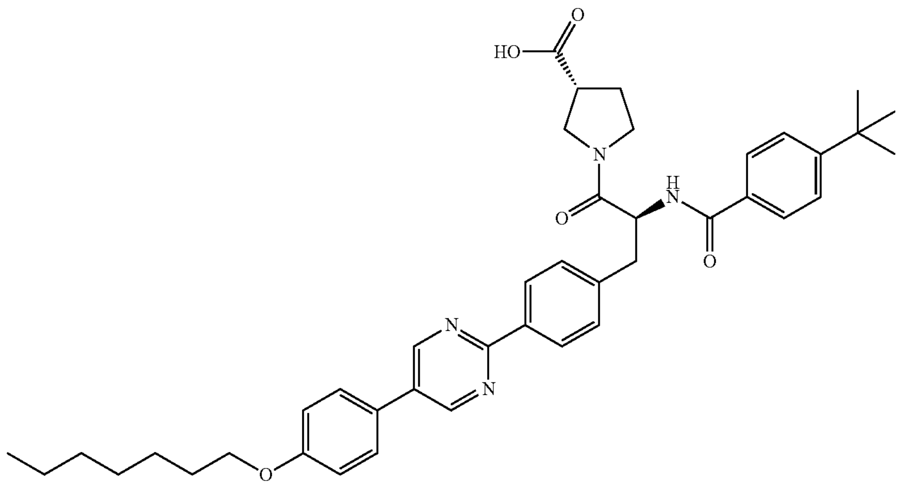 [SMILES: CCCCCCCOc1ccc(-c2cnc(-c3ccc(C[C@H](NC(=O)c4ccc(C(C)(C)C)cc4)C(=O)N4CC[C@@H](C(=O)O)C4)cc3)nc2)cc1] | 588 | 10.14 | 14 |
| 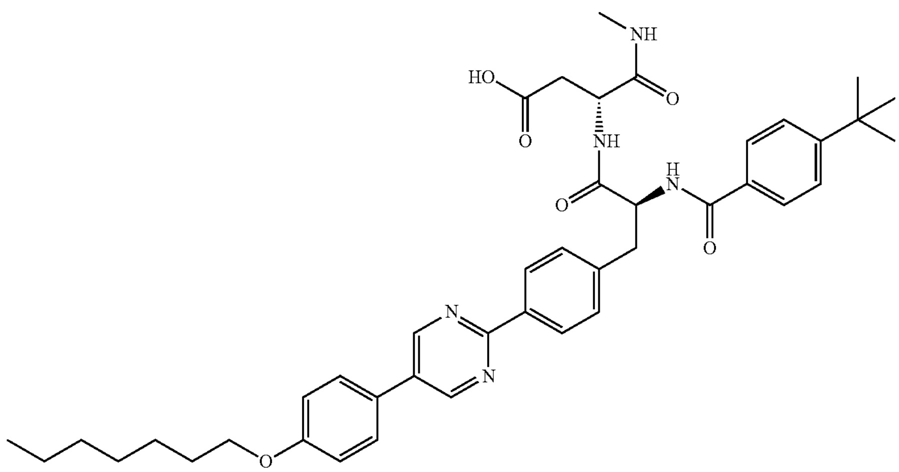 [SMILES: CCCCCCCOc1ccc(-c2cnc(-c3ccc(C[C@H](NC(=O)c4ccc(C(C)(C)C)cc4)C(=O)N[C@H](CC(=O)O)C(=O)NC)cc3)nc2)cc1] | 589 | 9.77 | 14 |
| 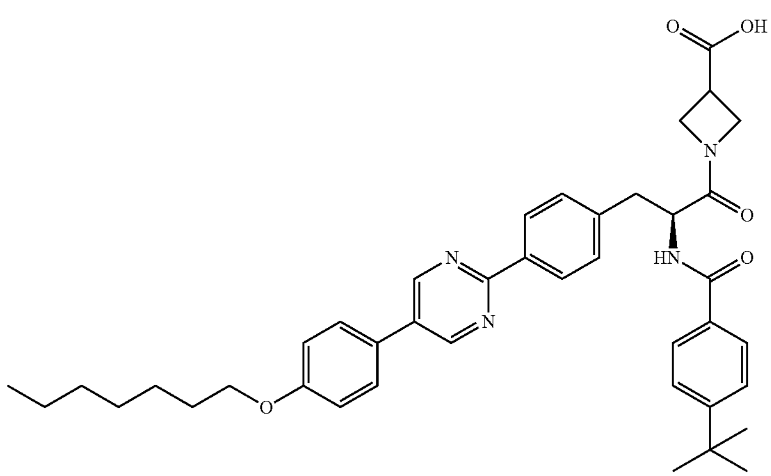 [SMILES: CCCCCCCOc1ccc(-c2cnc(-c3ccc(C[C@H](NC(=O)c4ccc(C(C)(C)C)cc4)C(=O)N4CC(C(=O)O)C4)cc3)nc2)cc1] | 590 | 10.23 | 10 |

| STRUCTURE | COMPOUND NUMBER | LCMS RETENTION TIME (min) | PURITY METHOD |
|---|---|---|---|
| 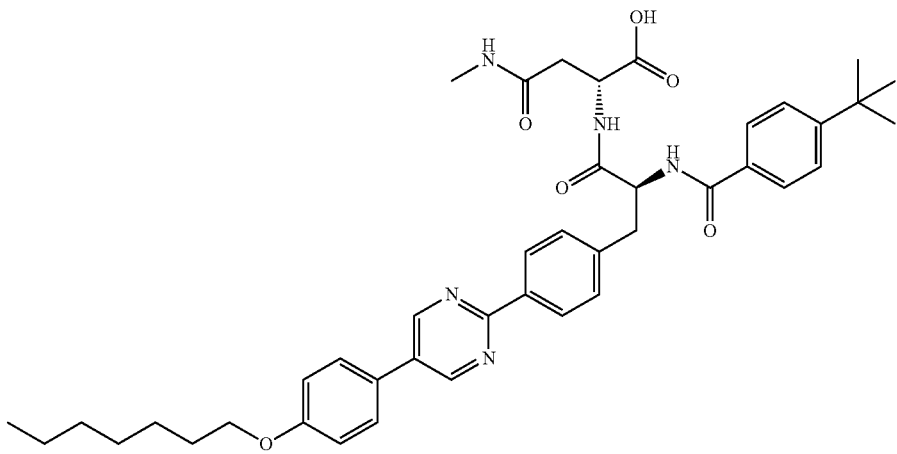 [SMILES: CCCCCCCOc1ccc(-c2cnc(-c3ccc(C[C@H](NC(=O)c4ccc(C(C)(C)C)cc4)C(=O)N[C@H](CC(=O)NC)C(=O)O)cc3)nc2)cc1] | 591 | 9.83 | 14 |
| 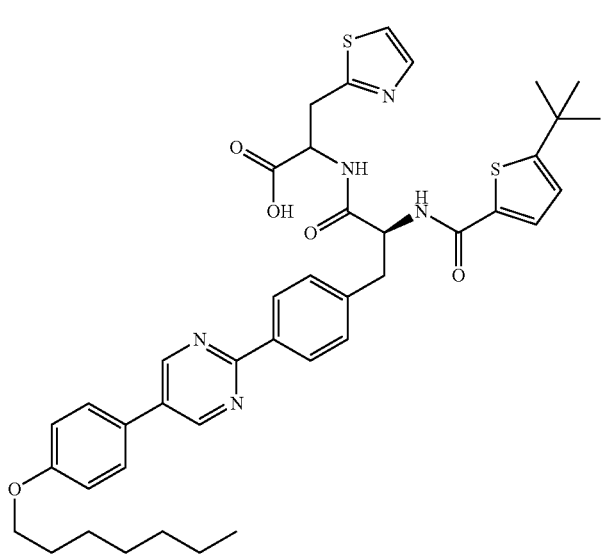 [SMILES: CCCCCCCOc1ccc(-c2cnc(-c3ccc(C[C@H](NC(=O)c4ccc(C(C)(C)C)s4)C(=O)NC(Cc4nccs4)C(=O)O)cc3)nc2)cc1] | 592 | 10.41 | 10 |

TABLE 1-continued
| STRUCTURE | COMPOUND NUMBER | LCMS RETENTION TIME (min) | PURITY METHOD |
|---|---|---|---|
| 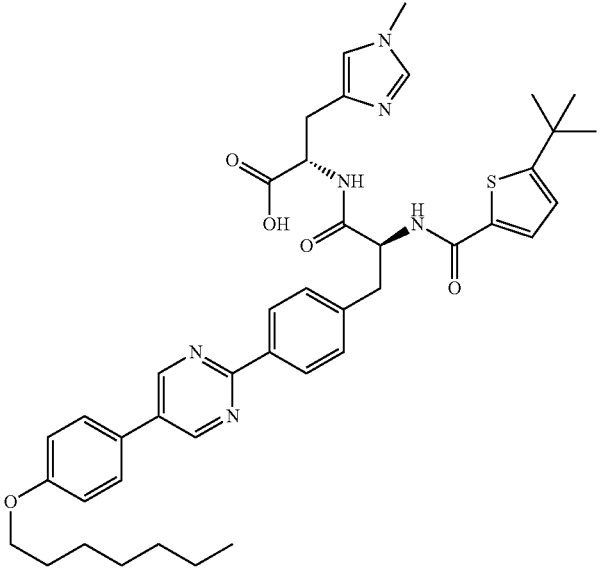 [SMILES: CCCCCCCOc1ccc(-c2cnc(-c3ccc(C[C@H](NC(=O)c4ccc(C(C)(C)C)s4)C(=O)N[C@@H](Cc4cn(C)cn4)C(=O)O)cc3)nc2)cc1] | 593 | 7.80 | 10 |
| 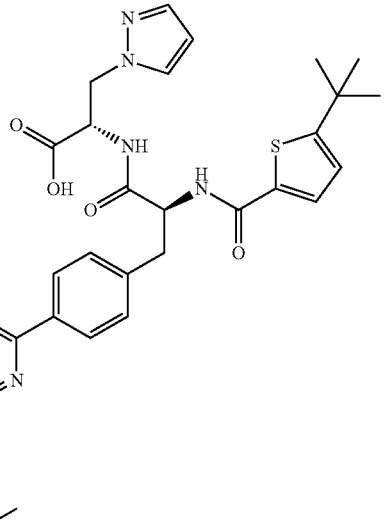 | 594 | 10.38 | 9 |

TABLE 1-continued
| STRUCTURE | COMPOUND NUMBER | LCMS RETENTION TIME (min) | PURITY METHOD |
|---|---|---|---|
| 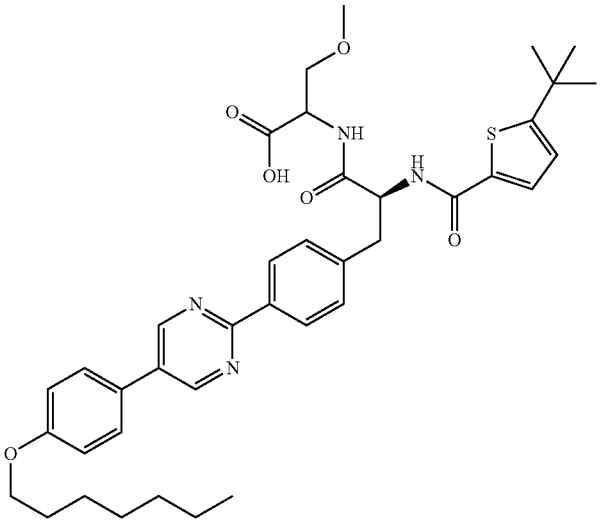 [SMILES: CCCCCCCOc1ccc(-c2cnc(-c3ccc(C[C@H](NC(=O)c4ccc(C(C)(C)C)s4)C(=O)NC(COC)C(=O)O)cc3)nc2)cc1] | 595 | 10.34 | 9 |
| 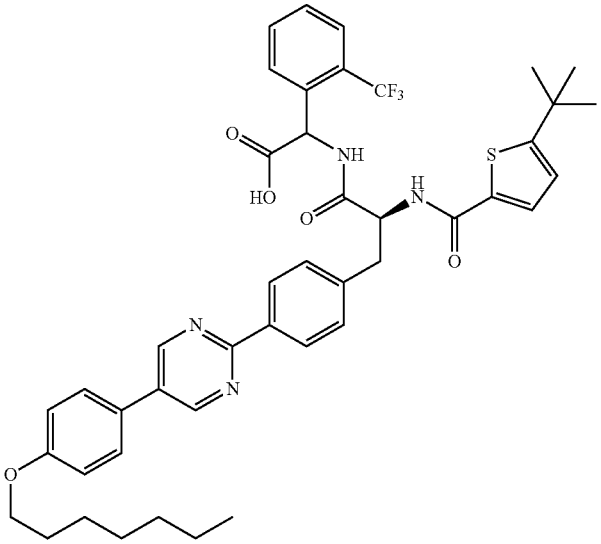 [SMILES: CCCCCCCOc1ccc(-c2cnc(-c3ccc(C[C@H](NC(=O)c4ccc(C(C)(C)C)s4)C(=O)NC(C(=O)O)c4ccccc4C(F)(F)F)cc3)nc2)cc1] | 596 | 10.27 | 9 |

TABLE 1-continued
| STRUCTURE | COMPOUND NUMBER | LCMS RETENTION TIME (min) | PURITY METHOD |
|---|---|---|---|
| 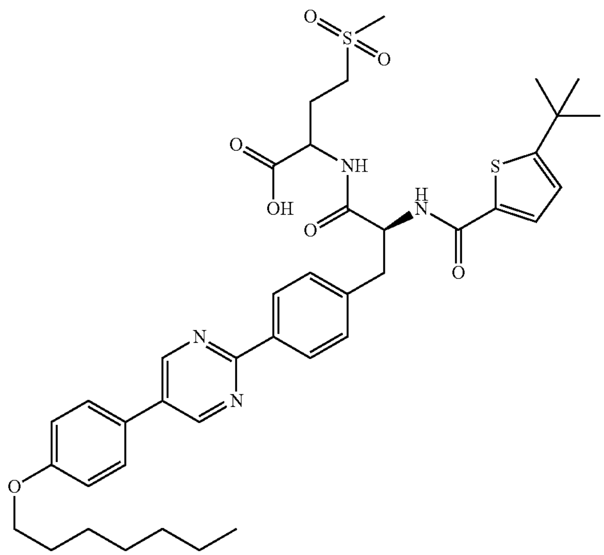 [SMILES: CCCCCCCOc1ccc(-c2cnc(-c3ccc(C[C@H](NC(=O)c4ccc(C(C)(C)C)s4)C(=O)NC(CCS(C)(=O)=O)C(=O)O)cc3)nc2)cc1] | 597 | 9.95 | 9 |
| 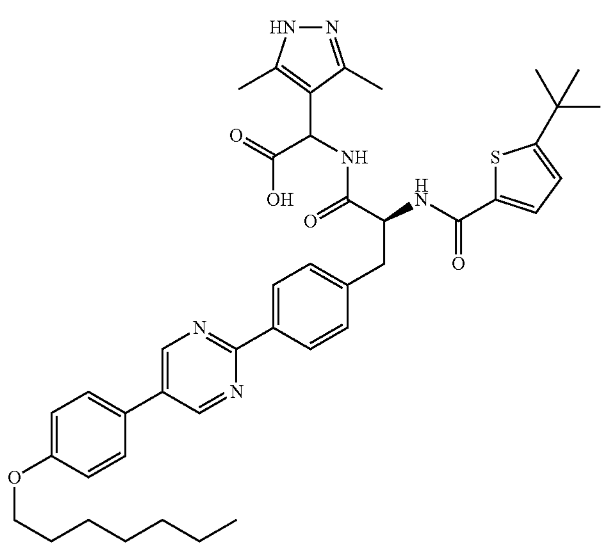 [SMILES: CCCCCCCOc1ccc(-c2cnc(-c3ccc(C[C@H](NC(=O)c4ccc(C(C)(C)C)s4)C(=O)NC(C(=O)O)c4c(C)n[nH]c4C)cc3)nc2)cc1] | 598 | 9.70 | 9 |

TABLE 1-continued
| STRUCTURE | COMPOUND NUMBER | LCMS RETENTION TIME (min) | PURITY METHOD |
|---|---|---|---|
| 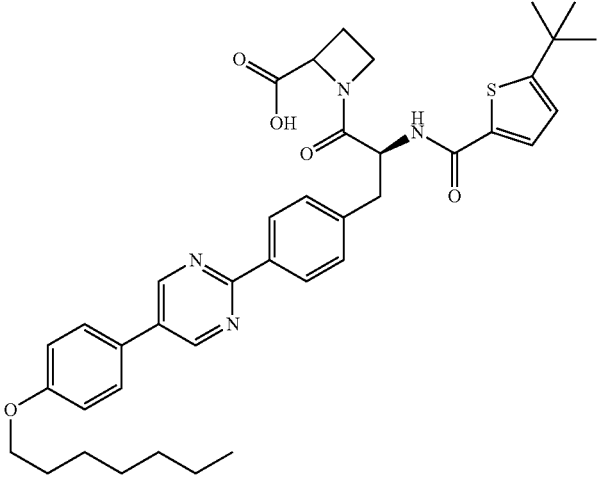 [SMILES: CCCCCCCOc1ccc(-c2cnc(-c3ccc(C[C@H](NC(=O)c4ccc(C(C)(C)C)s4)C(=O)N4CCC4C(=O)O)cc3)nc2)cc1] | 599 | 10.38 | 9 |
| 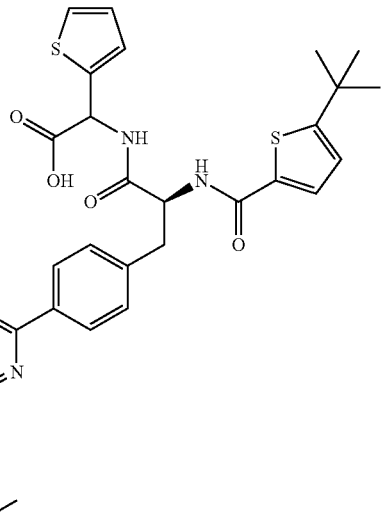 | 600 | 10.97 | 9 |

TABLE 1-continued

| STRUCTURE | COMPOUND NUMBER | LCMS RETENTION TIME (min) | PURITY METHOD |
|---|---|---|---|
| 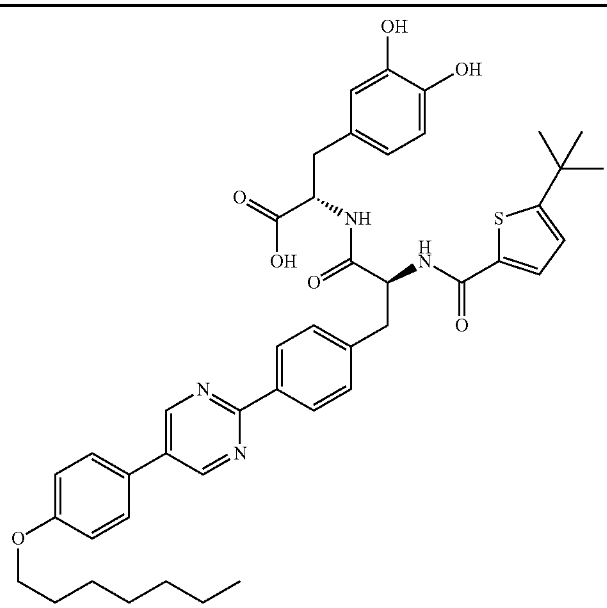 | 601 | 10.36 | 10 |
| 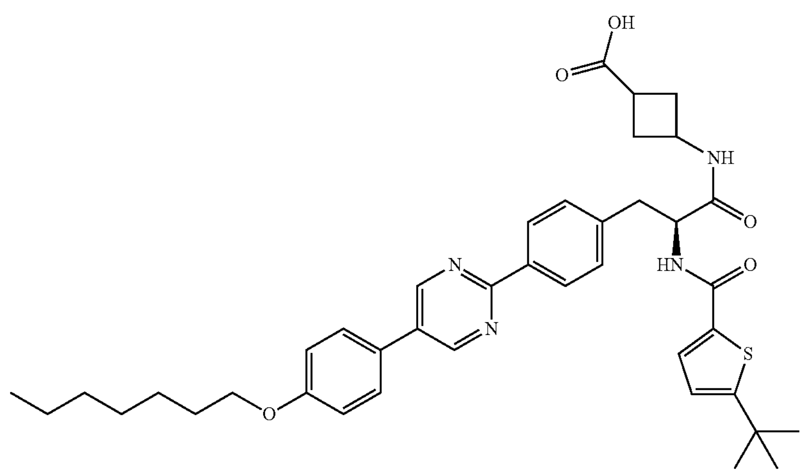 [SMILES: CCCCCCCOc1ccc(-c2cnc(-c3ccc(C[C@H](NC(=O)c4ccc(C(C)(C)C)s4)C(=O)NC4CC(C(=O)O)C4)cc3)nc2)cc1] | 602 | 10.72 | 2 |
| 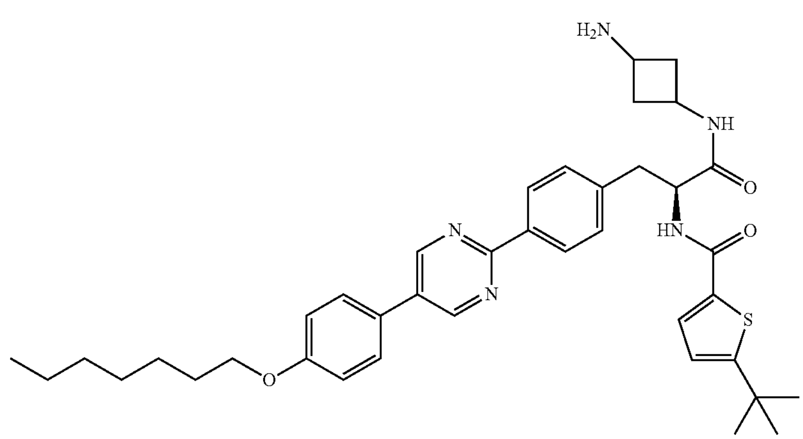 [SMILES: CCCCCCCOc1ccc(-c2cnc(-c3ccc(C[C@H](NC(=O)c4ccc(C(C)(C)C)s4)C(=O)NC4CC(N)C4)cc3)nc2)cc1] | 603 | 10.52 | 2 |

TABLE 1-continued

| STRUCTURE | COMPOUND NUMBER | LCMS RETENTION TIME (min) | PURITY METHOD |
|---|---|---|---|
| 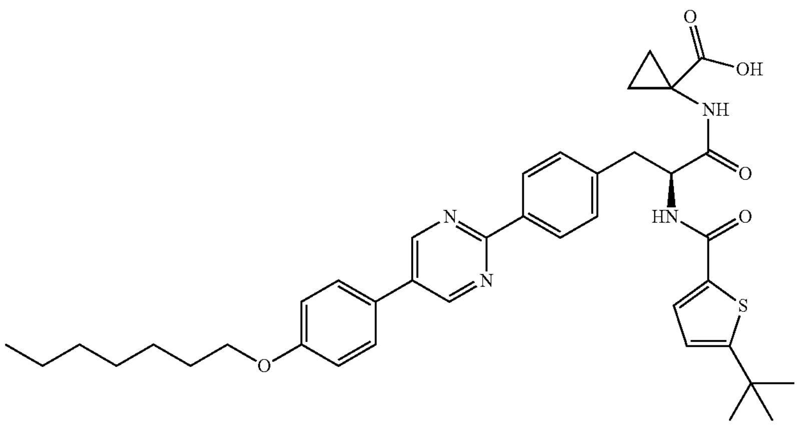 [SMILES: CCCCCCCOc1ccc(-c2cnc(-c3ccc(C[C@H](NC(=O)c4ccc(C(C)(C)C)s4)C(=O)NC4(C(=O)O)CC4)cc3)nc2)cc1] | 604 | 10.532 | 2 |
| 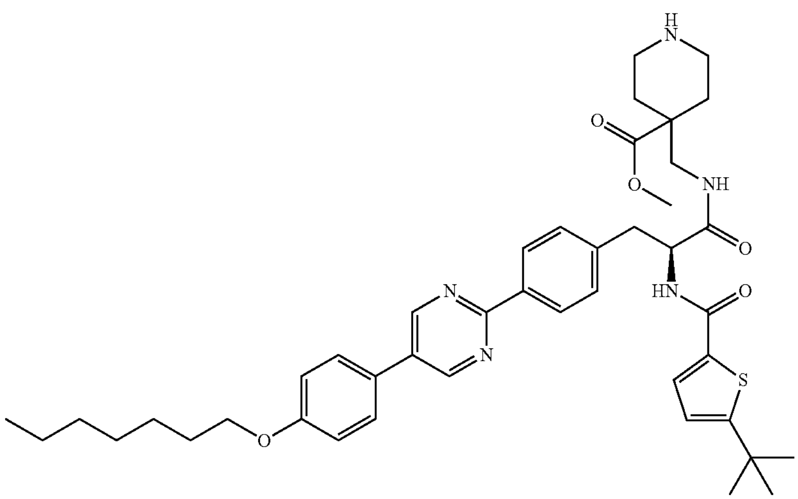 [SMILES: CCCCCCCOc1ccc(-c2cnc(-c3ccc(C[C@H](NC(=O)c4ccc(C(C)(C)C)s4)C(=O)NCC4(C(=O)OC)CCNCC4)cc3)nc2)cc1] | 605 | 10.91 | 2 |
| 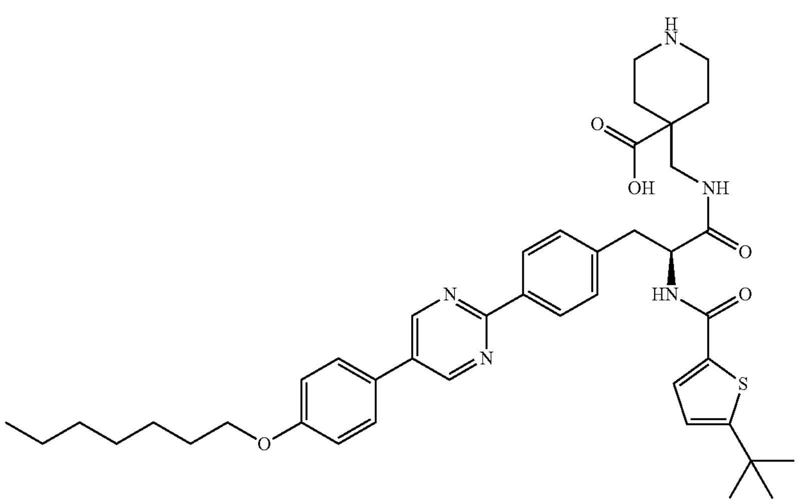 [SMILES: CCCCCCCOc1ccc(-c2cnc(-c3ccc(C[C@H](NC(=O)c4ccc(C(C)(C)C)s4)C(=O)NCC4(C(=O)O)CCNCC4)cc3)nc2)cc1] | 606 | 9.93 | 2 |

TABLE 1-continued
| STRUCTURE | COMPOUND NUMBER | LCMS RETENTION TIME (min) | PURITY METHOD |
|---|---|---|---|
| 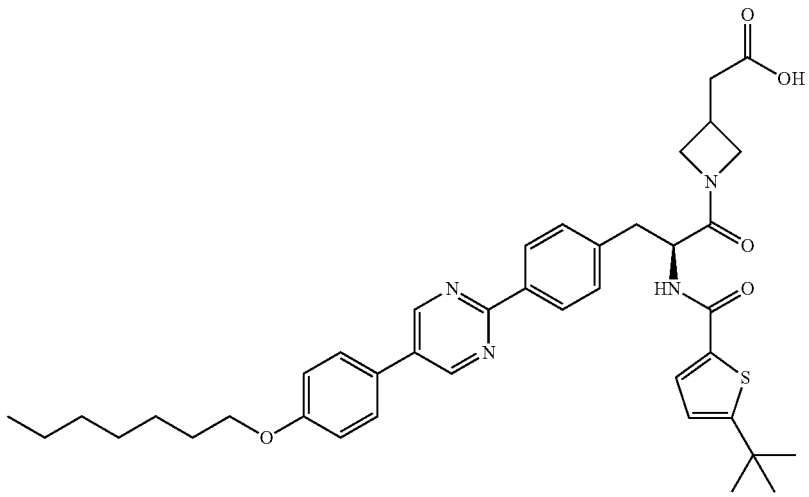 [SMILES: CCCCCCCOc1ccc(-c2cnc(-c3ccc(C[C@H](NC(=O)c4ccc(C(C)(C)C)s4)C(=O)N4CC(CC(=O)O)C4)cc3)nc2)cc1] | 607 | 10.61 | 2 |
| 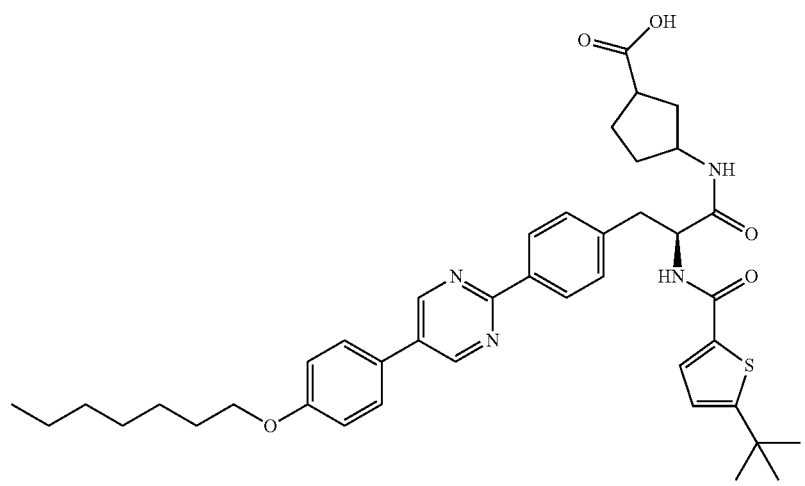 [SMILES: CCCCCCCOc1ccc(-c2cnc(-c3ccc(C[C@H](NC(=O)c4ccc(C(C)(C)C)s4)C(=O)NC4CCC(C(=O)O)C4)cc3)nc2)cc1] | 608 | 10.20 | 2 |
| 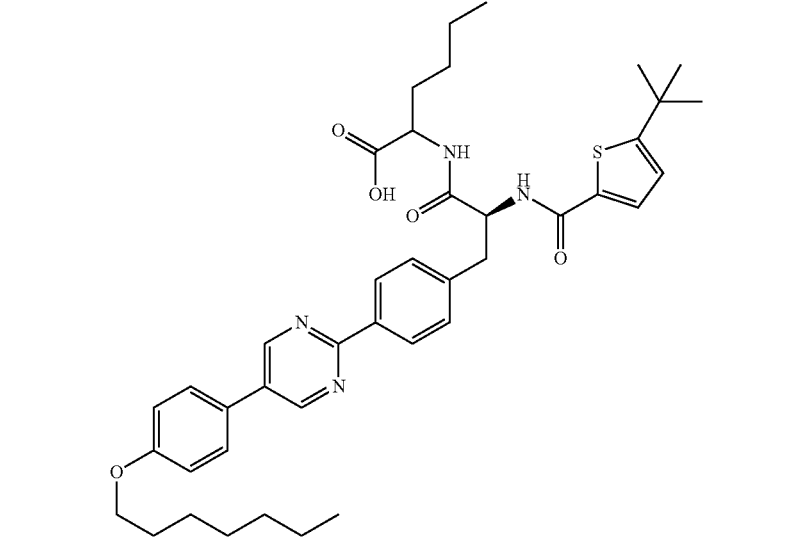 [SMILES: CCCCCCCOc1ccc(-c2cnc(-c3ccc(C[C@H](NC(=O)c4ccc(C(C)(C)C)s4)C(=O)NC(CCCC)C(=O)O)cc3)nc2)cc1] | 609 | 10.16 | 10 |

TABLE 1-continued

| STRUCTURE | COMPOUND NUMBER | LCMS RETENTION TIME (min) | PURITY METHOD |
|---|---|---|---|
| 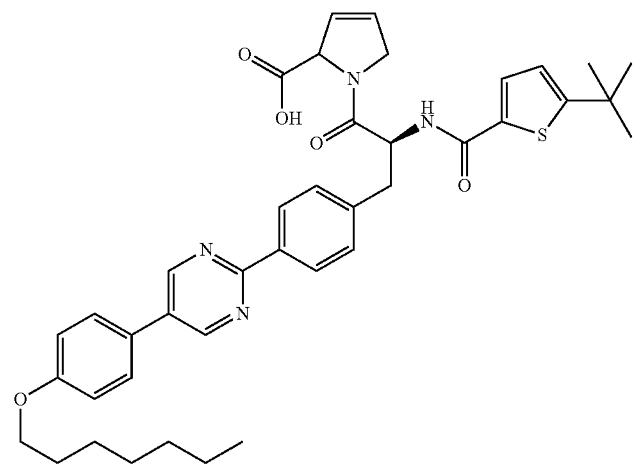 [SMILES: CCCCCCCOc1ccc(-c2cnc(-c3ccc(C[C@H](NC(=O)c4ccc(C(C)(C)C)s4)C(=O)N4CC=CC4C(=O)O)cc3)nc2)cc1] | 610 | 10.65 | 10 |
| 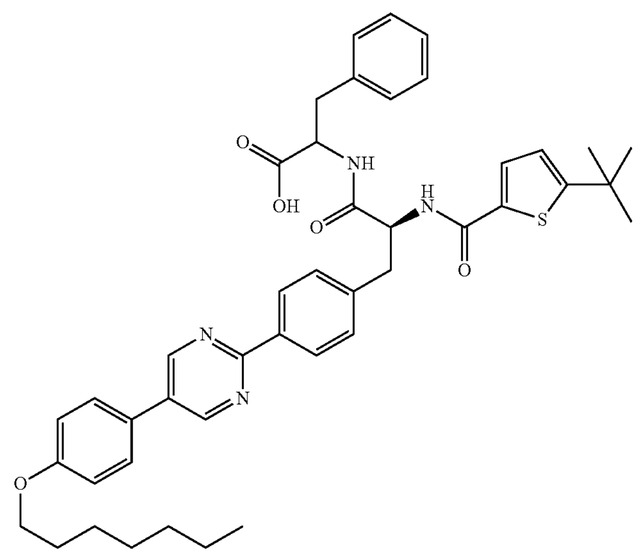 [SMILES: CCCCCCCOc1ccc(-c2cnc(-c3ccc(C[C@H](NC(=O)c4ccc(C(C)(C)C)s4)C(=O)NC(Cc4ccccc4)C(=O)O)cc3)nc2)cc1] | 611 | 10.15 | 10 |
| 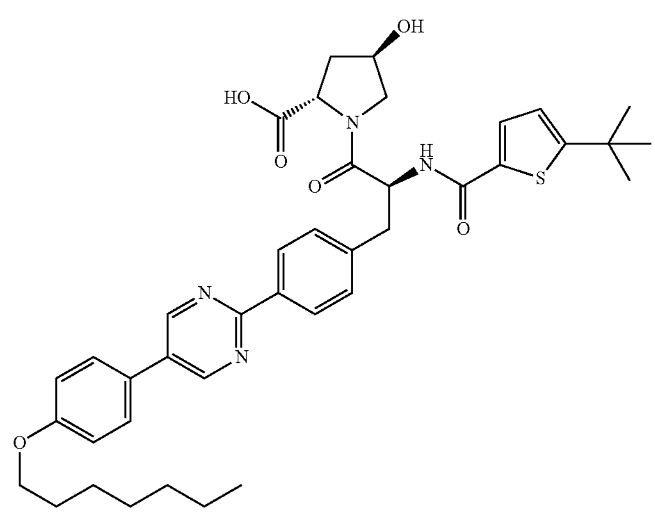 [SMILES: CCCCCCCOc1ccc(-c2cnc(-c3ccc(C[C@H](NC(=O)c4ccc(C(C)(C)C)s4)C(=O)N4C[C@H](O)C[C@H]4C(=O)O)cc3)nc2)cc1] | 612 | 9.91 | 10 |

TABLE 1-continued

| STRUCTURE | COMPOUND NUMBER | LCMS RETENTION TIME (min) | PURITY METHOD |
|---|---|---|---|
| 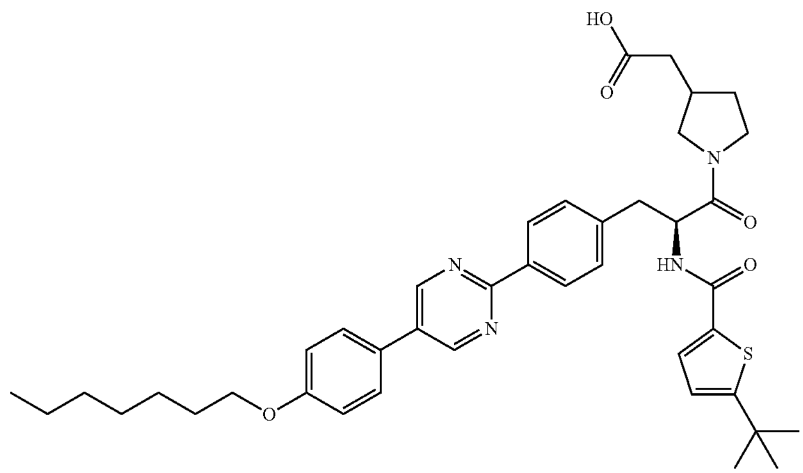 [SMILES: CCCCCCCOc1ccc(-c2cnc(-c3ccc(C[C@H](NC(=O)c4ccc(C(C)(C)C)s4)C(=O)N4CCC(CC(=O)O)C4)cc3)nc2)cc1] | 613 | 10.39 | 10 |
| 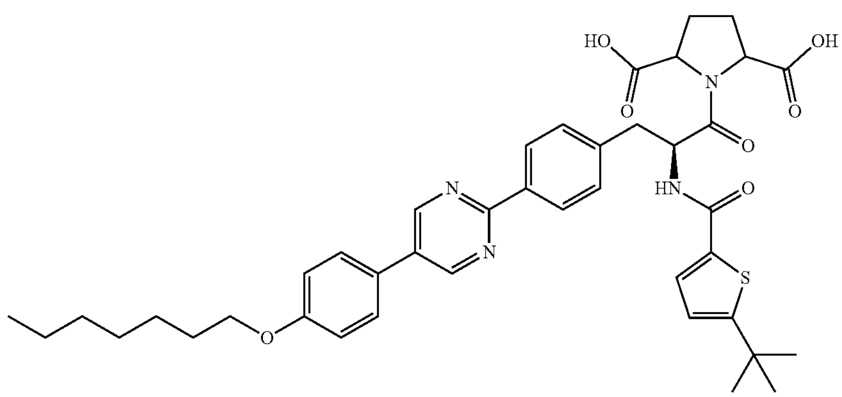 [SMILES: CCCCCCCOc1ccc(-c2cnc(-c3ccc(C[C@H](NC(=O)c4ccc(C(C)(C)C)s4)C(=O)N4C(C(=O)O)CCC4C(=O)O)cc3)nc2)cc1] | 614 | 9.25 | 10 |
| 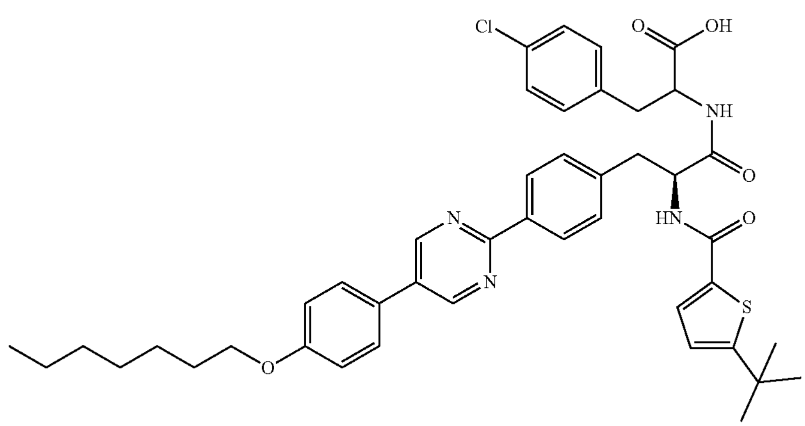 [SMILES: CCCCCCCOc1ccc(-c2cnc(-c3ccc(C[C@H](NC(=O)c4ccc(C(C)(C)C)s4)C(=O)NC(Cc4ccc(Cl)cc4)C(=O)O)cc3)nc2)cc1] | 615 | 10.53 | 10 |

TABLE 1-continued

| STRUCTURE | COMPOUND NUMBER | LCMS RETENTION TIME (min) | PURITY METHOD |
|---|---|---|---|
| 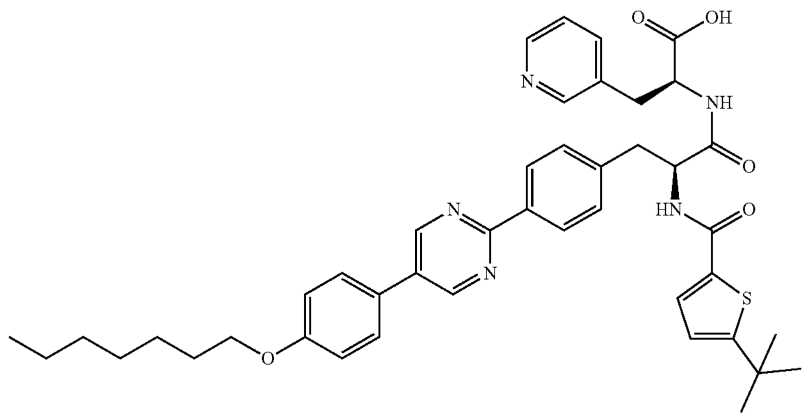 [SMILES: CCCCCCCOc1ccc(-c2cnc(-c3ccc(C[C@H](NC(=O)c4ccc(C(C)(C)C)s4)C(=O)N[C@@H](Cc4cccnc4)C(=O)O)cc3)nc2)cc1] | 616 | 8.55 | 10 |
| 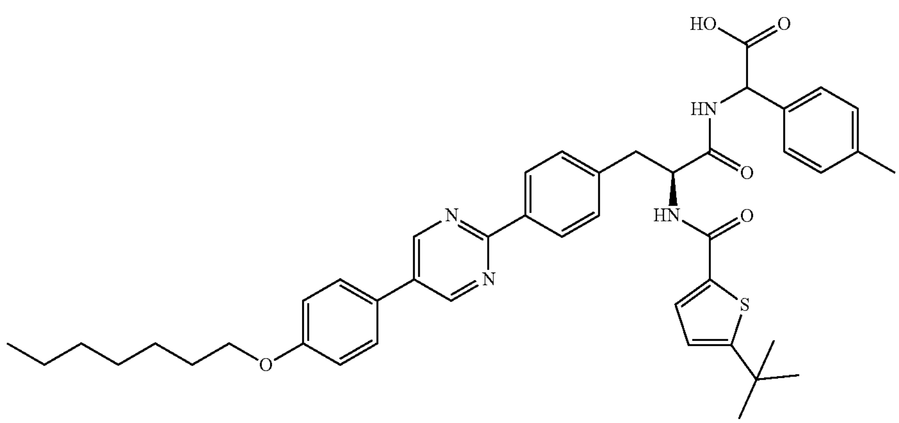 [SMILES: CCCCCCCOc1ccc(-c2cnc(-c3ccc(C[C@H](NC(=O)c4ccc(C(C)(C)C)s4)C(=O)NC(C(=O)O)c4ccc(C)cc4)cc3)nc2)cc1] | 617 | 10.27 | 10 |
| 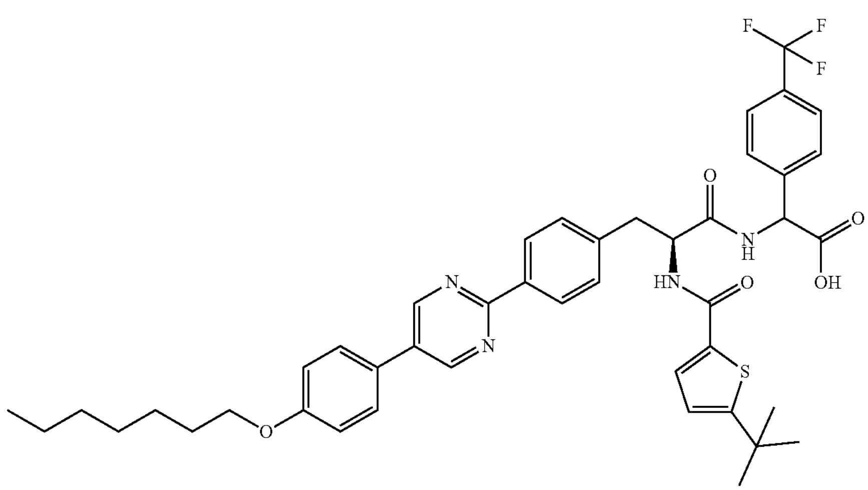 [SMILES: CCCCCCCOc1ccc(-c2cnc(-c3ccc(C[C@H](NC(=O)c4ccc(C(C)(C)C)s4)C(=O)NC(C(=O)O)c4ccc(C(F)(F)F)cc4)cc3)nc2)cc1] | 618 | 10.6 | 10 |

TABLE 1-continued
| STRUCTURE | COMPOUND NUMBER | LCMS RETENTION TIME (min) | PURITY METHOD |
|---|---|---|---|
| 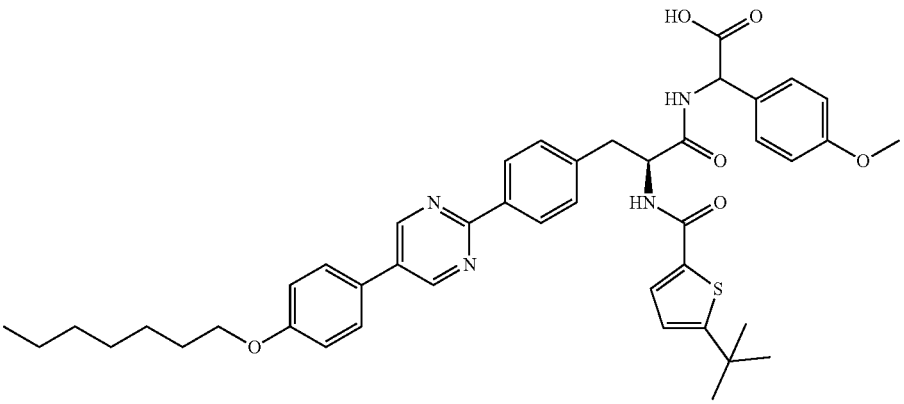 [SMILES: CCCCCCCOc1ccc(-c2cnc(-c3ccc(C[C@H](NC(=O)c4ccc(C(C)(C)C)s4)C(=O)NC(C(=O)O)c4ccc(OC)cc4)cc3)nc2)cc1] | 619 | 10.97 | 10 |
| 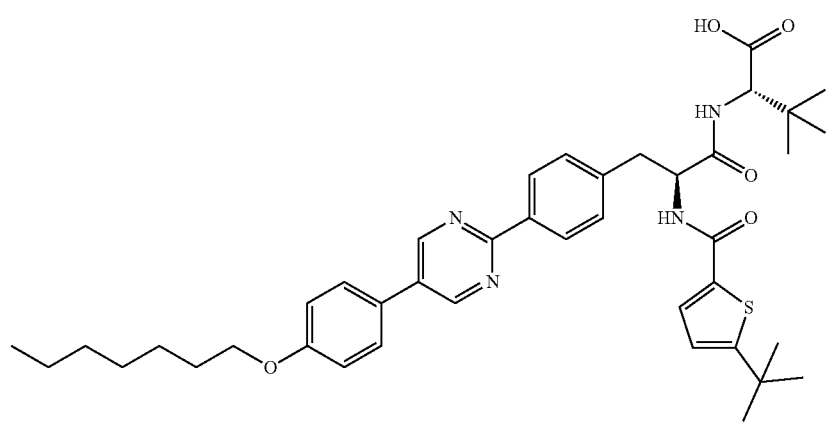 [SMILES: CCCCCCCOc1ccc(-c2cnc(-c3ccc(C[C@H](NC(=O)c4ccc(C(C)(C)C)s4)C(=O)N[C@H](C(=O)O)C(C)(C)C)cc3)nc2)cc1] | 620 | 10.10 | 10 |
| 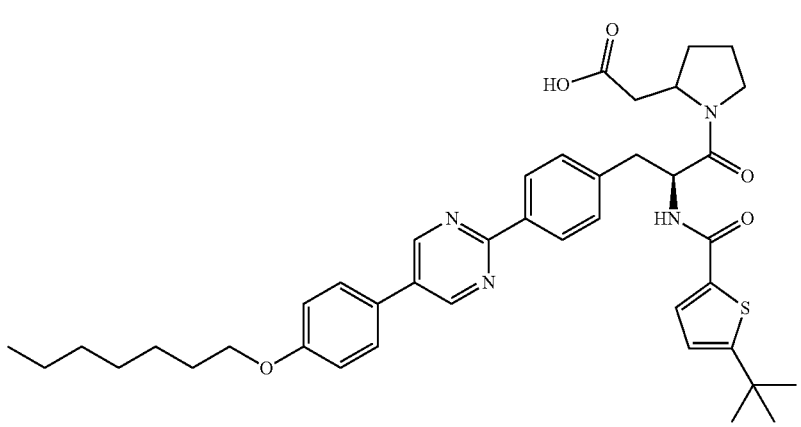 [SMILES: CCCCCCCOc1ccc(-c2cnc(-c3ccc(C[C@H](NC(=O)c4ccc(C(C)(C)C)s4)C(=O)N4CCCC4CC(=O)O)cc3)nc2)cc1] | 621 | 10.70 | 10 |

TABLE 1-continued

| STRUCTURE | COMPOUND NUMBER | LCMS RETENTION TIME (min) | PURITY METHOD |
|---|---|---|---|
| 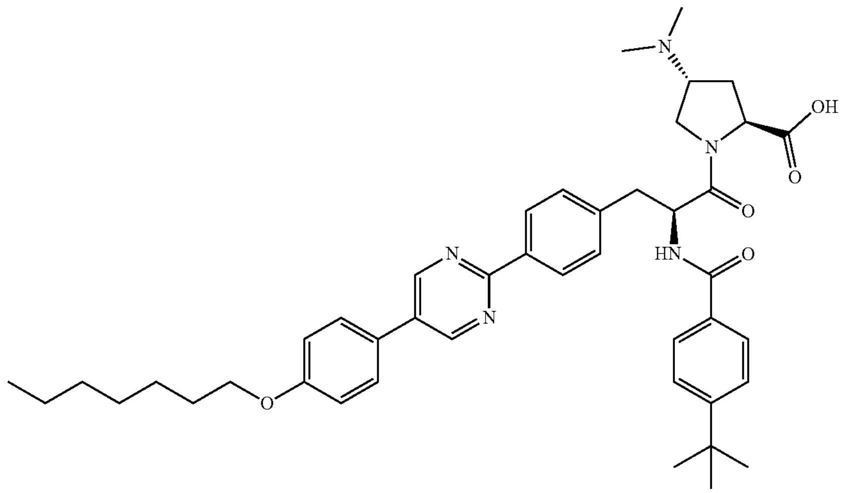 [SMILES: CCCCCCCOc1ccc(-c2cnc(-c3ccc(C[C@H](NC(=O)c4ccc(C(C)(C)C)cc4)C(=O)N4C[C@H](N(C)C)C[C@H]4C(=O)O)cc3)nc2)cc1] | 622 | 7.70 | 10 |
| 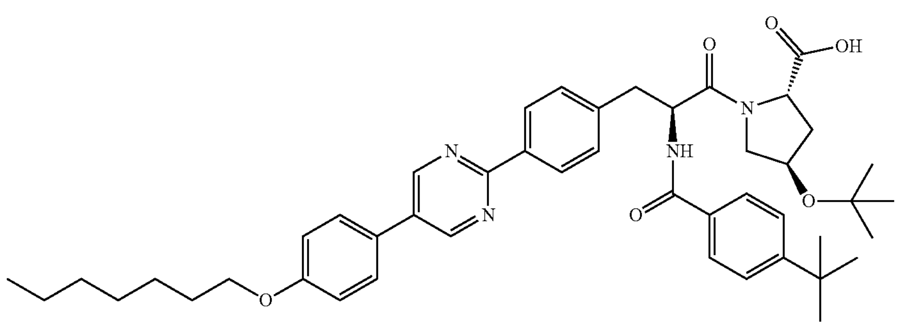 [SMILES: CCCCCCCOc1ccc(-c2cnc(-c3ccc(C[C@H](NC(=O)c4ccc(C(C)(C)C)cc4)C(=O)N4C[C@H](OC(C)(C)C)C[C@H]4C(=O)O)cc3)nc2)cc1] | 623 | 10.35 | 10 |
| 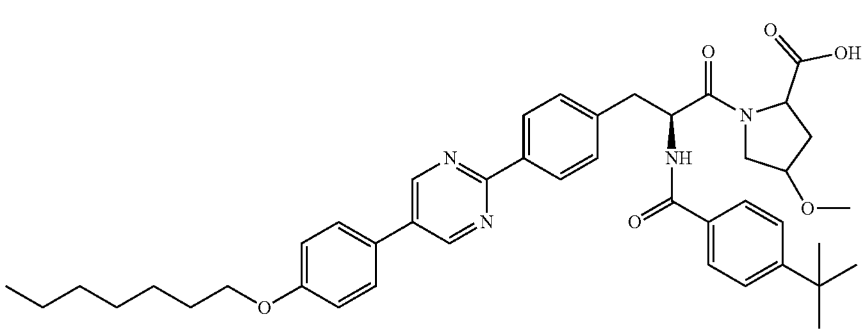 [SMILES: CCCCCCCOc1ccc(-c2cnc(-c3ccc(C[C@H](NC(=O)c4ccc(C(C)(C)C)cc4)C(=O)N4CC(OC)CC4C(=O)O)cc3)nc2)cc1] | 624 | 10.56 | 10 |

TABLE 1-continued
| STRUCTURE | COMPOUND NUMBER | LCMS RETENTION TIME (min) | PURITY METHOD |
|---|---|---|---|
| 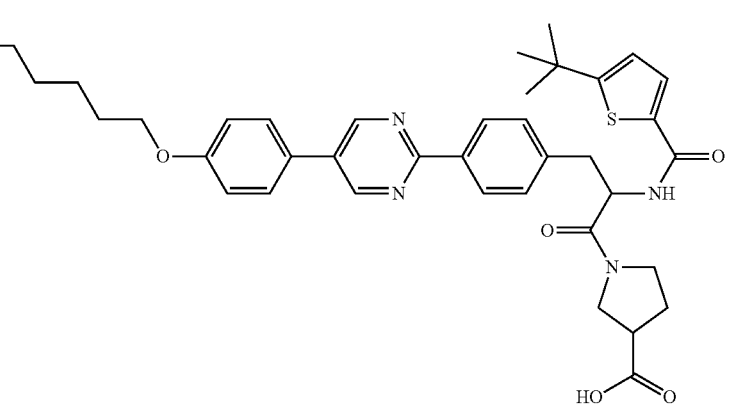 | 625 | 10.29 | 10 |
| 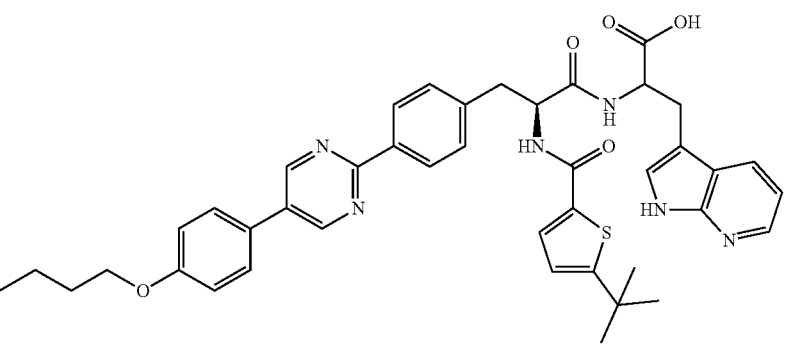 | 626 | 9.39 | 10 |
| 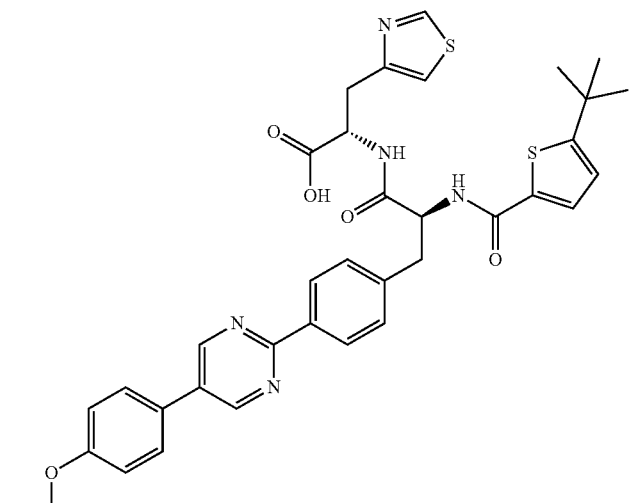 | 627 | 10.30 | 10 |

TABLE 1-continued
| STRUCTURE | COMPOUND NUMBER | LCMS RETENTION TIME (min) | PURITY METHOD |
|---|---|---|---|
| 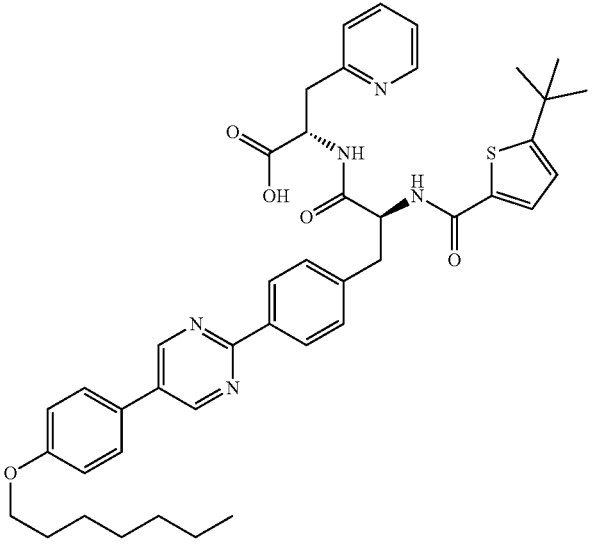 [SMILES: CCCCCCCOc1ccc(-c2cnc(-c3ccc(C[C@H](NC(=O)c4ccc(C(C)(C)C)s4)C(=O)N[C@@H](Cc4ccccn4)C(=O)O)cc3)nc2)cc1] | 628 | 9.20 | 10 |
| 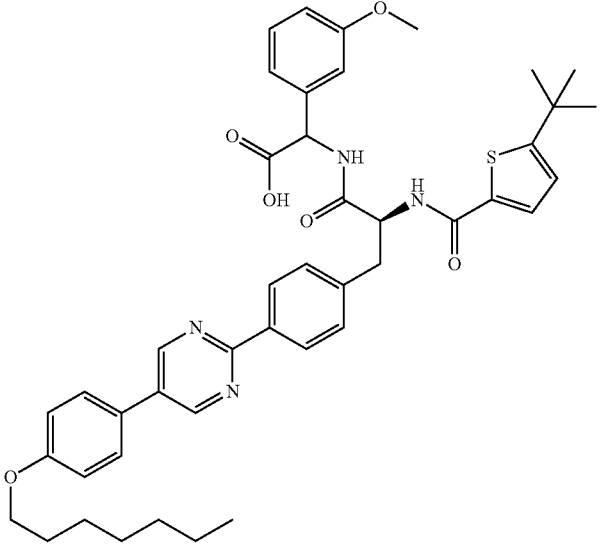 [SMILES: CCCCCCCOc1ccc(-c2cnc(-c3ccc(C[C@H](NC(=O)c4ccc(C(C)(C)C)s4)C(=O)NC(C(=O)O)c4cccc(OC)c4)cc3)nc2)cc1] | 629 | 10.90 | 10 |

TABLE 1-continued

| STRUCTURE | COMPOUND NUMBER | LCMS RETENTION TIME (min) | PURITY METHOD |
|---|---|---|---|
| 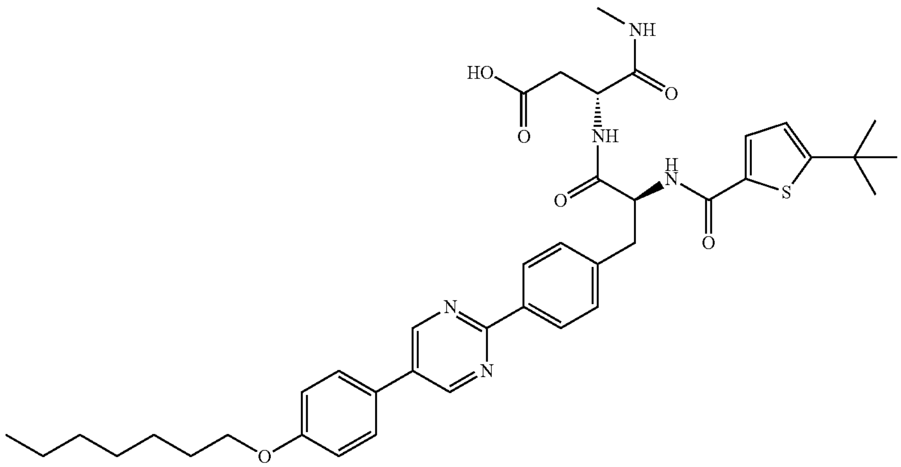 [SMILES: CCCCCCCOc1ccc(-c2cnc(-c3ccc(C[C@H](NC(=O)c4ccc(C(C)(C)C)s4)C(=O)N[C@H](CC(=O)O)C(=O)NC)cc3)nc2)cc1] | 630 | 9.66 | 14 |
| 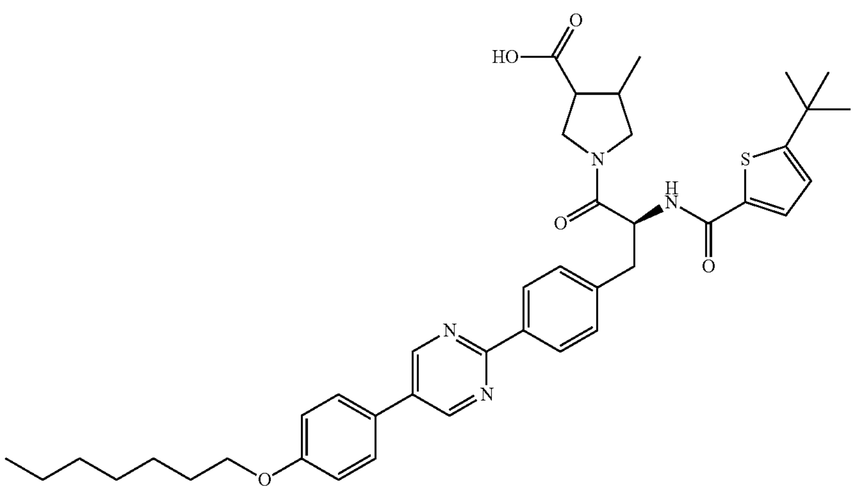 [SMILES: CCCCCCCOc1ccc(-c2cnc(-c3ccc(C[C@H](NC(=O)c4ccc(C(C)(C)C)s4)C(=O)N4CC(C)C(C(=O)O)C4)cc3)nc2)cc1] | 631 | 10.32 | 14 |
| 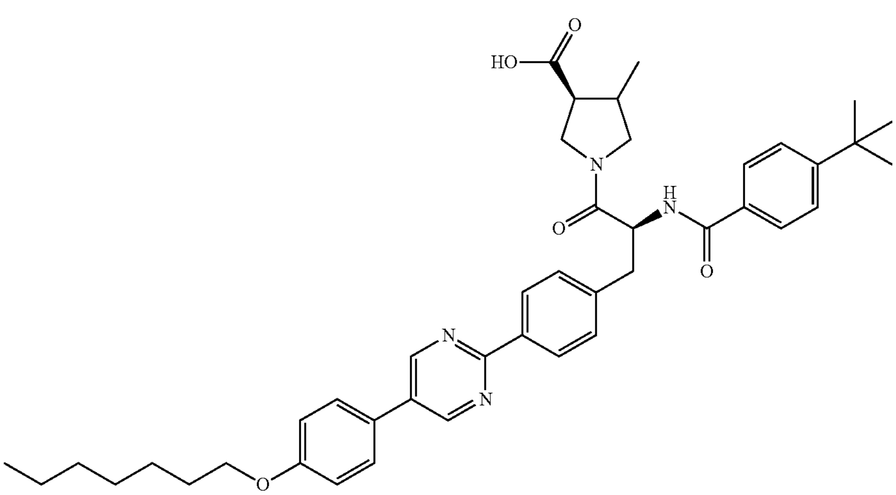 [SMILES: CCCCCCCOc1ccc(-c2cnc(-c3ccc(C[C@H](NC(=O)c4ccc(C(C)(C)C)cc4)C(=O)N4CC(C)[C@H](C(=O)O)C4)cc3)nc2)cc1] | 632 | 10.10 | 14 |

TABLE 1-continued
| STRUCTURE | COMPOUND NUMBER | LCMS RETENTION TIME (min) | PURITY METHOD |
|---|---|---|---|
| 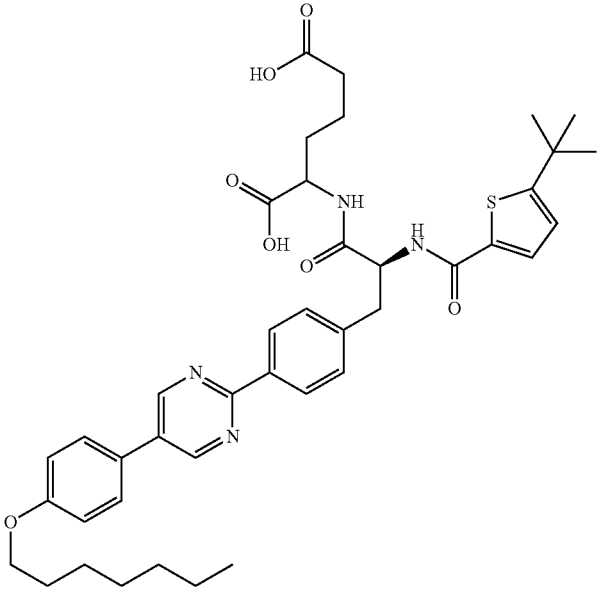 [SMILES: CCCCCCCOc1ccc(-c2cnc(-c3ccc(C[C@H](NC(=O)c4ccc(C(C)(C)C)s4)C(=O)NC(CCCC(=O)O)C(=O)O)cc3)nc2)cc1] | 633 | 9.80 | 10 |
| 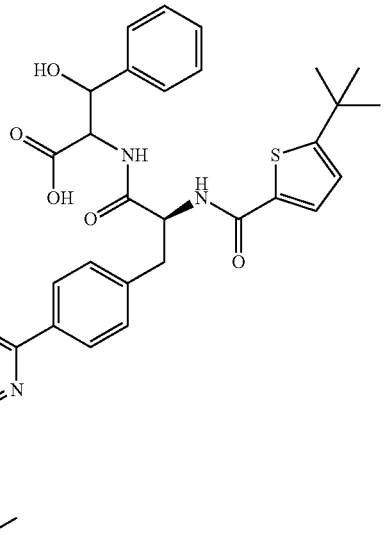 | 634 | 10.62 | 10 |

TABLE 1-continued
| STRUCTURE | COMPOUND NUMBER | LCMS RETENTION TIME (min) | PURITY METHOD |
|---|---|---|---|
| 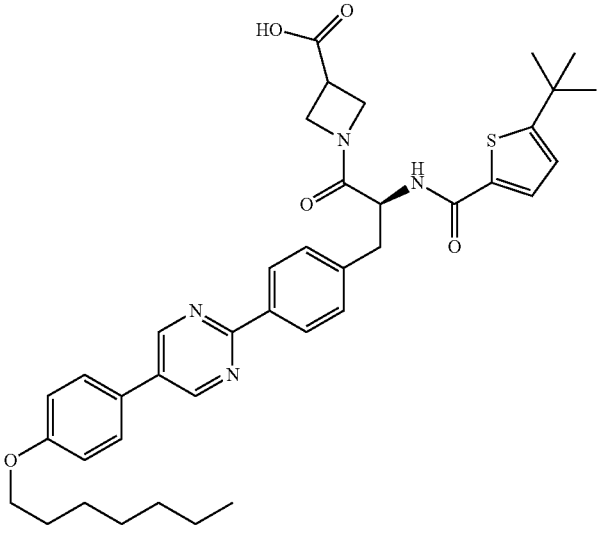 [SMILES: CCCCCCCOc1ccc(-c2cnc(-c3ccc(C[C@H](NC(=O)c4ccc(C(C)(C)C)s4)C(=O)N4CC(C(=O)O)C4)cc3)nc2)cc1] | 635 | 10.17 | 10 |
| 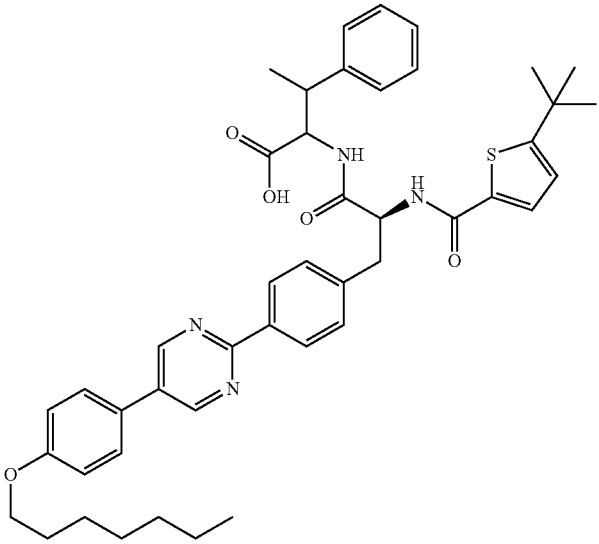 [SMILES: CCCCCCCOc1ccc(-c2cnc(-c3ccc(C[C@H](NC(=O)c4ccc(C(C)(C)C)s4)C(=O)NC(C(=O)O)C(C)c4ccccc4)cc3)nc2)cc1] | 636 | 10.25 | 10 |

TABLE 1-continued

| STRUCTURE | COMPOUND NUMBER | LCMS RETENTION TIME (min) | PURITY METHOD |
|---|---|---|---|
| 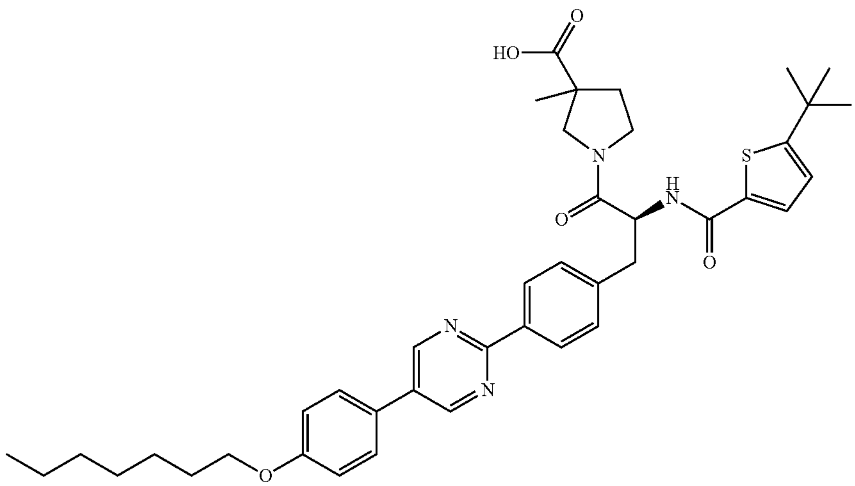 [SMILES: CCCCCCCOc1ccc(-c2cnc(-c3ccc(C[C@H](NC(=O)c4ccc(C(C)(C)C)s4)C(=O)N4CCC(C)(C(=O)O)C4)cc3)nc2)cc1] | 637 | 10.50 | 14 |
| 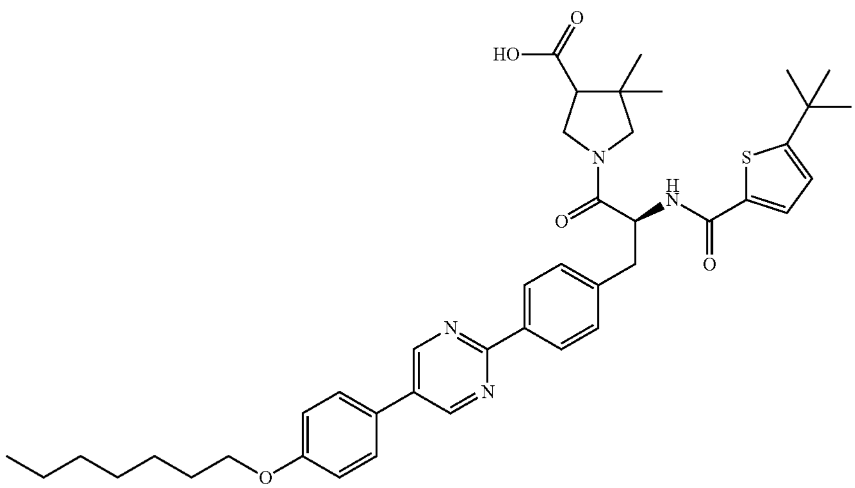 [SMILES: CCCCCCCOc1ccc(-c2cnc(-c3ccc(C[C@H](NC(=O)c4ccc(C(C)(C)C)s4)C(=O)N4CC(C(=O)O)C(C)(C)C4)cc3)nc2)cc1] | 638 | 10.94 | 14 |
| 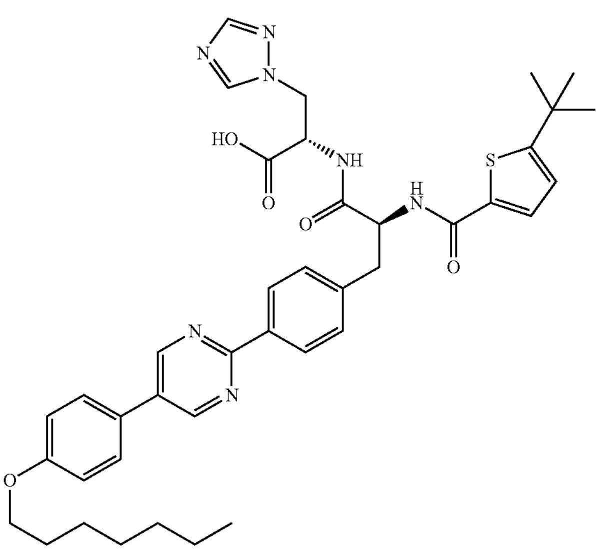 [SMILES: CCCCCCCOc1ccc(-c2cnc(-c3ccc(C[C@H](NC(=O)c4ccc(C(C)(C)C)s4)C(=O)N[C@@H](Cn4cncn4)C(=O)O)cc3)nc2)cc1] | 639 | 9.88 | 10 |

TABLE 1-continued

| STRUCTURE | COMPOUND NUMBER | LCMS RETENTION TIME (min) | PURITY METHOD |
|---|---|---|---|
| 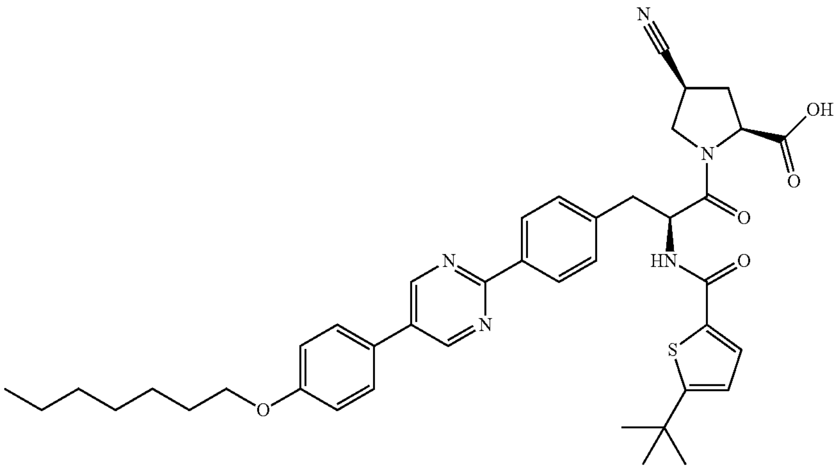 [SMILES: CCCCCCCOc1ccc(-c2cnc(-c3ccc(C[C@H](NC(=O)c4ccc(C(C)(C)C)s4)C(=O)N4C[C@@H](C#N)C[C@H]4C(=O)O)cc3)nc2)cc1] | 640 | 10.38 | 10 |
| 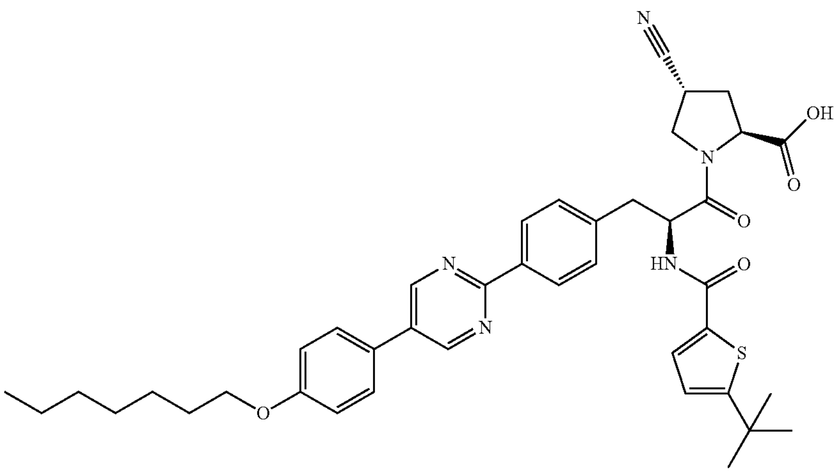 [SMILES: CCCCCCCOc1ccc(-c2cnc(-c3ccc(C[C@H](NC(=O)c4ccc(C(C)(C)C)s4)C(=O)N4C[C@H](C#N)C[C@H]4C(=O)O)cc3)nc2)cc1] | 641 | 10.45 | 10 |
| 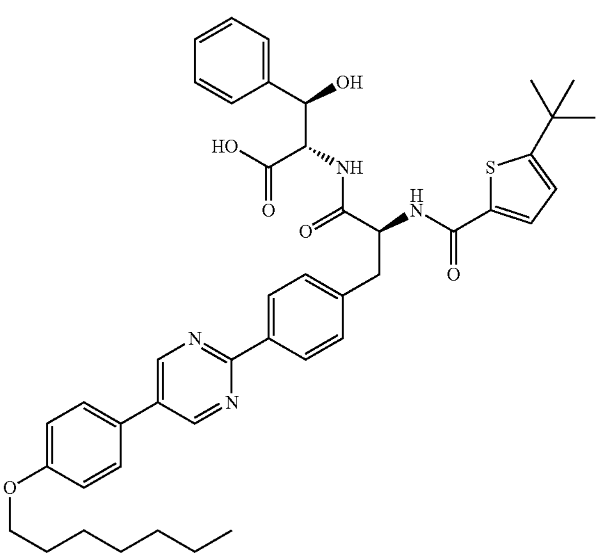 [SMILES: CCCCCCCOc1ccc(-c2cnc(-c3ccc(C[C@H](NC(=O)c4ccc(C(C)(C)C)s4)C(=O)N[C@H](C(=O)O)[C@H](O)c4ccccc4)cc3)nc2)cc1] | 642 | 10.523 | 10 |

TABLE 1-continued

| STRUCTURE | COMPOUND NUMBER | LCMS RETENTION TIME (min) | PURITY METHOD |
|---|---|---|---|
| 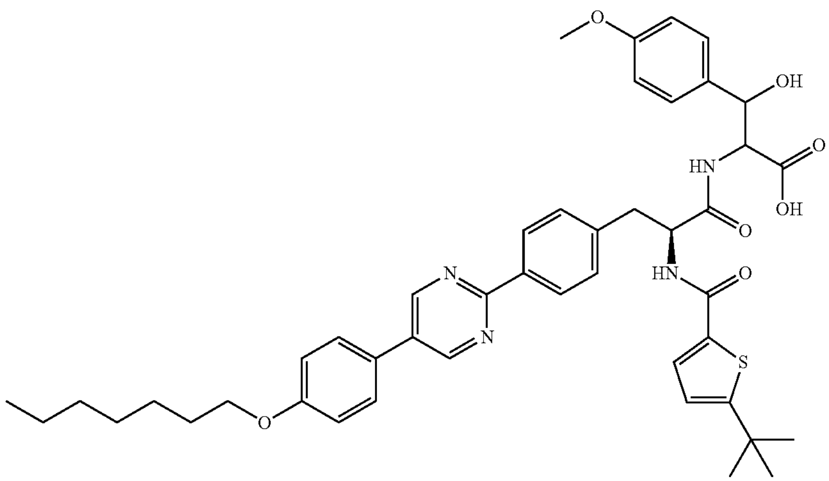 [SMILES: CCCCCCCOc1ccc(-c2cnc(-c3ccc(C[C@H](NC(=O)c4ccc(C(C)(C)C)s4)C(=O)NC(C(=O)O)C(O)c4ccc(OC)cc4)cc3)nc2)cc1] | 644 | 10.20 | 14 |
| 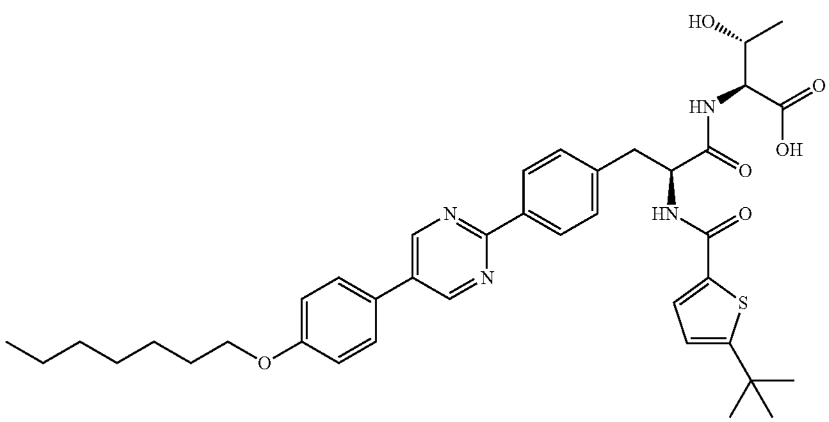 [SMILES: CCCCCCCOc1ccc(-c2cnc(-c3ccc(C[C@H](NC(=O)c4ccc(C(C)(C)C)s4)C(=O)N[C@H](C(=O)O)[C@@H](C)O)cc3)nc2)cc1] | 645 | 9.68 | 14 |
| 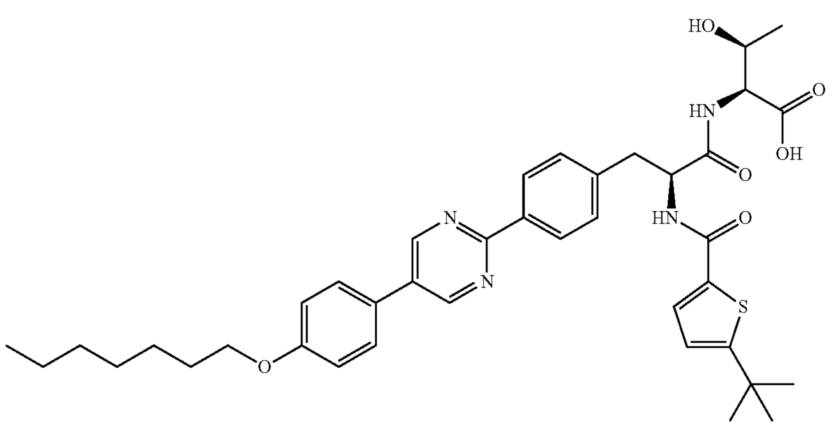 [SMILES: CCCCCCCOc1ccc(-c2cnc(-c3ccc(C[C@H](NC(=O)c4ccc(C(C)(C)C)s4)C(=O)N[C@H](C(=O)O)[C@H](C)O)cc3)nc2)cc1] | 646 | 9.80 | 14 |

TABLE 1-continued

| STRUCTURE | COMPOUND NUMBER | LCMS RETENTION TIME (min) | PURITY METHOD |
|---|---|---|---|
| 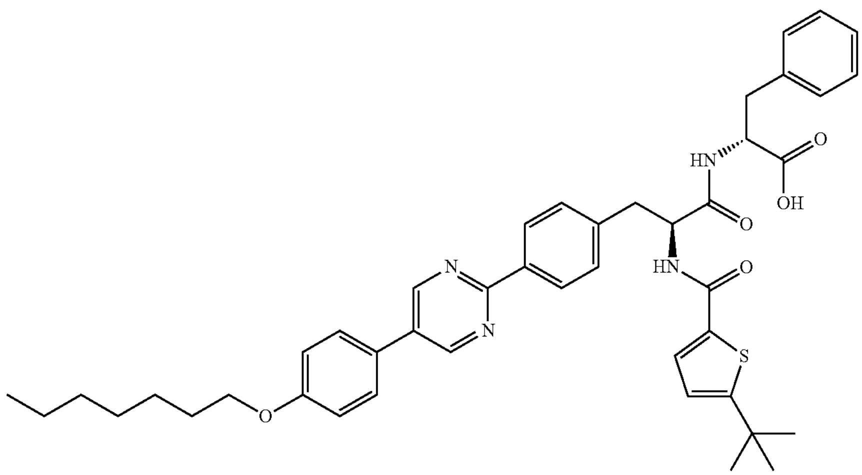 [SMILES: CCCCCCCOc1ccc(-c2cnc(-c3ccc(C[C@H](NC(=O)c4ccc(C(C)(C)C)s4)C(=O)N[C@H](Cc4ccccc4)C(=O)O)cc3)nc2)cc1] | 647 | 10.50 | 14 |
| 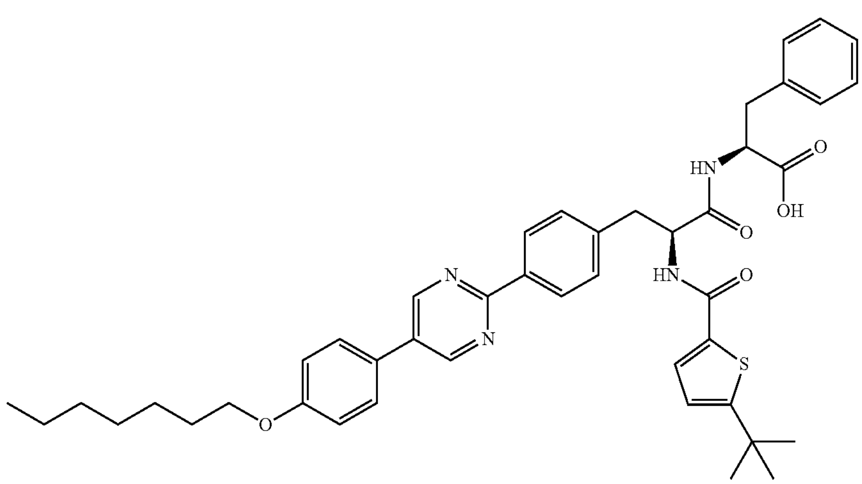 [SMILES: CCCCCCCOc1ccc(-c2cnc(-c3ccc(C[C@H](NC(=O)c4ccc(C(C)(C)C)s4)C(=O)N[C@@H](Cc4ccccc4)C(=O)O)cc3)nc2)cc1] | 648 | 10.50 | 14 |

TABLE 1-continued
| STRUCTURE | COMPOUND NUMBER | LCMS RETENTION TIME (min) | PURITY METHOD |
|---|---|---|---|
| 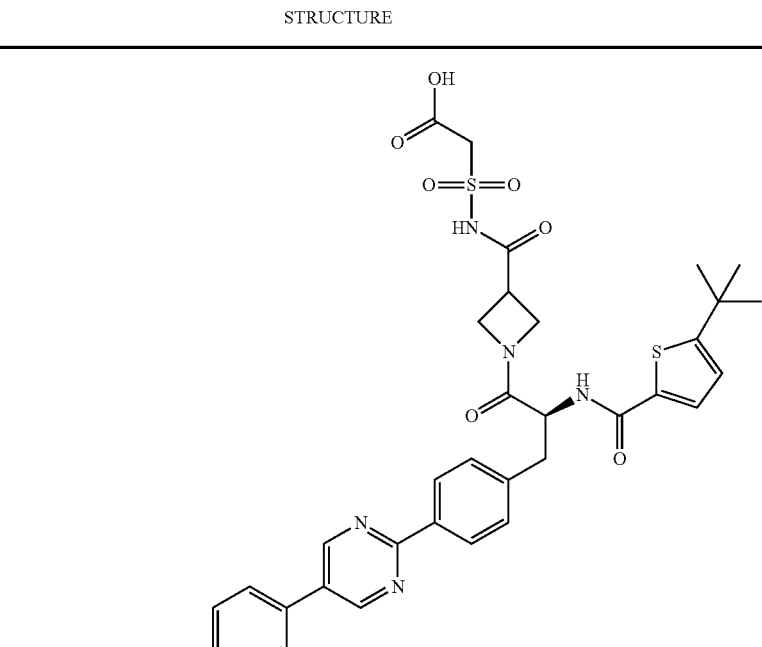 | 649 | 8.51 | 14 |
| 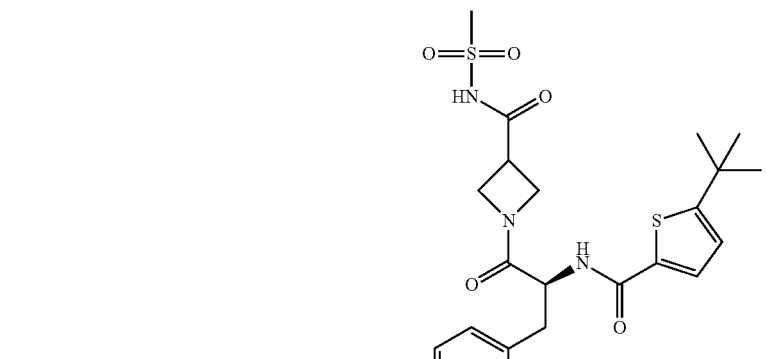 | 650 | 9.62 | 14 |

TABLE 1-continued

| STRUCTURE | COMPOUND NUMBER | LCMS RETENTION TIME (min) | PURITY METHOD |
|---|---|---|---|
| 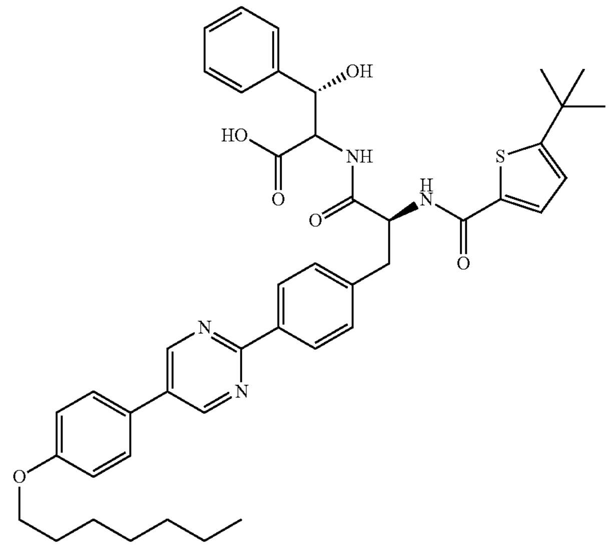 [SMILES: CCCCCCCOc1ccc(-c2cnc(-c3ccc(C[C@H](NC(=O)c4ccc(C(C)(C)C)s4)C(=O)NC(C(=O)O)[C@@H](O)c4ccccc4)cc3)nc2)cc1] | 651 | 10.65 | 10 |
| 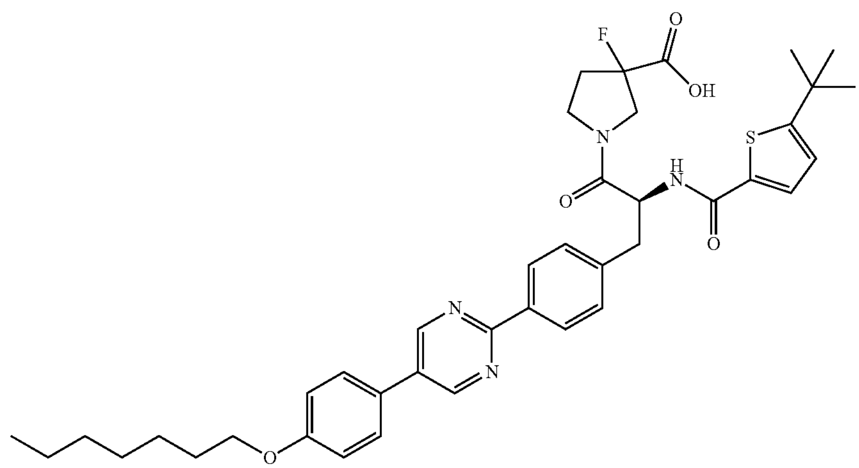 [SMILES: CCCCCCCOc1ccc(-c2cnc(-c3ccc(C[C@H](NC(=O)c4ccc(C(C)(C)C)s4)C(=O)N4CCC(F)(C(=O)O)C4)cc3)nc2)cc1] | 652 | 9.91 | 14 |
| 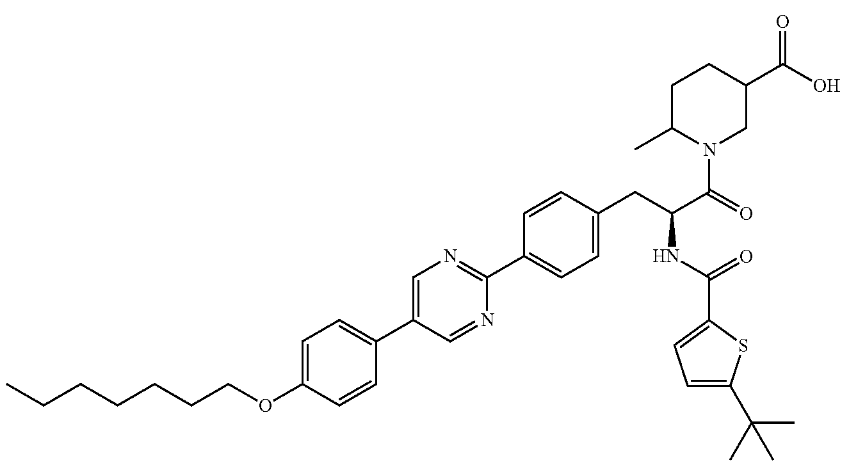 [SMILES: CCCCCCCOc1ccc(-c2cnc(-c3ccc(C[C@H](NC(=O)c4ccc(C(C)(C)C)s4)C(=O)N4CC(C(=O)O)CCC4C)cc3)nc2)cc1] | 653 | 10.81 | 14 |

| STRUCTURE | COMPOUND NUMBER | LCMS RETENTION TIME (min) | PURITY METHOD |
|---|---|---|---|
| 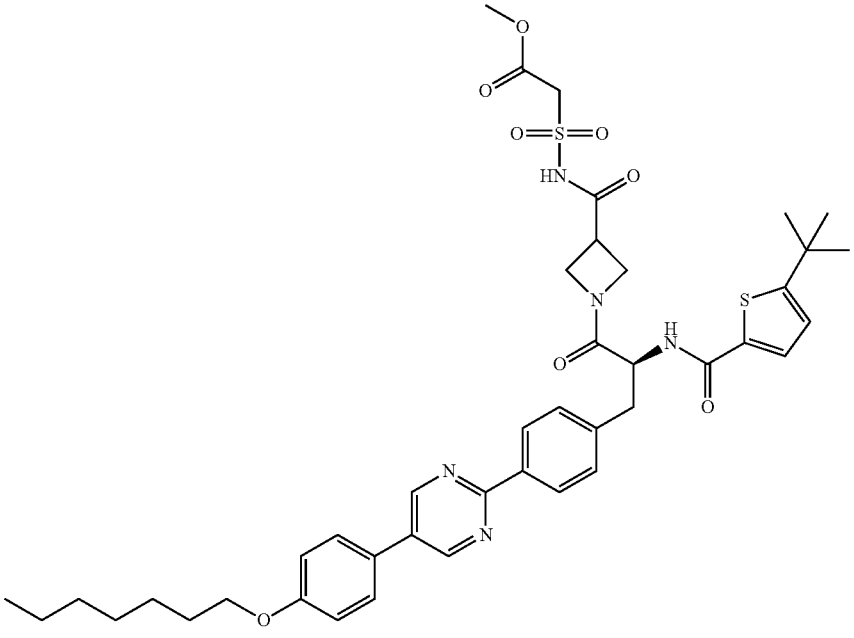 [SMILES: CCCCCCCOc1ccc(-c2cnc(-c3ccc(C[C@H](NC(=O)c4ccc(C(C)(C)C)s4)C(=O)N4CC(C(=O)NS(=O)(=O)CC(=O)OC)C4)cc3)nc2)cc1] | 654 | 10.10 | 14 |
| 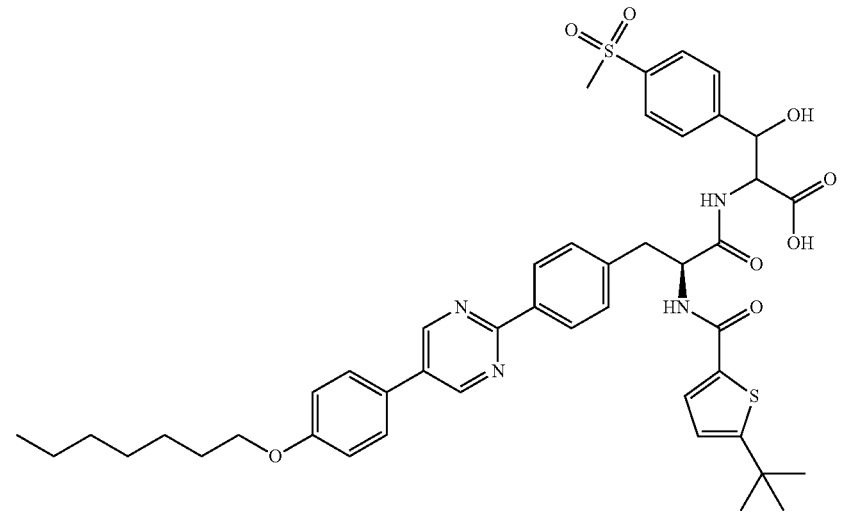 [SMILES: CCCCCCCOc1ccc(-c2cnc(-c3ccc(C[C@H](NC(=O)c4ccc(C(C)(C)C)s4)C(=O)NC(C(=O)O)C(O)c4ccc(S(C)(=O)=O)cc4)cc3)nc2)cc1] | 655 | 9.87 | 14 |

TABLE 1-continued

| STRUCTURE | COMPOUND NUMBER | LCMS RETENTION TIME (min) | PURITY METHOD |
|---|---|---|---|
| 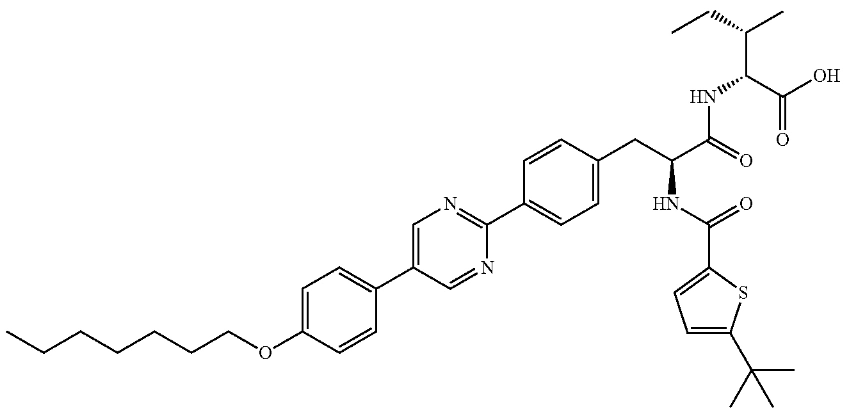 [SMILES: CCCCCCCOc1ccc(-c2cnc(-c3ccc(C[C@H](NC(=O)c4ccc(C(C)(C)C)s4)C(=O)N[C@@H](C(=O)O)[C@@H](C)CC)cc3)nc2)cc1] | 656 | 10.47 | 14 |
| 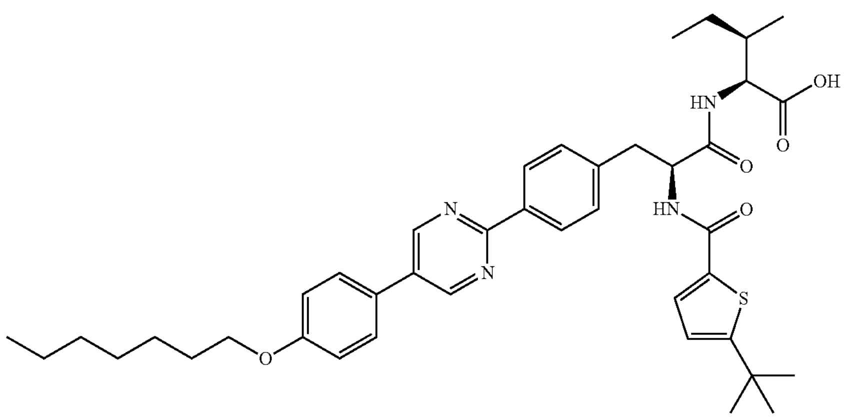 [SMILES: CCCCCCCOc1ccc(-c2cnc(-c3ccc(C[C@H](NC(=O)c4ccc(C(C)(C)C)s4)C(=O)N[C@H](C(=O)O)[C@H](C)CC)cc3)nc2)cc1] | 657 | 10.47 | 14 |
| 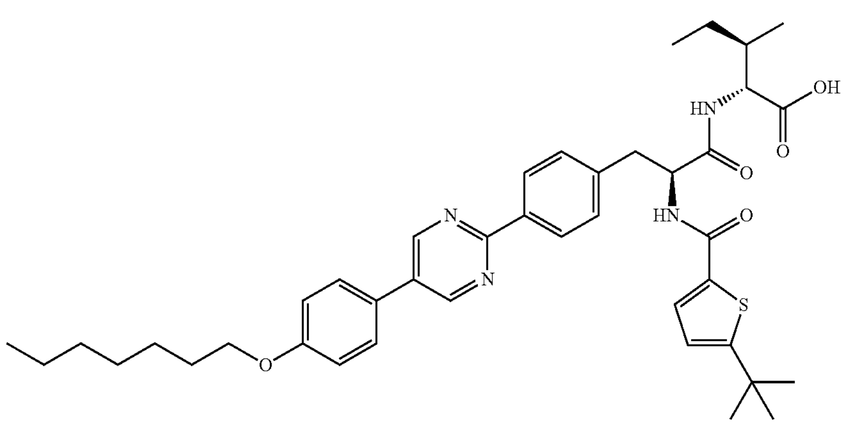 [SMILES: CCCCCCCOc1ccc(-c2cnc(-c3ccc(C[C@H](NC(=O)c4ccc(C(C)(C)C)s4)C(=O)N[C@@H](C(=O)O)[C@H](C)CC)cc3)nc2)cc1] | 658 | 10.43 | 14 |

TABLE 1-continued

| STRUCTURE | COMPOUND NUMBER | LCMS RETENTION TIME (min) | PURITY METHOD |
|---|---|---|---|
| 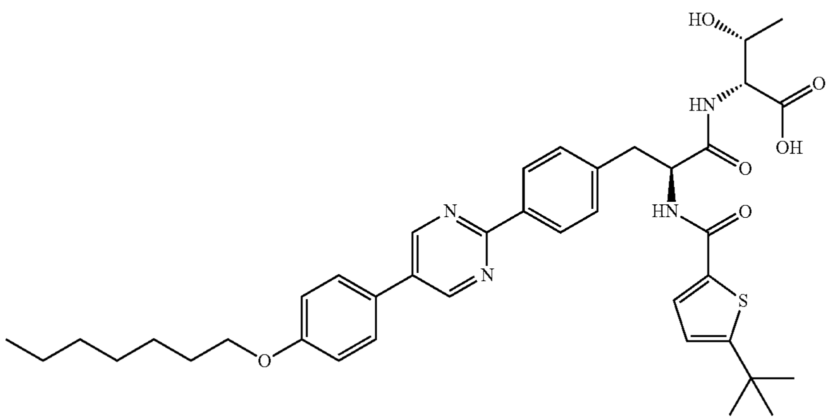 [SMILES: CCCCCCCOc1ccc(-c2cnc(-c3ccc(C[C@H](NC(=O)c4ccc(C(C)(C)C)s4)C(=O)N[C@@H](C(=O)O)[C@@H](C)O)cc3)nc2)cc1] | 659 | 9.57 | 14 |
| 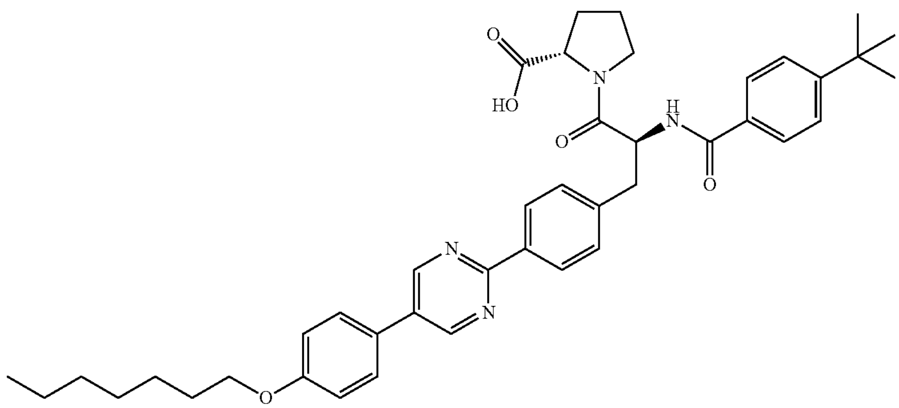 [SMILES: CCCCCCCOc1ccc(-c2cnc(-c3ccc(C[C@H](NC(=O)c4ccc(C(C)(C)C)cc4)C(=O)N4CCC[C@H]4C(=O)O)cc3)nc2)cc1] | 660 | 10.23 | 2 |
| 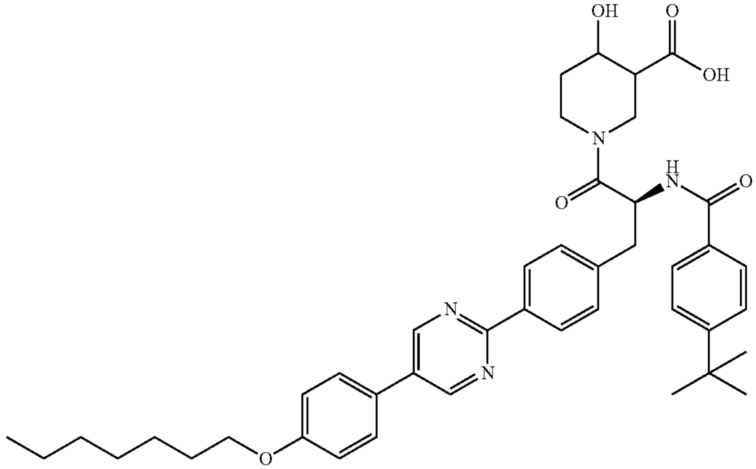 [SMILES: CCCCCCCOc1ccc(-c2cnc(-c3ccc(C[C@H](NC(=O)c4ccc(C(C)(C)C)cc4)C(=O)N4CCC(O)C(C(=O)O)C4)cc3)nc2)cc1] | 661 | 10.29 | 14 |

TABLE 1-continued

| STRUCTURE | COMPOUND NUMBER | LCMS RETENTION TIME (min) | PURITY METHOD |
|---|---|---|---|
| 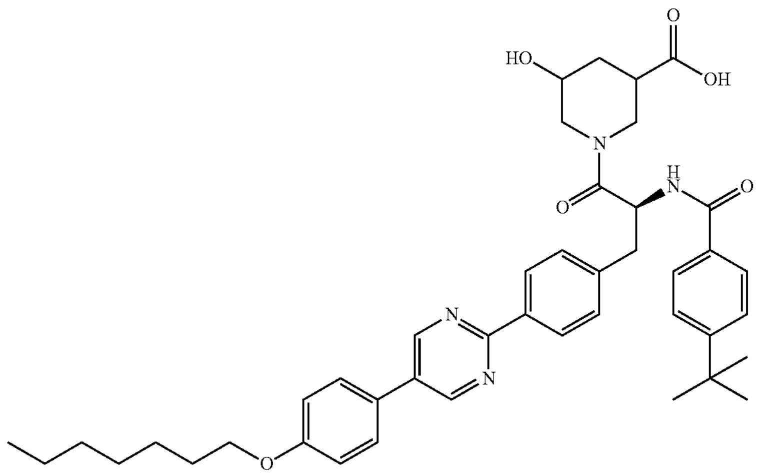 [SMILES: CCCCCCCOc1ccc(-c2cnc(-c3ccc(C[C@H](NC(=O)c4ccc(C(C)(C)C)cc4)C(=O)N4CC(O)CC(C(=O)O)C4)cc3)nc2)cc1] | 662 | 10.16 | 14 |
| 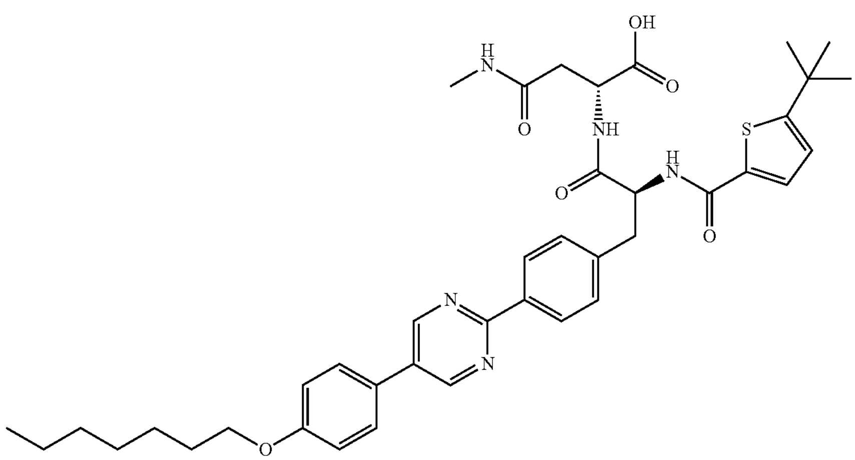 [SMILES: CCCCCCCOc1ccc(-c2cnc(-c3ccc(C[C@H](NC(=O)c4ccc(C(C)(C)C)s4)C(=O)N[C@H](CC(=O)NC)C(=O)O)cc3)nc2)cc1] | 663 | 9.79 | 14 |
| 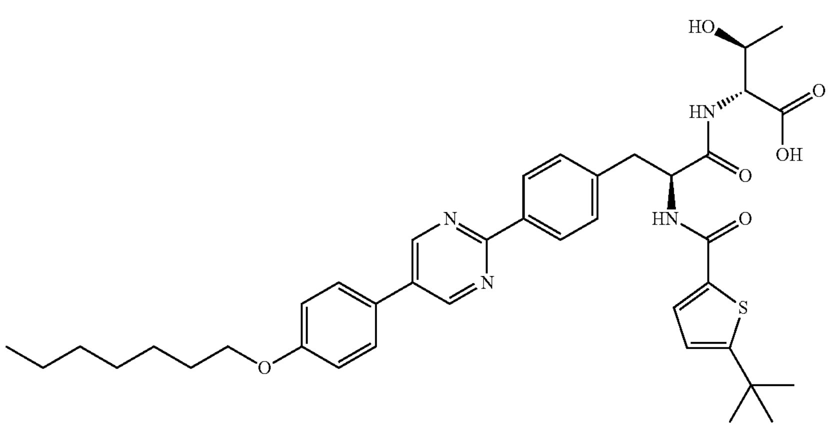 [SMILES: CCCCCCCOc1ccc(-c2cnc(-c3ccc(C[C@H](NC(=O)c4ccc(C(C)(C)C)s4)C(=O)N[C@@H](C(=O)O)[C@H](C)O)cc3)nc2)cc1] | 664 | 9.59 | 14 |

TABLE 1-continued
| STRUCTURE | COMPOUND NUMBER | LCMS RETENTION TIME (min) | PURITY METHOD |
|---|---|---|---|
| 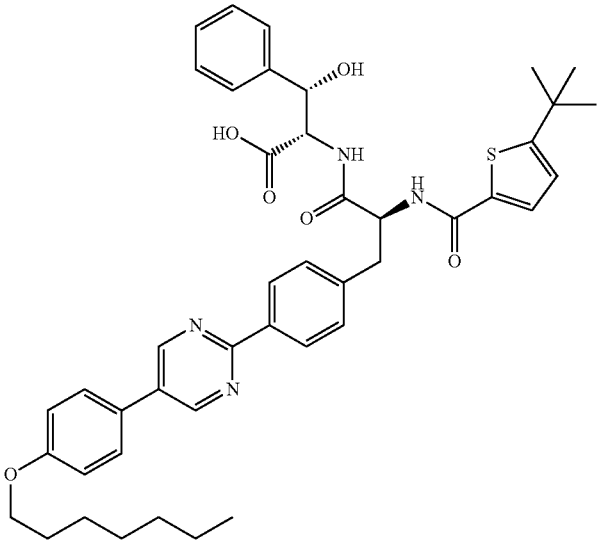 [SMILES: CCCCCCCOc1ccc(-c2cnc(-c3ccc(C[C@H](NC(=O)c4ccc(C(C)(C)C)s4)C(=O)N[C@H](C(=O)O)[C@@H](O)c4ccccc4)cc3)nc2)cc1] | 665 | 10.68 | 10 |
| 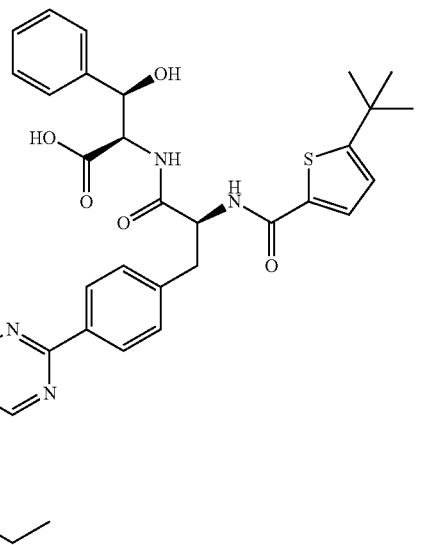 | 666 | 10.68 | 10 |

TABLE 1-continued

| STRUCTURE | COMPOUND NUMBER | LCMS RETENTION TIME (min) | PURITY METHOD |
|---|---|---|---|
| 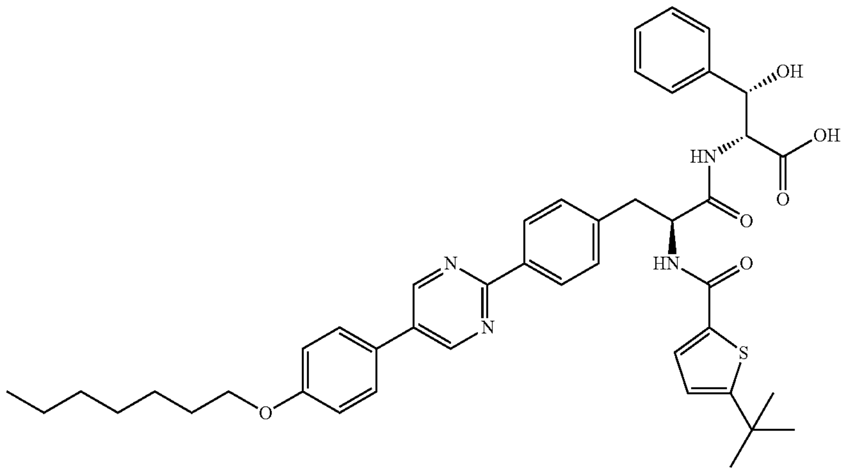 [SMILES: CCCCCCCOc1ccc(-c2cnc(-c3ccc(C[C@H](NC(=O)c4ccc(C(C)(C)C)s4)C(=O)N[C@@H](C(=O)O)[C@@H](O)c4ccccc4)cc3)nc2)cc1] | 667 | 10.63 | 10 |
| 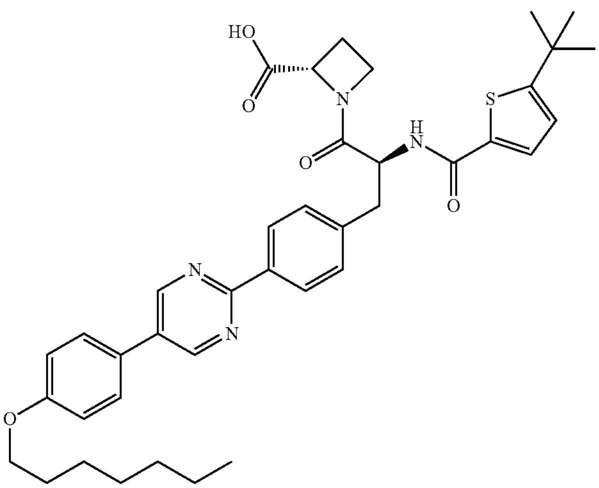 [SMILES: CCCCCCCOc1ccc(-c2cnc(-c3ccc(C[C@H](NC(=O)c4ccc(C(C)(C)C)s4)C(=O)N4CC[C@H]4C(=O)O)cc3)nc2)cc1] | 668 | 10.38 | 10 |
| 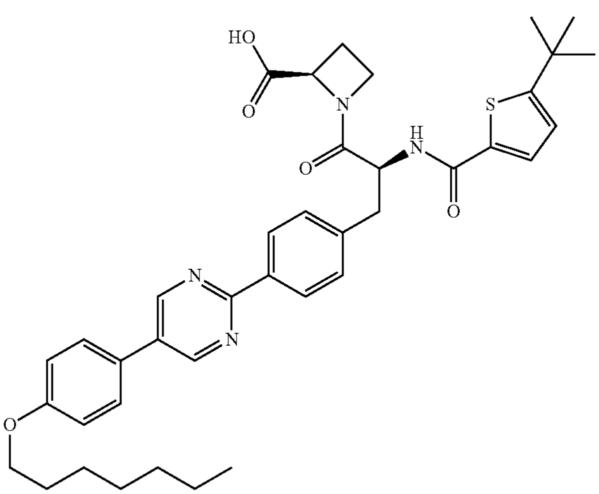 [SMILES: CCCCCCCOc1ccc(-c2cnc(-c3ccc(C[C@H](NC(=O)c4ccc(C(C)(C)C)s4)C(=O)N4CC[C@@H]4C(=O)O)cc3)nc2)cc1] | 669 | 10.33 | 10 |

TABLE 1-continued

| STRUCTURE | COMPOUND NUMBER | LCMS RETENTION TIME (min) | PURITY METHOD |
|---|---|---|---|
| 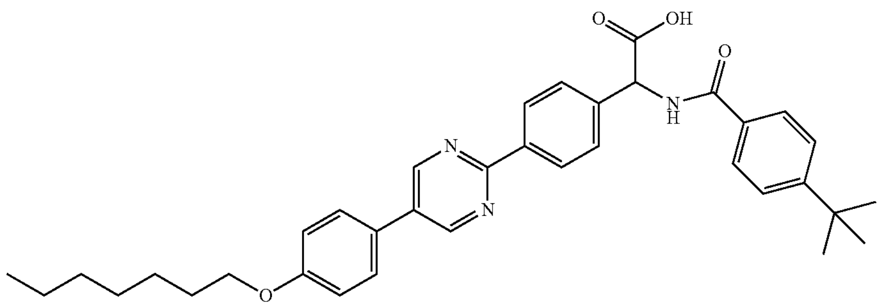 [SMILES: CCCCCCCOc1ccc(-c2cnc(-c3ccc(C(NC(=O)c4ccc(C(C)(C)C)cc4)C(=O)O)cc3)nc2)cc1] | 670 | 9.57 | 14 |
| 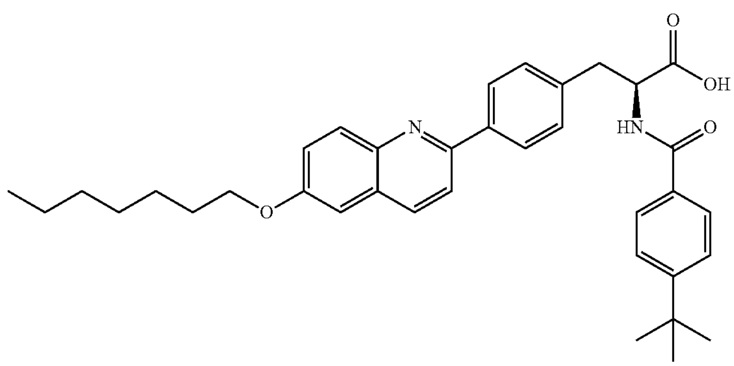 [SMILES: CCCCCCCOc1ccc2nc(-c3ccc(C[C@H](NC(=O)c4ccc(C(C)(C)C)cc4)C(=O)O)cc3)ccc2c1] | 671 | 9.38 | 14 |
| 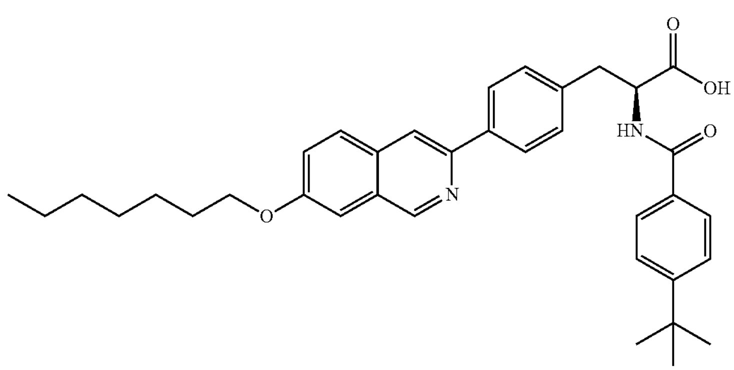 | 672 | 9.67 | 14 |
| 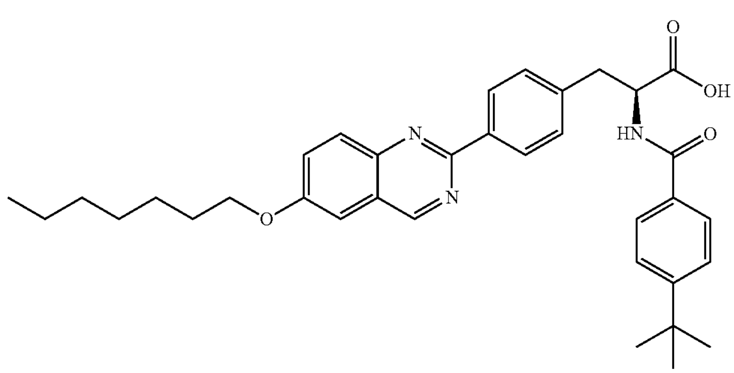 [SMILES: CCCCCCCOc1ccc2nc(-c3ccc(C[C@H](NC(=O)c4ccc(C(C)(C)C)cc4)C(=O)O)cc3)ncc2c1] | 673 | 9.40 | 14 |

TABLE 1-continued

| STRUCTURE | COMPOUND NUMBER | LCMS RETENTION TIME (min) | PURITY METHOD |
|---|---|---|---|
| 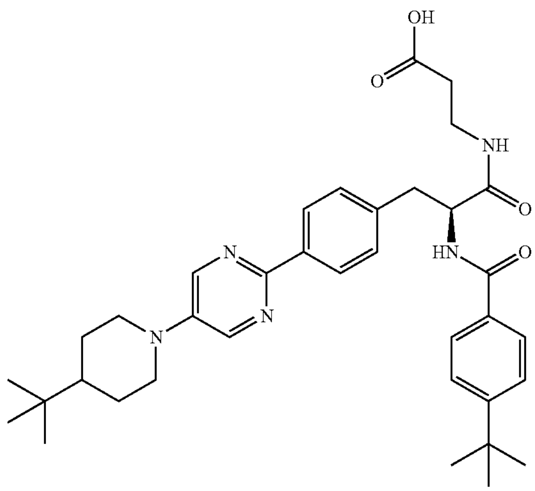 [SMILES: CC(C)(C)c1ccc(C(=O)N[C@@H](Cc2ccc(-c3ncc(N4CCC(C(C)(C)C)CC4)cn3)cc2)C(=O)NCCC(=O)O)cc1] | 674 | 8.92 | 14 |
| 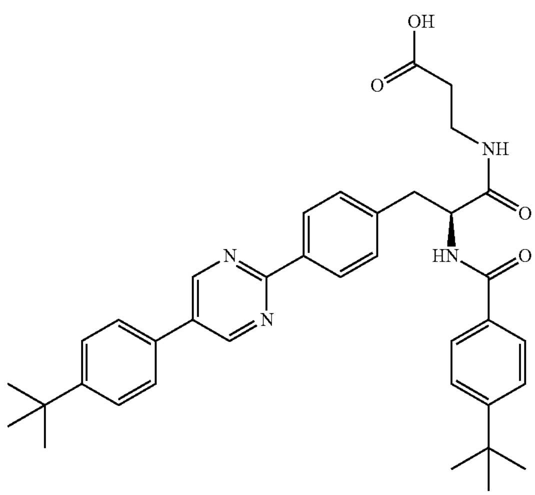 [SMILES: CC(C)(C)c1ccc(C(=O)N[C@@H](Cc2ccc(-c3ncc(-c4ccc(C(C)(C)C)cc4)cn3)cc2)C(=O)NCCC(=O)O)cc1] | 675 | 8.94 | 14 |
| 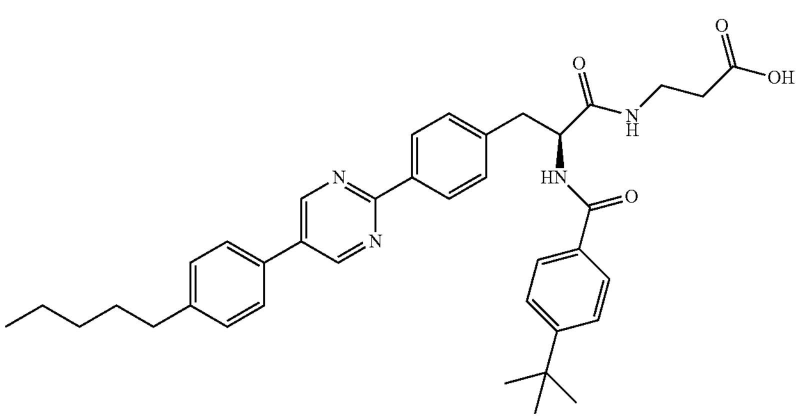 [SMILES: CCCCCc1ccc(-c2cnc(-c3ccc(C[C@H](NC(=O)c4ccc(C(C)(C)C)cc4)C(=O)NCCC(=O)O)cc3)nc2)cc1] | 676 | 10.34 | 14 |

TABLE 1-continued

| STRUCTURE | COMPOUND NUMBER | LCMS RETENTION TIME (min) | PURITY METHOD |
|---|---|---|---|
| (structure) | 677 | 9.79 | 14 |
| (structure) | 678 | 10.92 | 14 |
| (structure) | 679 | 10.45 | 14 |

TABLE 1-continued
| STRUCTURE | COMPOUND NUMBER | LCMS RETENTION TIME (min) | PURITY METHOD |
|---|---|---|---|
| 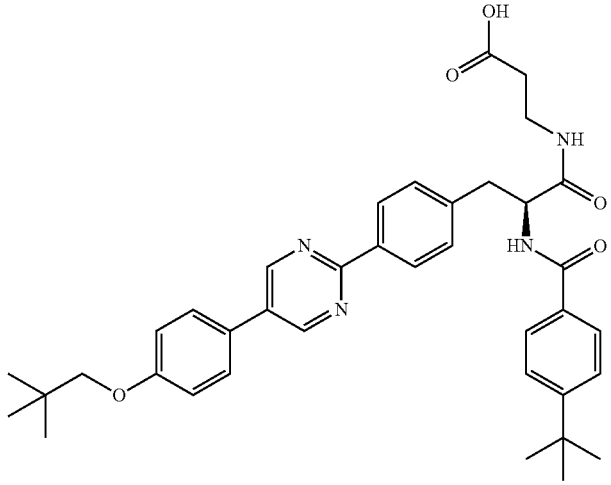 | 680 | 9.91 | 14 |
| 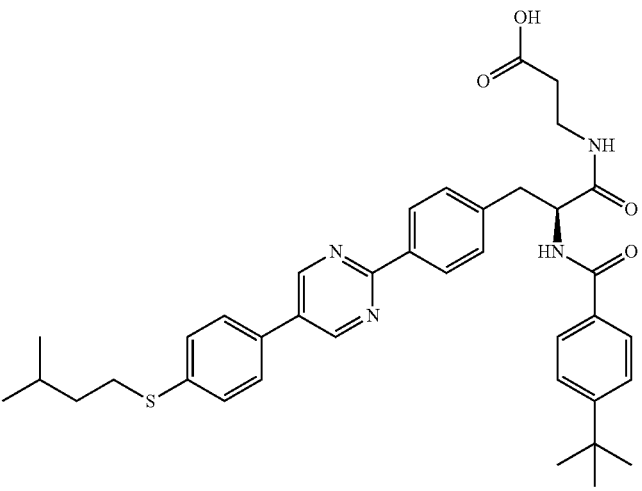 [SMILES: CC(C)CCSc1ccc(-c2cnc(-c3ccc(C[C@H](NC(=O)c4ccc(C(C)(C)C)cc4)C(=O)NCCC(=O)O)cc3)nc2)cc1] | 681 | 10.24 | 14 |
| 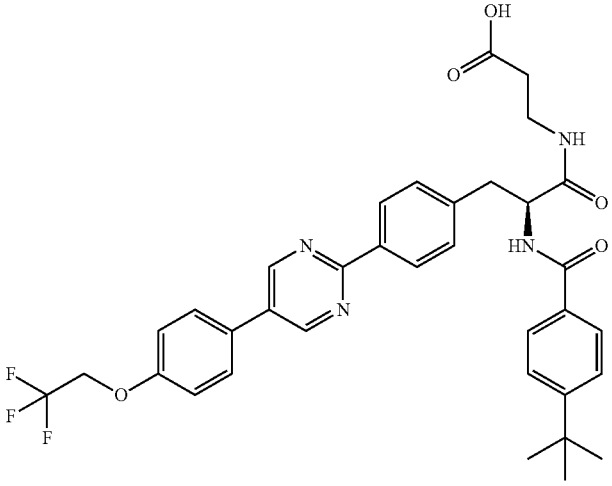 [SMILES: CC(C)(C)c1ccc(C(=O)N[C@@H](Cc2ccc(-c3ncc(-c4ccc(OCC(F)(F)F)cc4)cn3)cc2)C(=O)NCCC(=O)O)cc1] | 682 | 8.258 | 14 |

TABLE 1-continued

| STRUCTURE | COMPOUND NUMBER | LCMS RETENTION TIME (min) | PURITY METHOD |
|---|---|---|---|
| 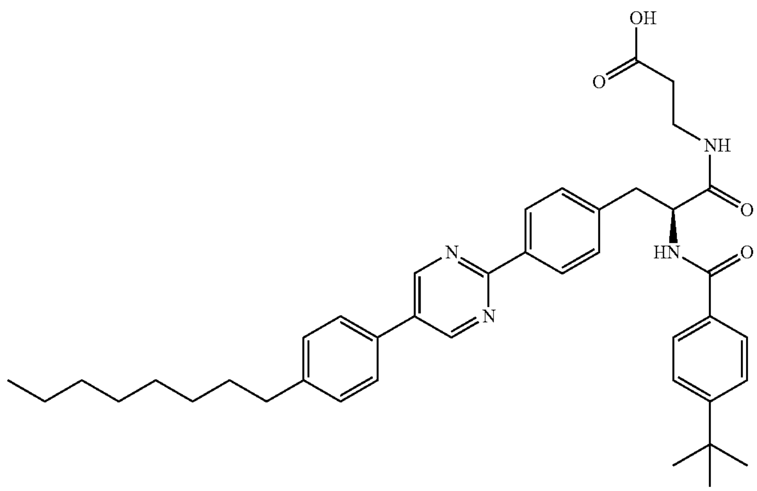 [SMILES: CCCCCCCCc1ccc(-c2cnc(-c3ccc(C[C@H](NC(=O)c4ccc(C(C)(C)C)cc4)C(=O)NCCC(=O)O)cc3)nc2)cc1] | 683 | 12.00 | 14 |
| 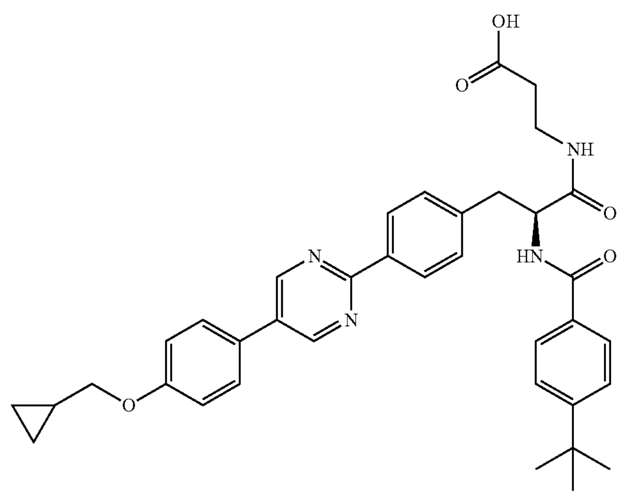 [SMILES: CC(C)(C)c1ccc(C(=O)N[C@@H](Cc2ccc(-c3ncc(-c4ccc(OCC5CC5)cc4)cn3)cc2)C(=O)NCCC(=O)O)cc1] | 684 | 11.47 | 14 |
| 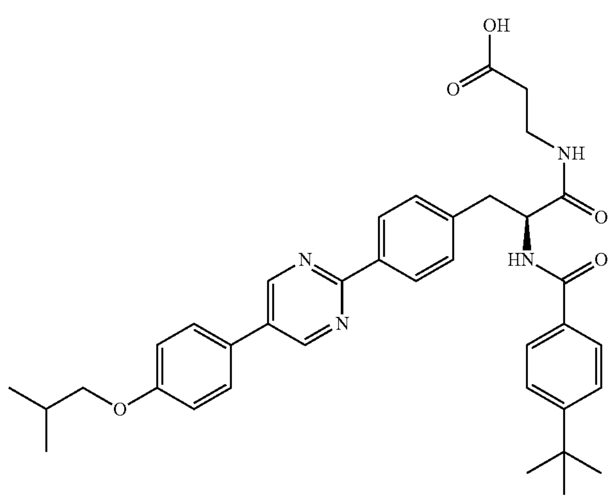 [SMILES: CC(C)COc1ccc(-c2cnc(-c3ccc(C[C@H](NC(=O)c4ccc(C(C)(C)C)cc4)C(=O)NCCC(=O)O)cc3)nc2)cc1] | 685 | 9.34 | 14 |

TABLE 1-continued

| STRUCTURE | COMPOUND NUMBER | LCMS RETENTION TIME (min) | PURITY METHOD |
|---|---|---|---|
| 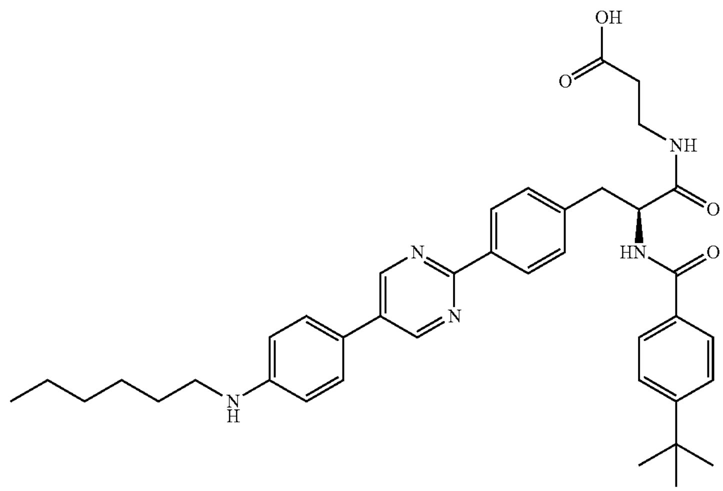 [SMILES: CCCCCCNc1ccc(-c2cnc(-c3ccc(C[C@H](NC(=O)c4ccc(C(C)(C)C)cc4)C(=O)NCCC(=O)O)cc3)nc2)cc1] | 686 | 9.88 | 14 |
| 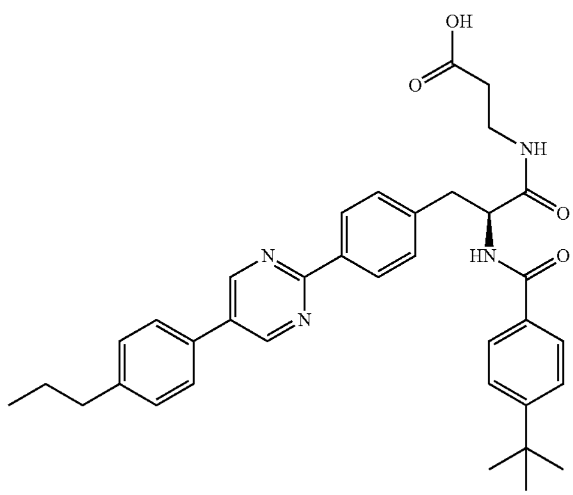 [SMILES: CCCc1ccc(-c2cnc(-c3ccc(C[C@H](NC(=O)c4ccc(C(C)(C)C)cc4)C(=O)NCCC(=O)O)cc3)nc2)cc1] | 687 | 9.29 | 14 |
| 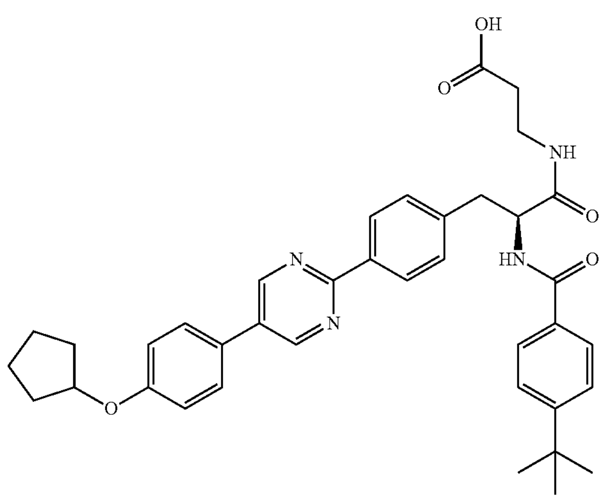 [SMILES: CC(C)(C)c1ccc(C(=O)N[C@@H](Cc2ccc(-c3ncc(-c4ccc(OC5CCCC5)cc4)cn3)cc2)C(=O)NCCC(=O)O)cc1] | 688 | 9.37 | 14 |

TABLE 1-continued

| STRUCTURE | COMPOUND NUMBER | LCMS RETENTION TIME (min) | PURITY METHOD |
|---|---|---|---|
| 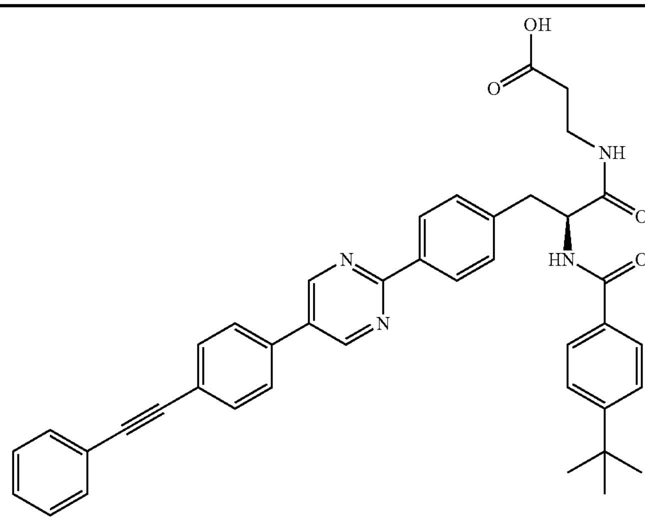 | 689 | 9.25 | 14 |
| 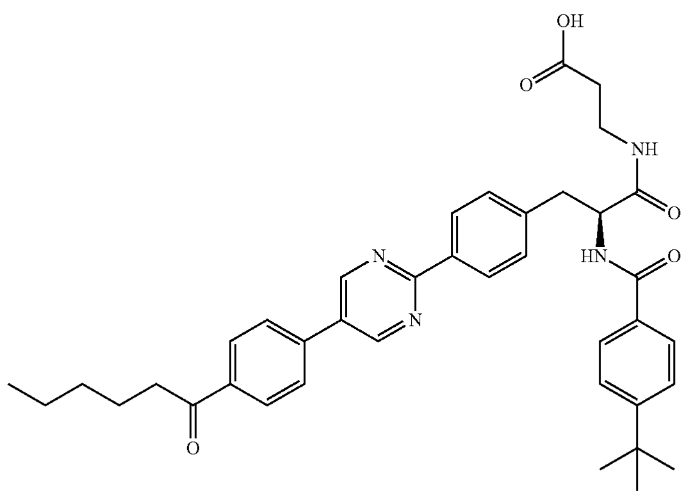 [SMILES: CCCCCC(=O)c1ccc(-c2cnc(-c3ccc(C[C@H](NC(=O)c4ccc(C(C)(C)C)cc4)C(=O)NCCC(=O)O)cc3)nc2)cc1] | 690 | 8.90 | 14 |
| 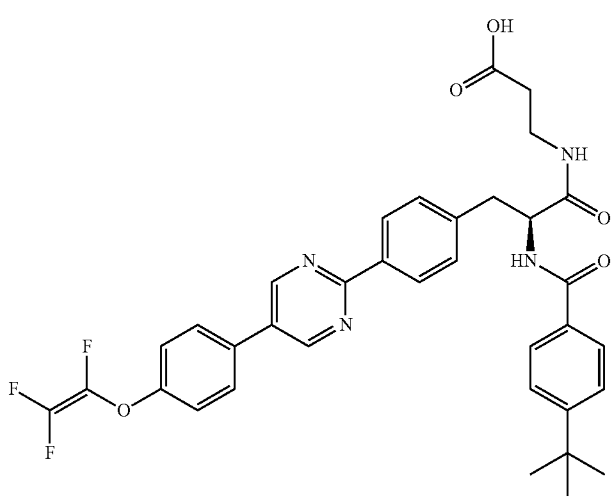 [SMILES: CC(C)(C)c1ccc(C(=O)N[C@@H](Cc2ccc(-c3ncc(-c4ccc(OC(F)=C(F)F)cc4)cn3)cc2)C(=O)NCCC(=O)O)cc1] | 691 | 8.03 | 14 |

TABLE 1-continued

| STRUCTURE | COMPOUND NUMBER | LCMS RETENTION TIME (min) | PURITY METHOD |
| --- | --- | --- | --- |
| 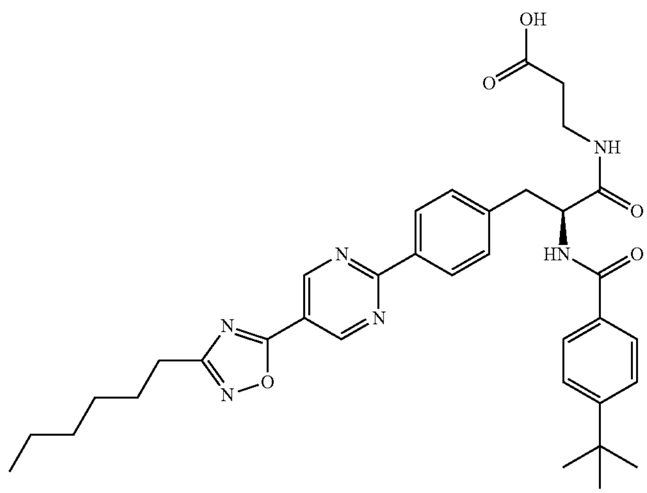 [SMILES: CCCCCCc1noc(-c2cnc(-c3ccc(C[C@H](NC(=O)c4ccc(C(C)(C)C)cc4)C(=O)NCCC(=O)O)cc3)nc2)n1] | 692 | 9.09 | 14 |
| 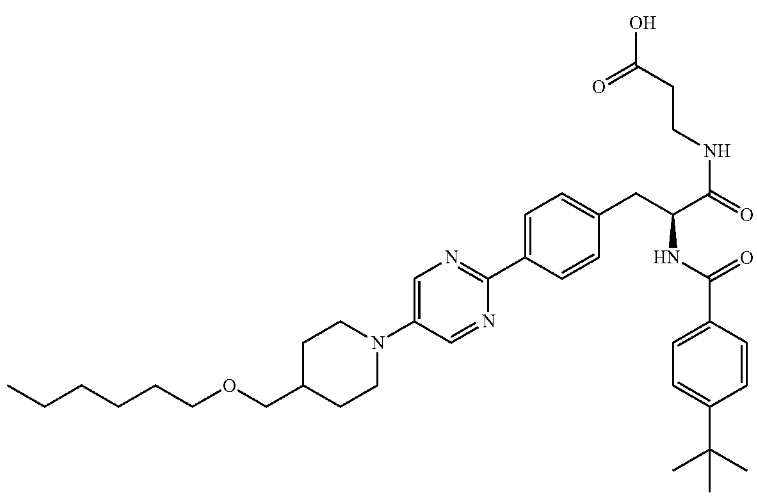 [SMILES: CCCCCCOCC1CCN(c2cnc(-c3ccc(C[C@H](NC(=O)c4ccc(C(C)(C)C)cc4)C(=O)NCCC(=O)O)cc3)nc2)CC1] | 693 | 9.26 | 14 |
| 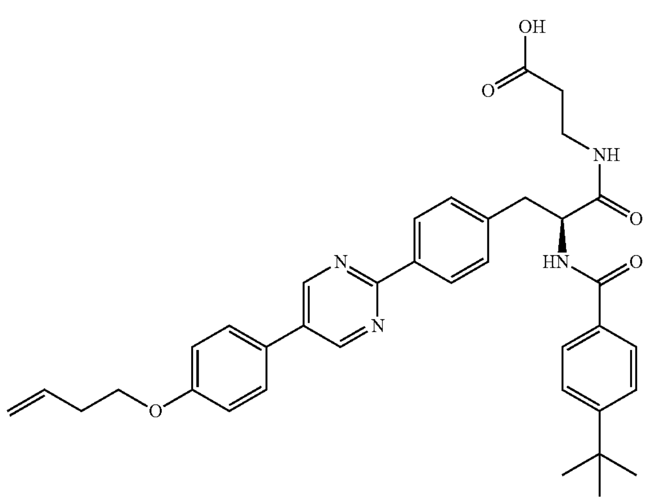 [SMILES: C=CCCOc1ccc(-c2cnc(-c3ccc(C[C@H](NC(=O)c4ccc(C(C)(C)C)cc4)C(=O)NCCC(=O)O)cc3)nc2)cc1] | 694 | 8.22 | 14 |

TABLE 1-continued

| STRUCTURE | COMPOUND NUMBER | LCMS RETENTION TIME (min) | PURITY METHOD |
|---|---|---|---|
| 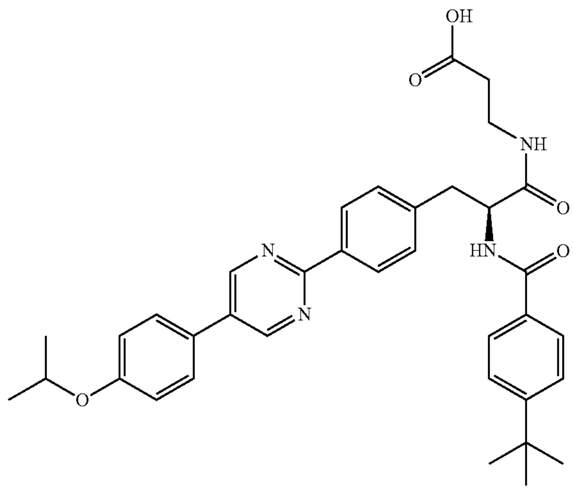 [SMILES: CC(C)Oc1ccc(-c2cnc(-c3ccc(C[C@H](NC(=O)c4ccc(C(C)(C)C)cc4)C(=O)NCCC(=O)O)cc3)nc2)cc1] | 695 | 7.82 | 14 |
| 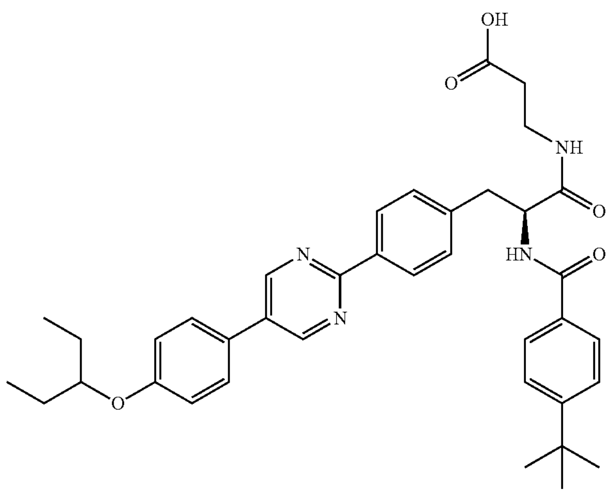 [SMILES: CCC(CC)Oc1ccc(-c2cnc(-c3ccc(C[C@H](NC(=O)c4ccc(C(C)(C)C)cc4)C(=O)NCCC(=O)O)cc3)nc2)cc1] | 696 | 8.82 | 14 |
| 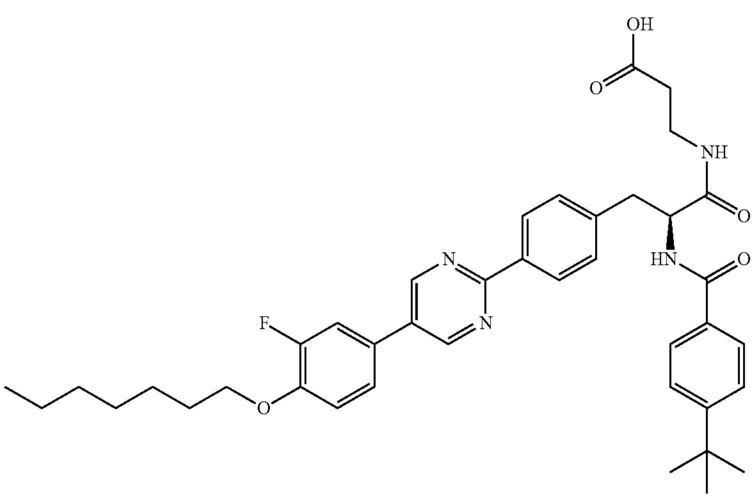 [SMILES: CCCCCCCOc1ccc(-c2cnc(-c3ccc(C[C@H](NC(=O)c4ccc(C(C)(C)C)cc4)C(=O)NCCC(=O)O)cc3)nc2)cc1C] | 697 | 10.53 | 14 |

TABLE 1-continued

| STRUCTURE | COMPOUND NUMBER | LCMS RETENTION TIME (min) | PURITY METHOD |
|---|---|---|---|
| 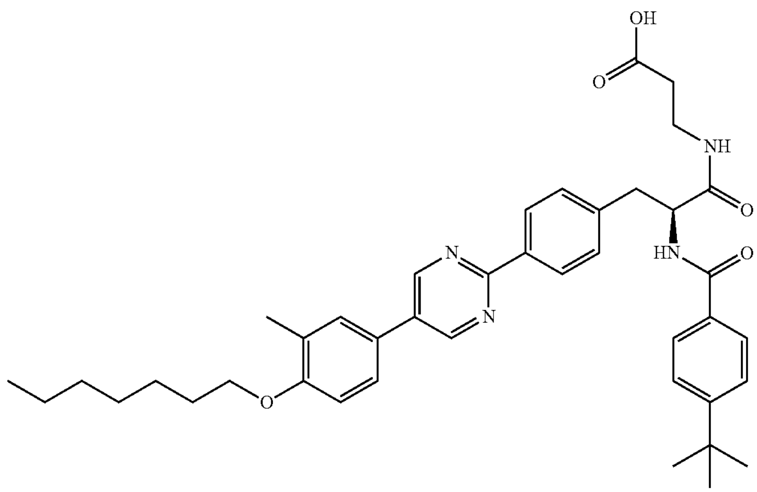 | 698 | 10.49 | 14 |
| 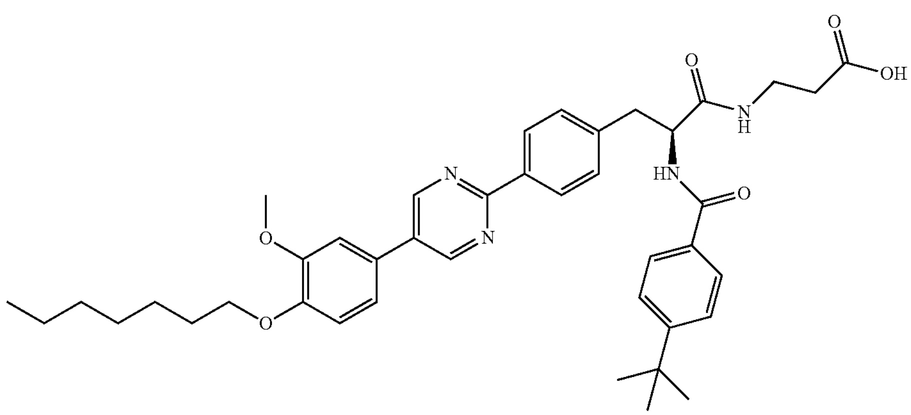 [SMILES: CCCCCCCOc1ccc(-c2cnc(-c3ccc(C[C@H](NC(=O)c4ccc(C(C)(C)C)cc4)C(=O)NCCC(=O)O)cc3)nc2)cc1OC] | 699 | 9.30 | 14 |
| 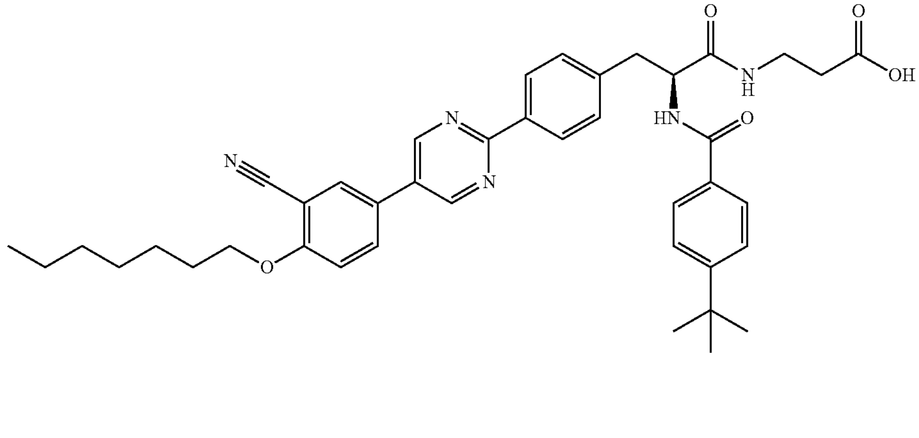 [SMILES: CCCCCCCOc1ccc(-c2cnc(-c3ccc(C[C@H](NC(=O)c4ccc(C(C)(C)C)cc4)C(=O)NCCC(=O)O)cc3)nc2)cc1C#N] | 700 | 9.14 | 14 |

TABLE 1-continued

| STRUCTURE | COMPOUND NUMBER | LCMS RETENTION TIME (min) | PURITY METHOD |
|---|---|---|---|
| 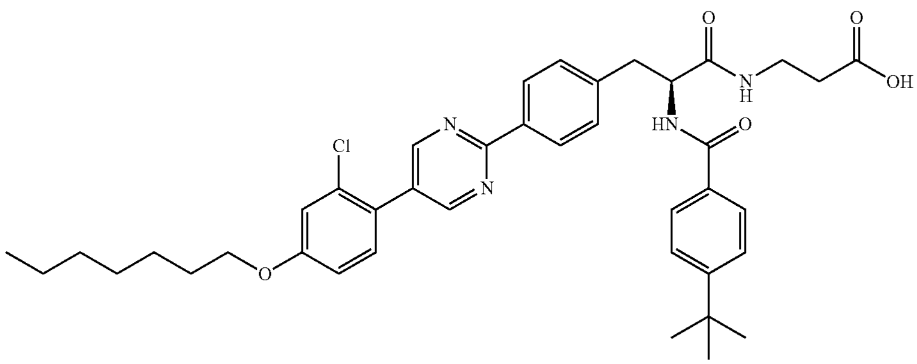 [SMILES: CCCCCCCOc1ccc(-c2cnc(-c3ccc(C[C@H](NC(=O)c4ccc(C(C)(C)C)cc4)C(=O)NCCC(=O)O)cc3)nc2)c(Cl)c1] | 701 | 10.30 | 14 |
| 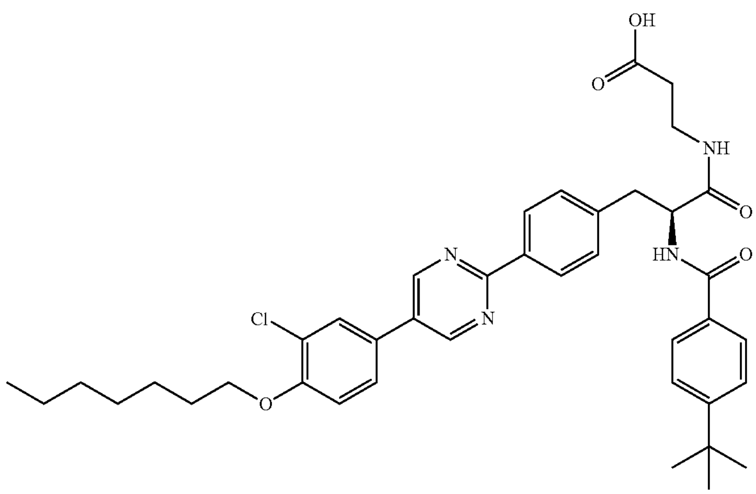 | 702 | 10.21 | 14 |
| 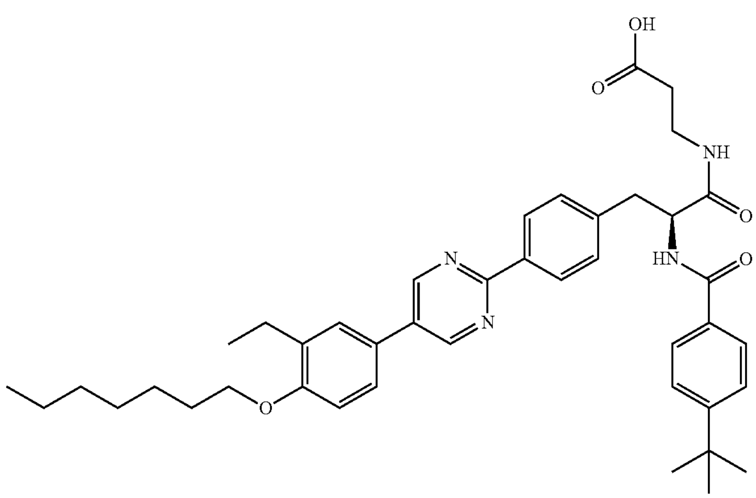 [SMILES: CCCCCCCOc1ccc(-c2cnc(-c3ccc(C[C@H](NC(=O)c4ccc(C(C)(C)C)cc4)C(=O)NCCC(=O)O)cc3)nc2)cc1CC] | 703 | 10.04 | 14 |

TABLE 1-continued
| STRUCTURE | COMPOUND NUMBER | LCMS RETENTION TIME (min) | PURITY METHOD |
|---|---|---|---|
| 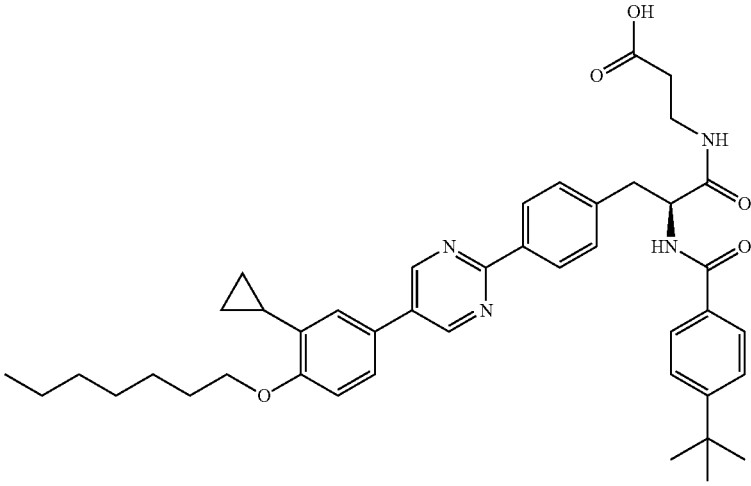 [SMILES: CCCCCCCOc1ccc(-c2cnc(-c3ccc(C[C@H](NC(=O)c4ccc(C(C)(C)C)cc4)C(=O)NCCC(=O)O)cc3)nc2)cc1C1CC1] | 704 | 13.49 | 14 |
| 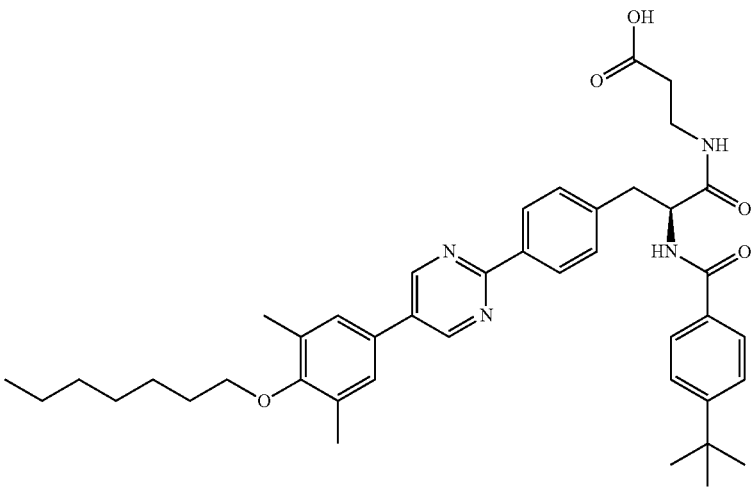 [SMILES: CCCCCCCOc1c(C)cc(-c2cnc(-c3ccc(C[C@H](NC(=O)c4ccc(C(C)(C)C)cc4)C(=O)NCCC(=O)O)cc3)nc2)cc1C] | 705 | 10.85 | 14 |
| 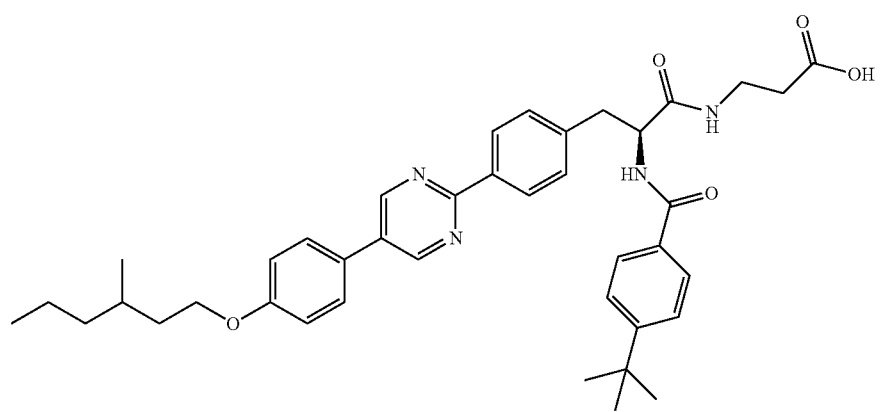 [SMILES: CCCC(C)CCOc1ccc(-c2cnc(-c3ccc(C[C@H](NC(=O)c4ccc(C(C)(C)C)cc4)C(=O)NCCC(=O)O)cc3)nc2)cc1] | 706 | 10.85 | 2 |

TABLE 1-continued

| STRUCTURE | COMPOUND NUMBER | LCMS RETENTION TIME (min) | PURITY METHOD |
|---|---|---|---|
| 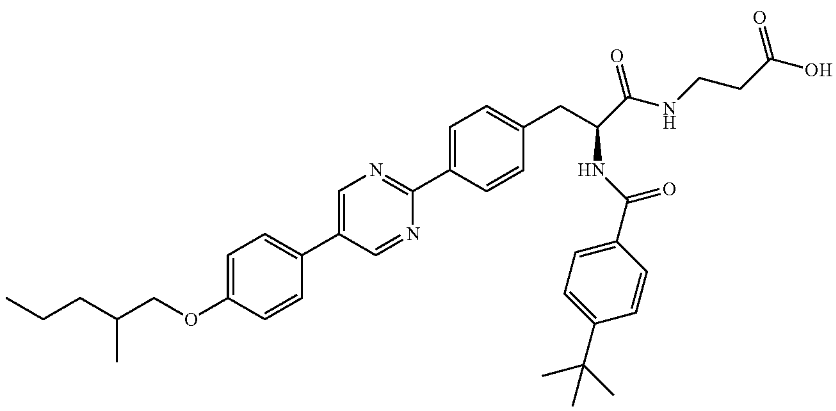 [SMILES: CCCC(C)COc1ccc(-c2cnc(-c3ccc(C[C@H](NC(=O)c4ccc(C(C)(C)C)cc4)C(=O)NCCC(=O)O)cc3)nc2)cc1] | 707 | 10.60 | 2 |
| 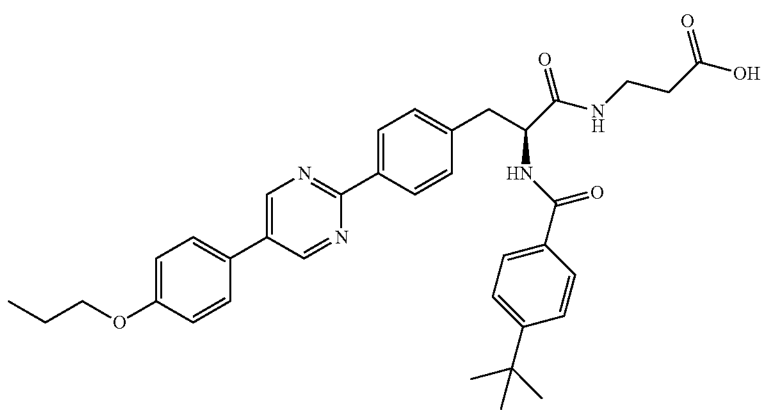 | 708 | 8.40 | 2 |
| 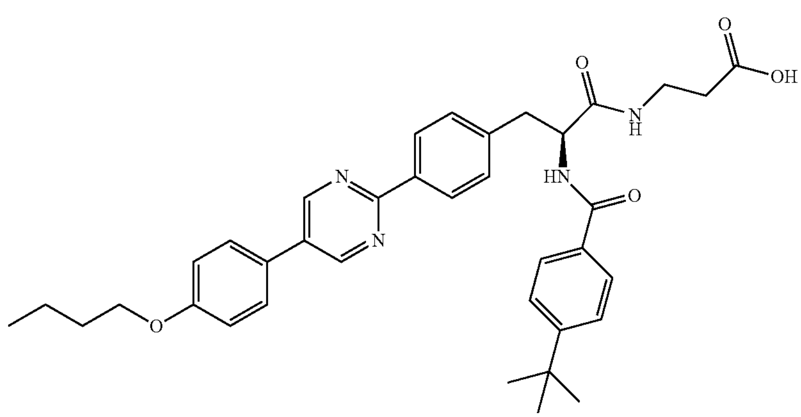 | 709 | 8.91 | 2 |

TABLE 1-continued
| STRUCTURE | COMPOUND NUMBER | LCMS RETENTION TIME (min) | PURITY METHOD |
|---|---|---|---|
| 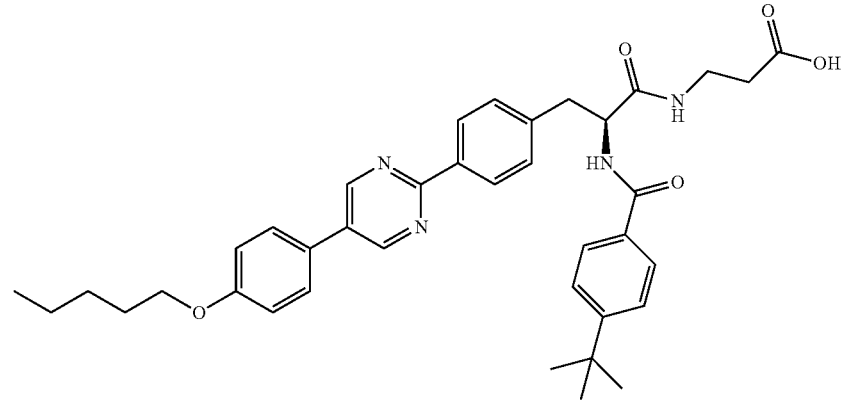 [SMILES: CCCCCOc1ccc(-c2cnc(-c3ccc(C[C@H](NC(=O)c4ccc(C(C)(C)C)cc4)C(=O)NCCC(=O)O)cc3)nc2)cc1] | 710 | 9.442 | 2 |
| 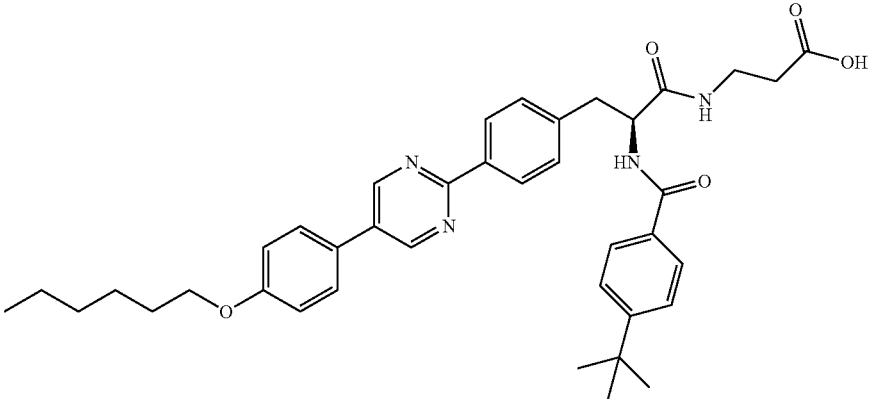 [SMILES: CCCCCCOc1ccc(-c2cnc(-c3ccc(C[C@H](NC(=O)c4ccc(C(C)(C)C)cc4)C(=O)NCCC(=O)O)cc3)nc2)cc1] | 711 | 9.937 | 2 |
| 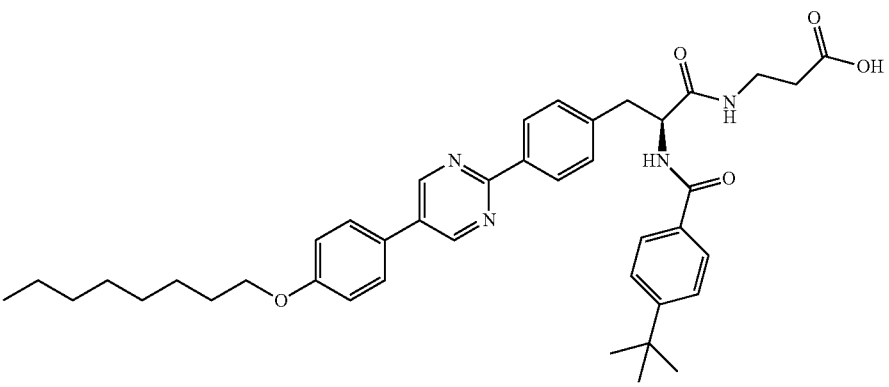 [SMILES: CCCCCCCCOc1ccc(-c2cnc(-c3ccc(C[C@H](NC(=O)c4ccc(C(C)(C)C)cc4)C(=O)NCCC(=O)O)cc3)nc2)cc1] | 712 | 10.943 | 2 |

TABLE 1-continued

| STRUCTURE | COMPOUND NUMBER | LCMS RETENTION TIME (min) | PURITY METHOD |
|---|---|---|---|
| 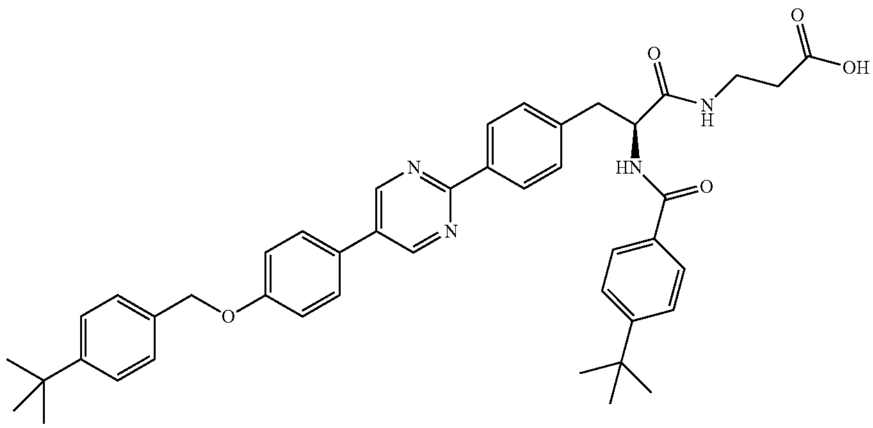 [SMILES: CC(C)(C)c1ccc(COc2ccc(-c3cnc(-c4ccc(C[C@H](NC(=O)c5ccc(C(C)(C)C)cc5)C(=O)NCCC(=O)O)cc4)nc3)cc2)cc1] | 713 | 10.11 | 14 |
| 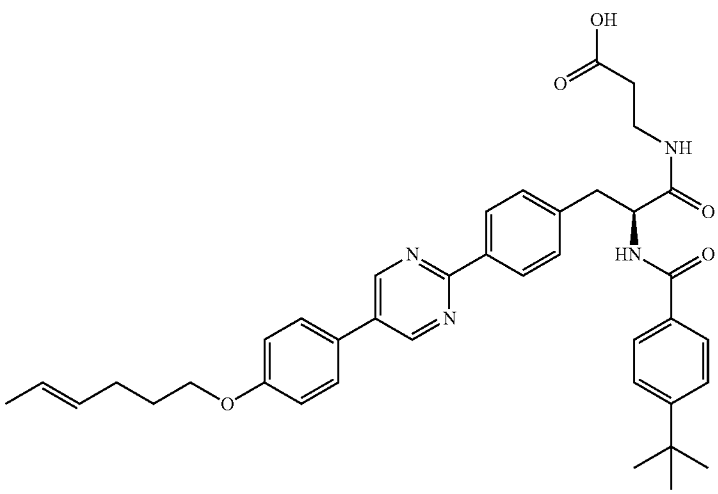 [SMILES: C/C=C/CCCOc1ccc(-c2cnc(-c3ccc(C[C@H](NC(=O)c4ccc(C(C)(C)C)cc4)C(=O)NCCC(=O)O)cc3)nc2)cc1] | 714 | 9.15 | 14 |
| 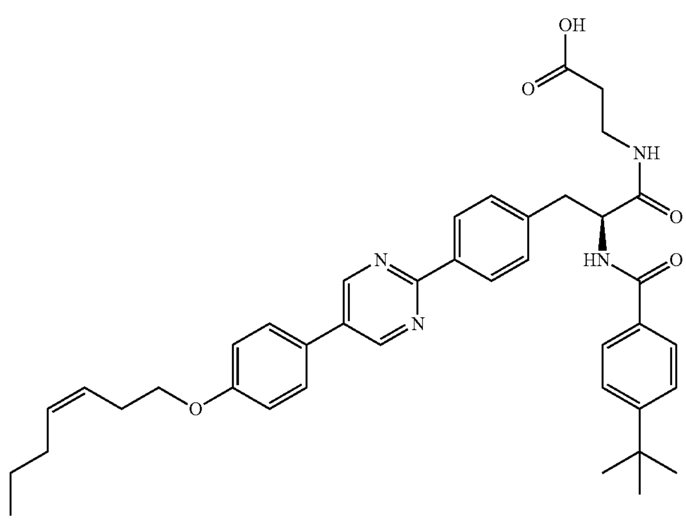 [SMILES: CCC/C=C\CCOc1ccc(-c2cnc(-c3ccc(C[C@H](NC(=O)c4ccc(C(C)(C)C)cc4)C(=O)NCCC(=O)O)cc3)nc2)cc1] | 715 | 10.02 | 14 |

TABLE 1-continued

| STRUCTURE | COMPOUND NUMBER | LCMS RETENTION TIME (min) | PURITY METHOD |
|---|---|---|---|
| 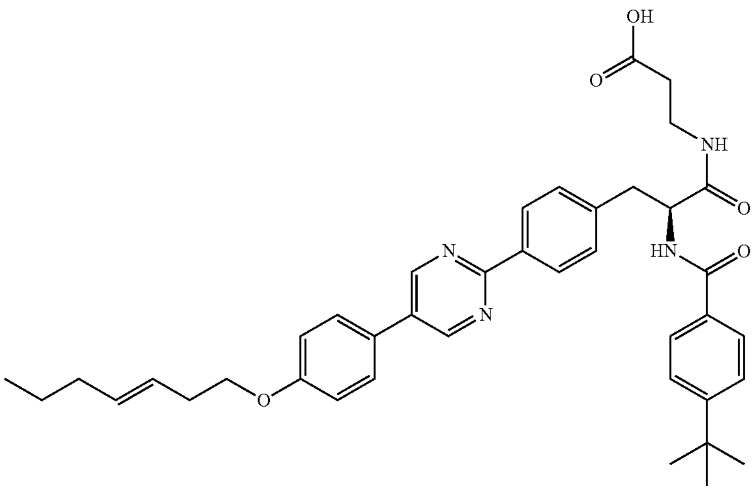 [SMILES: CCC/C=C/CCOc1ccc(-c2cnc(-c3ccc(C[C@H](NC(=O)c4ccc(C(C)(C)C)cc4)C(=O)NCCC(=O)O)cc3)nc2)cc1] | 716 | 10.09 | 14 |
| 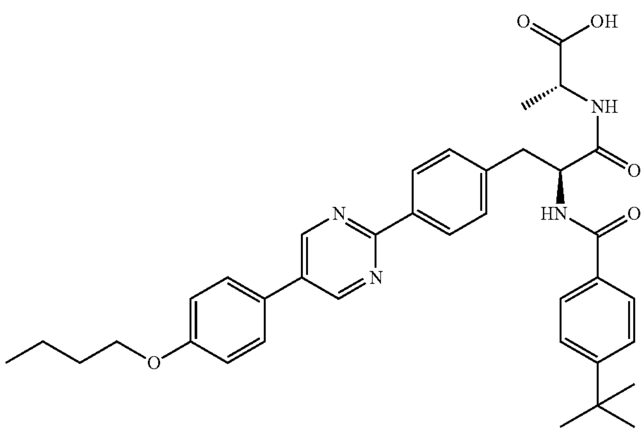 [SMILES: CCCCOc1ccc(-c2cnc(-c3ccc(C[C@H](NC(=O)c4ccc(C(C)(C)C)cc4)C(=O)N[C@H](C)C(=O)O)cc3)nc2)cc1] | 717 | 8.80 | 14 |
| 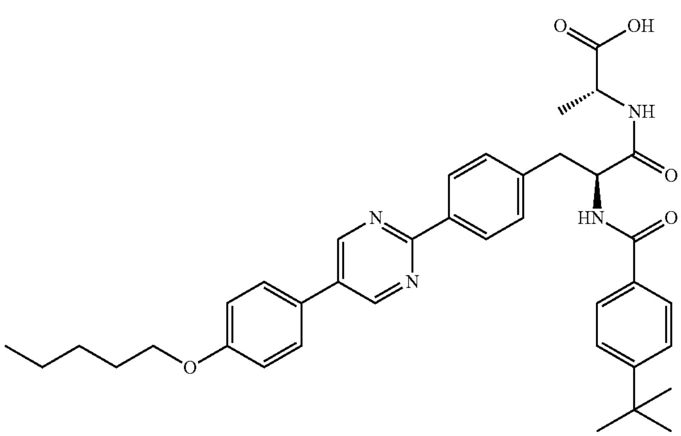 [SMILES: CCCCCOc1ccc(-c2cnc(-c3ccc(C[C@H](NC(=O)c4ccc(C(C)(C)C)cc4)C(=O)N[C@H](C)C(=O)O)cc3)nc2)cc1] | 718 | 9.35 | 14 |

TABLE 1-continued
| STRUCTURE | COMPOUND NUMBER | LCMS RETENTION TIME (min) | PURITY METHOD |
|---|---|---|---|
| 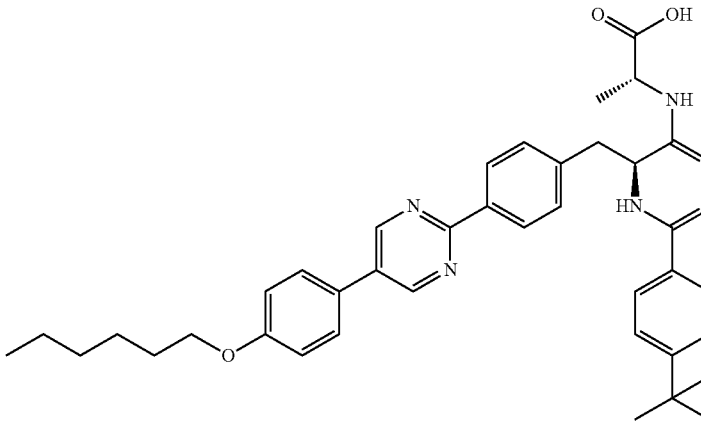 | 719 | 9.83 | 14 |
| 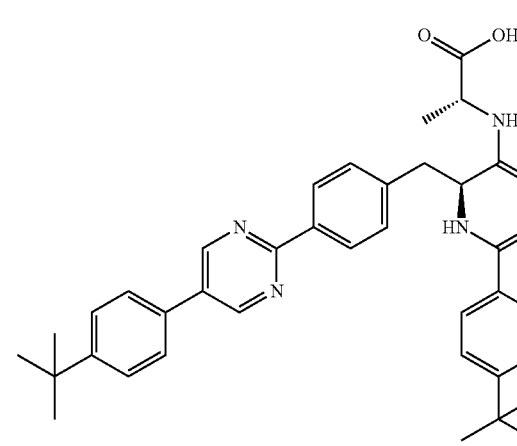 | 720 | 8.85 | 14 |
| 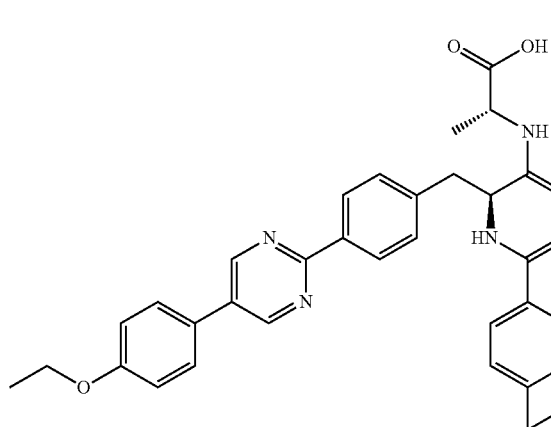 | 721 | 7.33 | 12 |

TABLE 1-continued

| STRUCTURE | COMPOUND NUMBER | LCMS RETENTION TIME (min) | PURITY METHOD |
|---|---|---|---|
| 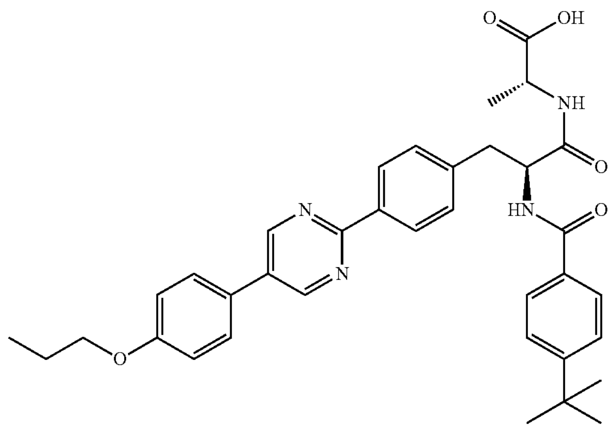 [SMILES: CCCOc1ccc(-c2cnc(-c3ccc(C[C@H](NC(=O)c4ccc(C(C)(C)C)cc4)C(=O)N[C@H](C)C(=O)O)cc3)nc2)cc1] | 722 | 7.88 | 14 |
| 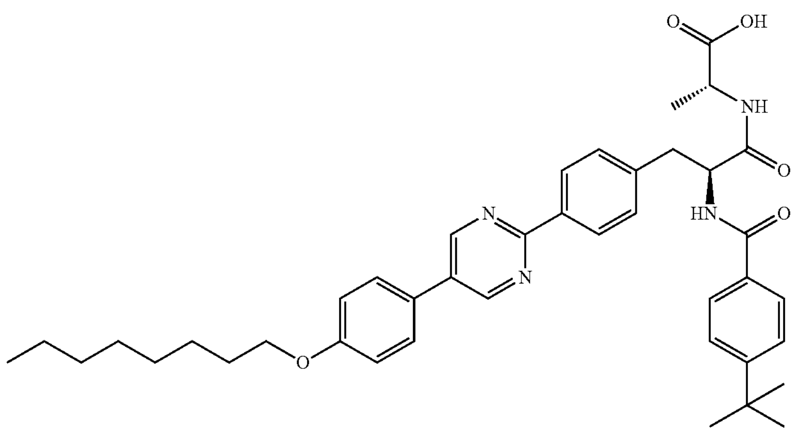 [SMILES: CCCCCCCCOc1ccc(-c2cnc(-c3ccc(C[C@H](NC(=O)c4ccc(C(C)(C)C)cc4)C(=O)N[C@H](C)C(=O)O)cc3)nc2)cc1] | 723 | 10.36 | 14 |
| 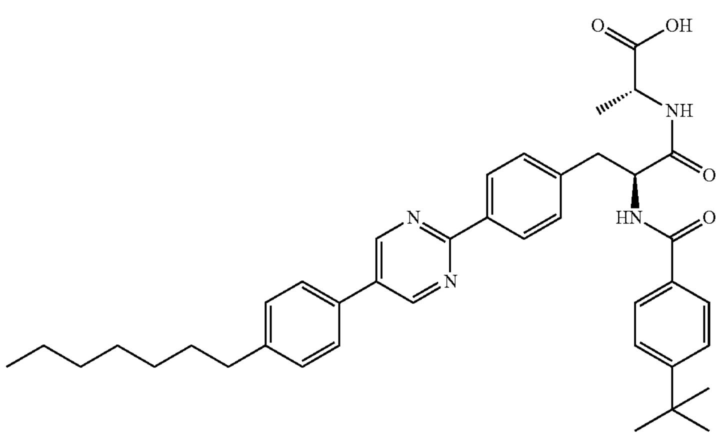 [SMILES: CCCCCCCc1ccc(-c2cnc(-c3ccc(C[C@H](NC(=O)c4ccc(C(C)(C)C)cc4)C(=O)N[C@H](C)C(=O)O)cc3)nc2)cc1] | 724 | 10.28 | 14 |

TABLE 1-continued

| STRUCTURE | COMPOUND NUMBER | LCMS RETENTION TIME (min) | PURITY METHOD |
|---|---|---|---|
| 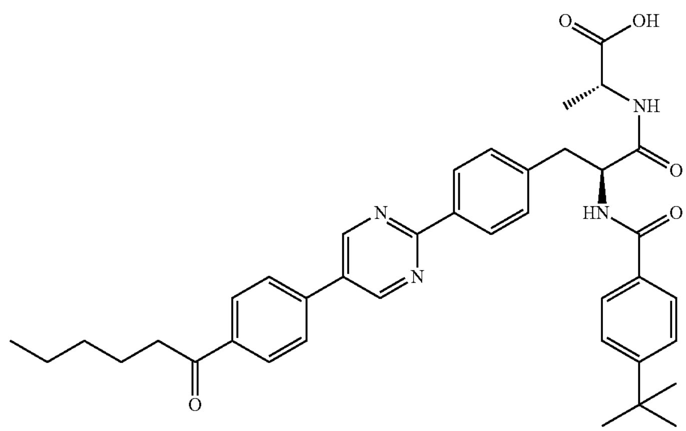 [SMILES: CCCCCC(=O)c1ccc(-c2cnc(-c3ccc(C[C@H](NC(=O)c4ccc(C(C)(C)C)cc4)C(=O)N[C@H](C)C(=O)O)cc3)nc2)cc1] | 725 | 8.32 | 14 |
| 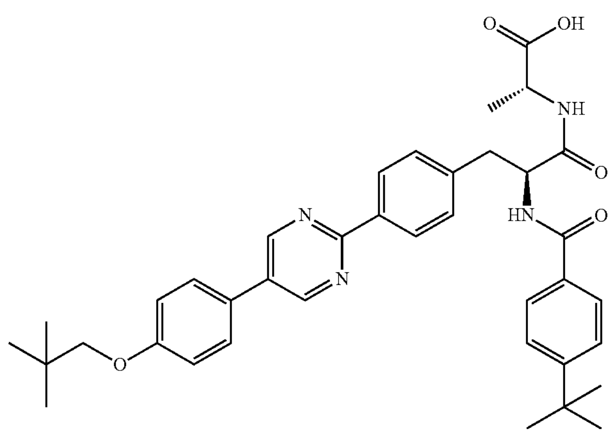 [SMILES: C[C@@H](NC(=O)[C@H](Cc1ccc(-c2ncc(-c3ccc(OCC(C)(C)C)cc3)cn2)cc1)NC(=O)c1ccc(C(C)(C)C)cc1)C(=O)O] | 726 | 8.84 | 14 |
| 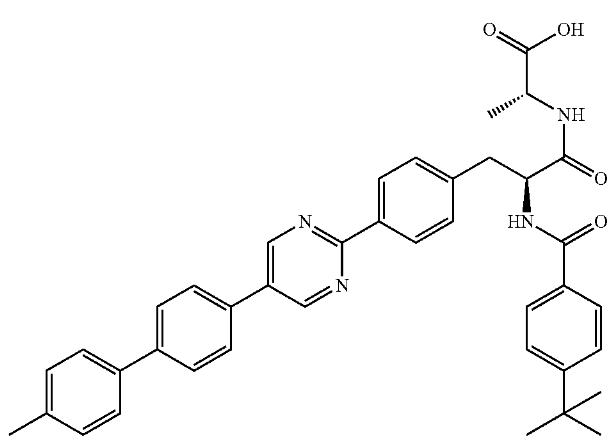 [SMILES: Cc1ccc(-c2ccc(-c3cnc(-c4ccc(C[C@H](NC(=O)c5ccc(C(C)(C)C)cc5)C(=O)N[C@H](C)C(=O)O)cc4)nc3)cc2)cc1] | 727 | 8.63 | 14 |

TABLE 1-continued

| STRUCTURE | COMPOUND NUMBER | LCMS RETENTION TIME (min) | PURITY METHOD |
|---|---|---|---|
| 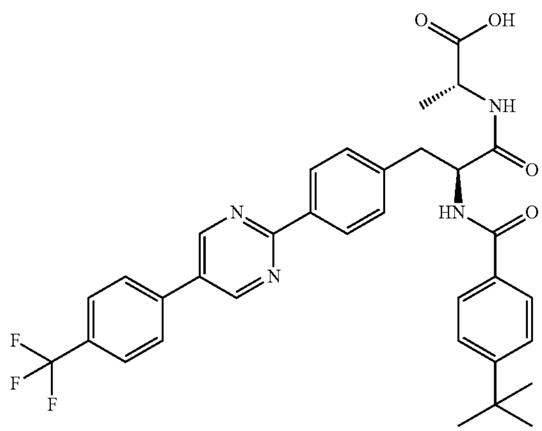 [SMILES: C[C@@H](NC(=O)[C@H](Cc1ccc(-c2ncc(-c3ccc(C(F)(F)F)cc3)cn2)cc1)NC(=O)c1ccc(C(C)(C)C)cc1)C(=O)O] | 728 | 7.72 | 14 |
| 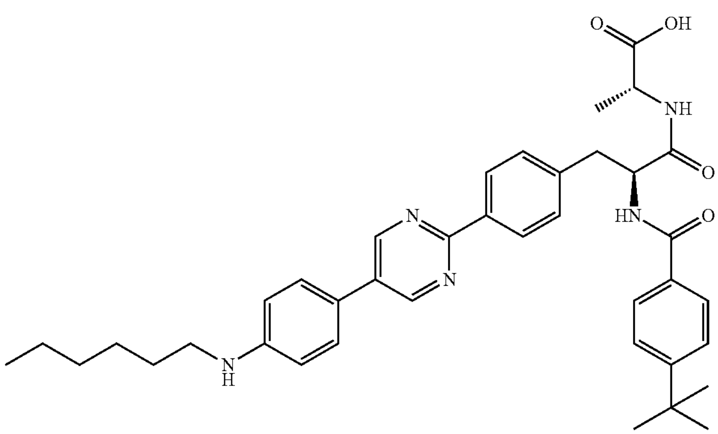 [SMILES: CCCCCCNc1ccc(-c2cnc(-c3ccc(C[C@H](NC(=O)c4ccc(C(C)(C)C)cc4)C(=O)N[C@H](C)C(=O)O)cc3)nc2)cc1] | 729 | 8.79 | 14 |
| 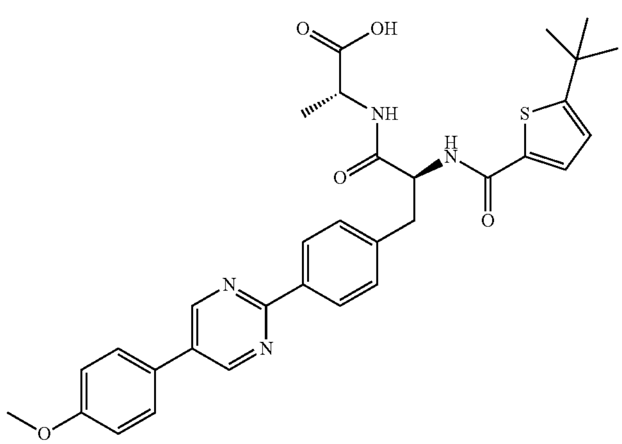 [SMILES: COc1ccc(-c2cnc(-c3ccc(C[C@H](NC(=O)c4ccc(C(C)(C)C)s4)C(=O)N[C@H](C)C(=O)O)cc3)nc2)cc1] | 730 | 6.91 | 14 |

TABLE 1-continued

| STRUCTURE | COMPOUND NUMBER | LCMS RETENTION TIME (min) | PURITY METHOD |
|---|---|---|---|
| (structure) | 731 | 7.30 | 14 |
| (structure) | 732 | 7.83 | 14 |
| (structure) | 733 | 8.31 | 14 |

TABLE 1-continued

| STRUCTURE | COMPOUND NUMBER | LCMS RETENTION TIME (min) | PURITY METHOD |
|---|---|---|---|
| 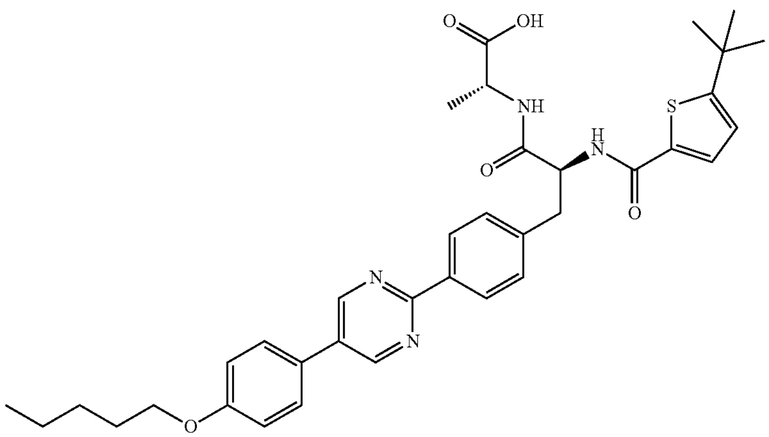 [SMILES: CCCCCOc1ccc(-c2cnc(-c3ccc(C[C@H](NC(=O)c4ccc(C(C)(C)C)s4)C(=O)N[C@H](C)C(=O)O)cc3)nc2)cc1] | 734 | 8.83 | 14 |
| 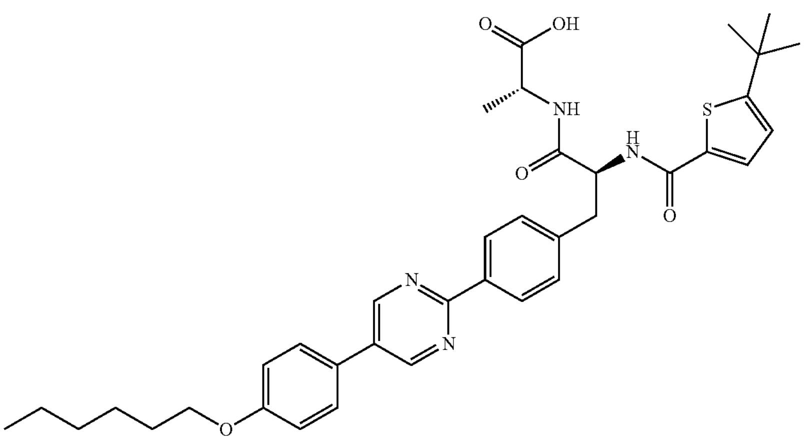 [SMILES: CCCCCCOc1ccc(-c2cnc(-c3ccc(C[C@H](NC(=O)c4ccc(C(C)(C)C)s4)C(=O)N[C@H](C)C(=O)O)cc3)nc2)cc1] | 735 | 9.33 | 14 |
| 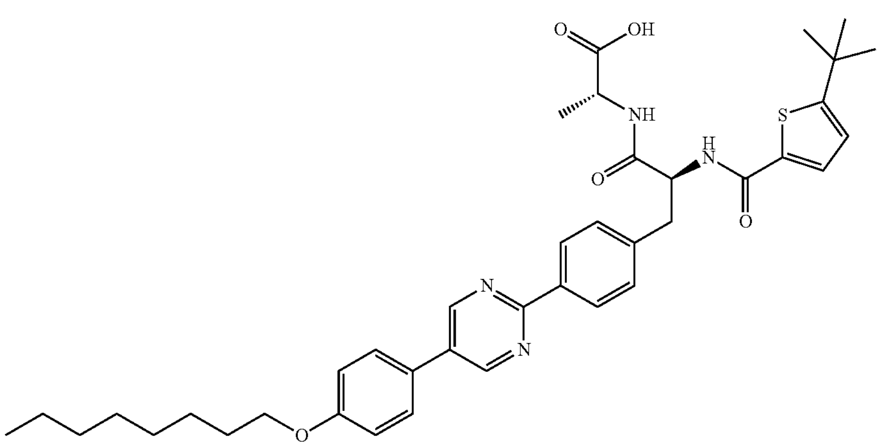 [SMILES: CCCCCCCCOc1ccc(-c2cnc(-c3ccc(C[C@H](NC(=O)c4ccc(C(C)(C)C)s4)C(=O)N[C@H](C)C(=O)O)cc3)nc2)cc1] | 736 | 10.33 | 14 |

TABLE 1-continued

| STRUCTURE | COMPOUND NUMBER | LCMS RETENTION TIME (min) | PURITY METHOD |
|---|---|---|---|
| 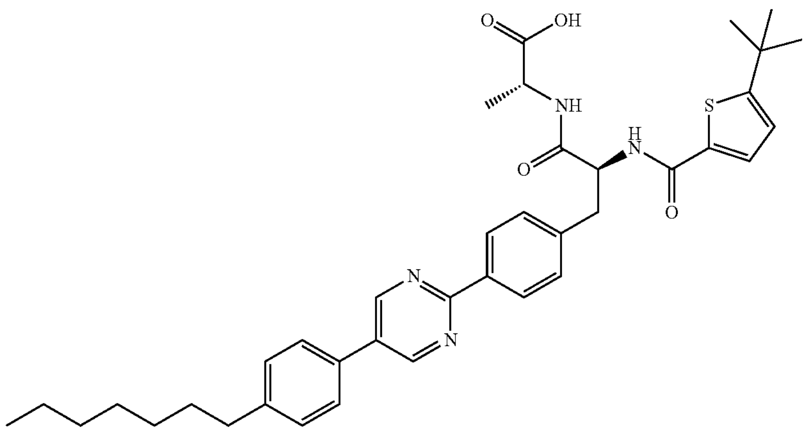 [SMILES: CCCCCCCc1ccc(-c2cnc(-c3ccc(C[C@H](NC(=O)c4ccc(C(C)(C)C)s4)C(=O)N[C@H](C)C(=O)O)cc3)nc2)cc1] | 737 | 10.23 | 14 |
| 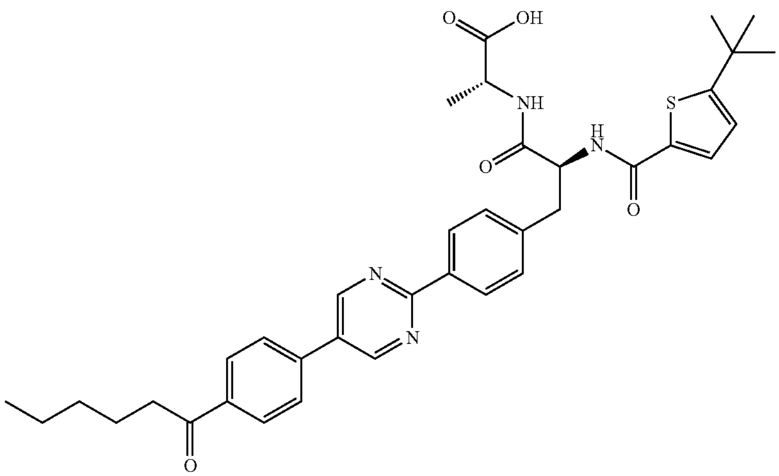 [SMILES: CCCCCC(=O)c1ccc(-c2cnc(-c3ccc(C[C@H](NC(=O)c4ccc(C(C)(C)C)s4)C(=O)N[C@H](C)C(=O)O)cc3)nc2)cc1] | 738 | 8.32 | 14 |
| 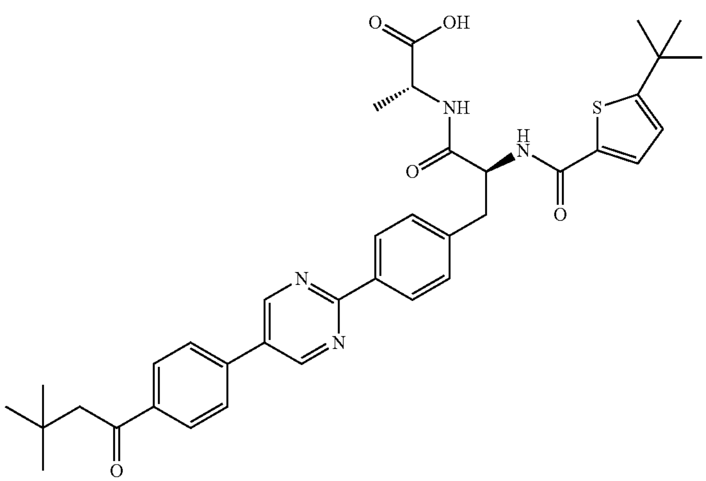 [SMILES: C[C@@H](NC(=O)[C@H](Cc1ccc(-c2ncc(-c3ccc(C(=O)CC(C)(C)C)cc3)cn2)cc1)NC(=O)c1ccc(C(C)(C)C)s1)C(=O)O] | 739 | 8.83 | 14 |

TABLE 1-continued

| STRUCTURE | COMPOUND NUMBER | LCMS RETENTION TIME (min) | PURITY METHOD |
|---|---|---|---|
| 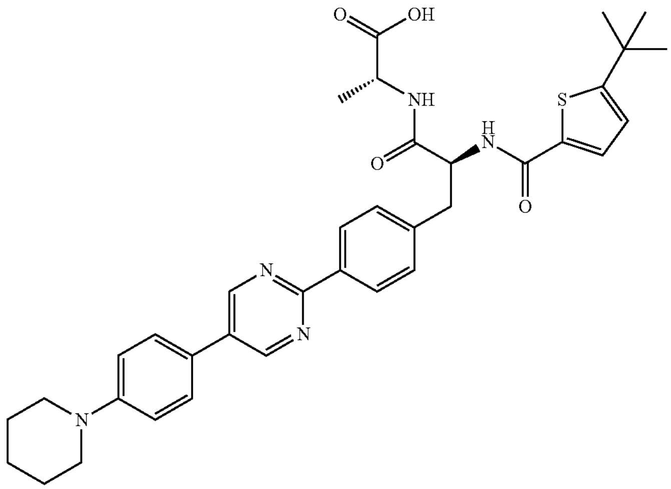 [SMILES: C[C@@H](NC(=O)[C@H](Cc1ccc(-c2ncc(-c3ccc(N4CCCCC4)cc3)cn2)cc1)NC(=O)c1ccc(C(C)(C)C)s1)C(=O)O] | 740 | 8.35 | 14 |
| 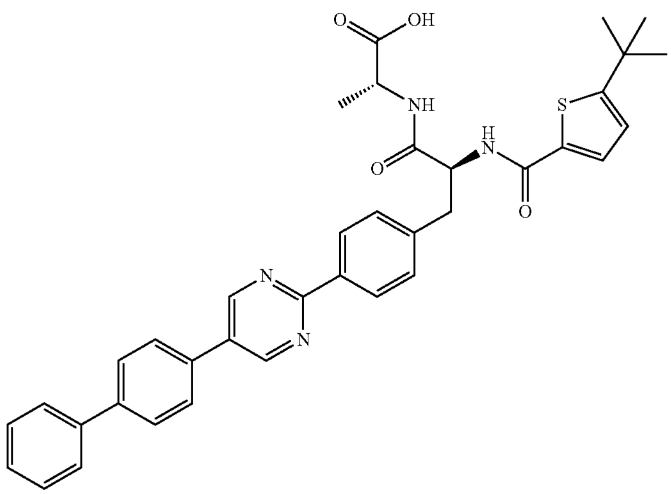 [SMILES: C[C@@H](NC(=O)[C@H](Cc1ccc(-c2ncc(-c3ccc(-c4ccccc4)cc3)cn2)cc1)NC(=O)c1ccc(C(C)(C)C)s1)C(=O)O] | 741 | 8.41 | 14 |
| 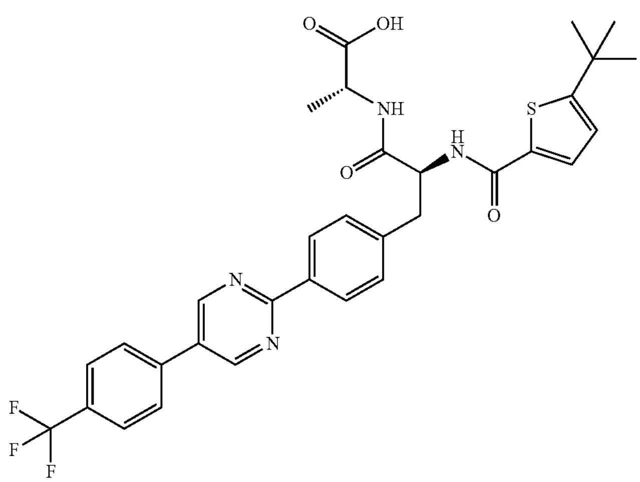 [SMILES: C[C@@H](NC(=O)[C@H](Cc1ccc(-c2ncc(-c3ccc(C(F)(F)F)cc3)cn2)cc1)NC(=O)c1ccc(C(C)(C)C)s1)C(=O)O] | 742 | 7.67 | 14 |

TABLE 1-continued

| STRUCTURE | COMPOUND NUMBER | LCMS RETENTION TIME (min) | PURITY METHOD |
|---|---|---|---|
| 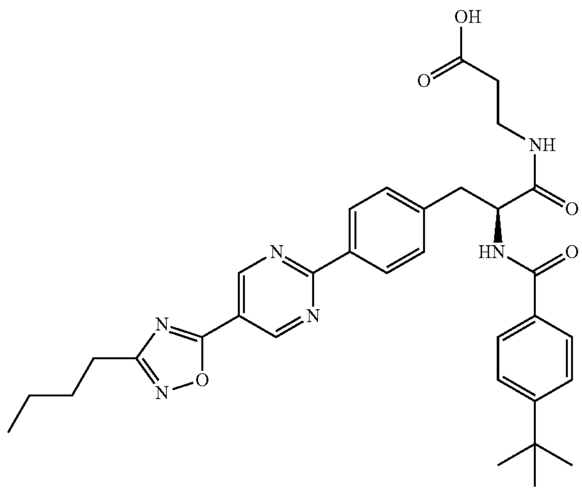 [SMILES: CCCCc1noc(-c2cnc(-c3ccc(C[C@H](NC(=O)c4ccc(C(C)(C)C)cc4)C(=O)NCCC(=O)O)cc3)nc2)n1] | 743 | 7.93 | 14 |
| 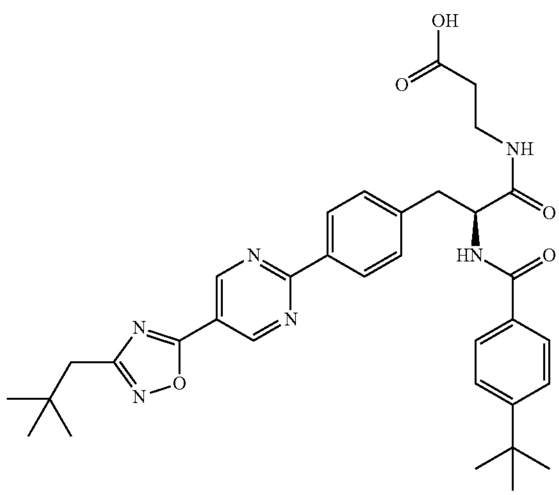 [SMILES: CC(C)(C)Cc1noc(-c2cnc(-c3ccc(C[C@H](NC(=O)c4ccc(C(C)(C)C)cc4)C(=O)NCCC(=O)O)cc3)nc2)n1] | 744 | 7.99 | 14 |
| 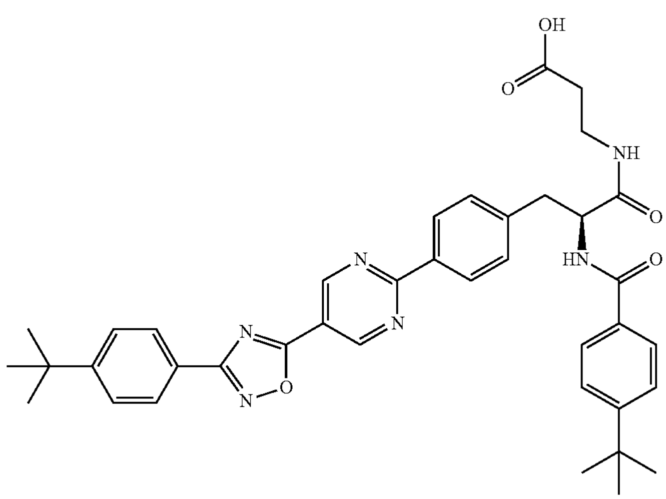 [SMILES: CC(C)(C)c1ccc(C(=O)N[C@@H](Cc2ccc(-c3ncc(-c4nc(-c5ccc(C(C)(C)C)cc5)no4)cn3)cc2)C(=O)NCCC(=O)O)cc1] | 745 | 9.45 | 14 |

TABLE 1-continued
| STRUCTURE | COMPOUND NUMBER | LCMS RETENTION TIME (min) | PURITY METHOD |
|---|---|---|---|
| 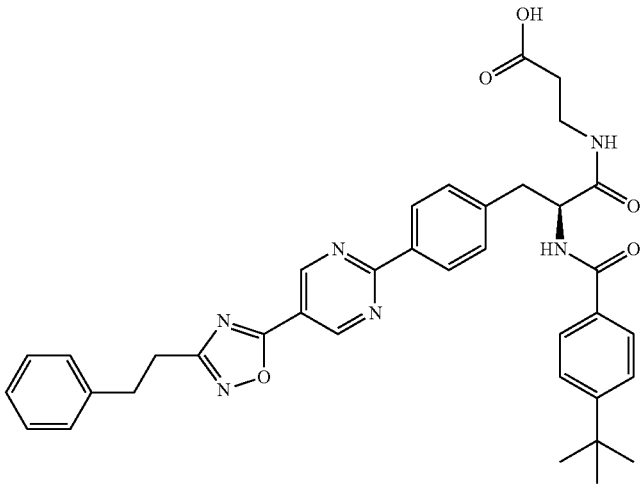 [SMILES: CC(C)(C)c1ccc(C(=O)N[C@@H](Cc2ccc(-c3ncc(-c4nc(CCc5ccccc5)no4)cn3)cc2)C(=O)NCCC(=O)O)cc1] | 746 | 7.88 | 14 |
| 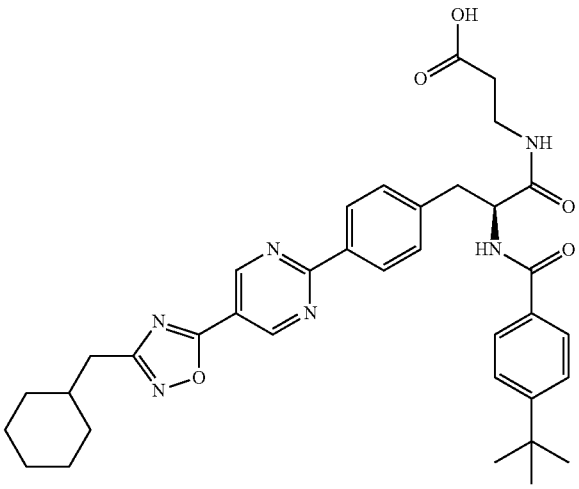 [SMILES: CC(C)(C)c1ccc(C(=O)N[C@@H](Cc2ccc(-c3ncc(-c4nc(CC5CCCCC5)no4)cn3)cc2)C(=O)NCCC(=O)O)cc1] | 747 | 8.71 | 14 |
| 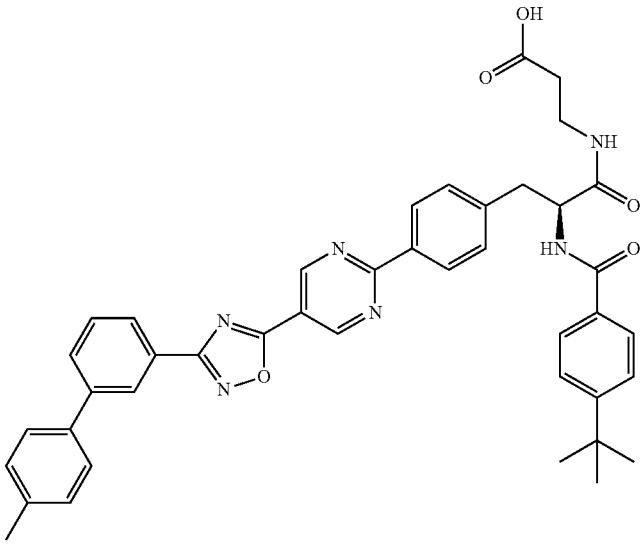 [SMILES: Cc1ccc(-c2cccc(-c3noc(-c4cnc(-c5ccc(C[C@H](NC(=O)c6ccc(C(C)(C)C)cc6)C(=O)NCCC(=O)O)cc5)nc4)n3)c2)cc1] | 748 | 9.64 | 14 |

TABLE 1-continued
| STRUCTURE | COMPOUND NUMBER | LCMS RETENTION TIME (min) | PURITY METHOD |
|---|---|---|---|
| 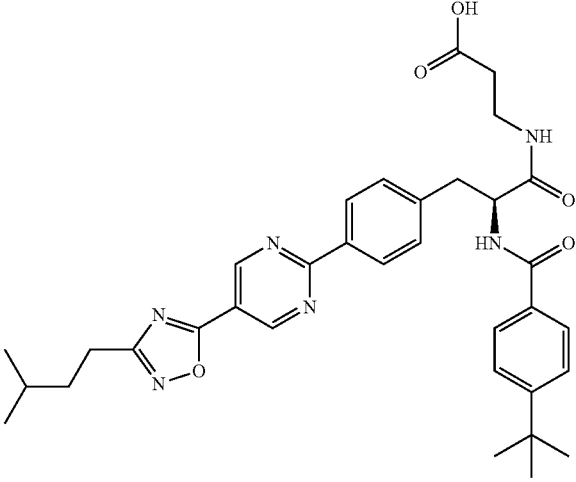 [SMILES: CC(C)CCc1noc(-c2cnc(-c3ccc(C[C@H](NC(=O)c4ccc(C(C)(C)C)cc4)C(=O)NCCC(=O)O)cc3)nc2)n1] | 749 | 8.10 | 14 |
| 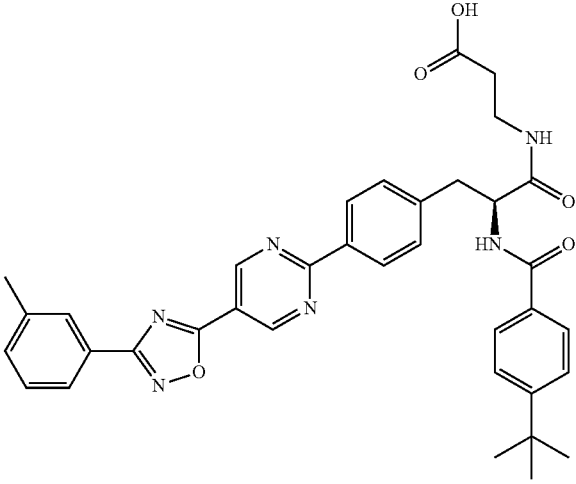 [SMILES: Cc1cccc(-c2noc(-c3cnc(-c4ccc(C[C@H](NC(=O)c5ccc(C(C)(C)C)cc5)C(=O)NCCC(=O)O)cc4)nc3)n2)c1] | 750 | 8.47 | 14 |
| 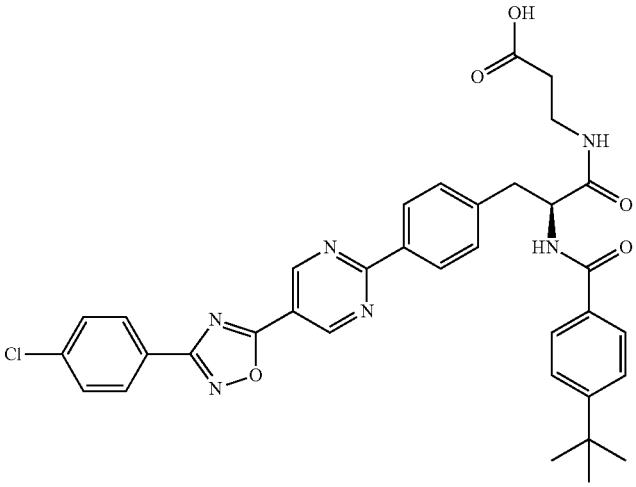 [SMILES: CC(C)(C)c1ccc(C(=O)N[C@@H](Cc2ccc(-c3ncc(-c4nc(-c5ccc(Cl)cc5)no4)cn3)cc2)C(=O)NCCC(=O)O)cc1] | 751 | 8.71 | 14 |

TABLE 1-continued
| STRUCTURE | COMPOUND NUMBER | LCMS RETENTION TIME (min) | PURITY METHOD |
|---|---|---|---|
| 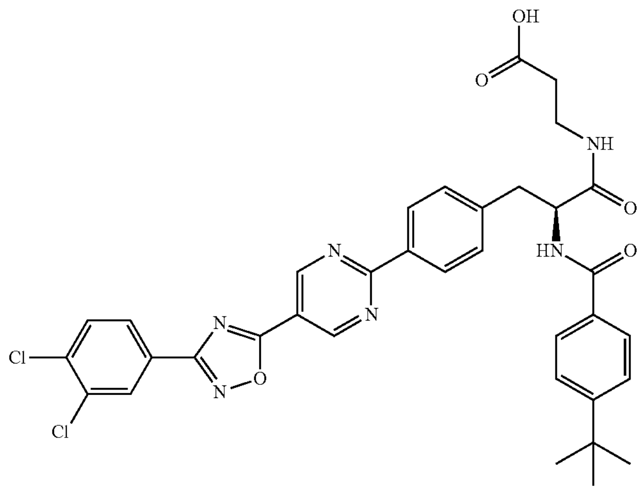 [SMILES: CC(C)(C)c1ccc(C(=O)N[C@@H](Cc2ccc(-c3ncc(-c4nc(-c5ccc(Cl)c(Cl)c5)no4)cn3)cc2)C(=O)NCCC(=O)O)cc1] | 752 | 9.33 | 14 |
| 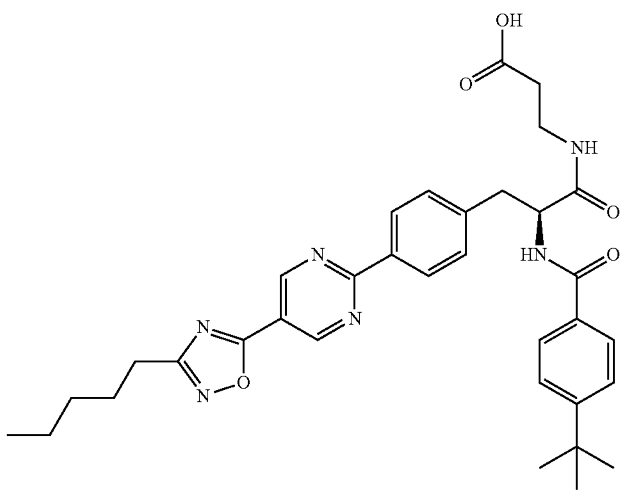 [SMILES: CCCCCc1noc(-c2cnc(-c3ccc(C[C@H](NC(=O)c4ccc(C(C)(C)C)cc4)C(=O)NCCC(=O)O)cc3)nc2)n1] | 753 | 8.33 | 14 |
| 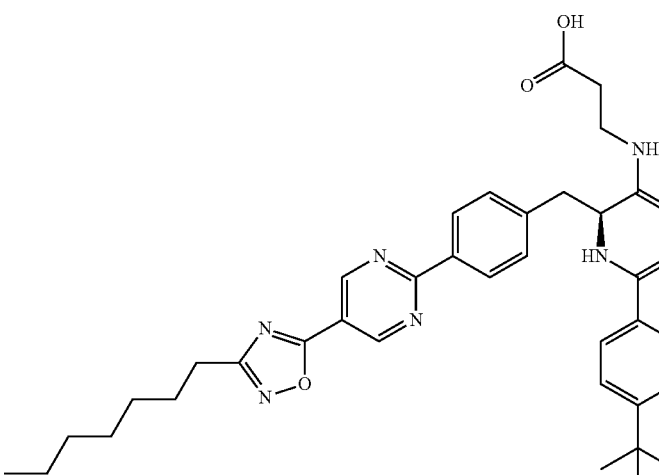 | 754 | 9.34 | 14 |

TABLE 1-continued

| STRUCTURE | COMPOUND NUMBER | LCMS RETENTION TIME (min) | PURITY METHOD |
|---|---|---|---|
| (structure) | 755 | 9.81 | 14 |
| (structure) | 756 | 9.40 | 14 |

TABLE 1-continued

| STRUCTURE | COMPOUND NUMBER | LCMS RETENTION TIME (min) | PURITY METHOD |
|---|---|---|---|
| 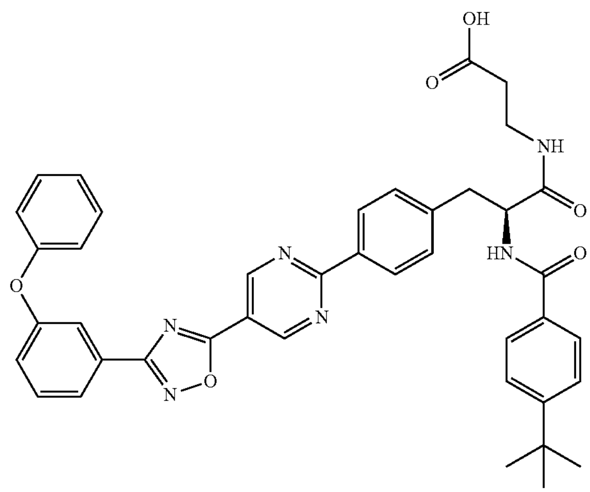 [SMILES: CC(C)(C)c1ccc(C(=O)N[C@@H](Cc2ccc(-c3ncc(-c4nc(-c5cccc(Oc6ccccc6)c5)no4)cn3)cc2)C(=O)NCCC(=O)O)cc1] | 757 | 9.78 | 14 |
| 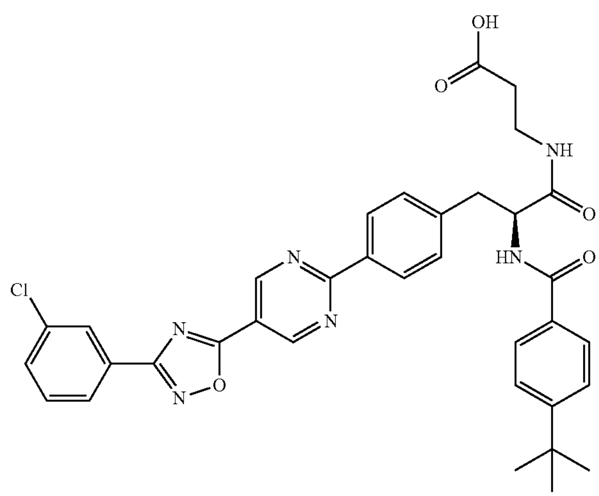 [SMILES: CC(C)(C)c1ccc(C(=O)N[C@@H](Cc2ccc(-c3ncc(-c4nc(-c5cccc(Cl)c5)no4)cn3)cc2)C(=O)NCCC(=O)O)cc1] | 758 | 9.24 | 14 |
| 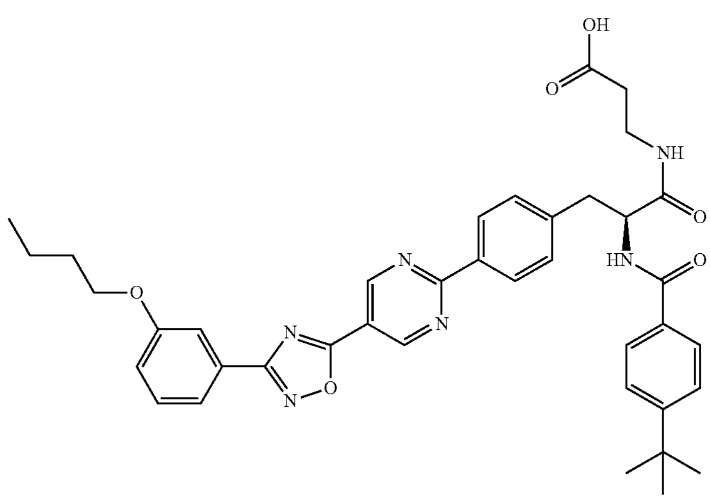 [SMILES: CCCCOc1cccc(-c2noc(-c3cnc(-c4ccc(C[C@H](NC(=O)c5ccc(C(C)(C)C)cc5)C(=O)NCCC(=O)O)cc4)nc3)n2)c1] | 759 | 10.11 | 14 |

TABLE 1-continued

| STRUCTURE | COMPOUND NUMBER | LCMS RETENTION TIME (min) | PURITY METHOD |
|---|---|---|---|
| 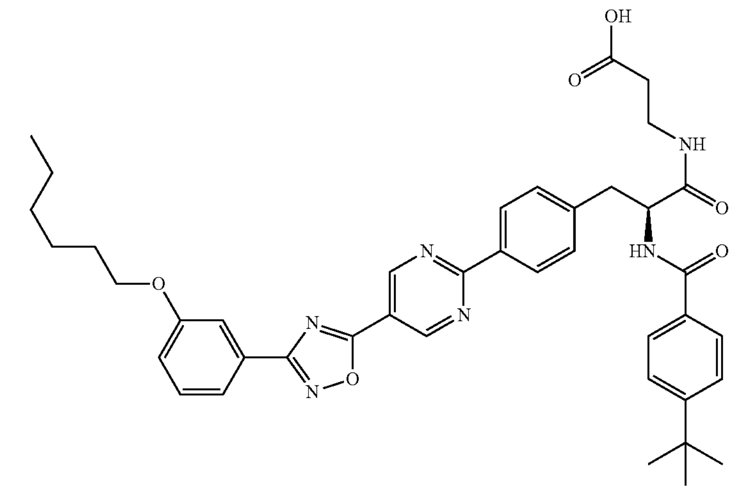 [SMILES: CCCCCCOc1cccc(-c2noc(-c3cnc(-c4ccc(C[C@H](NC(=O)c5ccc(C(C)(C)C)cc5)C(=O)NCCC(=O)O)cc4)nc3)n2)c1] | 760 | 10.10 | 14 |
| 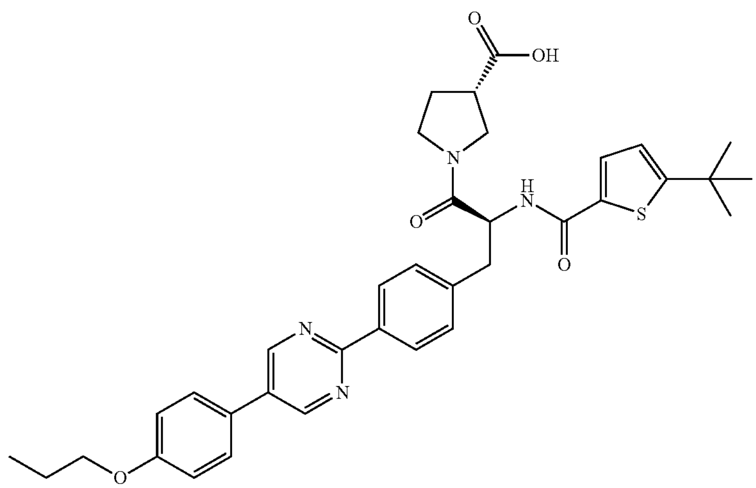 [SMILES: CCCOc1ccc(-c2cnc(-c3ccc(C[C@H](NC(=O)c4ccc(C(C)(C)C)s4)C(=O)N4CC[C@H](C(=O)O)C4)cc3)nc2)cc1] | 761 | 8.18 | 14 |
| 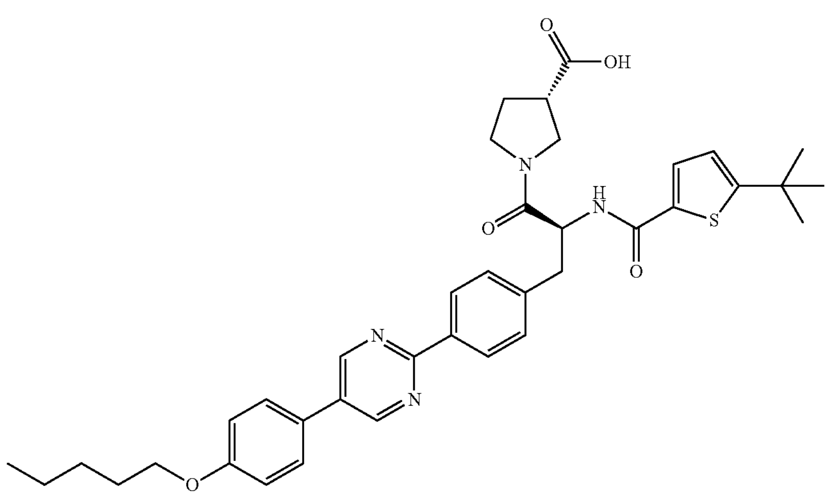 [SMILES: CCCCCOc1ccc(-c2cnc(-c3ccc(C[C@H](NC(=O)c4ccc(C(C)(C)C)s4)C(=O)N4CC[C@H](C(=O)O)C4)cc3)nc2)cc1] | 762 | 9.33 | 14 |

TABLE 1-continued
| STRUCTURE | COMPOUND NUMBER | LCMS RETENTION TIME (min) | PURITY METHOD |
|---|---|---|---|
| 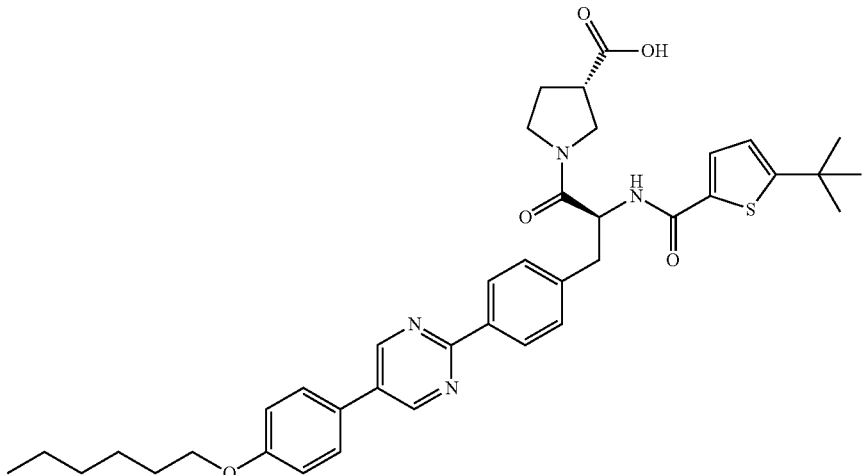 | 763 | 9.73 | 14 |
| 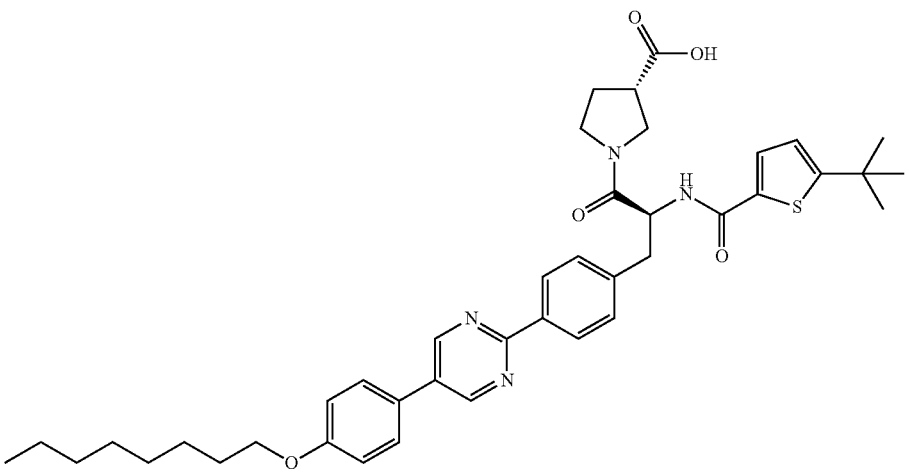 [SMILES: CCCCCCCCOc1ccc(-c2cnc(-c3ccc(C[C@H](NC(=O)c4ccc(C(C)(C)C)s4)C(=O)N4CC[C@H](C(=O)O)C4)cc3)nc2)cc1] | 764 | 10.78 | 14 |
| 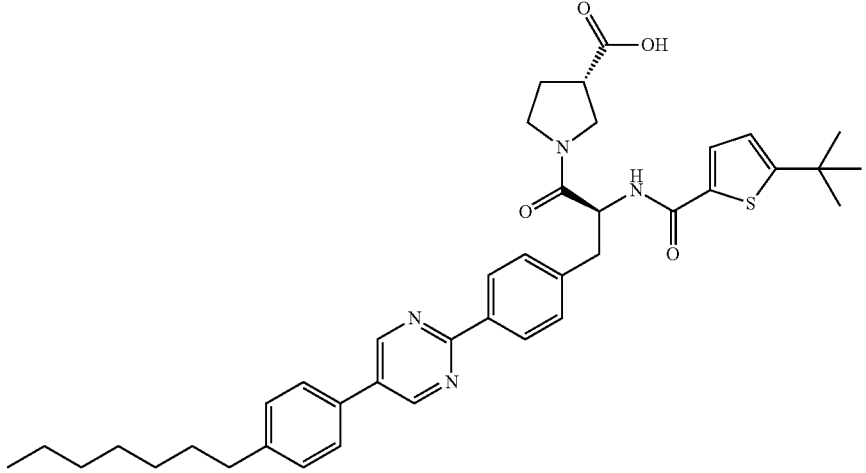 [SMILES: CCCCCCCc1ccc(-c2cnc(-c3ccc(C[C@H](NC(=O)c4ccc(C(C)(C)C)s4)C(=O)N4CC[C@H](C(=O)O)C4)cc3)nc2)cc1] | 765 | 10.71 | 14 |

TABLE 1-continued

| STRUCTURE | COMPOUND NUMBER | LCMS RETENTION TIME (min) | PURITY METHOD |
|---|---|---|---|
| 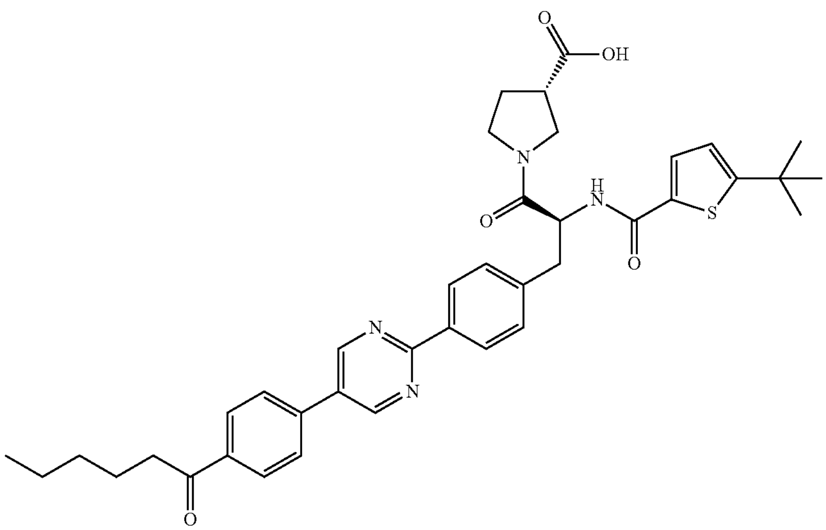 [SMILES: CCCCCC(=O)c1ccc(-c2cnc(-c3ccc(C[C@H](NC(=O)c4ccc(C(C)(C)C)s4)C(=O)N4CC[C@H](C(=O)O)C4)cc3)nc2)cc1] | 766 | 8.78 | 14 |
| 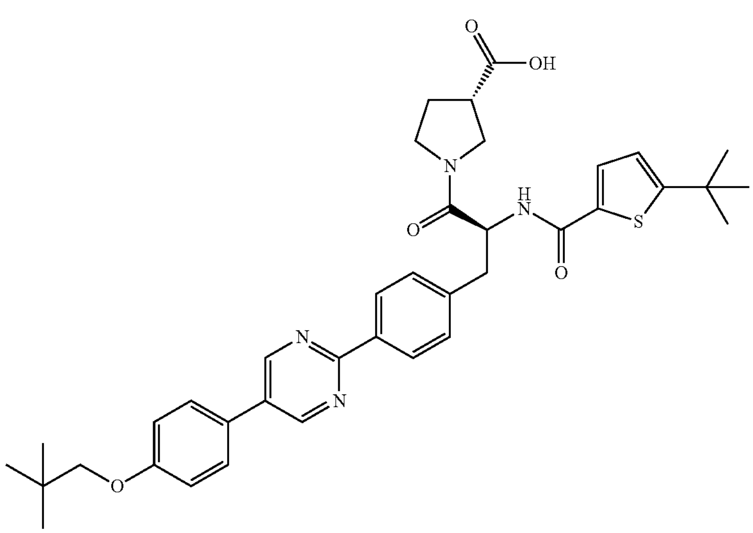 [SMILES: CC(C)(C)COc1ccc(-c2cnc(-c3ccc(C[C@H](NC(=O)c4ccc(C(C)(C)C)s4)C(=O)N4CC[C@H](C(=O)O)C4)cc3)nc2)cc1] | 767 | 9.24 | 14 |

TABLE 1-continued

| STRUCTURE | COMPOUND NUMBER | LCMS RETENTION TIME (min) | PURITY METHOD |
|---|---|---|---|
| 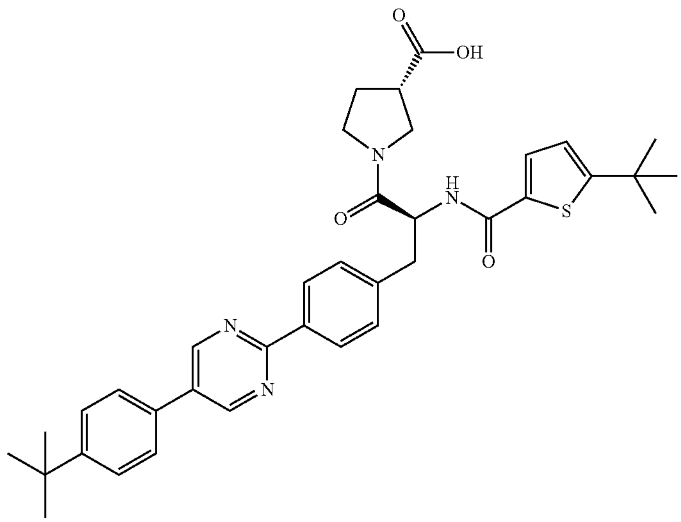 [SMILES: CC(C)(C)c1ccc(-c2cnc(-c3ccc(C[C@H](NC(=O)c4ccc(C(C)(C)C)s4)C(=O)N4CC[C@H](C(=O)O)C4)cc3)nc2)cc1] | 768 | 8.83 | 14 |
| 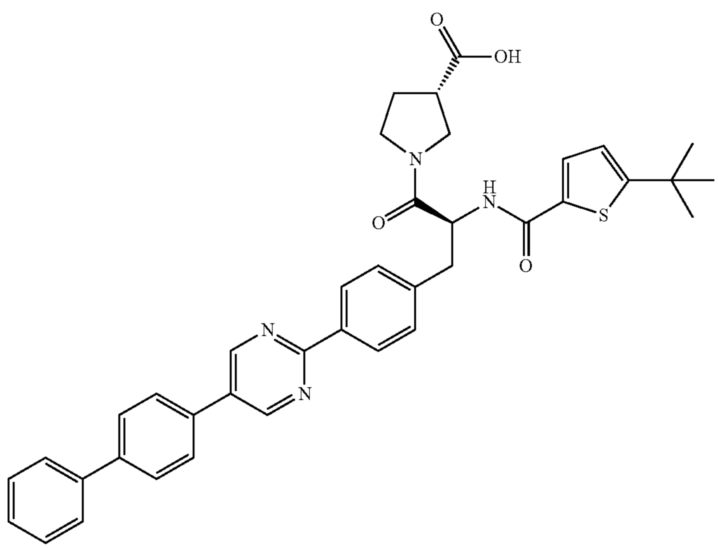 [SMILES: CC(C)(C)c1ccc(C(=O)N[C@@H](Cc2ccc(-c3ncc(-c4ccc(-c5ccccc5)cc4)cn3)cc2)C(=O)N2CC[C@H](C(=O)O)C2)s1] | 769 | 8.67 | 14 |
| 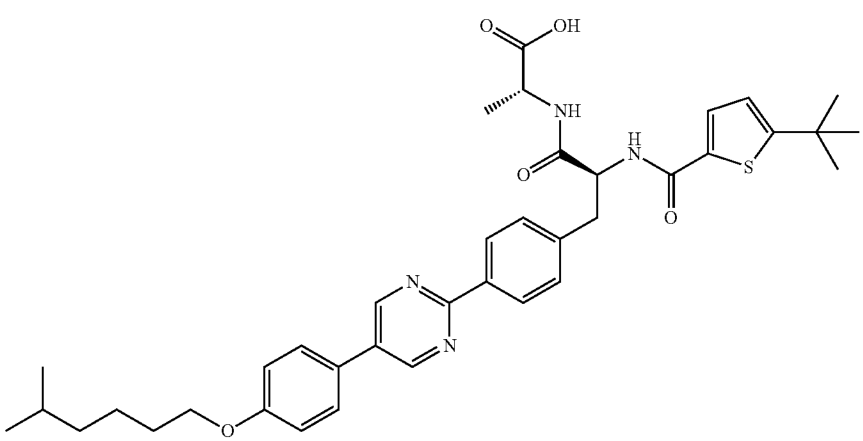 [SMILES: CC(C)CCCCOc1ccc(-c2cnc(-c3ccc(C[C@H](NC(=O)c4ccc(C(C)(C)C)s4)C(=O)N[C@H](C)C(=O)O)cc3)nc2)cc1] | 770 | 9.773 | 14 |

TABLE 1-continued

| STRUCTURE | COMPOUND NUMBER | LCMS RETENTION TIME (min) | PURITY METHOD |
|---|---|---|---|
| 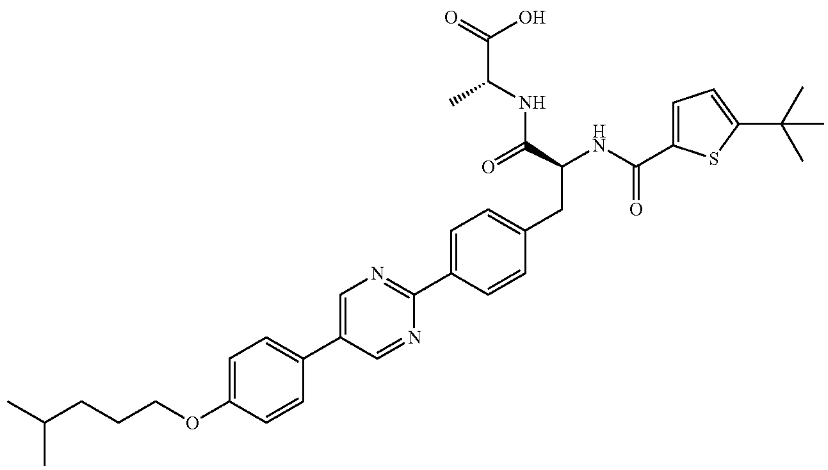 [SMILES: CC(C)CCCOc1ccc(-c2cnc(-c3ccc(C[C@H](NC(=O)c4ccc(C(C)(C)C)s4)C(=O)N[C@H](C)C(=O)O)cc3)nc2)cc1] | 771 | 9.32 | 14 |
| 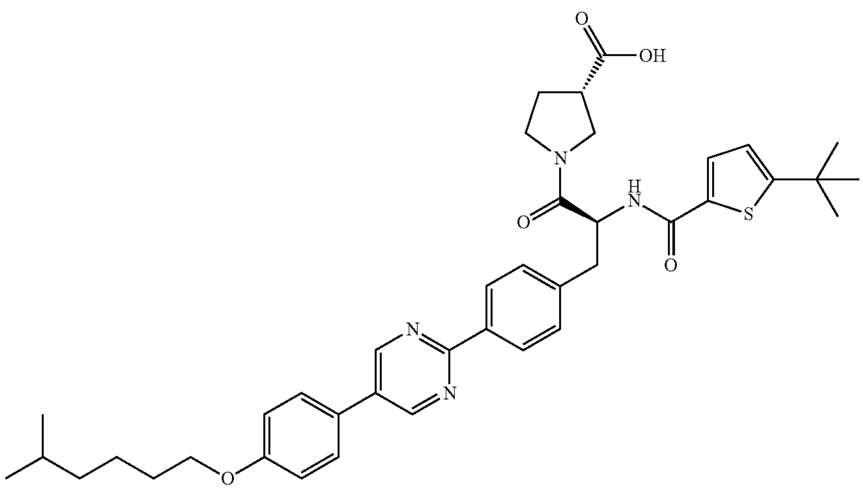 [SMILES: CC(C)CCCCOc1ccc(-c2cnc(-c3ccc(C[C@H](NC(=O)c4ccc(C(C)(C)C)s4)C(=O)N4CC[C@H](C(=O)O)C4)cc3)nc2)cc1] | 772 | 10.26 | 14 |
| 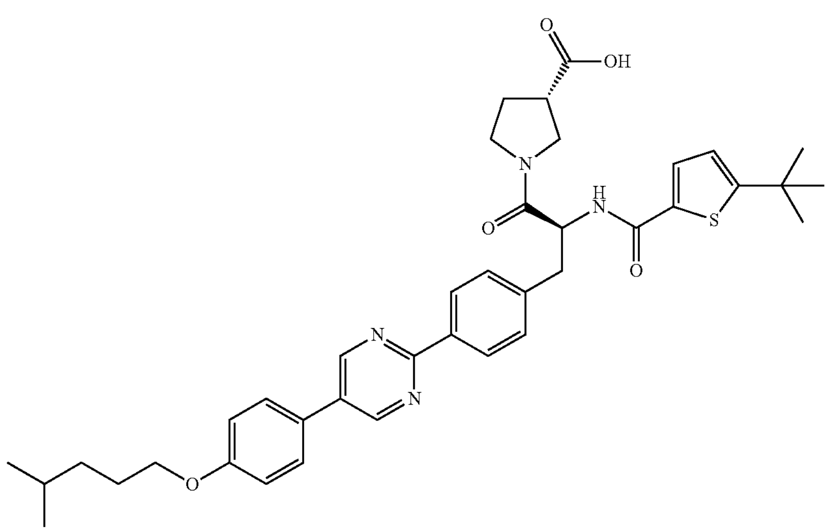 [SMILES: CC(C)CCCOc1ccc(-c2cnc(-c3ccc(C[C@H](NC(=O)c4ccc(C(C)(C)C)s4)C(=O)N4CC[C@H](C(=O)O)C4)cc3)nc2)cc1] | 773 | 9.72 | 14 |

TABLE 1-continued
| STRUCTURE | COMPOUND NUMBER | LCMS RETENTION TIME (min) | PURITY METHOD |
|---|---|---|---|
| 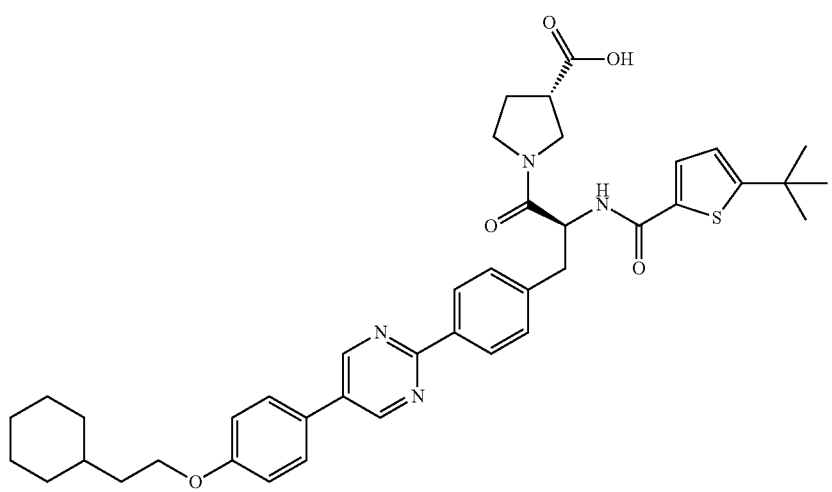 [SMILES: CC(C)(C)c1ccc(C(=O)N[C@@H](Cc2ccc(-c3ncc(-c4ccc(OCCC5CCCCC5)cc4)cn3)cc2)C(=O)N2CC[C@H](C(=O)O)C2)s1] | 774 | 10.19 | 10 |
| 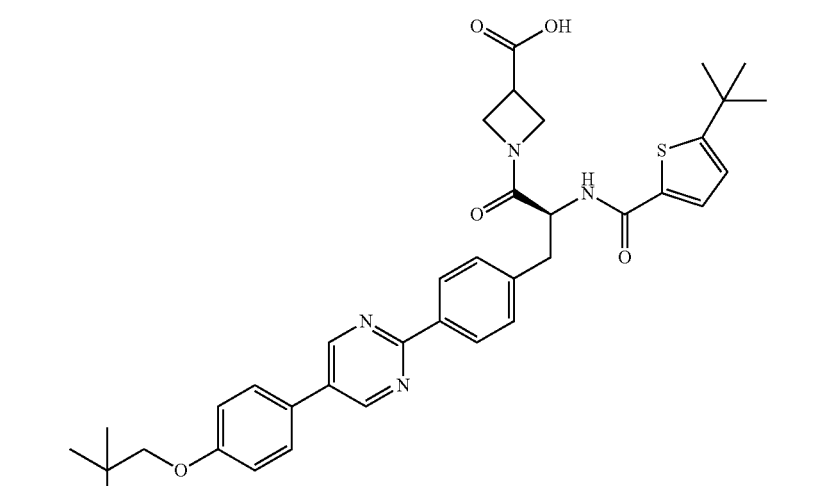 | 775 | 8.883 | 14 |
| 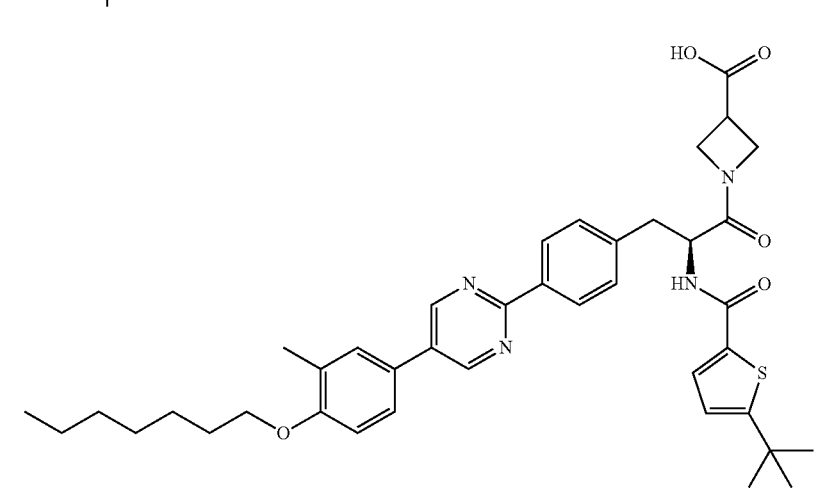 | 776 | 10.03 | 14 |

TABLE 1-continued

| STRUCTURE | COMPOUND NUMBER | LCMS RETENTION TIME (min) | PURITY METHOD |
|---|---|---|---|
| 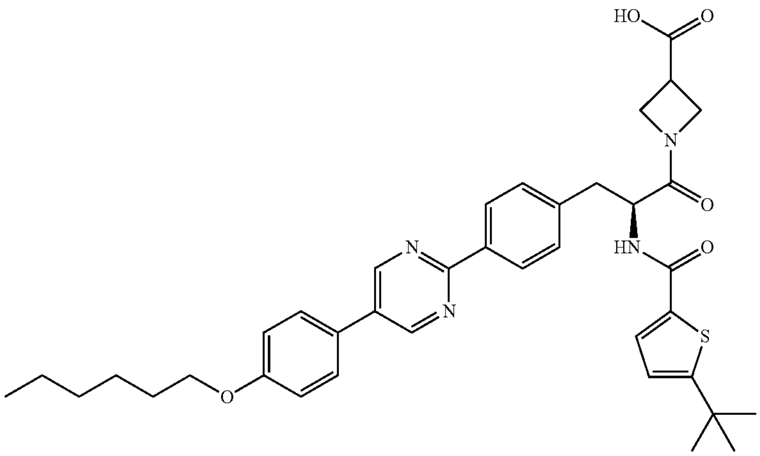 [SMILES: CCCCCCOc1ccc(-c2cnc(-c3ccc(C[C@H](NC(=O)c4ccc(C(C)(C)C)s4)C(=O)N4CC(C(=O)O)C4)cc3)nc2)cc1] | 777 | 9.19 | 14 |
| 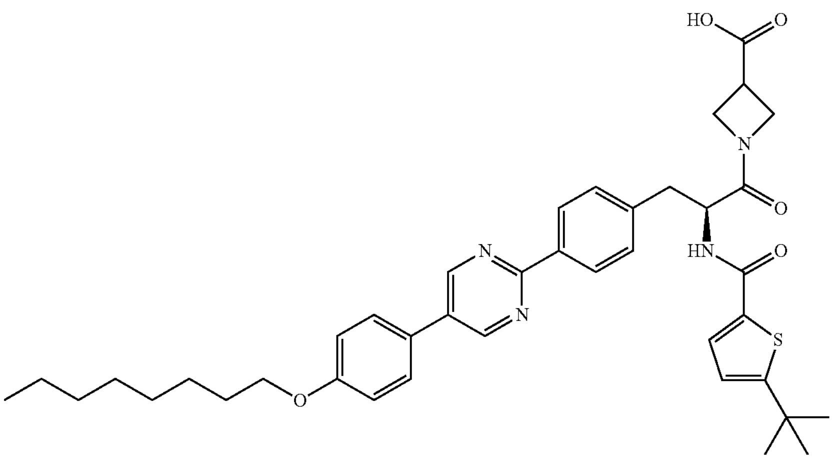 [SMILES: CCCCCCCCOc1ccc(-c2cnc(-c3ccc(C[C@H](NC(=O)c4ccc(C(C)(C)C)s4)C(=O)N4CC(C(=O)O)C4)cc3)nc2)cc1] | 778 | 10.31 | 14 |
| 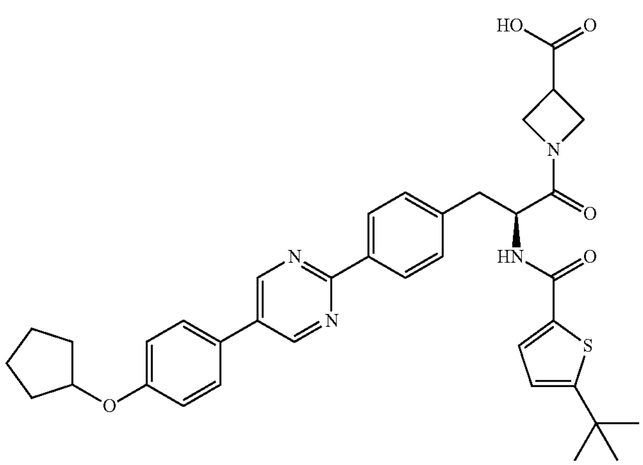 [SMILES: CC(C)(C)c1ccc(C(=O)N[C@@H](Cc2ccc(-c3ncc(-c4ccc(OC5CCCC5)cc4)cn3)cc2)C(=O)N2CC(C(=O)O)C2)s1] | 779 | 8.12 | 14 |

TABLE 1-continued

| STRUCTURE | COMPOUND NUMBER | LCMS RETENTION TIME (min) | PURITY METHOD |
|---|---|---|---|
| 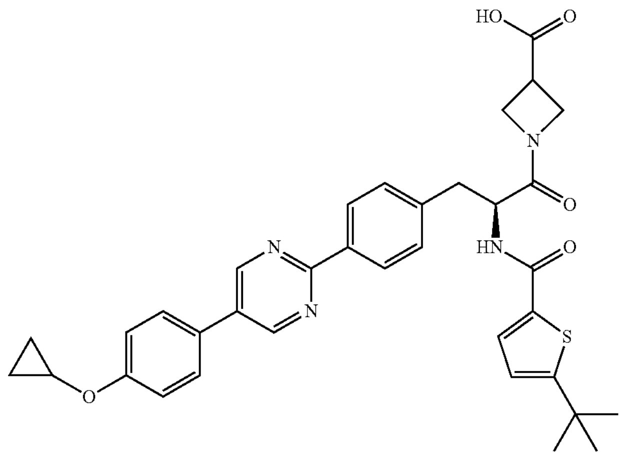 [SMILES: CC(C)(C)c1ccc(C(=O)N[C@@H](Cc2ccc(-c3ncc(-c4ccc(OC5CC5)cc4)cn3)cc2)C(=O)N2CC(C(=O)O)C2)s1] | 780 | 7.43 | 14 |
| 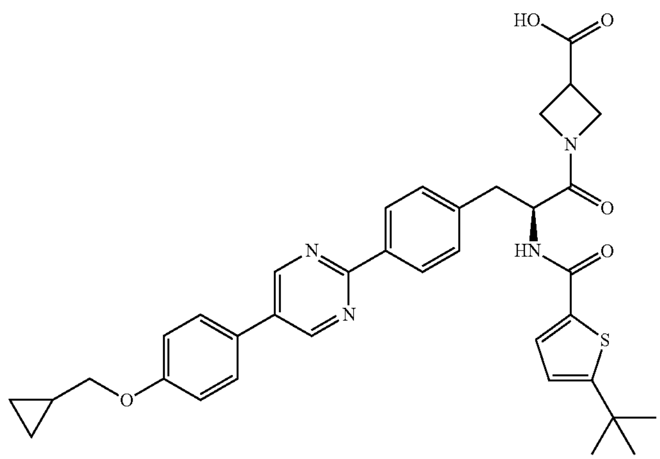 [SMILES: CC(C)(C)c1ccc(C(=O)N[C@@H](Cc2ccc(-c3ncc(-c4ccc(OCC5CC5)cc4)cn3)cc2)C(=O)N2CC(C(=O)O)C2)s1] | 781 | 7.63 | 14 |
| 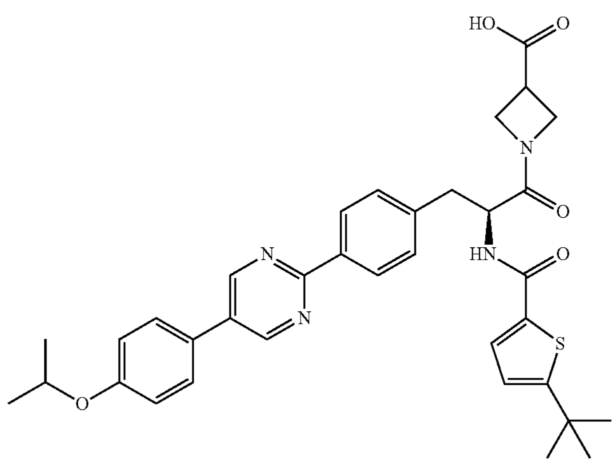 [SMILES: CC(C)Oc1ccc(-c2cnc(-c3ccc(C[C@H](NC(=O)c4ccc(C(C)(C)C)s4)C(=O)N4CC(C(=O)O)C4)cc3)nc2)cc1] | 782 | 7.59 | 14 |

TABLE 1-continued
| STRUCTURE | COMPOUND NUMBER | LCMS RETENTION TIME (min) | PURITY METHOD |
|---|---|---|---|
| 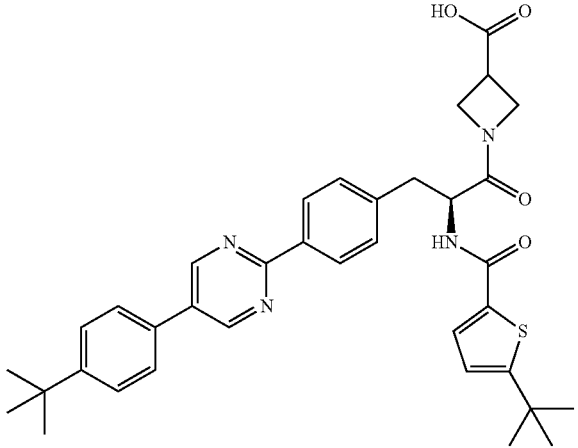 [SMILES: CC(C)(C)c1ccc(-c2cnc(-c3ccc(C[C@H](NC(=O)c4ccc(C(C)(C)C)s4)C(=O)N4CC(C(=O)O)C4)cc3)nc2)cc1] | 783 | 8.39 | 14 |
| 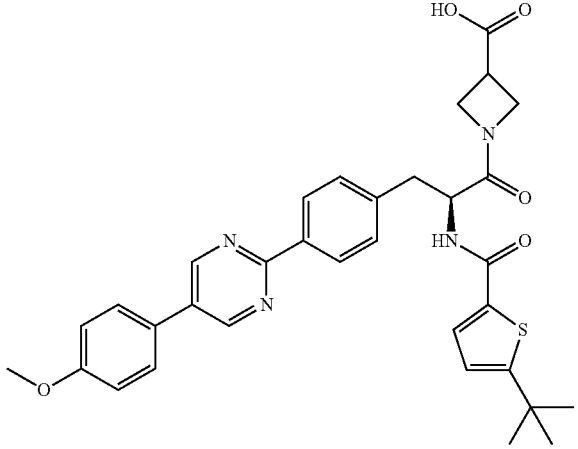 [SMILES: COc1ccc(-c2cnc(-c3ccc(C[C@H](NC(=O)c4ccc(C(C)(C)C)s4)C(=O)N4CC(C(=O)O)C4)cc3)nc2)cc1] | 784 | 6.75 | 14 |
| 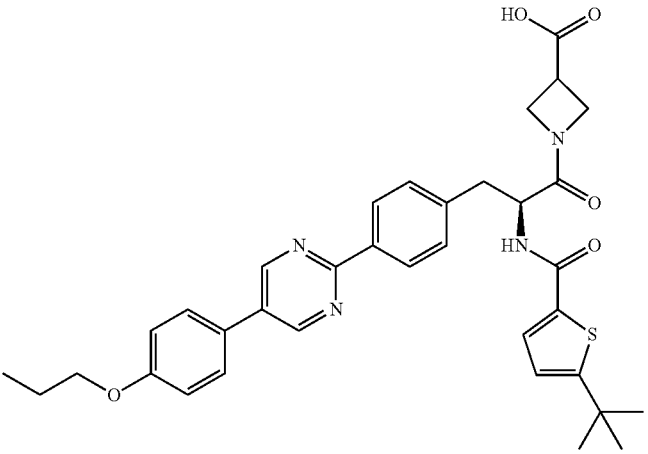 [SMILES: CCCOc1ccc(-c2cnc(-c3ccc(C[C@H](NC(=O)c4ccc(C(C)(C)C)s4)C(=O)N4CC(C(=O)O)C4)cc3)nc2)cc1] | 785 | 7.65 | 14 |

TABLE 1-continued

| STRUCTURE | COMPOUND NUMBER | LCMS RETENTION TIME (min) | PURITY METHOD |
|---|---|---|---|
| 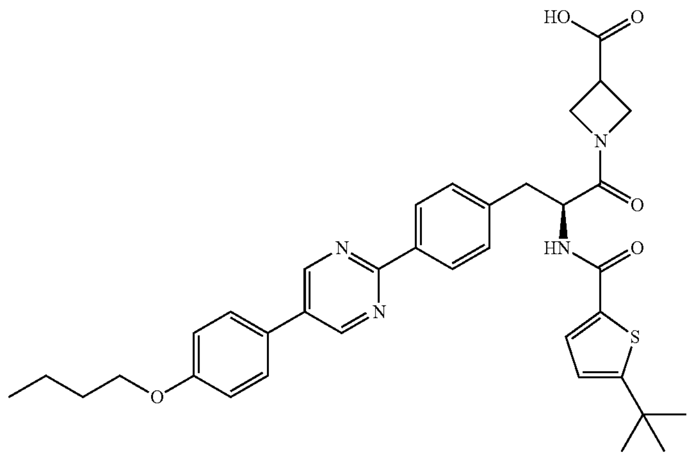 [SMILES: CCCCOc1ccc(-c2cnc(-c3ccc(C[C@H](NC(=O)c4ccc(C(C)(C)C)s4)C(=O)N4CC(C(=O)O)C4)cc3)nc2)cc1] | 786 | 8.14 | 14 |
| 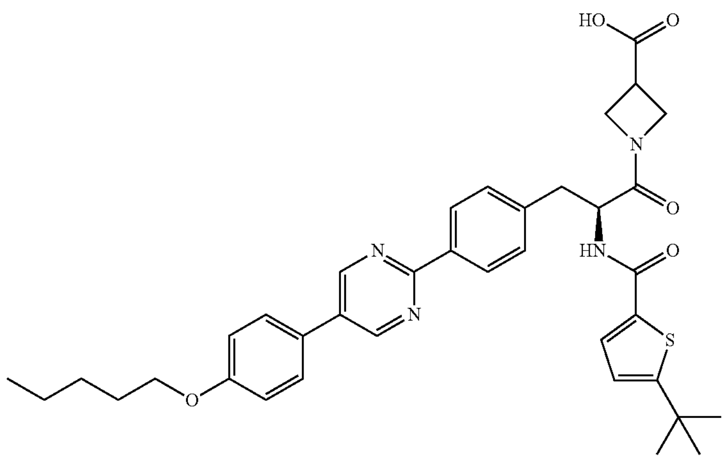 [SMILES: CCCCCOc1ccc(-c2cnc(-c3ccc(C[C@H](NC(=O)c4ccc(C(C)(C)C)s4)C(=O)N4CC(C(=O)O)C4)cc3)nc2)cc1] | 787 | 8.43 | 14 |
| 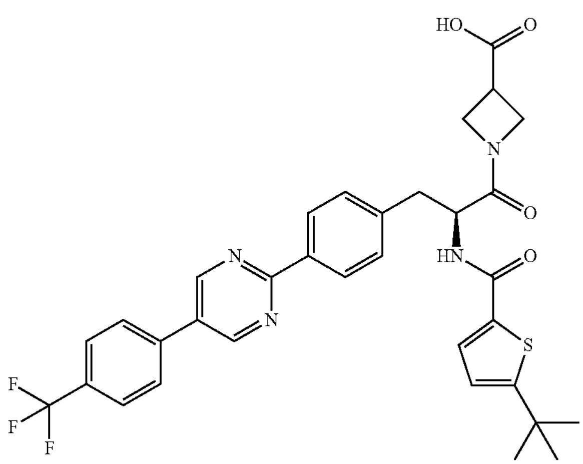 | 788 | 7.43 | 14 |

TABLE 1-continued
| STRUCTURE | COMPOUND NUMBER | LCMS RETENTION TIME (min) | PURITY METHOD |
|---|---|---|---|
| 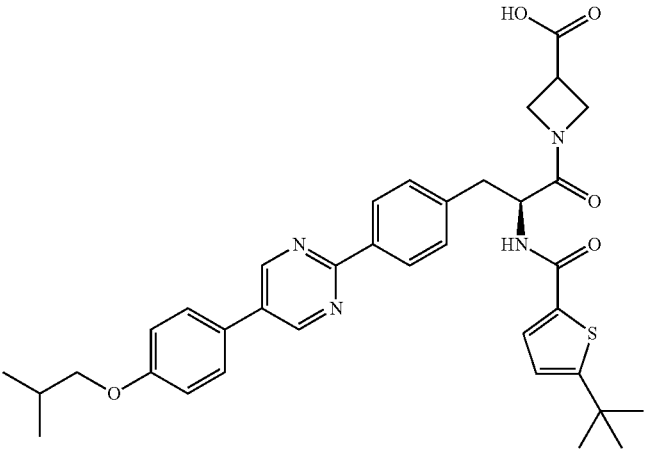 [SMILES: CC(C)COc1ccc(-c2cnc(-c3ccc(C[C@H](NC(=O)c4ccc(C(C)(C)C)s4)C(=O)N4CC(C(=O)O)C4)cc3)nc2)cc1] | 789 | 8.19 | 14 |
| 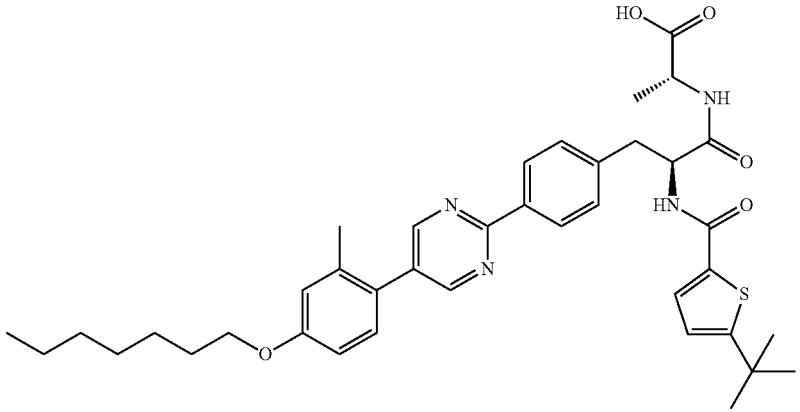 [SMILES: CCCCCCCOc1ccc(-c2cnc(-c3ccc(C[C@H](NC(=O)c4ccc(C(C)(C)C)s4)C(=O)N[C@H](C)C(=O)O)cc3)nc2)c(C)c1] | 790 | 10.67 | 10 |
| 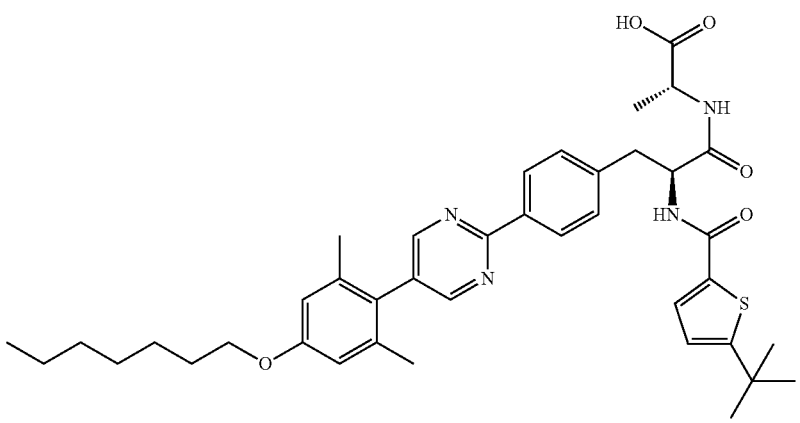 [SMILES: CCCCCCCOc1cc(C)c(-c2cnc(-c3ccc(C[C@H](NC(=O)c4ccc(C(C)(C)C)s4)C(=O)N[C@H](C)C(=O)O)cc3)nc2)c(C)c1] | 791 | 10.89 | 10 |

TABLE 1-continued

| STRUCTURE | COMPOUND NUMBER | LCMS RETENTION TIME (min) | PURITY METHOD |
|---|---|---|---|
| 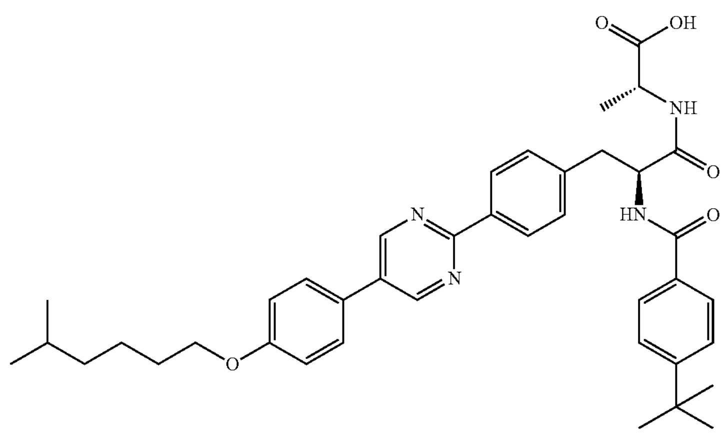 [SMILES: CC(C)CCCCOc1ccc(-c2cnc(-c3ccc(C[C@H](NC(=O)c4ccc(C(C)(C)C)cc4)C(=O)N[C@H](C)C(=O)O)cc3)nc2)cc1] | 792 | 10.02 | 14 |
| 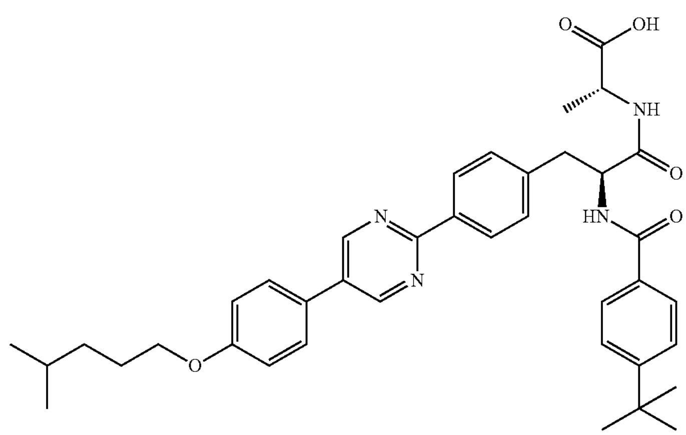 [SMILES: CC(C)CCCOc1ccc(-c2cnc(-c3ccc(C[C@H](NC(=O)c4ccc(C(C)(C)C)cc4)C(=O)N[C@H](C)C(=O)O)cc3)nc2)cc1] | 793 | 9.72 | 14 |
| 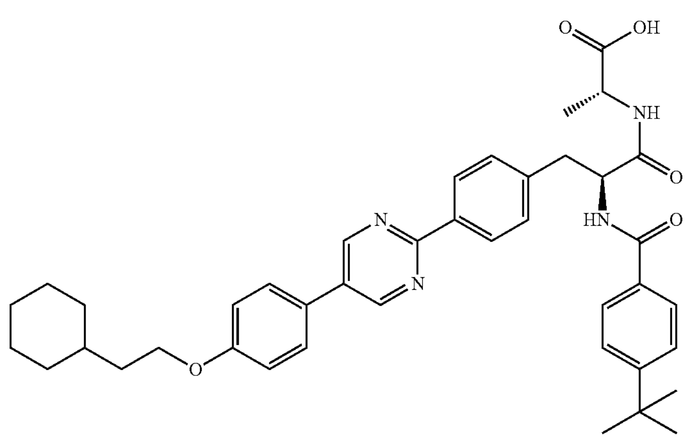 [SMILES: C[C@@H](NC(=O)[C@H](Cc1ccc(-c2ncc(-c3ccc(OCCC4CCCCC4)cc3)cn2)cc1)NC(=O)c1ccc(C(C)(C)C)cc1)C(=O)O] | 794 | 10.30 | 14 |

TABLE 1-continued

| STRUCTURE | COMPOUND NUMBER | LCMS RETENTION TIME (min) | PURITY METHOD |
|---|---|---|---|
| 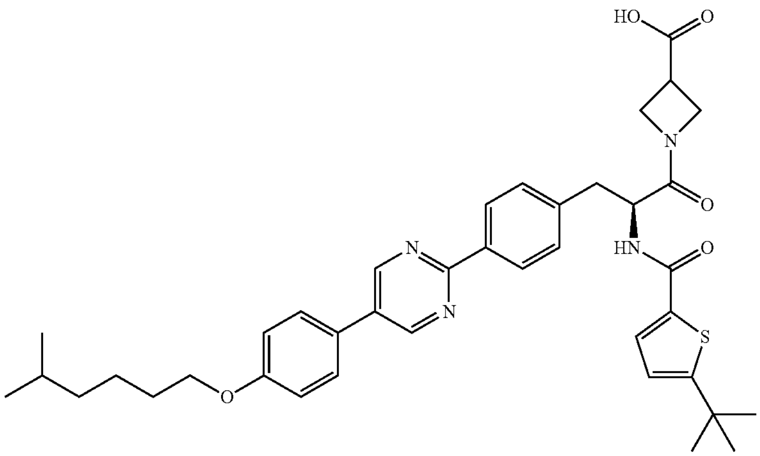 [SMILES: CC(C)CCCCOc1ccc(-c2cnc(-c3ccc(C[C@H](NC(=O)c4ccc(C(C)(C)C)s4)C(=O)N4CC(C(=O)O)C4)cc3)nc2)cc1] | 795 | 9.38 | 14 |
| 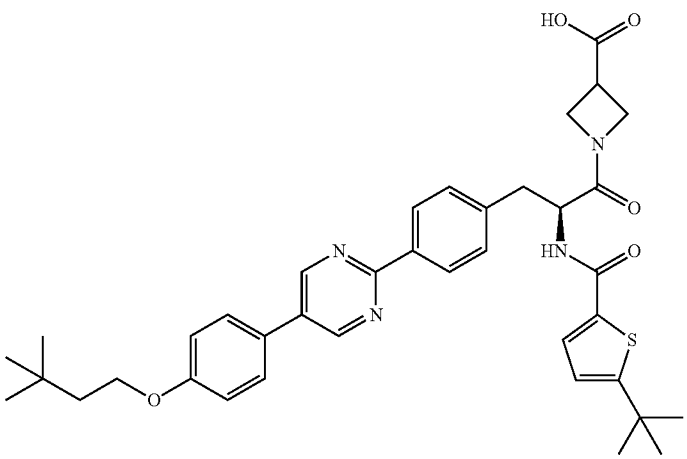 [SMILES: CC(C)(C)CCOc1ccc(-c2cnc(-c3ccc(C[C@H](NC(=O)c4ccc(C(C)(C)C)s4)C(=O)N4CC(C(=O)O)C4)cc3)nc2)cc1] | 796 | 8.90 | 14 |
| 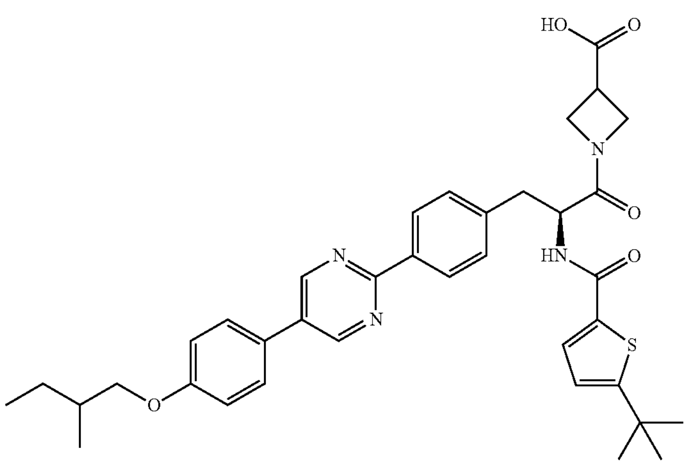 [SMILES: CCC(C)COc1ccc(-c2cnc(-c3ccc(C[C@H](NC(=O)c4ccc(C(C)(C)C)s4)C(=O)N4CC(C(=O)O)C4)cc3)nc2)cc1] | 797 | 8.69 | 14 |

TABLE 1-continued
| STRUCTURE | COMPOUND NUMBER | LCMS RETENTION TIME (min) | PURITY METHOD |
|---|---|---|---|
| 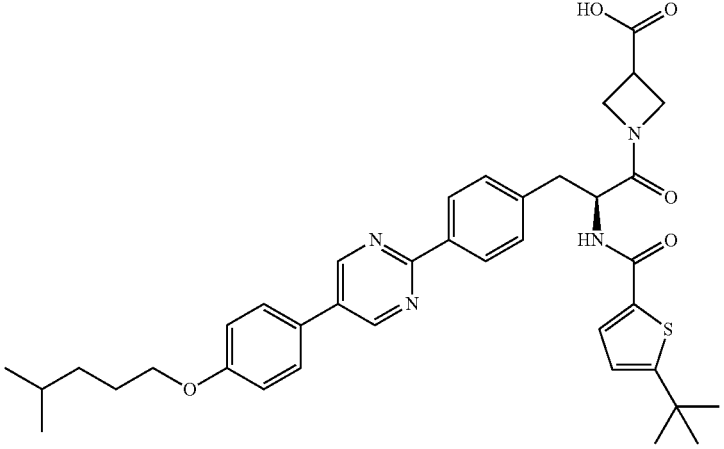 [SMILES: CC(C)CCCOc1ccc(-c2cnc(-c3ccc(C[C@H](NC(=O)c4ccc(C(C)(C)C)s4)C(=O)N4CC(C(=O)O)C4)cc3)nc2)cc1] | 798 | 9.05 | 14 |
| 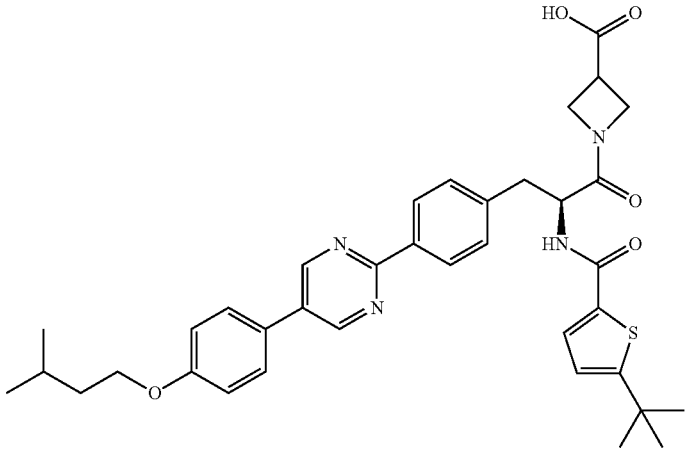 [SMILES: CC(C)CCOc1ccc(-c2cnc(-c3ccc(C[C@H](NC(=O)c4ccc(C(C)(C)C)s4)C(=O)N4CC(C(=O)O)C4)cc3)nc2)cc1] | 799 | 8.58 | 14 |
| 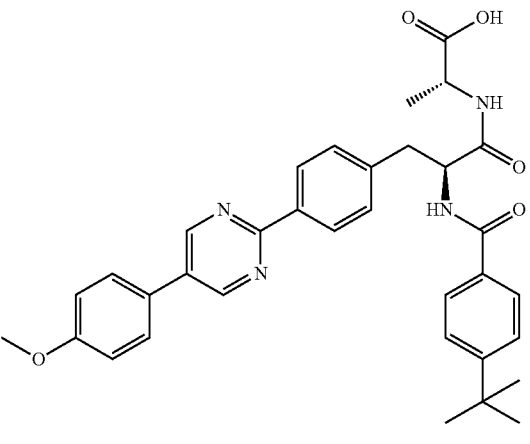 [SMILES: COc1ccc(-c2cnc(-c3ccc(C[C@H](NC(=O)c4ccc(C(C)(C)C)cc4)C(=O)N[C@H](C)C(=O)O)cc3)nc2)cc1] | 800 | 6.898 | 14 |

TABLE 1-continued

| STRUCTURE | COMPOUND NUMBER | LCMS RETENTION TIME (min) | PURITY METHOD |
|---|---|---|---|
| 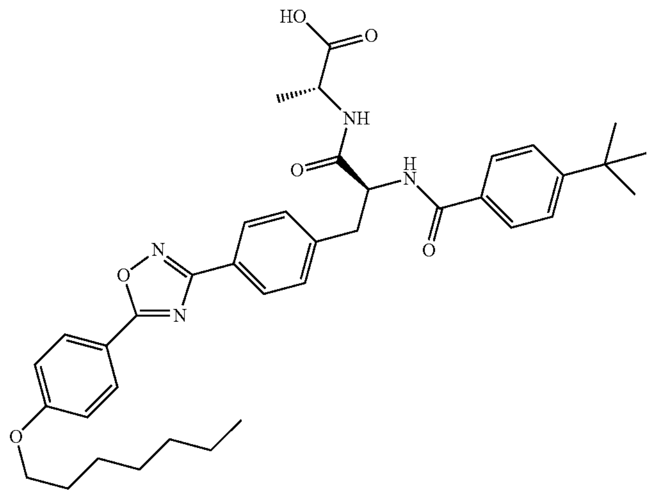 [SMILES: CCCCCCCOc1ccc(-c2nc(-c3ccc(C[C@H](NC(=O)c4ccc(C(C)(C)C)cc4)C(=O)N[C@H](C)C(=O)O)cc3)no2)cc1] | 801 | 10.18 | 14 |
| 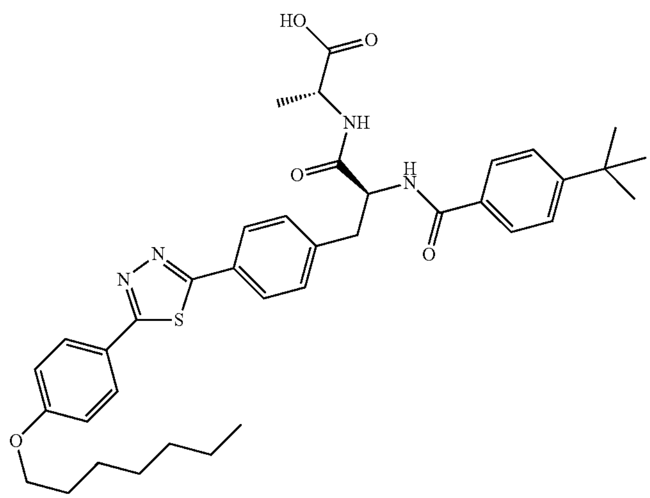 [SMILES: CCCCCCCOc1ccc(-c2nnc(-c3ccc(C[C@H](NC(=O)c4ccc(C(C)(C)C)cc4)C(=O)N[C@H](C)C(=O)O)cc3)s2)cc1] | 802 | 9.38 | 14 |
| 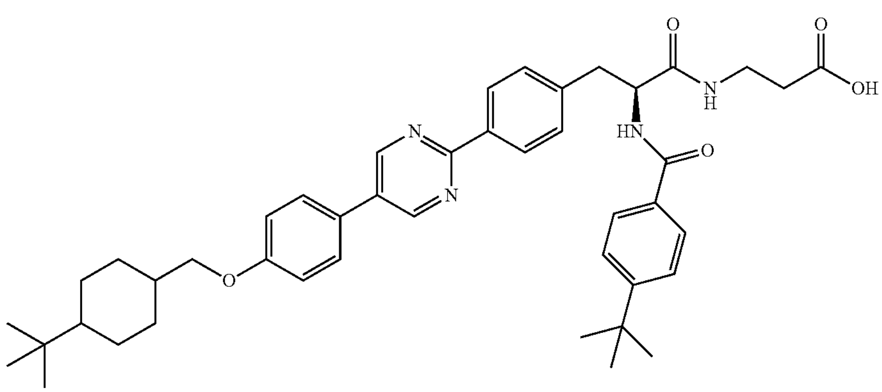 [SMILES: CC(C)(C)c1ccc(C(=O)N[C@@H](Cc2ccc(-c3ncc(-c4ccc(OCC5CCC(C(C)(C)C)CC5)cc4)cn3)cc2)C(=O)NCCC(=O)O)cc1] | 803 | 10.70 | 2 |

TABLE 1-continued

| STRUCTURE | COMPOUND NUMBER | LCMS RETENTION TIME (min) | PURITY METHOD |
|---|---|---|---|
| 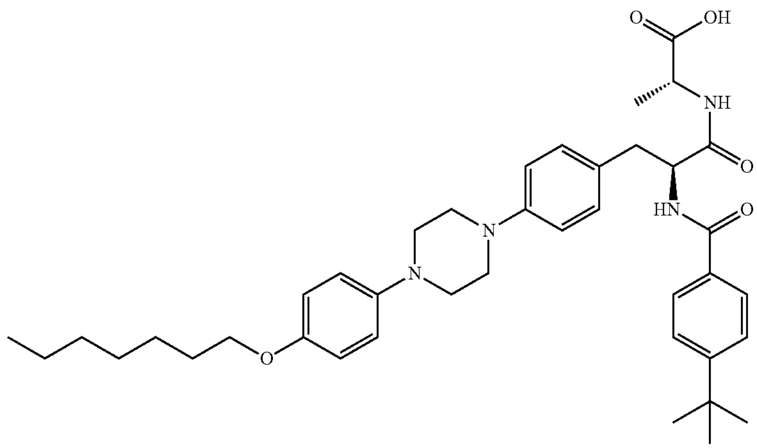 [SMILES: CCCCCCCOc1ccc(N2CCN(c3ccc(C[C@H](NC(=O)c4ccc(C(C)(C)C)cc4)C(=O)N[C@H](C)C(=O)O)cc3)CC2)cc1] | 804 | 9.66 | 14 |
| 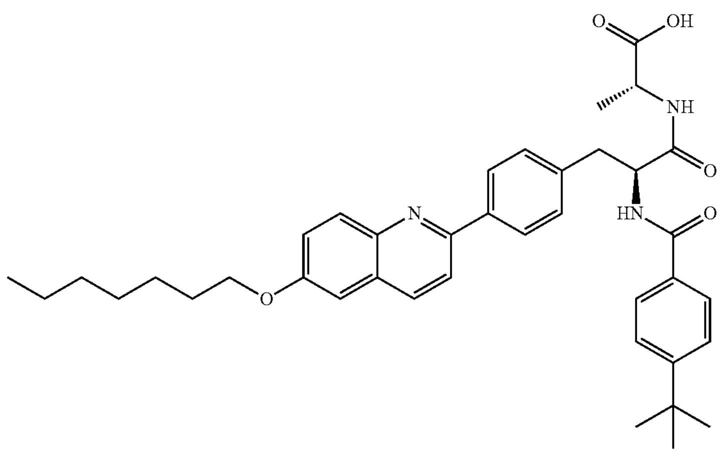 [SMILES: CCCCCCCOc1ccc2nc(-c3ccc(C[C@H](NC(=O)c4ccc(C(C)(C)C)cc4)C(=O)N[C@H](C)C(=O)O)cc3)ccc2c1] | 806 | 9.74 | 14 |
| 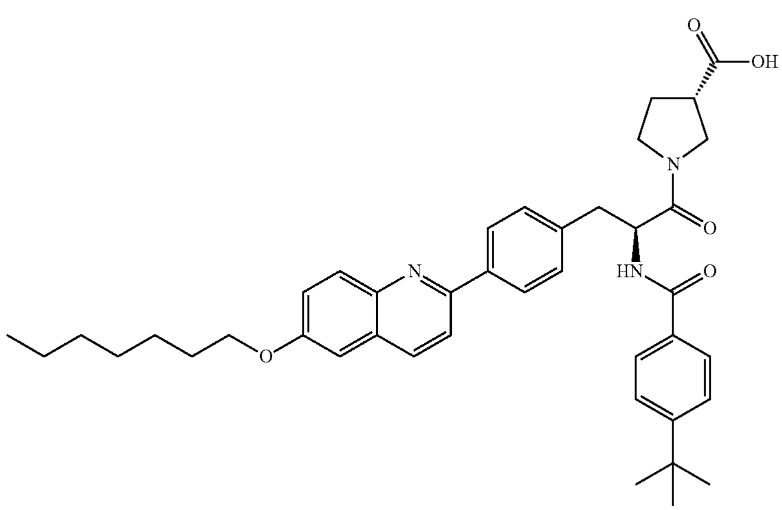 | 807 | 9.91 | 14 |

TABLE 1-continued

| STRUCTURE | COMPOUND NUMBER | LCMS RETENTION TIME (min) | PURITY METHOD |
|---|---|---|---|
| 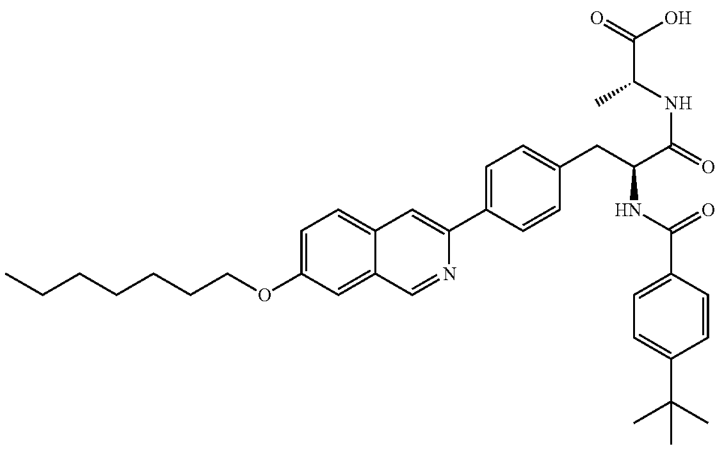 [SMILES: CCCCCCCOc1ccc2cc(-c3ccc(C[C@H](NC(=O)c4ccc(C(C)(C)C)cc4)C(=O)N[C@H](C)C(=O)O)cc3)ncc2c1] | 808 | 9.71 | 14 |
| 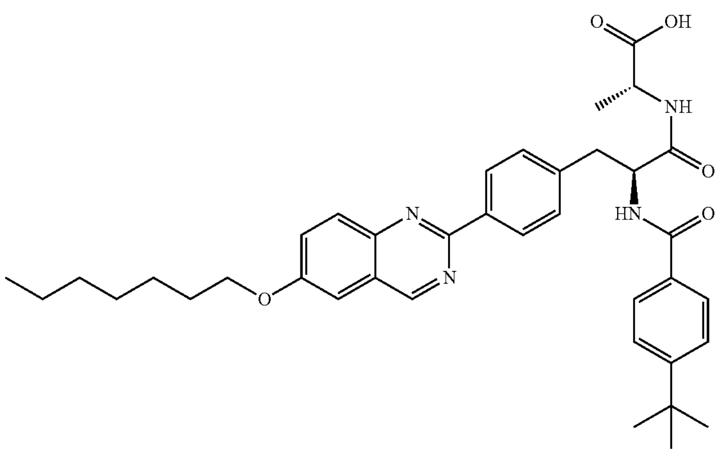 [SMILES: CCCCCCCOc1ccc2nc(-c3ccc(C[C@H](NC(=O)c4ccc(C(C)(C)C)cc4)C(=O)N[C@H](C)C(=O)O)cc3)ncc2c1] | 809 | 9.49 | 14 |
| 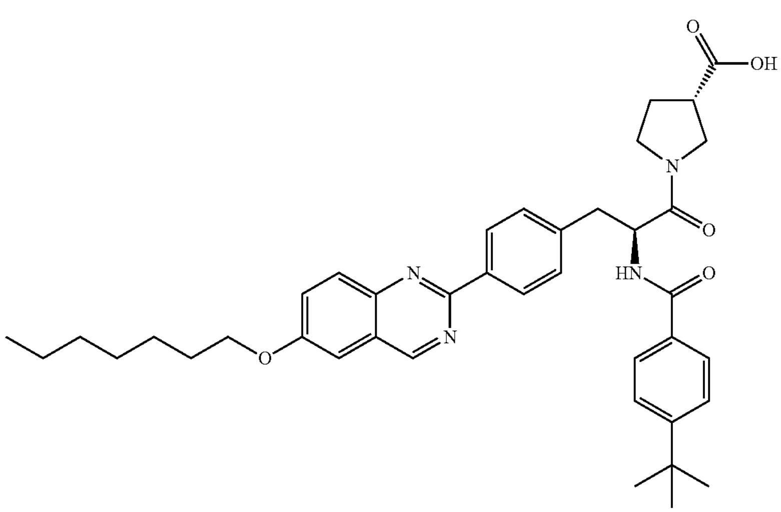 [SMILES: CCCCCCCOc1ccc2nc(-c3ccc(C[C@H](NC(=O)c4ccc(C(C)(C)C)cc4)C(=O)N4CC[C@H](C(=O)O)C4)cc3)ncc2c1] | 810 | 9.78 | 14 |

TABLE 1-continued

| STRUCTURE | COMPOUND NUMBER | LCMS RETENTION TIME (min) | PURITY METHOD |
|---|---|---|---|
| 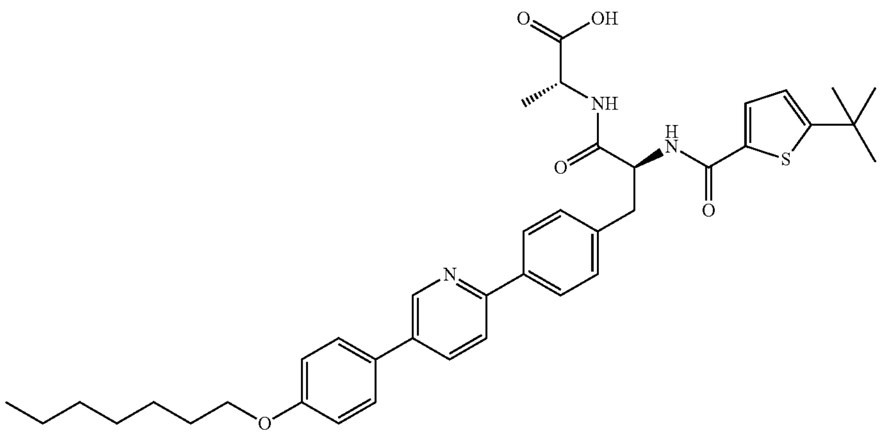 [SMILES: CCCCCCCOc1ccc(-c2ccc(-c3ccc(C[C@H](NC(=O)c4ccc(C(C)(C)C)s4)C(=O)N[C@H](C)C(=O)O)cc3)nc2)cc1] | 811 | 10.03 | 10 |
| 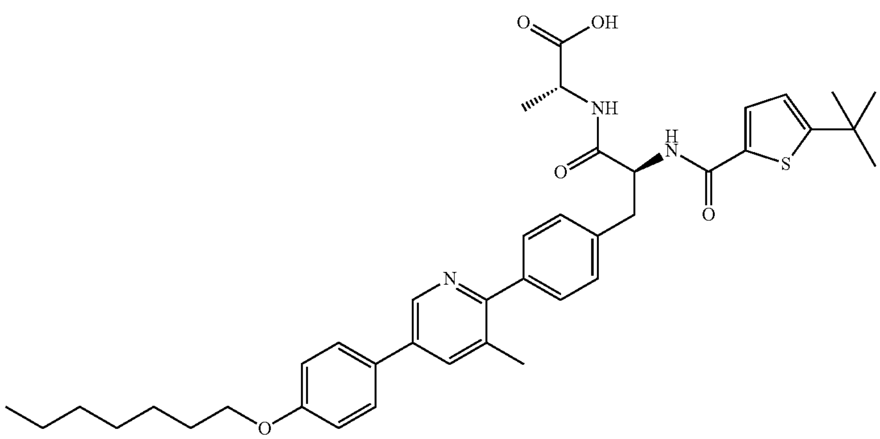 [SMILES: CCCCCCCOc1ccc(-c2cnc(-c3ccc(C[C@H](NC(=O)c4ccc(C(C)(C)C)s4)C(=O)N[C@H](C)C(=O)O)cc3)c(C)c2)cc1] | 812 | 9.00 | 10 |
| 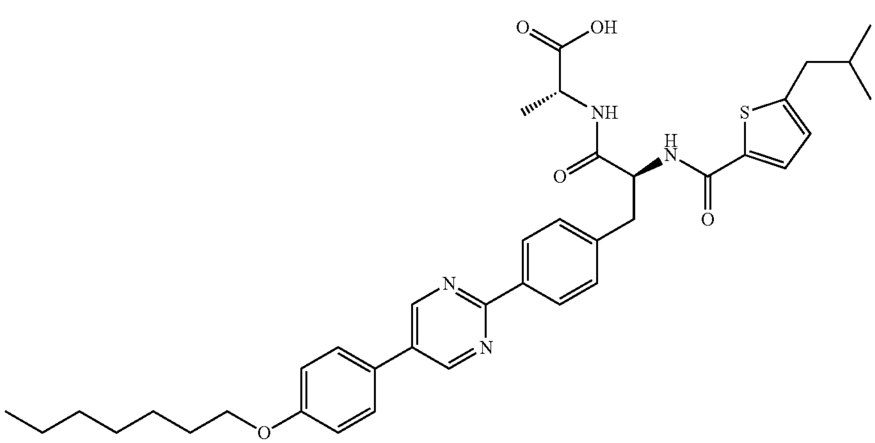 [SMILES: CCCCCCCOc1ccc(-c2cnc(-c3ccc(C[C@H](NC(=O)c4ccc(CC(C)C)s4)C(=O)N[C@H](C)C(=O)O)cc3)nc2)cc1] | 813 | 10.13 | 14 |

TABLE 1-continued

| STRUCTURE | COMPOUND NUMBER | LCMS RETENTION TIME (min) | PURITY METHOD |
|---|---|---|---|
| 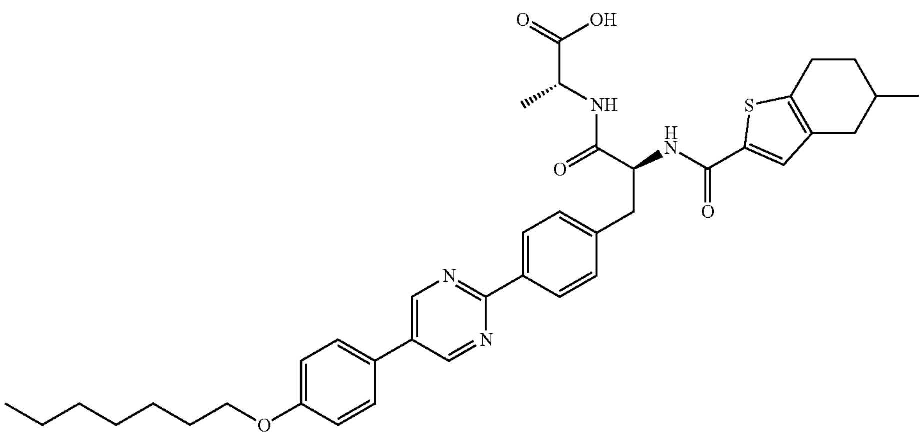 [SMILES: CCCCCCCOc1ccc(-c2cnc(-c3ccc(C[C@H](NC(=O)c4cc5c(s4)CCC(C)C5)C(=O)N[C@H](C)C(=O)O)cc3)nc2)cc1] | 814 | 10.18 | 14 |
| 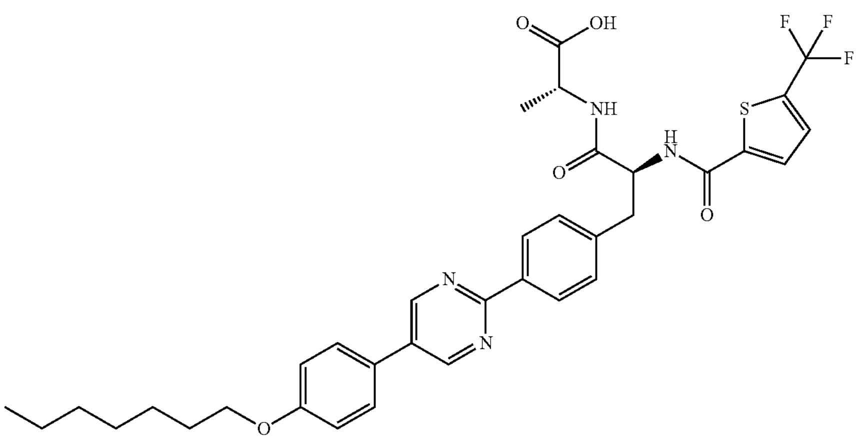 [SMILES: CCCCCCCOc1ccc(-c2cnc(-c3ccc(C[C@H](NC(=O)c4ccc(C(F)(F)F)s4)C(=O)N[C@H](C)C(=O)O)cc3)nc2)cc1] | 815 | 9.72 | 14 |
| 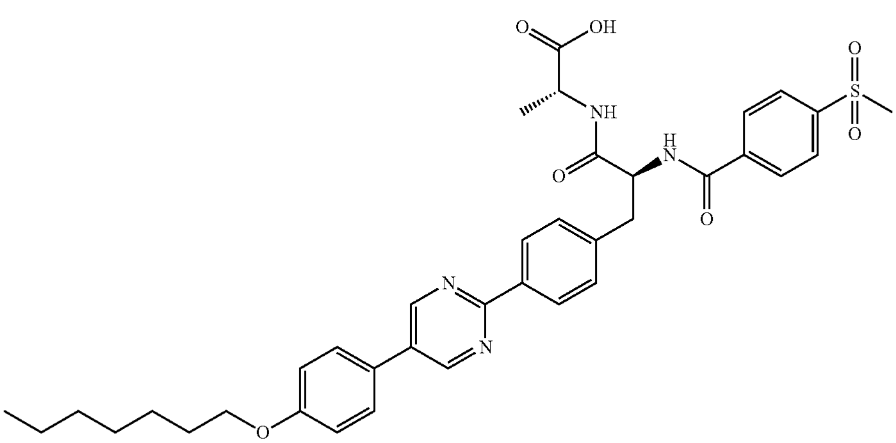 [SMILES: CCCCCCCOc1ccc(-c2cnc(-c3ccc(C[C@H](NC(=O)c4ccc(S(C)(=O)=O)cc4)C(=O)N[C@H](C)C(=O)O)cc3)nc2)cc1] | 816 | 8.59 | 14 |

TABLE 1-continued

| STRUCTURE | COMPOUND NUMBER | LCMS RETENTION TIME (min) | PURITY METHOD |
|---|---|---|---|
| 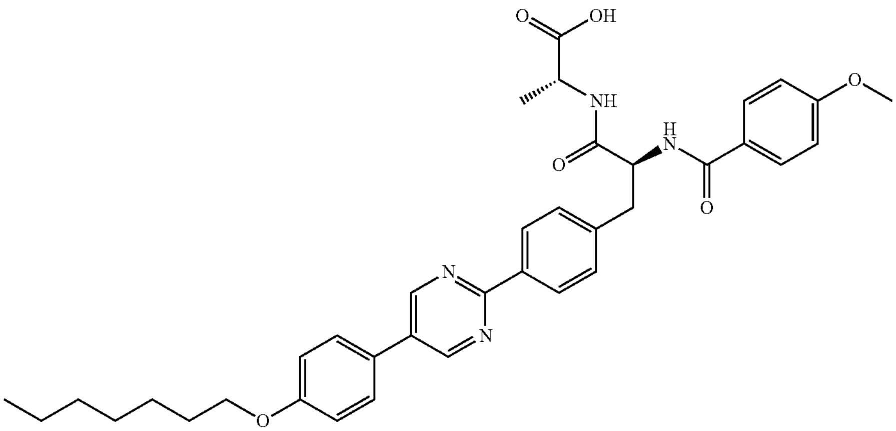 [SMILES: CCCCCCCOc1ccc(-c2cnc(-c3ccc(C[C@H](NC(=O)c4ccc(OC)cc4)C(=O)N[C@H](C)C(=O)O)cc3)nc2)cc1] | 817 | 8.97 | 14 |
| 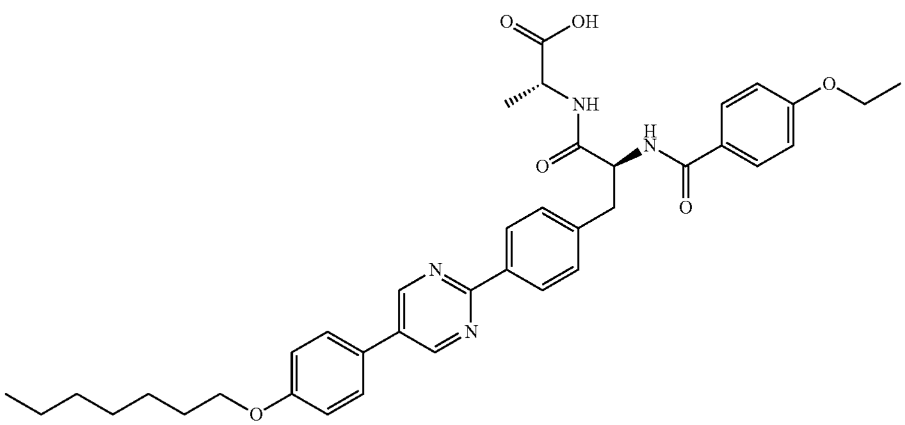 [SMILES: CCCCCCCOc1ccc(-c2cnc(-c3ccc(C[C@H](NC(=O)c4ccc(OCC)cc4)C(=O)N[C@H](C)C(=O)O)cc3)nc2)cc1] | 818 | 9.30 | 14 |
| 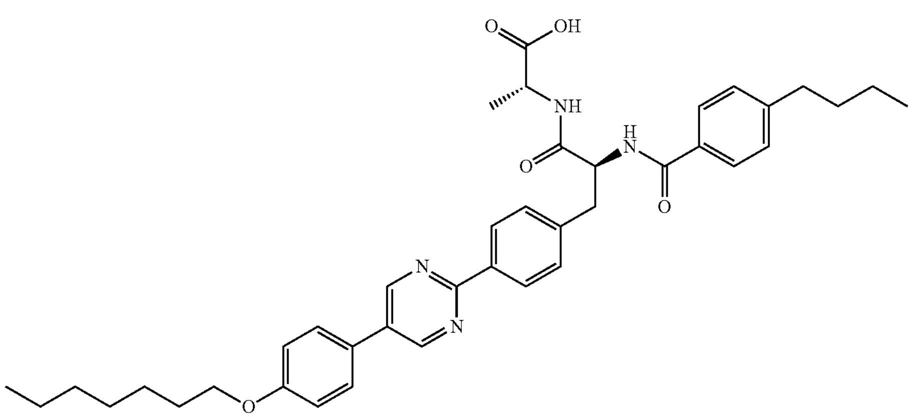 [SMILES: CCCCCCCOc1ccc(-c2cnc(-c3ccc(C[C@H](NC(=O)c4ccc(CCCC)cc4)C(=O)N[C@H](C)C(=O)O)cc3)nc2)cc1] | 819 | 10.35 | 14 |

TABLE 1-continued

| STRUCTURE | COMPOUND NUMBER | LCMS RETENTION TIME (min) | PURITY METHOD |
|---|---|---|---|
| (structure) | 820 | 9.56 | 14 |
| (structure) | 821 | 9.78 | 14 |
| (structure) | 822 | 9.70 | 14 |

TABLE 1-continued

| STRUCTURE | COMPOUND NUMBER | LCMS RETENTION TIME (min) | PURITY METHOD |
|---|---|---|---|
| 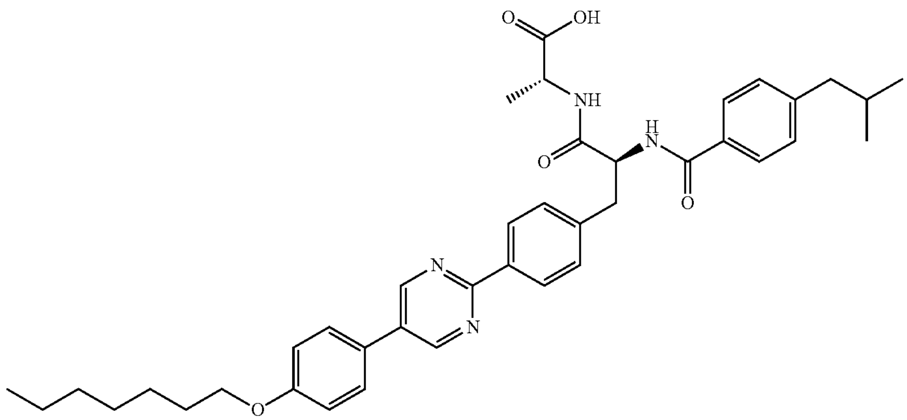 [SMILES: CCCCCCCOc1ccc(-c2cnc(-c3ccc(C[C@H](NC(=O)c4ccc(CC(C)C)cc4)C(=O)N[C@H](C)C(=O)O)cc3)nc2)cc1] | 823 | 10.30 | 14 |
| 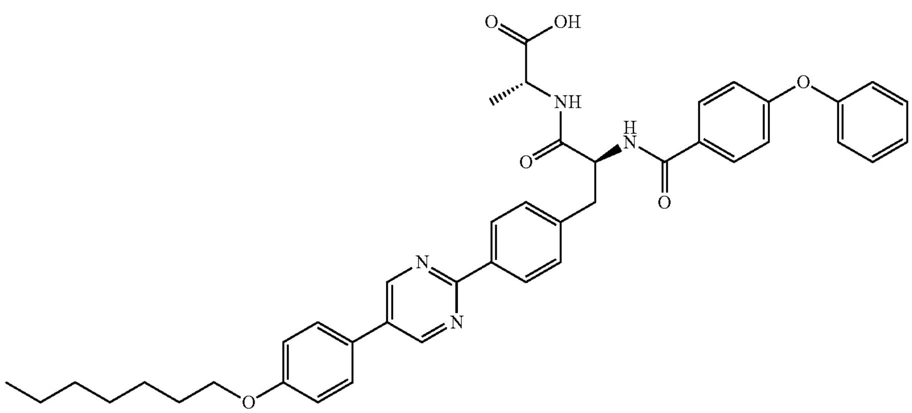 | 824 | 10.14 | 14 |
| 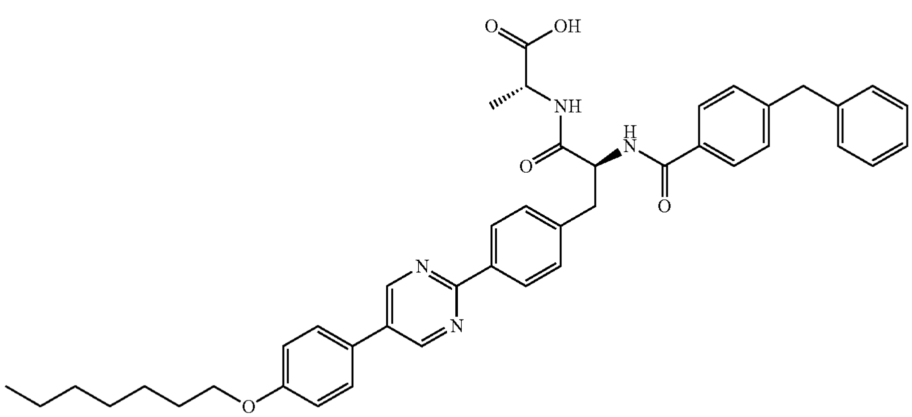 [SMILES: CCCCCCCOc1ccc(-c2cnc(-c3ccc(C[C@H](NC(=O)c4ccc(Oc5ccccc5)cc4)C(=O)N[C@H](C)C(=O)O)cc3)nc2)cc1] | 825 | 10.23 | 14 |

TABLE 1-continued

| STRUCTURE | COMPOUND NUMBER | LCMS RETENTION TIME (min) | PURITY METHOD |
|---|---|---|---|
| 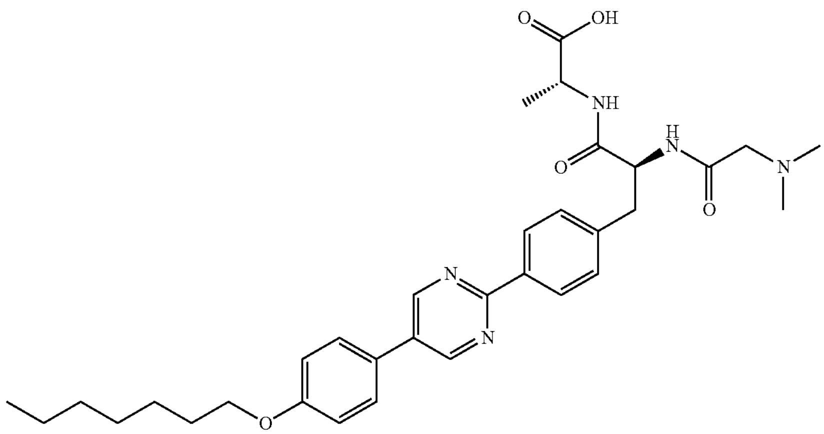 [SMILES: CCCCCCCOc1ccc(-c2cnc(-c3ccc(C[C@H](NC(=O)CN(C)C)C(=O)N[C@H](C)C(=O)O)cc3)nc2)cc1] | 826 | 8.21 | 14 |
| 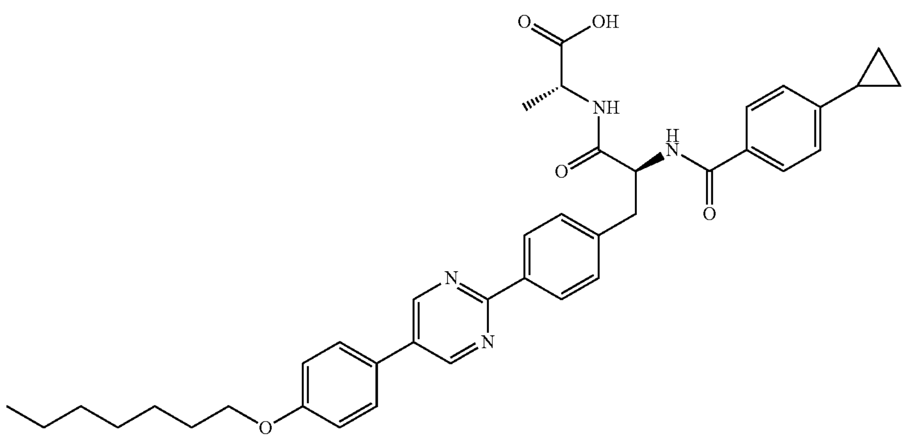 [SMILES: CCCCCCCOc1ccc(-c2cnc(-c3ccc(C[C@H](NC(=O)c4ccc(C5CC5)cc4)C(=O)N[C@H](C)C(=O)O)cc3)nc2)cc1] | 827 | 9.72 | 14 |
| 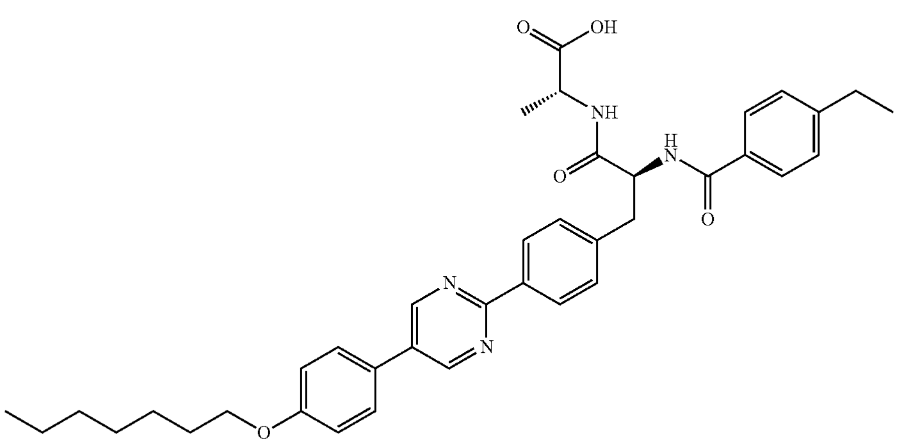 | 828 | 10.35 | 14 |

TABLE 1-continued

| STRUCTURE | COMPOUND NUMBER | LCMS RETENTION TIME (min) | PURITY METHOD |
|---|---|---|---|
| 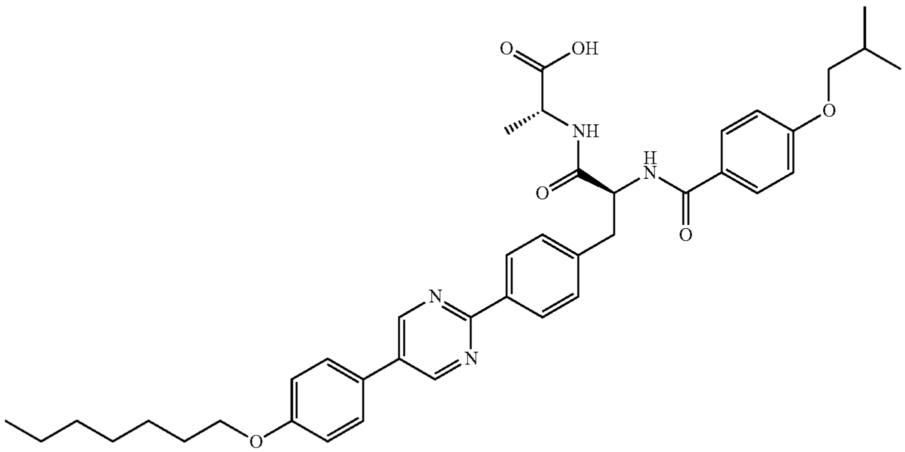 [SMILES: CCCCCCCOc1ccc(-c2cnc(-c3ccc(C[C@H](NC(=O)c4ccc(OCC(C)C)cc4)C(=O)N[C@H](C)C(=O)O)cc3)nc2)cc1] | 829 | 9.84 | 14 |
| 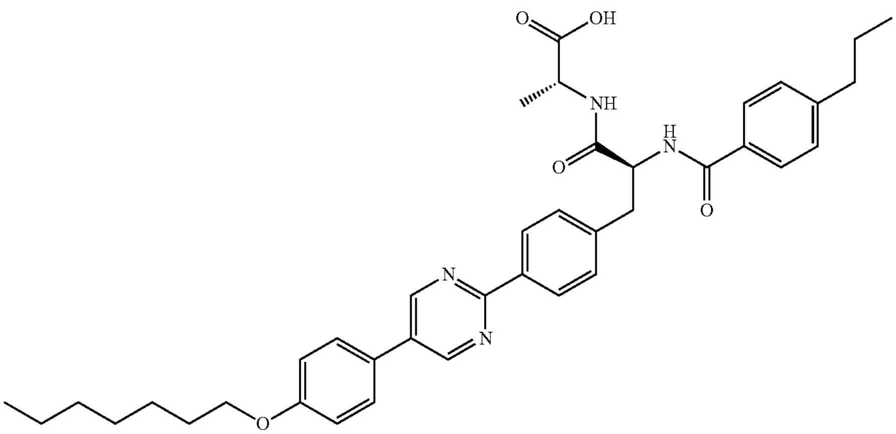 [SMILES: CCCCCCCOc1ccc(-c2cnc(-c3ccc(C[C@H](NC(=O)c4ccc(CCC)cc4)C(=O)N[C@H](C)C(=O)O)cc3)nc2)cc1] | 830 | 9.66 | 14 |
| 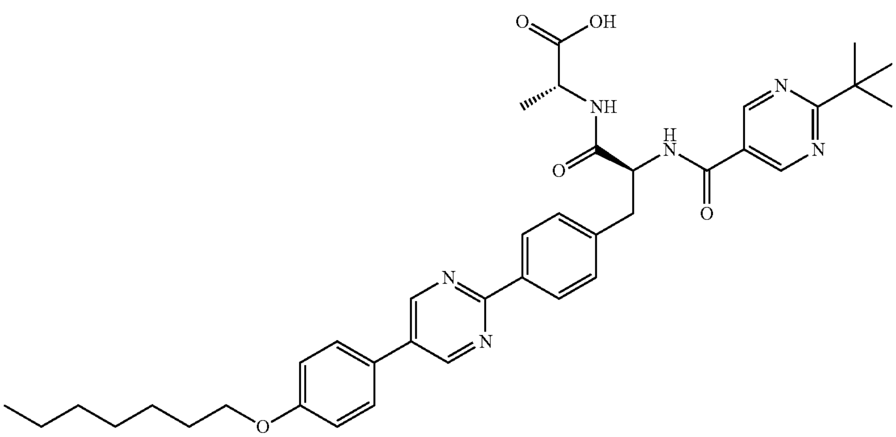 [SMILES: CCCCCCCOc1ccc(-c2cnc(-c3ccc(C[C@H](NC(=O)c4cnc(C(C)(C)C)nc4)C(=O)N[C@H](C)C(=O)O)cc3)nc2)cc1] | 832 | 9.20 | 14 |

TABLE 1-continued
| STRUCTURE | COMPOUND NUMBER | LCMS RETENTION TIME (min) | PURITY METHOD |
|---|---|---|---|
| 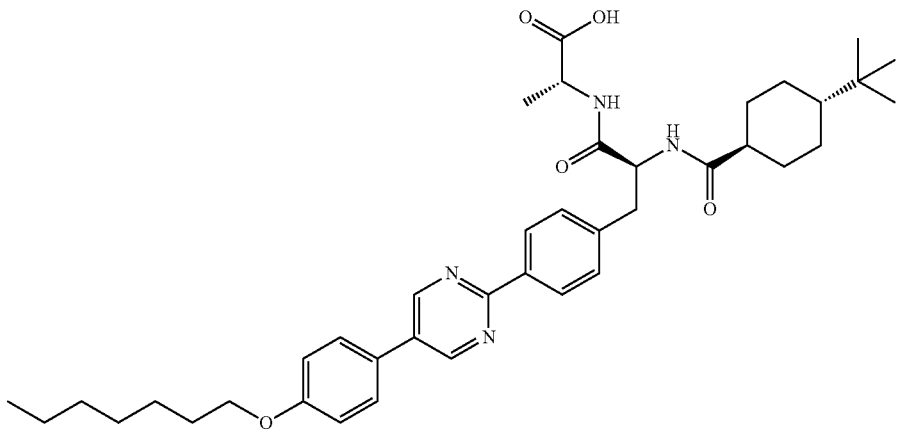 [SMILES: CCCCCCCOc1ccc(-c2cnc(-c3ccc(C[C@H](NC(=O)[C@H]4CC[C@H](C(C)(C)C)CC4)C(=O)N[C@H](C)C(=O)O)cc3)nc2)cc1] | 833 | 10.33 | 14 |
| 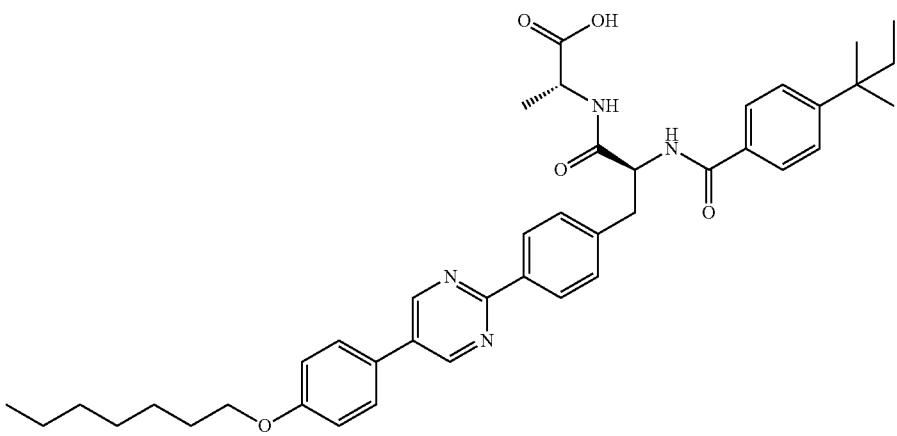 [SMILES: CCCCCCCOc1ccc(-c2cnc(-c3ccc(C[C@H](NC(=O)c4ccc(C(C)(C)CC)cc4)C(=O)N[C@H](C)C(=O)O)cc3)nc2)cc1] | 834 | 10.19 | 14 |
| 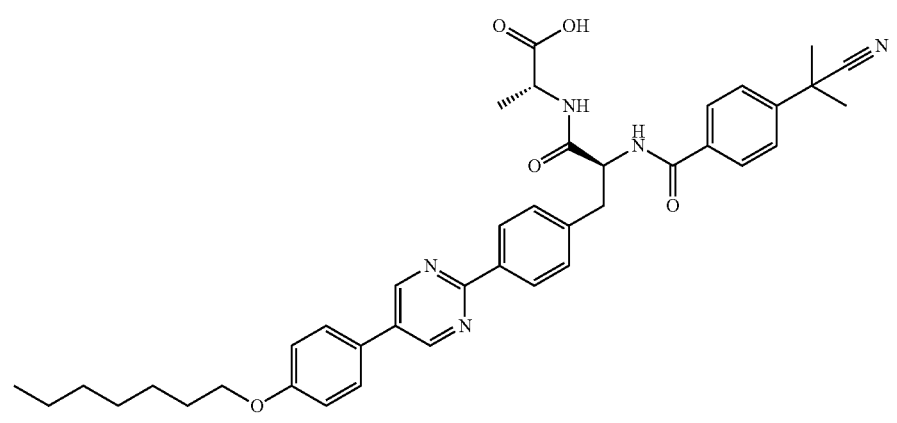 [SMILES: CCCCCCCOc1ccc(-c2cnc(-c3ccc(C[C@H](NC(=O)c4ccc(C(C)(C)C#N)cc4)C(=O)N[C@H](C)C(=O)O)cc3)nc2)cc1] | 835 | 9.04 | 14 |

TABLE 1-continued
| STRUCTURE | COMPOUND NUMBER | LCMS RETENTION TIME (min) | PURITY METHOD |
|---|---|---|---|
| 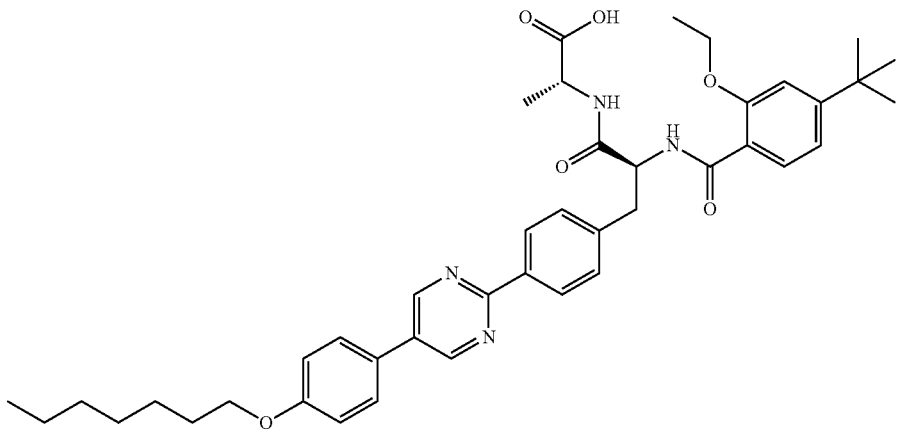 [SMILES: CCCCCCCOc1ccc(-c2cnc(-c3ccc(C[C@H](NC(=O)c4ccc(C(C)(C)C)cc4OCC)C(=O)N[C@H](C)C(=O)O)cc3)nc2)cc1] | 836 | 10.15 | 14 |
| 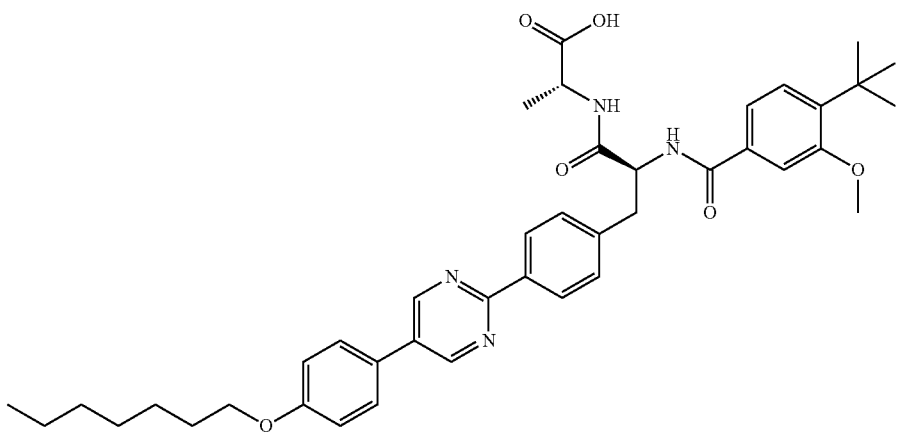 [SMILES: CCCCCCCOc1ccc(-c2cnc(-c3ccc(C[C@H](NC(=O)c4ccc(C(C)(C)C)c(OC)c4)C(=O)N[C@H](C)C(=O)O)cc3)nc2)cc1] | 837 | 10.02 | 14 |
| 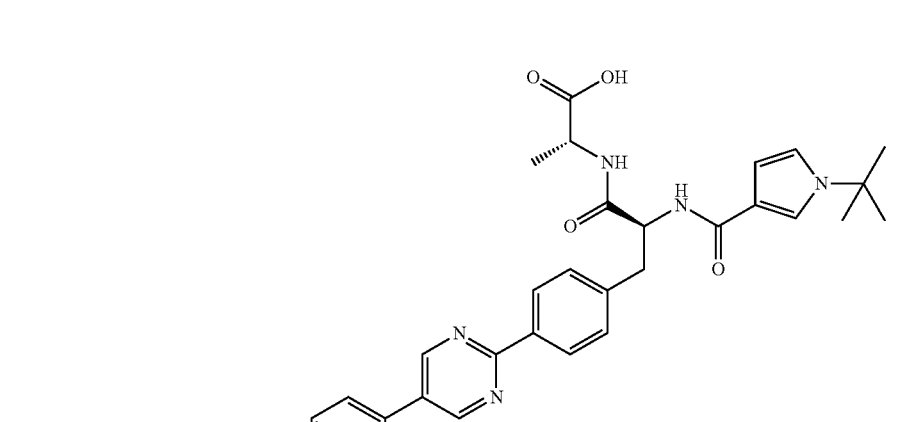 | 838 | 8.69 | 14 |

TABLE 1-continued

| STRUCTURE | COMPOUND NUMBER | LCMS RETENTION TIME (min) | PURITY METHOD |
|---|---|---|---|
| (structure) | 839 | 8.91 | 14 |
| (structure) | 840 | 9.35 | 14 |
| (structure) | 841 | 9.31 | 14 |

TABLE 1-continued

| STRUCTURE | COMPOUND NUMBER | LCMS RETENTION TIME (min) | PURITY METHOD |
|---|---|---|---|
| 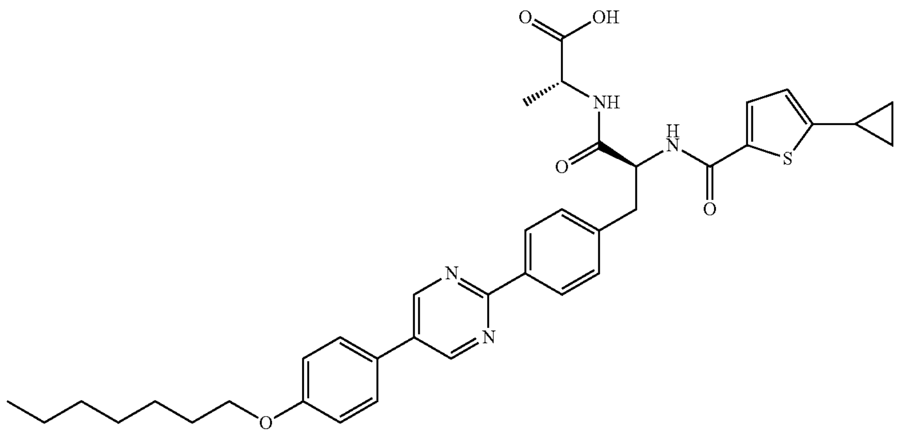 [SMILES: CCCCCCCOc1ccc(-c2cnc(-c3ccc(C[C@H](NC(=O)c4ccc(C5CC5)s4)C(=O)N[C@H](C)C(=O)O)cc3)nc2)cc1] | 842 | 9.01 | 14 |
| 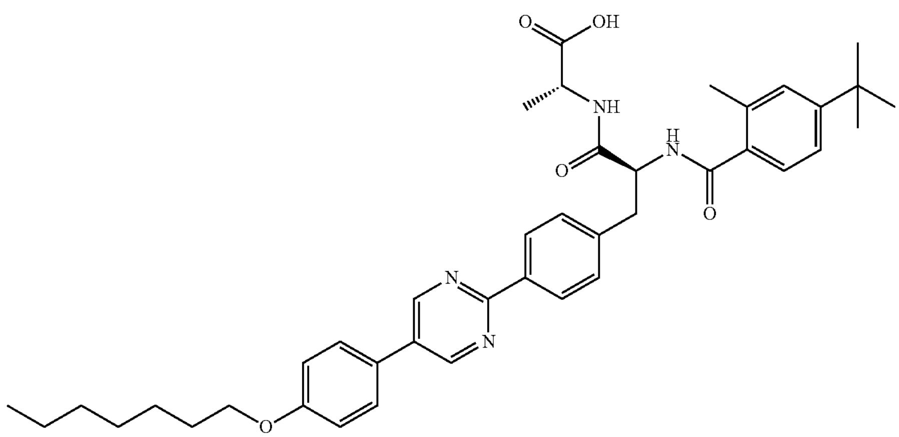 [SMILES: CCCCCCCOc1ccc(-c2cnc(-c3ccc(C[C@H](NC(=O)c4ccc(C(C)(C)C)cc4C)C(=O)N[C@H](C)C(=O)O)cc3)nc2)cc1] | 843 | 9.79 | 14 |
| 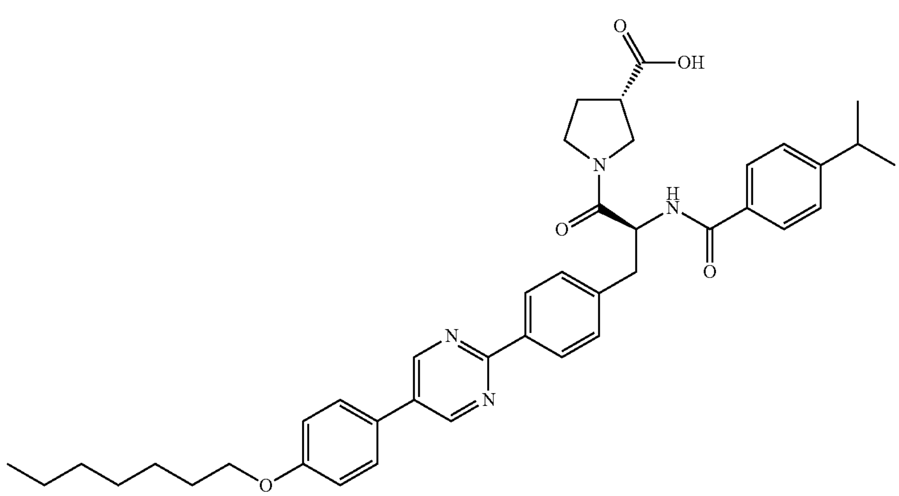 [SMILES: CCCCCCCOc1ccc(-c2cnc(-c3ccc(C[C@H](NC(=O)c4ccc(C(C)C)cc4)C(=O)N4CC[C@H](C(=O)O)C4)cc3)nc2)cc1] | 844 | 10.21 | 14 |

TABLE 1-continued

| STRUCTURE | COMPOUND NUMBER | LCMS RETENTION TIME (min) | PURITY METHOD |
|---|---|---|---|
| 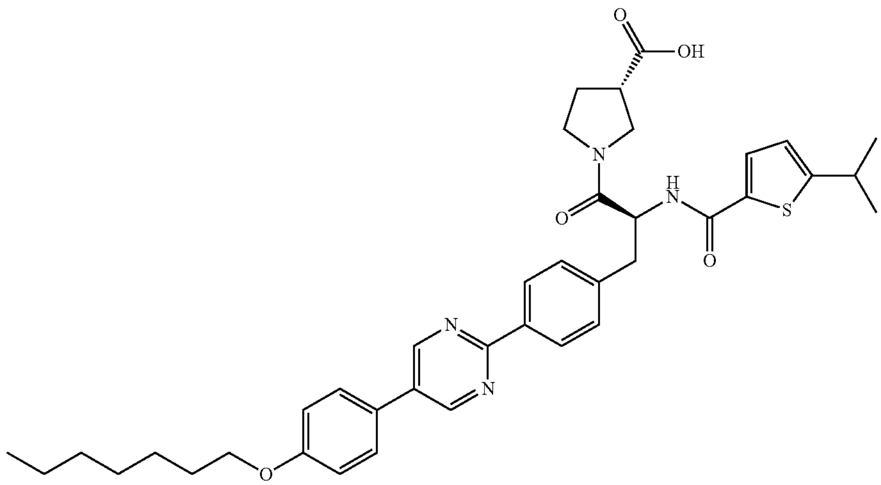 [SMILES: CCCCCCCOc1ccc(-c2cnc(-c3ccc(C[C@H](NC(=O)c4ccc(C(C)C)s4)C(=O)N4CC[C@H](C(=O)O)C4)cc3)nc2)cc1] | 845 | 10.11 | 14 |
| 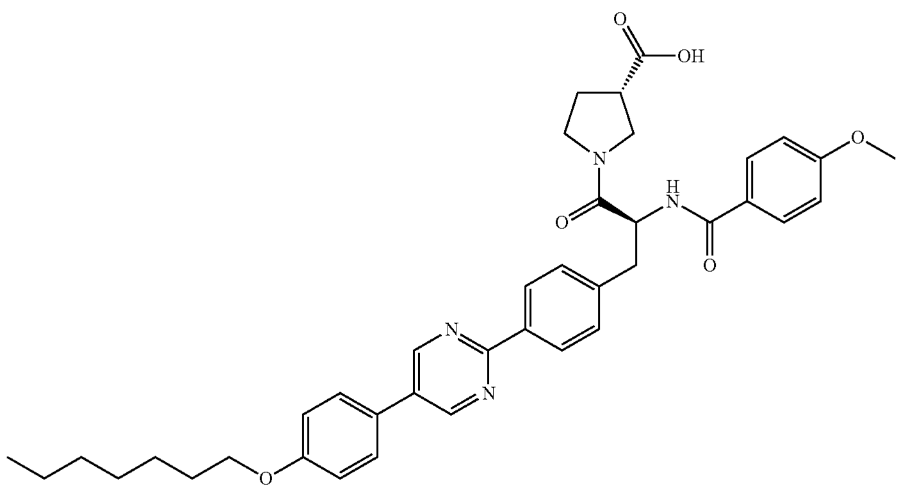 [SMILES: CCCCCCCOc1ccc(-c2cnc(-c3ccc(C[C@H](NC(=O)c4ccc(OC)cc4)C(=O)N4CC[C@H](C(=O)O)C4)cc3)nc2)cc1] | 846 | 9.38 | 14 |
| 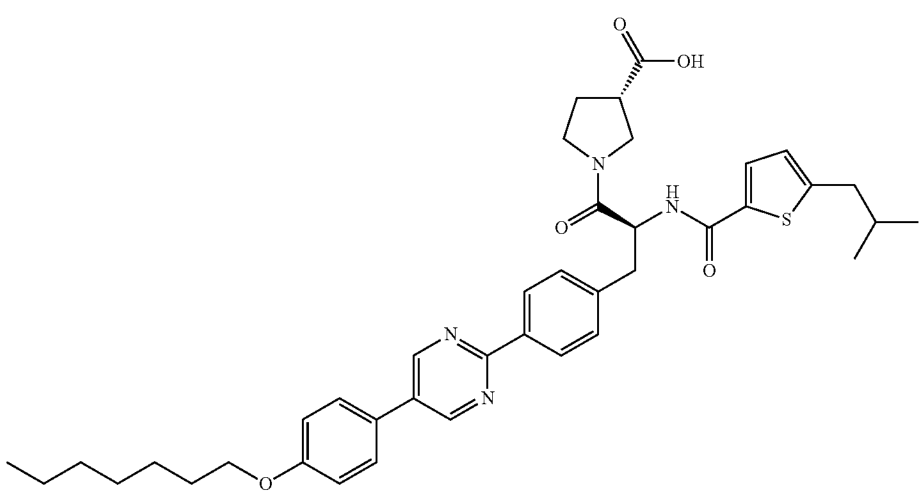 [SMILES: CCCCCCCOc1ccc(-c2cnc(-c3ccc(C[C@H](NC(=O)c4ccc(CC(C)C)s4)C(=O)N4CC[C@H](C(=O)O)C4)cc3)nc2)cc1] | 847 | 10.77 | 14 |

TABLE 1-continued

| STRUCTURE | COMPOUND NUMBER | LCMS RETENTION TIME (min) | PURITY METHOD |
|---|---|---|---|
| 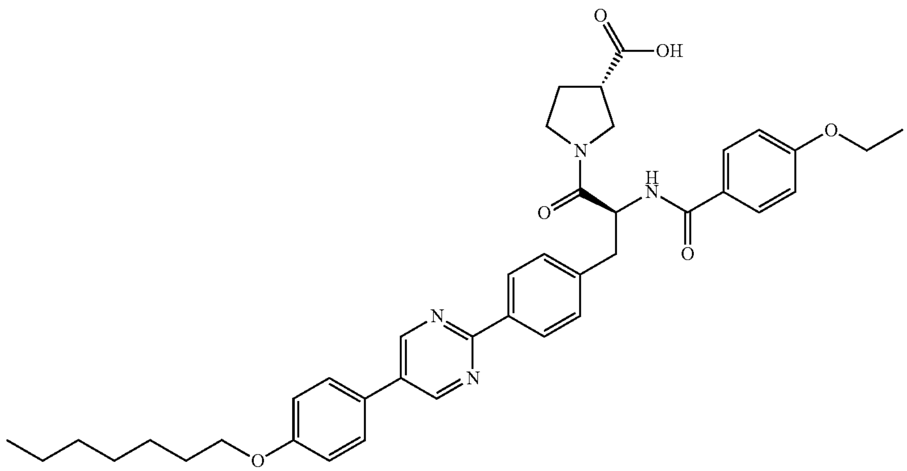 [SMILES: CCCCCCCOc1ccc(-c2cnc(-c3ccc(C[C@H](NC(=O)c4ccc(OCC)cc4)C(=O)N4CC[C@H](C(=O)O)C4)cc3)nc2)cc1] | 848 | 9.76 | 14 |
| 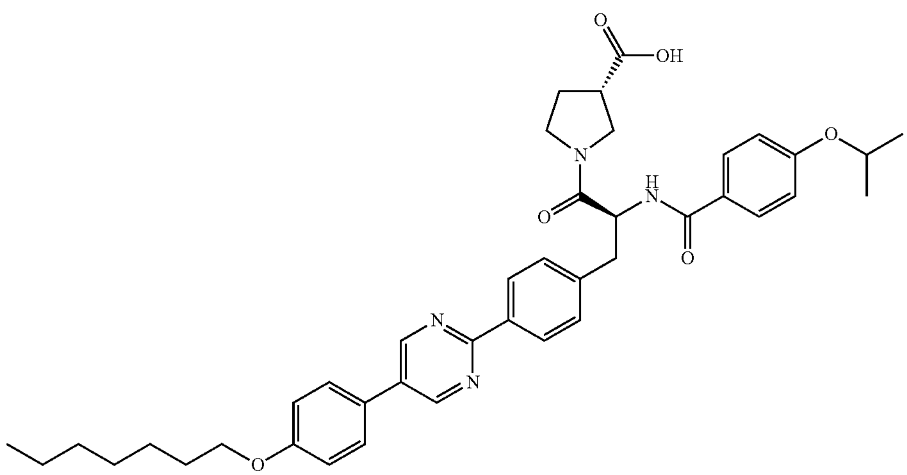 [SMILES: CCCCCCCOc1ccc(-c2cnc(-c3ccc(C[C@H](NC(=O)c4ccc(OC(C)C)cc4)C(=O)N4CC[C@H](C(=O)O)C4)cc3)nc2)cc1] | 849 | 10.06 | 14 |
| 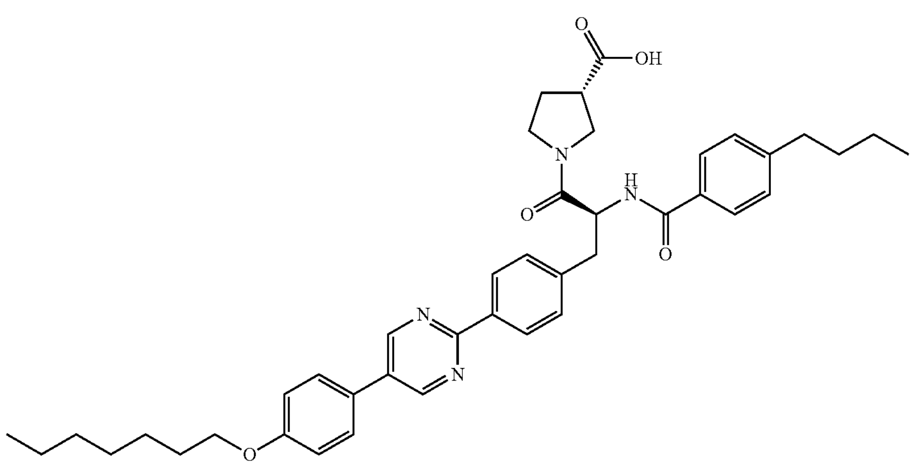 [SMILES: CCCCCCCOc1ccc(-c2cnc(-c3ccc(C[C@H](NC(=O)c4ccc(CCCC)cc4)C(=O)N4CC[C@H](C(=O)O)C4)cc3)nc2)cc1] | 850 | 10.93 | 14 |

TABLE 1-continued

| STRUCTURE | COMPOUND NUMBER | LCMS RETENTION TIME (min) | PURITY METHOD |
|---|---|---|---|
| 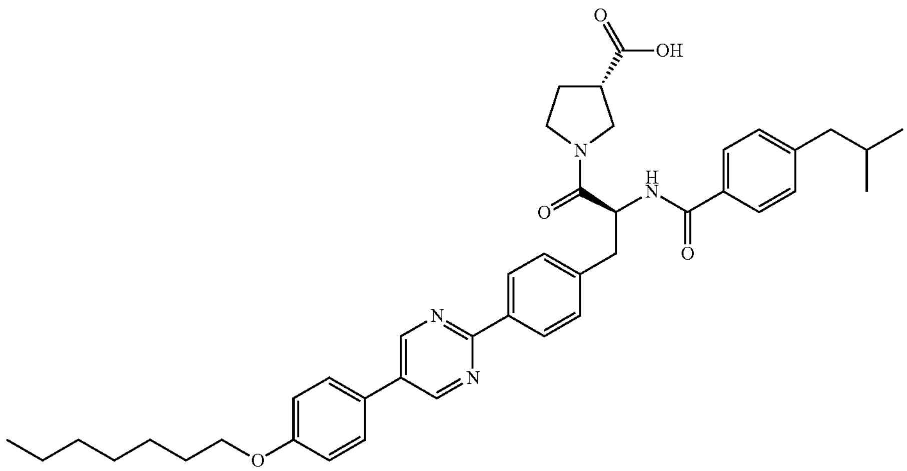 | 851 | 10.85 | 14 |
| 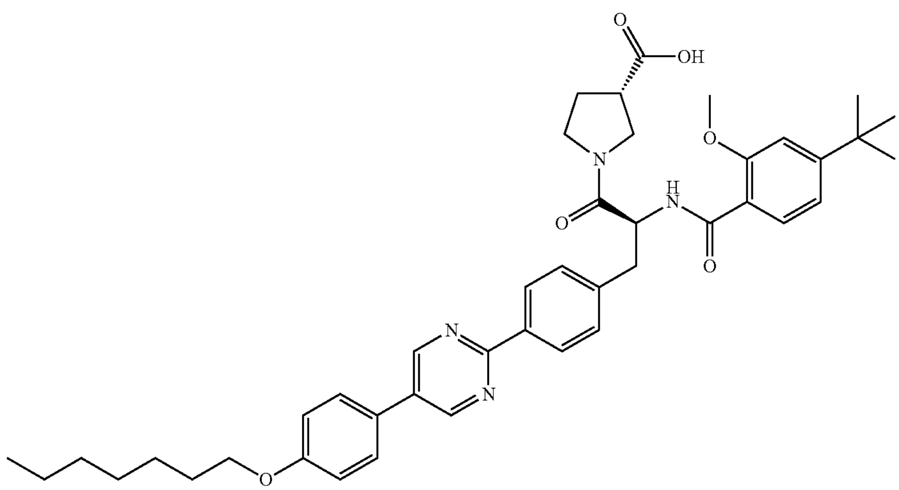 [SMILES: CCCCCCCOc1ccc(-c2cnc(-c3ccc(C[C@H](NC(=O)c4ccc(C(C)(C)C)cc4OC)C(=O)N4CC[C@H](C(=O)O)C4)cc3)nc2)cc1] | 852 | 10.92 | 14 |
| 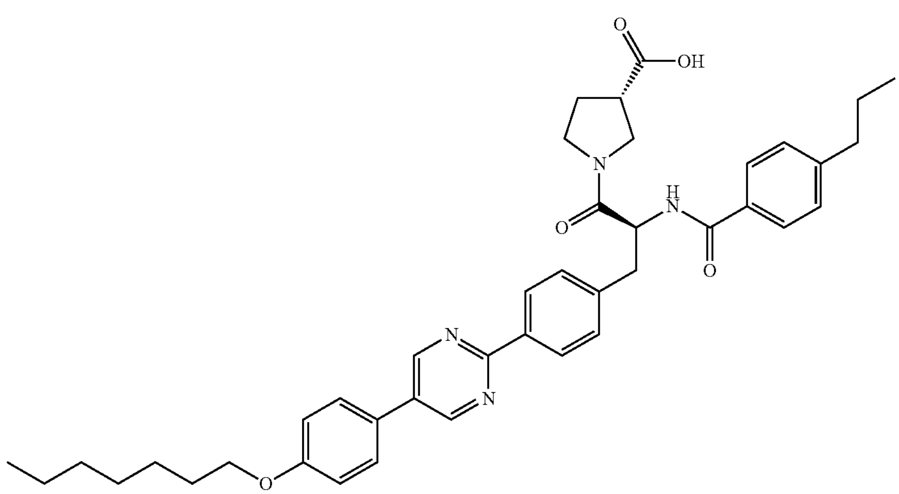 [SMILES: CCCCCCCOc1ccc(-c2cnc(-c3ccc(C[C@H](NC(=O)c4ccc(CCC)cc4)C(=O)N4CC[C@H](C(=O)O)C4)cc3)nc2)cc1] | 853 | 10.47 | 14 |

| STRUCTURE | COMPOUND NUMBER | LCMS RETENTION TIME (min) | PURITY METHOD |
|---|---|---|---|
| 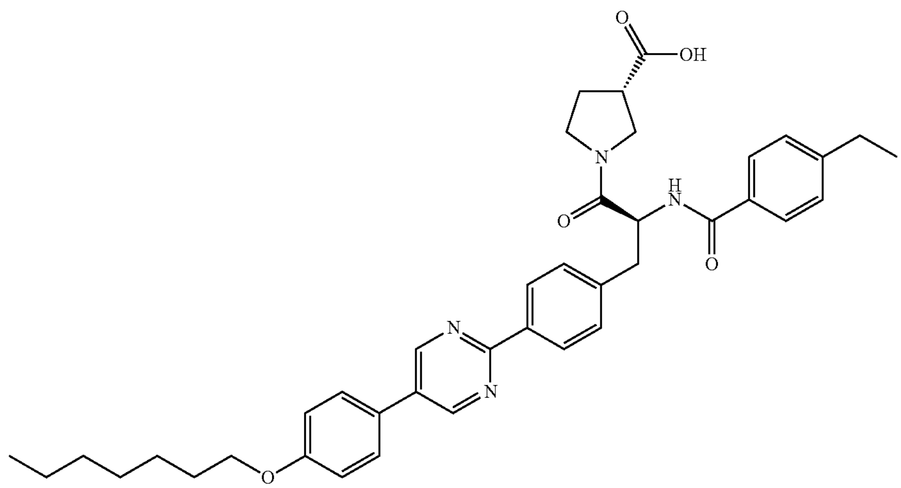 [SMILES: CCCCCCCOc1ccc(-c2cnc(-c3ccc(C[C@H](NC(=O)c4ccc(CC)cc4)C(=O)N4CC[C@H](C(=O)O)C4)cc3)nc2)cc1] | 855 | 9.34 | 14 |
| 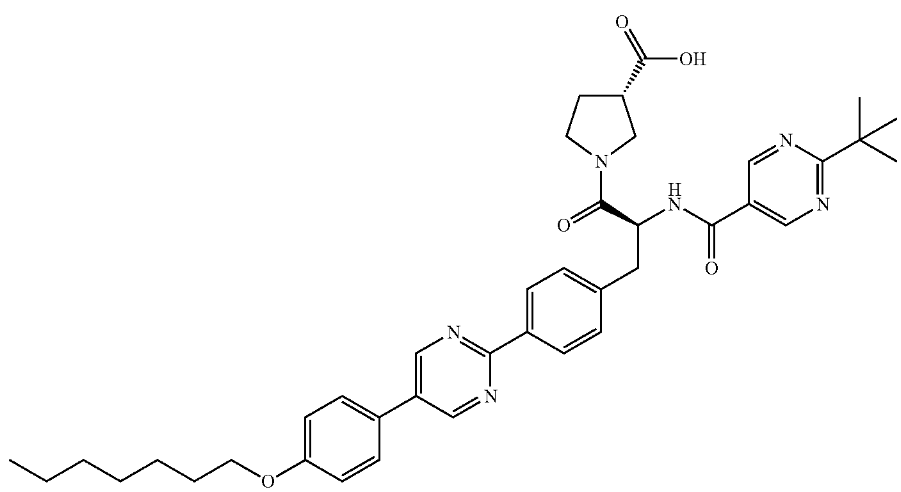 [SMILES: CCCCCCCOc1ccc(-c2cnc(-c3ccc(C[C@H](NC(=O)c4cnc(C(C)(C)C)nc4)C(=O)N4CC[C@H](C(=O)O)C4)cc3)nc2)cc1] | 856 | 9.18 | 14 |
| 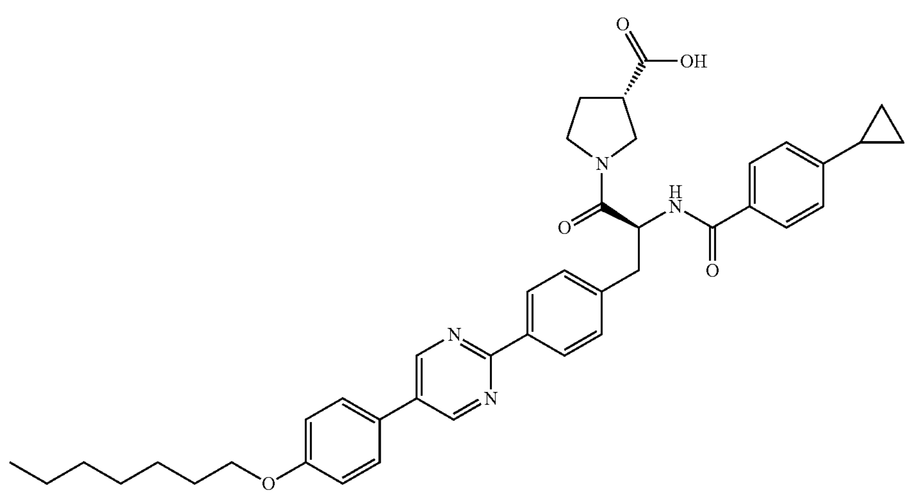 [SMILES: CCCCCCCOc1ccc(-c2cnc(-c3ccc(C[C@H](NC(=O)c4ccc(C5CC5)cc4)C(=O)N4CC[C@H](C(=O)O)C4)cc3)nc2)cc1] | 857 | 9.33 | 14 |

TABLE 1-continued

| STRUCTURE | COMPOUND NUMBER | LCMS RETENTION TIME (min) | PURITY METHOD |
|---|---|---|---|
| 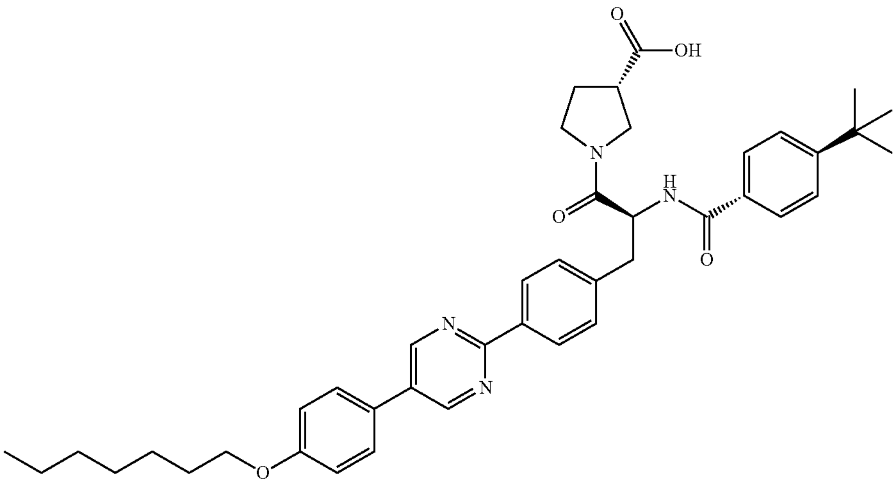 | 858 | 10.34 | 14 |
| 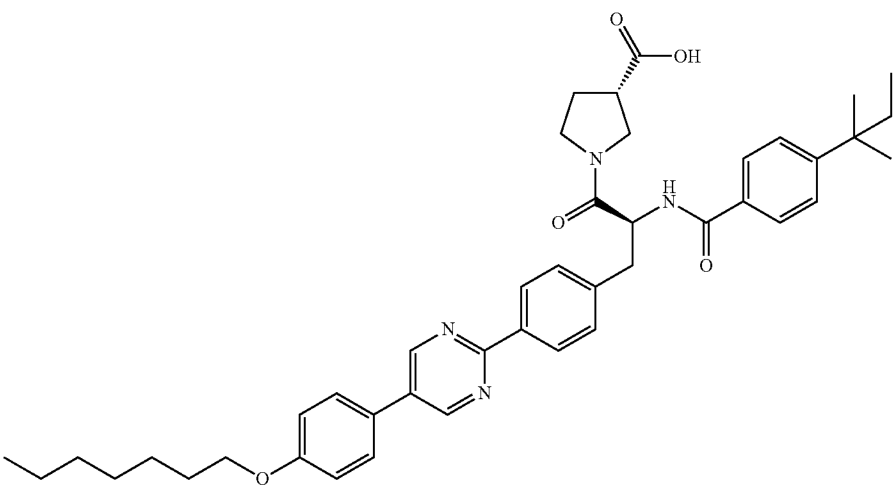 [SMILES: CCCCCCCOc1ccc(-c2cnc(-c3ccc(C[C@H](NC(=O)c4ccc(C(C)(C)CC)cc4)C(=O)N4CC[C@H](C(=O)O)C4)cc3)nc2)cc1] | 859 | 10.32 | 14 |
| 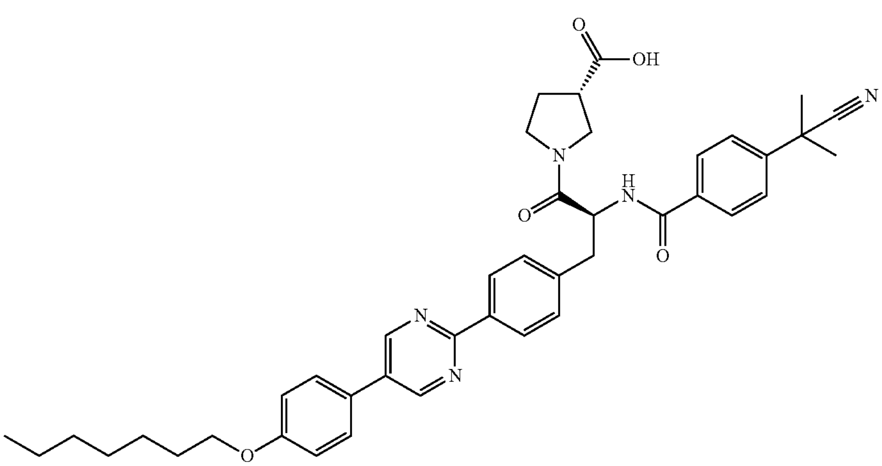 [SMILES: CCCCCCCOc1ccc(-c2cnc(-c3ccc(C[C@H](NC(=O)c4ccc(C(C)(C)C#N)cc4)C(=O)N4CC[C@H](C(=O)O)C4)cc3)nc2)cc1] | 860 | 9.02 | 14 |

TABLE 1-continued

| STRUCTURE | COMPOUND NUMBER | LCMS RETENTION TIME (min) | PURITY METHOD |
|---|---|---|---|
| 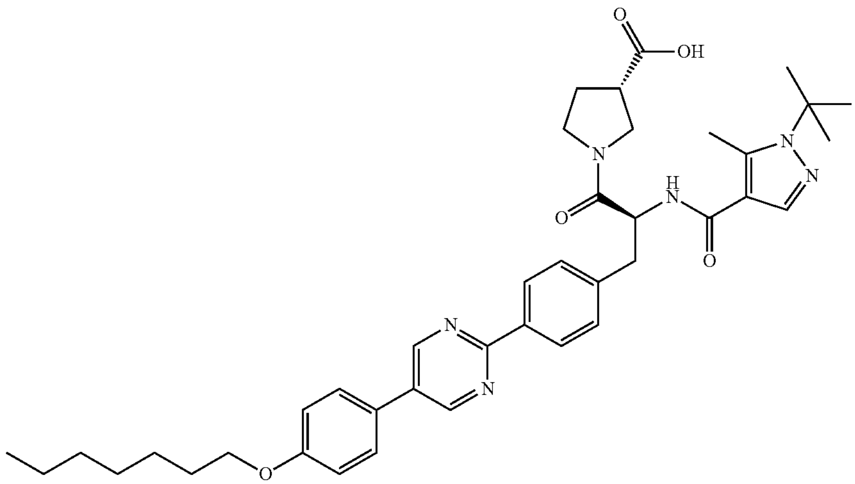 [SMILES: CCCCCCCOc1ccc(-c2cnc(-c3ccc(C[C@H](NC(=O)c4cnn(C(C)(C)C)c4C)C(=O)N4CC[C@H](C(=O)O)C4)cc3)nc2)cc1] | 861 | 8.85 | 14 |
| 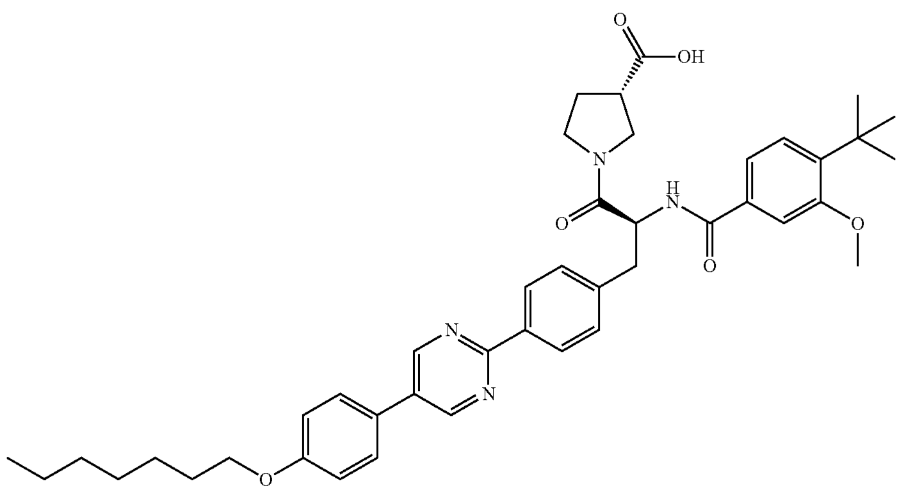 [SMILES: CCCCCCCOc1ccc(-c2cnc(-c3ccc(C[C@H](NC(=O)c4ccc(C(C)(C)C)c(OC)c4)C(=O)N4CC[C@H](C(=O)O)C4)cc3)nc2)cc1] | 862 | 10.34 | 14 |
| 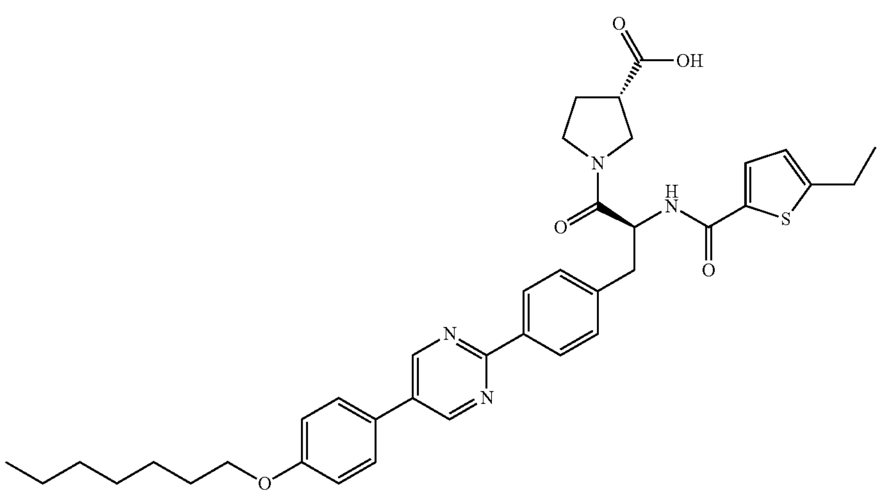 [SMILES: CCCCCCCOc1ccc(-c2cnc(-c3ccc(C[C@H](NC(=O)c4ccc(CC)s4)C(=O)N4CC[C@H](C(=O)O)C4)cc3)nc2)cc1] | 863 | 9.24 | 14 |

TABLE 1-continued

| STRUCTURE | COMPOUND NUMBER | LCMS RETENTION TIME (min) | PURITY METHOD |
|---|---|---|---|
| 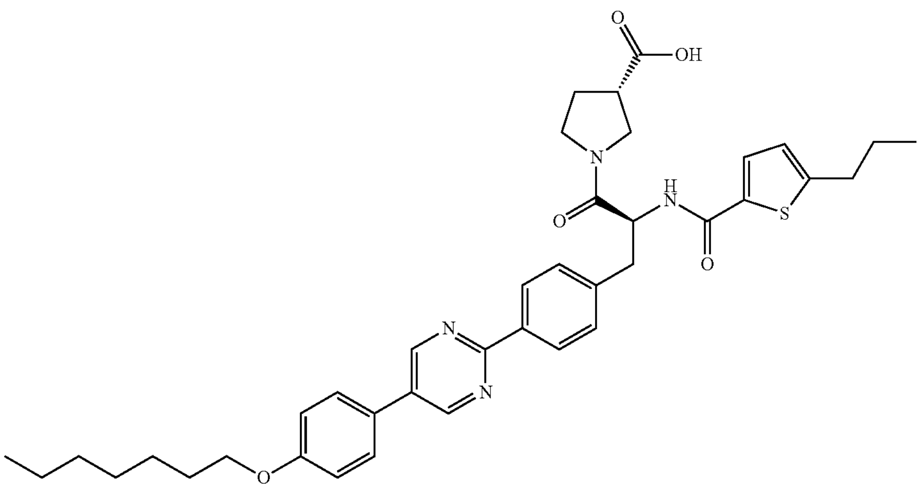 [SMILES: CCCCCCCOc1ccc(-c2cnc(-c3ccc(C[C@H](NC(=O)c4ccc(CCC)s4)C(=O)N4CC[C@H](C(=O)O)C4)cc3)nc2)cc1] | 864 | 9.61 | 14 |
| 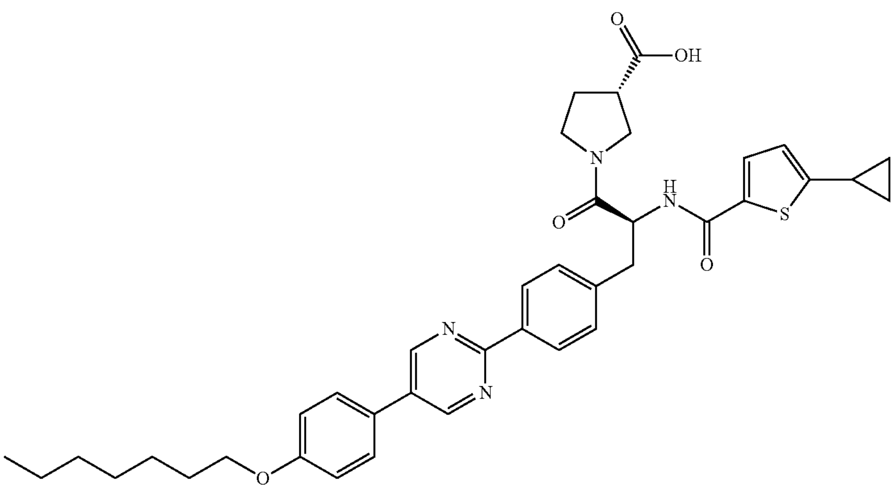 [SMILES: CCCCCCCOc1ccc(-c2cnc(-c3ccc(C[C@H](NC(=O)c4ccc(C5CC5)s4)C(=O)N4CC[C@H](C(=O)O)C4)cc3)nc2)cc1] | 865 | 9.25 | 14 |
| 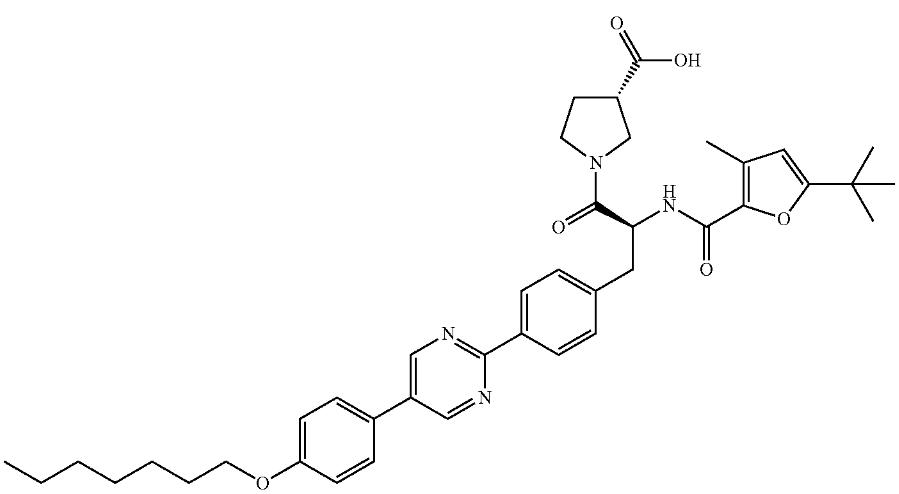 [SMILES: CCCCCCCOc1ccc(-c2cnc(-c3ccc(C[C@H](NC(=O)c4oc(C(C)(C)C)cc4C)C(=O)N4CC[C@H](C(=O)O)C4)cc3)nc2)cc1] | 866 | 10.07 | 14 |

| STRUCTURE | COMPOUND NUMBER | LCMS RETENTION TIME (min) | PURITY METHOD |
|---|---|---|---|
| 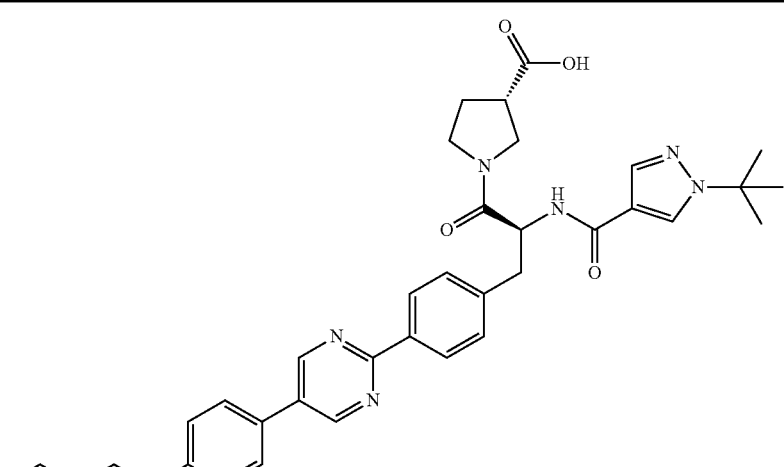 | 867 | 8.61 | 14 |
| 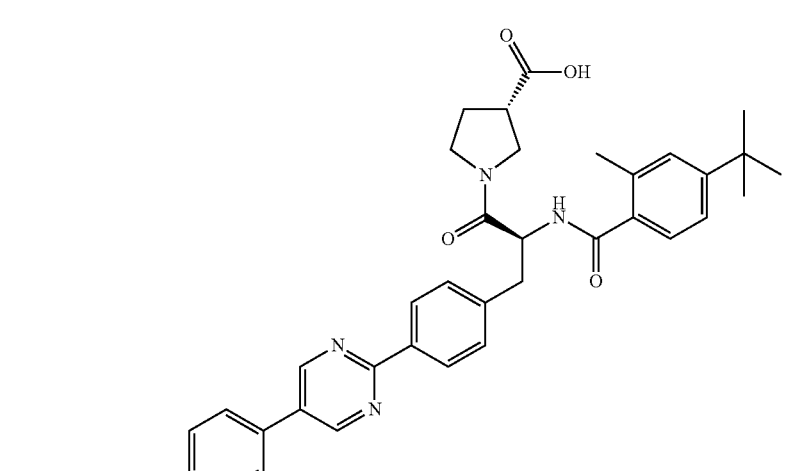 | 868 | 10.08 | 14 |
| 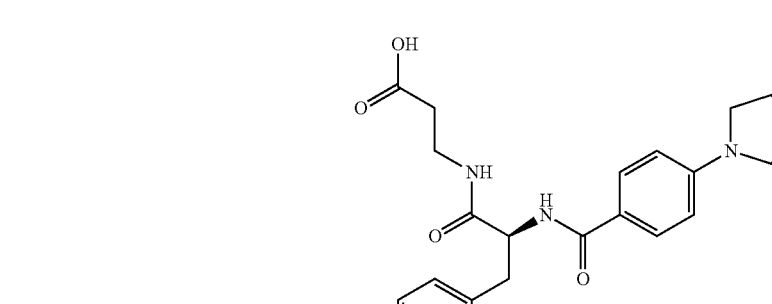 | 869 | 10.11 | 2 |

TABLE 1-continued
| STRUCTURE | COMPOUND NUMBER | LCMS RETENTION TIME (min) | PURITY METHOD |
|---|---|---|---|
| 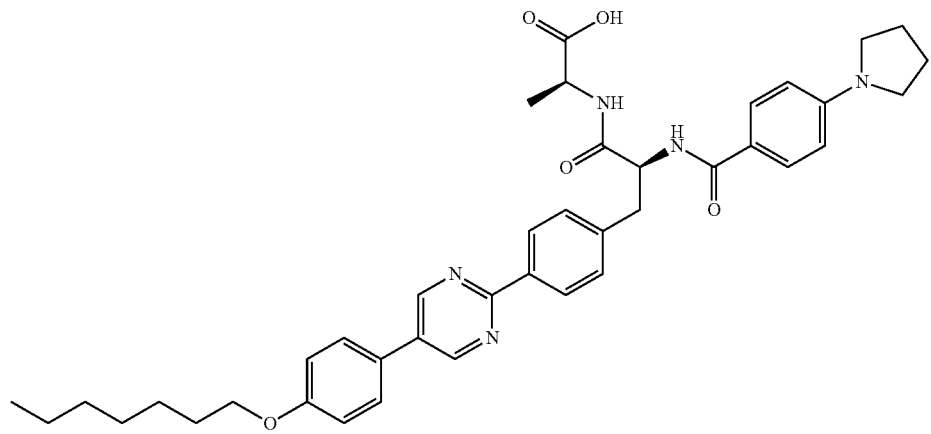 [SMILES: CCCCCCCOc1ccc(-c2cnc(-c3ccc(C[C@H](NC(=O)c4ccc(N5CCCC5)cc4)C(=O)N[C@@H](C)C(=O)O)cc3)nc2)cc1] | 870 | 9.84 | 2 |
| 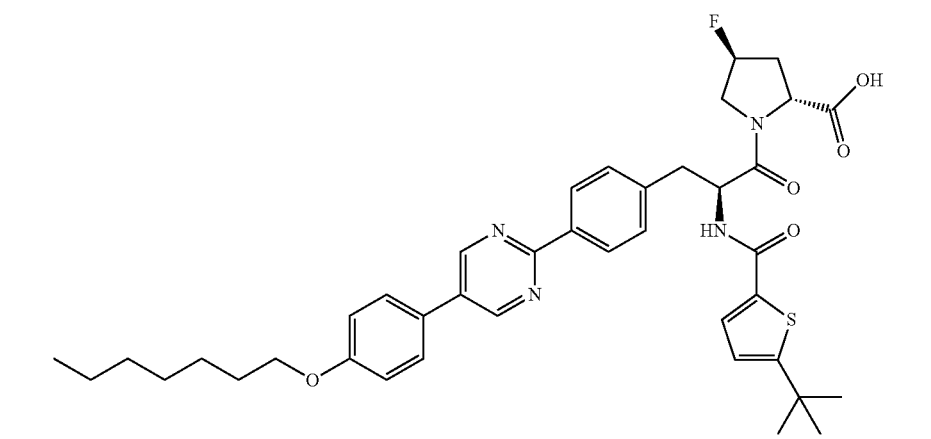 [SMILES: CCCCCCCOc1ccc(-c2cnc(-c3ccc(C[C@H](NC(=O)c4ccc(C(C)(C)C)s4)C(=O)N4C[C@@H](F)C[C@@H]4C(=O)O)cc3)nc2)cc1] | 871 | 9.78 | 14 |
| 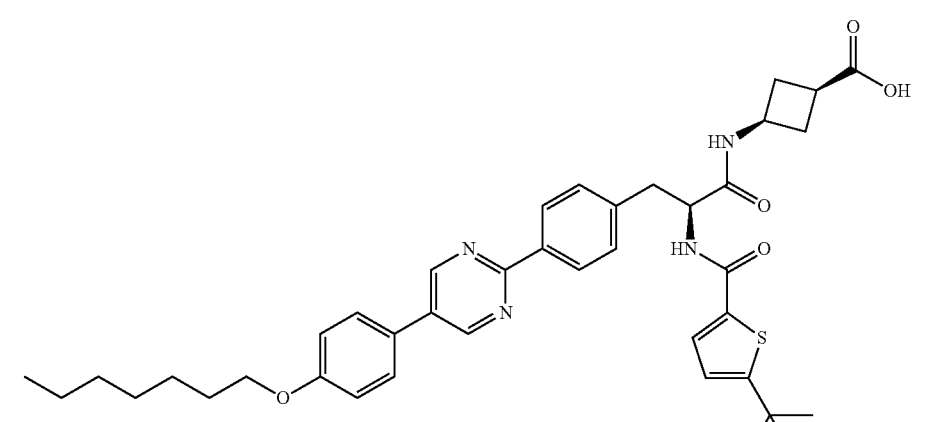 | 872 | 10.13 | 14 |

TABLE 1-continued

| STRUCTURE | COMPOUND NUMBER | LCMS RETENTION TIME (min) | PURITY METHOD |
|---|---|---|---|
| 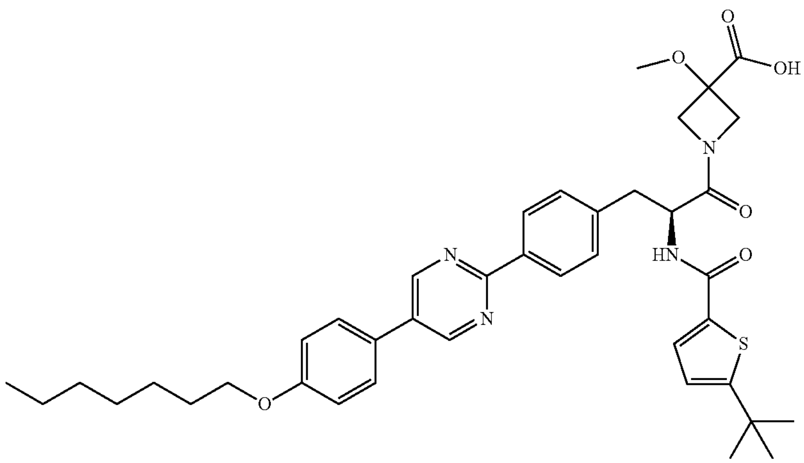 [SMILES: CCCCCCCOc1ccc(-c2cnc(-c3ccc(C[C@H](NC(=O)c4ccc(C(C)(C)C)s4)C(=O)N4CC(OC)(C(=O)O)C4)cc3)nc2)cc1] | 873 | 9.45 | 14 |
| 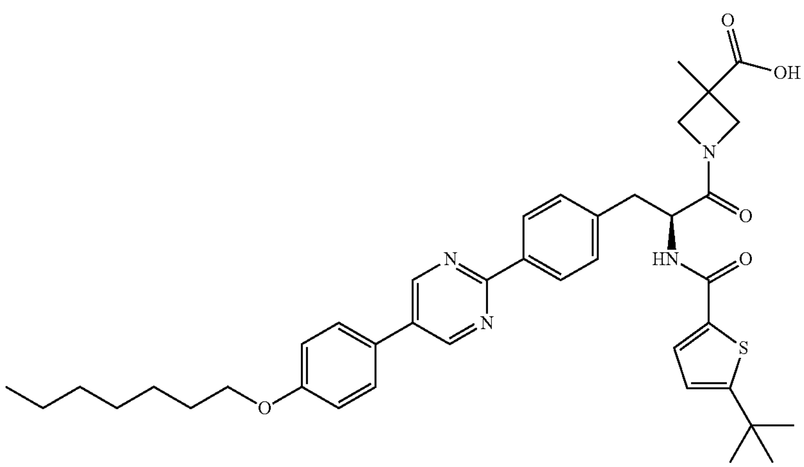 [SMILES: CCCCCCCOc1ccc(-c2cnc(-c3ccc(C[C@H](NC(=O)c4ccc(C(C)(C)C)s4)C(=O)N4CC(C)(C(=O)O)C4)cc3)nc2)cc1] | 874 | 9.48 | 14 |
| 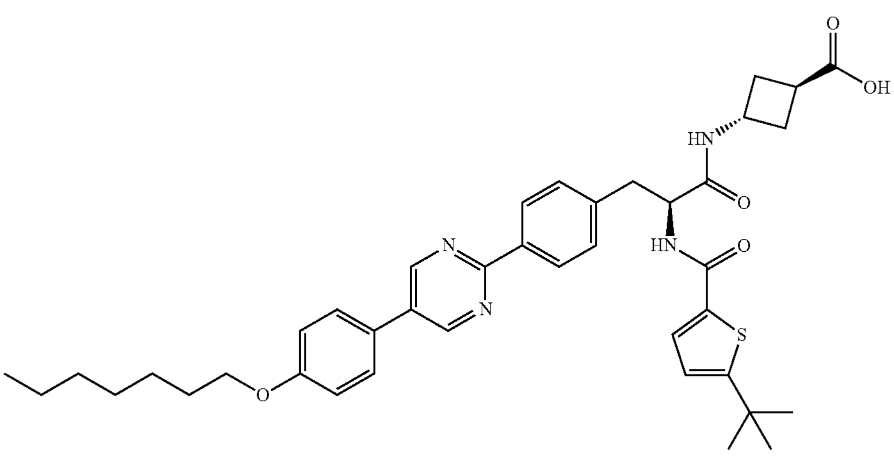 [SMILES: CCCCCCCOc1ccc(-c2cnc(-c3ccc(C[C@H](NC(=O)c4ccc(C(C)(C)C)s4)C(=O)N[C@H]4C[C@H](C(=O)O)C4)cc3)nc2)cc1] | 875 | 10.46 | 14 |

TABLE 1-continued

| STRUCTURE | COMPOUND NUMBER | LCMS RETENTION TIME (min) | PURITY METHOD |
|---|---|---|---|
| (structure) | 876 | 10.13 | 14 |
| (structure) | 877 | 10.59 | 14 |
| (structure) | 878 | 9.55 | 14 |

TABLE 1-continued

| STRUCTURE | COMPOUND NUMBER | LCMS RETENTION TIME (min) | PURITY METHOD |
|---|---|---|---|
| 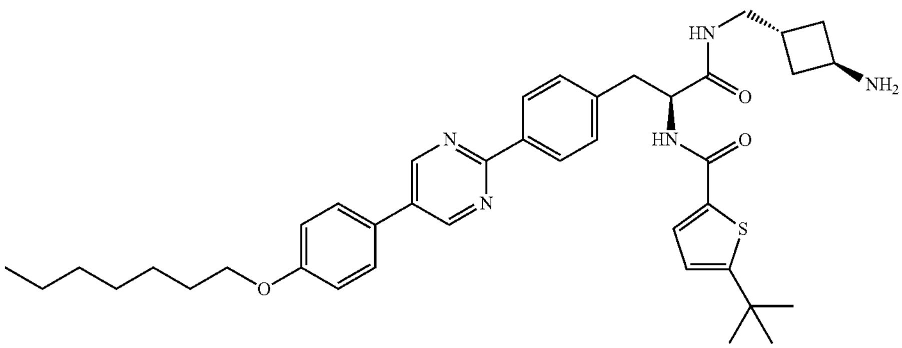 [SMILES: CCCCCCCOc1ccc(-c2cnc(-c3ccc(C[C@H](NC(=O)c4ccc(C(C)(C)C)s4)C(=O)NC[C@H]4C[C@H](N)C4)cc3)nc2)cc1] | 879 | 12.75 | 14 |
| 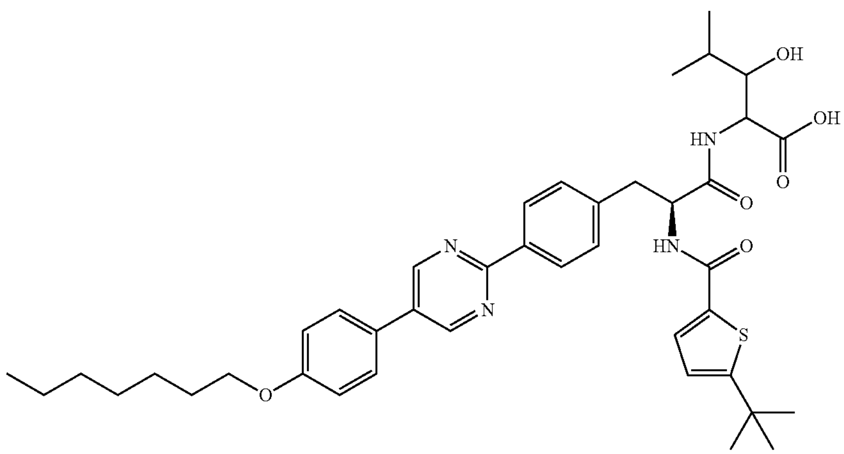 [SMILES: CCCCCCCOc1ccc(-c2cnc(-c3ccc(C[C@H](NC(=O)c4ccc(C(C)(C)C)s4)C(=O)NC(C(=O)O)C(O)C(C)C)cc3)nc2)cc1] | 880 | 10.25 | 14 |
| 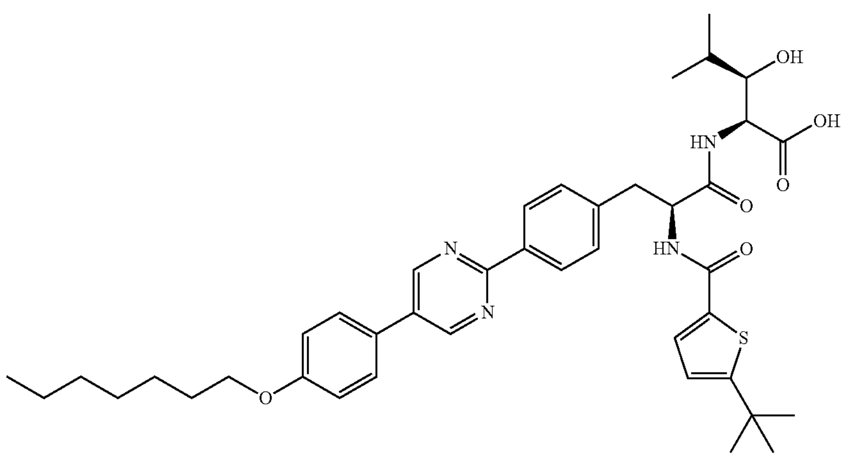 [SMILES: CCCCCCCOc1ccc(-c2cnc(-c3ccc(C[C@H](NC(=O)c4ccc(C(C)(C)C)s4)C(=O)N[C@H](C(=O)O)[C@H](O)C(C)C)cc3)nc2)cc1] | 881 | 10.23 | 14 |

TABLE 1-continued

| STRUCTURE | COMPOUND NUMBER | LCMS RETENTION TIME (min) | PURITY METHOD |
|---|---|---|---|
| 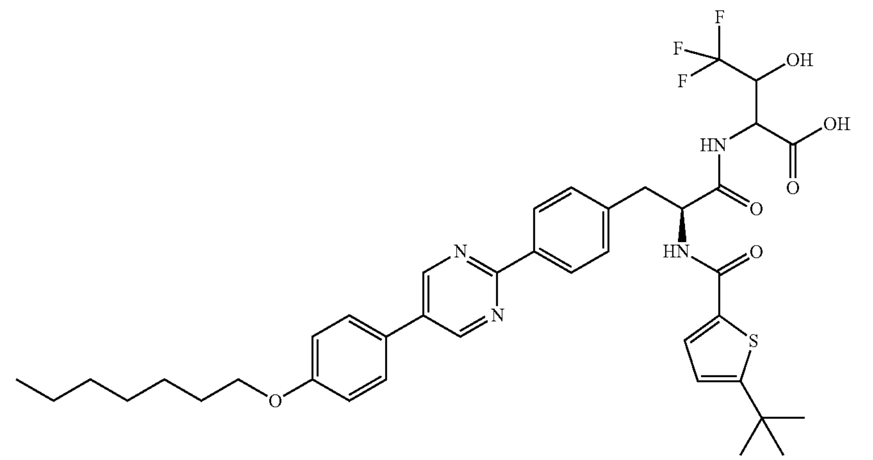 [SMILES: CCCCCCCOc1ccc(-c2cnc(-c3ccc(C[C@H](NC(=O)c4ccc(C(C)(C)C)s4)C(=O)NC(C(=O)O)C(O)C(F)(F)F)cc3)nc2)cc1] | 882 | 10.19 | 14 |
| 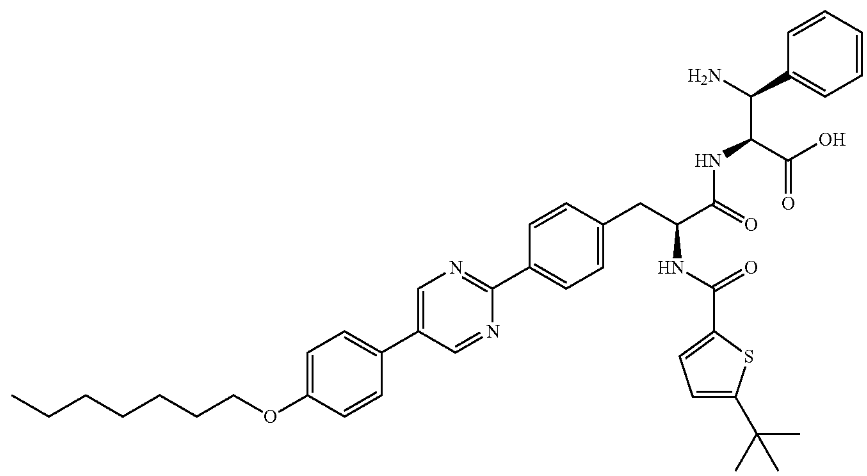 [SMILES: CCCCCCCOc1ccc(-c2cnc(-c3ccc(C[C@H](NC(=O)c4ccc(C(C)(C)C)s4)C(=O)N[C@H](C(=O)O)[C@@H](N)c4ccccc4)cc3)nc2)cc1] | 883 | 10.50 | 14 |
| 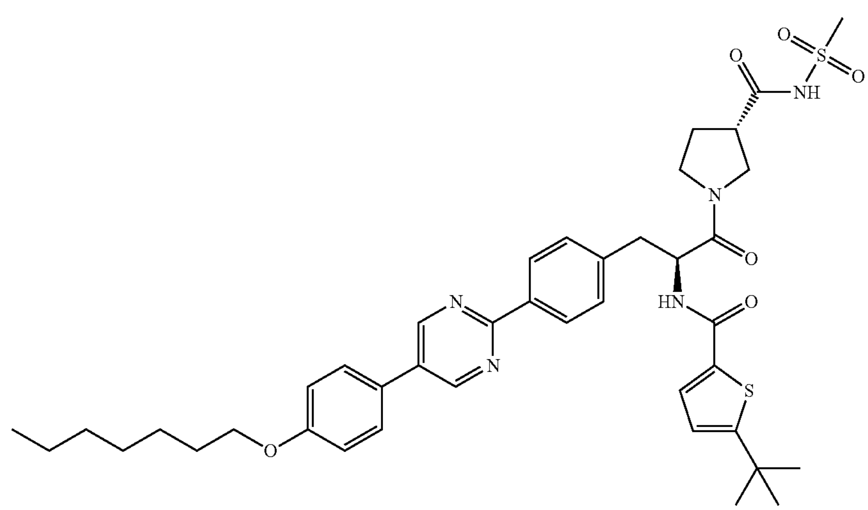 [SMILES: CCCCCCCOc1ccc(-c2cnc(-c3ccc(C[C@H](NC(=O)c4ccc(C(C)(C)C)s4)C(=O)N4CC[C@H](C(=O)NS(C)(=O)=O)C4)cc3)nc2)cc1] | 884 | 10.09 | 14 |

TABLE 1-continued
| STRUCTURE | COMPOUND NUMBER | LCMS RETENTION TIME (min) | PURITY METHOD |
|---|---|---|---|
| 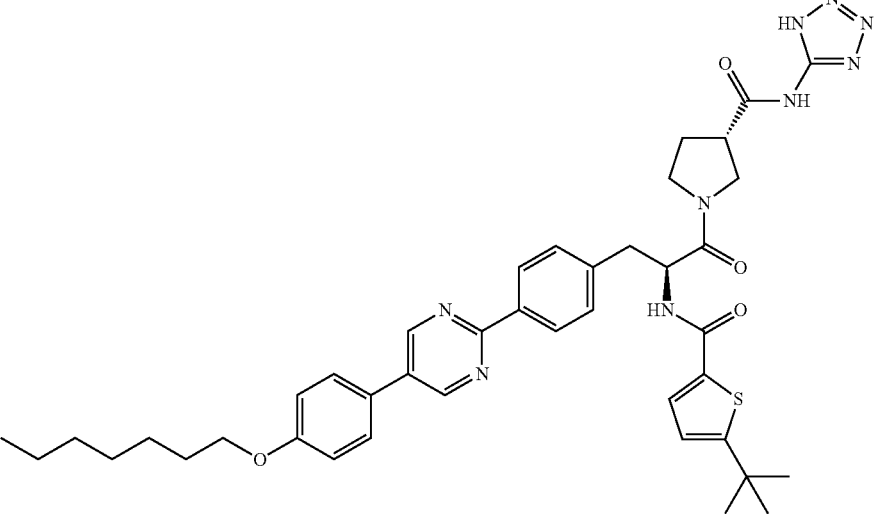 | 885 | 9.79 | 14 |
| 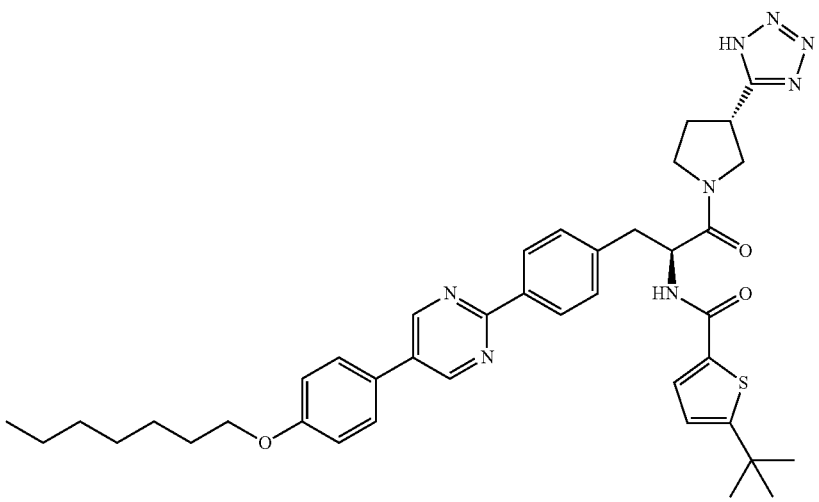 [SMILES: CCCCCCCOc1ccc(-c2cnc(-c3ccc(C[C@H](NC(=O)c4ccc(C(C)(C)C)s4)C(=O)N4CC[C@H](c5nnn[nH]5)C4)cc3)nc2)cc1] | 886 | 9.91 | 14 |

TABLE 1-continued

| STRUCTURE | COMPOUND NUMBER | LCMS RETENTION TIME (min) | PURITY METHOD |
|---|---|---|---|
| 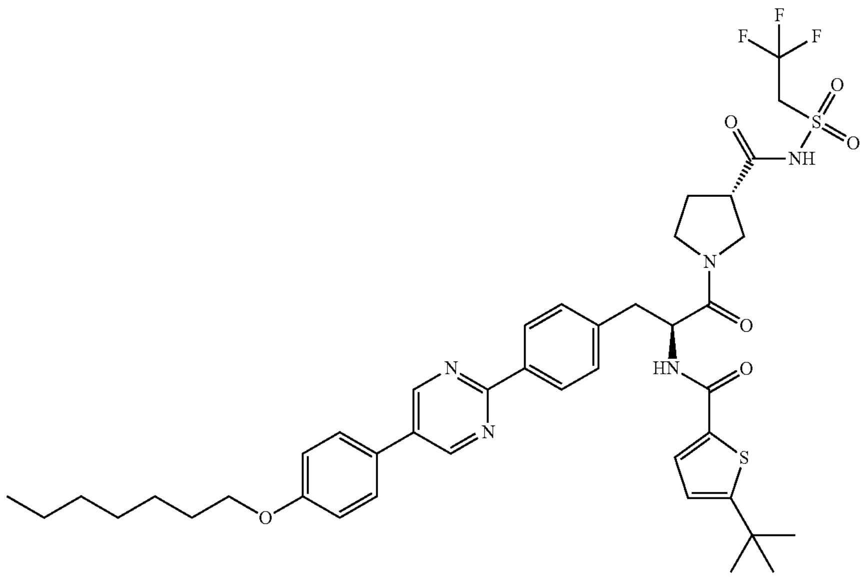 [SMILES: CCCCCCCOc1ccc(-c2cnc(-c3ccc(C[C@H](NC(=O)c4ccc(C(C)(C)C)s4)C(=O)N4CC[C@H](C(=O)NS(=O)(=O)CC(F)(F)F)C4)cc3)nc2)cc1] | 887 | 10.38 | 14 |
| 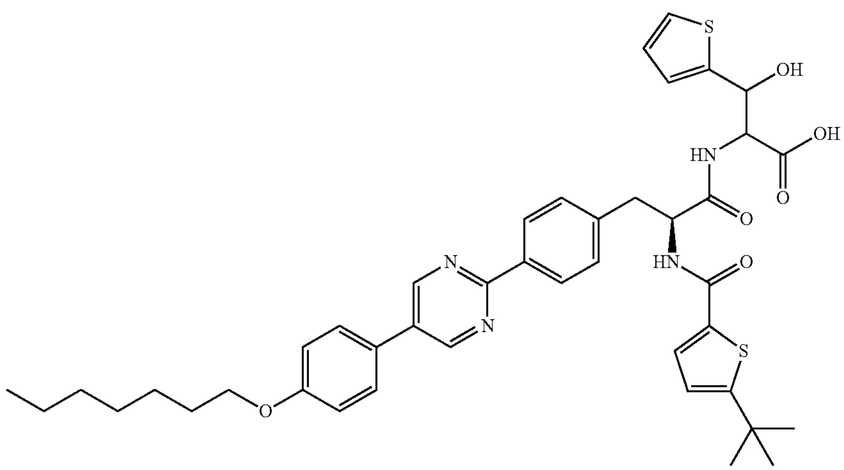 [SMILES: CCCCCCCOc1ccc(-c2cnc(-c3ccc(C[C@H](NC(=O)c4ccc(C(C)(C)C)s4)C(=O)NC(C(=O)O)C(O)c4cccs4)cc3)nc2)cc1] | 888 | 10.29 | 14 |
| 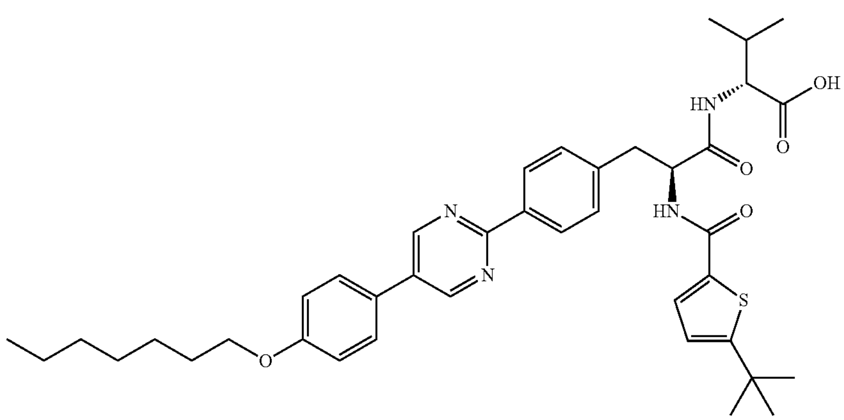 [SMILES: CCCCCCCOc1ccc(-c2cnc(-c3ccc(C[C@H](NC(=O)c4ccc(C(C)(C)C)s4)C(=O)N[C@@H](C(=O)O)C(C)C)cc3)nc2)cc1] | 889 | 10.13 | 14 |

TABLE 1-continued
| STRUCTURE | COMPOUND NUMBER | LCMS RETENTION TIME (min) | PURITY METHOD |
|---|---|---|---|
| 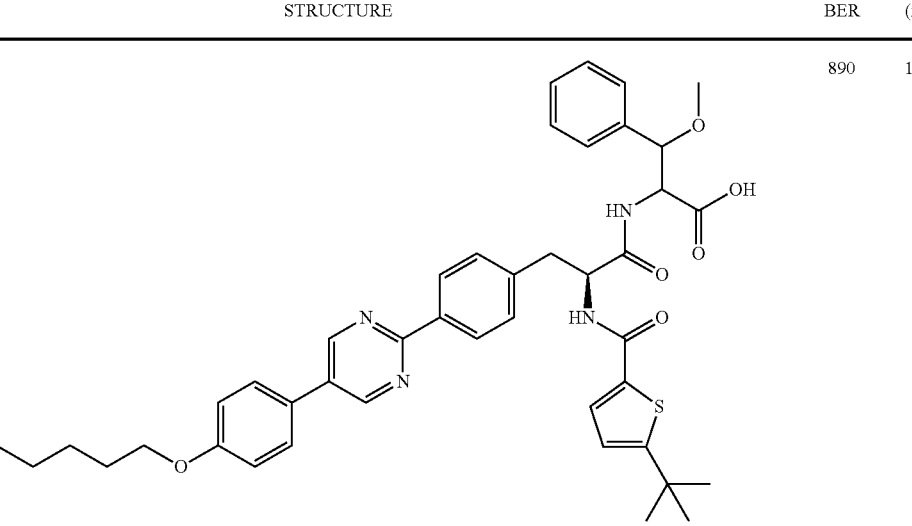 | 890 | 10.30 | 14 |
| 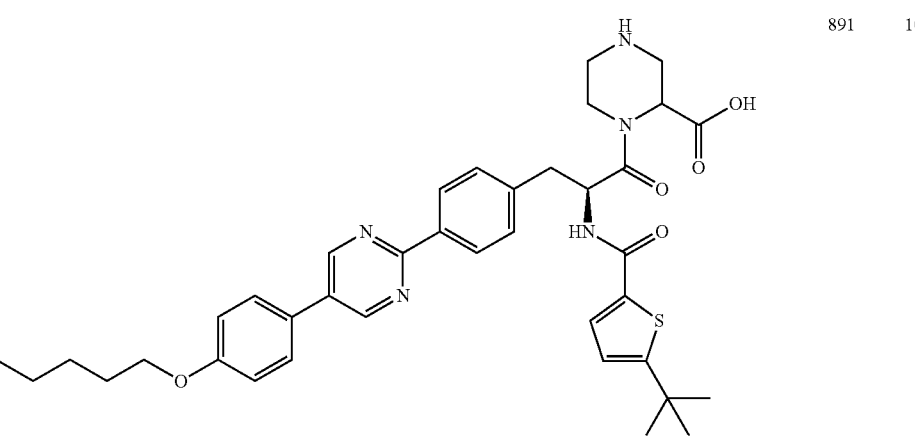 | 891 | 10.13 | 14 |
| 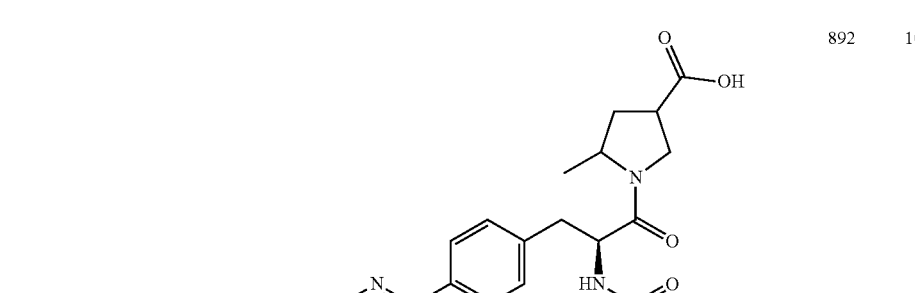 | 892 | 10.33 | 14 |

TABLE 1-continued

| STRUCTURE | COMPOUND NUMBER | LCMS RETENTION TIME (min) | PURITY METHOD |
|---|---|---|---|
| 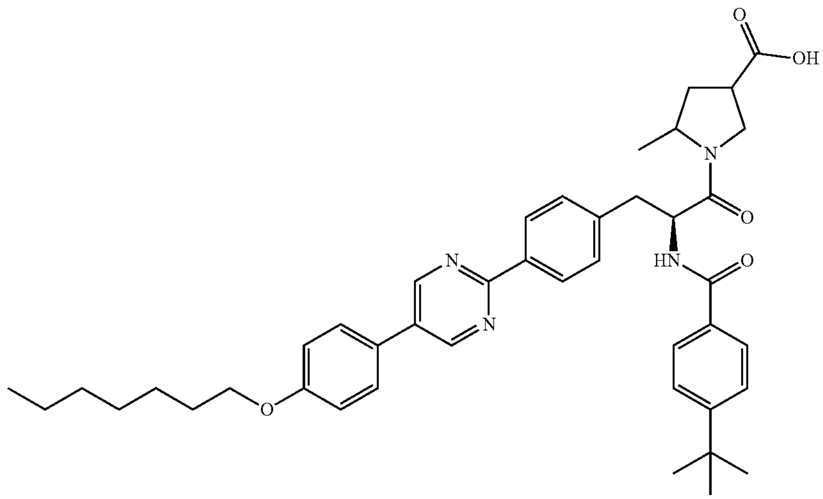 [SMILES: CCCCCCCOc1ccc(-c2cnc(-c3ccc(C[C@H](NC(=O)c4ccc(C(C)(C)C)cc4)C(=O)N4CC(C(=O)O)CC4C)cc3)nc2)cc1] | 893 | 10.38 | 14 |
| 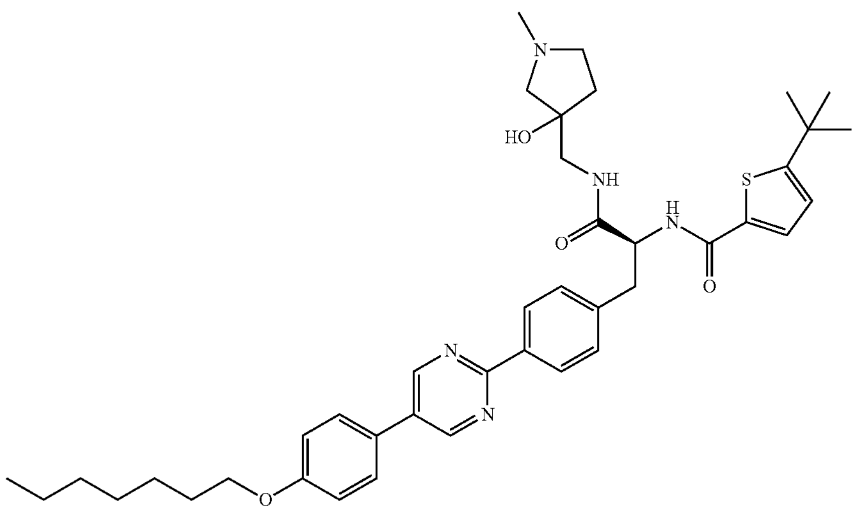 [SMILES: CCCCCCCOc1ccc(-c2cnc(-c3ccc(C[C@H](NC(=O)c4ccc(C(C)(C)C)s4)C(=O)NCC4(O)CCN(C)C4)cc3)nc2)cc1] | 894 | 10.49 | 14 |
| 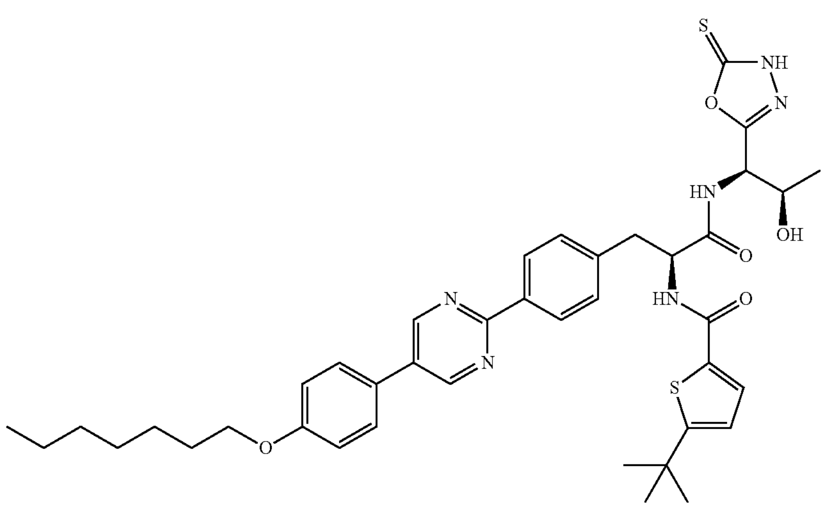 [SMILES: CCCCCCCOc1ccc(-c2cnc(-c3ccc(C[C@H](NC(=O)c4ccc(C(C)(C)C)s4)C(=O)N[C@@H](c4n[nH]c(=S)o4)[C@@H](C)O)cc3)nc2)cc1] | 895 | 10.28 | 11 |

TABLE 1-continued

| STRUCTURE | COMPOUND NUMBER | LCMS RETENTION TIME (min) | PURITY METHOD |
|---|---|---|---|
| 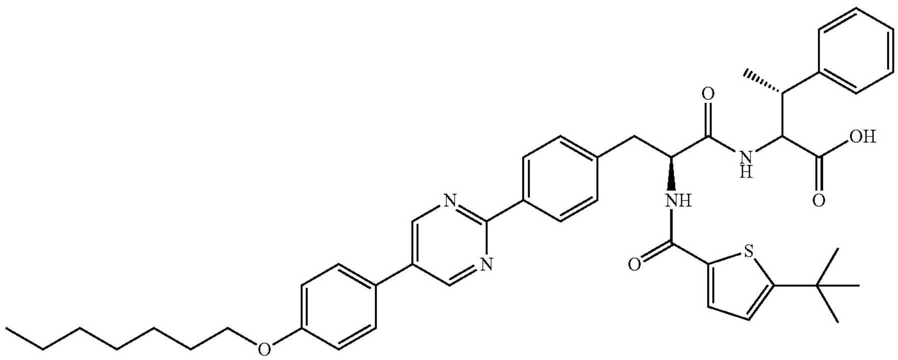 | 896 | 11.10 | 11 |
| 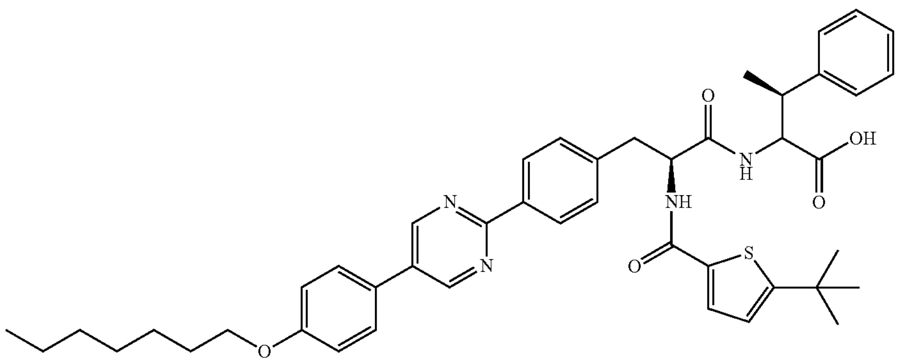 [SMILES: CCCCCCCOc1ccc(-c2cnc(-c3ccc(C[C@H](NC(=O)c4ccc(C(C)(C)C)s4)C(=O)NC(C(=O)O)[C@@H](C)c4ccccc4)cc3)nc2)cc1] | 897 | 11.09 | 11 |
| 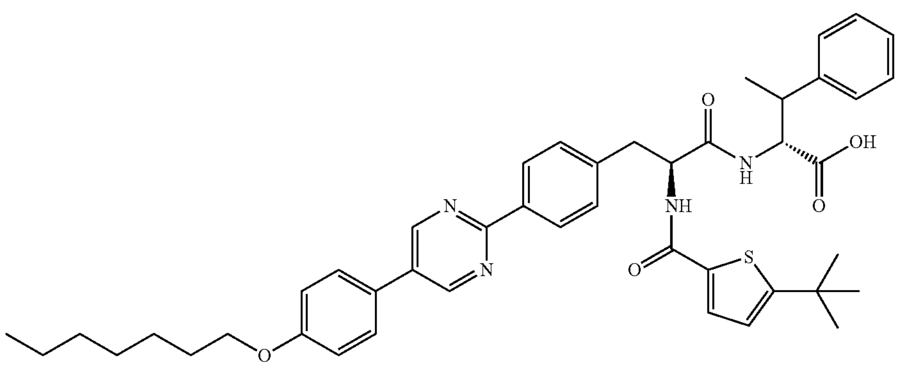 [SMILES: CCCCCCCOc1ccc(-c2cnc(-c3ccc(C[C@H](NC(=O)c4ccc(C(C)(C)C)s4)C(=O)N[C@@H](C(=O)O)C(C)c4ccccc4)cc3)nc2)cc1] | 898 | 11.19 | 11 |
| 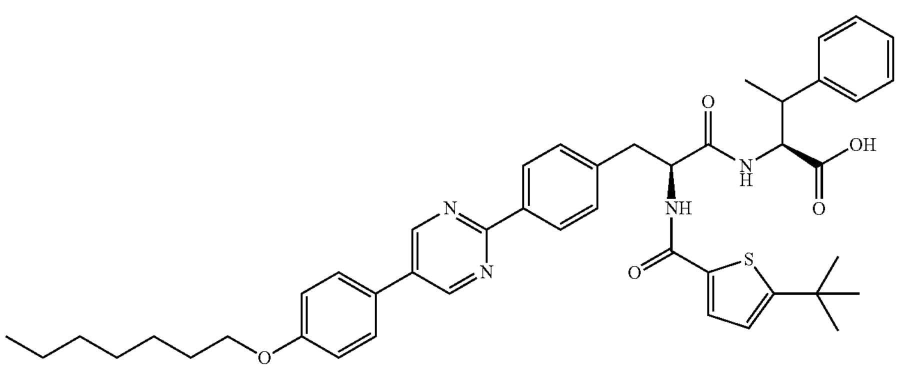 [SMILES: CCCCCCCOc1ccc(-c2cnc(-c3ccc(C[C@H](NC(=O)c4ccc(C(C)(C)C)s4)C(=O)N[C@H](C(=O)O)C(C)c4ccccc4)cc3)nc2)cc1] | 899 | 11.16 | 11 |

TABLE 1-continued
| STRUCTURE | COMPOUND NUMBER | LCMS RETENTION TIME (min) | PURITY METHOD |
|---|---|---|---|
| 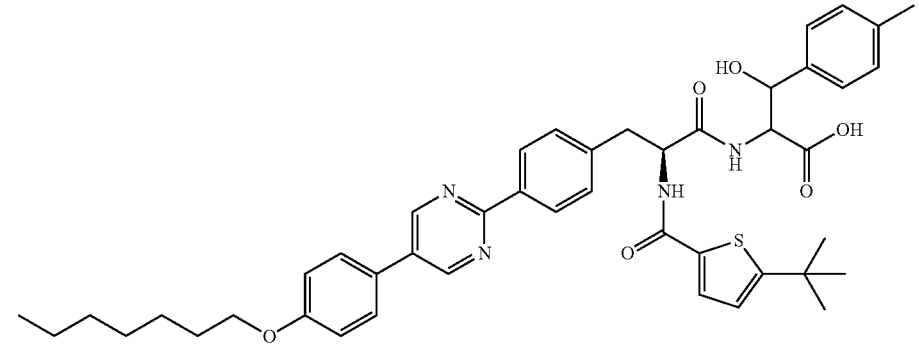 [SMILES: CCCCCCCOc1ccc(-c2cnc(-c3ccc(C[C@H](NC(=O)c4ccc(C(C)(C)C)s4)C(=O)NC(C(=O)O)C(O)c4ccc(C)cc4)cc3)nc2)cc1] | 900 | 10.75 | 11 |
| 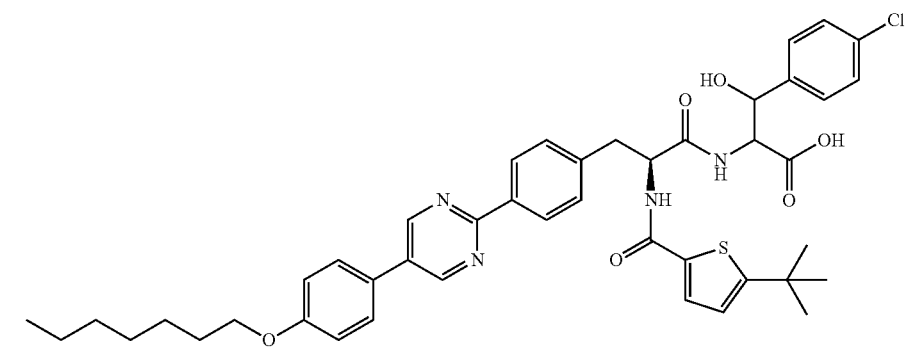 [SMILES: CCCCCCCOc1ccc(-c2cnc(-c3ccc(C[C@H](NC(=O)c4ccc(C(C)(C)C)s4)C(=O)NC(C(=O)O)C(O)c4ccc(Cl)cc4)cc3)nc2)cc1] | 901 | 10.90 | 11 |
| 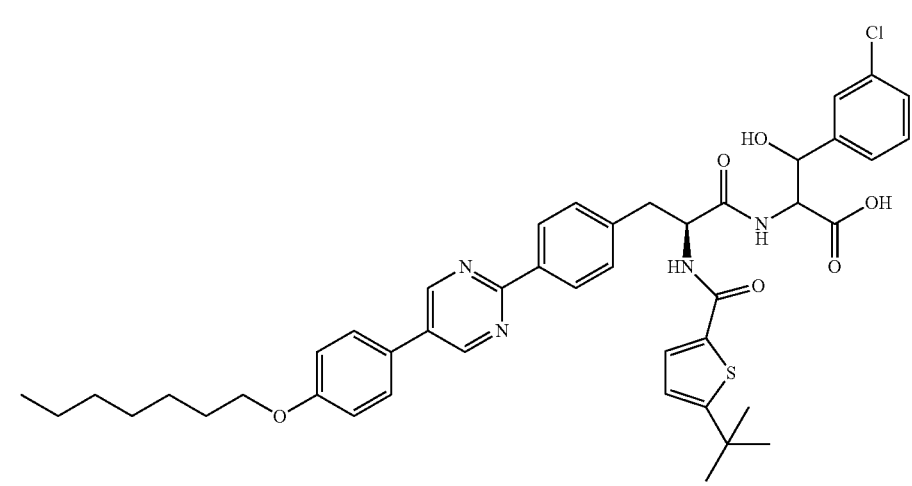 [SMILES: CCCCCCCOc1ccc(-c2cnc(-c3ccc(C[C@H](NC(=O)c4ccc(C(C)(C)C)s4)C(=O)NC(C(=O)O)C(O)c4cccc(Cl)c4)cc3)nc2)cc1] | 902 | 10.96 | 11 |

TABLE 1-continued

| STRUCTURE | COMPOUND NUMBER | LCMS RETENTION TIME (min) | PURITY METHOD |
|---|---|---|---|
| 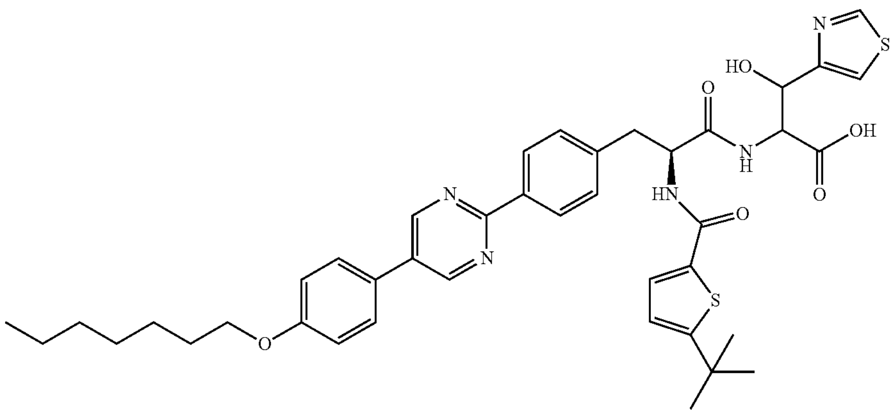 [SMILES: CCCCCCCOc1ccc(-c2cnc(-c3ccc(C[C@H](NC(=O)c4ccc(C(C)(C)C)s4)C(=O)NC(C(=O)O)C(O)c4cscn4)cc3)nc2)cc1] | 903 | 10.02 | 11 |
| 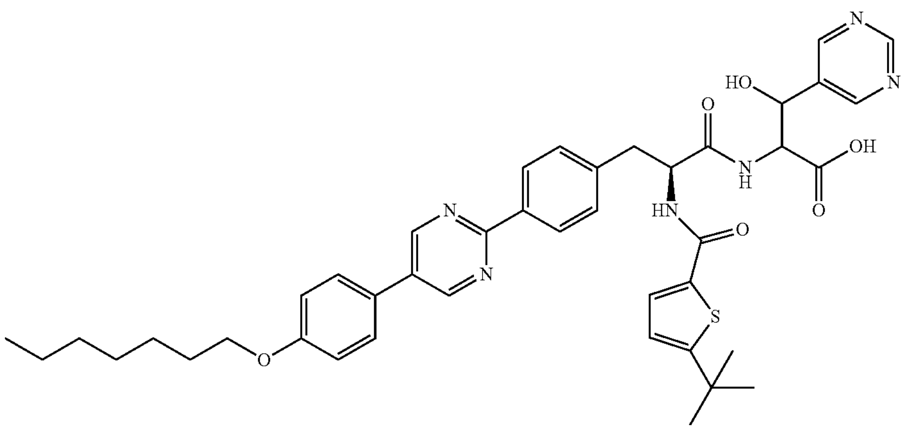 [SMILES: CCCCCCCOc1ccc(-c2cnc(-c3ccc(C[C@H](NC(=O)c4ccc(C(C)(C)C)s4)C(=O)NC(C(=O)O)C(O)c4cncnc4)cc3)nc2)cc1] | 904 | 9.62 | 11 |
| 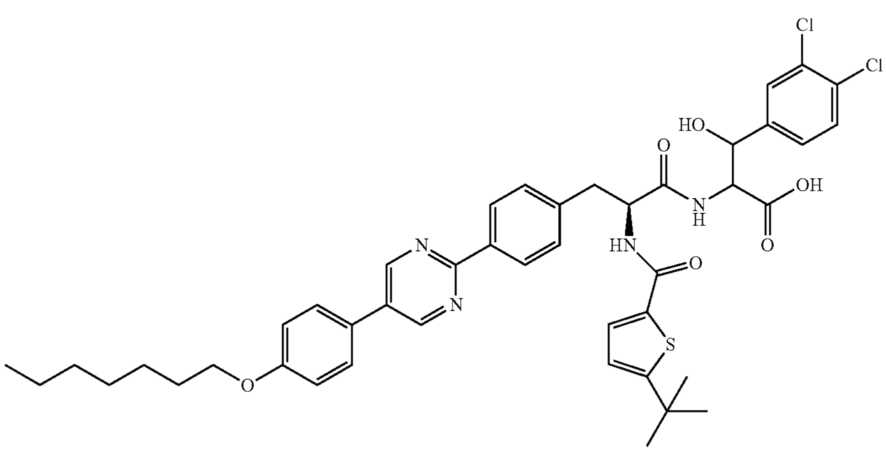 [SMILES: CCCCCCCOc1ccc(-c2cnc(-c3ccc(C[C@H](NC(=O)c4ccc(C(C)(C)C)s4)C(=O)NC(C(=O)O)C(O)c4ccc(Cl)c(Cl)c4)cc3)nc2)cc1] | 905 | 11.30 | 11 |

TABLE 1-continued

| STRUCTURE | COMPOUND NUMBER | LCMS RETENTION TIME (min) | PURITY METHOD |
|---|---|---|---|
| 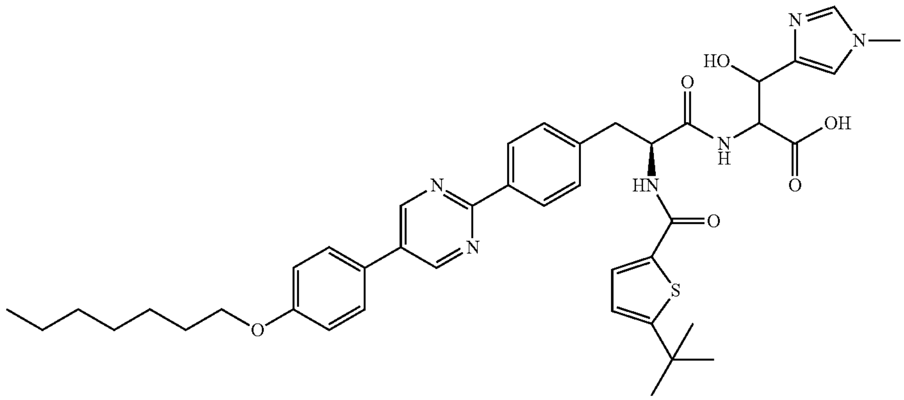 [SMILES: CCCCCCCOc1ccc(-c2cnc(-c3ccc(C[C@H](NC(=O)c4ccc(C(C)(C)C)s4)C(=O)NC(C(=O)O)C(O)c4cn(C)cn4)cc3)nc2)cc1] | 906 | 7.72 | 11 |
| 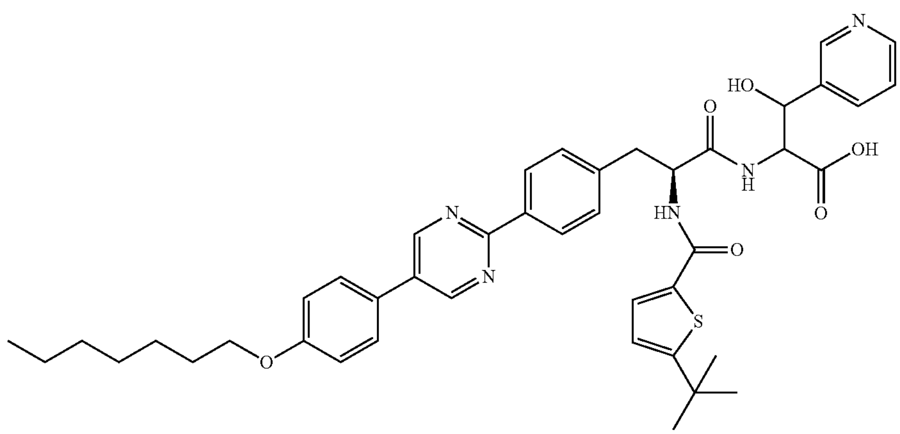 [SMILES: CCCCCCCOc1ccc(-c2cnc(-c3ccc(C[C@H](NC(=O)c4ccc(C(C)(C)C)s4)C(=O)NC(C(=O)O)C(O)c4cccnc4)cc3)nc2)cc1] | 907 | 8.30 | 11 |
| 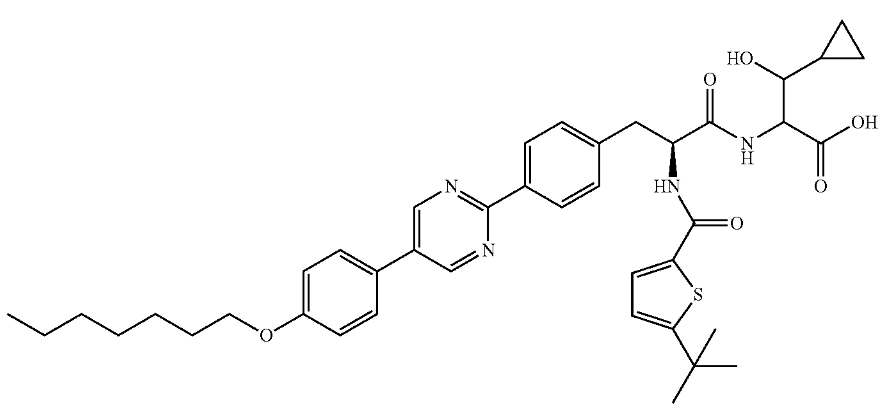 [SMILES: CCCCCCCOc1ccc(-c2cnc(-c3ccc(C[C@H](NC(=O)c4ccc(C(C)(C)C)s4)C(=O)NC(C(=O)O)C(O)C4CC4)cc3)nc2)cc1] | 908 | 10.21 | 11 |

TABLE 1-continued

| STRUCTURE | COMPOUND NUMBER | LCMS RETENTION TIME (min) | PURITY METHOD |
|---|---|---|---|
| 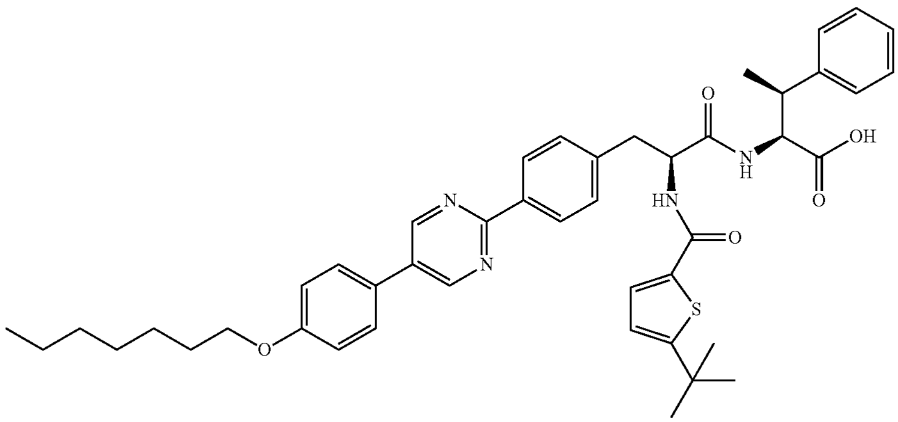 [SMILES: CCCCCCCOc1ccc(-c2cnc(-c3ccc(C[C@H](NC(=O)c4ccc(C(C)(C)C)s4)C(=O)N[C@H](C(=O)O)[C@@H](C)c4ccccc4)cc3)nc2)cc1] | 909 | 11.18 | 11 |
| 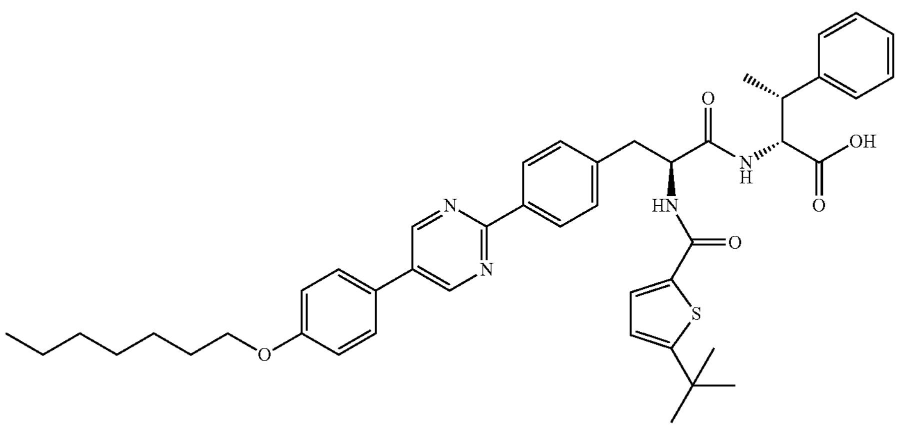 [SMILES: CCCCCCCOc1ccc(-c2cnc(-c3ccc(C[C@H](NC(=O)c4ccc(C(C)(C)C)s4)C(=O)N[C@@H](C(=O)O)[C@H](C)c4ccccc4)cc3)nc2)cc1] | 910 | 11.33 | 11 |
| 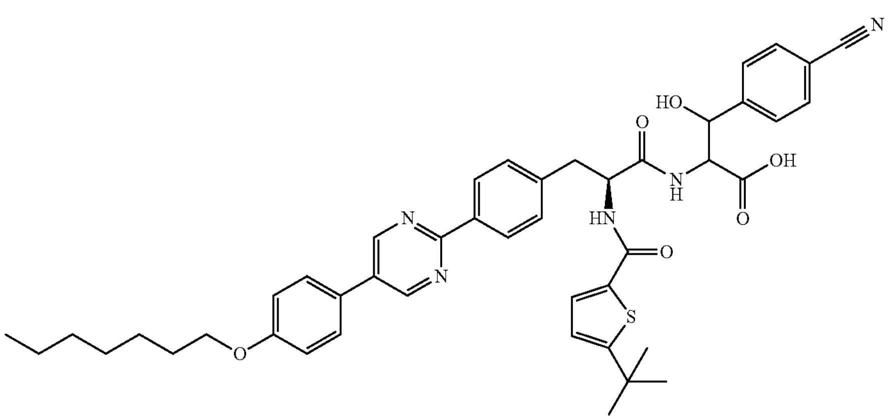 [SMILES: CCCCCCCOc1ccc(-c2cnc(-c3ccc(C[C@H](NC(=O)c4ccc(C(C)(C)C)s4)C(=O)NC(C(=O)O)C(O)c4ccc(C#N)cc4)cc3)nc2)cc1] | 911 | 9.90 | 11 |

TABLE 1-continued

| STRUCTURE | COMPOUND NUMBER | LCMS RETENTION TIME (min) | PURITY METHOD |
|---|---|---|---|
| 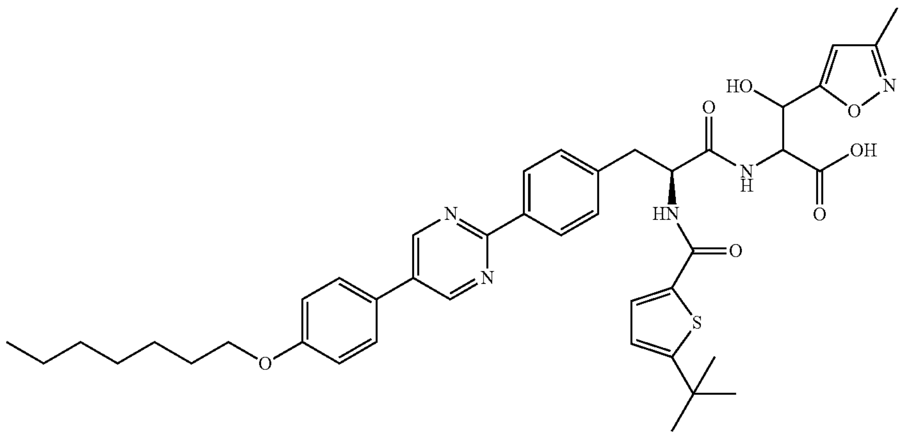 [SMILES: CCCCCCCOc1ccc(-c2cnc(-c3ccc(C[C@H](NC(=O)c4ccc(C(C)(C)C)s4)C(=O)NC(C(=O)O)C(O)c4cc(C)no4)cc3)nc2)cc1] | 912 | 10.08 | 11 |
| 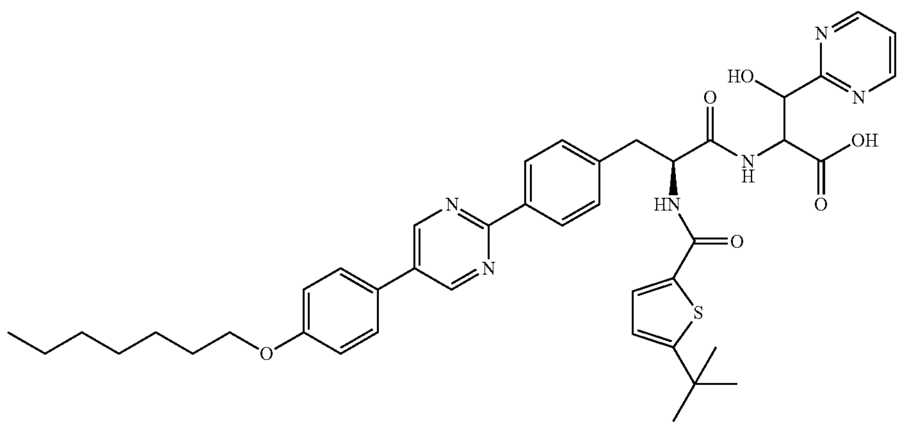 [SMILES: CCCCCCCOc1ccc(-c2cnc(-c3ccc(C[C@H](NC(=O)c4ccc(C(C)(C)C)s4)C(=O)NC(C(=O)O)C(O)c4ncccn4)cc3)nc2)cc1] | 913 | 9.80 | 11 |
| 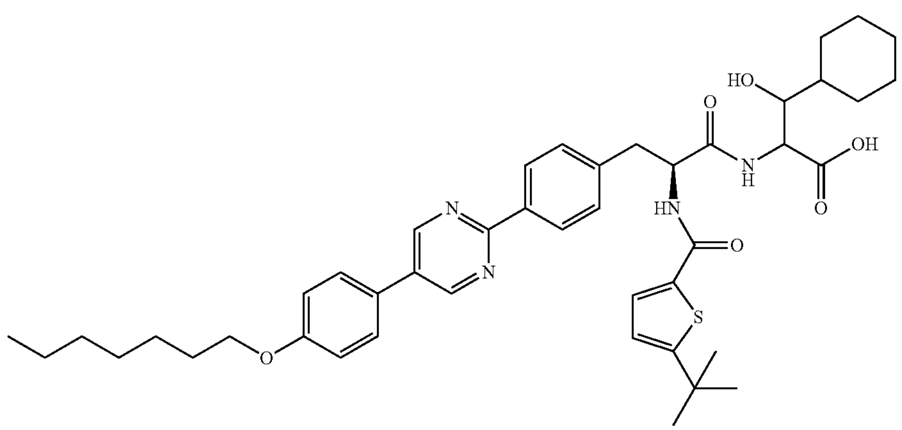 [SMILES: CCCCCCCOc1ccc(-c2cnc(-c3ccc(C[C@H](NC(=O)c4ccc(C(C)(C)C)s4)C(=O)NC(C(=O)O)C(O)C4CCCCC4)cc3)nc2)cc1] | 914 | 11.02 | 11 |

TABLE 1-continued
| STRUCTURE | COMPOUND NUMBER | LCMS RETENTION TIME (min) | PURITY METHOD |
|---|---|---|---|
| 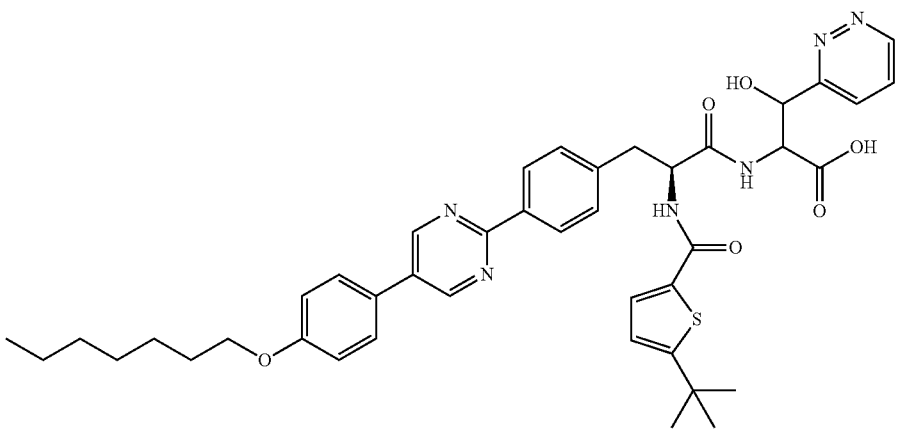 [SMILES: CCCCCCCOc1ccc(-c2cnc(-c3ccc(C[C@H](NC(=O)c4ccc(C(C)(C)C)s4)C(=O)NC(C(=O)O)C(O)c4cccnn4)cc3)nc2)cc1] | 915 | 9.51 | 11 |
| 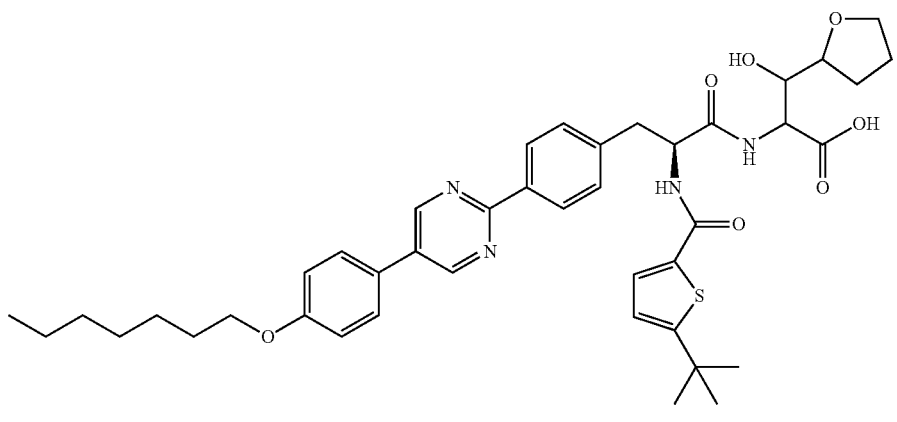 [SMILES: CCCCCCCOc1ccc(-c2cnc(-c3ccc(C[C@H](NC(=O)c4ccc(C(C)(C)C)s4)C(=O)NC(C(=O)O)C(O)C4CCCO4)cc3)nc2)cc1] | 916 | 10.14 | 11 |
| 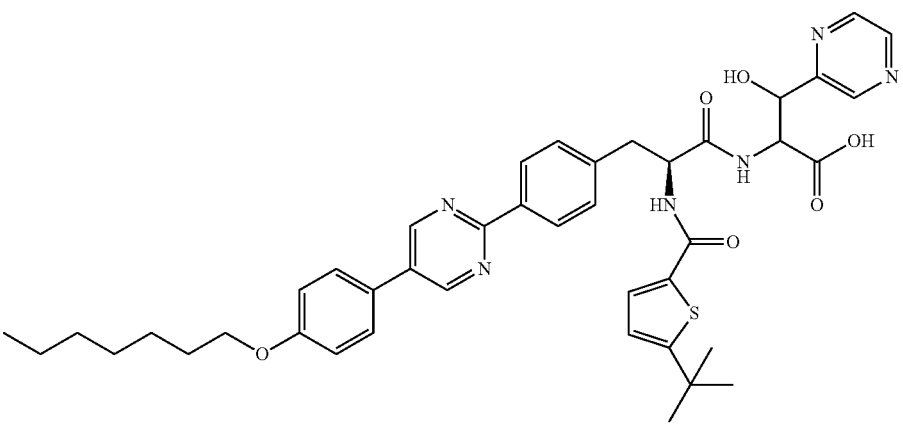 [SMILES: CCCCCCCOc1ccc(-c2cnc(-c3ccc(C[C@H](NC(=O)c4ccc(C(C)(C)C)s4)C(=O)NC(C(=O)O)C(O)c4cnccn4)cc3)nc2)cc1] | 917 | 9.70 | 11 |

TABLE 1-continued

| STRUCTURE | COMPOUND NUMBER | LCMS RETENTION TIME (min) | PURITY METHOD |
|---|---|---|---|
| 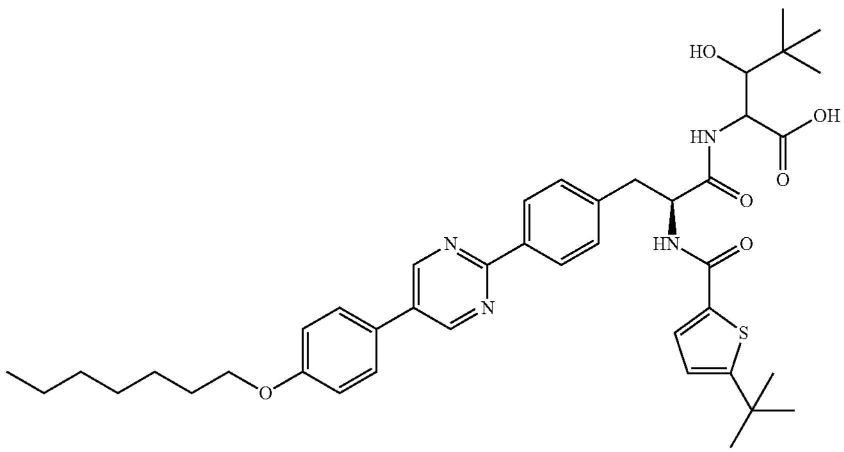 [SMILES: CCCCCCCOc1ccc(-c2cnc(-c3ccc(C[C@H](NC(=O)c4ccc(C(C)(C)C)s4)C(=O)NC(C(=O)O)C(O)C(C)(C)C)cc3)nc2)cc1] | 918 | 10.68 | 11 |
| 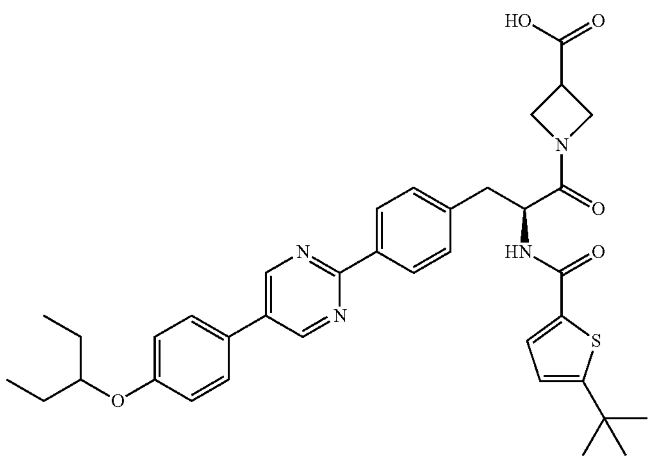 [SMILES: CCC(CC)Oc1ccc(-c2cnc(-c3ccc(C[C@H](NC(=O)c4ccc(C(C)(C)C)s4)C(=O)N4CC(C(=O)O)C4)cc3)nc2)cc1] | 919 | 8.49 | 14 |
| 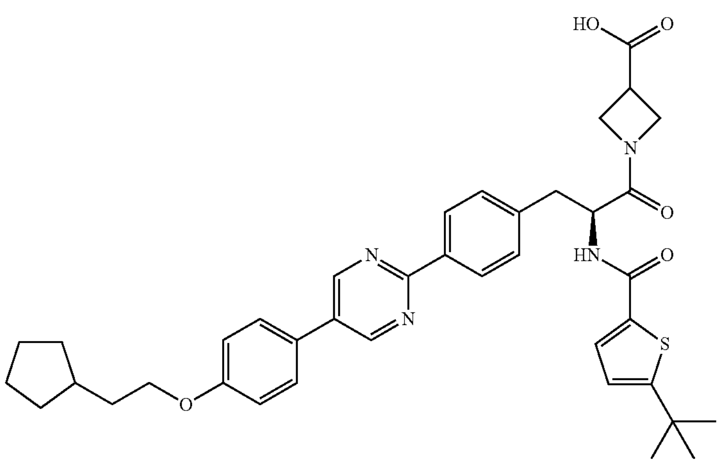 [SMILES: CC(C)(C)c1ccc(C(=O)N[C@@H](Cc2ccc(-c3ncc(-c4ccc(OCCC5CCCC5)cc4)cn3)cc2)C(=O)N2CC(C(=O)O)C2)s1] | 920 | 9.31 | 14 |

TABLE 1-continued

| STRUCTURE | COMPOUND NUMBER | LCMS RETENTION TIME (min) | PURITY METHOD |
|---|---|---|---|
| 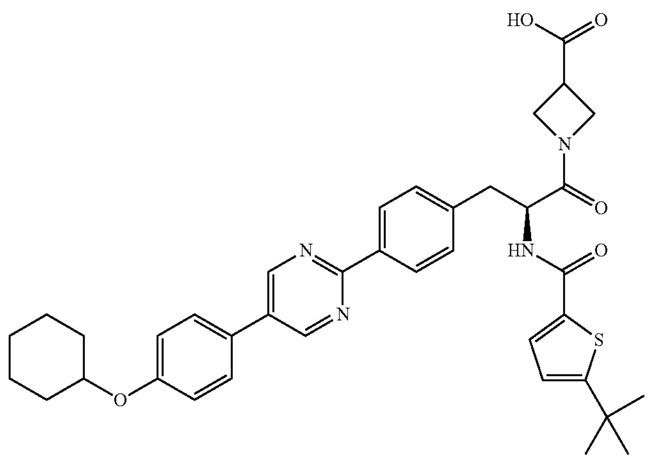 [SMILES: CC(C)(C)c1ccc(C(=O)N[C@@H](Cc2ccc(-c3ncc(-c4ccc(OC5CCCCC5)cc4)cn3)cc2)C(=O)N2CC(C(=O)O)C2)s1] | 921 | 8.63 | 14 |
| 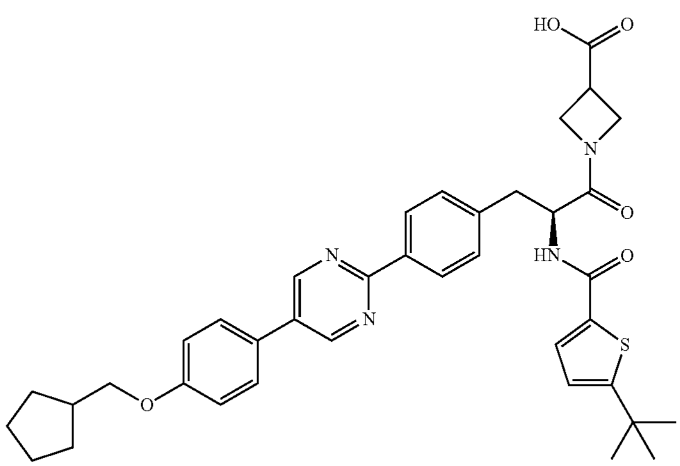 [SMILES: CC(C)(C)c1ccc(C(=O)N[C@@H](Cc2ccc(-c3ncc(-c4ccc(OCC5CCCC5)cc4)cn3)cc2)C(=O)N2CC(C(=O)O)C2)s1] | 922 | 8.80 | 14 |
| 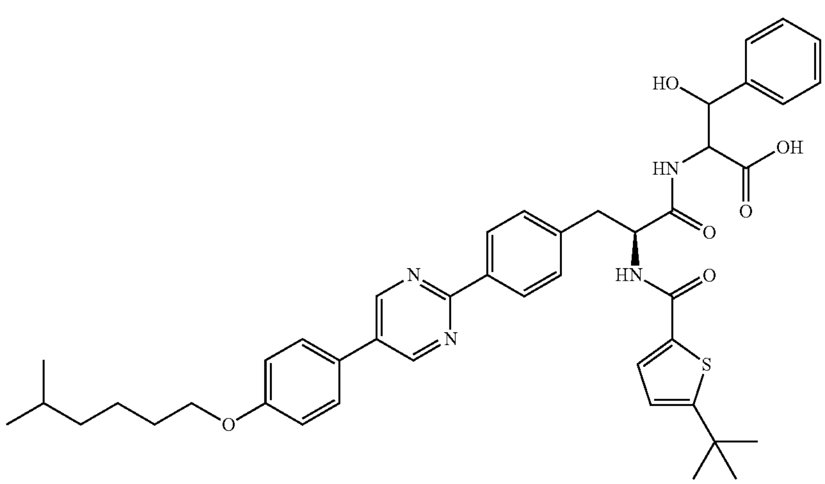 [SMILES: CC(C)CCCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 923 | 9.75 | 14 |

TABLE 1-continued

| STRUCTURE | COMPOUND NUMBER | LCMS RETENTION TIME (min) | PURITY METHOD |
|---|---|---|---|
| 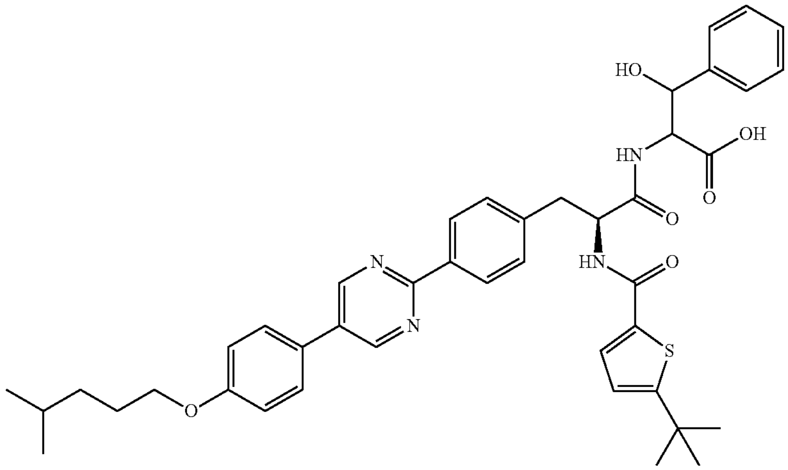 | 924 | 9.52 | 14 |
| 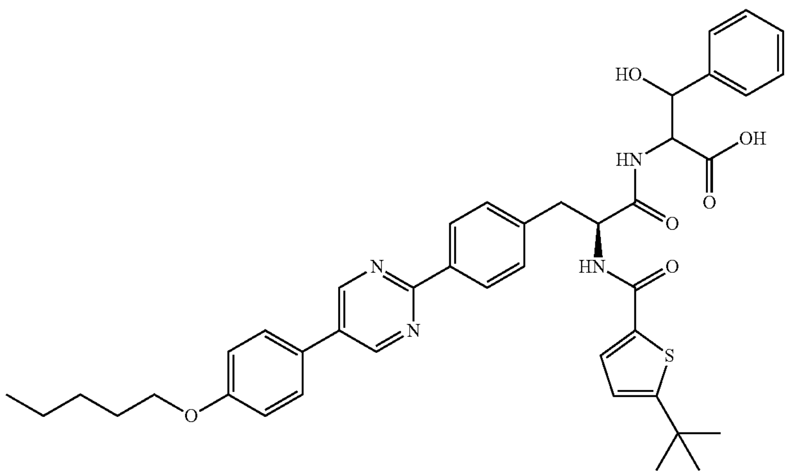 [SMILES: CCCCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 925 | 8.86 | 14 |
| 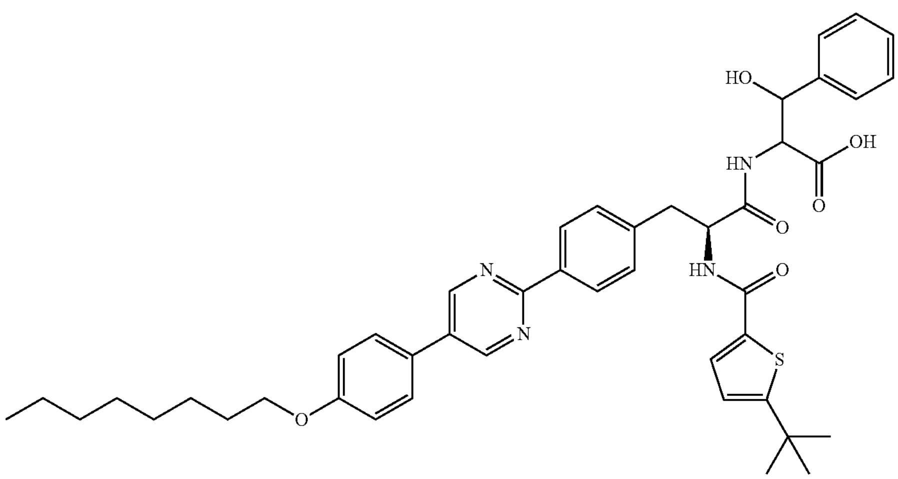 [SMILES: CCCCCCCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 926 | 10.49 | 14 |

TABLE 1-continued

| STRUCTURE | COMPOUND NUMBER | LCMS RETENTION TIME (min) | PURITY METHOD |
|---|---|---|---|
| 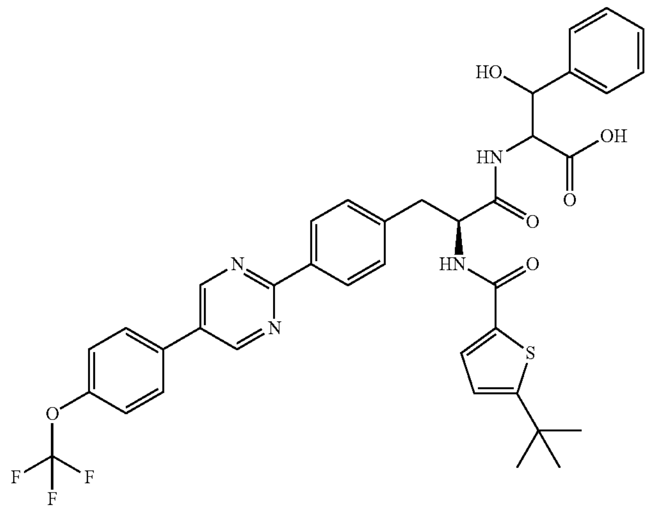 [SMILES: CC(C)(C)c1ccc(C(=O)N[C@@H](Cc2ccc(-c3ncc(-c4ccc(OC(F)(F)F)cc4)cn3)cc2)C(=O)NC(C(=O)O)C(O)c2ccccc2)s1] | 927 | 8.11 | 14 |
| 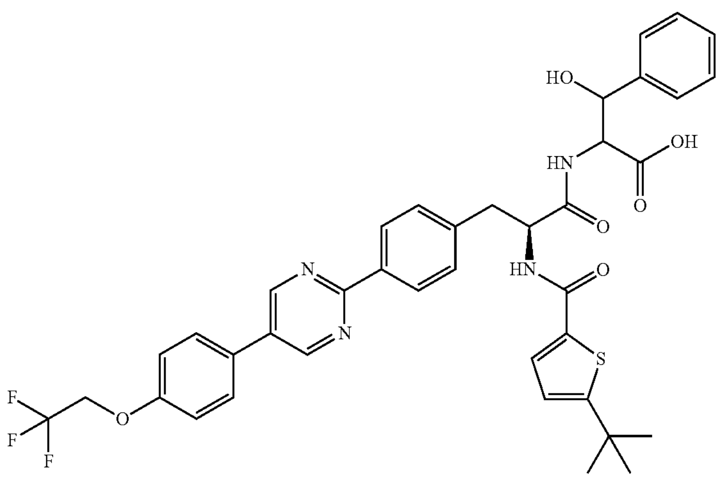 [SMILES: CC(C)(C)c1ccc(C(=O)N[C@@H](Cc2ccc(-c3ncc(-c4ccc(OCC(F)(F)F)cc4)cn3)cc2)C(=O)NC(C(=O)O)C(O)c2ccccc2)s1] | 928 | 7.81 | 14 |
| 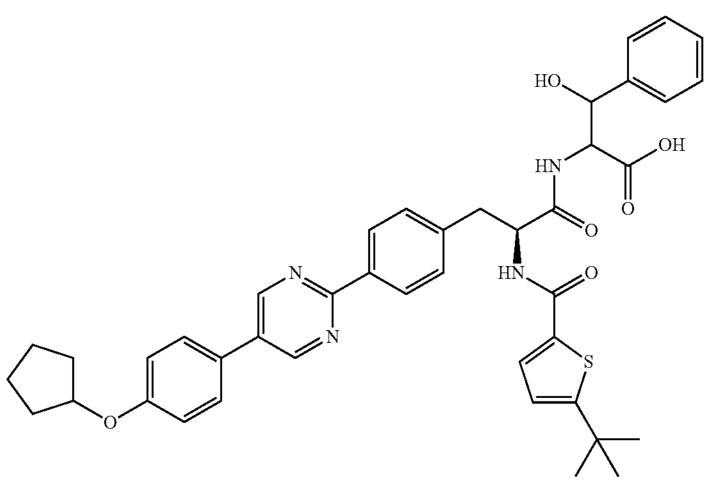 [SMILES: CC(C)(C)c1ccc(C(=O)N[C@@H](Cc2ccc(-c3ncc(-c4ccc(OC5CCCC5)cc4)cn3)cc2)C(=O)NC(C(=O)O)C(O)c2ccccc2)s1] | 929 | 8.77 | 14 |

TABLE 1-continued

| STRUCTURE | COMPOUND NUMBER | LCMS RETENTION TIME (min) | PURITY METHOD |
|---|---|---|---|
| 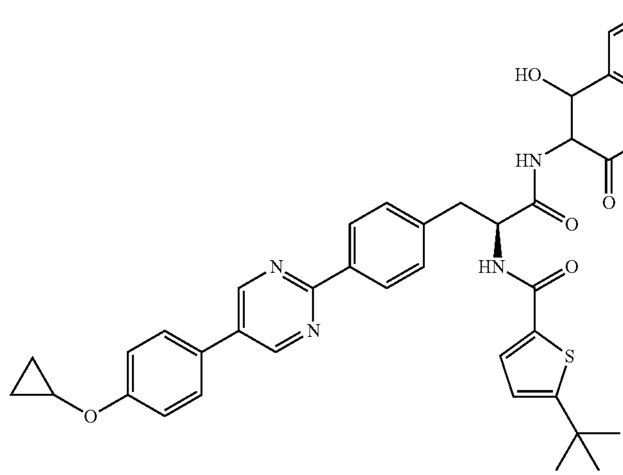 | 930 | 7.80 | 14 |
| 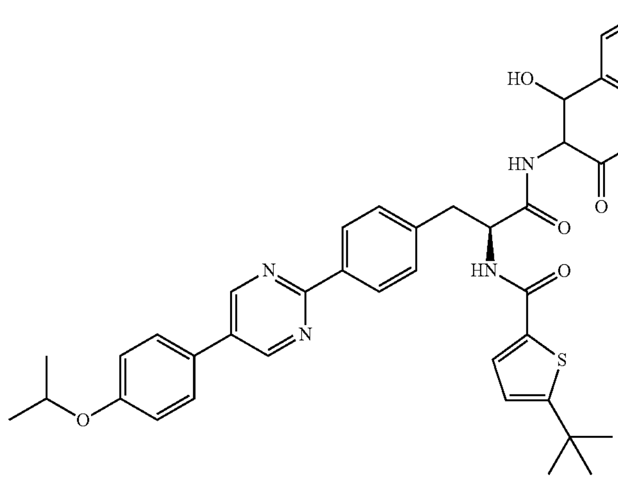 | 931 | 8.06 | 14 |
| 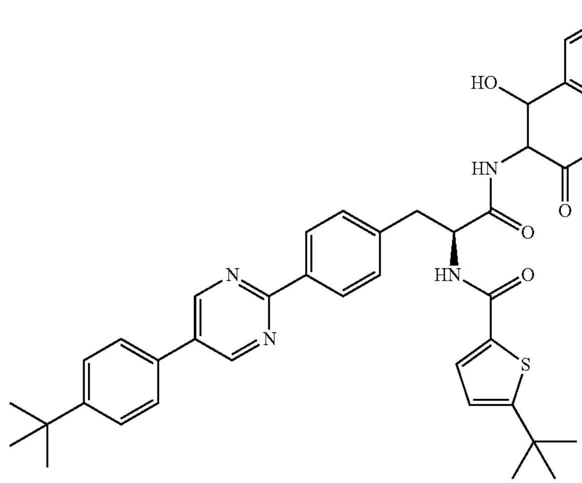 | 932 | 8.89 | 14 |

TABLE 1-continued

| STRUCTURE | COMPOUND NUMBER | LCMS RETENTION TIME (min) | PURITY METHOD |
|---|---|---|---|
| 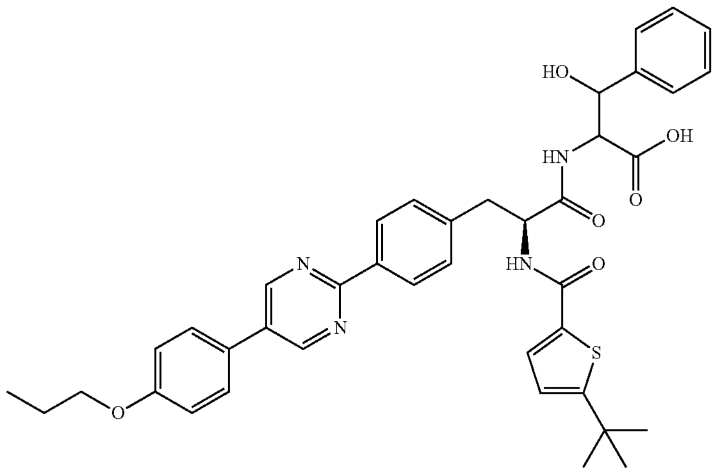 [SMILES: CCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 933 | 8.81 | 14 |
| 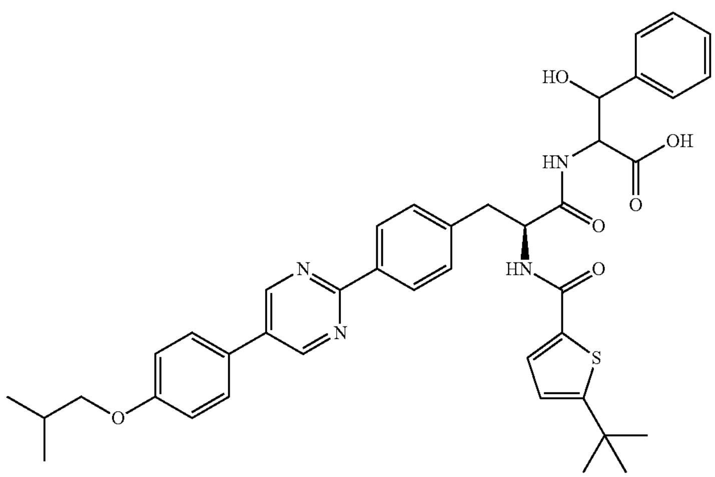 [SMILES: CC(C)COc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 934 | 8.60 | 14 |
| 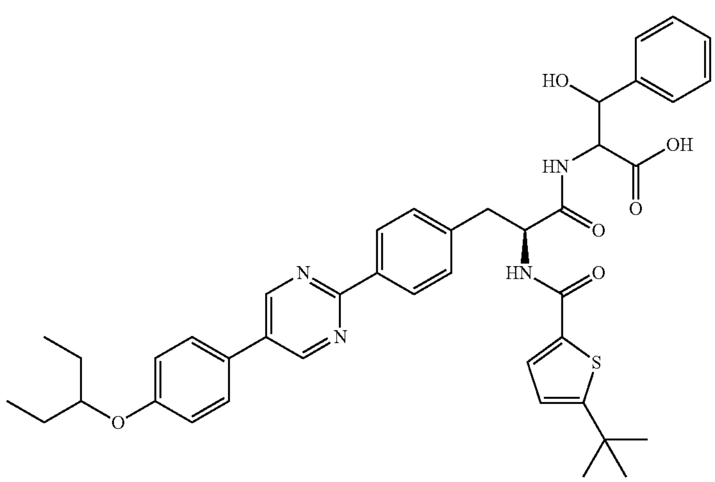 [SMILES: CCC(CC)Oc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 935 | 8.98 | 14 |

TABLE 1-continued
| STRUCTURE | COMPOUND NUMBER | LCMS RETENTION TIME (min) | PURITY METHOD |
|---|---|---|---|
| 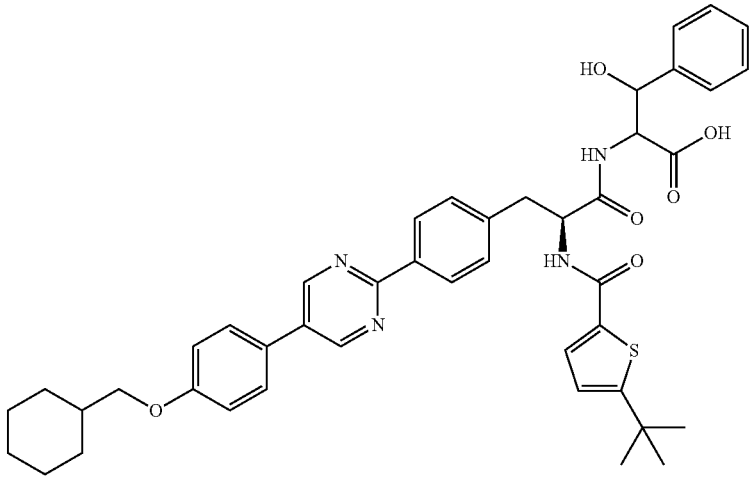 [SMILES: CC(C)(C)c1ccc(C(=O)N[C@@H](Cc2ccc(-c3ncc(-c4ccc(OCC5CCCCC5)cc4)cn3)cc2)C(=O)NC(C(=O)O)C(O)c2ccccc2)s1] | 936 | 9.90 | 14 |
| 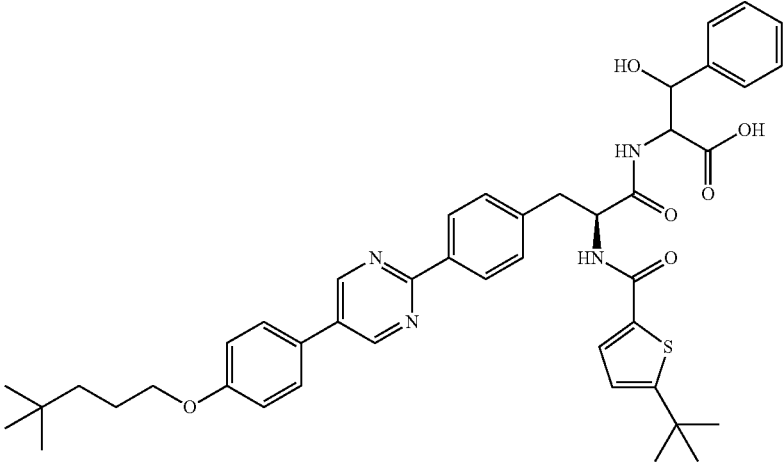 [SMILES: CC(C)(C)CCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 937 | 10.05 | 14 |
| 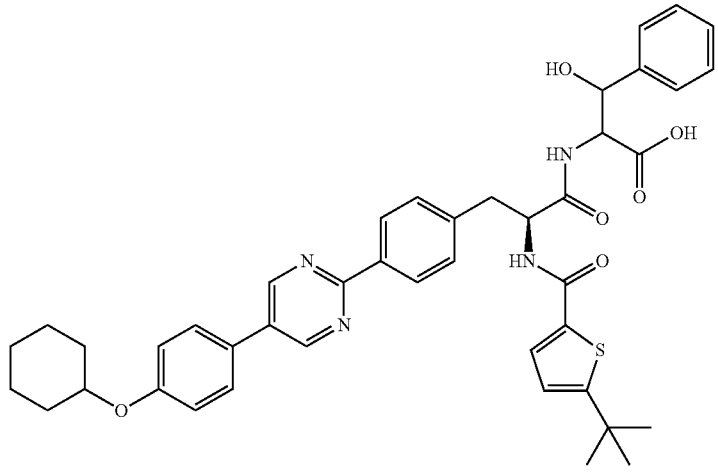 [SMILES: CC(C)(C)c1ccc(C(=O)N[C@@H](Cc2ccc(-c3ncc(-c4ccc(OC5CCCCC5)cc4)cn3)cc2)C(=O)NC(C(=O)O)C(O)c2ccccc2)s1] | 938 | 9.26 | 14 |

TABLE 1-continued
| STRUCTURE | COMPOUND NUMBER | LCMS RETENTION TIME (min) | PURITY METHOD |
|---|---|---|---|
| 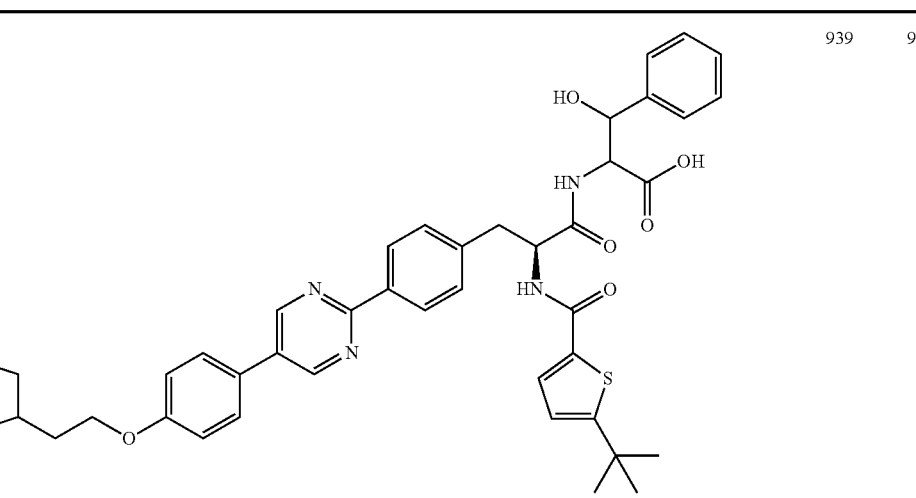 | 939 | 9.98 | 14 |
| 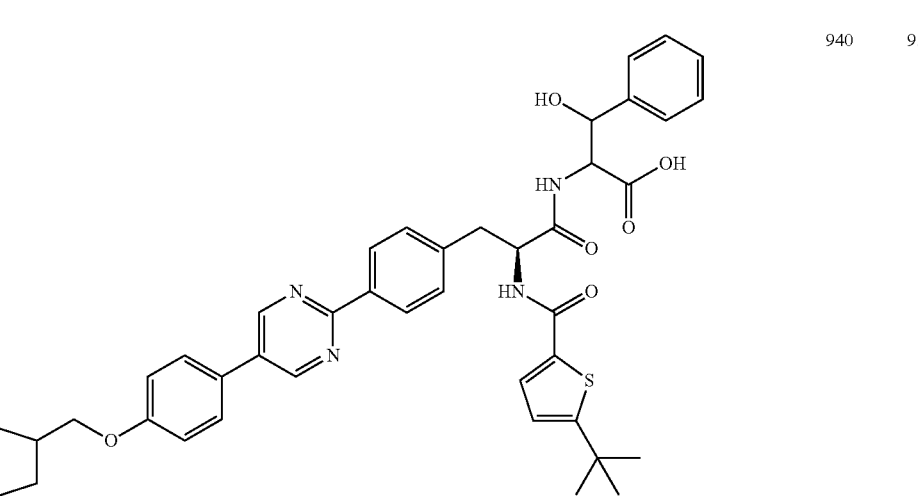 | 940 | 9.32 | 14 |
| 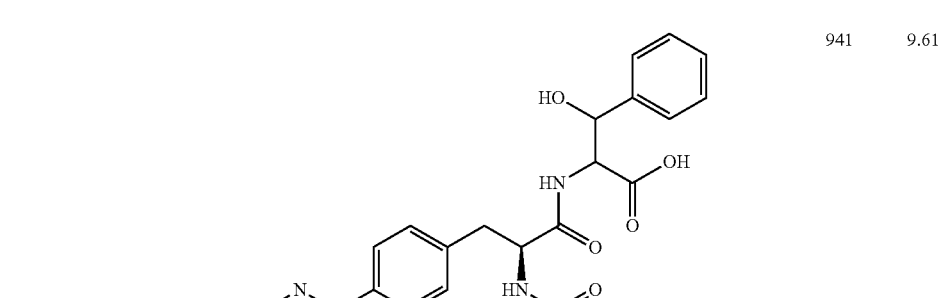 | 941 | 9.61 | 14 |

TABLE 1-continued

| STRUCTURE | COMPOUND NUMBER | LCMS RETENTION TIME (min) | PURITY METHOD |
|---|---|---|---|
| 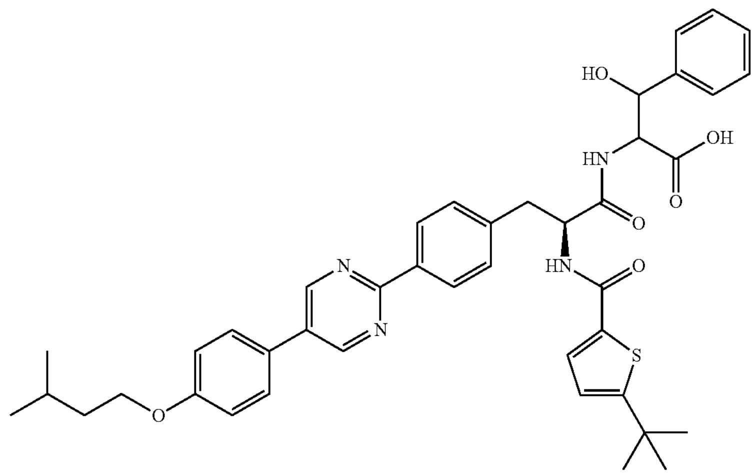 [SMILES: CC(C)CCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 942 | 9.07 | 14 |
| 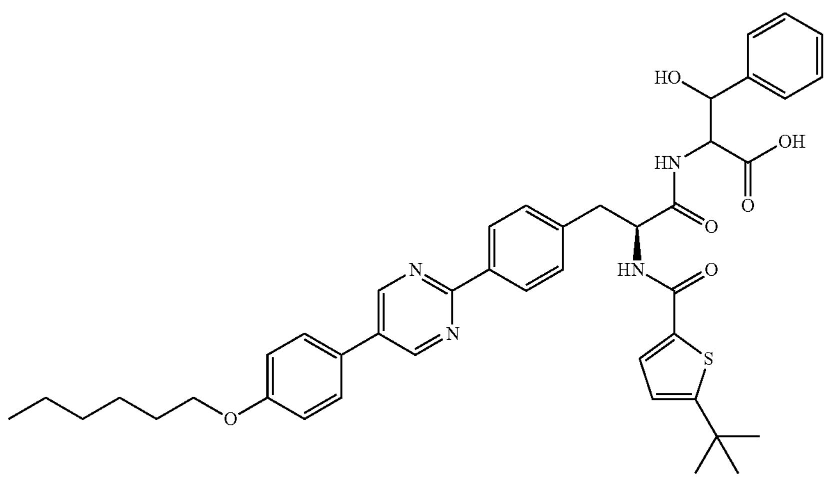 [SMILES: CCCCCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 943 | 9.42 | 14 |
| 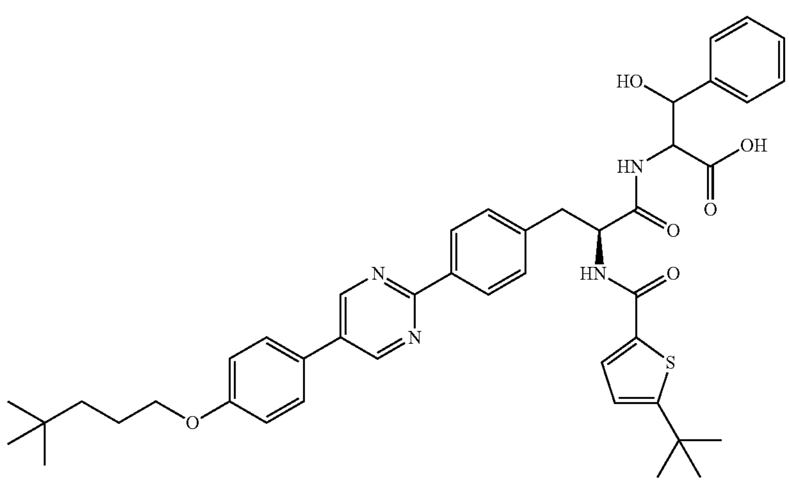 [SMILES: CC(C)(C)CCCOc1ccc(-c2cnc(-c3ccc(C[C@H](NC(=O)c4ccc(C(C)(C)C)s4)C(=O)NC(C(=O)O)C(O)c4ccccc4)cc3)nc2)cc1] | 944 | 9.47 | 14 |

TABLE 1-continued

| STRUCTURE | COMPOUND NUMBER | LCMS RETENTION TIME (min) | PURITY METHOD |
|---|---|---|---|
| 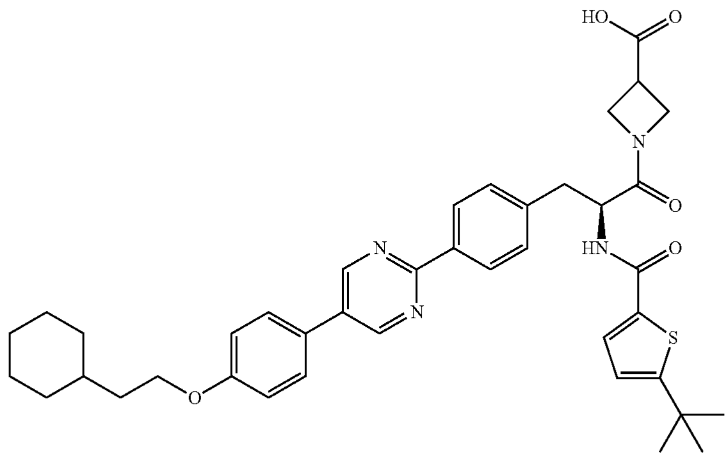 [SMILES: CC(C)(C)c1ccc(C(=O)N[C@@H](Cc2ccc(-c3ncc(-c4ccc(OCCC5CCCCC5)cc4)cn3)cc2)C(=O)N2CC(C(=O)O)C2)s1] | 945 | 9.773 | 14 |
| 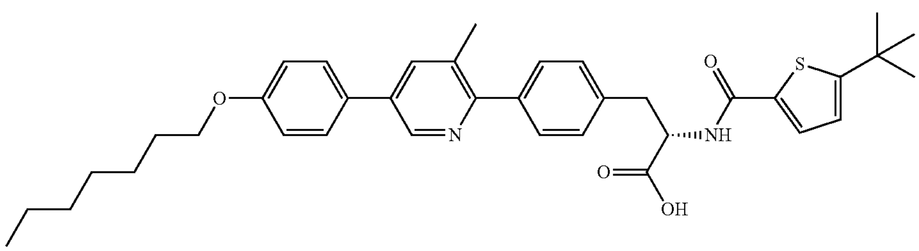 [SMILES: CCCCCCCOc1ccc(-c2cnc(-c3ccc(C[C@H](NC(=O)c4ccc(C(C)(C)C)s4)C(=O)O)cc3)c(C)c2)cc1] | 946 | 8.61 | 11 |
| 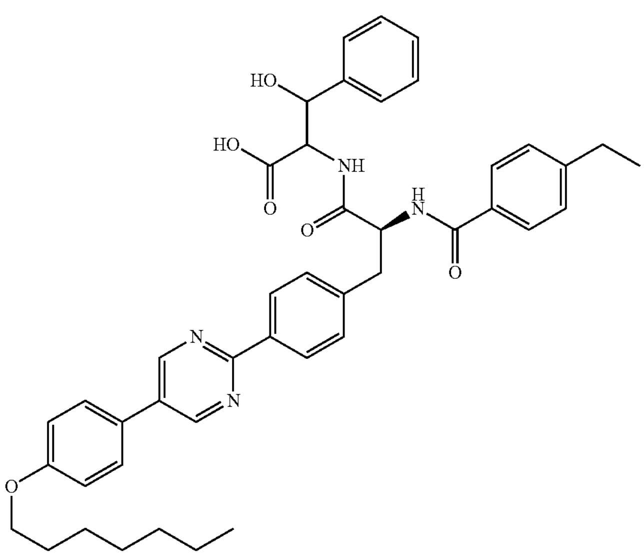 [SMILES: CCCCCCCOc1ccc(-c2cnc(-c3ccc(C[C@H](NC(=O)c4ccc(CC)cc4)C(=O)NC(C(=O)O)C(O)c4ccccc4)cc3)nc2)cc1] | 947 | 9.77 | 14 |

TABLE 1-continued

| STRUCTURE | COMPOUND NUMBER | LCMS RETENTION TIME (min) | PURITY METHOD |
|---|---|---|---|
| 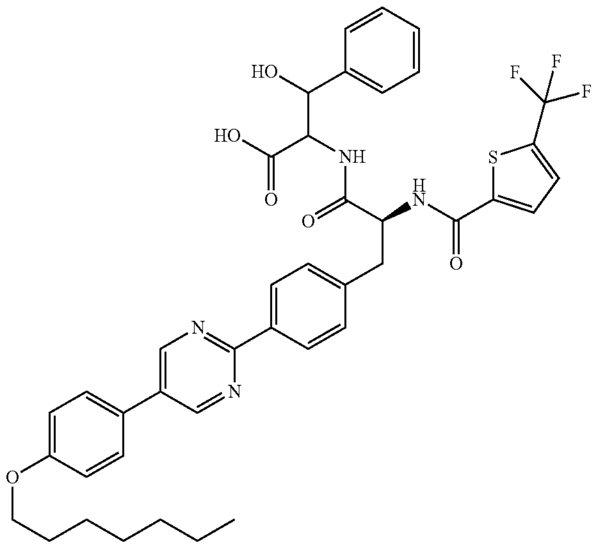 [SMILES: CCCCCCCOc1ccc(-c2cnc(-c3ccc(C[C@H](NC(=O)c4ccc(C(F)(F)F)s4)C(=O)NC(C(=O)O)C(O)c4ccccc4)cc3)nc2)cc1] | 948 | 10.12 | 14 |
| 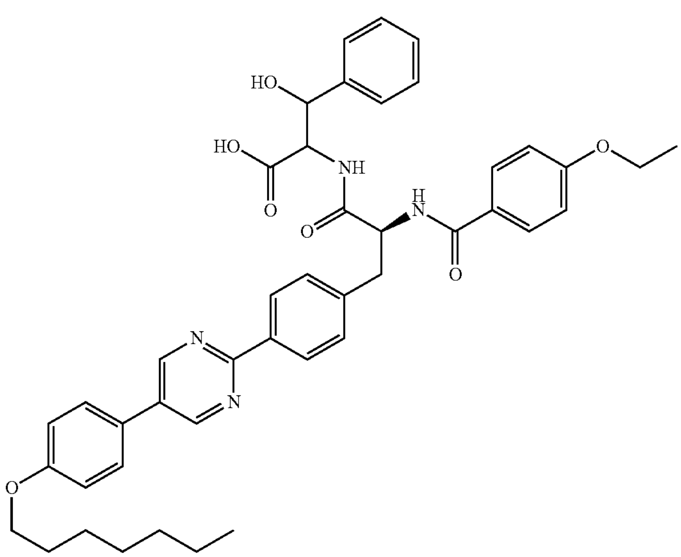 [SMILES: CCCCCCCOc1ccc(-c2cnc(-c3ccc(C[C@H](NC(=O)c4ccc(OCC)cc4)C(=O)NC(C(=O)O)C(O)c4ccccc4)cc3)nc2)cc1] | 949 | 9.55 | 14 |

TABLE 1-continued
| STRUCTURE | COMPOUND NUMBER | LCMS RETENTION TIME (min) | PURITY METHOD |
|---|---|---|---|
| 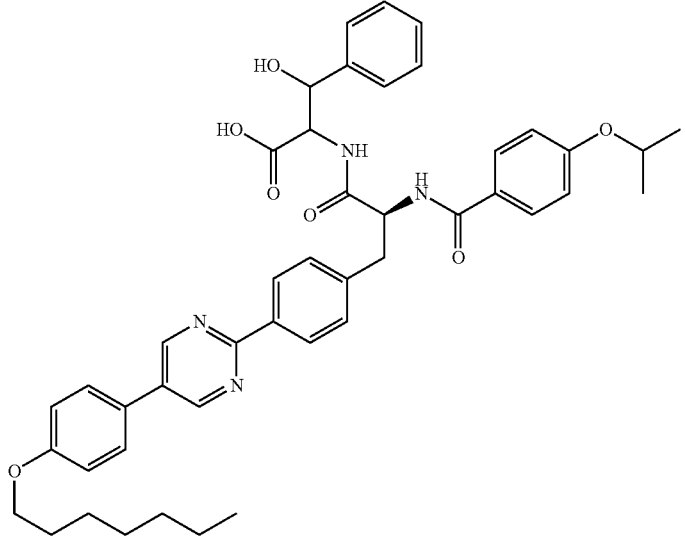 [SMILES: CCCCCCCOc1ccc(-c2cnc(-c3ccc(C[C@H](NC(=O)c4ccc(OC(C)C)cc4)C(=O)NC(C(=O)O)C(O)c4ccccc4)cc3)nc2)cc1] | 950 | 9.83 | 14 |
| 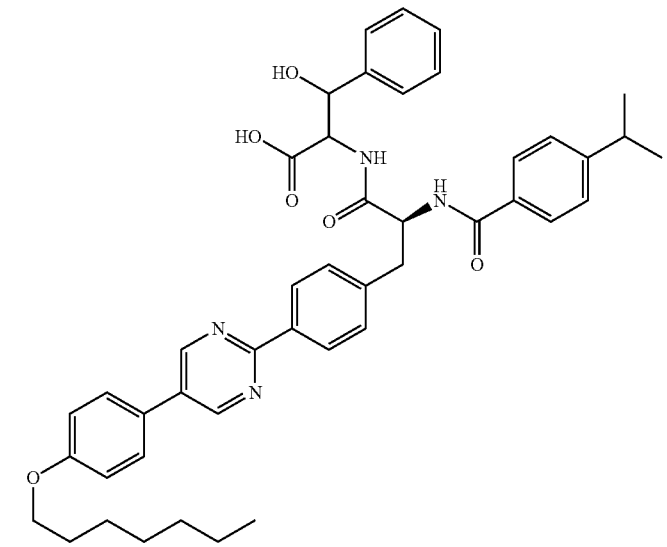 [SMILES: CCCCCCCOc1ccc(-c2cnc(-c3ccc(C[C@H](NC(=O)c4ccc(C(C)C)cc4)C(=O)NC(C(=O)O)C(O)c4ccccc4)cc3)nc2)cc1] | 951 | 10.15 | 14 |

TABLE 1-continued

| STRUCTURE | COMPOUND NUMBER | LCMS RETENTION TIME (min) | PURITY METHOD |
|---|---|---|---|
| 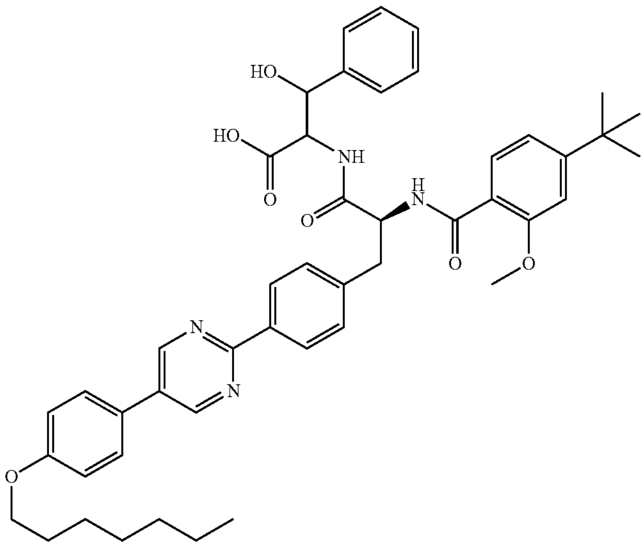 [SMILES: CCCCCCCOc1ccc(-c2cnc(-c3ccc(C[C@H](NC(=O)c4ccc(C(C)(C)C)cc4OC)C(=O)NC(C(=O)O)C(O)c4ccccc4)cc3)nc2)cc1] | 952 | 10.52 | 14 |
| 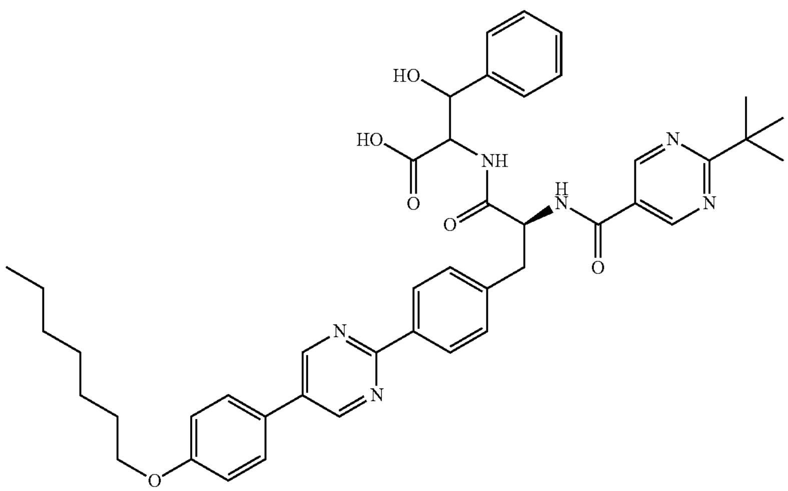 [SMILES: CCCCCCCOc1ccc(-c2cnc(-c3ccc(C[C@H](NC(=O)c4cnc(C(C)(C)C)nc4)C(=O)NC(C(=O)O)C(O)c4ccccc4)cc3)nc2)cc1] | 953 | 9.75 | 14 |
| 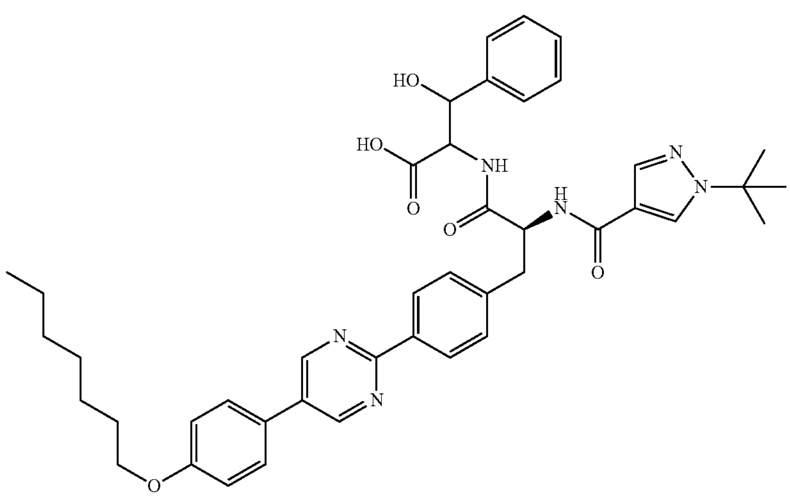 [SMILES: CCCCCCCOc1ccc(-c2cnc(-c3ccc(C[C@H](NC(=O)c4cnn(C(C)(C)C)c4)C(=O)NC(C(=O)O)C(O)c4ccccc4)cc3)nc2)cc1] | 954 | 9.12 | 14 |

TABLE 1-continued

| STRUCTURE | COMPOUND NUMBER | LCMS RETENTION TIME (min) | PURITY METHOD |
|---|---|---|---|
| 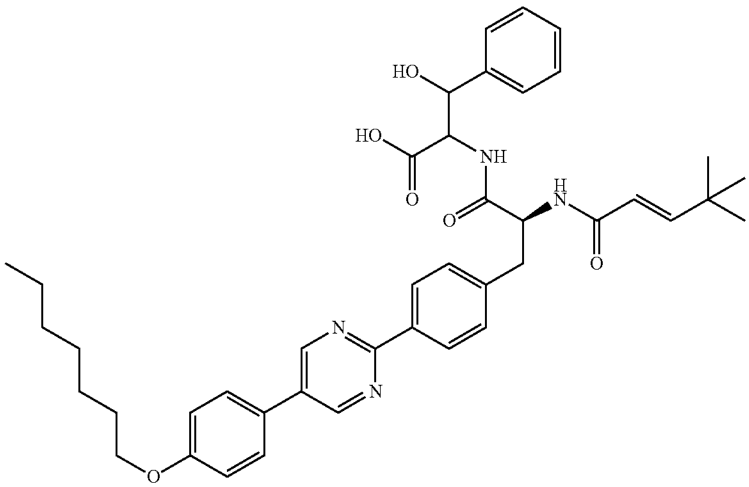 [SMILES: CCCCCCCOc1ccc(-c2cnc(-c3ccc(C[C@H](NC(=O)/C=C/C(C)(C)C)C(=O)NC(C(=O)O)C(O)c4ccccc4)cc3)nc2)cc1] | 955 | 9.67 | 14 |
| 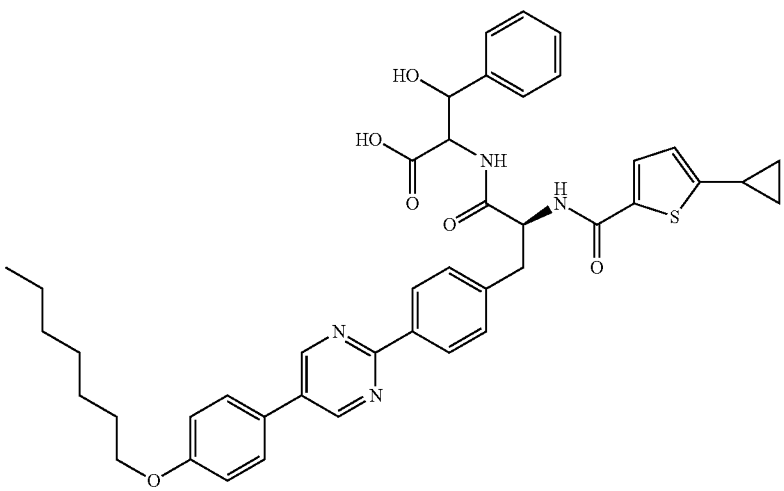 [SMILES: CCCCCCCOc1ccc(-c2cnc(-c3ccc(C[C@H](NC(=O)c4ccc(C5CC5)s4)C(=O)NC(C(=O)O)C(O)c4ccccc4)cc3)nc2)cc1] | 956 | 9.61 | 14 |
| 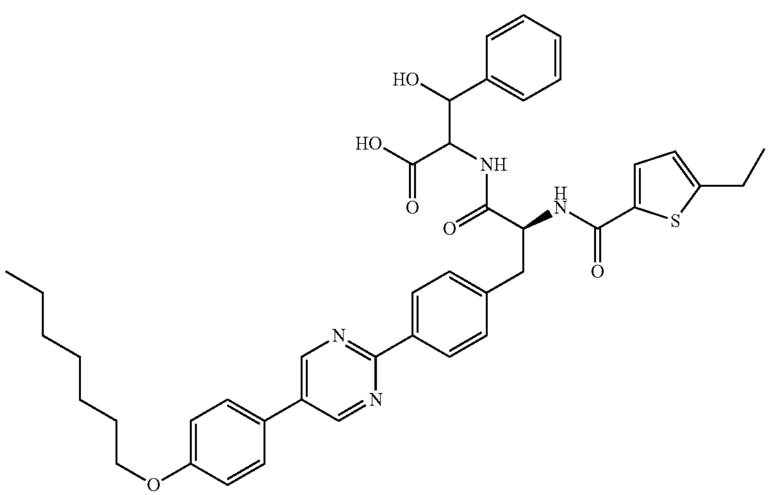 [SMILES: CCCCCCCOc1ccc(-c2cnc(-c3ccc(C[C@H](NC(=O)c4ccc(CC)s4)C(=O)NC(C(=O)O)C(O)c4ccccc4)cc3)nc2)cc1] | 957 | 9.69 | 14 |

TABLE 1-continued

| STRUCTURE | COMPOUND NUMBER | LCMS RETENTION TIME (min) | PURITY METHOD |
|---|---|---|---|
| 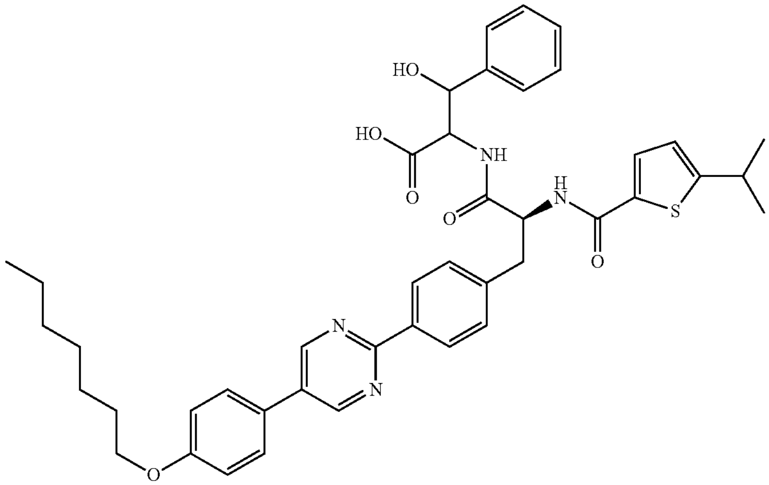 [SMILES: CCCCCCCOc1ccc(-c2cnc(-c3ccc(C[C@H](NC(=O)c4ccc(C(C)C)s4)C(=O)NC(C(=O)O)C(O)c4ccccc4)cc3)nc2)cc1] | 958 | 10.01 | 14 |
| 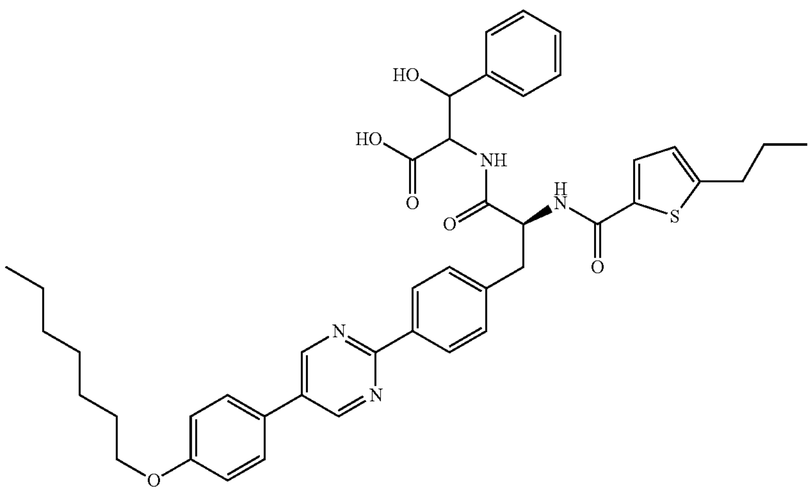 [SMILES: CCCCCCCOc1ccc(-c2cnc(-c3ccc(C[C@H](NC(=O)c4ccc(CCC)s4)C(=O)NC(C(=O)O)C(O)c4ccccc4)cc3)nc2)cc1] | 959 | 10.06 | 14 |
| 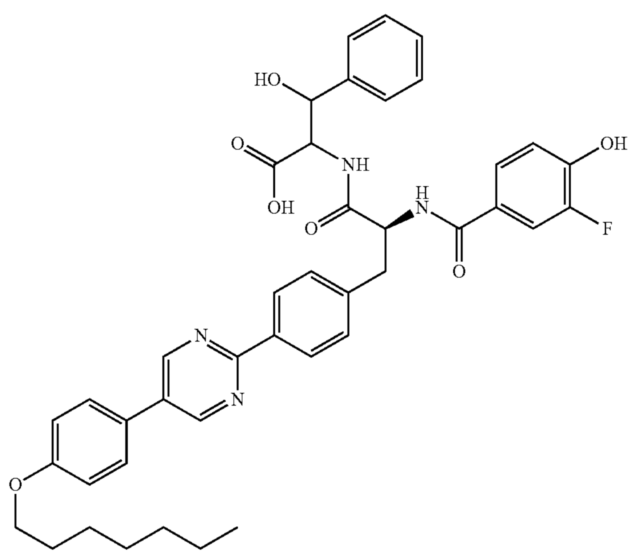 [SMILES: CCCCCCCOc1ccc(-c2cnc(-c3ccc(C[C@H](NC(=O)c4ccc(O)c(F)c4)C(=O)NC(C(=O)O)C(O)c4ccccc4)cc3)nc2)cc1] | 960 | 8.61 | 14 |

TABLE 1-continued
| STRUCTURE | COMPOUND NUMBER | LCMS RETENTION TIME (min) | PURITY METHOD |
|---|---|---|---|
| 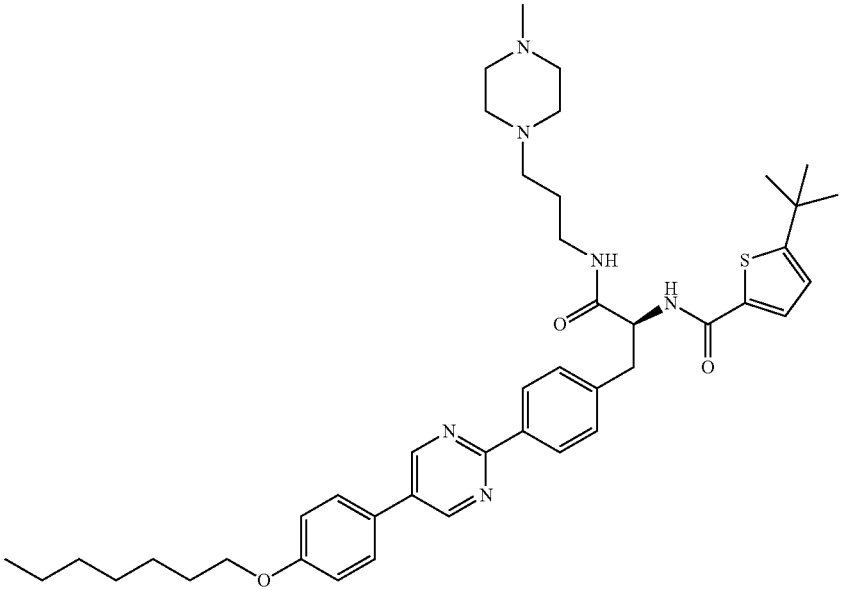 [SMILES: CCCCCCCOc1ccc(-c2cnc(-c3ccc(C[C@H](NC(=O)c4ccc(C(C)(C)C)s4)C(=O)NCCCN4CCN(C)CC4)cc3)nc2)cc1] | 961 | 2.38 | 20 |
| 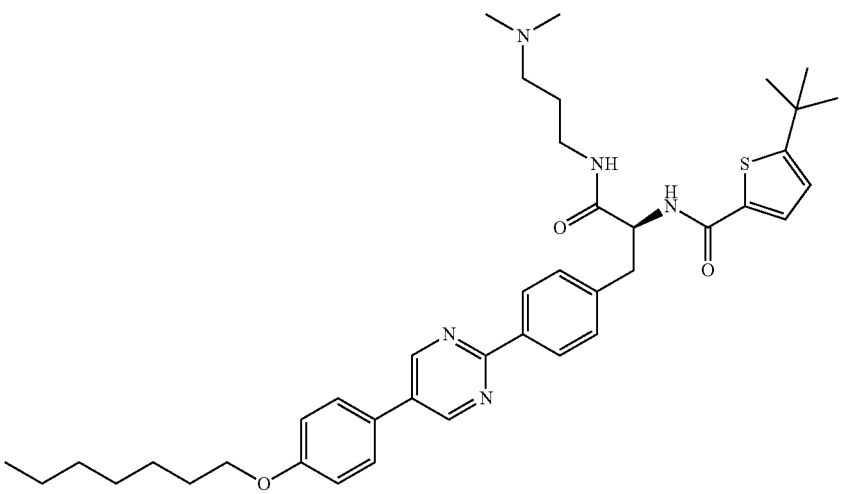 [SMILES: CCCCCCCOc1ccc(-c2cnc(-c3ccc(C[C@H](NC(=O)c4ccc(C(C)(C)C)s4)C(=O)NCCCN(C)C)cc3)nc2)cc1] | 962 | 2.61 | 20 |

TABLE 1-continued
| STRUCTURE | COMPOUND NUMBER | LCMS RETENTION TIME (min) | PURITY METHOD |
|---|---|---|---|
| 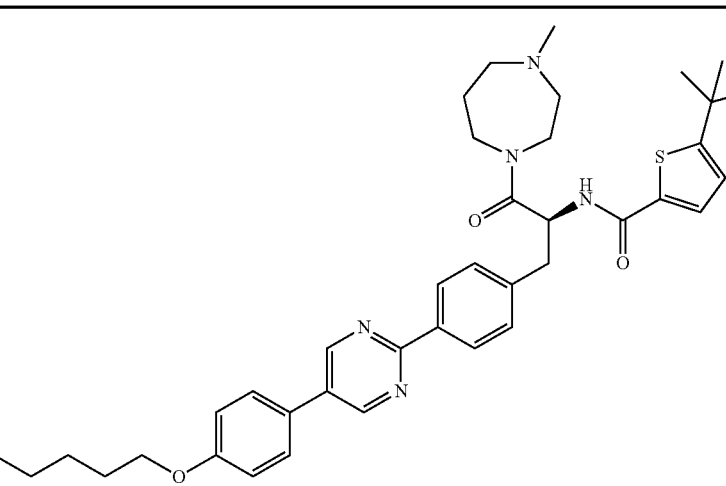 | 963 | 2.64 | 20 |
| 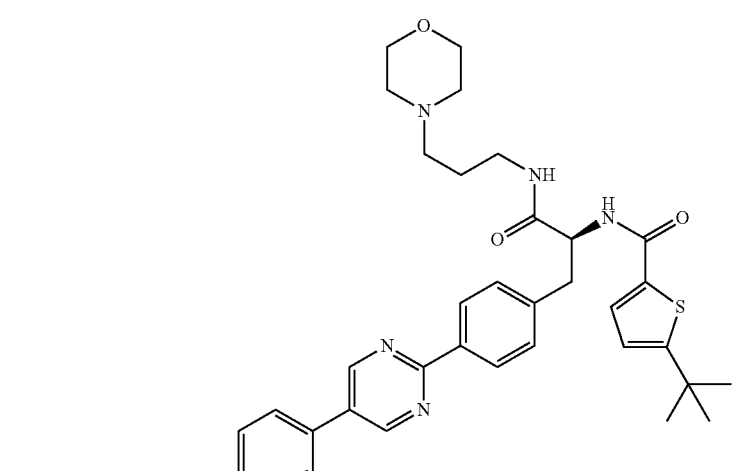 | 964 | 2.91 | 20 |
| 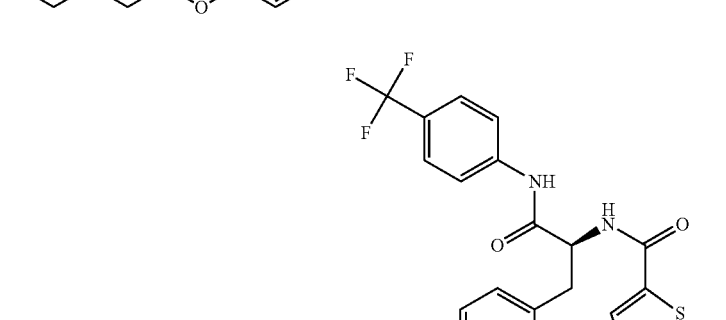 | 965 | 3.11 | 20 |

TABLE 1-continued

| STRUCTURE | COMPOUND NUMBER | LCMS RETENTION TIME (min) | PURITY METHOD |
|---|---|---|---|
| 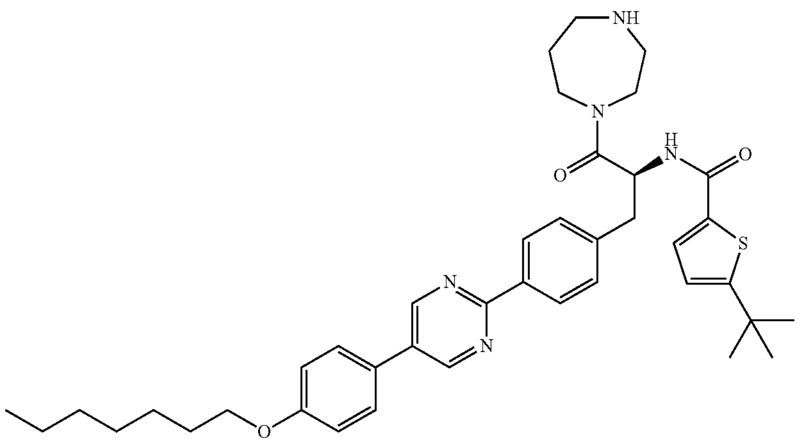 [SMILES: CCCCCCCOc1ccc(-c2cnc(-c3ccc(C[C@H](NC(=O)c4ccc(C(C)(C)C)s4)C(=O)N4CCCNCC4)cc3)nc2)cc1] | 966 | 2.66 | 20 |
| 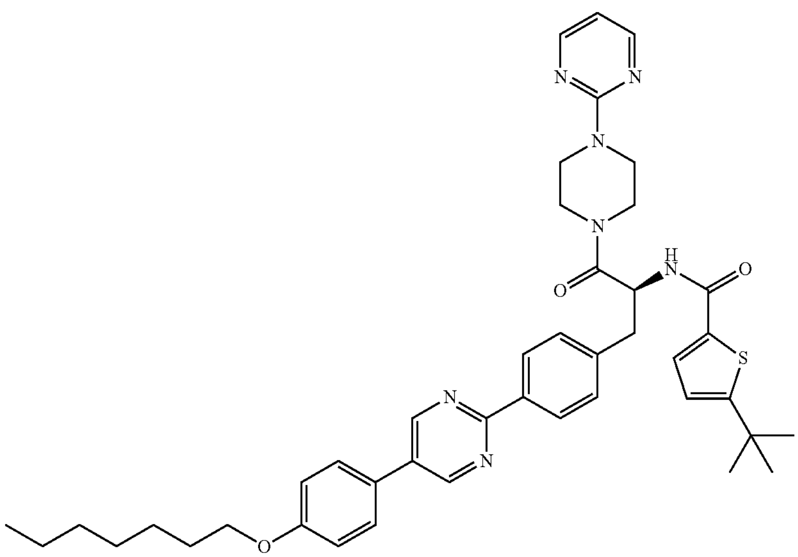 [SMILES: CCCCCCCOc1ccc(-c2cnc(-c3ccc(C[C@H](NC(=O)c4ccc(C(C)(C)C)s4)C(=O)N4CCN(c5ncccn5)CC4)cc3)nc2)cc1] | 967 | 2.96 | 20 |
| 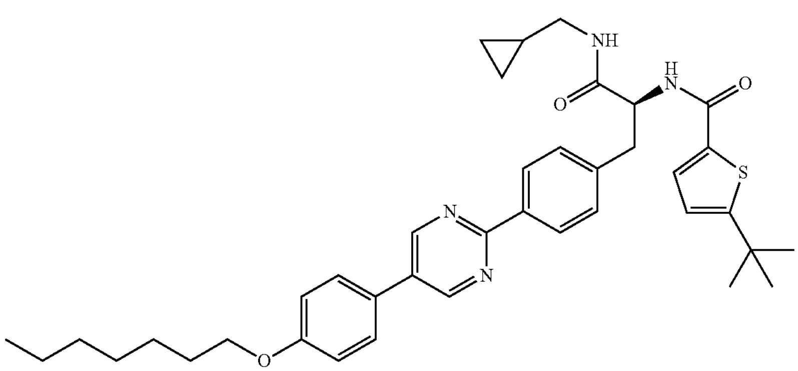 [SMILES: CCCCCCCOc1ccc(-c2cnc(-c3ccc(C[C@H](NC(=O)c4ccc(C(C)(C)C)s4)C(=O)NCC4CC4)cc3)nc2)cc1] | 968 | 2.88 | 20 |

TABLE 1-continued

| STRUCTURE | COMPOUND NUMBER | LCMS RETENTION TIME (min) | PURITY METHOD |
|---|---|---|---|
| 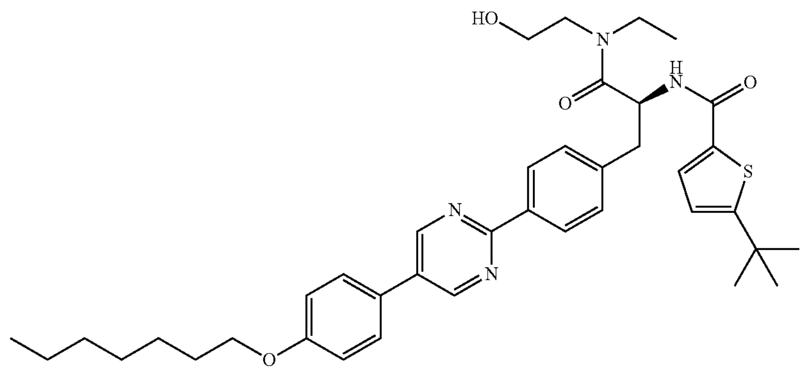 [SMILES: CCCCCCCOc1ccc(-c2cnc(-c3ccc(C[C@H](NC(=O)c4ccc(C(C)(C)C)s4)C(=O)N(CC)CCO)cc3)nc2)cc1] | 969 | 2.36 | 20 |
| 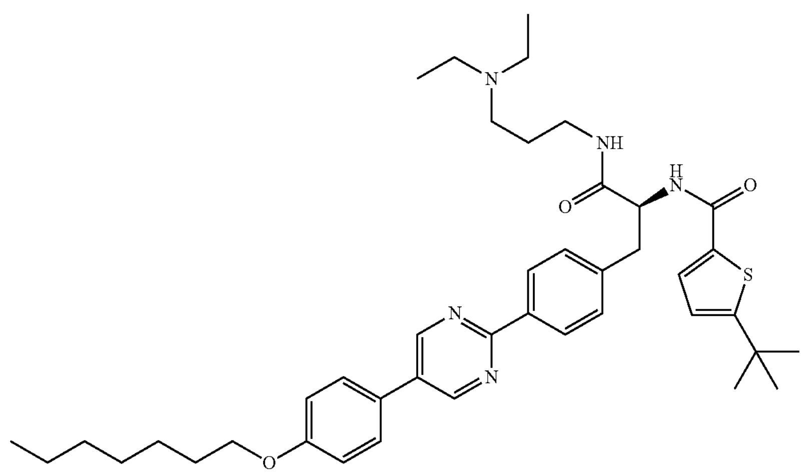 [SMILES: CCCCCCCOc1ccc(-c2cnc(-c3ccc(C[C@H](NC(=O)c4ccc(C(C)(C)C)s4)C(=O)NCCCN(CC)CC)cc3)nc2)cc1] | 970 | 2.76 | 20 |
| 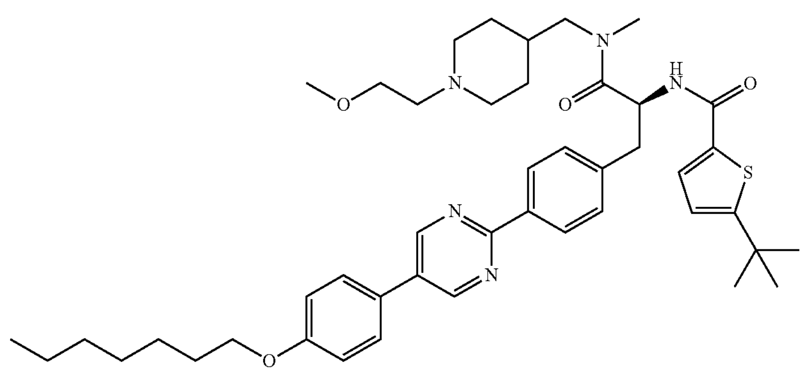 [SMILES: CCCCCCCOc1ccc(-c2cnc(-c3ccc(C[C@H](NC(=O)c4ccc(C(C)(C)C)s4)C(=O)N(C)CC4CCN(CCOC)CC4)cc3)nc2)cc1] | 971 | 2.31 | 20 |

TABLE 1-continued

| STRUCTURE | COMPOUND NUMBER | LCMS RETENTION TIME (min) | PURITY METHOD |
|---|---|---|---|
| 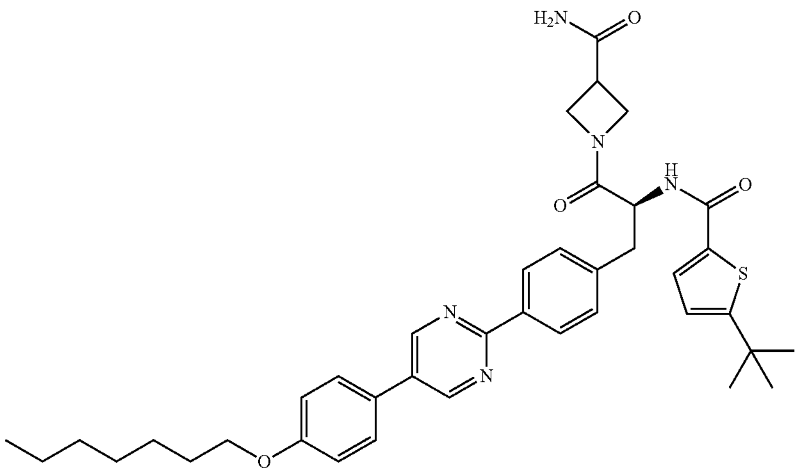 [SMILES: CCCCCCCOc1ccc(-c2cnc(-c3ccc(C[C@H](NC(=O)c4ccc(C(C)(C)C)s4)C(=O)N4CC(C(N)=O)C4)cc3)nc2)cc1] | 972 | 2.30 | 20 |
| 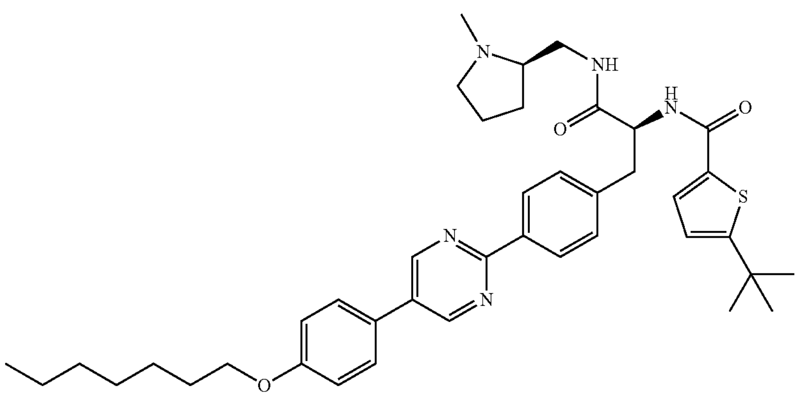 [SMILES: CCCCCCCOc1ccc(-c2cnc(-c3ccc(C[C@H](NC(=O)c4ccc(C(C)(C)C)s4)C(=O)NC[C@H]4CCCN4C)cc3)nc2)cc1] | 973 | 2.02 | 20 |
| 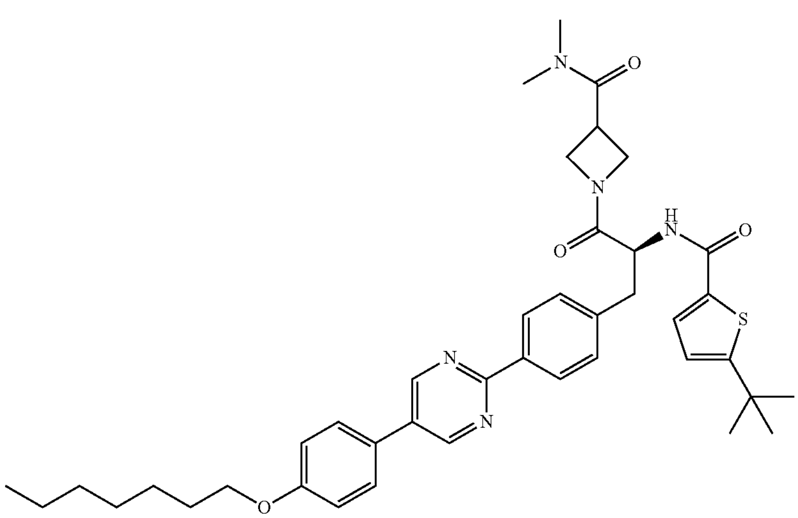 [SMILES: CCCCCCCOc1ccc(-c2cnc(-c3ccc(C[C@H](NC(=O)c4ccc(C(C)(C)C)s4)C(=O)N4CC(C(=O)N(C)C)C4)cc3)nc2)cc1] | 974 | 2.42 | 20 |

TABLE 1-continued

| STRUCTURE | COMPOUND NUMBER | LCMS RETENTION TIME (min) | PURITY METHOD |
|---|---|---|---|
| 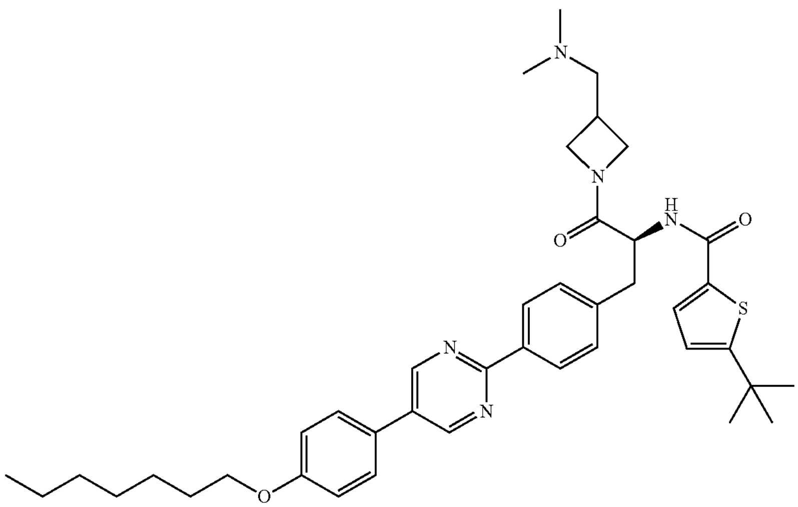 [SMILES: CCCCCCCOc1ccc(-c2cnc(-c3ccc(C[C@H](NC(=O)c4ccc(C(C)(C)C)s4)C(=O)N4CC(CN(C)C)C4)cc3)nc2)cc1] | 975 | 2.38 | 19 |
| 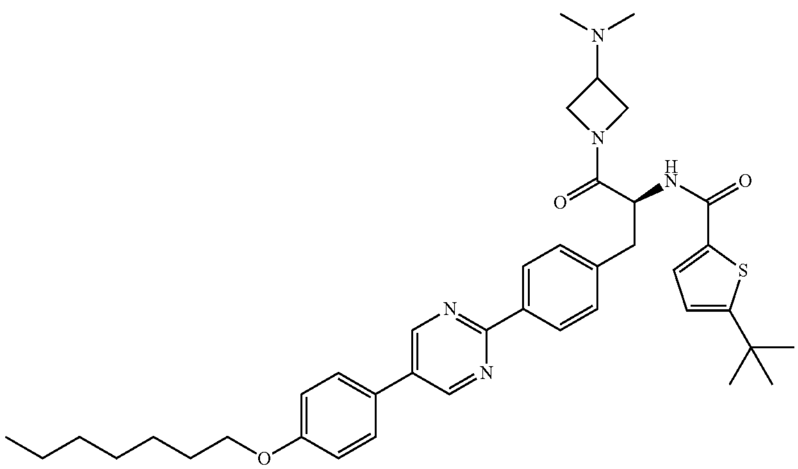 [SMILES: CCCCCCCOc1ccc(-c2cnc(-c3ccc(C[C@H](NC(=O)c4ccc(C(C)(C)C)s4)C(=O)N4CC(N(C)C)C4)cc3)nc2)cc1] | 976 | 2.38 | 17 |
| 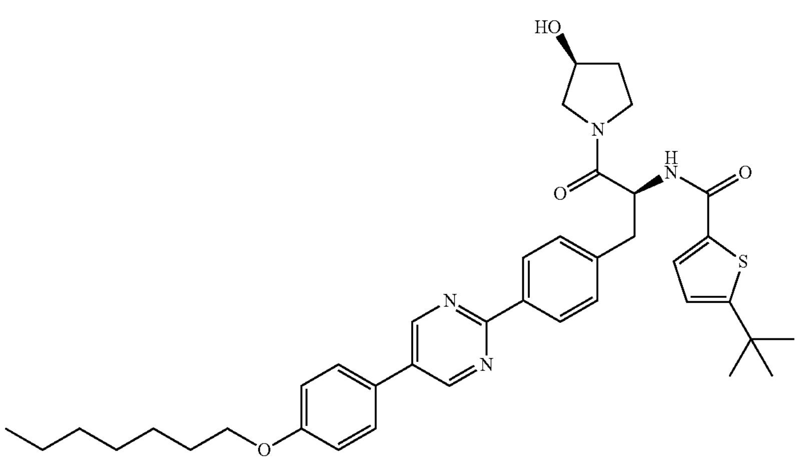 [SMILES: CCCCCCCOc1ccc(-c2cnc(-c3ccc(C[C@H](NC(=O)c4ccc(C(C)(C)C)s4)C(=O)N4CC[C@H](O)C4)cc3)nc2)cc1] | 977 | 2.38 | 22 |

TABLE 1-continued

| STRUCTURE | COMPOUND NUMBER | LCMS RETENTION TIME (min) | PURITY METHOD |
|---|---|---|---|
| 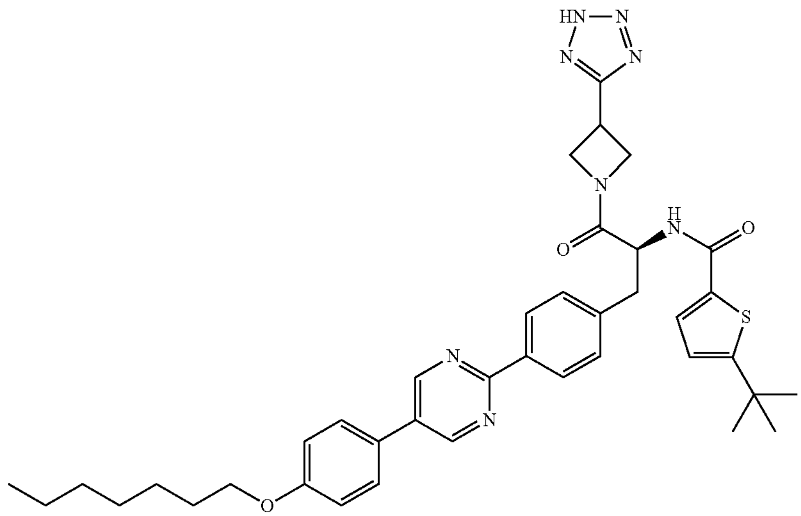 [SMILES: CCCCCCCOc1ccc(-c2cnc(-c3ccc(C[C@H](NC(=O)c4ccc(C(C)(C)C)s4)C(=O)N4CC(c5nn[nH]n5)C4)cc3)nc2)cc1] | 978 | 3.25 | 20 |
| 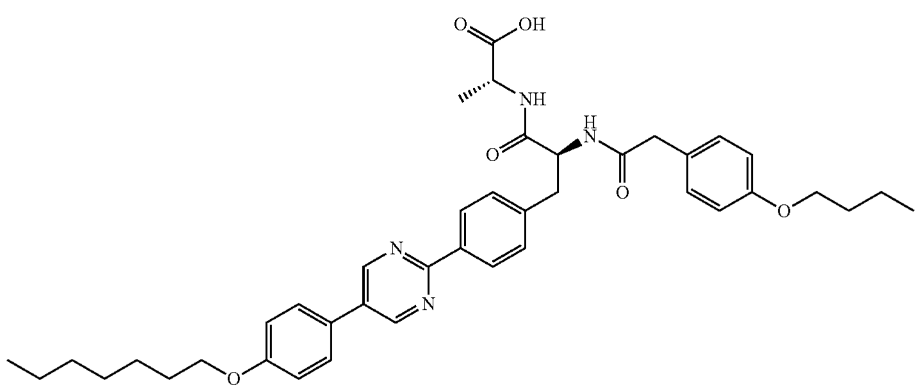 [SMILES: CCCCCCCOc1ccc(-c2cnc(-c3ccc(C[C@H](NC(=O)Cc4ccc(OCCCC)cc4)C(=O)N[C@H](C)C(=O)O)cc3)nc2)cc1] | 979 | 2.28 | 18 |
| 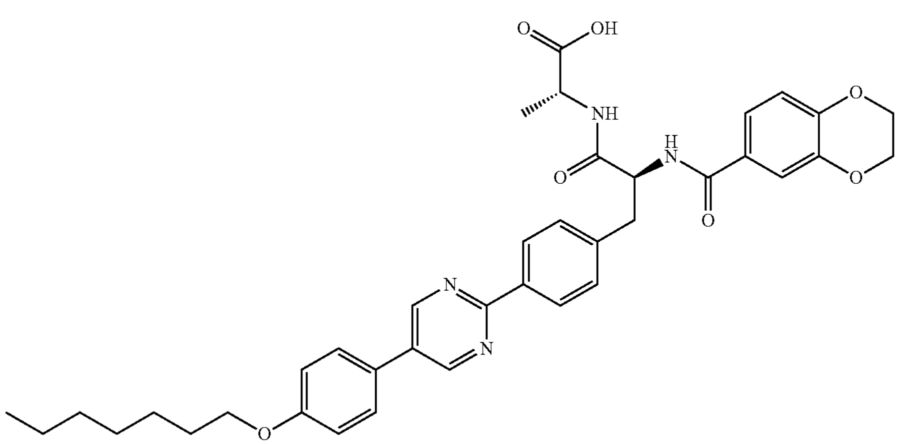 [SMILES: CCCCCCCOc1ccc(-c2cnc(-c3ccc(C[C@H](NC(=O)c4ccc5c(c4)OCCO5)C(=O)N[C@H](C)C(=O)O)cc3)nc2)cc1] | 980 | 2.04 | 18 |

TABLE 1-continued

| STRUCTURE | COMPOUND NUMBER | LCMS RETENTION TIME (min) | PURITY METHOD |
|---|---|---|---|
| 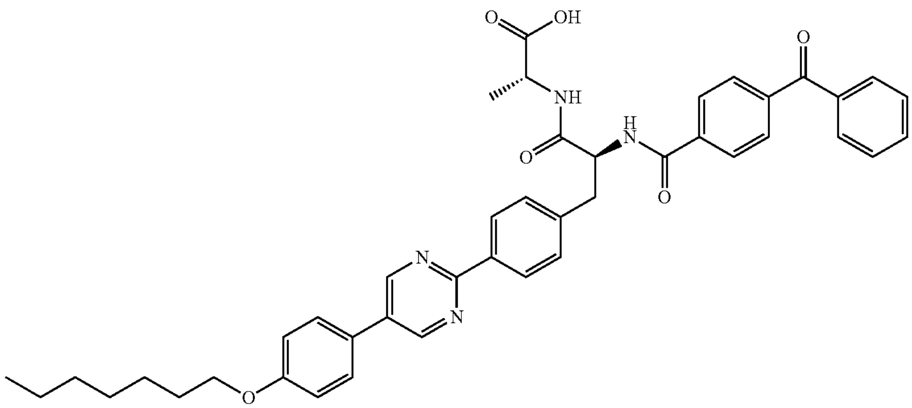 [SMILES: CCCCCCCOc1ccc(-c2cnc(-c3ccc(C[C@H](NC(=O)c4ccc(C(=O)c5ccccc5)cc4)C(=O)N[C@H](C)C(=O)O)cc3)nc2)cc1] | 981 | 2.23 | 18 |
| 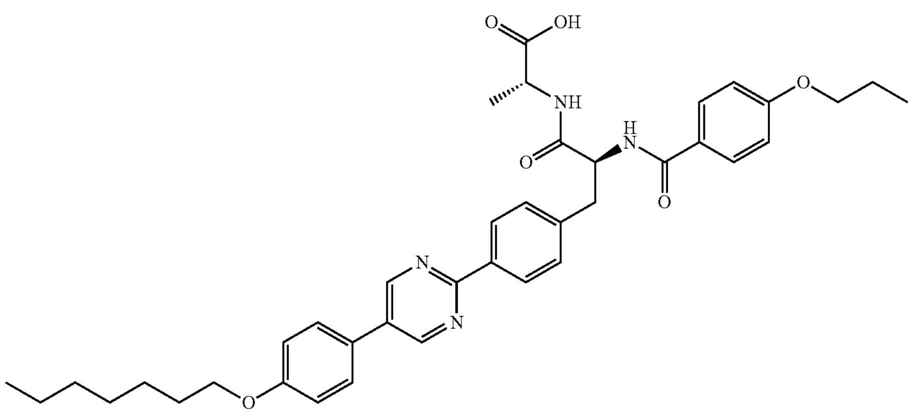 [SMILES: CCCCCCCOc1ccc(-c2cnc(-c3ccc(C[C@H](NC(=O)c4ccc(OCCC)cc4)C(=O)N[C@H](C)C(=O)O)cc3)nc2)cc1] | 982 | 2.24 | 18 |
| 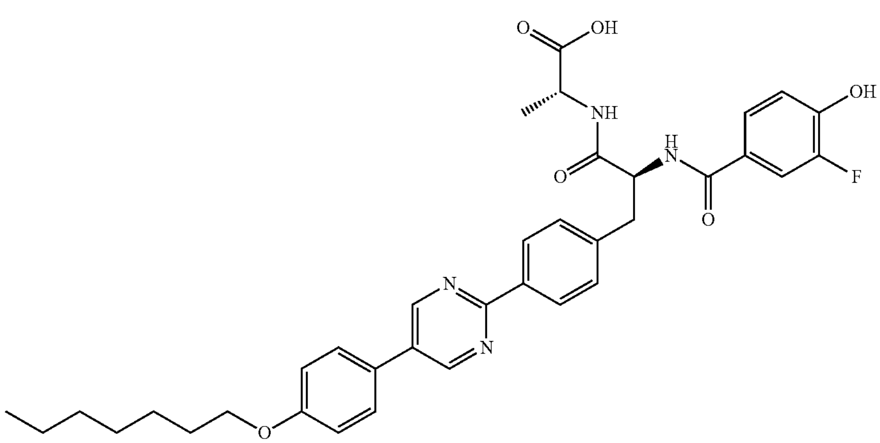 [SMILES: CCCCCCCOc1ccc(-c2cnc(-c3ccc(C[C@H](NC(=O)c4ccc(O)c(F)c4)C(=O)N[C@H](C)C(=O)O)cc3)nc2)cc1] | 983 | 1.74 | 19 |

TABLE 1-continued

| STRUCTURE | COMPOUND NUMBER | LCMS RETENTION TIME (min) | PURITY METHOD |
|---|---|---|---|
| 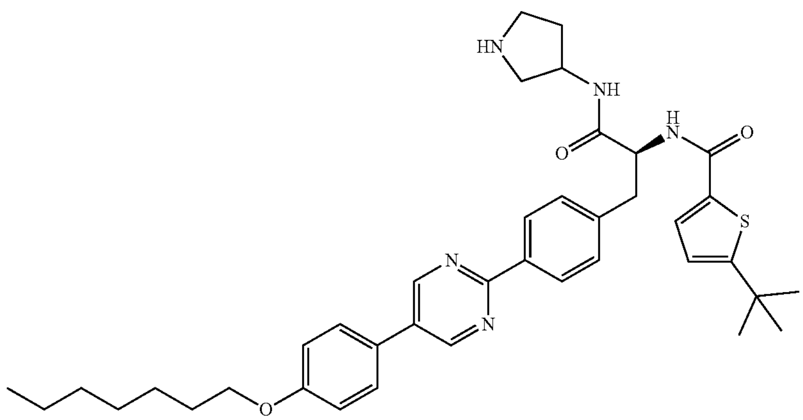 [SMILES: CCCCCCCOc1ccc(-c2cnc(-c3ccc(C[C@H](NC(=O)c4ccc(C(C)(C)C)s4)C(=O)NC4CCNC4)cc3)nc2)cc1] | 984 | 2.38 | 18 |
| 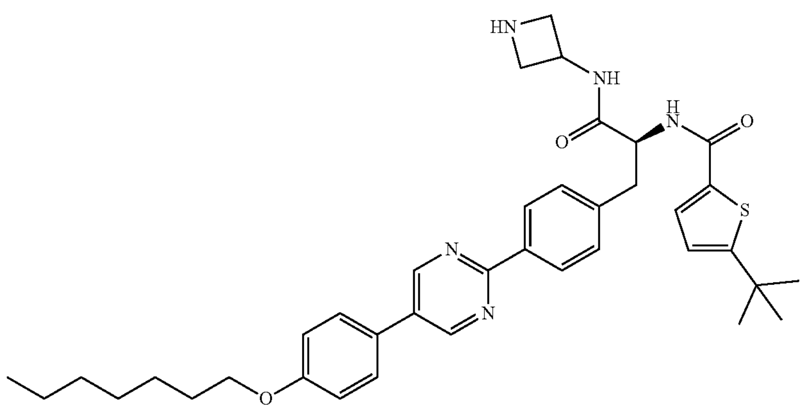 [SMILES: CCCCCCCOc1ccc(-c2cnc(-c3ccc(C[C@H](NC(=O)c4ccc(C(C)(C)C)s4)C(=O)NC4CNC4)cc3)nc2)cc1] | 985 | 2.38 | 19 |
| 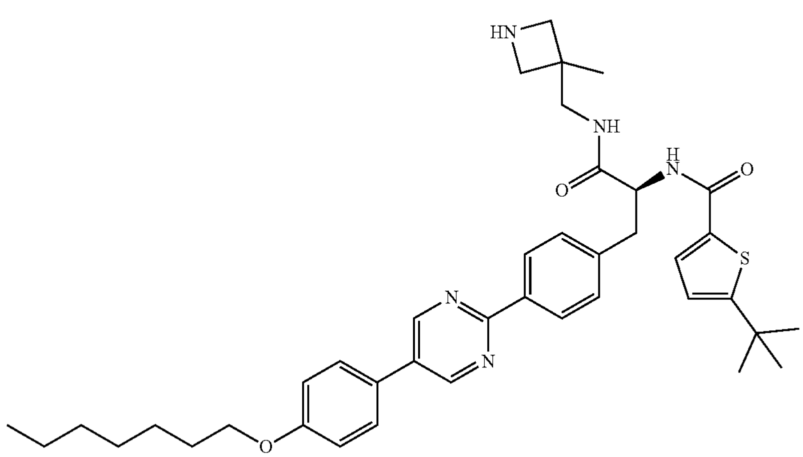 [SMILES: CCCCCCCOc1ccc(-c2cnc(-c3ccc(C[C@H](NC(=O)c4ccc(C(C)(C)C)s4)C(=O)NCC4(C)CNC4)cc3)nc2)cc1] | 986 | 2.38 | 18 |

TABLE 1-continued

| STRUCTURE | COMPOUND NUMBER | LCMS RETENTION TIME (min) | PURITY METHOD |
|---|---|---|---|
| 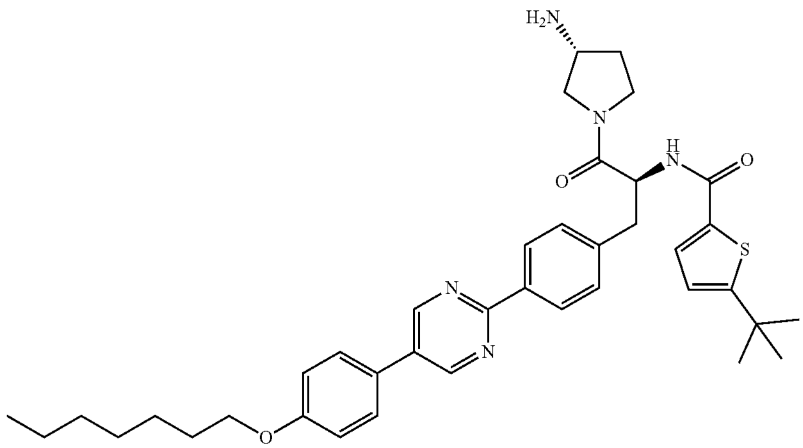 [SMILES: CCCCCCCOc1ccc(-c2cnc(-c3ccc(C[C@H](NC(=O)c4ccc(C(C)(C)C)s4)C(=O)N4CC[C@@H](N)C4)cc3)nc2)cc1] | 987 | 2.38 | 18 |
| 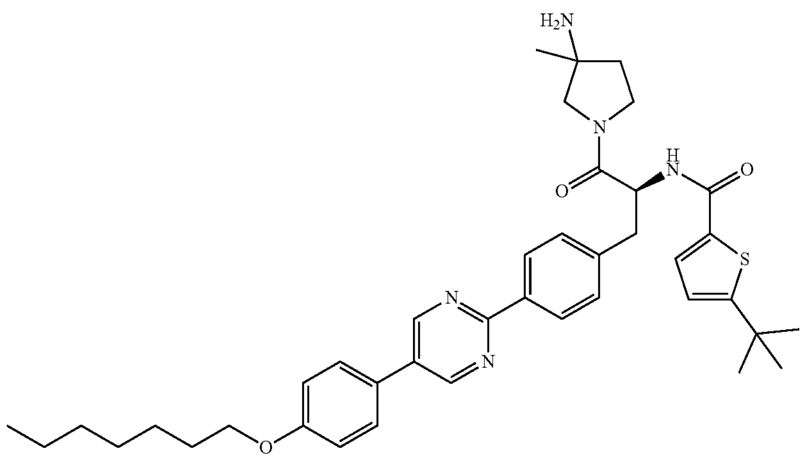 [SMILES: CCCCCCCOc1ccc(-c2cnc(-c3ccc(C[C@H](NC(=O)c4ccc(C(C)(C)C)s4)C(=O)N4CCC(C)(N)C4)cc3)nc2)cc1] | 988 | 2.38 | 18 |
| 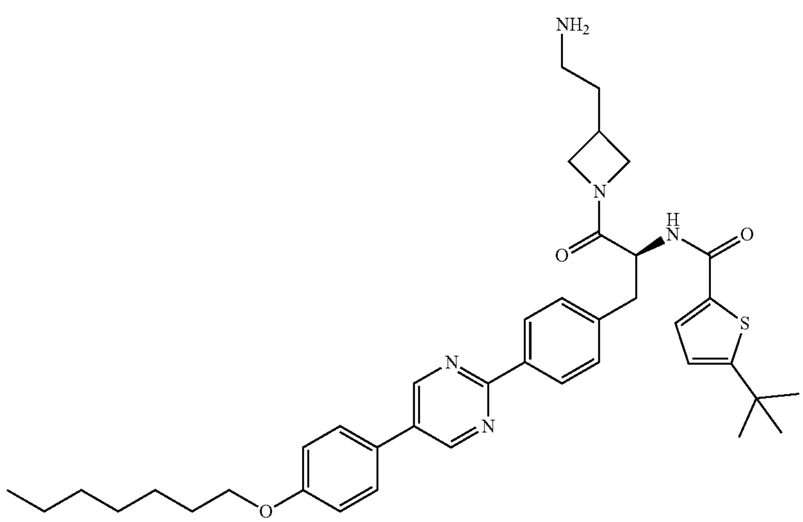 [SMILES: CCCCCCCOc1ccc(-c2cnc(-c3ccc(C[C@H](NC(=O)c4ccc(C(C)(C)C)s4)C(=O)N4CC(CCN)C4)cc3)nc2)cc1] | 989 | 2.12 | 20 |

TABLE 1-continued
| STRUCTURE | COMPOUND NUMBER | LCMS RETENTION TIME (min) | PURITY METHOD |
|---|---|---|---|
| 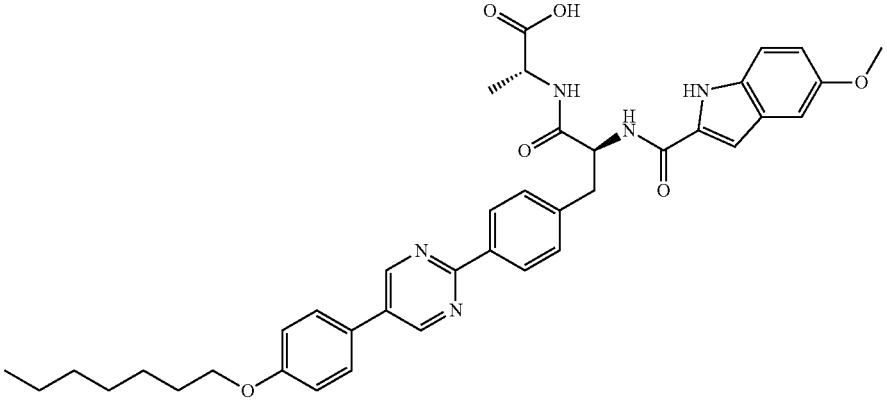 [SMILES: CCCCCCCOc1ccc(-c2cnc(-c3ccc(C[C@H](NC(=O)c4cc5cc(OC)ccc5[nH]4)C(=O)N[C@H](C)C(=O)O)cc3)nc2)cc1] | 990 | 2.95 | 19 |
| 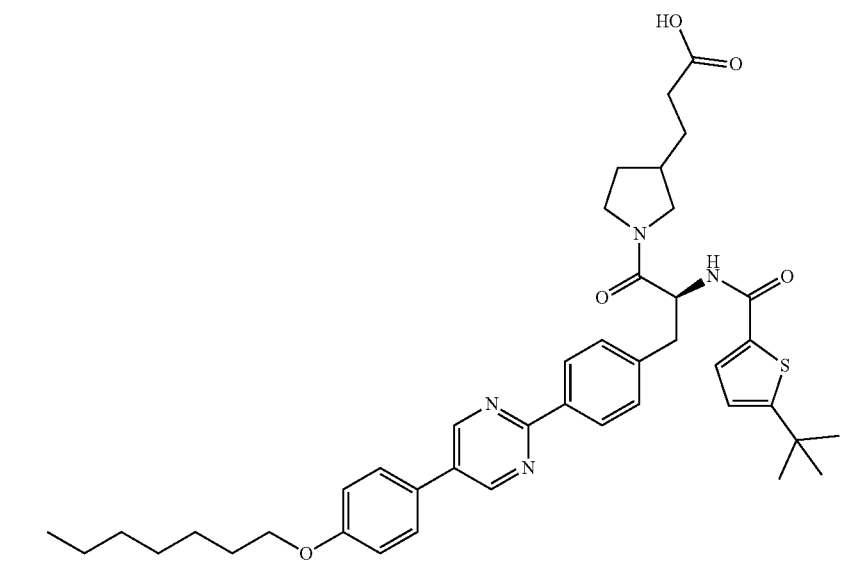 [SMILES: CCCCCCCOc1ccc(-c2cnc(-c3ccc(C[C@H](NC(=O)c4ccc(C(C)(C)C)s4)C(=O)N4CCC(CCC(=O)O)C4)cc3)nc2)cc1] | 991 | 2.00 | 20 |
| 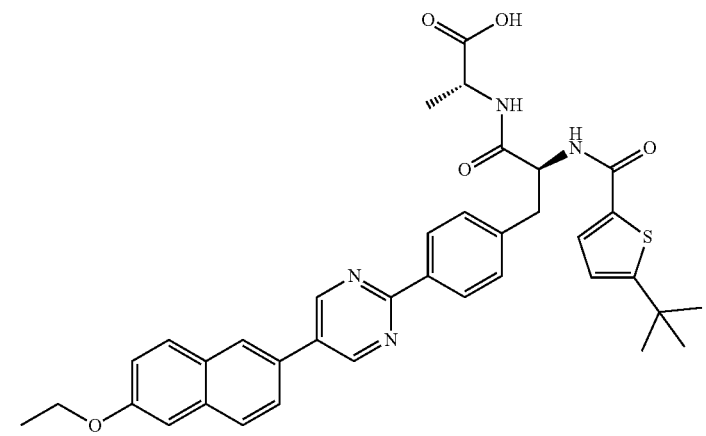 [SMILES: CCOc1ccc2cc(-c3cnc(-c4ccc(C[C@H](NC(=O)c5ccc(C(C)(C)C)s5)C(=O)N[C@H](C)C(=O)O)cc4)nc3)ccc2c1] | 992 | 2.41 | 17 |

TABLE 1-continued

| STRUCTURE | COMPOUND NUMBER | LCMS RETENTION TIME (min) | PURITY METHOD |
|---|---|---|---|
| 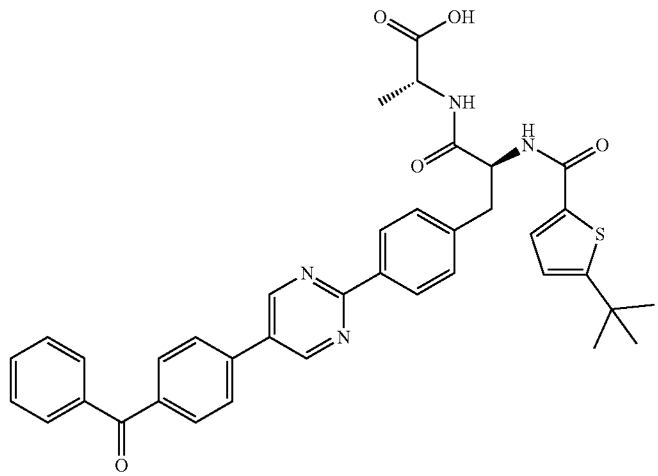 [SMILES: C[C@@H](NC(=O)[C@H](Cc1ccc(-c2ncc(-c3ccc(C(=O)c4ccccc4)cc3)cn2)cc1)NC(=O)c1ccc(C(C)(C)C)s1)C(=O)O] | 993 | 2.19 | 17 |
| 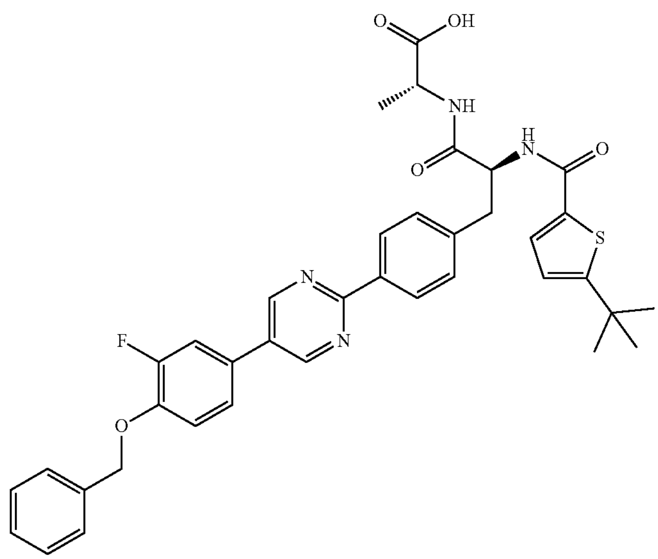 [SMILES: C[C@@H](NC(=O)[C@H](Cc1ccc(-c2ncc(-c3ccc(OCc4ccccc4)c(F)c3)cn2)cc1)NC(=O)c1ccc(C(C)(C)C)s1)C(=O)O] | 994 | 2.13 | 17 |
| 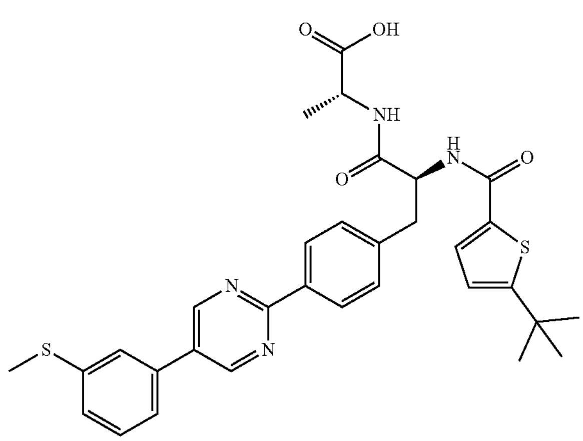 [SMILES: CSc1cccc(-c2cnc(-c3ccc(C[C@H](NC(=O)c4ccc(C(C)(C)C)s4)C(=O)N[C@H](C)C(=O)O)cc3)nc2)c1] | 995 | 2.06 | 17 |

TABLE 1-continued
| STRUCTURE | COMPOUND NUMBER | LCMS RETENTION TIME (min) | PURITY METHOD |
|---|---|---|---|
| 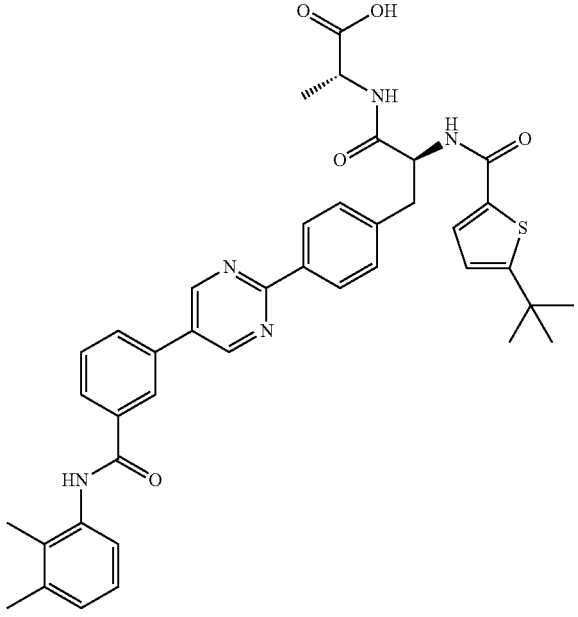 [SMILES: Cc1cccc(NC(=O)c2cccc(-c3cnc(-c4ccc(C[C@H](NC(=O)c5ccc(C(C)(C)C)s5)C(=O)N[C@H](C)C(=O)O)cc4)nc3)c2)c1C] | 996 | 1.88 | 17 |
| 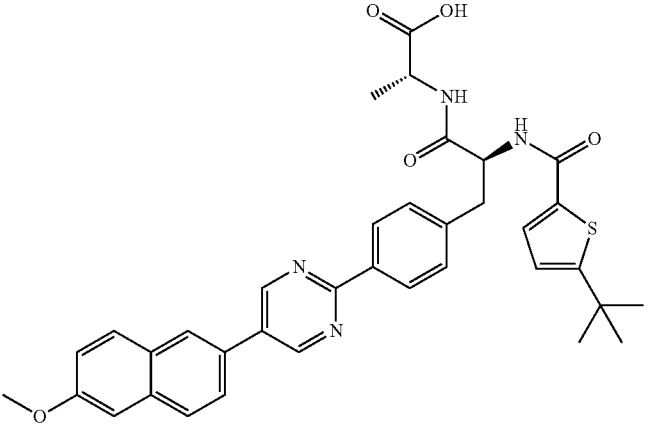 [SMILES: COc1ccc2cc(-c3cnc(-c4ccc(C[C@H](NC(=O)c5ccc(C(C)(C)C)s5)C(=O)N[C@H](C)C(=O)O)cc4)nc3)ccc2c1] | 997 | 2.01 | 17 |

TABLE 1-continued

| STRUCTURE | COMPOUND NUMBER | LCMS RETENTION TIME (min) | PURITY METHOD |
|---|---|---|---|
| 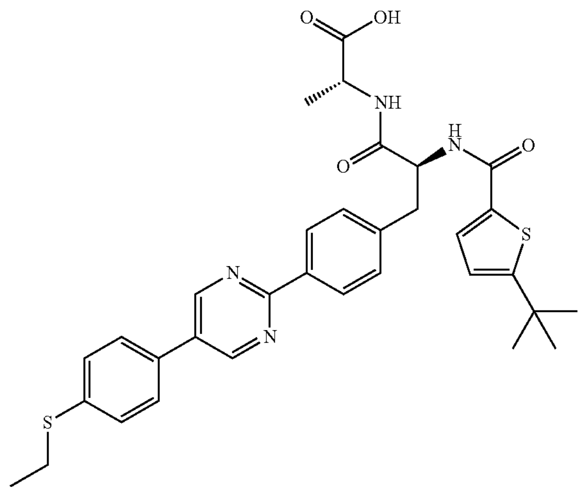 [SMILES: CCSc1ccc(-c2cnc(-c3ccc(C[C@H](NC(=O)c4ccc(C(C)(C)C)s4)C(=O)N[C@H](C)C(=O)O)cc3)nc2)cc1] | 998 | 2.18 | 17 |
| 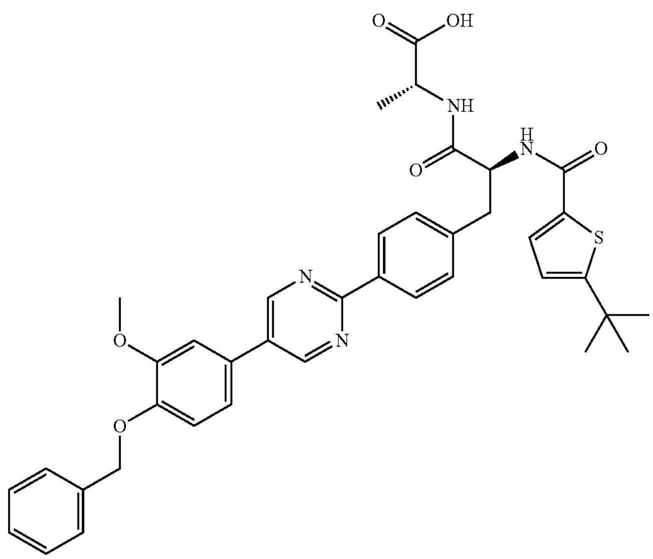 [SMILES: COc1cc(-c2cnc(-c3ccc(C[C@H](NC(=O)c4ccc(C(C)(C)C)s4)C(=O)N[C@H](C)C(=O)O)cc3)nc2)ccc1OCc1ccccc1] | 999 | 2.26 | 17 |
| 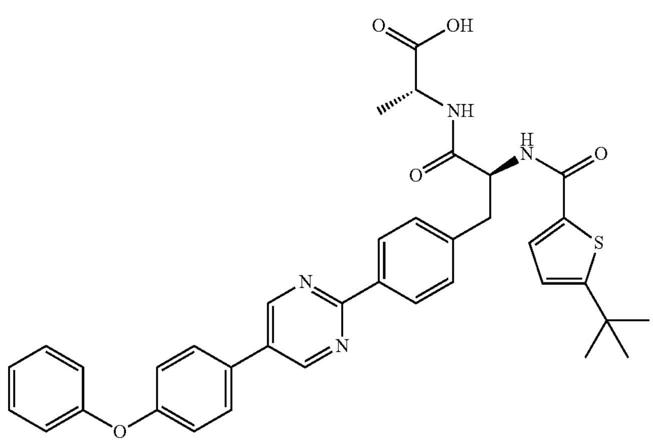 [SMILES: C[C@@H](NC(=O)[C@H](Cc1ccc(-c2ncc(-c3ccc(Oc4ccccc4)cc3)cn2)cc1)NC(=O)c1ccc(C(C)(C)C)s1)C(=O)O] | 1000 | 2.13 | 17 |

TABLE 1-continued

| STRUCTURE | COMPOUND NUMBER | LCMS RETENTION TIME (min) | PURITY METHOD |
|---|---|---|---|
| 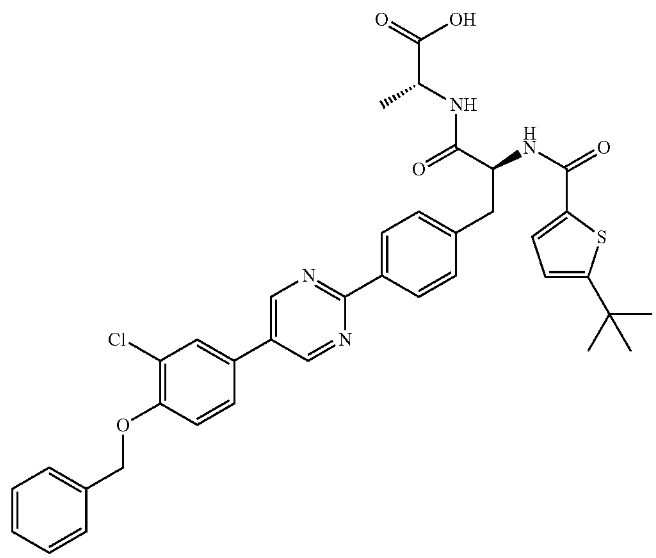 [SMILES: C[C@@H](NC(=O)[C@H](Cc1ccc(-c2ncc(-c3ccc(OCc4ccccc4)c(Cl)c3)cn2)cc1)NC(=O)c1ccc(C(C)(C)C)s1)C(=O)O] | 1001 | 2.38 | 17 |
| 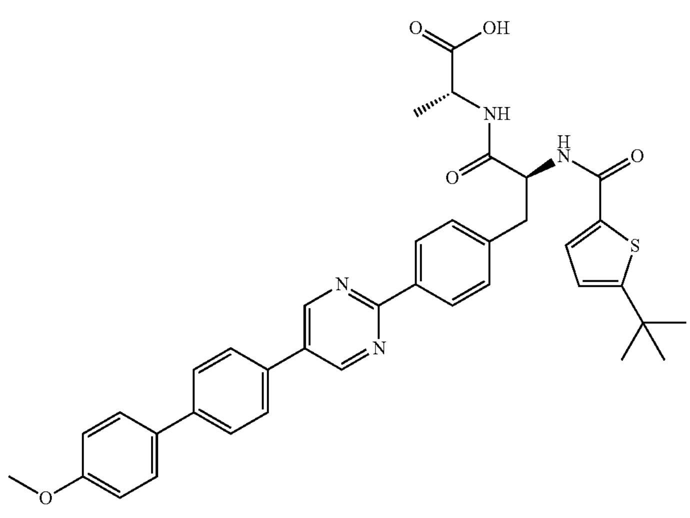 [SMILES: COc1ccc(-c2ccc(-c3cnc(-c4ccc(C[C@H](NC(=O)c5ccc(C(C)(C)C)s5)C(=O)N[C@H](C)C(=O)O)cc4)nc3)cc2)cc1] | 1002 | 1.98 | 17 |

TABLE 1-continued
| STRUCTURE | COMPOUND NUMBER | LCMS RETENTION TIME (min) | PURITY METHOD |
|---|---|---|---|
| 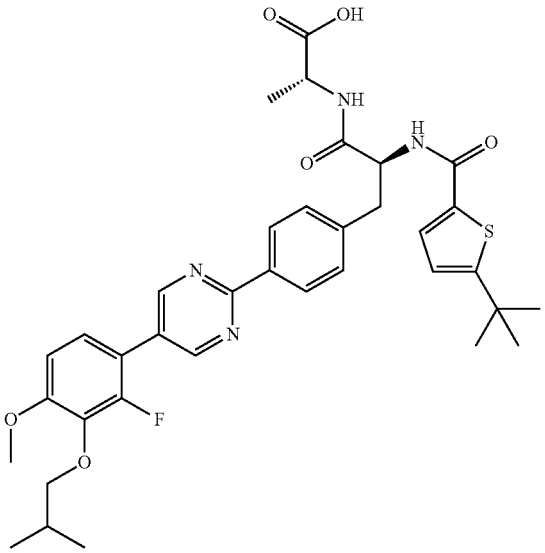 [SMILES: COc1ccc(-c2cnc(-c3ccc(C[C@H](NC(=O)c4ccc(C(C)(C)C)s4)C(=O)N[C@H](C)C(=O)O)cc3)nc2)c(F)c1OCC(C)C] | 1003 | 2.03 | 17 |
| 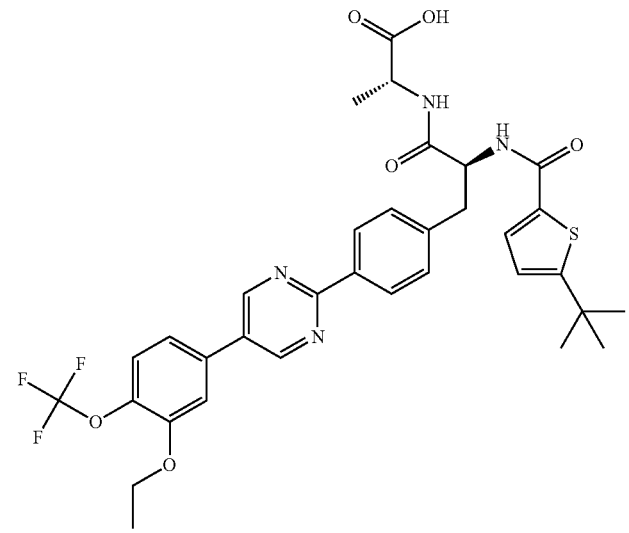 [SMILES: CCOc1cc(-c2cnc(-c3ccc(C[C@H](NC(=O)c4ccc(C(C)(C)C)s4)C(=O)N[C@H](C)C(=O)O)cc3)nc2)ccc1OC(F)(F)F] | 1004 | 2.01 | 17 |

TABLE 1-continued

| STRUCTURE | COMPOUND NUMBER | LCMS RETENTION TIME (min) | PURITY METHOD |
|---|---|---|---|
| 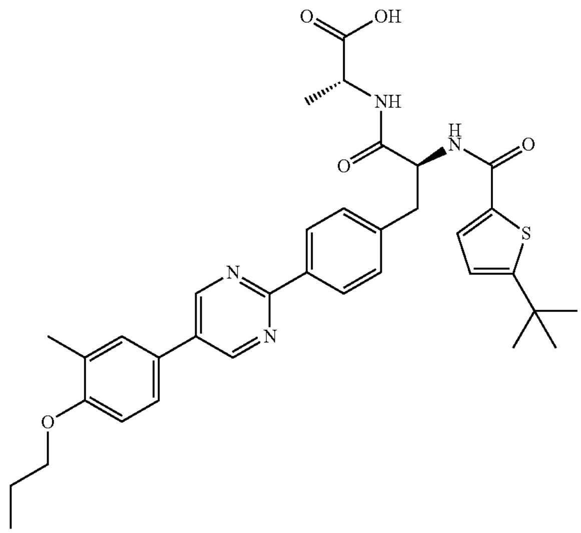 [SMILES: CCCOc1ccc(-c2cnc(-c3ccc(C[C@H](NC(=O)c4ccc(C(C)(C)C)s4)C(=O)N[C@H](C)C(=O)O)cc3)nc2)cc1C] | 1005 | 1.83 | 17 |
| 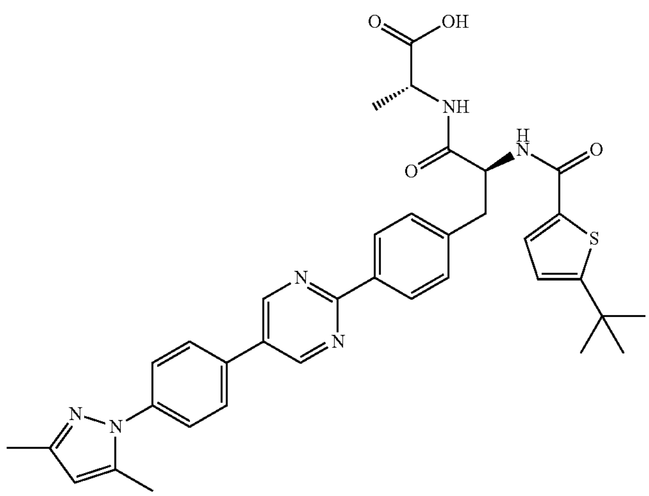 [SMILES: Cc1cc(C)n(-c2ccc(-c3cnc(-c4ccc(C[C@H](NC(=O)c5ccc(C(C)(C)C)s5)C(=O)N[C@H](C)C(=O)O)cc4)nc3)cc2)n1] | 1006 | 1.96 | 17 |
| 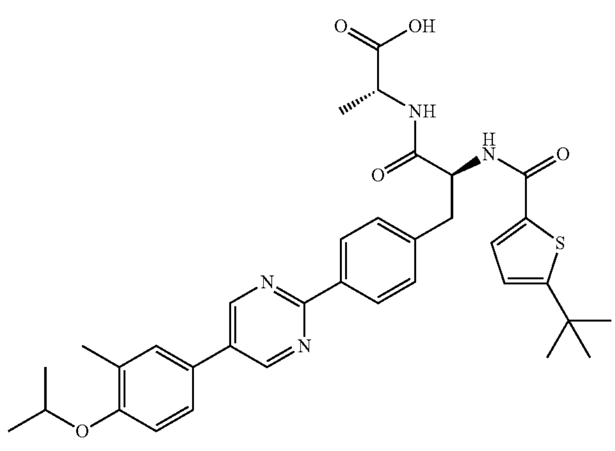 [SMILES: Cc1cc(-c2cnc(-c3ccc(C[C@H](NC(=O)c4ccc(C(C)(C)C)s4)C(=O)N[C@H](C)C(=O)O)cc3)nc2)ccc1OC(C)C] | 1007 | 2.31 | 17 |

TABLE 1-continued
| STRUCTURE | COMPOUND NUMBER | LCMS RETENTION TIME (min) | PURITY METHOD |
|---|---|---|---|
| 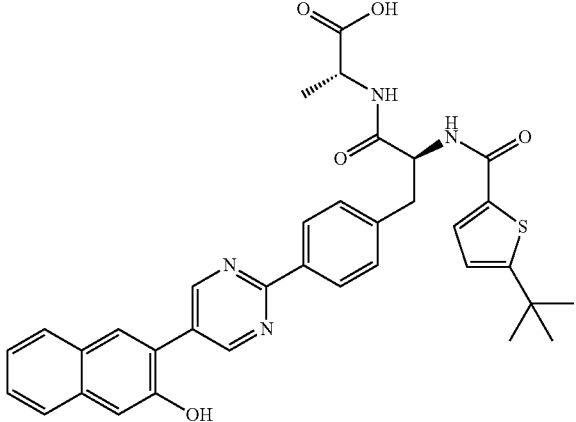 [SMILES: C[C@@H](NC(=O)[C@H](Cc1ccc(-c2ncc(-c3cc4ccccc4cc3O)cn2)cc1)NC(=O)c1ccc(C(C)(C)C)s1)C(=O)O] | 1008 | 2.38 | 21 |
| 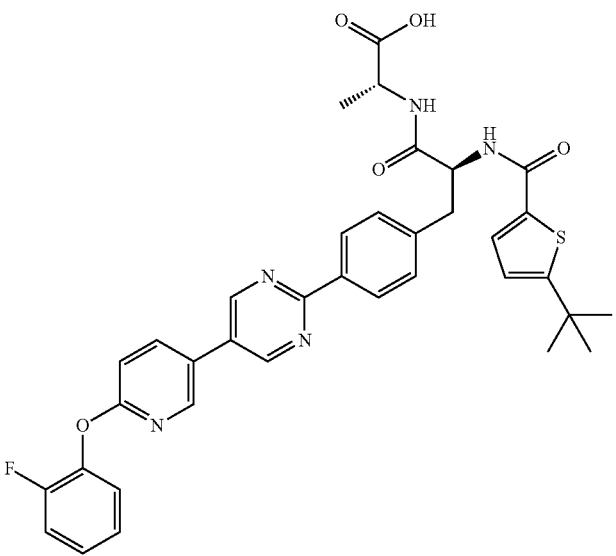 [SMILES: C[C@@H](NC(=O)[C@H](Cc1ccc(-c2ncc(-c3ccc(Oc4ccccc4F)nc3)cn2)cc1)NC(=O)c1ccc(C(C)(C)C)s1)C(=O)O] | 1009 | 2.38 | 18 |
| 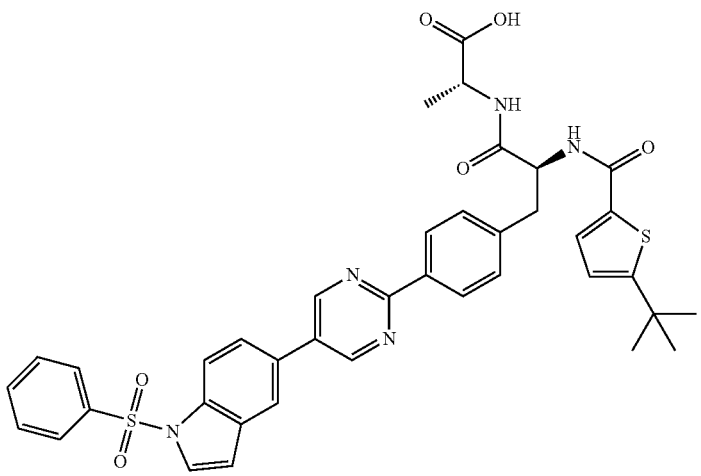 [SMILES: C[C@@H](NC(=O)[C@H](Cc1ccc(-c2ncc(-c3ccc4c(ccn4S(=O)(=O)c4ccccc4)c3)cn2)cc1)NC(=O)c1ccc(C(C)(C)C)s1)C(=O)O] | 1010 | 2.38 | 18 |

TABLE 1-continued
| STRUCTURE | COMPOUND NUMBER | LCMS RETENTION TIME (min) | PURITY METHOD |
|---|---|---|---|
| 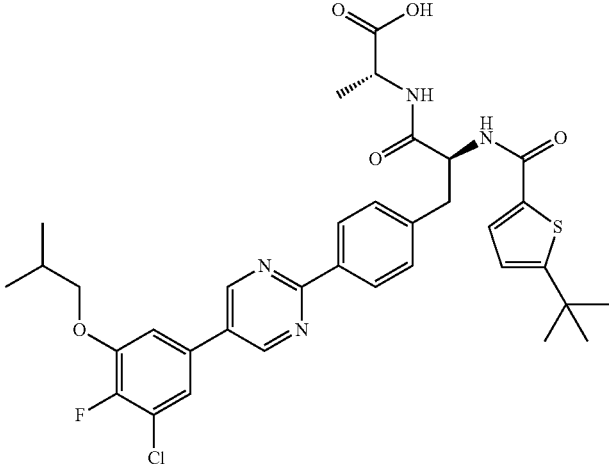 [SMILES: CC(C)COc1cc(-c2cnc(-c3ccc(C[C@H](NC(=O)c4ccc(C(C)(C)C)s4)C(=O)N[C@H](C)C(=O)O)cc3)nc2)cc(Cl)c1F] | 1011 | 2.38 | 17 |
| 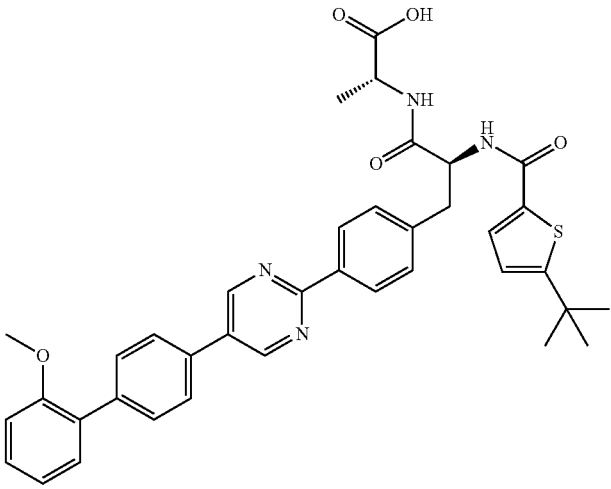 [SMILES: COc1ccccc1-c1ccc(-c2cnc(-c3ccc(C[C@H](NC(=O)c4ccc(C(C)(C)C)s4)C(=O)N[C@H](C)C(=O)O)cc3)nc2)cc1] | 1012 | 2.08 | 17 |
| 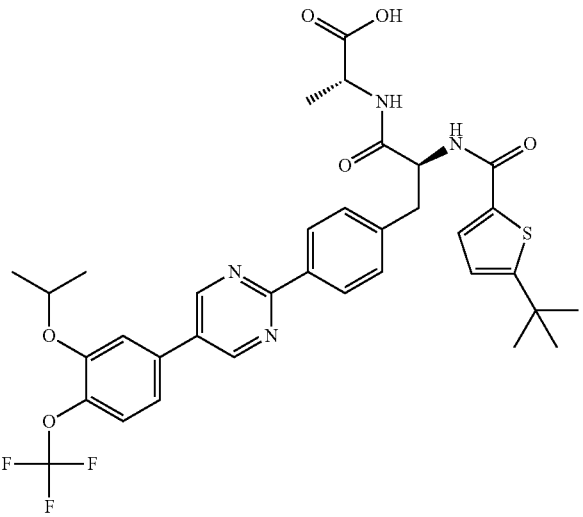 [SMILES: CC(C)Oc1cc(-c2cnc(-c3ccc(C[C@H](NC(=O)c4ccc(C(C)(C)C)s4)C(=O)N[C@H](C)C(=O)O)cc3)nc2)ccc1OC(F)(F)F] | 1013 | 2.22 | 17 |

TABLE 1-continued

| STRUCTURE | COMPOUND NUMBER | LCMS RETENTION TIME (min) | PURITY METHOD |
|---|---|---|---|
| (structure) | 1014 | 2.50 | 17 |
| (structure) | 1015 | 2.45 | 17 |
| (structure) | 1016 | 2.57 | 17 |

TABLE 1-continued

| STRUCTURE | COMPOUND NUMBER | LCMS RETENTION TIME (min) | PURITY METHOD |
|---|---|---|---|
| 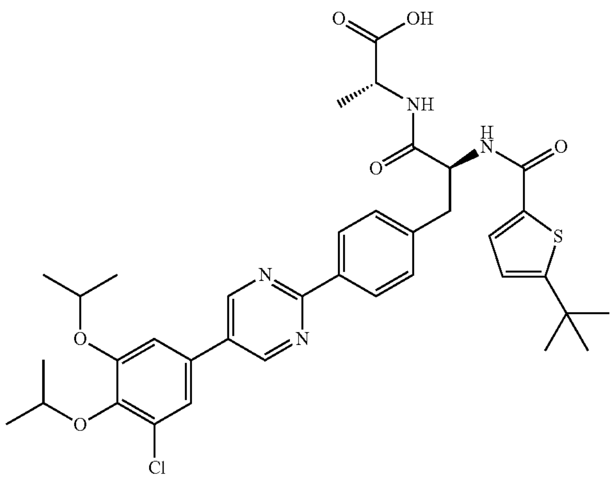 [SMILES: CC(C)Oc1cc(-c2cnc(-c3ccc(C[C@H](NC(=O)c4ccc(C(C)(C)C)s4)C(=O)N[C@H](C)C(=O)O)cc3)nc2)cc(Cl)c1OC(C)C] | 1017 | 2.93 | 17 |
| 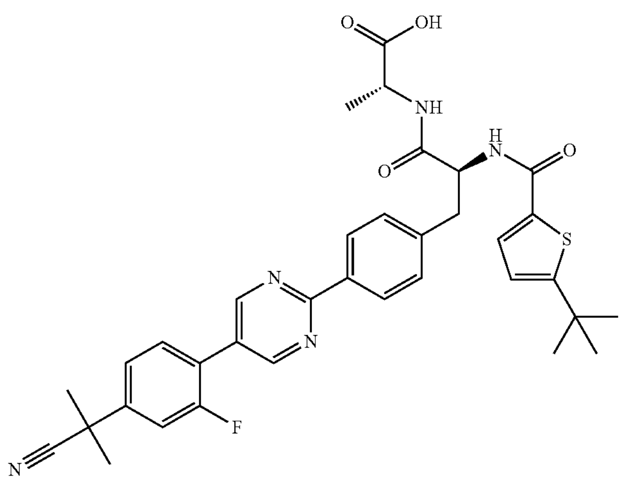 [SMILES: C[C@@H](NC(=O)[C@H](Cc1ccc(-c2ncc(-c3ccc(C(C)(C)C#N)cc3F)cn2)cc1)NC(=O)c1ccc(C(C)(C)C)s1)C(=O)O] | 1018 | 2.35 | 17 |
| 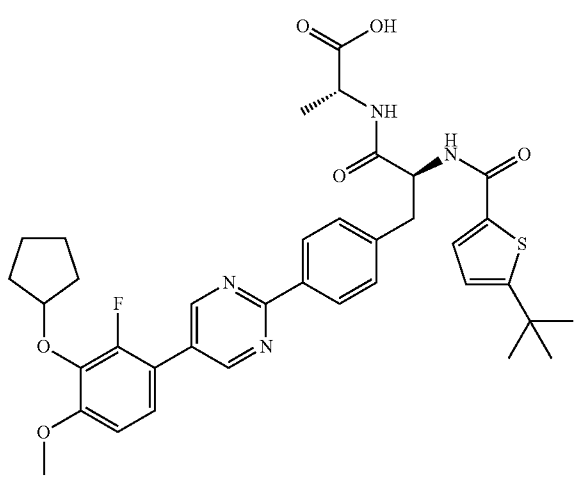 [SMILES: COc1ccc(-c2cnc(-c3ccc(C[C@H](NC(=O)c4ccc(C(C)(C)C)s4)C(=O)N[C@H](C)C(=O)O)cc3)nc2)c(F)c1OC1CCCC1] | 1019 | 2.46 | 17 |

TABLE 1-continued

| STRUCTURE | COMPOUND NUMBER | LCMS RETENTION TIME (min) | PURITY METHOD |
|---|---|---|---|
| 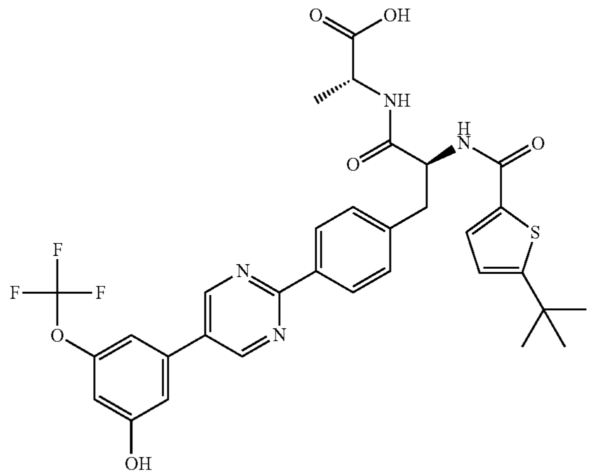 [SMILES: C[C@@H](NC(=O)[C@H](Cc1ccc(-c2ncc(-c3cc(O)cc(OC(F)(F)F)c3)cn2)cc1)NC(=O)c1ccc(C(C)(C)C)s1)C(=O)O] | 1020 | 2.35 | 17 |
| 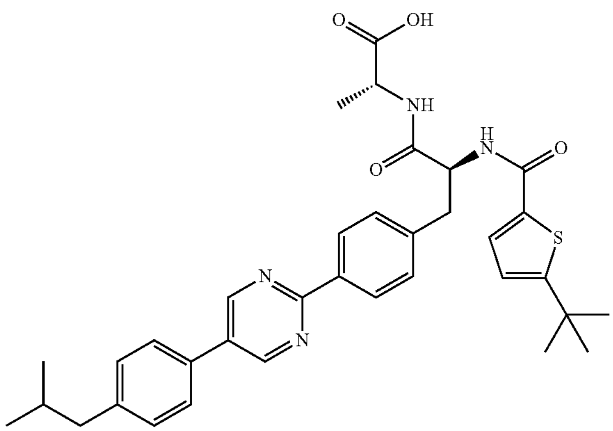 [SMILES: CC(C)Cc1ccc(-c2cnc(-c3ccc(C[C@H](NC(=O)c4ccc(C(C)(C)C)s4)C(=O)N[C@H](C)C(=O)O)cc3)nc2)cc1] | 1021 | 2.88 | 17 |
| 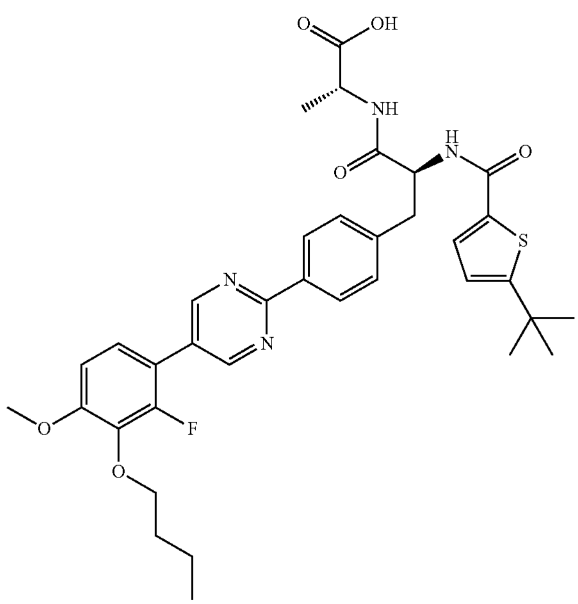 [SMILES: CCCCOc1c(OC)ccc(-c2cnc(-c3ccc(C[C@H](NC(=O)c4ccc(C(C)(C)C)s4)C(=O)N[C@H](C)C(=O)O)cc3)nc2)c1F] | 1022 | 2.67 | 17 |

TABLE 1-continued

| STRUCTURE | COMPOUND NUMBER | LCMS RETENTION TIME (min) | PURITY METHOD |
|---|---|---|---|
| 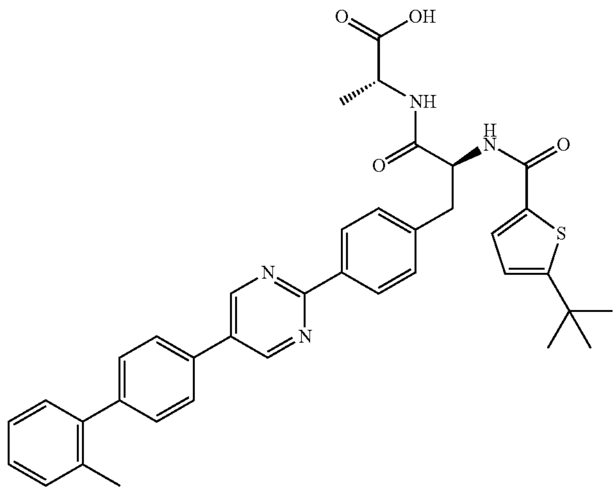 [SMILES: Cc1ccccc1-c1ccc(-c2cnc(-c3ccc(C[C@H](NC(=O)c4ccc(C(C)(C)C)s4)C(=O)N[C@H](C)C(=O)O)cc3)nc2)cc1] | 1023 | 2.83 | 17 |
| 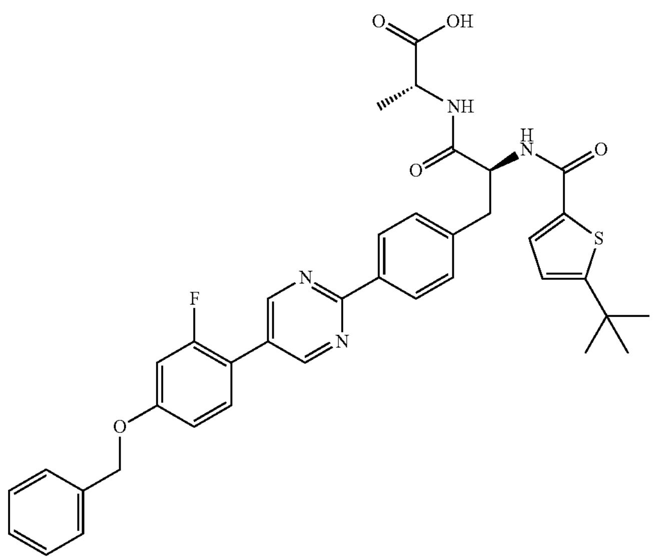 [SMILES: C[C@@H](NC(=O)[C@H](Cc1ccc(-c2ncc(-c3ccc(OCc4ccccc4)cc3F)cn2)cc1)NC(=O)c1ccc(C(C)(C)C)s1)C(=O)O] | 1024 | 2.70 | 17 |
| 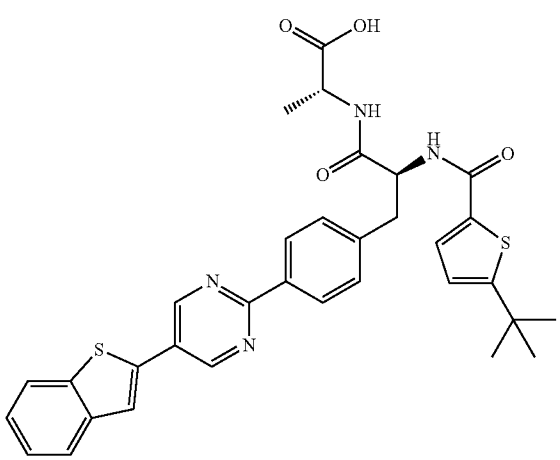 [SMILES: C[C@@H](NC(=O)[C@H](Cc1ccc(-c2ncc(-c3cc4ccccc4s3)cn2)cc1)NC(=O)c1ccc(C(C)(C)C)s1)C(=O)O] | 1025 | 2.65 | 17 |

TABLE 1-continued

| STRUCTURE | COMPOUND NUMBER | LCMS RETENTION TIME (min) | PURITY METHOD |
|---|---|---|---|
| 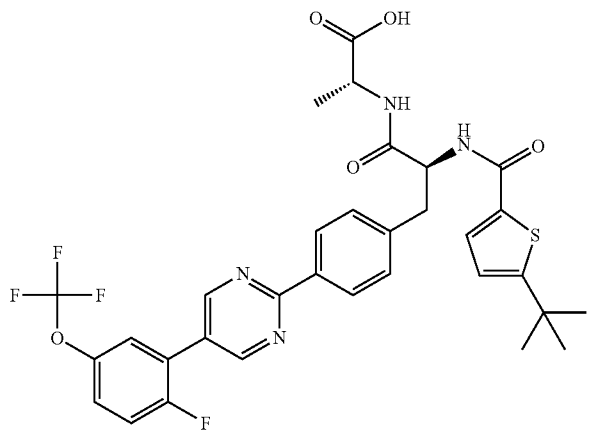 [SMILES: C[C@@H](NC(=O)[C@H](Cc1ccc(-c2ncc(-c3cc(OC(F)(F)F)ccc3F)cn2)cc1)NC(=O)c1ccc(C(C)(C)C)s1)C(=O)O] | 1026 | 2.60 | 18 |
| 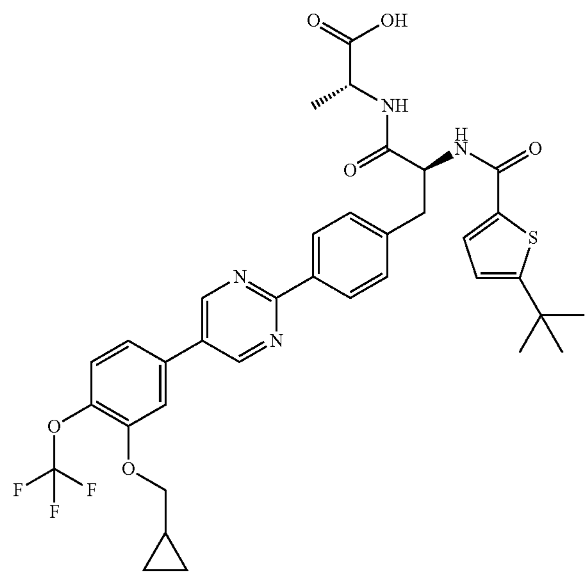 [SMILES: C[C@@H](NC(=O)[C@H](Cc1ccc(-c2ncc(-c3ccc(OC(F)(F)F)c(OCC4CC4)c3)cn2)cc1)NC(=O)c1ccc(C(C)(C)C)s1)C(=O)O] | 1027 | 2.87 | 19 |
| 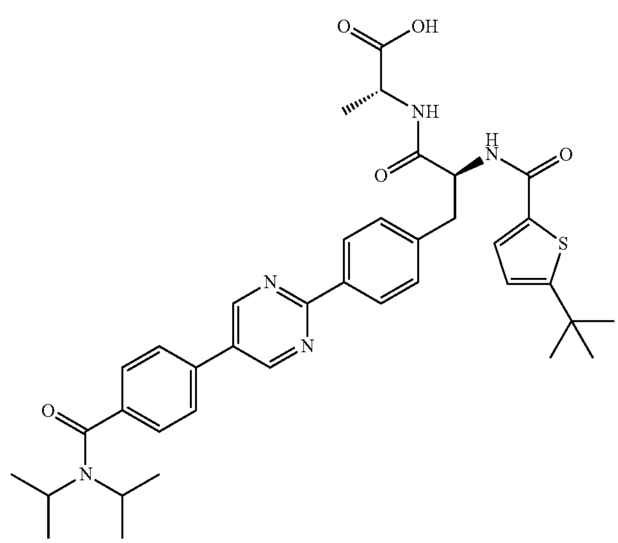 [SMILES: CC(C)N(C(=O)c1ccc(-c2cnc(-c3ccc(C[C@H](NC(=O)c4ccc(C(C)(C)C)s4)C(=O)N[C@H](C)C(=O)O)cc3)nc2)cc1)C(C)C] | 1028 | 2.40 | 19 |

TABLE 1-continued
| STRUCTURE | COMPOUND NUMBER | LCMS RETENTION TIME (min) | PURITY METHOD |
|---|---|---|---|
| 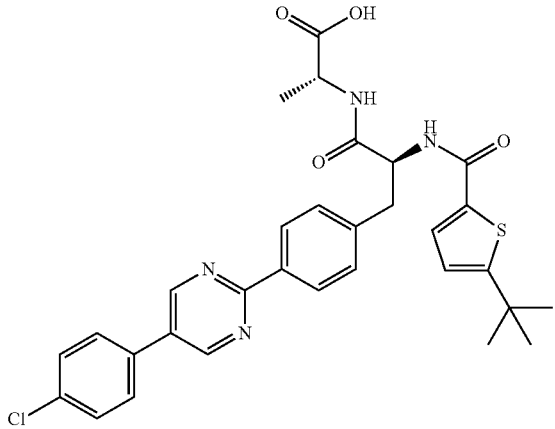 [SMILES: C[C@@H](NC(=O)[C@H](Cc1ccc(-c2ncc(-c3ccc(Cl)cc3)cn2)cc1)NC(=O)c1ccc(C(C)(C)C)s1)C(=O)O] | 1029 | 2.53 | 18 |
| 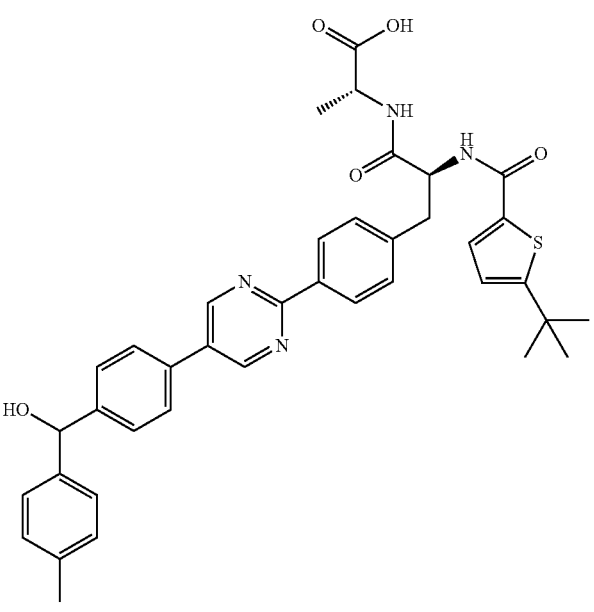 [SMILES: Cc1ccc(C(O)c2ccc(-c3cnc(-c4ccc(C[C@H](NC(=O)c5ccc(C(C)(C)C)s5)C(=O)N[C@H](C)C(=O)O)cc4)nc3)cc2)cc1] | 1030 | 2.40 | 18 |

TABLE 1-continued
| STRUCTURE | COMPOUND NUMBER | LCMS RETENTION TIME (min) | PURITY METHOD |
|---|---|---|---|
| 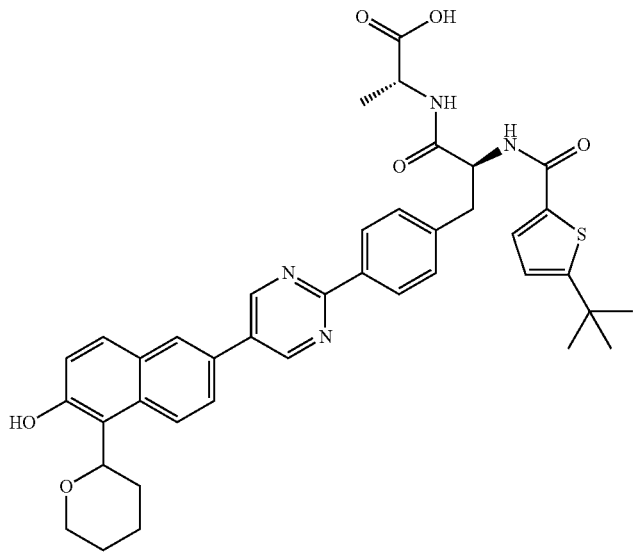 [SMILES: C[C@@H](NC(=O)[C@H](Cc1ccc(-c2ncc(-c3ccc4c(C5CCCCO5)c(O)ccc4c3)cn2)cc1)NC(=O)c1ccc(C(C)(C)C)s1)C(=O)O] | 1031 | 2.68 | 18 |
| 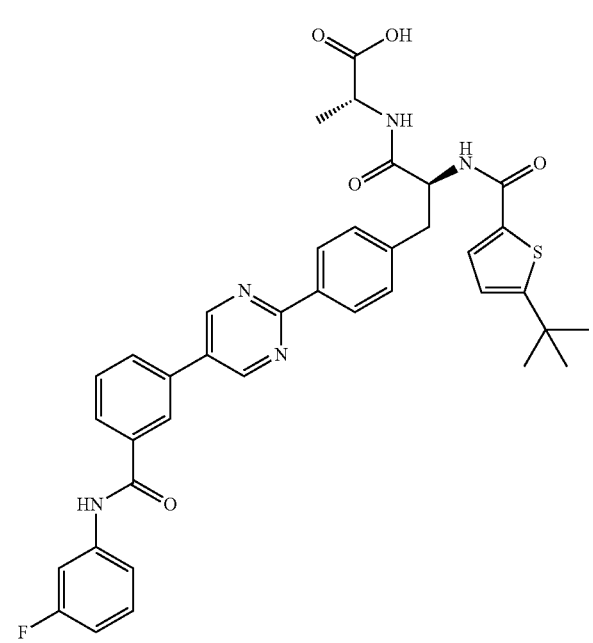 [SMILES: C[C@@H](NC(=O)[C@H](Cc1ccc(-c2ncc(-c3cccc(C(=O)Nc4cccc(F)c4)c3)cn2)cc1)NC(=O)c1ccc(C(C)(C)C)s1)C(=O)O] | 1032 | 2.43 | 17 |

TABLE 1-continued

| STRUCTURE | COMPOUND NUMBER | LCMS RETENTION TIME (min) | PURITY METHOD |
|---|---|---|---|
| 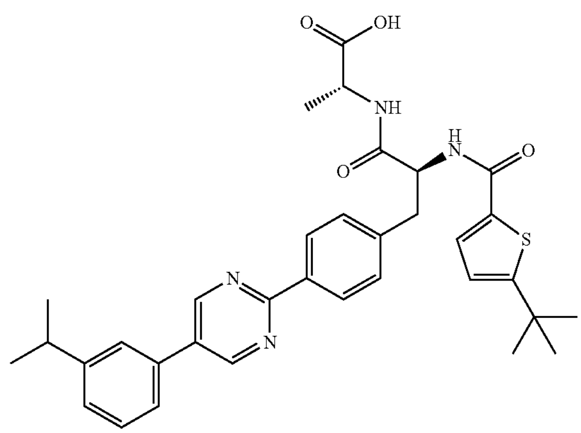 [SMILES: CC(C)c1cccc(-c2cnc(-c3ccc(C[C@H](NC(=O)c4ccc(C(C)(C)C)s4)C(=O)N[C@H](C)C(=O)O)cc3)nc2)c1] | 1033 | 2.73 | 17 |
| 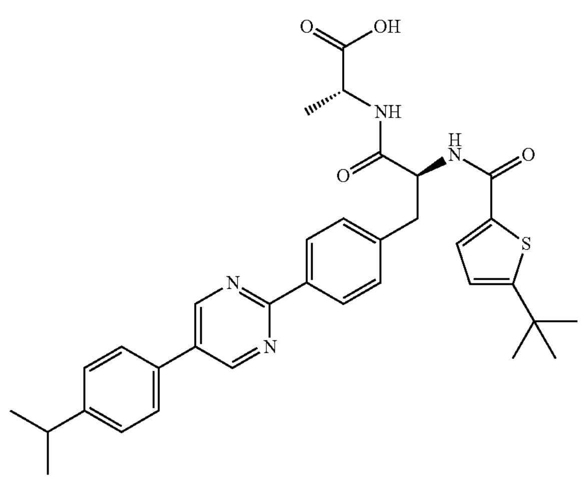 [SMILES: CC(C)c1ccc(-c2cnc(-c3ccc(C[C@H](NC(=O)c4ccc(C(C)(C)C)s4)C(=O)N[C@H](C)C(=O)O)cc3)nc2)cc1] | 1034 | 2.72 | 17 |
| 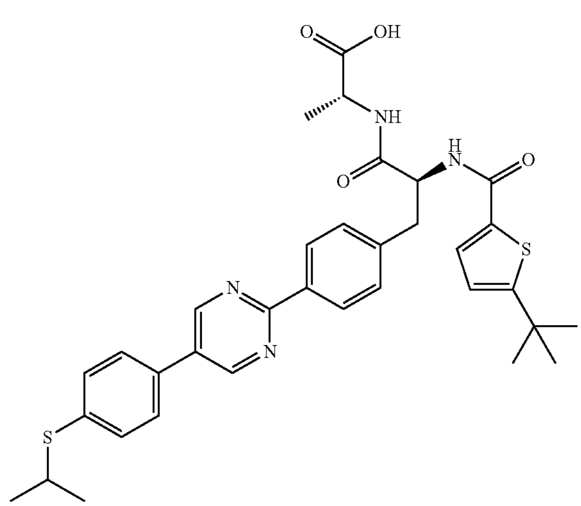 [SMILES: CC(C)Sc1ccc(-c2cnc(-c3ccc(C[C@H](NC(=O)c4ccc(C(C)(C)C)s4)C(=O)N[C@H](C)C(=O)O)cc3)nc2)cc1] | 1035 | 2.73 | 17 |

TABLE 1-continued
| STRUCTURE | COMPOUND NUMBER | LCMS RETENTION TIME (min) | PURITY METHOD |
|---|---|---|---|
| 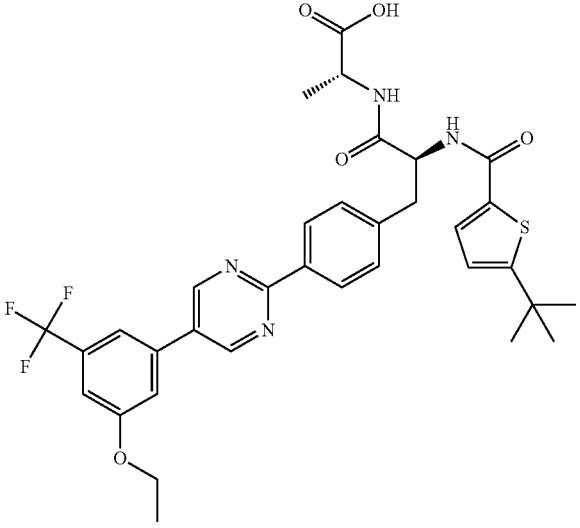 [SMILES: CCOc1cc(-c2cnc(-c3ccc(C[C@H](NC(=O)c4ccc(C(C)(C)C)s4)C(=O)N[C@H](C)C(=O)O)cc3)nc2)cc(C(F)(F)F)c1] | 1036 | 2.75 | 18 |
| 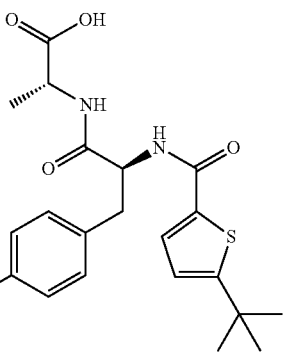 | 1037 | 2.80 | 18 |

TABLE 1-continued

| STRUCTURE | COMPOUND NUMBER | LCMS RETENTION TIME (min) | PURITY METHOD |
|---|---|---|---|
| 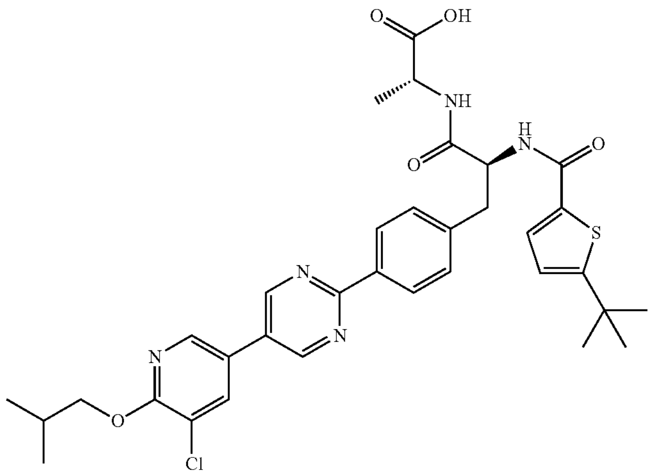 [SMILES: CC(C)COc1ncc(-c2cnc(-c3ccc(C[C@H](NC(=O)c4ccc(C(C)(C)C)s4)C(=O)N[C@H](C)C(=O)O)cc3)nc2)cc1Cl] | 1038 | 2.90 | 17 |
| 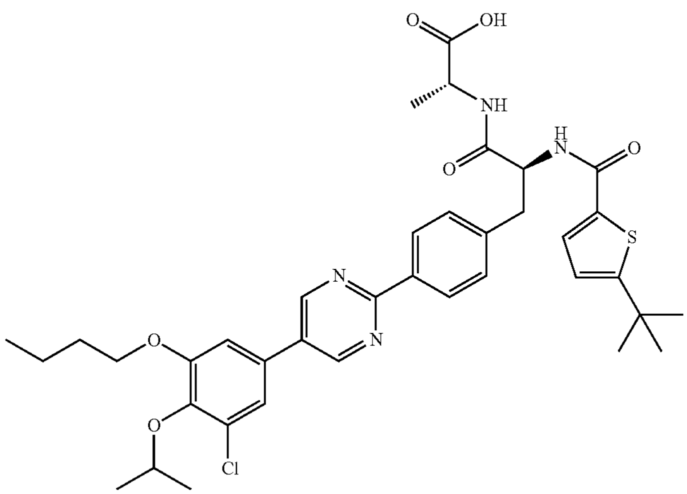 [SMILES: CCCCOc1cc(-c2cnc(-c3ccc(C[C@H](NC(=O)c4ccc(C(C)(C)C)s4)C(=O)N[C@H](C)C(=O)O)cc3)nc2)cc(Cl)c1OC(C)C] | 1039 | 3.18 | 17 |
| 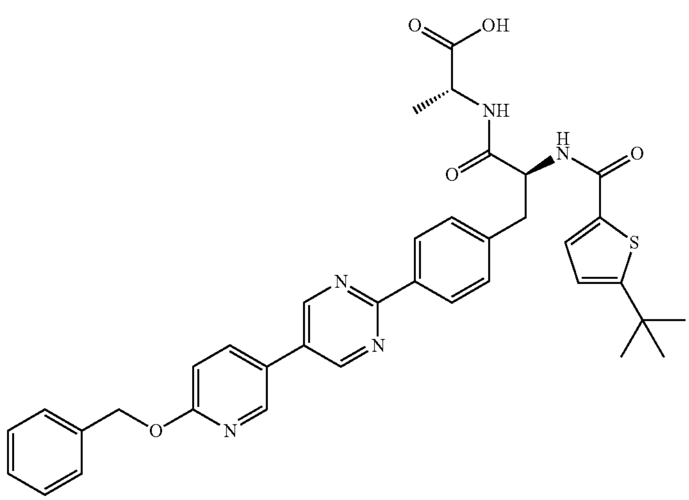 [SMILES: C[C@@H](NC(=O)[C@H](Cc1ccc(-c2ncc(-c3ccc(OCc4ccccc4)nc3)cn2)cc1)NC(=O)c1ccc(C(C)(C)C)s1)C(=O)O] | 1040 | 2.63 | 17 |

TABLE 1-continued

| STRUCTURE | COMPOUND NUMBER | LCMS RETENTION TIME (min) | PURITY METHOD |
|---|---|---|---|
| 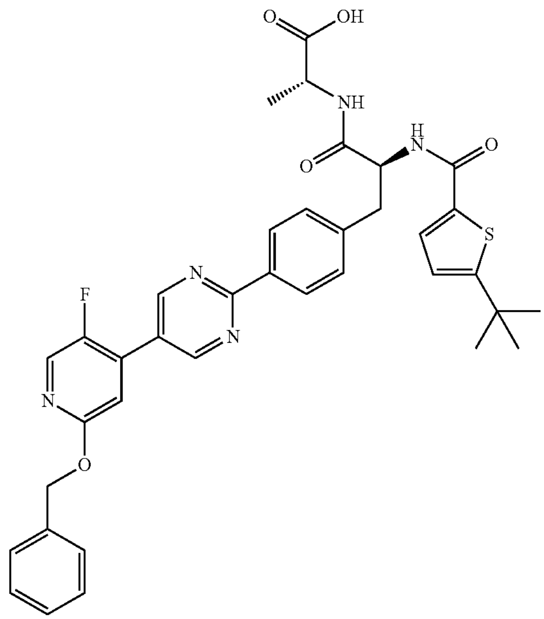 [SMILES: C[C@@H](NC(=O)[C@H](Cc1ccc(-c2ncc(-c3cc(OCc4ccccc4)ncc3F)cn2)cc1)NC(=O)c1ccc(C(C)(C)C)s1)C(=O)O] | 1041 | 2.73 | 17 |
| 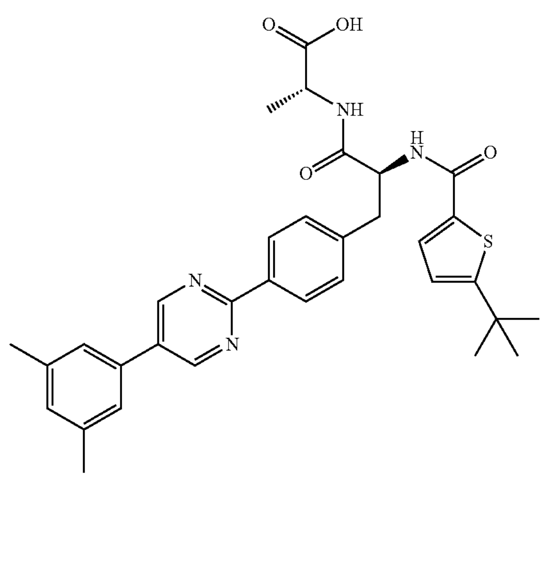 [SMILES: Cc1cc(C)cc(-c2cnc(-c3ccc(C[C@H](NC(=O)c4ccc(C(C)(C)C)s4)C(=O)N[C@H](C)C(=O)O)cc3)nc2)c1] | 1042 | 2.67 | 17 |

TABLE 1-continued
| STRUCTURE | COMPOUND NUMBER | LCMS RETENTION TIME (min) | PURITY METHOD |
|---|---|---|---|
| 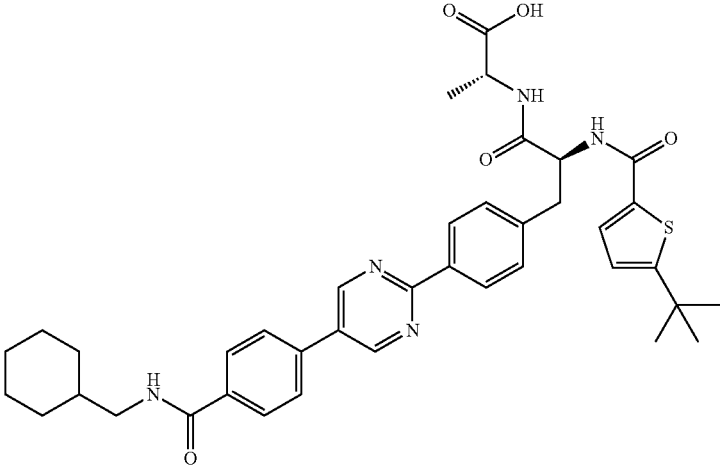 [SMILES: C[C@@H](NC(=O)[C@H](Cc1ccc(-c2ncc(-c3ccc(C(=O)NCC4CCCCC4)cc3)cn2)cc1)NC(=O)c1ccc(C(C)(C)C)s1)C(=O)O] | 1043 | 2.47 | 17 |
| 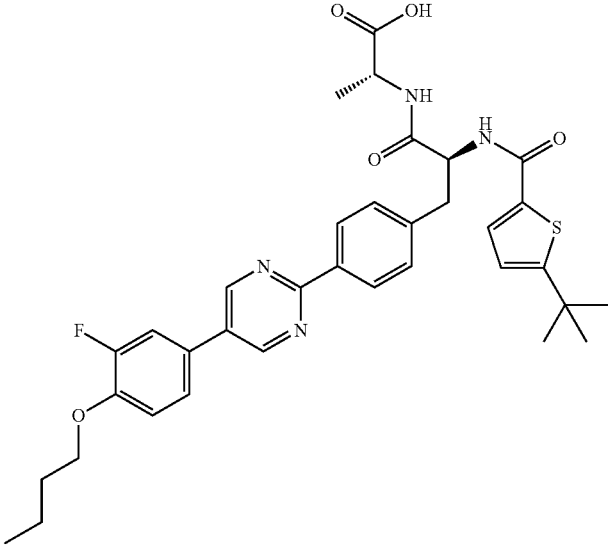 [SMILES: CCCCOc1ccc(-c2cnc(-c3ccc(C[C@H](NC(=O)c4ccc(C(C)(C)C)s4)C(=O)N[C@H](C)C(=O)O)cc3)nc2)cc1F] | 1044 | 2.80 | 17 |

TABLE 1-continued

| STRUCTURE | COMPOUND NUMBER | LCMS RETENTION TIME (min) | PURITY METHOD |
|---|---|---|---|
| (structure) | 1045 | 2.75 | 17 |
| (structure) | 1046 | 2.98 | 17 |
| (structure) | 1047 | 2.01 | 19 |

TABLE 1-continued

| STRUCTURE | COMPOUND NUMBER | LCMS RETENTION TIME (min) | PURITY METHOD |
|---|---|---|---|
| 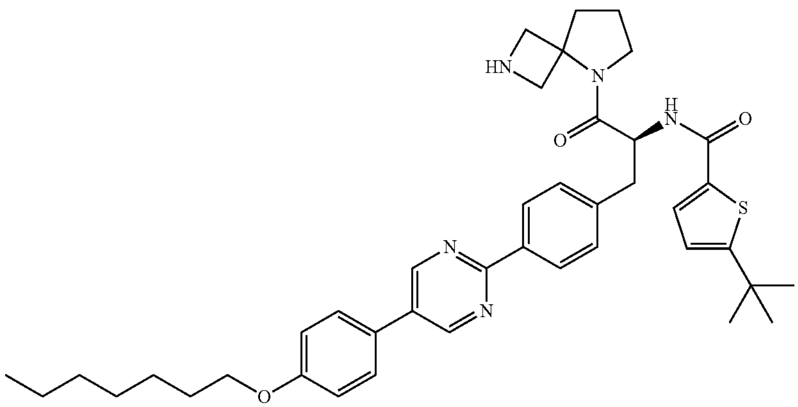 [SMILES: CCCCCCCOc1ccc(-c2cnc(-c3ccc(C[C@H](NC(=O)c4ccc(C(C)(C)C)s4)C(=O)N4CCCC45CNC5)cc3)nc2)cc1] | 1048 | 2.38 | 17 |
| 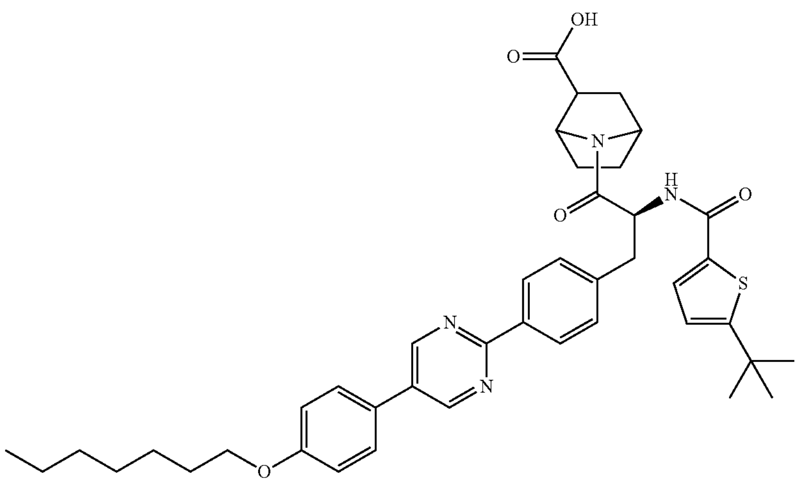 [SMILES: CCCCCCCOc1ccc(-c2cnc(-c3ccc(C[C@H](NC(=O)c4ccc(C(C)(C)C)s4)C(=O)N4C5CCC4C(C(=O)O)C5)cc3)nc2)cc1] | 1049 | 1.80 | 20 |
| 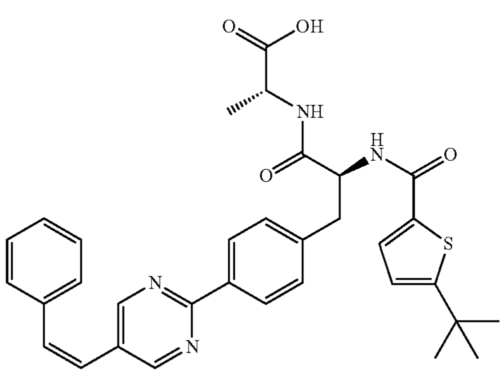 [SMILES: C[C@@H](NC(=O)[C@H](Cc1ccc(-c2ncc(/C=C\c3ccccc3)cn2)cc1)NC(=O)c1ccc(C(C)(C)C)s1)C(=O)O] | 1050 | 1.71 | 17 |

TABLE 1-continued

| STRUCTURE | COMPOUND NUMBER | LCMS RETENTION TIME (min) | PURITY METHOD |
|---|---|---|---|
| 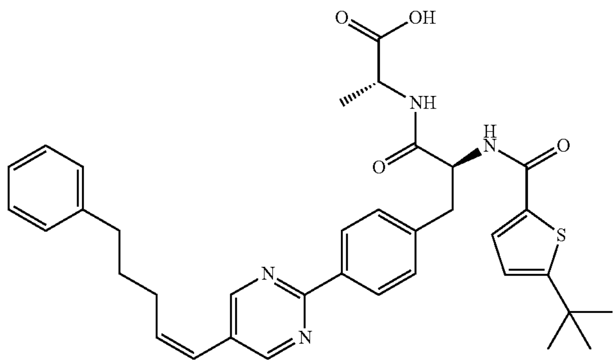 [SMILES: C[C@@H](NC(=O)[C@H](Cc1ccc(-c2ncc(/C=C\CCCc3ccccc3)cn2)cc1)NC(=O)c1ccc(C(C)(C)C)s1)C(=O)O] | 1051 | 2.38 | 18 |
| 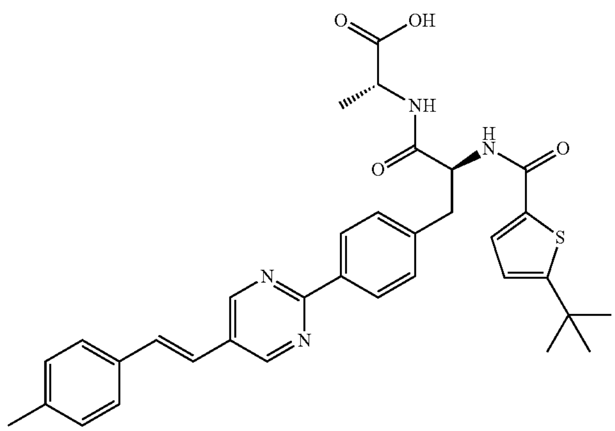 [SMILES: Cc1ccc(/C=C/c2cnc(-c3ccc(C[C@H](NC(=O)c4ccc(C(C)(C)C)s4)C(=O)N[C@H](C)C(=O)O)cc3)nc2)cc1] | 1052 | 2.90 | 17 |
| 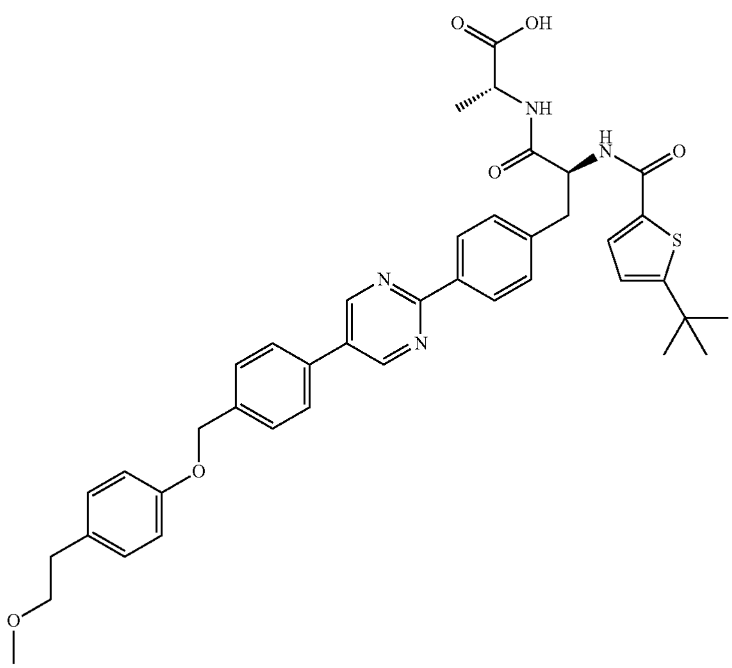 [SMILES: COCCc1ccc(OCc2ccc(-c3cnc(-c4ccc(C[C@H](NC(=O)c5ccc(C(C)(C)C)s5)C(=O)N[C@H](C)C(=O)O)cc4)nc3)cc2)cc1] | 1053 | 2.70 | 17 |

TABLE 1-continued

| STRUCTURE | COMPOUND NUMBER | LCMS RETENTION TIME (min) | PURITY METHOD |
|---|---|---|---|
| 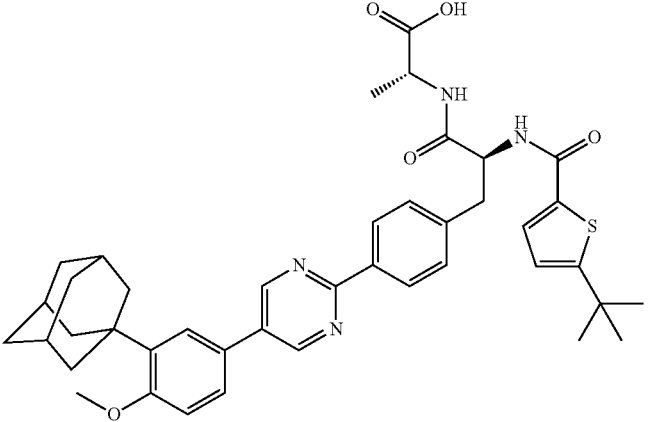 [SMILES: COc1ccc(-c2cnc(-c3ccc(C[C@H](NC(=O)c4ccc(C(C)(C)C)s4)C(=O)N[C@H](C)C(=O)O)cc3)nc2)cc1C12CC3CC(CC(C3)C1)C2] | 1054 | 3.43 | 17 |
| 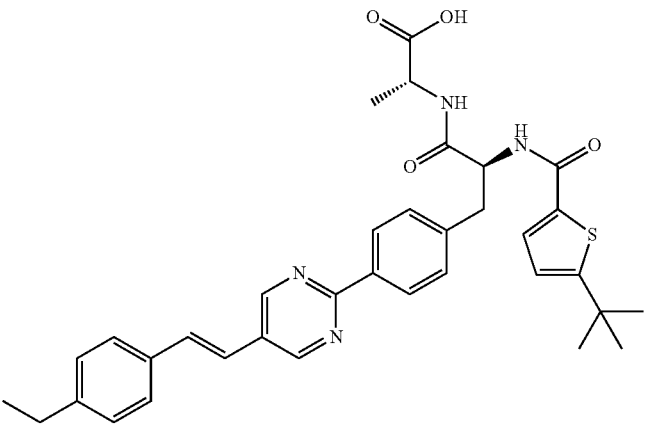 [SMILES: CCc1ccc(/C=C/c2cnc(-c3ccc(C[C@H](NC(=O)c4ccc(C(C)(C)C)s4)C(=O)N[C@H](C)C(=O)O)cc3)nc2)cc1] | 1055 | 2.78 | 17 |

Biological Assays

Assay Procedures

GLP-1 PAM Shift cAMP Assay: Dose Response of Peptide Ligand in Presence of Fixed Concentration of Compound.

A GLP-1R expressing CRB-bla CHO-K1 cell line was purchased from Invitrogen. Cells were seeded into 384-well white flat bottom plates at 5000 cells/well/20 µL growth media (DMEM-High glucose, 10% dialyzed FBS, 0.1 mM NEAA, 25 mM Hepes, 100 U/mL penicillin/100 µg/mL streptomycin, 5 µg/mL Blasticidin, 600 µg/mL Hygromycin) and incubated for 18 h at 37° C. in 5% $CO_2$. Growth medium was replaced with 12 µL assay buffer (Hanks Balanced Salt solution, 10 mM Hepes, 0.1% BSA, pH 7.4). A 5× peptide dose response curve (12-point) was generated in assay buffer containing 1.5 mM IBMX, 12.5% DMSO, and 50 µM compound. Peptide ligand was GLP-1 (9-36). The 5× peptide dose response plus compound mix was added (3 µL) and cells were incubated for 30 min at 37° C. Direct detection of cAMP was carried out using DiscoveRx HitHunter cAMP kit according to manufacturer's instructions and luminescence was read using a SpectraMax M5 plate reader. Luminescence was analyzed by non-linear regression to determine the $EC_{50}$ and Emax. A GLP-1(7-36) dose response was included to determine maximum efficacy.

$EC_{20}$ GLP-1(9-36) PAM cAMP Assay: Dose Response of Compound in the Presence of Fixed Concentration of GLP-1(9-36).

GLP-1R CRE-bla CHO-K1 cells cultured in growth medium (DMEM-High glucose, 10% dialyzed FBS, 0.1 mM NEAA, 25 mM Hepes, 100 U/mL penicillin/100 µg/mL streptomycin, 5 µg/mL Blasticidin, 600 µg/mL Hygromycin) were trypsinized and plated in suspension into 384 well white flat bottom plates at 5000 cells/well in 12 µL assay buffer (Hanks Balanced Salt solution, 10 mM hepes, 0.1% BSA, pH 7.4). A 5× compound dose response curve (12-point) was generated in assay buffer containing 1.5 mM IBMX, 4% DMSO. GLP-1(9-36) was diluted to 4.2 M in assay buffer containing 1.5 mM IMBX and 4% DMSO. The 5× compound dose response was added (3 µL), followed by 0.5 µL of GLP-1(9-36) and cells were incubated for 30 min at 37° C. Direct detection of cAMP was carried out using DiscoveRx HitHunter cAMP kit according to manufacturer's instructions and luminescence was read using a SpectraMax M5 plate reader. Luminescence was converted to total cAMP using a cAMP standard curve and data was analyzed by non-linear regression to determine the $EC_{50}$ and Emax.

Peptide Sequences

GLP-1(7-36): HAEGTFTSDVSSYLEGQAAKEFI-AWLVKGR-NH$_2$ (SEQ ID NO: 2) GLP-1(9-36): EGTFTSDVSSYLEGQAAKEFIAWLVKGR-NH$_2$ (SEQ ID NC: 3) GLP-1(7-36) was purchased from GenScript. GLP-1(9-36) was purchased from Biopeptide Co., Inc.

Reported GLP-1 Activity

Activity data for selected GLP-1 modulators are displayed in Table 2. The EC$_{20}$GLP-1(9-36) PAM Activity range is denoted as follows: + denotes activity <0.8 μM, ++ denotes activity between 0.8 and 2.5 μM, +++ denotes activity between 2.5 and 5 μM, and ++++ denotes activity 5 to 10 μM.

TABLE 2

| COMPOUND NUMBER | EC$_{20}$ GLP-1(9-36) PAM EC$_{50}$ |
|---|---|
| 1 | ++ |
| 2 | +++ |
| 3 | ++++ |
| 4 | ++++ |
| 5 | +++ |
| 6 | ++++ |
| 7 | ++++ |
| 8 | ++ |
| 9 | ++++ |
| 10 | +++ |
| 11 | ++ |
| 13 | ++ |
| 14 | +++ |
| 15 | +++ |
| 16 | ++++ |
| 17 | +++ |
| 18 | ++ |
| 19 | ++ |
| 20 | ++ |
| 21 | +++ |
| 22 | +++ |
| 23 | +++ |
| 24 | ++ |
| 25 | ++ |
| 26 | +++ |
| 27 | ++ |
| 28 | +++ |
| 29 | ++ |
| 30 | ++ |
| 31 | ++ |
| 32 | ++++ |
| 33 | +++ |
| 34 | +++ |
| 35 | +++ |
| 36 | +++ |
| 37 | +++ |
| 38 | ++ |
| 39 | ++ |
| 40 | +++ |
| 41 | +++ |
| 42 | +++ |
| 43 | +++ |
| 44 | +++ |
| 45 | ++ |
| 46 | ++ |
| 47 | +++ |
| 48 | ++++ |
| 49 | ++++ |
| 50 | +++ |
| 51 | +++ |
| 52 | ++ |
| 53 | +++ |
| 54 | +++ |
| 55 | +++ |
| 56 | +++ |
| 57 | +++ |
| 58 | +++ |
| 59 | +++ |
| 60 | +++ |

TABLE 2-continued

| COMPOUND NUMBER | EC$_{20}$ GLP-1(9-36) PAM EC$_{50}$ |
|---|---|
| 61 | +++ |
| 62 | +++ |
| 63 | ++ |
| 64 | ++ |
| 65 | +++ |
| 66 | +++ |
| 67 | ++ |
| 68 | +++ |
| 69 | ++++ |
| 70 | ++++ |
| 71 | +++ |
| 72 | ++++ |
| 73 | ++ |
| 74 | +++ |
| 75 | +++ |
| 76 | ++ |
| 77 | ++ |
| 78 | ++ |
| 79 | ++ |
| 80 | ++ |
| 81 | ++++ |
| 82 | ++ |
| 83 | ++ |
| 84 | ++ |
| 85 | ++ |
| 86 | ++ |
| 87 | ++ |
| 88 | ++++ |
| 89 | ++ |
| 90 | +++ |
| 91 | ++ |
| 92 | ++ |
| 93 | ++++ |
| 94 | ++ |
| 95 | ++ |
| 96 | +++ |
| 97 | ++ |
| 98 | ++ |
| 99 | ++ |
| 100 | ++ |
| 101 | ++ |
| 102 | ++ |
| 104 | ++ |
| 105 | ++++ |
| 106 | ++ |
| 107 | ++ |
| 108 | ++ |
| 109 | ++ |
| 110 | ++ |
| 111 | ++ |
| 112 | ++ |
| 113 | ++ |
| 114 | ++ |
| 115 | ++ |
| 116 | ++ |
| 117 | + |
| 118 | + |
| 119 | + |
| 120 | ++ |
| 121 | ++ |
| 122 | ++ |
| 123 | ++ |
| 124 | ++ |
| 125 | ++ |
| 126 | ++ |
| 127 | ++ |
| 128 | ++ |
| 129 | ++ |
| 130 | + |
| 131 | ++ |
| 132 | ++ |
| 133 | ++ |
| 134 | ++ |
| 135 | ++ |
| 136 | ++++ |
| 137 | ++ |
| 138 | ++ |

TABLE 2-continued

| COMPOUND NUMBER | EC$_{20}$ GLP-1(9-36) PAM EC$_{50}$ |
|---|---|
| 139 | ++ |
| 140 | +++ |
| 141 | ++ |
| 142 | + |
| 143 | + |
| 144 | ++ |
| 145 | ++ |
| 146 | +++ |
| 147 | +++ |
| 148 | ++ |
| 149 | ++ |
| 150 | ++ |
| 151 | ++ |
| 152 | ++ |
| 153 | ++ |
| 154 | + |
| 155 | ++ |
| 156 | ++ |
| 157 | ++ |
| 158 | + |
| 159 | ++ |
| 160 | ++ |
| 161 | ++ |
| 162 | ++ |
| 163 | ++ |
| 164 | ++ |
| 165 | ++ |
| 166 | ++ |
| 167 | ++ |
| 168 | ++ |
| 169 | ++++ |
| 170 | ++ |
| 171 | ++ |
| 172 | ++ |
| 173 | ++ |
| 174 | + |
| 175 | + |
| 176 | ++++ |
| 177 | ++ |
| 178 | ++ |
| 179 | ++++ |
| 180 | + |
| 181 | ++ |
| 182 | ++ |
| 183 | ++ |
| 184 | ++ |
| 185 | ++ |
| 186 | ++ |
| 187 | +++ |
| 188 | +++ |
| 189 | ++ |
| 190 | +++ |
| 191 | ++ |
| 192 | + |
| 193 | ++ |
| 194 | ++ |
| 195 | ++ |
| 196 | +++ |
| 197 | +++ |
| 198 | ++++ |
| 199 | ++ |
| 200 | +++ |
| 201 | +++ |
| 202 | ++++ |
| 203 | ++++ |
| 204 | +++ |
| 205 | ++ |
| 206 | +++ |
| 207 | +++ |
| 208 | +++ |
| 209 | ++ |
| 210 | +++ |
| 211 | ++++ |
| 212 | ++++ |
| 213 | +++ |
| 214 | +++ |
| 215 | +++ |

TABLE 2-continued

| COMPOUND NUMBER | EC$_{20}$ GLP-1(9-36) PAM EC$_{50}$ |
|---|---|
| 216 | +++ |
| 217 | ++++ |
| 218 | +++ |
| 219 | ++ |
| 220 | +++ |
| 221 | +++ |
| 222 | ++ |
| 223 | ++ |
| 224 | ++ |
| 225 | + |
| 226 | ++ |
| 227 | +++ |
| 228 | ++ |
| 229 | ++ |
| 230 | ++ |
| 231 | ++++ |
| 232 | ++ |
| 233 | +++ |
| 234 | ++++ |
| 235 | +++ |
| 236 | ++++ |
| 237 | ++ |
| 238 | ++ |
| 239 | ++ |
| 240 | +++ |
| 241 | ++ |
| 242 | ++ |
| 243 | ++ |
| 244 | +++ |
| 245 | ++ |
| 246 | ++ |
| 247 | ++ |
| 248 | +++ |
| 249 | ++++ |
| 250 | ++ |
| 251 | ++++ |
| 252 | ++++ |
| 253 | +++ |
| 254 | ++ |
| 255 | ++++ |
| 256 | ++++ |
| 257 | ++ |
| 258 | ++++ |
| 259 | ++ |
| 260 | + |
| 261 | +++ |
| 262 | +++ |
| 263 | ++ |
| 264 | ++ |
| 265 | ++++ |
| 266 | ++++ |
| 267 | ++ |
| 268 | ++ |
| 269 | ++ |
| 270 | +++ |
| 271 | ++ |
| 272 | ++ |
| 273 | ++ |
| 274 | ++ |
| 275 | ++ |
| 276 | ++ |
| 277 | + |
| 278 | +++ |
| 279 | ++++ |
| 280 | +++ |
| 281 | + |
| 282 | ++ |
| 283 | ++++ |
| 284 | ++ |
| 285 | ++ |
| 286 | +++ |
| 287 | ++++ |
| 288 | +++ |
| 289 | +++ |
| 291 | ++ |
| 292 | ++ |
| 293 | +++ |

TABLE 2-continued

| COMPOUND NUMBER | $EC_{20}$ GLP-1(9-36) PAM $EC_{50}$ |
|---|---|
| 294 | ++ |
| 295 | ++ |
| 296 | ++ |
| 297 | + |
| 298 | + |
| 299 | + |
| 300 | + |
| 301 | ++ |
| 302 | +++ |
| 303 | ++ |
| 304 | ++ |
| 305 | ++ |
| 306 | + |
| 307 | ++ |
| 308 | ++ |
| 309 | + |
| 310 | + |
| 311 | ++ |
| 312 | ++ |
| 313 | ++ |
| 314 | ++ |
| 315 | ++ |
| 316 | + |
| 317 | + |
| 318 | + |
| 319 | + |
| 320 | + |
| 321 | + |
| 322 | ++ |
| 323 | + |
| 324 | ++ |
| 325 | ++++ |
| 326 | + |
| 327 | + |
| 328 | + |
| 329 | ++ |
| 330 | ++ |
| 331 | ++ |
| 332 | ++ |
| 333 | + |
| 334 | ++ |
| 335 | ++ |
| 336 | + |
| 337 | ++ |
| 338 | ++ |
| 339 | ++ |
| 340 | ++ |
| 341 | + |
| 342 | ++ |
| 343 | ++ |
| 344 | + |
| 345 | + |
| 346 | ++ |
| 347 | + |
| 348 | ++ |
| 349 | + |
| 350 | + |
| 351 | + |
| 352 | + |
| 353 | ++ |
| 354 | + |
| 355 | ++ |
| 356 | ++ |
| 357 | ++ |
| 358 | ++ |
| 359 | ++ |
| 360 | ++ |
| 361 | ++ |
| 362 | +++ |
| 363 | ++ |
| 364 | ++ |
| 365 | +++ |
| 366 | +++ |
| 367 | ++ |
| 368 | + |
| 369 | ++ |
| 370 | ++ |

TABLE 2-continued

| COMPOUND NUMBER | $EC_{20}$ GLP-1(9-36) PAM $EC_{50}$ |
|---|---|
| 371 | + |
| 372 | + |
| 373 | ++ |
| 374 | ++ |
| 375 | + |
| 376 | ++ |
| 377 | + |
| 378 | + |
| 379 | + |
| 380 | ++ |
| 381 | ++ |
| 382 | ++ |
| 383 | +++ |
| 384 | ++++ |
| 385 | ++++ |
| 386 | ++ |
| 387 | ++++ |
| 388 | +++ |
| 389 | ++ |
| 390 | ++ |
| 391 | +++ |
| 392 | +++ |
| 393 | ++ |
| 394 | +++ |
| 395 | ++ |
| 396 | + |
| 397 | +++ |
| 398 | + |
| 399 | + |
| 400 | + |
| 401 | + |
| 402 | + |
| 403 | ++ |
| 404 | + |
| 405 | + |
| 406 | ++ |
| 407 | + |
| 408 | ++ |
| 409 | ++ |
| 410 | ++ |
| 411 | ++ |
| 412 | + |
| 413 | ++++ |
| 414 | + |
| 415 | + |
| 416 | + |
| 417 | + |
| 418 | + |
| 419 | + |
| 420 | + |
| 421 | ++ |
| 422 | + |
| 423 | ++ |
| 424 | + |
| 425 | +++ |
| 426 | ++ |
| 427 | ++ |
| 428 | ++ |
| 429 | +++ |
| 430 | ++++ |
| 431 | + |
| 432 | + |
| 433 | +++ |
| 434 | ++ |
| 435 | ++ |
| 436 | + |
| 437 | + |
| 438 | ++++ |
| 439 | +++ |
| 440 | + |
| 441 | ++ |
| 442 | ++ |
| 443 | ++ |
| 444 | + |
| 445 | + |
| 446 | ++ |
| 447 | ++ |

TABLE 2-continued

| COMPOUND NUMBER | $EC_{20}$ GLP-1(9-36) PAM $EC_{50}$ |
|---|---|
| 448 | + |
| 449 | ++ |
| 450 | + |
| 451 | + |
| 452 | +++ |
| 453 | ++ |
| 454 | ++ |
| 455 | + |
| 456 | ++ |
| 457 | +++ |
| 458 | ++ |
| 459 | ++ |
| 460 | ++++ |
| 461 | ++ |
| 462 | ++++ |
| 463 | ++++ |
| 464 | ++++ |
| 465 | ++ |
| 466 | ++ |
| 467 | + |
| 468 | + |
| 469 | ++ |
| 470 | + |
| 471 | ++++ |
| 472 | ++ |
| 473 | ++++ |
| 474 | ++ |
| 475 | ++ |
| 476 | +++ |
| 477 | + |
| 478 | + |
| 479 | + |
| 480 | ++ |
| 481 | ++ |
| 482 | + |
| 483 | ++ |
| 484 | ++ |
| 485 | ++++ |
| 486 | + |
| 487 | + |
| 488 | ++ |
| 489 | ++ |
| 490 | ++ |
| 491 | + |
| 492 | ++++ |
| 493 | + |
| 494 | + |
| 495 | + |
| 496 | + |
| 497 | + |
| 498 | ++ |
| 499 | + |
| 500 | ++ |
| 501 | + |
| 502 | + |
| 503 | ++ |
| 504 | +++ |
| 505 | ++ |
| 506 | ++ |
| 507 | ++ |
| 508 | + |
| 509 | ++ |
| 510 | +++ |
| 511 | ++ |
| 512 | + |
| 513 | + |
| 514 | + |
| 515 | + |
| 516 | + |
| 517 | + |
| 518 | ++ |
| 519 | ++ |
| 520 | ++ |
| 521 | + |
| 522 | ++ |
| 523 | + |
| 524 | + |
| 525 | + |
| 526 | + |
| 527 | + |
| 528 | + |
| 529 | + |
| 530 | + |
| 531 | ++ |
| 532 | + |
| 533 | + |
| 534 | ++ |
| 535 | ++++ |
| 536 | ++ |
| 537 | ++++ |
| 538 | ++++ |
| 539 | ++++ |
| 540 | + |
| 541 | ++ |
| 542 | + |
| 543 | + |
| 544 | + |
| 545 | + |
| 546 | ++ |
| 547 | ++ |
| 548 | + |
| 549 | + |
| 550 | ++ |
| 551 | + |
| 552 | ++ |
| 553 | ++ |
| 554 | + |
| 555 | +++ |
| 556 | + |
| 557 | + |
| 558 | + |
| 559 | ++++ |
| 560 | ++ |
| 561 | + |
| 562 | + |
| 563 | + |
| 564 | ++ |
| 565 | ++ |
| 566 | + |
| 567 | + |
| 568 | + |
| 569 | + |
| 570 | + |
| 571 | ++ |
| 572 | ++ |
| 573 | ++ |
| 574 | ++ |
| 575 | +++ |
| 576 | ++ |
| 577 | +++ |
| 578 | +++ |
| 579 | + |
| 580 | + |
| 581 | ++ |
| 582 | ++ |
| 583 | ++++ |
| 584 | ++ |
| 585 | ++ |
| 586 | + |
| 587 | + |
| 588 | ++ |
| 589 | ++ |
| 590 | + |
| 591 | + |
| 592 | ++ |
| 593 | + |
| 594 | + |
| 595 | + |
| 596 | ++ |
| 597 | + |
| 598 | + |
| 599 | + |
| 600 | + |
| 601 | ++ |

TABLE 2-continued

| COMPOUND NUMBER | $EC_{20}$ GLP-1(9-36) PAM $EC_{50}$ |
|---|---|
| 602 | + |
| 603 | ++ |
| 604 | ++ |
| 605 | + |
| 606 | ++ |
| 607 | ++ |
| 608 | ++ |
| 609 | + |
| 610 | + |
| 611 | + |
| 612 | + |
| 613 | ++ |
| 614 | ++ |
| 615 | ++++ |
| 616 | ++ |
| 617 | + |
| 618 | ++++ |
| 619 | ++ |
| 620 | ++++ |
| 621 | +++ |
| 622 | ++ |
| 623 | ++ |
| 624 | + |
| 625 | + |
| 626 | + |
| 627 | + |
| 628 | ++ |
| 629 | ++ |
| 630 | + |
| 631 | ++ |
| 632 | ++ |
| 633 | ++ |
| 634 | + |
| 635 | + |
| 636 | + |
| 637 | ++ |
| 638 | +++ |
| 639 | + |
| 640 | + |
| 641 | + |
| 642 | + |
| 644 | + |
| 645 | + |
| 646 | + |
| 647 | + |
| 648 | ++ |
| 649 | ++ |
| 650 | + |
| 651 | + |
| 652 | + |
| 653 | + |
| 654 | + |
| 655 | ++ |
| 656 | ++ |
| 657 | ++ |
| 658 | + |
| 659 | + |
| 660 | ++ |
| 661 | + |
| 662 | + |
| 663 | ++ |
| 664 | +++ |
| 665 | ++ |
| 666 | ++ |
| 667 | ++ |
| 668 | ++ |
| 669 | ++ |
| 670 | +++ |
| 671 | +++ |
| 672 | +++ |
| 673 | ++++ |
| 674 | ++++ |
| 675 | ++++ |
| 676 | +++ |
| 677 | +++ |
| 678 | ++ |
| 679 | ++ |
| 680 | ++++ |
| 681 | ++++ |
| 682 | +++ |
| 683 | ++ |
| 684 | ++++ |
| 685 | +++ |
| 686 | +++ |
| 687 | +++ |
| 688 | +++ |
| 689 | +++ |
| 690 | +++ |
| 691 | +++ |
| 692 | ++++ |
| 693 | ++++ |
| 694 | +++ |
| 695 | +++ |
| 696 | +++ |
| 697 | +++ |
| 698 | + |
| 699 | ++++ |
| 700 | ++++ |
| 701 | +++ |
| 702 | ++ |
| 703 | + |
| 704 | ++ |
| 705 | ++ |
| 706 | ++ |
| 707 | ++++ |
| 708 | ++ |
| 709 | ++ |
| 710 | ++++ |
| 711 | +++ |
| 712 | ++ |
| 713 | ++ |
| 714 | +++ |
| 715 | +++ |
| 716 | ++ |
| 717 | ++ |
| 718 | +++ |
| 719 | ++ |
| 720 | +++ |
| 721 | ++ |
| 722 | ++ |
| 723 | ++ |
| 724 | ++ |
| 725 | ++ |
| 726 | ++ |
| 727 | +++ |
| 728 | ++ |
| 729 | ++ |
| 730 | +++ |
| 731 | +++ |
| 732 | ++ |
| 733 | ++ |
| 734 | ++ |
| 735 | ++ |
| 736 | + |
| 737 | + |
| 738 | + |
| 739 | + |
| 740 | +++ |
| 741 | +++ |
| 742 | +++ |
| 743 | ++++ |
| 744 | ++++ |
| 745 | ++ |
| 746 | +++ |
| 747 | +++ |
| 748 | +++ |
| 749 | ++ |
| 750 | +++ |
| 751 | +++ |
| 752 | ++++ |
| 753 | +++ |
| 754 | ++++ |
| 755 | +++ |
| 756 | ++++ |

TABLE 2-continued

| COMPOUND NUMBER | EC$_{20}$ GLP-1(9-36) PAM EC$_{50}$ |
|---|---|
| 757 | ++ |
| 758 | +++ |
| 759 | ++ |
| 760 | ++ |
| 761 | +++ |
| 762 | ++++ |
| 763 | ++ |
| 764 | + |
| 765 | ++ |
| 766 | +++ |
| 767 | +++ |
| 768 | ++ |
| 769 | ++++ |
| 770 | + |
| 771 | ++ |
| 772 | + |
| 773 | ++ |
| 774 | ++ |
| 775 | + |
| 776 | + |
| 777 | ++ |
| 778 | + |
| 779 | ++ |
| 780 | +++ |
| 781 | +++ |
| 782 | ++ |
| 783 | ++ |
| 784 | ++++ |
| 785 | +++ |
| 786 | ++ |
| 787 | ++ |
| 788 | ++++ |
| 789 | +++ |
| 790 | ++ |
| 791 | ++ |
| 792 | ++ |
| 793 | ++ |
| 794 | ++ |
| 795 | + |
| 796 | + |
| 797 | ++ |
| 798 | ++ |
| 799 | ++ |
| 800 | ++++ |
| 801 | ++++ |
| 802 | +++ |
| 803 | ++ |
| 804 | ++ |
| 806 | ++ |
| 807 | ++++ |
| 808 | +++ |
| 809 | ++ |
| 810 | ++++ |
| 811 | ++ |
| 812 | ++ |
| 813 | ++ |
| 814 | ++ |
| 815 | + |
| 816 | ++ |
| 817 | ++ |
| 818 | ++ |
| 819 | +++ |
| 820 | +++ |
| 821 | ++ |
| 822 | +++ |
| 823 | ++ |
| 824 | + |
| 825 | + |
| 826 | +++ |
| 827 | ++ |
| 828 | + |
| 829 | ++++ |
| 830 | ++++ |
| 832 | +++ |
| 833 | ++++ |
| 834 | ++ |
| 835 | +++ |
| 836 | +++ |
| 837 | + |
| 838 | ++ |
| 839 | ++ |
| 840 | ++ |
| 841 | ++ |
| 842 | ++ |
| 843 | ++ |
| 844 | ++ |
| 845 | +++ |
| 846 | +++ |
| 847 | +++ |
| 848 | +++ |
| 849 | +++ |
| 850 | +++ |
| 851 | +++ |
| 852 | +++ |
| 853 | ++ |
| 855 | ++ |
| 856 | ++ |
| 857 | ++++ |
| 858 | ++ |
| 859 | +++ |
| 860 | ++ |
| 861 | +++ |
| 862 | ++ |
| 863 | ++ |
| 864 | ++ |
| 865 | ++ |
| 866 | +++ |
| 867 | ++ |
| 868 | ++ |
| 869 | +++ |
| 870 | ++ |
| 871 | +++ |
| 872 | ++ |
| 873 | + |
| 874 | ++ |
| 875 | ++ |
| 876 | ++ |
| 877 | ++ |
| 878 | + |
| 879 | +++ |
| 880 | + |
| 881 | ++ |
| 882 | ++ |
| 883 | ++++ |
| 884 | ++ |
| 885 | ++++ |
| 886 | ++ |
| 887 | + |
| 888 | ++ |
| 889 | ++ |
| 890 | ++ |
| 891 | ++ |
| 892 | + |
| 893 | +++ |
| 894 | ++++ |
| 895 | + |
| 896 | ++++ |
| 897 | ++++ |
| 898 | +++ |
| 899 | +++ |
| 900 | ++ |
| 901 | ++ |
| 902 | +++ |
| 903 | ++++ |
| 904 | +++ |
| 905 | ++++ |
| 906 | +++ |
| 907 | ++ |
| 908 | ++ |
| 909 | +++ |
| 910 | ++ |
| 911 | ++ |
| 912 | + |
| 913 | + |

TABLE 2-continued

| COMPOUND NUMBER | EC$_{20}$ GLP-1(9-36) PAM EC$_{50}$ |
|---|---|
| 914 | +++ |
| 915 | ++ |
| 916 | ++ |
| 917 | ++ |
| 918 | ++++ |
| 919 | ++++ |
| 920 | ++ |
| 921 | ++++ |
| 922 | ++++ |
| 923 | ++ |
| 924 | +++ |
| 925 | +++ |
| 926 | ++ |
| 927 | +++ |
| 928 | +++ |
| 929 | ++++ |
| 930 | ++++ |
| 931 | +++ |
| 932 | +++ |
| 933 | ++++ |
| 934 | ++++ |
| 935 | +++ |
| 936 | ++ |
| 937 | ++ |
| 938 | ++++ |
| 939 | +++ |
| 940 | ++ |
| 941 | +++ |
| 942 | +++ |
| 943 | ++ |
| 944 | + |
| 945 | + |
| 946 | +++ |
| 947 | ++ |
| 948 | +++ |
| 949 | ++ |
| 950 | ++ |
| 951 | ++ |
| 952 | +++ |
| 953 | ++ |
| 954 | ++ |
| 955 | ++++ |
| 956 | +++ |
| 957 | ++ |
| 958 | ++ |
| 959 | ++ |
| 960 | ++ |
| 961 | +++ |
| 962 | ++ |
| 963 | ++++ |
| 964 | +++ |
| 965 | ++++ |
| 966 | ++++ |
| 967 | +++ |
| 968 | ++++ |
| 969 | +++ |
| 970 | +++ |
| 971 | +++ |
| 972 | ++++ |
| 973 | ++++ |
| 974 | +++ |
| 975 | ++++ |
| 976 | +++ |
| 977 | ++++ |
| 978 | ++ |
| 979 | +++ |
| 980 | ++ |
| 981 | +++ |
| 982 | ++++ |
| 983 | ++++ |
| 984 | +++ |
| 985 | +++ |
| 986 | ++ |
| 987 | ++++ |
| 988 | ++++ |
| 989 | ++ |
| 990 | +++ |
| 991 | ++ |
| 992 | +++ |
| 993 | +++ |
| 994 | ++ |
| 995 | ++++ |
| 996 | ++ |
| 997 | ++++ |
| 998 | +++ |
| 999 | +++ |
| 1000 | ++++ |
| 1001 | +++ |
| 1002 | ++ |
| 1003 | ++++ |
| 1004 | ++ |
| 1005 | ++ |
| 1006 | ++ |
| 1007 | ++ |
| 1008 | ++++ |
| 1009 | +++ |
| 1010 | +++ |
| 1011 | +++ |
| 1012 | +++ |
| 1013 | ++++ |
| 1014 | ++++ |
| 1015 | ++ |
| 1016 | ++++ |
| 1017 | +++ |
| 1018 | ++++ |
| 1019 | +++ |
| 1020 | ++++ |
| 1021 | +++ |
| 1022 | +++ |
| 1023 | +++ |
| 1024 | ++ |
| 1025 | ++ |
| 1026 | +++ |
| 1027 | ++++ |
| 1028 | +++ |
| 1029 | +++ |
| 1030 | ++++ |
| 1031 | +++ |
| 1032 | ++ |
| 1033 | ++++ |
| 1034 | +++ |
| 1035 | ++ |
| 1036 | +++ |
| 1037 | ++ |
| 1038 | +++ |
| 1039 | ++ |
| 1040 | ++++ |
| 1041 | ++ |
| 1042 | ++++ |
| 1043 | +++ |
| 1044 | +++ |
| 1045 | +++ |
| 1046 | ++ |
| 1047 | +++ |
| 1048 | +++ |
| 1049 | ++ |
| 1050 | ++ |
| 1051 | ++++ |
| 1052 | +++ |
| 1053 | +++ |
| 1054 | +++ |
| 1055 | +++ |

In Vivo Assays

In Vivo Procedures

The Oral Glucose Tolerance Test in C57Bl/6 Mice.

Fasted C57BL/6 female mice were 8-10 weeks of age. Sitagliptin, compound, or vehicle was dosed at least 1 hr prior to the oGTT. Mice receive a bolus of glucose (3 g/kg) by oral gavage (time 0). Blood samples are collected at frequent time intervals from the tail tip for glucose measurement (BD glucometer; Becton-Dickinson, Lincoln Park, N.J.).

The Oral Glucose Tolerance Test in Ob/Ob Mice.

Fasted ob/ob female mice were 7-10 weeks of age. Sitagliptin, compound, or vehicle was dosed at least 1 hr prior to the oGTT. Mice receive a bolus of glucose (0.2 g/kg) by oral gavage (time 0). Blood samples are collected at frequent time intervals from the tail tip for glucose measurement (BD glucometer; Becton-Dickinson, Lincoln Park, N.J.).

The Oral Glucose Tolerance Test in Fa/Fa Rats.

The use of these compounds to lower glucose can be evaluated in rats using the protocol described by Pederson et. al. (Diabetes, Vol. 47, August 1998, 1253-1258). After an overnight fast, lean or obese animals are administered oral glucose by syringe and feeding tube (1 g/kg) as a 40% solution (wt/vol). Compound is dissolved and administered along with the glucose. In control experiments, vehicle is administered along with oral glucose. Blood samples are collected from the tail veins of conscious unrestrained rats into heparinized capillary tubes at 0 and 5, 10, 20, 30, and 60 min after glucose administration. Blood samples are centrifuged at 4° C., and plasma is stored at −20° C. until analysis for glucose and insulin measurement. Glucose levels are measured using the glucose oxidase procedure (Beckman glucose analyzer; Fullerton, Calif.).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method of treating type II diabetes in a patient, comprising administering an effective amount of a compound to the patient at a frequency and for a duration of time sufficient to provide a beneficial effect to the patient, wherein the compound has the structure of Formula I-R or I-S or a pharmaceutically acceptable isolated optical isomer, enantiomer, racemate, salt, hydrate or solvate thereof:

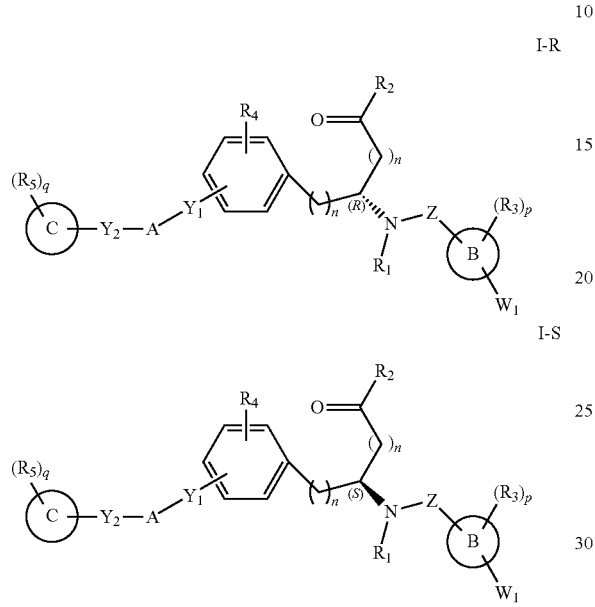

wherein
- A is pyrimidine optionally substituted with one or more of $R_4$;
- B is aryl, aralkyl, heterocyclyl, or heterocyclylalkyl;
- C is aryl, aralkyl, heterocyclyl or heterocyclylalkyl;
- $Y_1$ and $Y_2$ are both null, or one of $Y_1$ or $Y_2$ is —NH— or —O— and the other $Y_1$ or $Y_2$ is null;
- Z is —C(O)— or —S(O)$_2$—;
- each $R_1$ is independently H or $C_{1-4}$ alkyl;
- $R_2$ is —OH, —O—$R_8$, —N($R_1$)—SO$_2$—$R_7$, —N$R_{41}R_{42}$, —N($R_1$)—(CR$_a$R$_b$)$_m$—COOR$_8$, —N($R_1$)—(CR$_a$R$_b$)$_m$—CO—N($R_1$)($R_{40}$), —N($R_1$)—(CR$_a$R$_b$)$_m$—N($R_1$)C(O)O($R_8$), —N($R_1$)—(CR$_a$R$_b$)$_m$—N($R_1$)($R_{40}$), —N($R_1$)—(CR$_a$R$_b$)$_m$—CO—N($R_1$)— heterocyclyl, or —N($R_1$)—(CR$_a$R$_b$)$_m$-heterocyclyl, which heterocyclyl may be optionally (singly or multiply) substituted with $R_7$;
- each $R_3$ and $R_4$ is independently H, halo, alkyl, alkyl substituted (singly or multiply) with $R_{31}$, alkoxy, haloalkyl, perhaloalkyl, haloalkoxy, perhaloalkoxy, aryl, heterocyclyl, —OH, —OR$_7$, —CN, —NO$_2$, —NR$_1$R$_7$, —C(O)R$_7$, —C(O)NR$_1$R$_7$, —NR$_1$C(O)R$_7$, —SR$_7$, —S(O)R$_7$, —S(O)$_2$R$_7$, —OS(O)$_2$R$_7$, —S(O)$_2$NR$_1$R$_7$, —NR$_1$S(O)$_2$R$_7$, —(CR$_a$R$_b$)$_m$NR$_1$R$_7$, —(CR$_a$R$_b$)$_m$O(CR$_a$R$_b$)$_m$R$_7$, —(CR$_a$R$_b$)$_m$NR$_1$(CR$_a$R$_b$)$_m$R$_7$ or —(CR$_a$R$_b$)$_m$NR$_1$(CR$_a$R$_b$)$_m$COOR$_8$; or any two $R_3$ or $R_4$ groups on the same carbon atom taken together form oxo;
- each $R_{31}$ is independently H, halo, hydroxyl, —NR$_{41}$R$_{42}$, or alkoxy;
- each $R_{40}$ is independently H, $R_7$, alkyl which may be optionally (singly or multiply) substituted with $R_7$, or $R_{40}$ and $R_1$ taken together with the N atom to which they are attached form a 3- to 7-membered heterocyclyl which may be optionally (singly or multiply) substituted with $R_7$;
- each $R_{41}$ and $R_{42}$ is independently $R_{40}$, —(CHR$_{40}$)$_n$—C(O)O—R$_{40}$, —(CHR$_{40}$)$_n$—C(O)—R$_{40}$, —(CH$_2$)$_n$—N(R$_1$)(R$_7$), aryl or heteroaryl any of which aryl or heteroaryl may be optionally (singly or multiply) substituted with $R_7$; or any two $R_{41}$ and $R_{42}$ taken together with the N atom to which they are attached form a 3- to 7-membered heterocyclyl which may be optionally (singly or multiply) substituted with $R_7$;
- $W_1$ is null or 1$_1$-(CR$_a$R$_b$)$_m$-L$_1$-R$_6$;
- each $L_1$ is independently, from the proximal to distal end of the structure of Formula I-R or I-S, null, —C(O)O—, —S(O$_2$)—, —S(O)—, —S—, —N(R$_1$)—C(O)—N(R$_1$)—, C(O)—O—, —C(O)— or —S(O$_2$)—NR$_1$—;
- each $R_a$ and $R_b$ is independently H, halo, alkyl, alkoxy, aryl, aralkyl, heterocyclyl, heterocyclylalkyl (any of which alkyl, alkoxy, aryl, aralkyl, heterocyclyl or heterocyclylalkyl may be optionally (singly or multiply) substituted with $R_7$), —(CHR$_{40}$)$_m$C(O)OR$_{40}$, —(CHR$_{40}$)$_m$OR$_{40}$, —(CHR$_{40}$)$_m$SR$_{40}$, —(CHR$_{40}$)$_m$NR$_{41}$R$_{42}$, —(CHR$_{40}$)$_m$C(O)NR$_{41}$R$_{42}$, —(CHR$_{40}$)$_m$C(O)N(R$_1$)(CHR$_{40}$)$_m$—NR$_{41}$R$_{42}$, —(CHR$_{40}$)$_m$C(O)—N(R$_1$)(CHR$_{40}$)$_m$C(O)NR$_{41}$R$_{42}$, —(CHR$_{40}$)$_m$C(O)N(R$_1$)—(CHR$_{40}$)$_m$C(O)OR$_{40}$, or —(CHR$_{40}$)$_m$—S—S—R$_{40}$; or any two $R_a$ and $R_b$ taken together with the carbon atom(s) to which they are attached form a cycloalkyl or heterocyclyl optionally substituted (singly or multiply) with $R_7$; or $R_1$ and any one of $R_a$ or $R_b$ taken together with the atom(s) to which they are attached form heterocyclyl optionally substituted (singly or multiply) with $R_7$;
- $R_5$ is $R_7$, —(CR$_a$R$_b$)$_m$-L$_2$-(CR$_a$R$_b$)$_m$—R$_7$, or -(-L$_3$-(CR$_a$R$_b$)$_r$-)$_s$-L$_3$-R$_7$, wherein the carbon atoms of any two adjacent —(CR$_a$R$_b$)$_m$ or —(CR$_a$R$_b$)$_r$ groups may be taken together to form a double bond (—(C(R$_a$)═(C(R$_a$)—) or triple bond (—C≡C—);
- $R_6$ is H, alkyl, aryl, heteroaryl, heterocyclyl, heterocyloalkyl, any of which may be optionally substituted (singly or multiply) with $R_7$ or —(CR$_a$R$_b$)$_m$-L$_2$-(CR$_a$R$_b$)$_m$—R$_7$;
- each $R_7$ is independently $R_{10}$; a ring moiety selected from cycloalkyl, aryl, aralkyl, heterocyclyl or heterocyclylalkyl, where such ring moiety is optionally singly or multiply substituted with $R_{10}$; or when a carbon atom bears two $R_7$ groups such two $R_7$ groups are taken together to form oxo or thioxo, or are taken together to form a ring moiety selected from cycloalkyl, aryl, heterocyclyl or heterocyclyl, wherein such ring moiety is optionally singly or multiply substituted with $R_{10}$;
- each $R_{10}$ is independently H, halo, alkyl, haloalkyl, perhaloalkyl, —(CR$_a$R$_b$)$_m$OH, —(CR$_a$R$_b$)$_m$OR$_8$, —(CR$_a$R$_b$)$_m$CN, —(CR$_a$R$_b$)$_m$NH(C═NH)NH$_2$, —(CR$_a$R$_b$)$_m$NR$_1$R$_8$, —(CR$_a$R$_b$)$_m$O(CR$_a$R$_b$)$_m$R$_8$, —(CR$_a$R$_b$)$_m$NR$_1$(CR$_a$R$_b$)$_m$R$_8$, —(CR$_a$R$_b$)$_m$C(O)R$_8$, —(CR$_a$R$_b$)$_m$C(O)OR$_8$, —(CR$_a$R$_b$)$_m$C(O)NR$_1$R$_8$, —(CR$_a$R$_b$)$_m$NR$_1$(CR$_a$R$_b$)$_m$C(O)OR$_8$, —(CR$_a$R$_b$)$_m$NR$_1$C(O)R$_8$, —(CR$_a$R$_b$)$_m$C(O)NR$_1$S(O)$_2$R$_8$, —(CR$_a$R$_b$)$_m$SR$_8$, —(CR$_a$R$_b$)$_m$S(O)R$_8$, —(CR$_a$R$_b$)$_m$S(O)$_2$R$_8$, —(CR$_a$R$_b$)$_m$S(O)$_2$NR$_1$R$_8$ or —(CR$_a$R$_b$)$_m$NR$_1$S(O)$_2$R$_8$;
- each $R_8$ is independently H, alkyl, aryl, —(CR$_a$R$_b$)$_m$-L$_2$-(CR$_a$R$_b$)$_m$—R$_1$ or -(-L$_3$-(CR$_a$R$_b$)$_r$-)$_s$-L$_3$-R$_1$;

L₂ is independently, from the proximal to distal end of the structure of Formula I-R or I-S, null, —O—, —OC(O)—, —NR₁—, —C(O)NR₁—, —N(R₁)—C(O)—, —S(O₂)—, —S(O)—, —S—, —C(O)— or —S(O₂)—N(R₁)—;

each L₃ is independently null, —O—, or —N(R₁)— each m is independently 0, 1, 2, 3, 4, 5 or 6;

each n is independently 0 or 1 or 2;

p is 0, 1, 2 or 3;

q is 0, 1, 2 or 3;

each r is independently 2, 3, or 4; and each s is independently 1, 2, 3, or 4.

2. The method of claim 1 wherein the compound has the following structure:

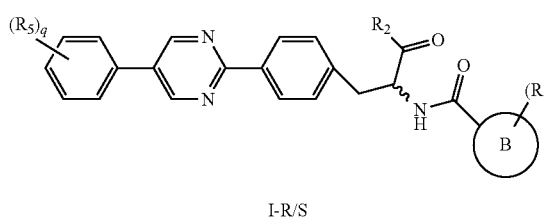

(64)

I-R/S

3. The method of claim 1 wherein the compound has the following structure:

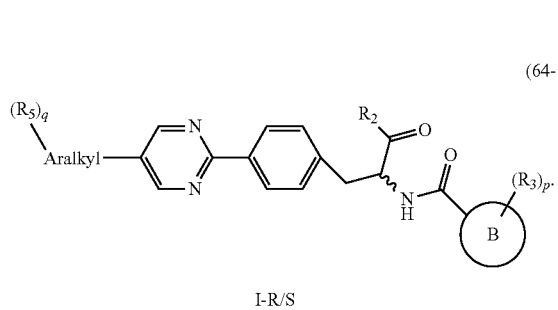

(64-1)

I-R/S

4. The method of claim 2 wherein B is phenyl and the compound has the following structure:

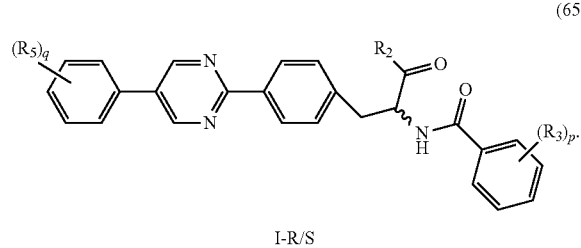

(65)

I-R/S

5. The method of claim 3 wherein B is phenyl and the compound has the following structure:

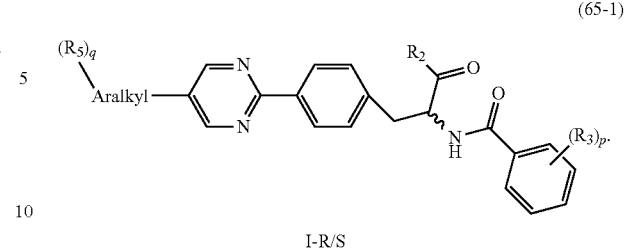

(65-1)

I-R/S

6. The method of claim 2 wherein B is thiophenyl and the compound has following structure:

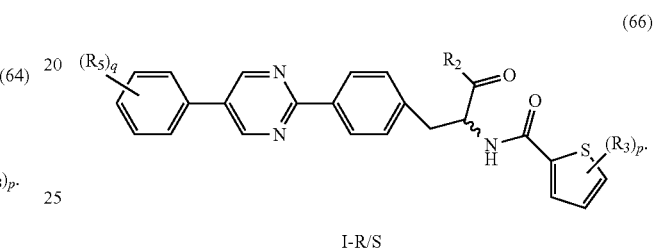

(66)

I-R/S

7. The method of claim 3 wherein B is thiophenyl and the compound has following structure:

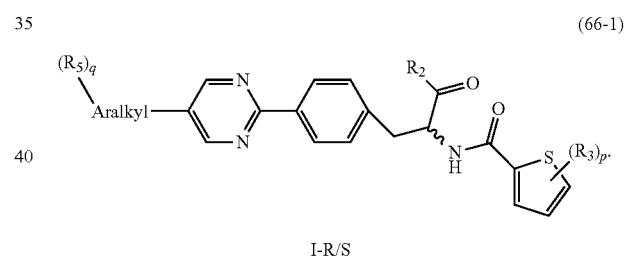

(66-1)

I-R/S

8. The method of claim 4 wherein the compound has the following structure:

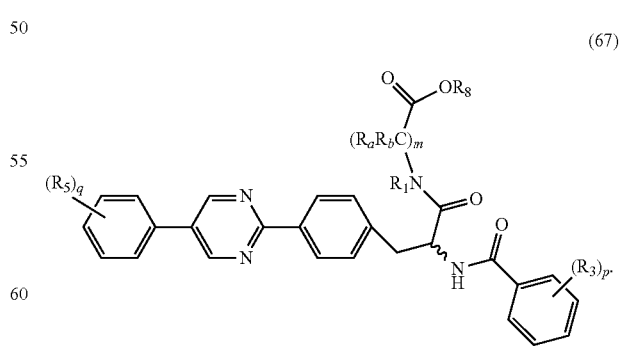

(67)

I-R/S

9. The method of claim 5 wherein the compound has the following structure:

10. The method of claim 6 wherein the compound has the following structure:

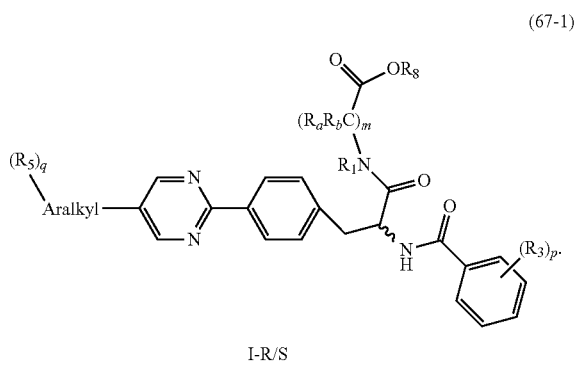
(67-1)

11. The method of claim 7 wherein the compound has the following structure:

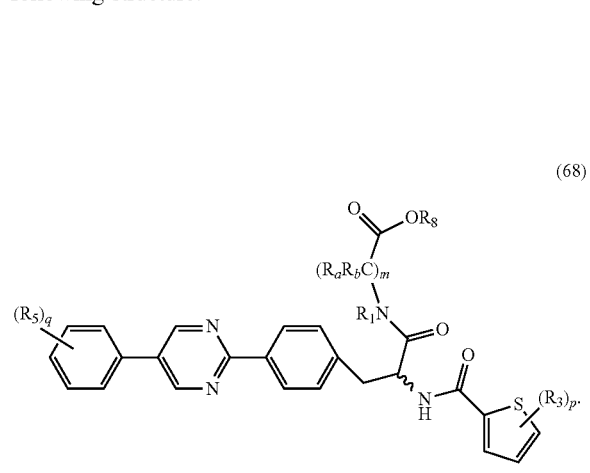
(68)

12. The method of claim 8 wherein the compound has the following structure:

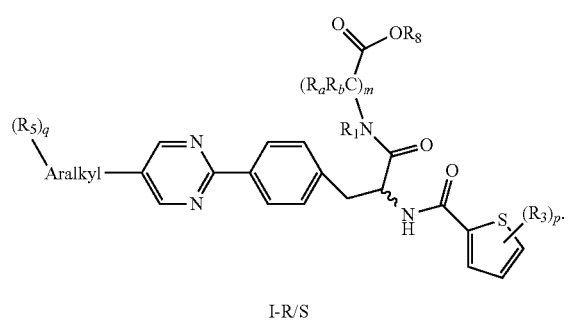
(68-1)

13. The method of claim 10 wherein the compound has the following structure:

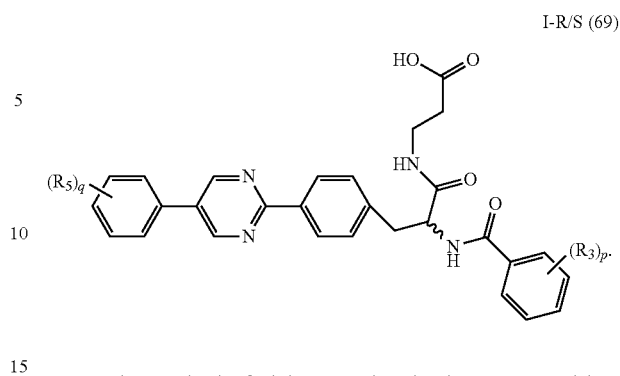
I-R/S (69)

14. The method of claim 8 wherein the compound has the following structure:

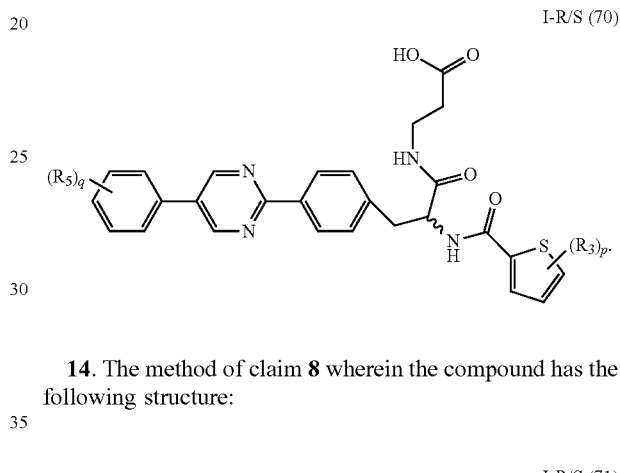
I-R/S (70)

15. The method of claim 10 wherein the compound has the following structure:

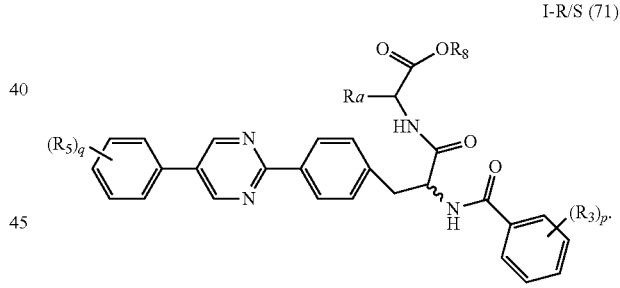
I-R/S (71)

16. The method of claim 8 wherein the compound has the following structure:

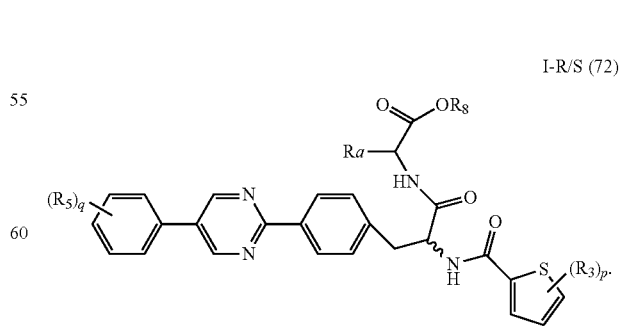
I-R/S (72)

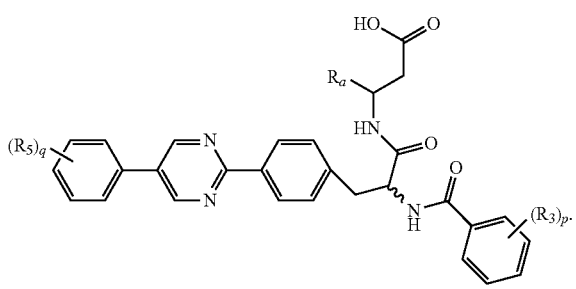

I-R/S (73)

17. The method of claim 10 wherein the compound has the following structure:

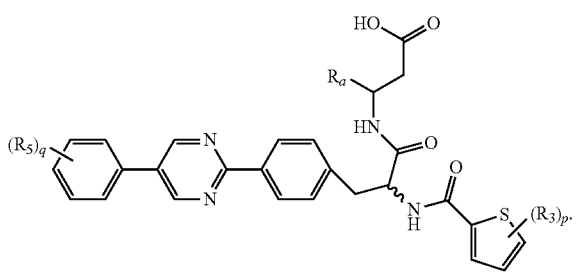

I-R/S (74)

18. The method of claim 8 wherein the compound has the following structure:

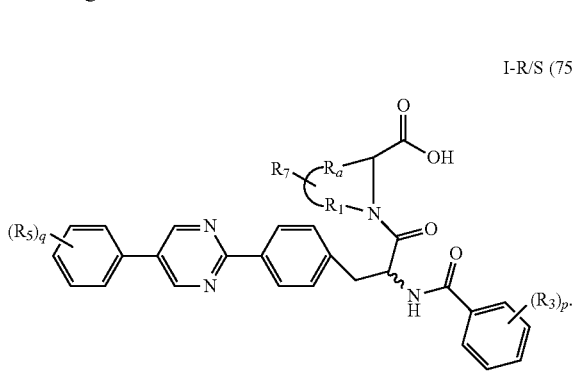

I-R/S (75)

19. The method of claim 10 wherein the compound has the following structure:

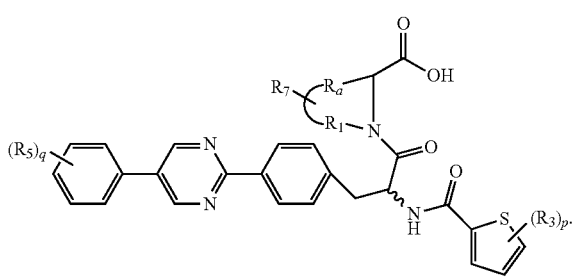

I-R/S (76)

20. The method of claim 8 wherein the compound has the following structure:

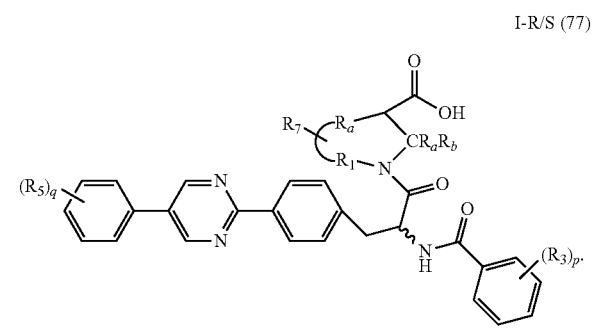

I-R/S (77)

21. The method of claim 10 wherein the compound has the following structure:

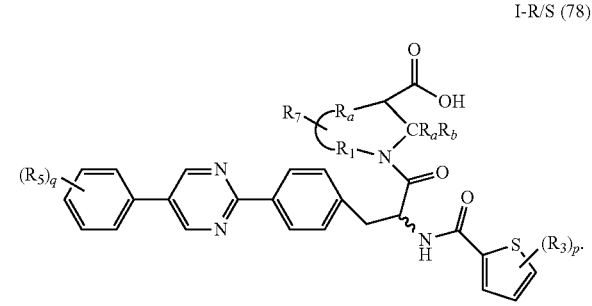

I-R/S (78)

22. The method of claim 18 wherein the compound has the following structure:

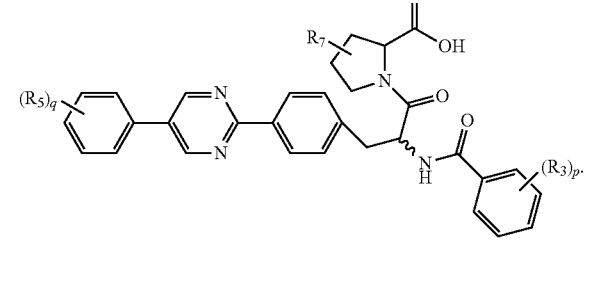

I-R/S (79)

23. The method of claim 19 wherein the compound has the following structure:

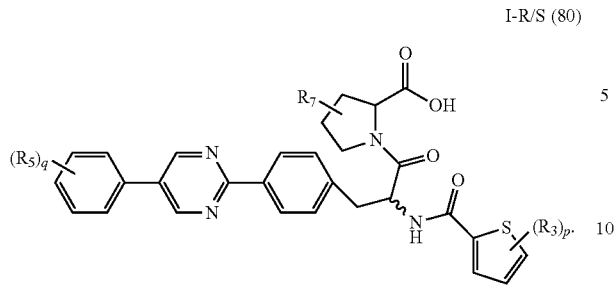

24. The method of claim 8 wherein the compound has the following structure:

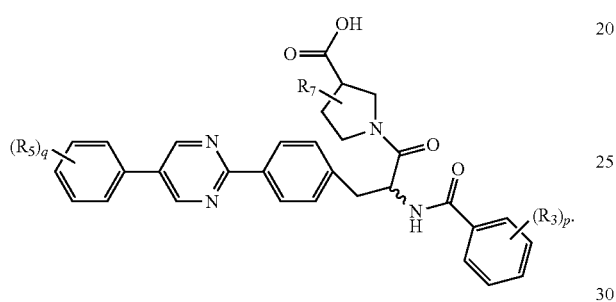

25. The method of claim 10 wherein the compound has the following structure:

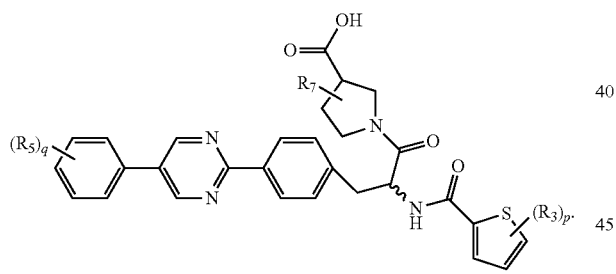

26. The method of claim 8 wherein the compound has the following structure:

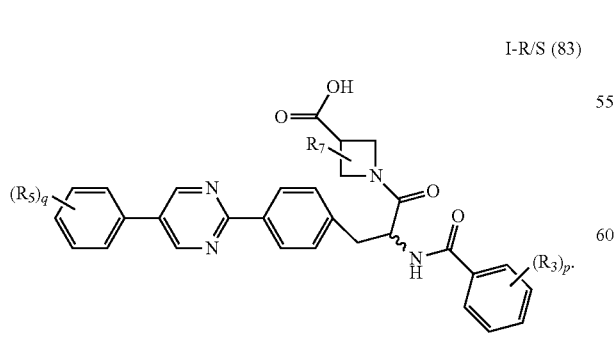

27. The method of claim 10 wherein the compound has the following structure:

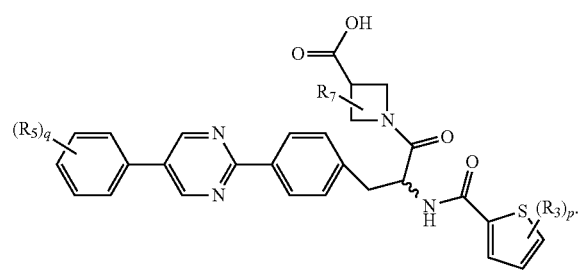

28. The method of claim 8 wherein the compound has the following structure:

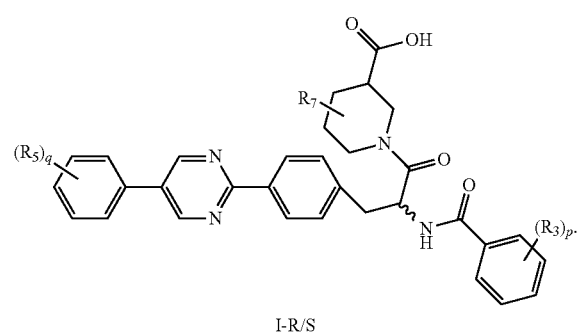

29. The method of claim 10 wherein the compound has the following structure:

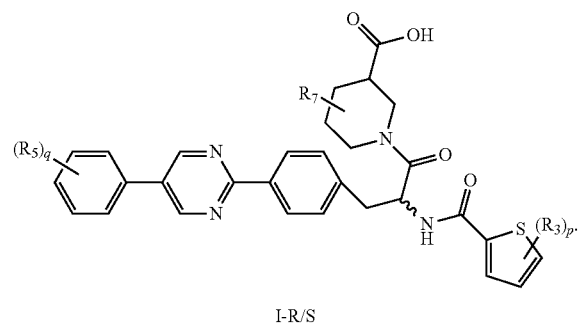

30. The method of claim 1 wherein the compound has the following structure:

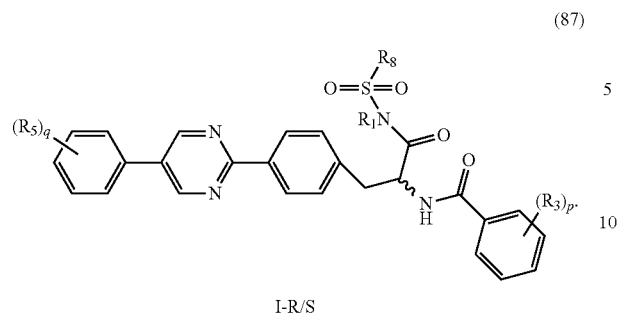

(87)

31. The method of claim 1 wherein the compound has the following structure:

(88)

32. The method of claim 1 wherein the compound has the following structure:

(89)

33. The method of claim 1 wherein the compound has the following structure:

(90)

34. The method of claim 1 wherein the compound has the following structure:

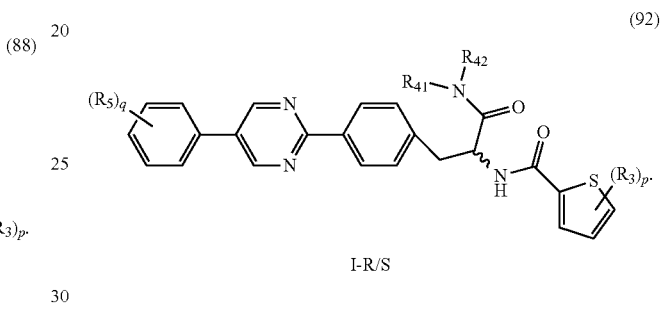

(91)

35. The method of claim 1 wherein the compound has the following structure:

(92)

36. The method of claim 1 wherein the compound has the following structure:


(93)

37. The method of claim 1 wherein the compound has the following structure:

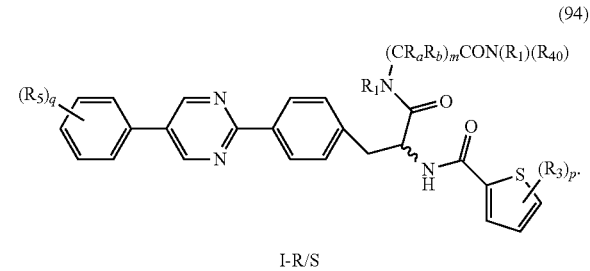

(94)

38. The method of claim 1 wherein the compound has the following structure:

39. The method of claim 1 wherein the compound has the following structure:

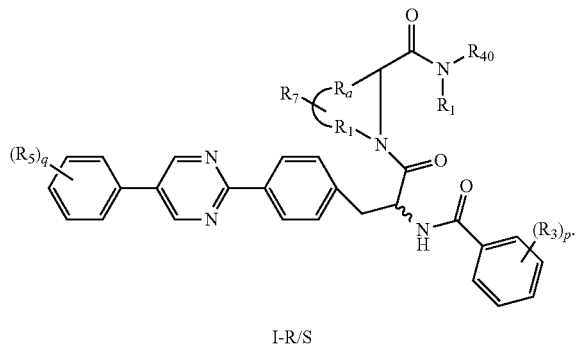
(95)

I-R/S

40. The method of claim 1 wherein the compound has the following structure:

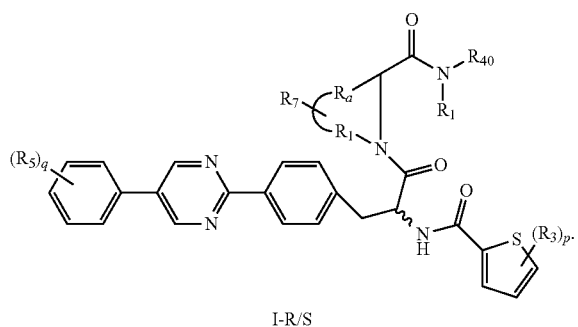
(96)

I-R/S

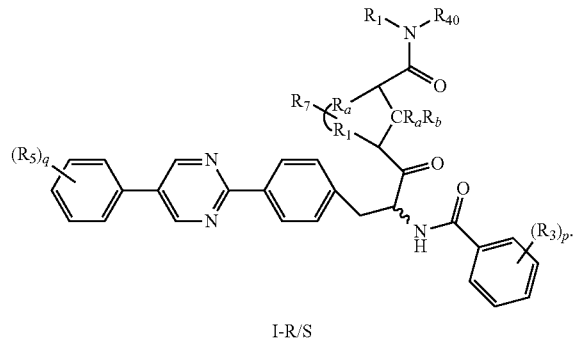
(97)

I-R/S

41. The method of claim 1 wherein the compound has the following structure:

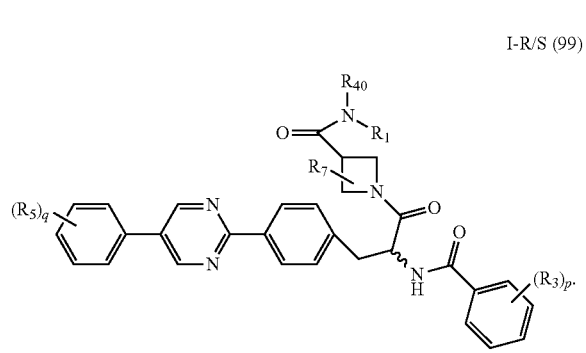
(98)

I-R/S

42. The method of claim 40 wherein the compound has the following structure:

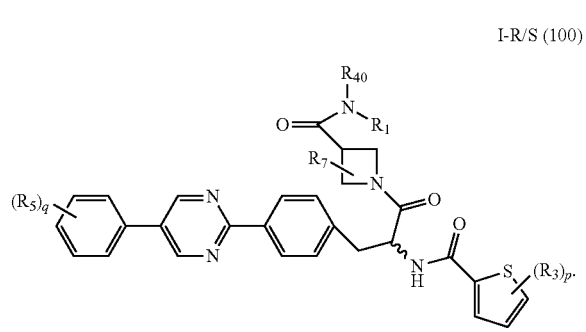
I-R/S (99)

43. The method of claim 41 wherein the compound has the following structure:

I-R/S (100)

44. The method of claim 40 wherein the compound has the following structure:

45. The method of claim 41 wherein the compound has the following structure:

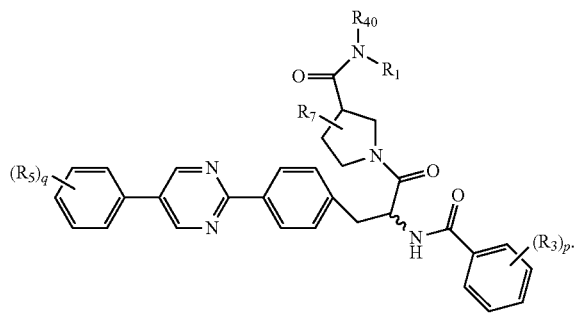
I-R/S (101)

46. The method of claim 40 wherein the compound has the following structure:

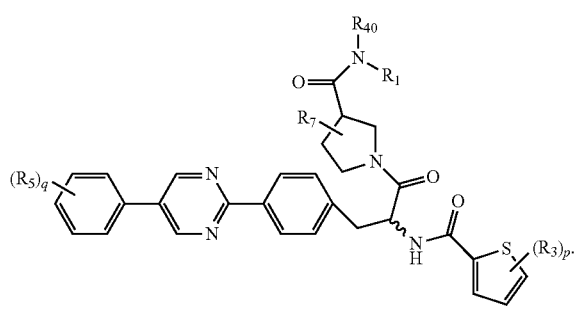
I-R/S (102)

47. The method of claim 41 wherein the compound has the following structure:

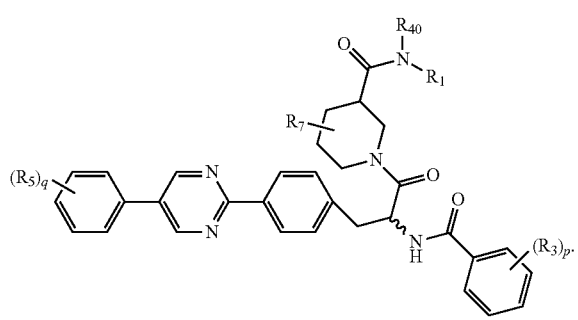
I-R/S (103)

48. The method of claim 1 wherein the compound has the following structure:

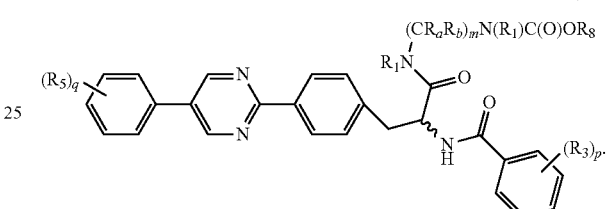
I-R/S (104)

49. The method of claim 1 wherein the compound has the following structure:

I-R/S (105)

50. The method of claim 1 wherein the compound has the following structure:

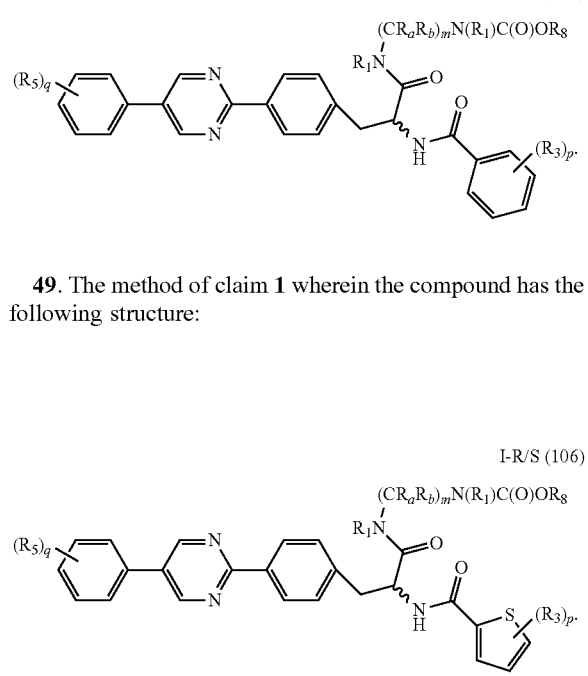
I-R/S (106)

51. The method of claim 1 wherein the compound has the following structure:

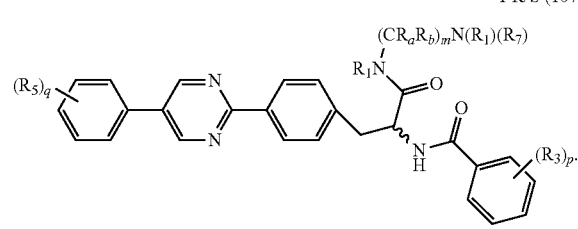
I-R/S (107)

52. The method of claim 1 wherein the compound has the following structure:
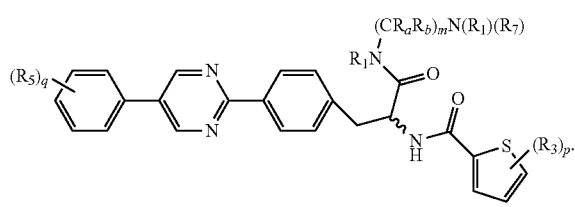
53. The method of claim 1 wherein the compound has the following structure:
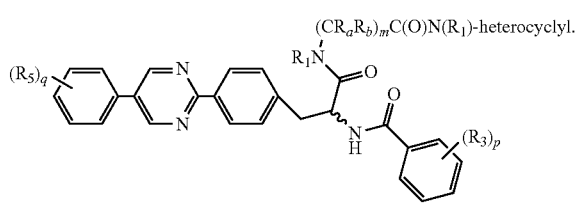
54. The method of claim 1 wherein the compound has the following structure:

55. The method of claim 1 wherein the compound has the following structure:
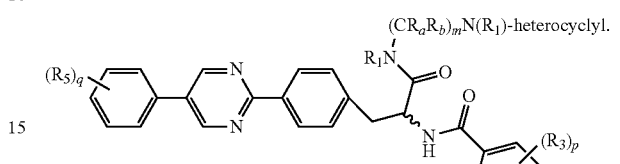
56. The method of claim 1 wherein the compound has one of the following structures:
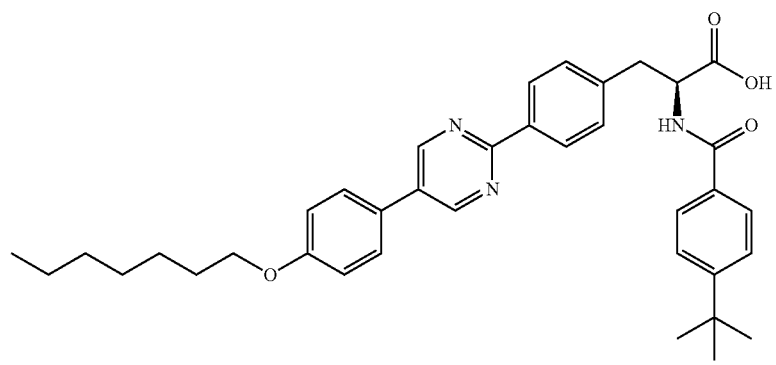

-continued
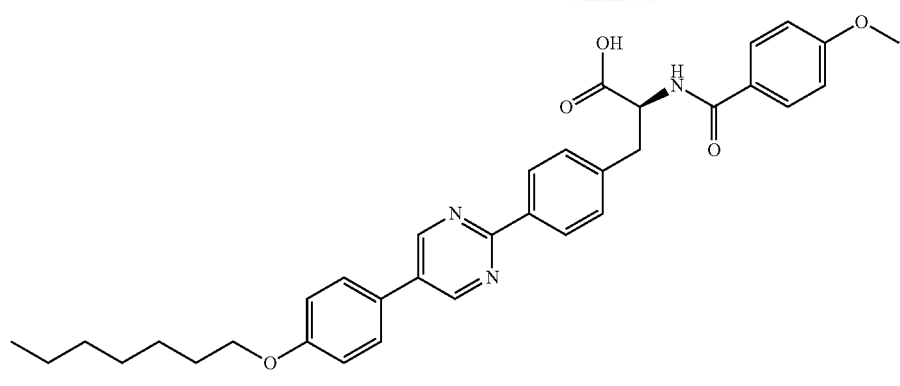
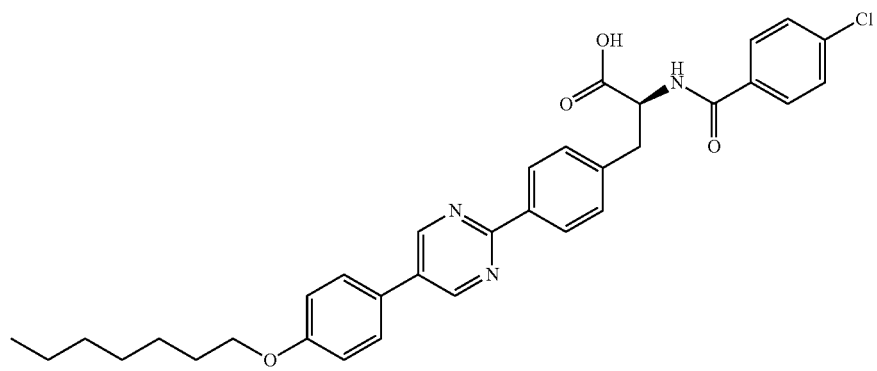
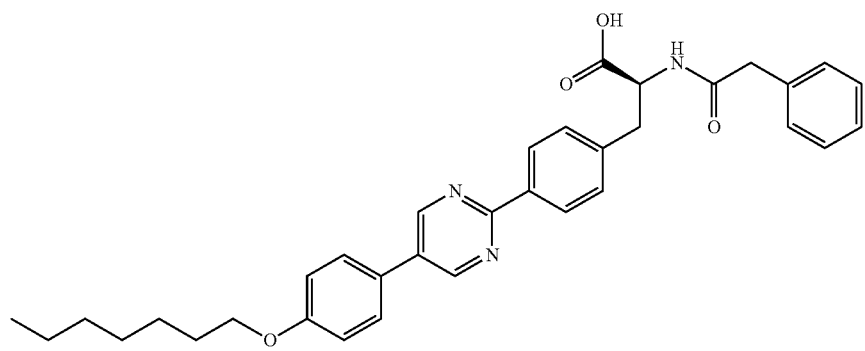
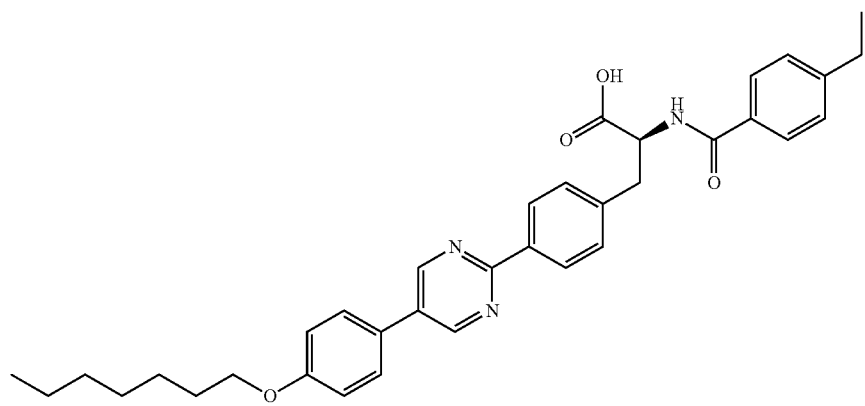

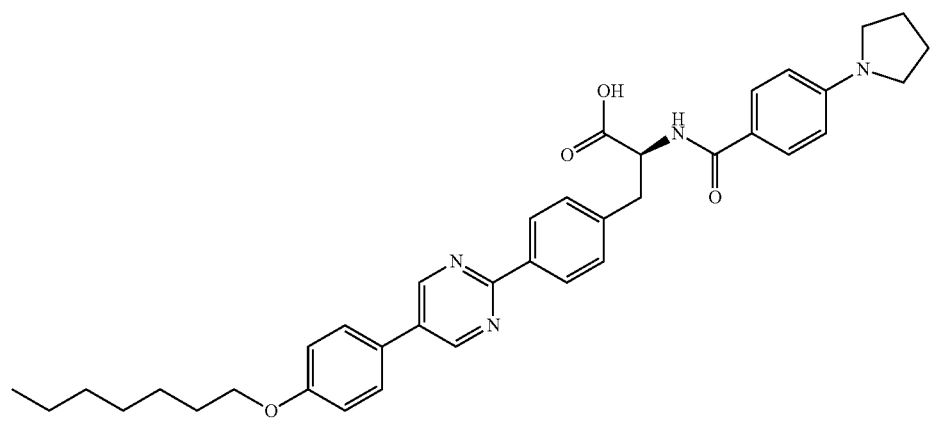
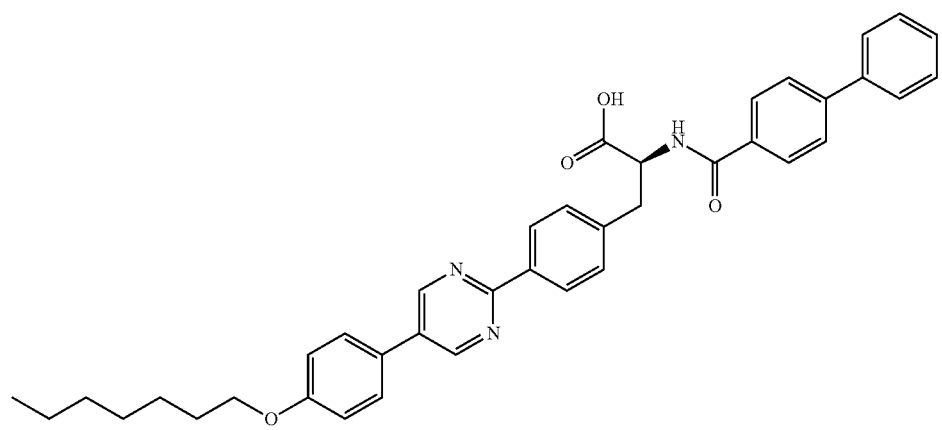
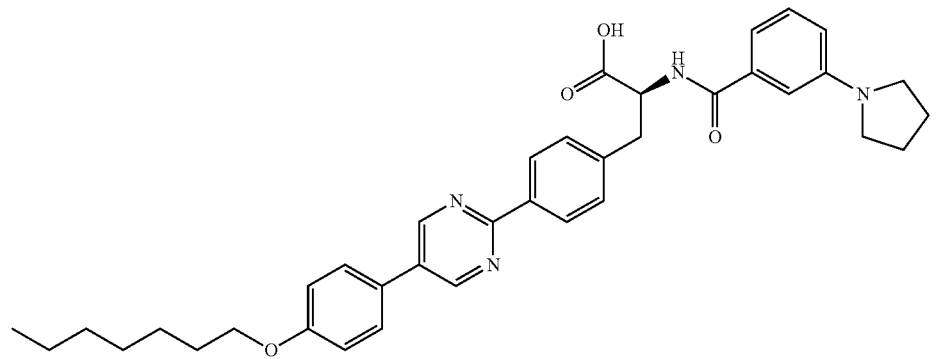
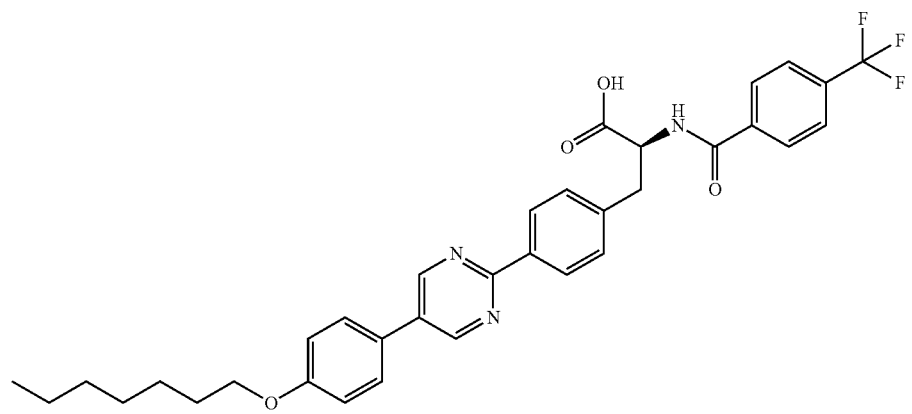

| 1041 | 1042 |
|---|---|
-continued
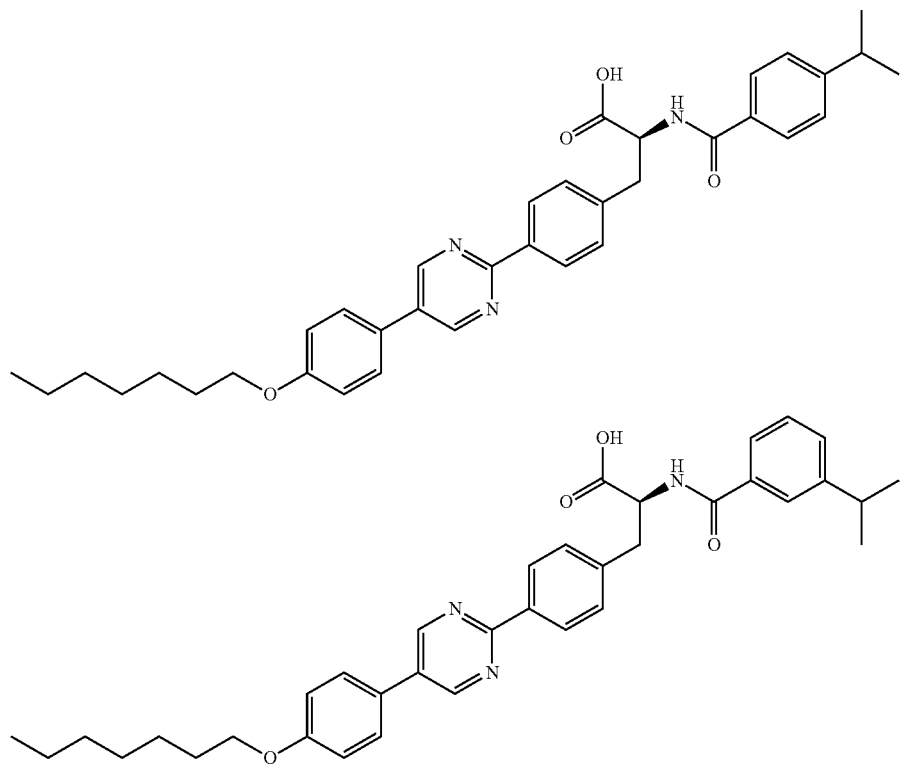
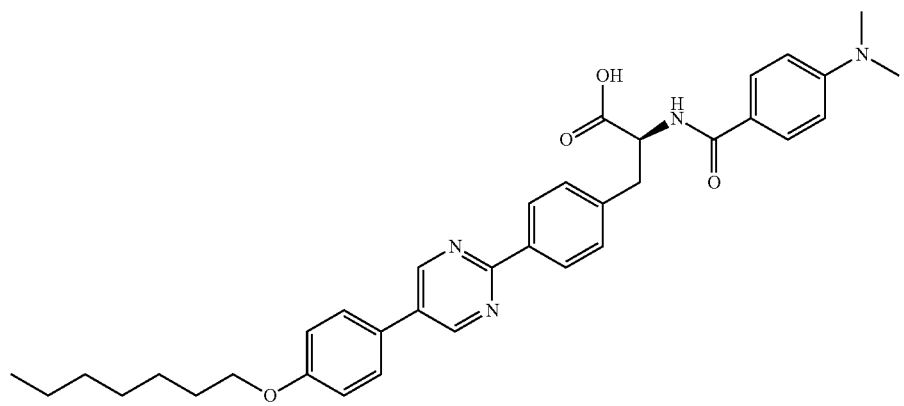
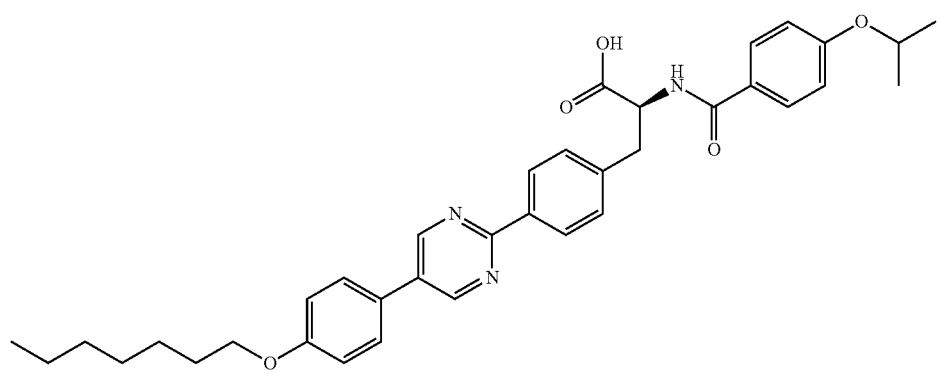

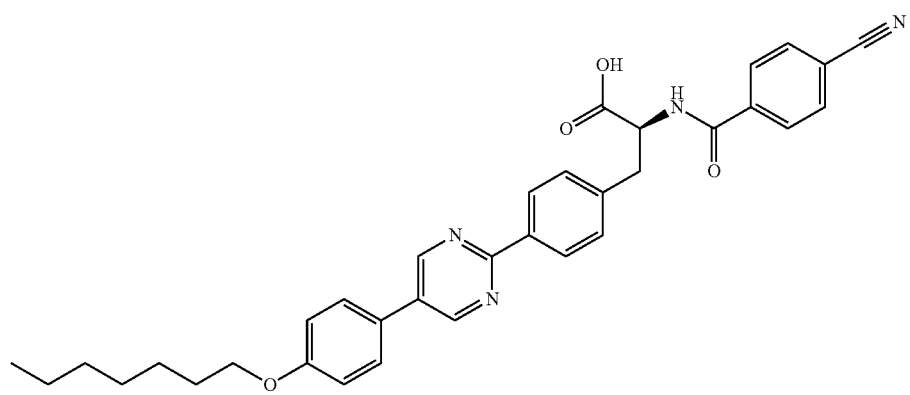
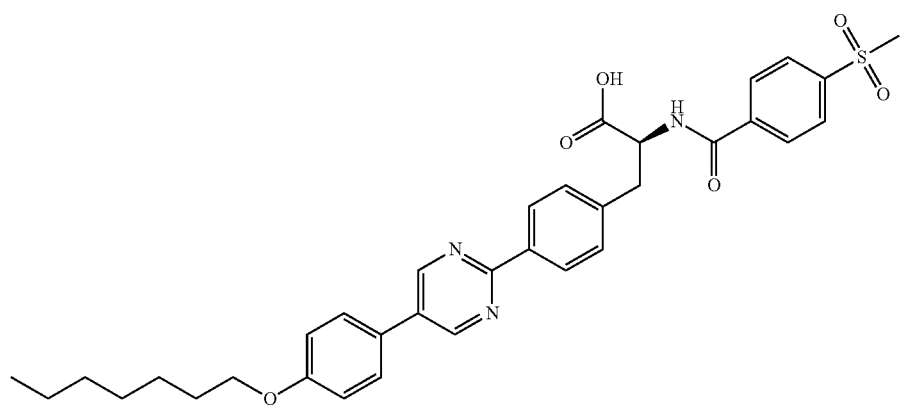
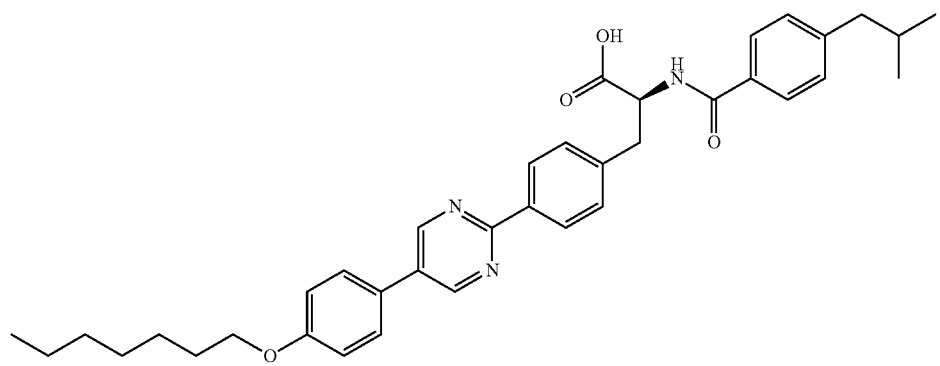
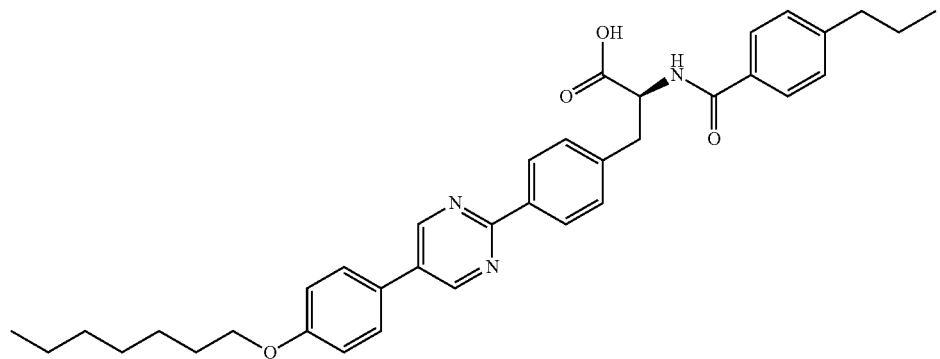

1045 1046
-continued
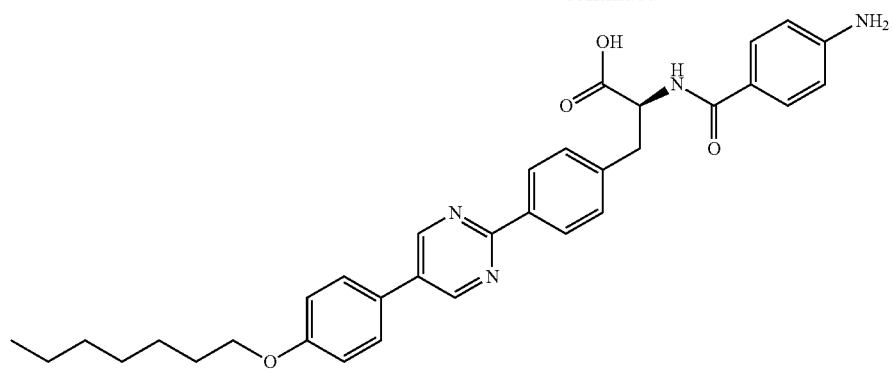
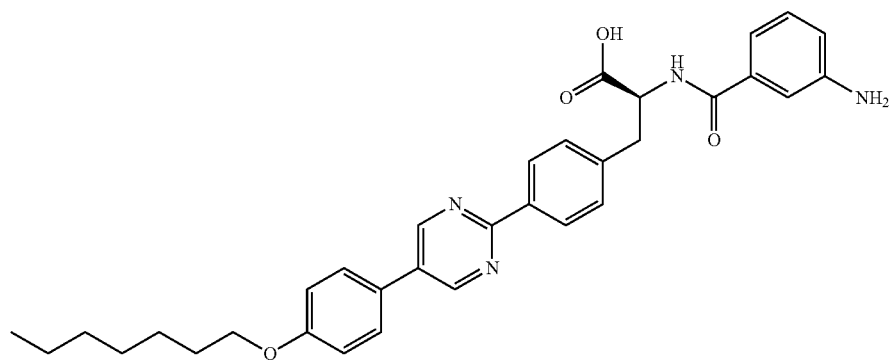
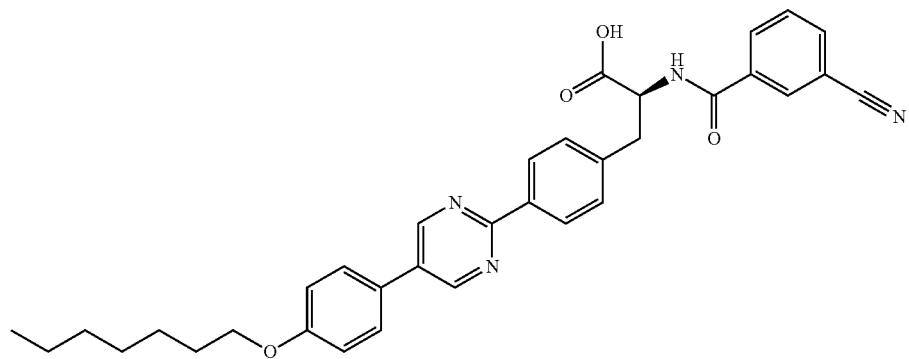
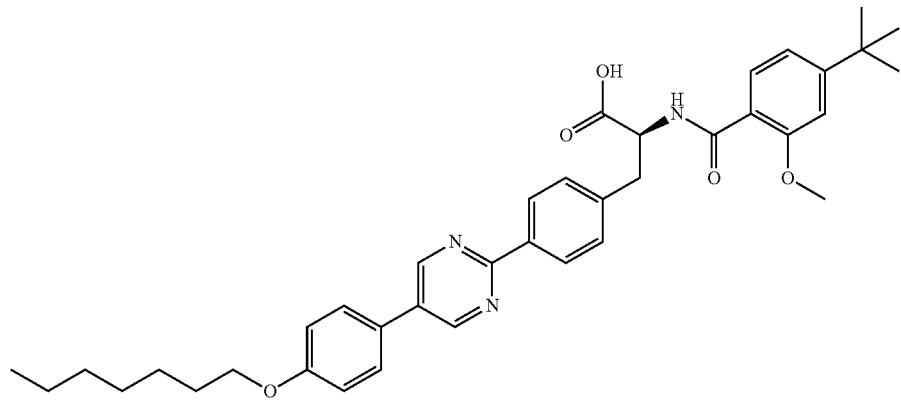

-continued
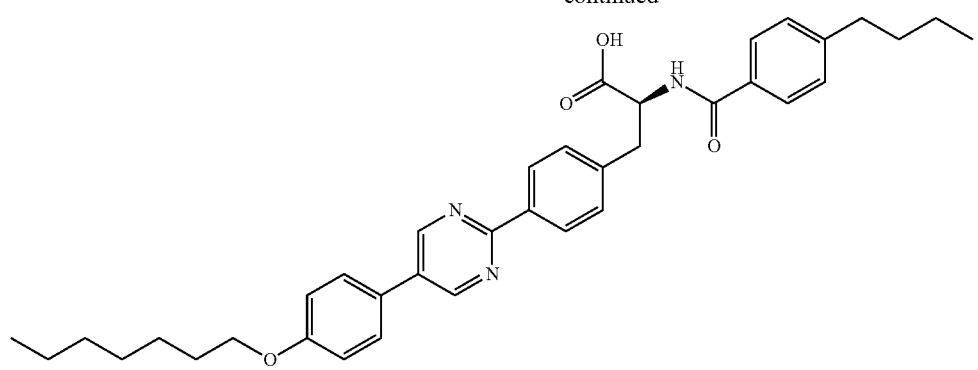
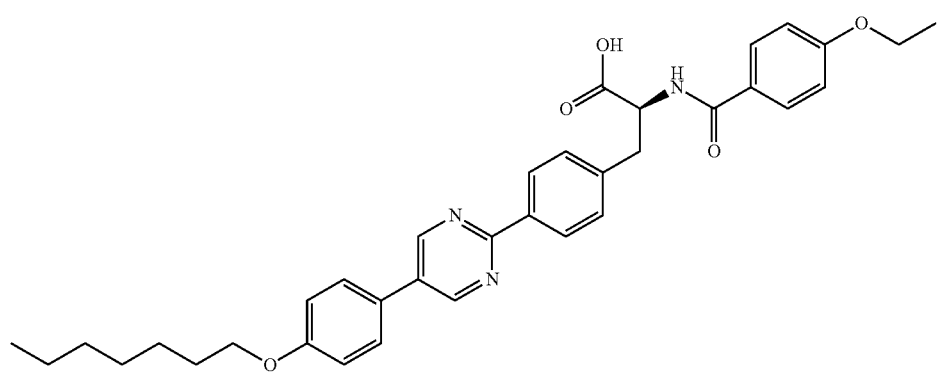
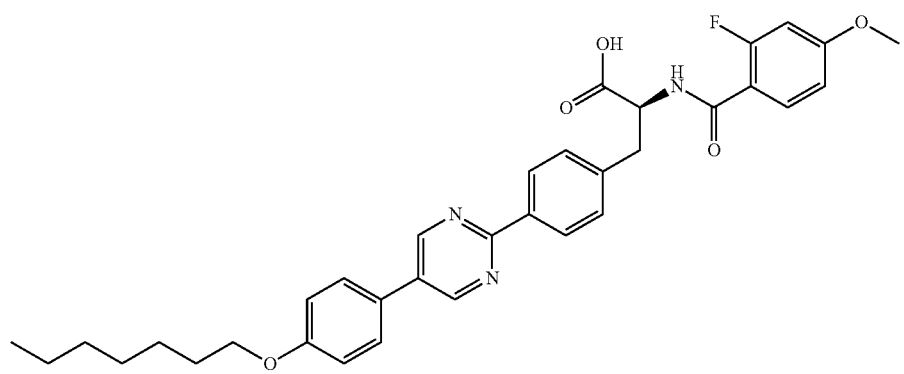
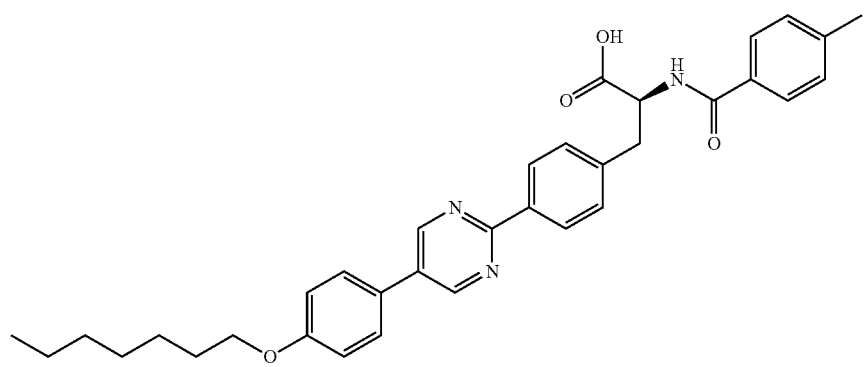

-continued
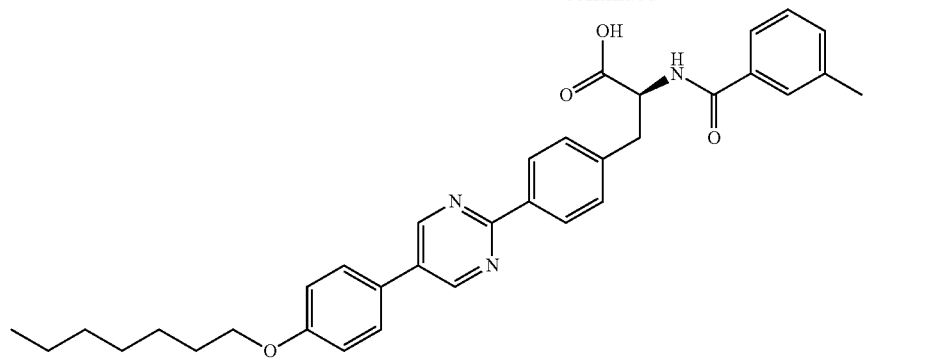
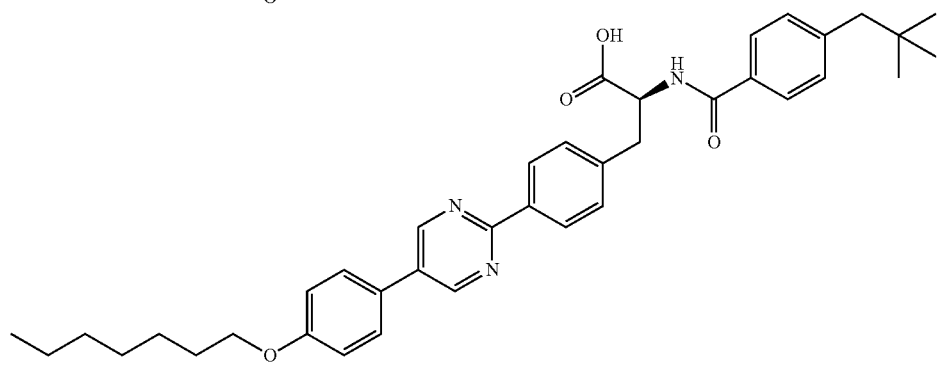
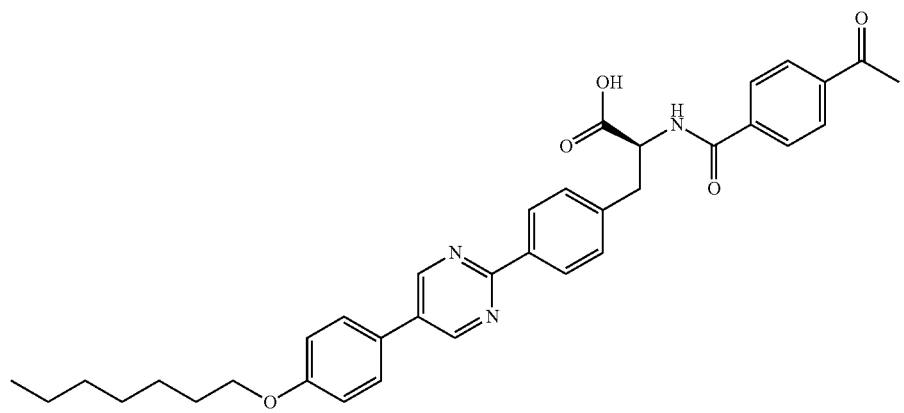
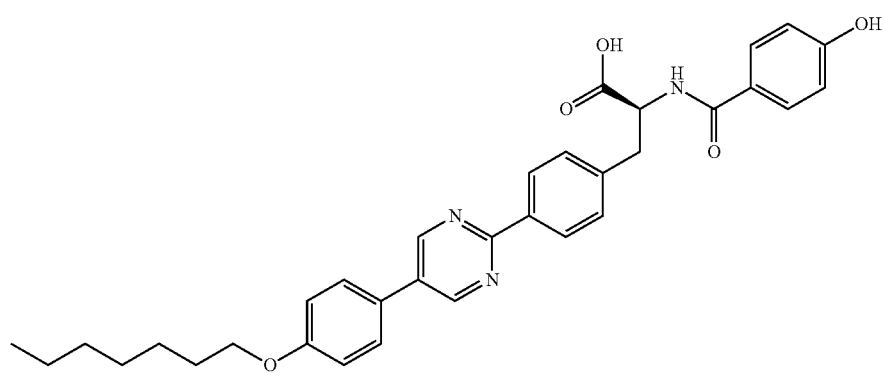

1051
1052
-continued
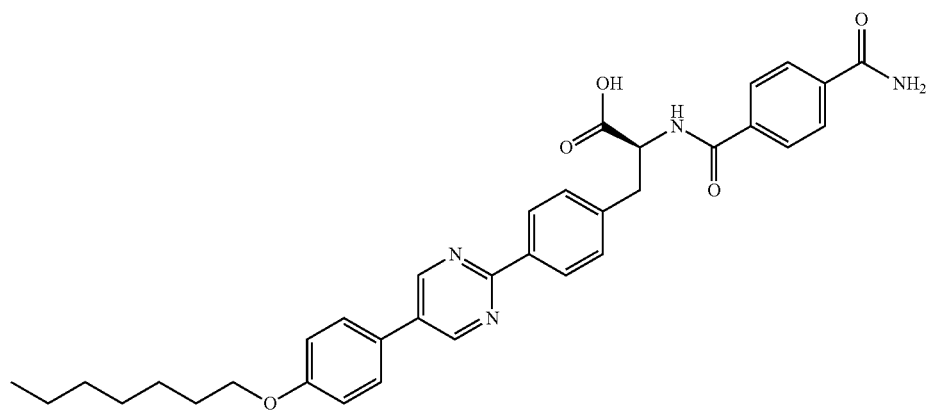
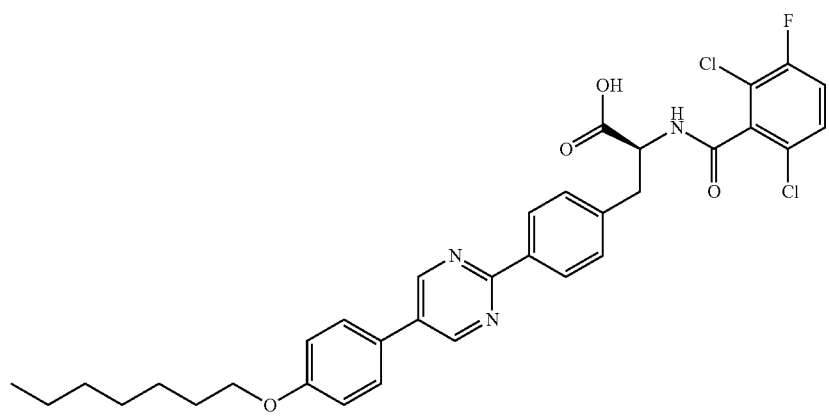
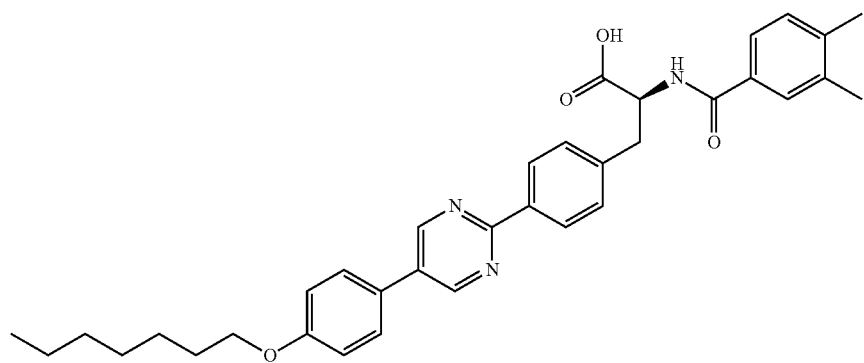
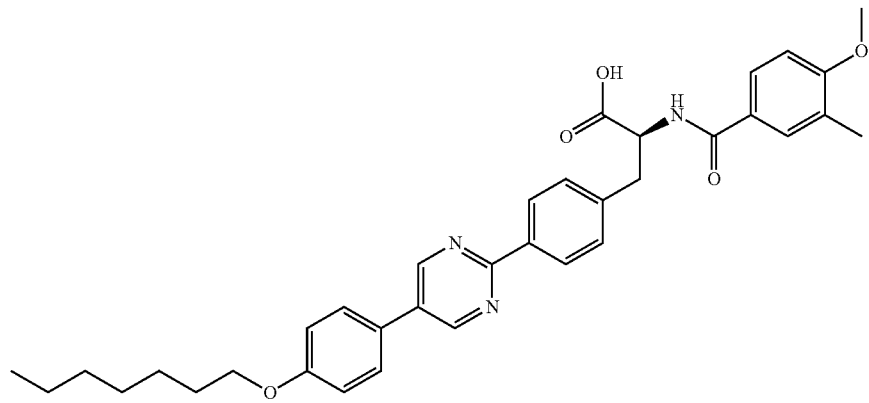

1053
-continued
1054
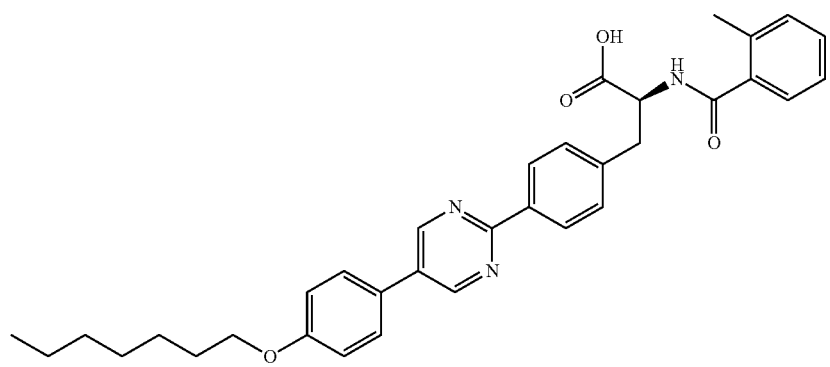
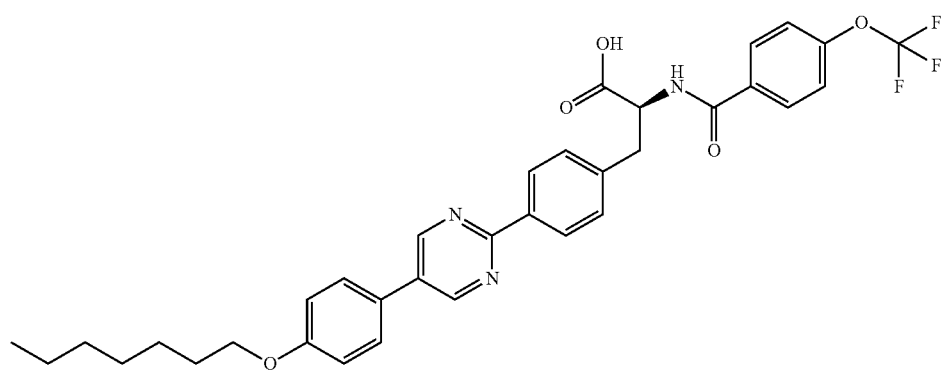
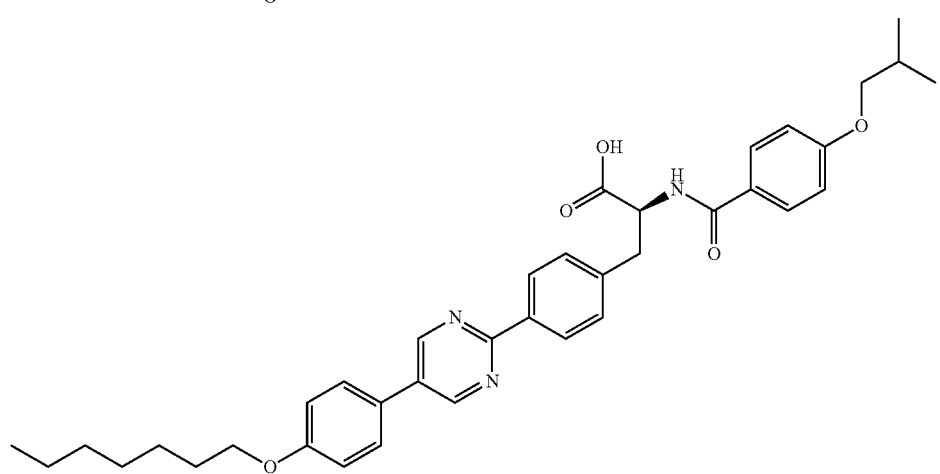
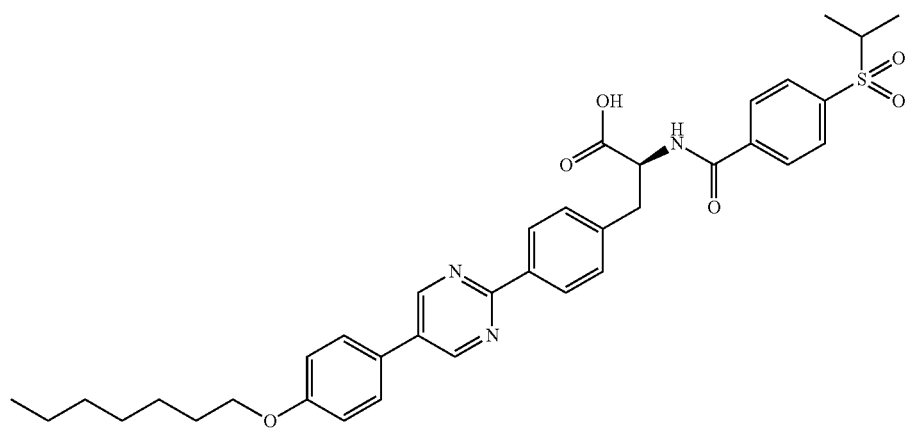

1055
-continued
1056
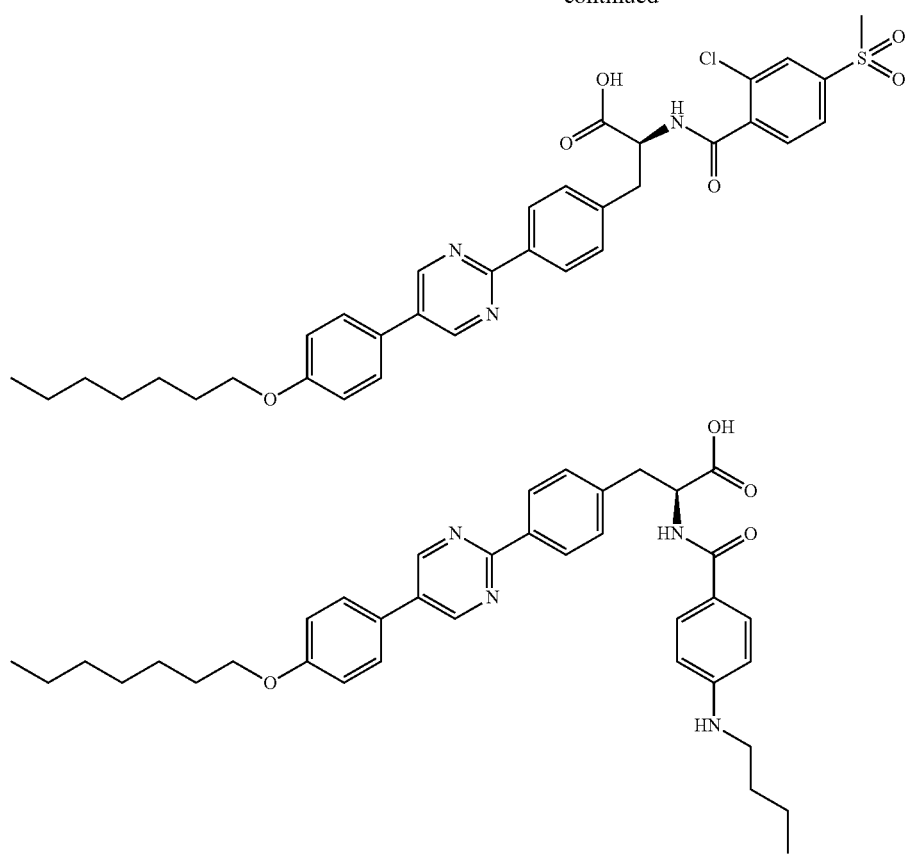
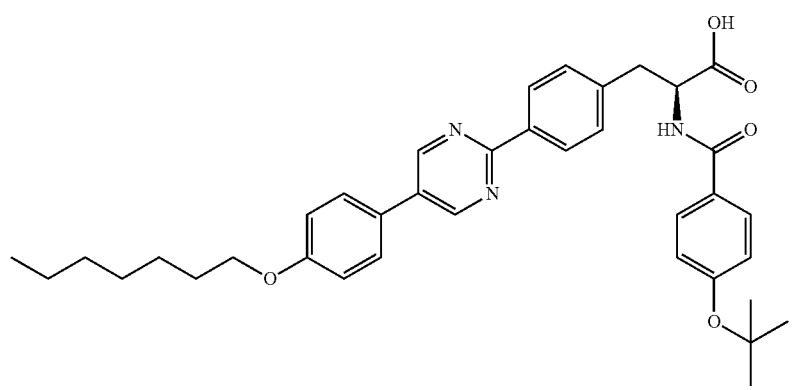
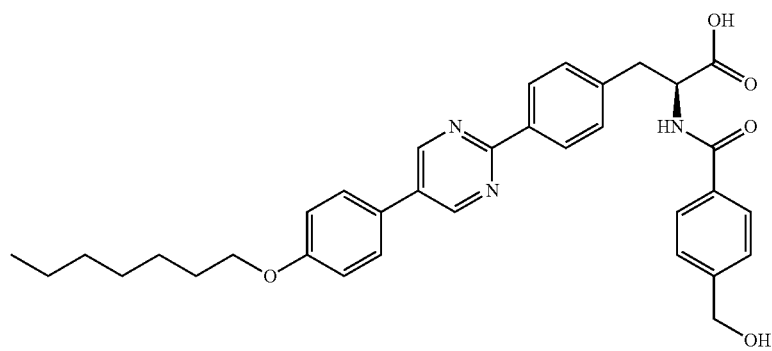

-continued
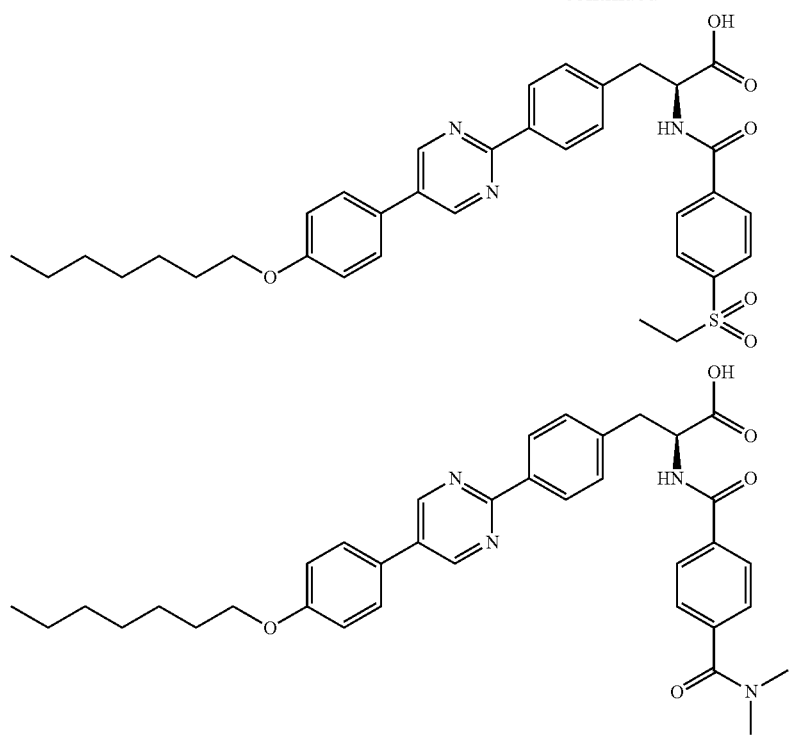
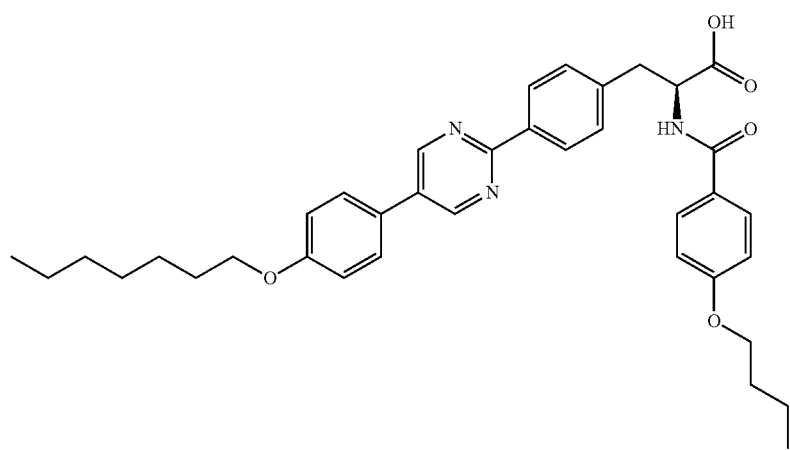
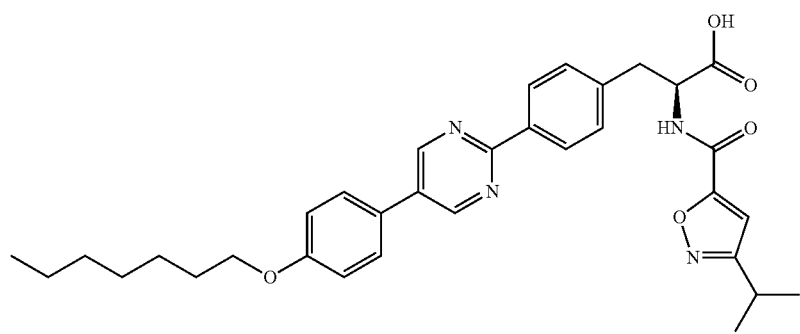

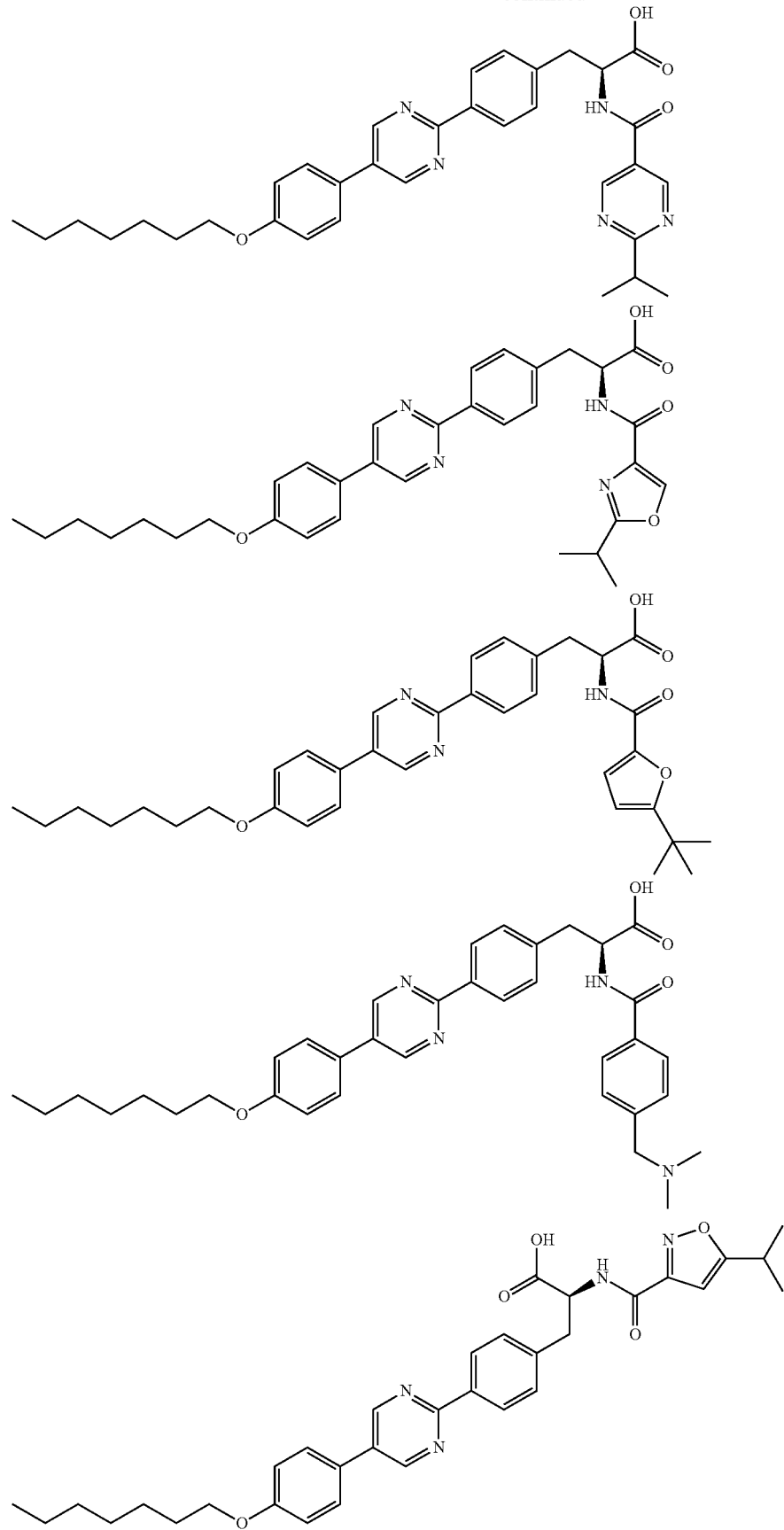

1061
-continued
1062
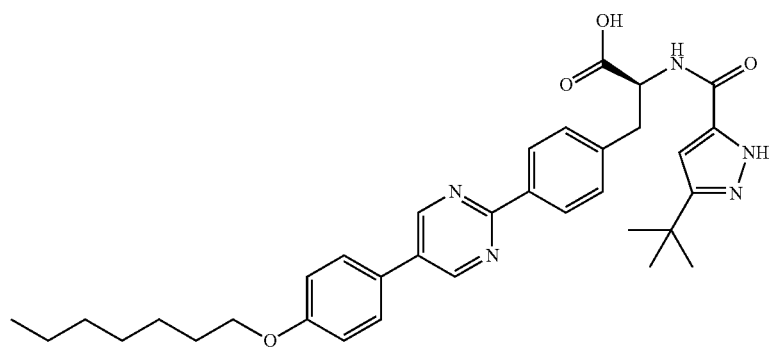
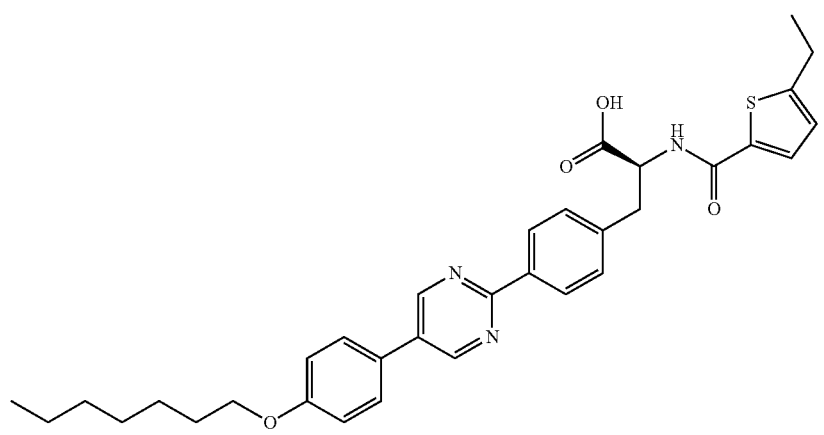
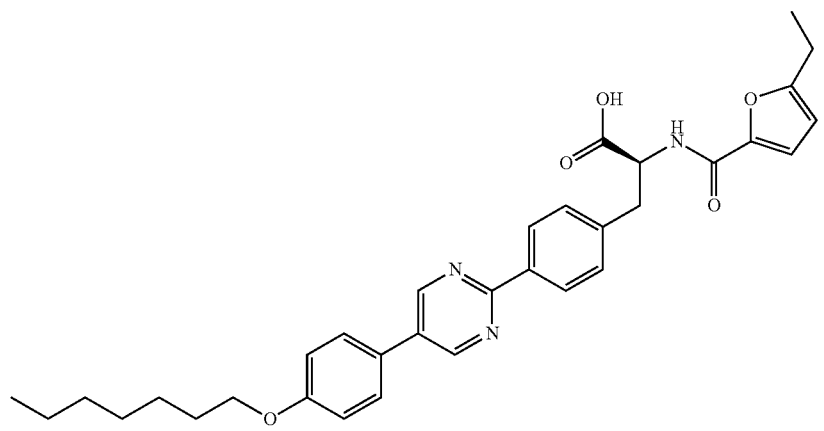
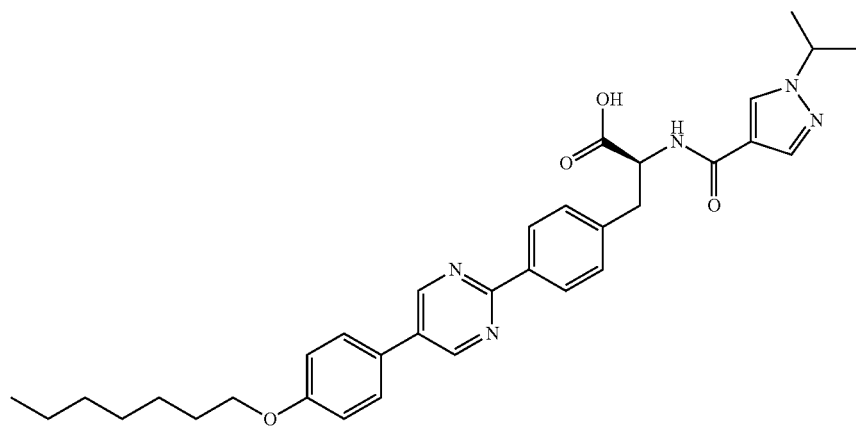

-continued
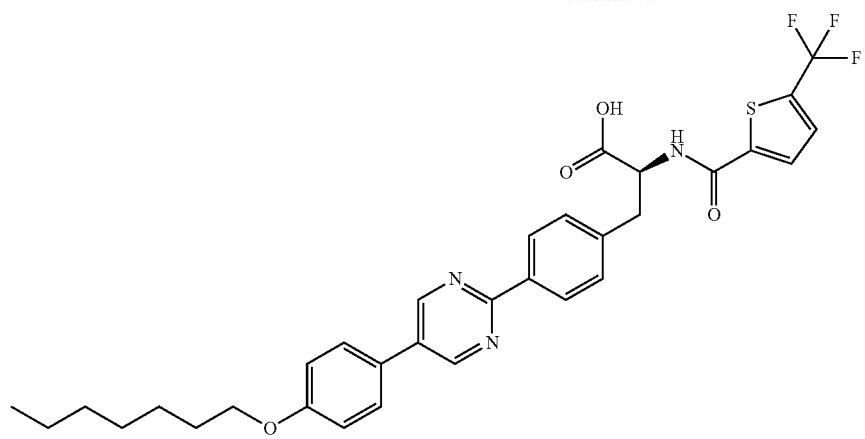
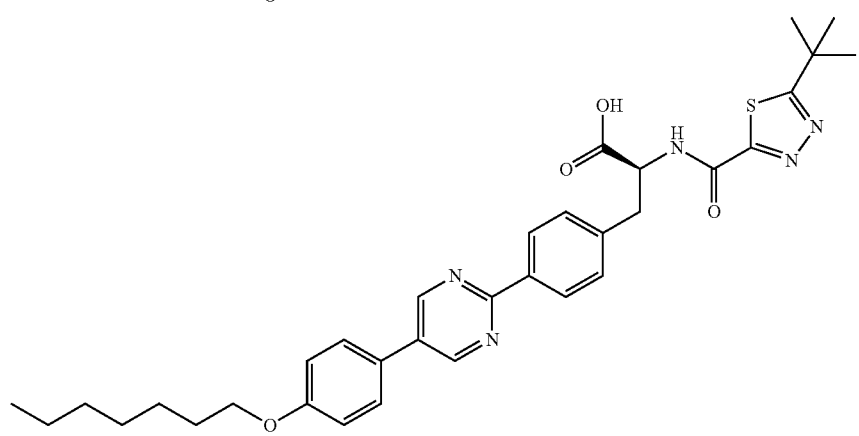
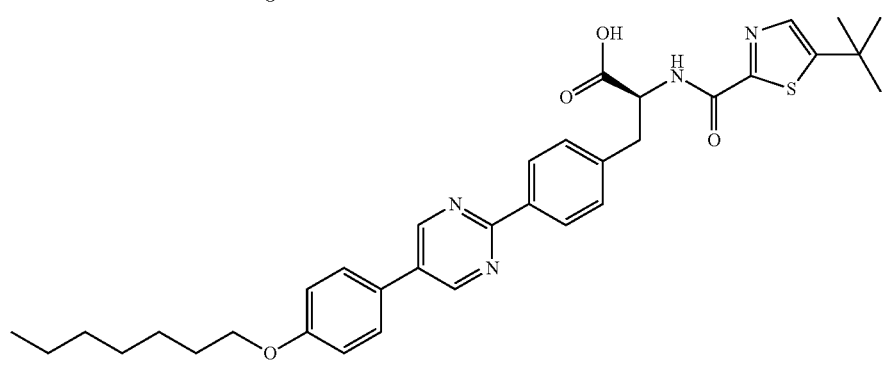
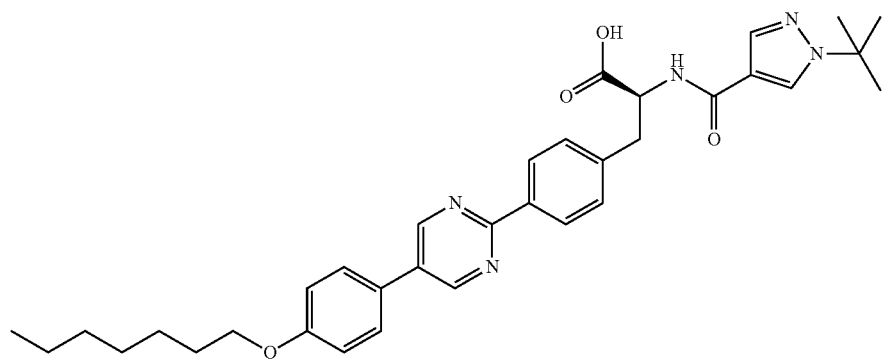

1065 | 1066
-continued
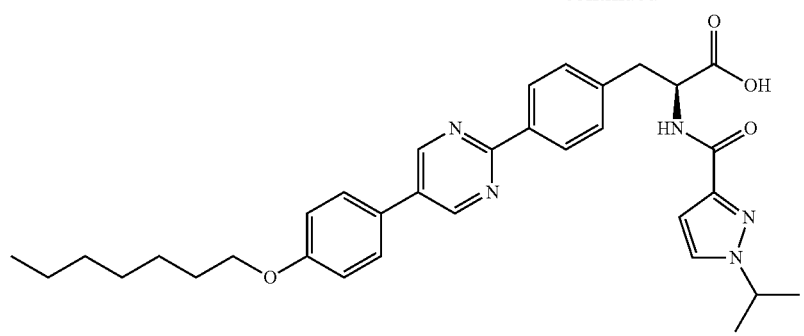
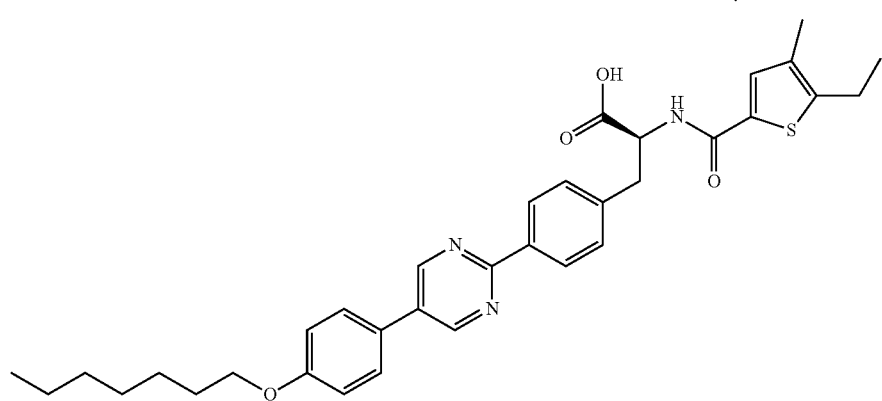
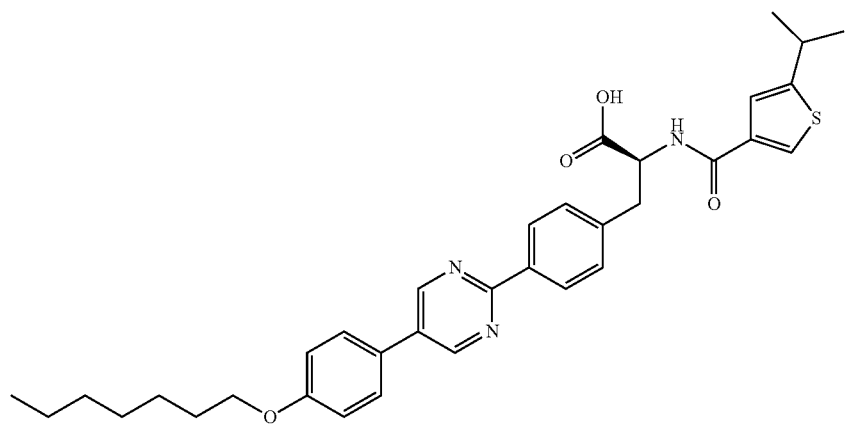
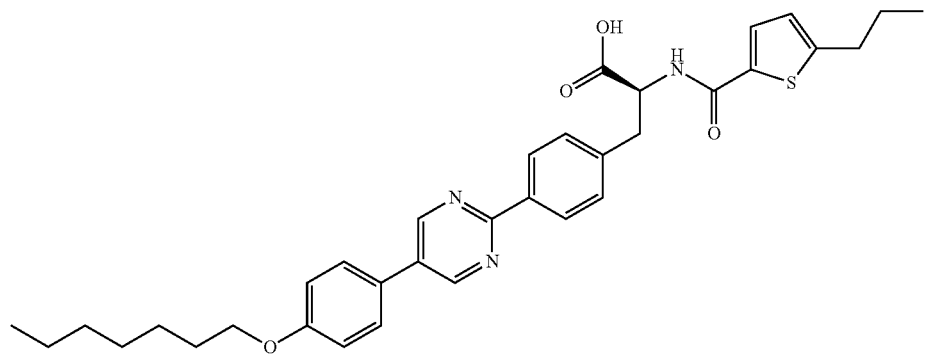

-continued
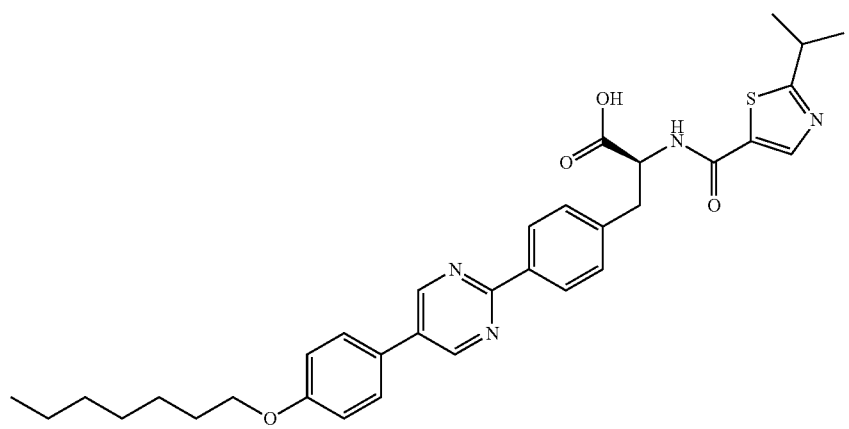
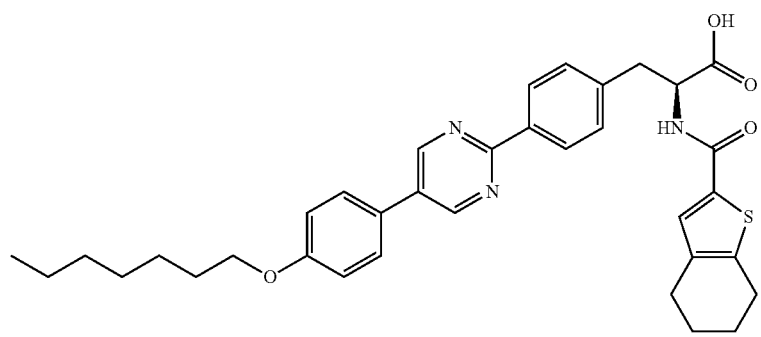
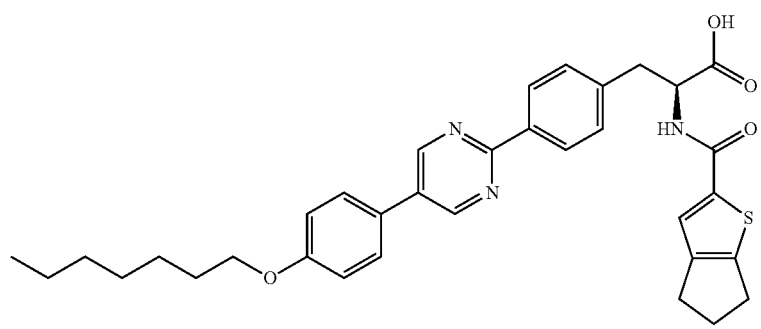
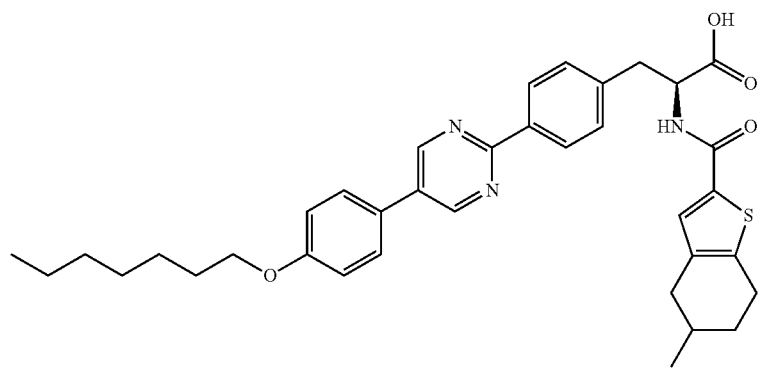

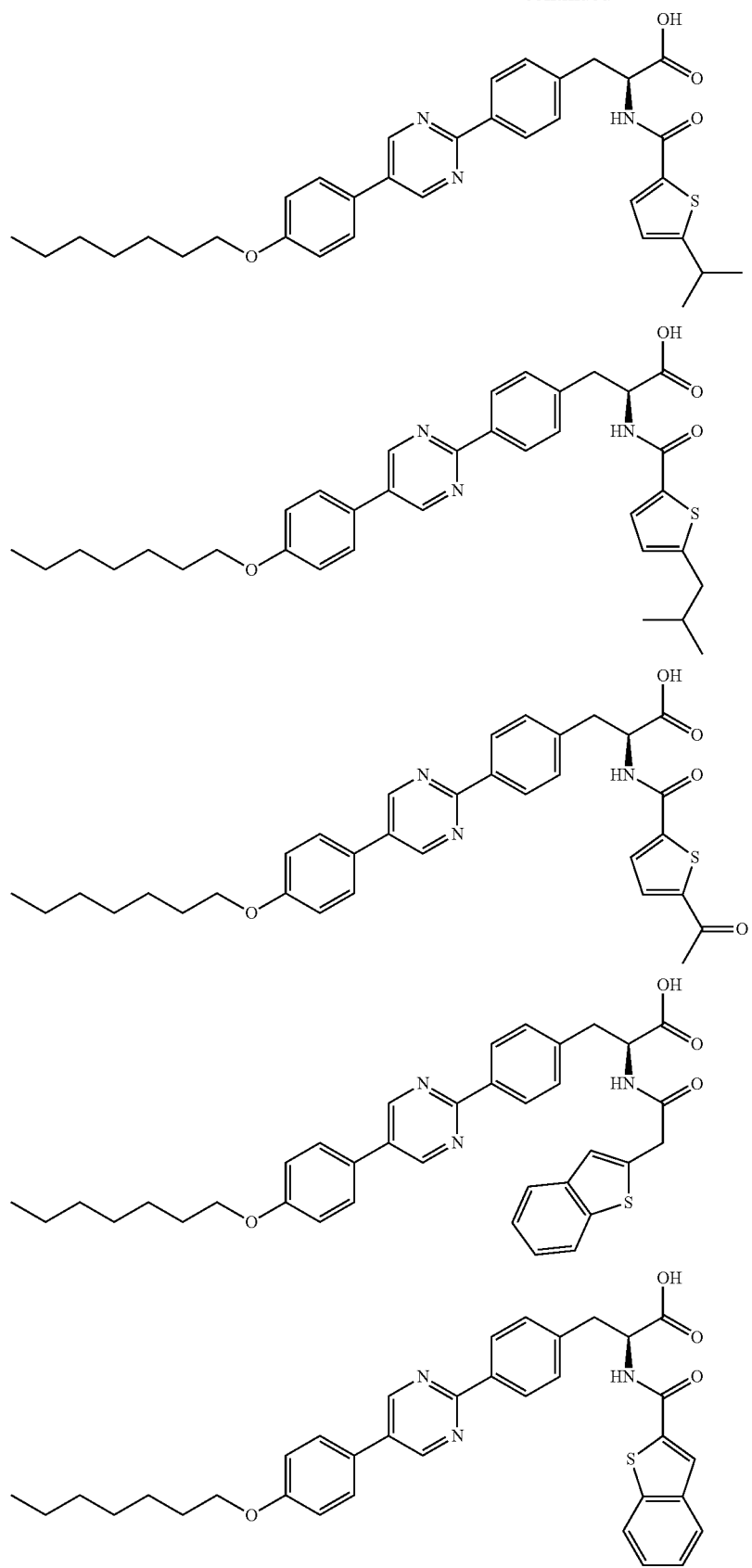

1071                              -continued                              1072
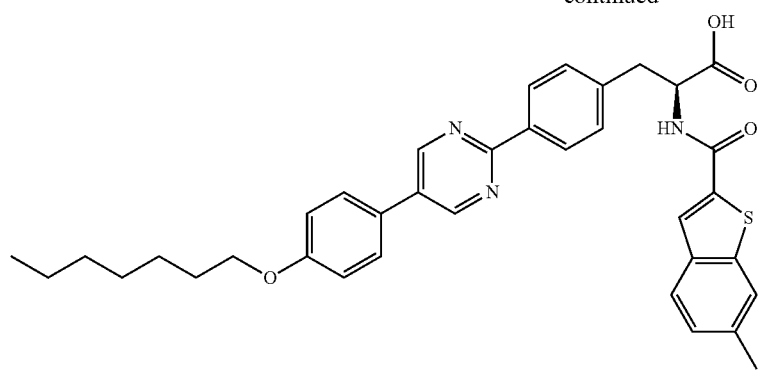
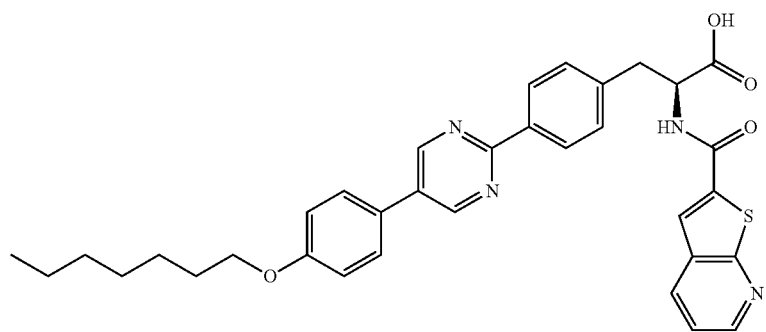
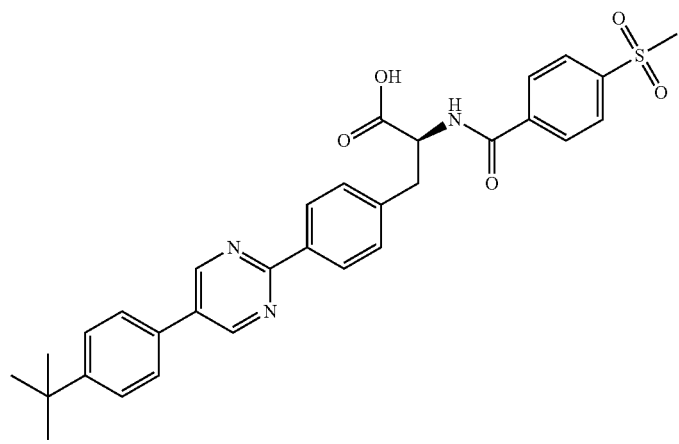
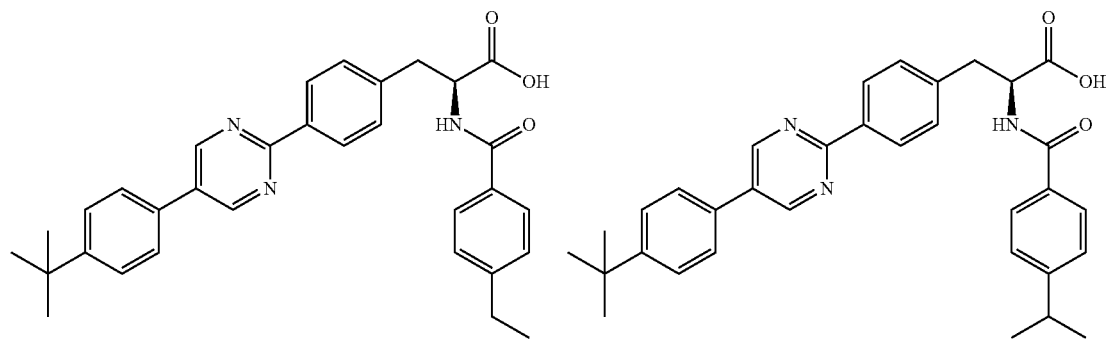

1073 1074
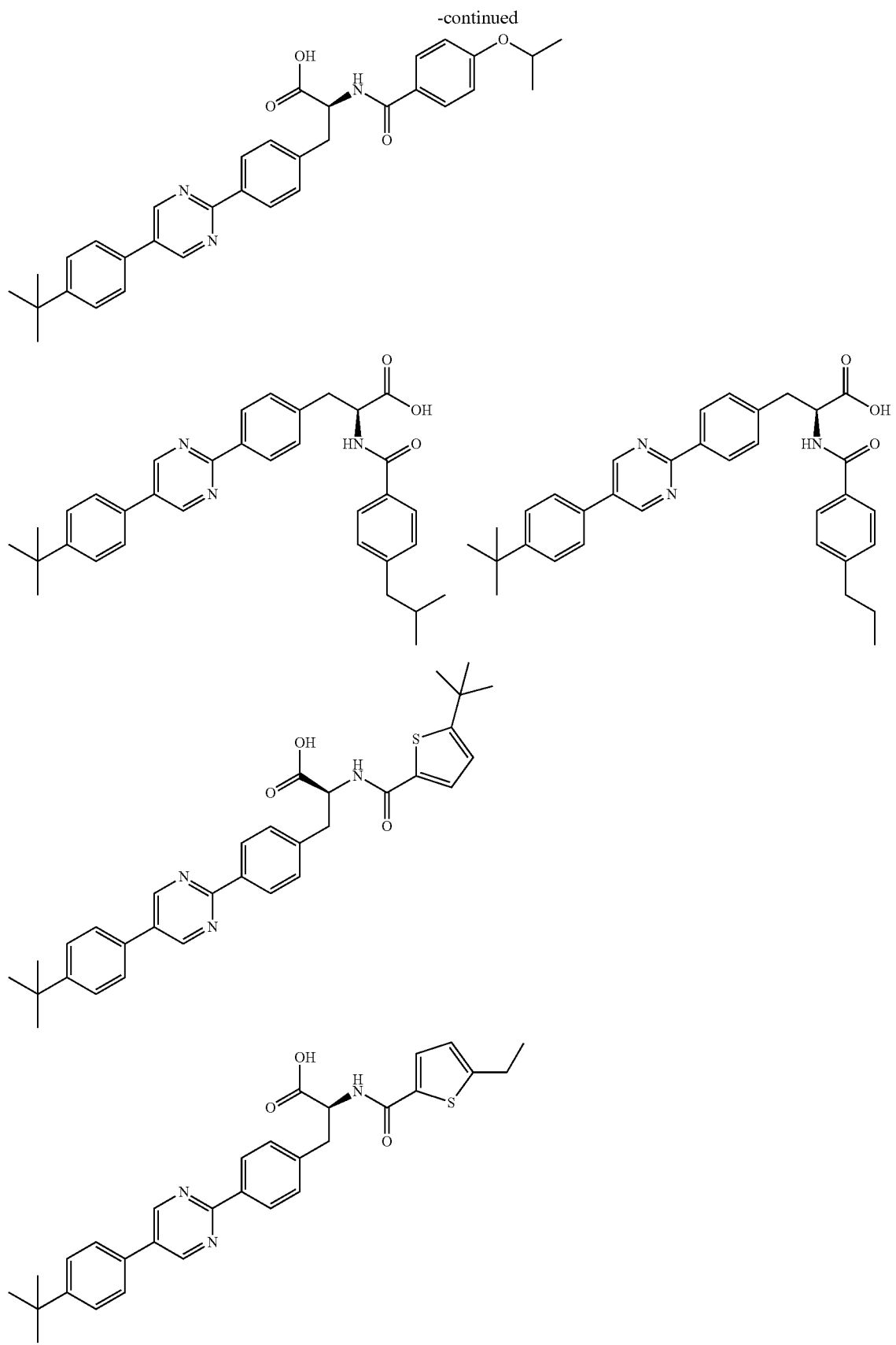

1075
-continued
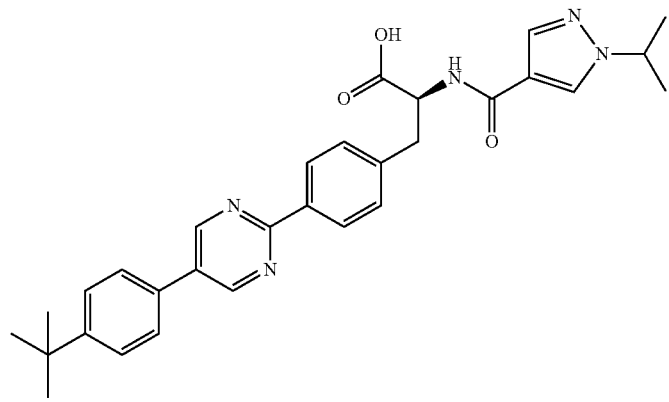
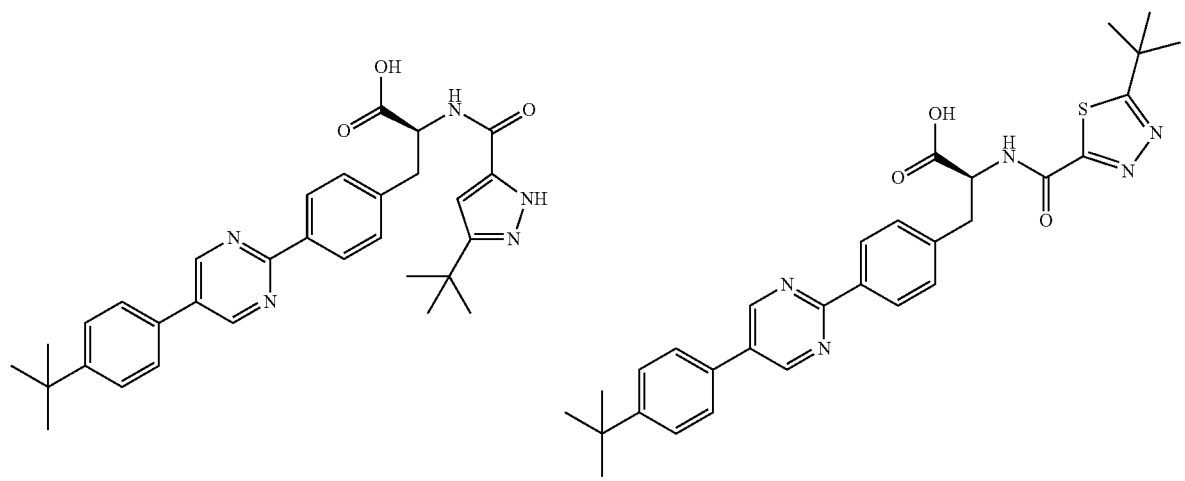
1076
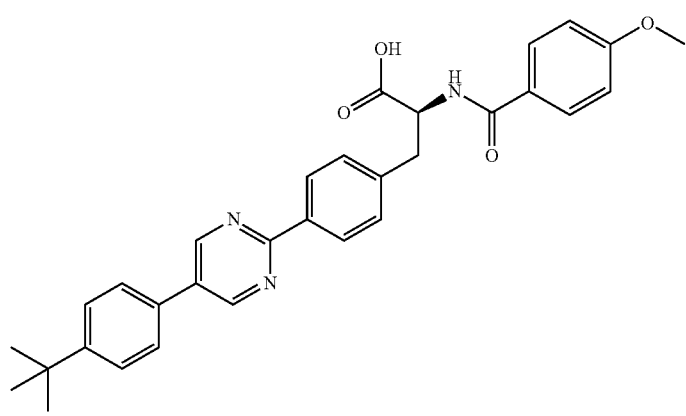
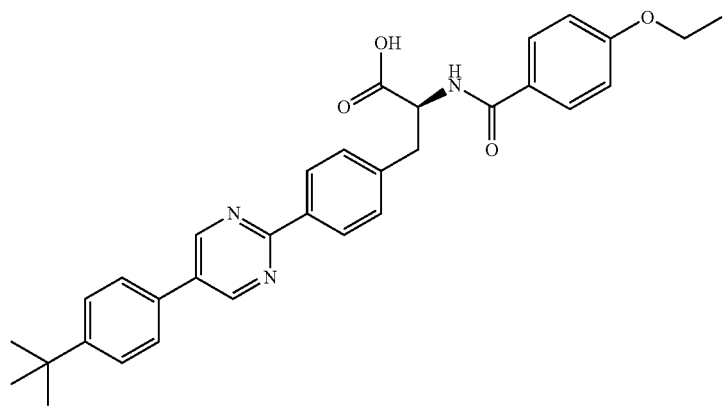

1077
-continued
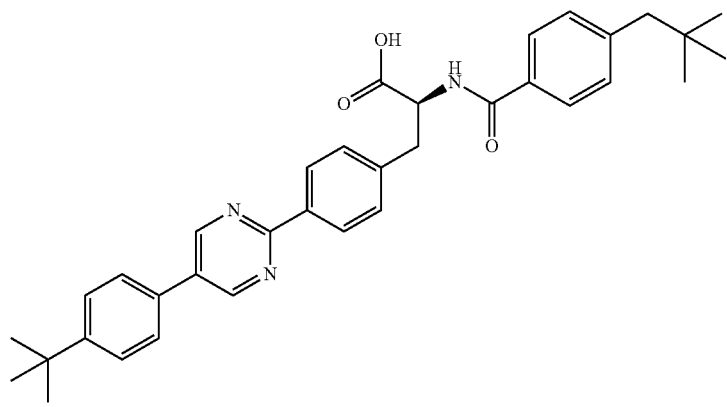
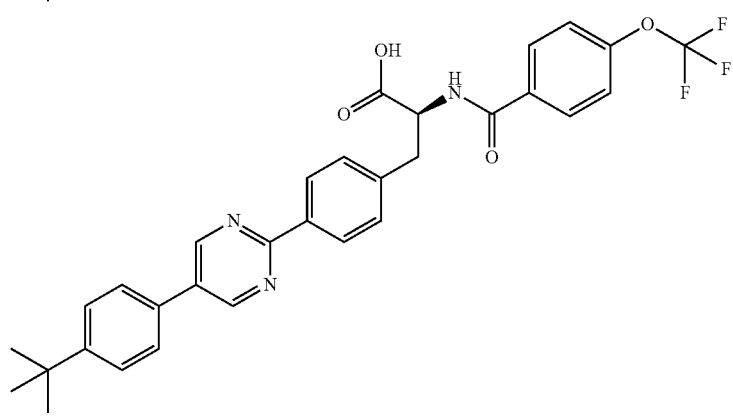
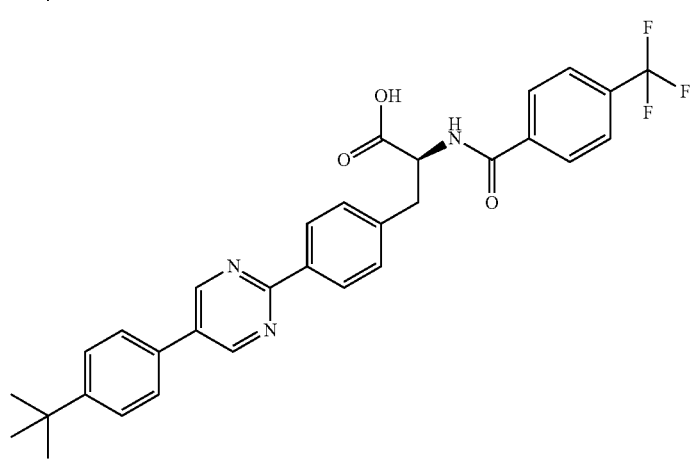
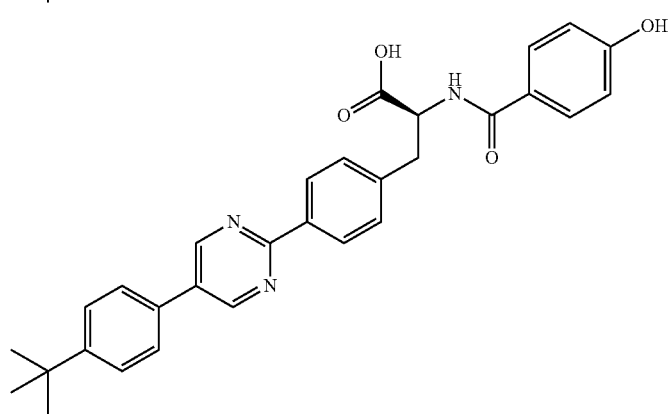
1078

1079
-continued
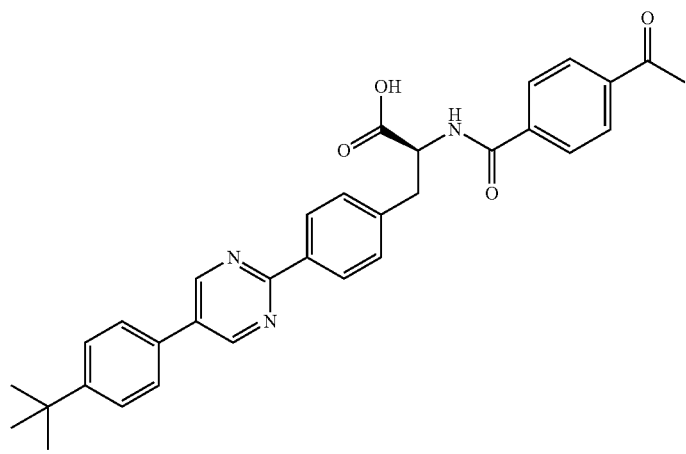
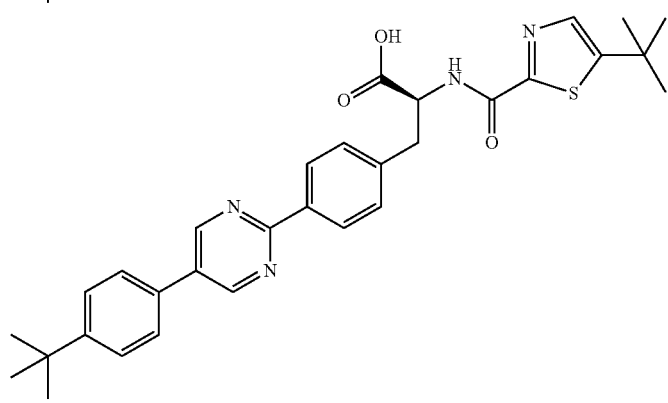
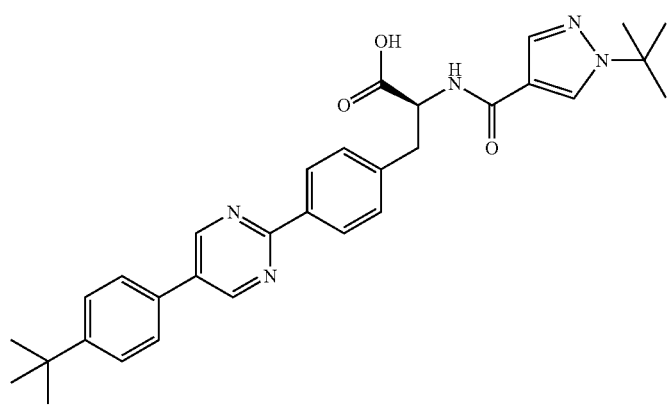
1080
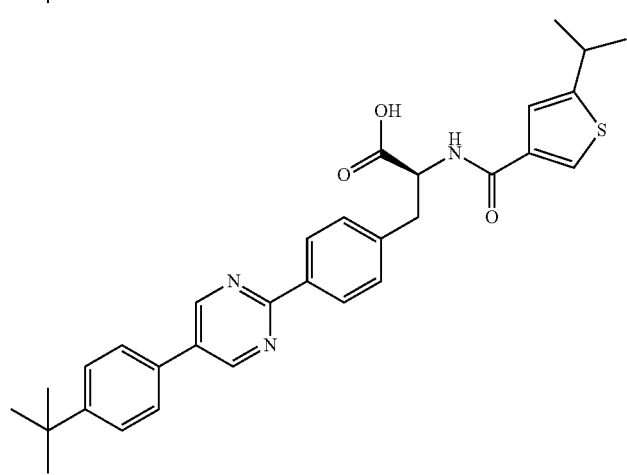

-continued
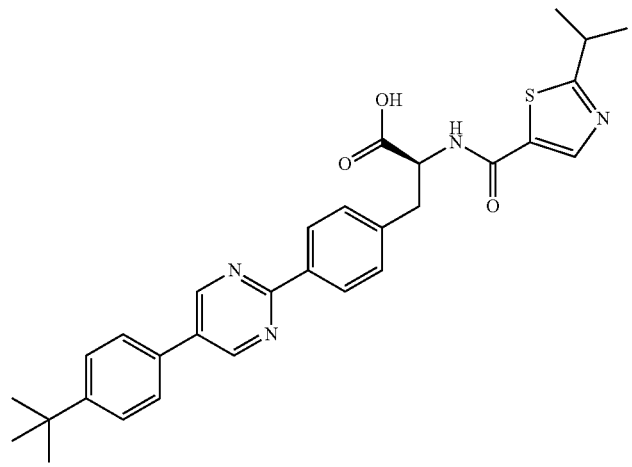
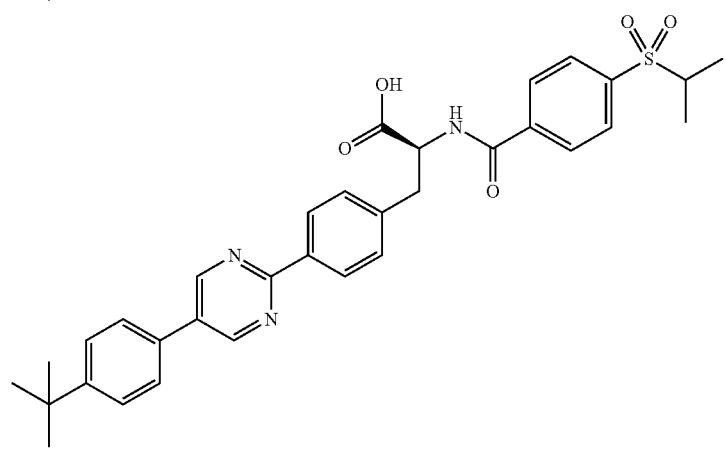
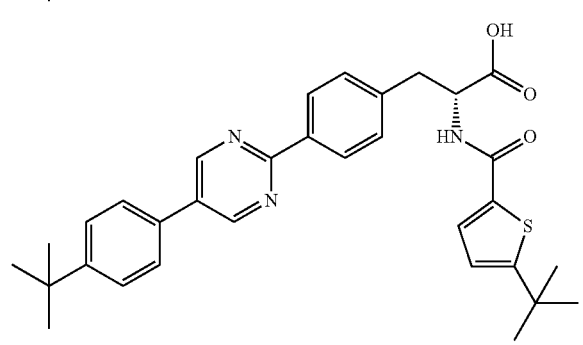
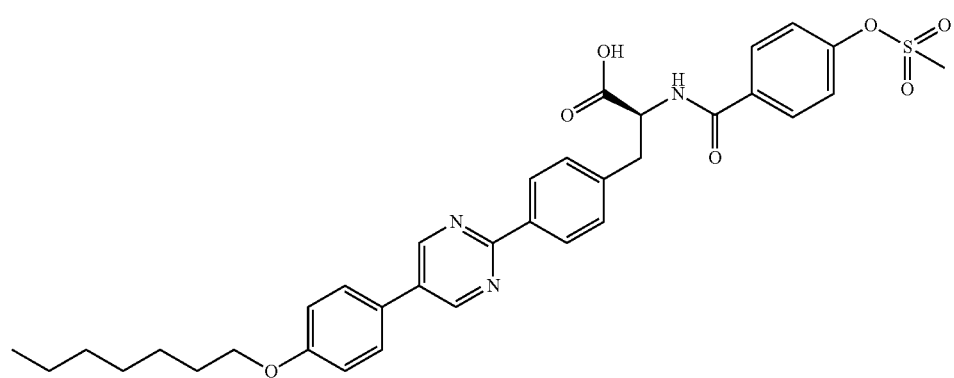

-continued
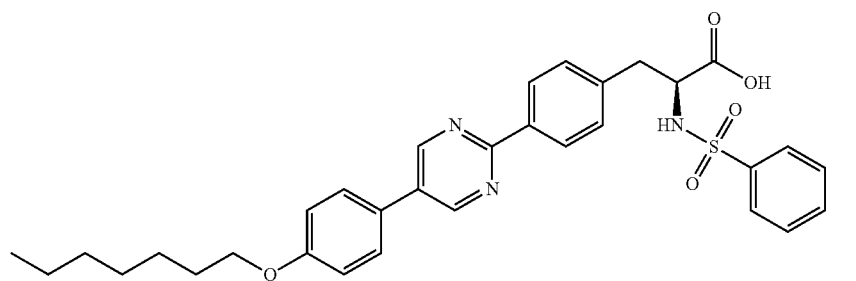
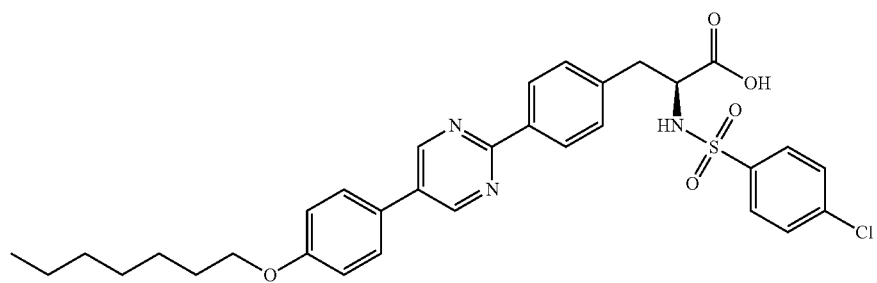
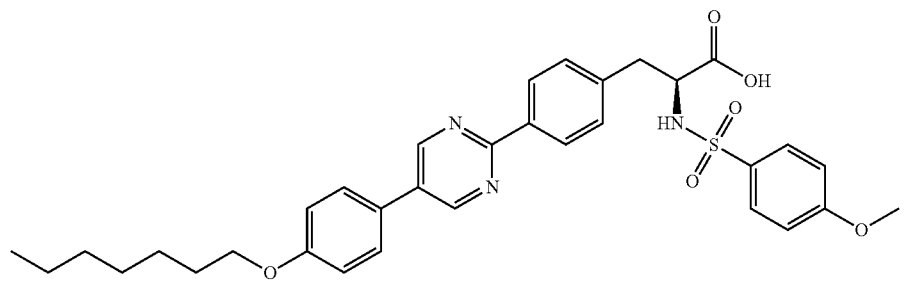
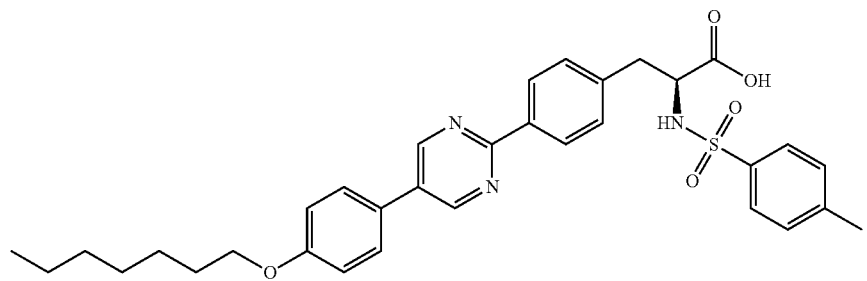
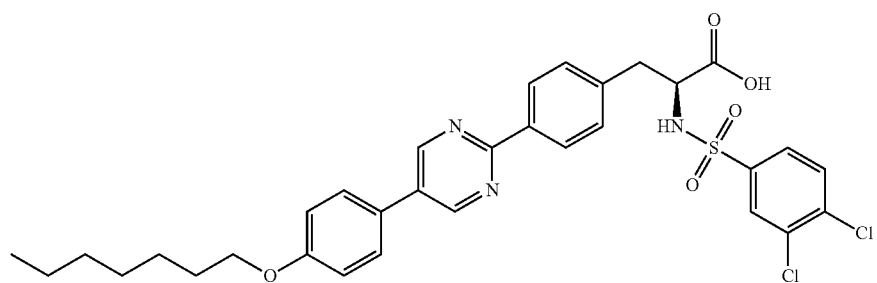
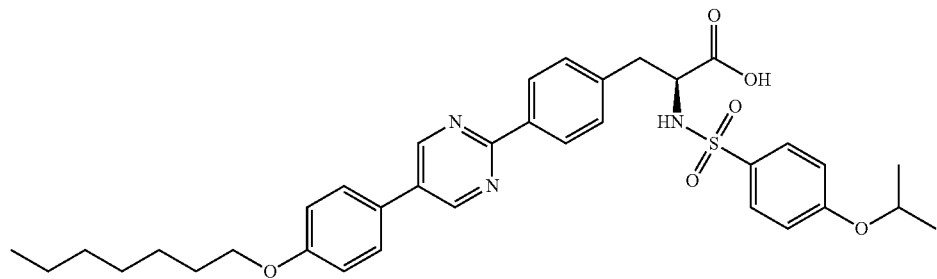

-continued
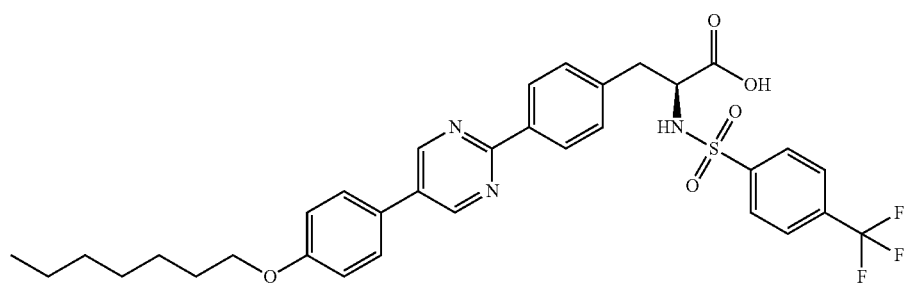
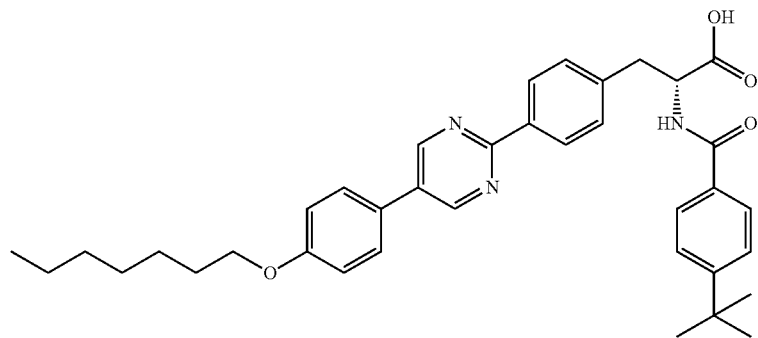
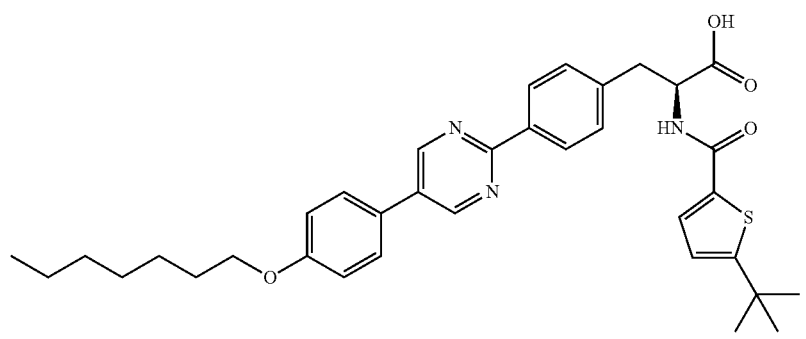
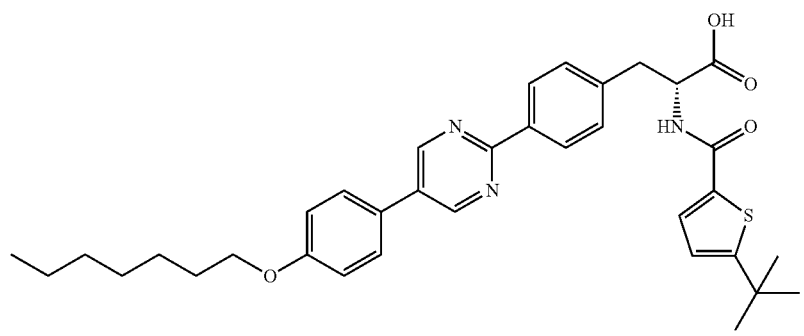
1085
1086
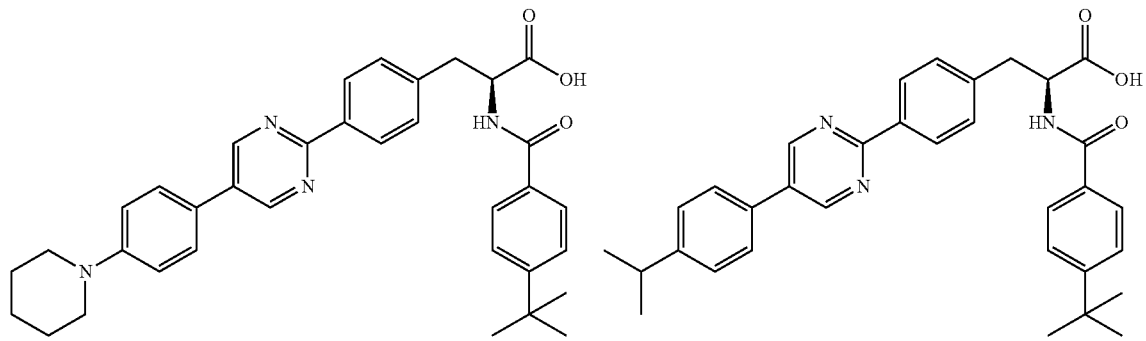

1087    1088
-continued
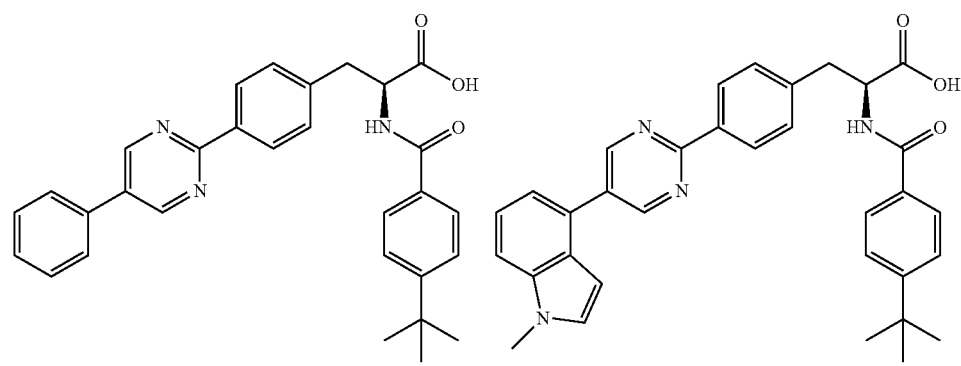
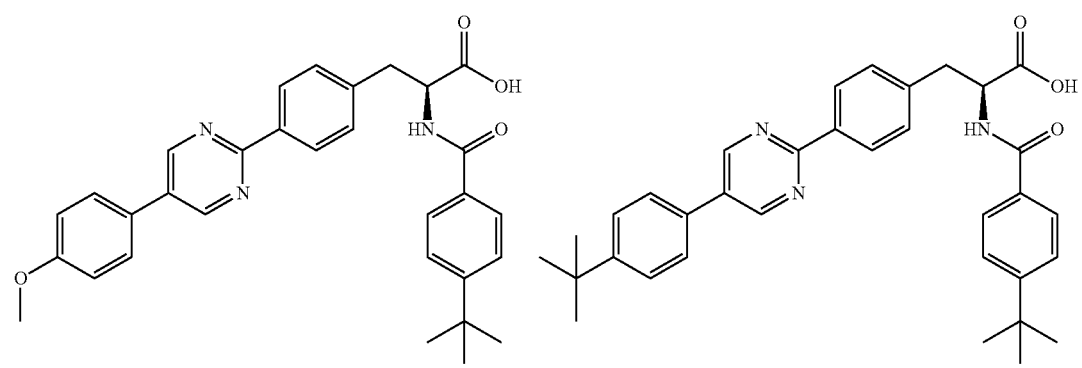
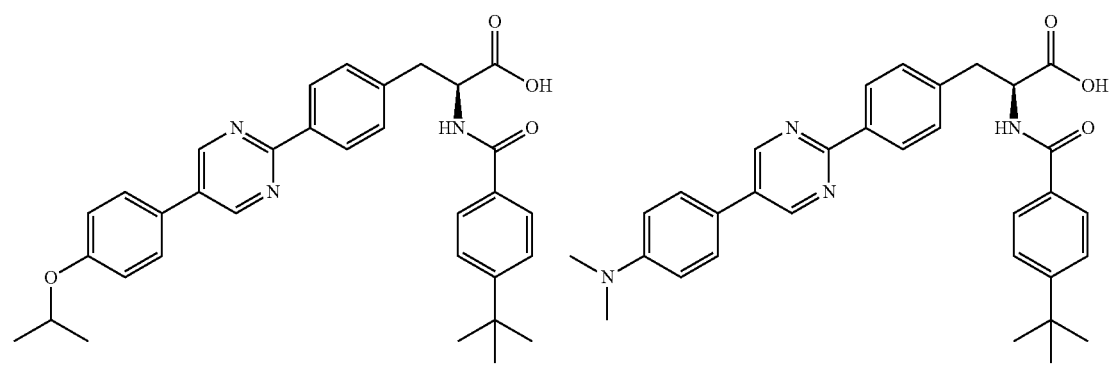
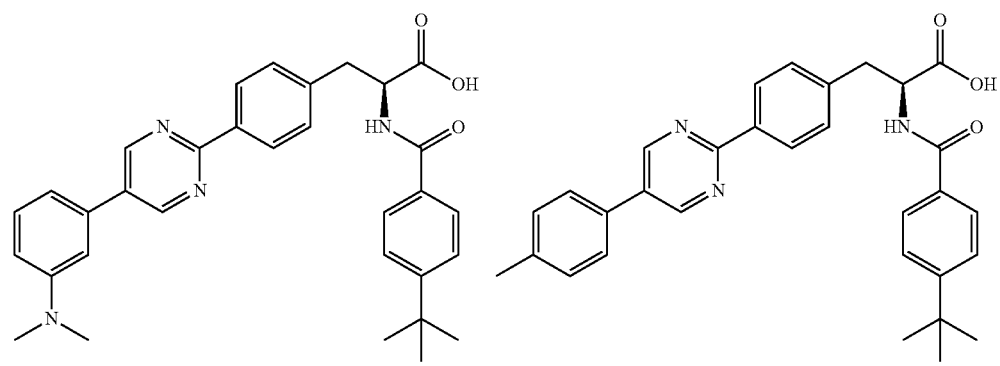

| 1089 | 1090 |
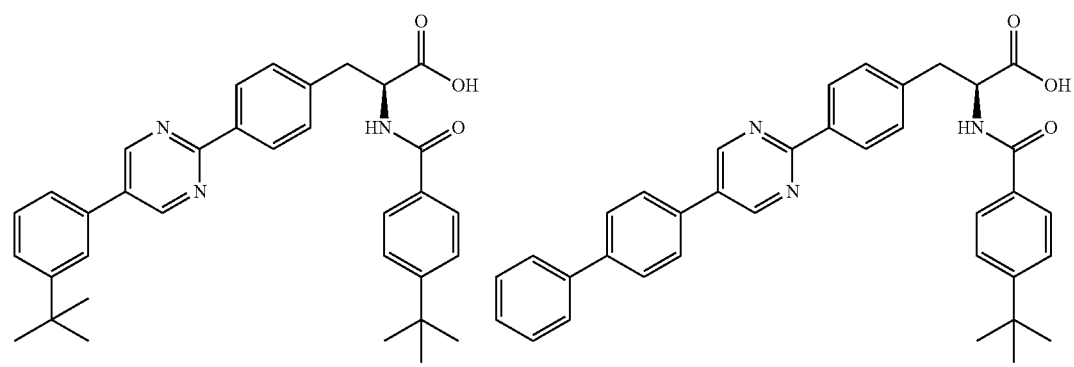
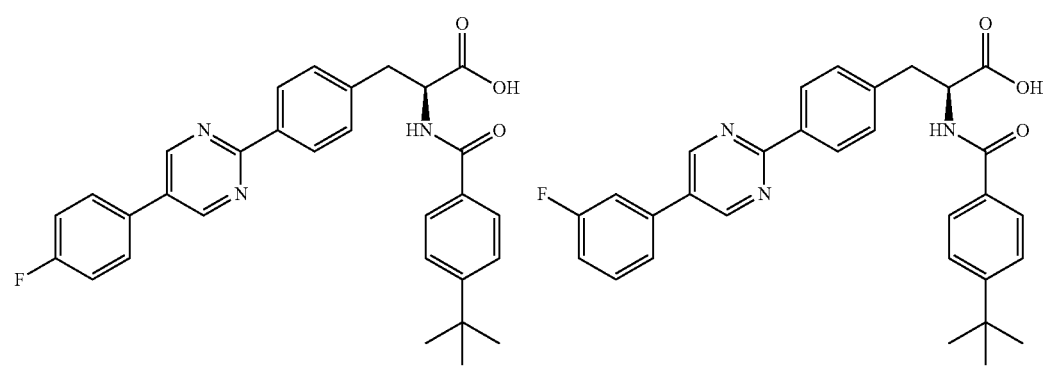
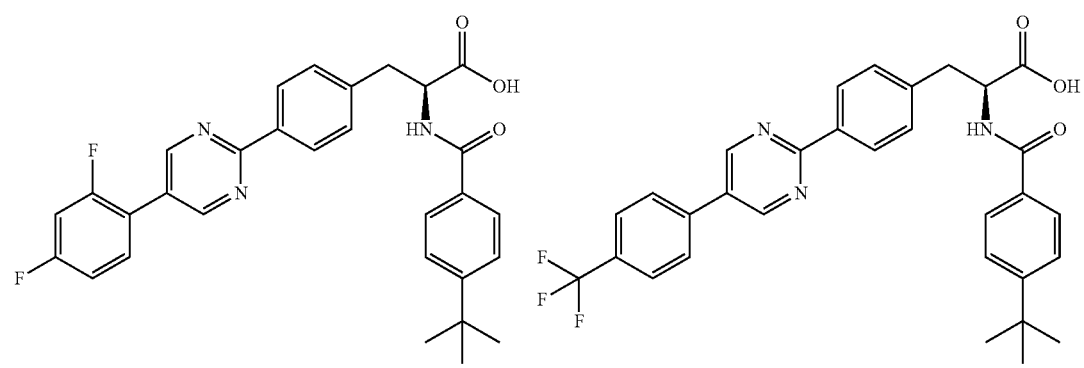
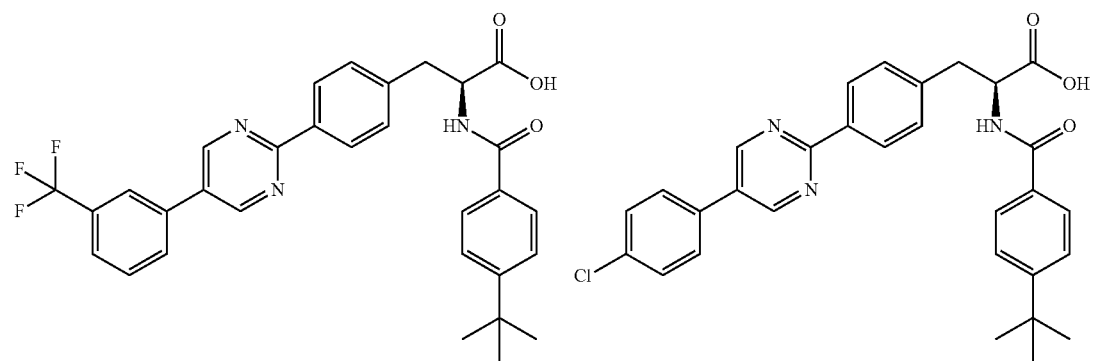

1091  1092
-continued
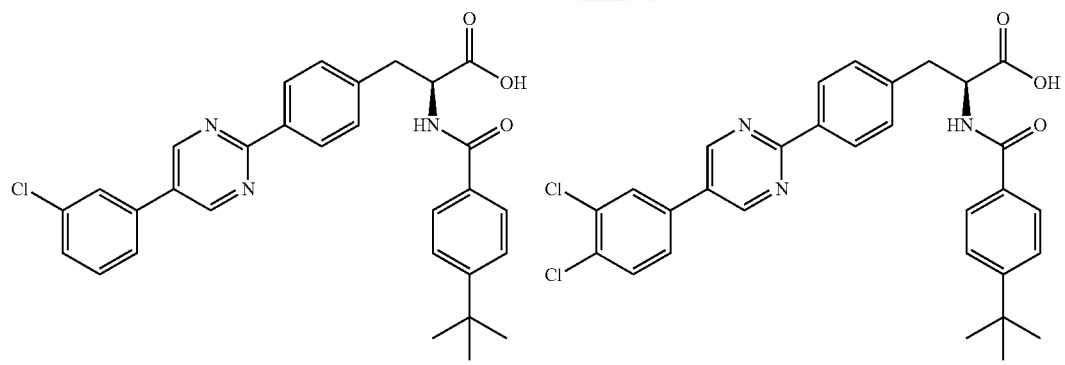
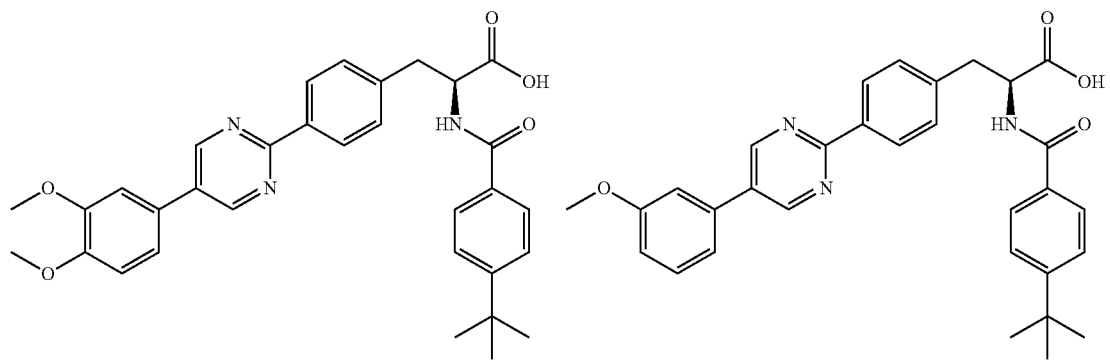
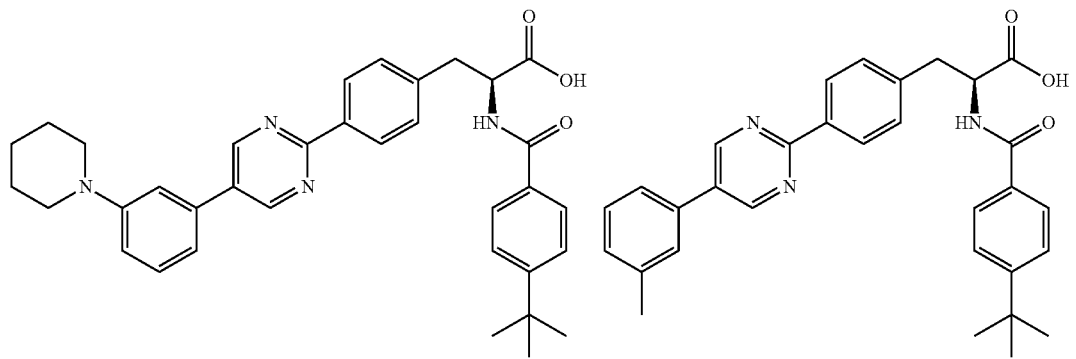
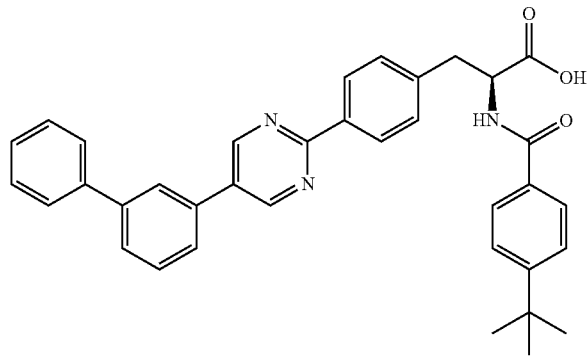

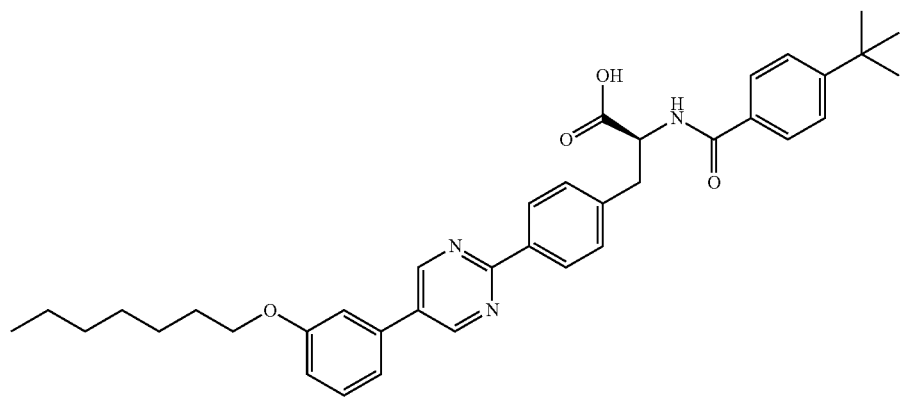
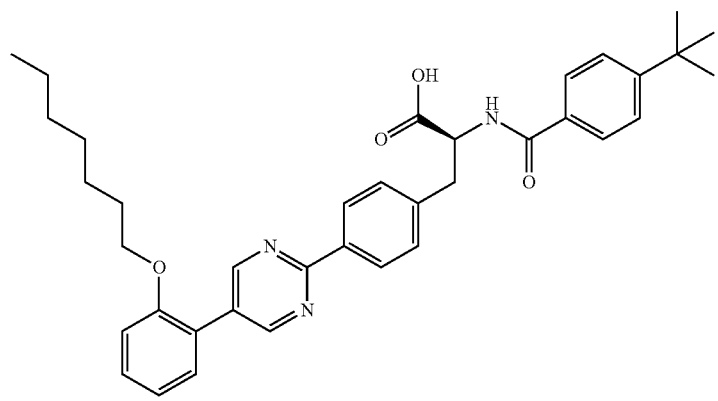
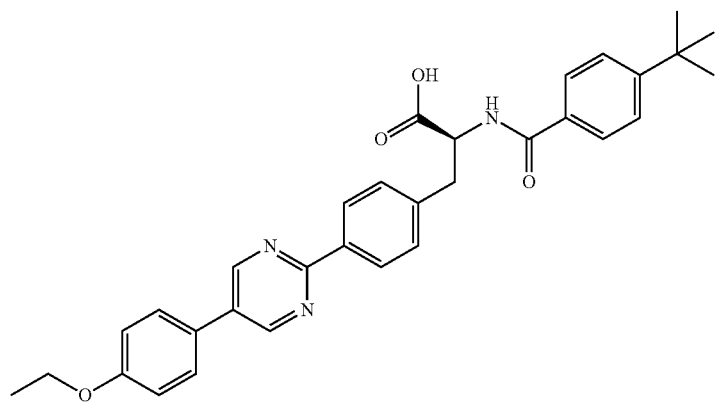
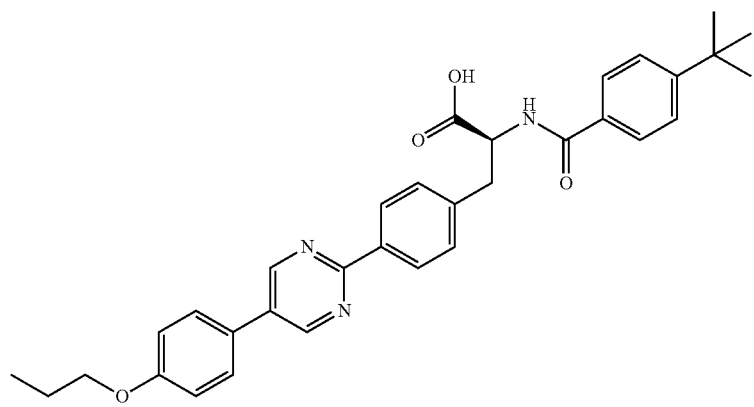

-continued
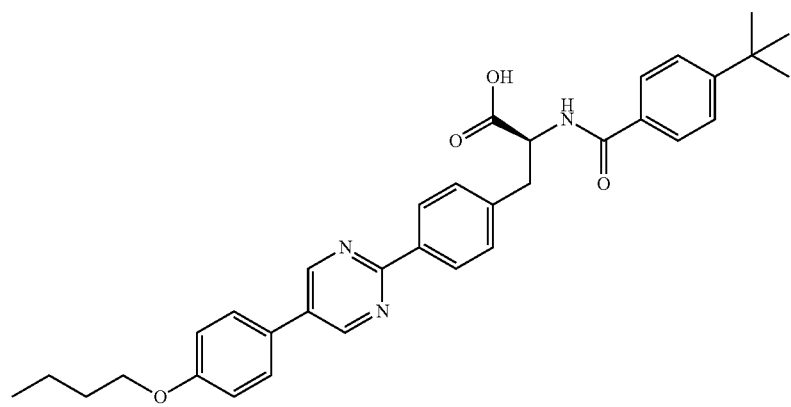
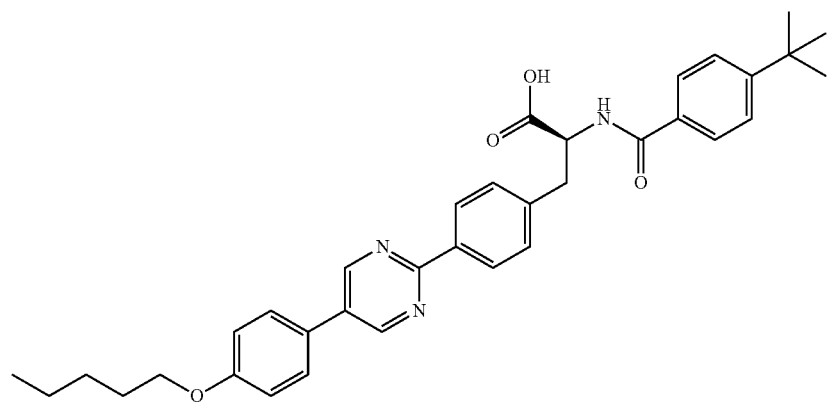
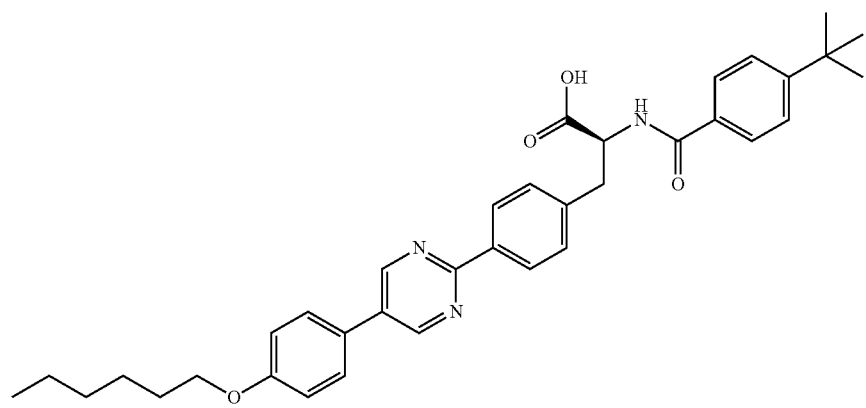
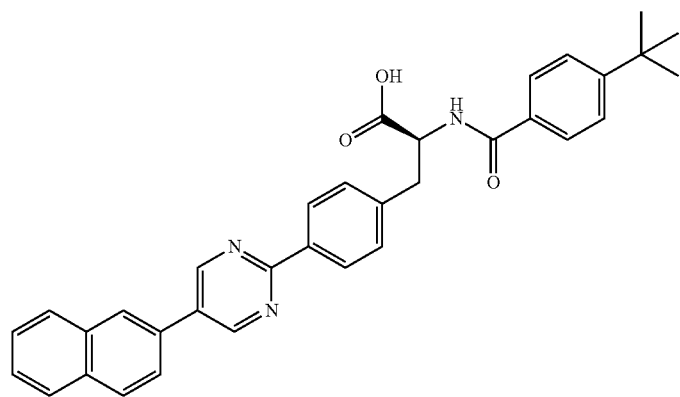

-continued
1097
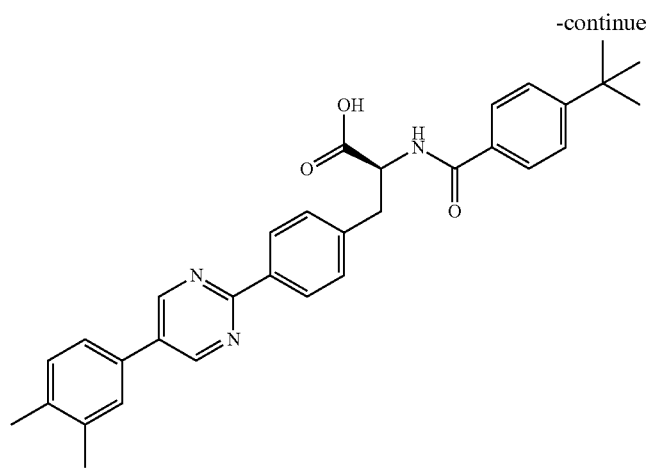
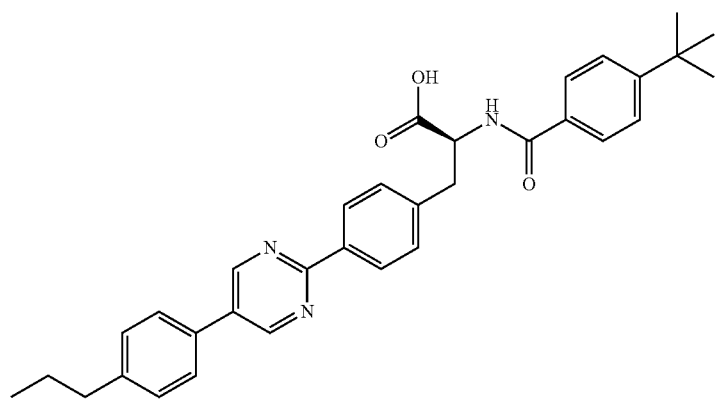
1098
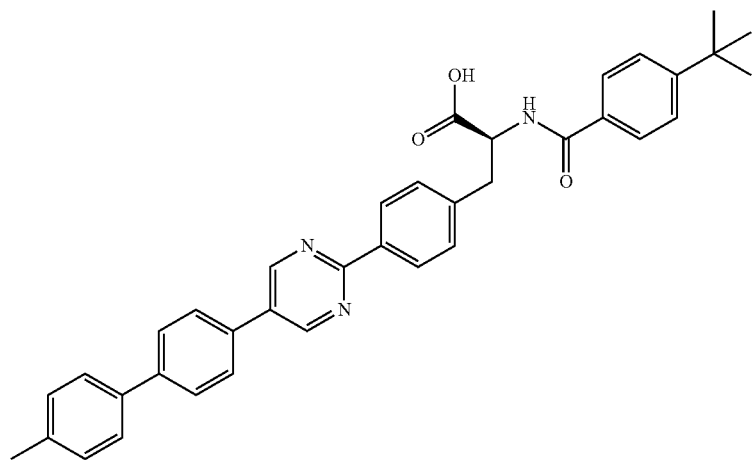

-continued
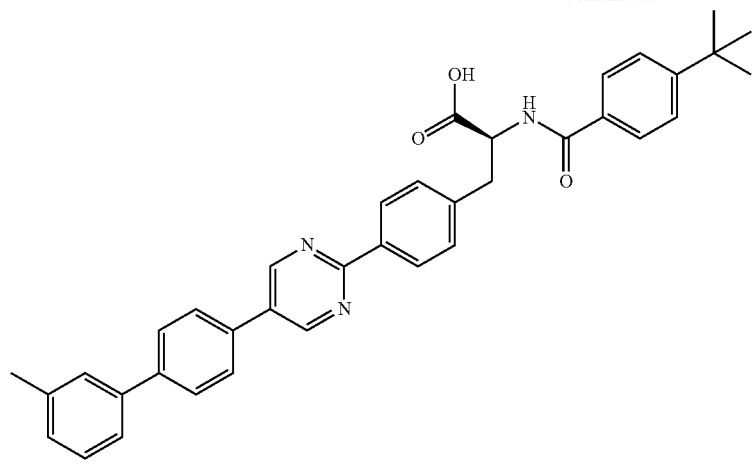
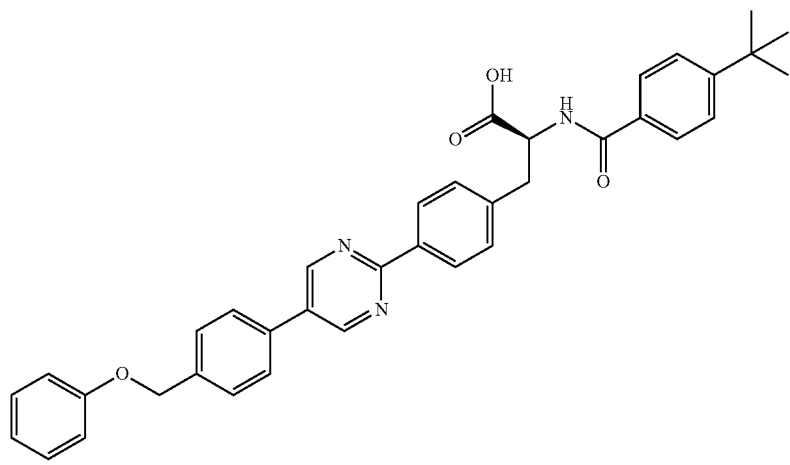
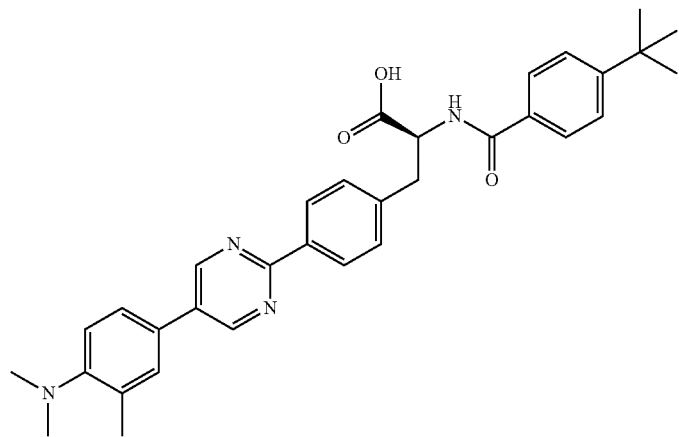
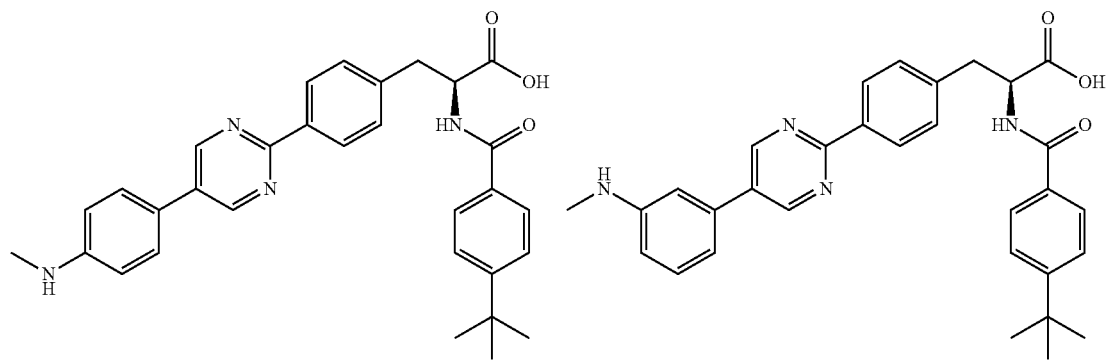
1099 1100

1101
-continued
1102
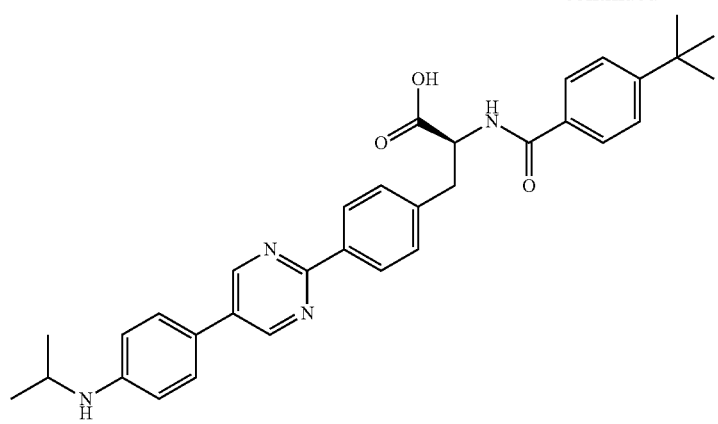
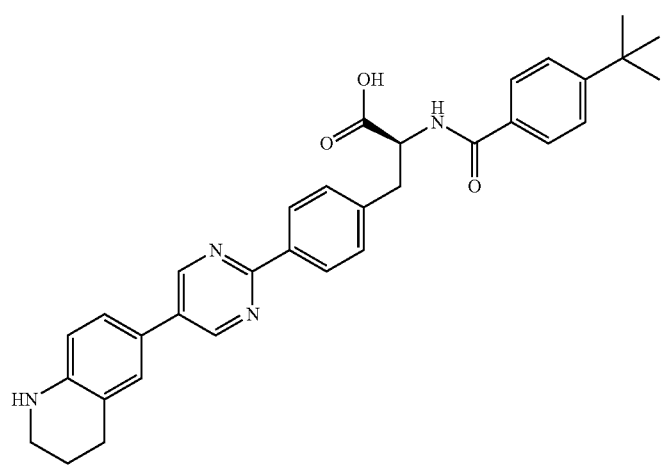
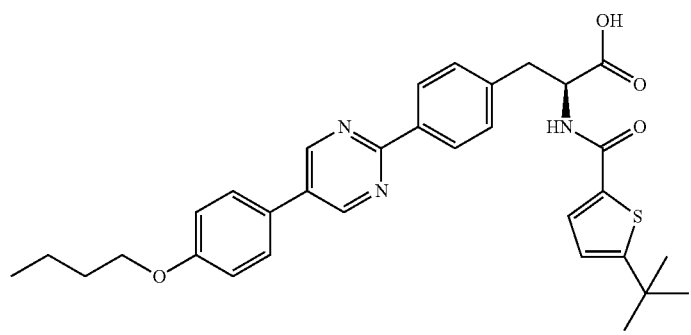
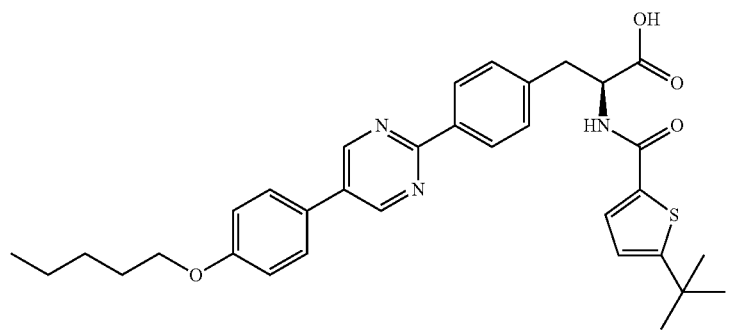

1103 1104
-continued
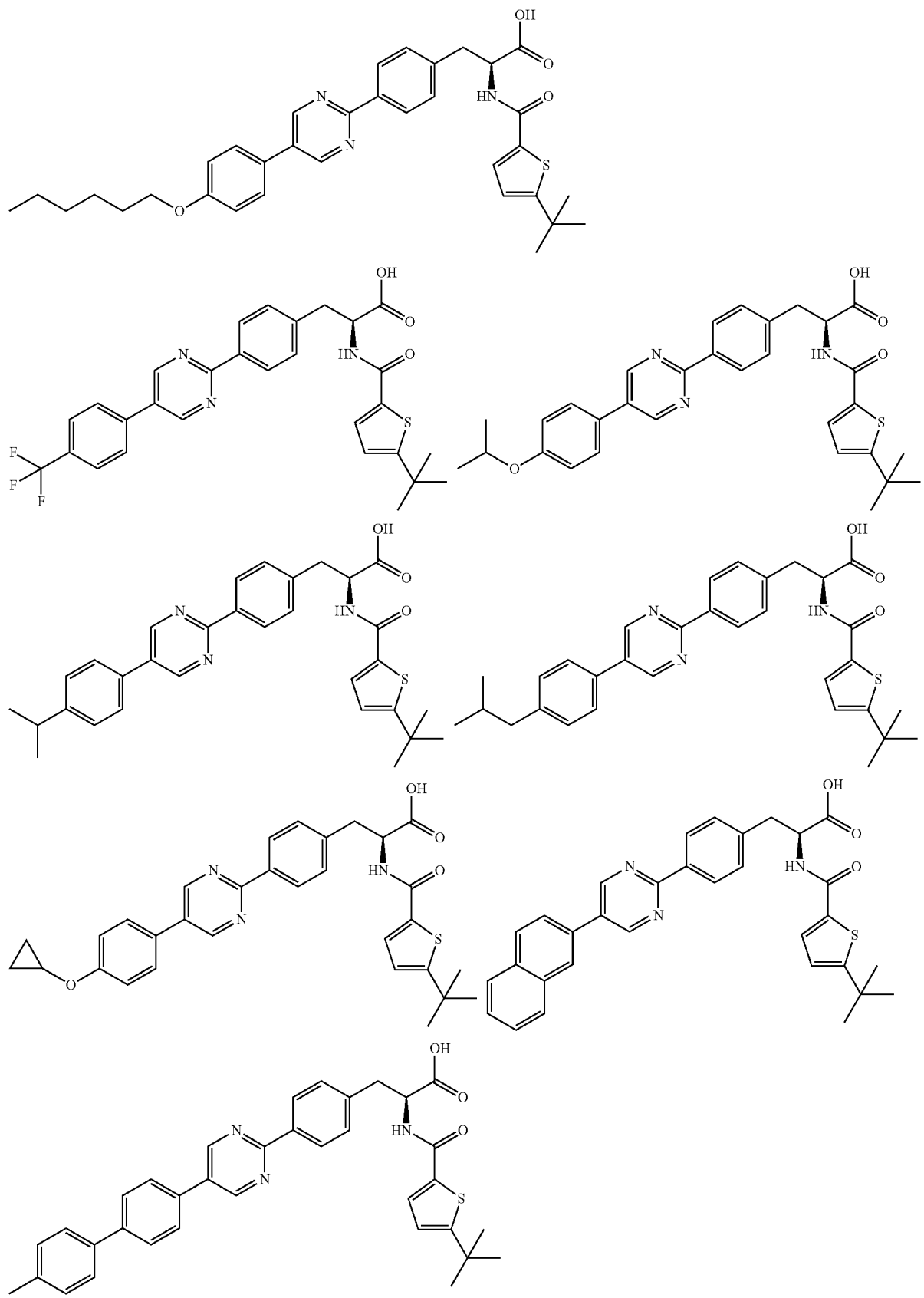

1105
1106
-continued
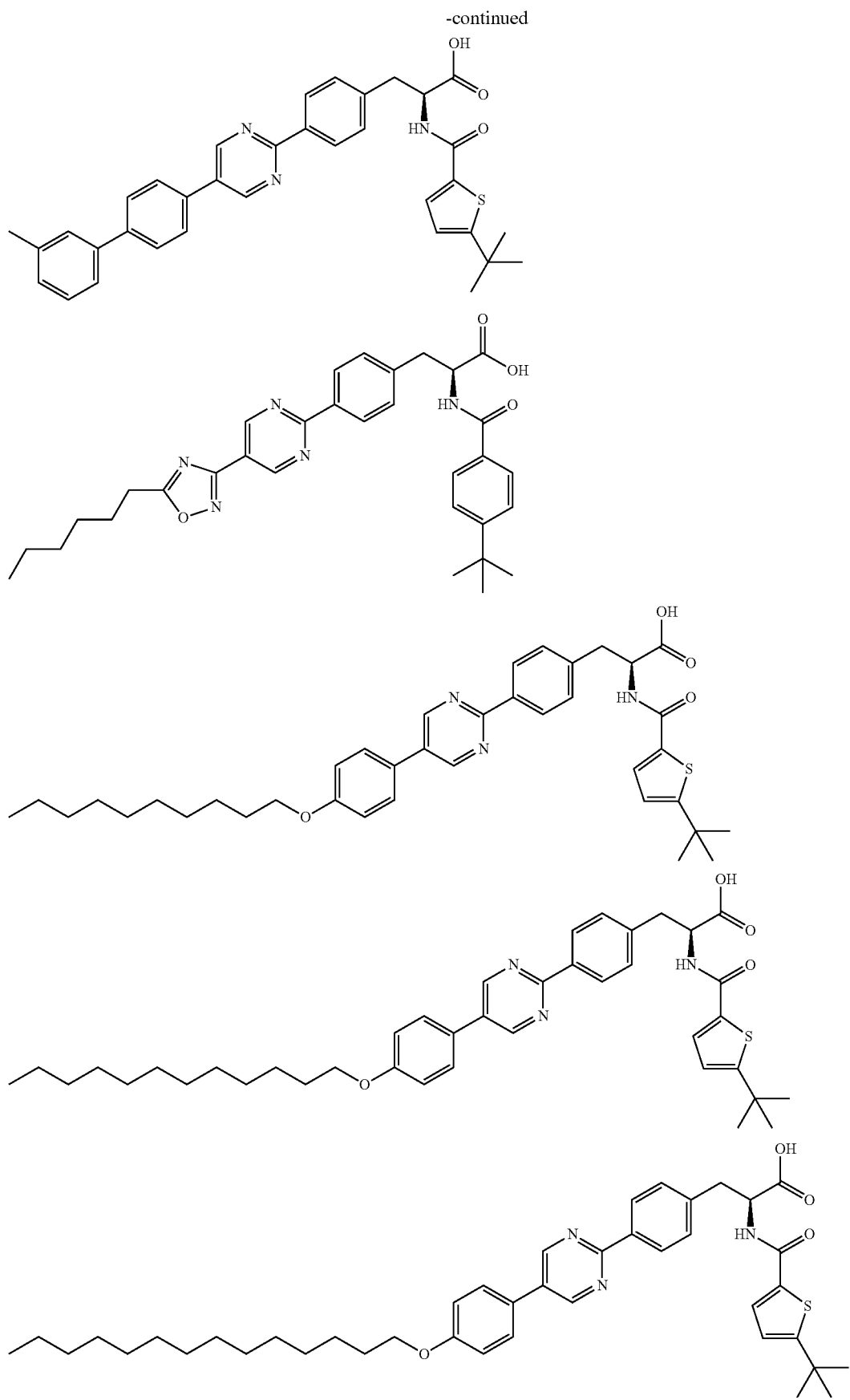

1107 1108
-continued
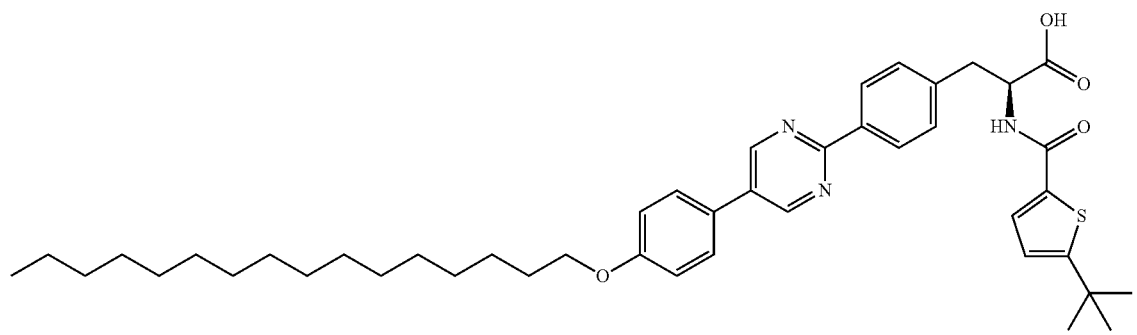
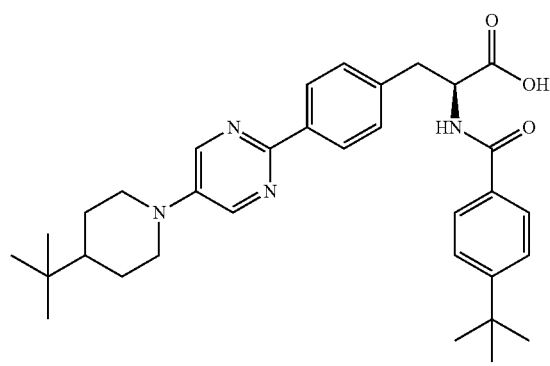
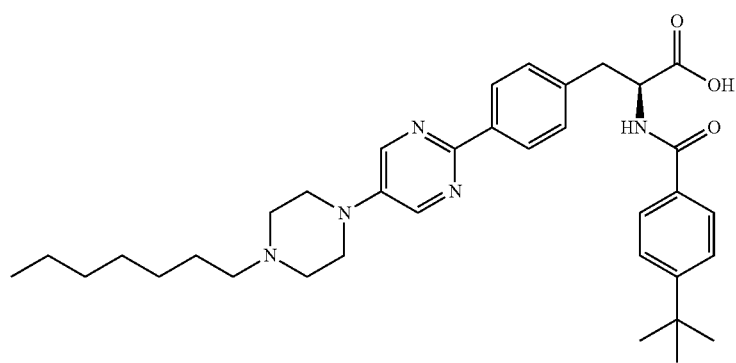
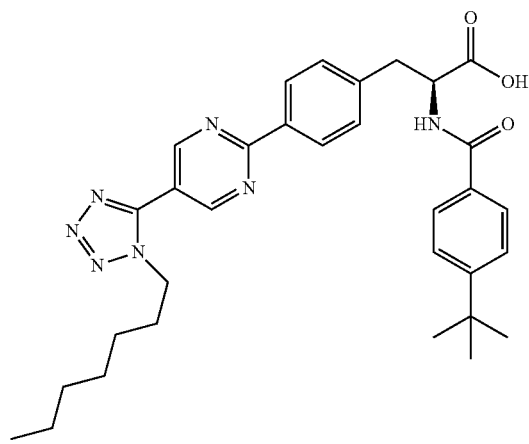

1109
-continued
1110
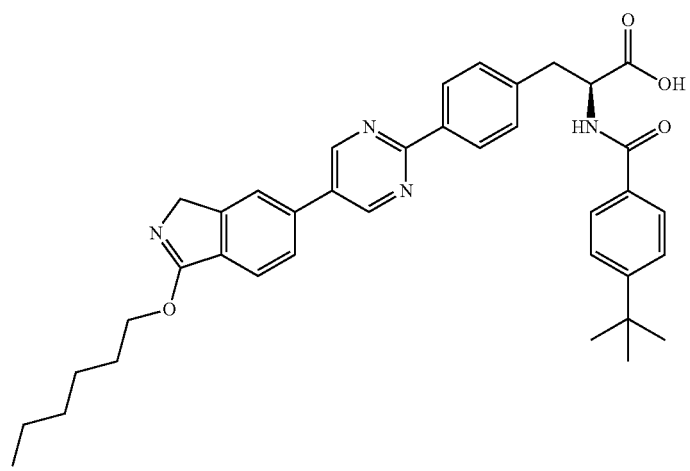
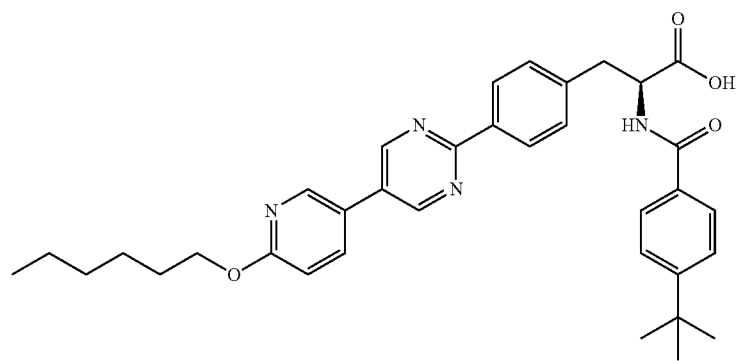
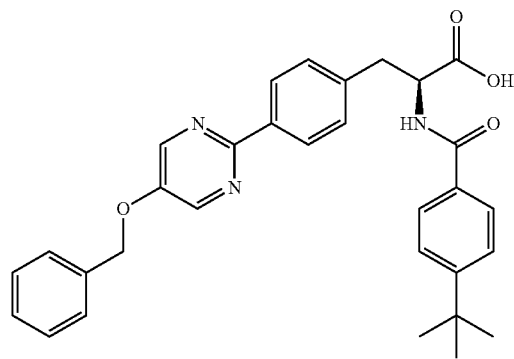
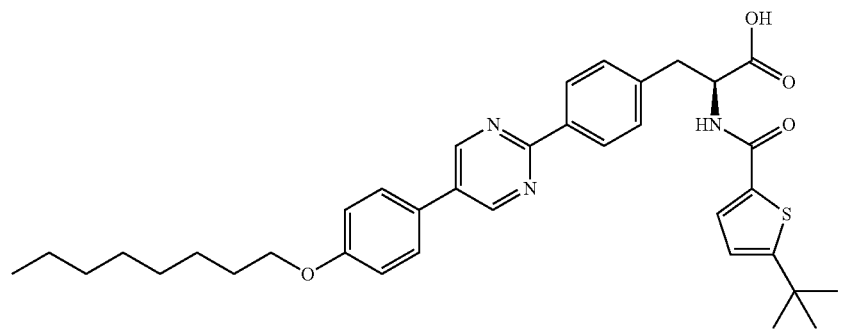

-continued
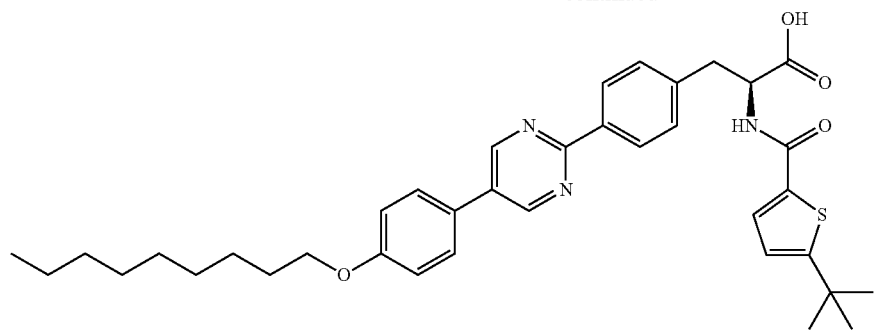
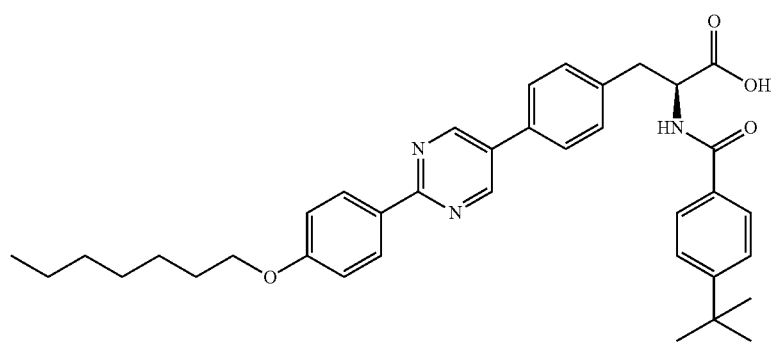
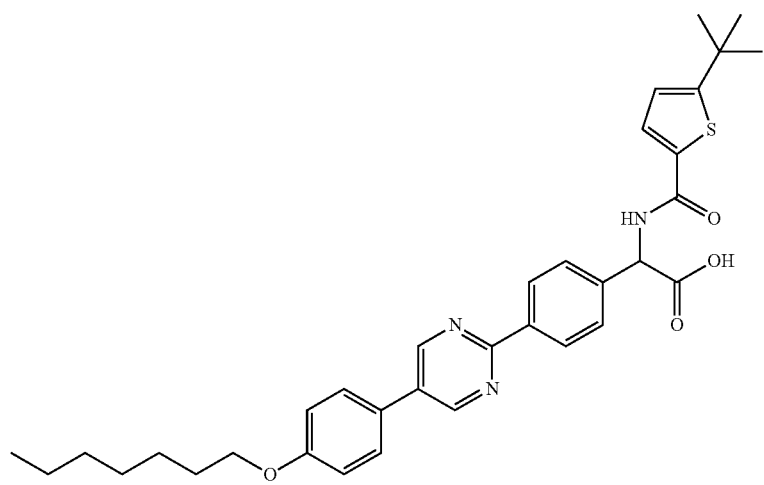
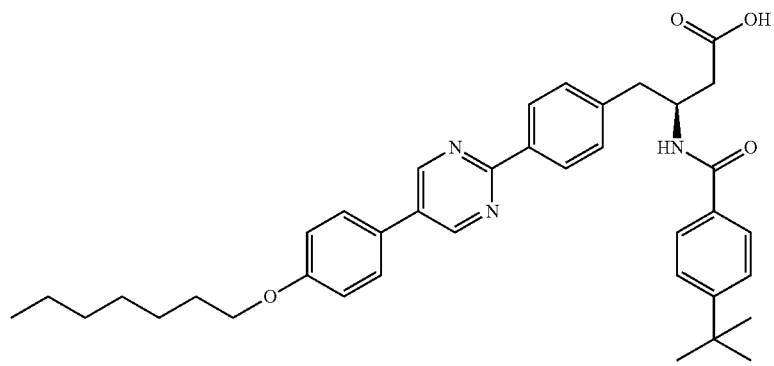

1113
-continued
1114
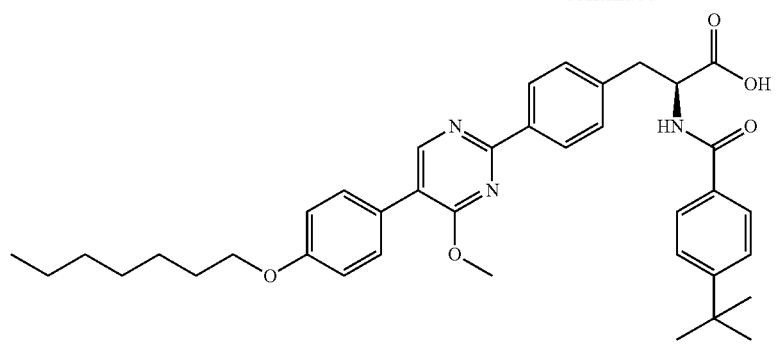
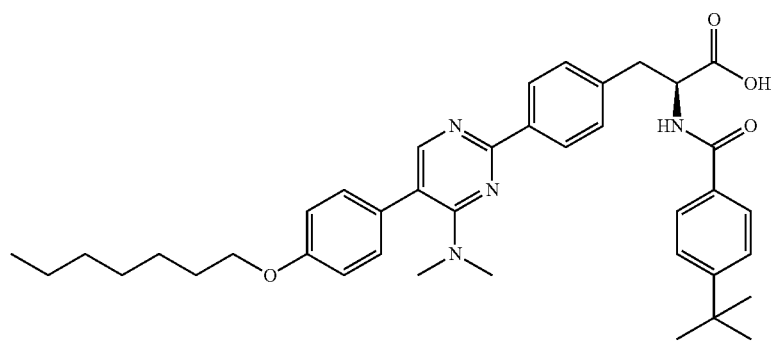
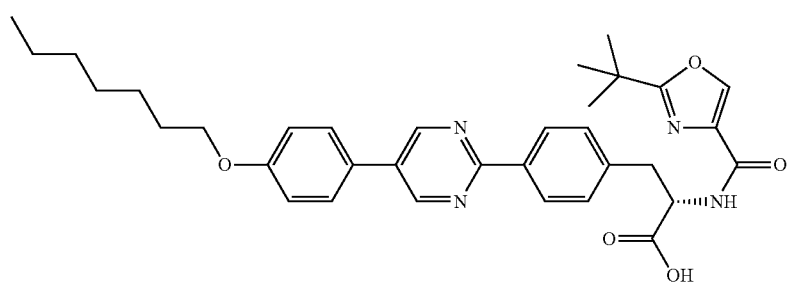
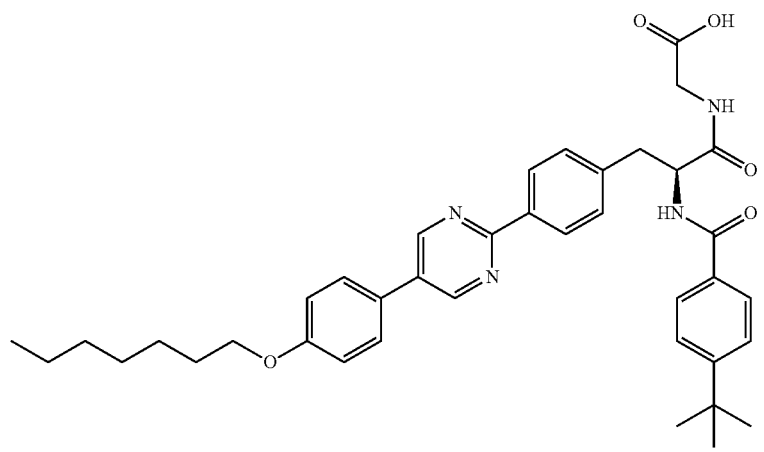

| 1115 | 1116 |
|---|---|
| 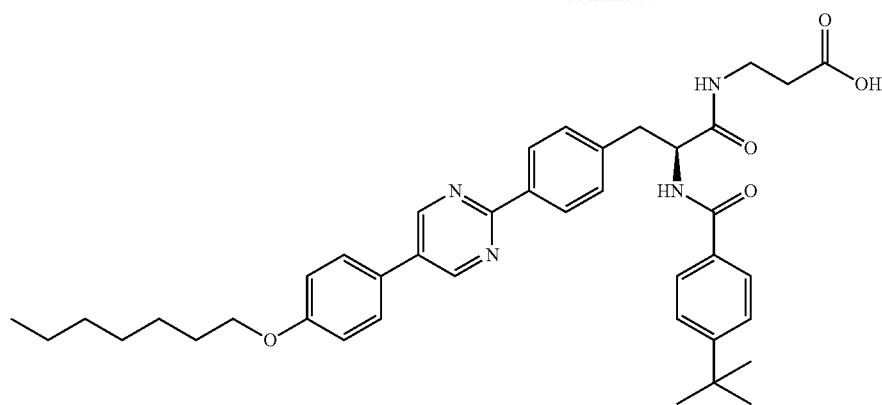 | 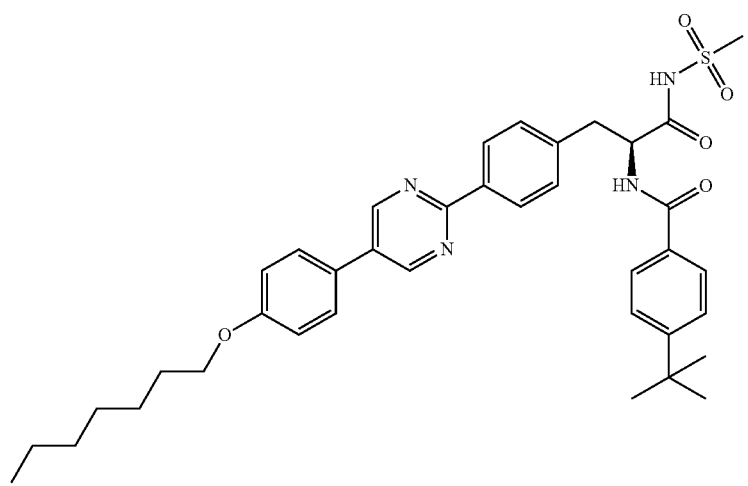 |
| | 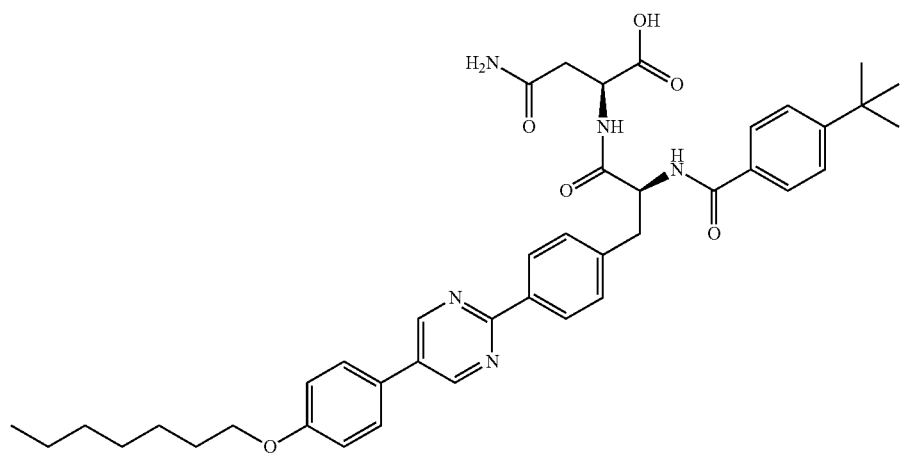 |

1117
1118
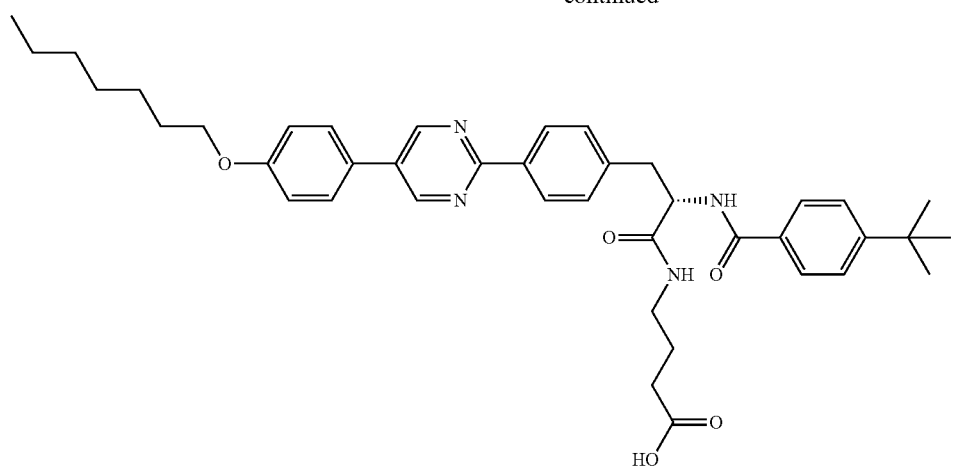
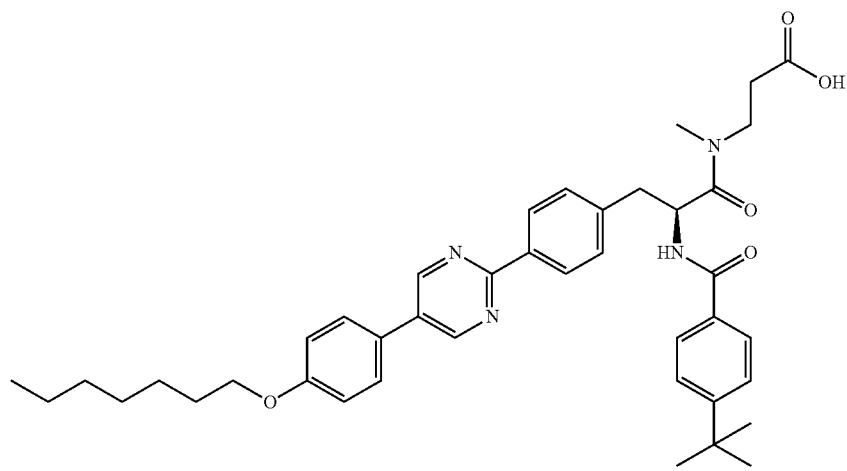
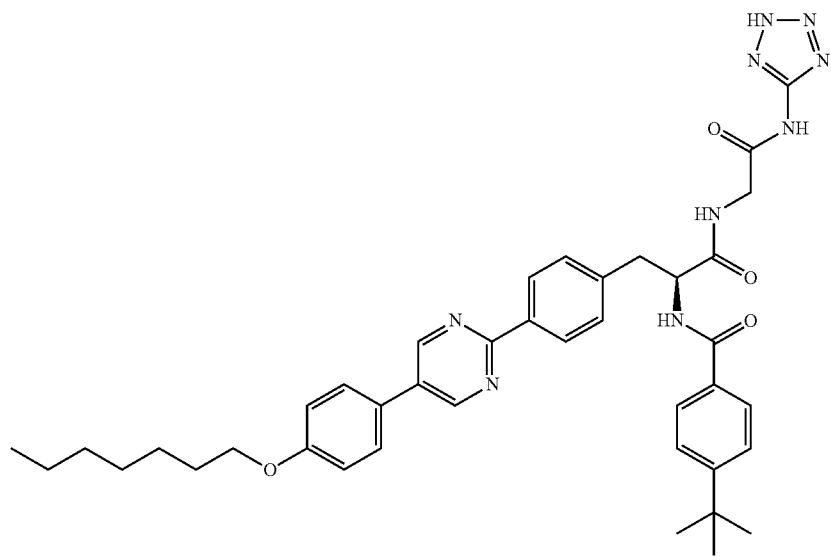

-continued
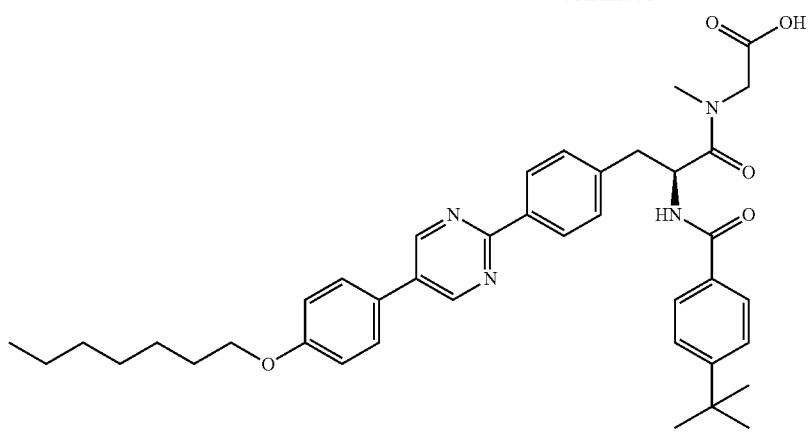
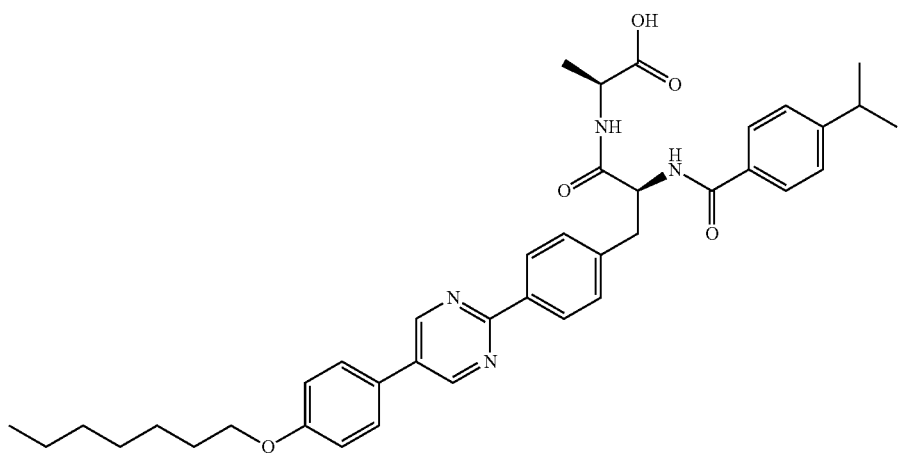
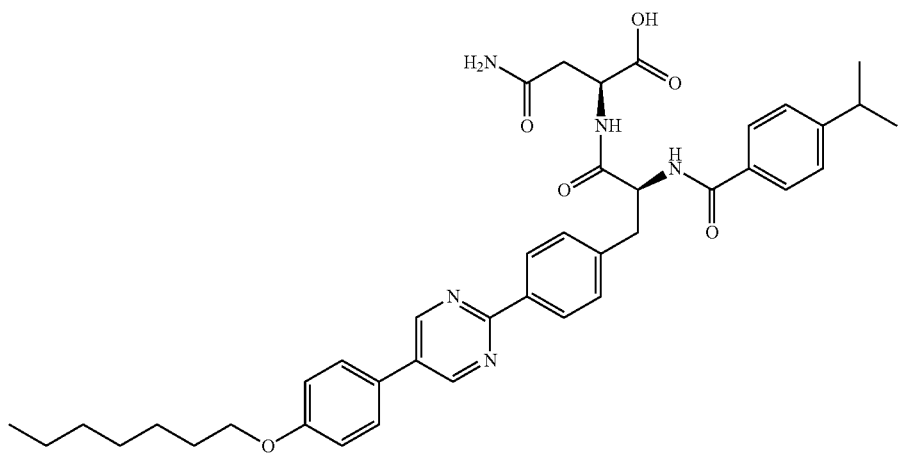

1121
-continued
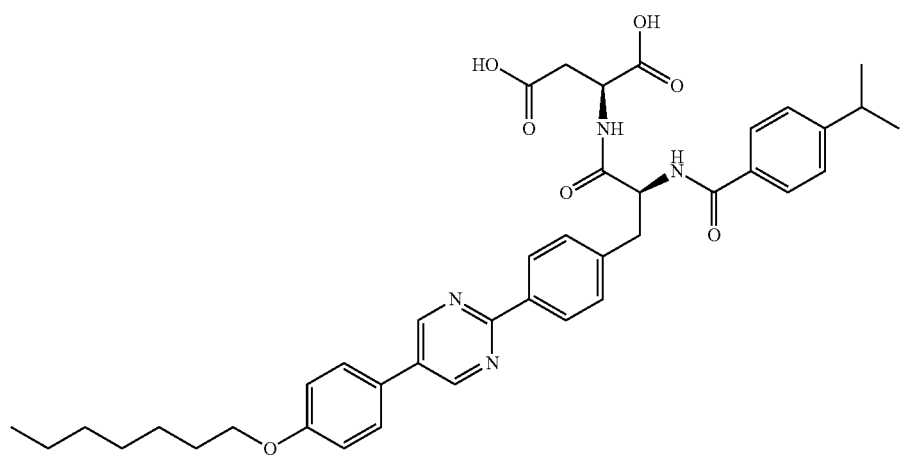
1122
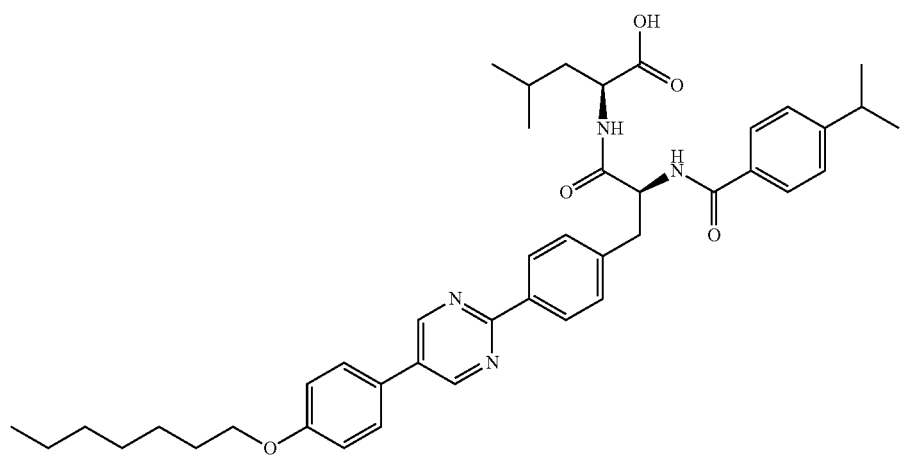
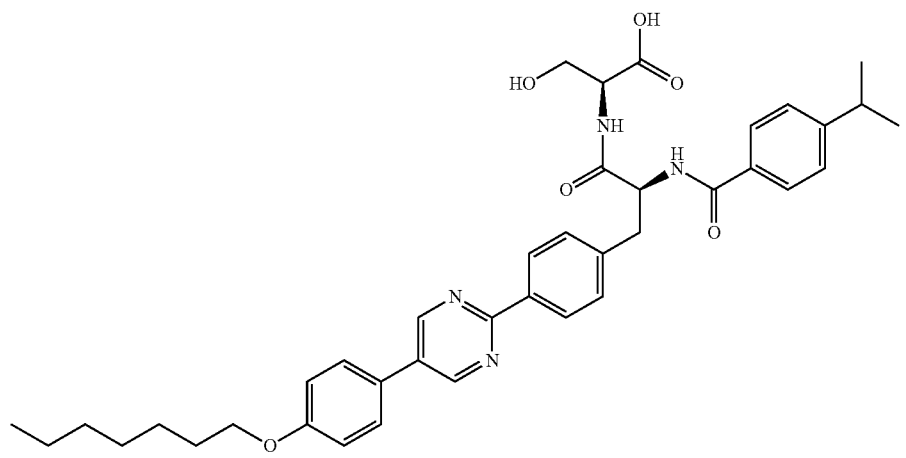

-continued
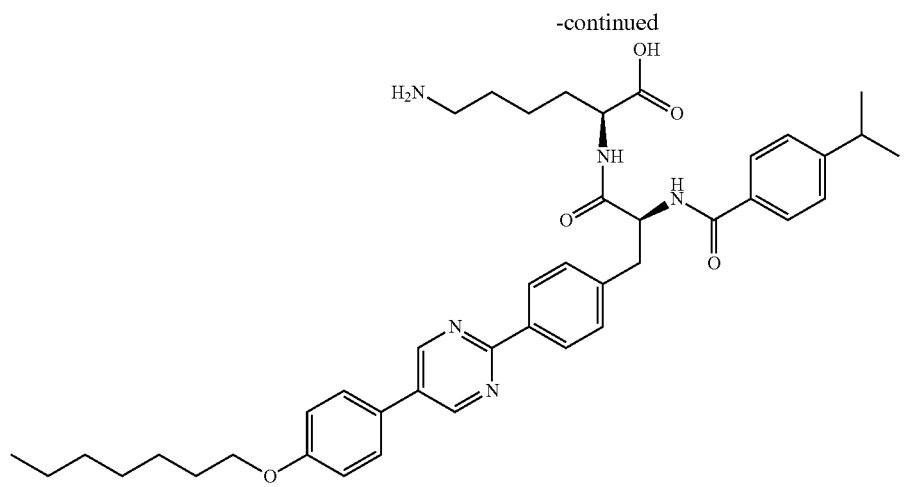
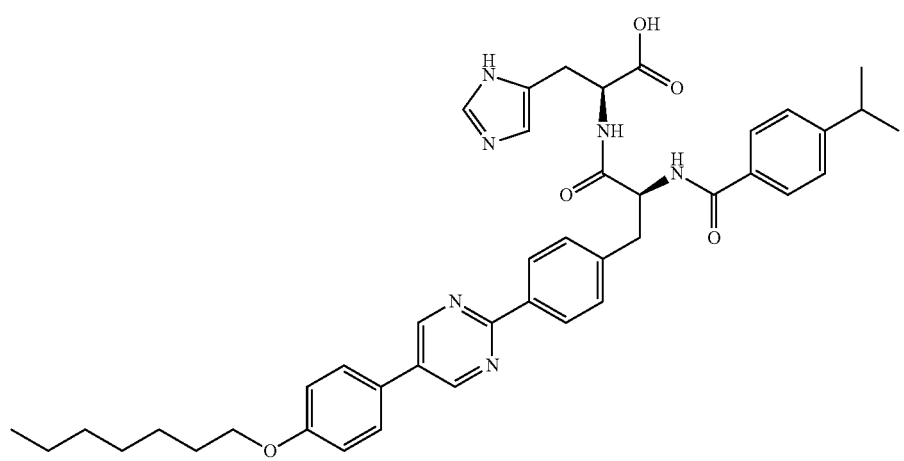
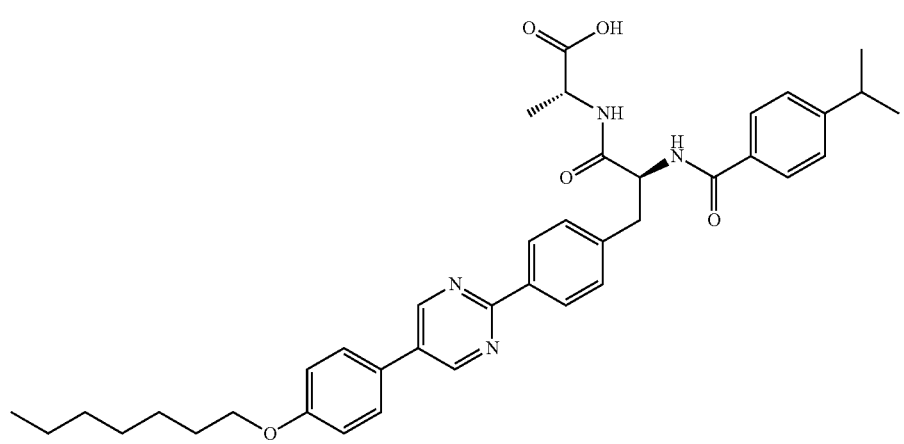

-continued
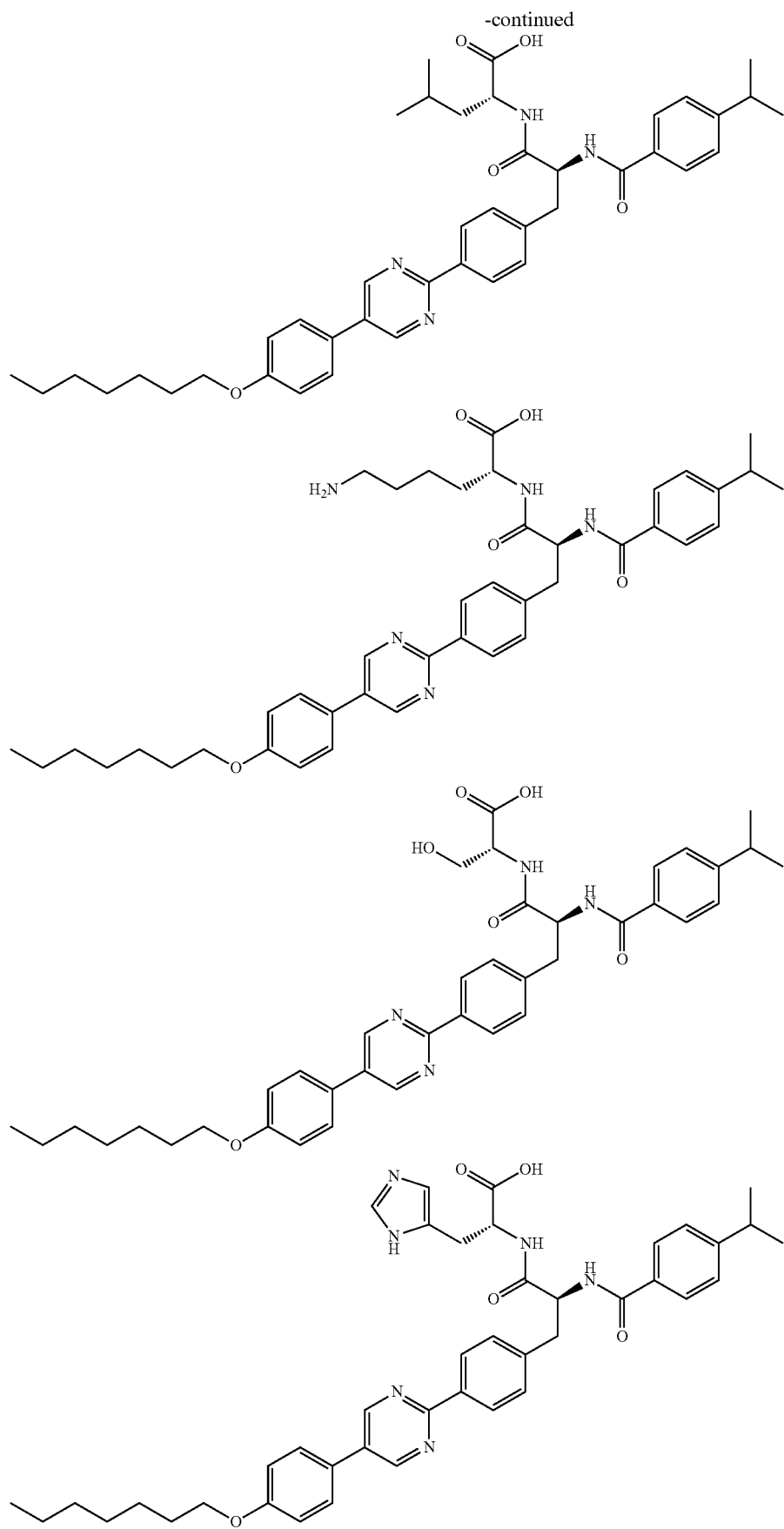

1127
-continued
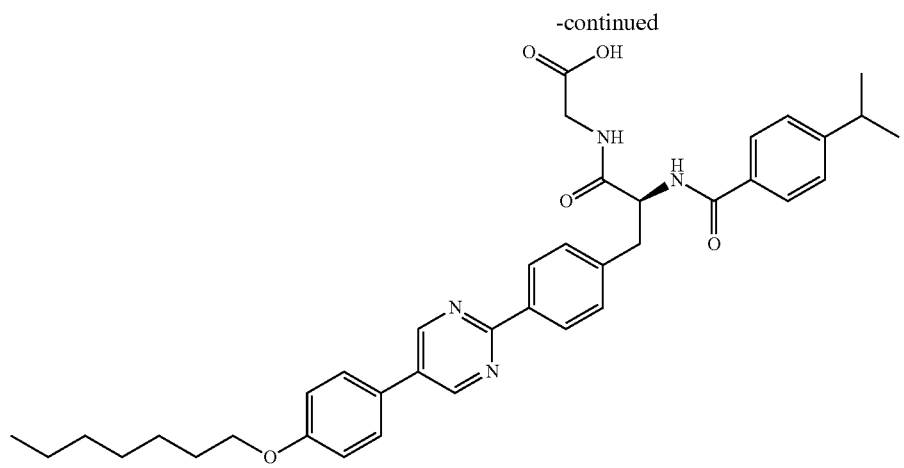
1128
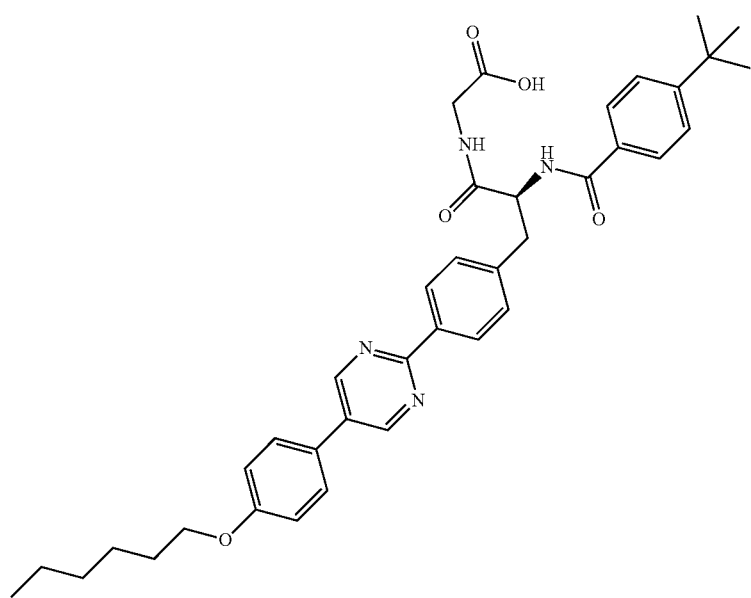
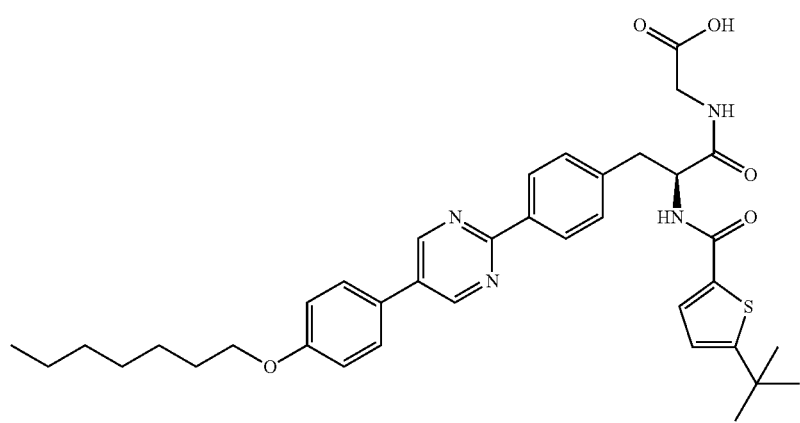

-continued
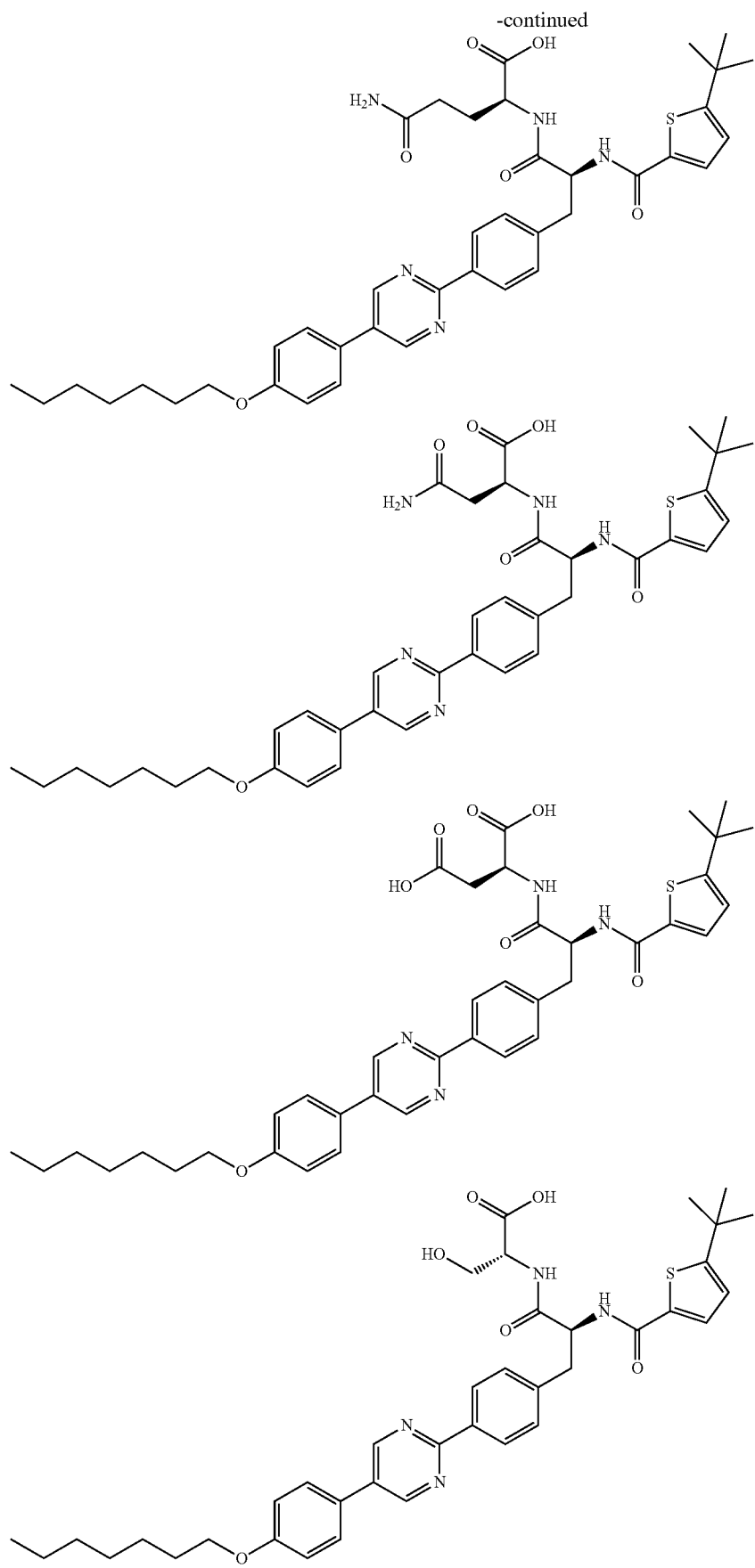

-continued
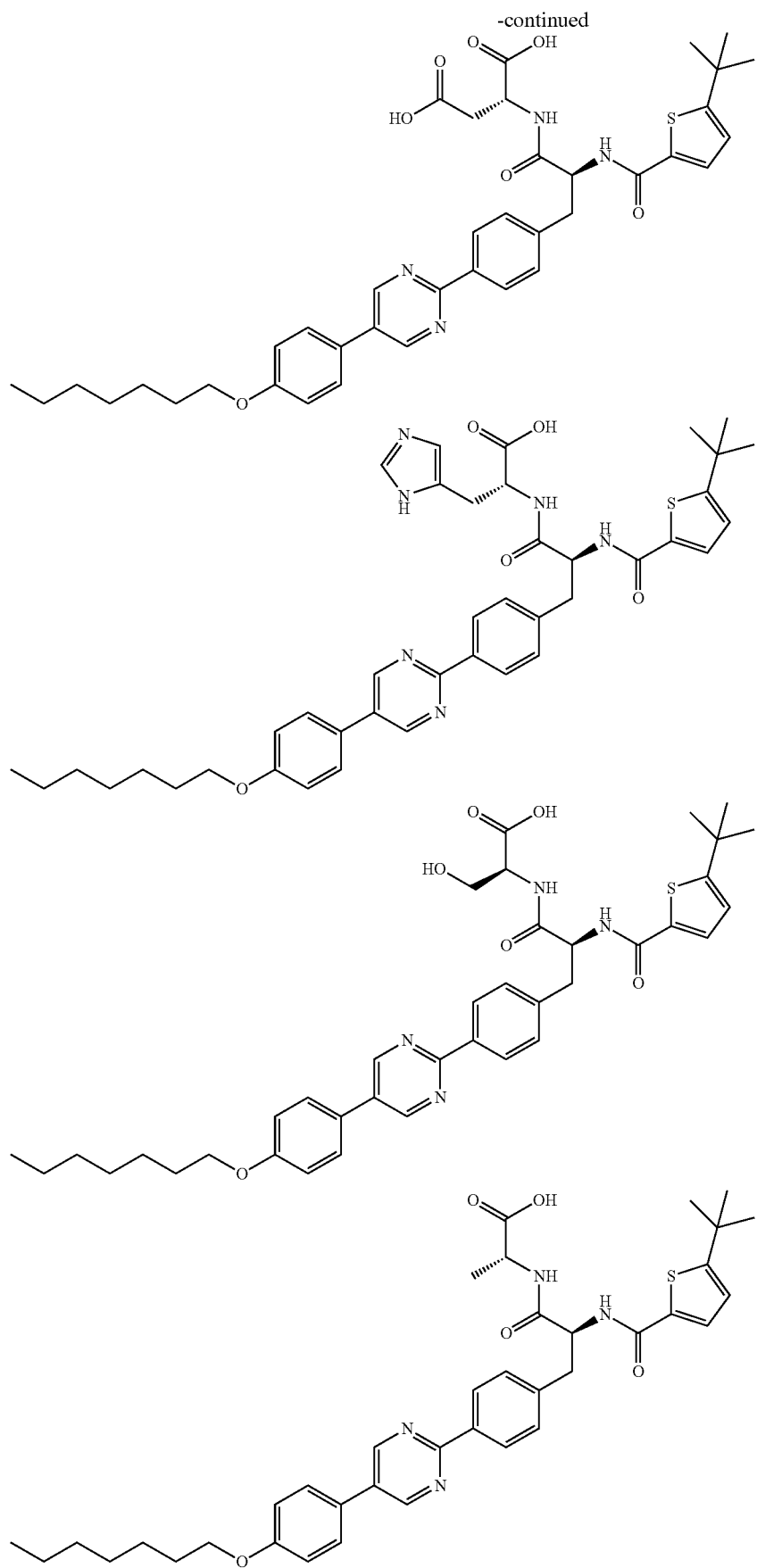

-continued
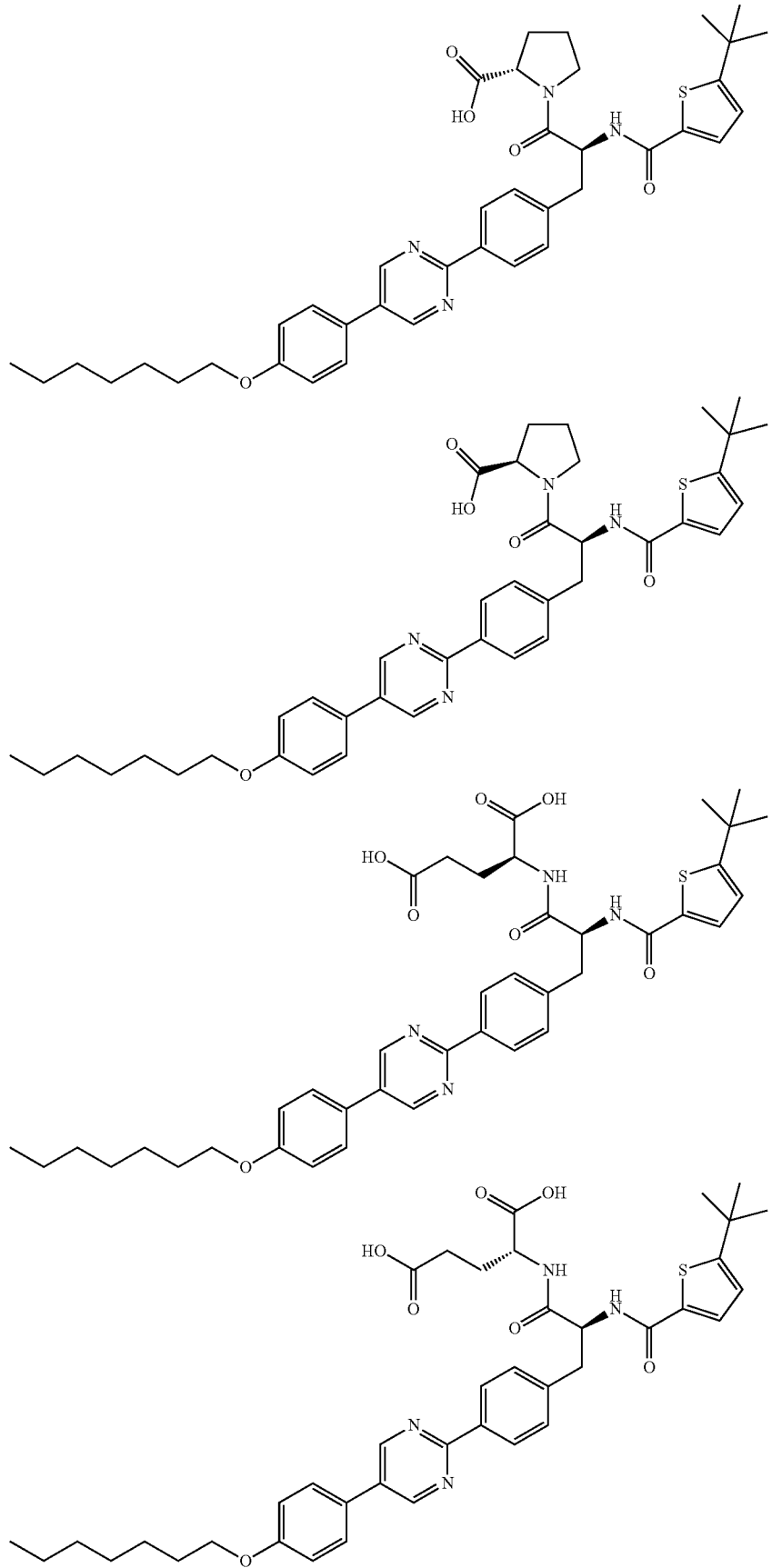

-continued
1135
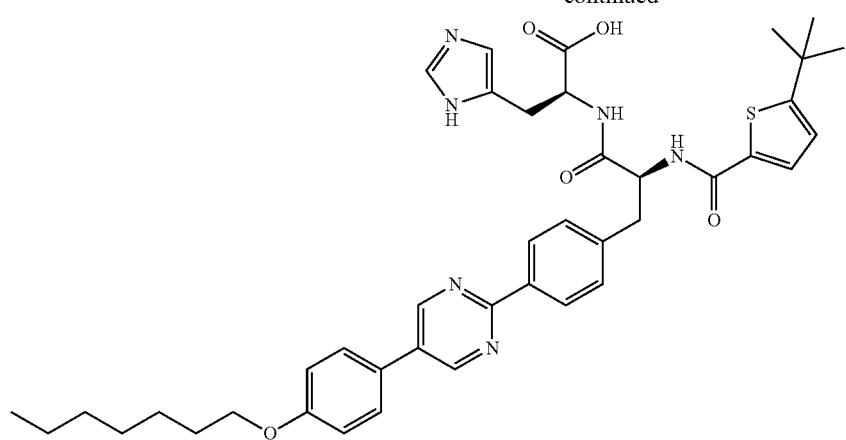
1136
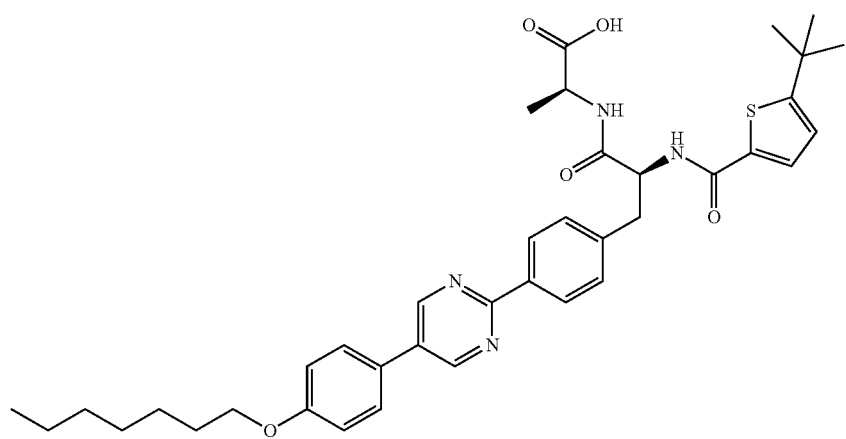
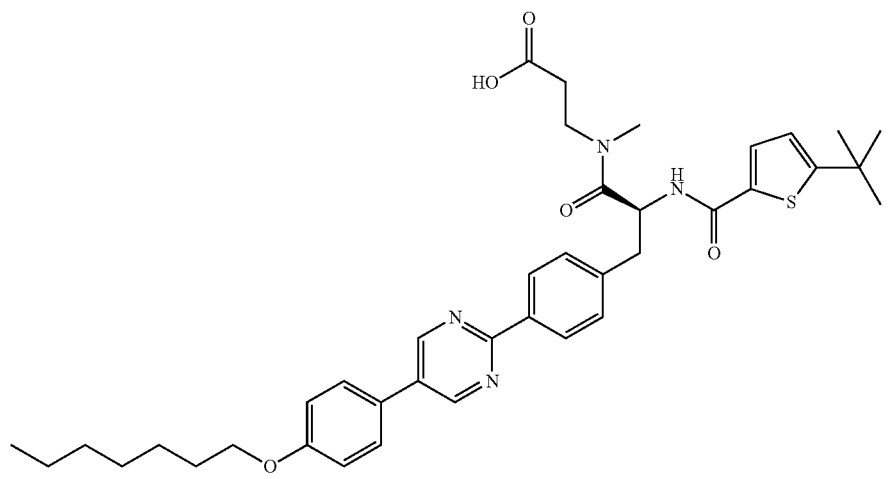

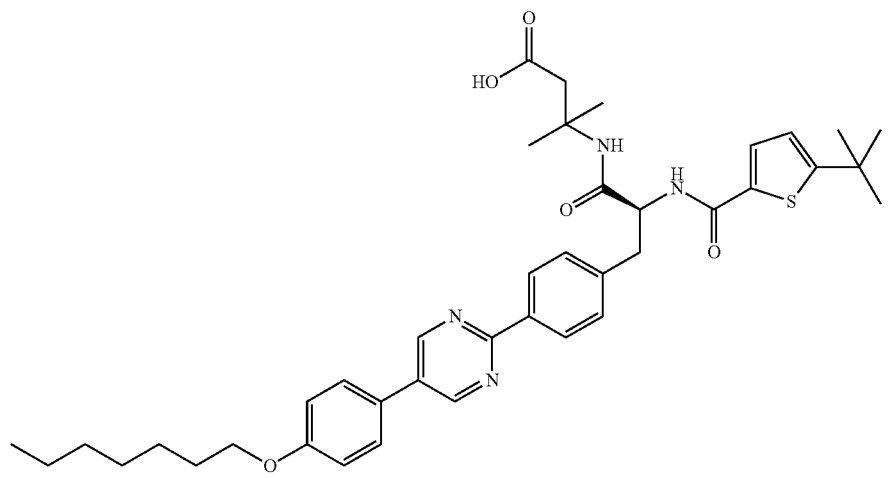
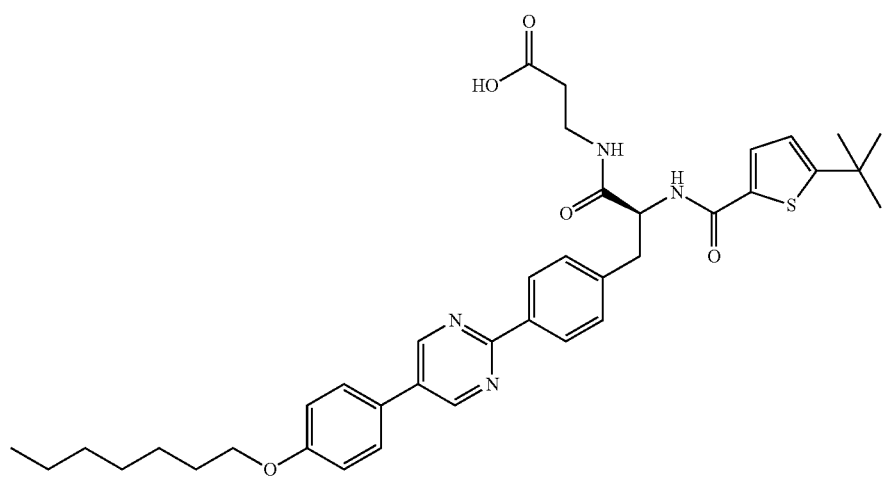
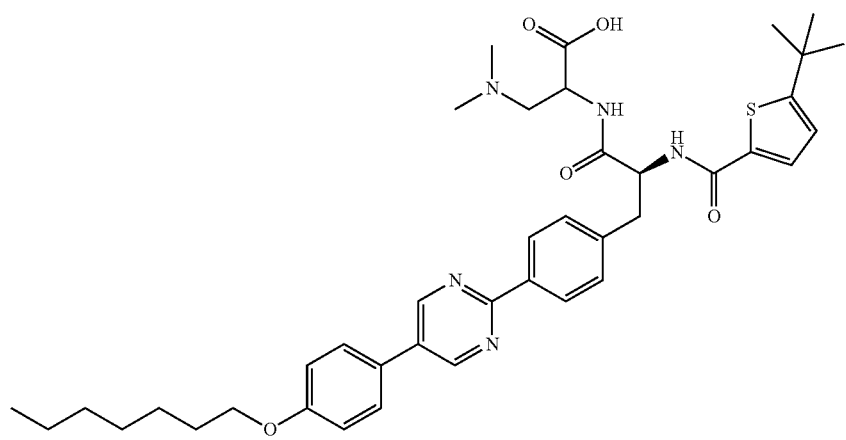

-continued
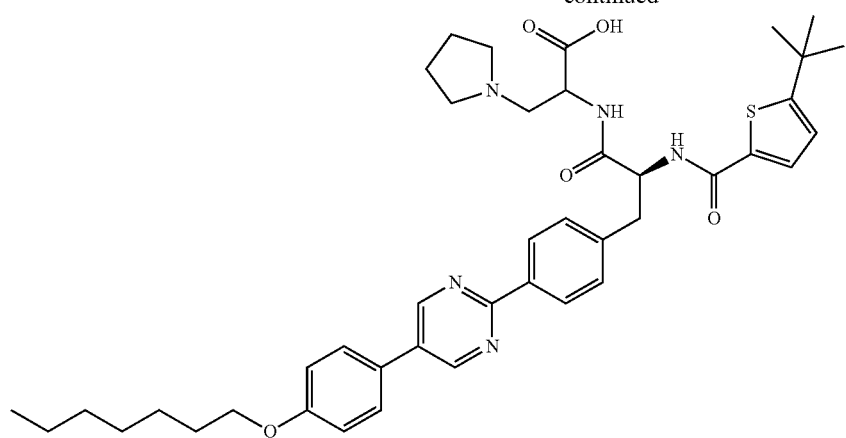
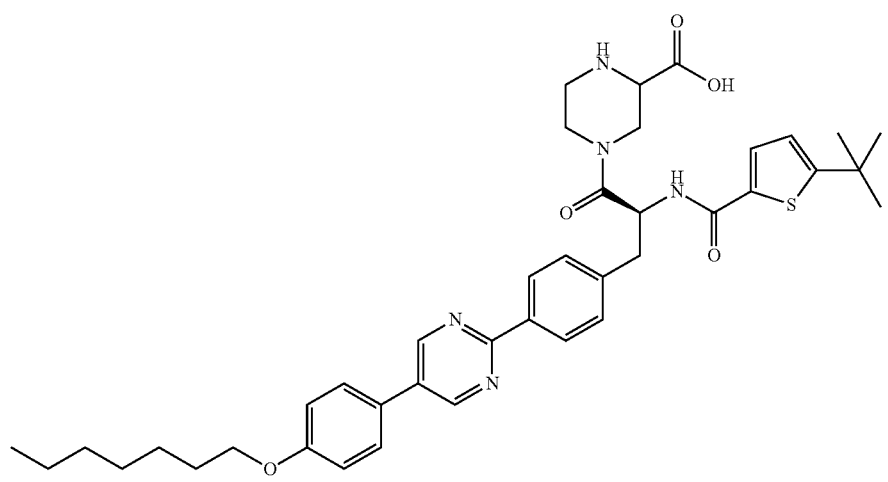
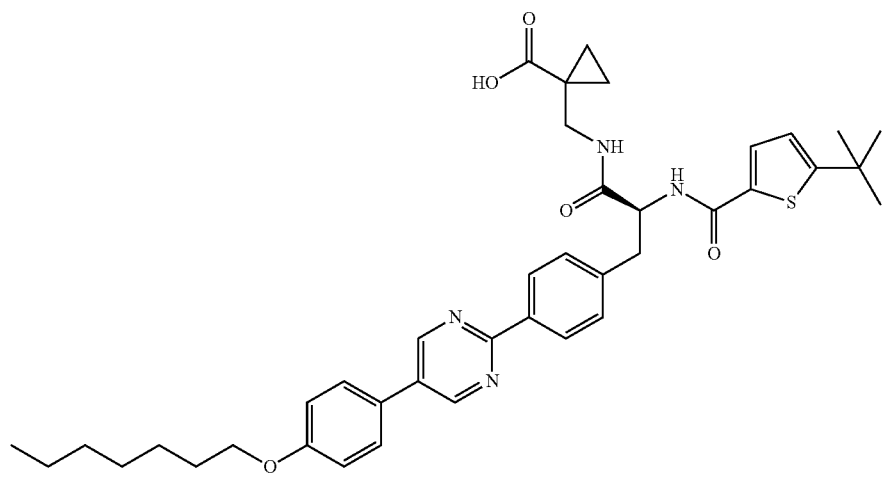

1141
-continued
1142
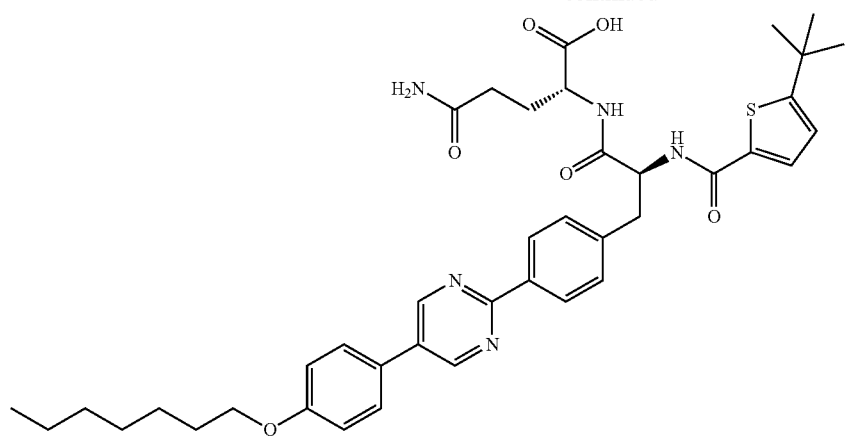
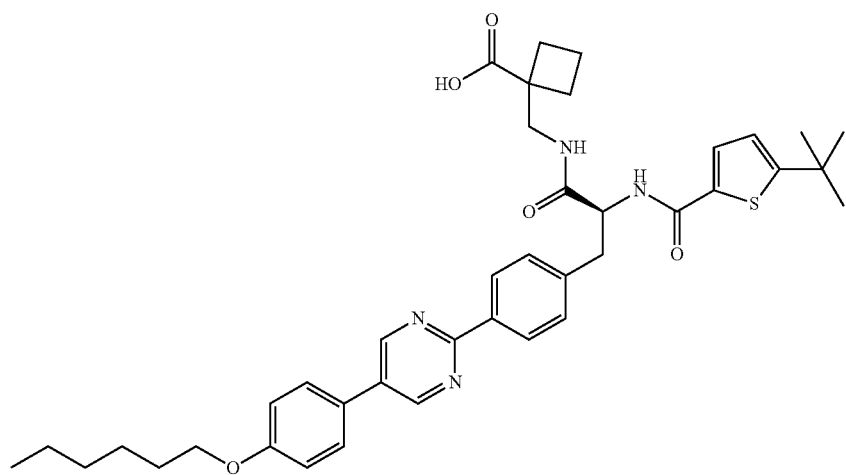
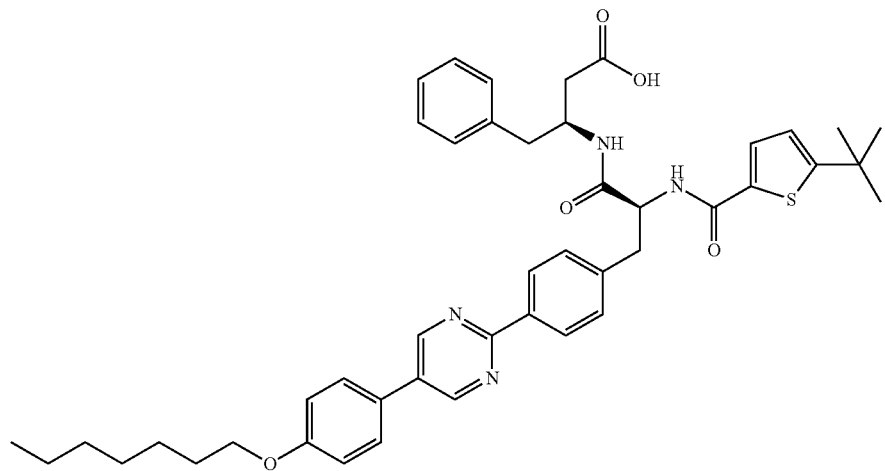

-continued
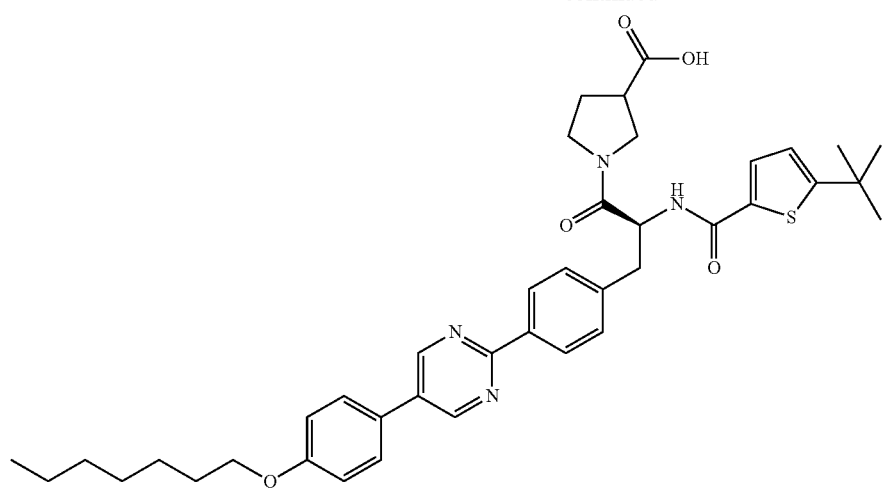
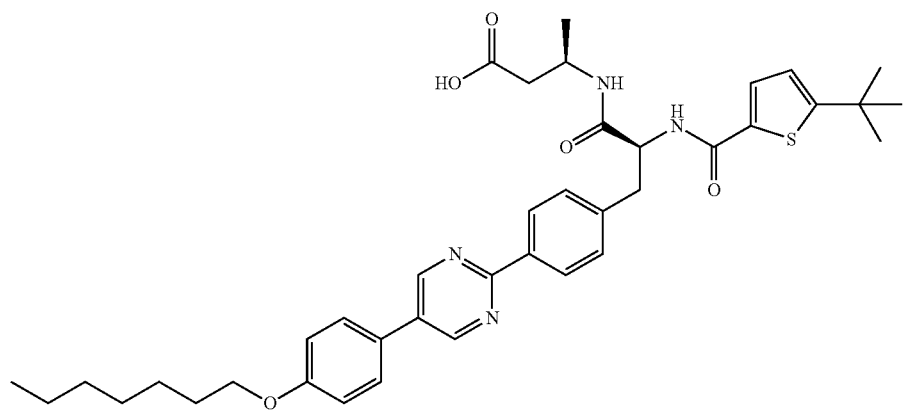
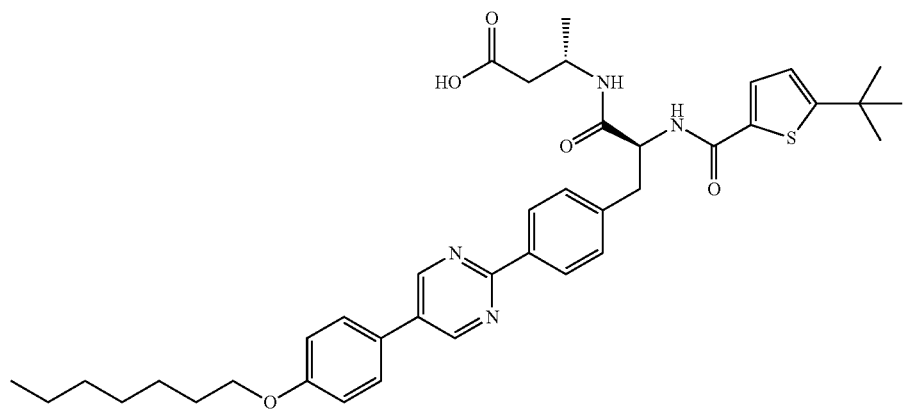

1145
-continued
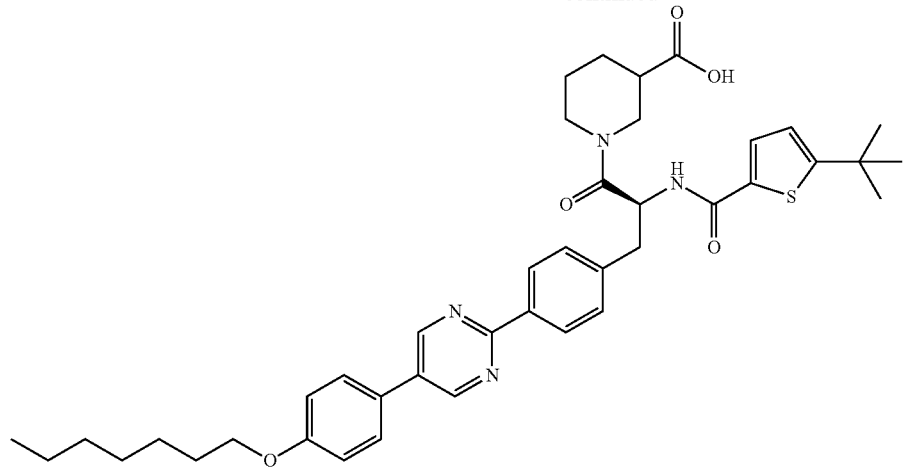
1146
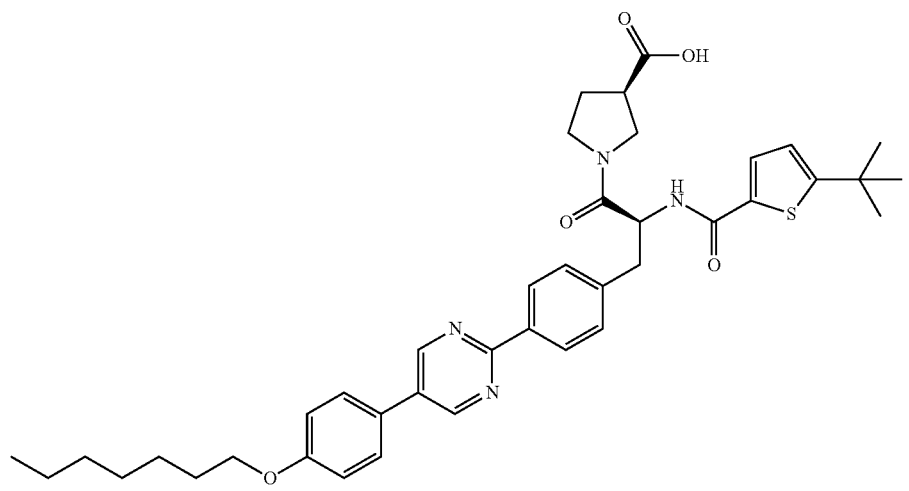
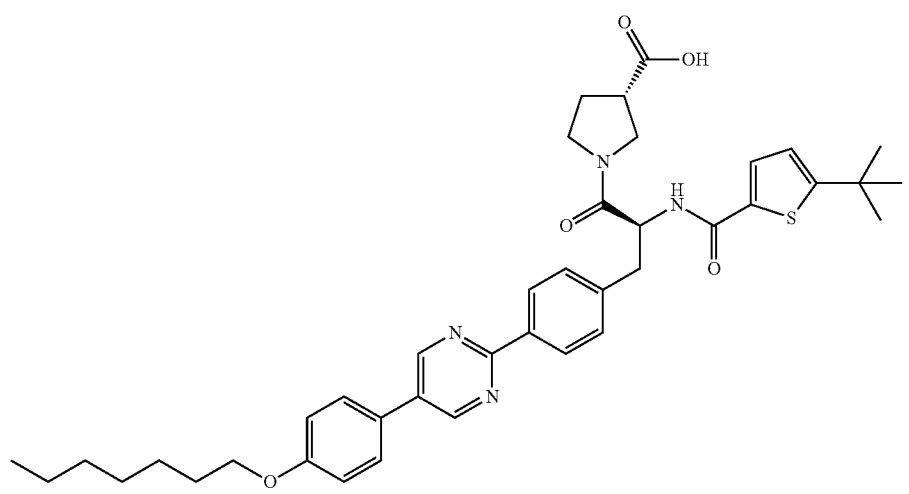

1147
1148
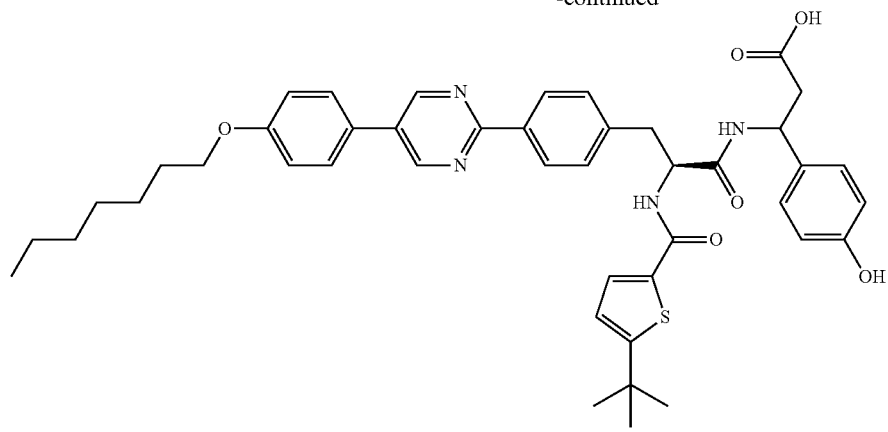
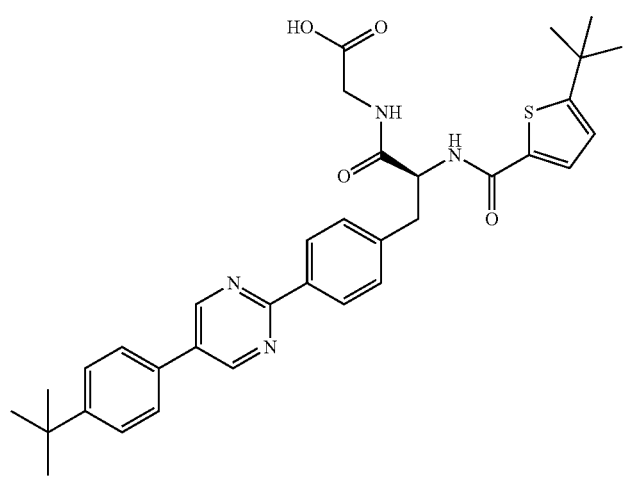
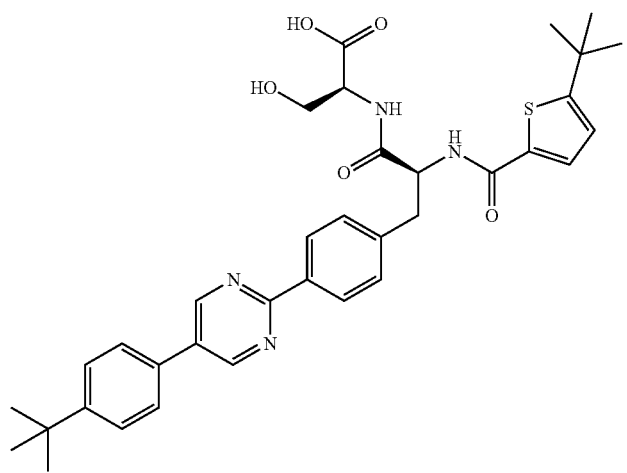

1149
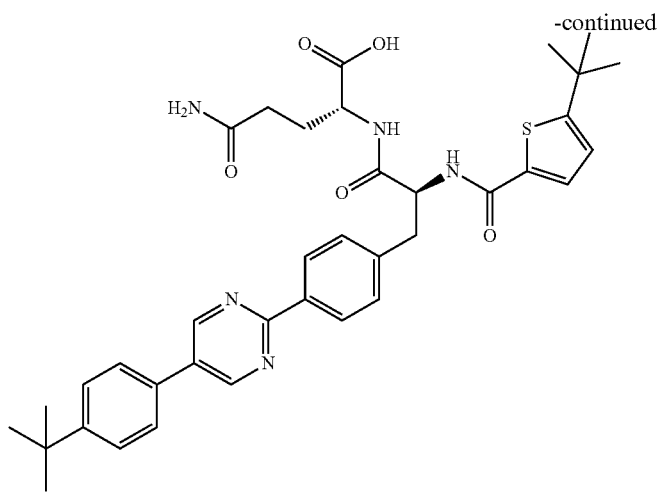
-continued
1150
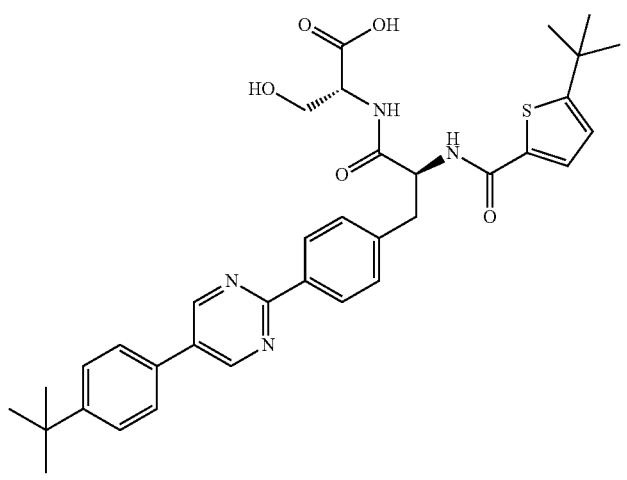
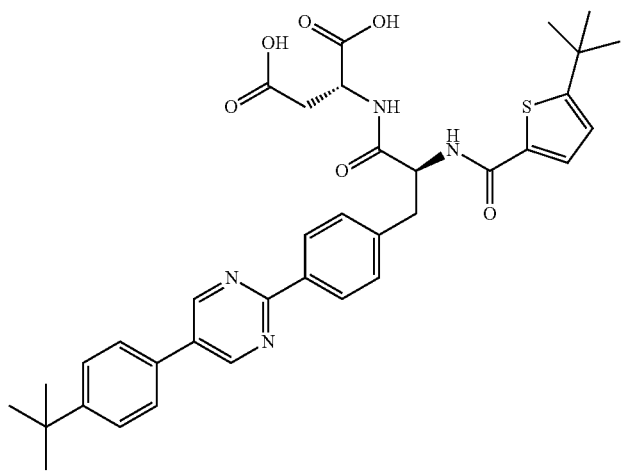

1151
-continued
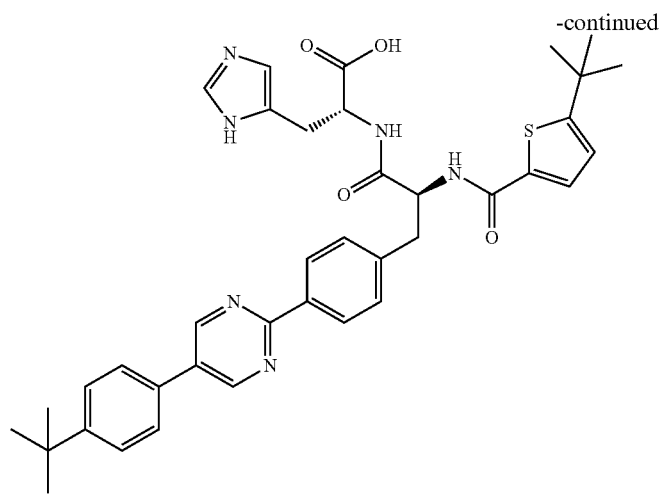
1152
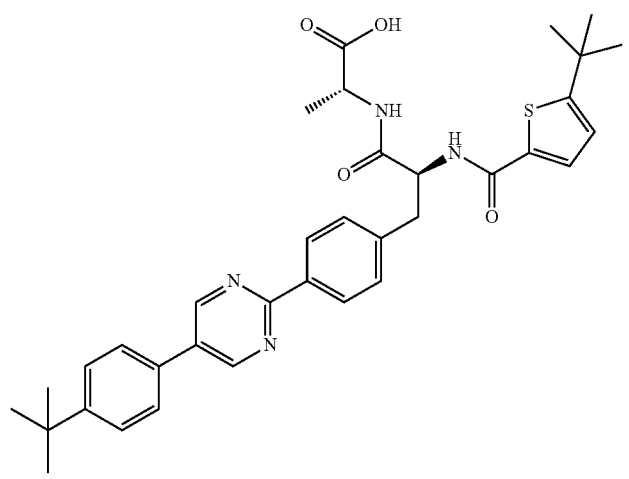
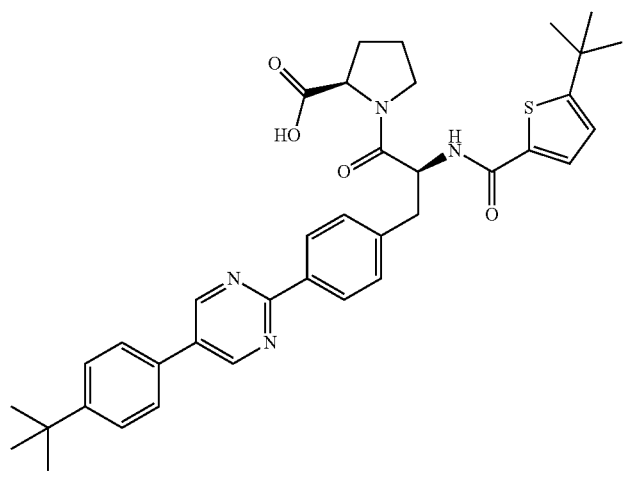

1153
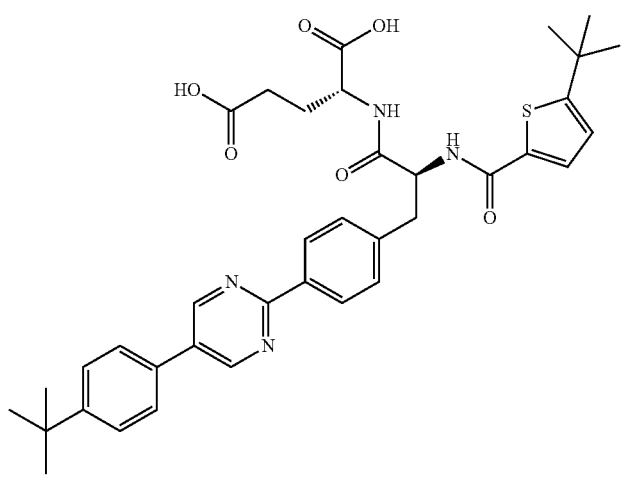
-continued
1154
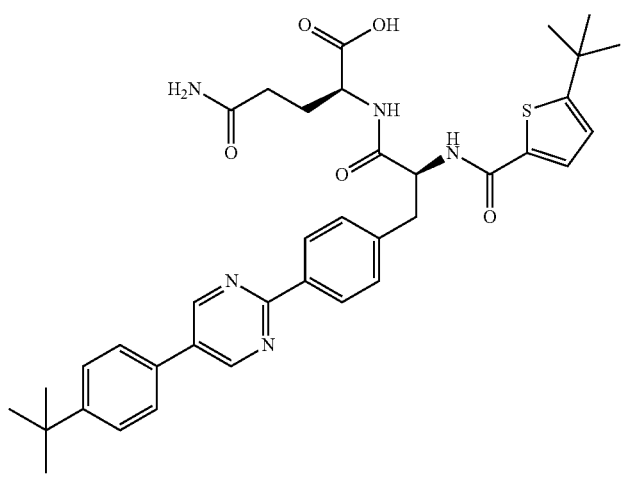
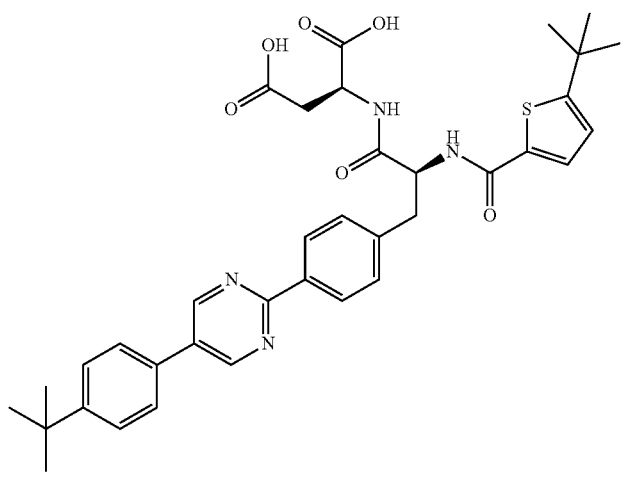

1155
-continued
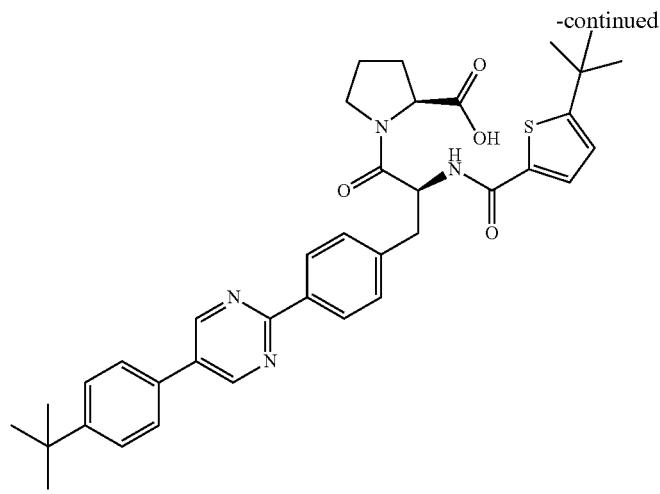
1156
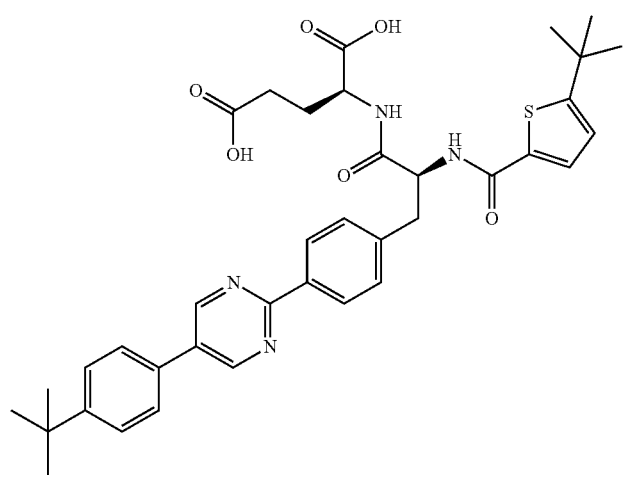
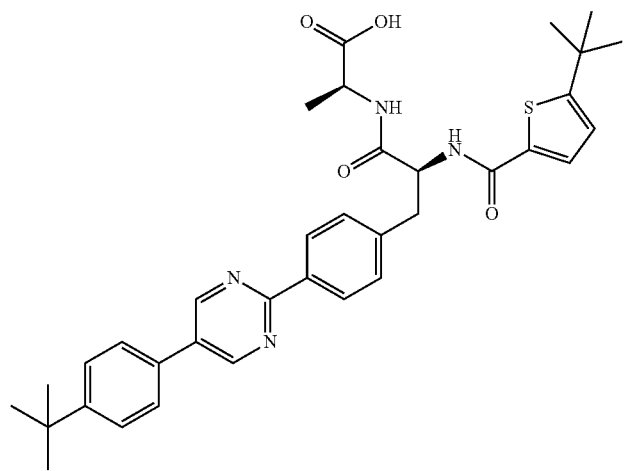

1157
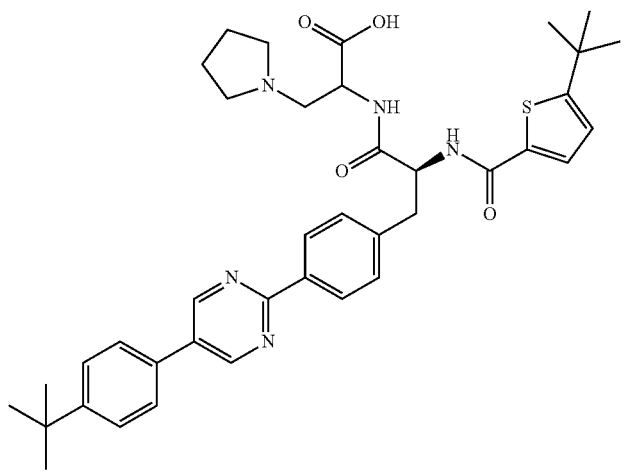
-continued
1158
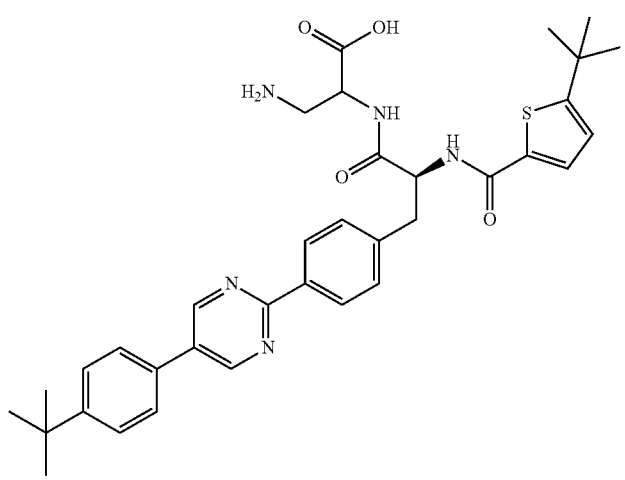
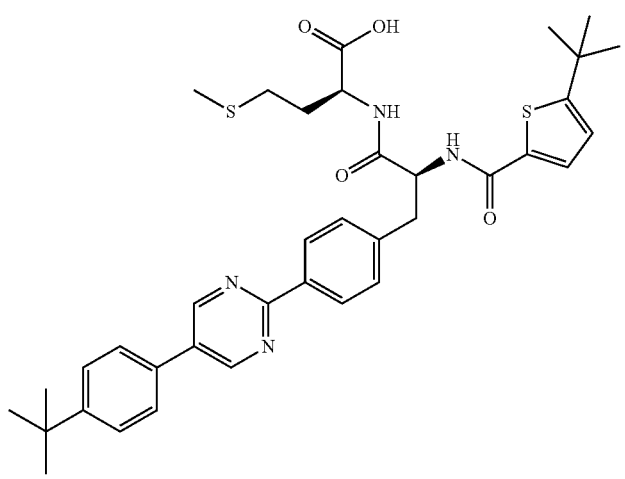

1159
-continued
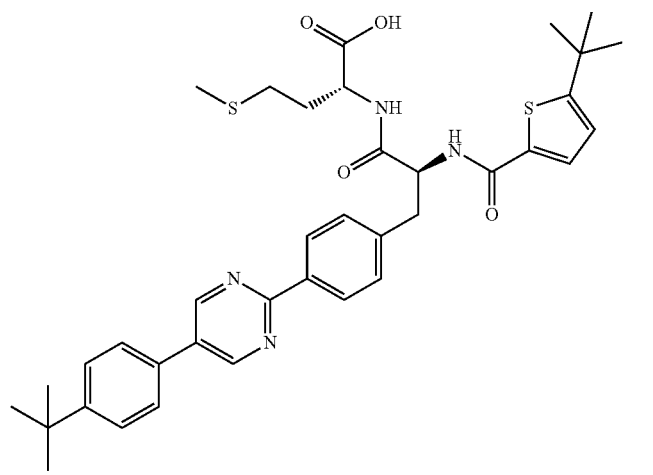
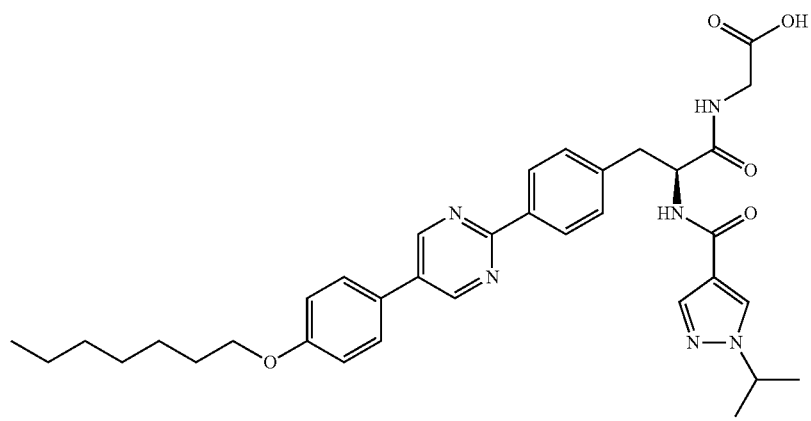
1160
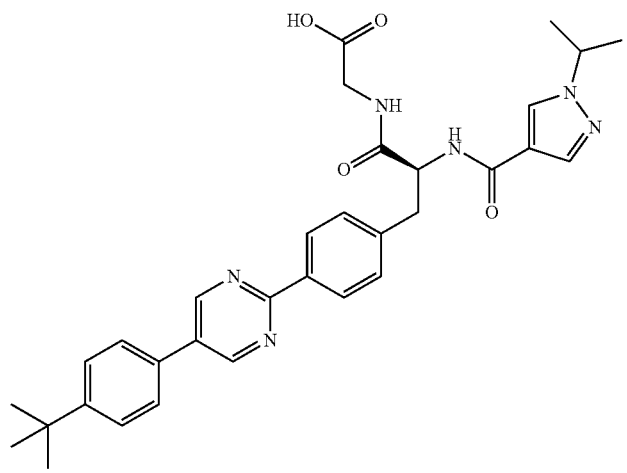
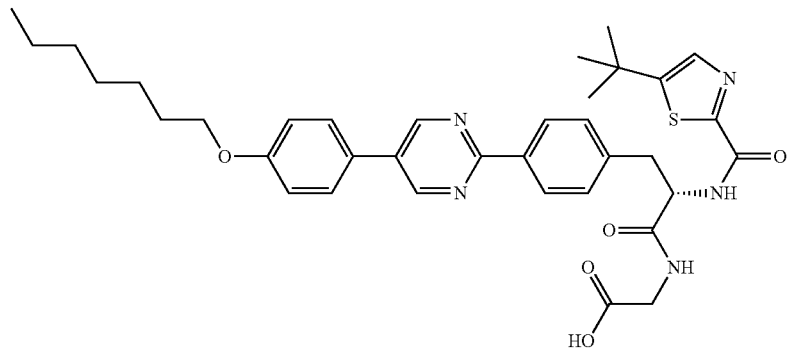

1161
-continued
1162
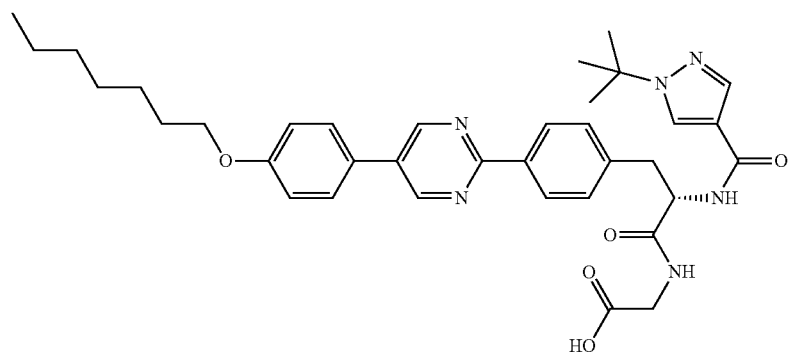
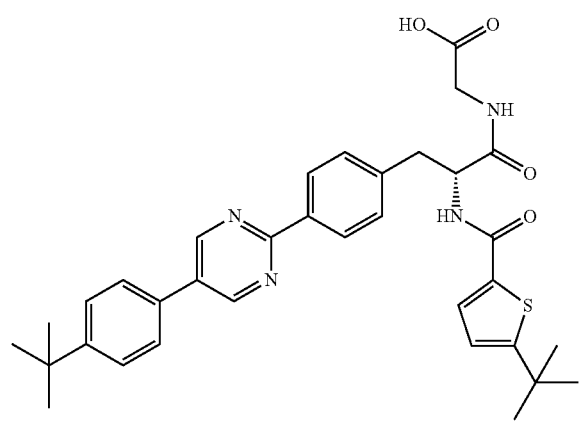
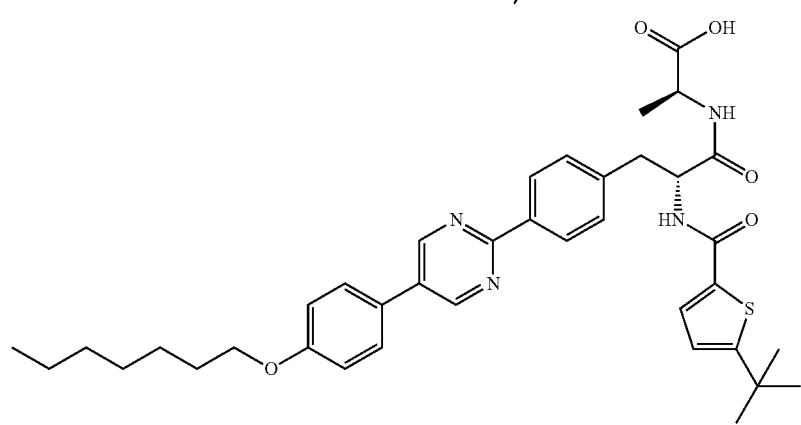
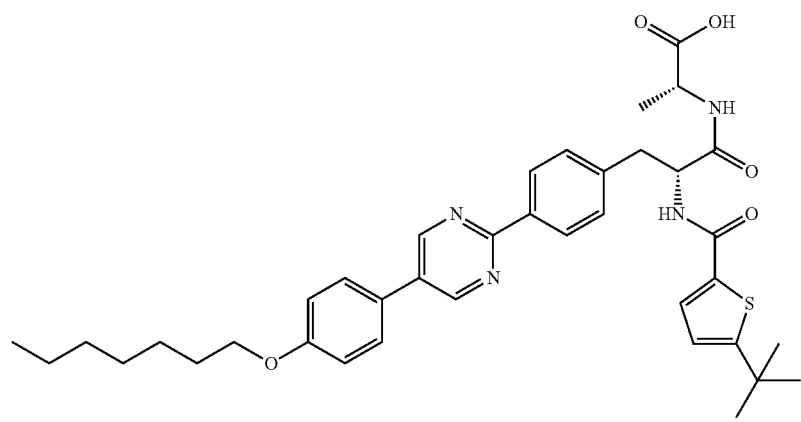

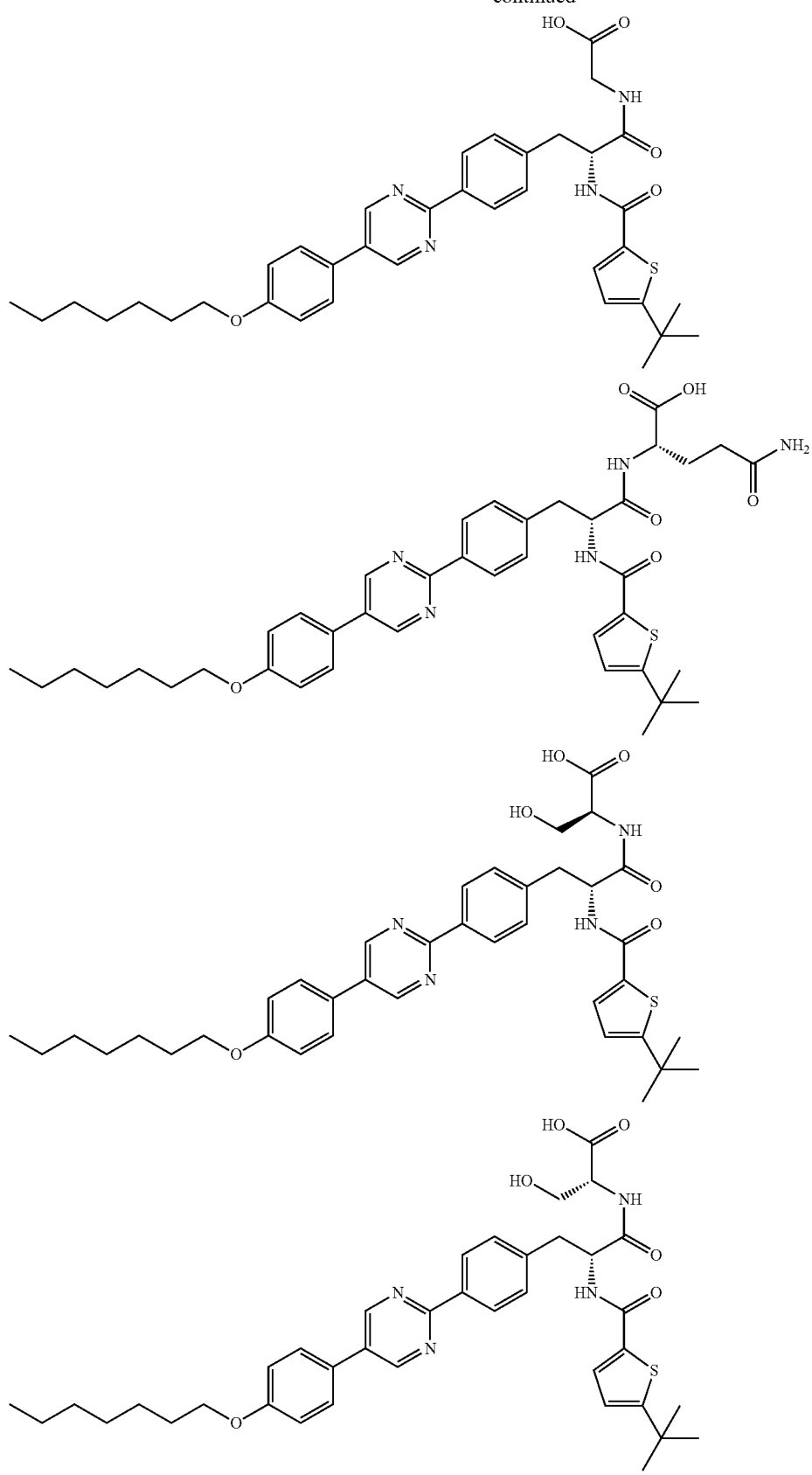

1165
1166
-continued
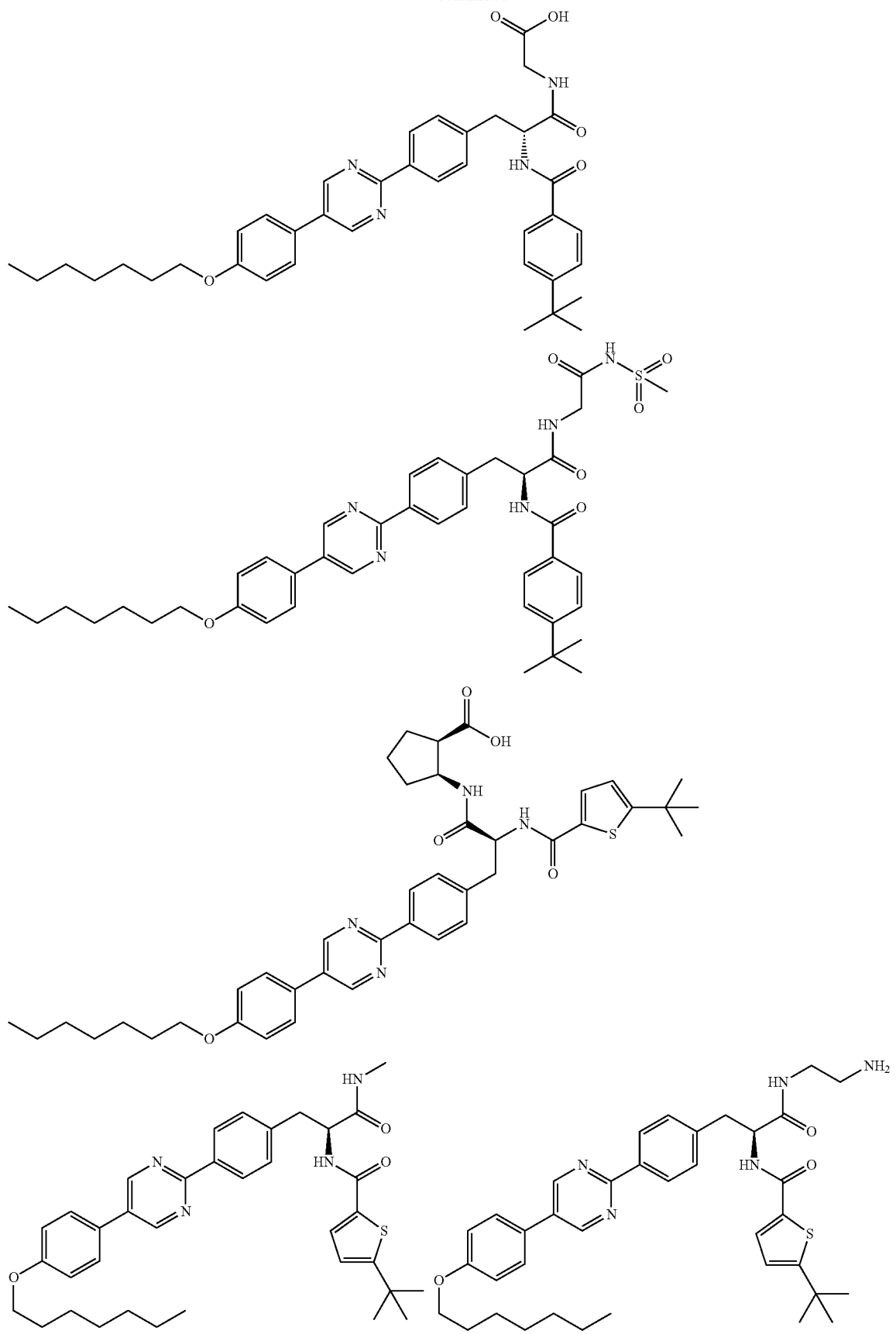

1167 1168
-continued
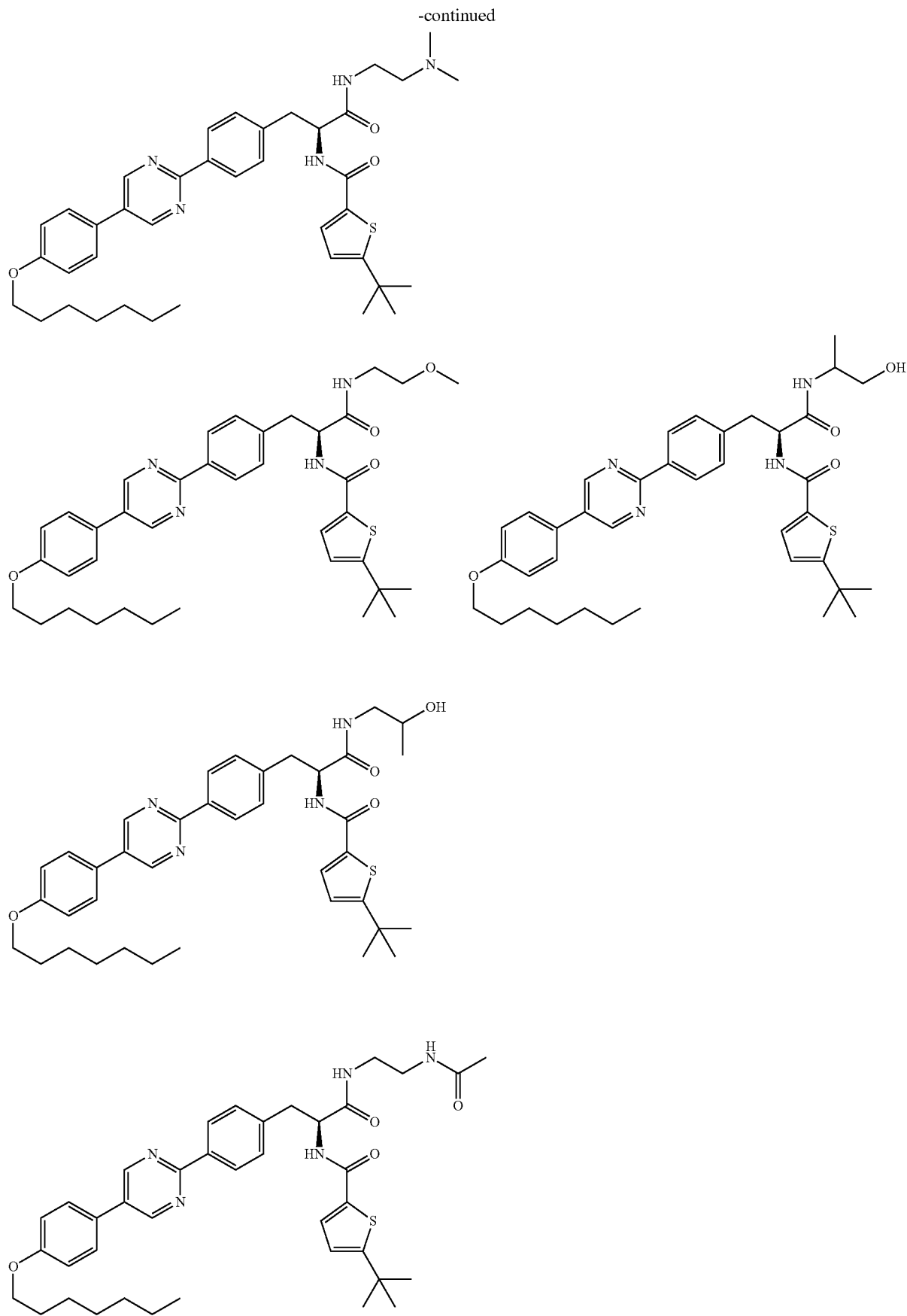

1169 1170
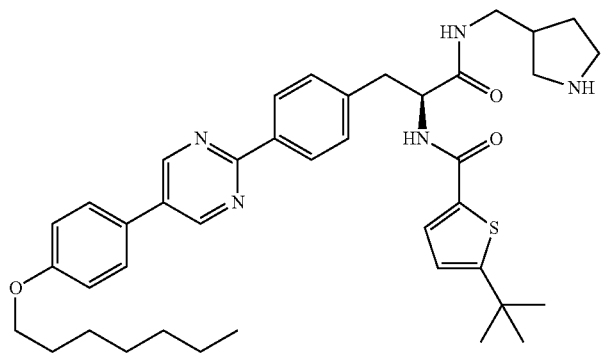
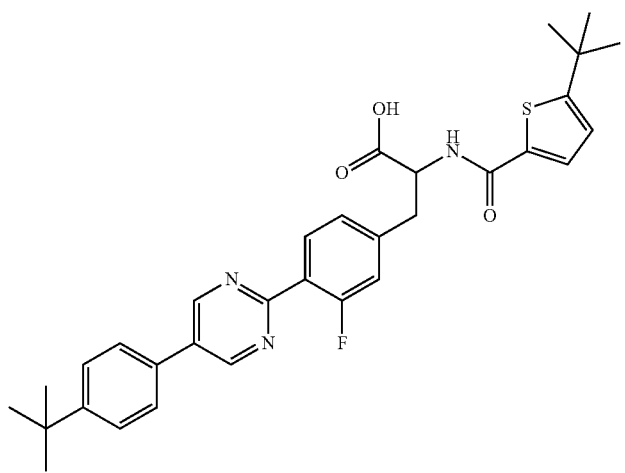
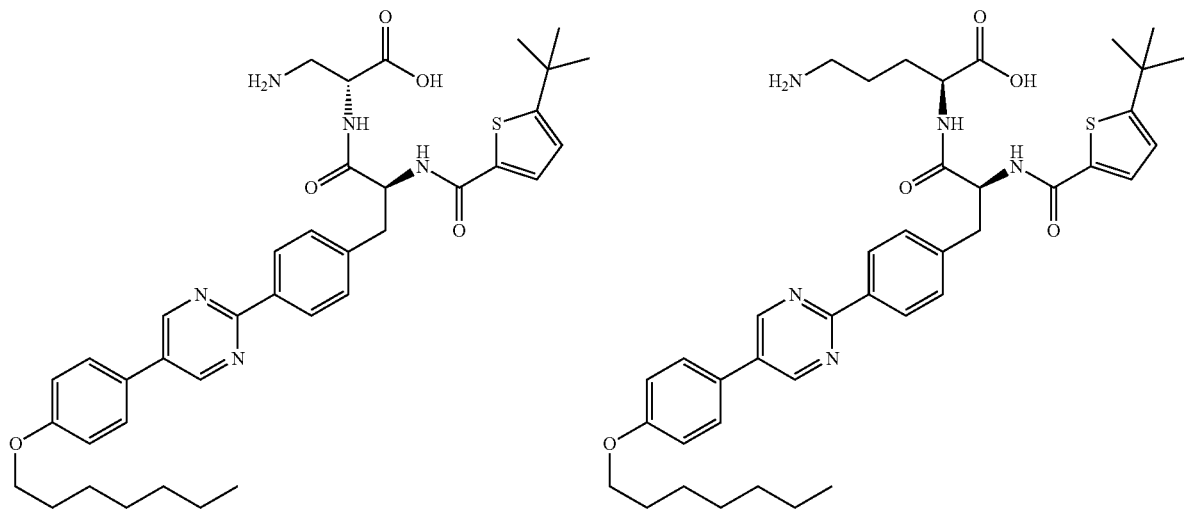

1171
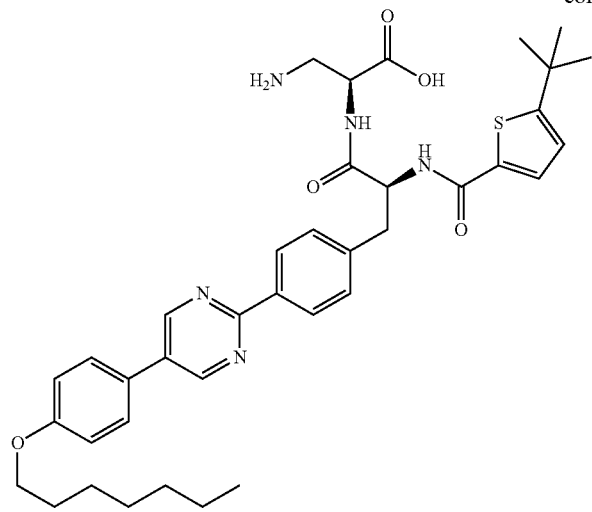
1172
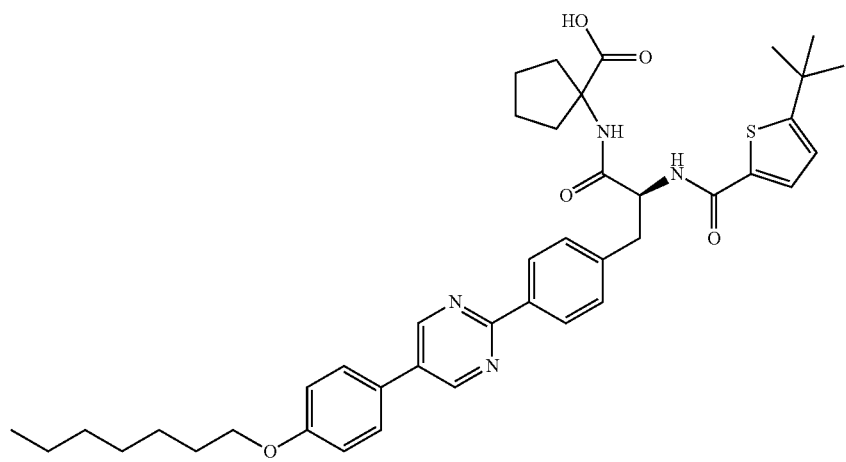
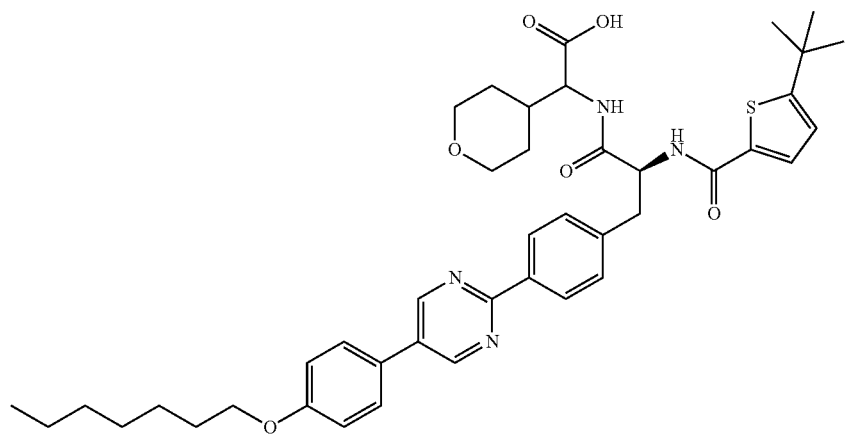

-continued
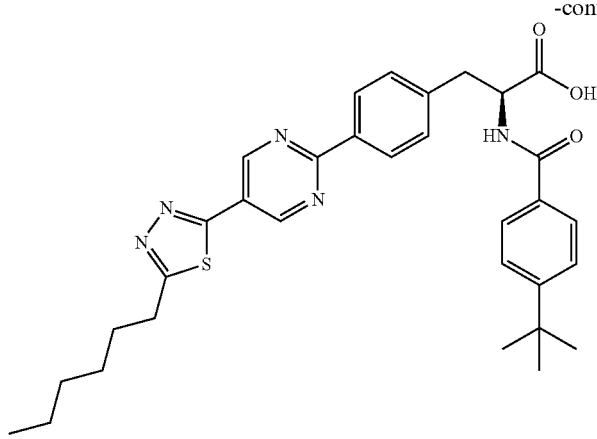
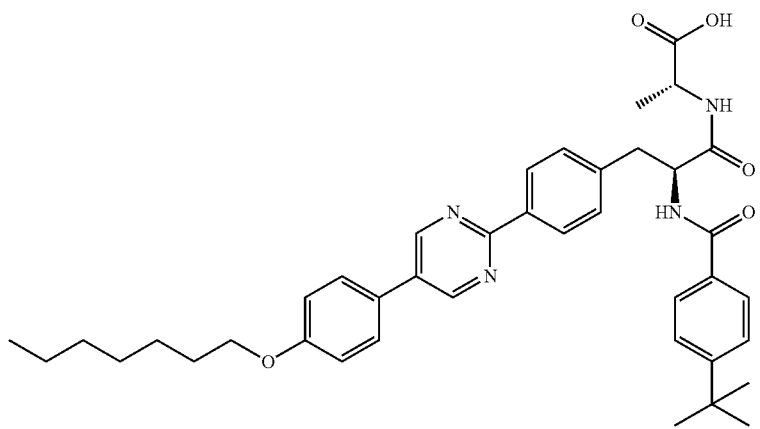
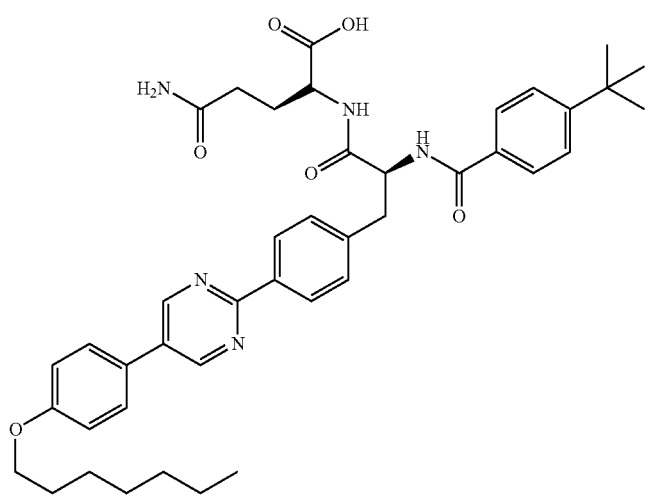

-continued
1175
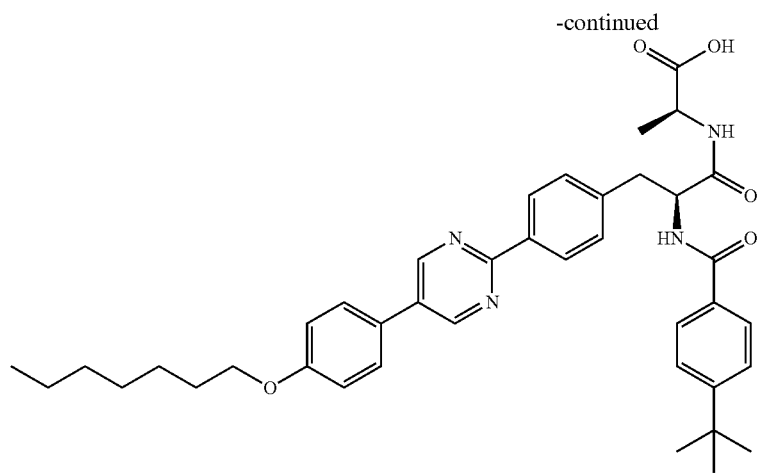
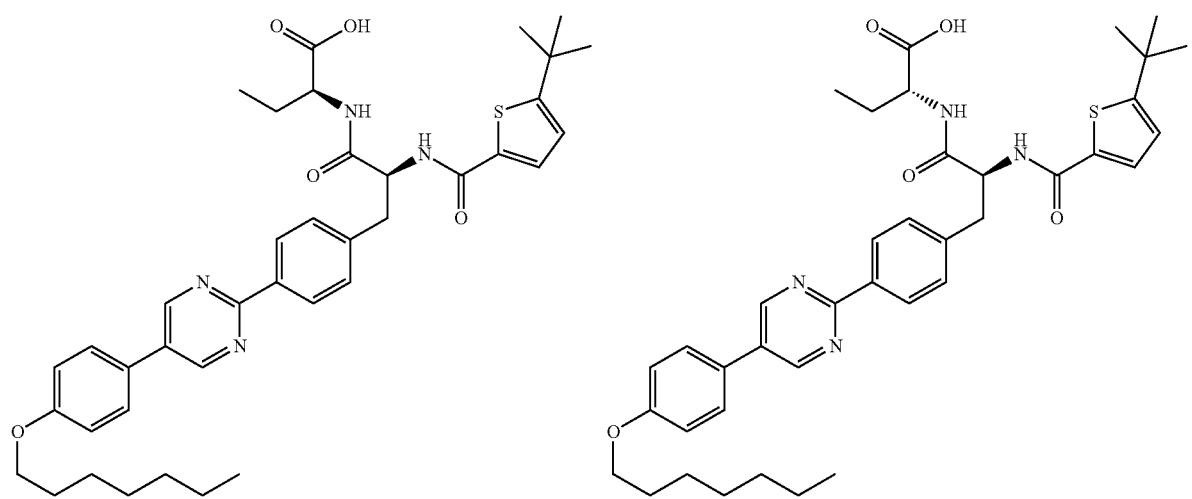
1176
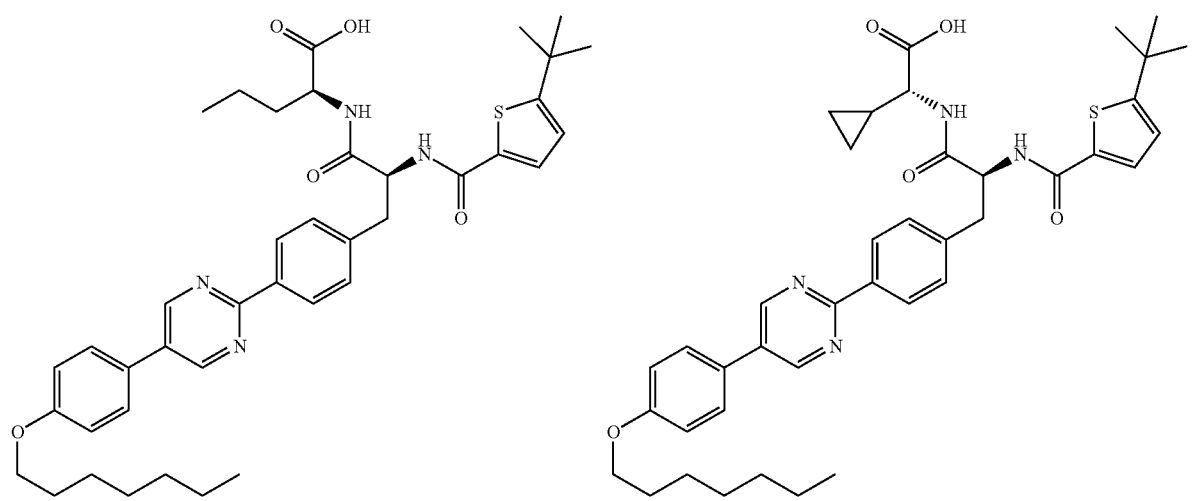

1177
-continued
1178
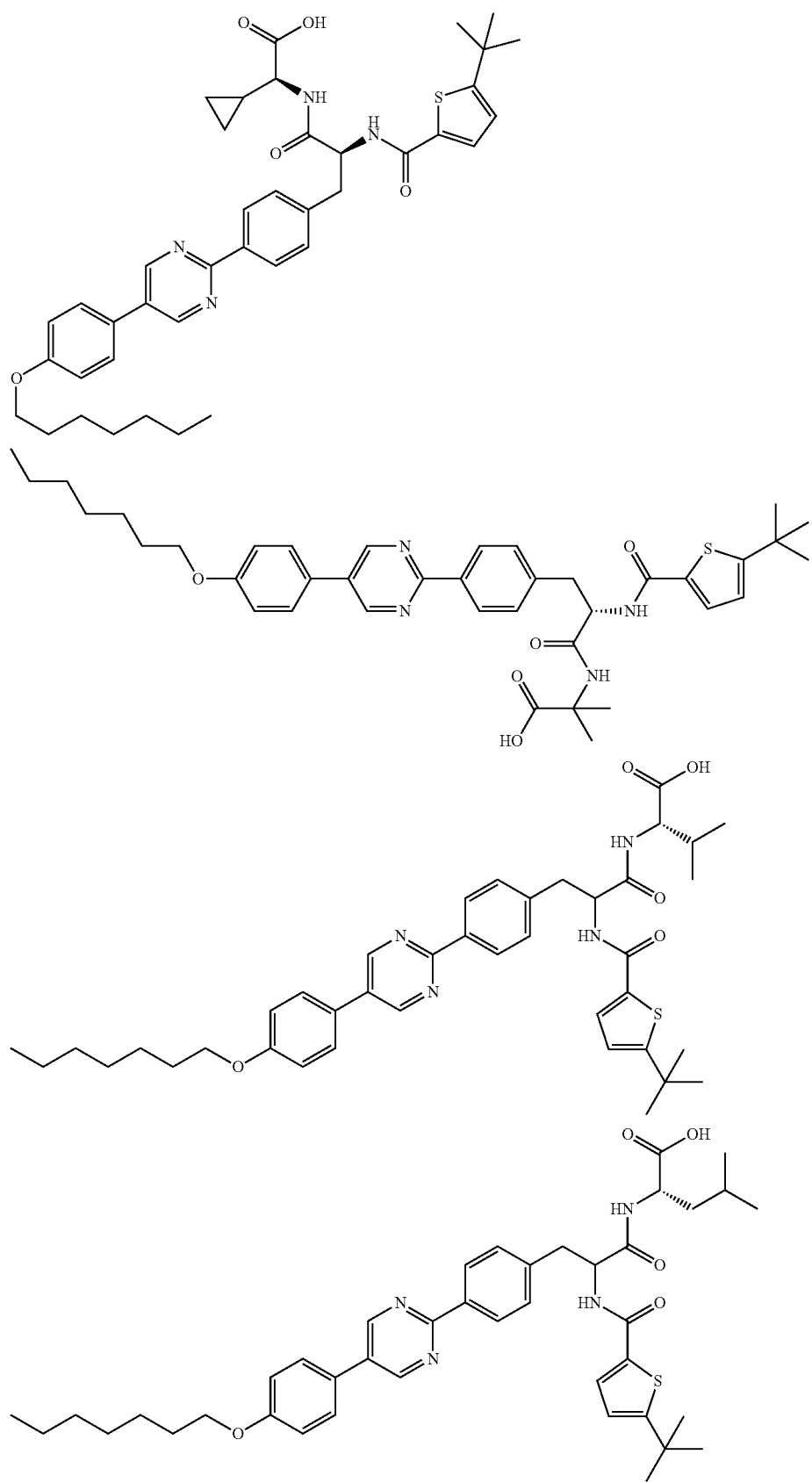

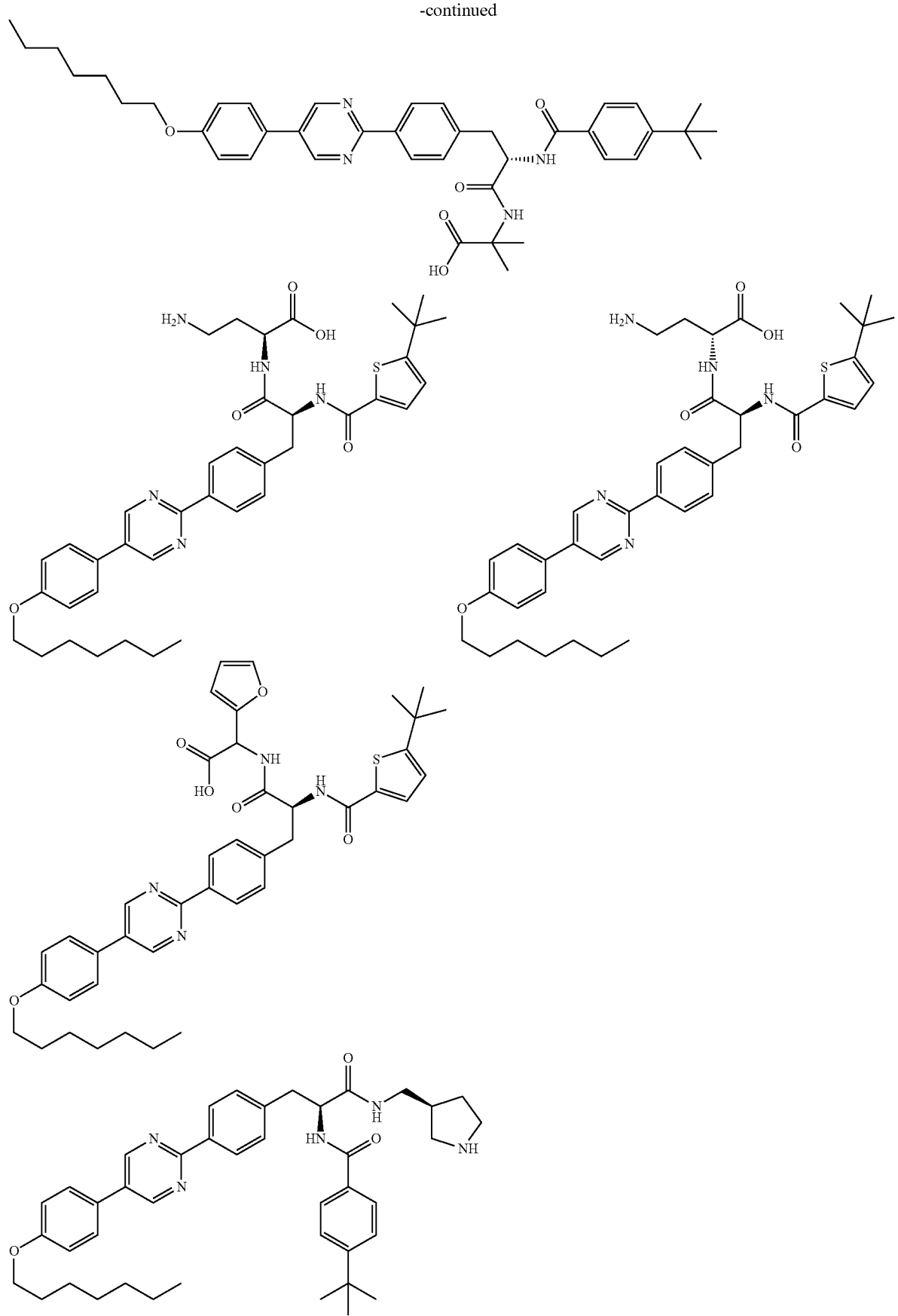

-continued
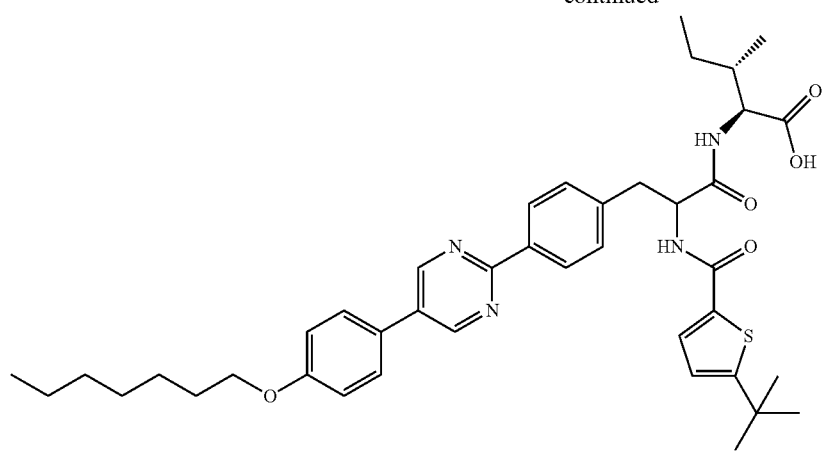
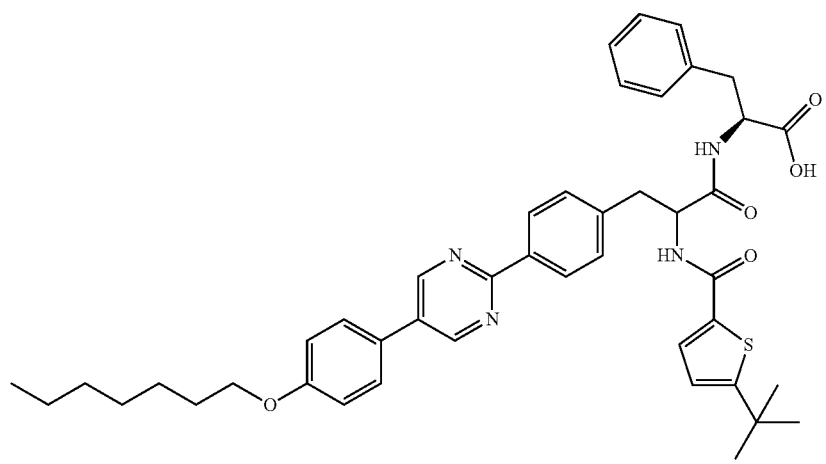
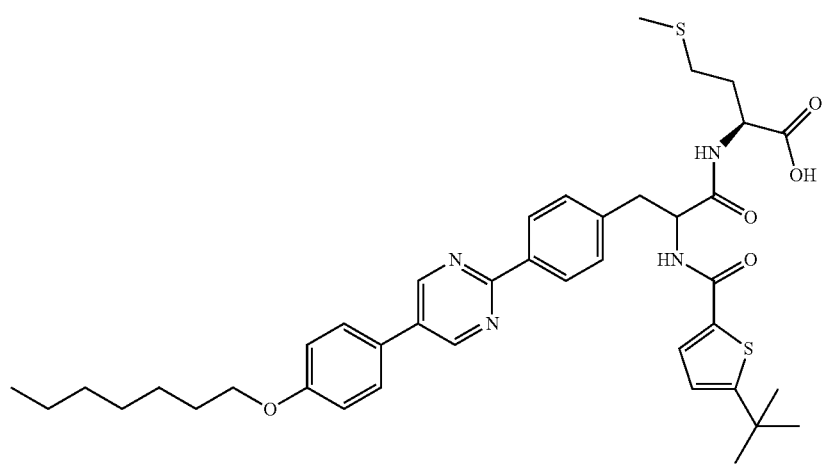

-continued
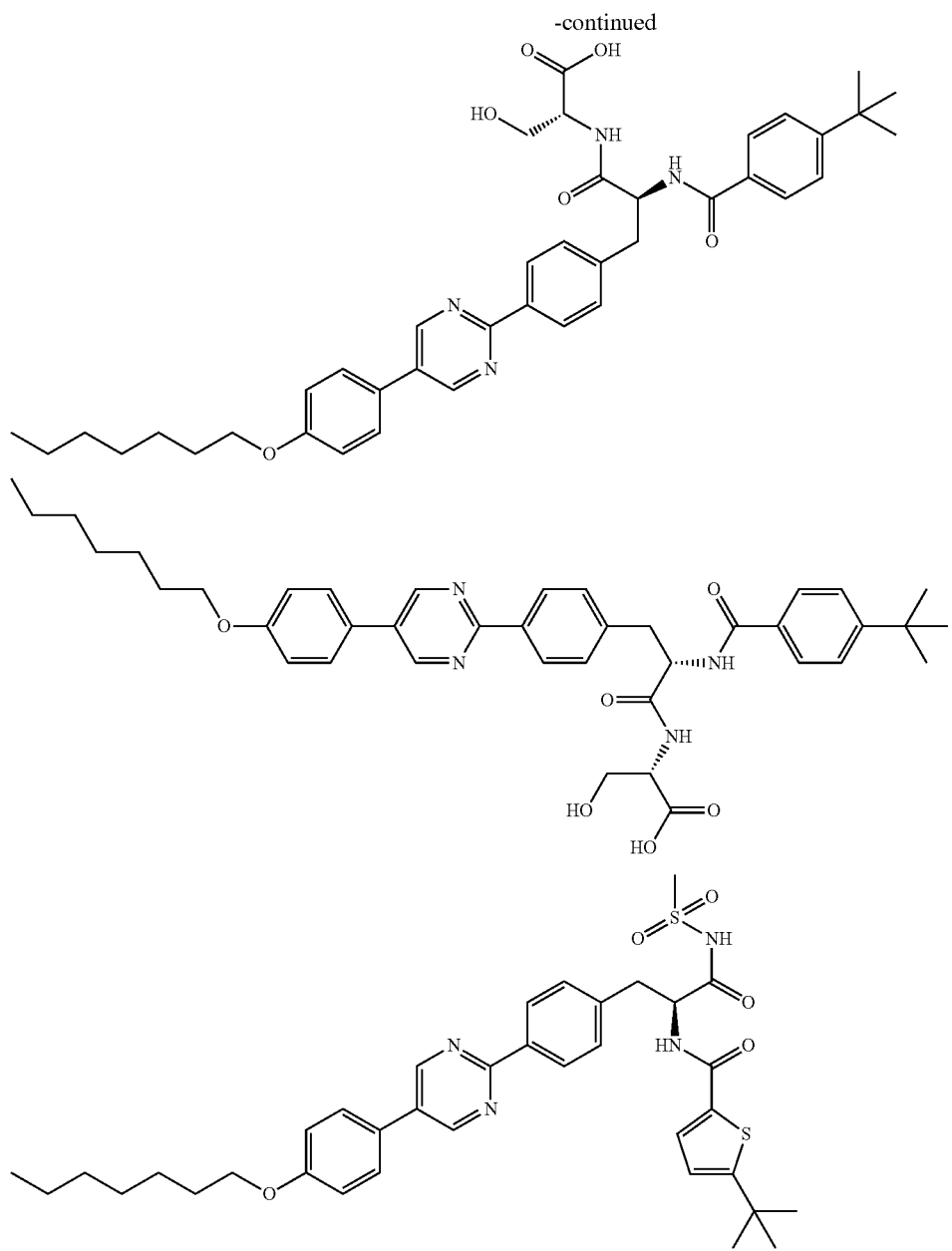
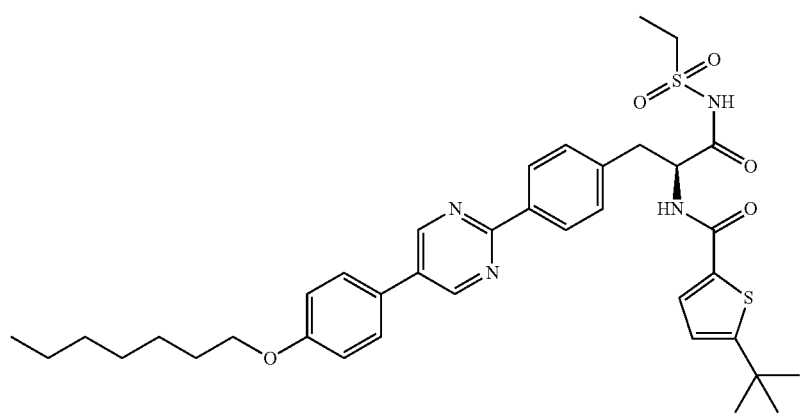

-continued
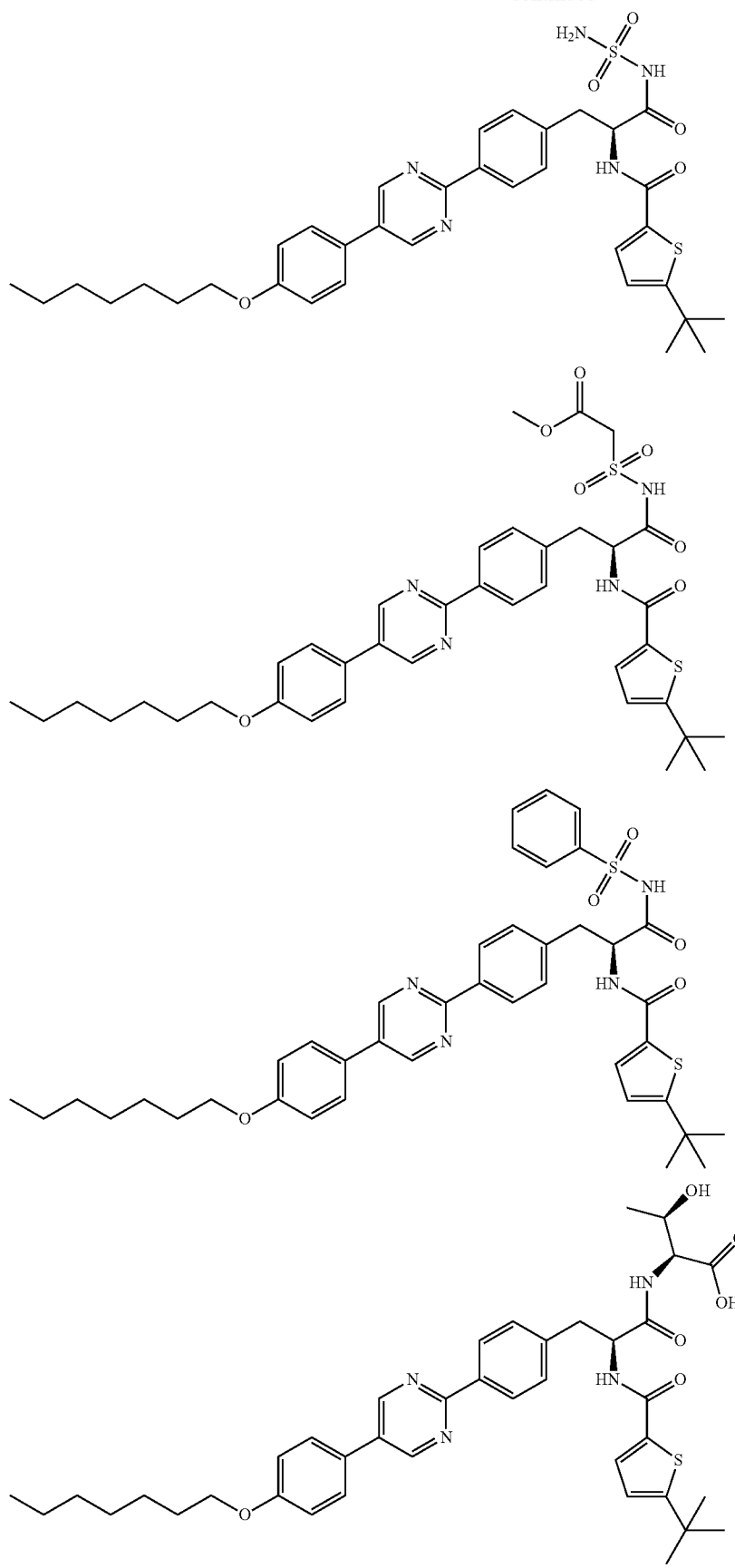

-continued
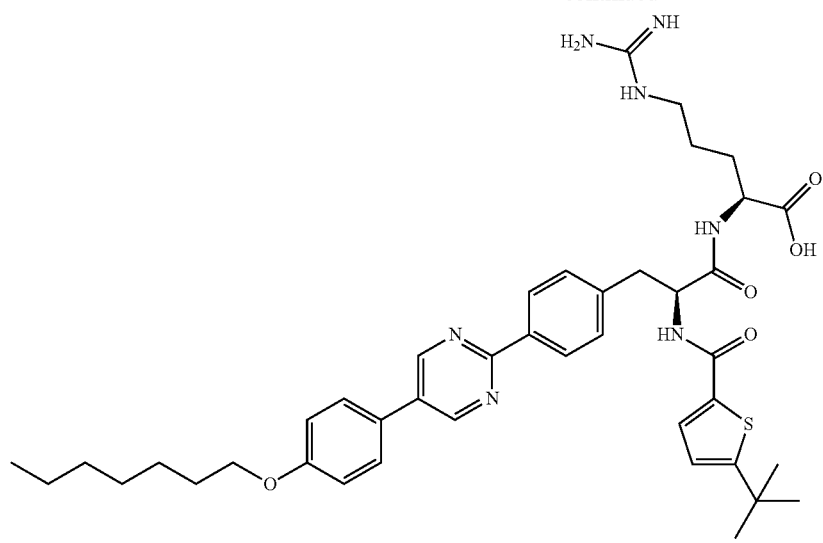
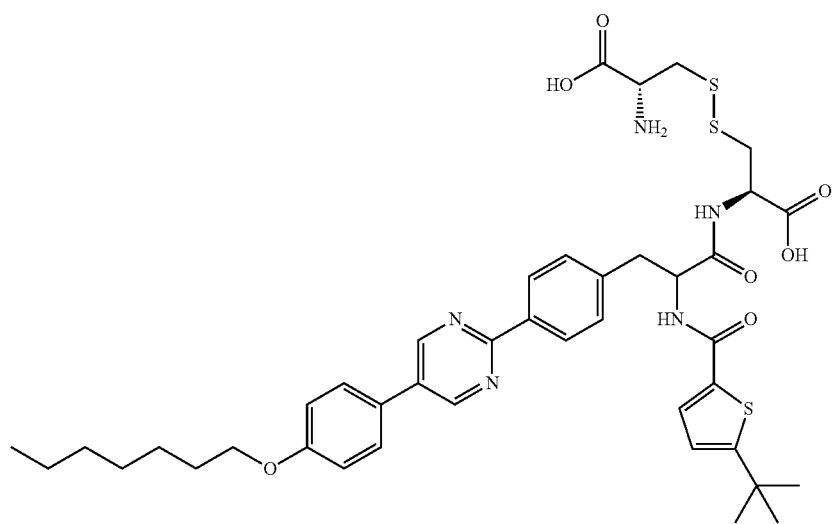
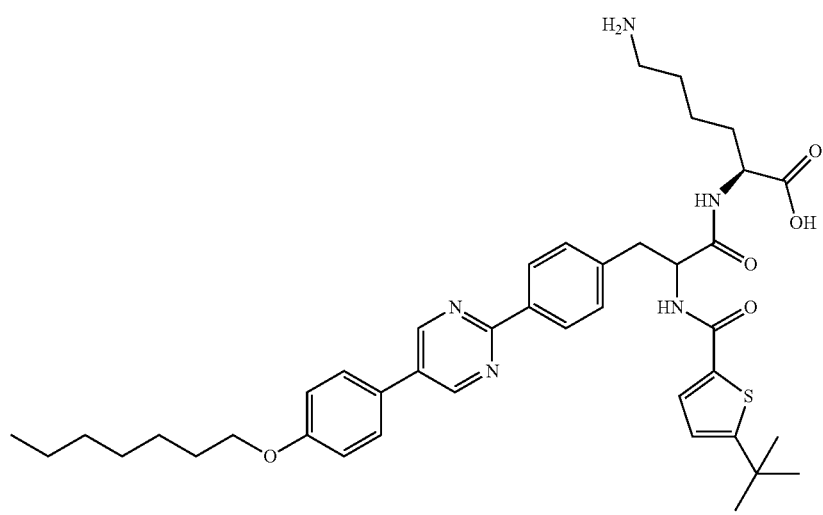

-continued
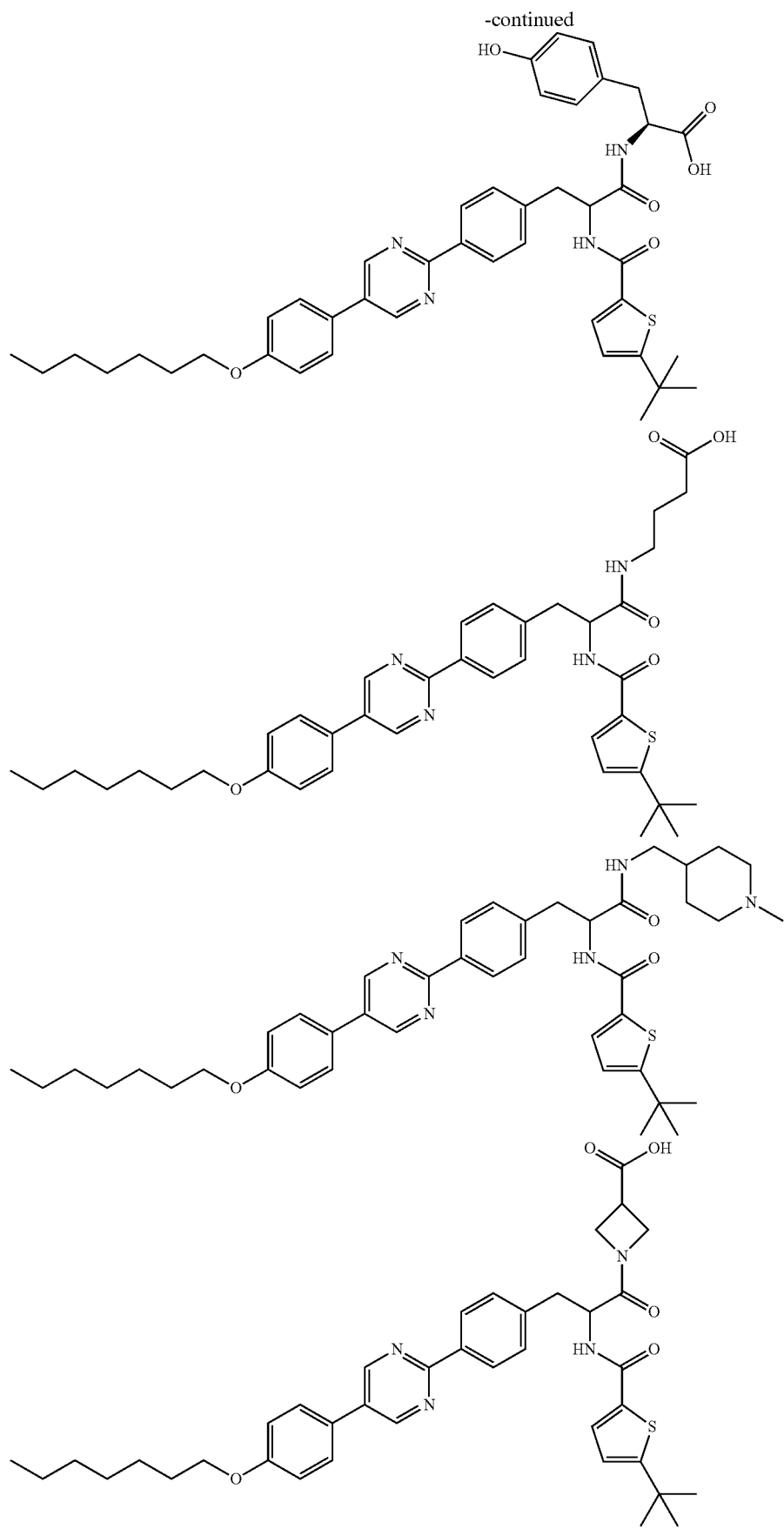

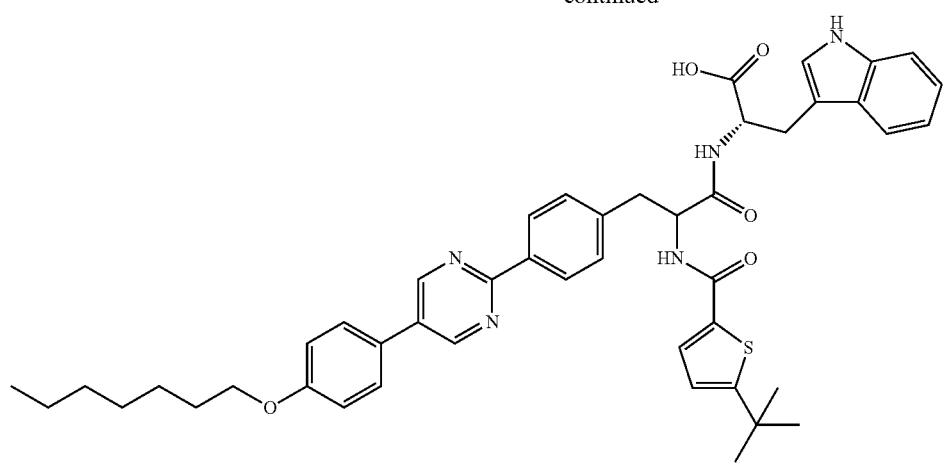
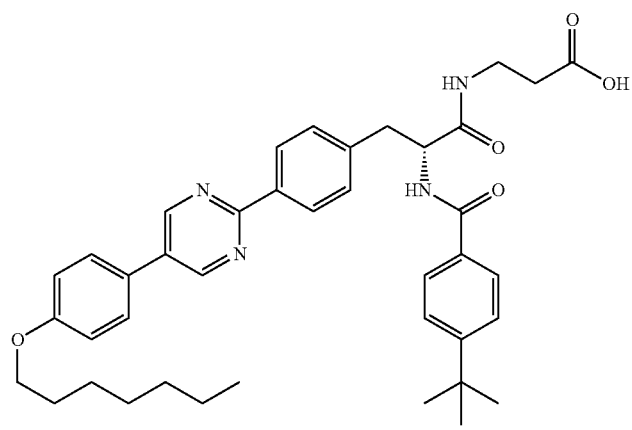
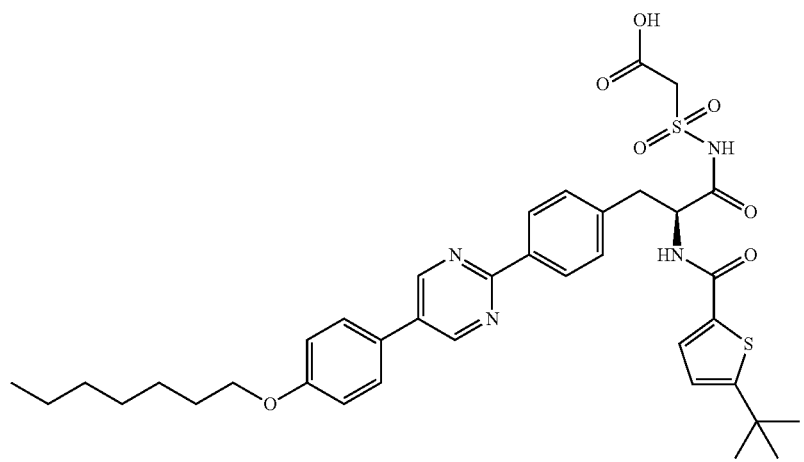

1193 1194
-continued
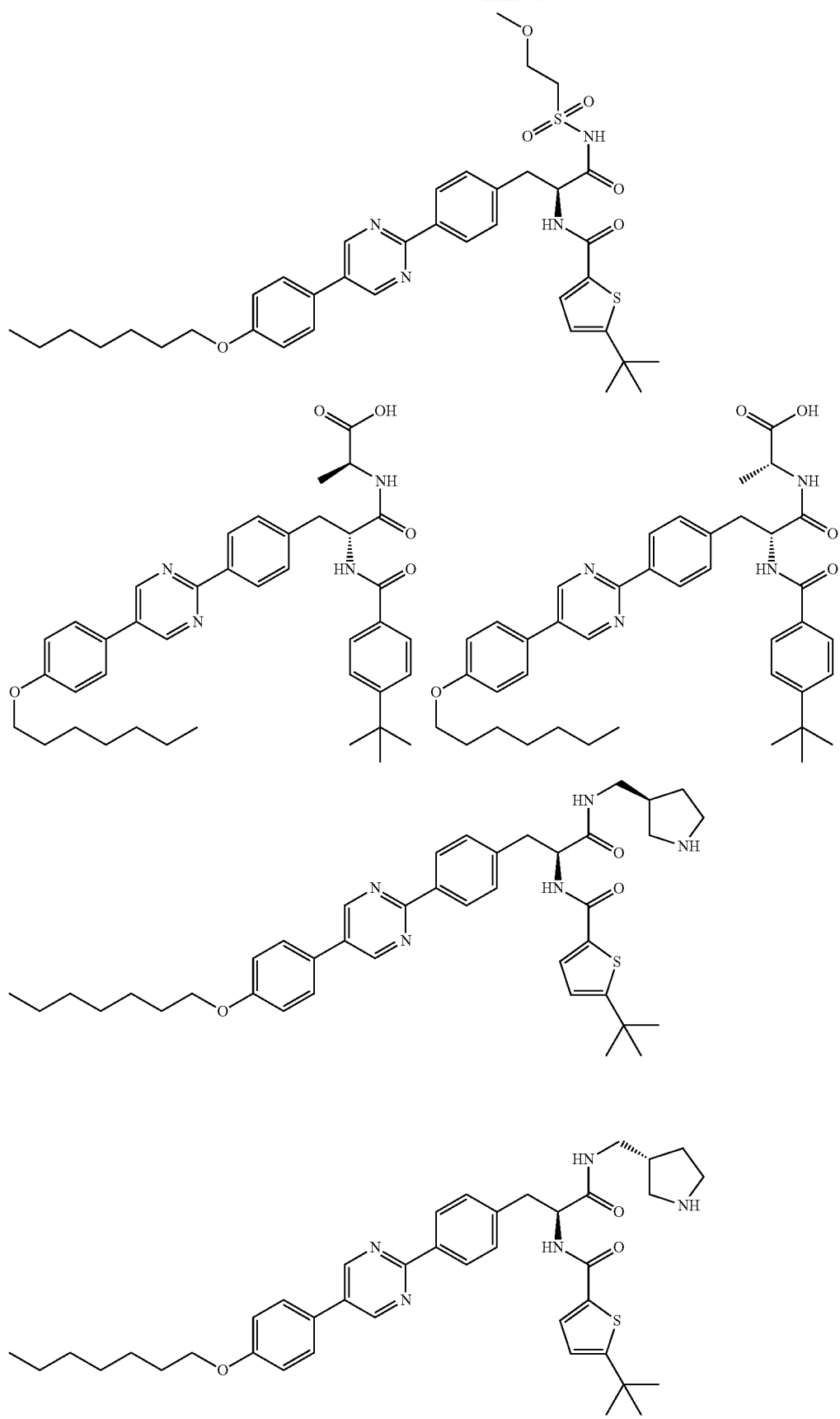

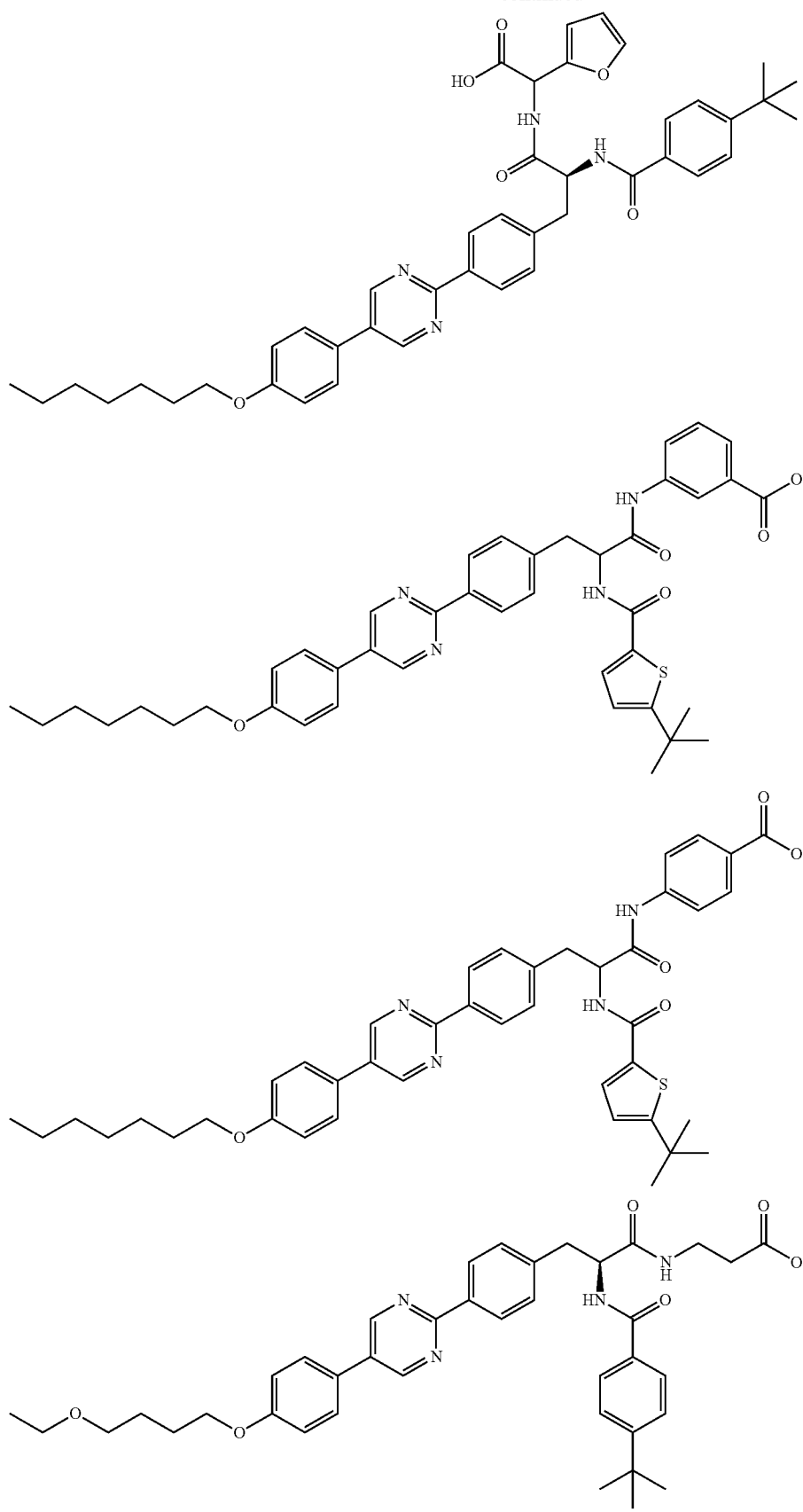

-continued
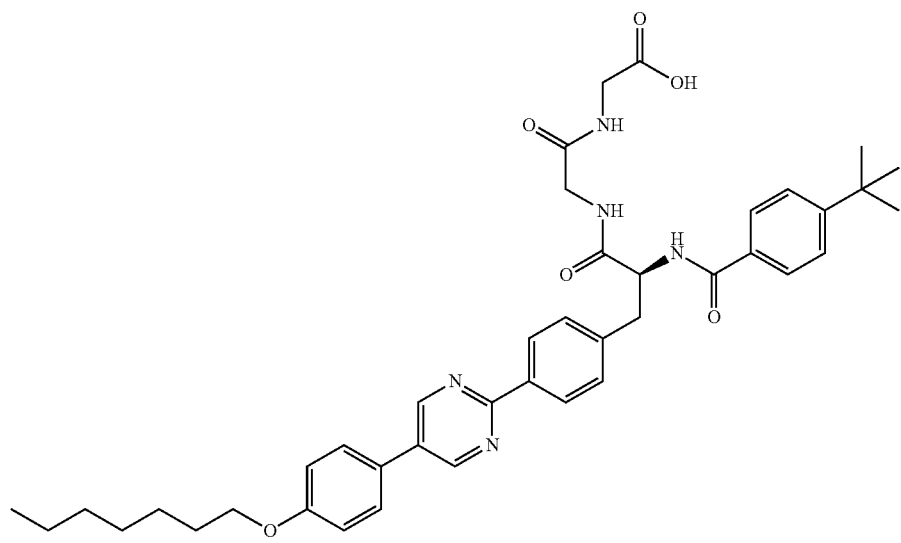
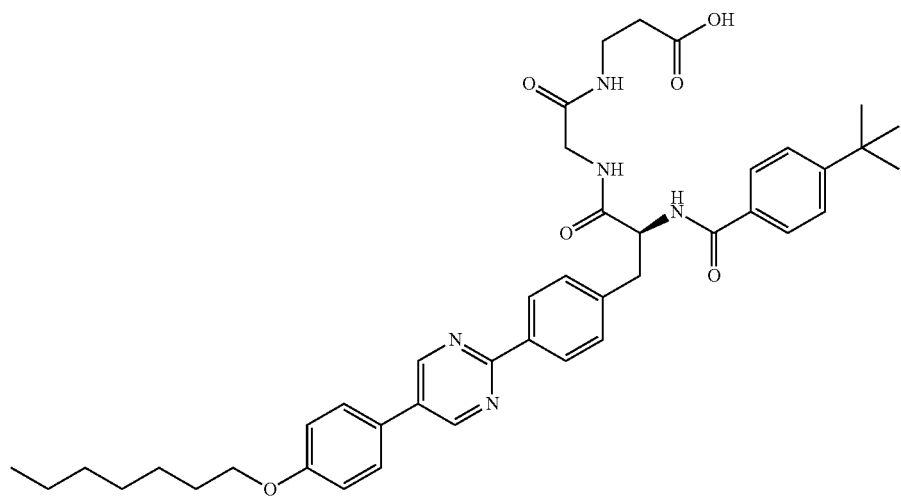
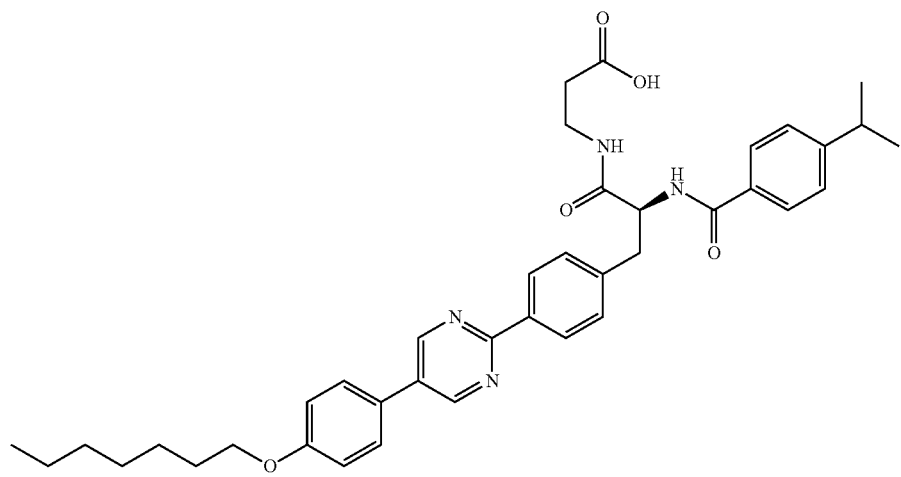

-continued
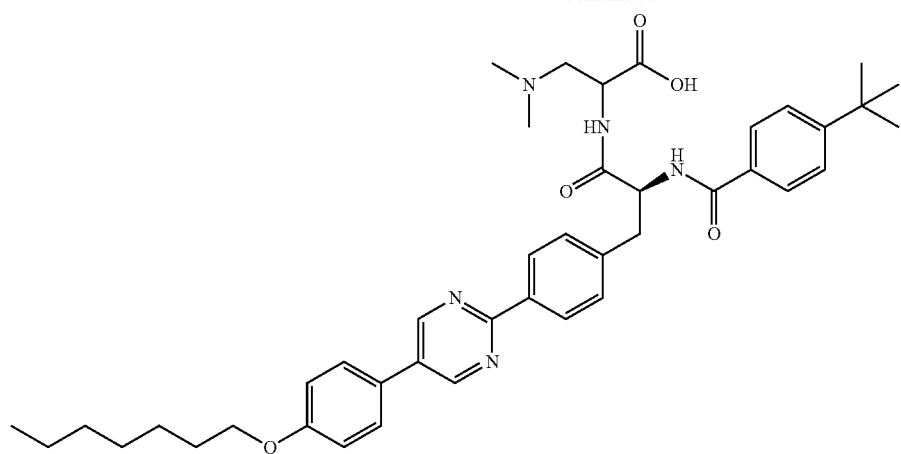
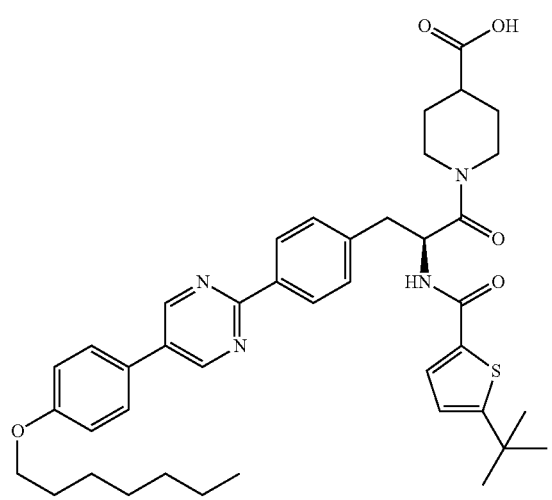
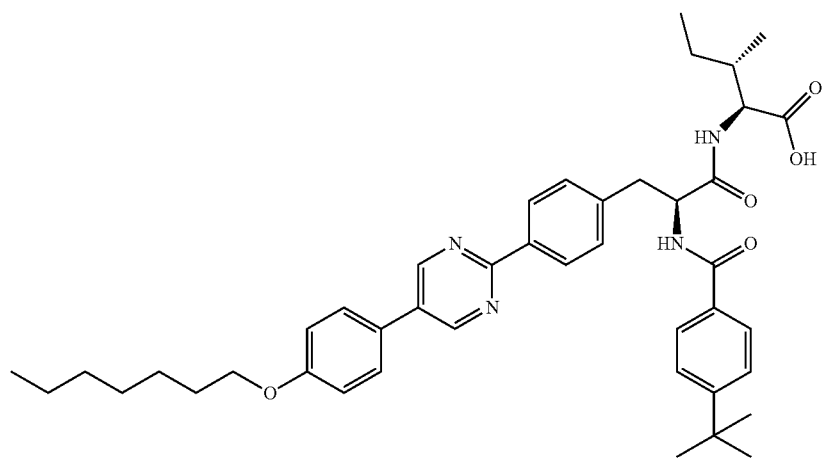

1201
-continued
1202
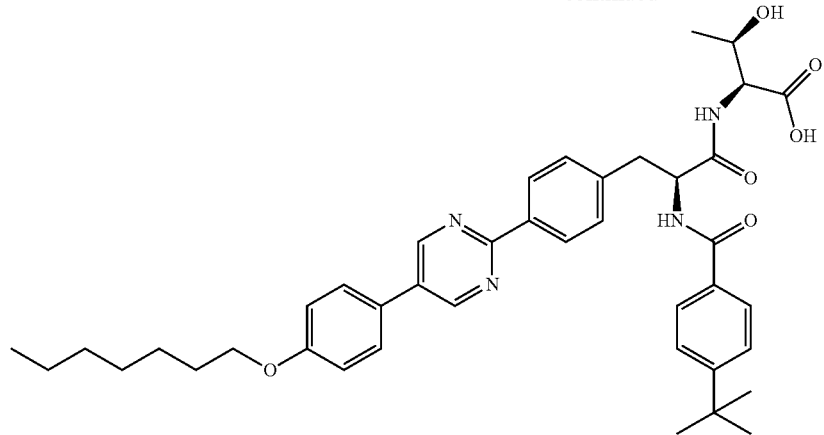
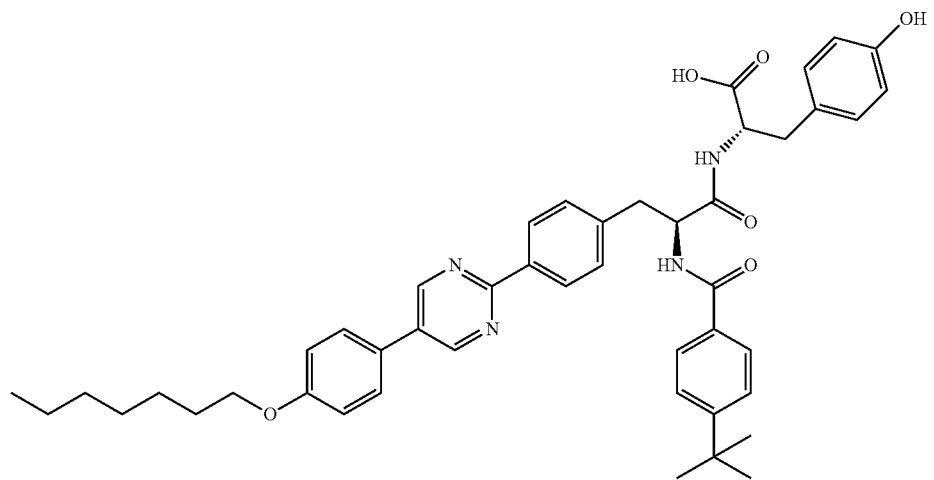
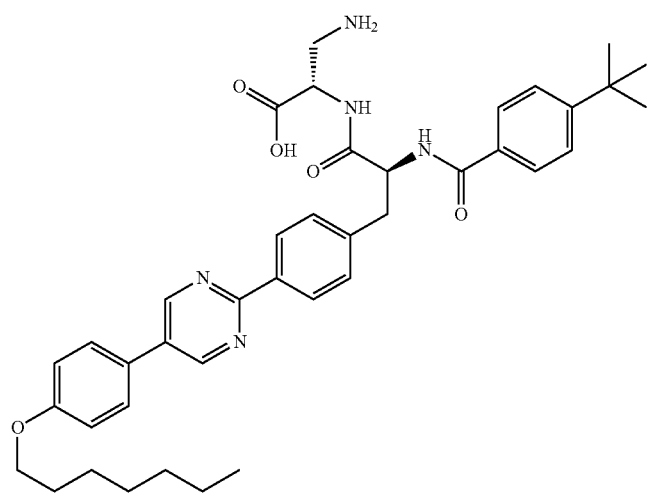

1203
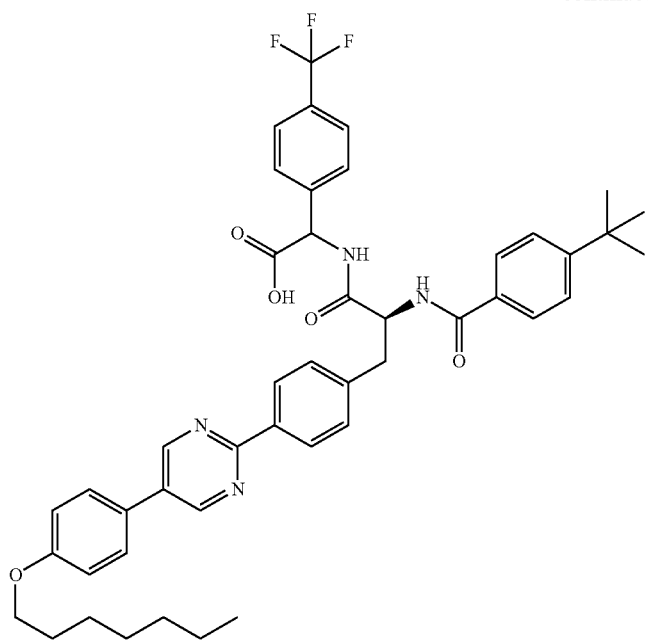
1204
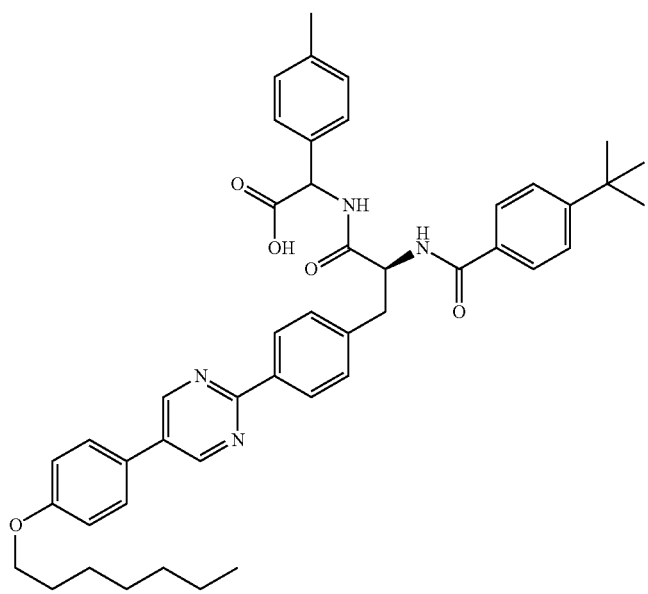
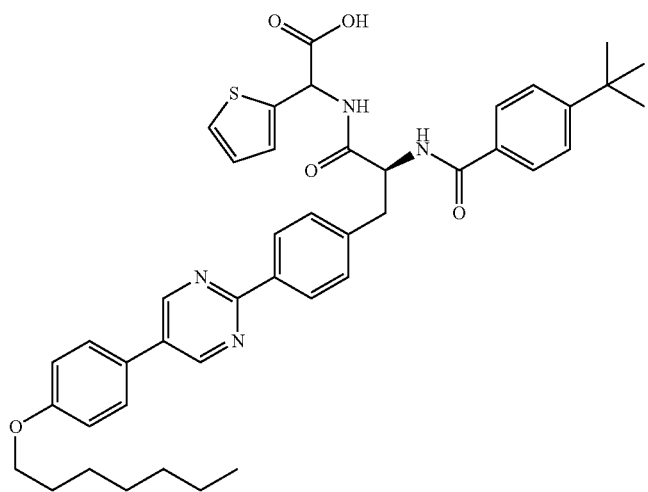

-continued
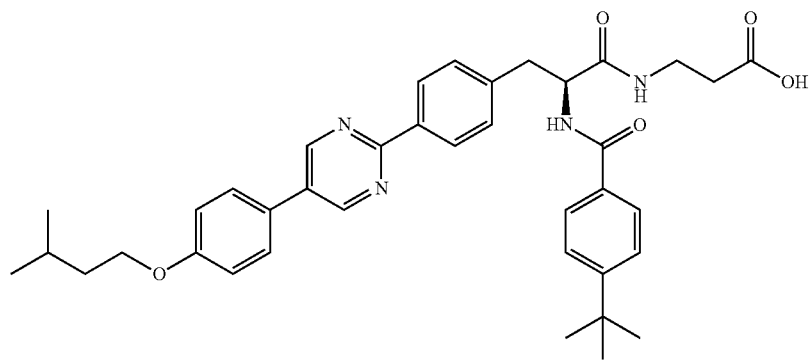
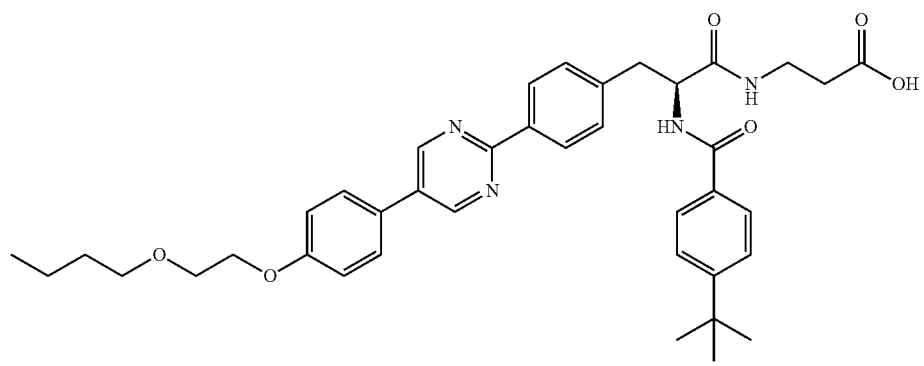
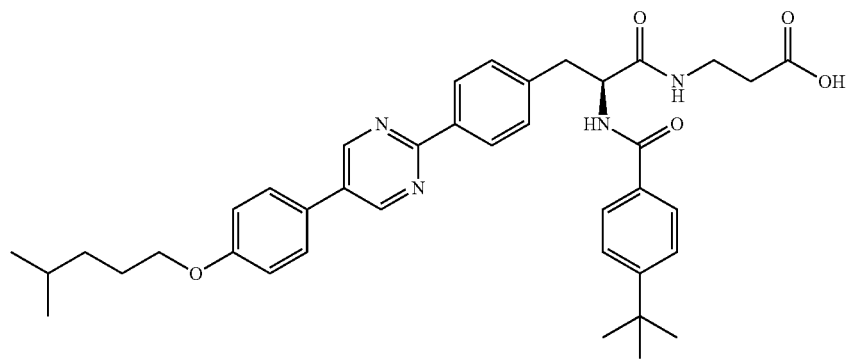
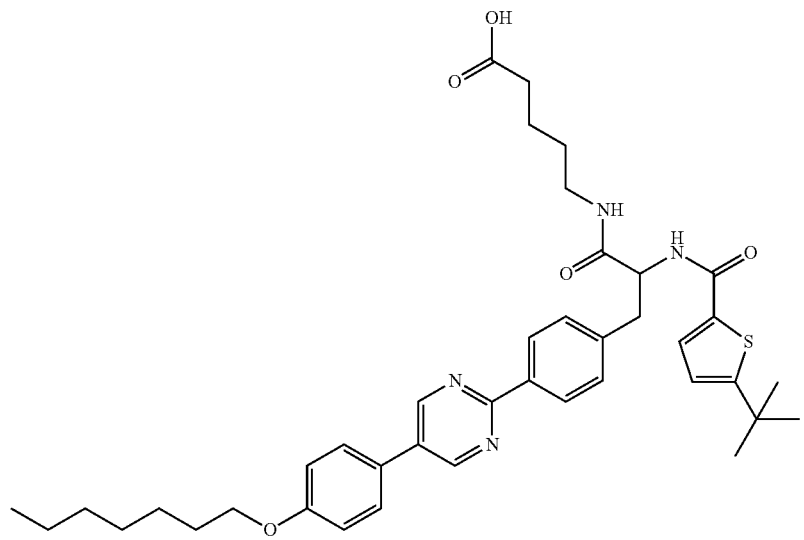

-continued
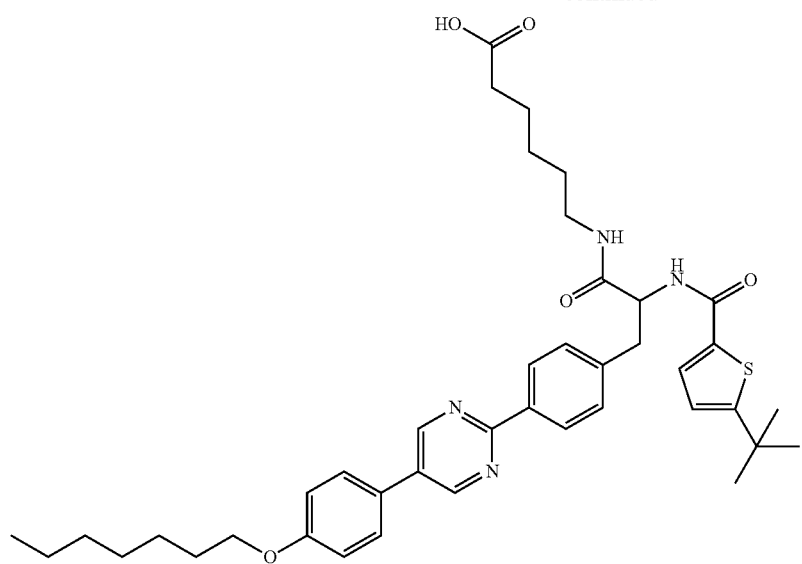
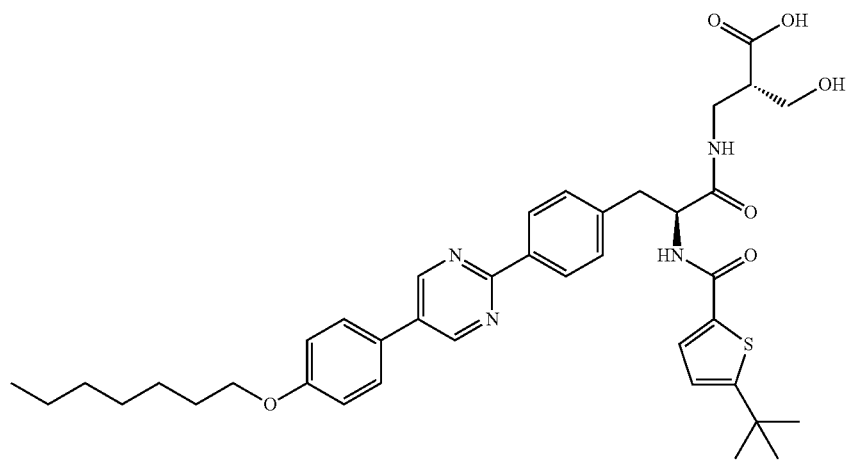
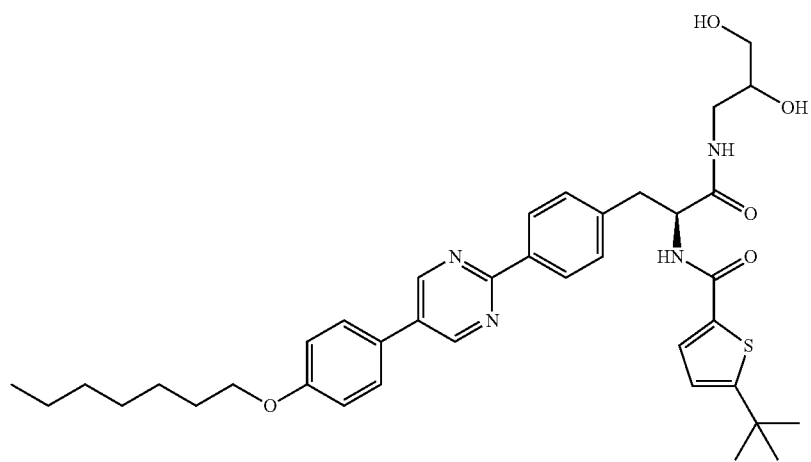

-continued
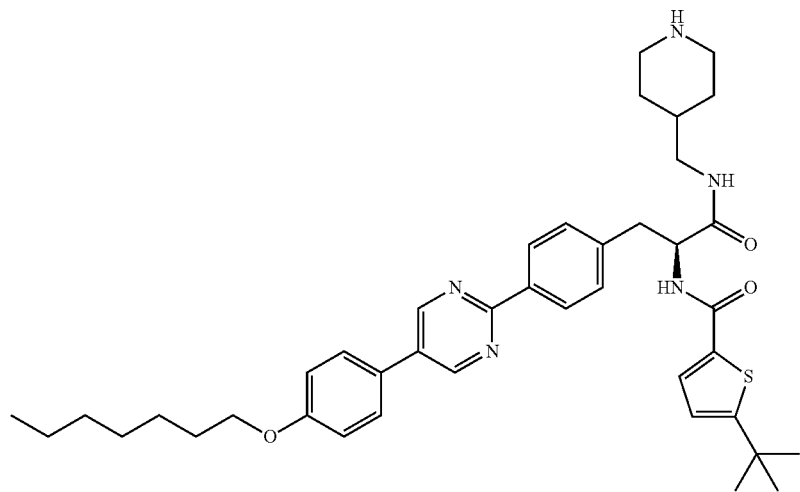
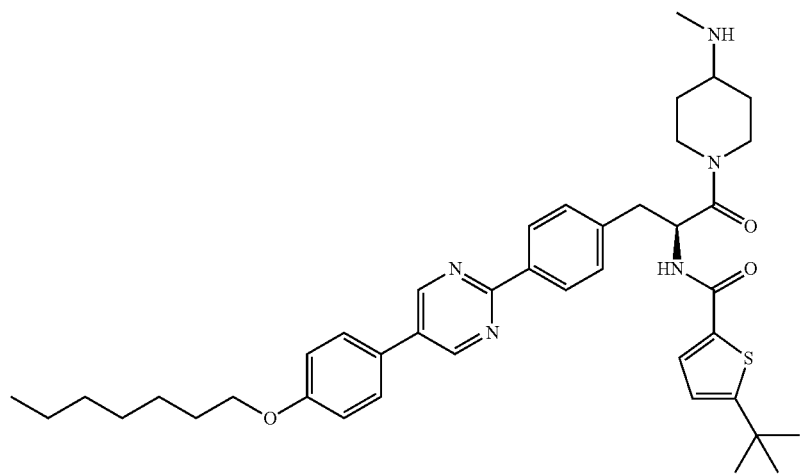
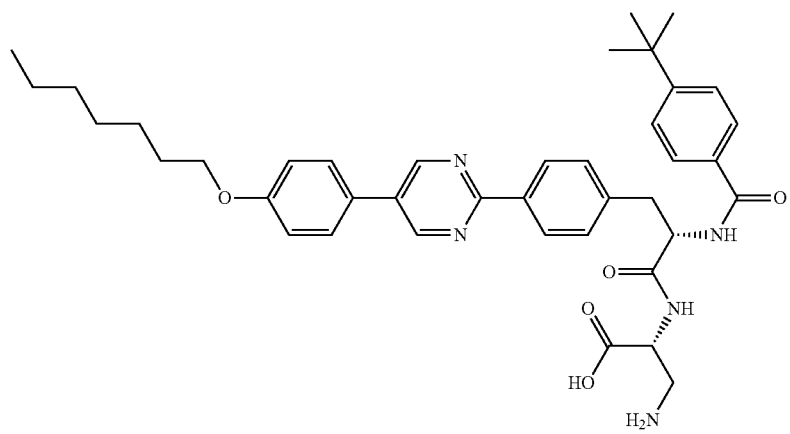

1211
-continued
1212
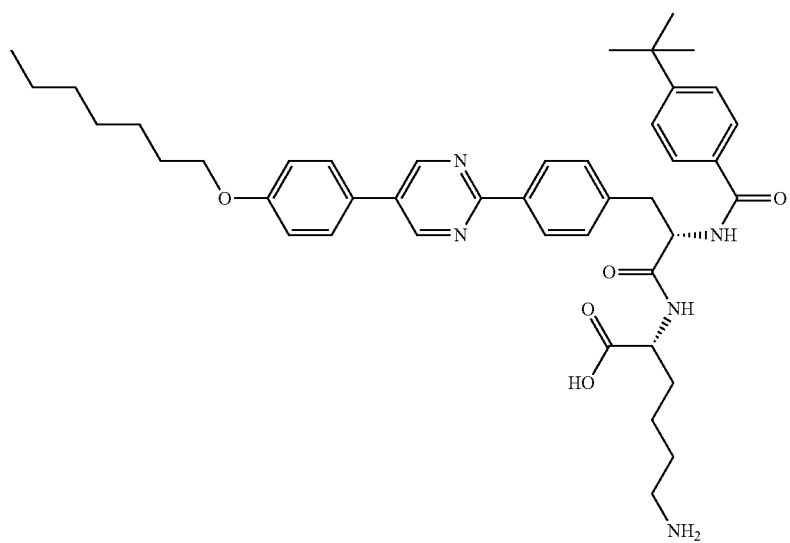
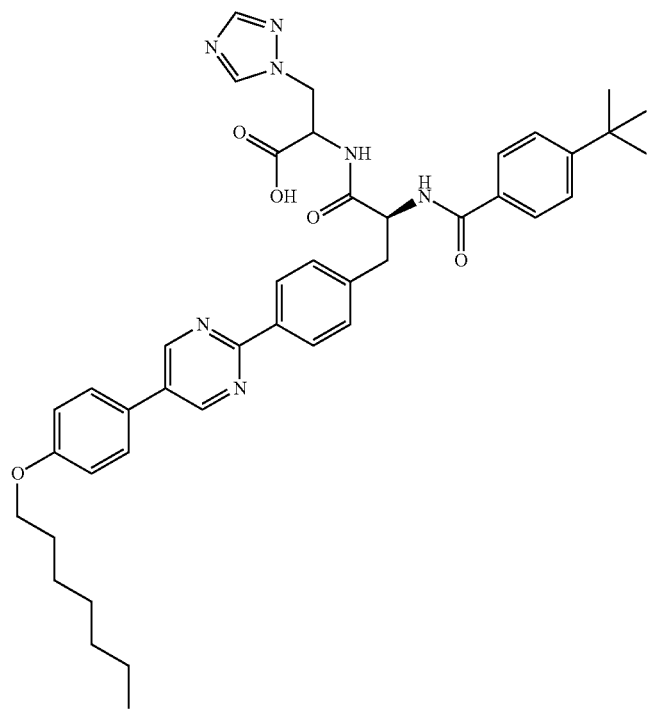

1213
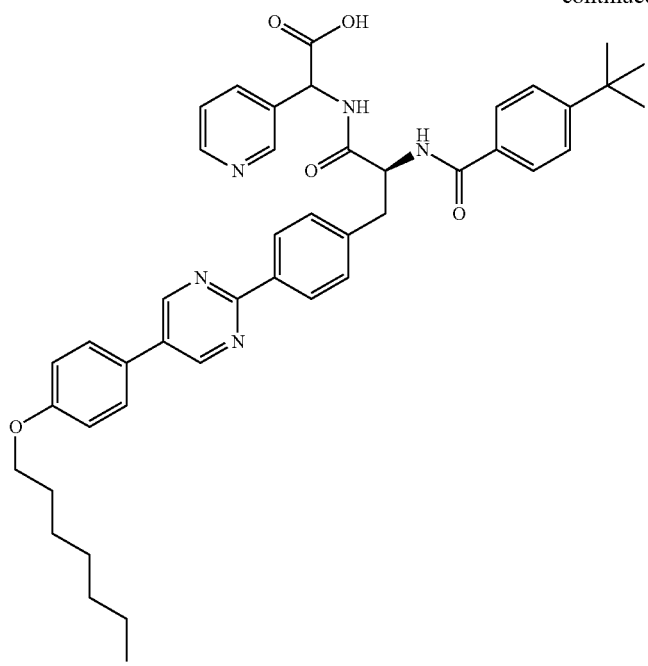
-continued
1214
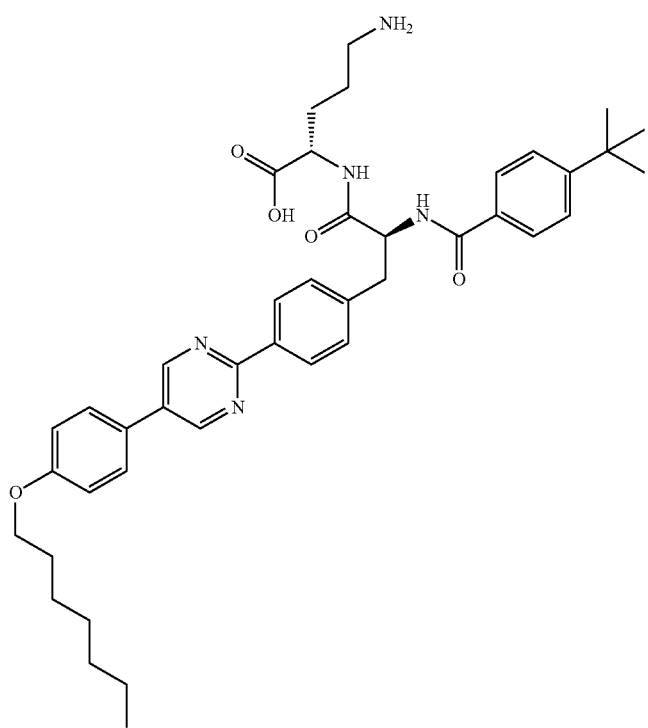

1215
-continued
1216
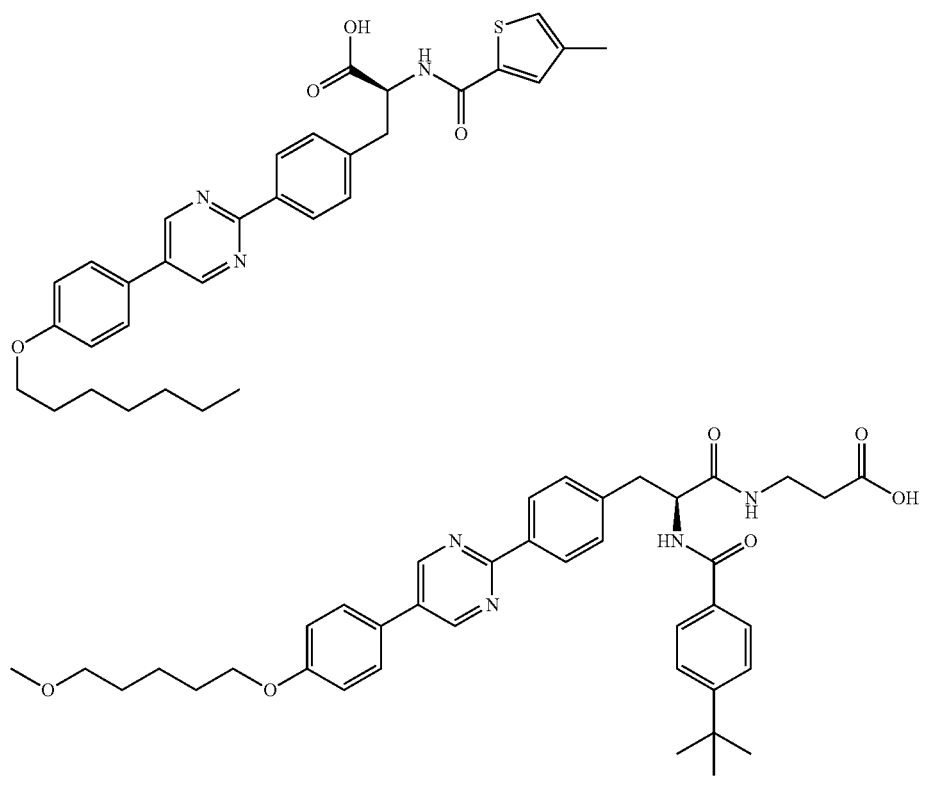
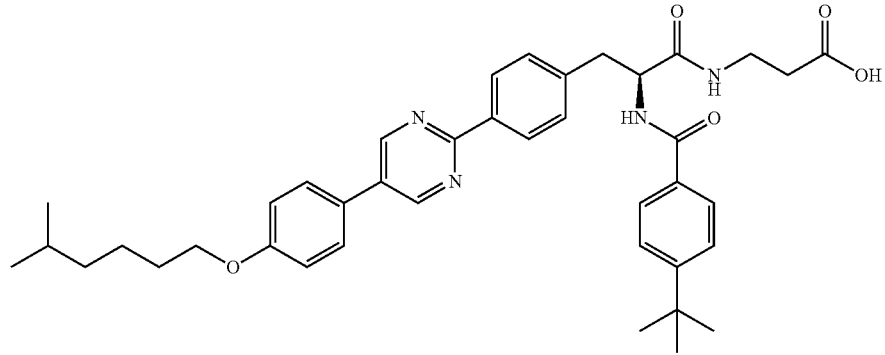
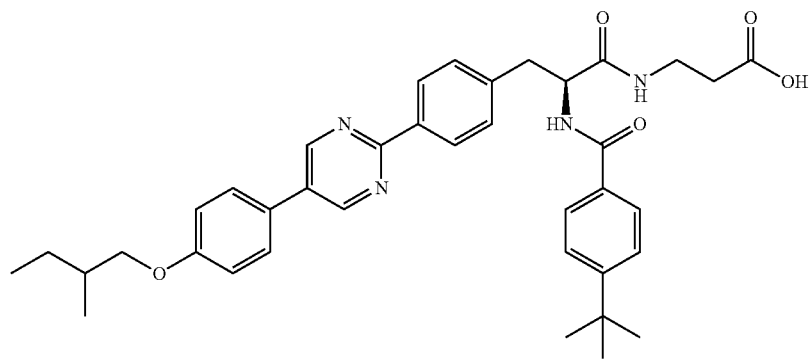

-continued
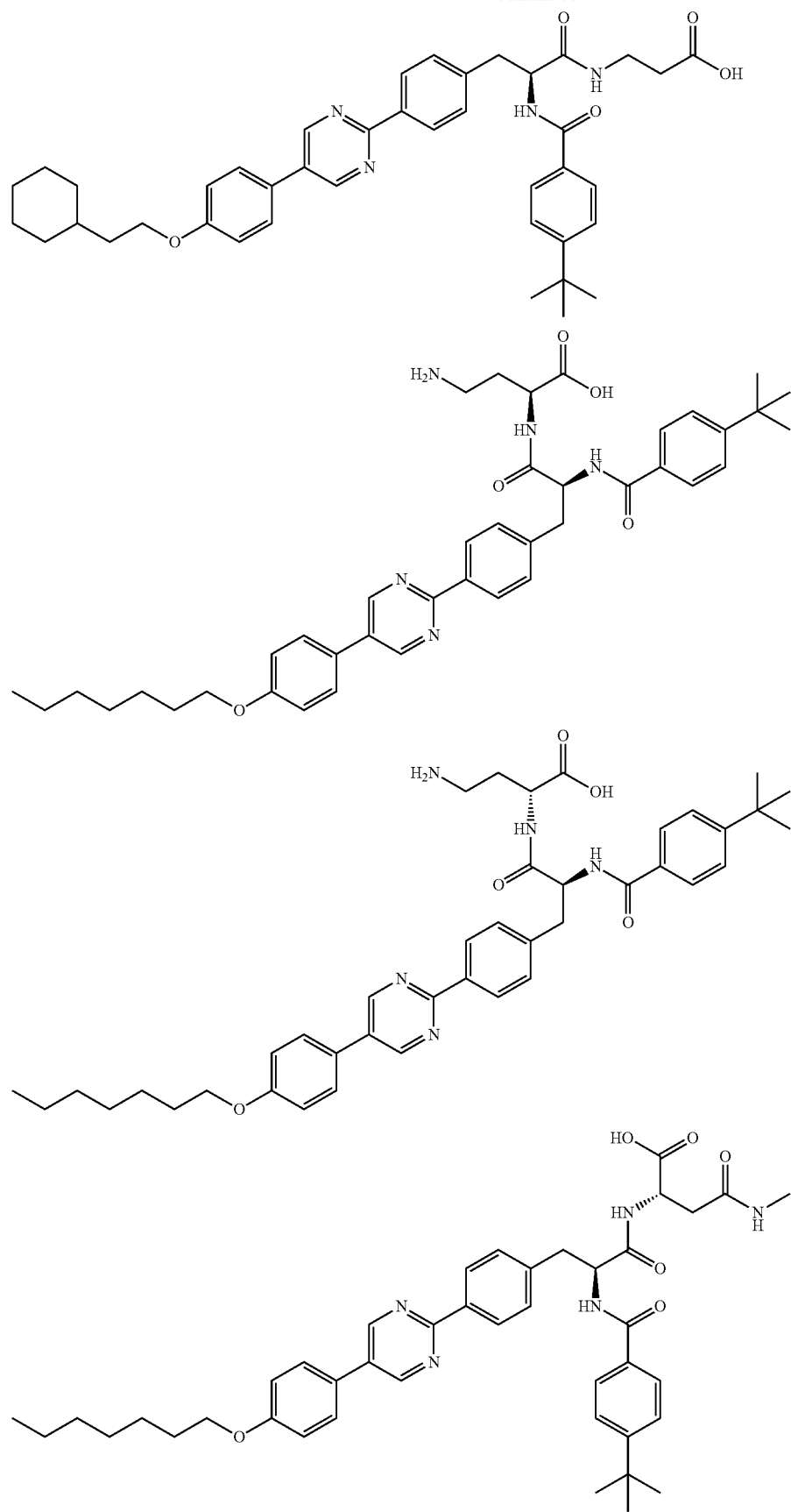

1219 1220
-continued
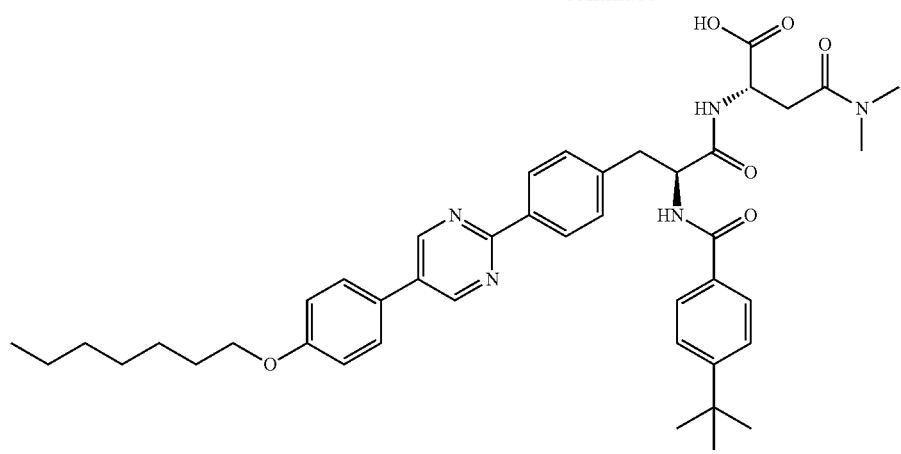
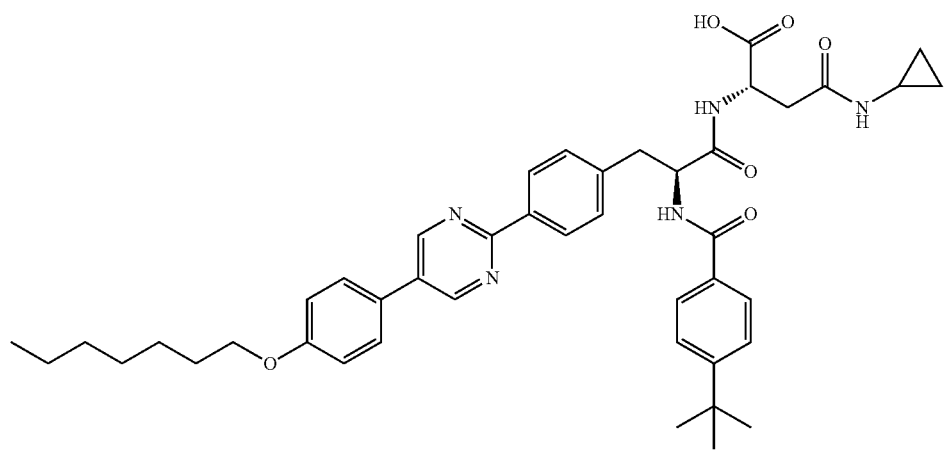
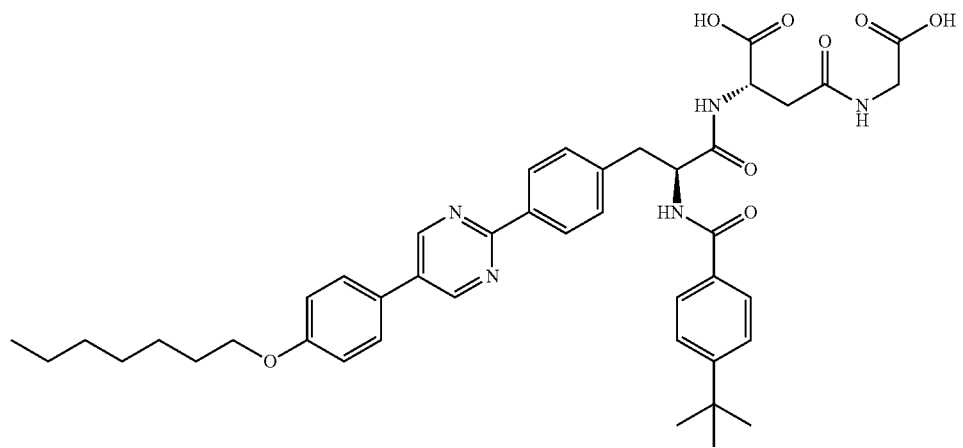

-continued
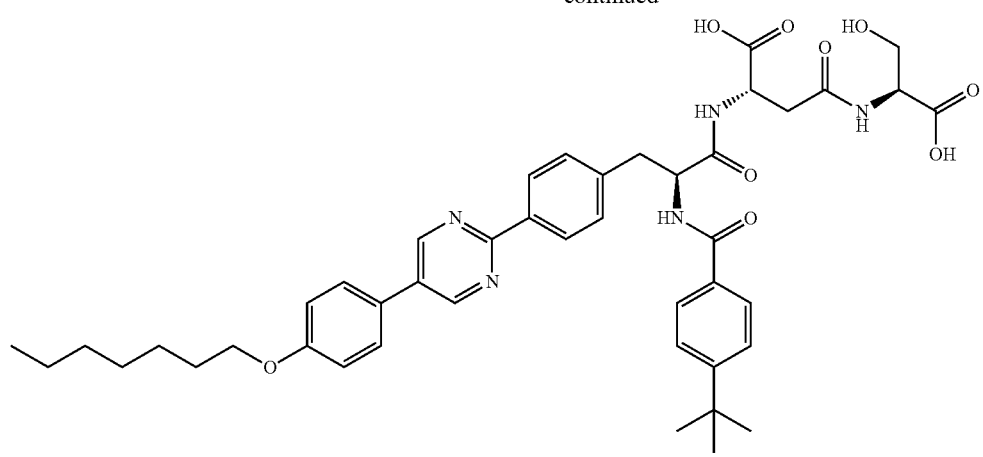
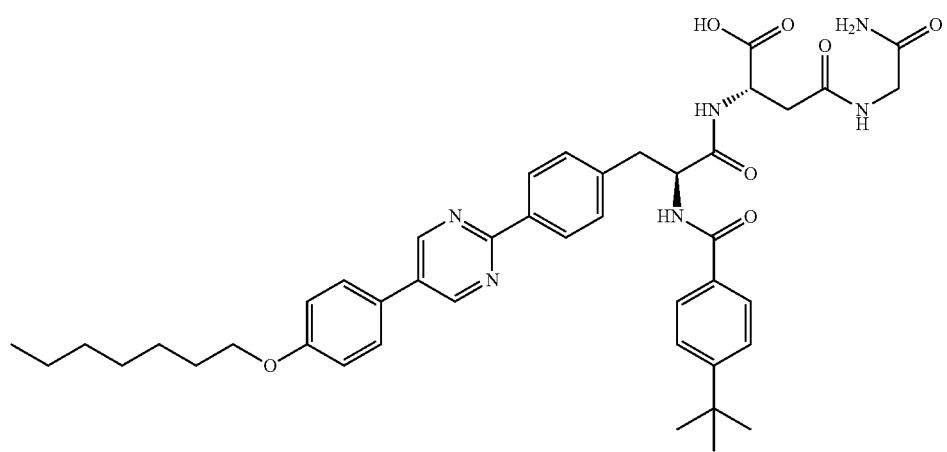
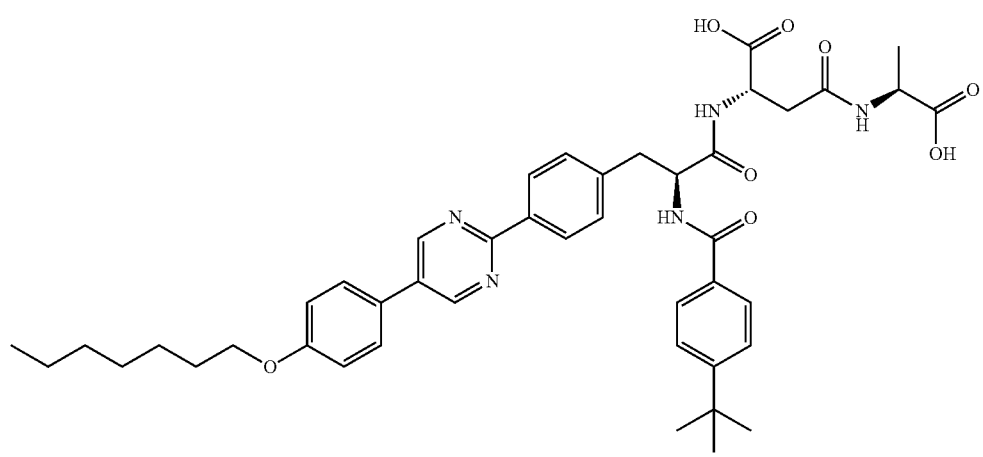

1223
1224
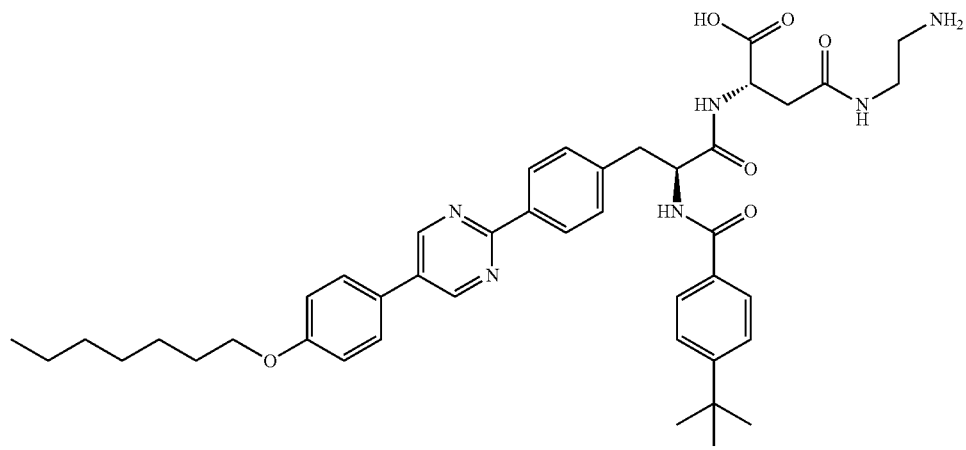
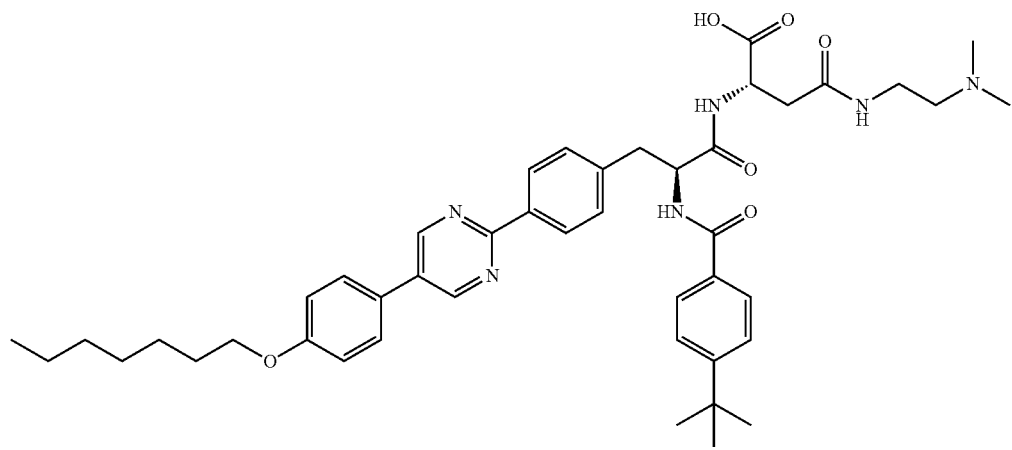
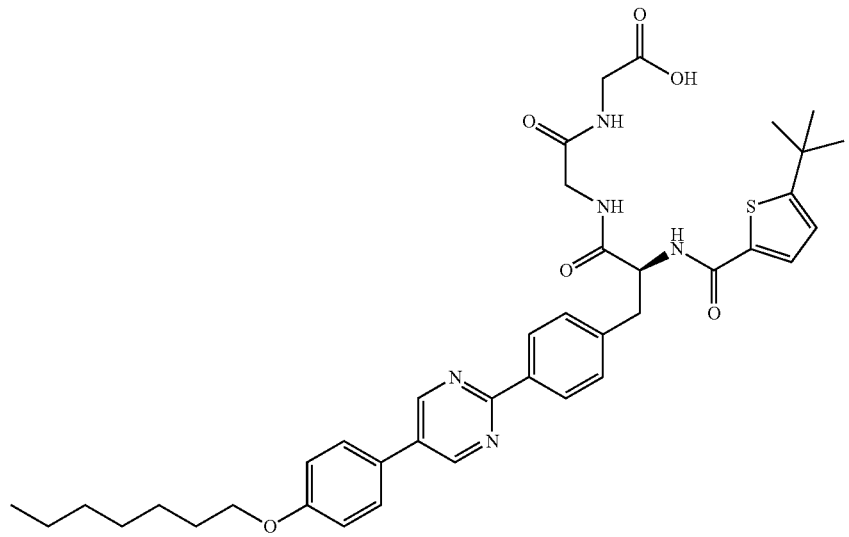

1225
-continued
1226
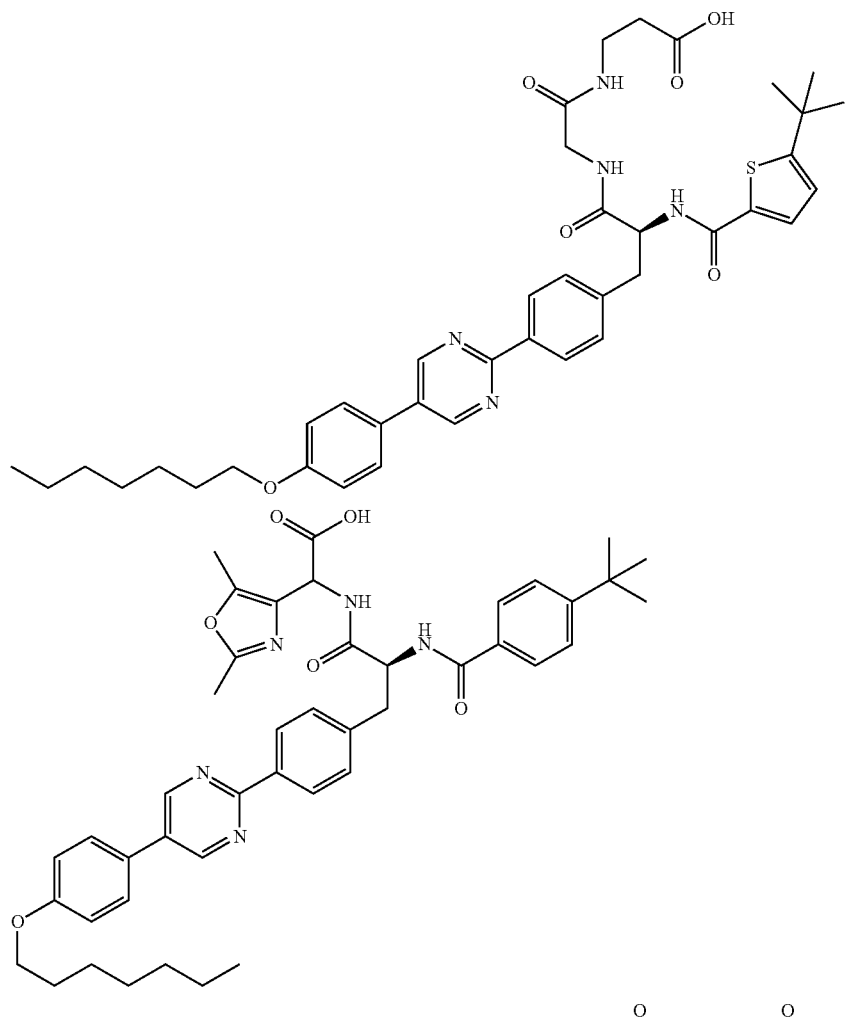
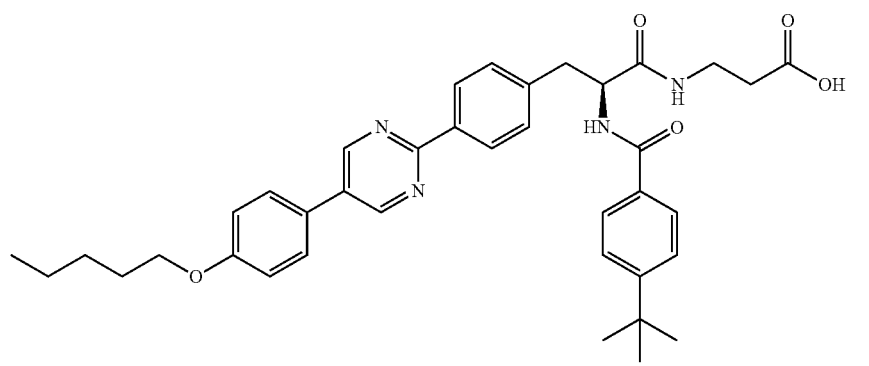
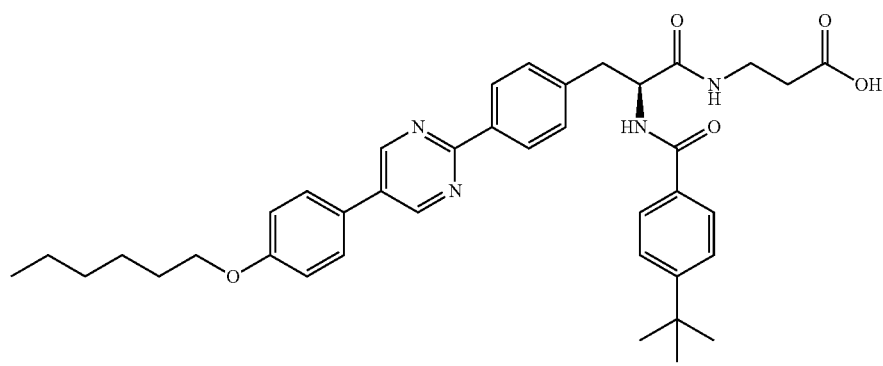

1227 1228
-continued
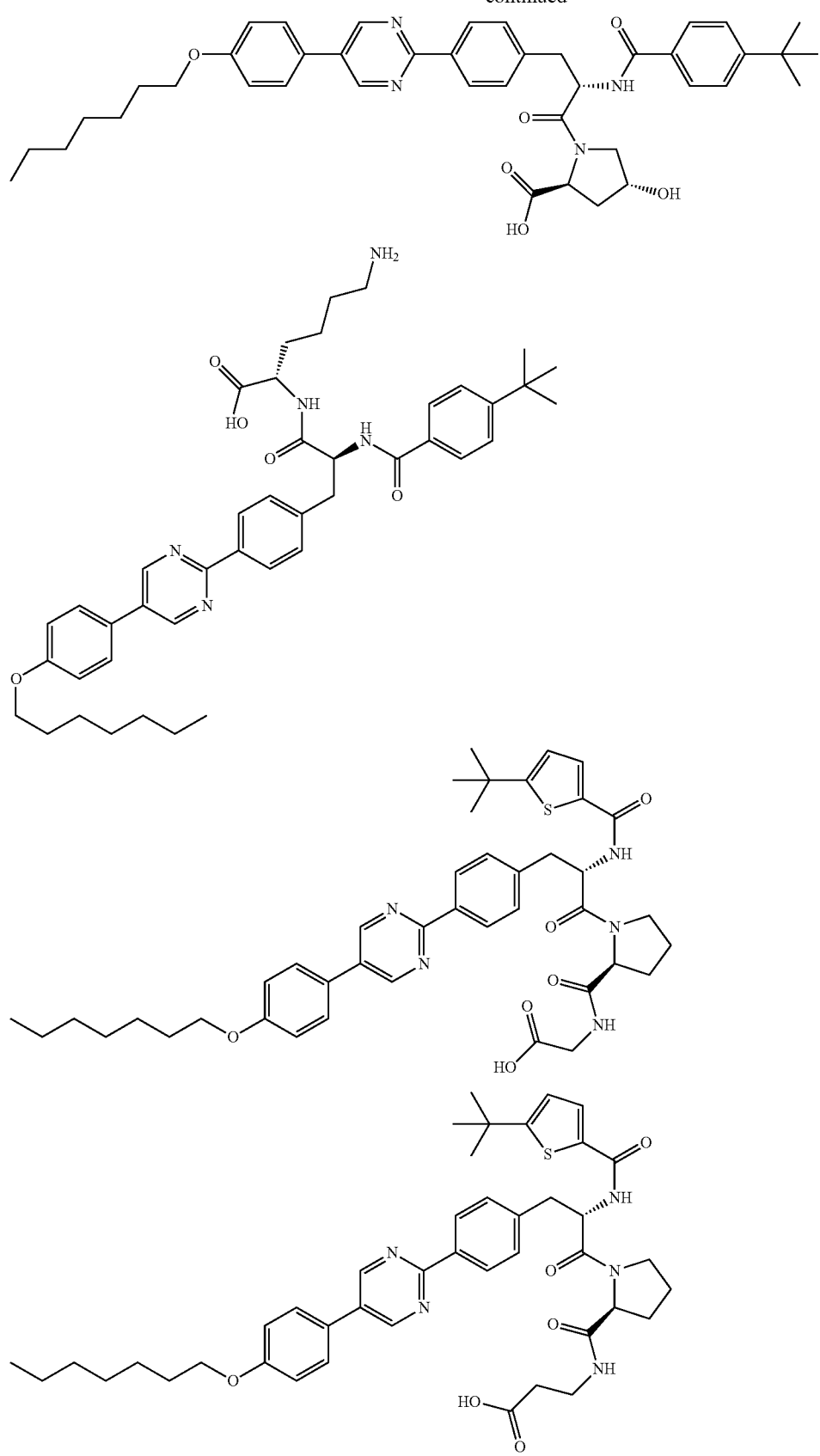

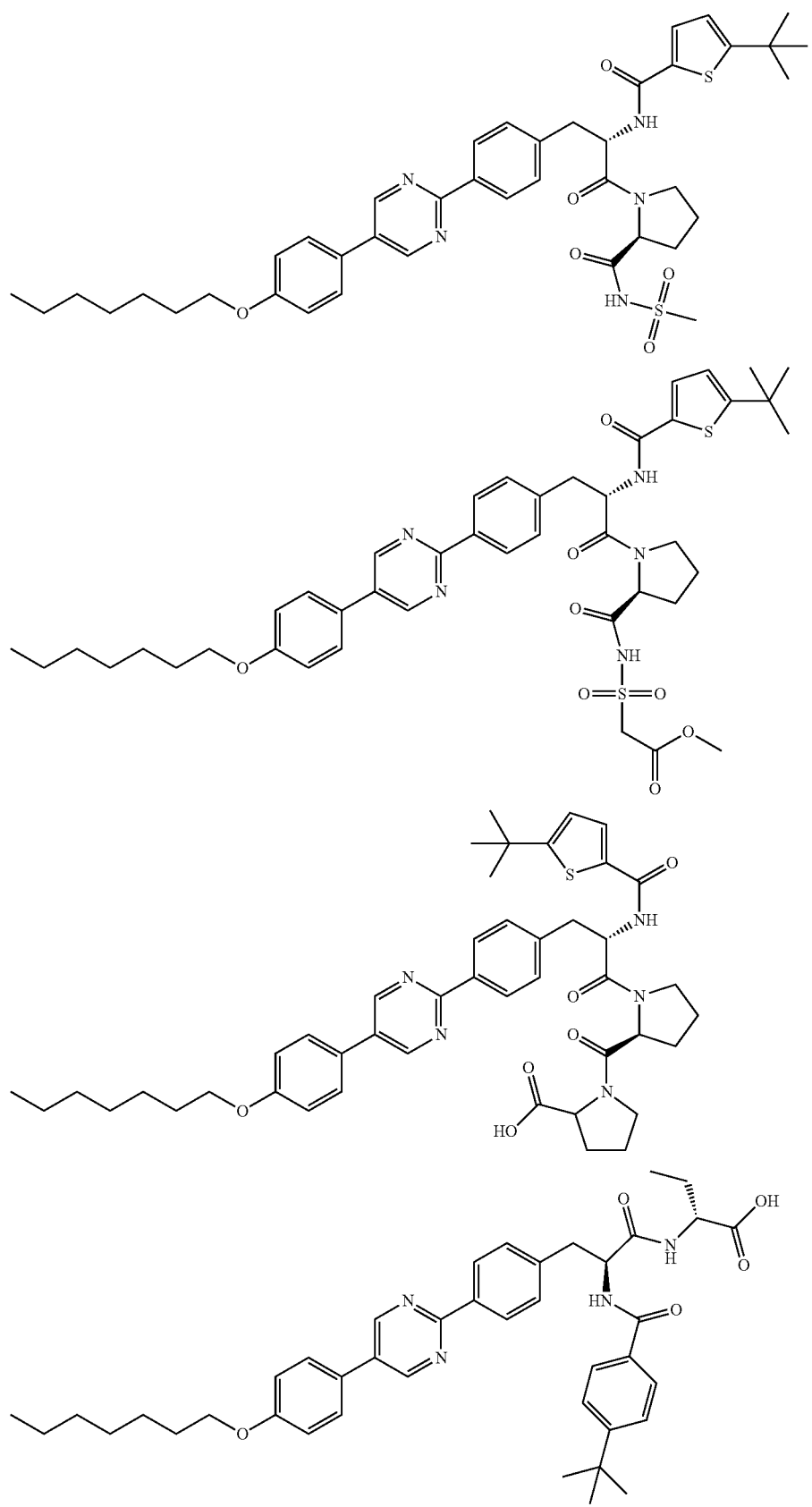

| 1231 | | 1232 |
|---|---|---|
-continued
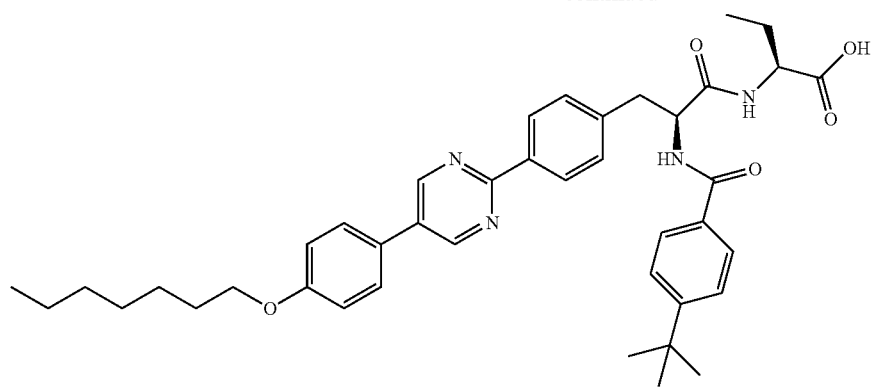
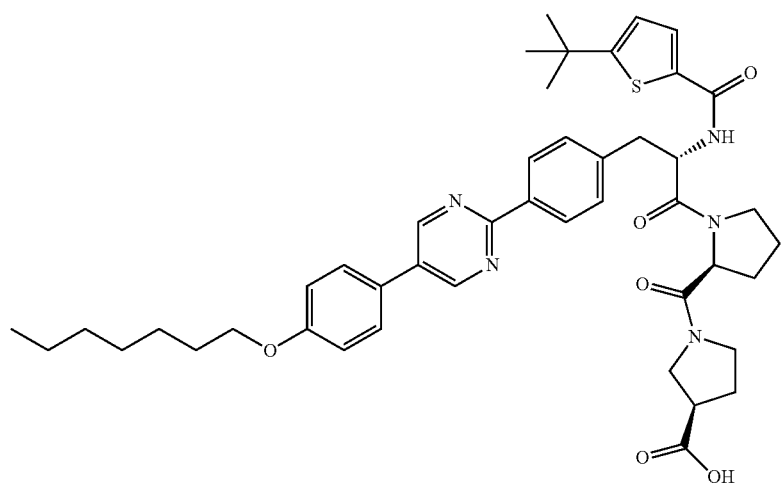
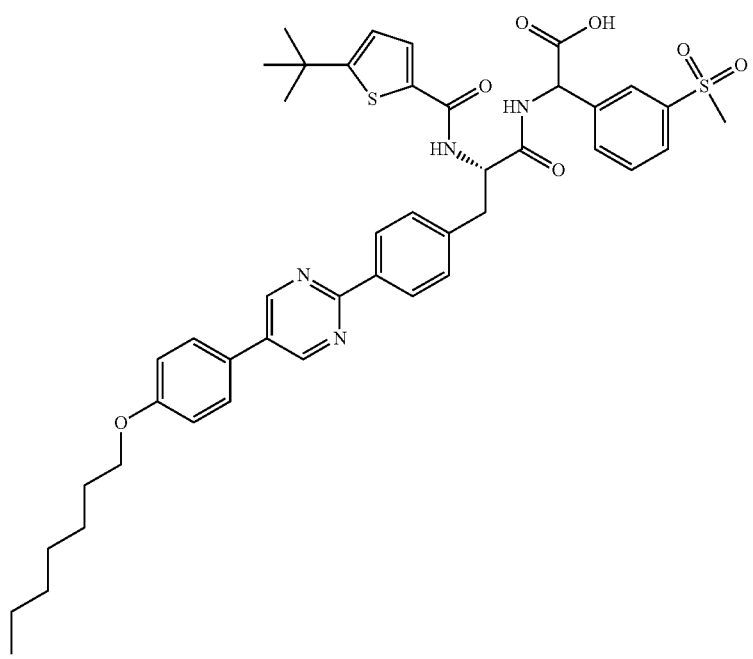

1233
-continued
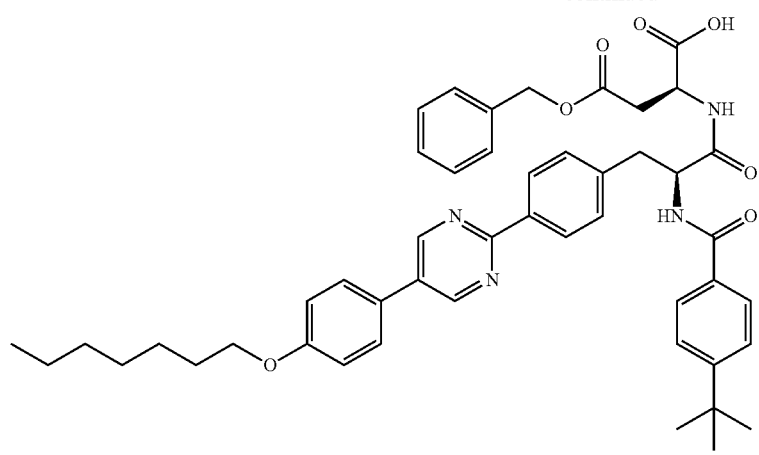
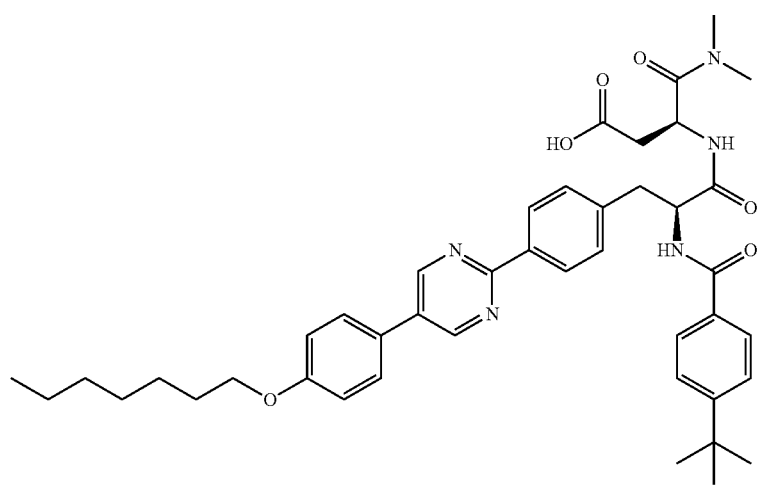
1234
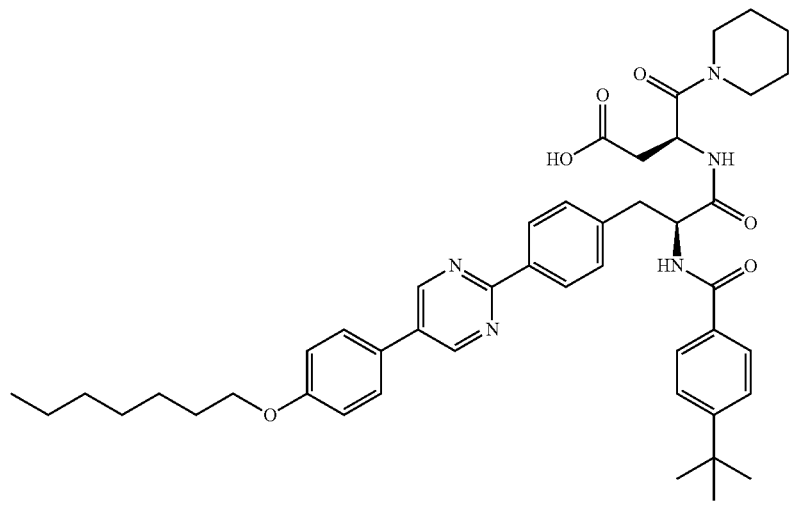

1235
-continued
1236
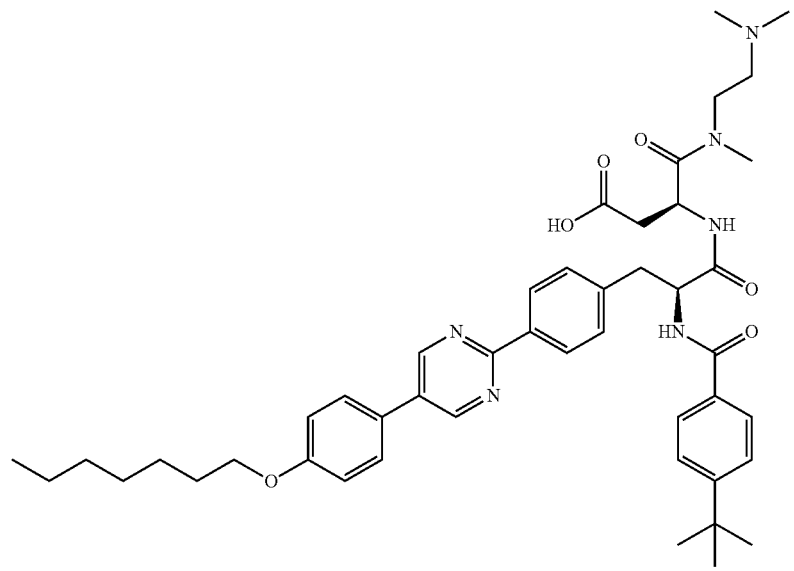
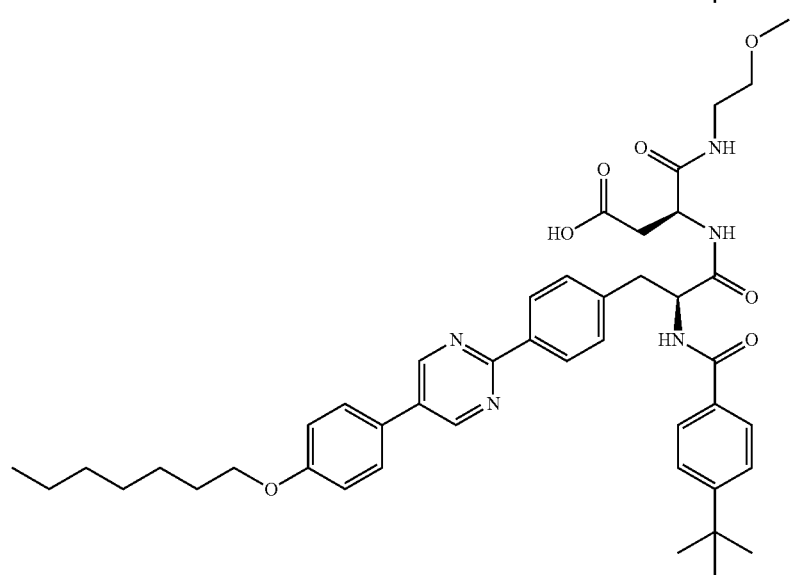
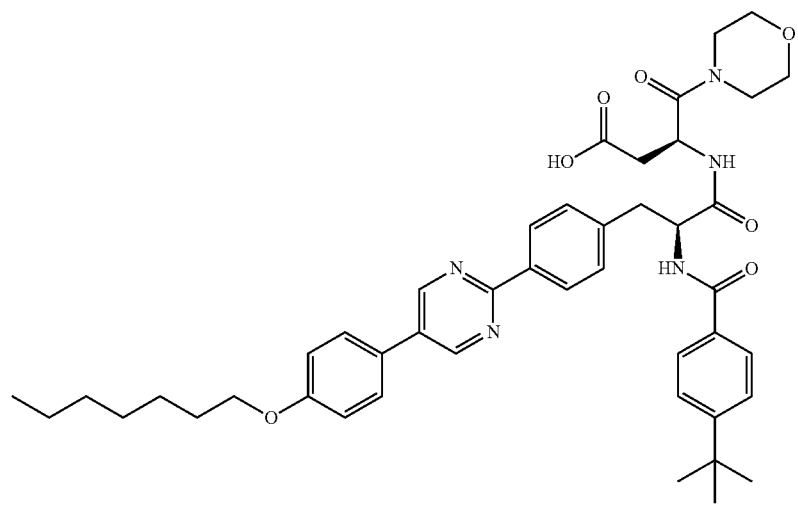

1237 1238
-continued
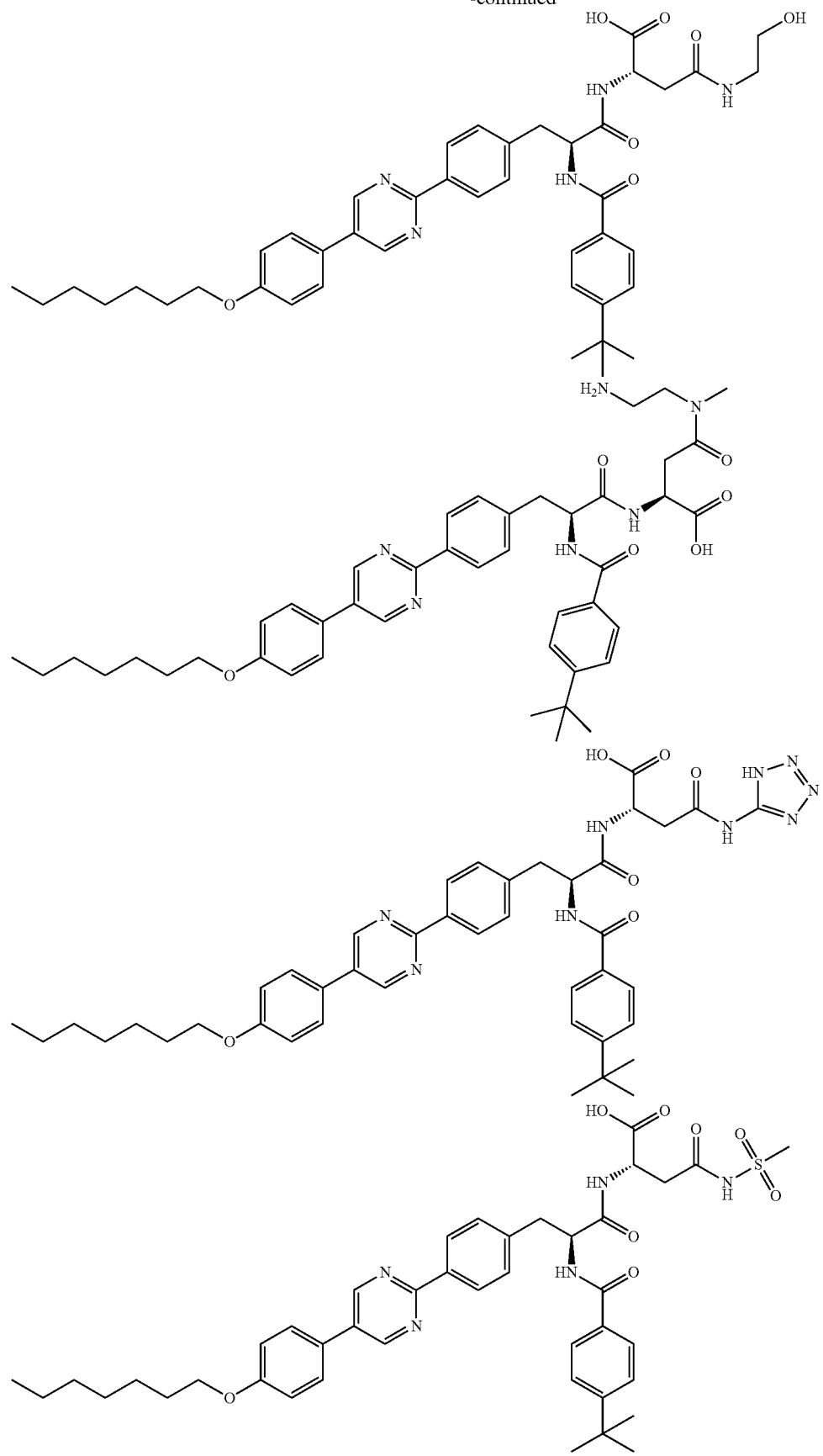

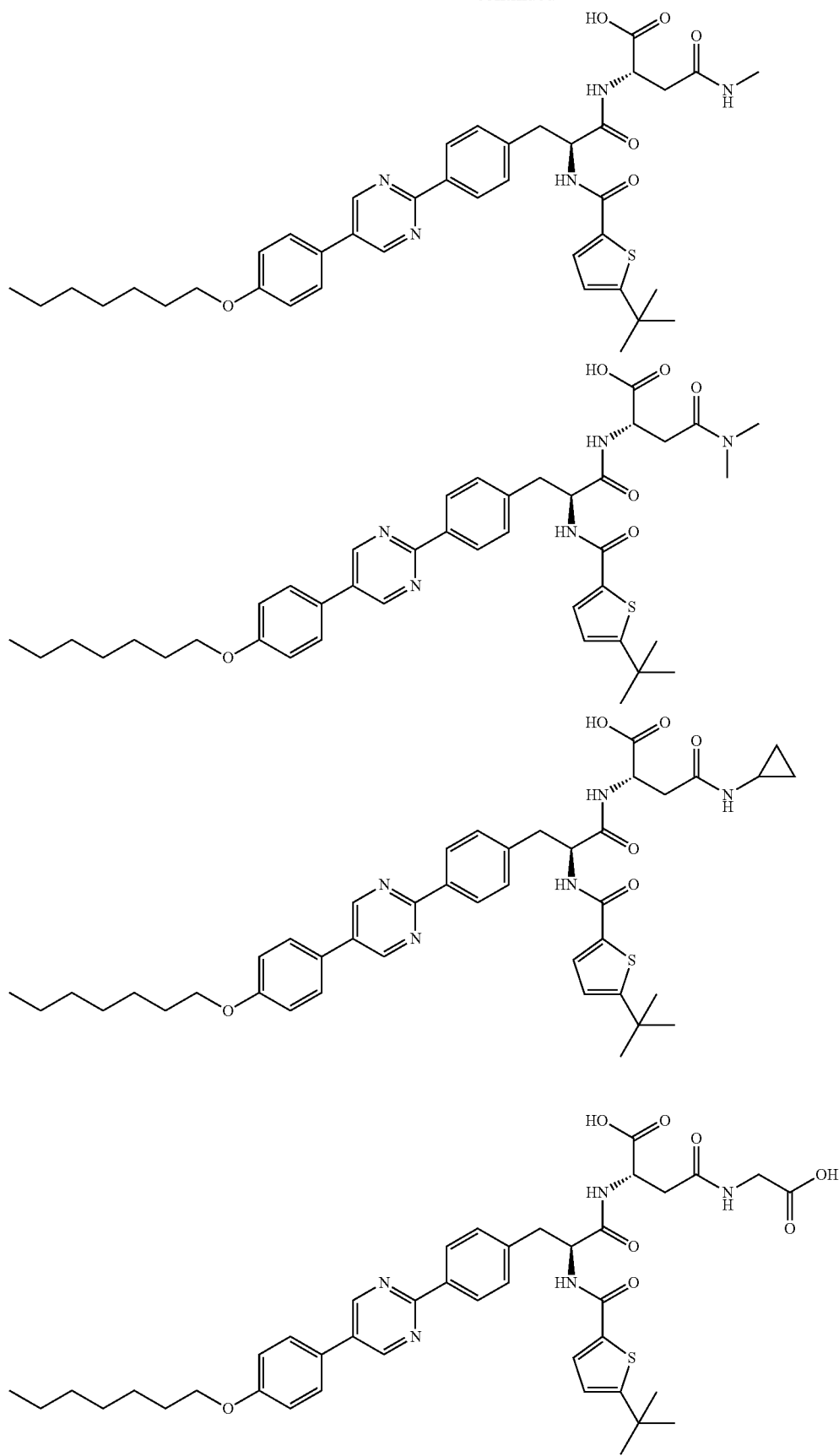

-continued
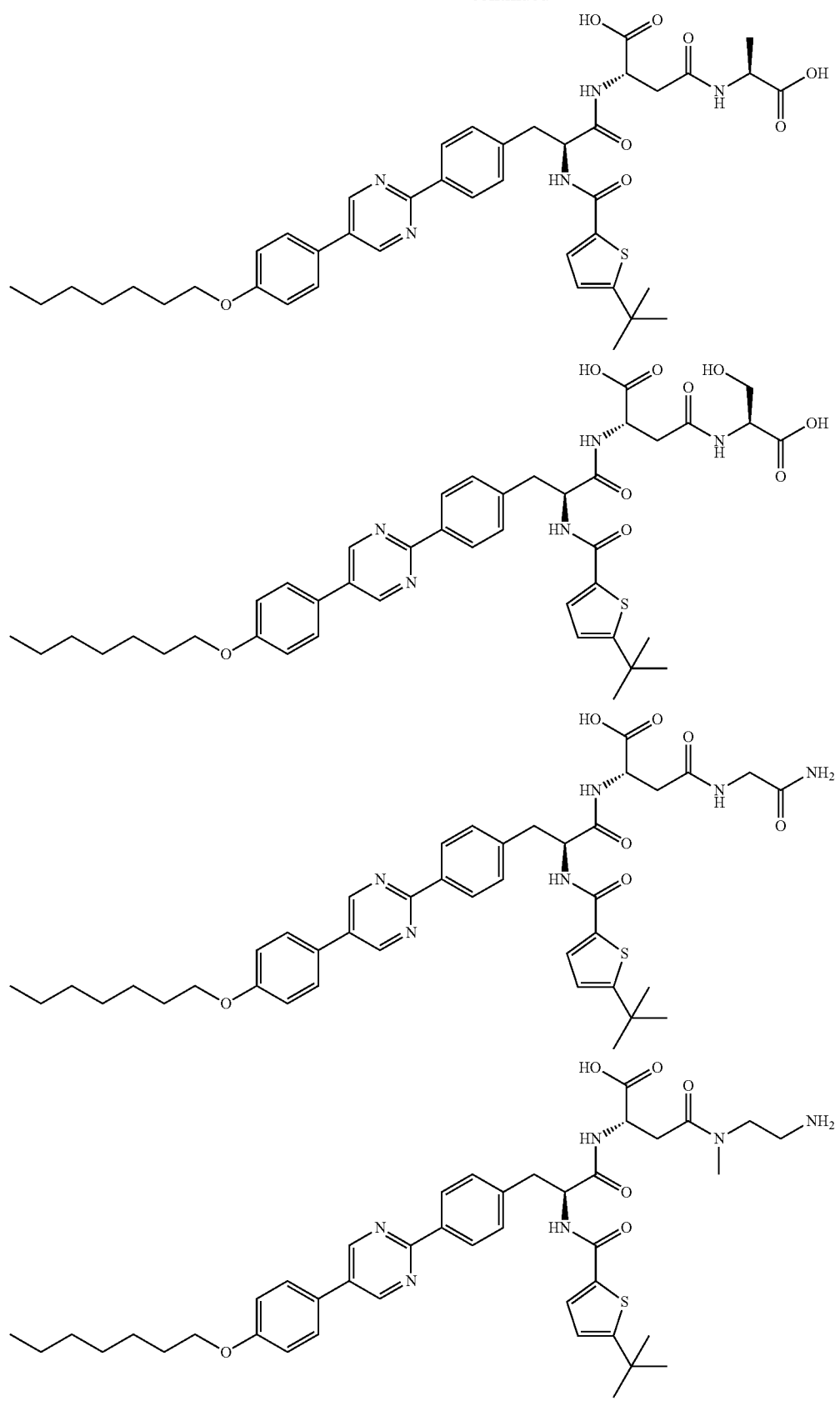

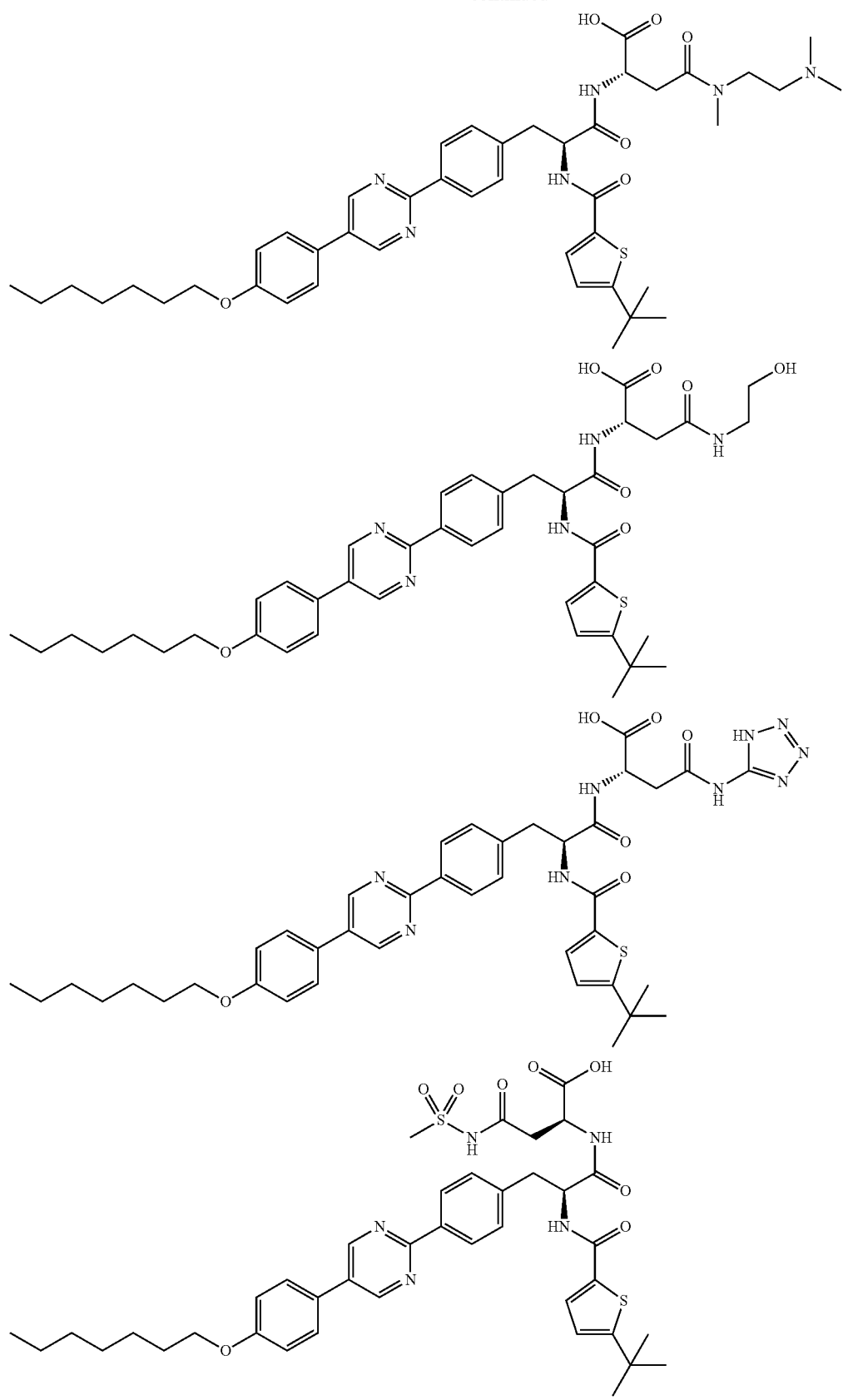

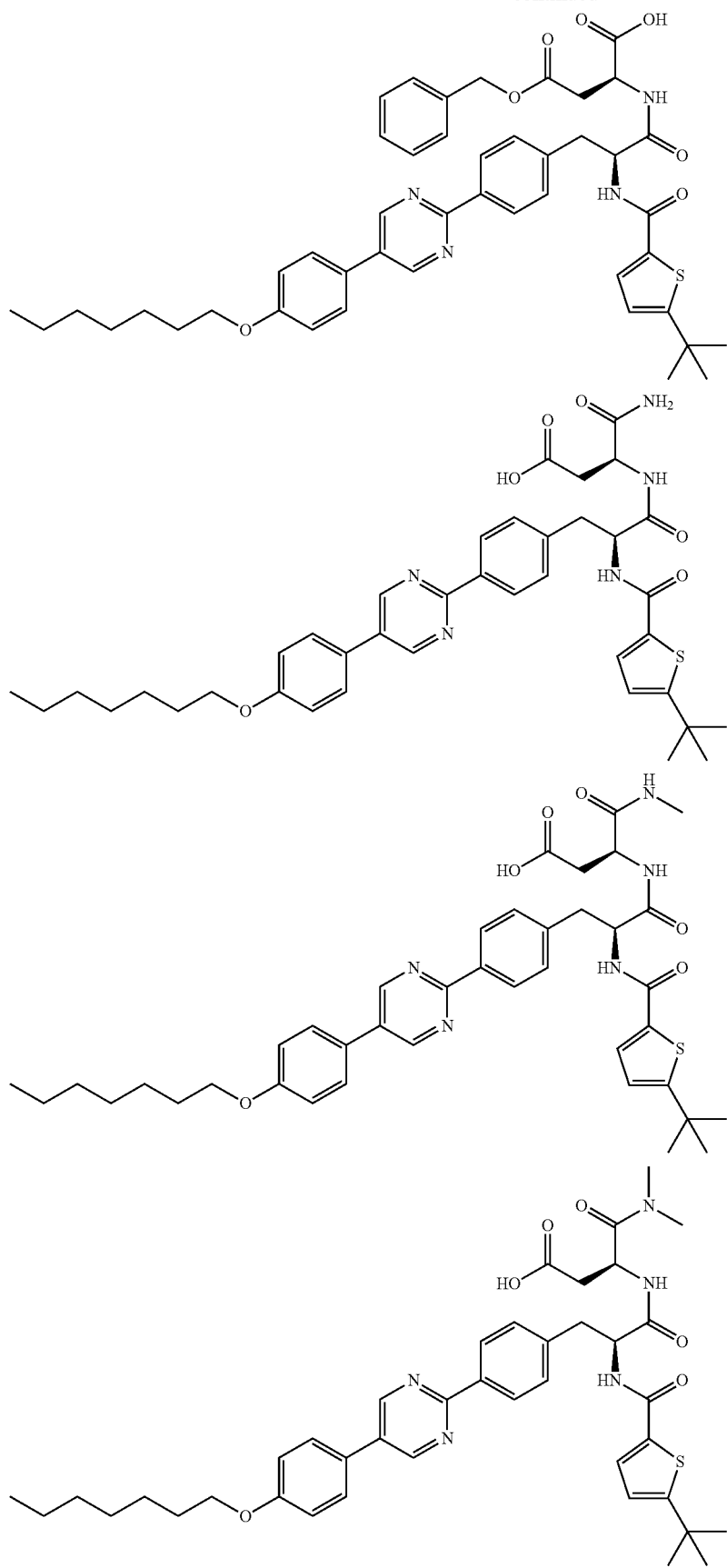

1247
-continued
1248
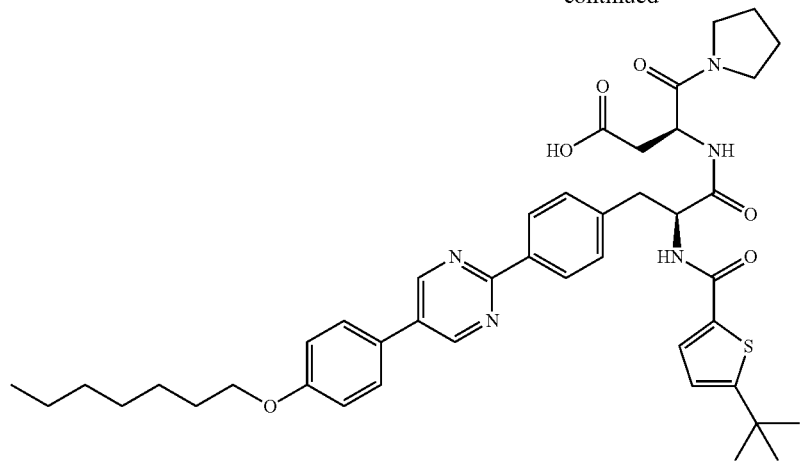
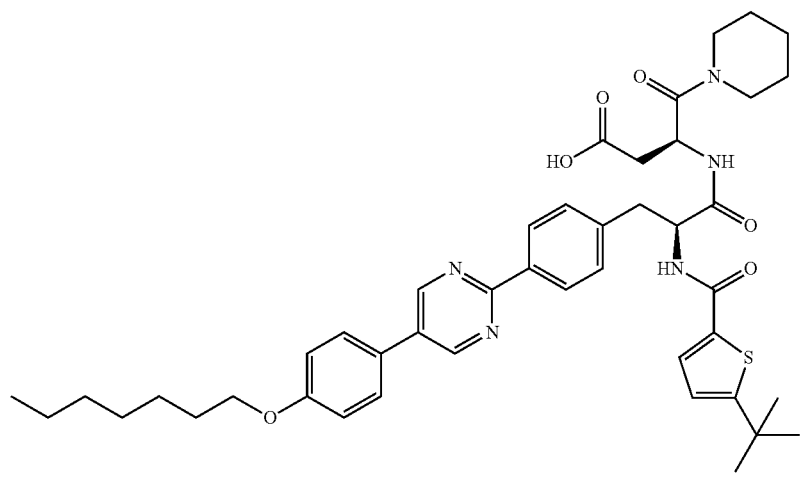
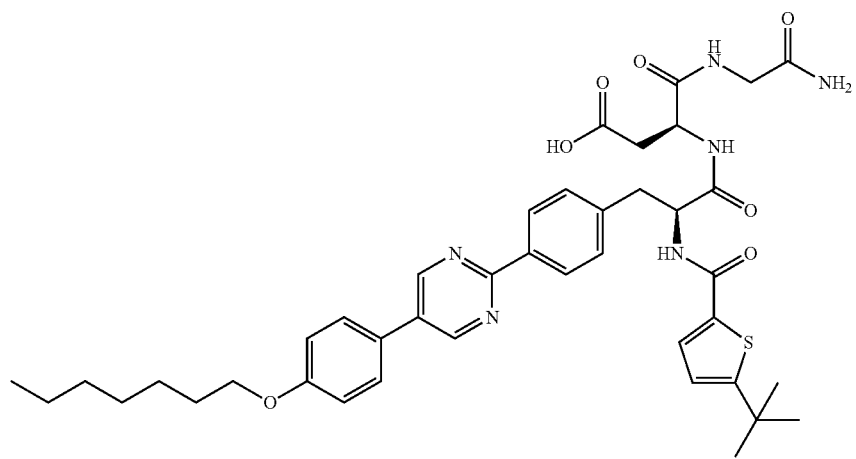

-continued
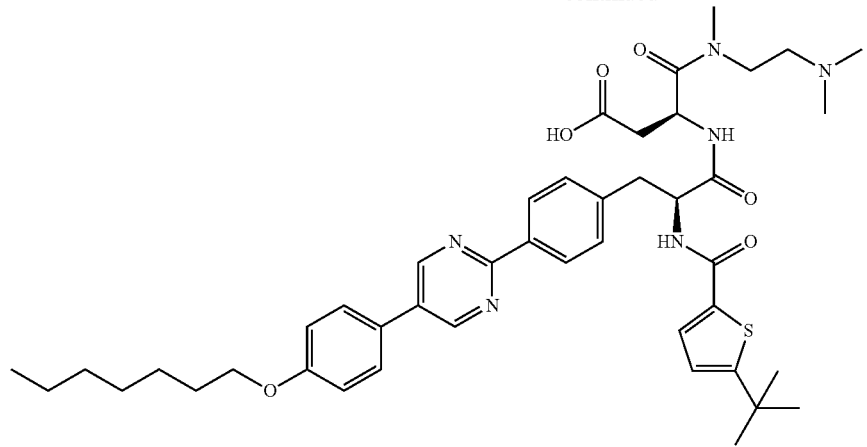
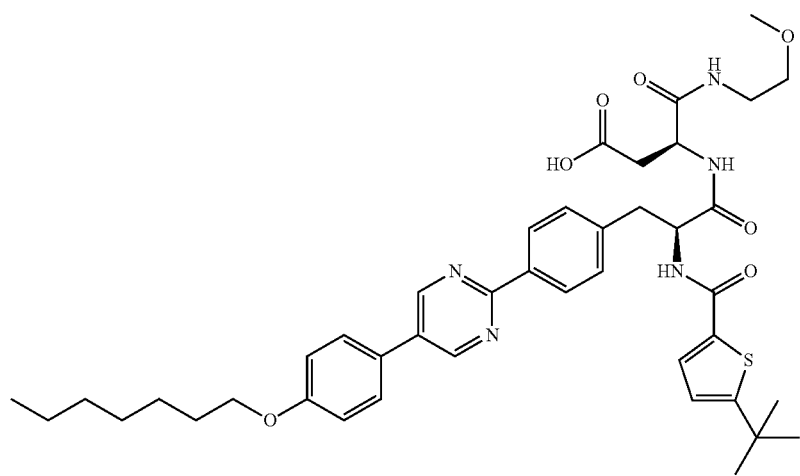
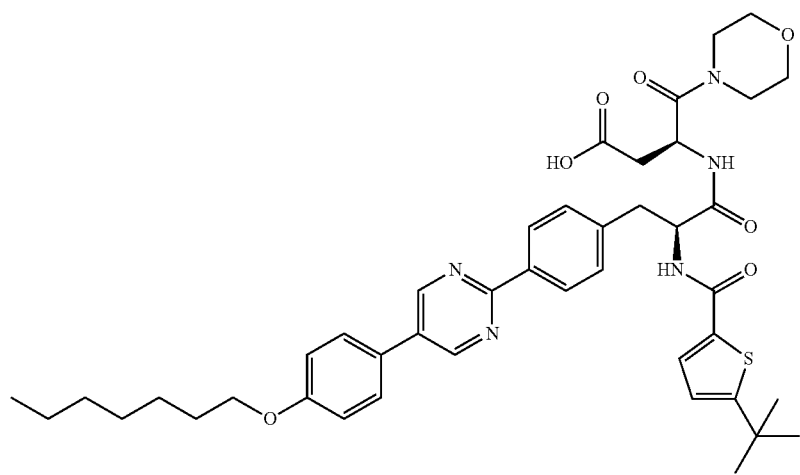

-continued
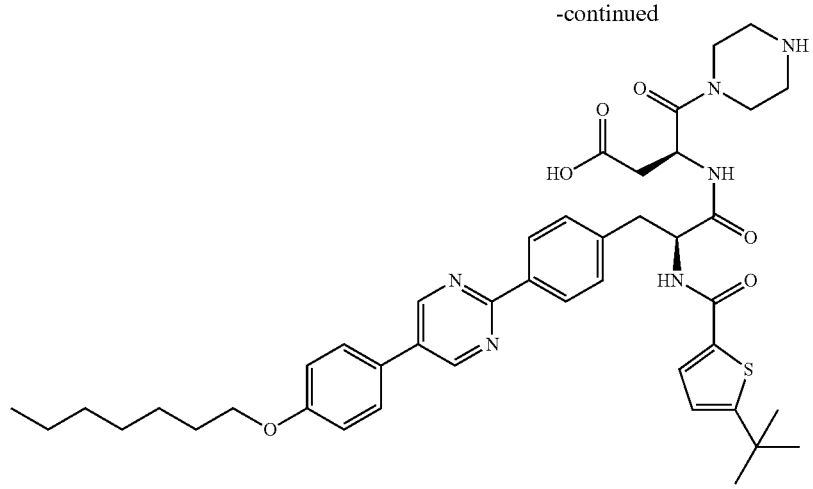
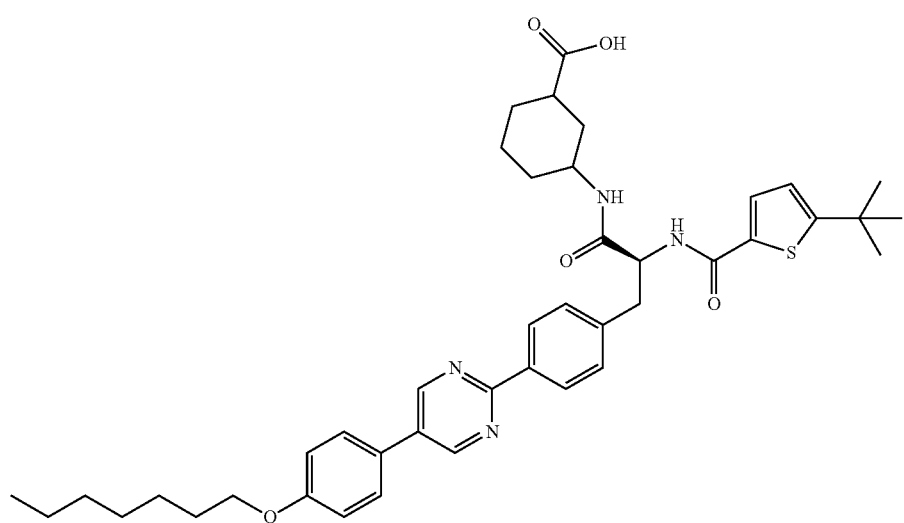
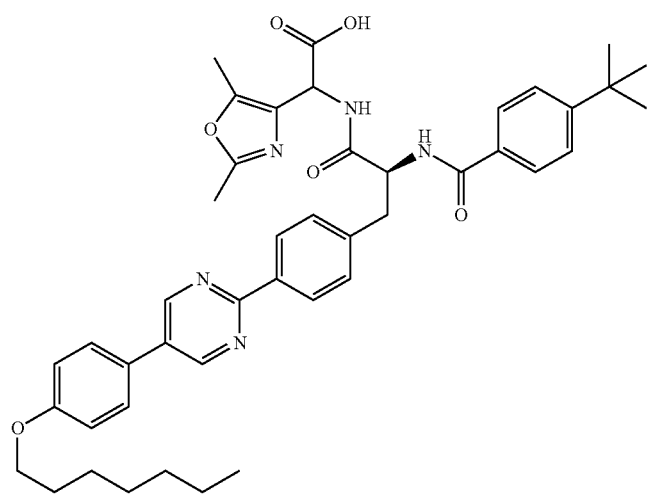

-continued
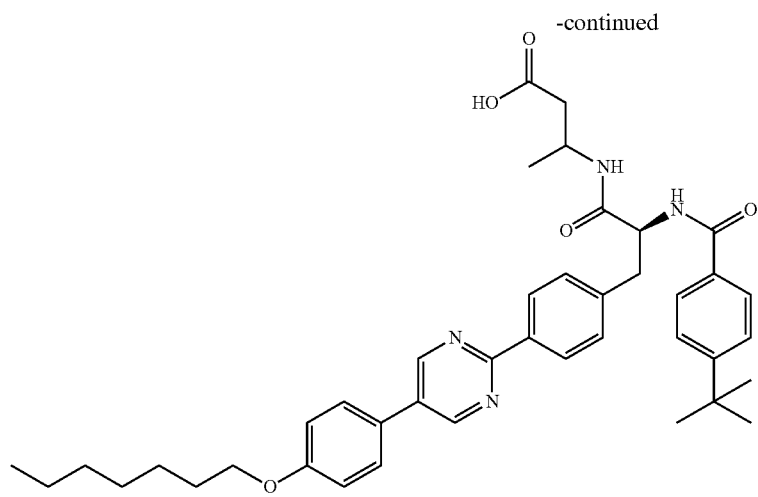
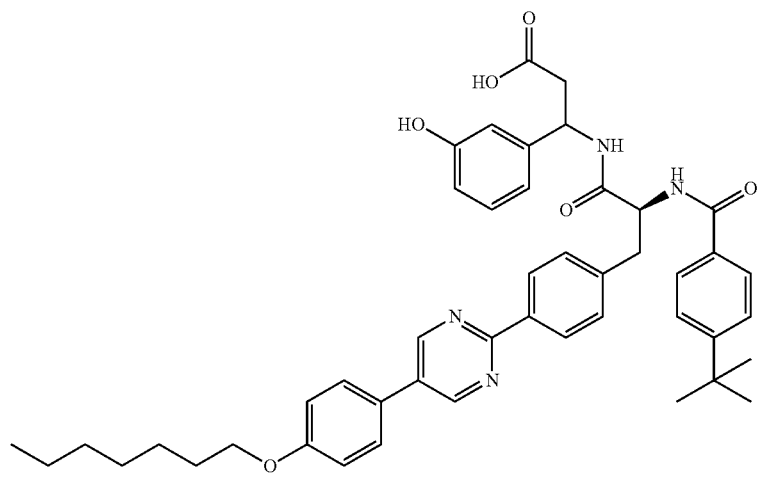
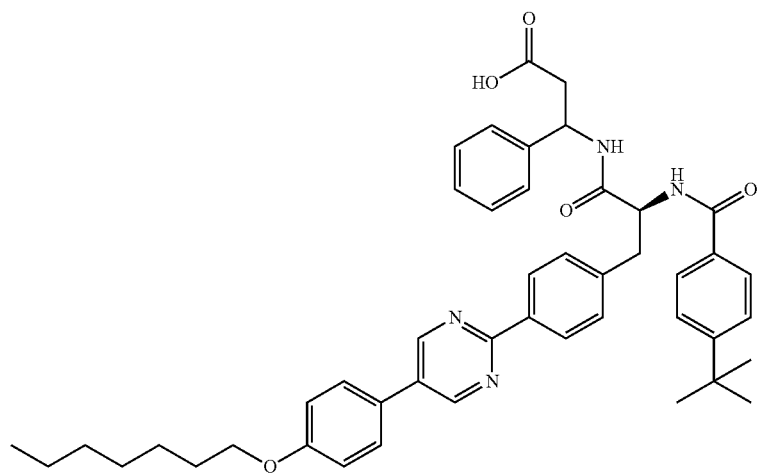

1255
1256
-continued
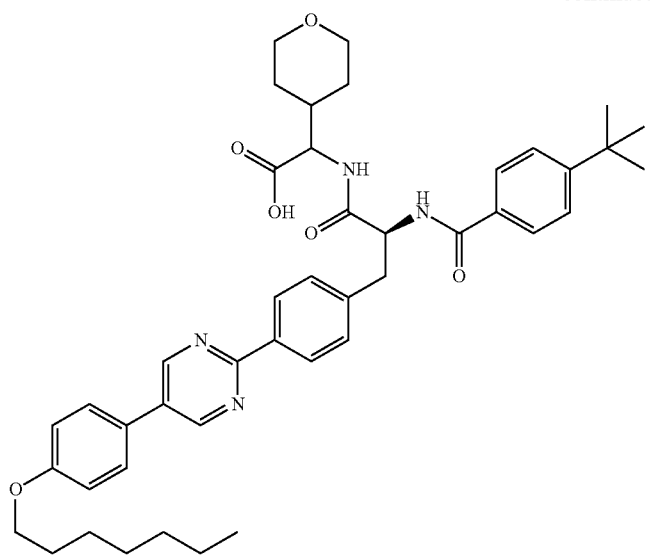
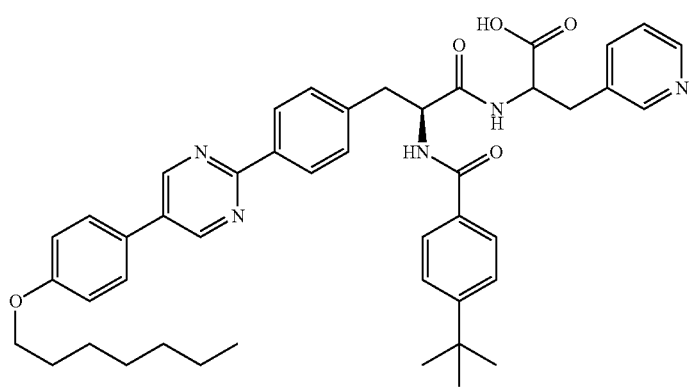
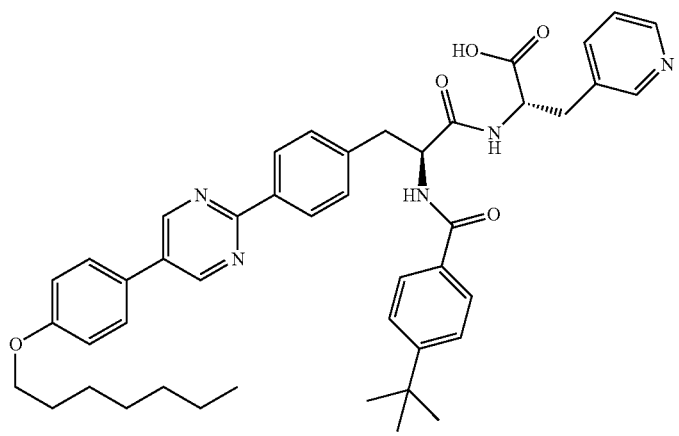

-continued
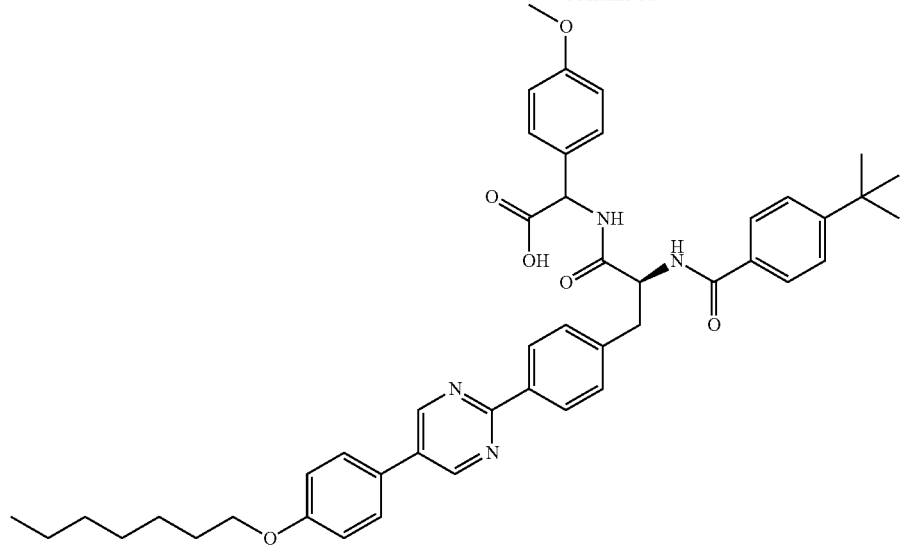
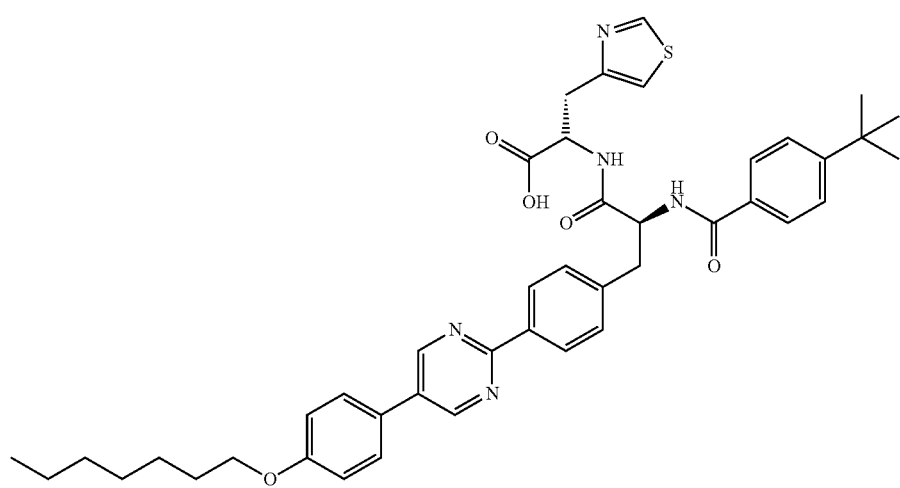
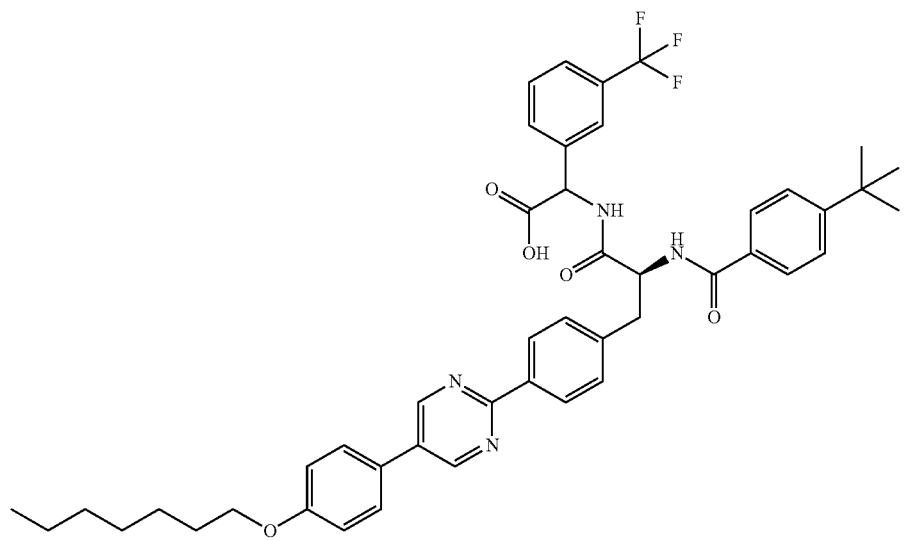

-continued
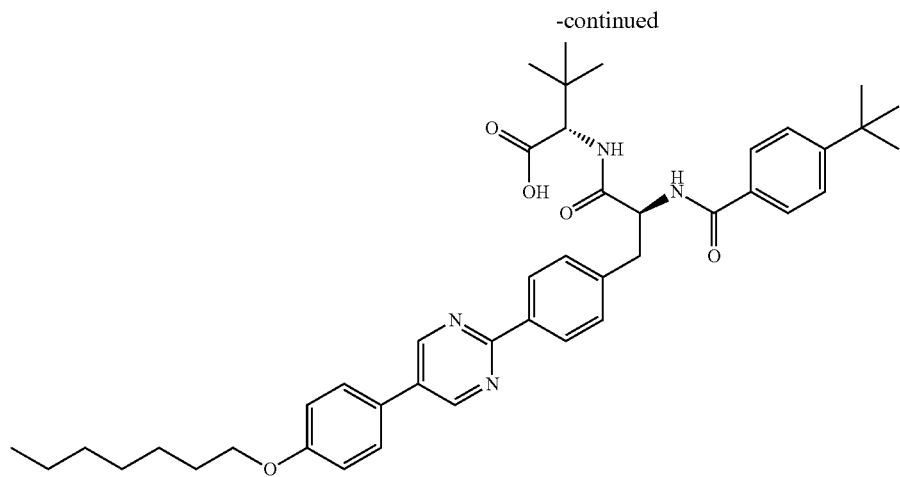
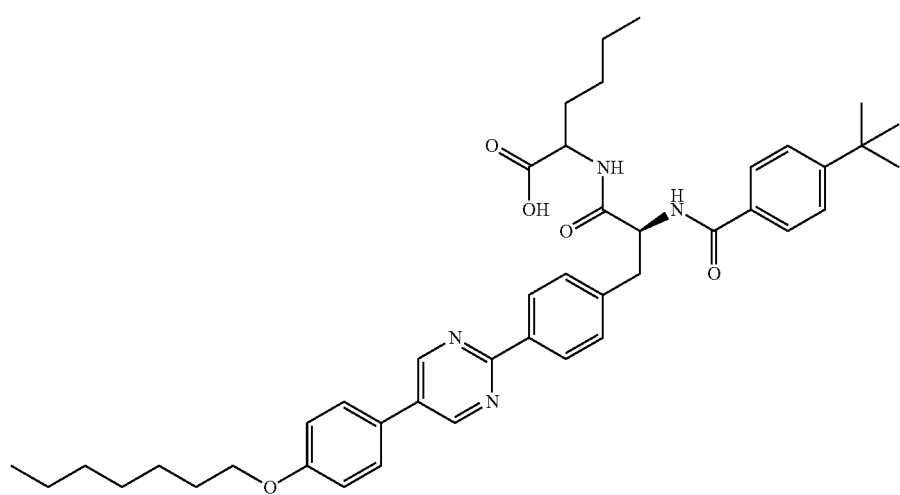
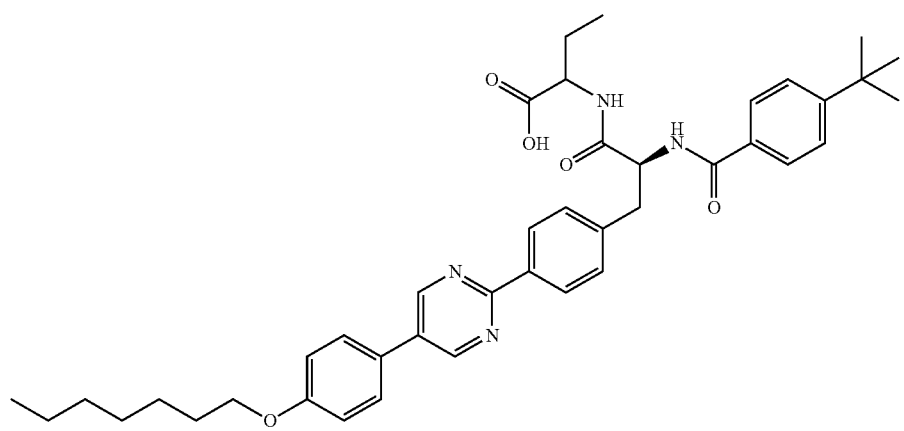

1261
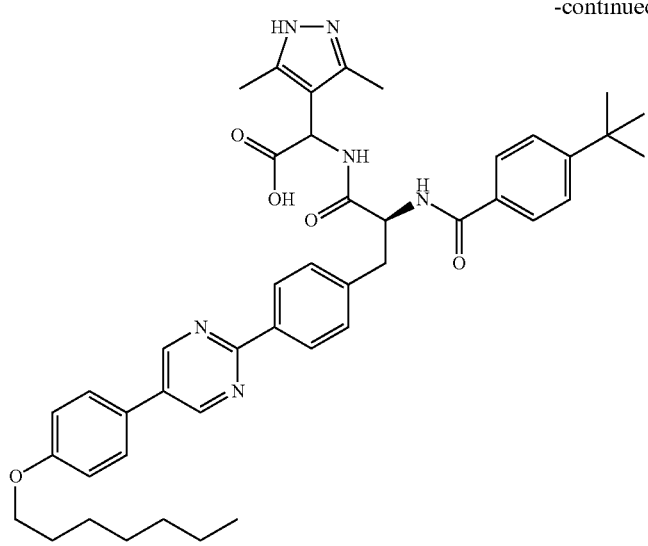
1262
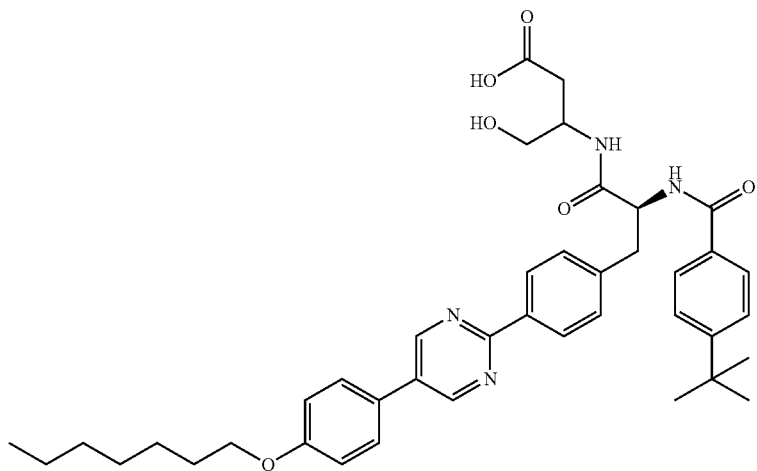
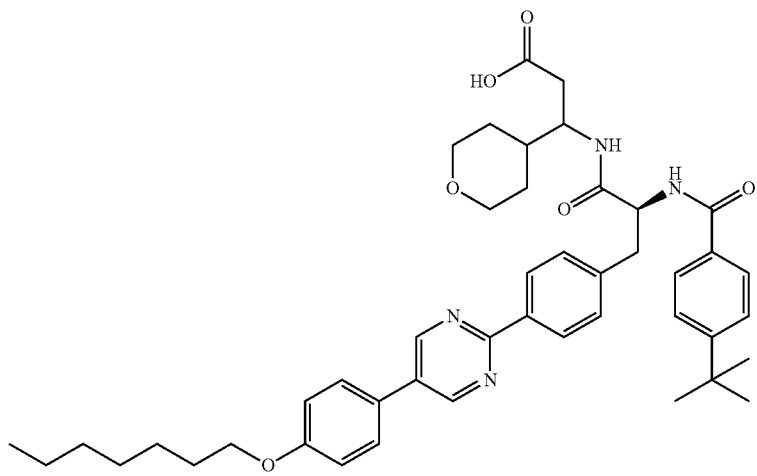

1263
1264
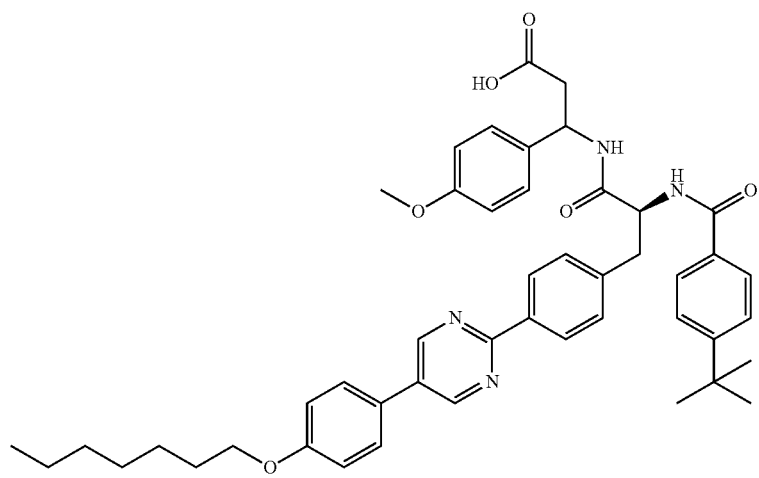
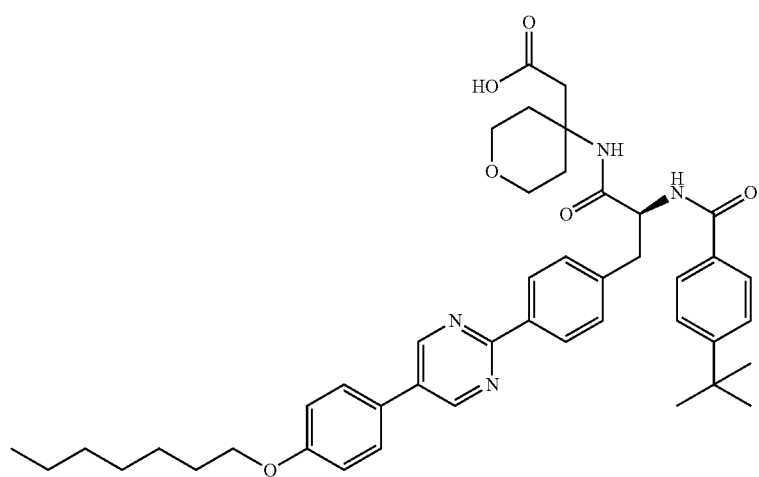
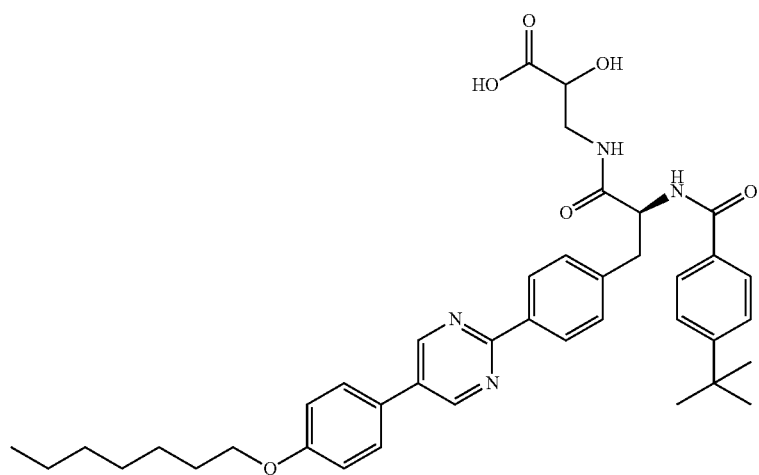

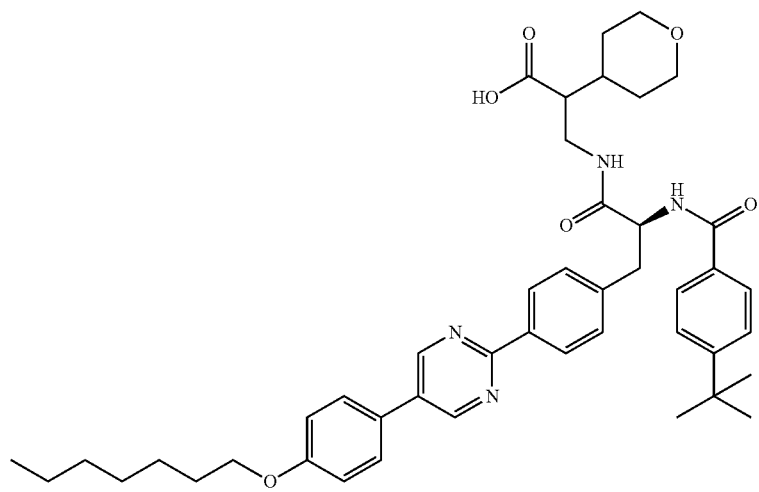
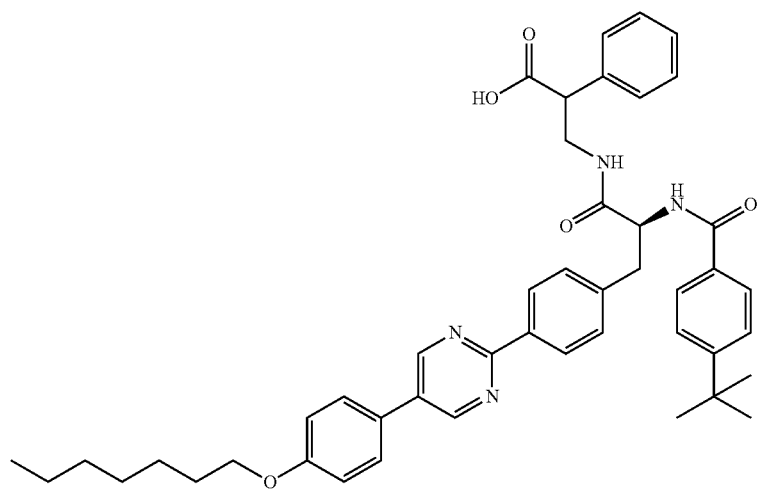
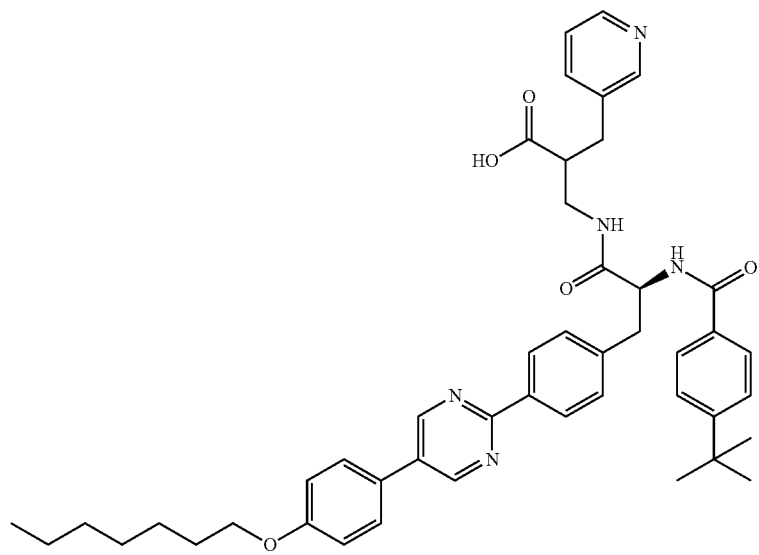

-continued
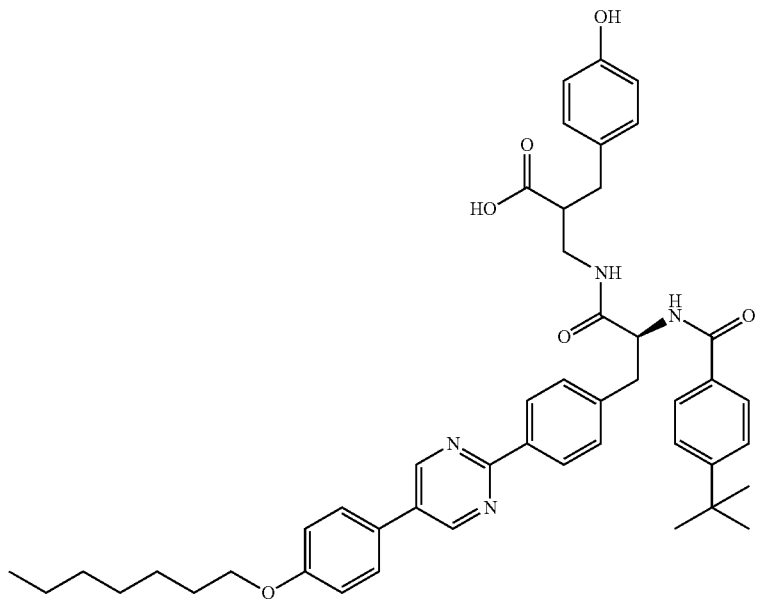
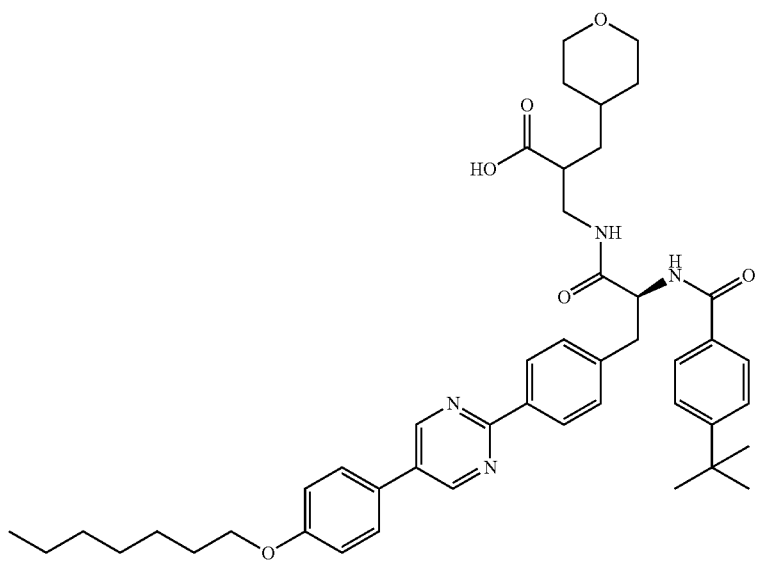
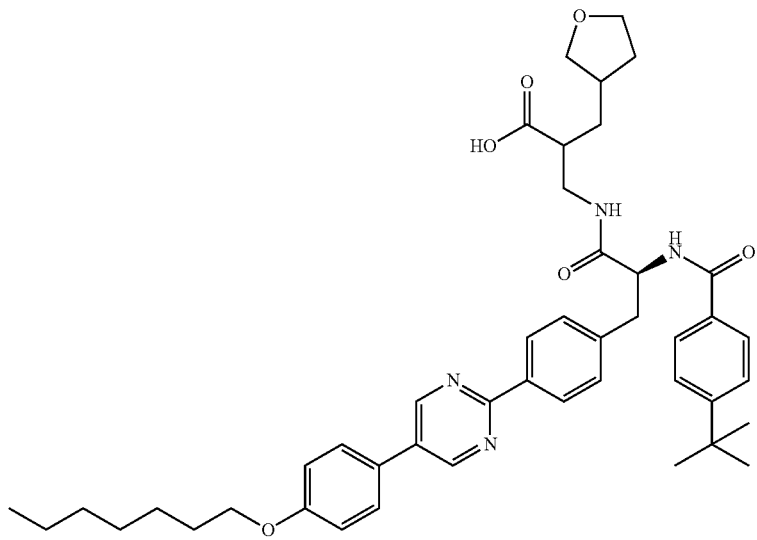

-continued
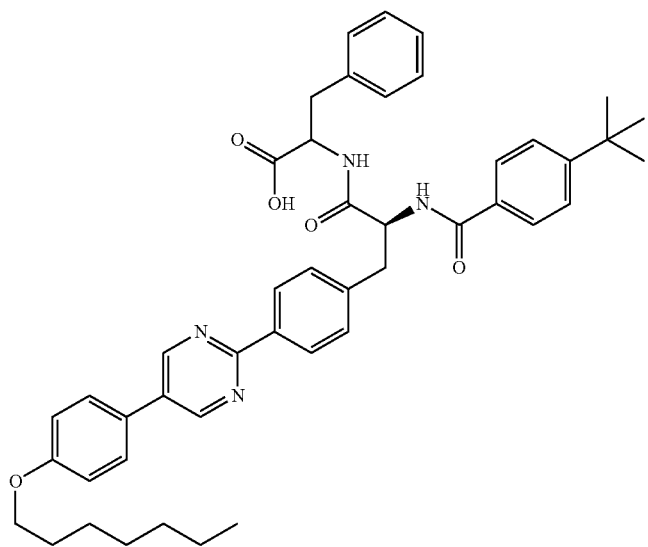
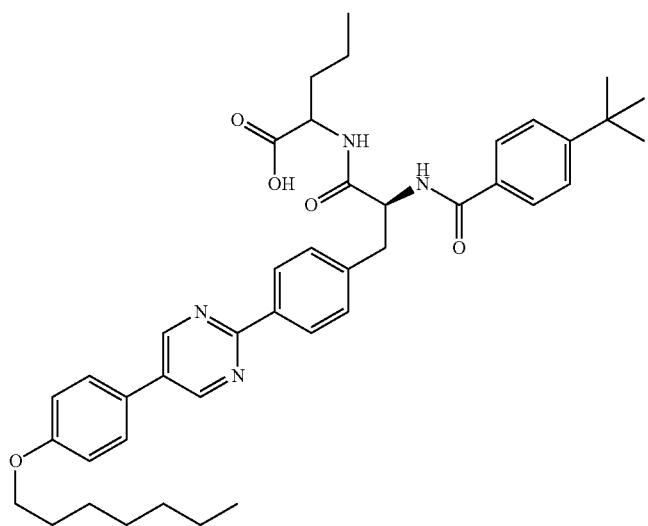
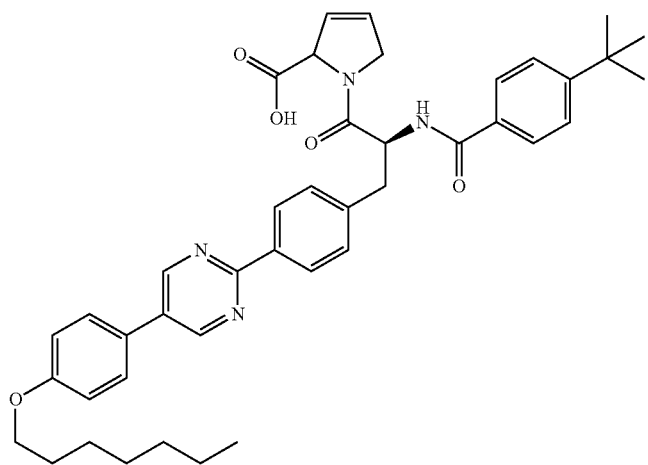

| 1271 | 1272 |
|---|---|
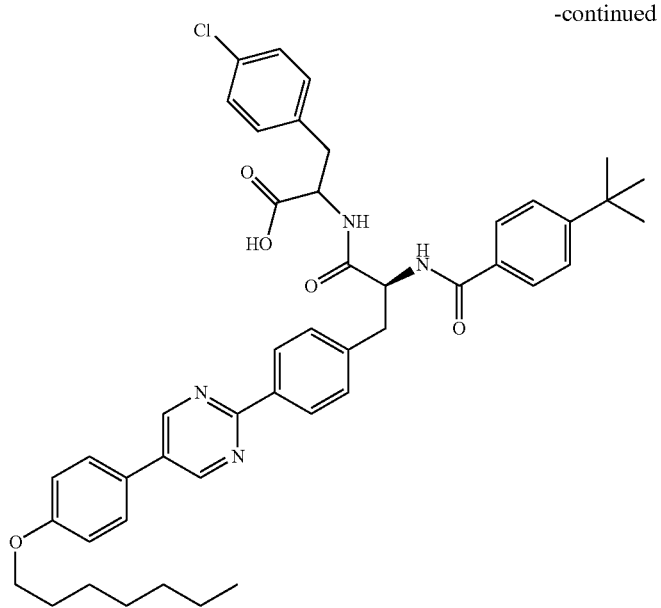
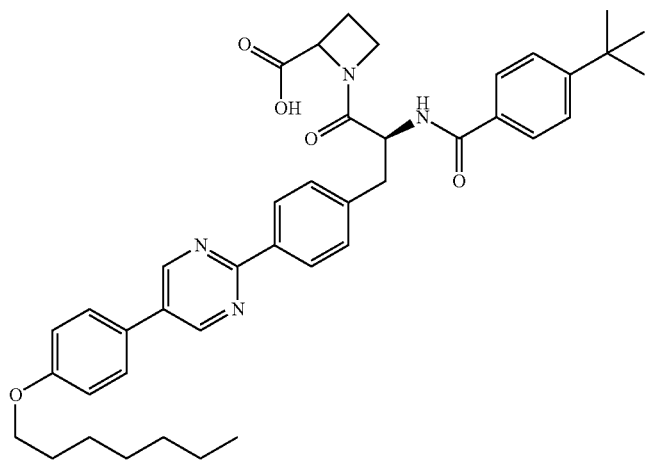
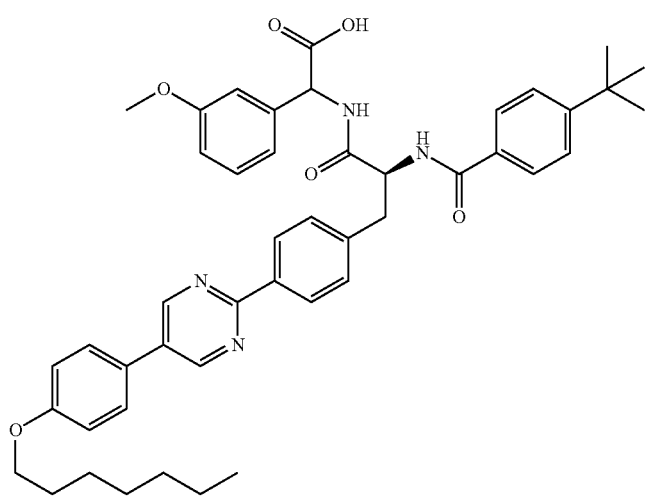

-continued
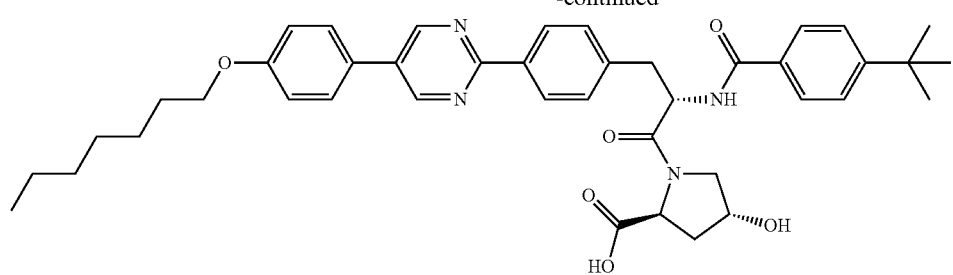
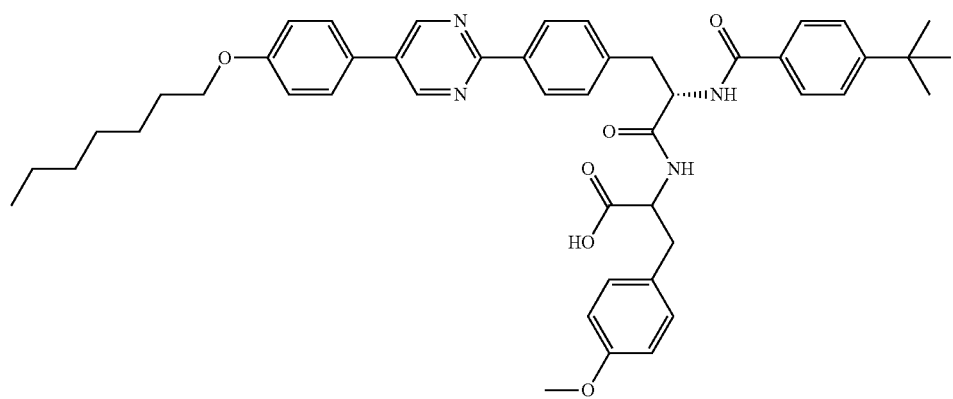
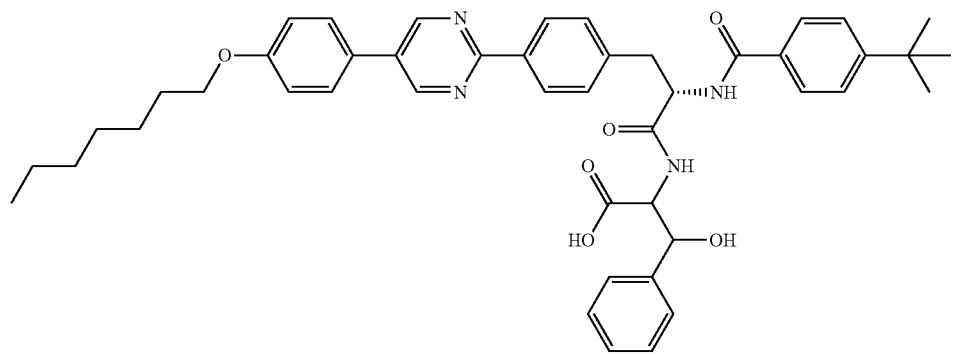
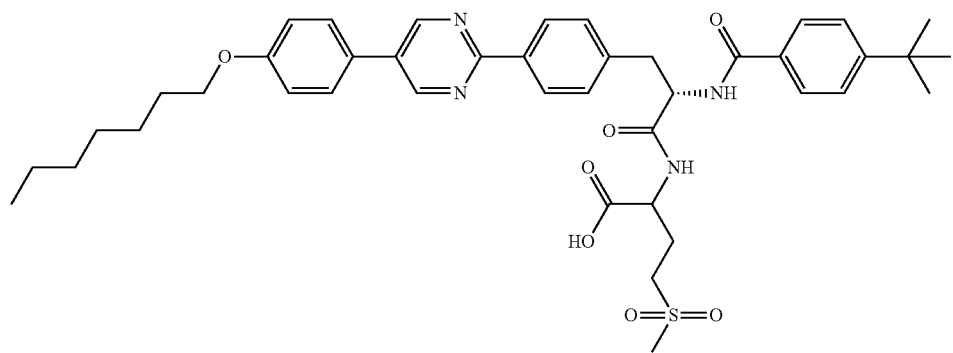

-continued
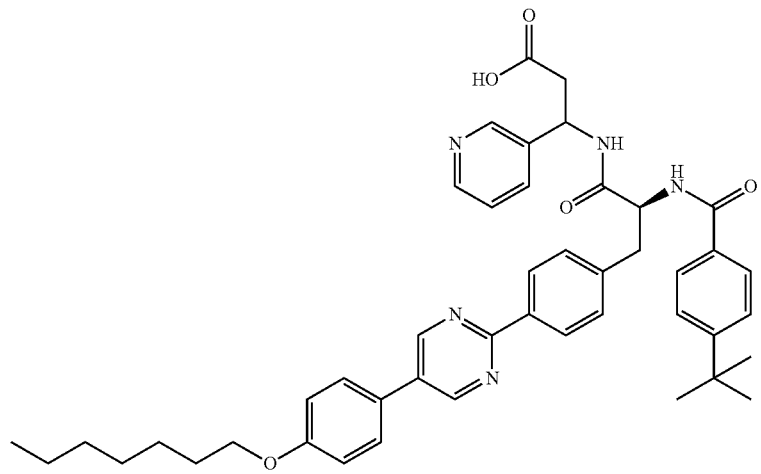
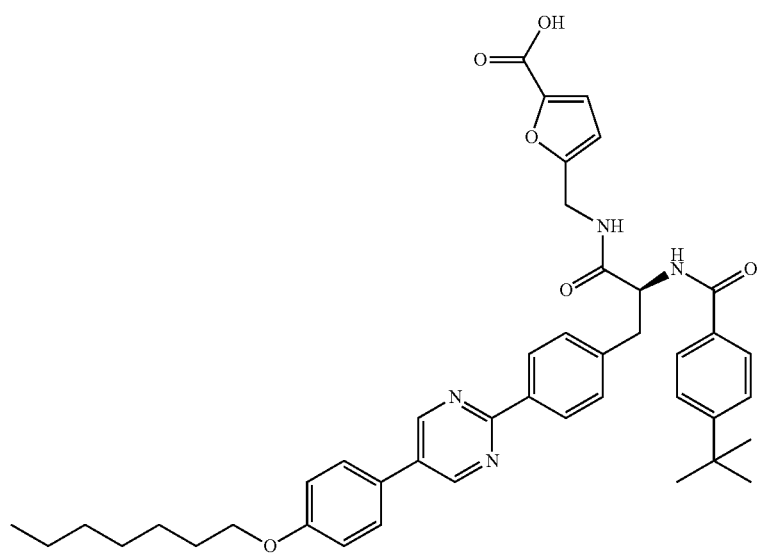
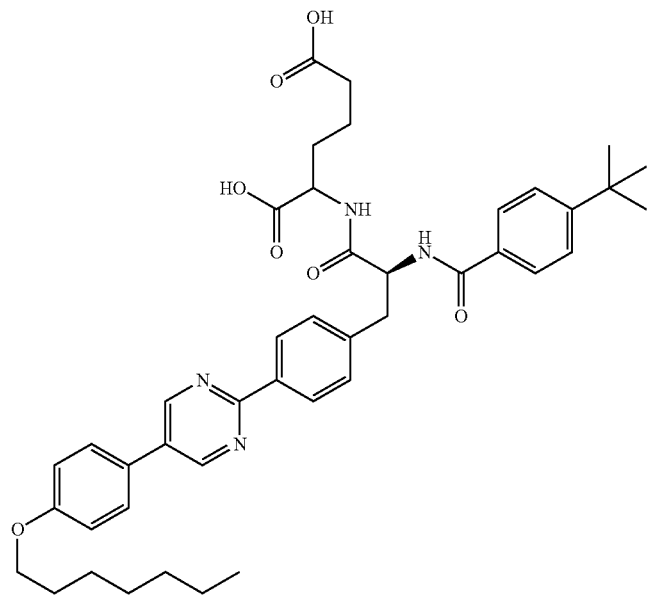

1277
1278
-continued
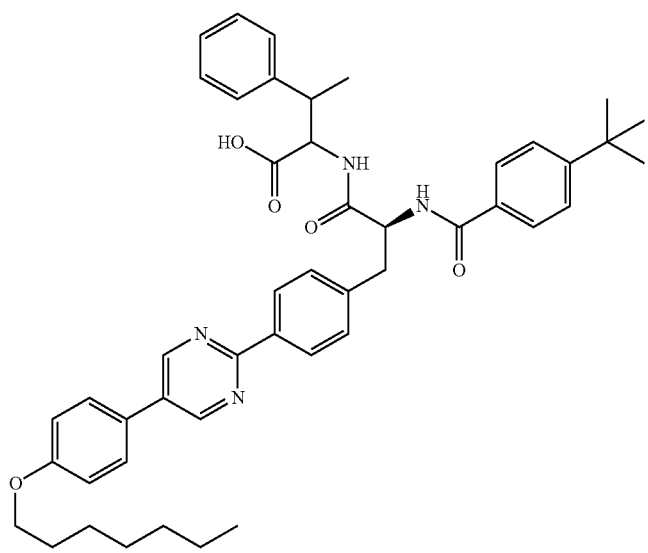
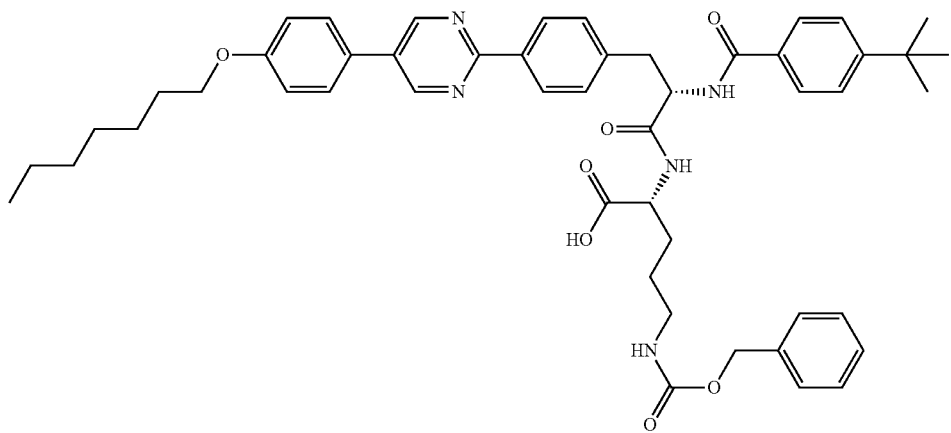
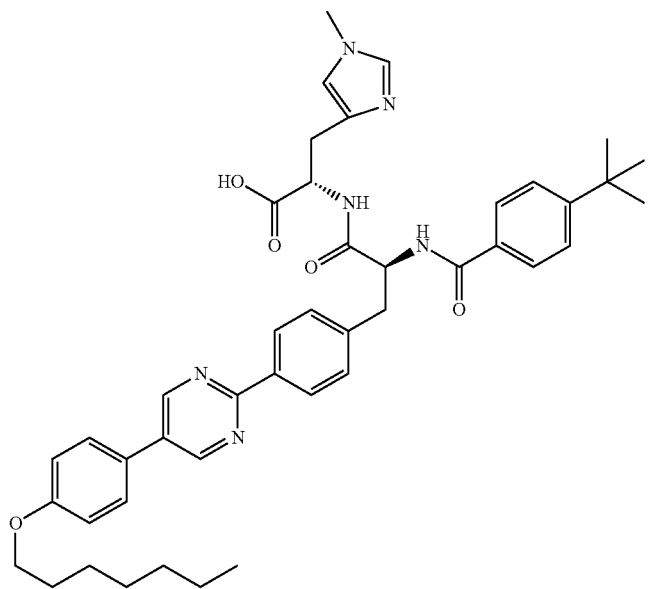

1279
1280
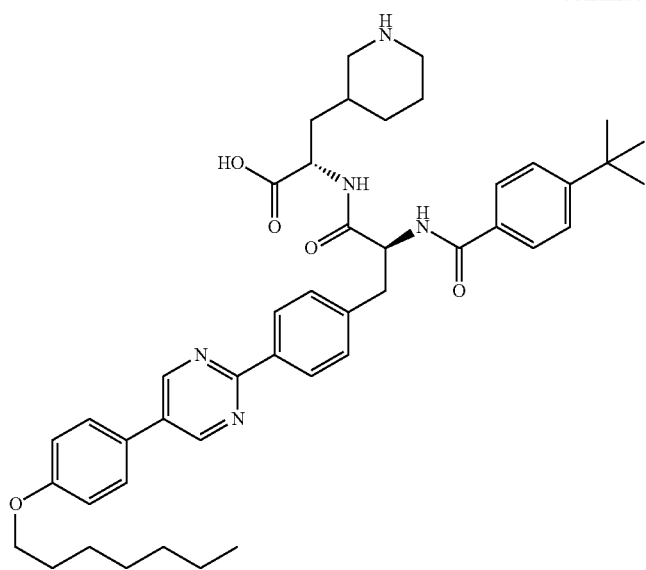
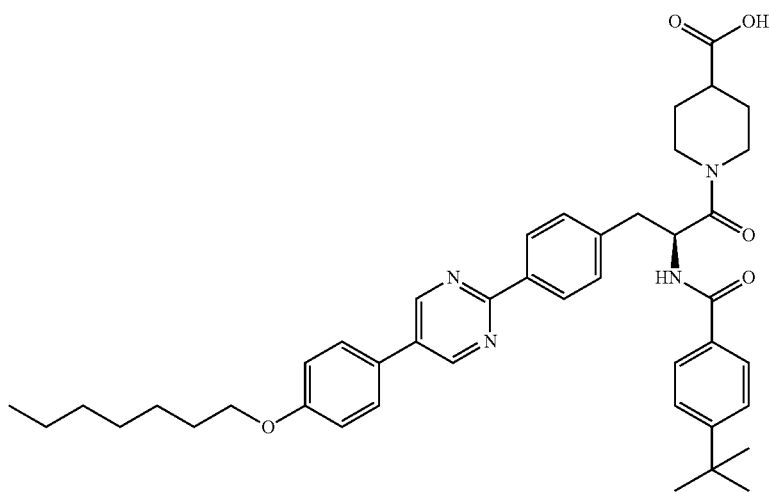
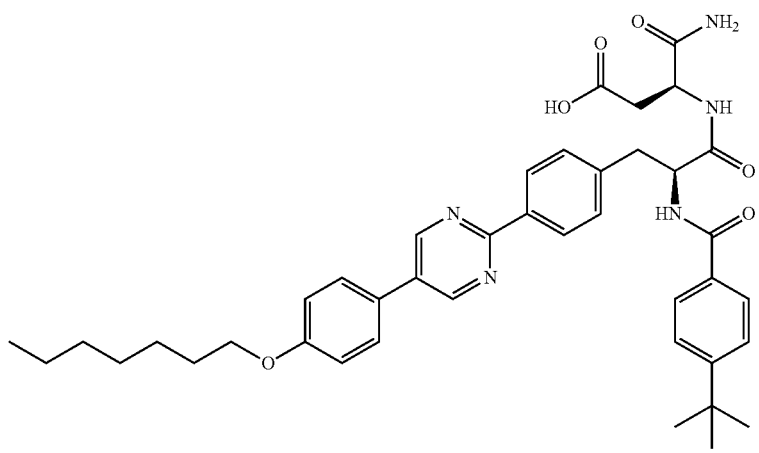

1281
-continued
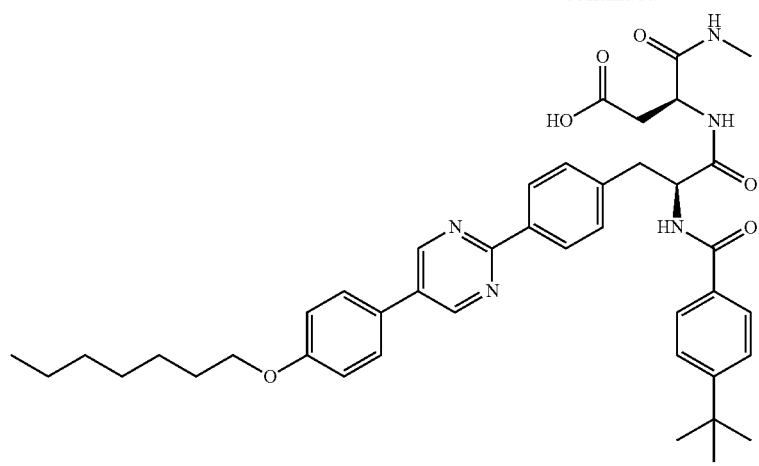
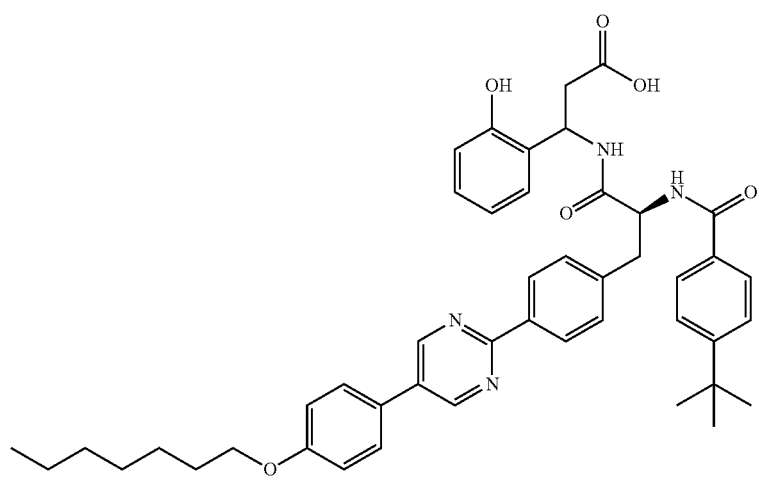
1282
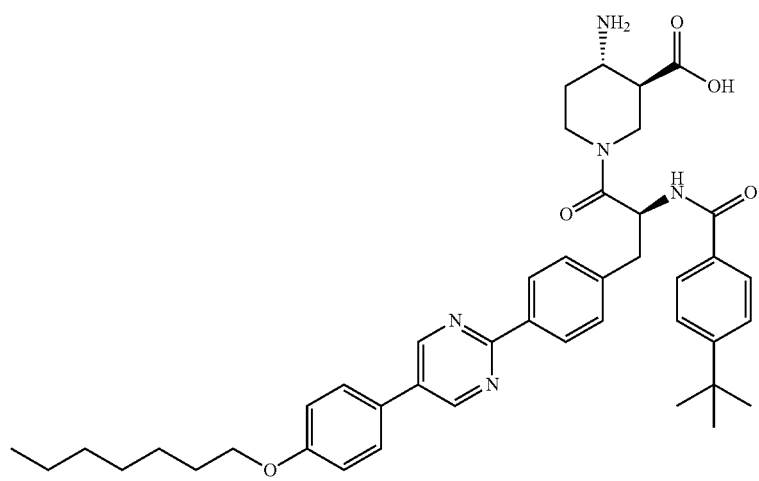

-continued
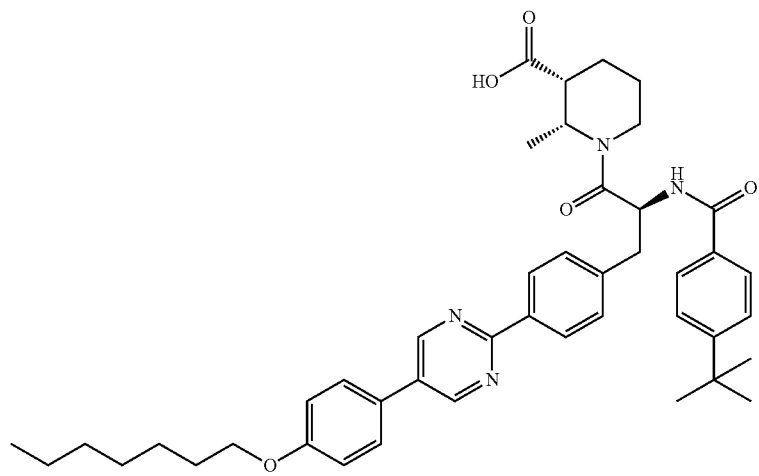
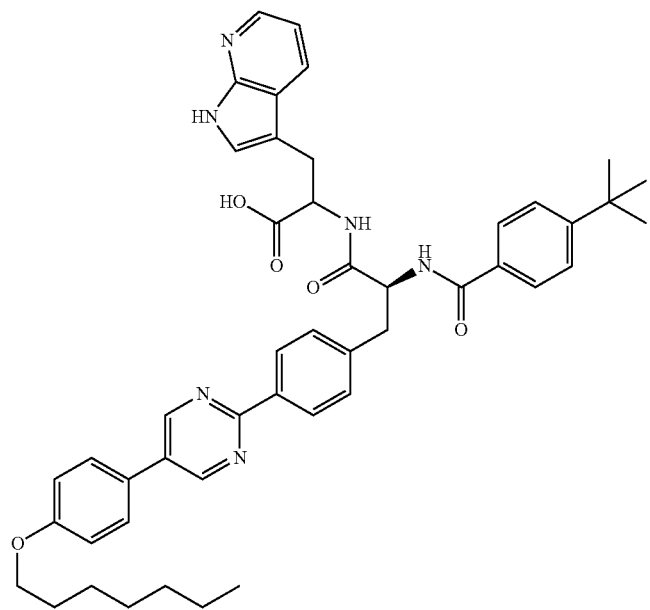
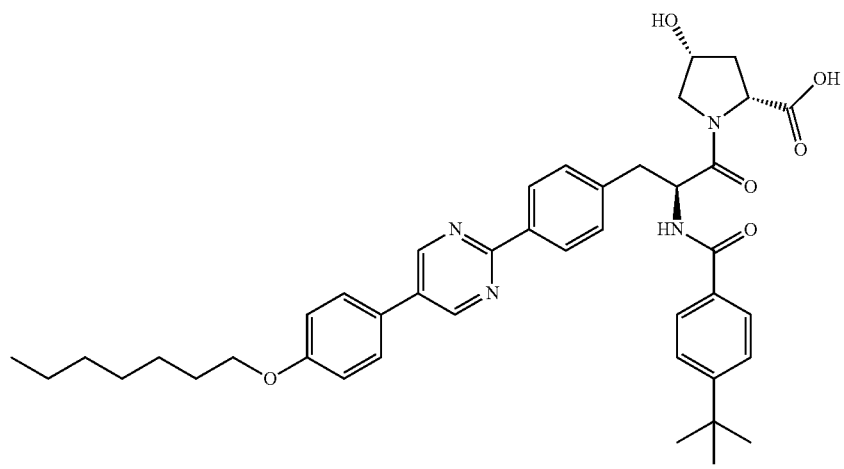

-continued
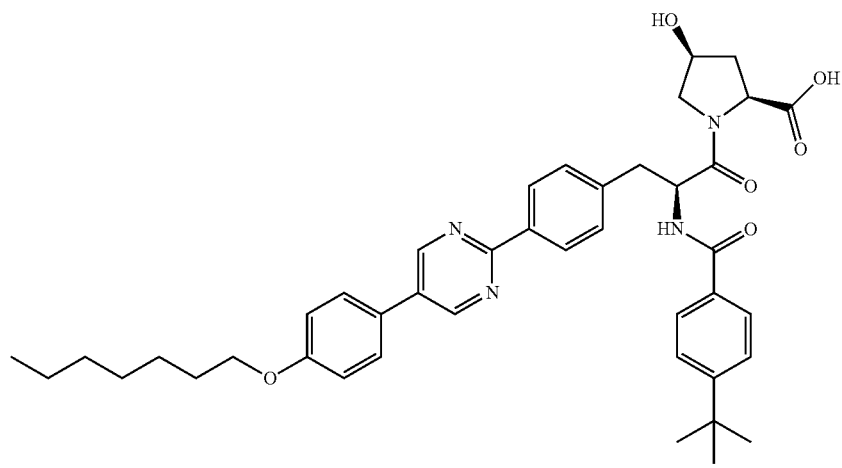
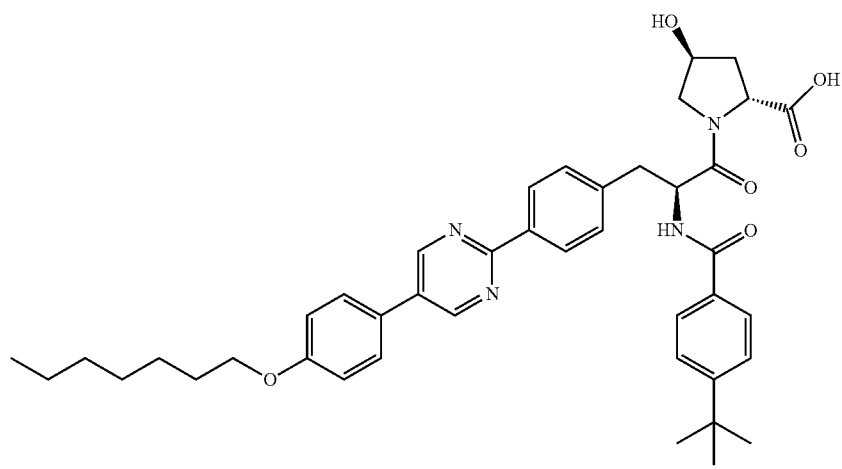
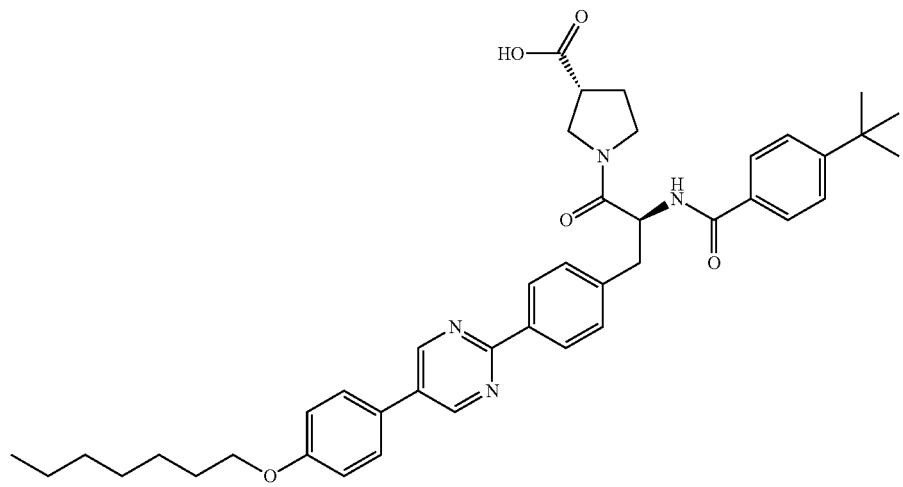

-continued
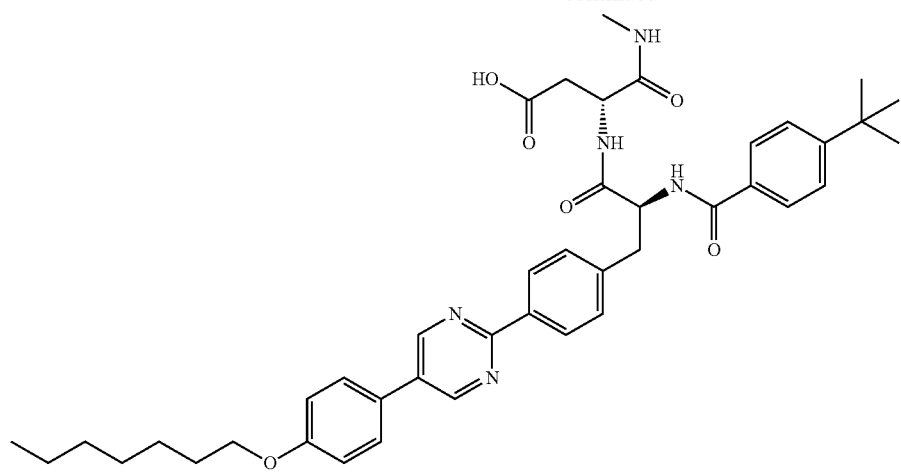
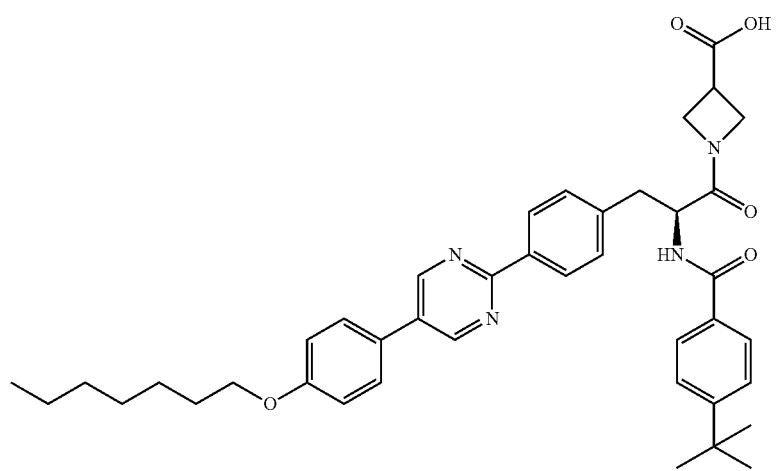
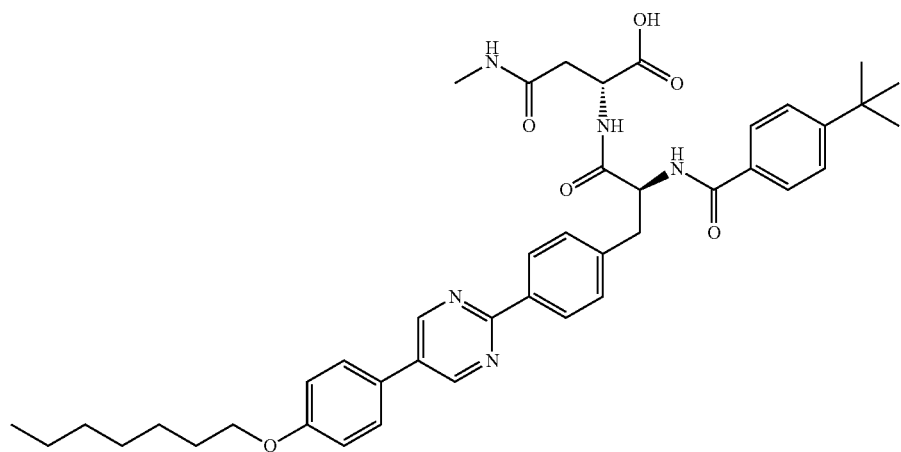

1289
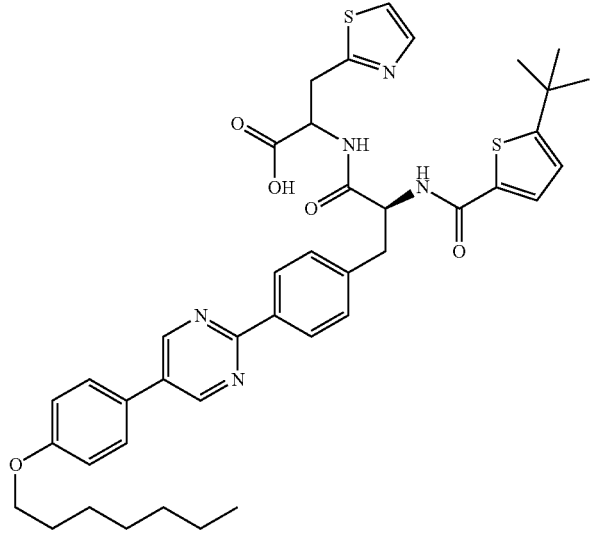
1290
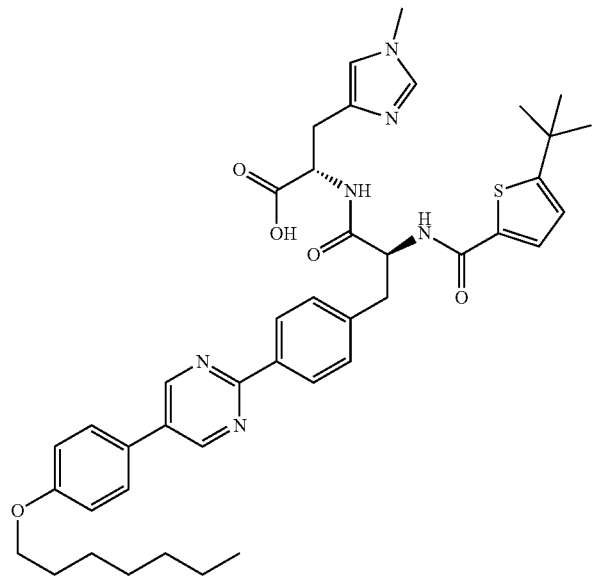
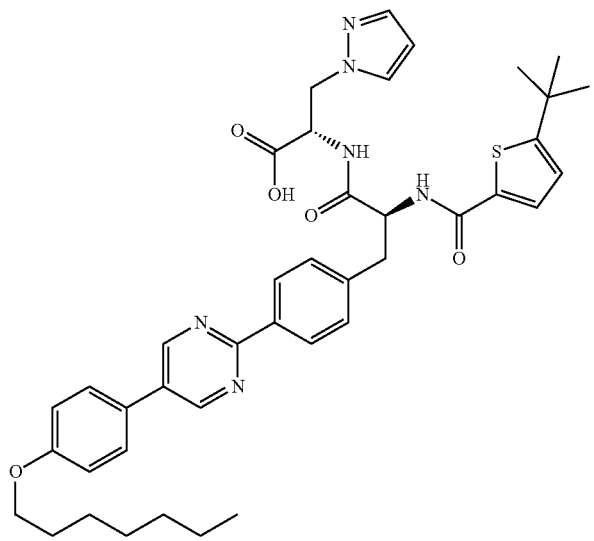
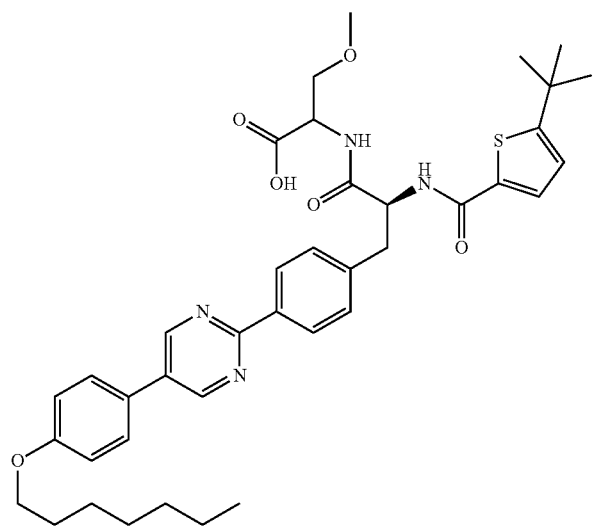
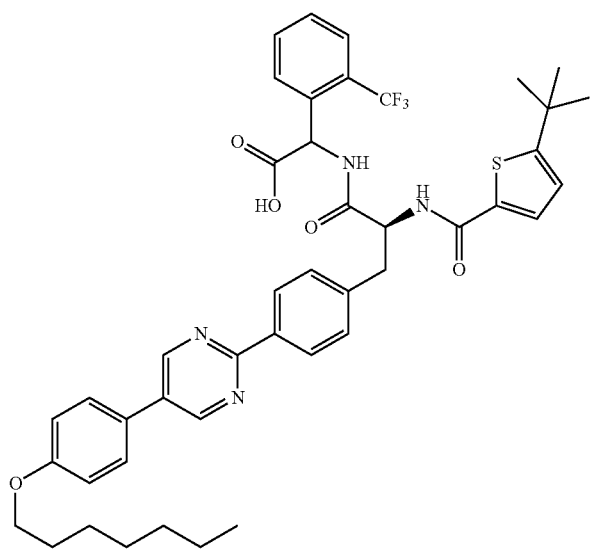
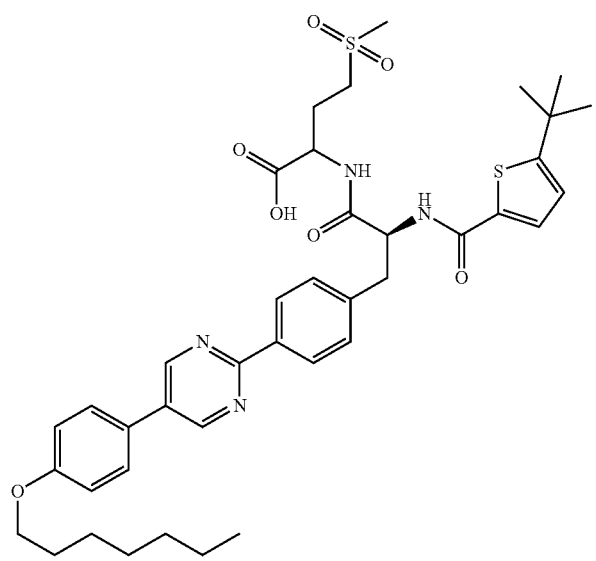

1291 1292
-continued
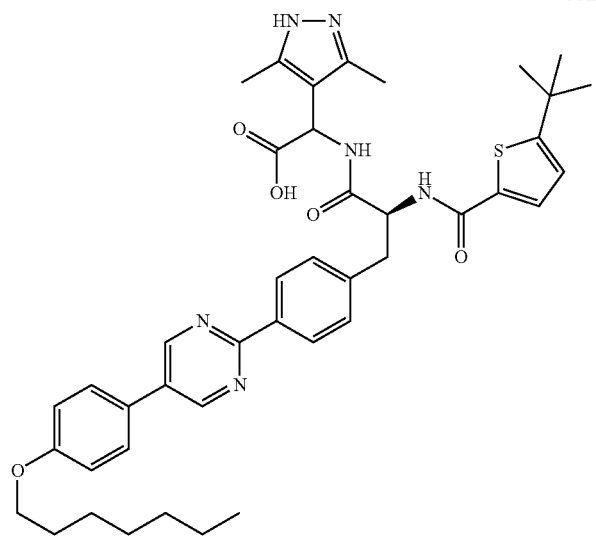
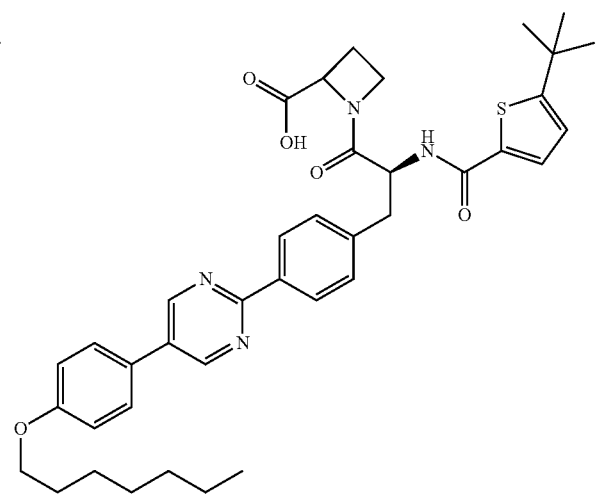
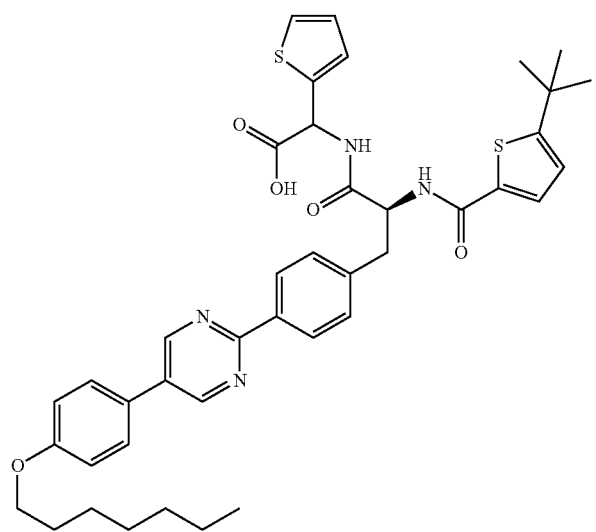
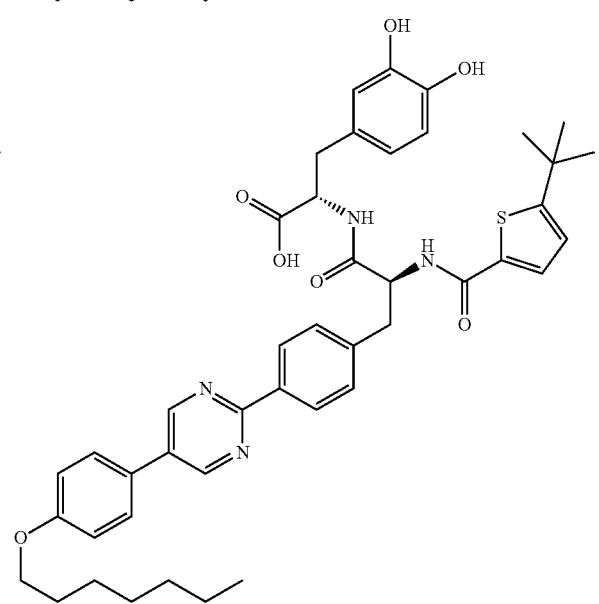
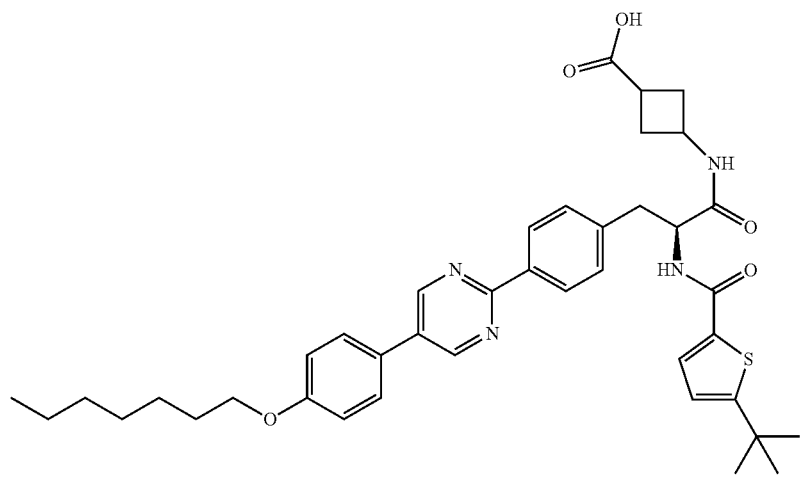

1293
-continued
1294
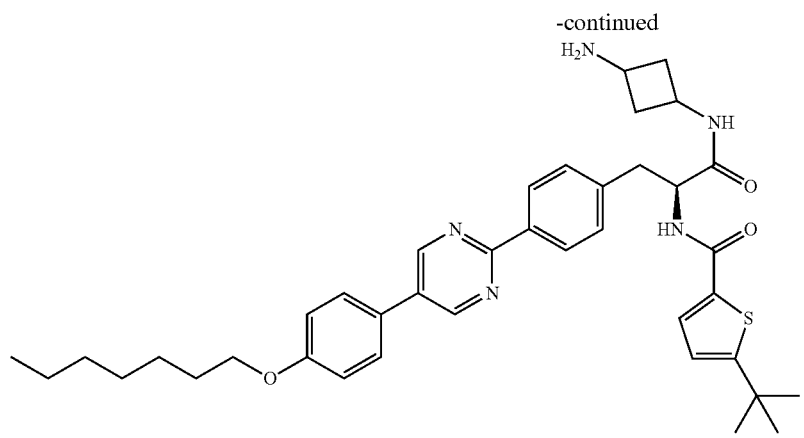
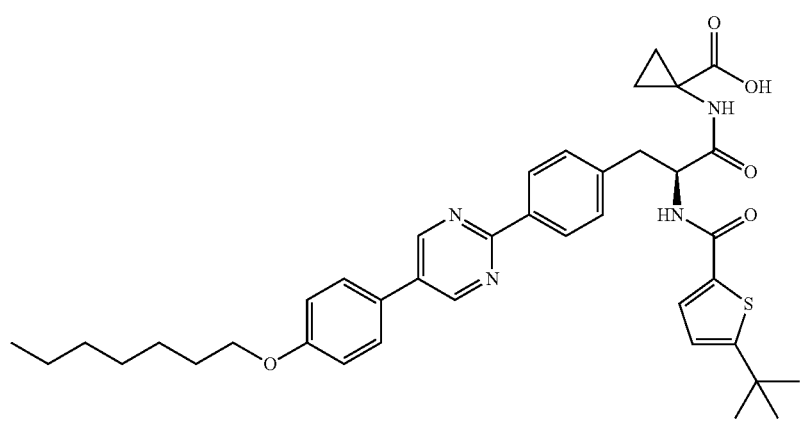
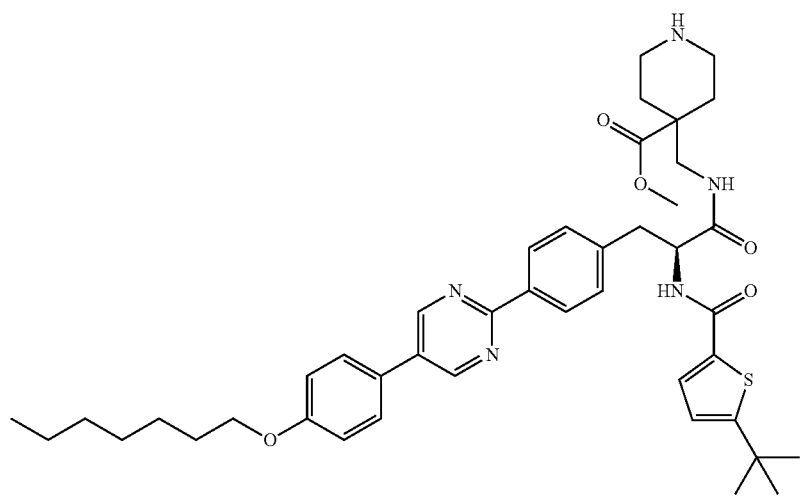

1295
-continued
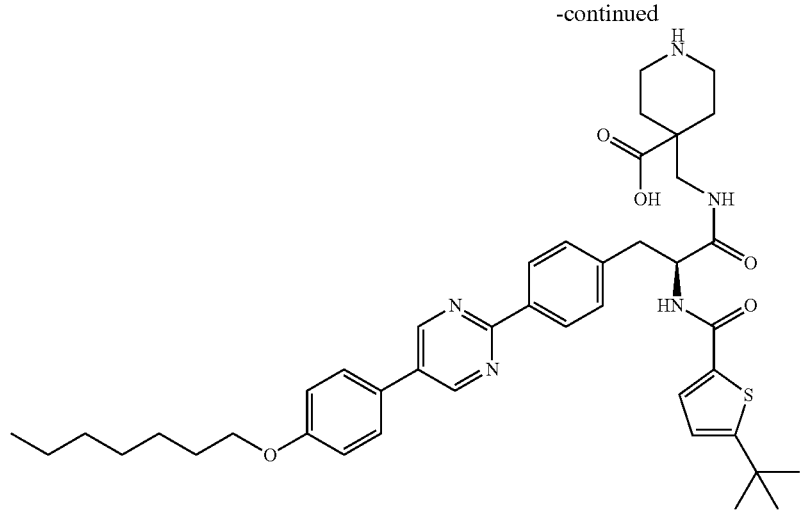
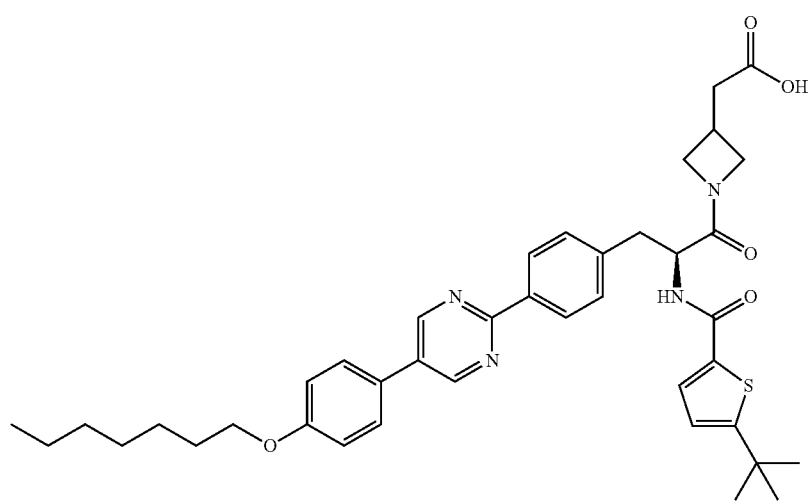
1296
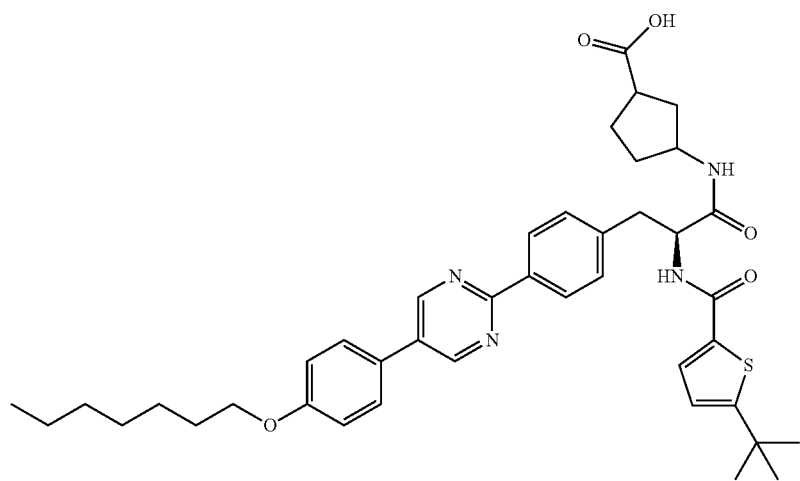

1297
1298
-continued
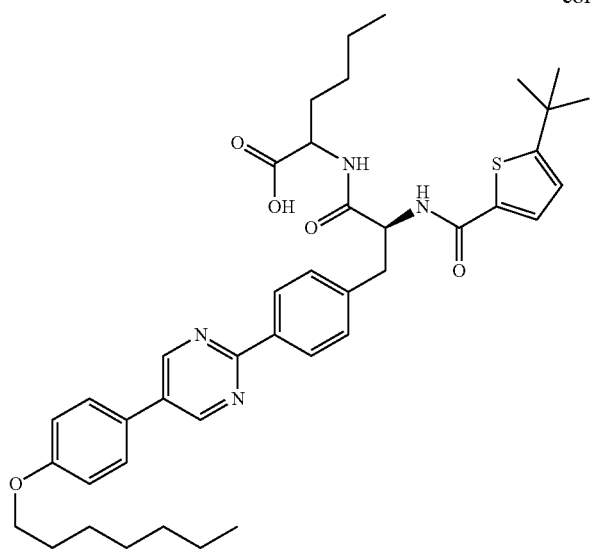
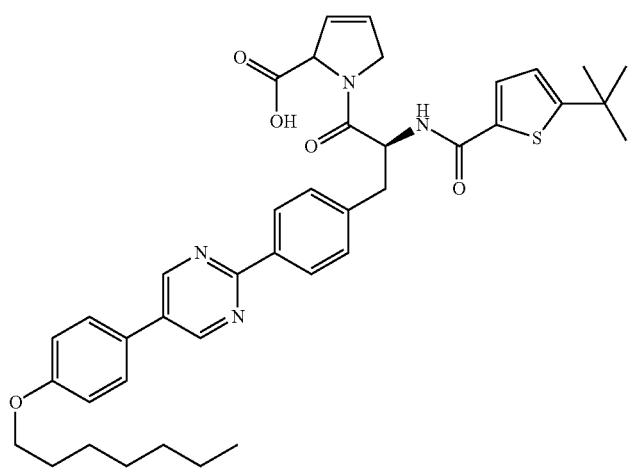
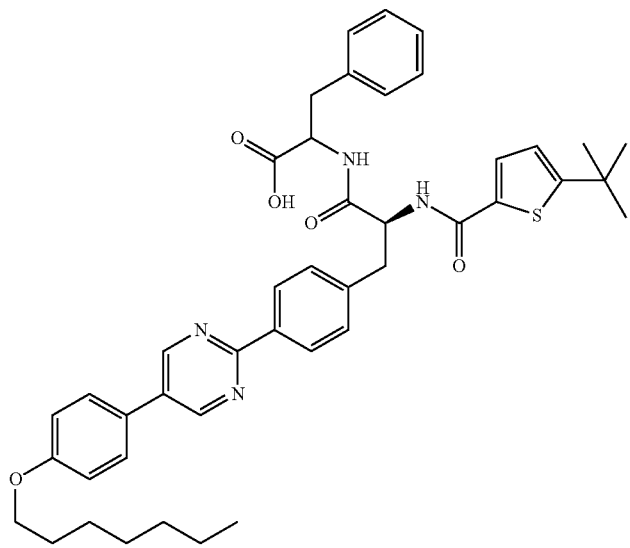

1299
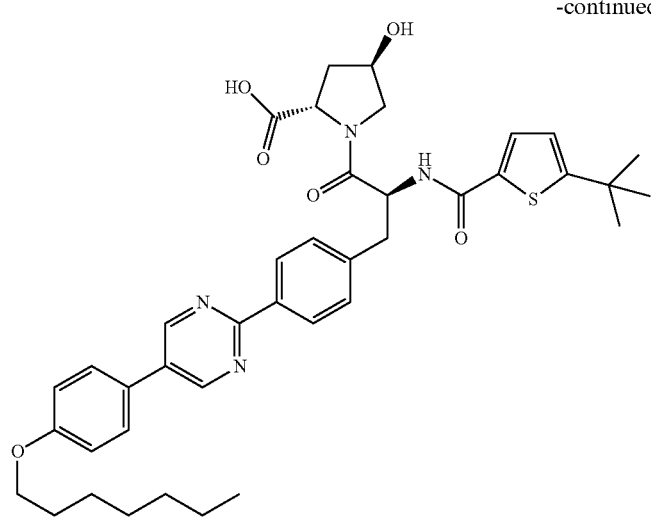
1300
-continued
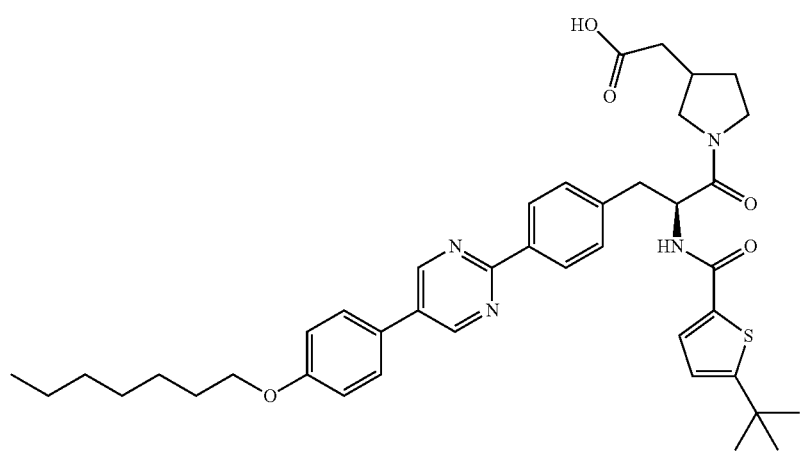
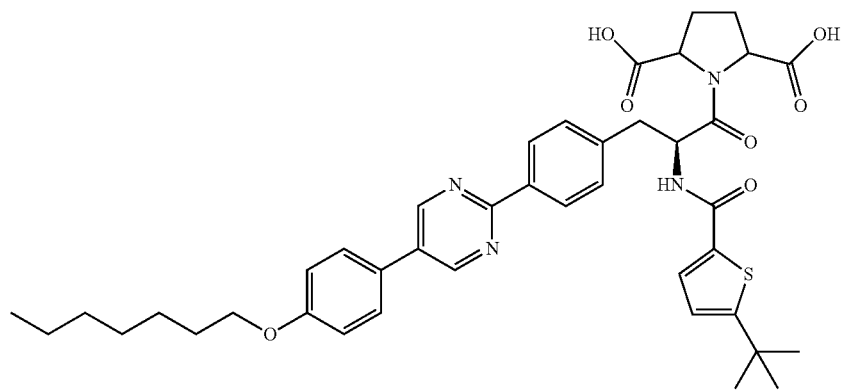

-continued
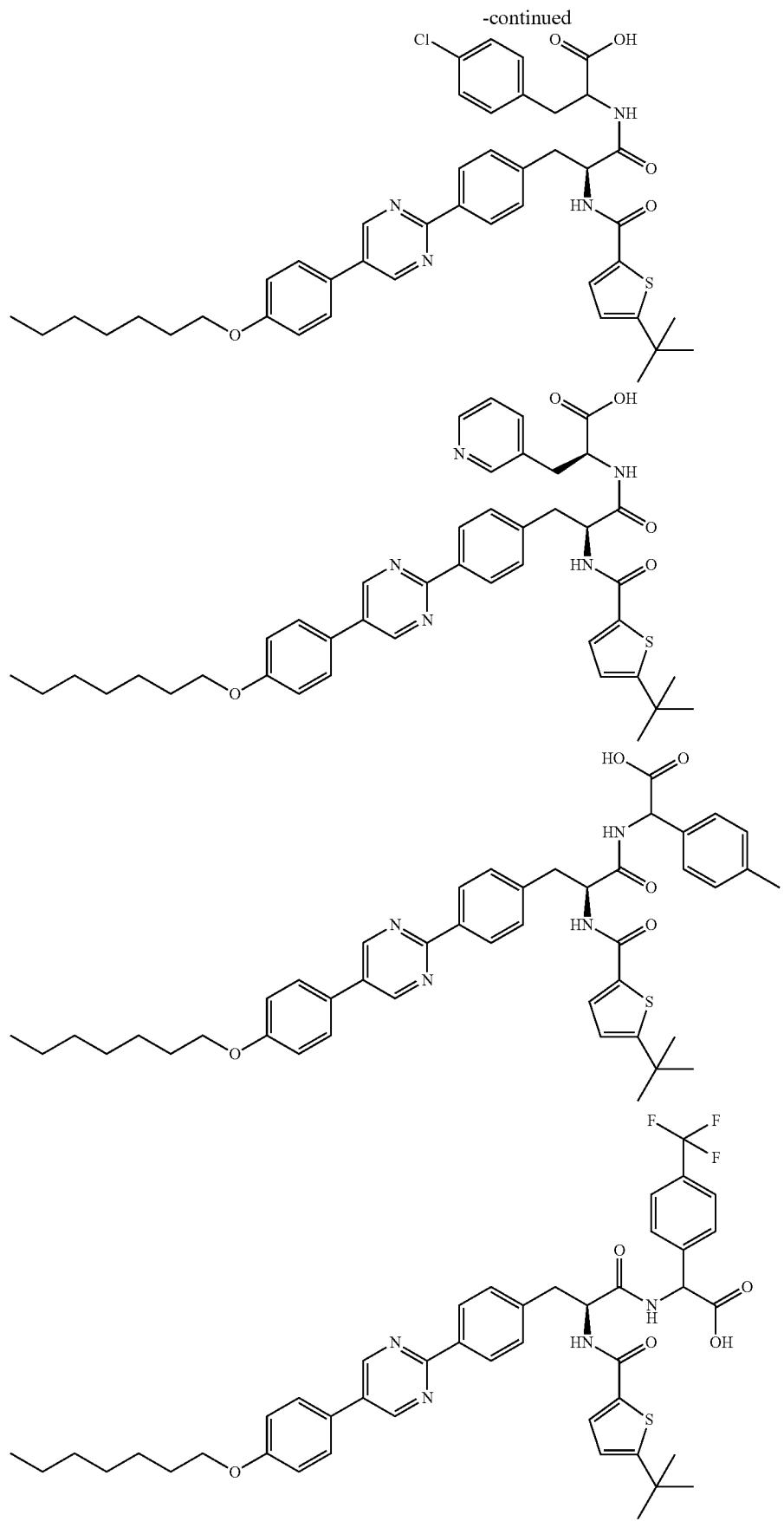

-continued
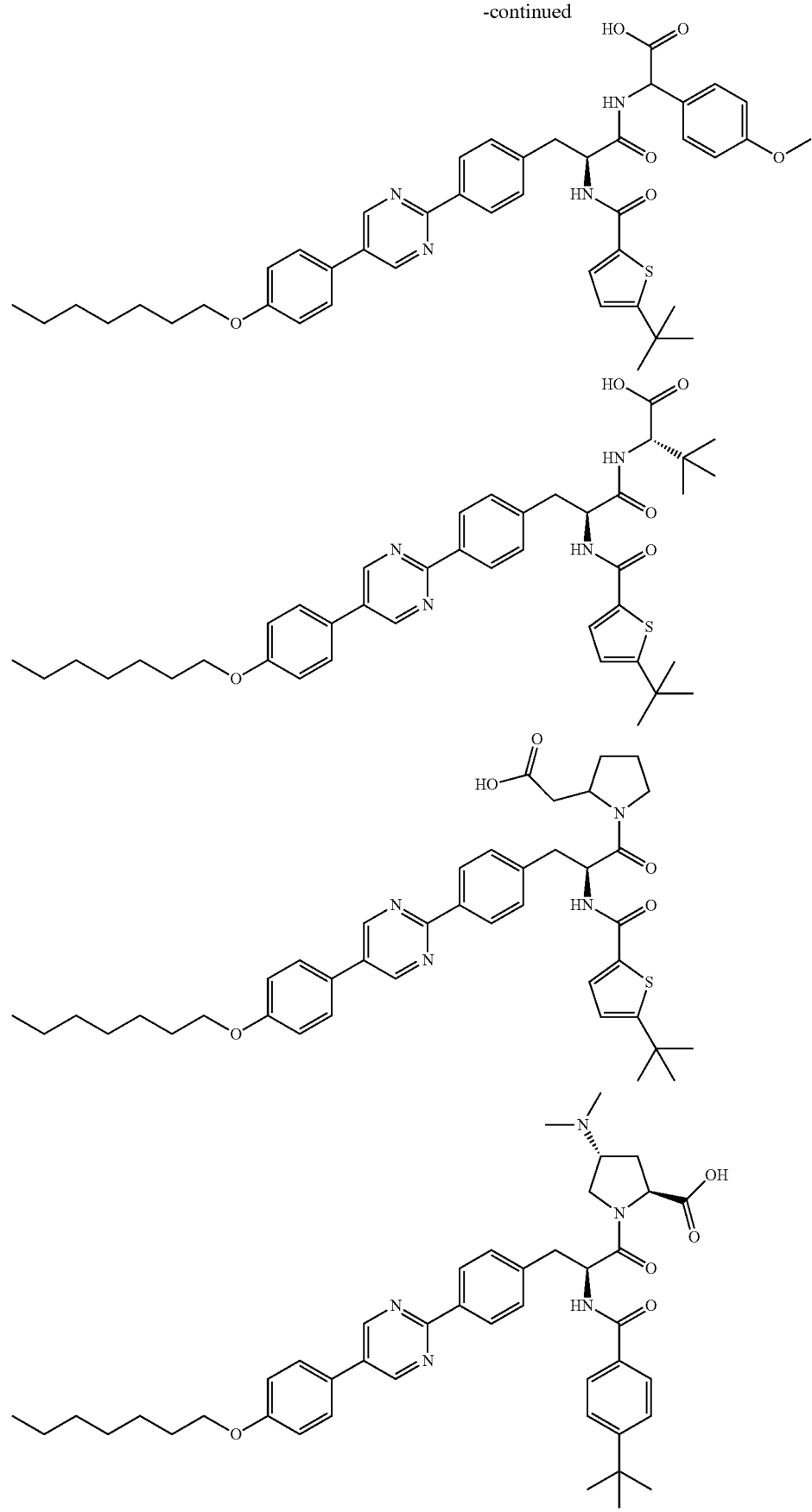

1305　　　　　　　　　　　　　　　　　　　　1306
-continued
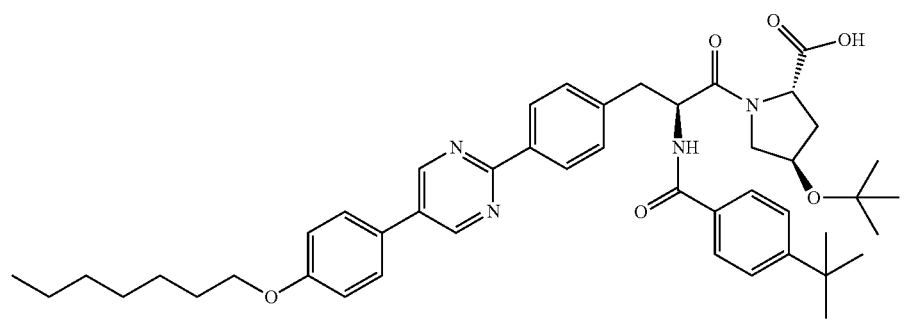
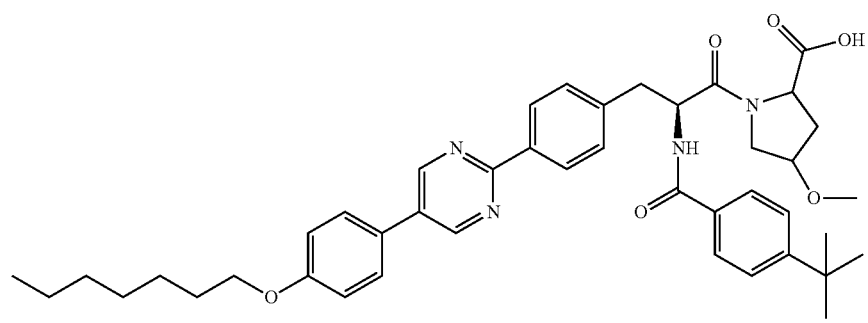
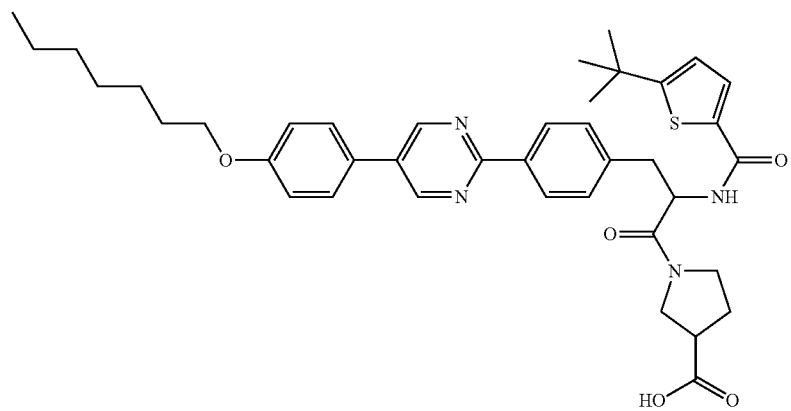
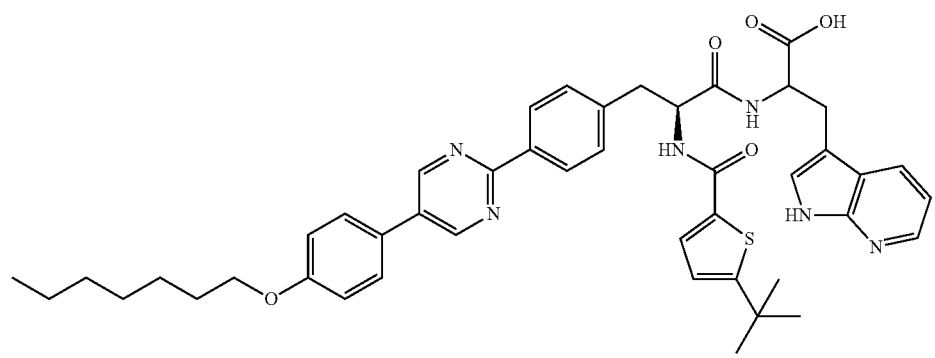

1307
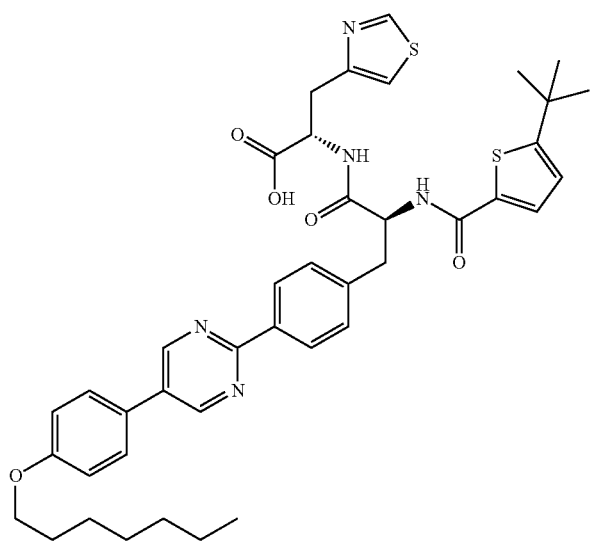
1308
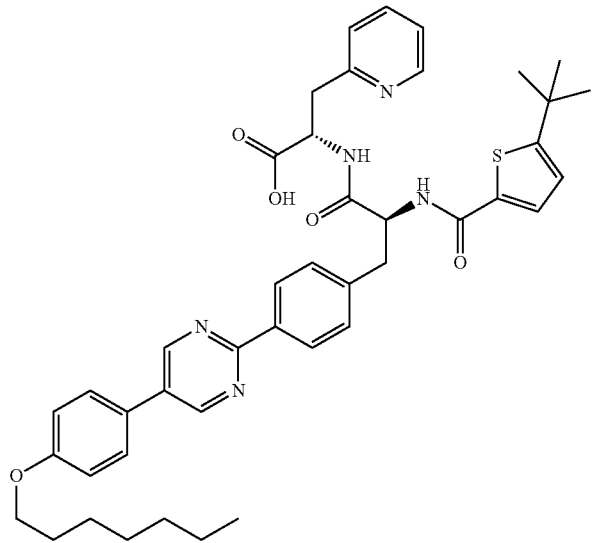
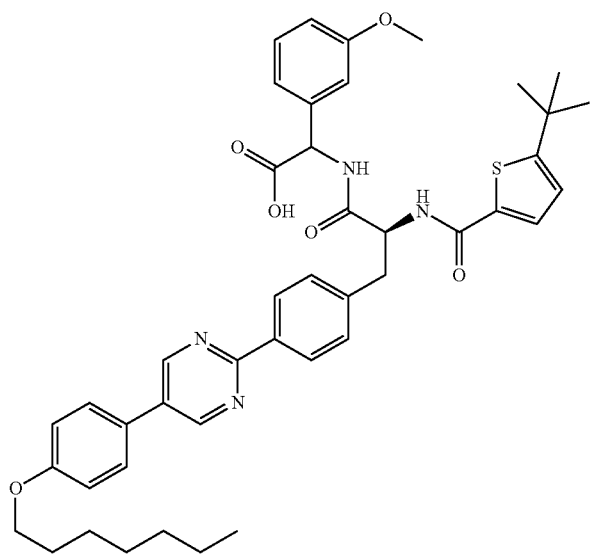
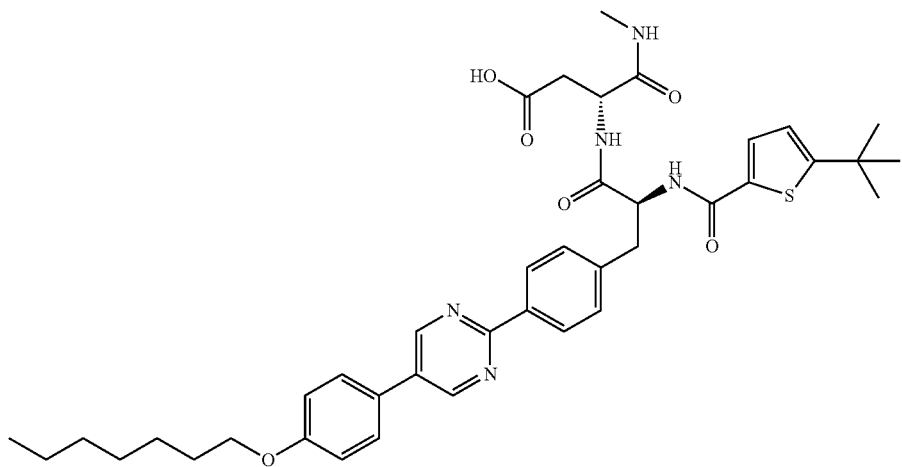

1309
-continued
1310
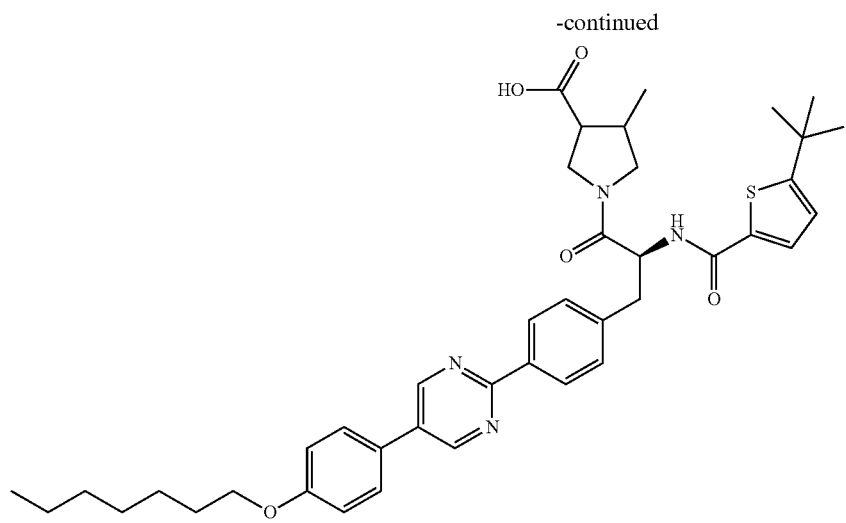
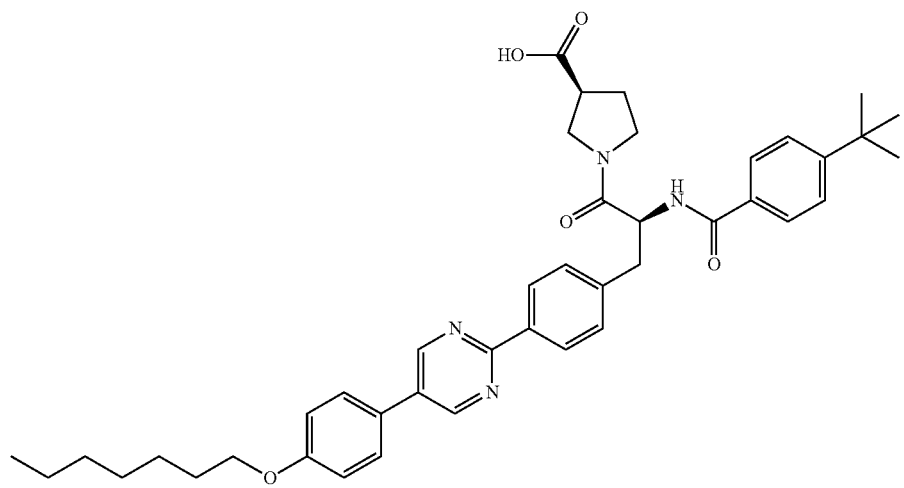
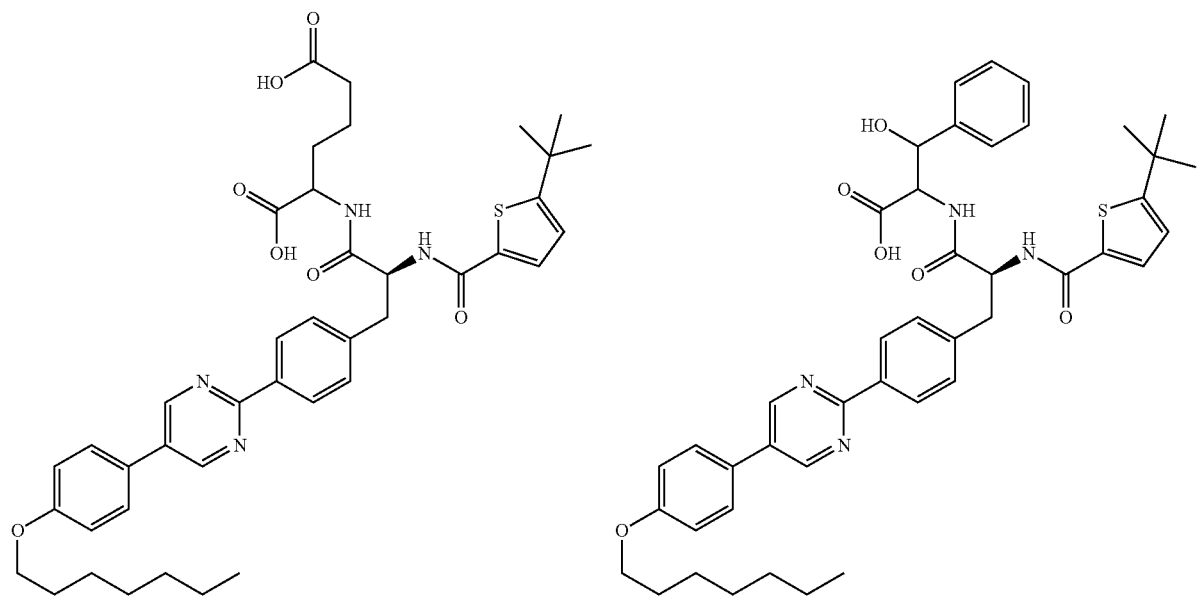

1311 1312
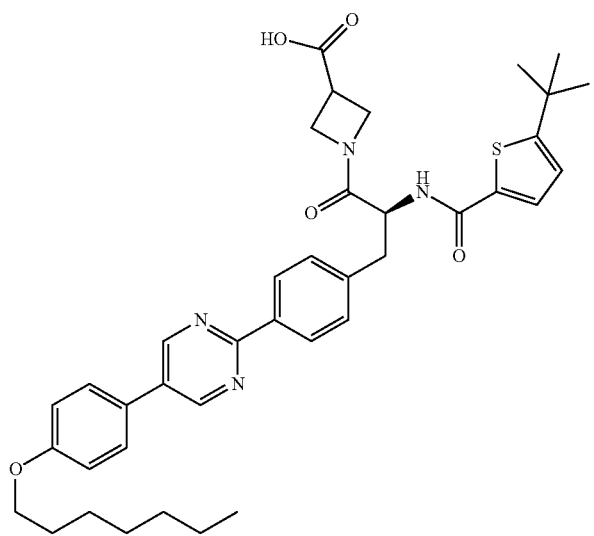
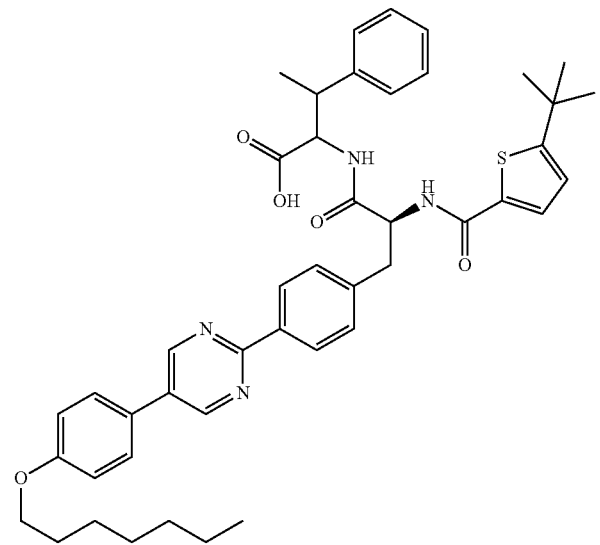
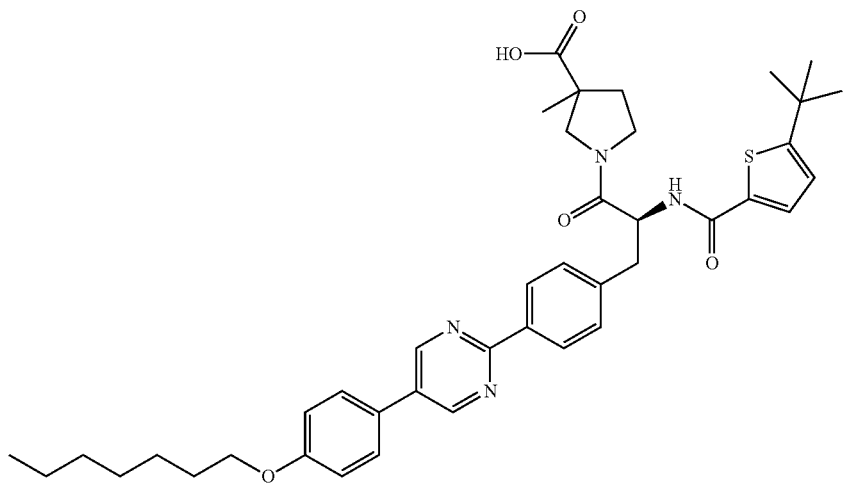
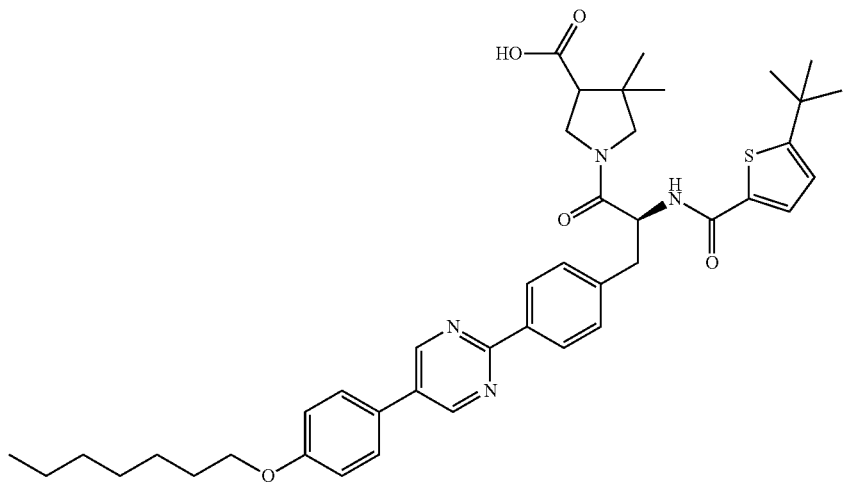

1313
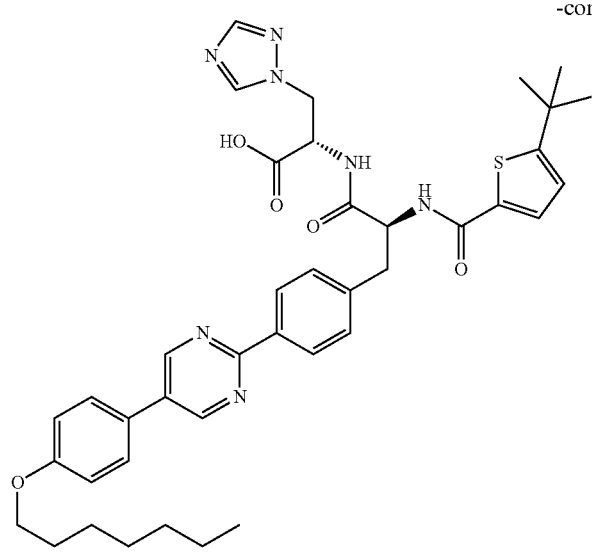
1314
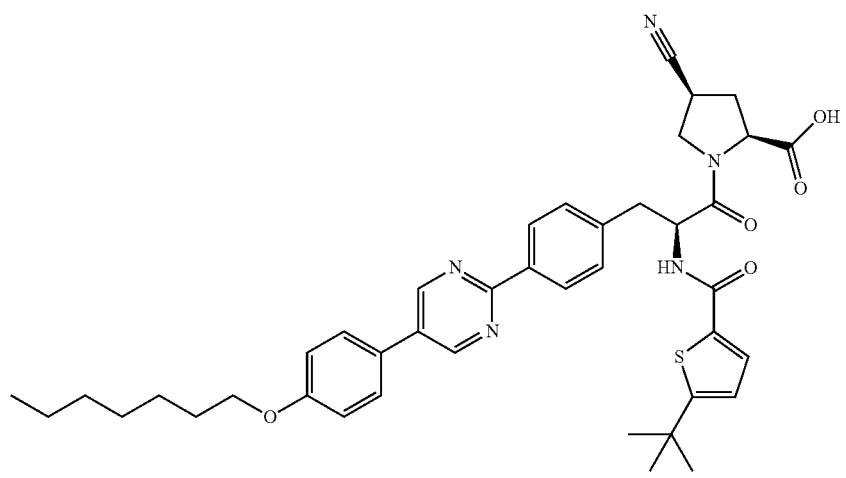
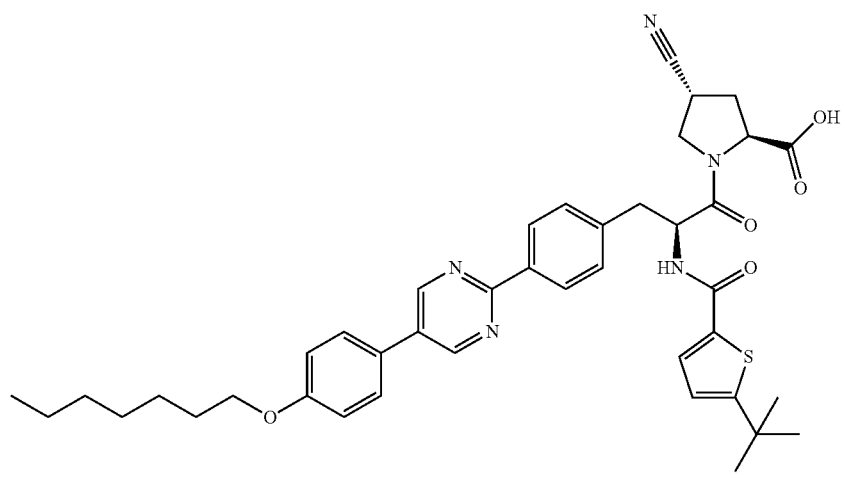

1315
-continued
1316
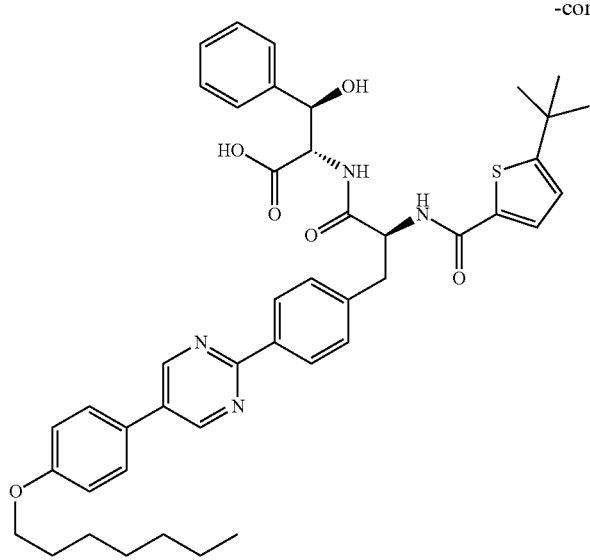
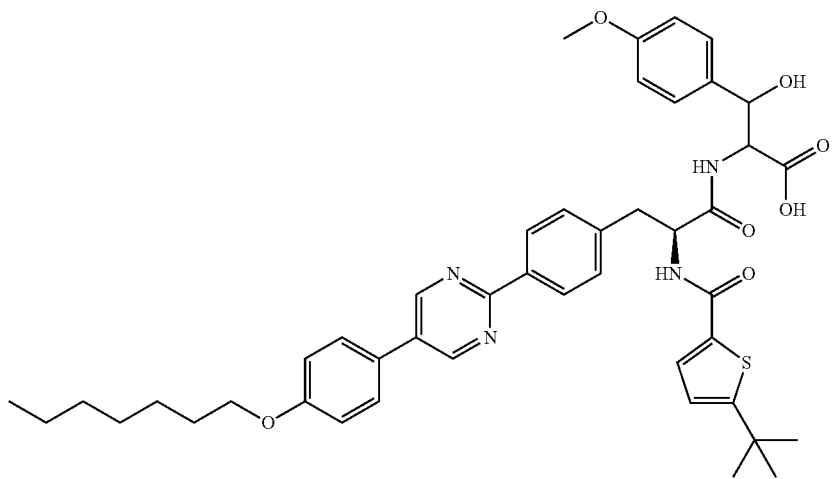
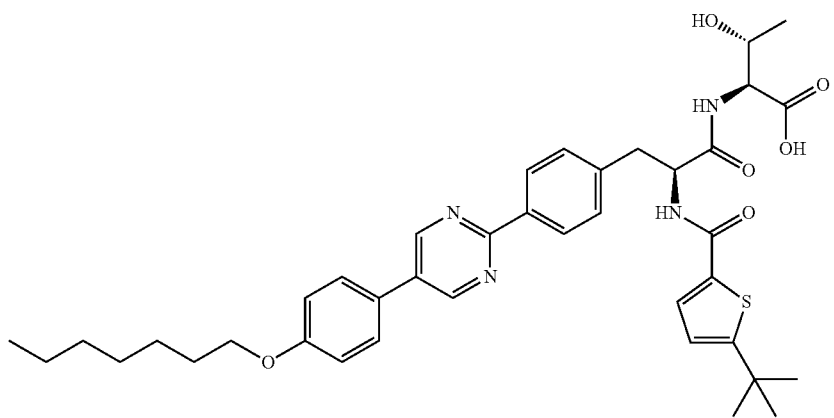

1317 1318
-continued
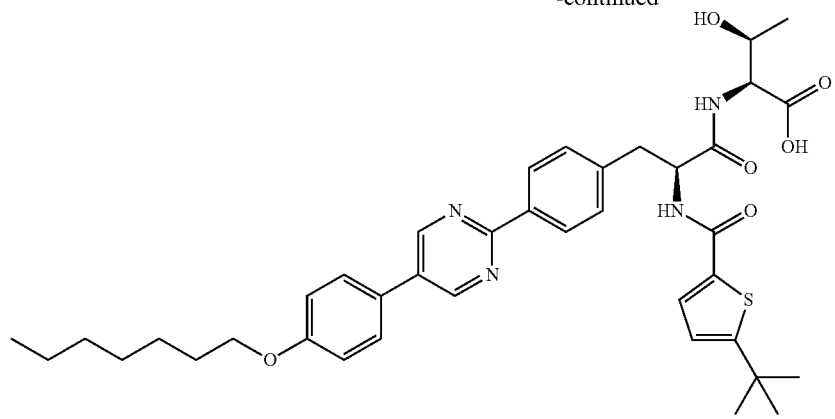
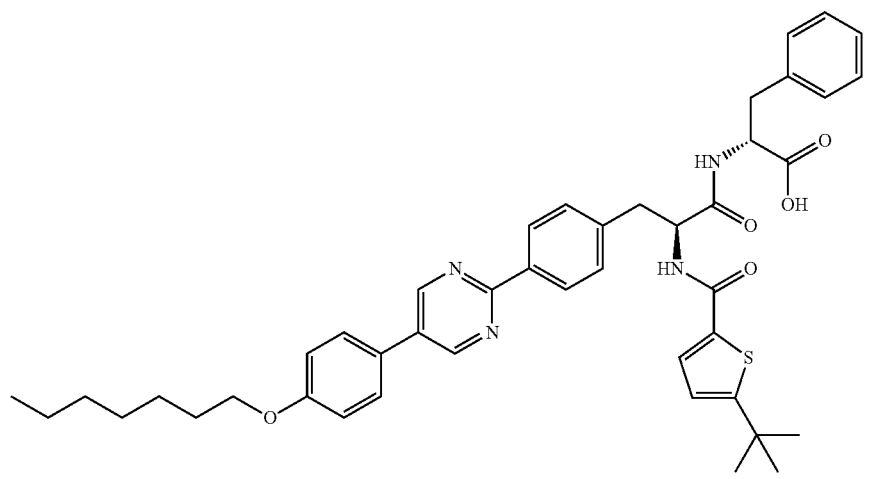
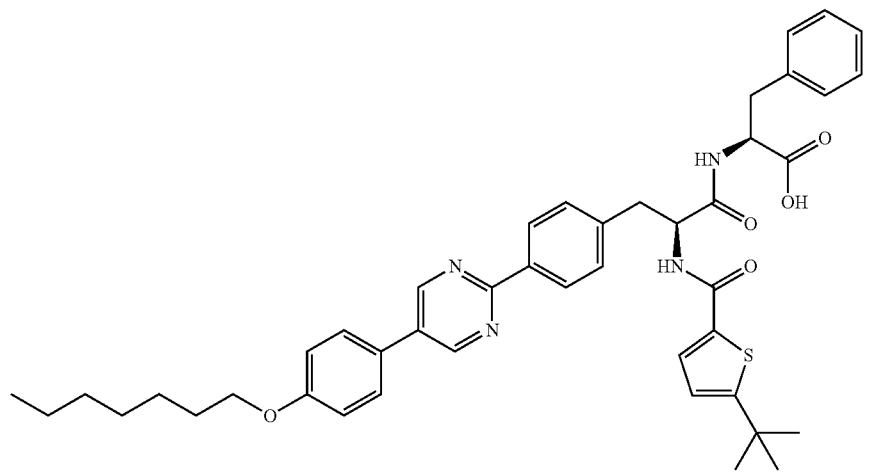

-continued
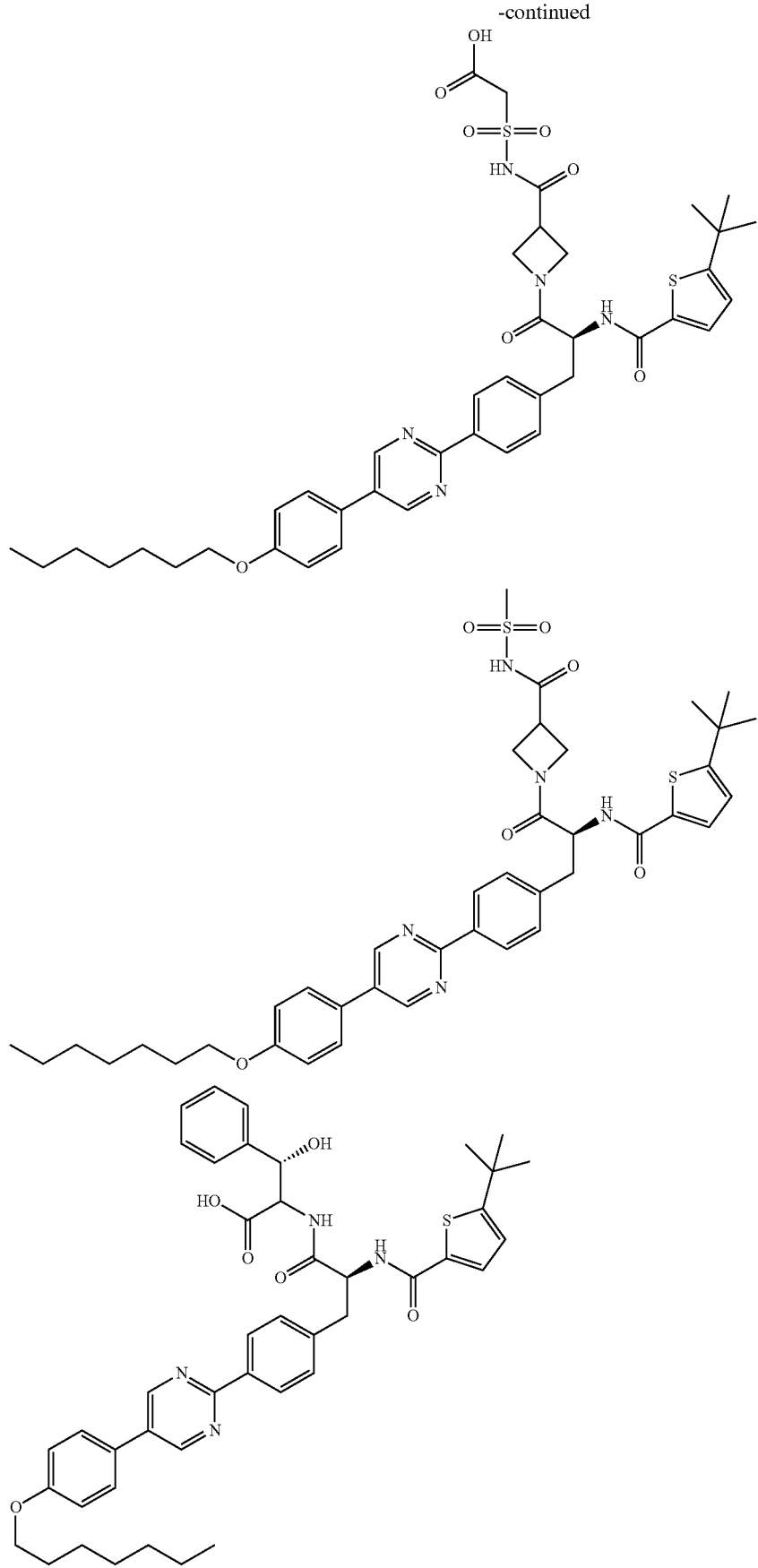

1321
-continued
1322
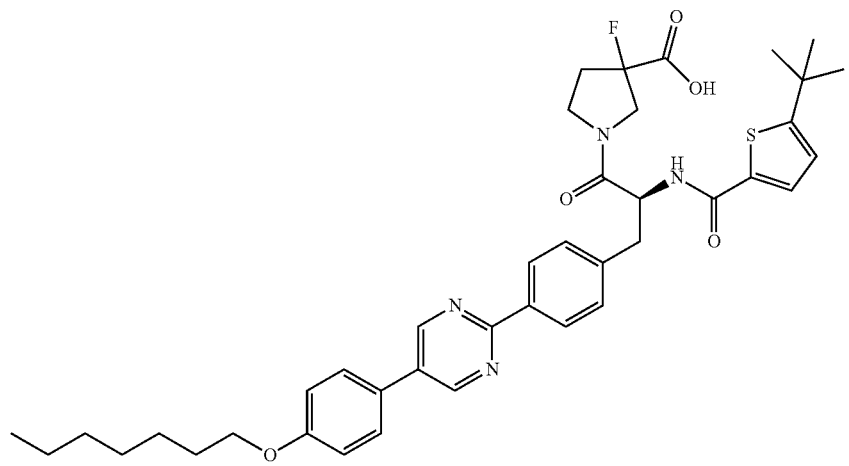
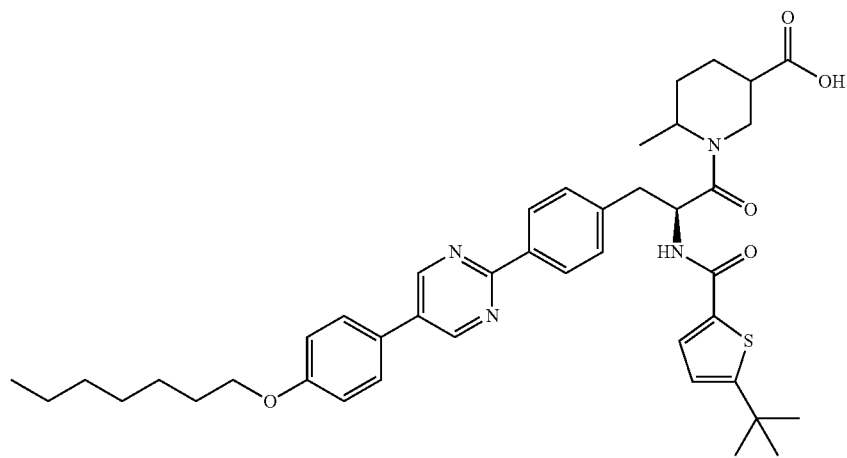
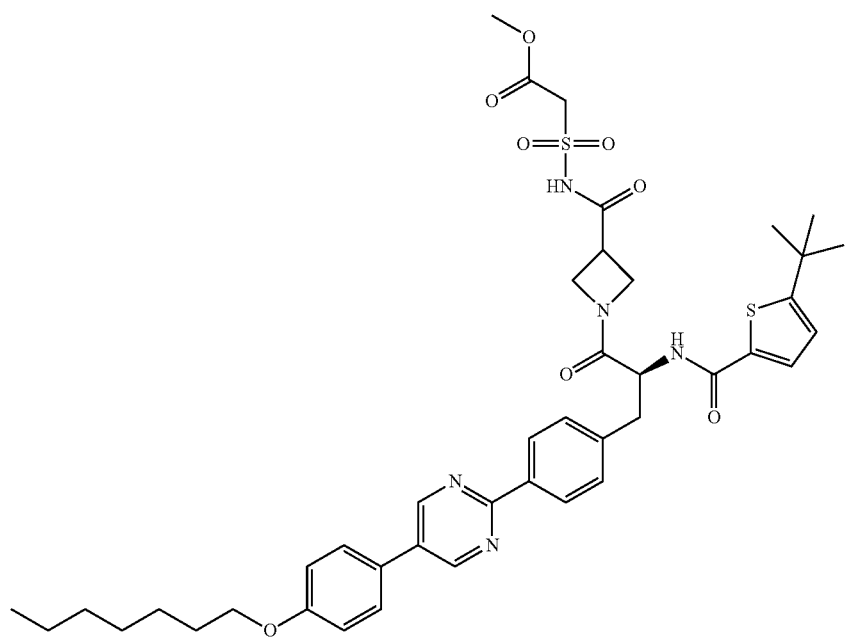

-continued
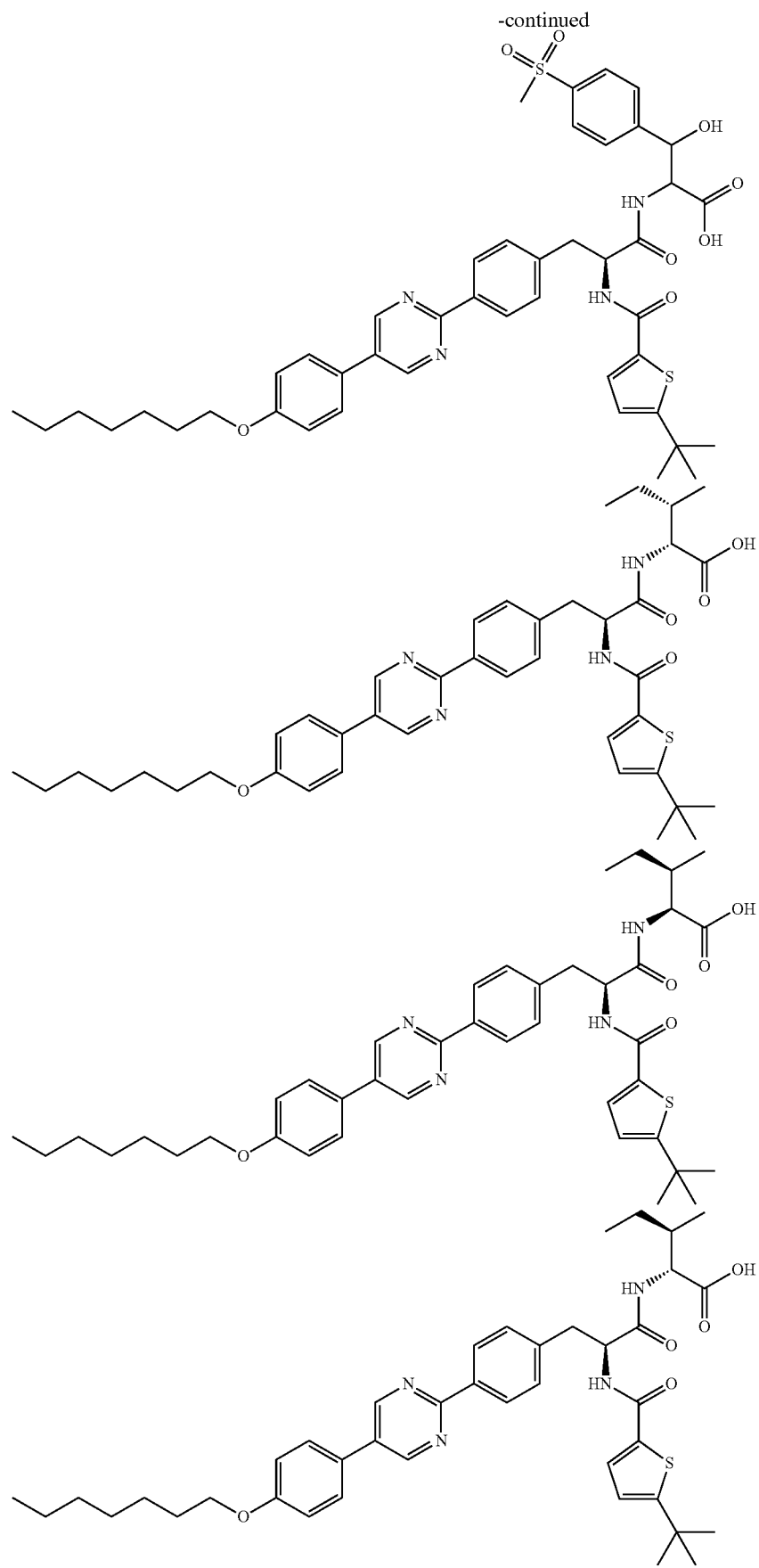

1325
-continued
1326
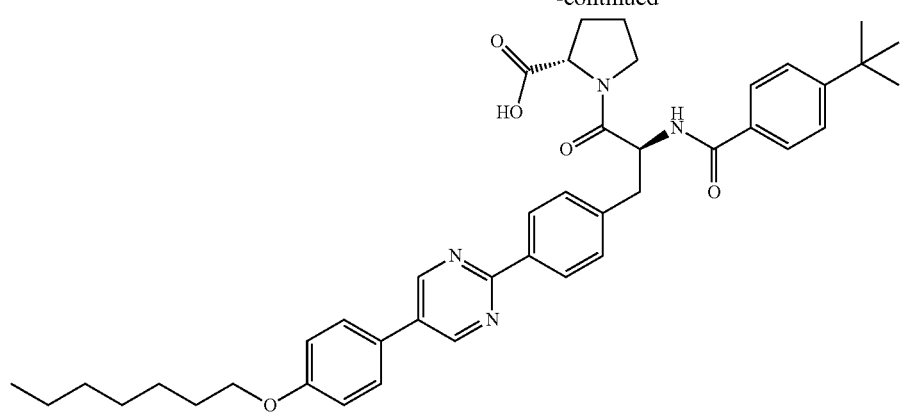
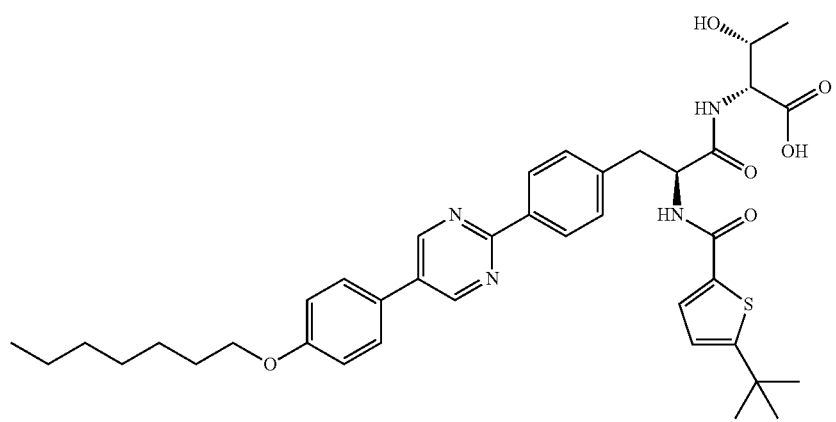
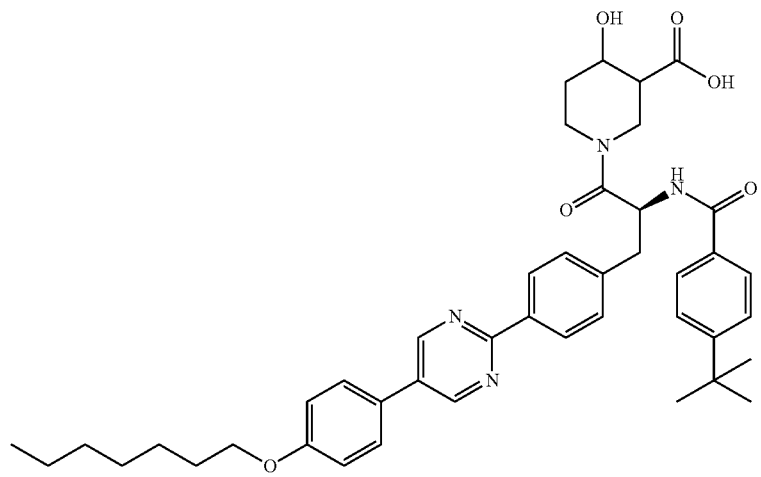

-continued
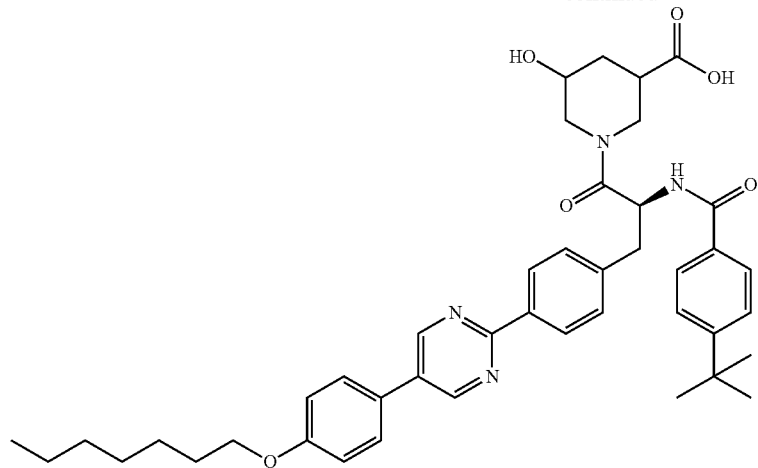
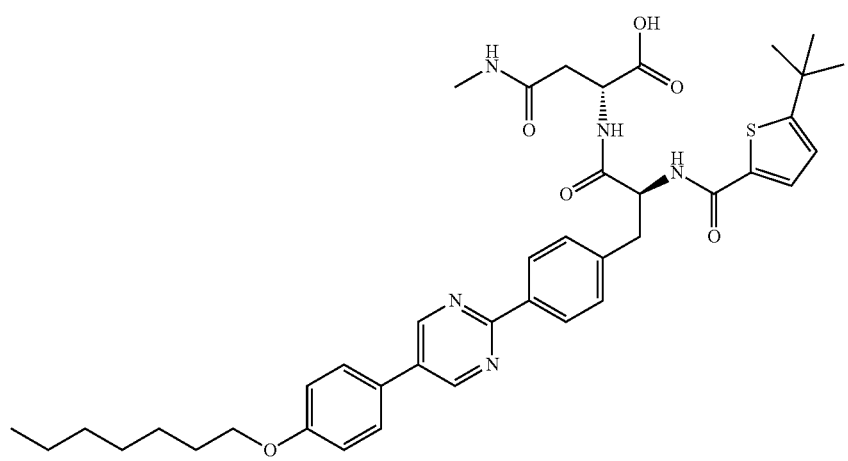
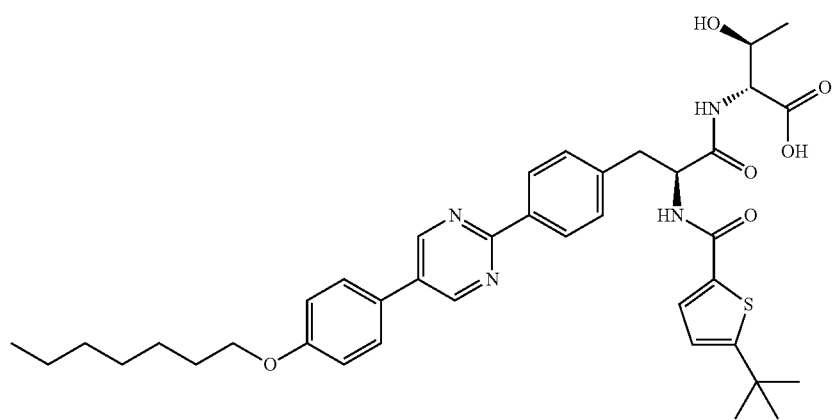

-continued
1329
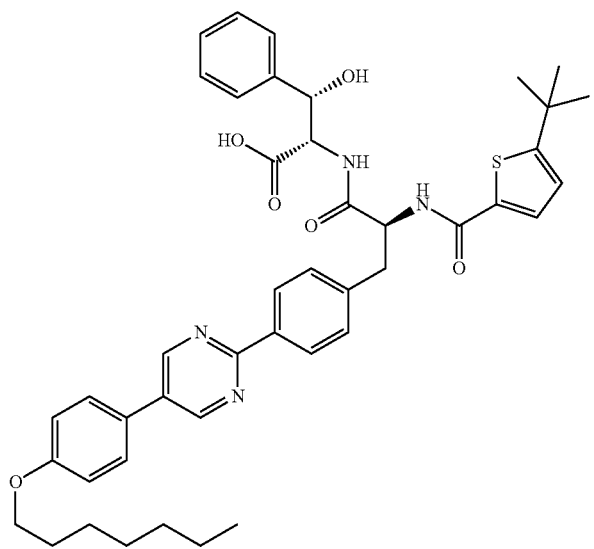
1330
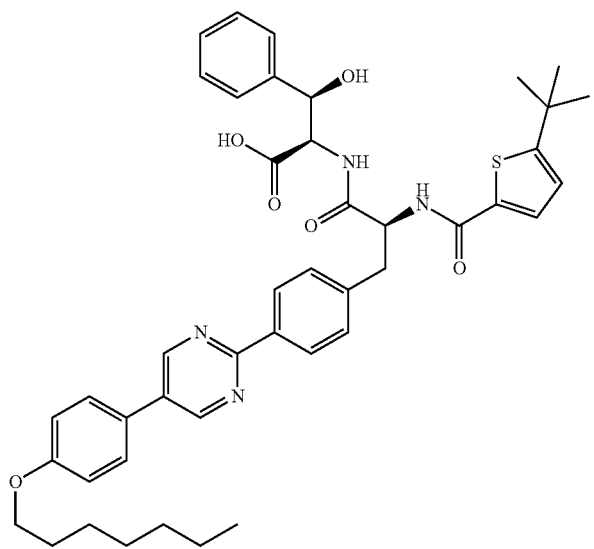
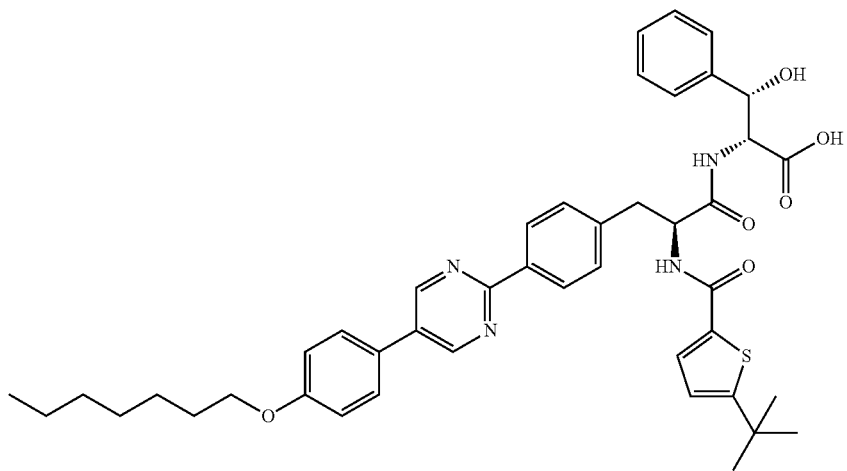
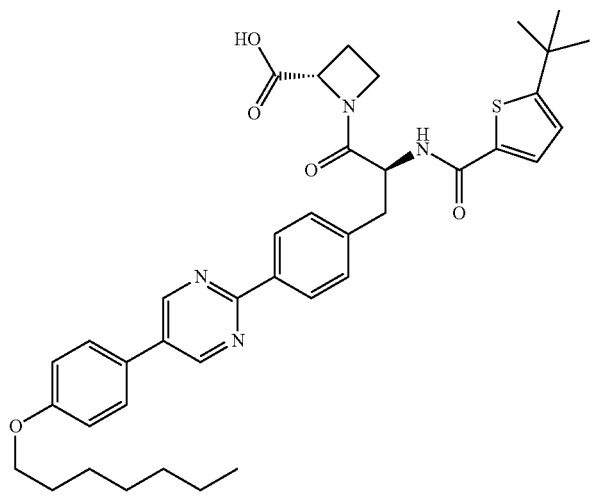
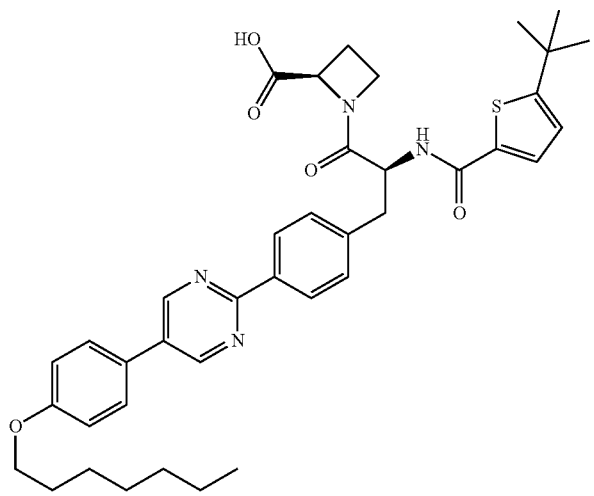

1331
1332
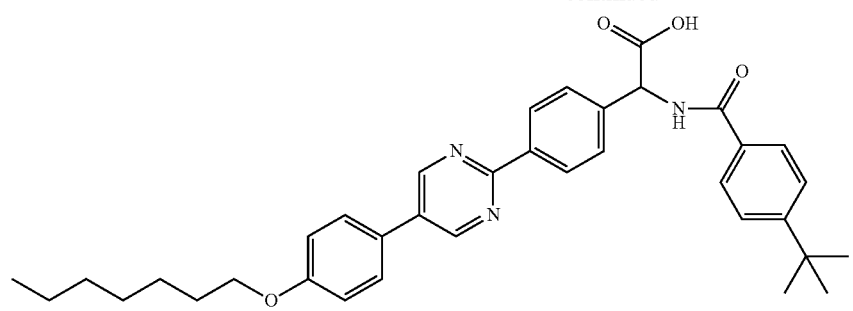
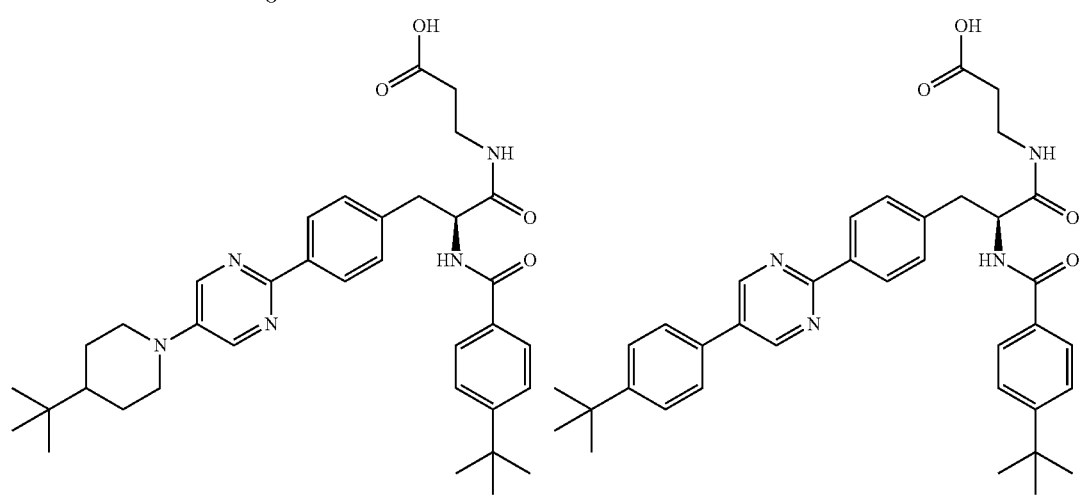
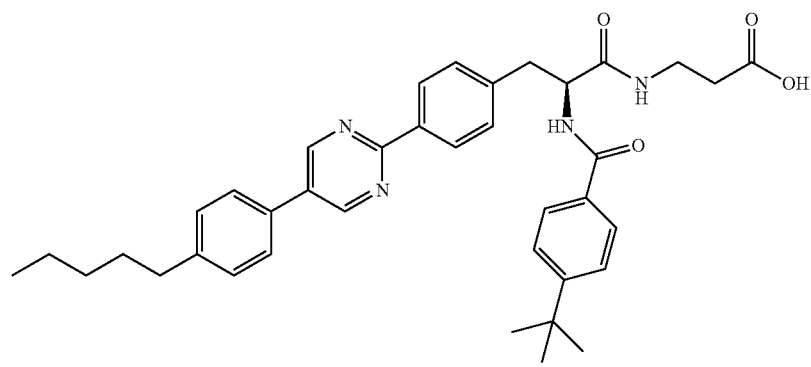
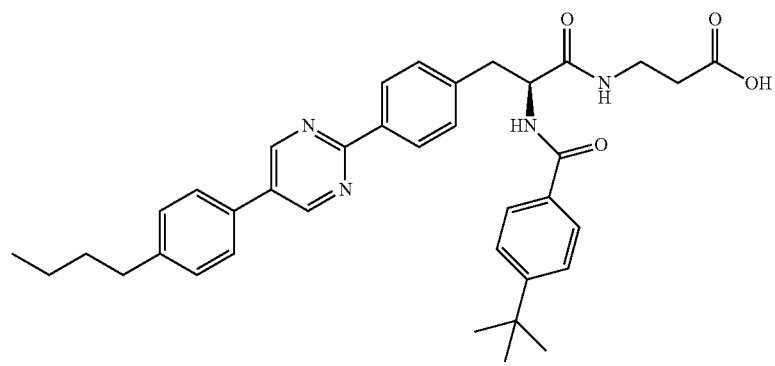

1333
-continued
1334
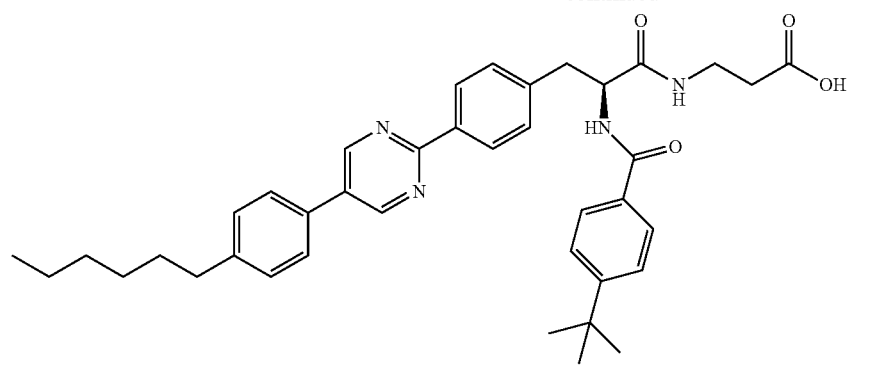
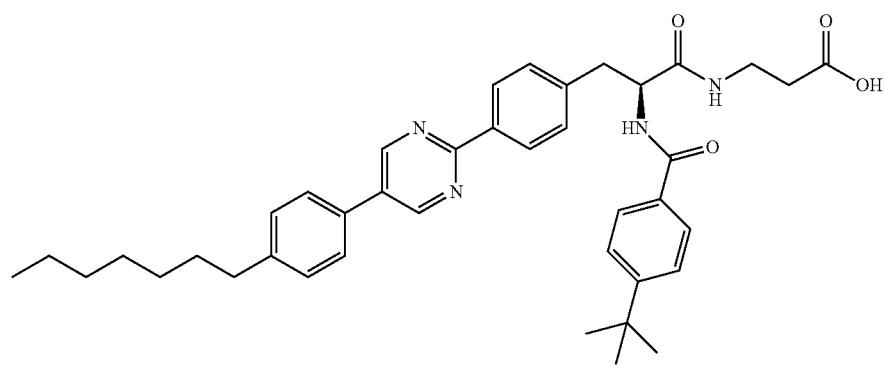
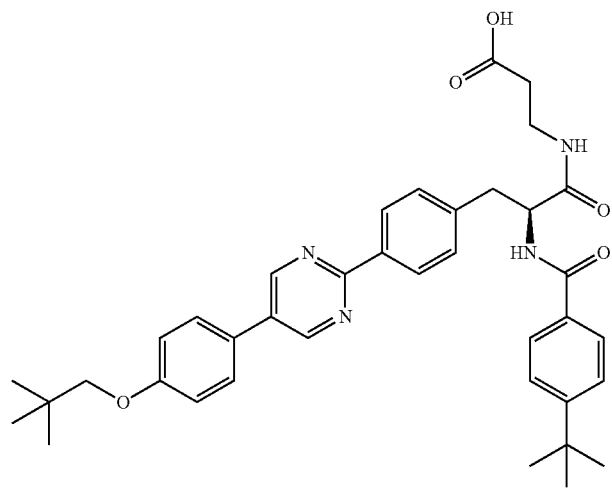
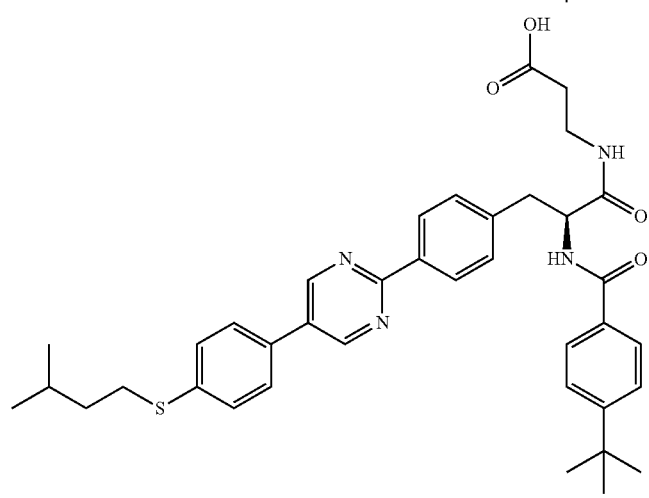

1335
-continued
1336
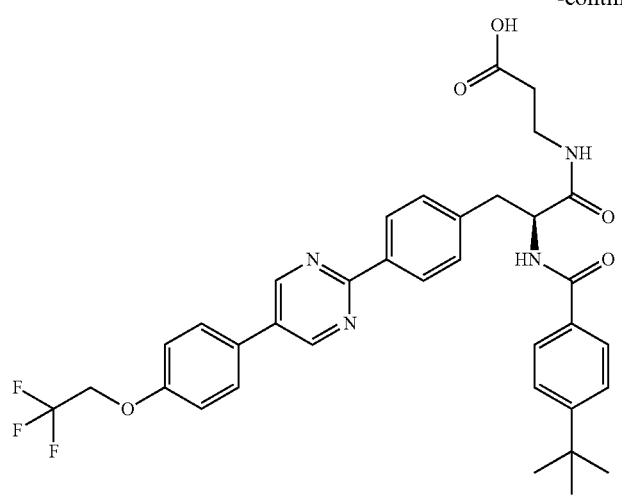
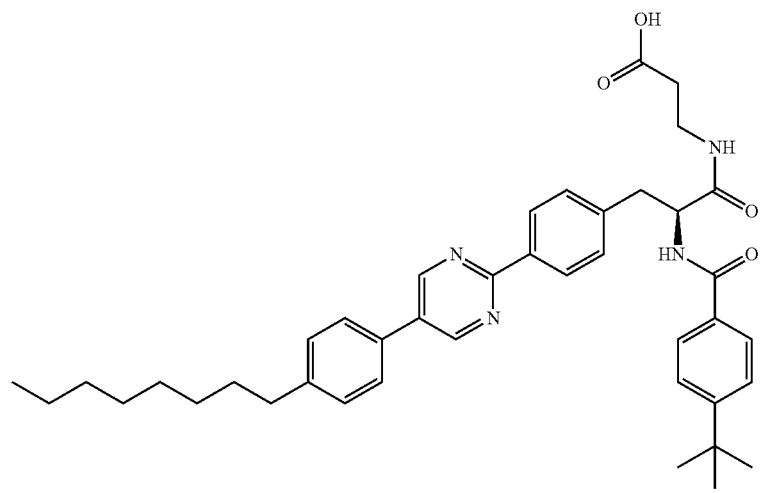
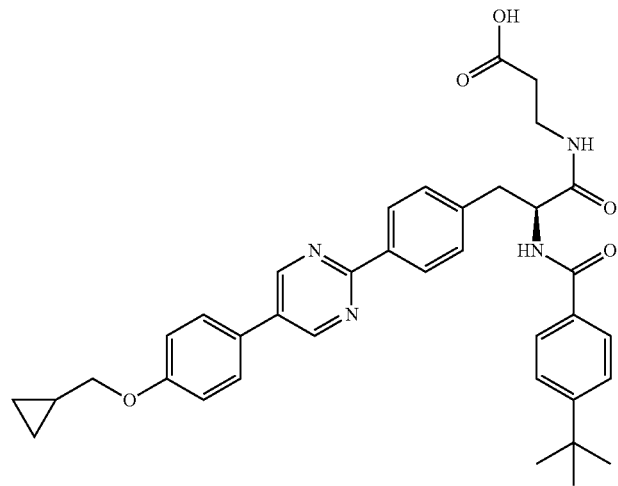

1337 1338
-continued
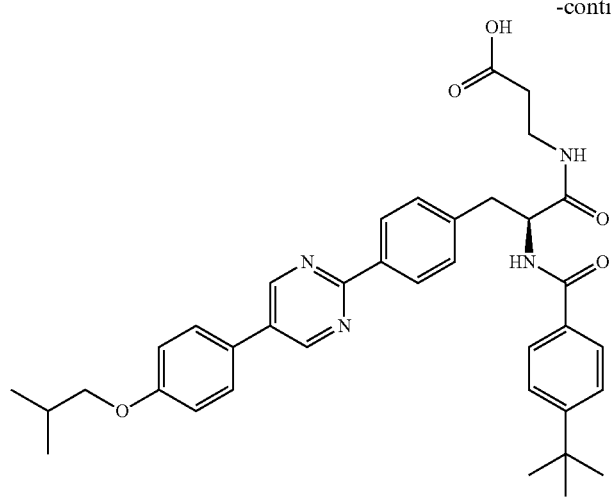
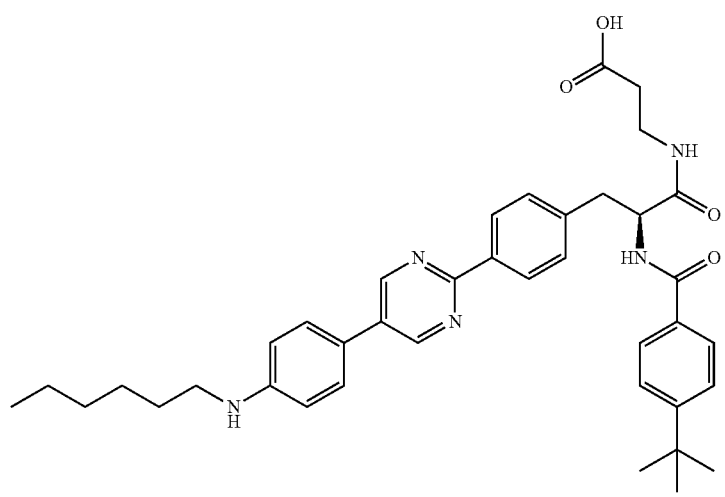
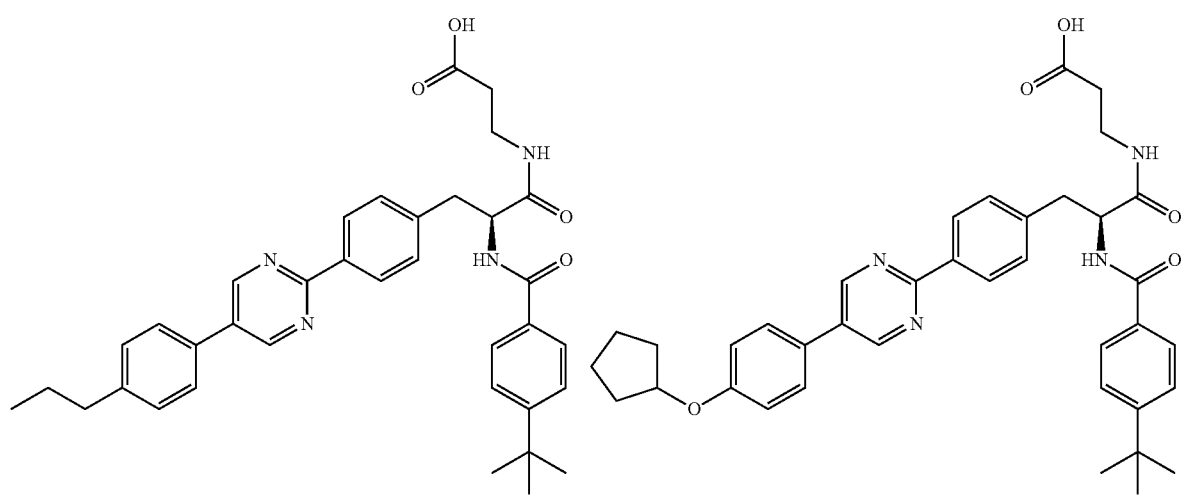

1339 1340
-continued
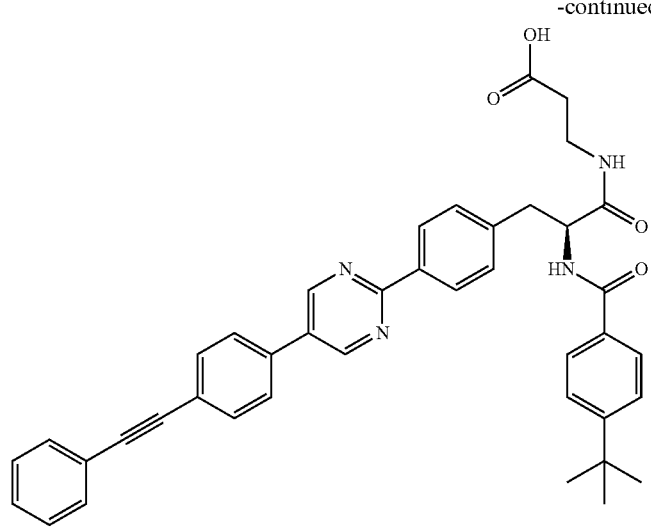
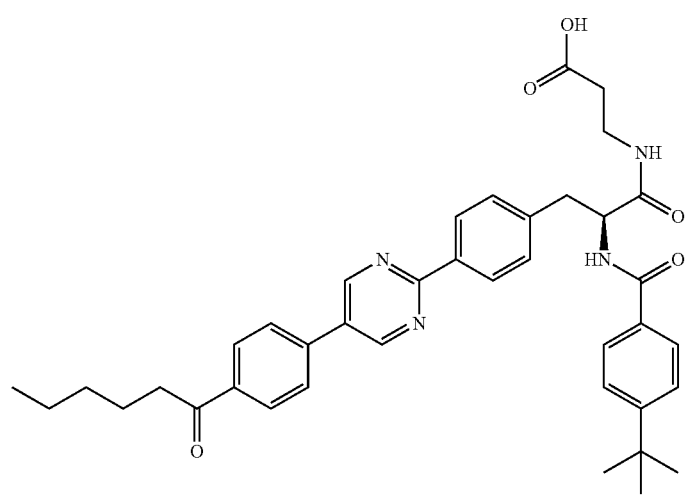
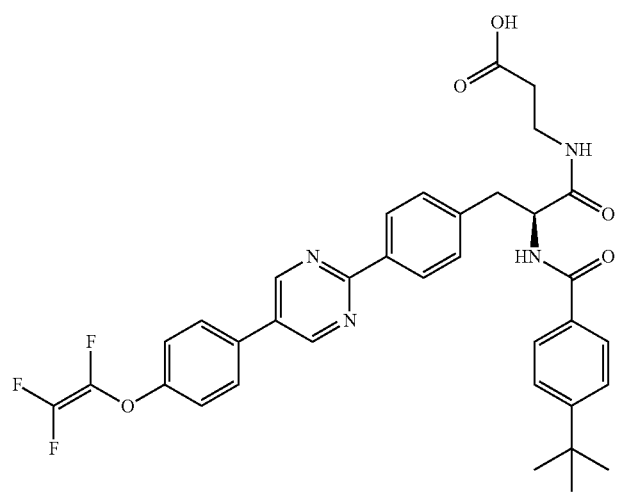

1341
-continued
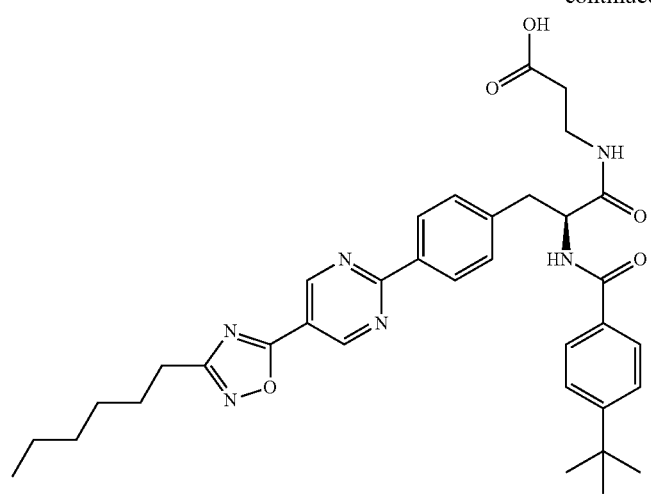
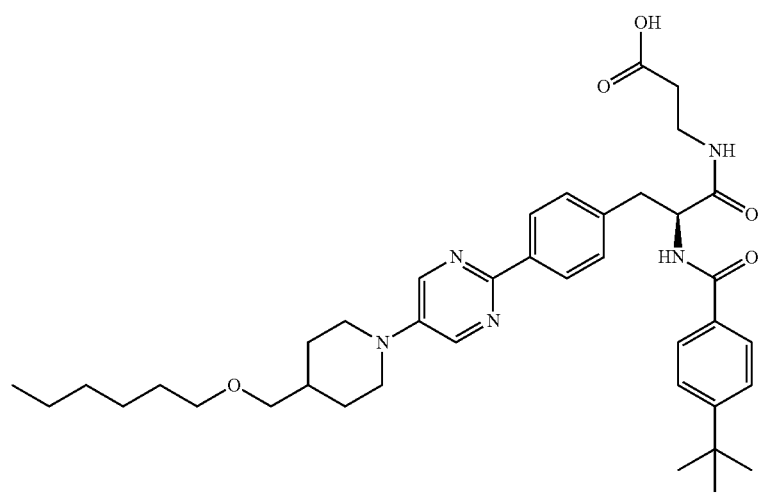
1342
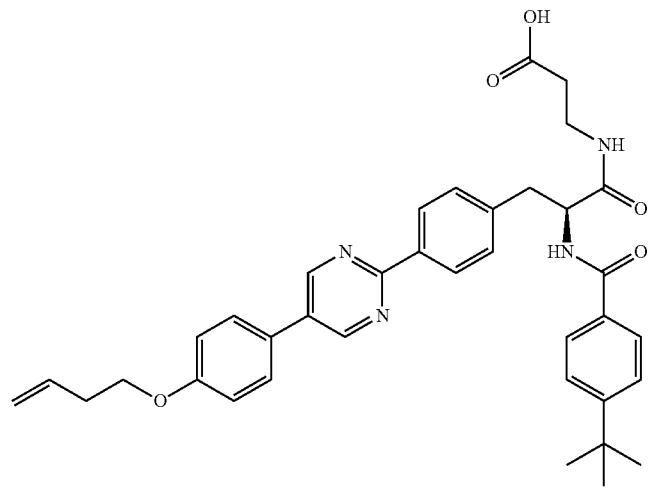

1343 1344
-continued
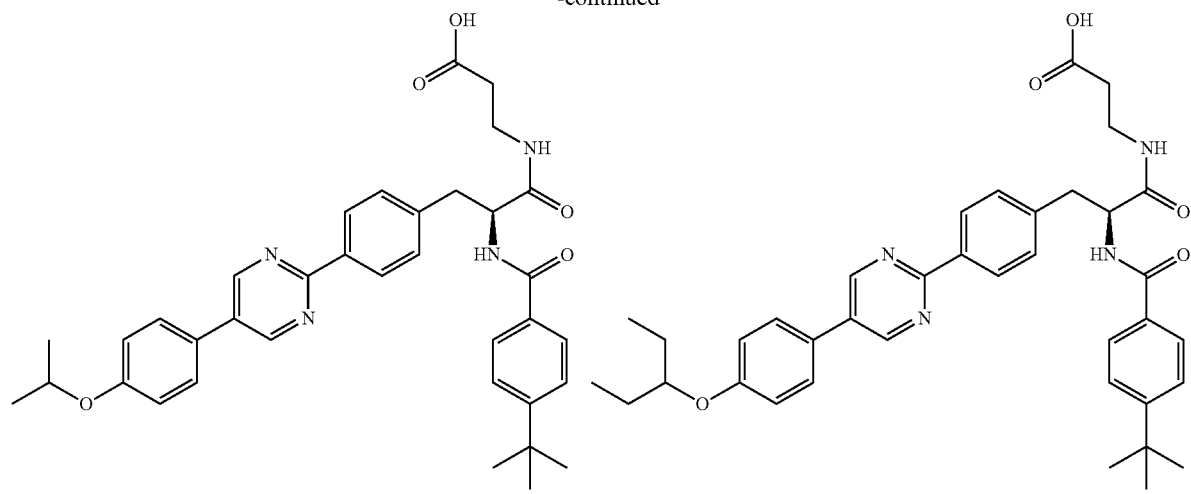
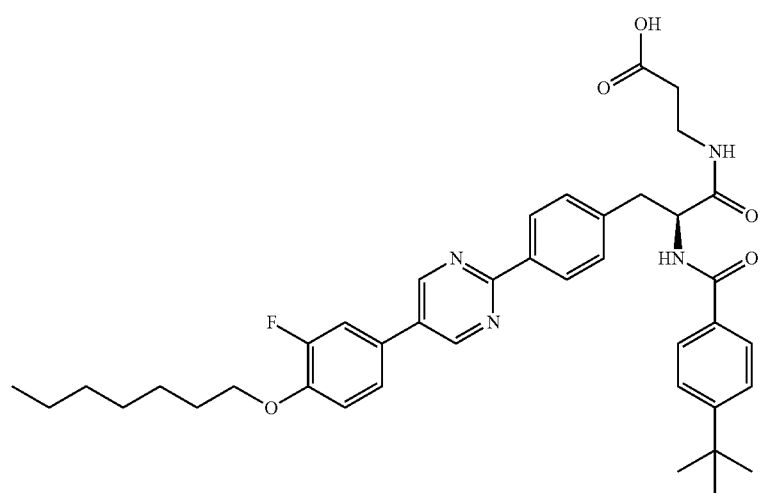
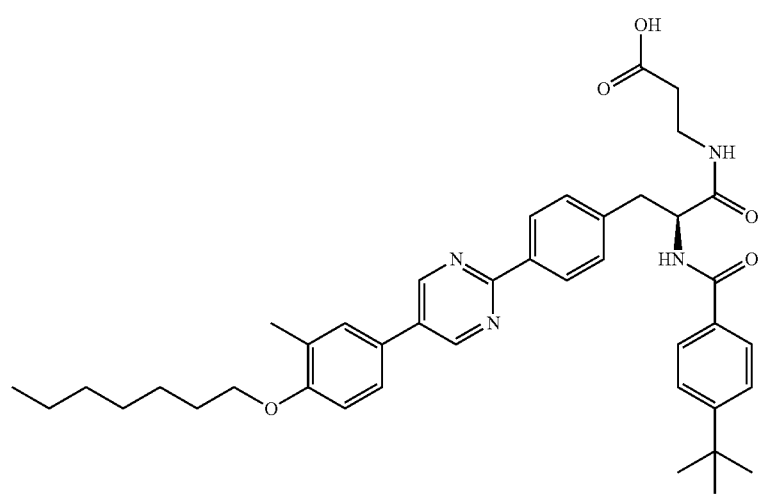

-continued
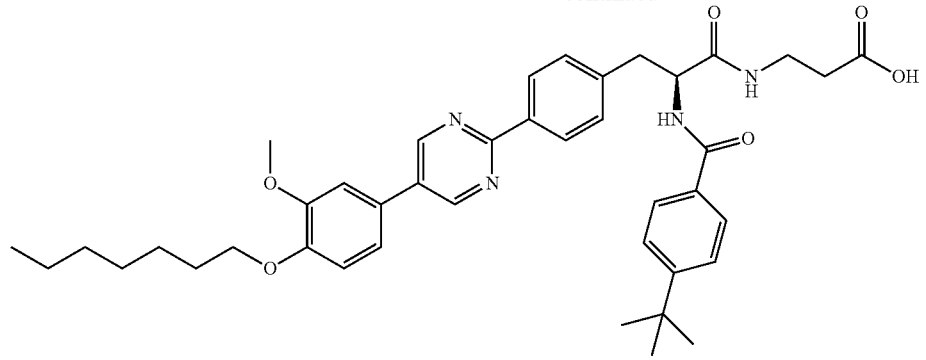
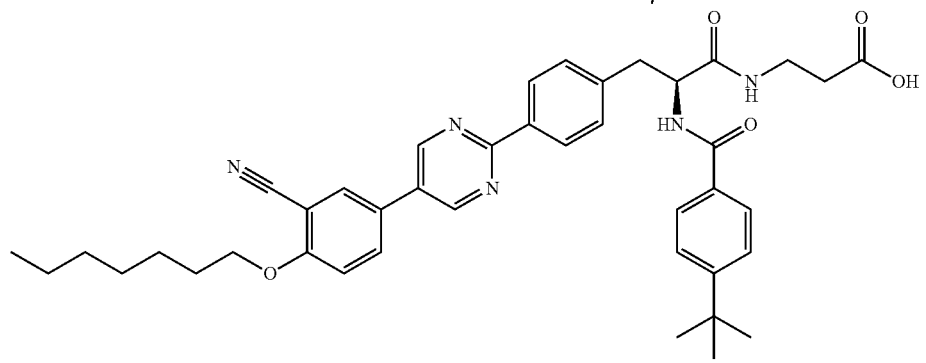
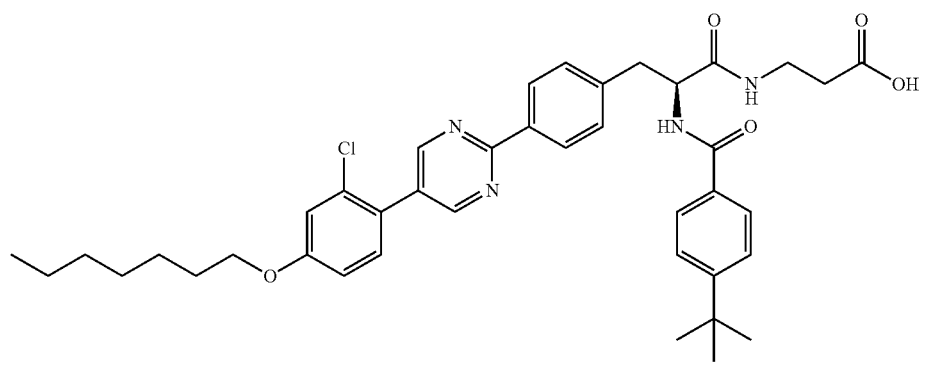
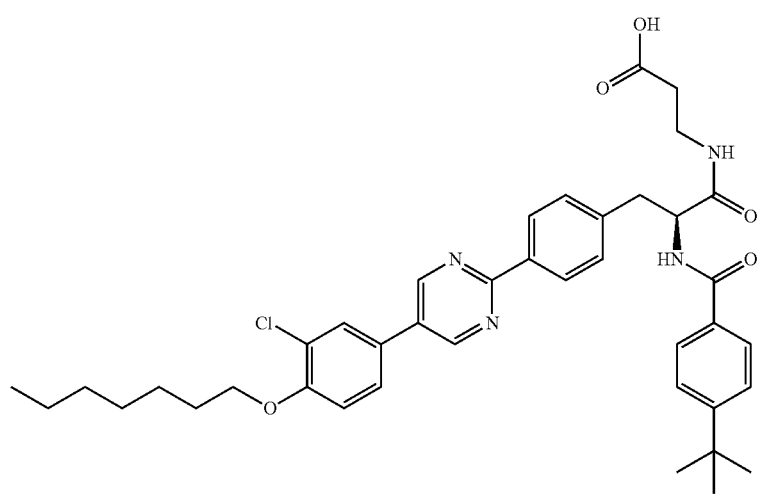

-continued
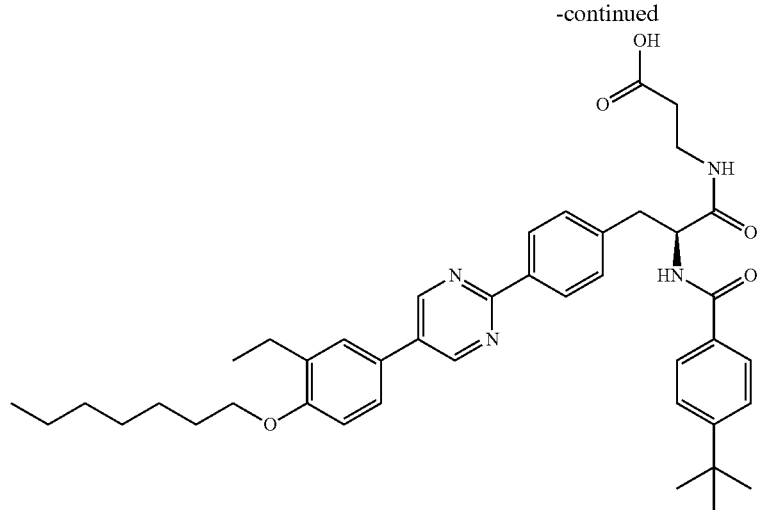
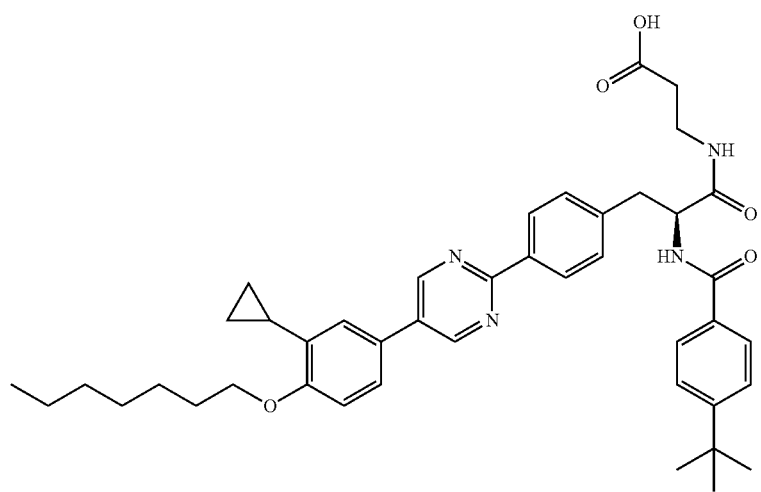
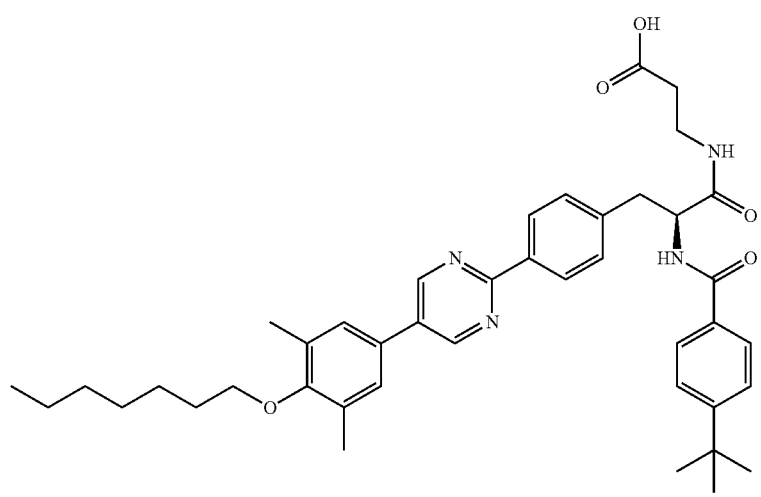

-continued
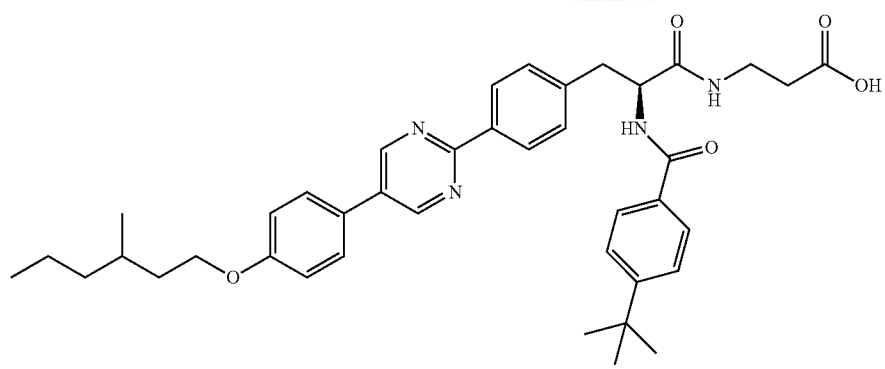
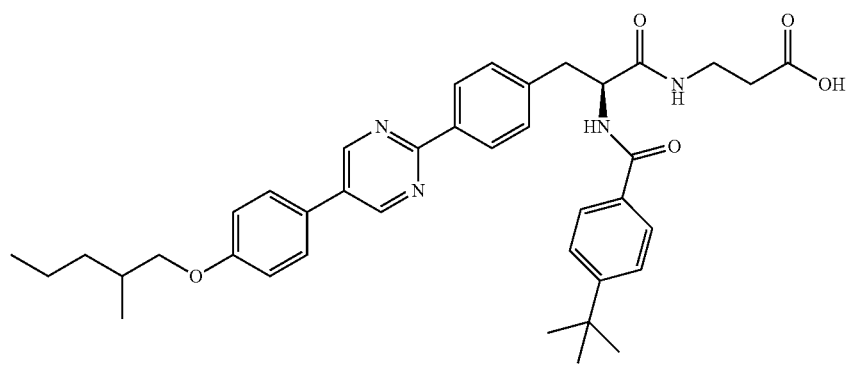
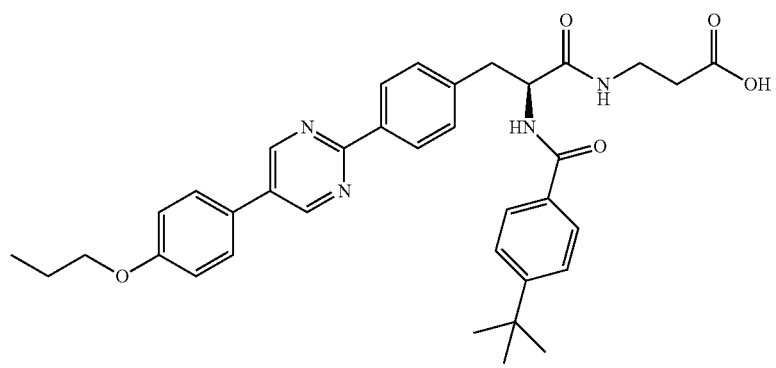
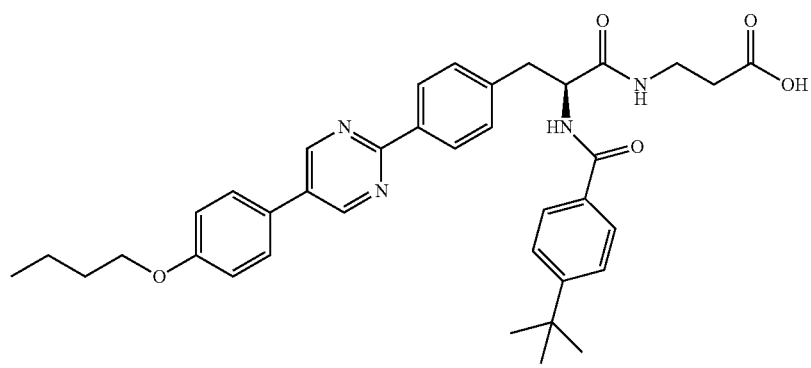

| 1351 | 1352 |
-continued
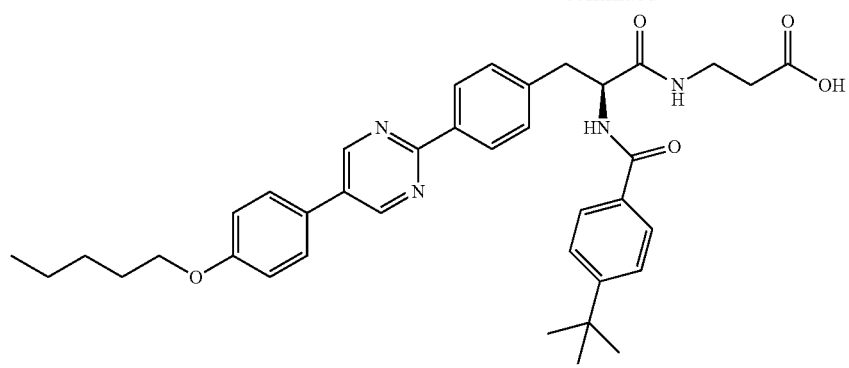
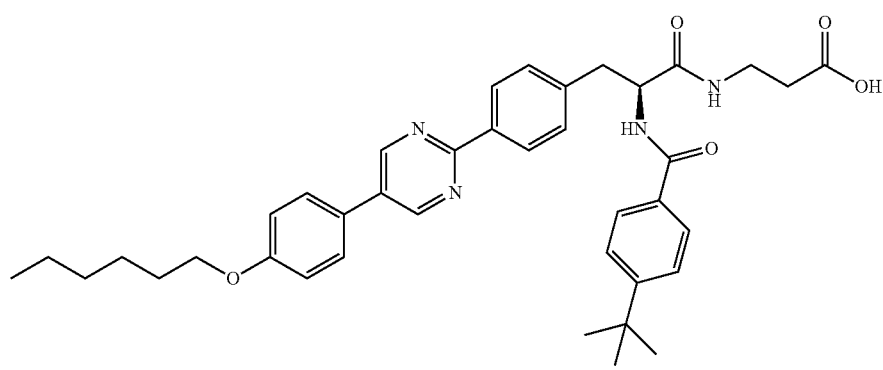
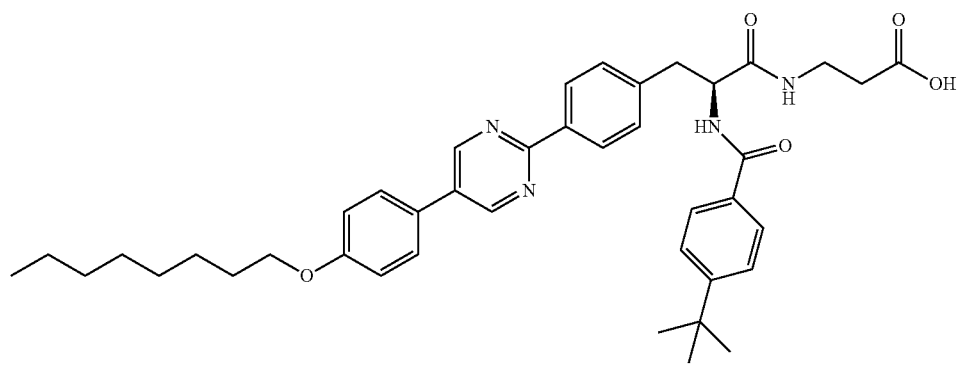
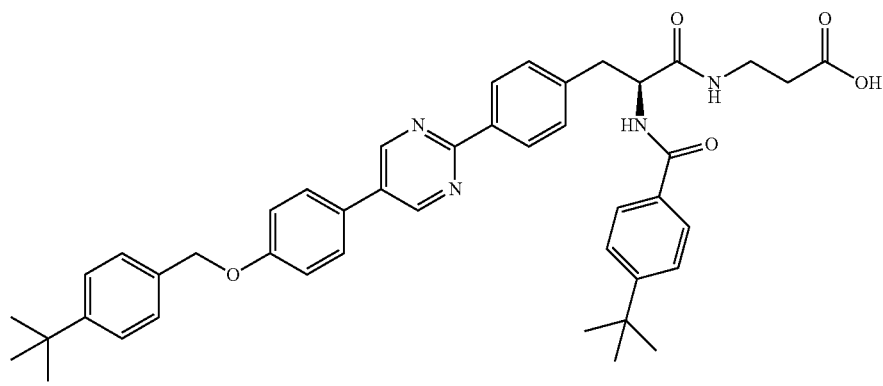

-continued
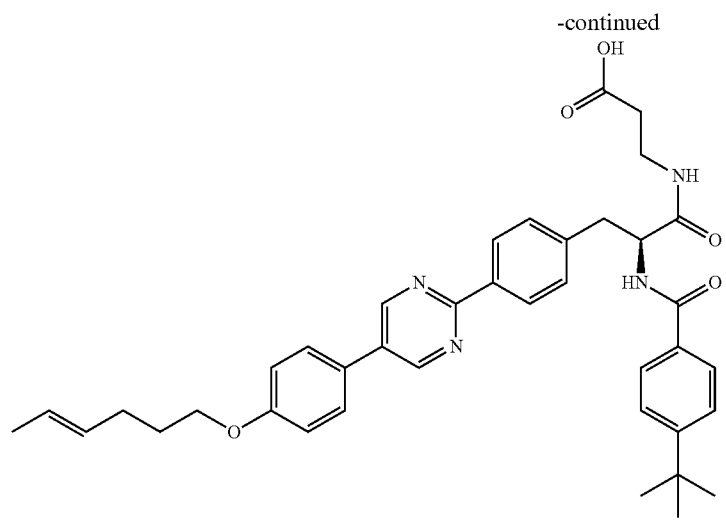
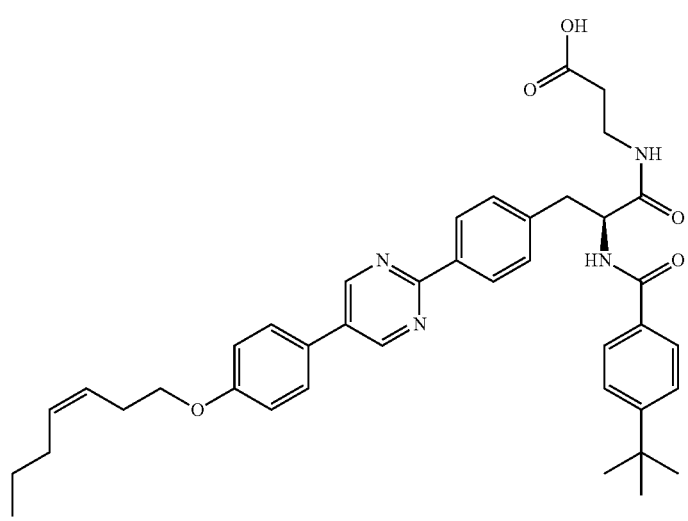
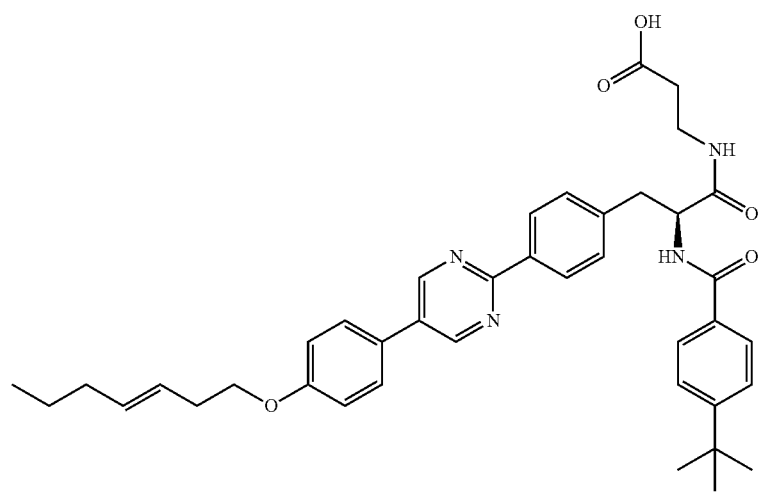

1355 1356
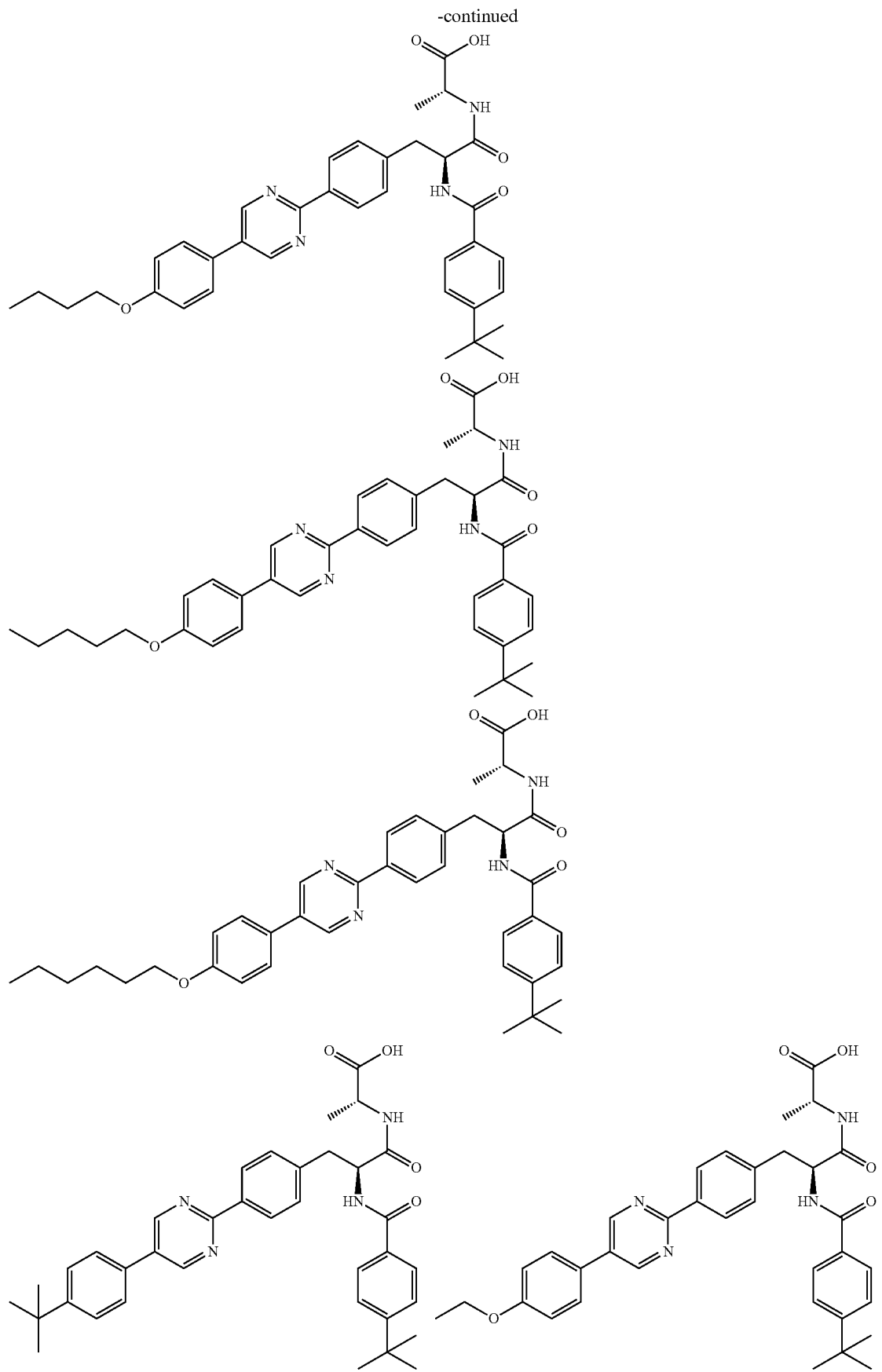

-continued
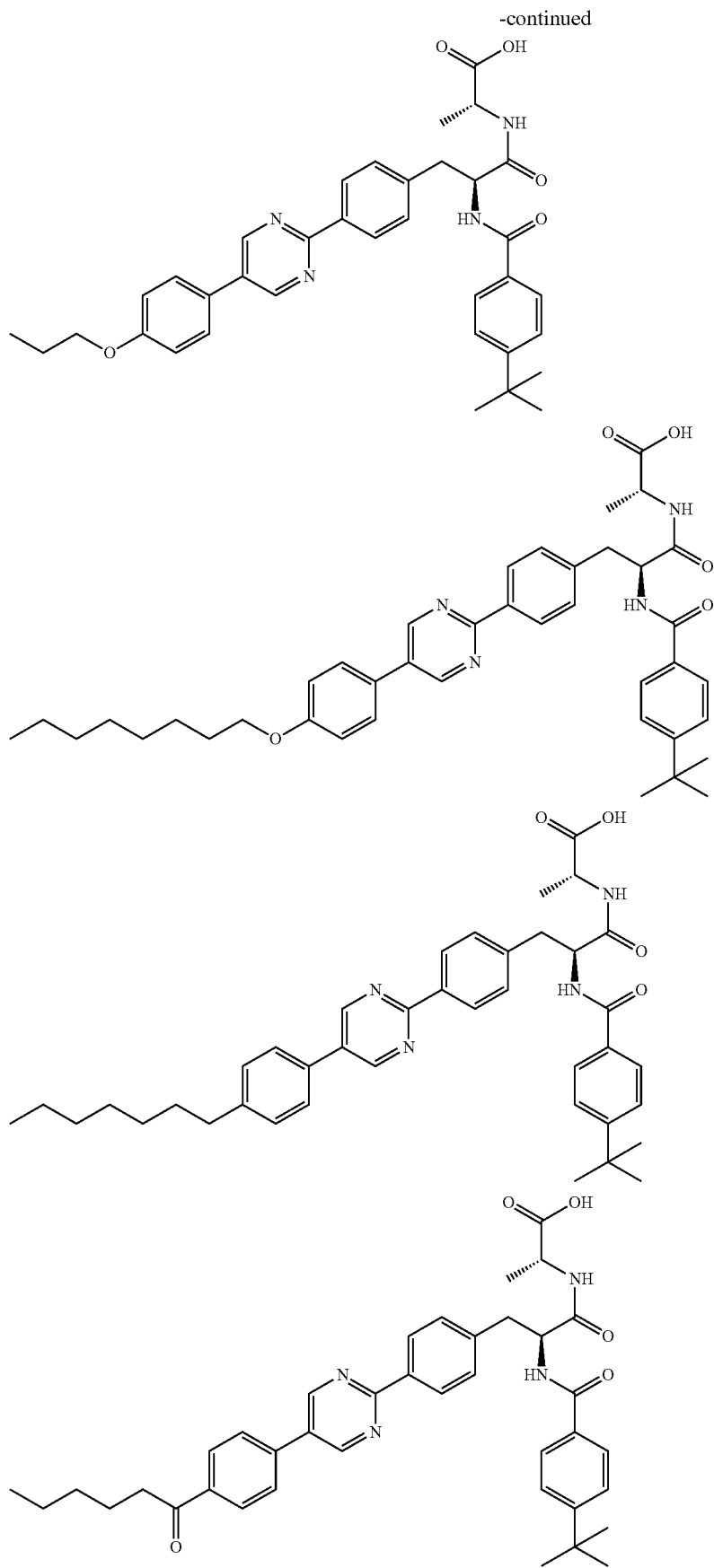

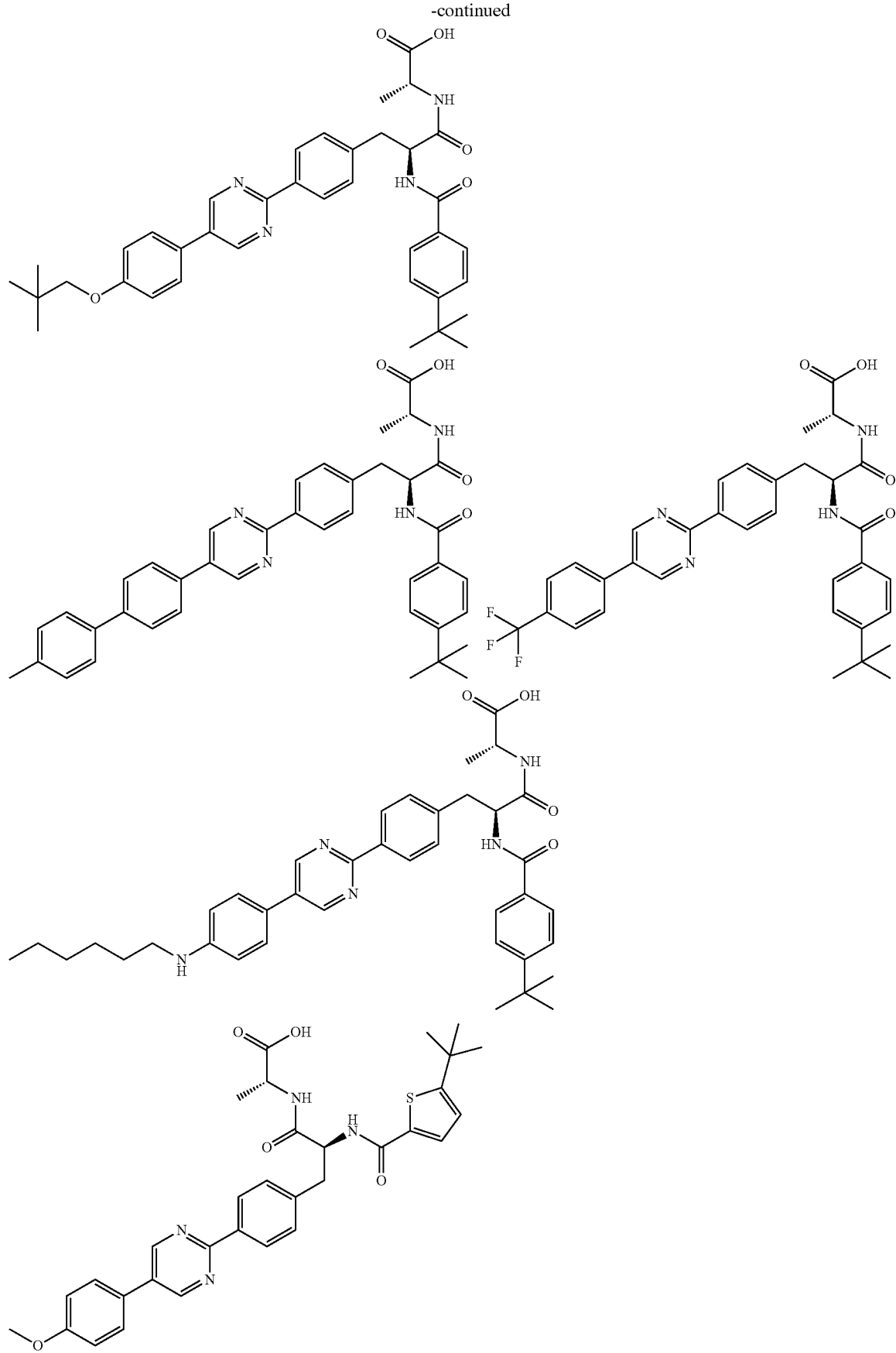

1361 -continued 1362
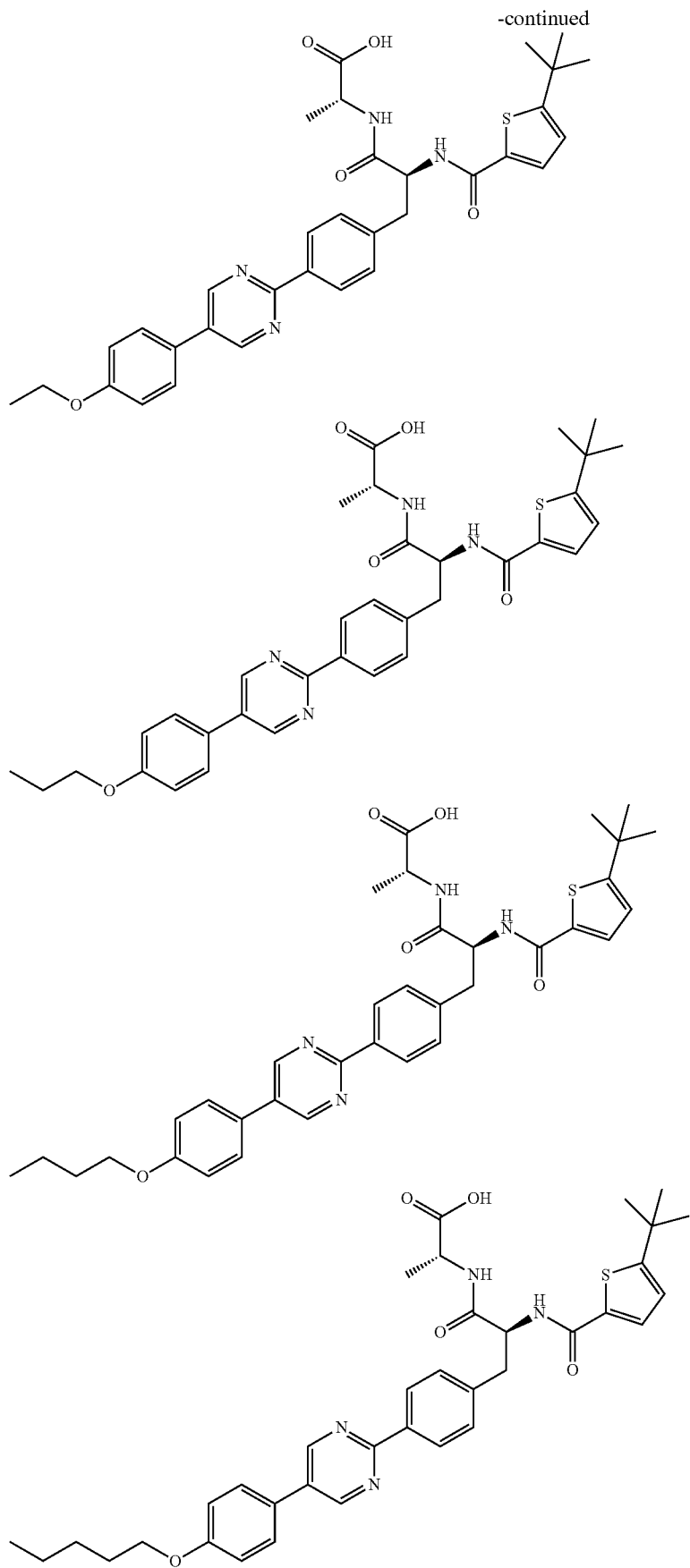

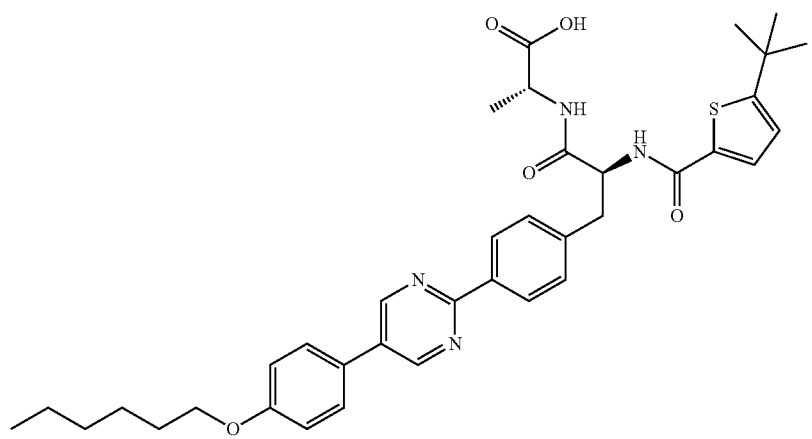
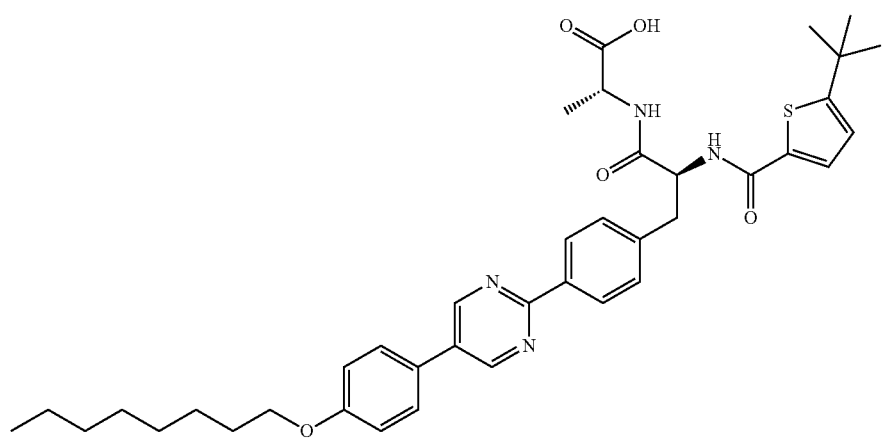
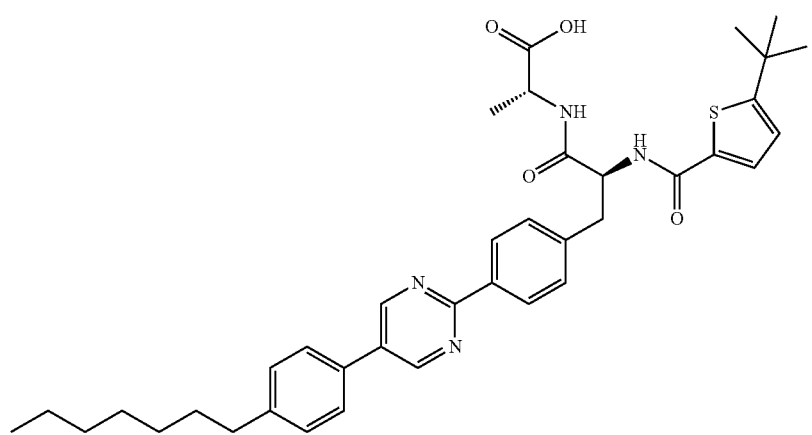

1365
-continued
1366
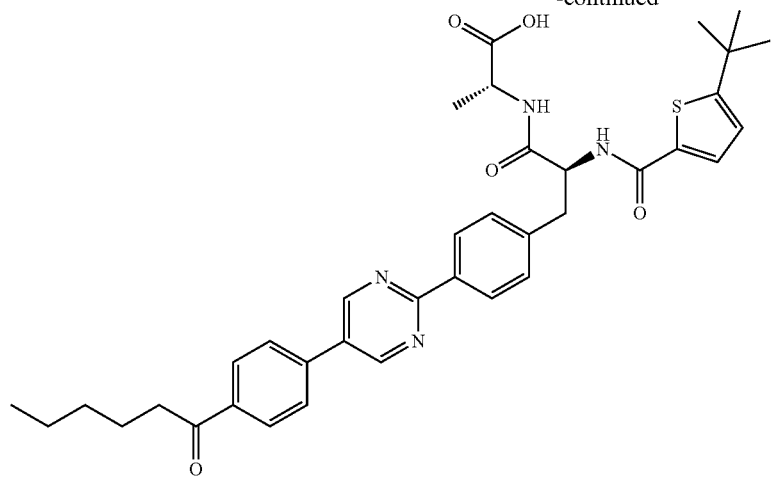
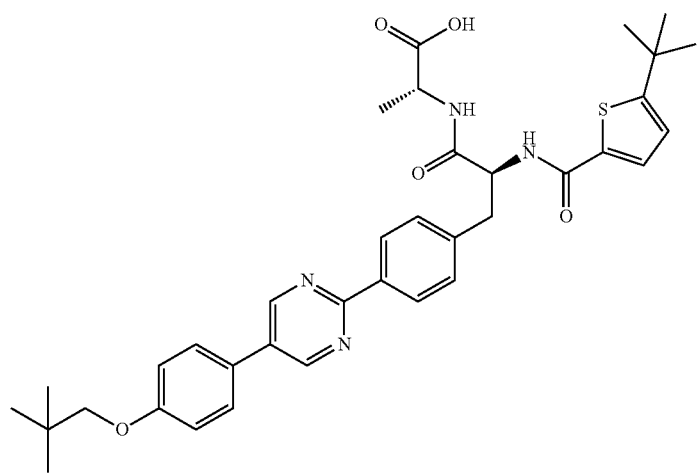
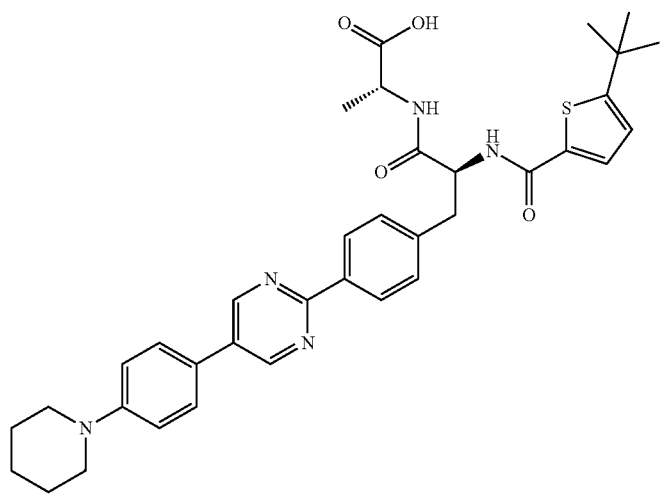

1367
-continued
1368
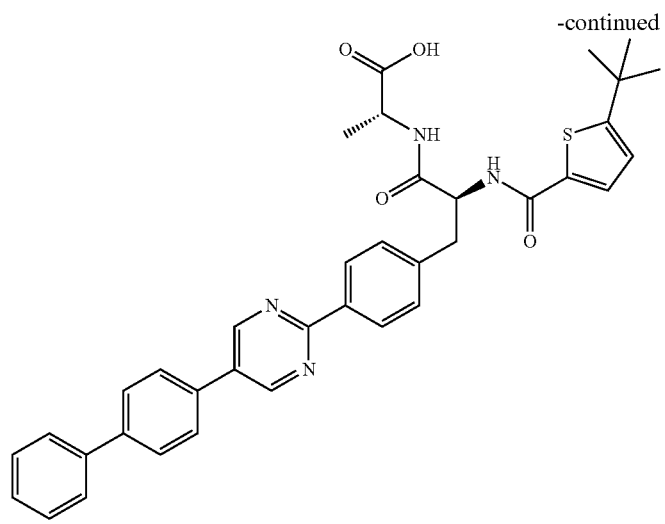
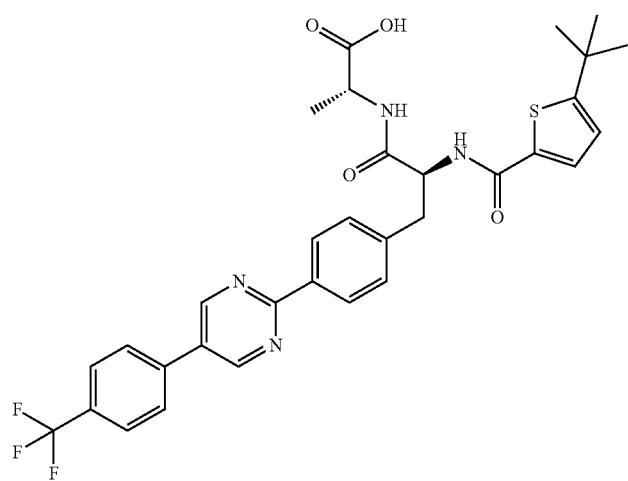
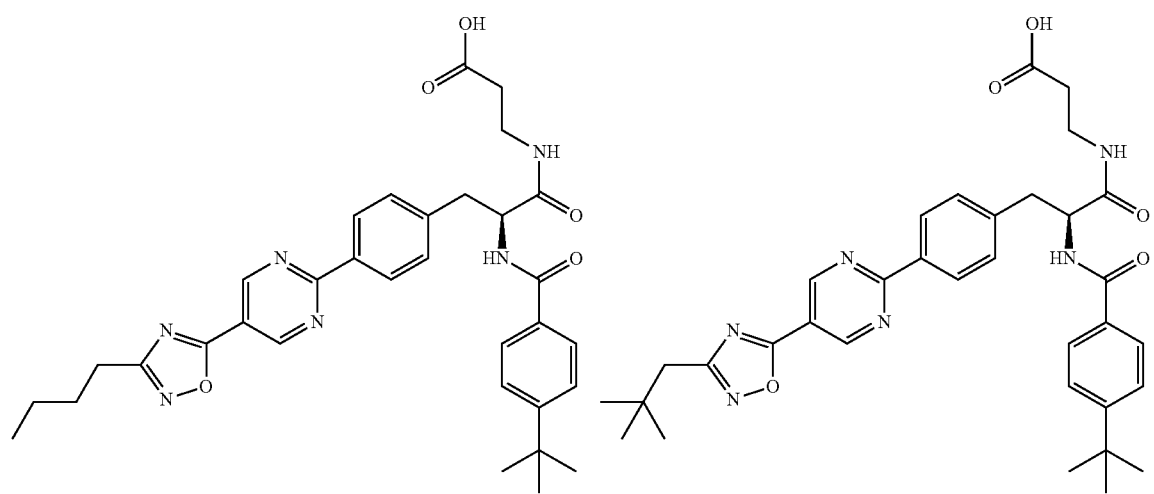

-continued
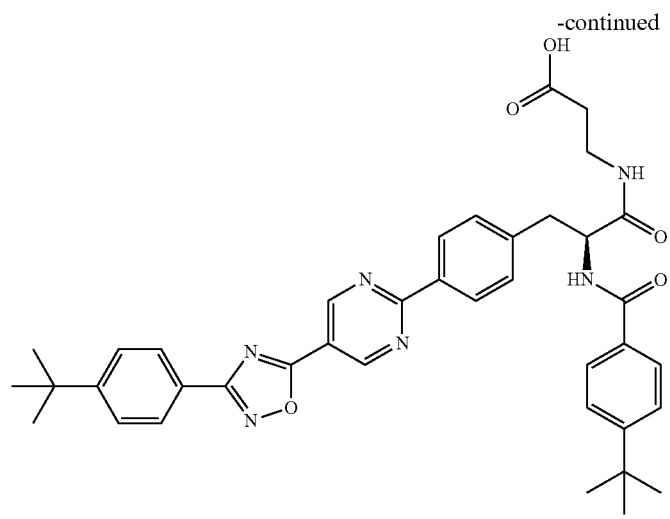
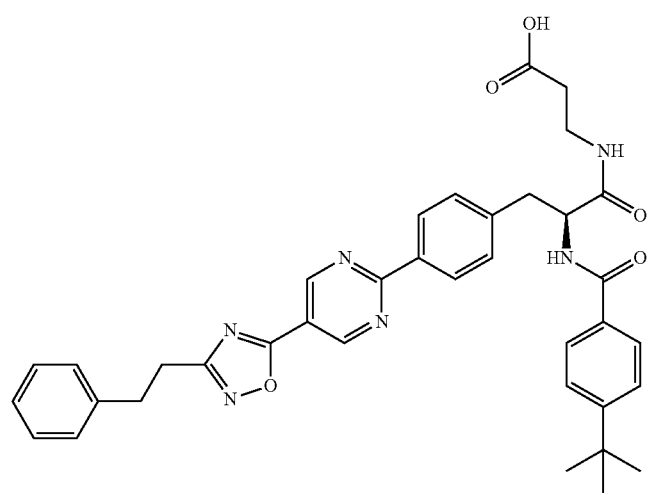
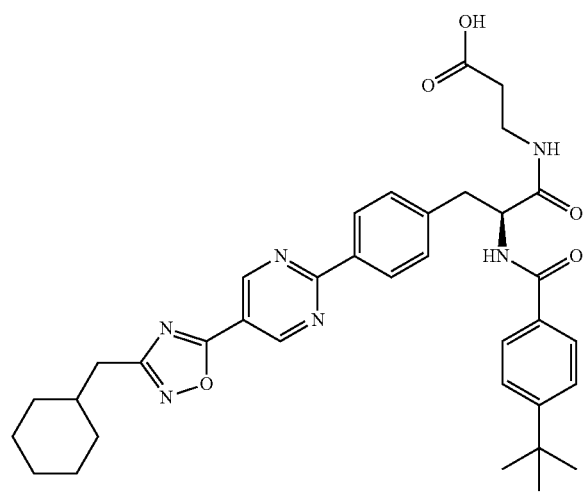

1371
1372
-continued
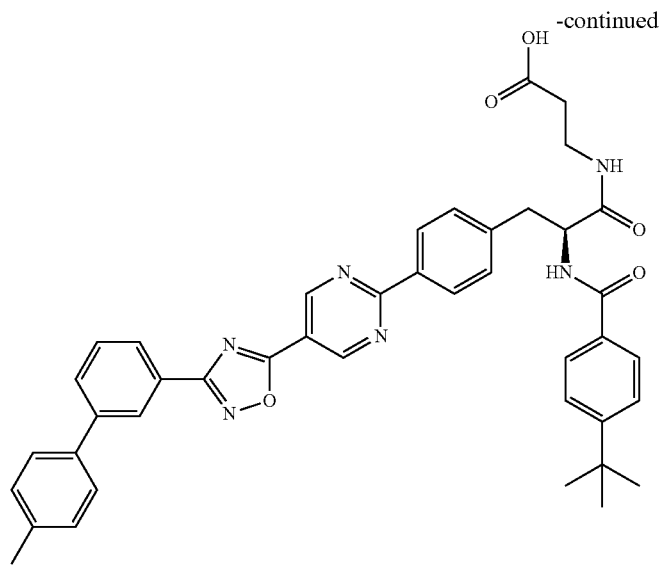
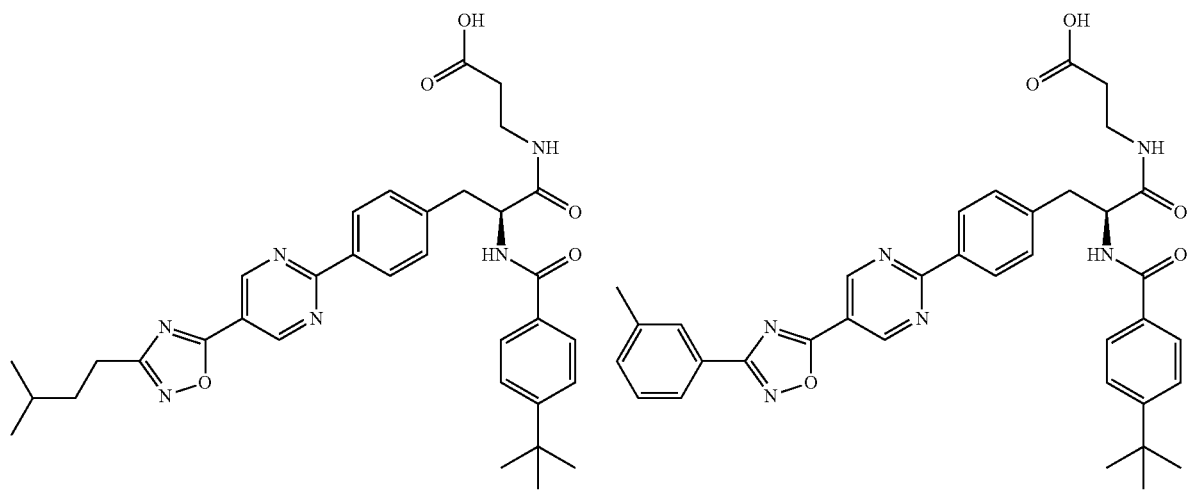
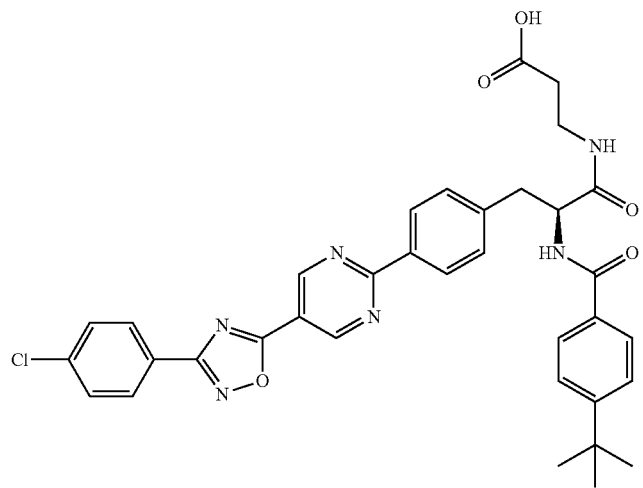

1373
-continued
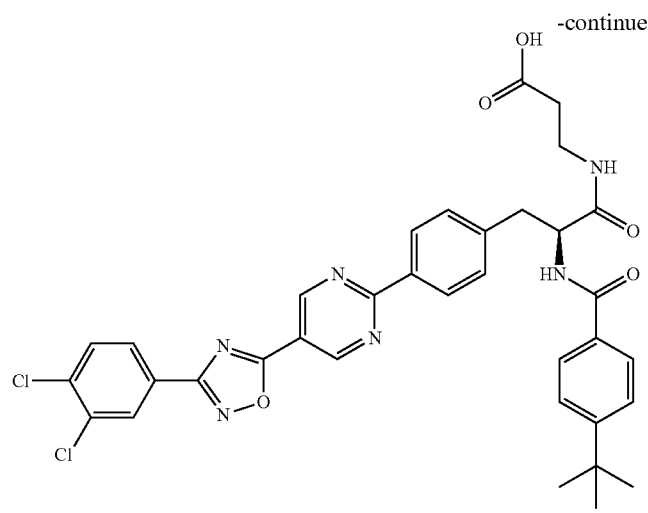
1374
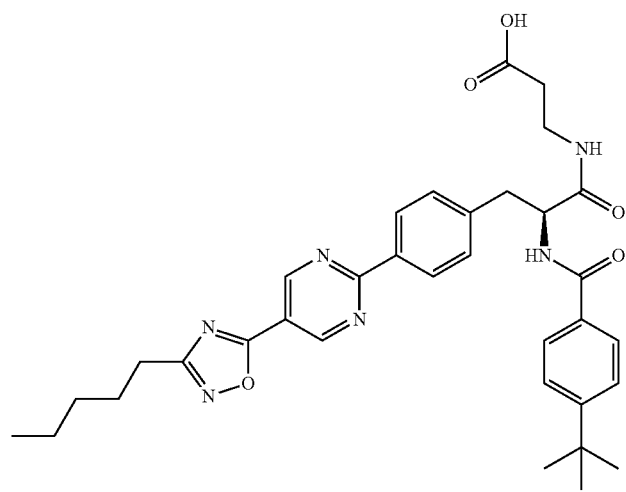
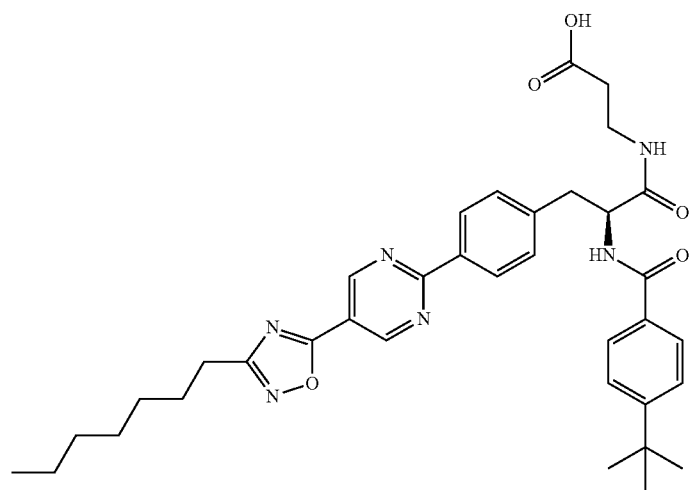

-continued
1375
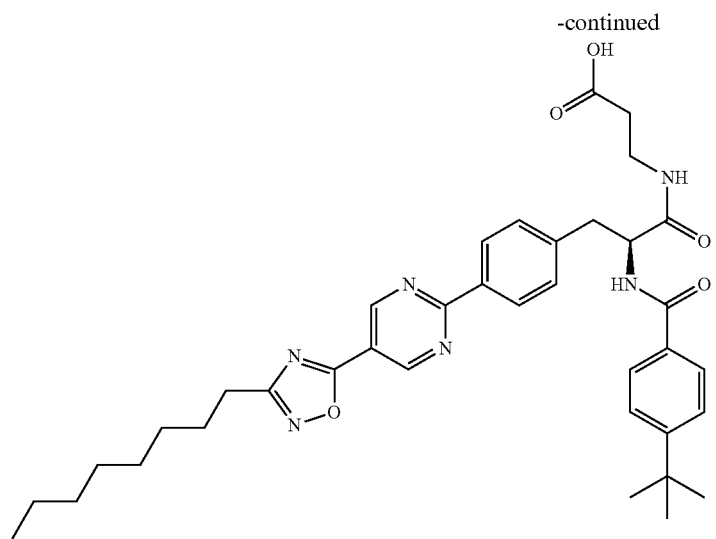
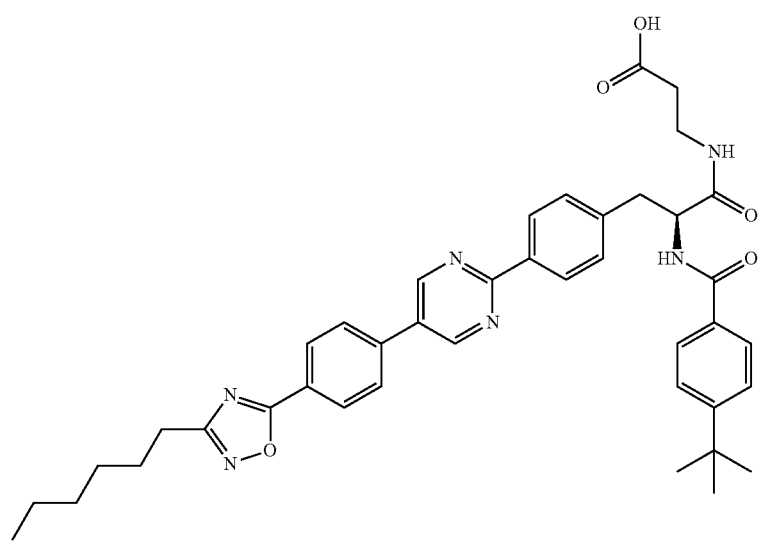
1376
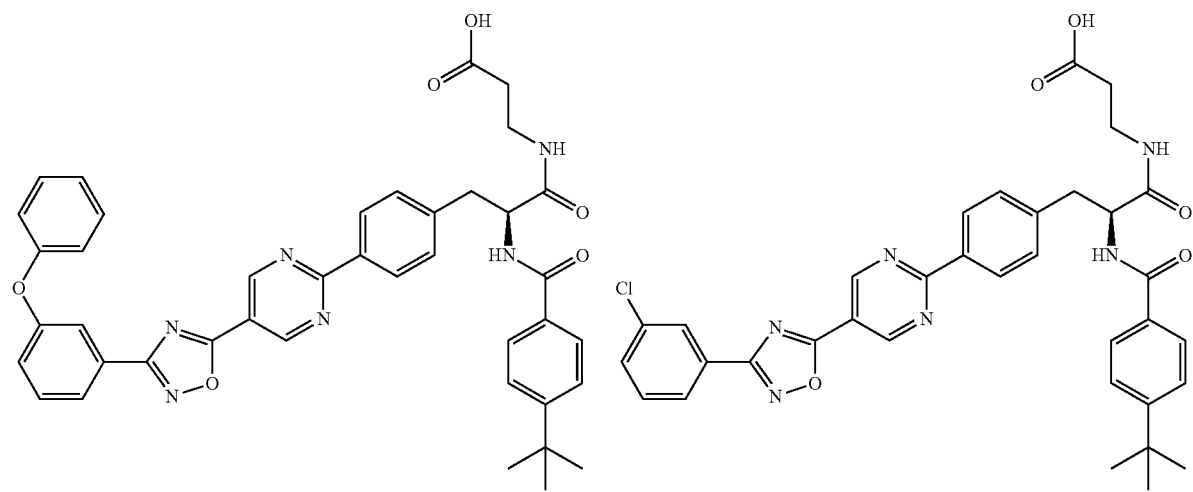

-continued
1377
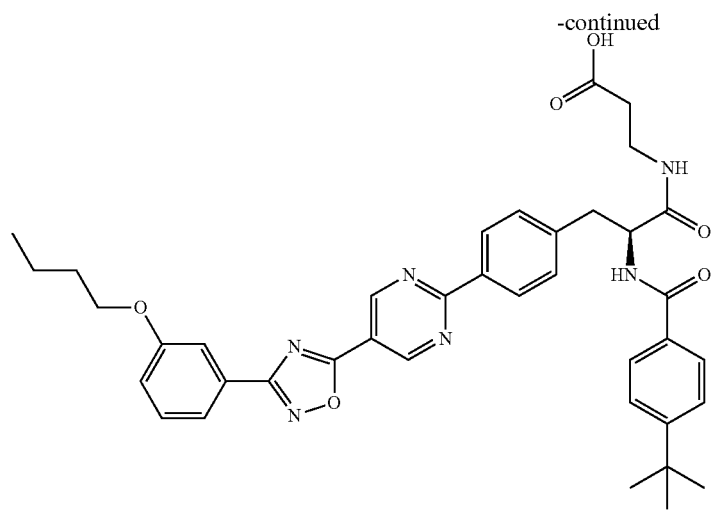
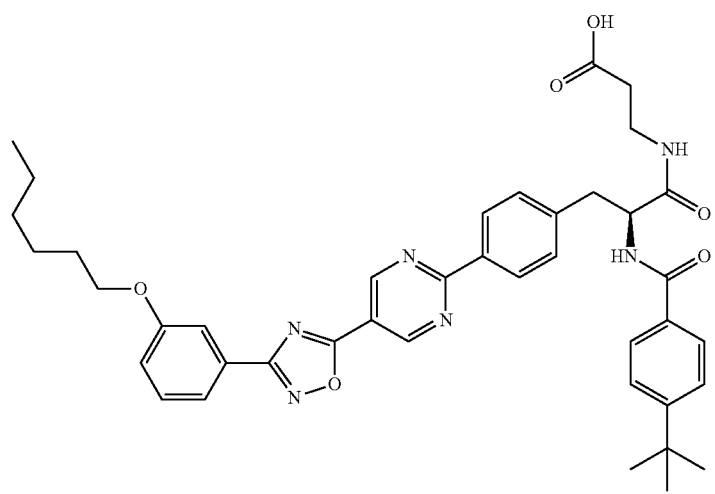
1378
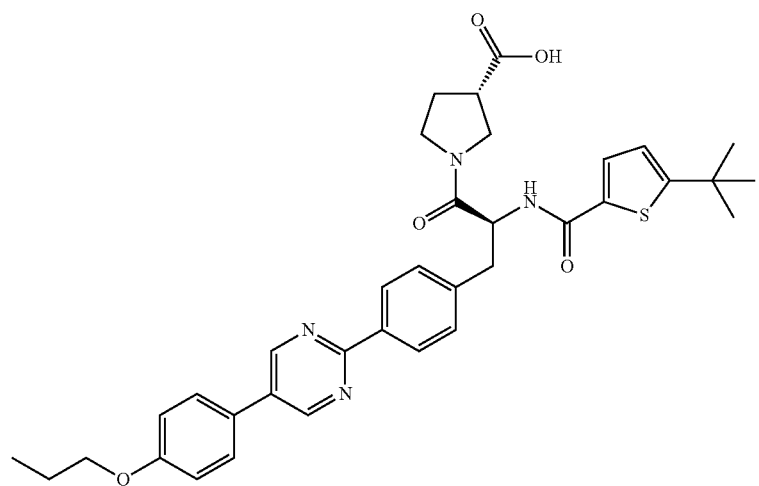

-continued
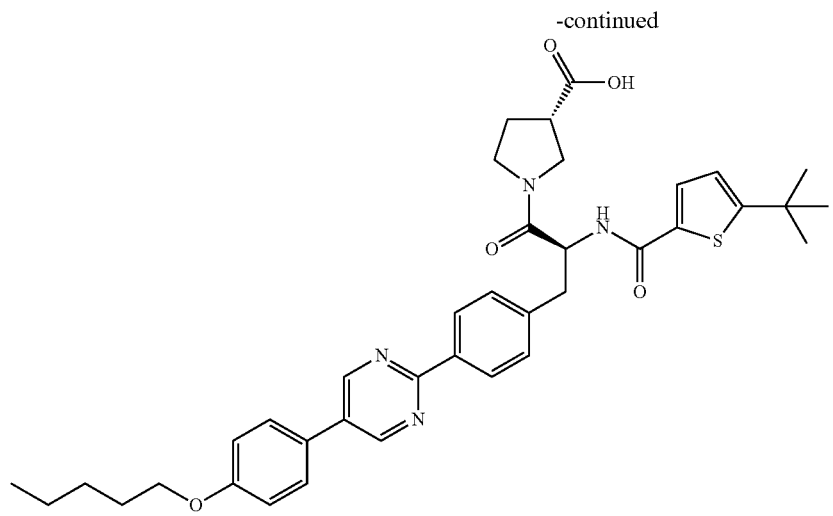
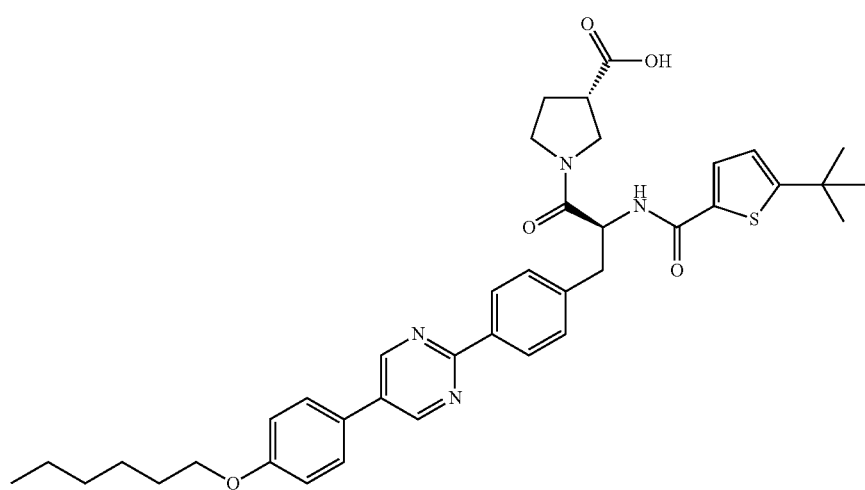
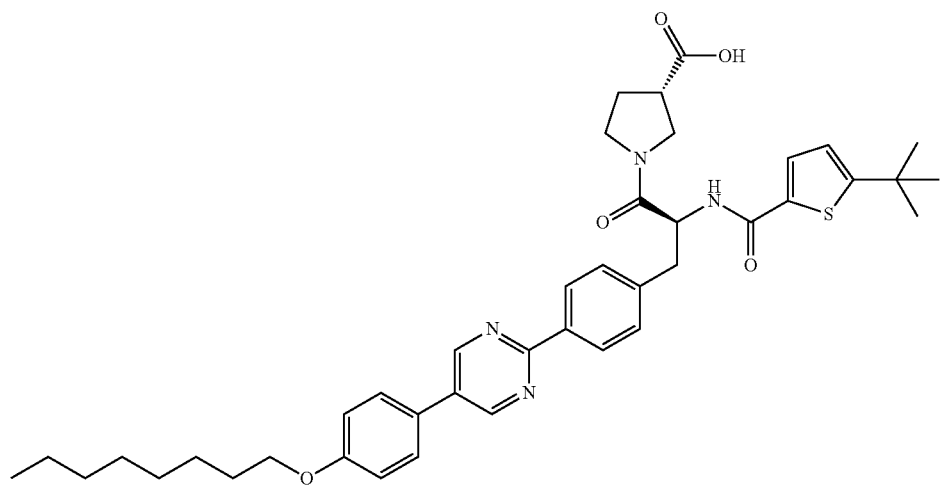

1381
-continued
1382
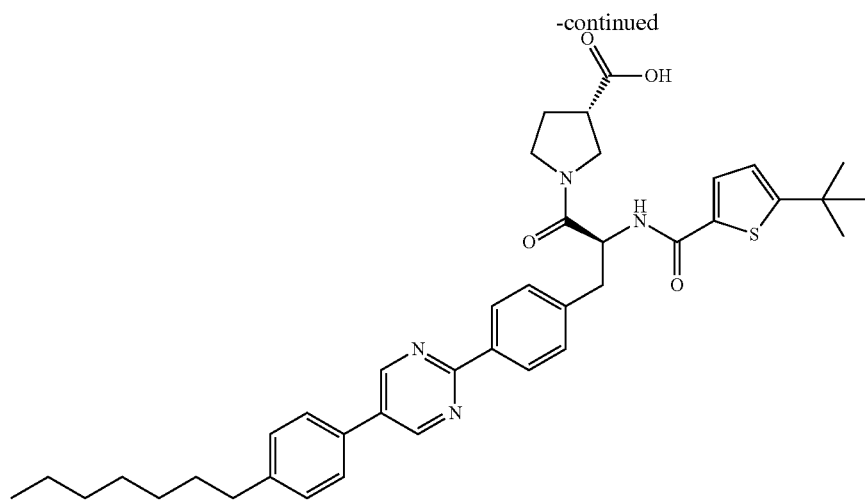
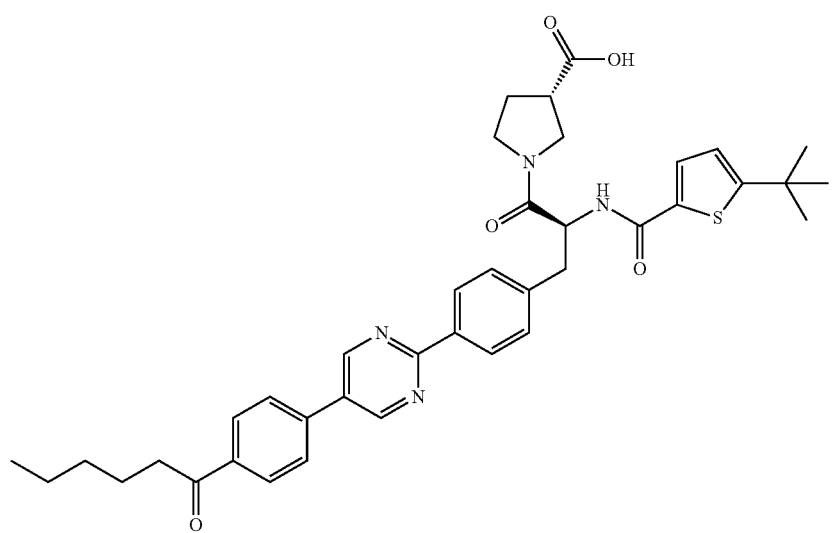
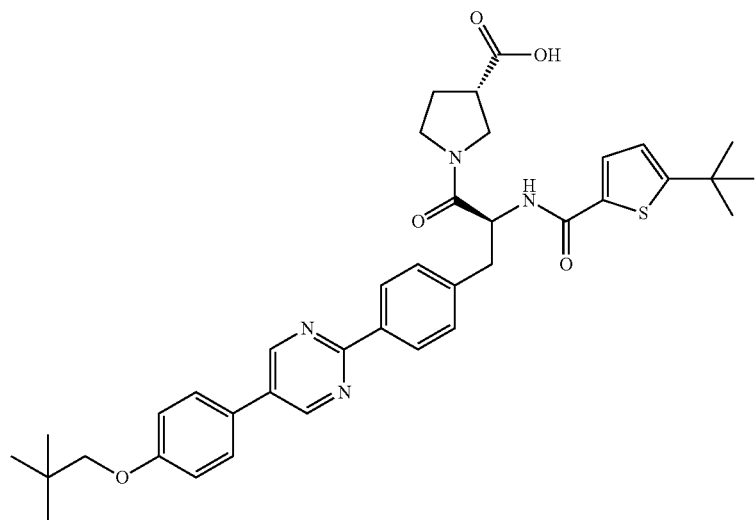

1383
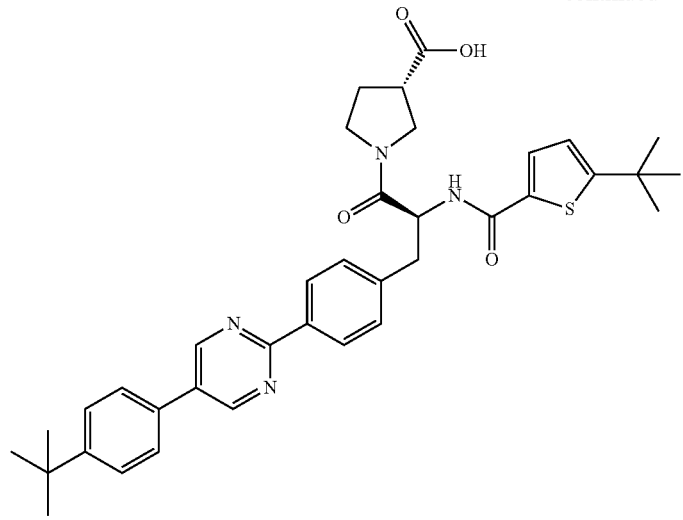
1384
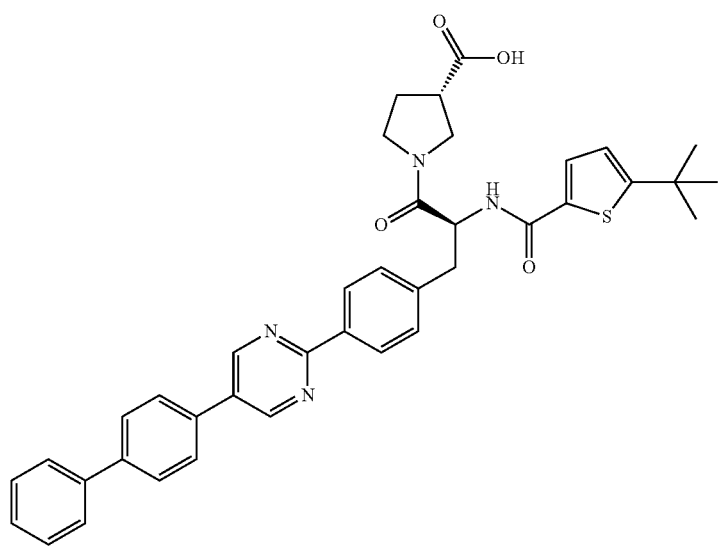
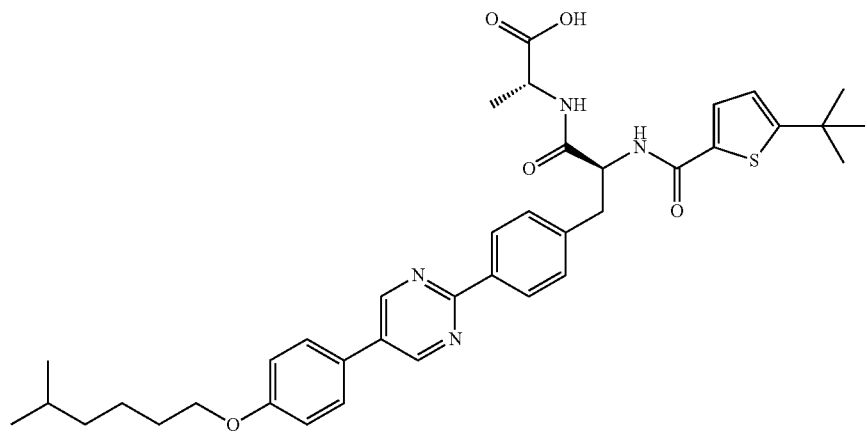

-continued
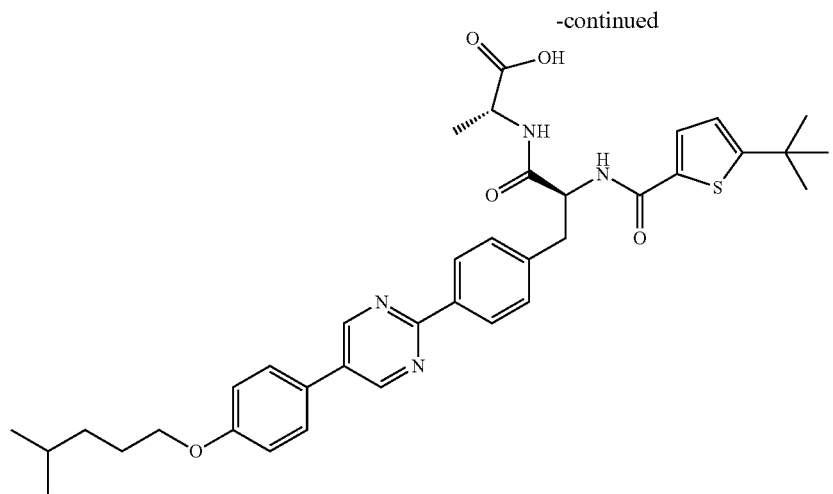
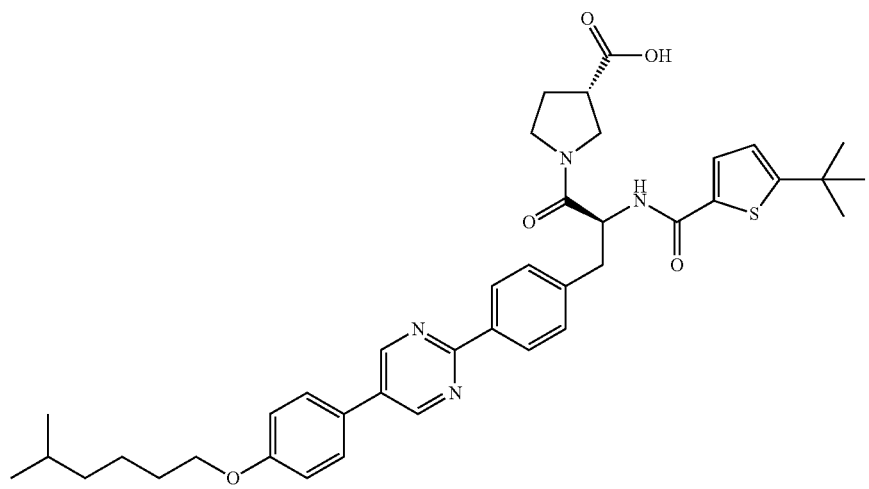
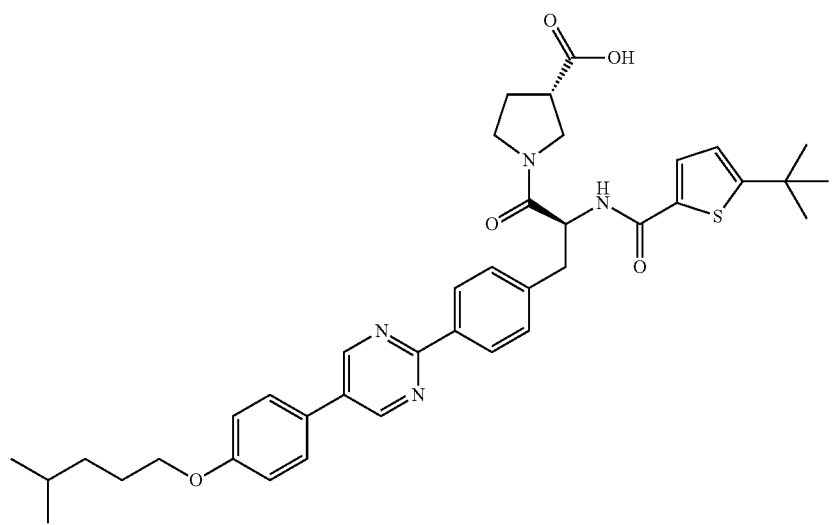

1387
-continued
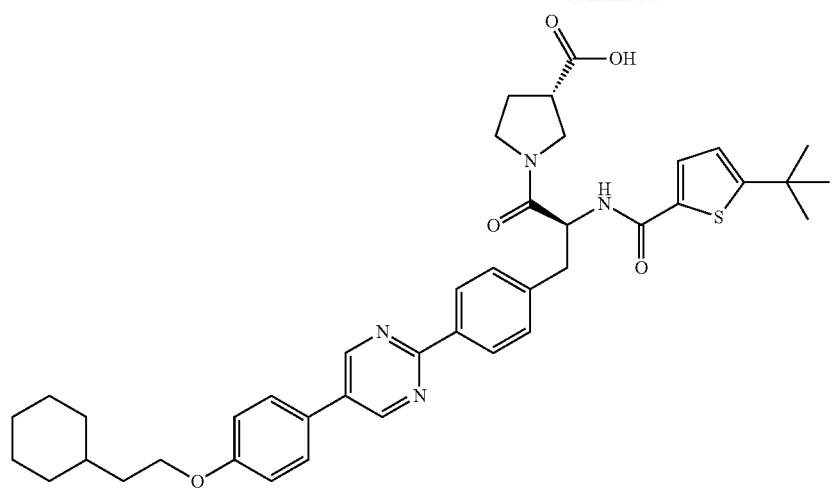
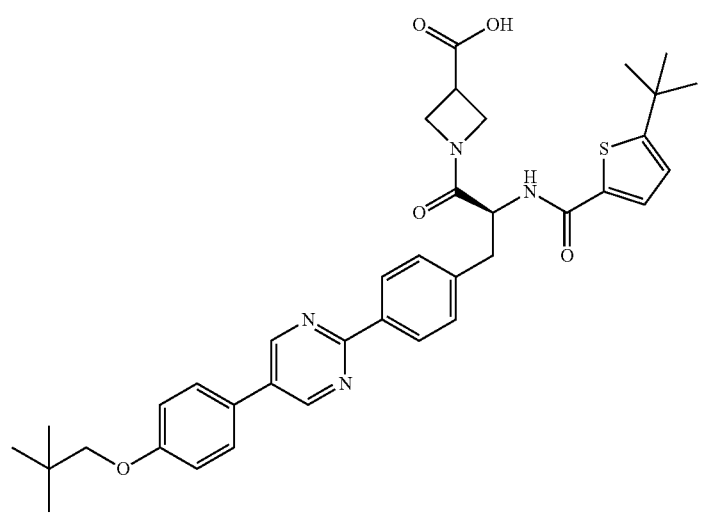
1388
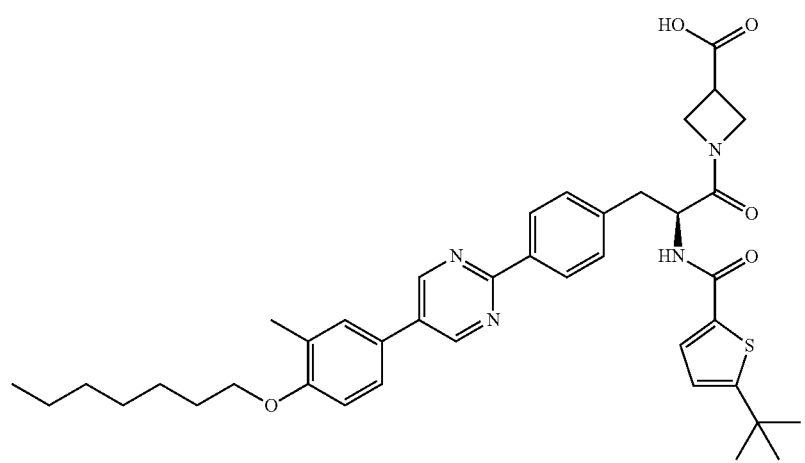

-continued
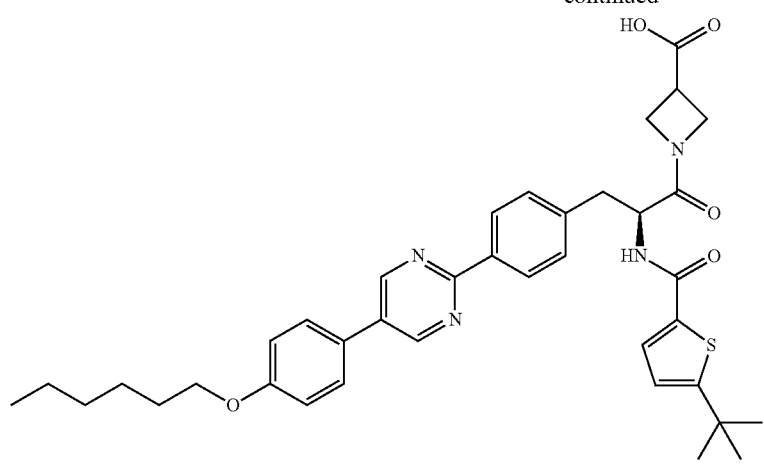
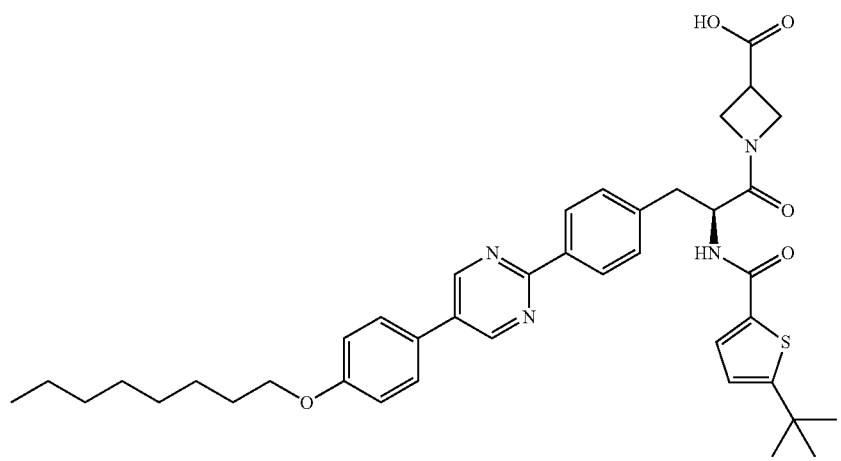
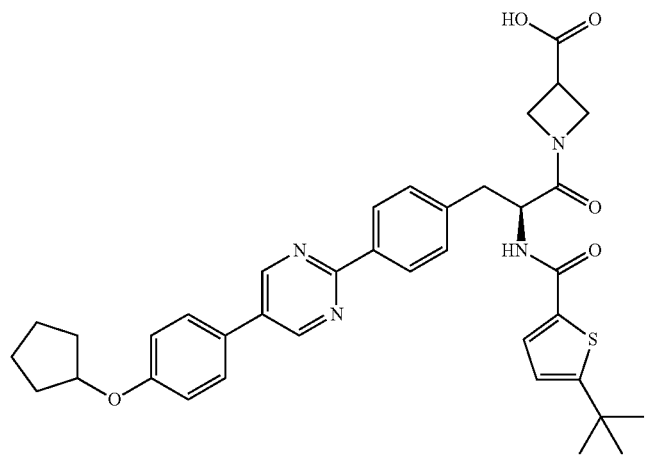

1391
-continued
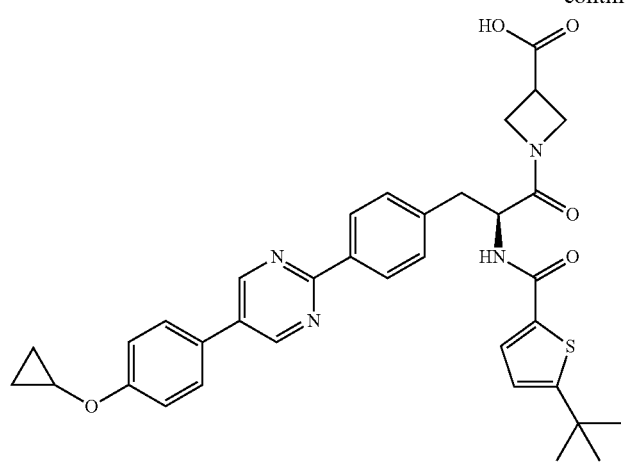
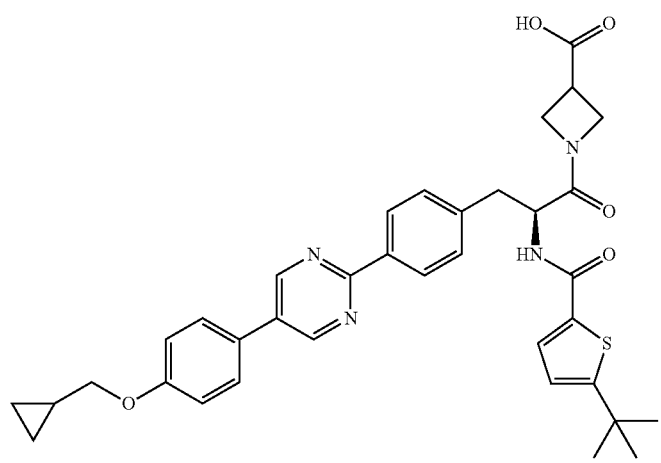
1392
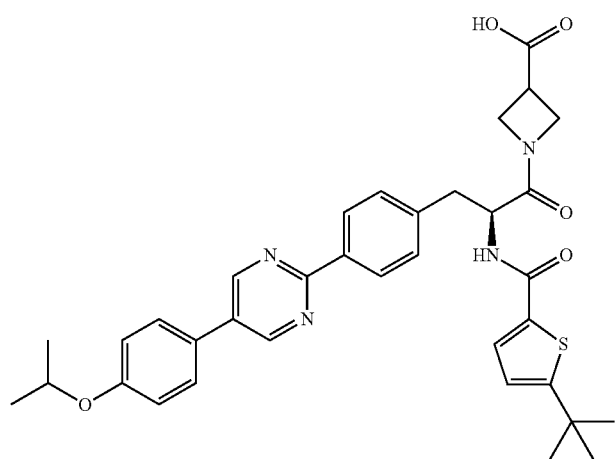

-continued
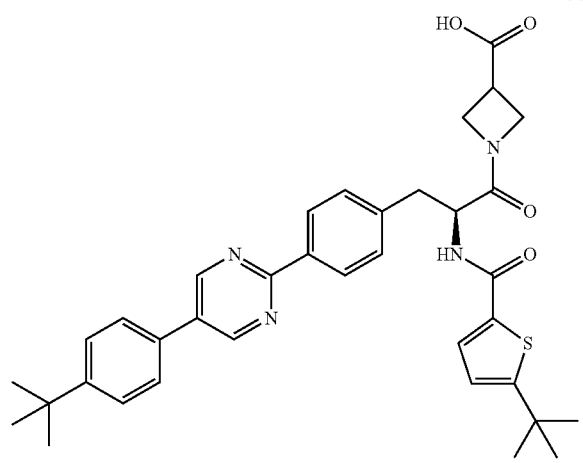
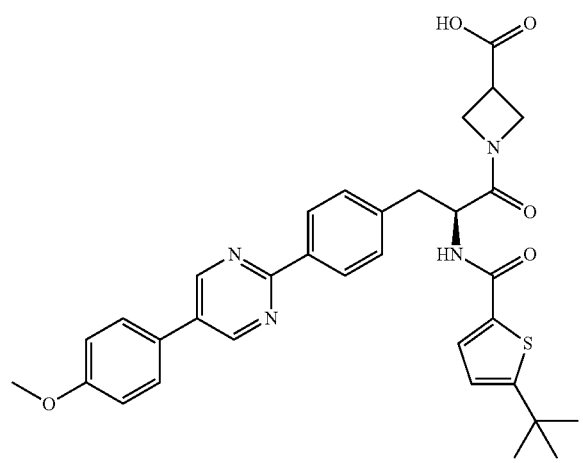
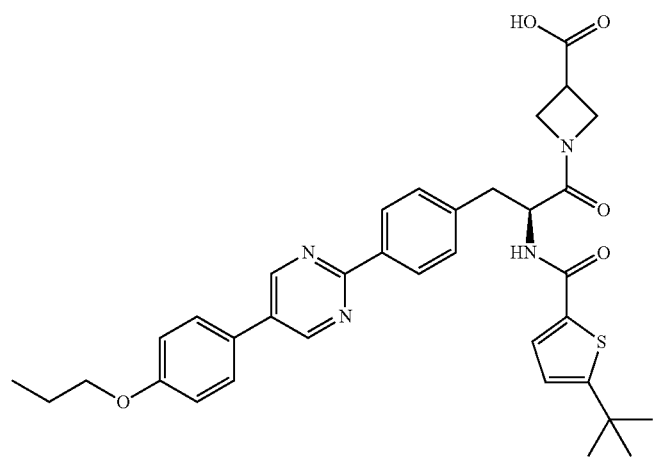

-continued
1395
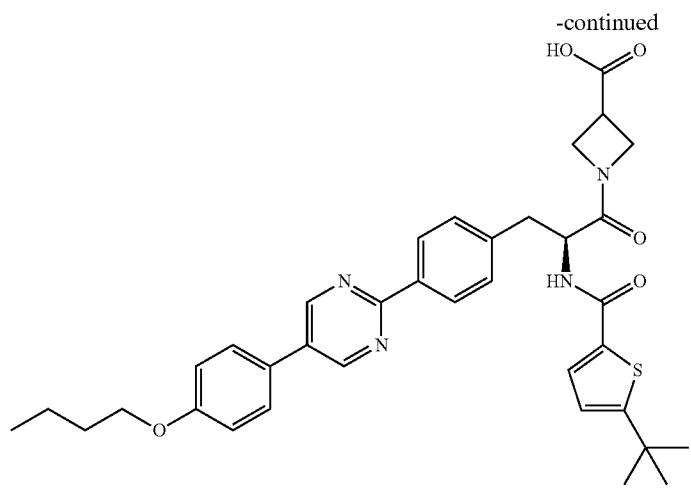
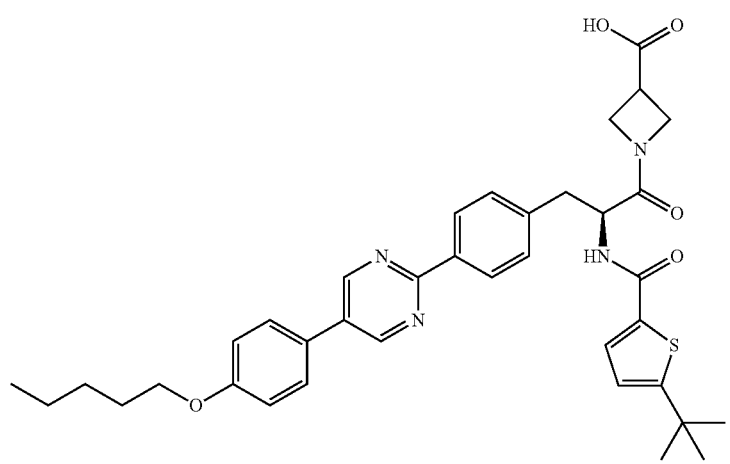
1396
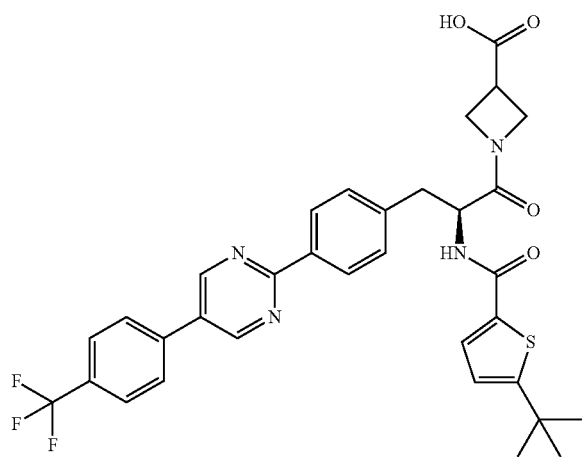

-continued
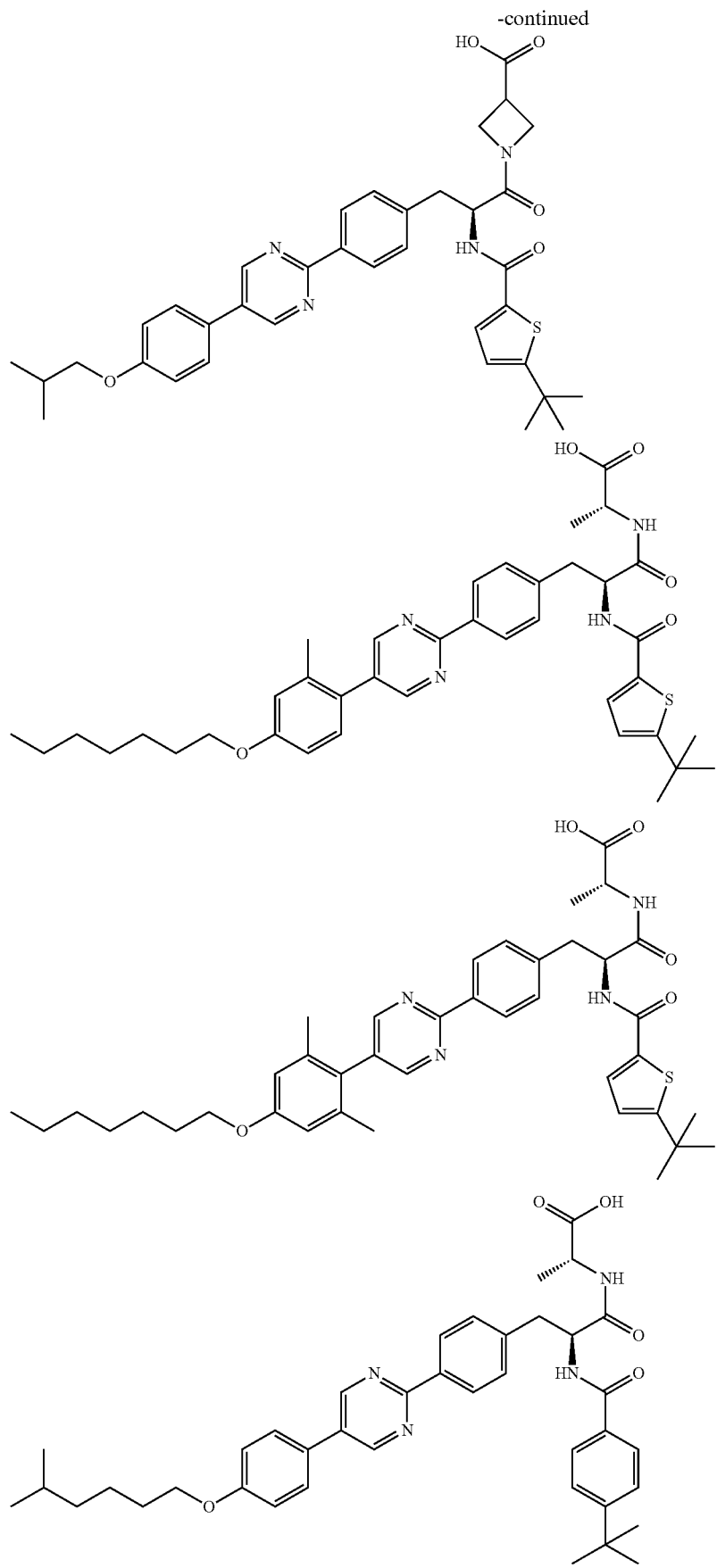

1399
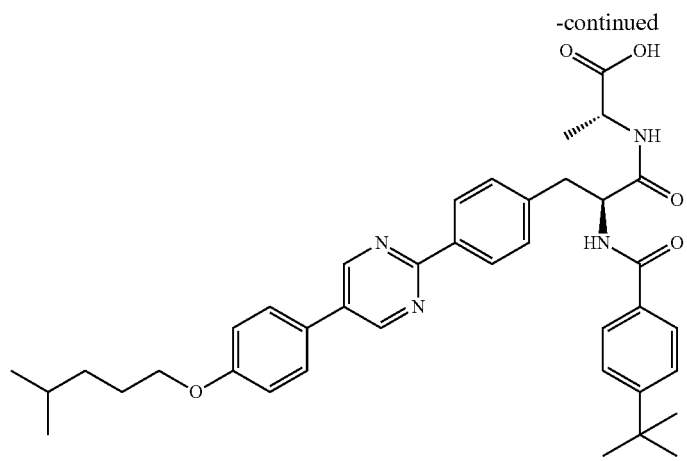
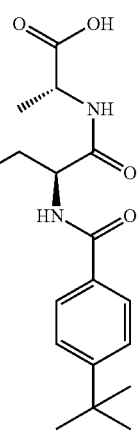
1400
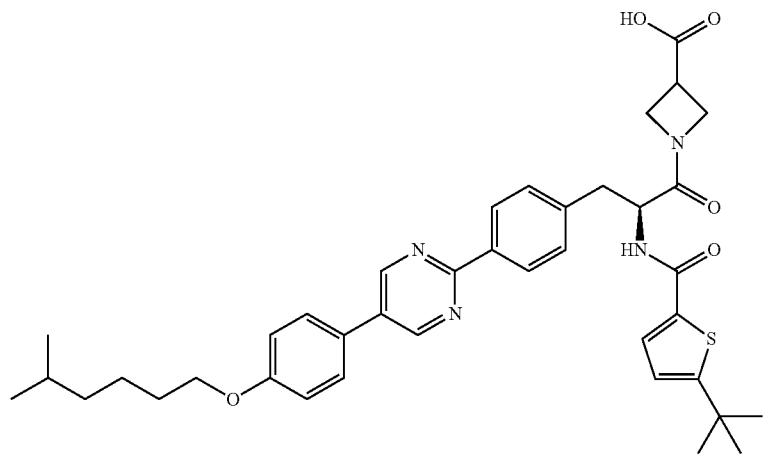

1401
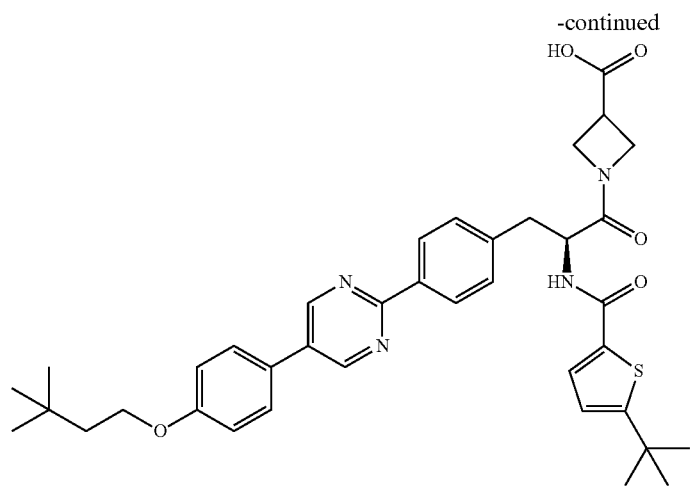
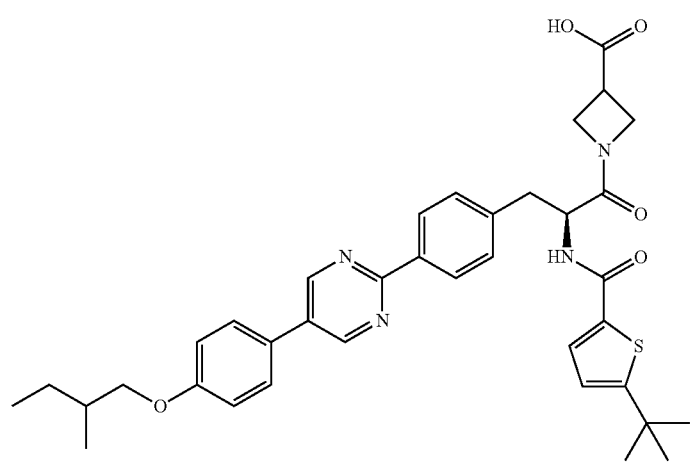
1402
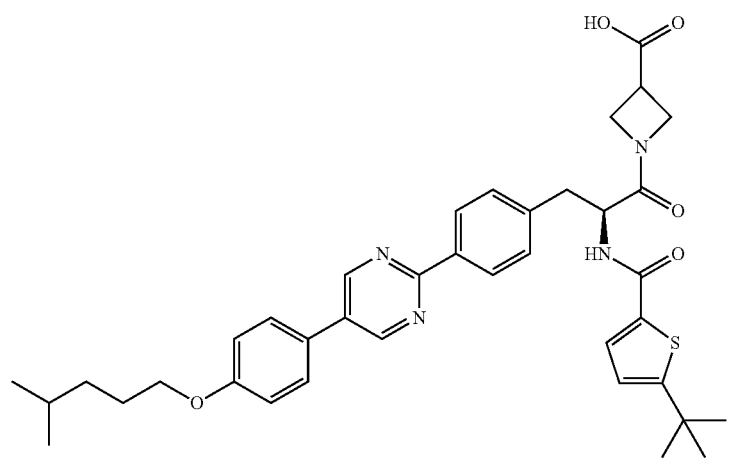

1403                                           1404
-continued
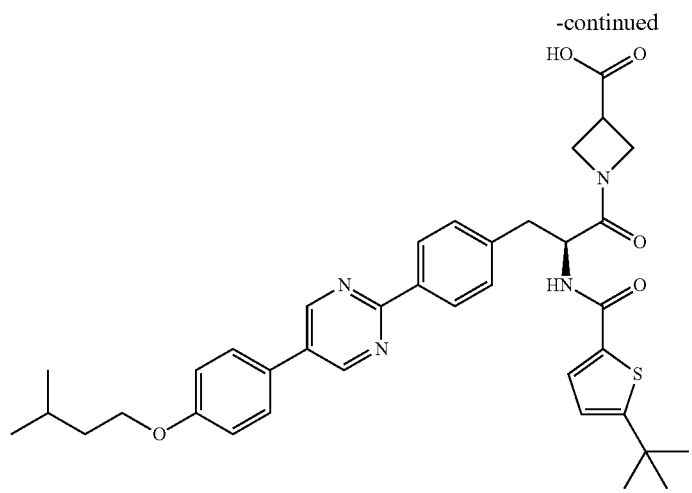
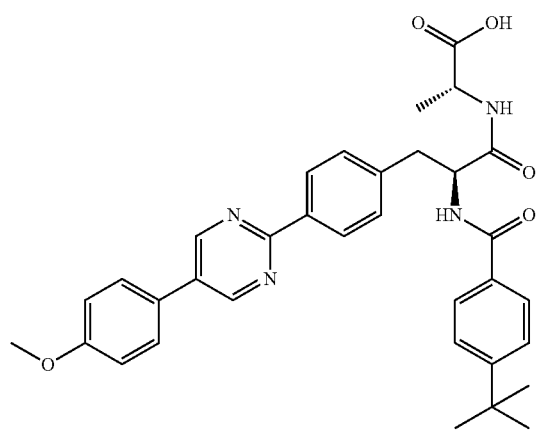
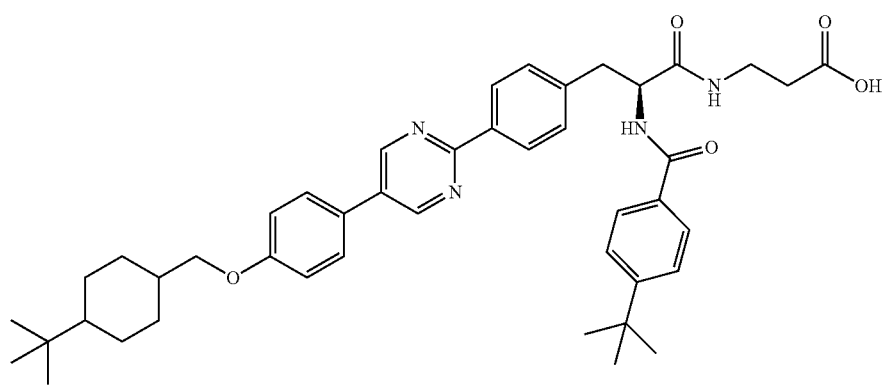
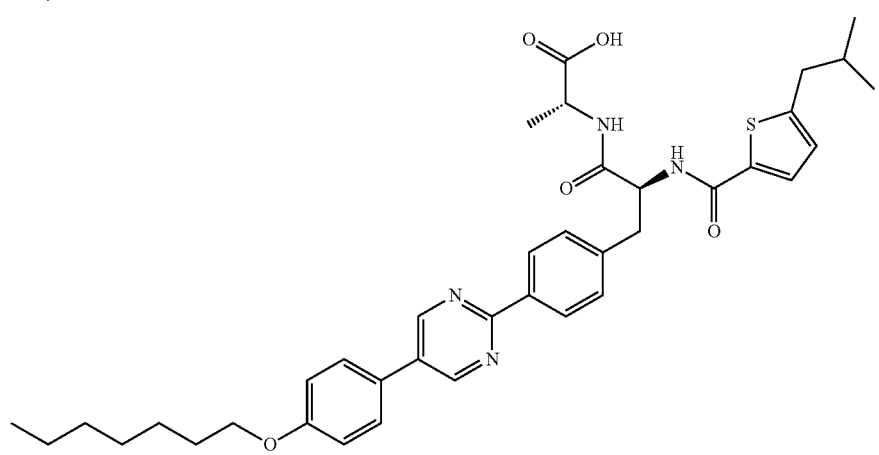

-continued
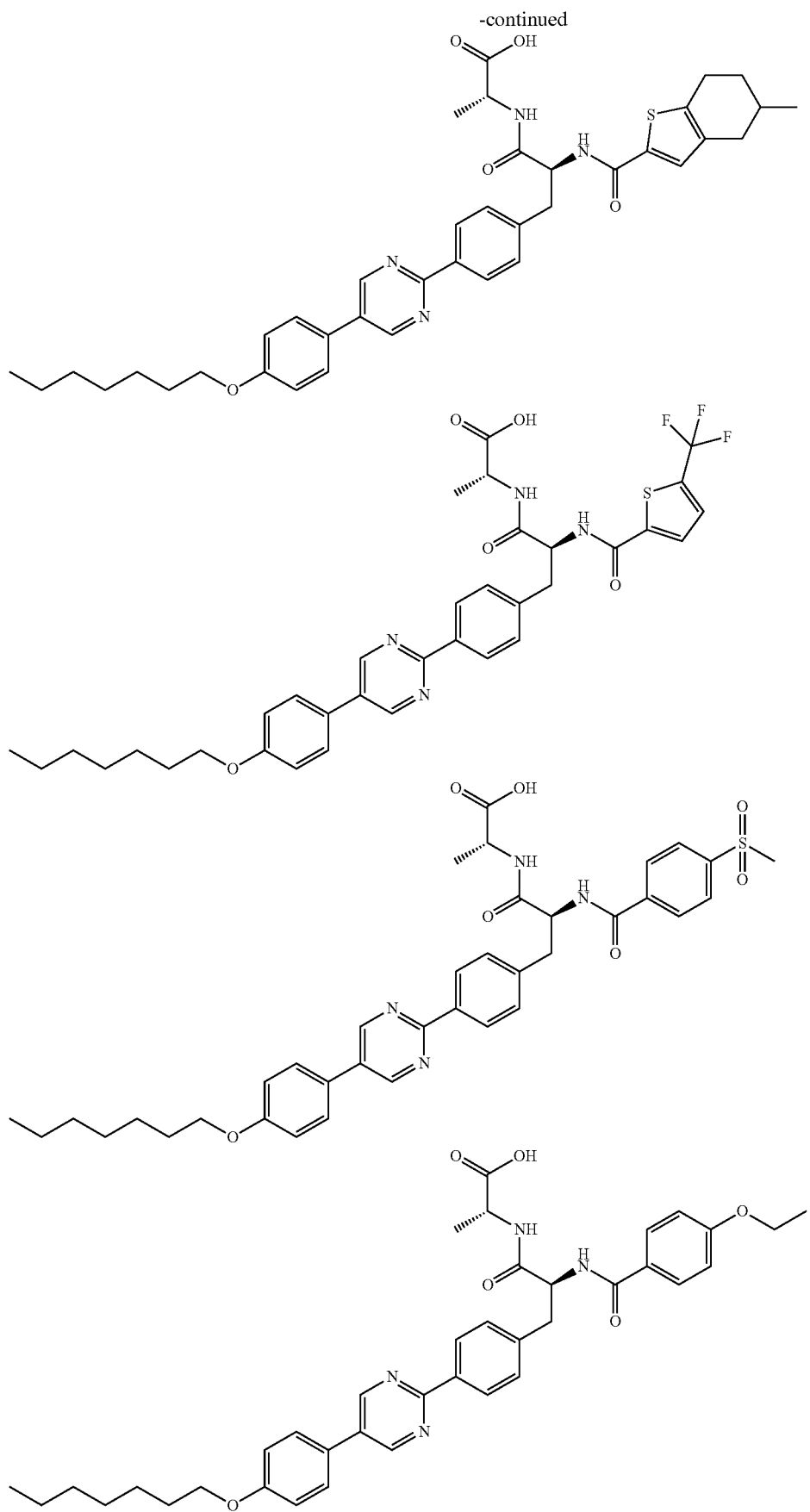

-continued
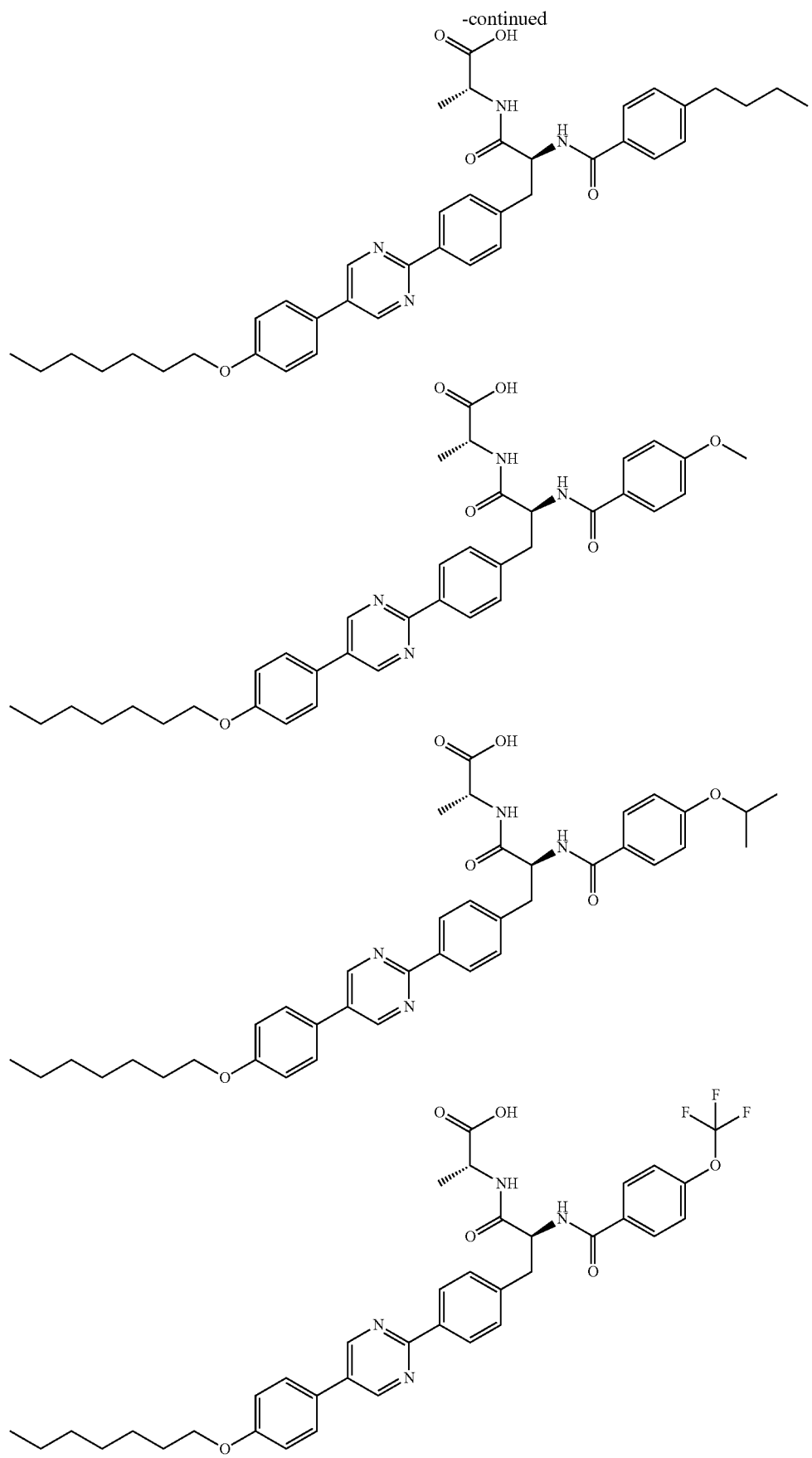

-continued
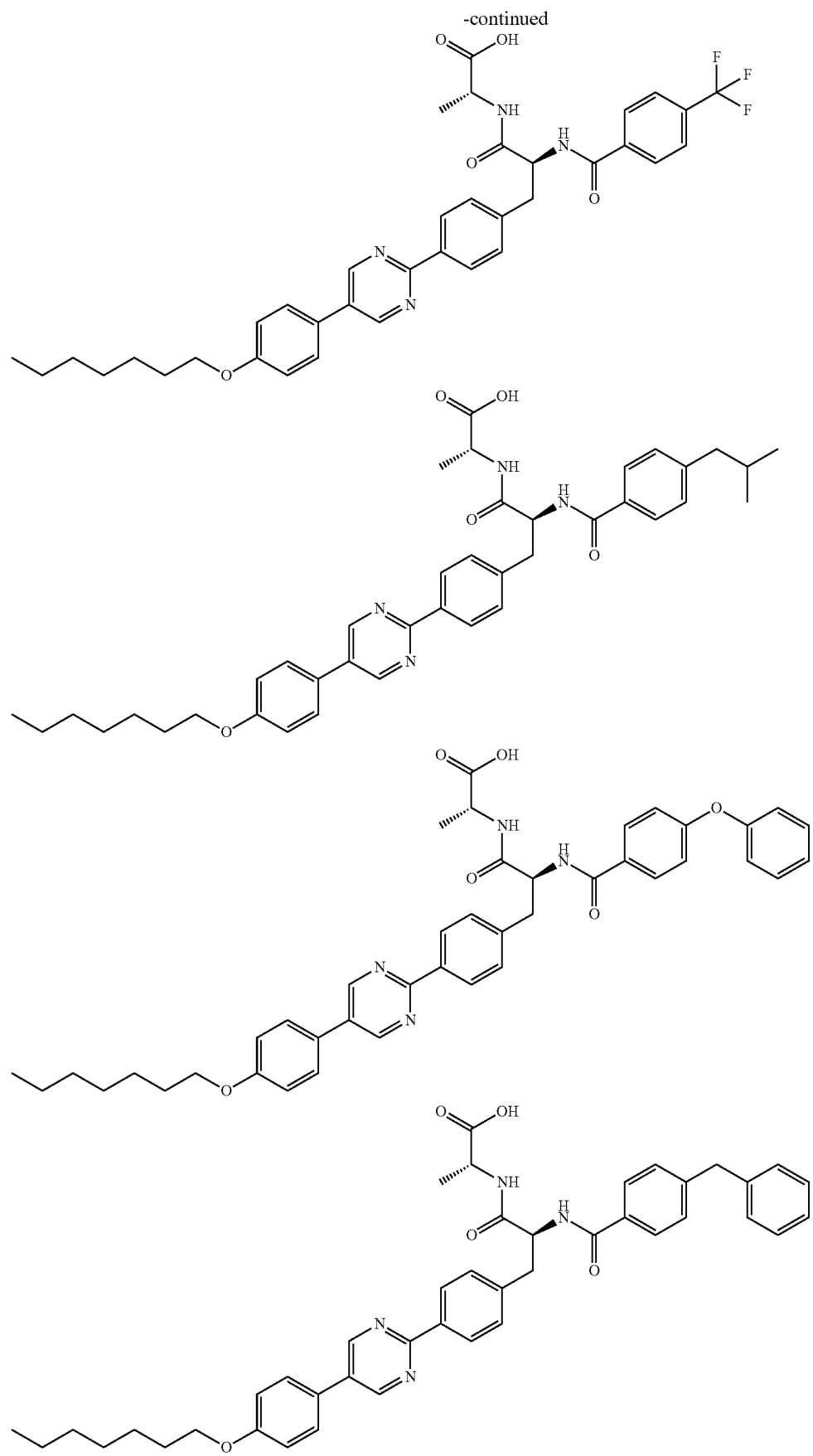

-continued
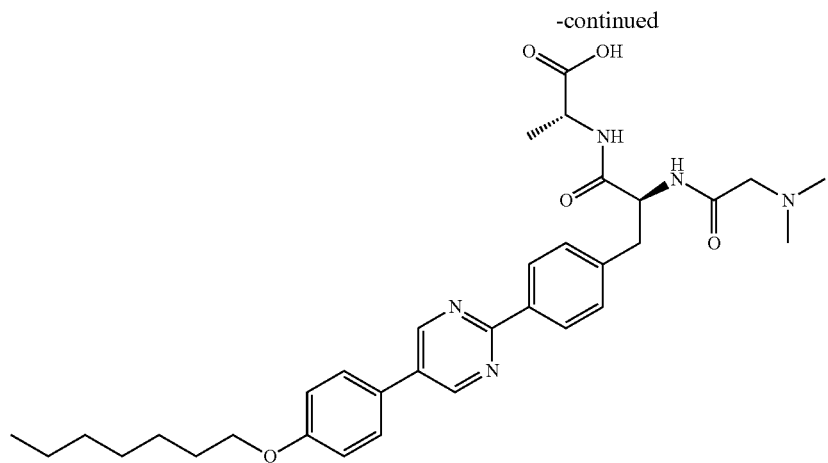
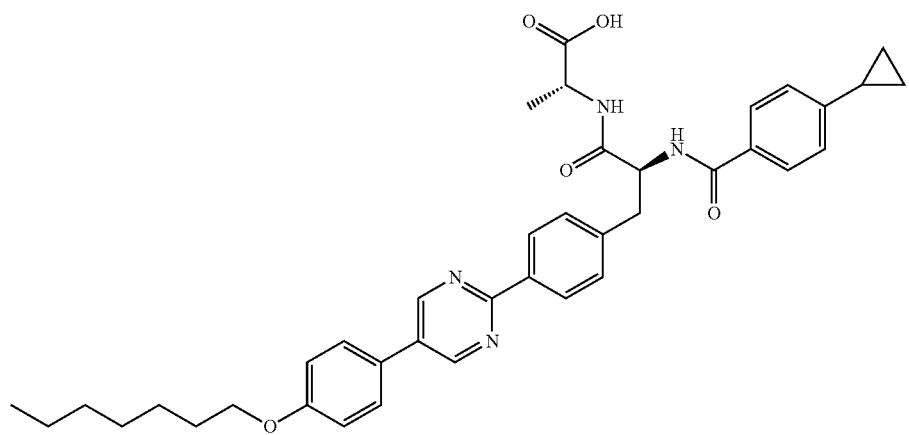
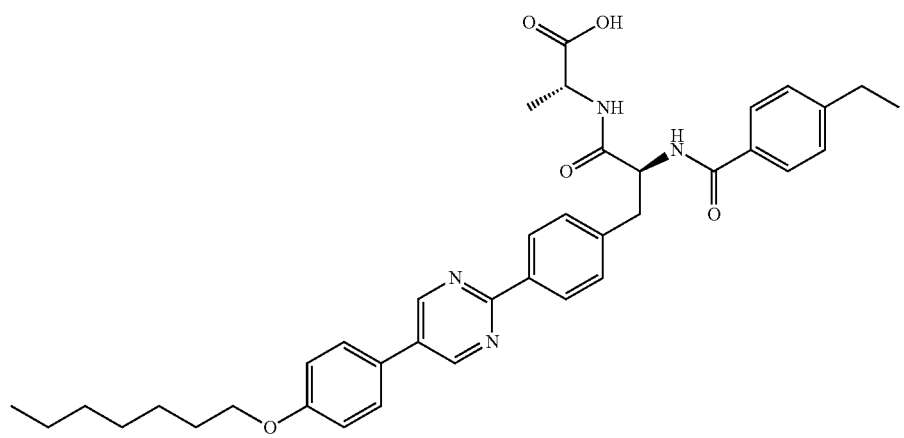

1413 1414
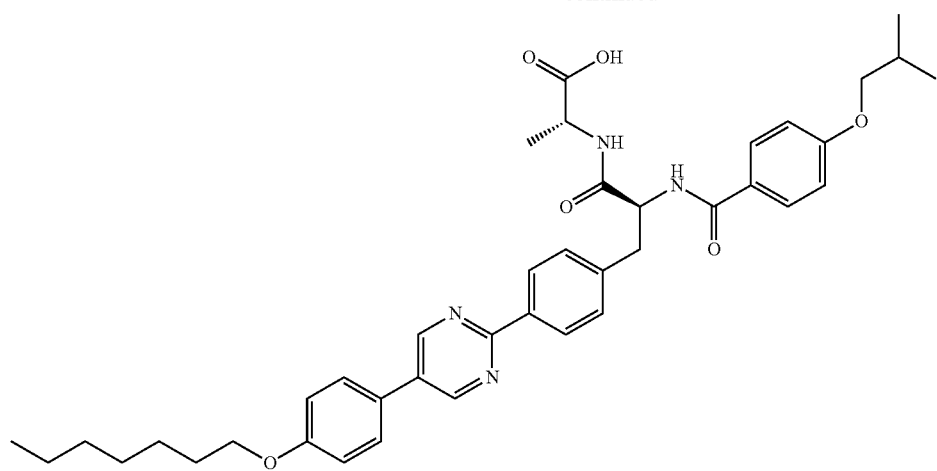
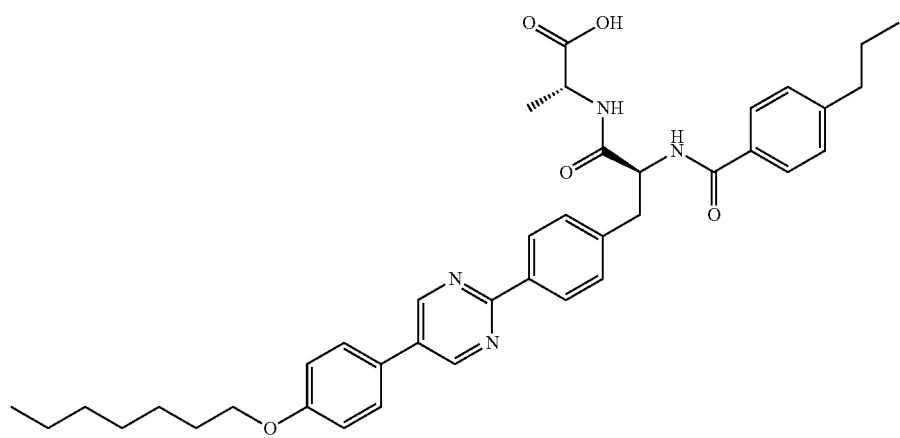
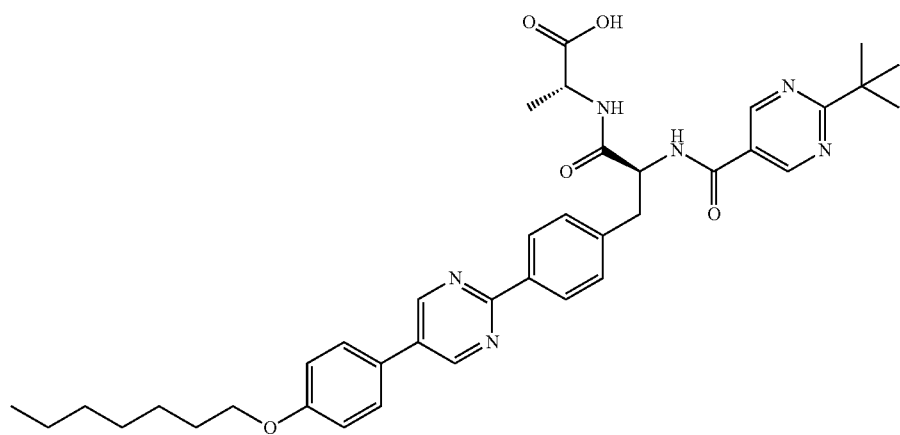

-continued
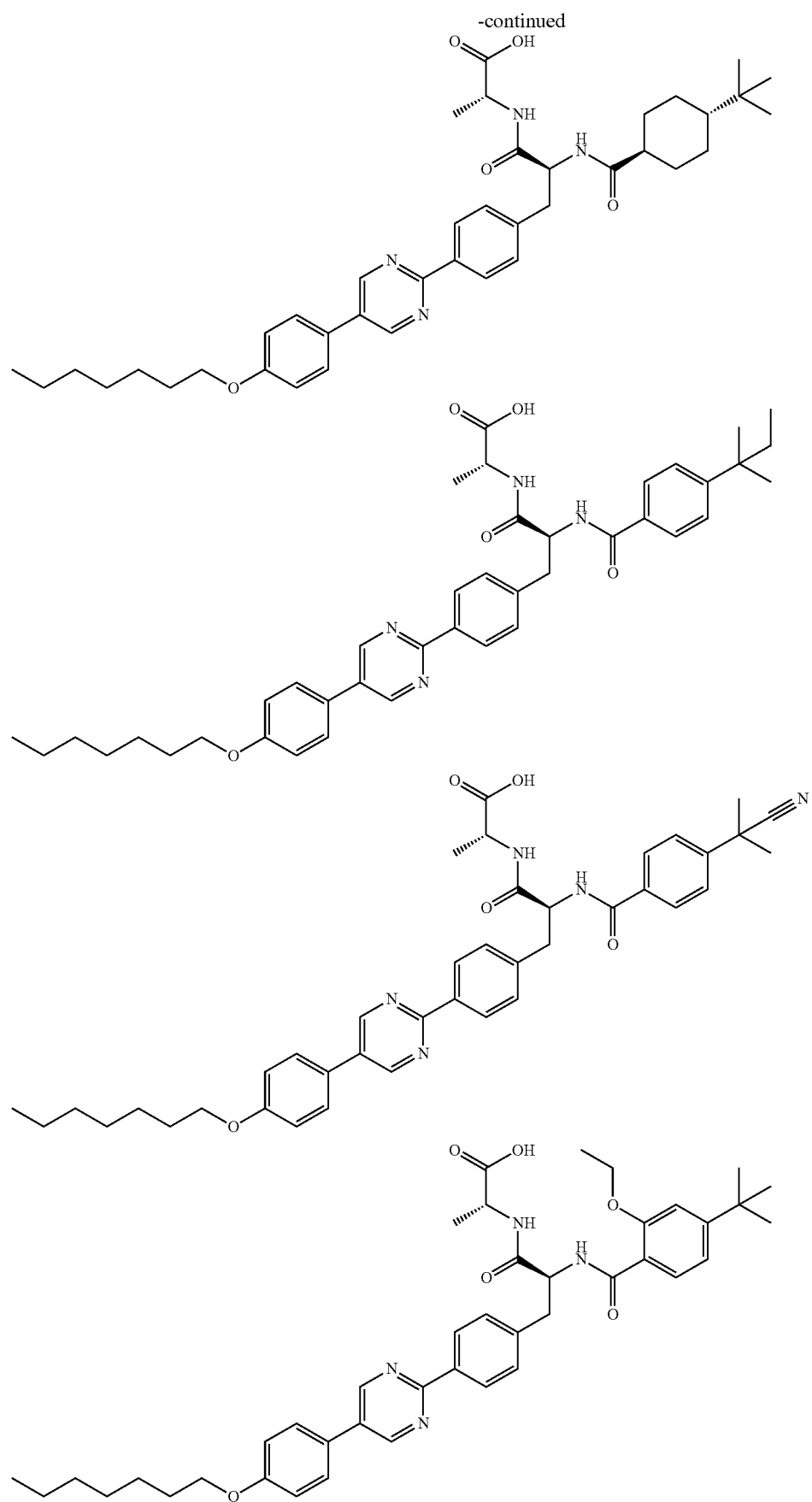

-continued
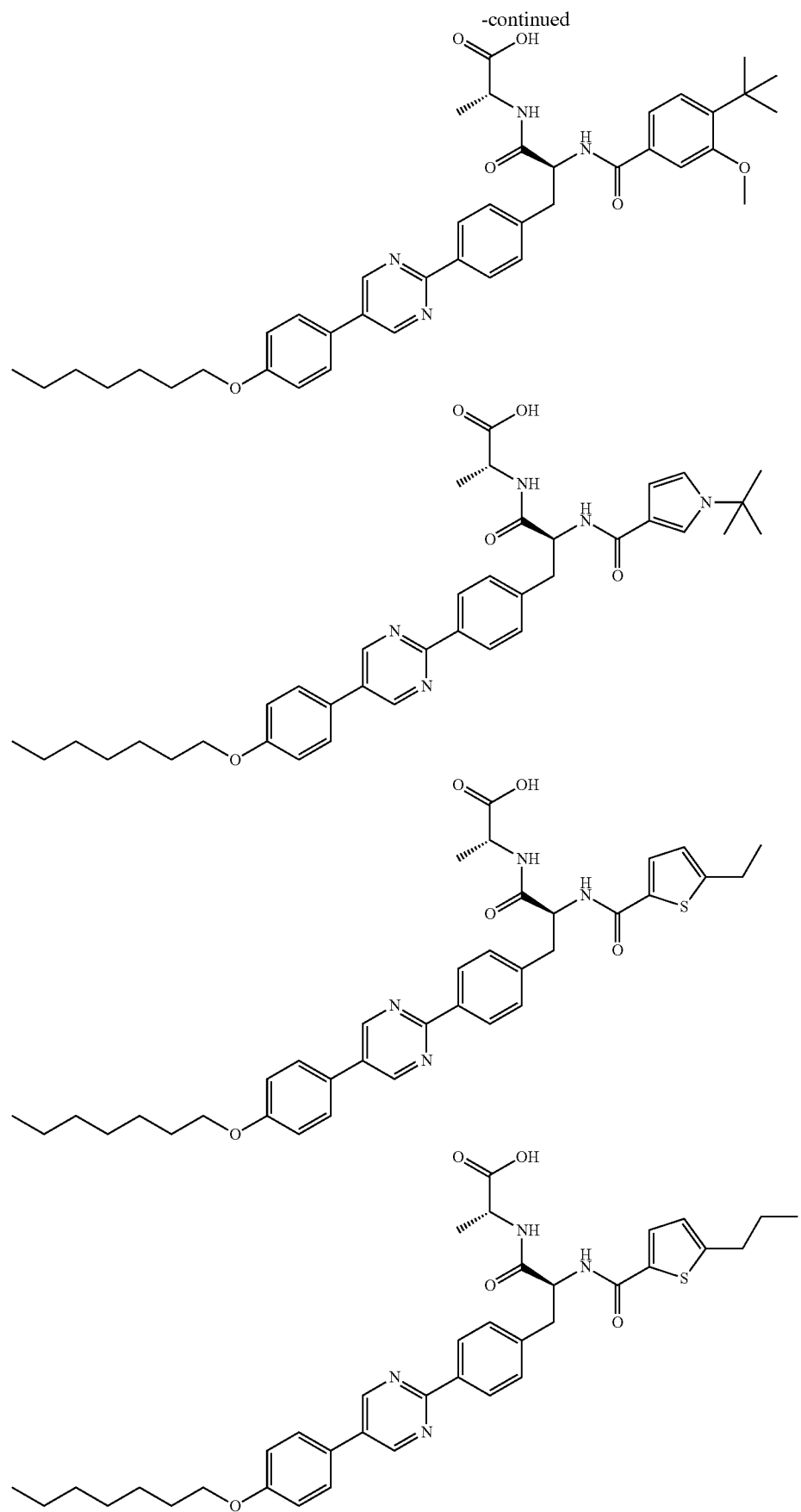

-continued
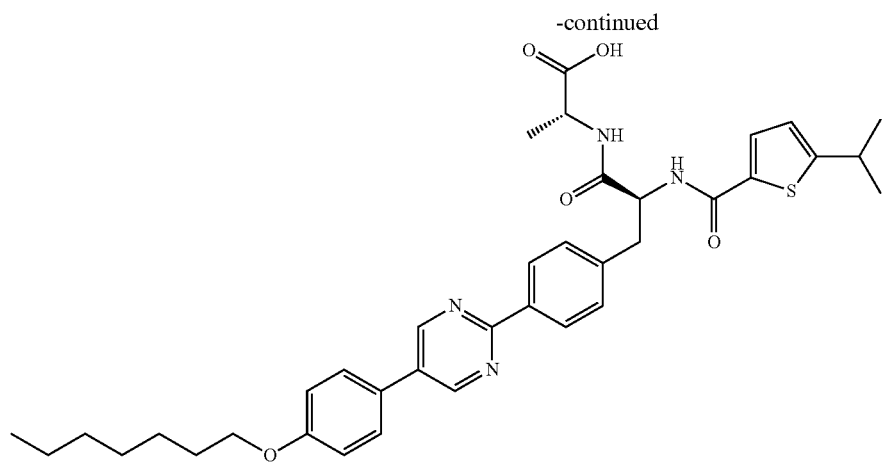
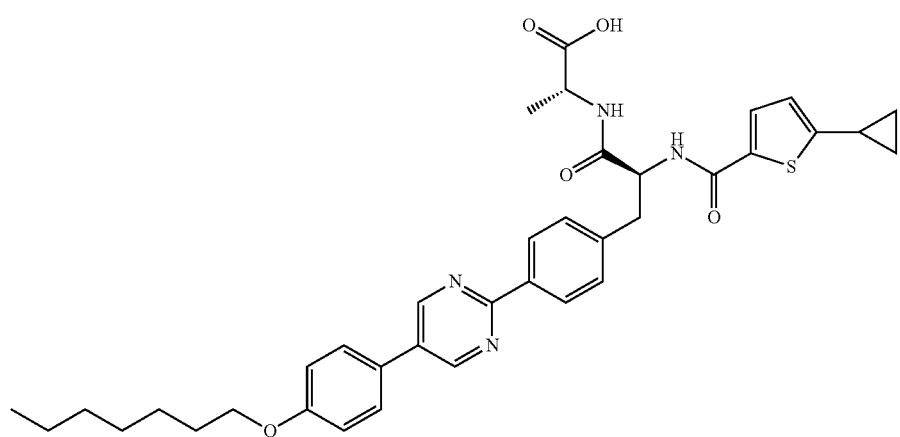
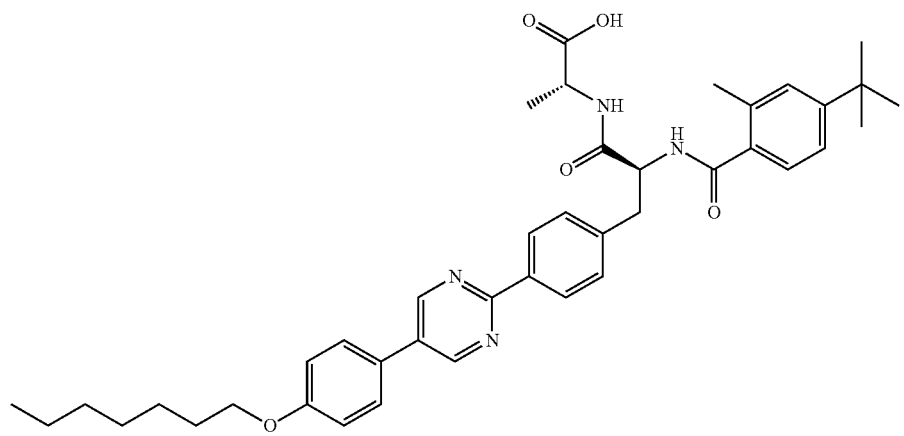

1421
-continued
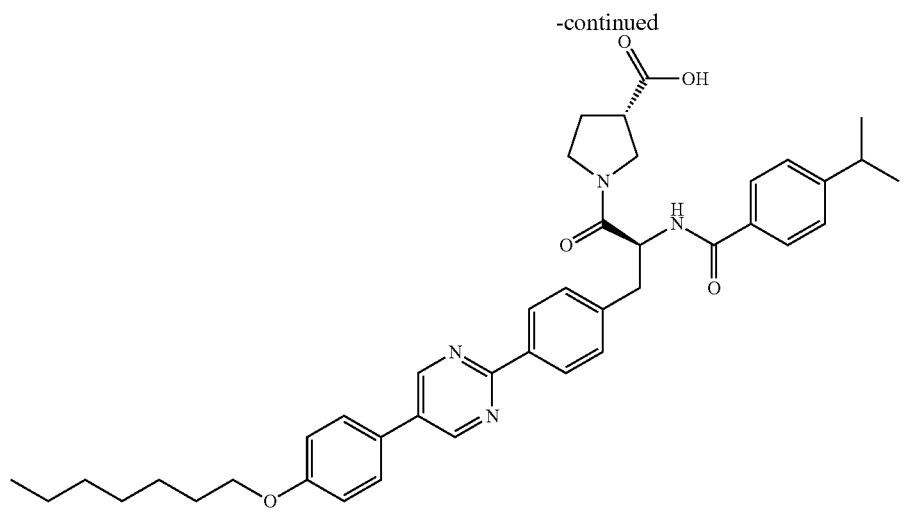
1422
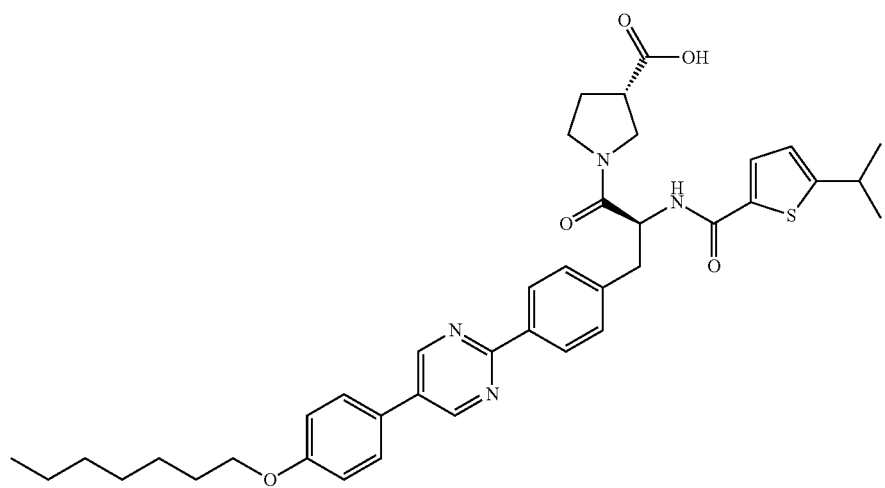
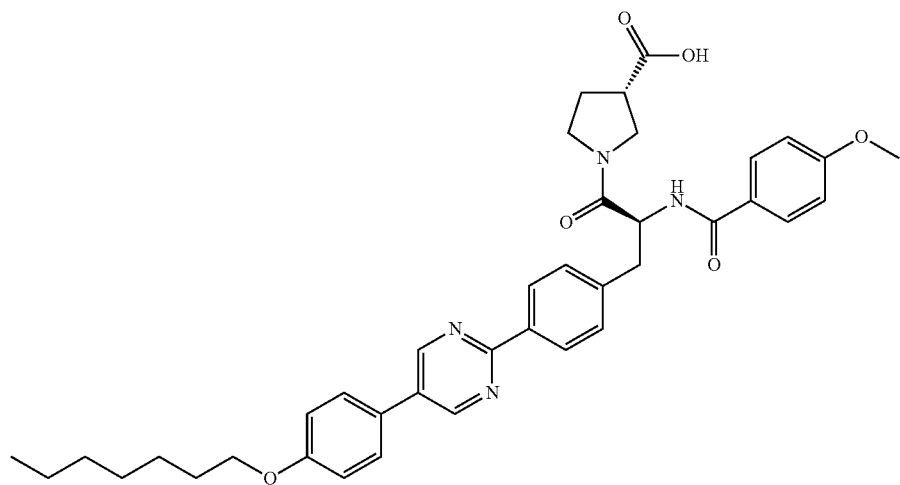

-continued
1423
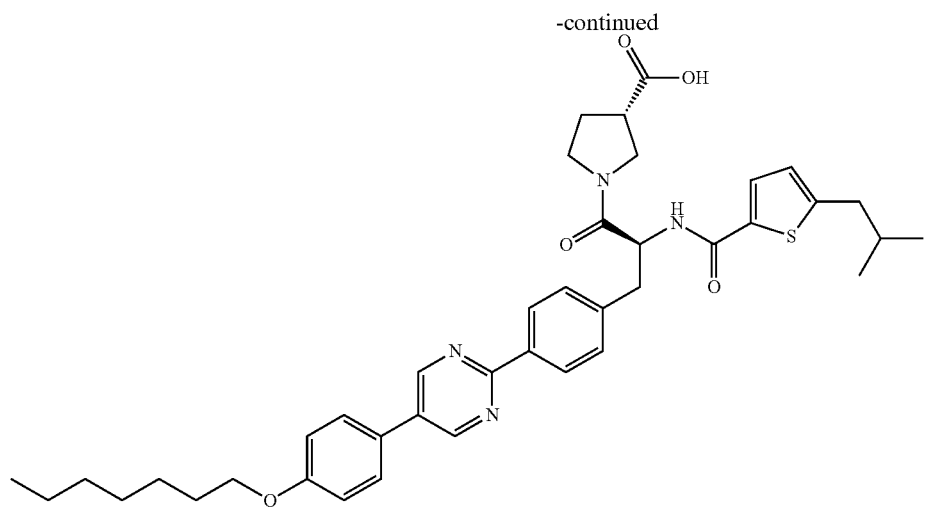
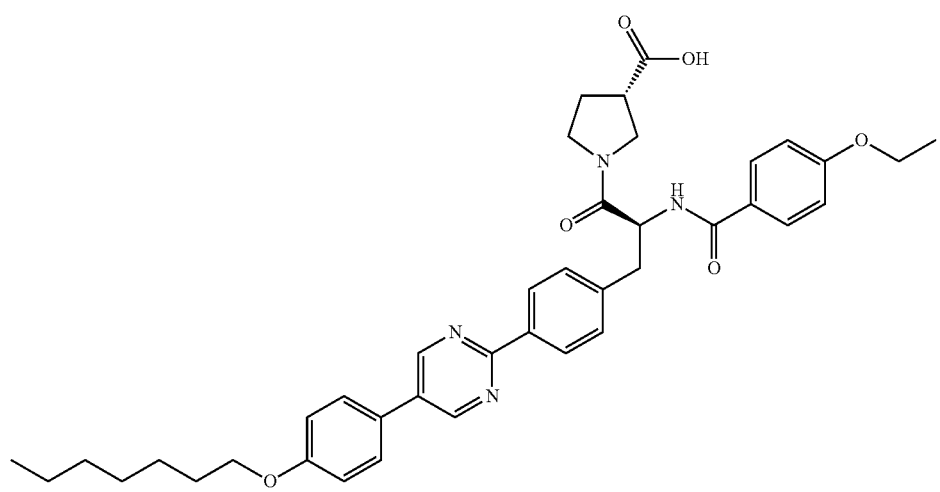
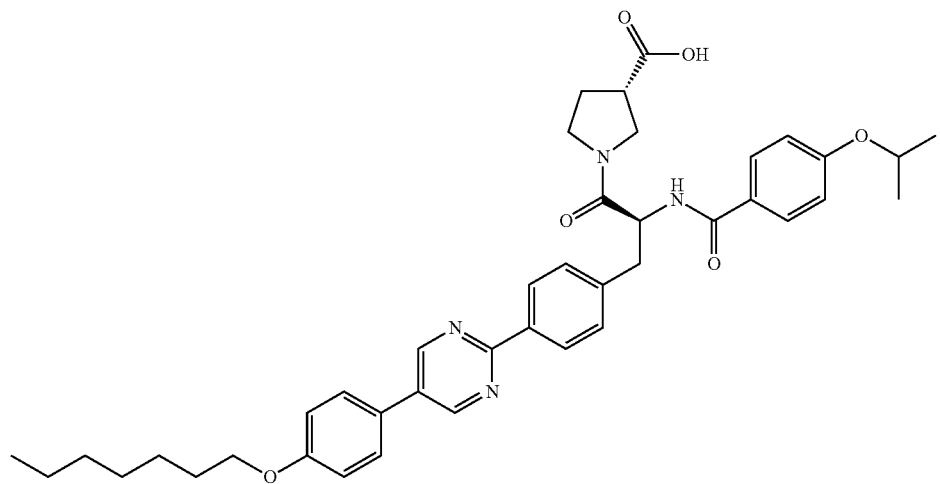
1424

-continued
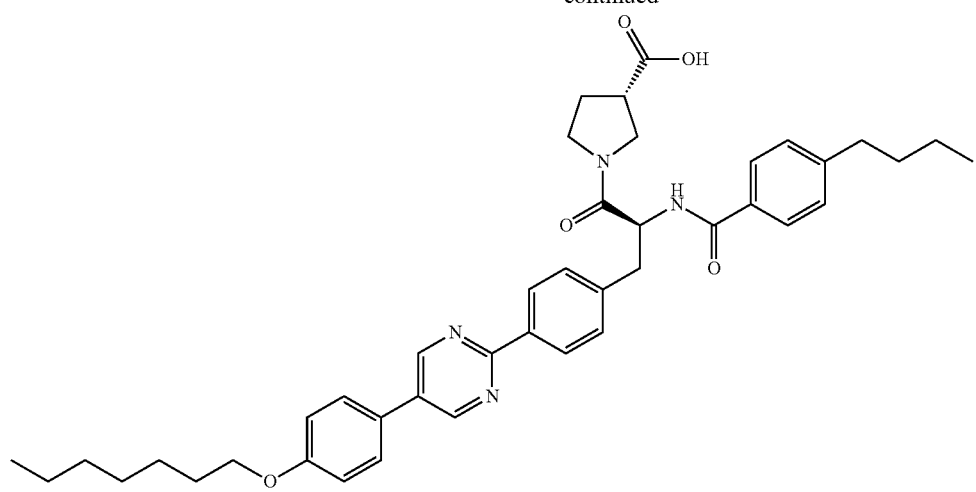
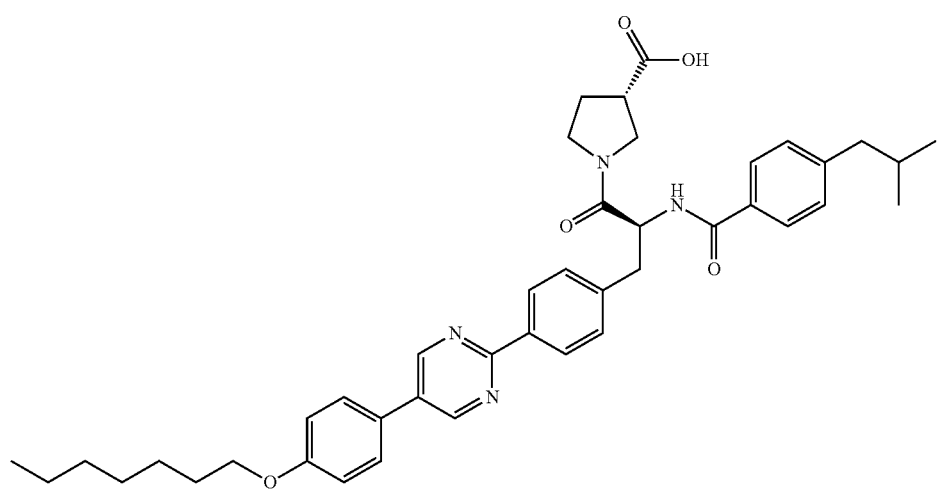
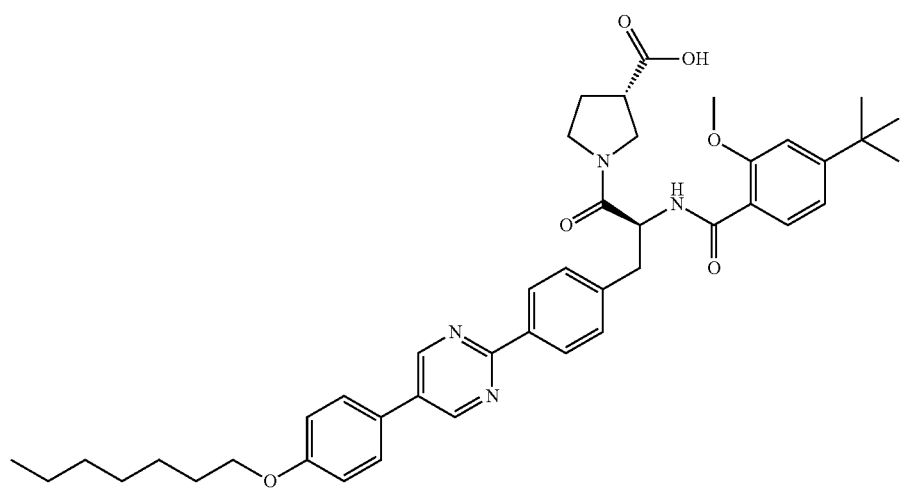

-continued
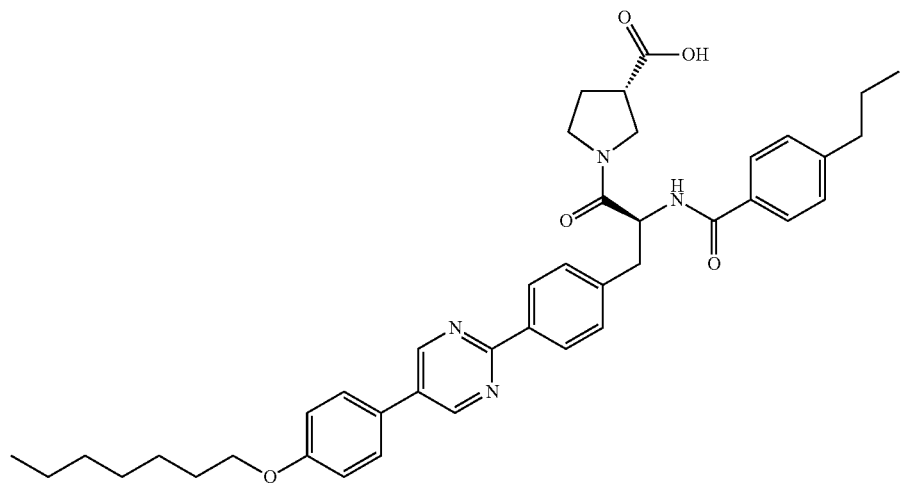
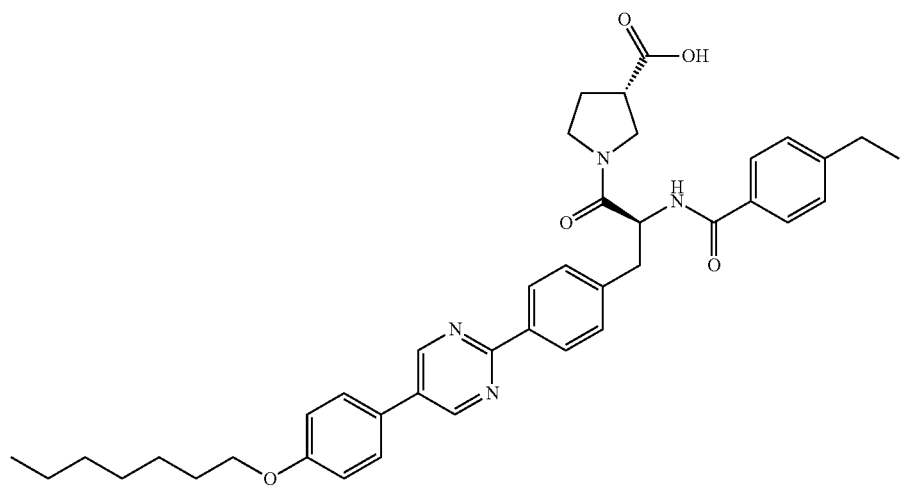
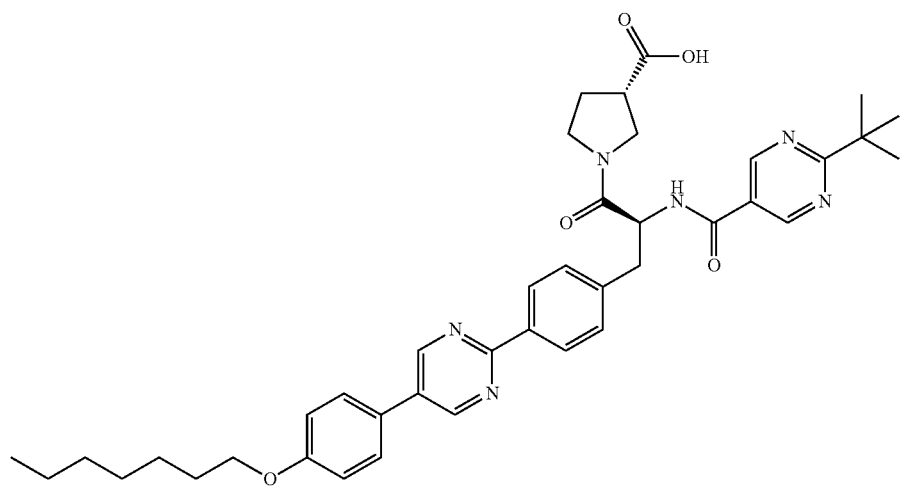

-continued
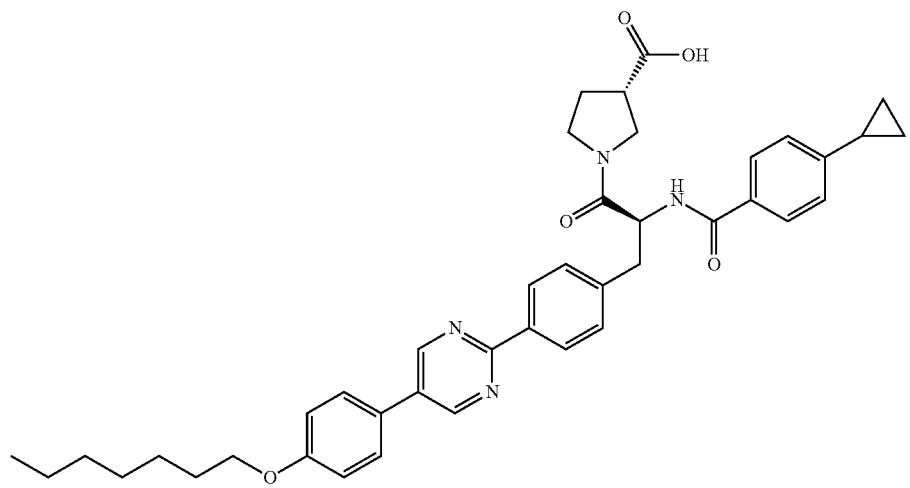
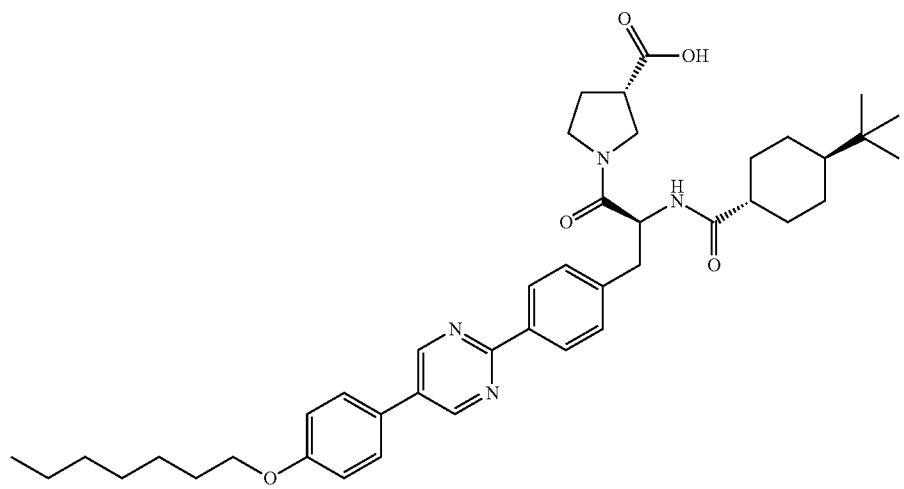
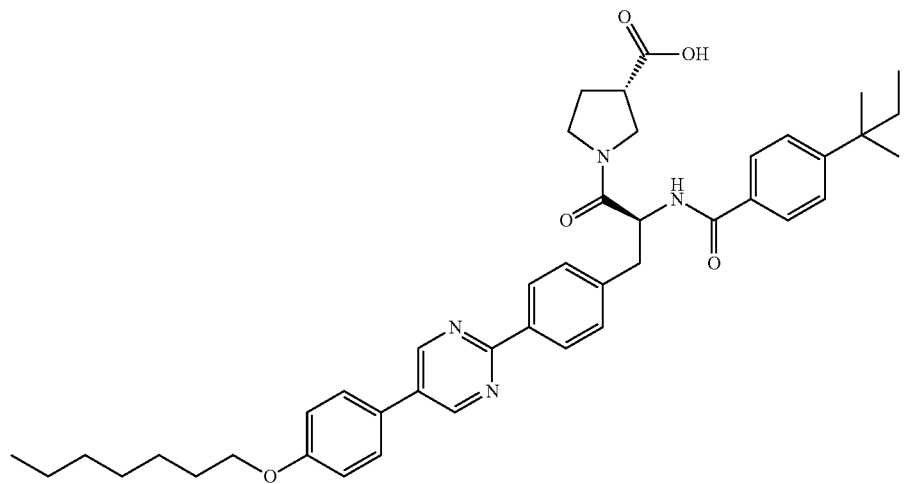

-continued
| 1431 | 1432 |
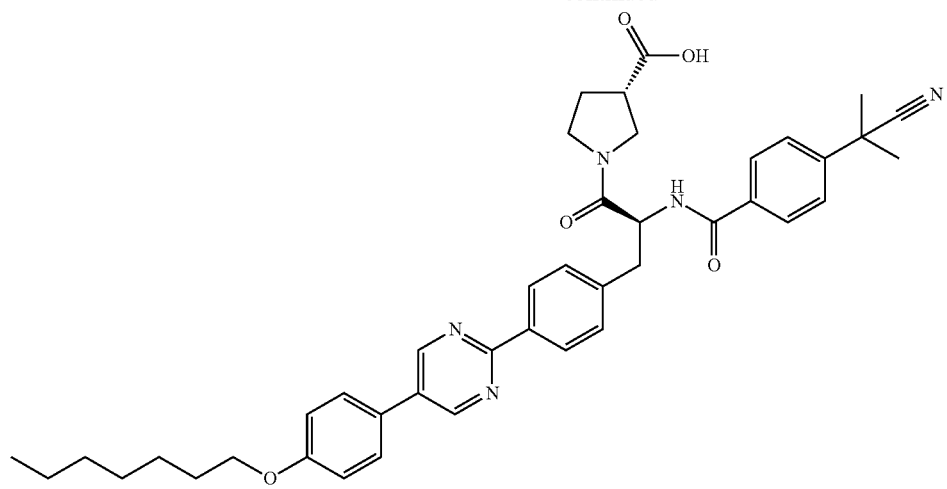
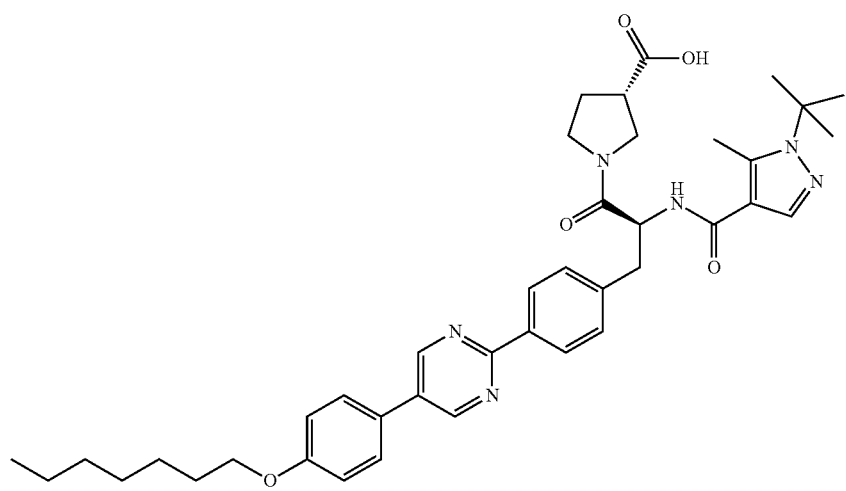
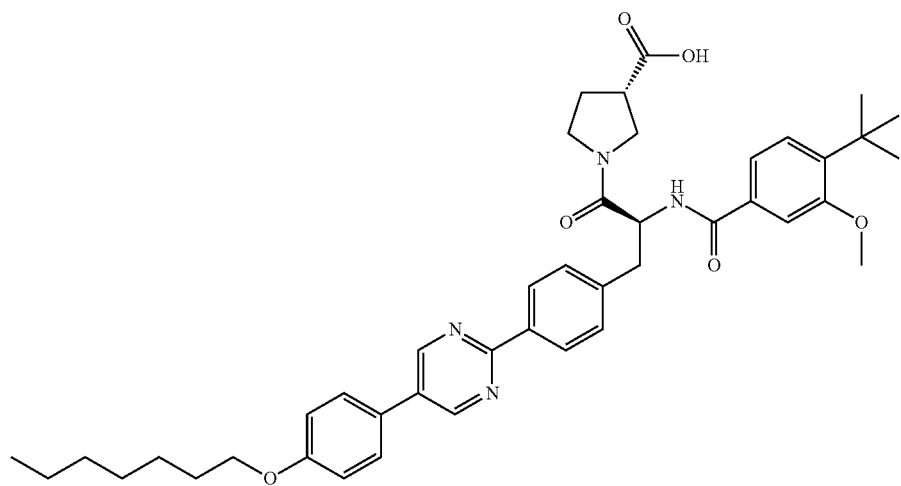

-continued
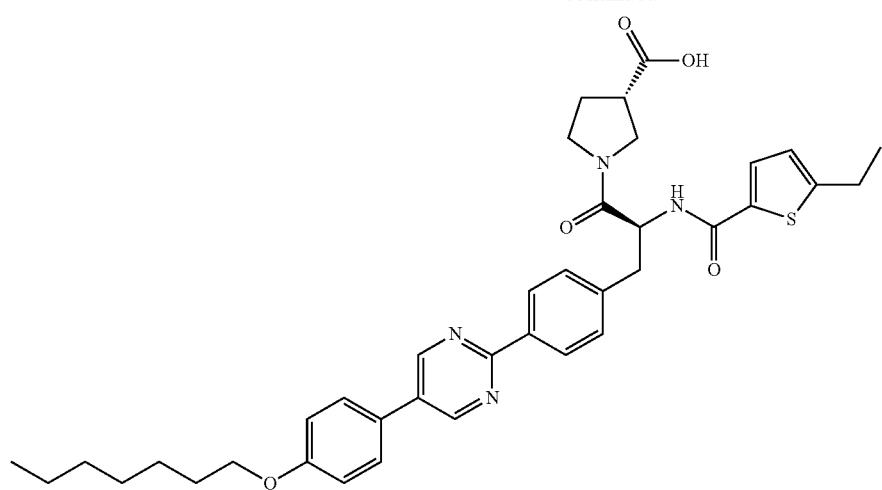
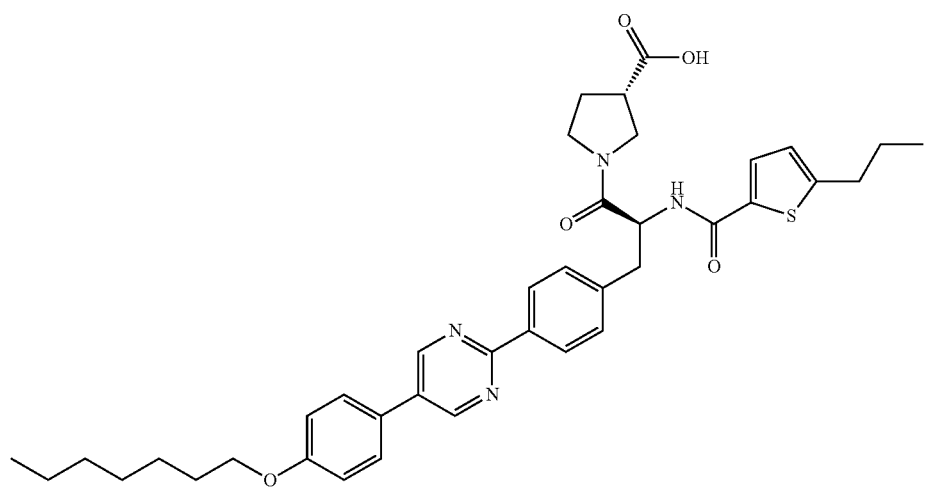
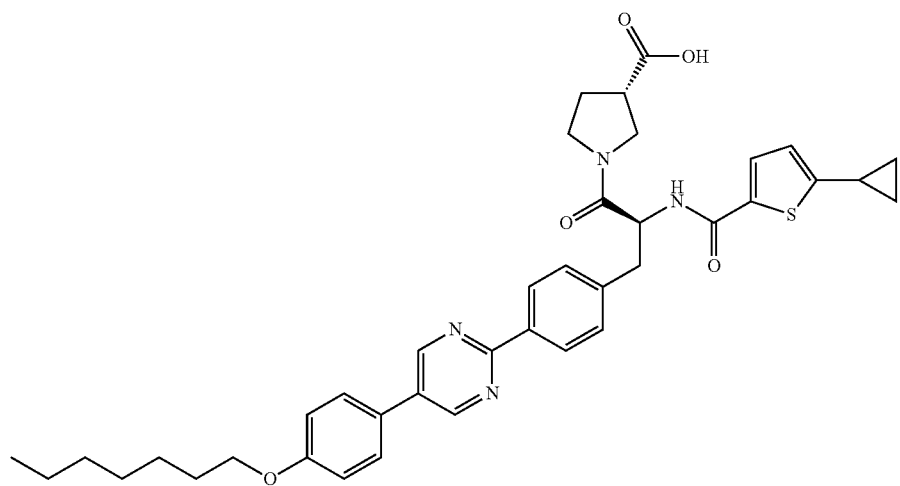

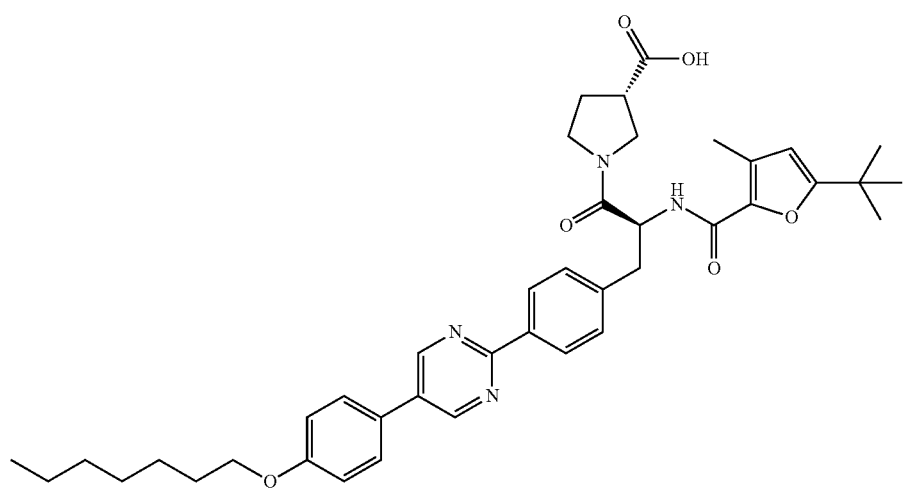
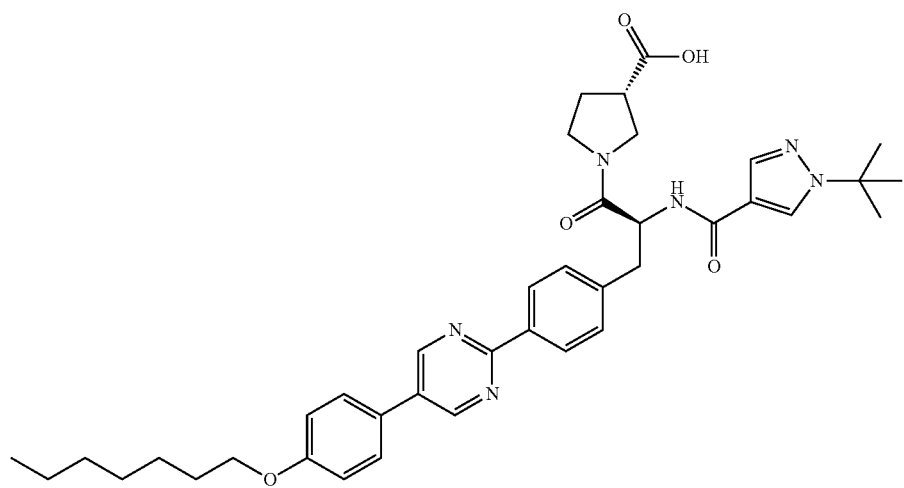
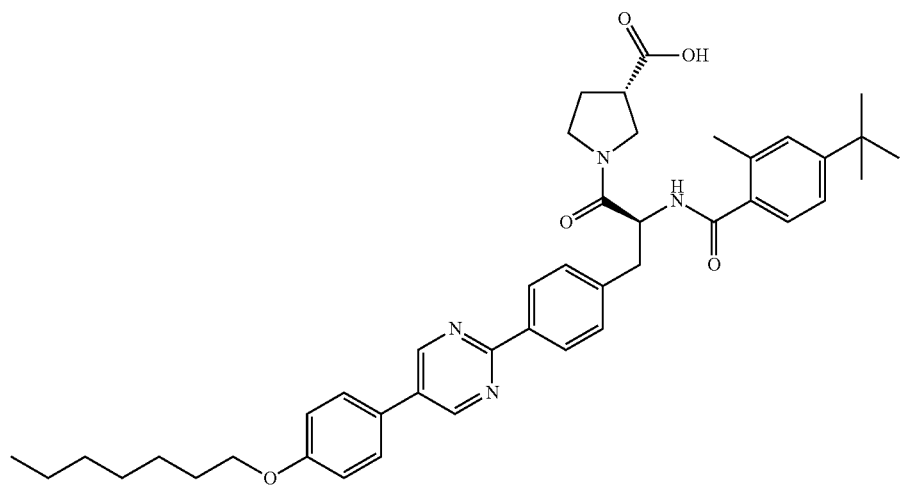

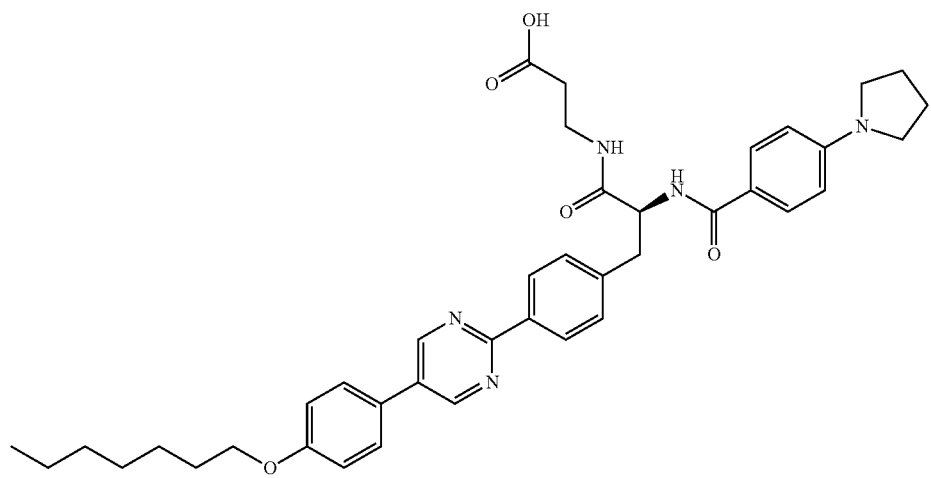
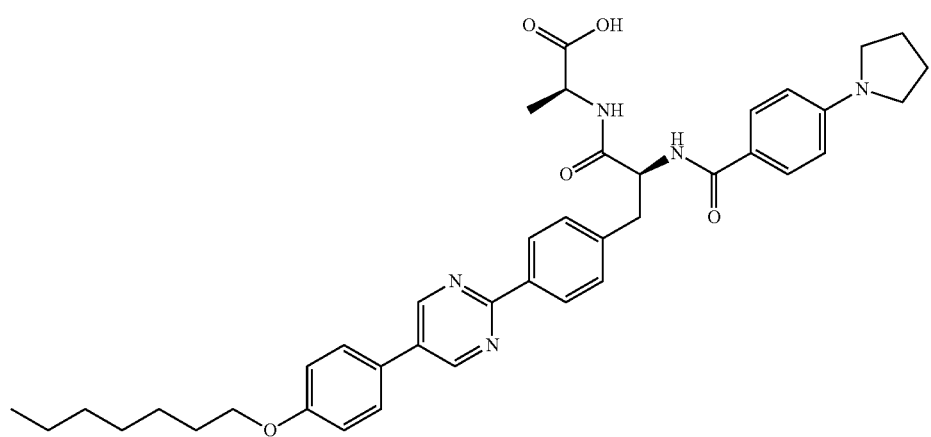
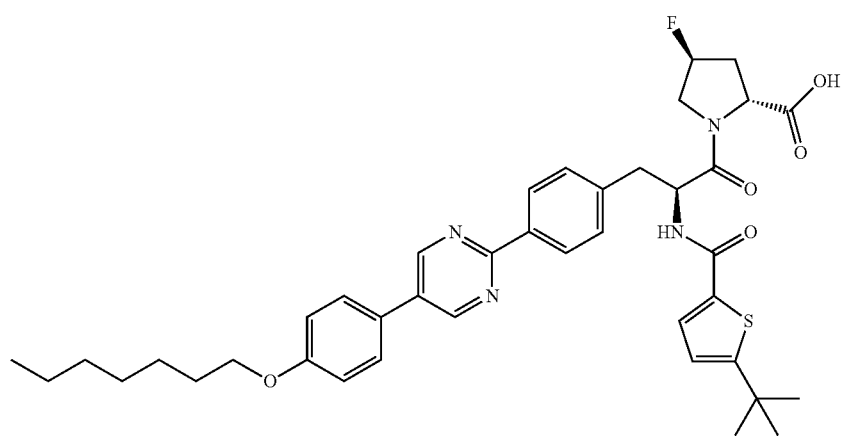

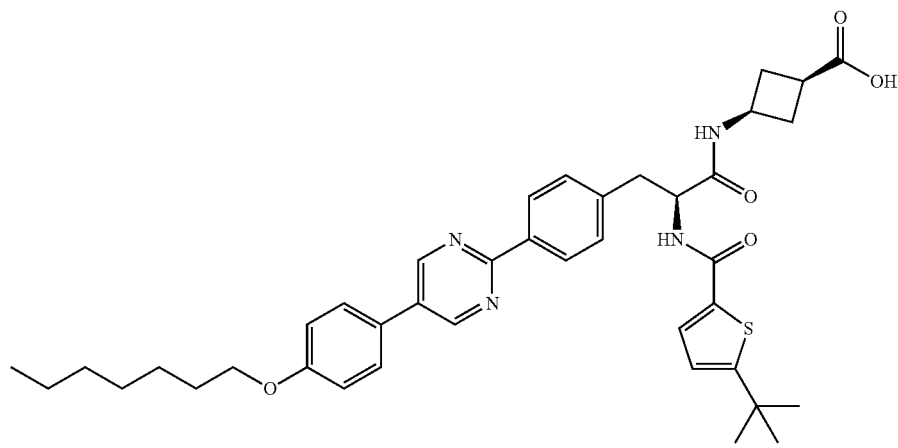
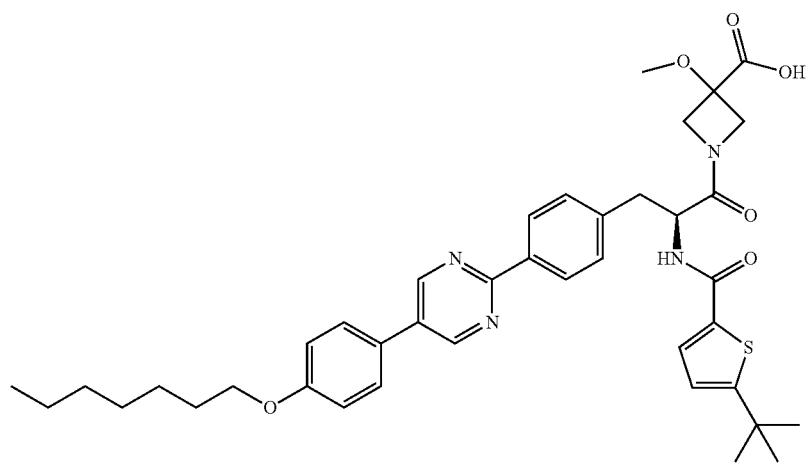
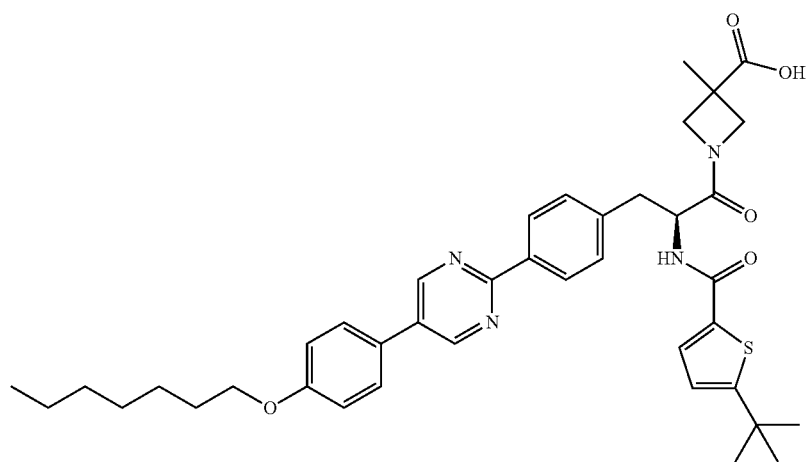

-continued
| 1441 | 1442 |
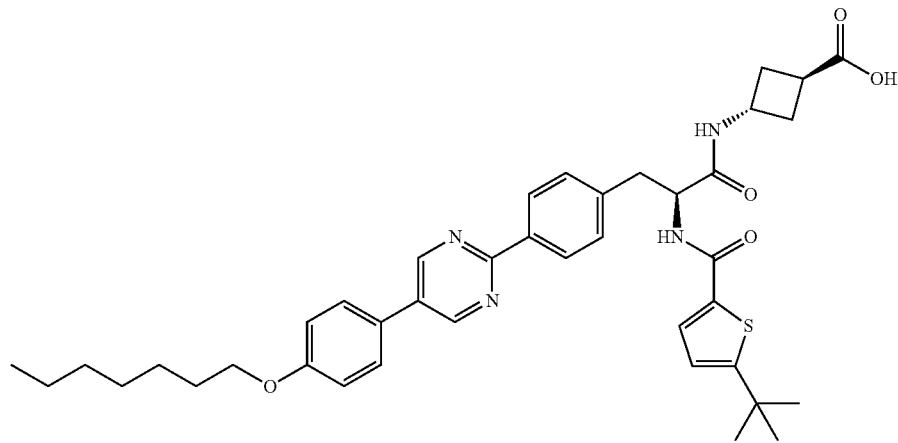
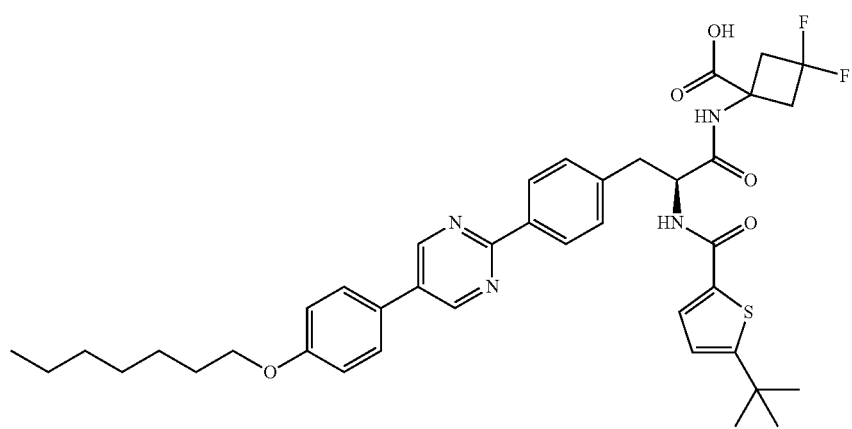
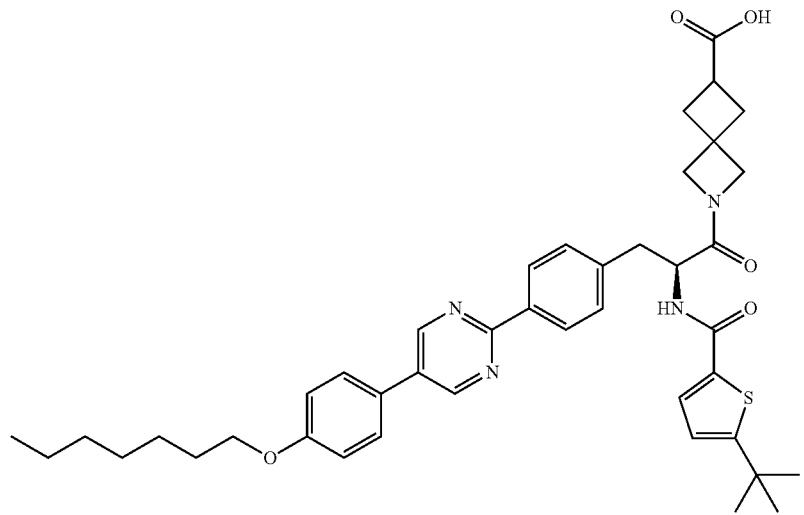 [SMILES: CCCCCCCOc1ccc(-c2cnc(-c3ccc(C[C@H](NC(=O)c4ccc(C(C)(C)C)s4)C(=O)N4CC5(CC(C(=O)O)C5)C4)cc3)nc2)cc1]

1443
-continued
1444
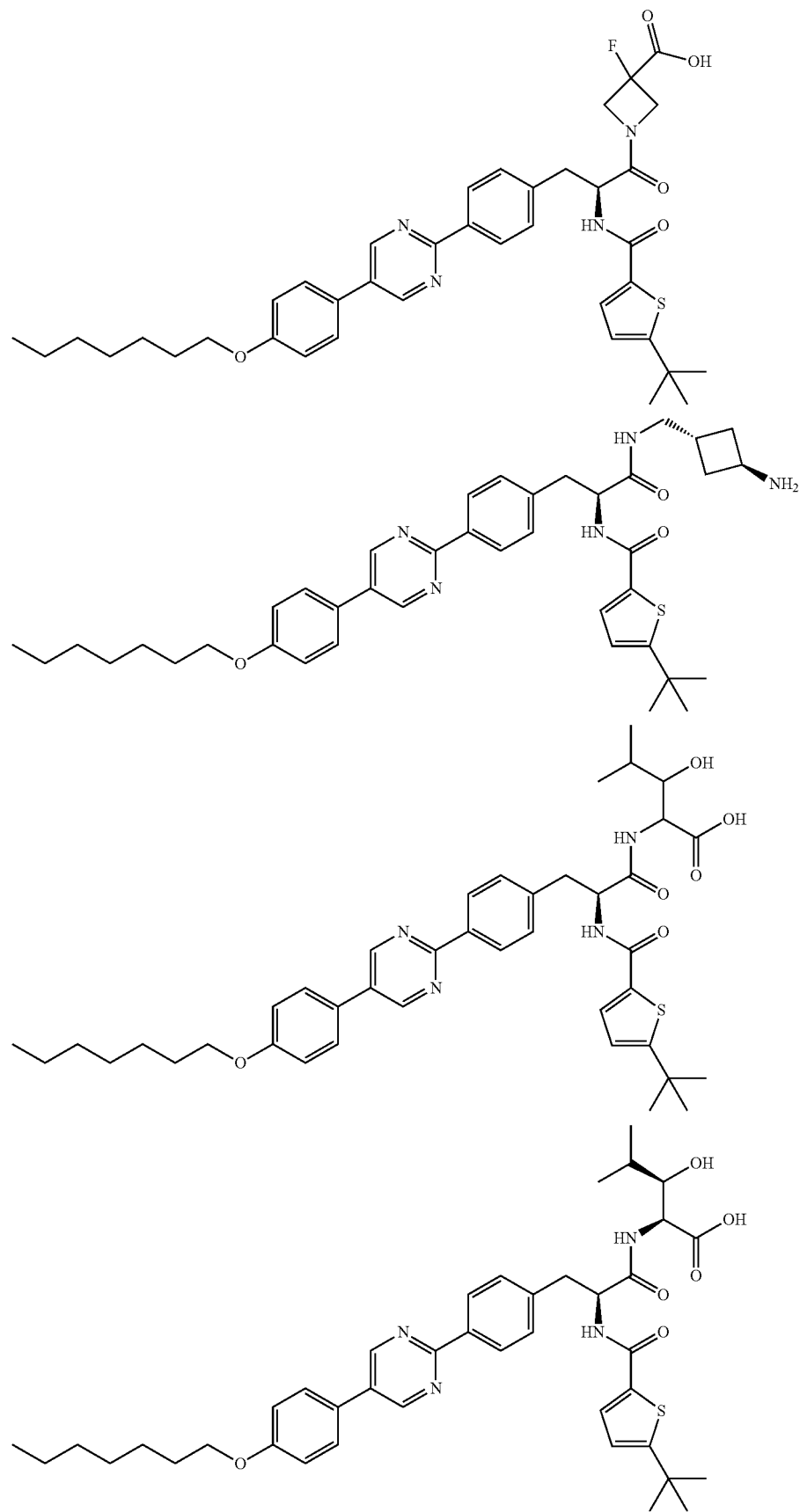

1445
-continued
1446
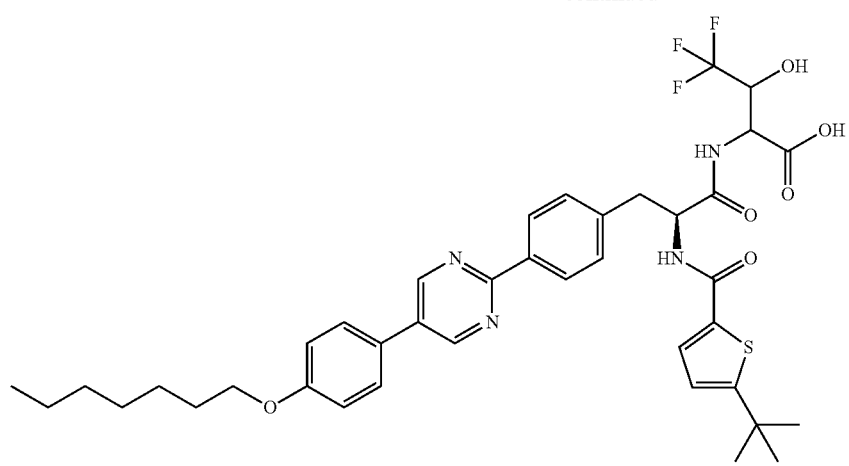
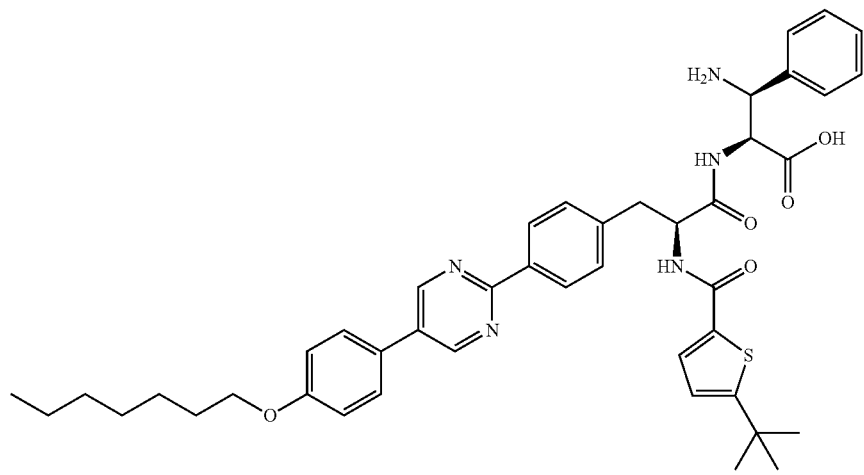
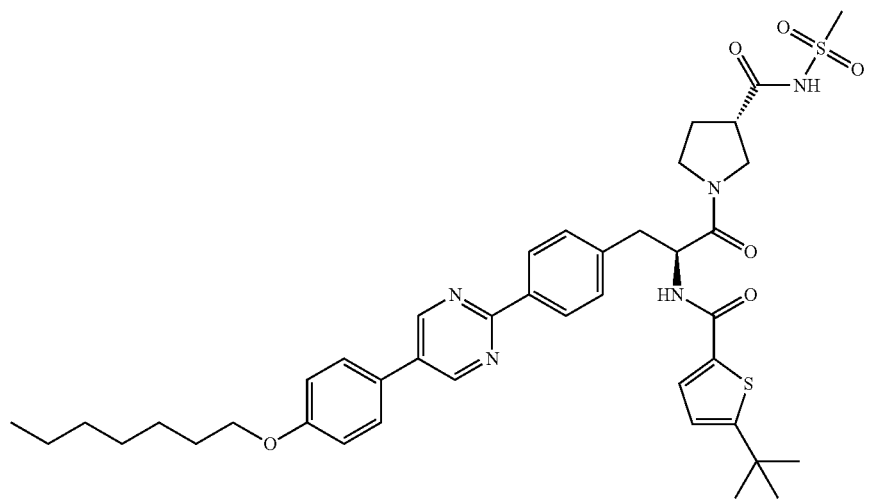

-continued
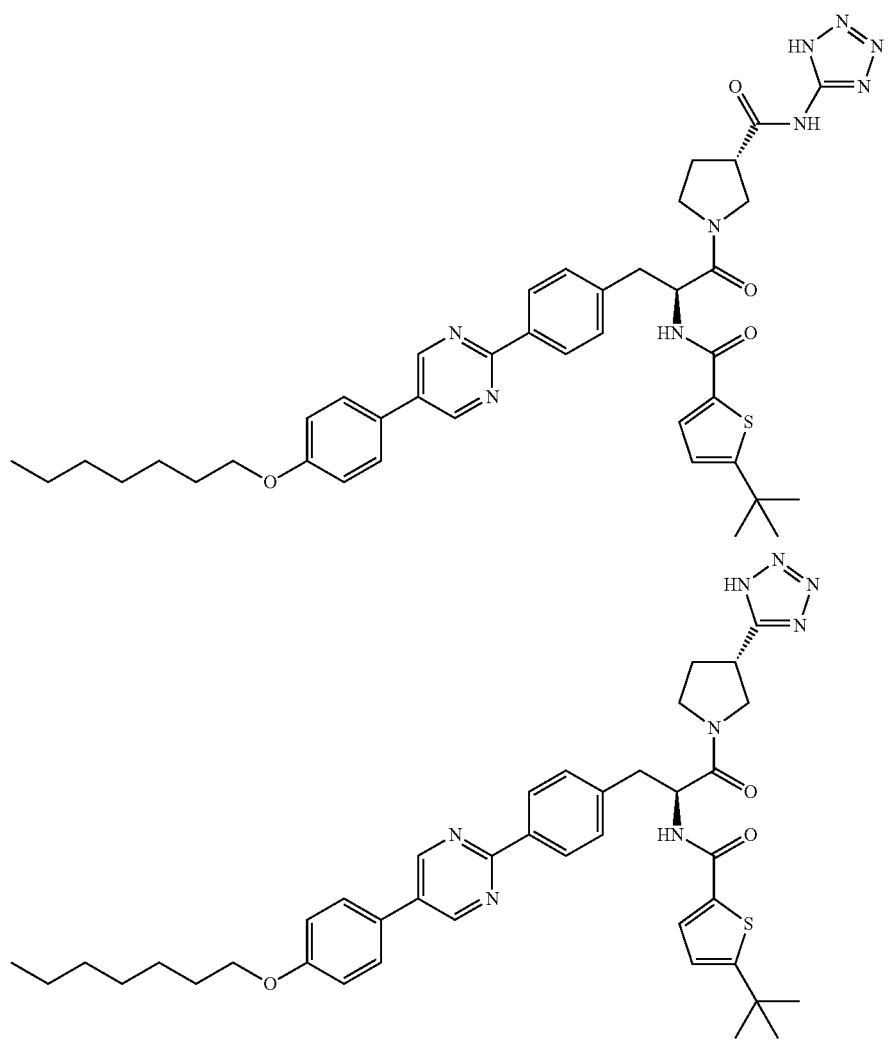
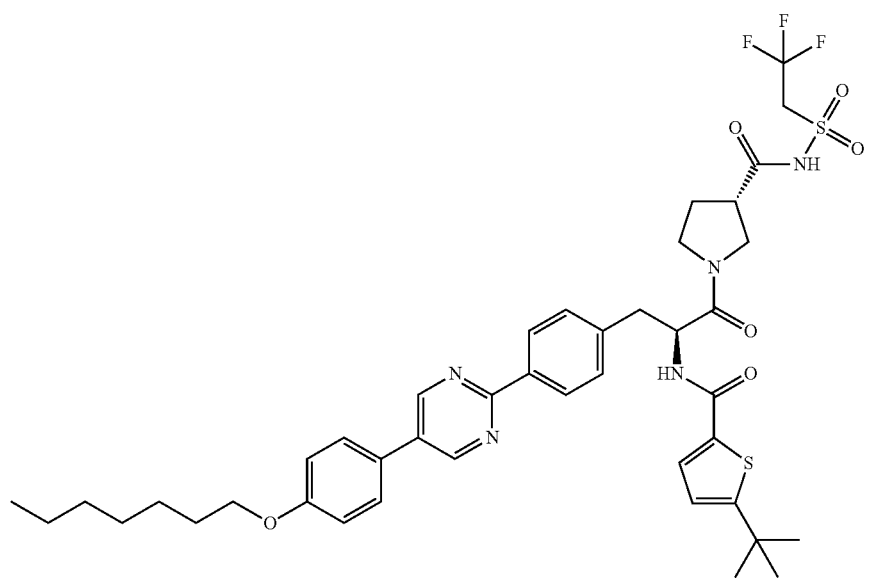

-continued
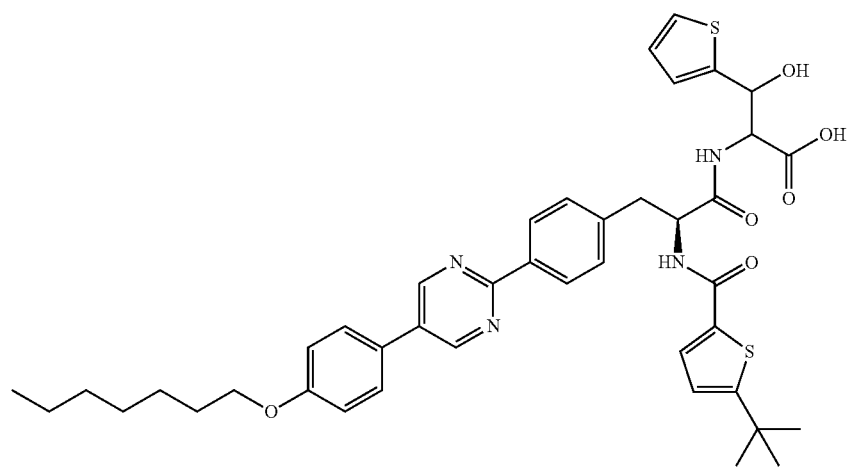
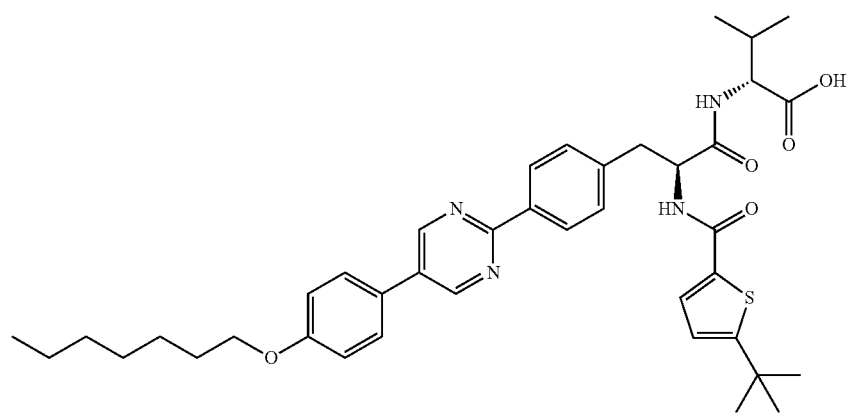
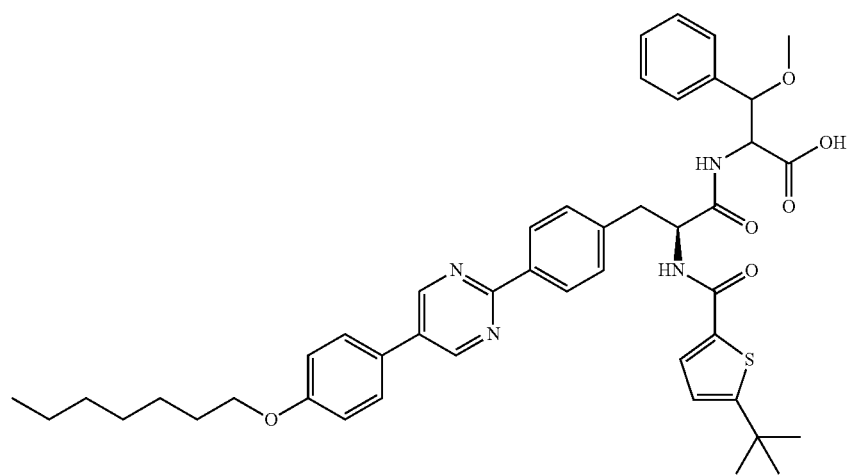

1451
1452
-continued
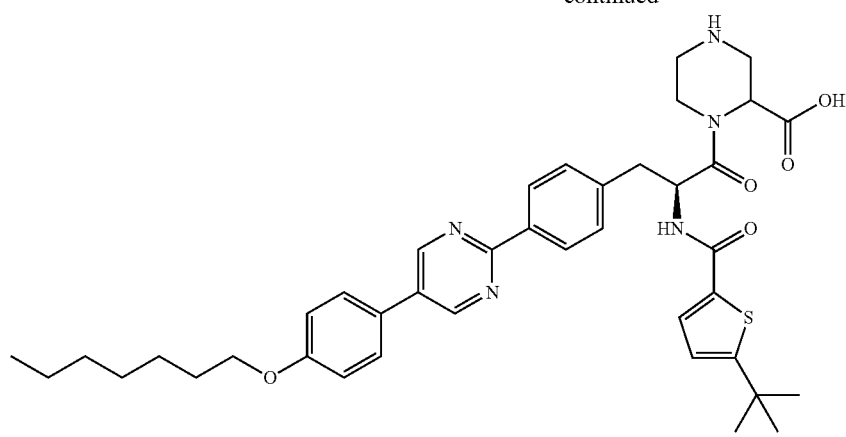
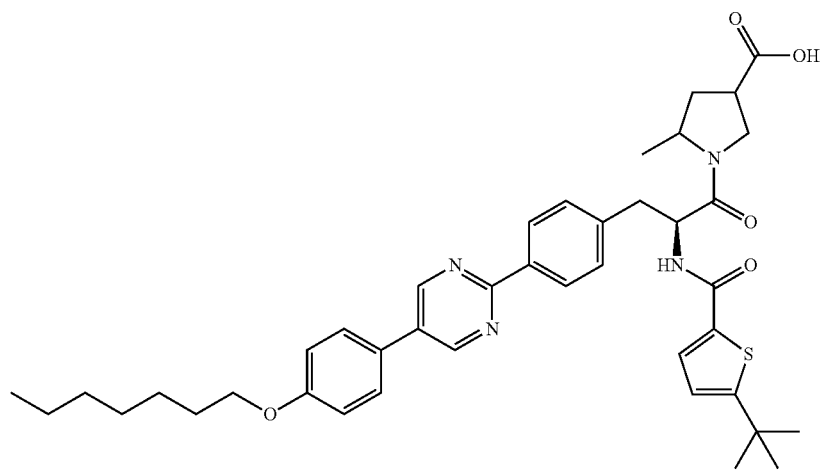
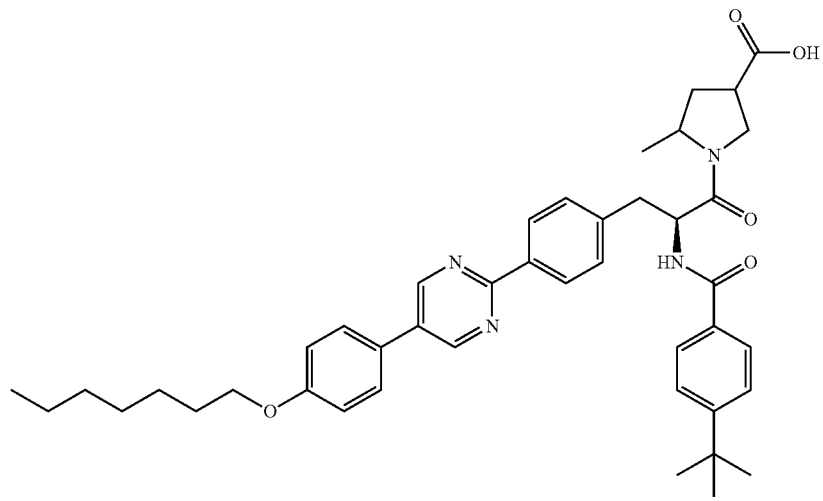

-continued
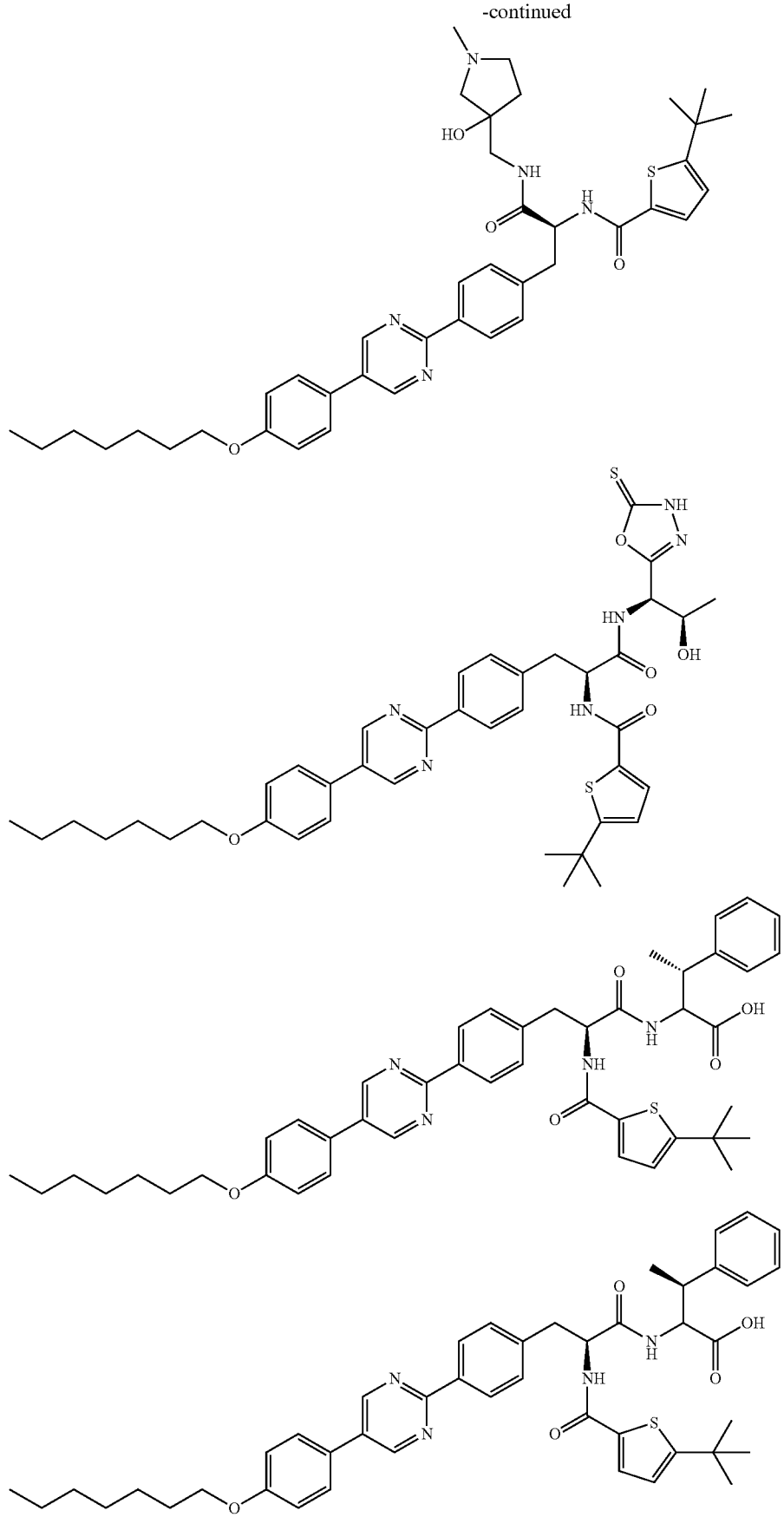

-continued
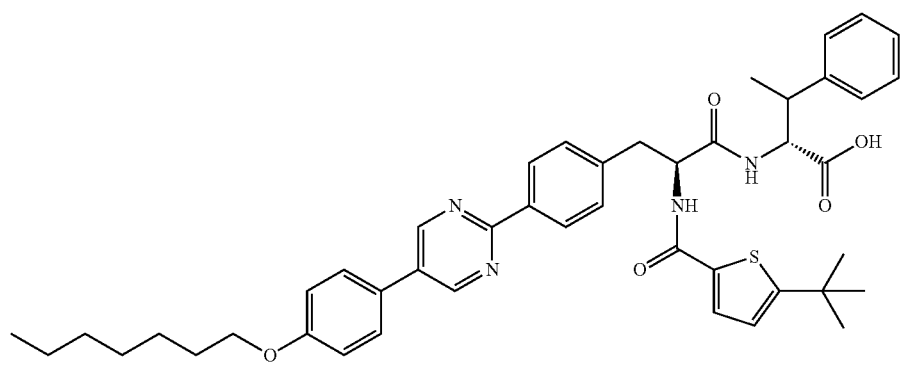
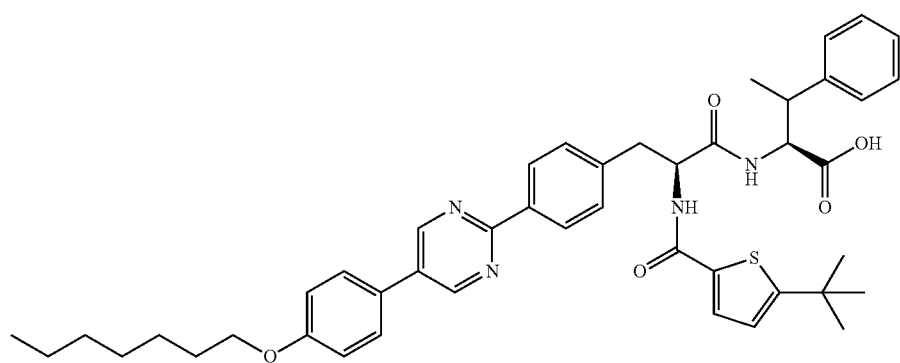
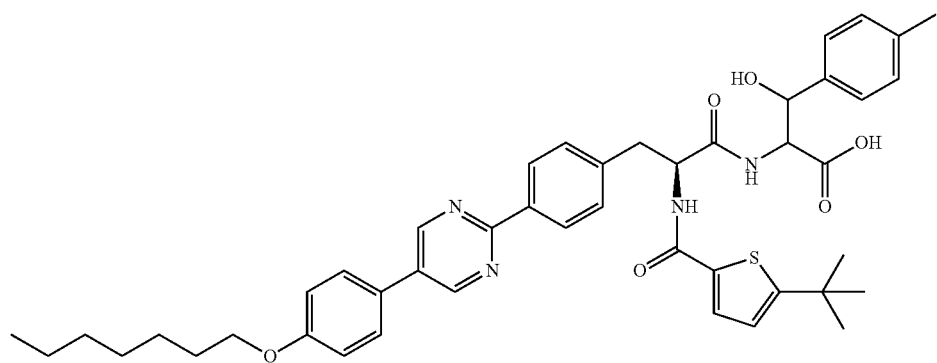
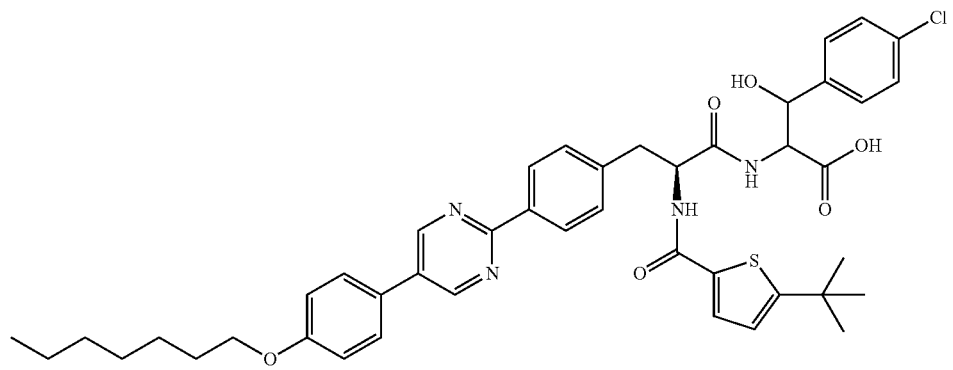

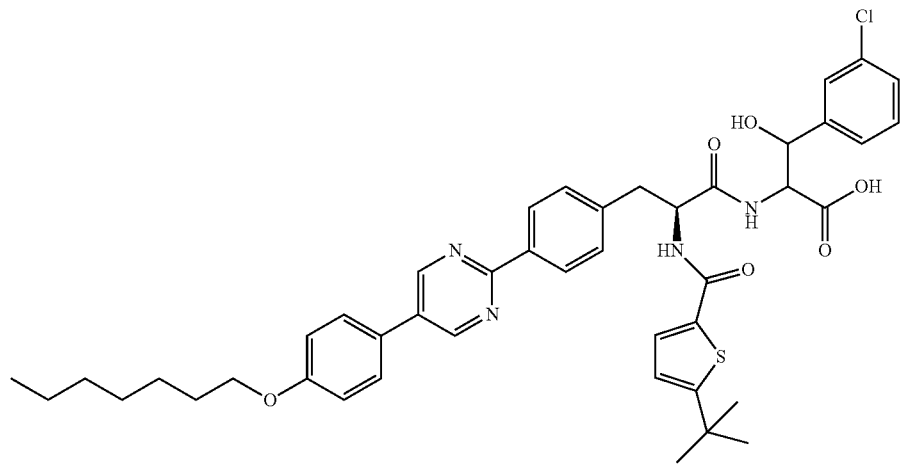
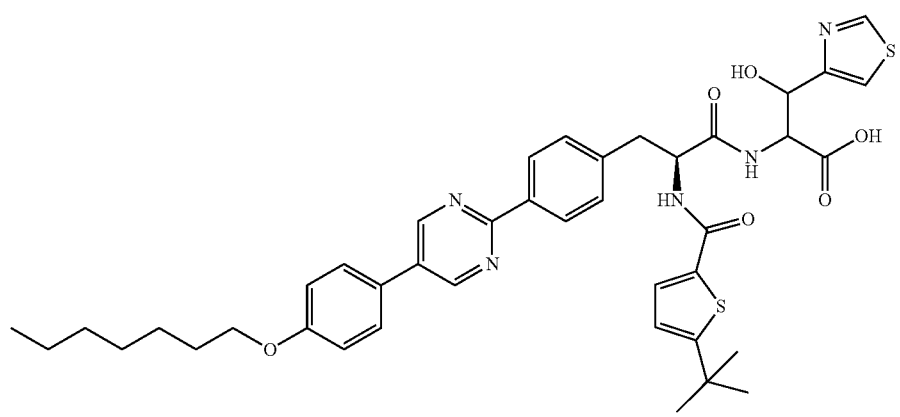
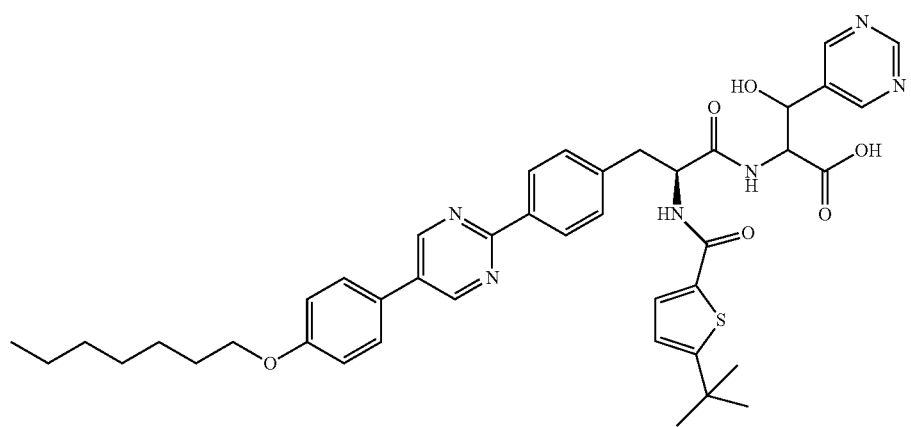

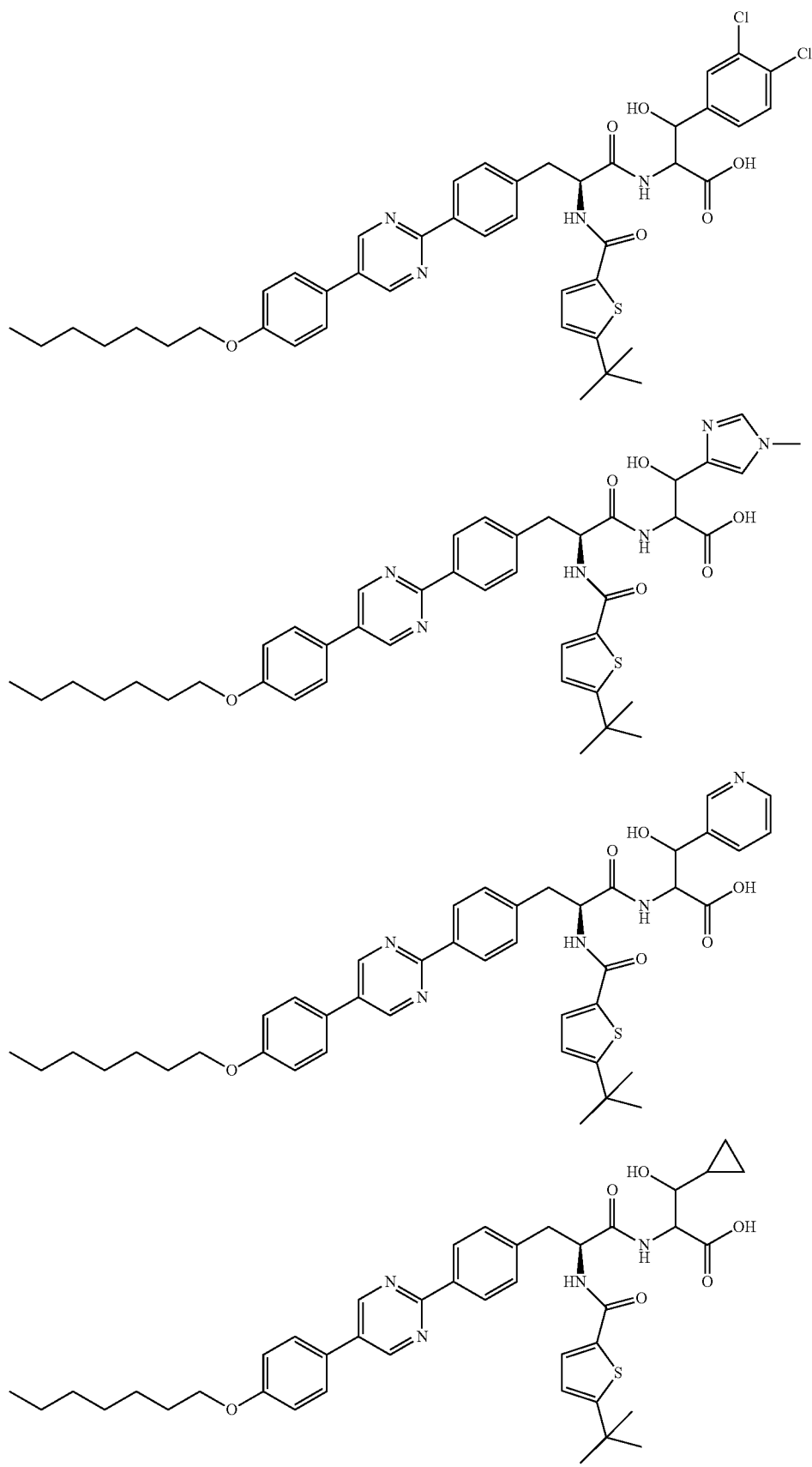

1461 1462
-continued
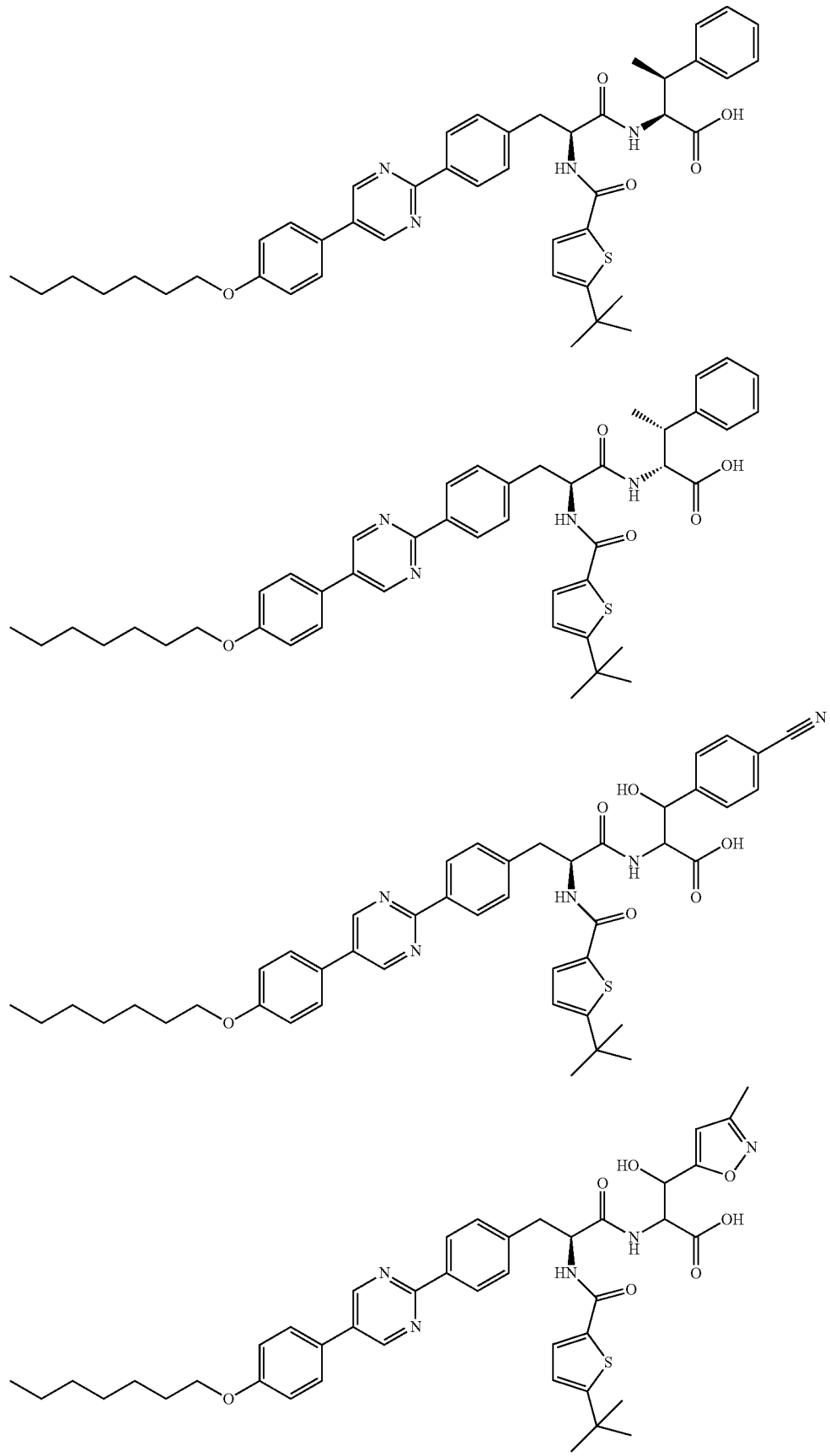

-continued
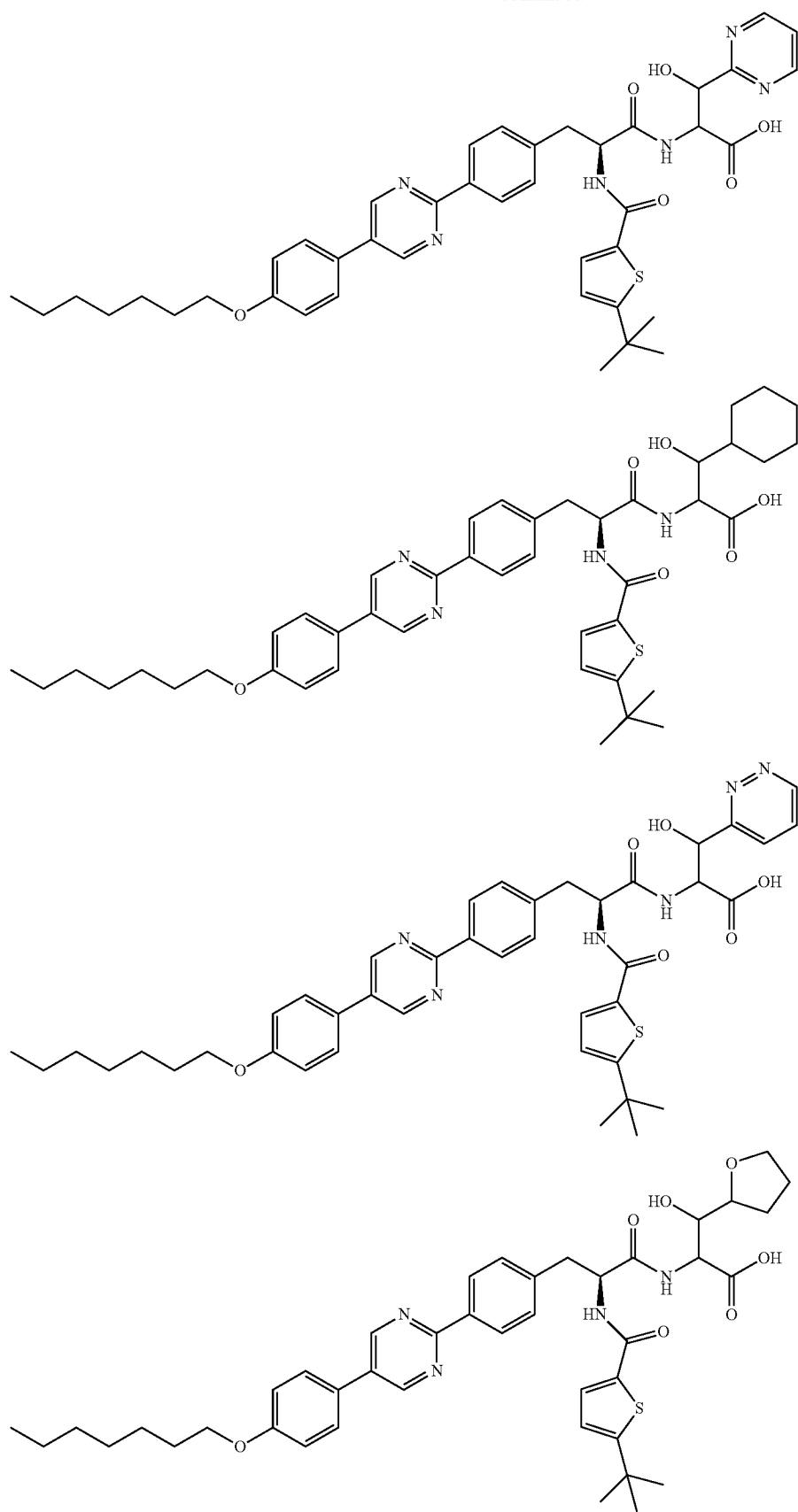

-continued
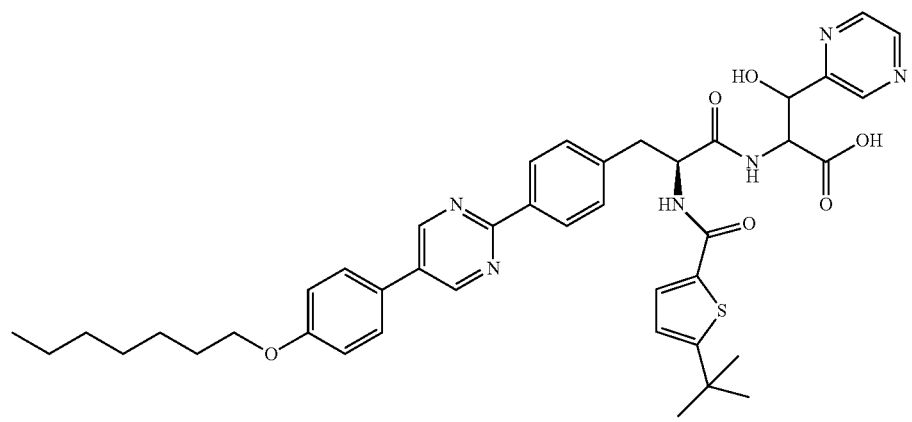
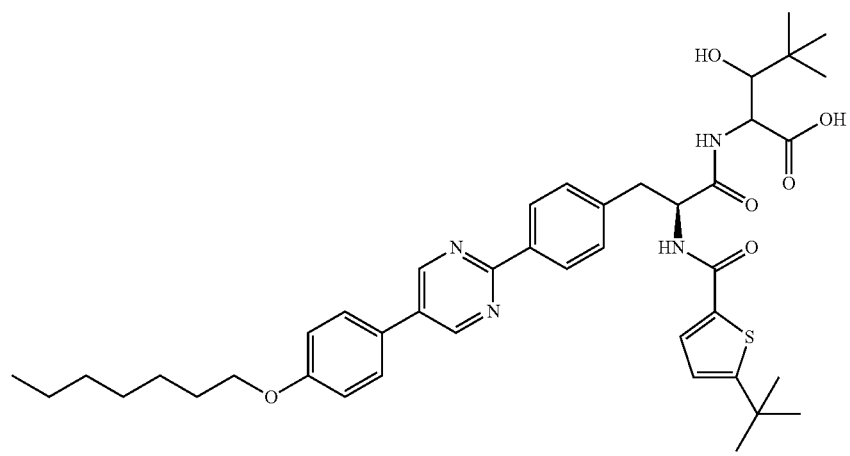
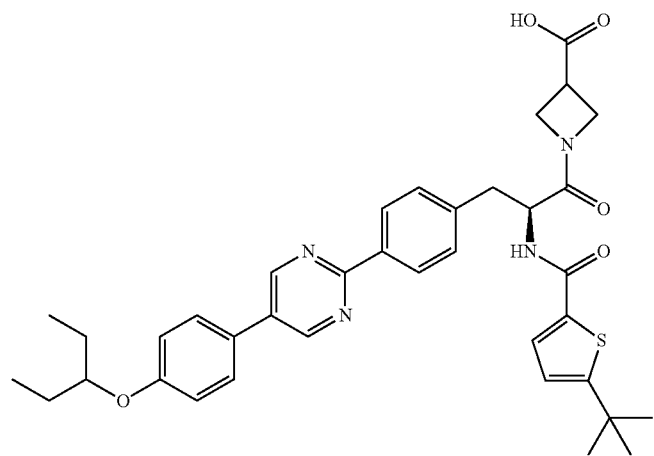

1467
-continued
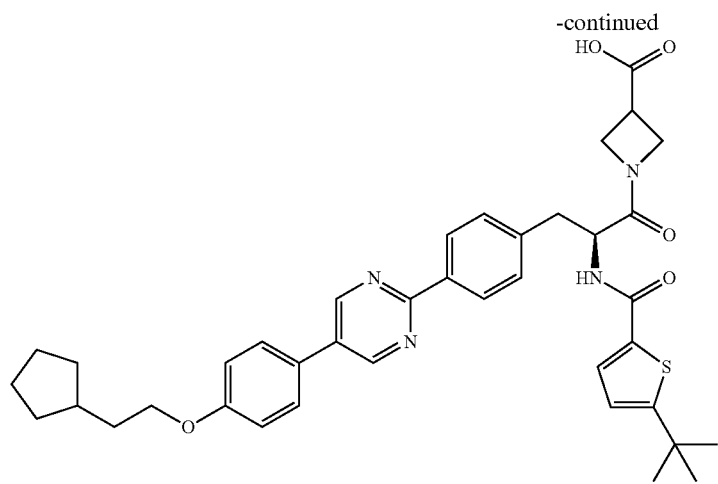
1468
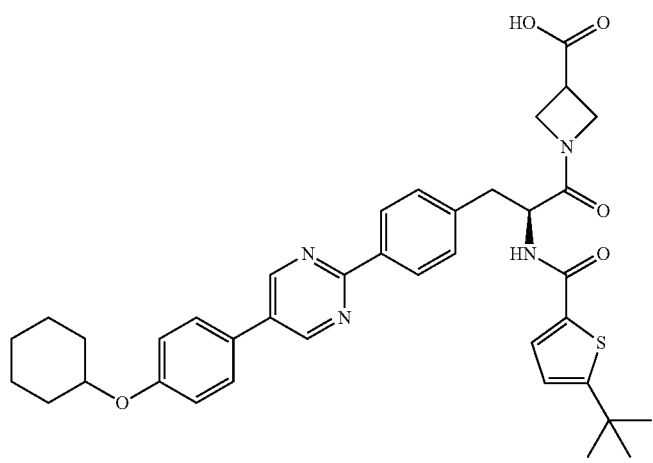
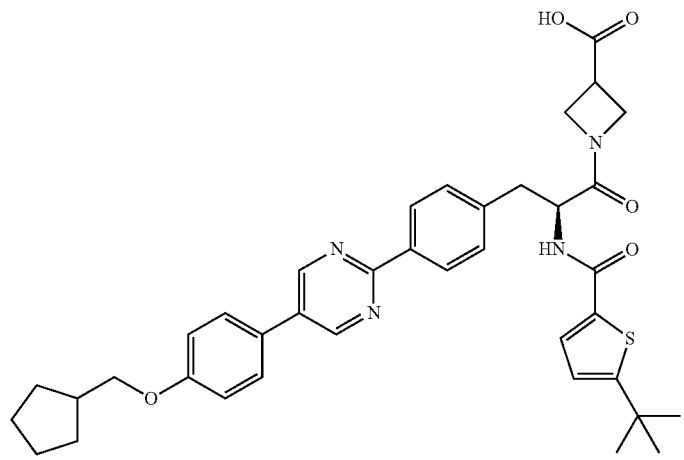

1469
1470
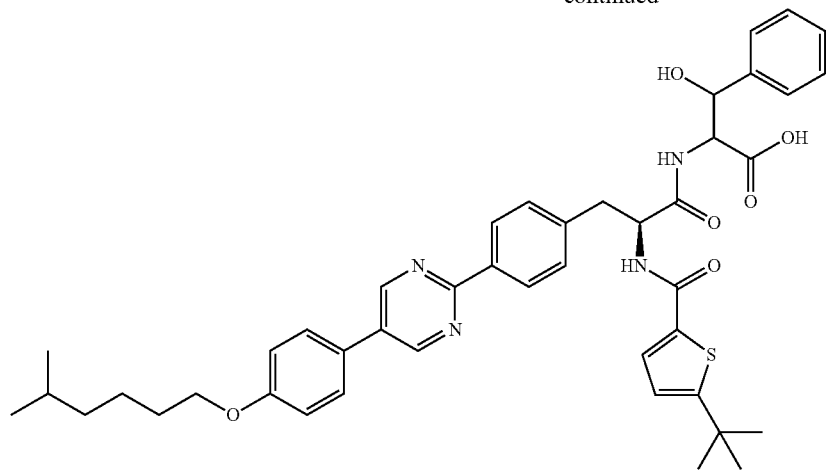
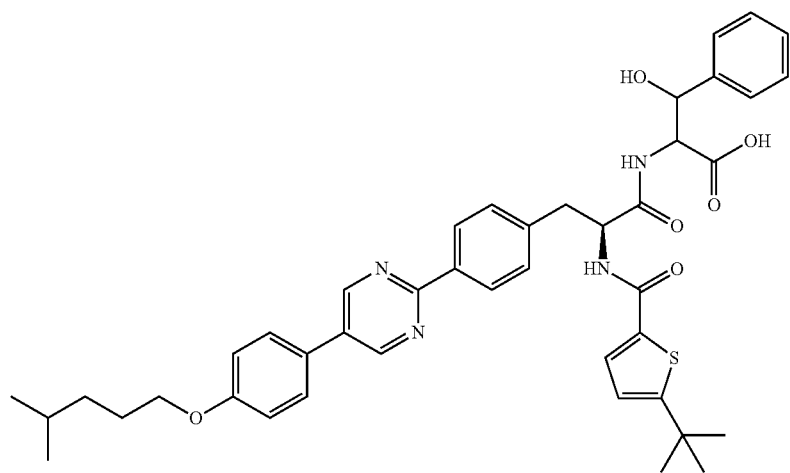
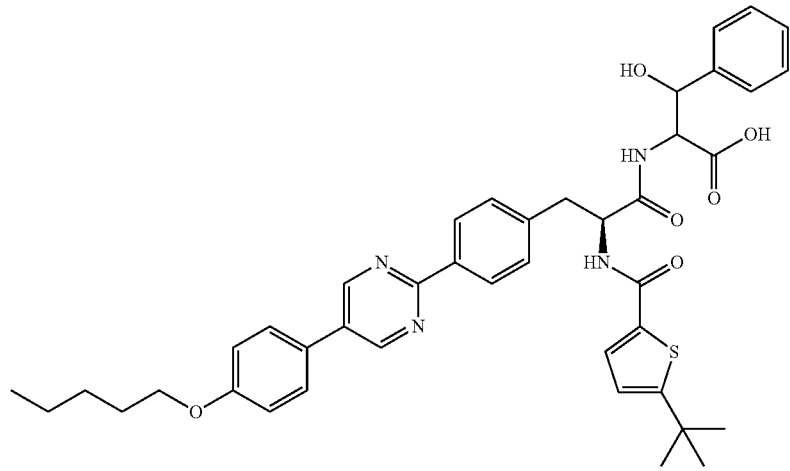

-continued
1471
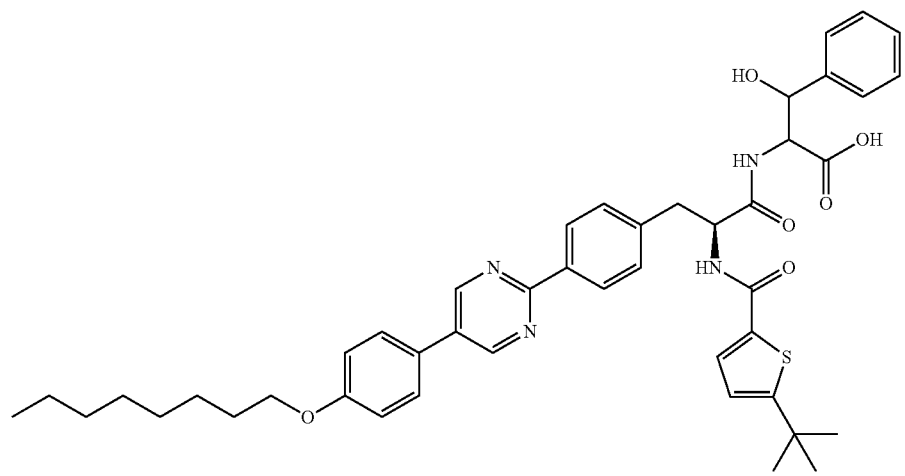
1472
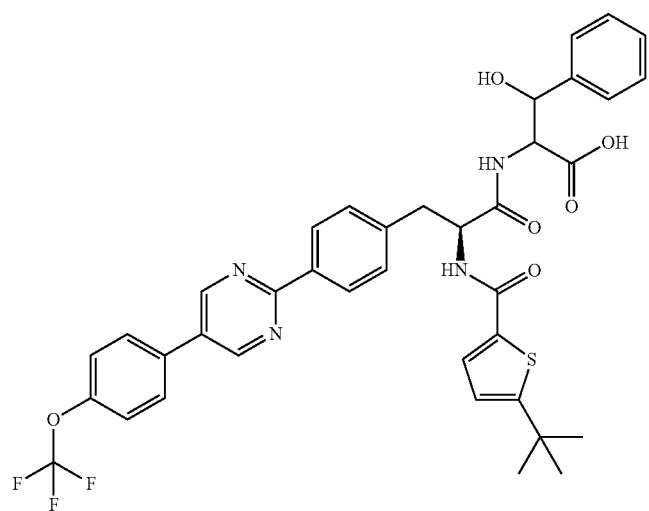
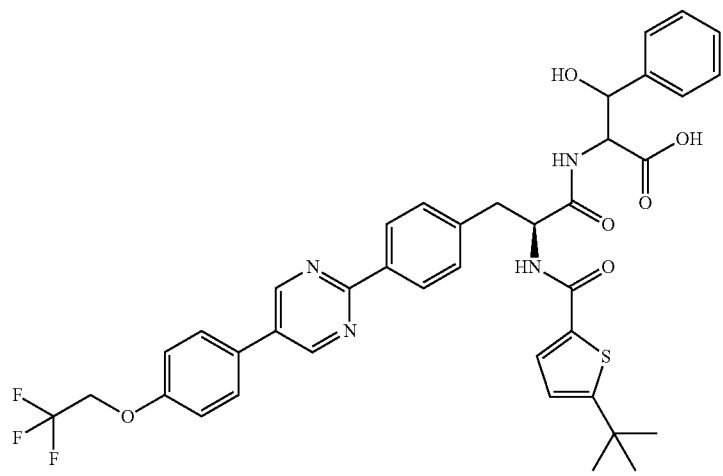

1473
-continued
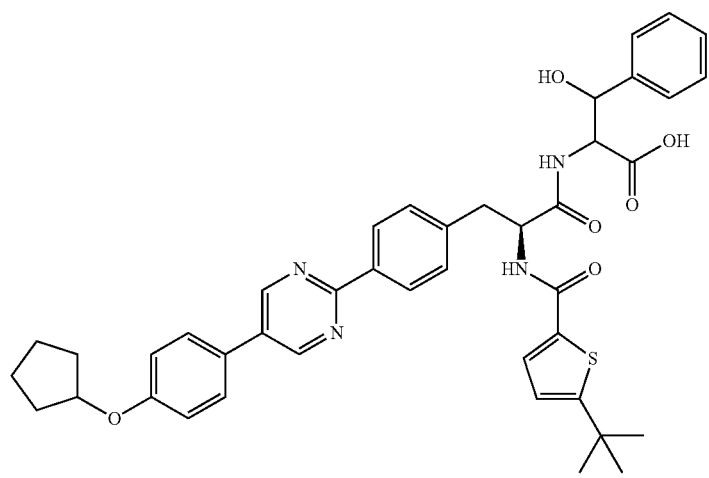
1474
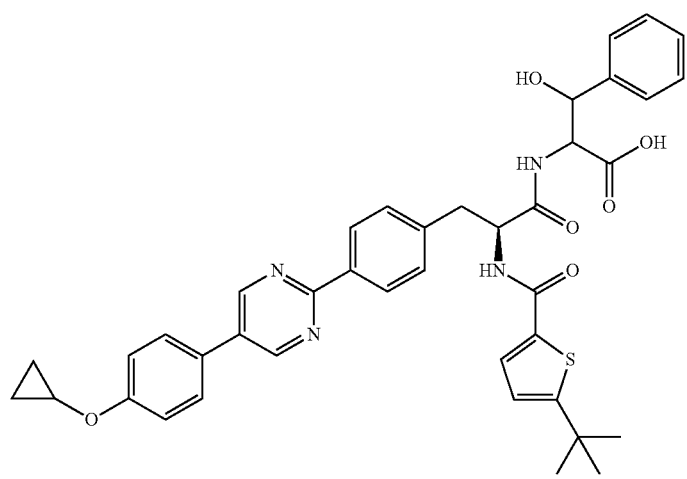
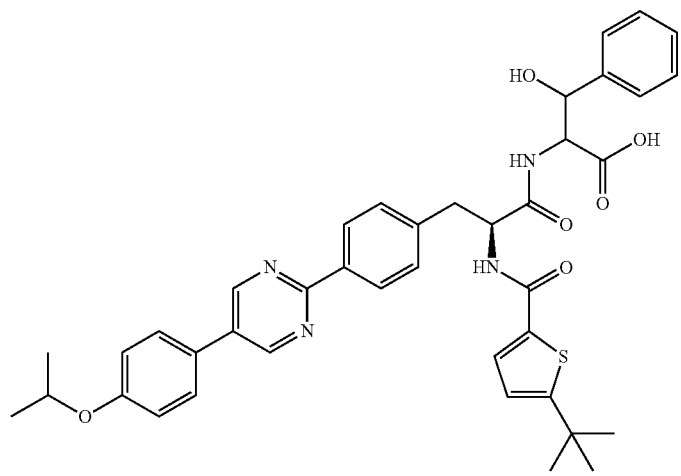

1475
-continued
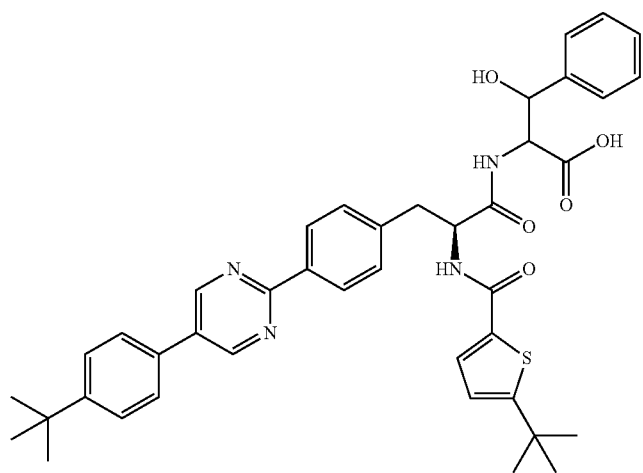
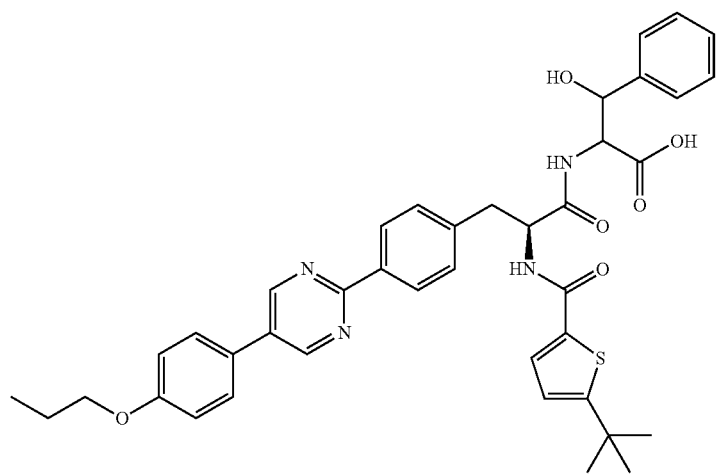
1476
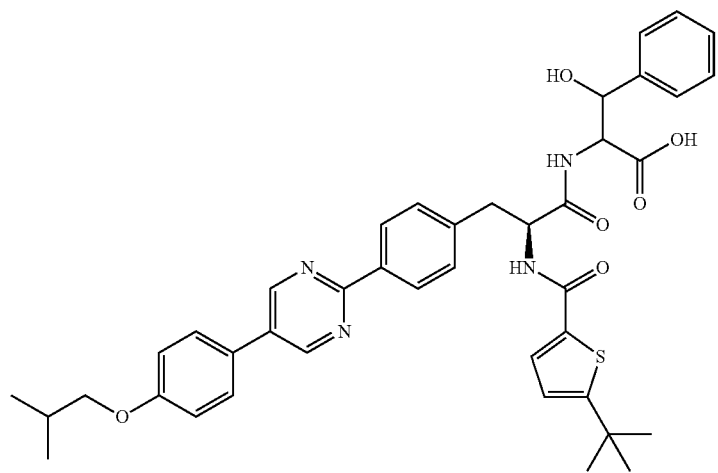

-continued
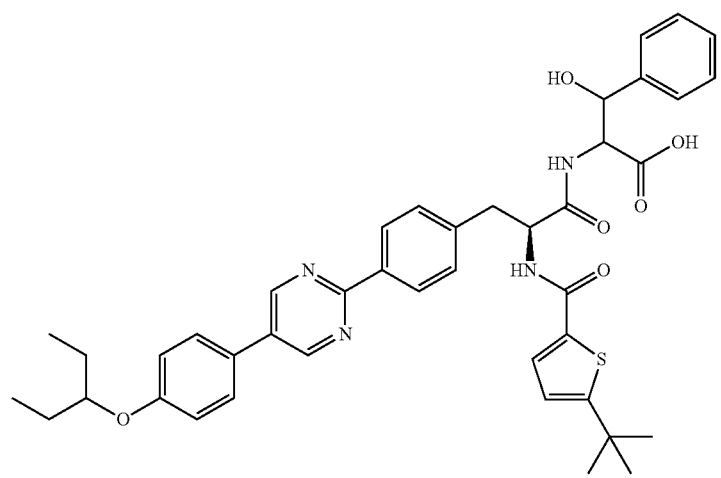
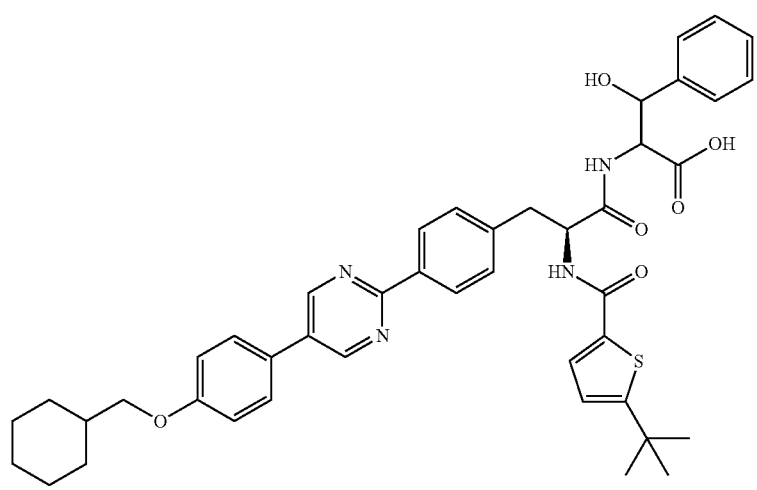
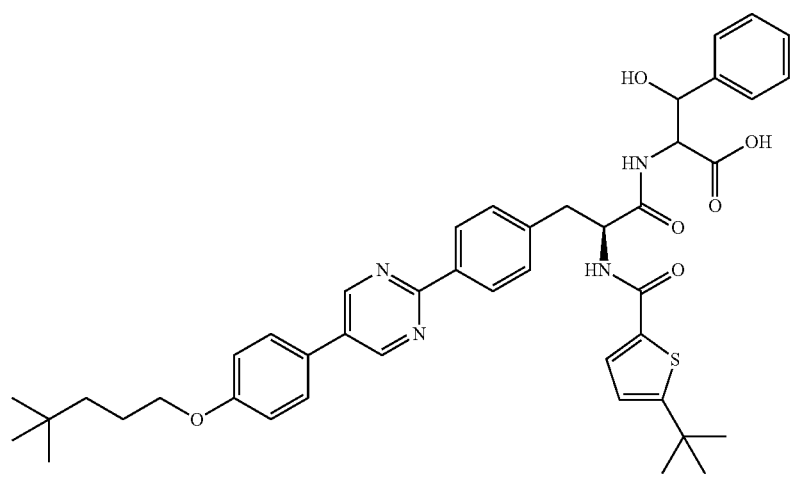

-continued
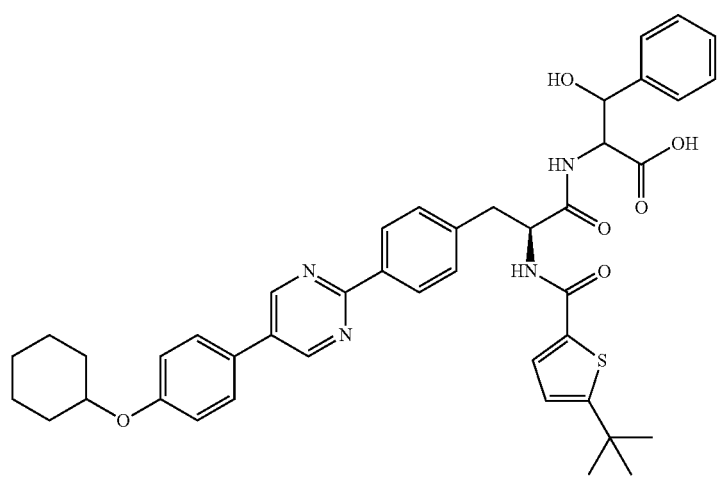
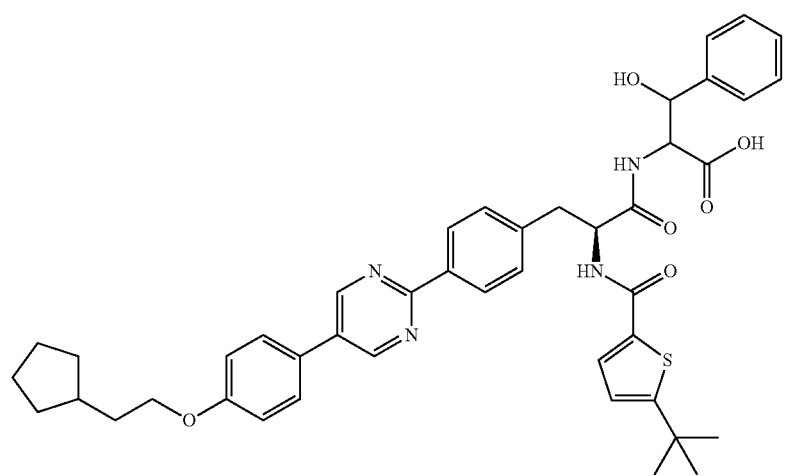
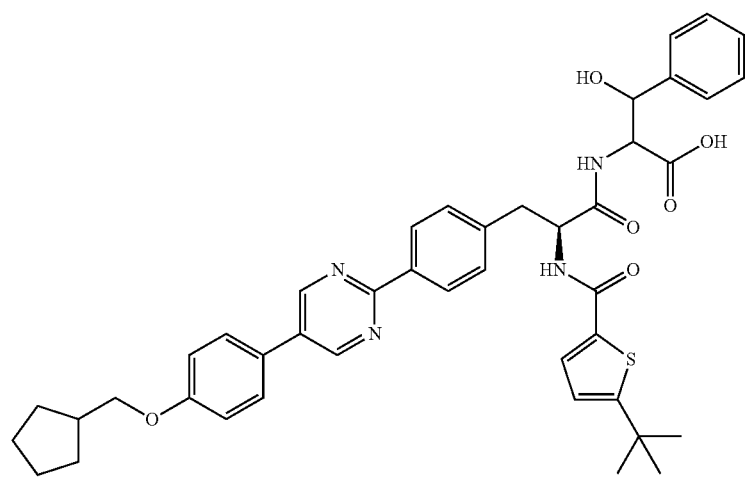

-continued
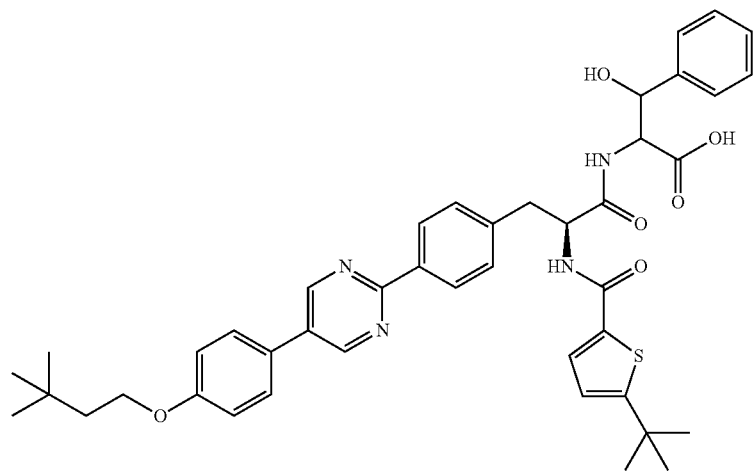
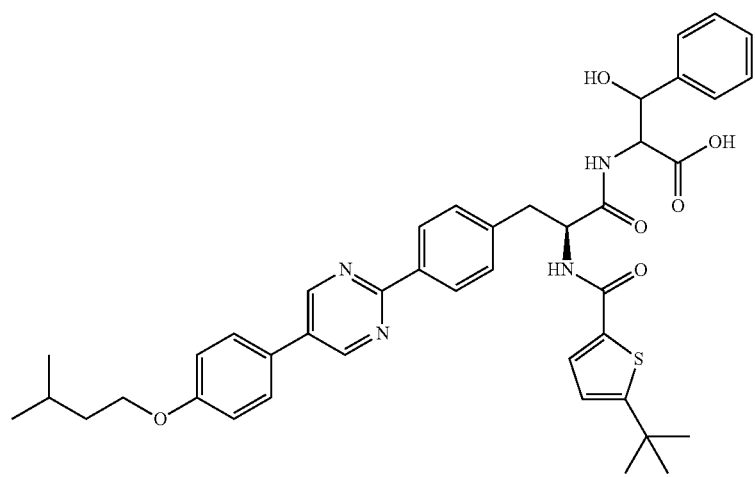
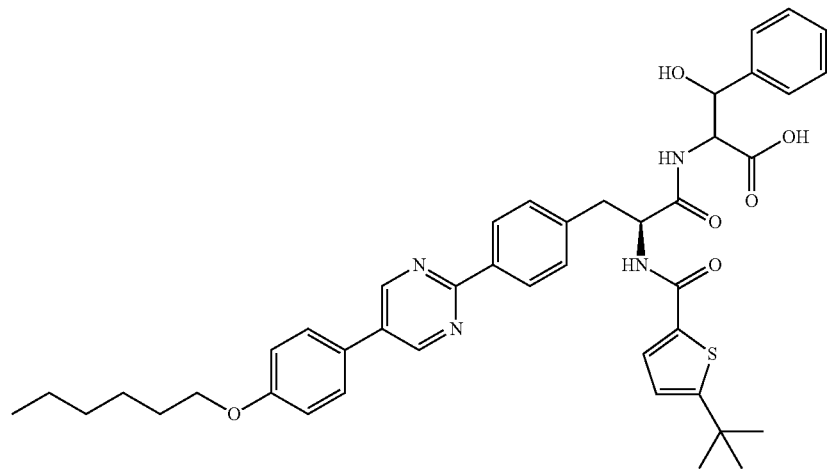

1483
-continued
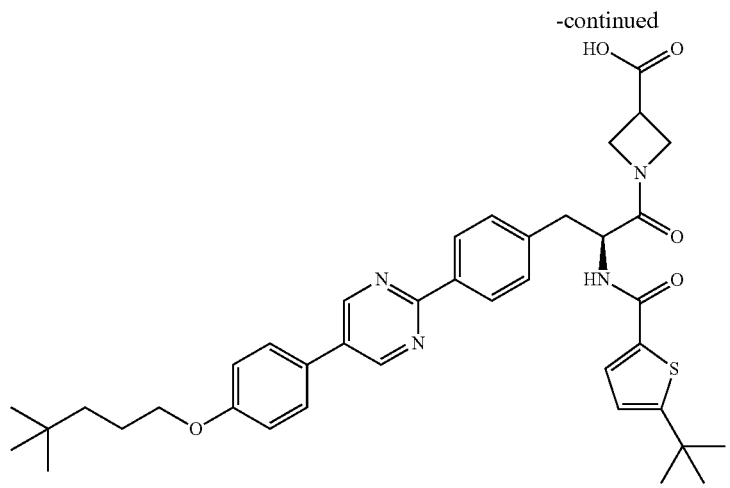
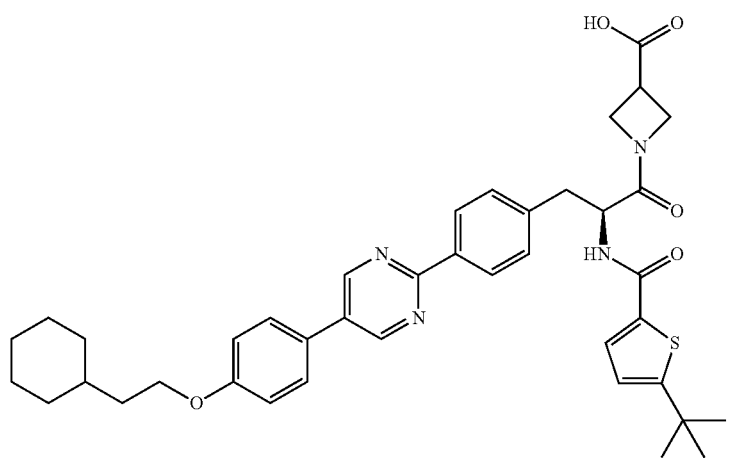
1484
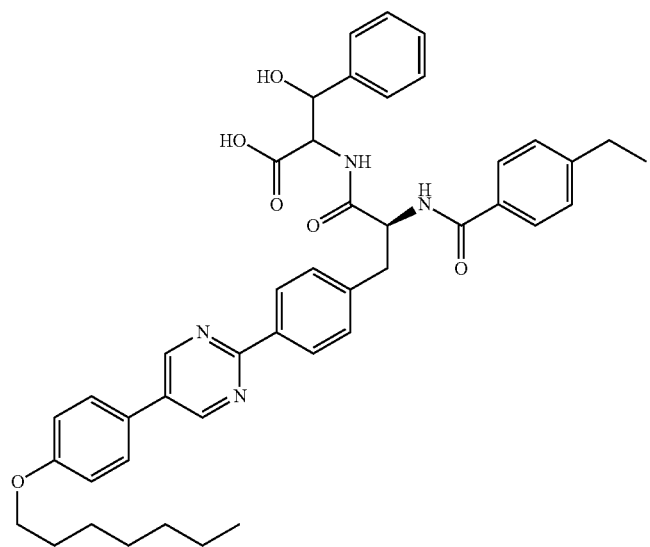

1485
-continued
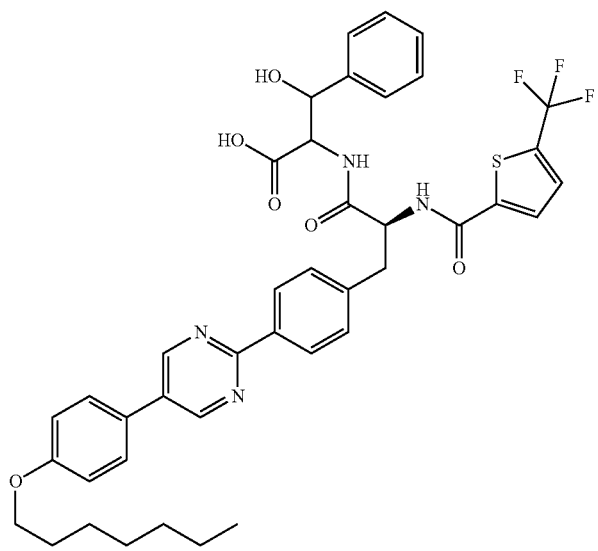
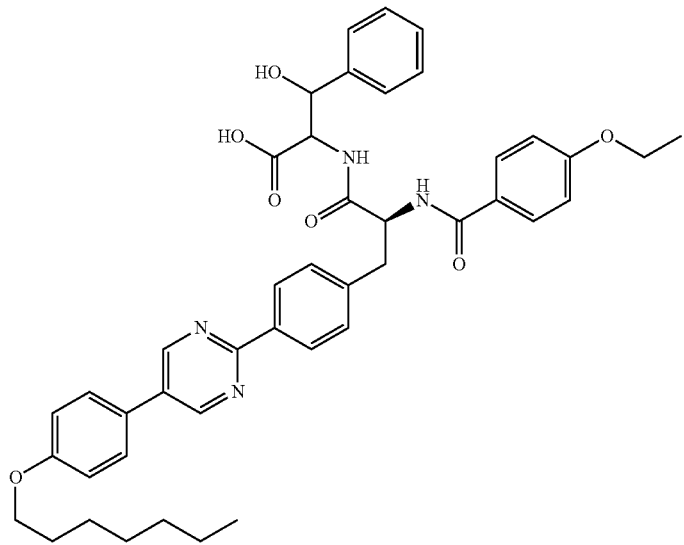
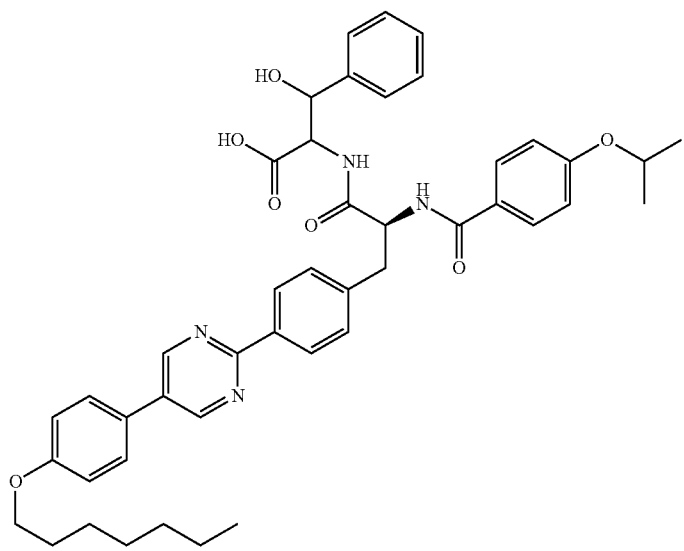
1486

1487
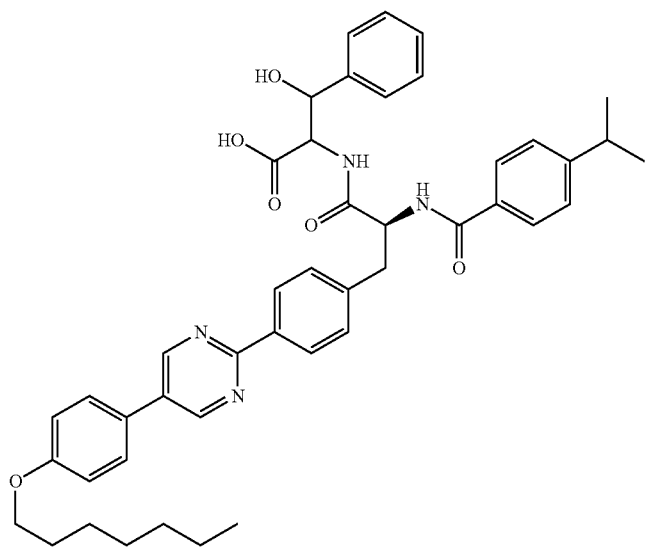
1488
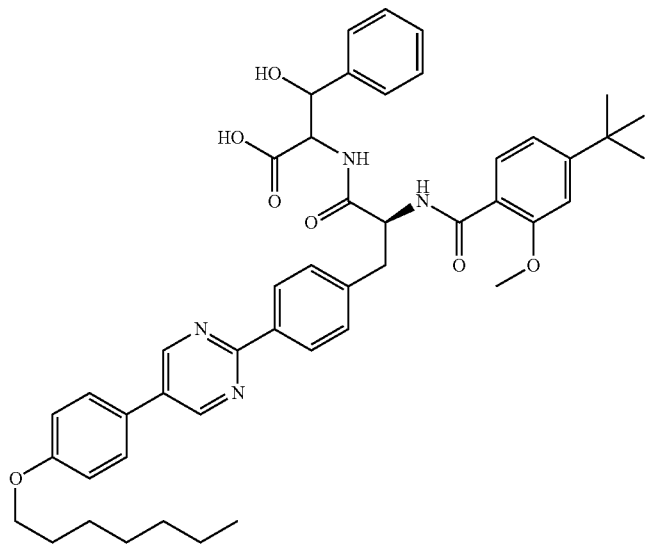
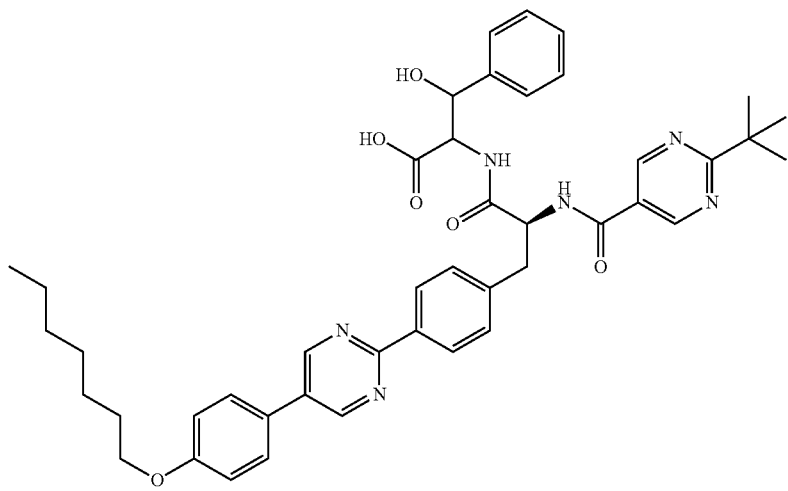

-continued
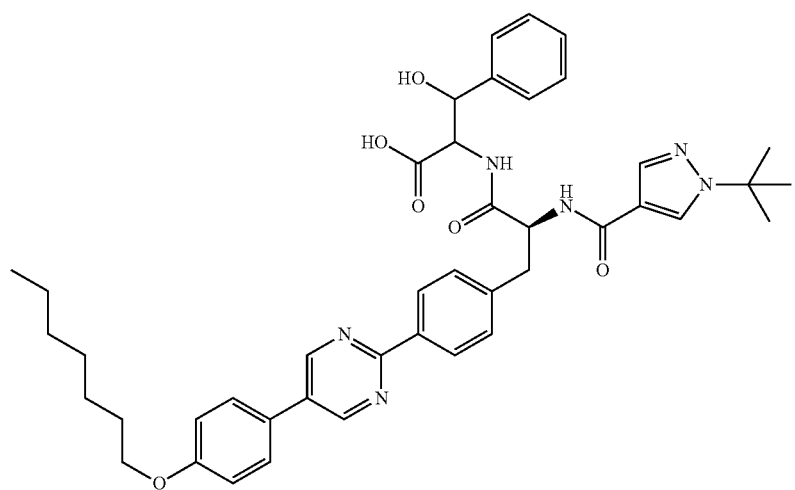
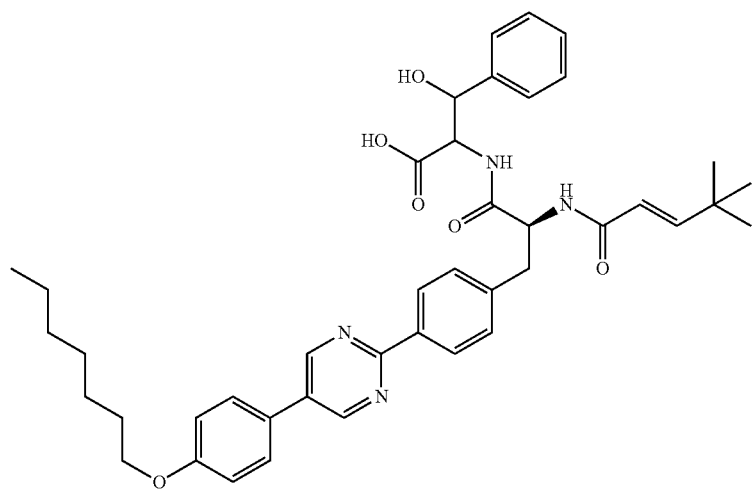
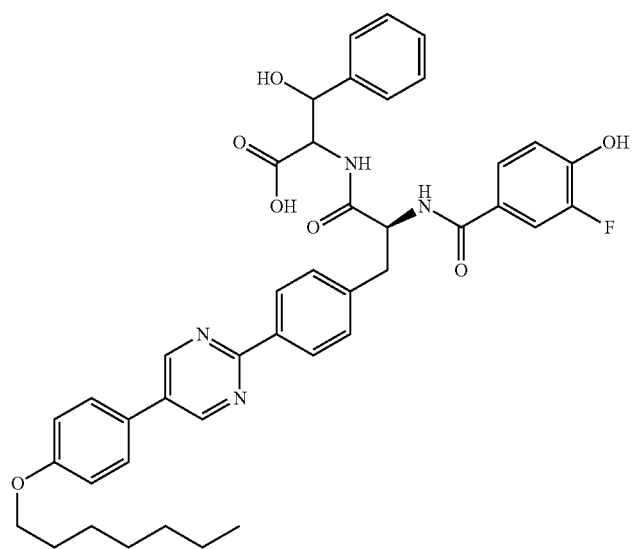

-continued
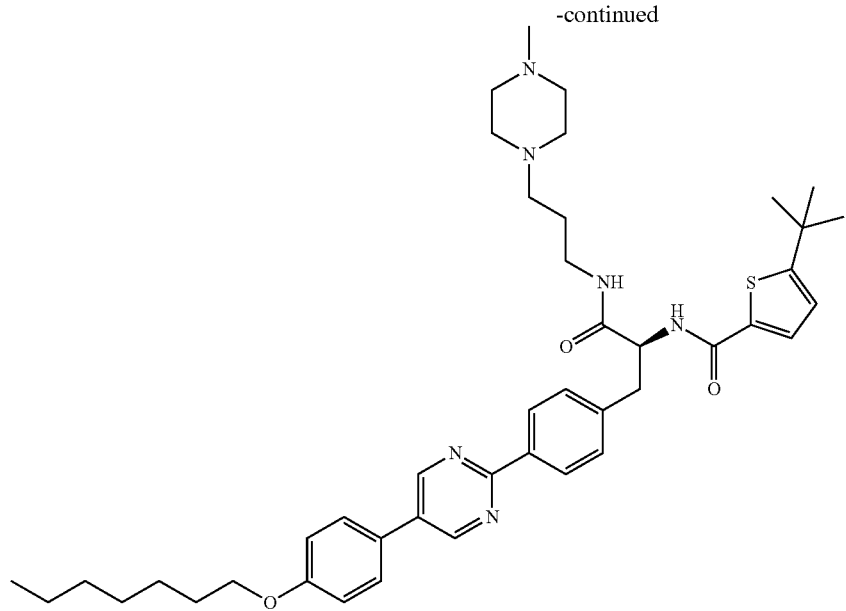
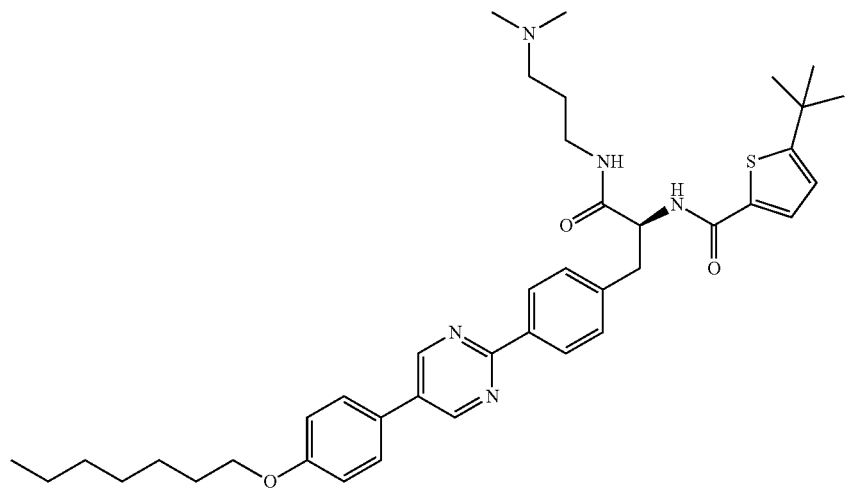
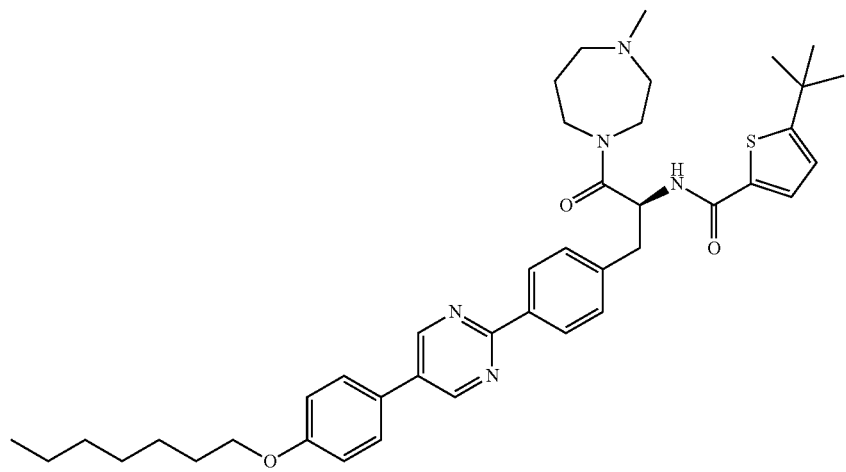

1493
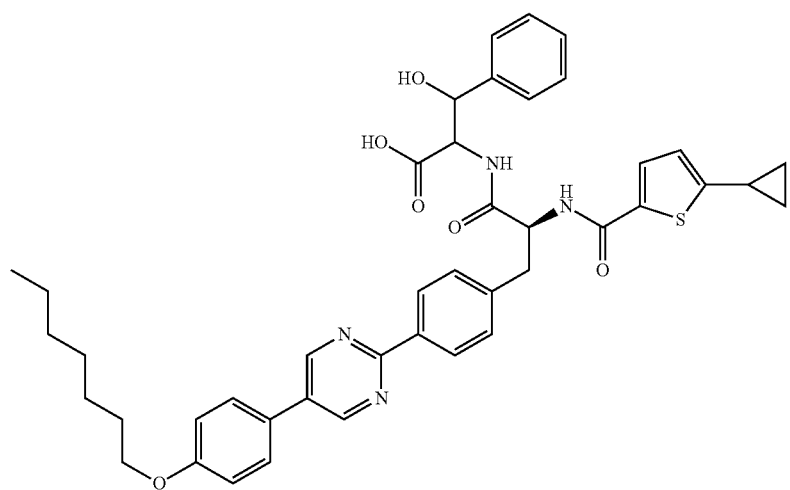
1494
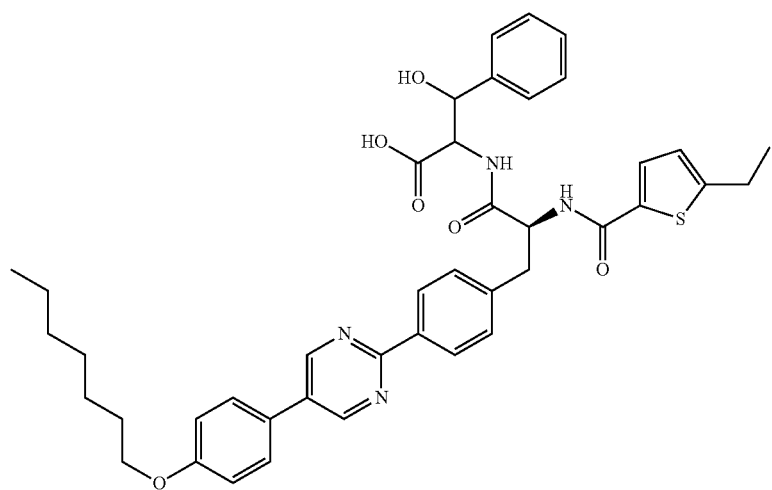
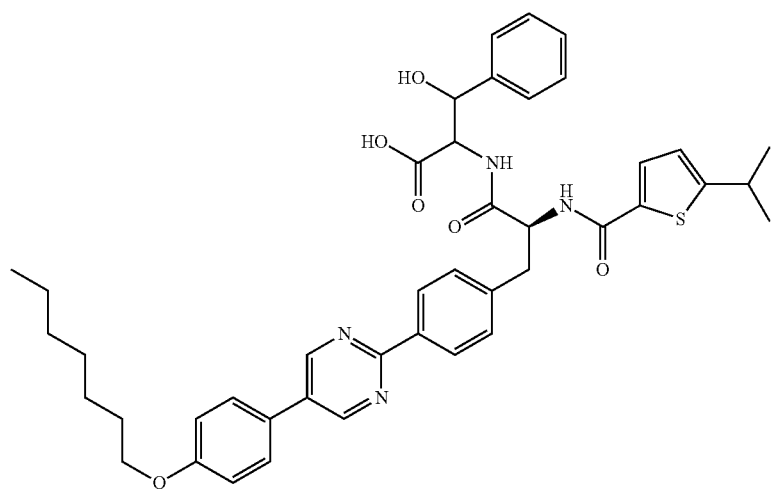

-continued
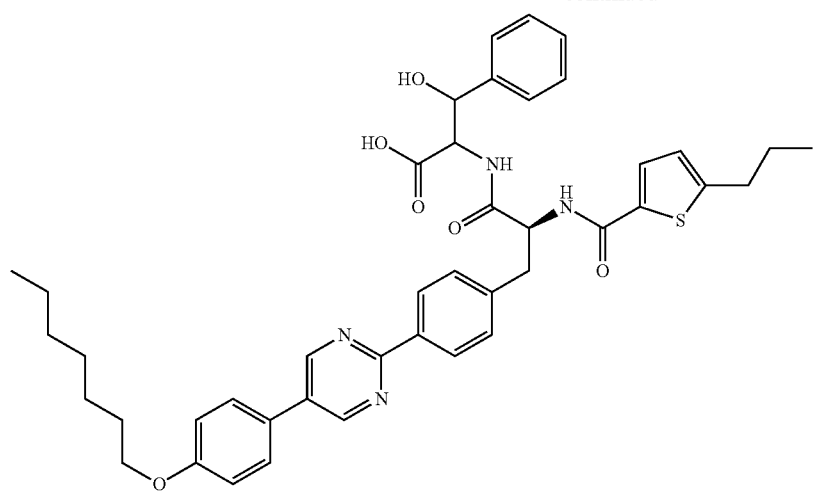
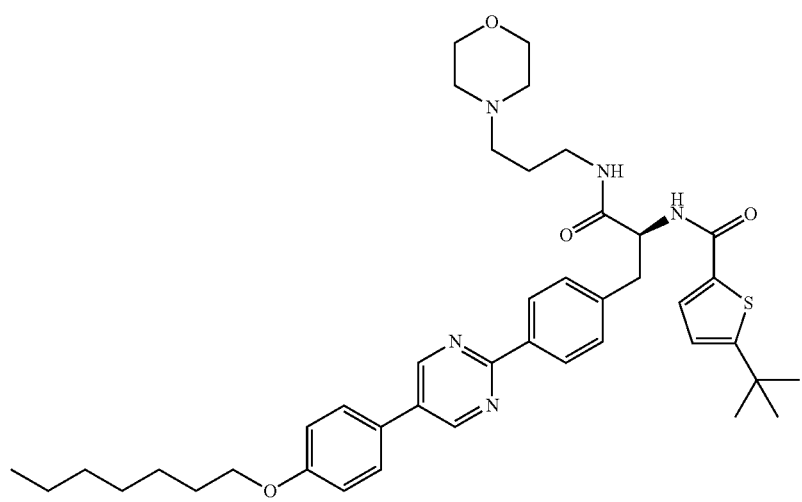
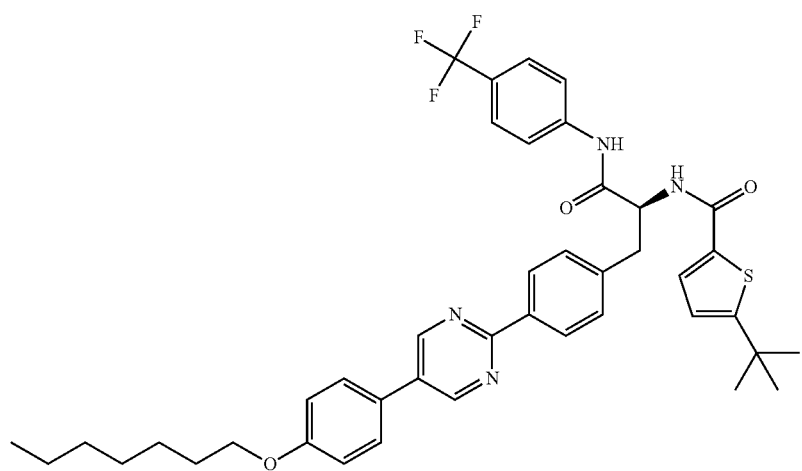

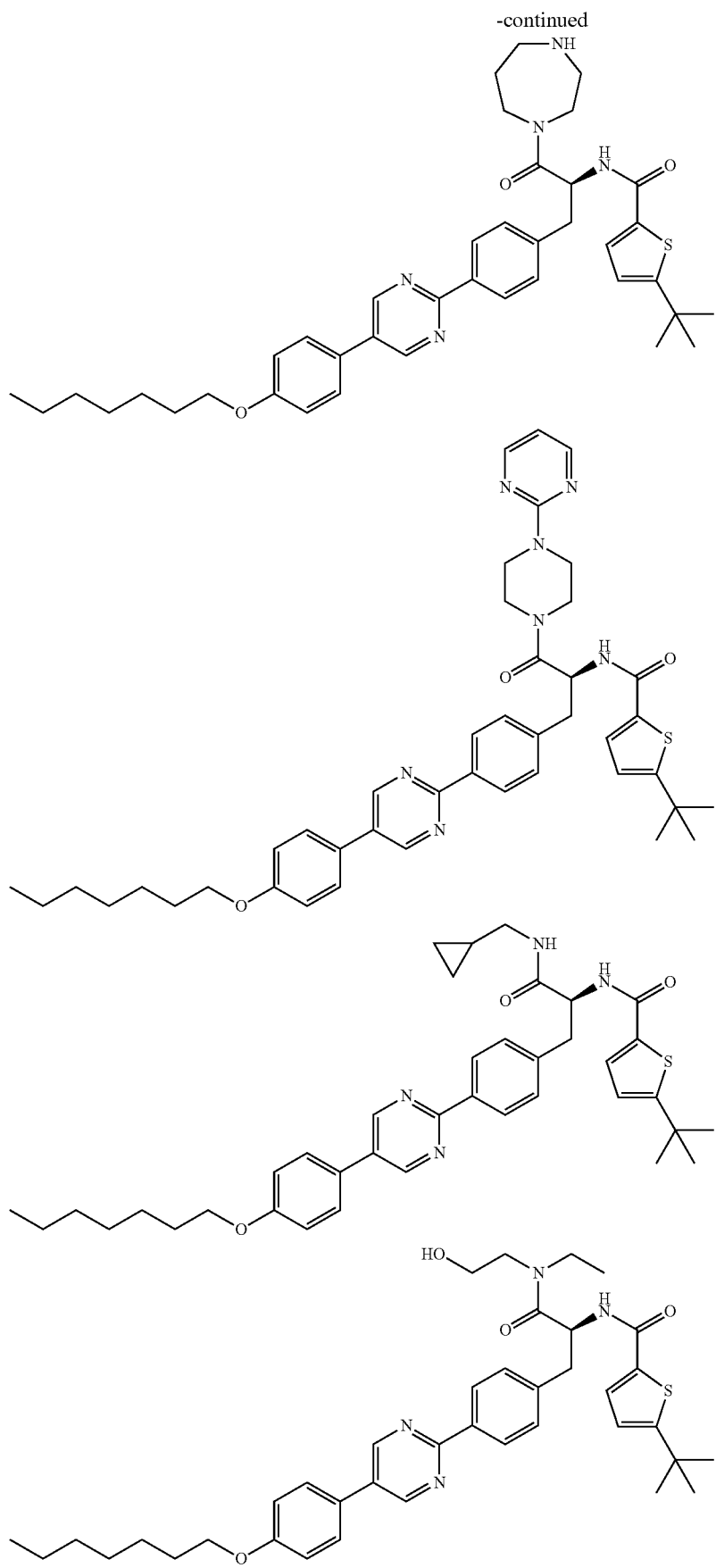

-continued
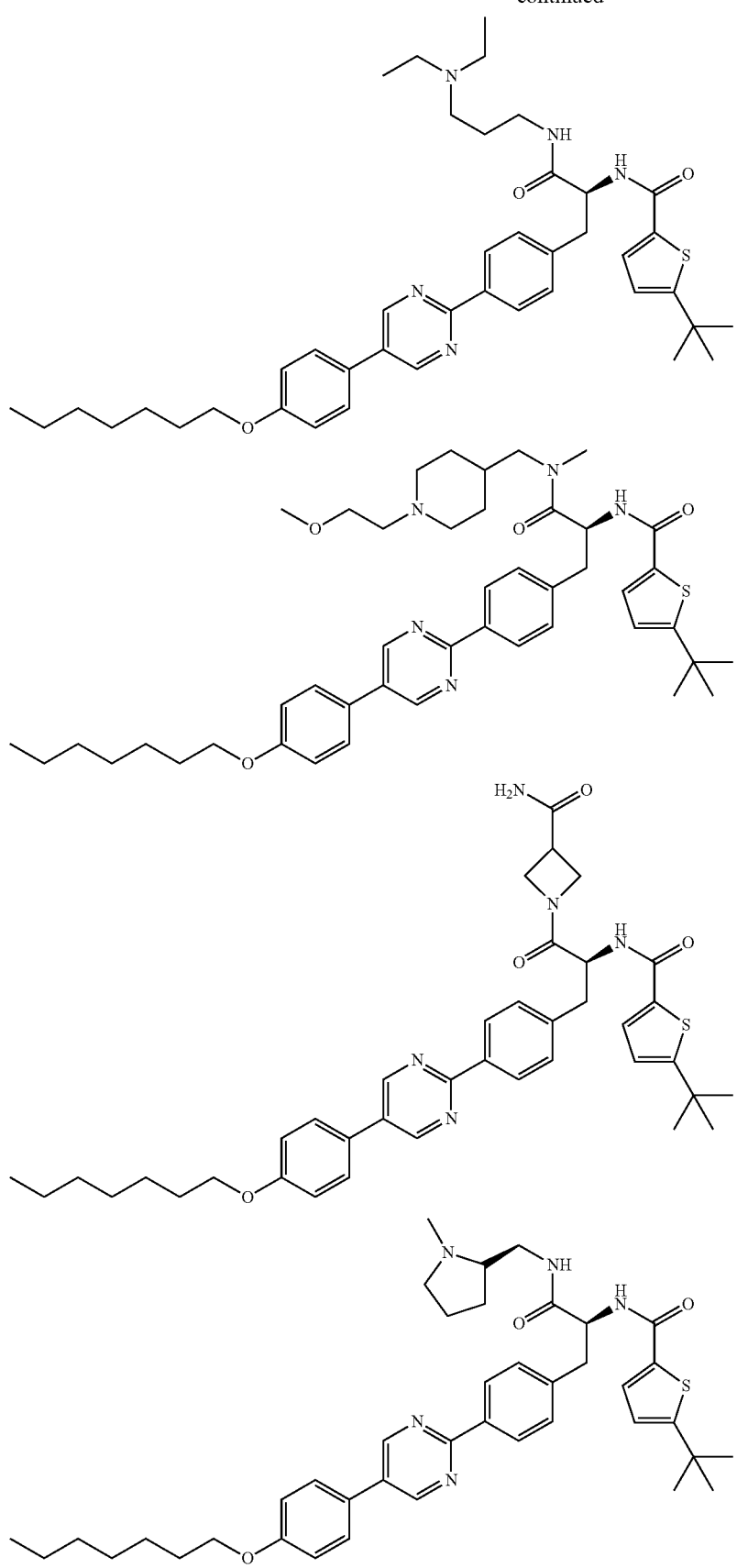

1501
-continued
1502
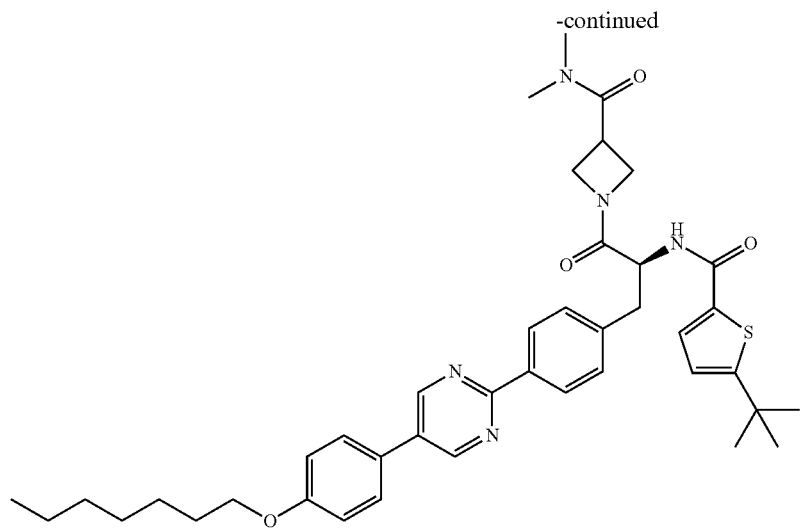
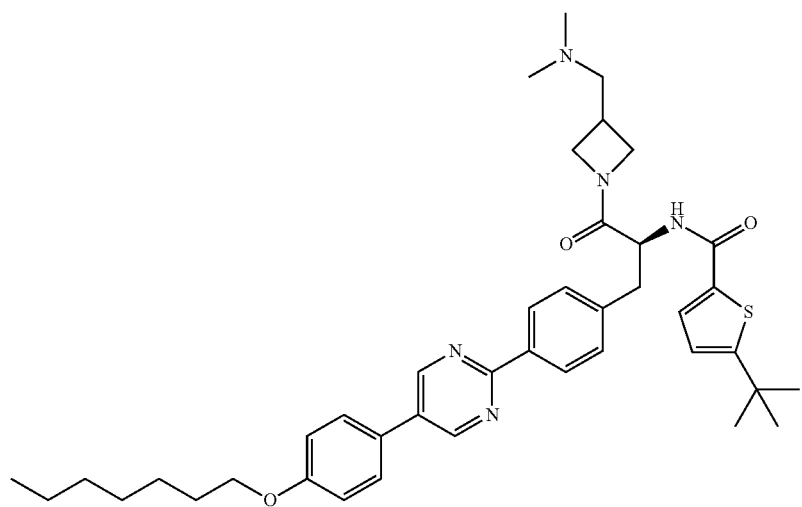
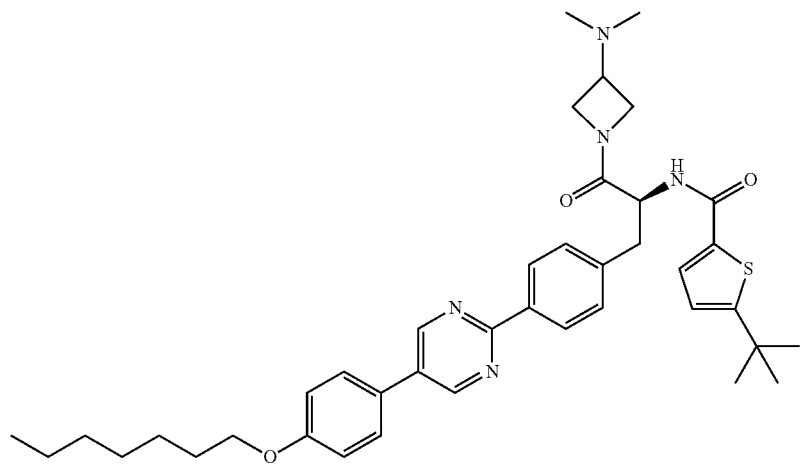

1503 1504
-continued
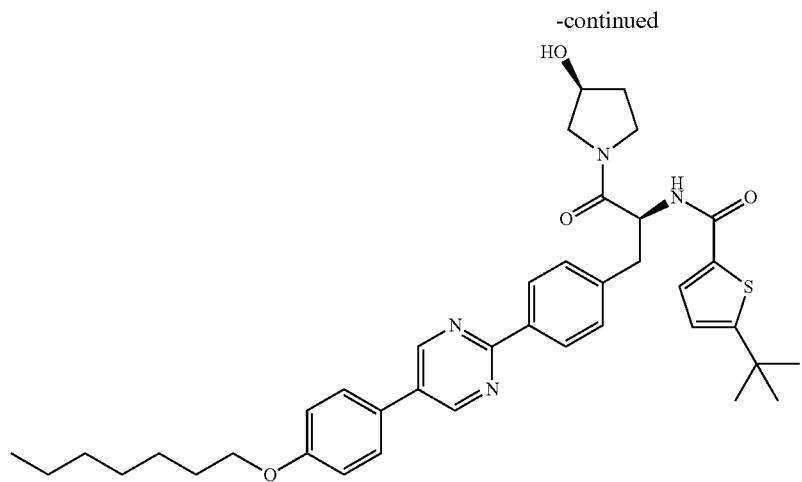
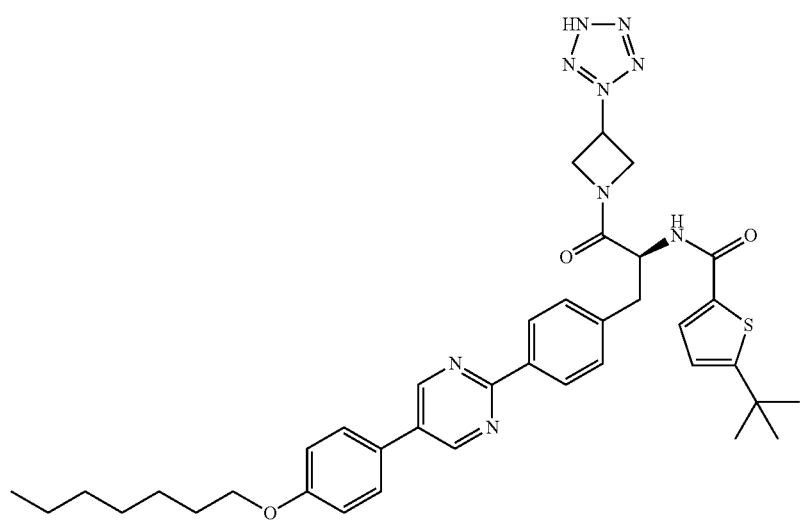
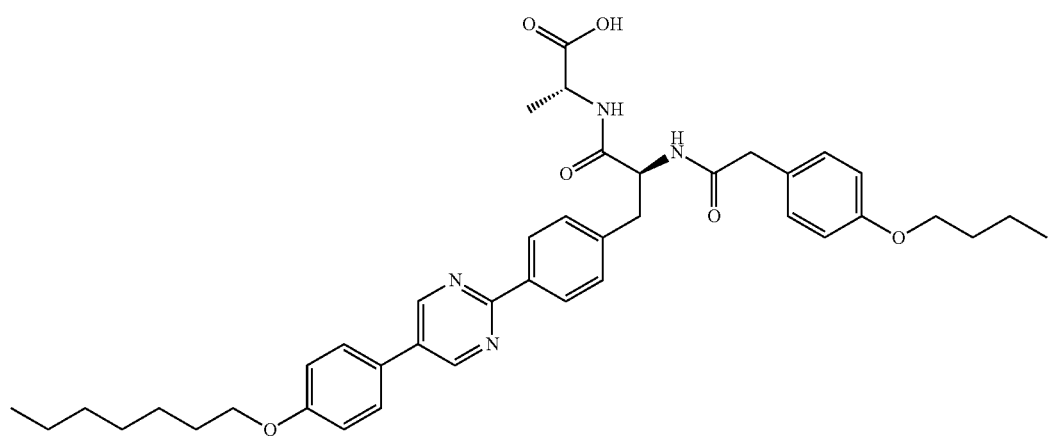

1505	1506
-continued
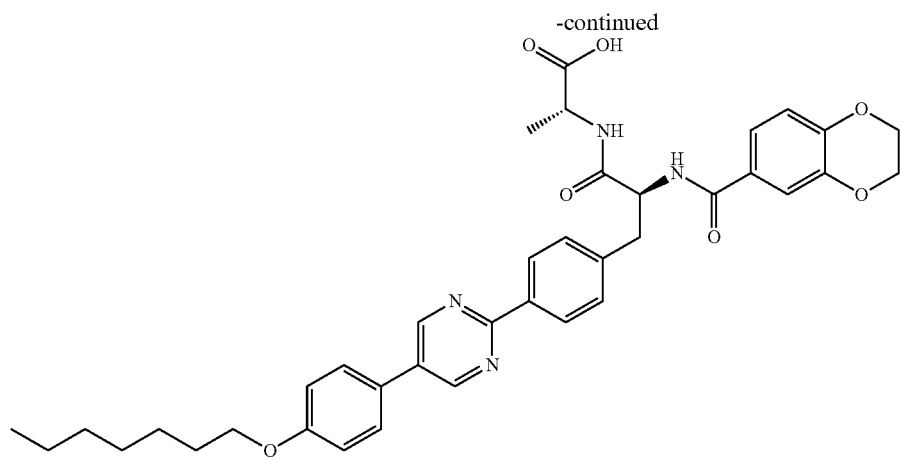
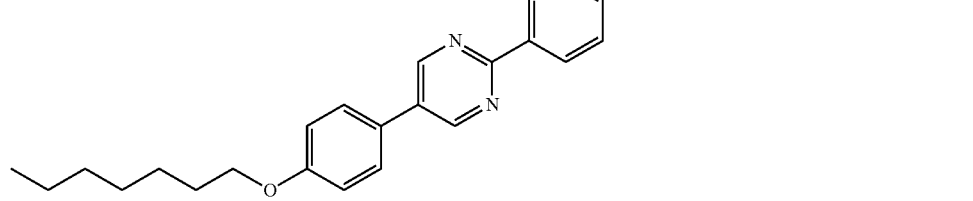
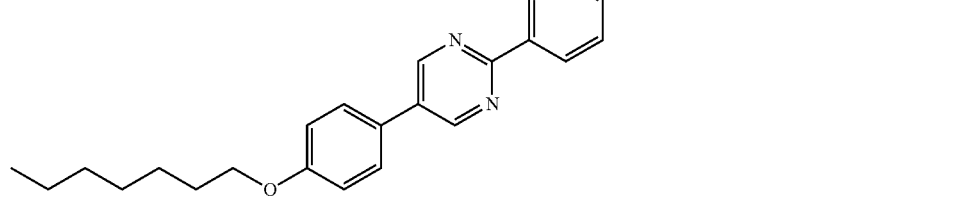
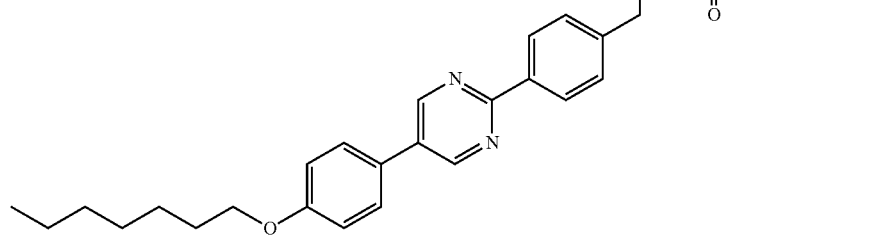

-continued
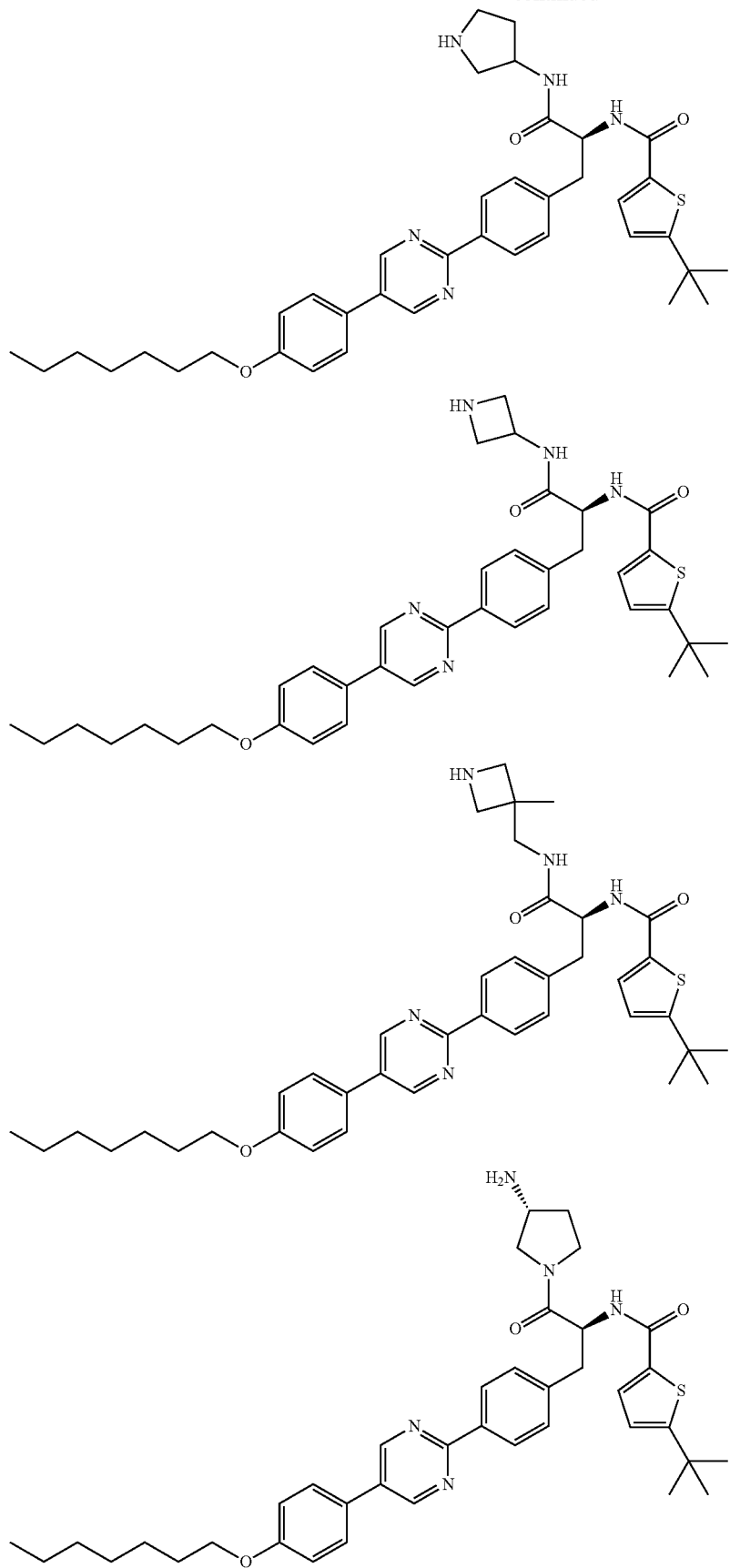

1509
-continued
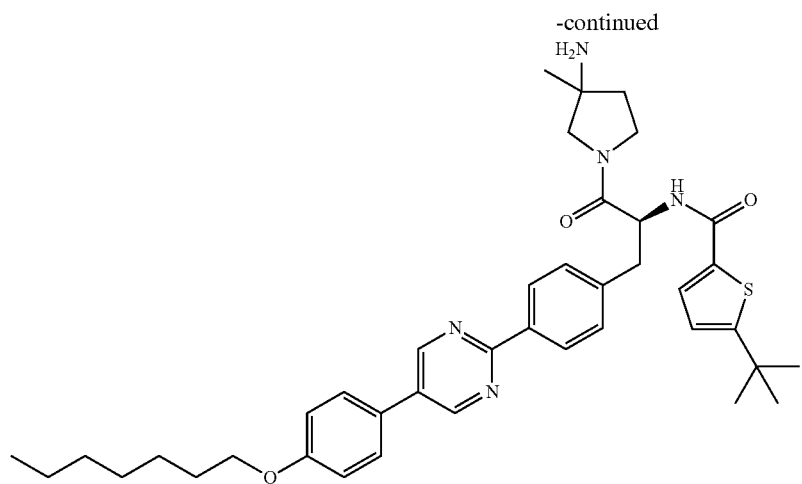
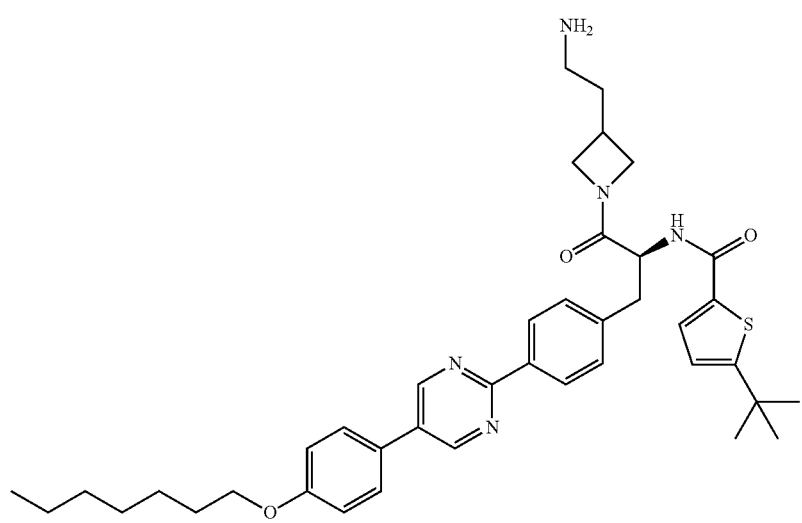
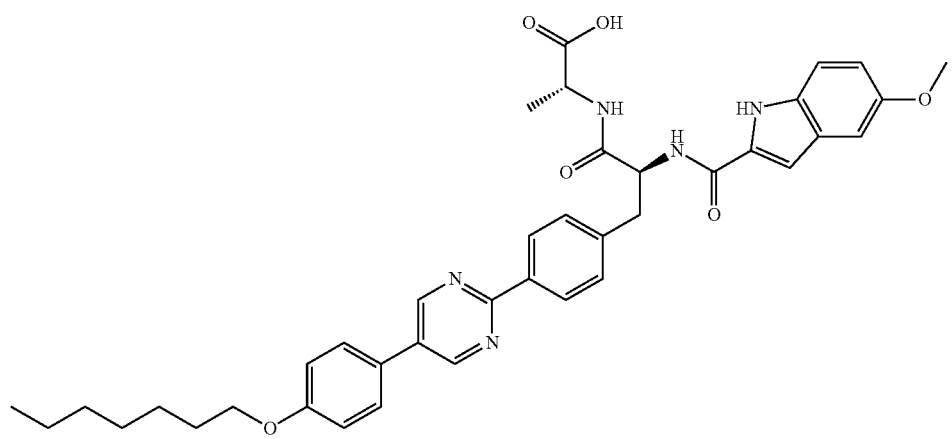
1510

1511
-continued
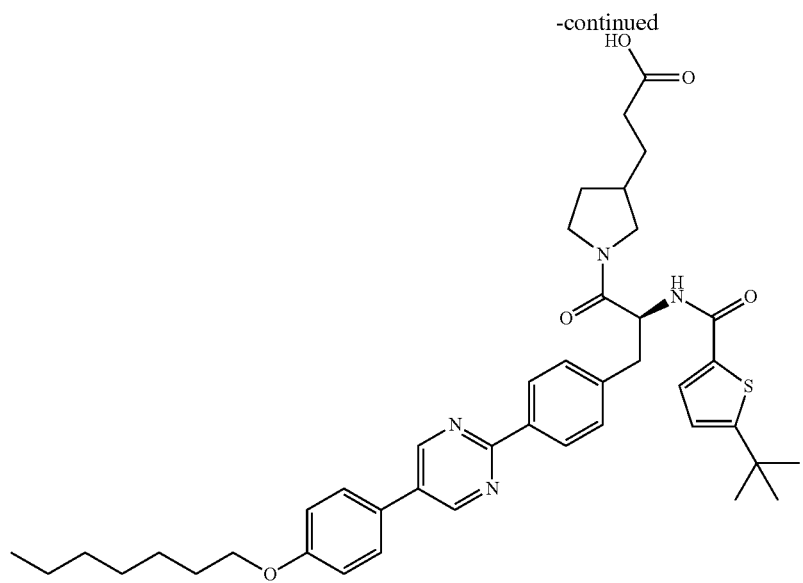
1512
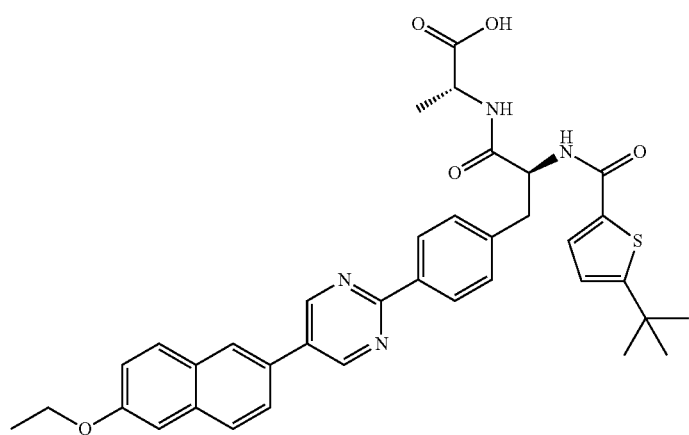
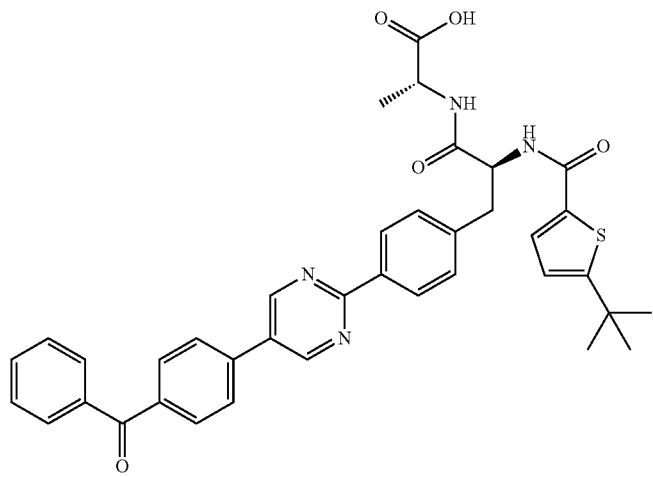

1513 1514
-continued
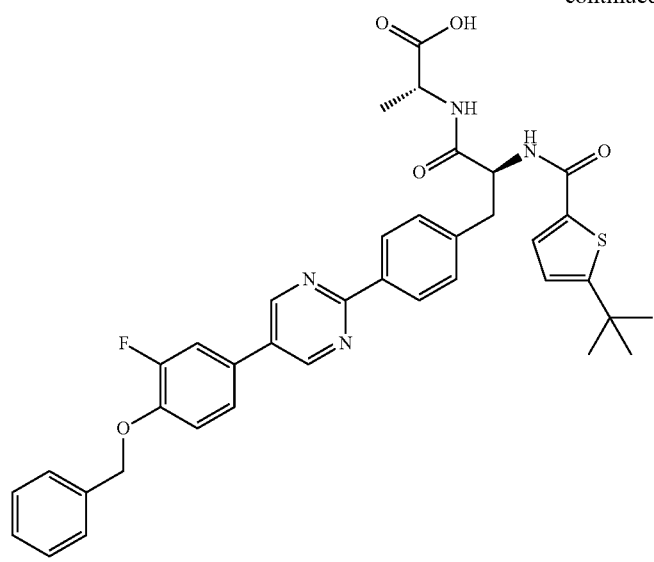
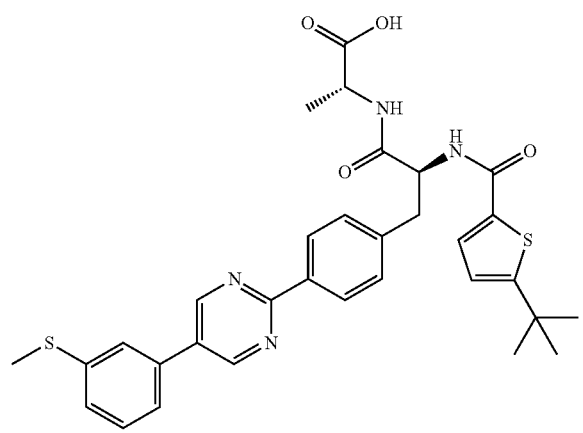
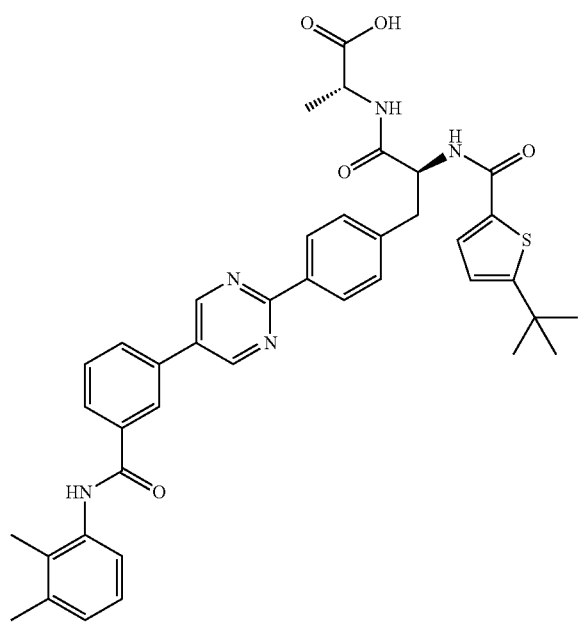
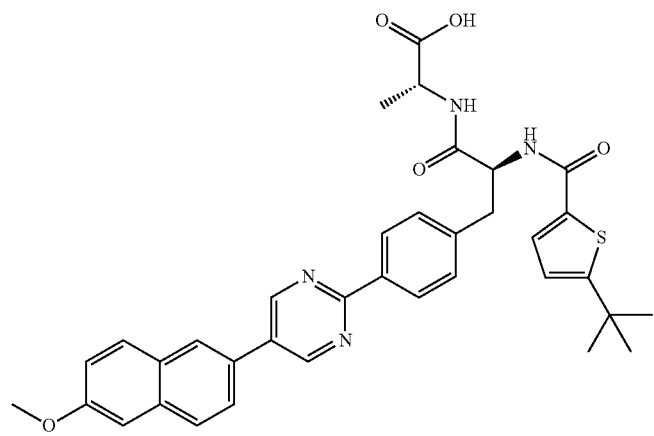

1515
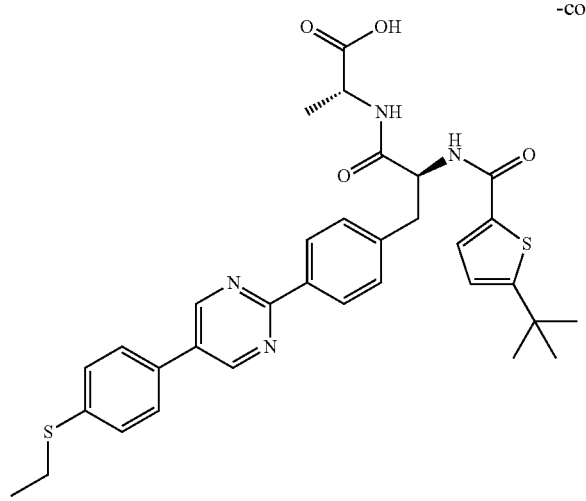
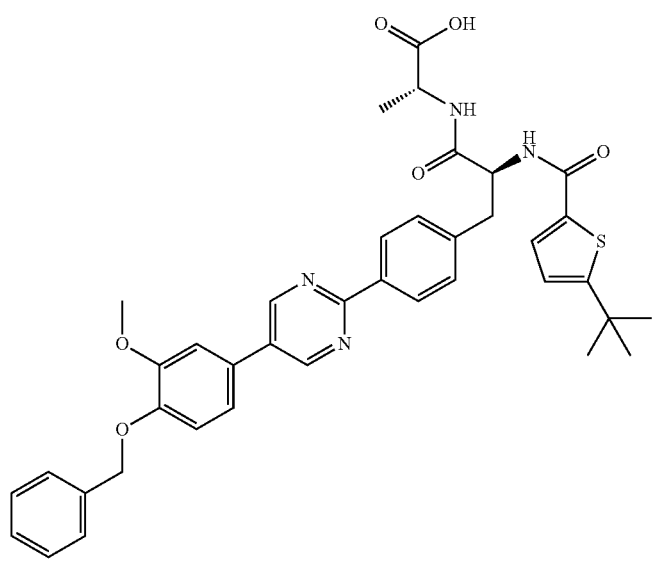
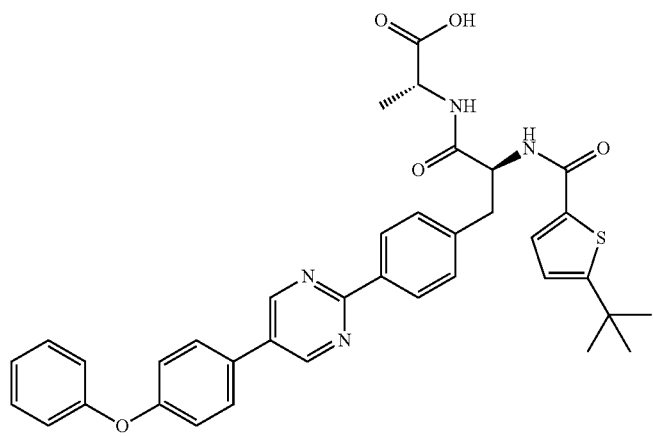
1516

1517 1518
-continued
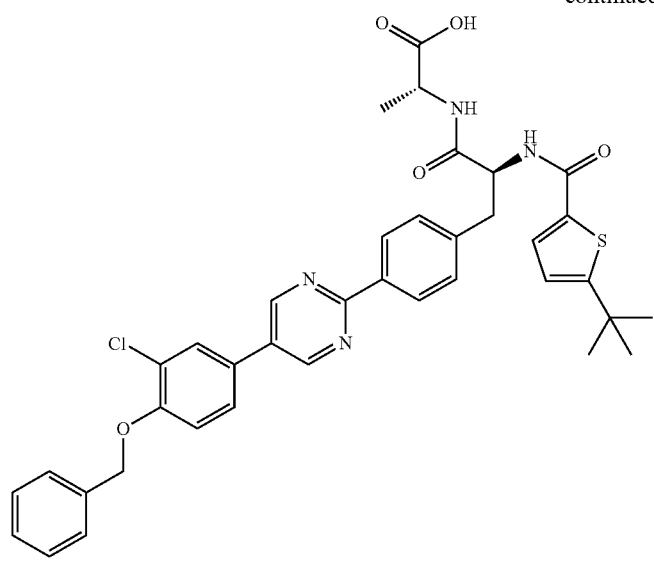
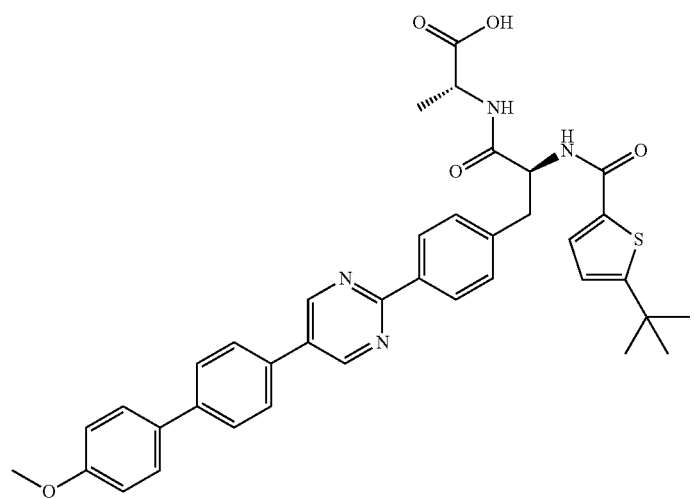
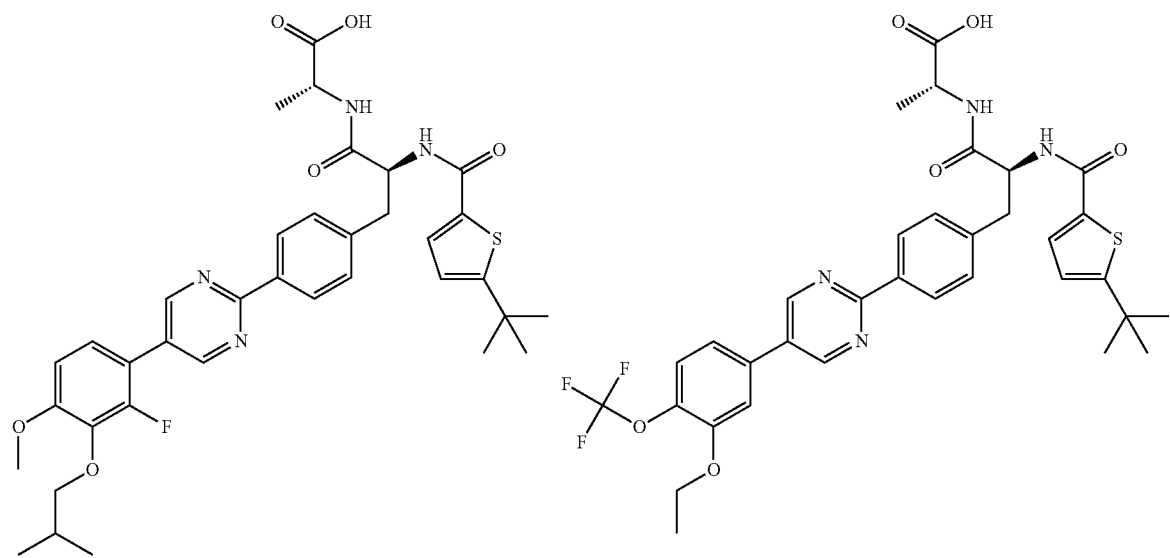

1519                    1520
-continued
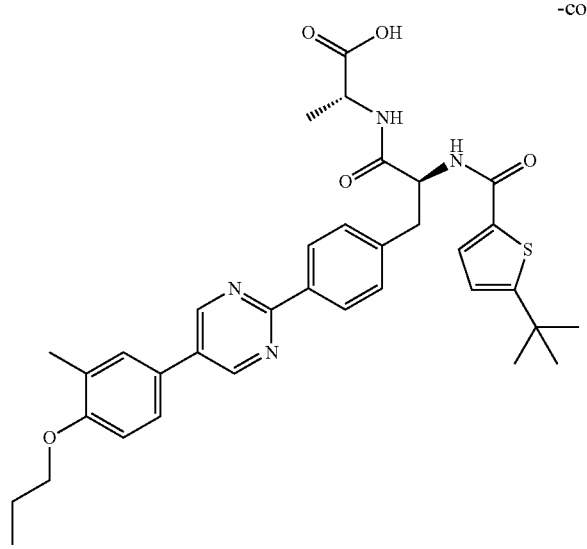
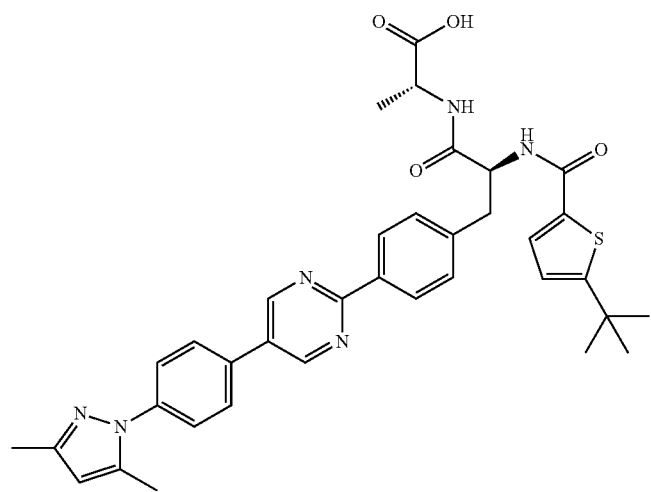
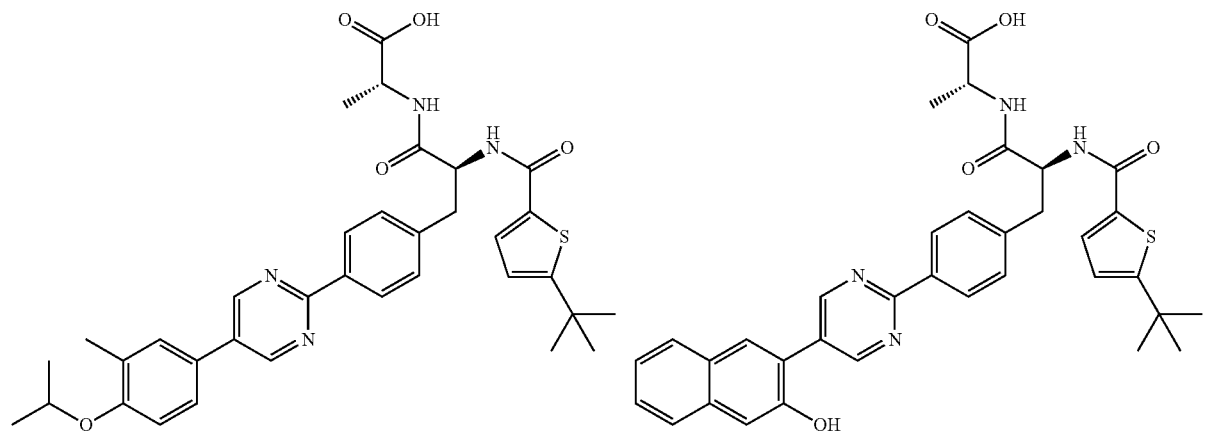

1521
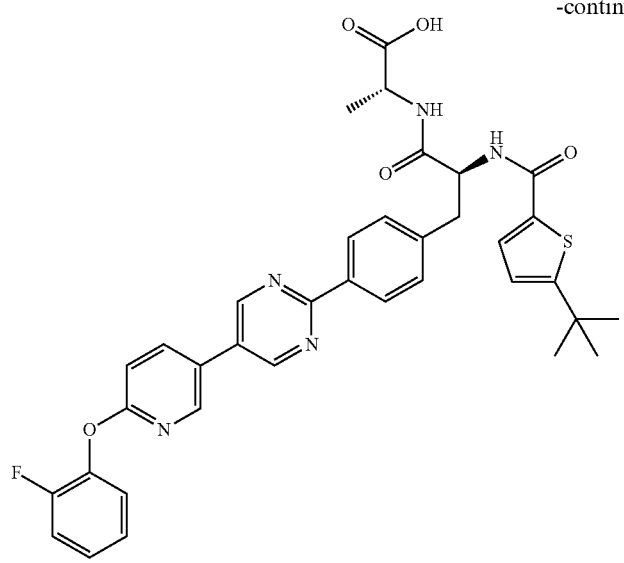
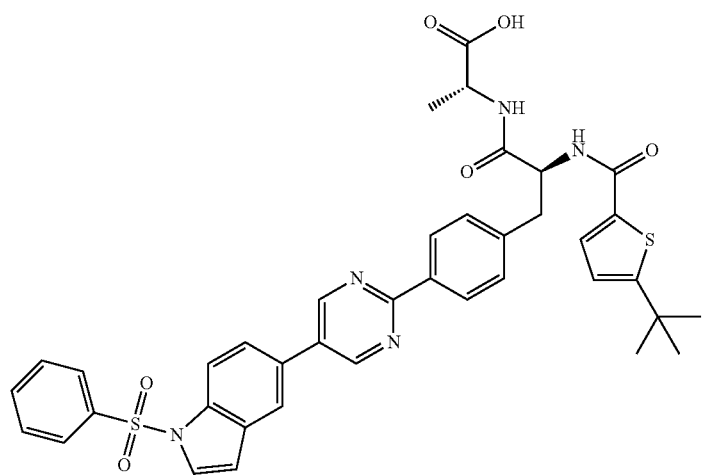
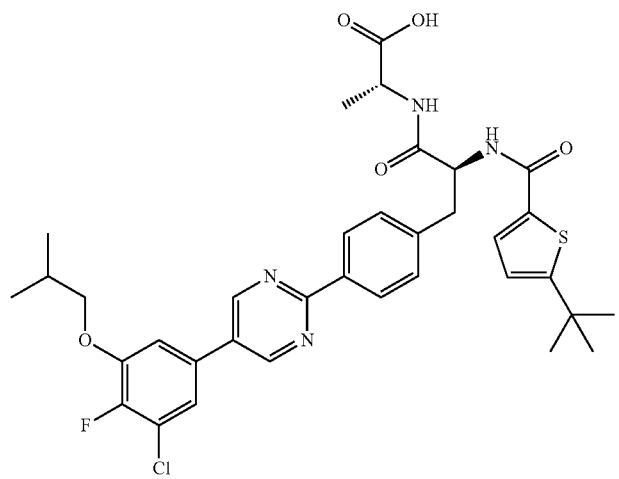
1522

-continued
1523
1524
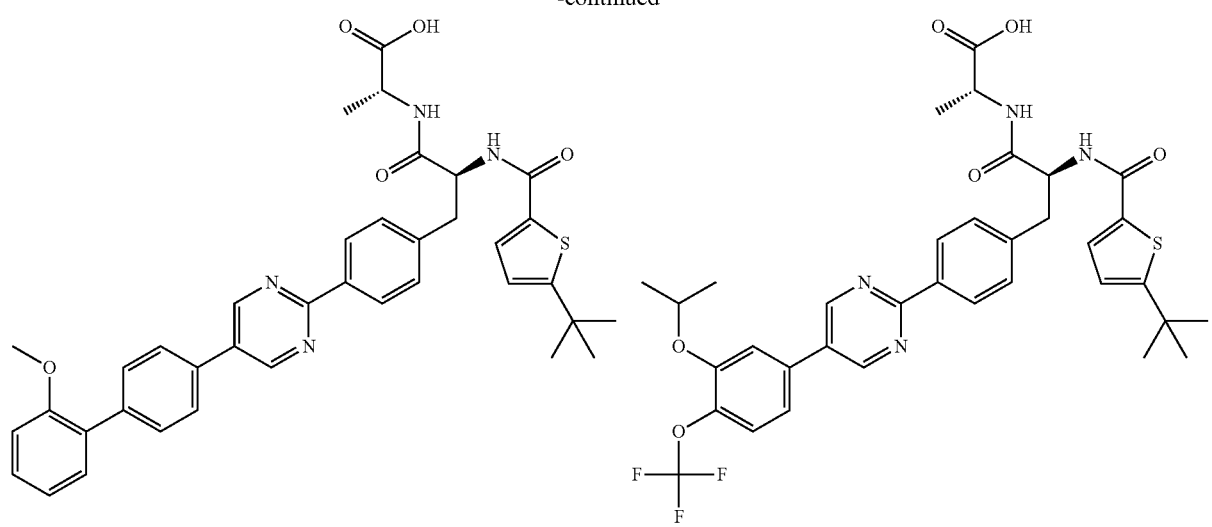
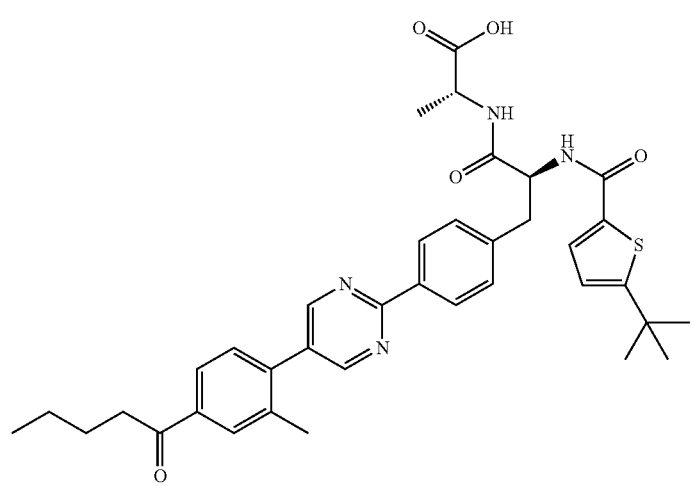
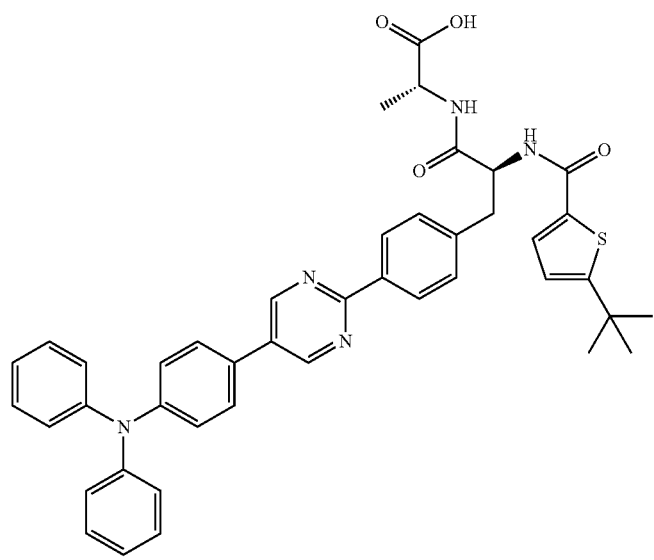

1525
-continued
1526
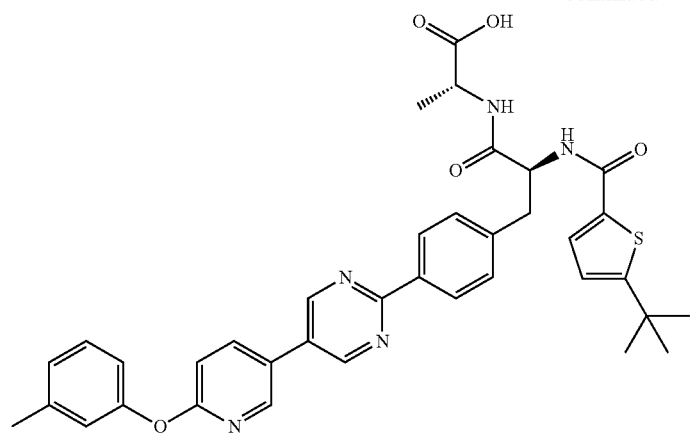
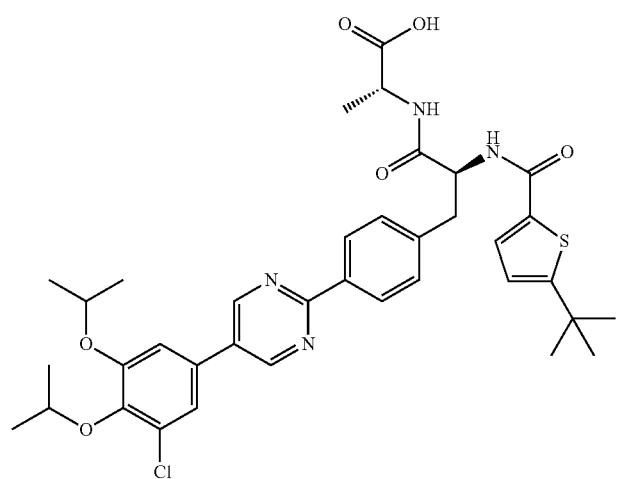
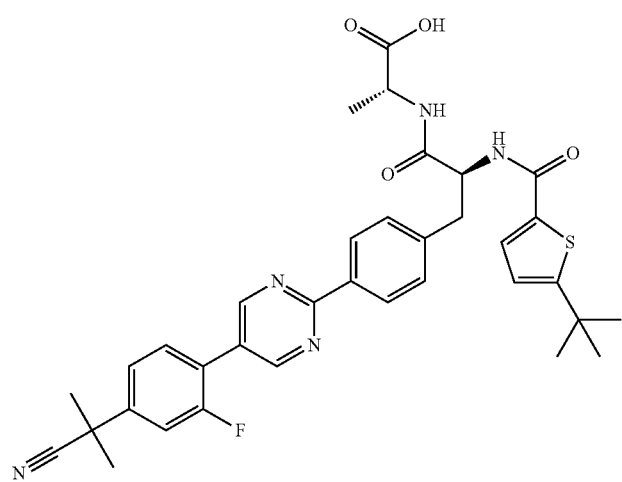

1527 1528
-continued
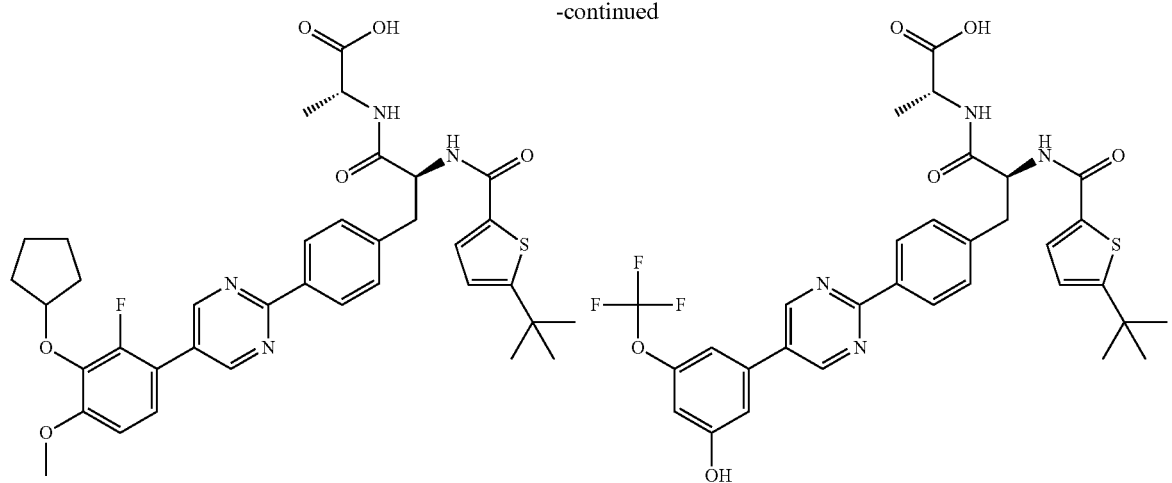
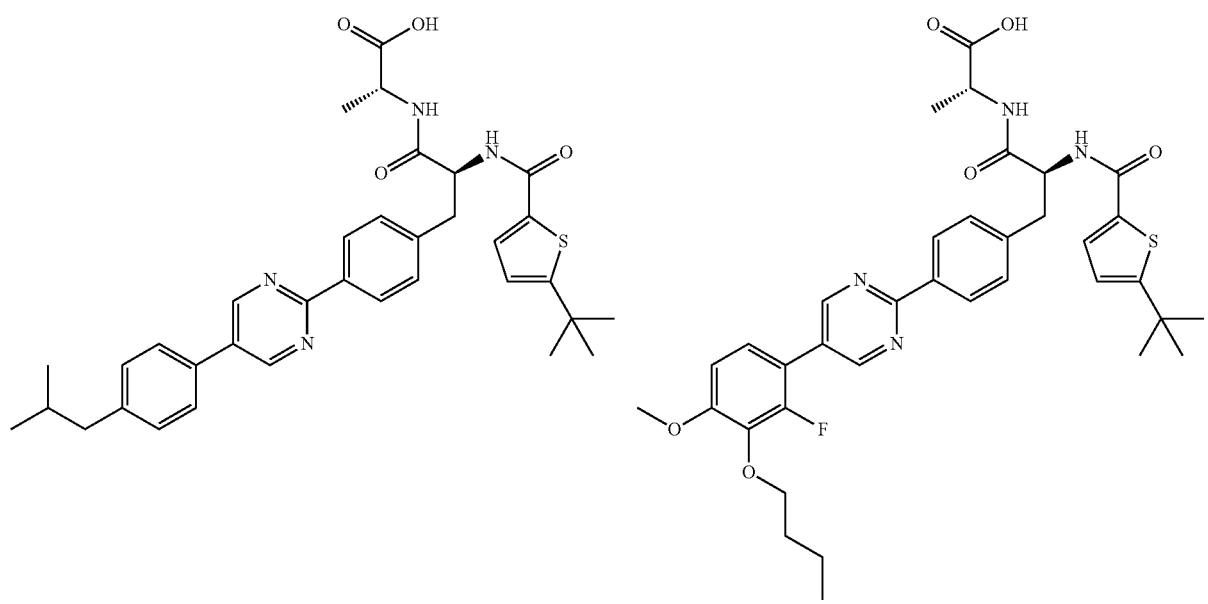
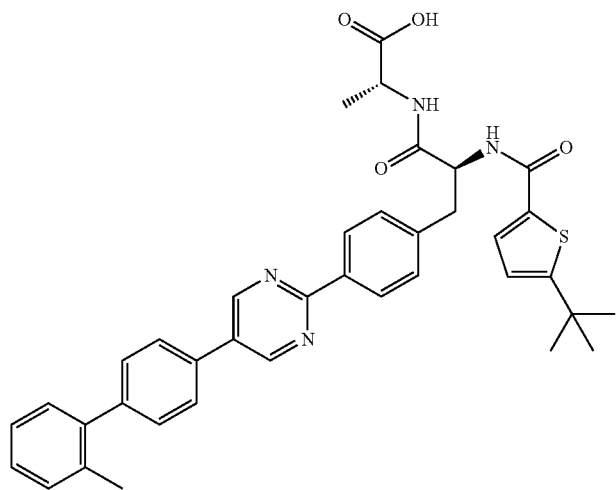

1529 -continued 1530
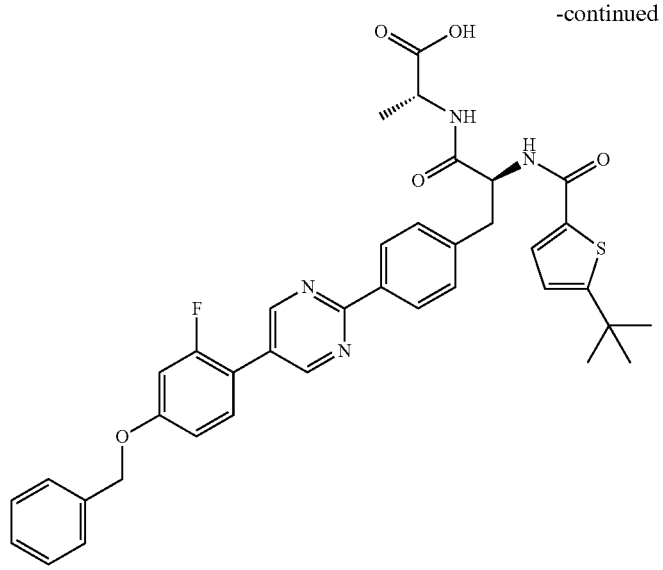
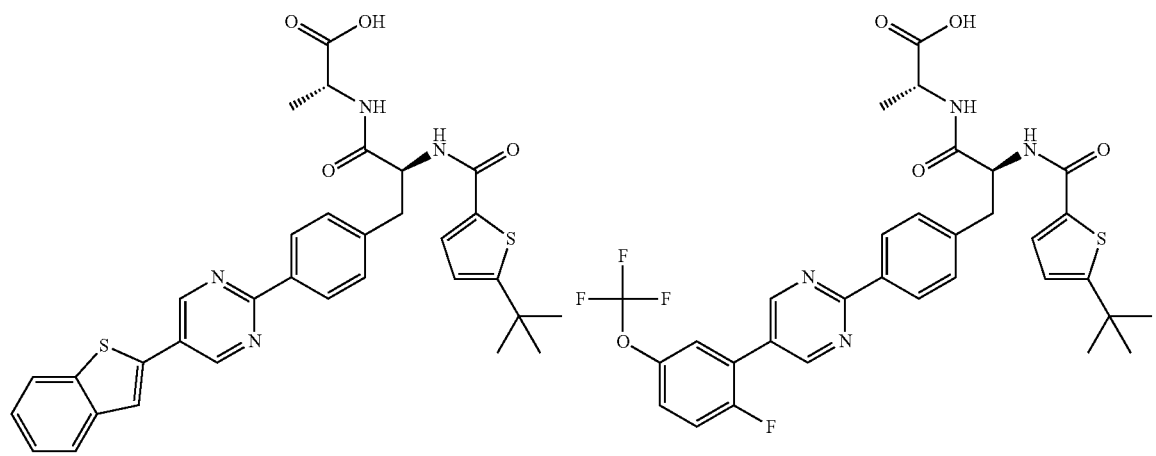
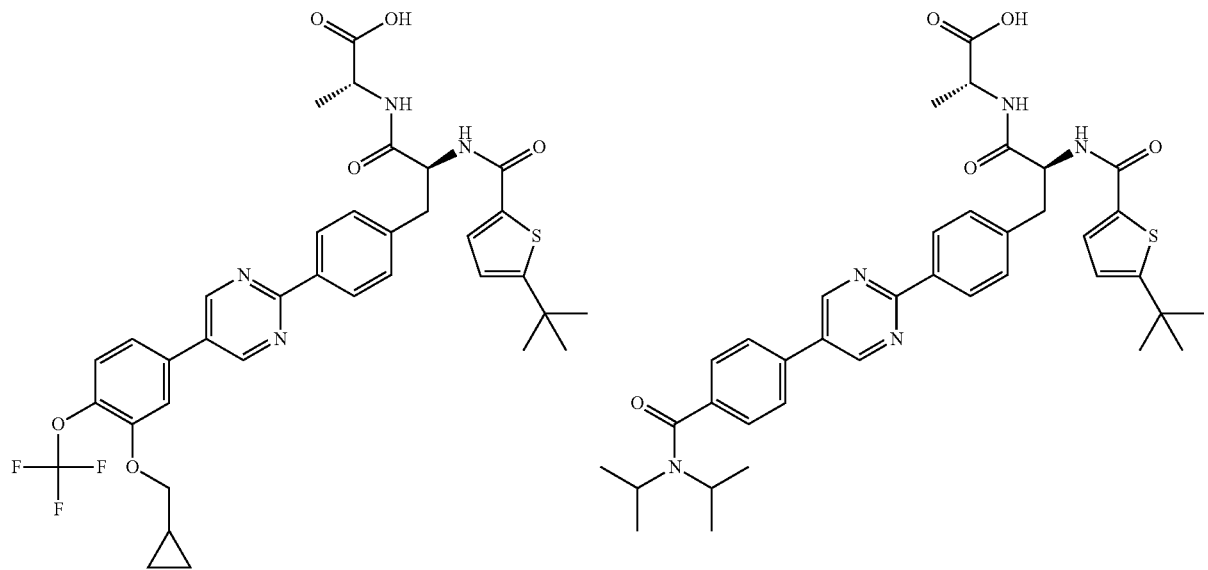

-continued
1531
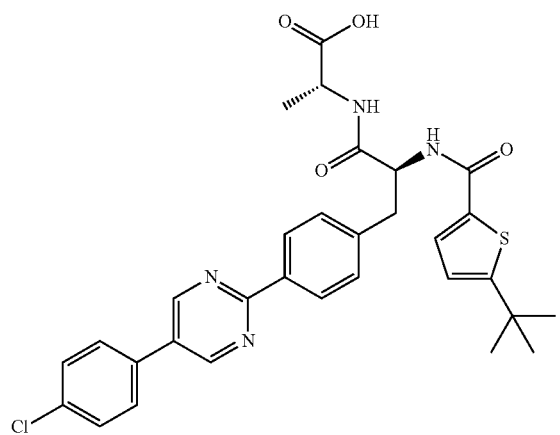
1532
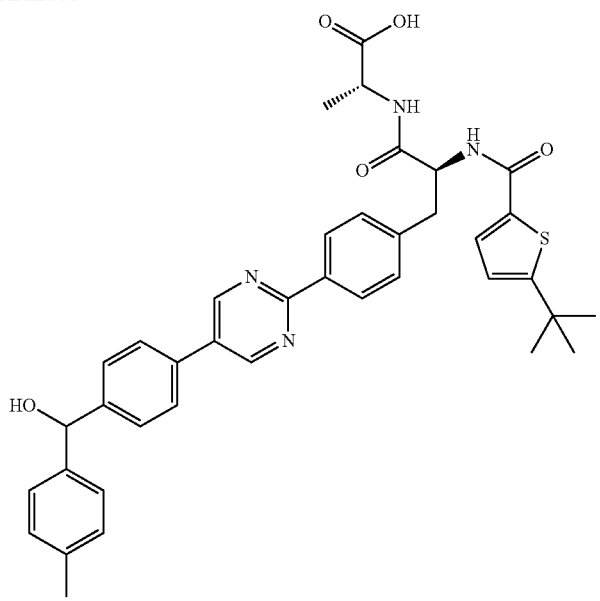
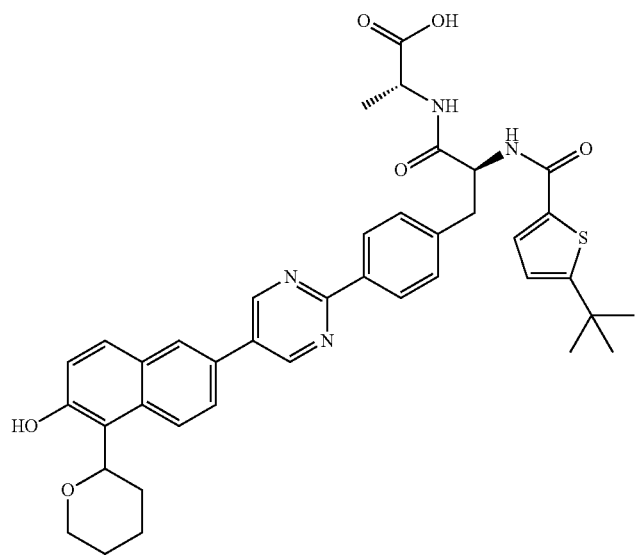

1533 1534
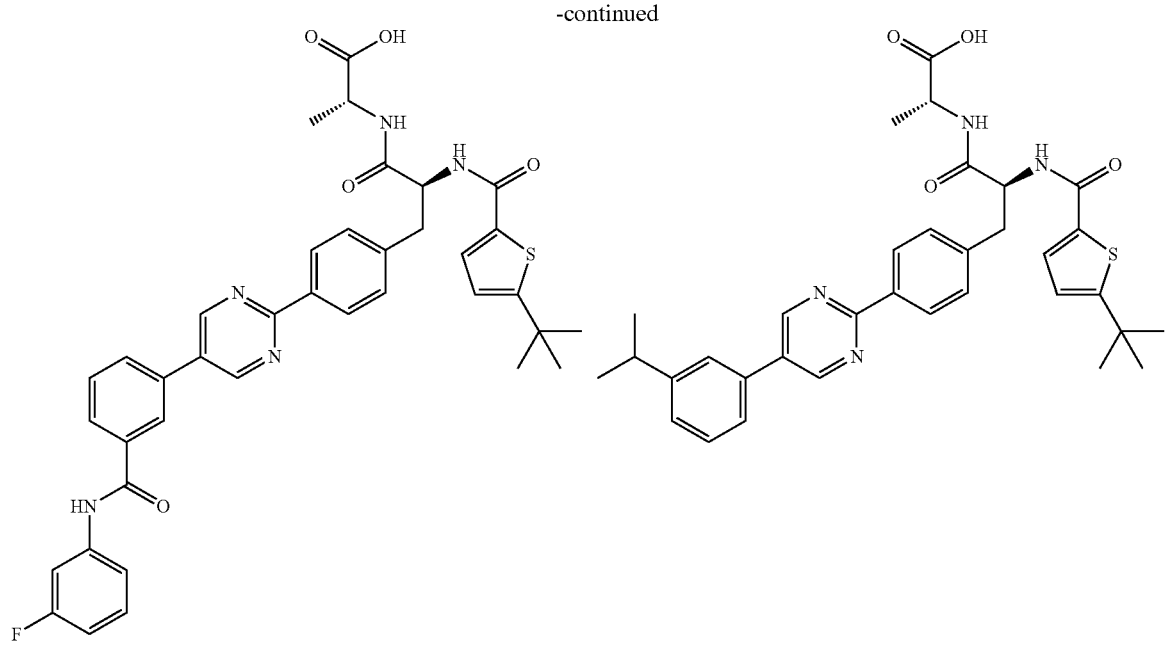
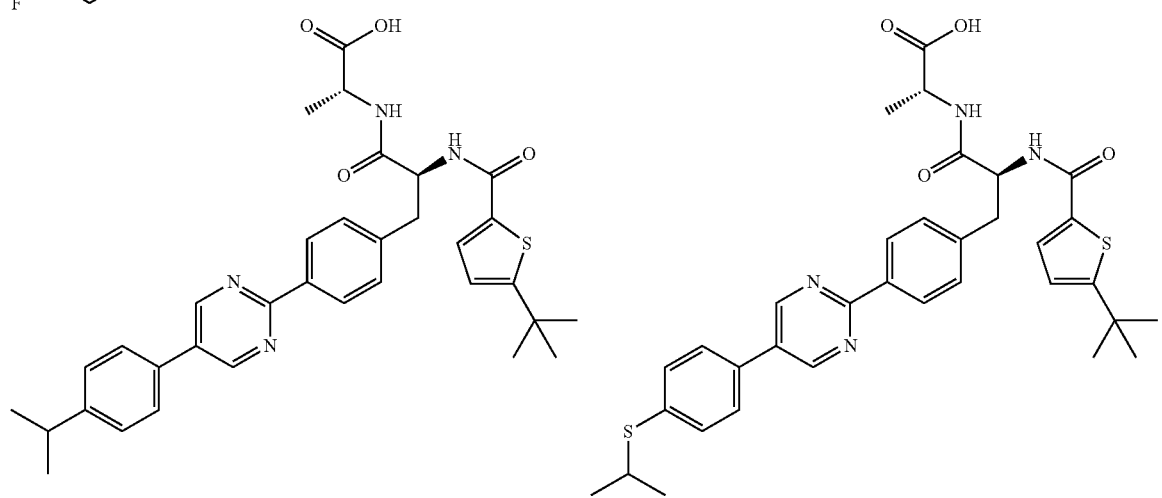
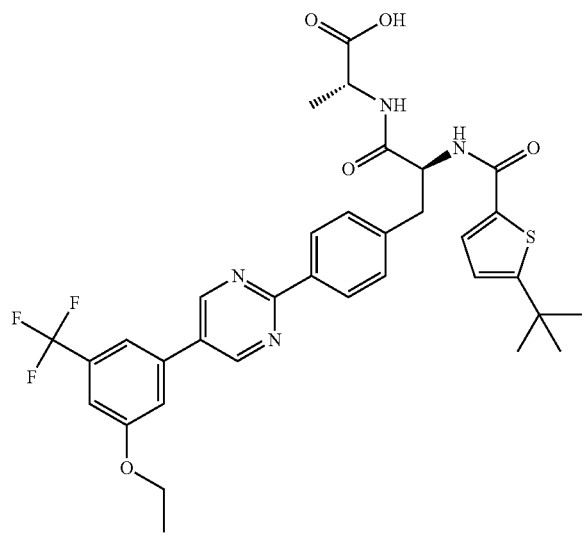

-continued
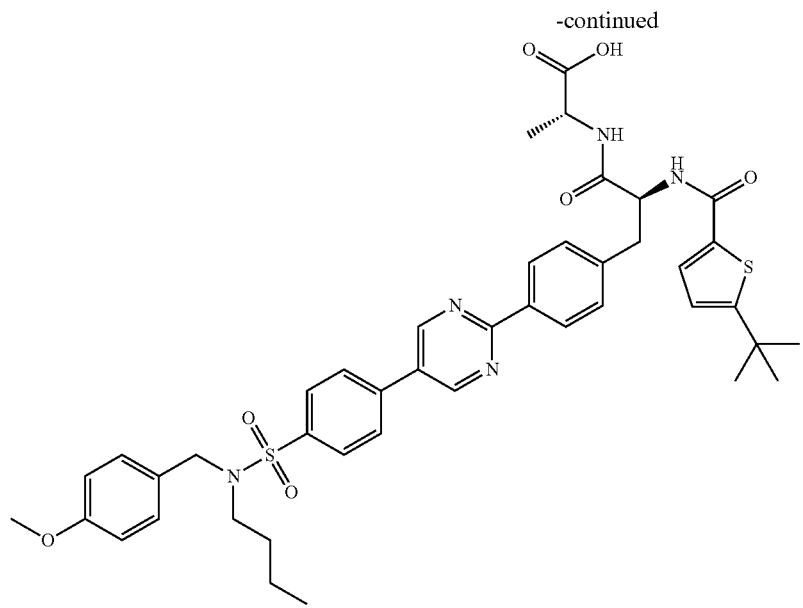
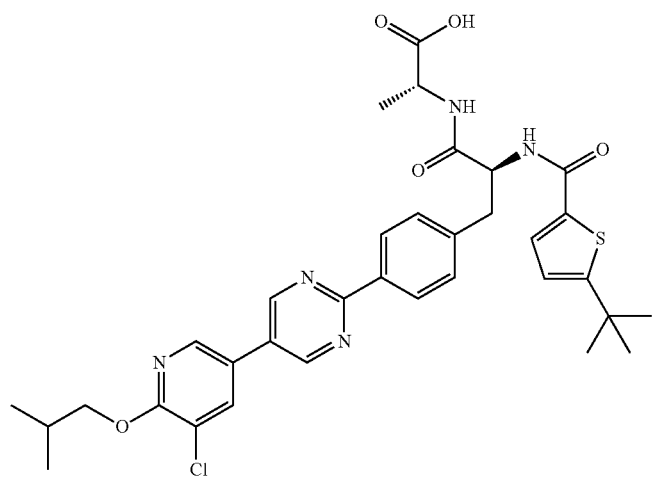
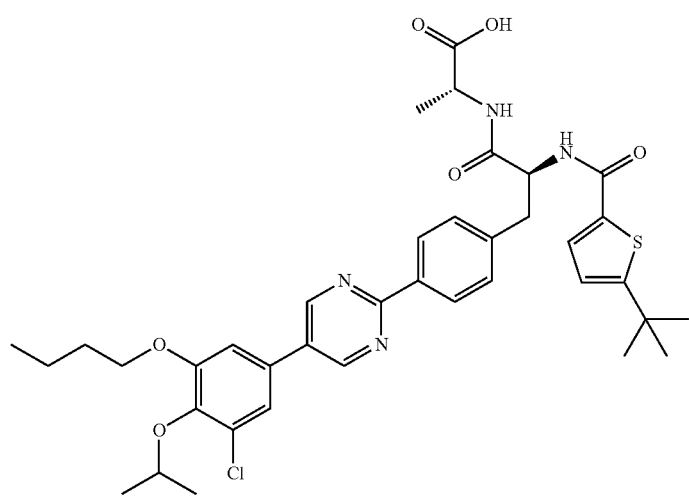

1537
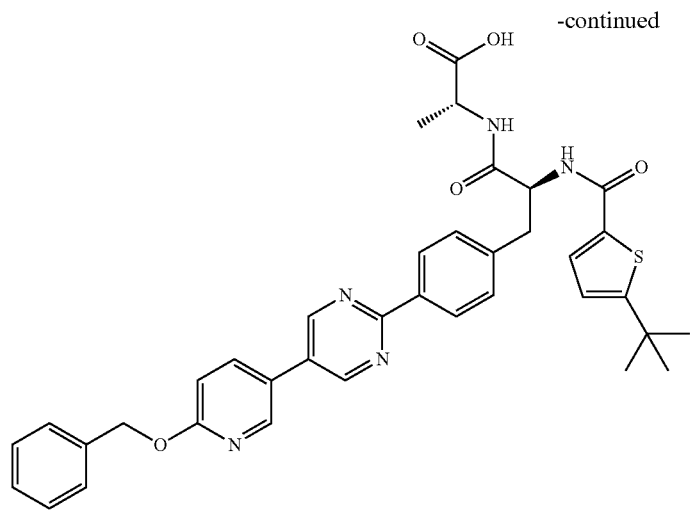
-continued
1538
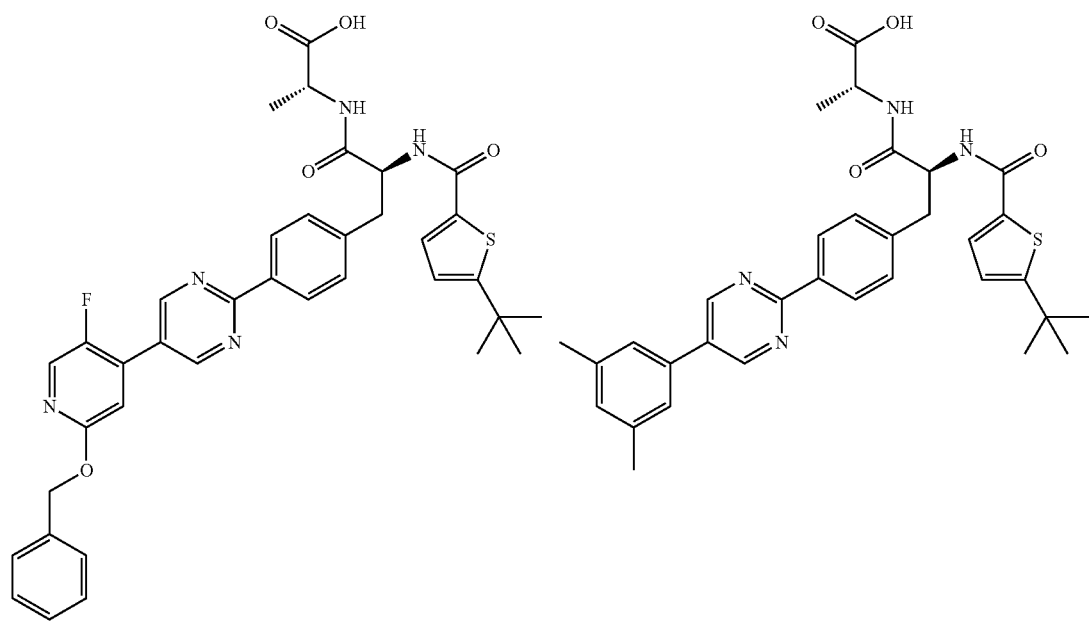
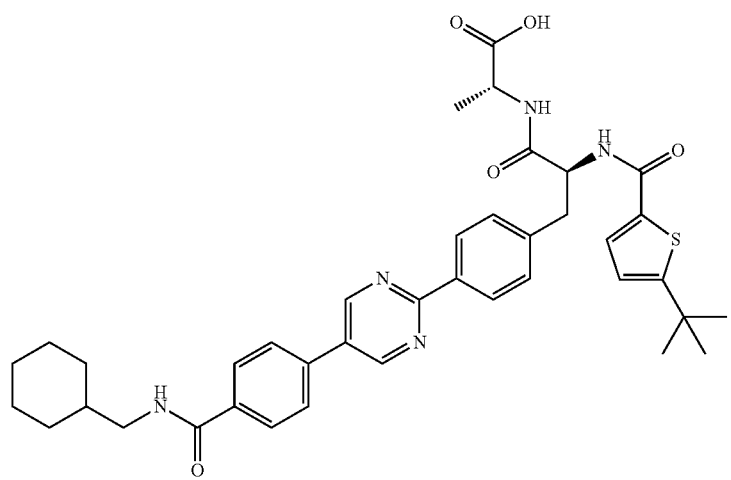

1539
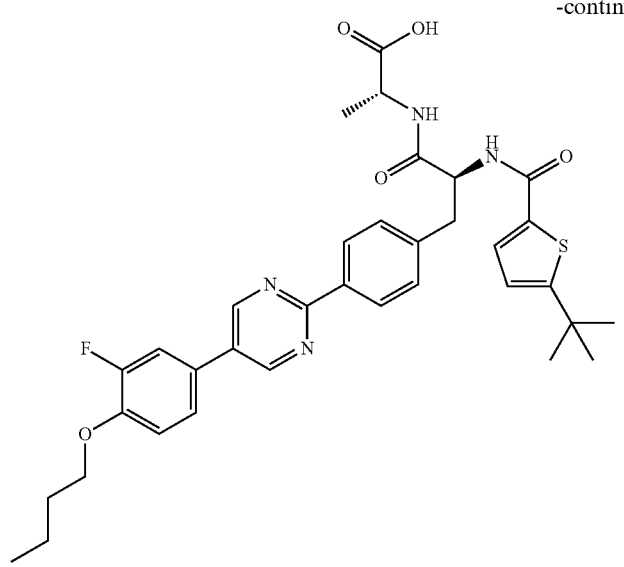
-continued
1540
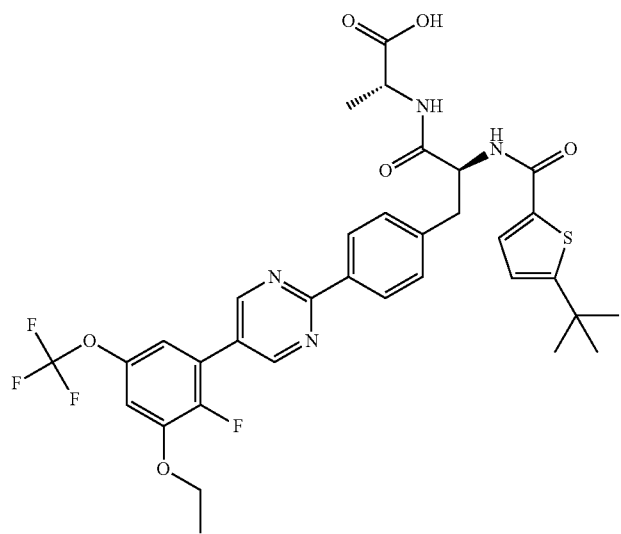
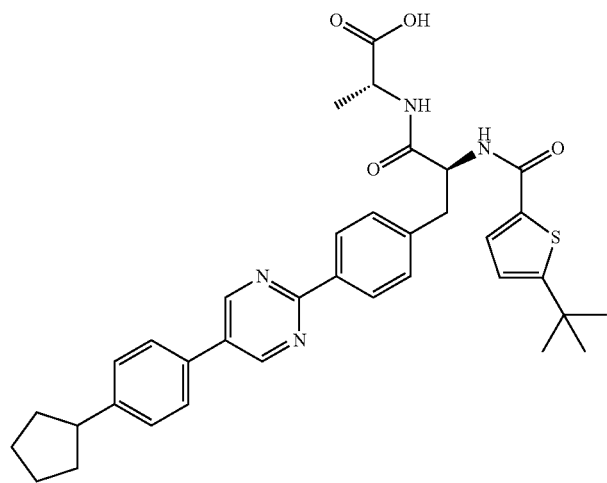

1541 | 1542
-continued
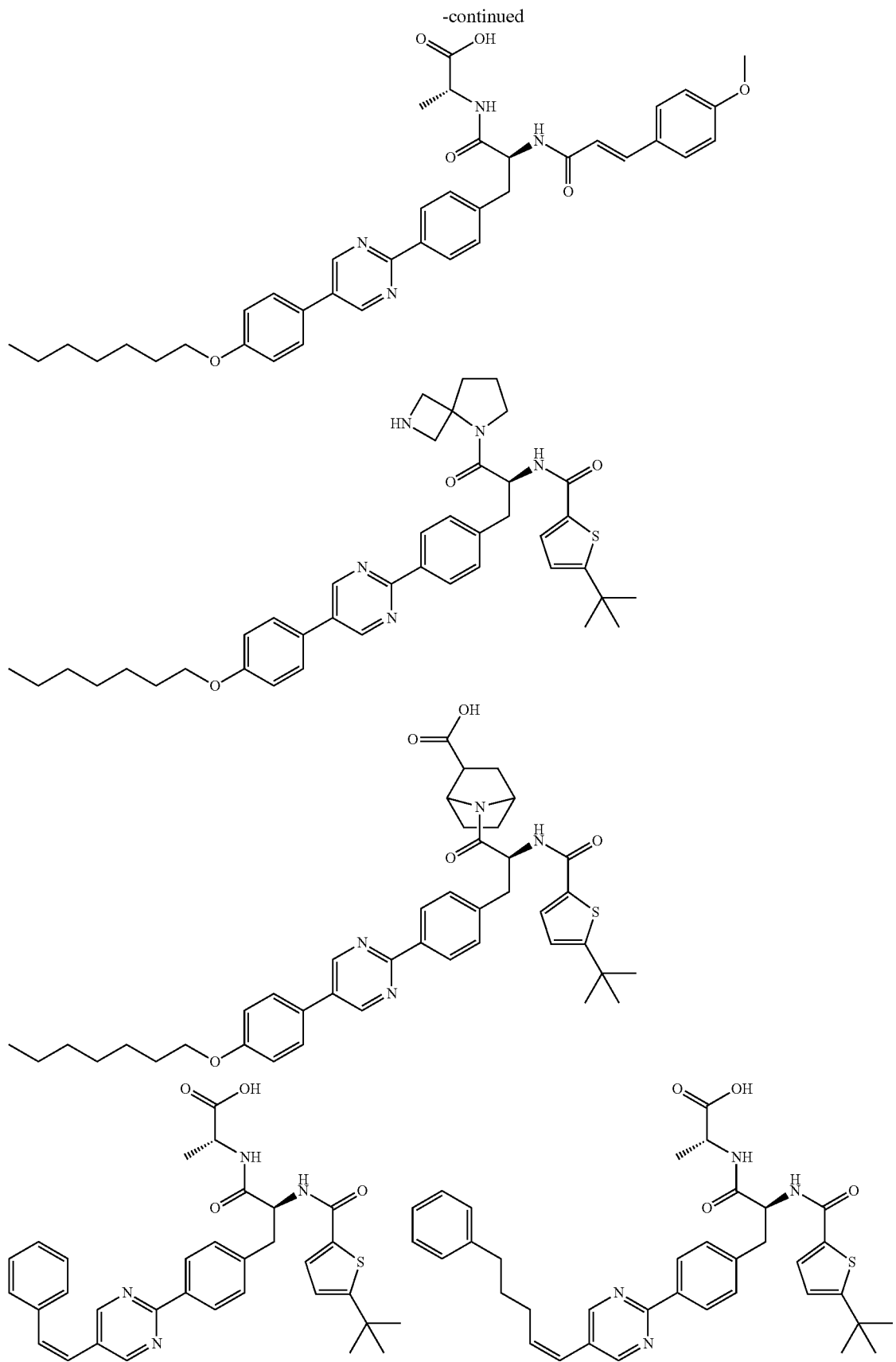

1543
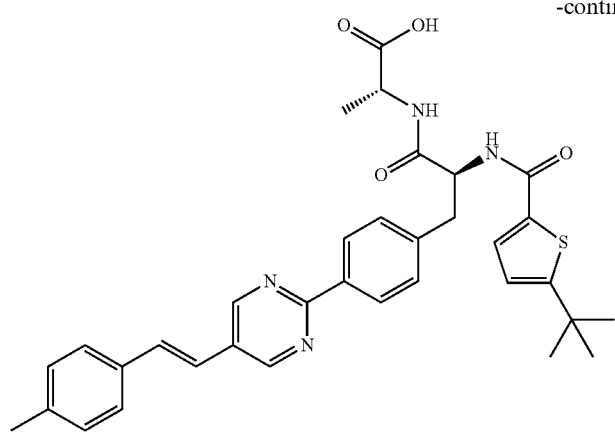
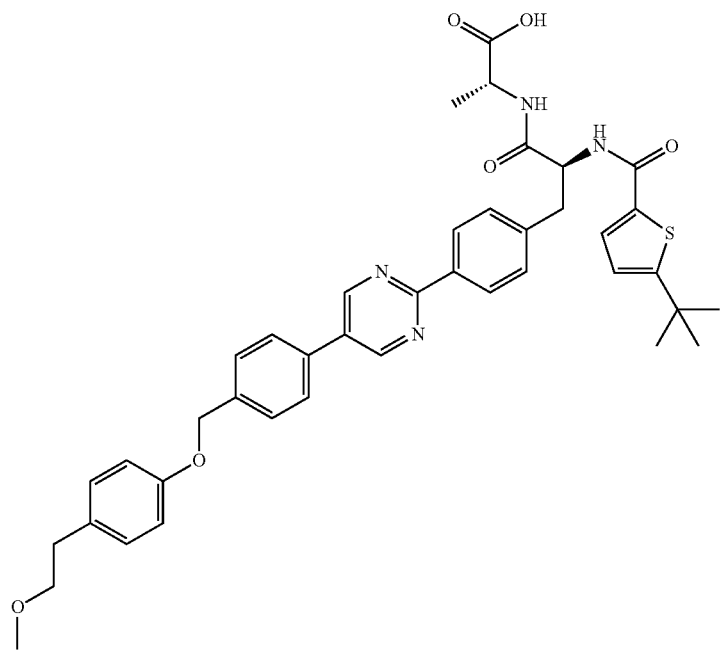
1544
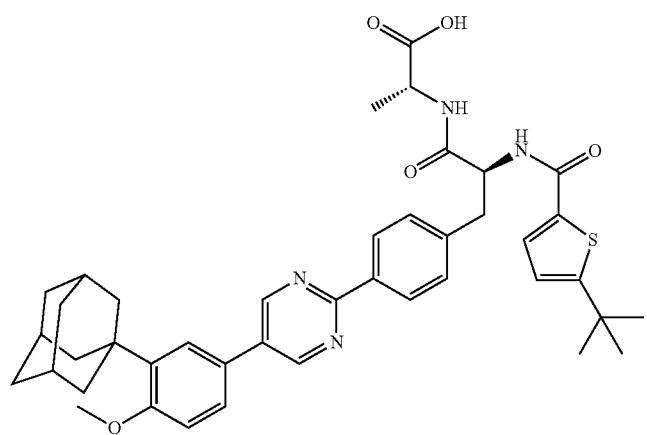

-continued
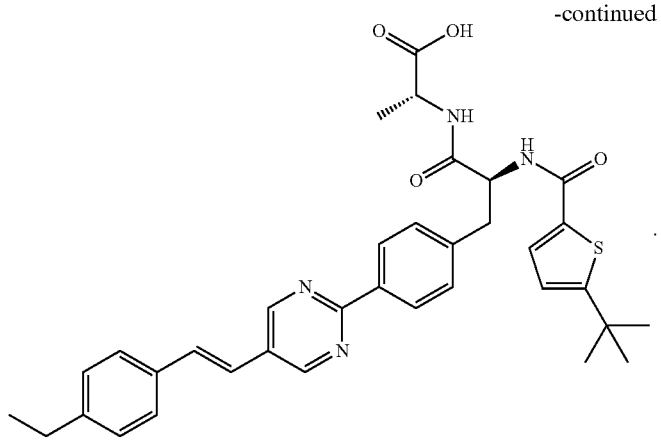
* * * * *

UNITED STATES PATENT AND TRADEMARK OFFICE
CERTIFICATE OF CORRECTION

| | | |
|---|---|---|
| PATENT NO. | : 9,598,430 B2 | Page 1 of 1 |
| APPLICATION NO. | : 14/958513 | |
| DATED | : March 21, 2017 | |
| INVENTOR(S) | : Marcus F. Boehm et al. | |

It is certified that error appears in the above-identified patent and that said Letters Patent is hereby corrected as shown below:

Column 1020, Line 15:
"$W_1$ is null or $I_1$-$(CR_aR_b)$m-$L_1$-$R_6$;" should read, -- $W_1$ is null or $L_1$-$(CR_aR_b)$m-$L_1$-$R_6$; --.

Column 1020, Lines 16-18:
"-C(O)O-, -S(O$_2$)-, -S(O)-, -S-, -N(R$_1$)-C(O)-N(R$_1$)-, C(O)-O-, -C(O)- or -S(O$_2$)-NR$_1$-;" should read, -- C(O)O-, -S(O$_2$)-, -S(O)-, -S-, -N(R$_1$)-C(O)-N(R$_1$)-, -N(R$_1$)-C(O)-O-, -C(O)- or -S(O$_2$)-NR$_1$-; --.

Column 1022, Line 15:
"compound has following structure:" should read, -- compound has the following structure: --.

Column 1022, Line 30:
"compound has following structure:" should read, -- compound has the following structure: --.

Signed and Sealed this
Fifth Day of December, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: the GLP-1agonist (liraglutide(VICTOZA)

<400> SEQUENCE: 1

His Ala Glu Gly Thr Phe Thr Ser Asp Val Ser Ser Tyr Leu Glu Gly
 1               5                   10                  15

Gln Ala Ala Lys Glu Phe Ile Ala Trp Lys Val Arg Gly Arg Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Peptide sequence GLP-1(7-36)

<400> SEQUENCE: 2

His Ala Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Gly Arg
            20                  25                  30

<210> SEQ ID NO 3
<211> LENGTH: 28
<212> TYPE: PRT
<213> ORGANISM: Artificial Sequence
<220> FEATURE:
<223> OTHER INFORMATION: Peptide sequence GLP-1(9-36)

<400> SEQUENCE: 3

Glu Gly Thr Phe Thr Ser Asp Val Ser Ser Tyr Leu Glu Gly Gln Ala
 1               5                   10                  15

Ala Lys Glu Phe Ile Ala Trp Leu Val Lys Gly Arg
            20                  25
```